US009916538B2

(12) United States Patent
Zadeh et al.

(10) Patent No.: US 9,916,538 B2
(45) Date of Patent: Mar. 13, 2018

(54) METHOD AND SYSTEM FOR FEATURE DETECTION

(71) Applicants: Lotfi A. Zadeh, Berkeley, CA (US); Saied Tadayon, Potomac, MD (US); Bijan Tadayon, Potomac, MD (US)

(72) Inventors: Lotfi A. Zadeh, Berkeley, CA (US); Saied Tadayon, Potomac, MD (US); Bijan Tadayon, Potomac, MD (US)

(73) Assignee: Z ADVANCED COMPUTING, INC., Potomac, MD (US)

( * ) Notice: Subject to any disclaimer, the term of this patent is extended or adjusted under 35 U.S.C. 154(b) by 650 days.

(21) Appl. No.: 14/218,923

(22) Filed: Mar. 18, 2014

(65) Prior Publication Data
US 2014/0201126 A1 Jul. 17, 2014

Related U.S. Application Data

(63) Continuation-in-part of application No. 13/781,303, filed on Feb. 28, 2013, now Pat. No. 8,873,813, which
(Continued)

(51) Int. Cl.
*G06N 7/00* (2006.01)
*G06K 9/62* (2006.01)

(52) U.S. Cl.
CPC ............ *G06N 7/005* (2013.01); *G06K 9/627* (2013.01)

(58) Field of Classification Search
None
See application file for complete search history.

(56) References Cited

U.S. PATENT DOCUMENTS 5,212,730 A * 5/1993 Wheatley ............ G10L 15/063
704/232
5,295,228 A 3/1994 Koda et al.
(Continued)

OTHER PUBLICATIONS

Ali Sanayei, titled "Towards a complexity theory: Theoratical foundations and practical applications", submitted to Satellite Meeting Unravelling and Controlling Discrete Dynamical Systems, on Jun. 17, 2011. No page number, volume number, or publisher's location mentioned. (Paper dedicated to Professor Lotfi A. Zadeh, et al., by the author.).
(Continued)

*Primary Examiner* — Kakali Chaki
*Assistant Examiner* — Michael Zidanic
(74) *Attorney, Agent, or Firm* — Bijan Tadayon; Saied Tadayon

(57) ABSTRACT

Specification covers new algorithms, methods, and systems for artificial intelligence, soft computing, and deep learning/recognition, e.g., image recognition (e.g., for action, gesture, emotion, expression, biometrics, fingerprint, facial, OCR (text), background, relationship, position, pattern, and object), Big Data analytics, machine learning, training schemes, crowd-sourcing (experts), feature space, clustering, classification, SVM, similarity measures, modified Boltzmann Machines, optimization, search engine, ranking, question-answering system, soft (fuzzy or unsharp) boundaries/impreciseness/ambiguities/fuzziness in language, Natural Language Processing (NLP), Computing-with-Words (CWW), parsing, machine translation, sound and speech recognition, video search and analysis (e.g. tracking), image annotation, geometrical abstraction, image correction, semantic web, context analysis, data reliability, Z-number, Z-Web, Z-factor, rules engine, control system, autonomous vehicle, self-diagnosis and self-repair robots, system diagnosis, medical diagnosis, biomedicine, data mining,
(Continued)

event prediction, financial forecasting, economics, risk assessment, e-mail management, database management, indexing and join operation, memory management, data compression, event-centric social network, Image Ad Network.

29 Claims, 320 Drawing Sheets

Related U.S. Application Data is a continuation-in-part of application No. 14/201,974, filed on Mar. 10, 2014, now Pat. No. 8,949,170, which is a continuation of application No. 13/953,047, filed on Jul. 29, 2013, now Pat. No. 8,694,459, which is a continuation of application No. 13/621,135, filed on Sep. 15, 2012, now Pat. No. 8,515,890.

(60) Provisional application No. 61/802,810, filed on Mar. 18, 2013, provisional application No. 61/832,816, filed on Jun. 8, 2013, provisional application No. 61/864,633, filed on Aug. 11, 2013, provisional application No. 61/871,860, filed on Aug. 29, 2013, provisional application No. 61/701,789, filed on Sep. 17, 2012.

(56) References Cited

U.S. PATENT DOCUMENTS

| | | | |
|---|---|---|---|
| 5,329,611 A | 7/1994 | Pechanek et al. |
| 5,517,596 A | 5/1996 | Pechanek et al. |
| 6,157,921 A | 12/2000 | Barnhill |
| 7,542,947 B2 | 6/2009 | Guyon et al. |
| 7,689,529 B2 | 3/2010 | Fung et al. |
| 7,697,761 B2 | 4/2010 | Napper |
| 7,698,236 B2 | 4/2010 | Cox et al. |
| 7,721,336 B1 | 5/2010 | Adjaoute |
| 7,734,400 B2 | 6/2010 | Gayme et al. |
| 7,734,451 B2 | 6/2010 | MacArthur et al. |
| 7,739,337 B1 | 6/2010 | Jensen |
| 7,742,103 B1 | 6/2010 | He et al. |
| 7,761,742 B2 | 7/2010 | Di Palma et al. |
| 7,769,512 B2 | 8/2010 | Norris et al. |
| 7,783,580 B2 | 8/2010 | Huang et al. |
| 7,784,295 B2 | 8/2010 | McCormick et al. |
| 7,792,746 B2 | 9/2010 | Del Callar et al. |
| 7,792,750 B2 | 9/2010 | Moeller |
| 7,797,268 B2 | 9/2010 | Bigus et al. |
| 7,801,840 B2 | 9/2010 | Repasi et al. |
| 7,805,396 B2 | 9/2010 | Wagner et al. |
| 7,805,397 B2 | 9/2010 | Kurian et al. |
| 7,805,984 B2 | 10/2010 | McLain et al. |
| 7,817,854 B2 | 10/2010 | Taylor |
| 7,832,511 B2 | 11/2010 | Syed et al. |
| 7,836,496 B2 | 11/2010 | Chesla et al. |
| 7,840,500 B2 | 11/2010 | Khanbaghi |
| 7,844,564 B2 | 11/2010 | Donohue et al. |
| 7,853,538 B2 | 12/2010 | Hildebrand |
| 7,856,356 B2 | 12/2010 | Chung et al. |
| 7,857,976 B2 | 12/2010 | Bissler et al. |
| 7,864,552 B2 | 1/2011 | Heber et al. |
| 7,869,989 B1 | 1/2011 | Harvey et al. |
| 7,895,135 B2 | 2/2011 | Norris et al. |
| 7,921,068 B2 | 4/2011 | Guyon et al. |
| 7,925,874 B1 | 4/2011 | Zaitsev |
| 7,929,771 B2 | 4/2011 | Ko et al. |
| 7,930,265 B2 | 4/2011 | Akelbein et al. |
| 7,934,499 B2 | 5/2011 | Berthon-Jones |
| 7,936,906 B2 | 5/2011 | Hua et al. |
| 7,941,350 B2 | 5/2011 | Ginsburg et al. |
| 7,966,061 B2 | 6/2011 | Al-Abed et al. |
| 7,974,455 B2 | 7/2011 | Peters et al. |
| 7,991,754 B2 | 8/2011 | Maizel et al. |
| 7,999,857 B2 | 8/2011 | Bunn et al. |
| 8,004,544 B1 | 8/2011 | Zhang et al. |
| 8,015,196 B2 | 9/2011 | Taranenko et al. |
| 8,016,319 B2 | 9/2011 | Winkler et al. |
| 8,023,974 B1 | 9/2011 | Diao et al. |
| 8,054,592 B2 | 11/2011 | Rivers, Jr. |
| 8,060,456 B2 | 11/2011 | Gao et al. |
| 8,063,889 B2 | 11/2011 | Anderson |
| 8,077,983 B2 | 12/2011 | Qiu et al. |
| 8,081,844 B2 | 12/2011 | Steinberg et al. |
| 8,095,483 B2 | 1/2012 | Weston et al. |
| 8,108,207 B1 | 1/2012 | Harvey et al. |
| 8,108,324 B2 | 1/2012 | Krupka et al. |
| 8,116,534 B2 | 2/2012 | Nishiyama et al. |
| 8,150,109 B2 | 4/2012 | Sung et al. |
| 8,165,354 B1 | 4/2012 | Zhao |
| 8,199,203 B2 | 6/2012 | Sugimoto |
| 8,199,242 B2 | 6/2012 | Sugihara |
| 8,199,979 B2 | 6/2012 | Steinberg et al. |
| 8,204,310 B2 | 6/2012 | Zou et al. |
| 8,208,764 B2 | 6/2012 | Guckenberger |
| 8,209,179 B2 | 6/2012 | Aoyama et al. |
| 8,224,040 B2 | 7/2012 | Li |
| 8,224,042 B2 | 7/2012 | Wang |
| 8,233,676 B2 | 7/2012 | Ngan et al. |
| 8,244,040 B2 | 8/2012 | Imagawa |
| 8,249,313 B2 | 8/2012 | Yanagi |
| 8,254,691 B2 | 8/2012 | Kaneda et al. |
| 8,259,168 B2 | 9/2012 | Wu et al. |
| 8,265,399 B2 | 9/2012 | Steinberg et al. |
| 8,275,175 B2 | 9/2012 | Baltatu et al. |
| 8,285,006 B2 | 10/2012 | Tang |
| 8,289,546 B2 | 10/2012 | Hayasaki |
| 8,295,558 B2 | 10/2012 | Su et al. |
| 8,300,898 B2 | 10/2012 | Bak et al. |
| 8,300,900 B2 | 10/2012 | Lai et al. |
| 8,265,474 B2 | 11/2012 | Kanayama |
| 8,306,279 B2 | 11/2012 | Hanna |
| 8,316,436 B2 | 11/2012 | Shirai et al. |
| 8,320,682 B2 | 11/2012 | Froeba et al. |
| 8,325,999 B2 | 12/2012 | Kapoor et al. |
| 8,326,001 B2 | 12/2012 | Free |
| 8,331,632 B1 | 12/2012 | Mohanty et al. |
| 8,332,422 B2 | 12/2012 | Chang et al. |
| 8,340,366 B2 | 12/2012 | Masuda et al. |
| 8,352,467 B1 | 1/2013 | Guha |
| 8,359,611 B2 | 1/2013 | Johnson et al. |
| 8,370,352 B2 | 2/2013 | Lita et al. |
| 8,374,405 B2 | 2/2013 | Lee et al. |
| 8,379,074 B2 | 2/2013 | Currivan et al. |
| 8,379,920 B2 | 2/2013 | Yang et al. |
| 8,379,940 B2 | 2/2013 | Wechsler et al. |
| 8,386,446 B1 | 2/2013 | Pasupathy et al. |
| 9,031,844 B2 * | 5/2015 | Yu ............... G06K 9/6296 704/232 |
| 2009/0276263 A1* | 11/2009 | Deb ............... G06Q 10/06 717/101 |
| 2012/0057779 A1* | 3/2012 | El Dokor ......... G06K 9/00221 382/154 |
| 2012/0065976 A1* | 3/2012 | Deng ............... G10L 15/14 704/256.1 |
| 2012/0150626 A1* | 6/2012 | Zhang ............ G06Q 30/0243 705/14.42 |

OTHER PUBLICATIONS

Ronald Yager, titled "On Z-valuations using Zadeh's Z-numbers", International Journal of Intelligent Systems, vol. 27, Issue 3, pp. 259-278, Mar. 2012, Wiley Periodicals, Inc. The online version first published on Jan. 20, 2012. No publisher's location mentioned.

* cited by examiner

And type hierarchy continues

Data, e.g., sparse units approximating low res. thumbnail

Data, e.g., sparse V units fed from thumbnail

Thumbnail pixel

Data, e.g., thumbnail wide pixels on V units ately 9,916,538 B2

METHOD AND SYSTEM FOR FEATURE DETECTION

RELATED APPLICATION

The current application is a CIP (Continuation-in-part) of another co-pending U.S. application Ser. No. 13/781,303, filed Feb. 28, 2013, called ZAdvanced-1, which claims the benefit of and takes the priority of the earlier filing date of the following U.S. provisional application No. 61/701,789, filed Sep. 17, 2012, called ZAdvanced-1-prov. The current application claims the benefit of and takes the priority of the earlier filing dates of the following U.S. provisional application No. 61/802,810, filed Mar. 18, 2013, called ZAdvanced-2-prov; and 61/832,816, filed Jun. 8, 2013, called ZAdvanced-3-prov; and 61/864,633, filed Aug. 11, 2013, called ZAdvanced-4-prov; and 61/871,860, filed Aug. 29, 2013, called ZAdvanced-5-prov. The current application is a CIP (Continuation-in-part) of another co-pending U.S. application Ser. No. 14/201,974, filed 10 Mar. 2014, called Zadeh-101-Cont-4, which is a Continuation of another U.S. application Ser. No. 13/953,047, filed Jul. 29, 2013, called Zadeh-101-Cont-3, now allowed, which is also a Continuation of another application Ser. No. 13/621,135, filed Sep. 15, 2012, now issued as U.S. Pat. No. 8,515,890, on Aug. 20, 2013, which is also a Continuation of Ser. No. 13/621,164, filed Sep. 15, 2012, now issued as U.S. Pat. No. 8,463,735, which is a Continuation of another application Ser. No. 13/423,758, filed Mar. 19, 2012, now issued as U.S. Pat. No. 8,311,973, which, in turn, claims the benefit of the U.S. provisional application No. 61/538,824, filed on Sep. 24, 2011. The current application incorporates by reference all of the applications and patents/provisionals mentioned above, including all their Appendices and attachments (Packages), and it claims benefits to and takes the priority of the earlier filing dates of all the provisional and utility applications or patents mentioned above. Please note that most of the Appendices and attachments (Packages) to the specifications for the above-mentioned applications and patents (such as U.S. Pat. No. 8,311,973) are available for public view, e.g., through Public Pair system at the USPTO web site (www.uspto.gov), with some of their listings given below in the next section.
Attached Packages to Prior Specifications (e.g., U.S. Pat. No. 8,311,973)

In addition to the provisional cases above, the teachings of all 33 packages (the PDF files, named "Packages 1-33") attached with some of the parent cases' filings (as Appendices) (such as U.S. Pat. No. 8,311,973) are incorporated herein by reference to this current disclosure. Please note that Packages 1-33 are also one of the inventor's (Prof. Lotfi Zadeh's) own teachings, and thus, they may be referred to (from time-to-time) for further details or explanations, by the reader, if needed.

Please note that Packages 1-25 had already been submitted (and filed) with our provisional application for one of the parent cases.

Packages 1-12 and 15-22 are marked accordingly at the bottom of each page or slide (as the identification). The other Packages (Packages 13-14 and 23-33) are identified here:
  Package 13: 1 page, with 3 slides, starting with "Figure 1. Membership function of A and probability density function of X"
  Package 14: 1 page, with 5 slides, starting with "Fig.1. f-transformation and f-geometry. Note that fuzzy figures, as shown, are not hand drawn. They should be visualized as hand drawn figures."
  Package 23: 2-page text, titled "The Concept of a Z-number—a New Direction in Computation, Lotfi A. Zadeh, Abstract" (dated Mar. 28, 2011)
  Package 24: 2-page text, titled "Prof. Lotfi Zadeh, The Z-mouse—a visual means of entry and retrieval of fuzzy data"
  Package 25: 12-page article, titled "Toward Extended Fuzzy Logic—A First Step, Abstract"
  Package 26: 2-page text, titled "Can mathematics deal with computational problems which are stated in a natural language?, Lotfi A. Zadeh, Sep. 30, 2011, Abstract" (Abstract dated Sep. 30, 2011)
  Package 27: 15 pages, with 131 slides, titled "Can Mathematics Deal with Computational Problems Which are Stated in a Natural Language?, Lotfi A. Zadeh" (dated Feb. 2, 2012)
  Package 28: 14 pages, with 123 slides, titled "Can Mathematics Deal with Computational Problems Which are Stated in a Natural Language?, Lotfi A. Zadeh" (dated Oct. 6, 2011)
  Package 29: 33 pages, with 289 slides, titled "Computing with Words—Principal Concepts and Ideas, Lotfi A. Zadeh" (dated Jan. 9, 2012)
  Package 30: 23 pages, with 205 slides, titled "Computing with Words—Principal Concepts and Ideas, Lotfi A. Zadeh" (dated May 10, 2011)
  Package 31: 3 pages, with 25 slides, titled "Computing with Words—Principal Concepts and Ideas, Lotfi A. Zadeh" (dated Nov. 29, 2011)
  Package 32: 9 pages, with 73 slides, titled "Z-NUMBERS—A NEW DIRECTION IN THE ANALYSIS OF UNCERTAIN AND IMPRECISE SYSTEMS, Lotfi A. Zadeh" (dated Jan. 20, 2012)
  Package 33: 15 pages, with 131 slides, titled "PRECISIATION OF MEANING—A KEY TO SEMANTIC COMPUTING, Lotfi A. Zadeh" (dated Jul. 22, 2011)

BACKGROUND OF THE INVENTION

Professor Lotfi A. Zadeh, one of the inventors of the current disclosure and some of the parent cases, is the "Father of Fuzzy Logic". He first introduced the concept of Fuzzy Set and Fuzzy Theory in his famous paper, in 1965 (as a professor of University of California, at Berkeley). Since then, many people have worked on the Fuzzy Logic technology and science. Dr. Zadeh has also developed many other concepts related to Fuzzy Logic. He has invented Computation-with-Words (CWW or CW), e.g., for natural language processing and analysis, for many applications, which we address here, as well, as some of our new innovative methods and systems. One of his last revolutionary inventions is called Z-numbers, named after him ("Z" from Zadeh), which is one of the subjects of the current many inventions. That is, some of the embodiments of the current invention are based on or related to Z-numbers and Fuzzy Logic. The concept of Z-numbers was first published in a recent paper, by Dr. Zadeh, called "A Note on Z-Numbers", Information Sciences 181 (2011) 2923-2932.

In the real world, uncertainty is a pervasive phenomenon. Much of the information on which decisions are based is uncertain. Humans have a remarkable capability to make rational decisions based on information which is uncertain, imprecise and/or incomplete. Formalization of this capability is one of the goals of these current inventions.

Here are some of the publications on the related subjects:
[1] R. Ash, Basic Probability Theory, Dover Publications, 2008.

[2] J-C. Buisson, Nutri-Educ, a nutrition software application for balancing meals, using fuzzy arithmetic and heuristic search algorithms, Artificial Intelligence in Medicine 42, (3), (2008) 213-227.

[3] E. Trillas, C. Moraga, S. Guadarrama, S. Cubillo and E. Castiñeira, Computing with Antonyms, In: M. Nikravesh, J. Kacprzyk and L. A. Zadeh (Eds.), Forging New Frontiers: Fuzzy Pioneers I, Studies in Fuzziness and Soft Computing Vol 217, Springer-Verlag, Berlin Heidelberg 2007, pp. 133-153.

[4] R. R. Yager, On measures of specificity, In: O. Kaynak, L. A. Zadeh, B. Turksen, I. J. Rudas (Eds.), Computational Intelligence: Soft Computing and Fuzzy-Neuro Integration with Applications, Springer-Verlag, Berlin, 1998, pp. 94-113.

[5] L. A. Zadeh, Calculus of fuzzy restrictions, In: L. A. Zadeh, K. S. Fu, K. Tanaka, and M. Shimura (Eds.), Fuzzy sets and Their Applications to Cognitive and Decision Processes, Academic Press, New York, 1975, pp. 1-39.

[6] L. A. Zadeh, The concept of a linguistic variable and its application to approximate reasoning,
Part I: Information Sciences 8 (1975) 199-249;
Part II: Information Sciences 8 (1975) 301-357;
Part III: Information Sciences 9 (1975) 43-80.

[7] L. A. Zadeh, Fuzzy logic and the calculi of fuzzy rules and fuzzy graphs, Multiple-Valued Logic 1, (1996) 1-38.

[8] L. A. Zadeh, From computing with numbers to computing with words—from manipulation of measurements to manipulation of perceptions, IEEE Transactions on Circuits and Systems 45, (1999) 105-119.

[9] L. A. Zadeh, The Z-mouse—a visual means of entry and retrieval of fuzzy data, posted on BISC Forum, Jul. 30, 2010. A more detailed description may be found in Computing with Words—principal concepts and ideas, Colloquium PowerPoint presentation, University of Southern California, Los Angeles, Calif., Oct. 22, 2010.

As one of the applications mentioned here in this disclosure, for comparisons, some of the search engines or question-answering engines in the market (in the recent years) are (or were): Google®, Yahoo®, Autonomy, IBM®, Fast Search, Powerset® (by Xerox® PARC and bought by Microsoft®), Microsoft® Bing, Wolfram®, AskJeeves, Collarity, Vivisimo®, Endeca®, Media River, Hakia®, Ask.com®, AltaVista, Excite, Go Network, HotBot®, Lycos®, Northern Light, and Like.com.

Other references on related subjects are:

[1] A. R. Aronson, B. E. Jacobs, J. Minker, A note on fuzzy deduction, J. ACM27 (4) (1980), 599-603.

[2] A. Bardossy, L. Duckstein, Fuzzy Rule-based Modelling with Application to Geophysical, Biological and Engineering Systems, CRC Press, 1995.

[3] T. Berners-Lee, J. Hendler, O. Lassila, The semantic web, Scientific American 284 (5) (2001), 34-43.

[4] S. Brin, L. Page, The anatomy of a large-scale hypertextual web search engine, Computer Networks 30 (1-7) (1998), 107-117.

[5] W. J. H. J. Bronnenberg, M. C. Bunt, S. P. J. Lendsbergen, R. H. J. Scha, W. J. Schoenmakers, E. P. C. van Utteren, The question answering system PHLIQA1, in: L. Bola (Ed.), Natural Language Question Answering Systems, Macmillan, 1980.

[6] L. S. Coles, Techniques for information retrieval using an inferential question-answering system with natural language input, SRI Report, 1972.

[7] A. Di Nola, S. Sessa, W. Pedrycz, W. Pei-Zhuang, Fuzzy relation equation under a class of triangular norms: a survey and new results, in: Fuzzy Sets for Intelligent Systems, Morgan Kaufmann Publishers, San Mateo, Calif., 1993, pp. 166-189.

[8] A. Di Nola, S. Sessa, W. Pedrycz, E. Sanchez, Fuzzy Relation Equations and their Applications to Knowledge Engineering, Kluwer Academic Publishers, Dordrecht, 1989.

[9] D. Dubois, H. Prade, Gradual inference rules in approximate reasoning, Inform. Sci. 61 (1-2) (1992), 103-122.

[10] D. Filev, R. R. Yager, Essentials of Fuzzy Modeling and Control, Wiley-Interscience, 1994.

[11] J. A. Goguen, The logic of inexact concepts, Synthese 19 (1969), 325-373.

[12] M. Jamshidi, A. Titli, L. A. Zadeh, S. Boverie (Eds.), Applications of Fuzzy Logic—Towards High Machine Intelligence Quotient Systems, Environmental and Intelligent Manufacturing Systems Series, vol. 9, Prentice-Hall, Upper Saddle River, N.J., 1997.

[13] A. Kaufmann, M. M. Gupta, Introduction to Fuzzy Arithmetic: Theory and Applications, Van Nostrand, New York, 1985.

[14] D. B. Lenat, CYC: a large-scale investment in knowledge infrastructure, Comm. ACM38 (11) (1995), 32-38.

[15] E. H. Mamdani, S. Assilian, An experiment in linguistic synthesis with a fuzzy logic controller, Int. J. Man-Machine Studies 7 (1975), 1-13.

[16] J. R. McSkimin, J. Minker, The use of a semantic network in a deductive question-answering system, in: IJCAI, 1977, pp. 50-58.

[17] R. E. Moore, Interval Analysis, SIAM Studies in Applied Mathematics, vol. 2, Philadelphia, Pa., 1979.

[18] M. Nagao, J. Tsujii, Mechanism of deduction in a question-answering system with natural language input, in: ICJAI, 1973, pp. 285-290.

[19] B. H. Partee (Ed.), Montague Grammar, Academic Press, New York, 1976.

[20] W. Pedrycz, F. Gomide, Introduction to Fuzzy Sets, MIT Press, Cambridge, Mass., 1998.

[21] F. Rossi, P. Codognet (Eds.), Soft Constraints, Special issue on Constraints, vol. 8, N. 1, Kluwer Academic Publishers, 2003.

[22] G. Shafer, A Mathematical Theory of Evidence, Princeton University Press, Princeton, N.J., 1976.

[23] M. K. Smith, C. Welty, D. McGuinness (Eds.), OWL Web Ontology Language Guide, W3C Working Draft 31, 2003.

[24] L. A. Zadeh, Fuzzy sets, Inform. and Control 8 (1965), 338-353.

[25] L. A. Zadeh, Probability measures of fuzzy events, J. Math. Anal. Appl. 23 (1968), 421-427.

[26] L. A. Zadeh, Outline of a new approach to the analysis of complex systems and decision processes, IEEE Trans. on Systems Man Cybernet. 3 (1973), 28-44.

[27] L. A. Zadeh, On the analysis of large scale systems, in: H. Gottinger (Ed.), Systems Approaches and Environment Problems, Vandenhoeck and Ruprecht, Gottingen, 1974, pp. 23-37.

[28] L. A. Zadeh, The concept of a linguistic variable and its application to approximate reasoning, Part I, Inform. Sci. 8 (1975), 199-249; Part II, Inform. Sci. 8 (1975), 301-357; Part III, Inform. Sci. 9 (1975), 43-80.

[29] L. A. Zadeh, Fuzzy sets and information granularity, in: M. Gupta, R. Ragade, R. Yager (Eds.), Advances in Fuzzy Set Theory and Applications, North-Holland Publishing Co, Amsterdam, 1979, pp. 3-18.

[30] L. A. Zadeh, A theory of approximate reasoning, in: J. Hayes, D. Michie, L. I. Mikulich (Eds.), Machine Intelligence, vol. 9, Halstead Press, New York, 1979, pp. 149-194.

[31] L. A. Zadeh, Test-score semantics for natural languages and meaning representation via PRUF, in: B. Rieger (Ed.), Empirical Semantics, Brockmeyer, Bochum, W. Germany, 1982, pp. 281-349. Also Technical Memorandum 246, AI Center, SRI International, Menlo Park, Calif., 1981.

[32] L. A. Zadeh, A computational approach to fuzzy quantifiers in natural languages, Computers and Mathematics 9 (1983), 149-184.

[33] L. A. Zadeh, A fuzzy-set-theoretic approach to the compositionality of meaning: propositions, dispositions and canonical forms, J. Semantics 3 (1983), 253-272.

[34] L. A. Zadeh, Precisiation of meaning via translation into PRUF, in: L. Vaina, J. Hintikka (Eds.), Cognitive Constraints on Communication, Reidel, Dordrecht, 1984, pp. 373-402.

[35] L. A. Zadeh, Outline of a computational approach to meaning and knowledge representation based on a concept of a generalized assignment statement, in: M. Thoma, A. Wyner (Eds.), Proceedings of the International Seminar on Artificial Intelligence and Man-Machine Systems, Springer-Verlag, Heidelberg, 1986, pp. 198-211.

[36] L. A. Zadeh, Fuzzy logic and the calculi of fuzzy rules and fuzzy graphs, Multiple-Valued Logic 1 (1996), 1-38.

[37] L. A. Zadeh, Toward a theory of fuzzy information granulation and its centrality in human reasoning and fuzzy logic, Fuzzy Sets and Systems 90 (1997), 111-127.

[38] L. A. Zadeh, From computing with numbers to computing with words—from manipulation of measurements to manipulation of perceptions, IEEE Trans. on Circuits and Systems 45 (1) (1999), 105-119.

[39] L. A. Zadeh, Toward a perception-based theory of probabilistic reasoning with imprecise probabilities, J. Statist. Plann. Inference 105 (2002), 233-264.

[40] L. A. Zadeh, Precisiated natural language (PNL), AI Magazine 25 (3) (2004), 74-91.

[41] L. A. Zadeh, A note on web intelligence, world knowledge and fuzzy logic, Data and Knowledge Engineering 50 (2004), 291-304.

[42] L. A. Zadeh, Toward a generalized theory of uncertainty (GTU)—an outline, Inform. Sci. 172 (2005), 1-40.

[43] J. Arjona, R. Corchuelo, J. Pena, D. Ruiz, Coping with web knowledge, in: Advances in Web Intelligence, Springer-Verlag, Berlin, 2003, pp. 165-178.

[44] A. Bargiela, W. Pedrycz, Granular Computing—An Introduction, Kluwer Academic Publishers, Boston, 2003.

[45] Z. Bubnicki, Analysis and Decision Making in Uncertain Systems, Springer-Verlag, 2004.

[46] P. P. Chen, Entity-relationship Approach to Information Modeling and Analysis, North-Holland, 1983.

[47] M. Craven, D. DiPasquo, D. Freitag, A. McCallum, T. Mitchell, K. Nigam, S. Slattery, Learning to construct knowledge bases from the world wide web, Artificial Intelligence 118 (1-2) (2000), 69-113.

[48] M. J. Cresswell, Logic and Languages, Methuen, London, UK, 1973.

[49] D. Dubois, H. Prade, On the use of aggregation operations in information fusion processes, Fuzzy Sets and Systems 142 (1) (2004), 143-161.

[50] T. F. Gamat, Language, Logic and Linguistics, University of Chicago Press, 1996.

[51] M. Mares, Computation over Fuzzy Quantities, CRC, Boca Raton, Fla., 1994.

[52] V. Novak, I. Perfilieva, J. Mockor, Mathematical Principles of Fuzzy Logic, Kluwer Academic Publishers, Boston, 1999.

[53] V. Novak, I. Perfilieva (Eds.), Discovering the World with Fuzzy Logic, Studies in Fuzziness and Soft Computing, Physica-Verlag, Heidelberg, 2000.

[54] Z. Pawlak, Rough Sets: Theoretical Aspects of Reasoning about Data, Kluwer Academic Publishers, Dordrecht, 1991.

[55] M. K. Smith, C. Welty, What is ontology? Ontology: towards a new synthesis, in: Proceedings of the Second International Conference on Formal Ontology in Information Systems, 2002.

However, none of the prior art teaches the features mentioned in our invention disclosure.

There are a lot of research going on today, focusing on the search engine, analytics, Big Data processing, natural language processing, economy forecasting, dealing with reliability and certainty, medical diagnosis, pattern recognition, object recognition, biometrics, security analysis, risk analysis, fraud detection, satellite image analysis, machine generated data, machine learning, training samples, and the like.

For example, see the article by Technology Review, published by MIT, "Digging deeper in search web", Jan. 29, 2009, by Kate Greene, or search engine by GOOGLE®, MICROSOFT® (BINGO), or YAHOO®, or APPLE® SIRI, or WOLFRAM® ALPHA computational knowledge engine, or AMAZON engine, or FACEBOOK® engine, or ORACLE® database, or YANDEX® search engine in Russia, or PICASA® (GOOGLE®) web albums, or YOUTUBE® (GOOGLE®) engine, or ALIBABA (Chinese supplier connection), or SPLUNK® (for Big Data), or MICROSTRATEGY® (for business intelligence), or QUID (or KAGGLE, ZESTFINANCE, APIXIO, DATAMEER, BLUEKAI, GNIP, RETAILNEXT, or RECOMMIND) (for Big Data), or paper by Viola-Jones, Viola et al., at Conference on Computer Vision and Pattern Recognition, 2001, titled "Rapid object detection using a boosted cascade of simple features", from Mitsubishi and Compaq research labs, or paper by Alex Pentland et al., February 2000, at Computer, IEEE, titled "Face recognition for smart environments", or GOOGLE® official blog publication, May 16, 2012, titled "Introducing the knowledge graph: things, not strings", or the article by Technology Review, published by MIT, "The future of search", Jul. 16, 2007, by Kate Greene, or the article by Technology Review, published by MIT, "Microsoft searches for group advantage", Jan. 30, 2009, by Robert Lemos, or the article by Technology Review, published by MIT, "WOLFRAM ALPHA and GOOGLE face off", May 5, 2009, by David Talbot, or the paper by Devarakonda et al., at International Journal of Software Engineering (IJSE), Vol. 2, Issue 1, 2011, titled "Next generation search engines for information retrieval", or paper by Nair-Hinton, titled "Implicit mixtures of restricted Boltzmann machines", NIPS, pp. 1145-1152, 2009, or paper by Nair, V. and Hinton, G. E., titled "3-D Object recognition with deep belief nets", published in Advances in Neural Information Processing Systems 22, (Y. Bengio, D. Schuurmans, J. Lafferty, C. K. I. Williams, and A. Culotta (Eds.)), pp 1339-1347.

However, none of the prior art teaches the features mentioned in our invention disclosure.

SUMMARY OF THE INVENTION

Decisions are based on information. To be useful, information must be reliable. Basically, the concept of a Z-number relates to the issue of reliability of information. A Z-number, Z, has two components, Z=(A,B). The first component, A, is a restriction (constraint) on the values which a real-valued uncertain variable, X, is allowed to take. The second component, B, is a measure of reliability (certainty) of the first component. Typically, A and B are described in a natural language. Example: (about 45 minutes, very sure). An important issue relates to computation with Z-numbers. Examples are: What is the sum of (about 45 minutes, very sure) and (about 30 minutes, sure)? What is the square root of (approximately 100, likely)? Computation with Z-numbers falls within the province of Computing with Words (CW or CWW). In this disclosure, the concept of a Z-number is introduced and methods of computation with Z-numbers are shown. The concept of a Z-number has many applications, especially in the realms of economics, decision analysis, risk assessment, prediction, anticipation, rule-based characterization of imprecise functions and relations, and biomedicine. Different methods, applications, and systems are discussed. Other Fuzzy inventions and concepts are also discussed. Many non-Fuzzy-related inventions and concepts are also discussed.

Specification also covers new algorithms, methods, and systems for artificial intelligence, soft computing, and deep learning/recognition, e.g., image recognition (e.g., for action, gesture, emotion, expression, biometrics, fingerprint, facial, OCR (text), background, relationship, position, pattern, and object), large number of images ("Big Data") analytics, machine learning, training schemes, crowd-sourcing (using experts or humans), feature space, clustering, classification, similarity measures, optimization, search engine, ranking, question-answering system, soft (fuzzy or unsharp) boundaries/impreciseness/ambiguities/fuzziness in language, Natural Language Processing (NLP), Computing-with-Words (CWW), parsing, machine translation, sound and speech recognition, video search and analysis (e.g. tracking), image annotation, geometrical abstraction, image correction, semantic web, context analysis, data reliability (e.g., using Z-number (e.g., "About 45 minutes; Very sure")), rules engine, control system, autonomous vehicle, self-diagnosis and self-repair robots, system diagnosis, medical diagnosis, biomedicine, data mining, event prediction, financial forecasting, economics, risk assessment, e-mail management, database management, indexing and join operation, memory management, and data compression.

Other topics/inventions covered are, e.g.:
Method and System for Identification or Verification for an Object, a Person, or their Attributes
System and Method for Image Recognition and Matching for Targeted Advertisement
System and Method for Analyzing Ambiguities in Language for Natural Language Processing
Application of Z-Webs and Z-factors to Analytics, Search Engine, Learning, Recognition, Natural Language, and Other Utilities
Method and System for Approximate Z-Number Evaluation based on Categorical Sets of Probability Distributions
Image and Video Recognition and Application to Social Network and Image and Video Repositories
System and Method for Image Recognition for Event-Centric Social Networks
System and Method for Image Recognition for Image Ad Network
System and Method for Increasing Efficiency of Support Vector Machine Classifiers
Other topics/inventions covered are, e.g.:
Deep Machine Learning and training schemes
Image recognition (e.g., for action, gesture, emotion, expression, biometrics, fingerprint, facial (e.g. using eigenface), monument and landmark, OCR, background, partial object, relationship, position, pattern, texture, and object)
Basis functions
Image and video auto-annotation
Focus window
Modified Boltzmann Machines
Feature space translation
Geometrical abstraction
Image correction
Semantic web
Context analysis
Data reliability
Correlation layer
Clustering
Classification
Support Vector Machines
Similarity measures
Optimization
Z-number
Z-factor
Z-web
Rules engine
Control system
Robotics
Search engine
Ranking
Question-answering system
Soft boundaries & Fuzziness in language
Natural Language Processing (NLP)
System diagnosis
Medical diagnosis
Big Data analytics
Event prediction
Financial forecasting
Computing with Words (CWW)
Parsing
Soft boundaries & Fuzziness in clustering
Soft boundaries & Fuzziness in recognition
Machine translation
Risk assessment
e-mail management
Database management
Indexing and join operation
Memory management
Sound and speech recognition
Video search & analysis (e.g. tracking)
Data compression
Crowd sourcing (experts)
Event-centric social networking (based on image)
We also introduced the first Image Ad Network, powered by next generation image search engine, based on deep learning.

The industries/applications for our inventions are, e.g.:
Mobile devices (e.g., phones, wearable devices, eyeglasses, tablets)
Smart devices & connected/Internet appliances
Natural Language Processing
Photo albums & web sites containing pictures
Video libraries & web sites
Image and video search & summarization & directory & archiving & storage
Image & video Big Data analytics
Smart Camera Smart Scanning Device
Social networks
Dating sites
Tourism
Real estate
Manufacturing
Biometrics
Security
Satellite or aerial images
Medical
Financial forecasting
Robotics vision & control
Control systems & optimization
Autonomous vehicles We have the following usage examples: object/face recognition; rules engines & control modules; Computation with Words & soft boundaries; classification & search; information web; data search & organizer & data mining & marketing data analysis; search for similar-looking locations or monuments; search for similar-looking properties; defect analysis; fingerprint, iris, and face recognition; Face/emotion/expression recognition, monitoring, tracking; recognition & information extraction, for security & map; diagnosis, using images & rules engines; and Pattern and data analysis & prediction; image ad network; smart cameras and phones; mobile and wearable devices; searchable albums and videos; marketing analytics; social network analytics; dating sites; security; tracking and monitoring; medical records and diagnosis and analysis, based on images; real estate and tourism, based on building, structures, and landmarks; maps and location services and security/intelligence, based on satellite or aerial images; big data analytics; deep image recognition and search platform; deep machine learning; object recognition (e.g., shoe, bag, clothing, watch, earring, tattoo, pants, hat, cap, jacket, tie, medal, wrist band, necklace, pin, decorative objects, fashion accessories, ring, food, appliances, equipment, tools, machines, cars, electrical devices, electronic devices, office supplies, office objects, factory objects, and the like).

Here, we also introduce Z-webs, including Z-factors and Z-nodes, for the understanding of relationships between objects, subjects, abstract ideas, concepts, or the like, including face, car, images, people, emotions, mood, text, natural language, voice, music, video, locations, formulas, facts, historical data, landmarks, personalities, ownership, family, friends, love, happiness, social behavior, voting behavior, and the like, to be used for many applications in our life, including on the search engine, analytics, Big Data processing, natural language processing, economy forecasting, face recognition, dealing with reliability and certainty, medical diagnosis, pattern recognition, object recognition, biometrics, security analysis, risk analysis, fraud detection, satellite image analysis, machine generated data analysis, machine learning, training samples, extracting data or patterns (from the video, images, text, or music, and the like), editing video or images, and the like. Z-factors include reliability factor, confidence factor, expertise factor, bias factor, truth factor, trust factor, validity factor, "trustworthiness of speaker", "sureness of speaker", "statement helpfulness", "expertise of speaker", "speaker's truthfulness", "perception of speaker (or source of information)", "apparent confidence of speaker", "broadness of statement", and the like, which is associated with each Z-node in the Z-web.

For the current inventions, we can combine any and all the systems and methods of our own prior applications, which we have priority claim for, as mentioned on the current spec/application, to provide very efficient and fast algorithms for image processing, learning machines, NLP, pattern recognition, classification, SVM, deep learning, and the like, for all the applications and usages mentioned here in this disclosure, with all tools, systems, and methods provided here.

BRIEF DESCRIPTION OF THE DRAWINGS

FIGS. 12(k)-(l) depict a restriction on probability measure, in one embodiment.

FIG. 84 is a system for the search engine.

FIG. 85 is a system for the pattern recognition and search engine.

FIG. 86 is a system of relationships and designations for the pattern recognition and search engine.

FIG. 87 is a system for the search engine.

FIG. 88 is a system for the recognition and search engine.

FIG. 89 is a system for the recognition and search engine.

FIG. 90 is a method for the multi-step recognition and search engine.

FIG. 91 is a method for the multi-step recognition and search engine.

FIG. 92 is a method for the multi-step recognition and search engine.

FIG. 93 is an expert system.

FIG. 94 is a system for stock market.

FIG. 95 is a system for insurance.

Figure 96:
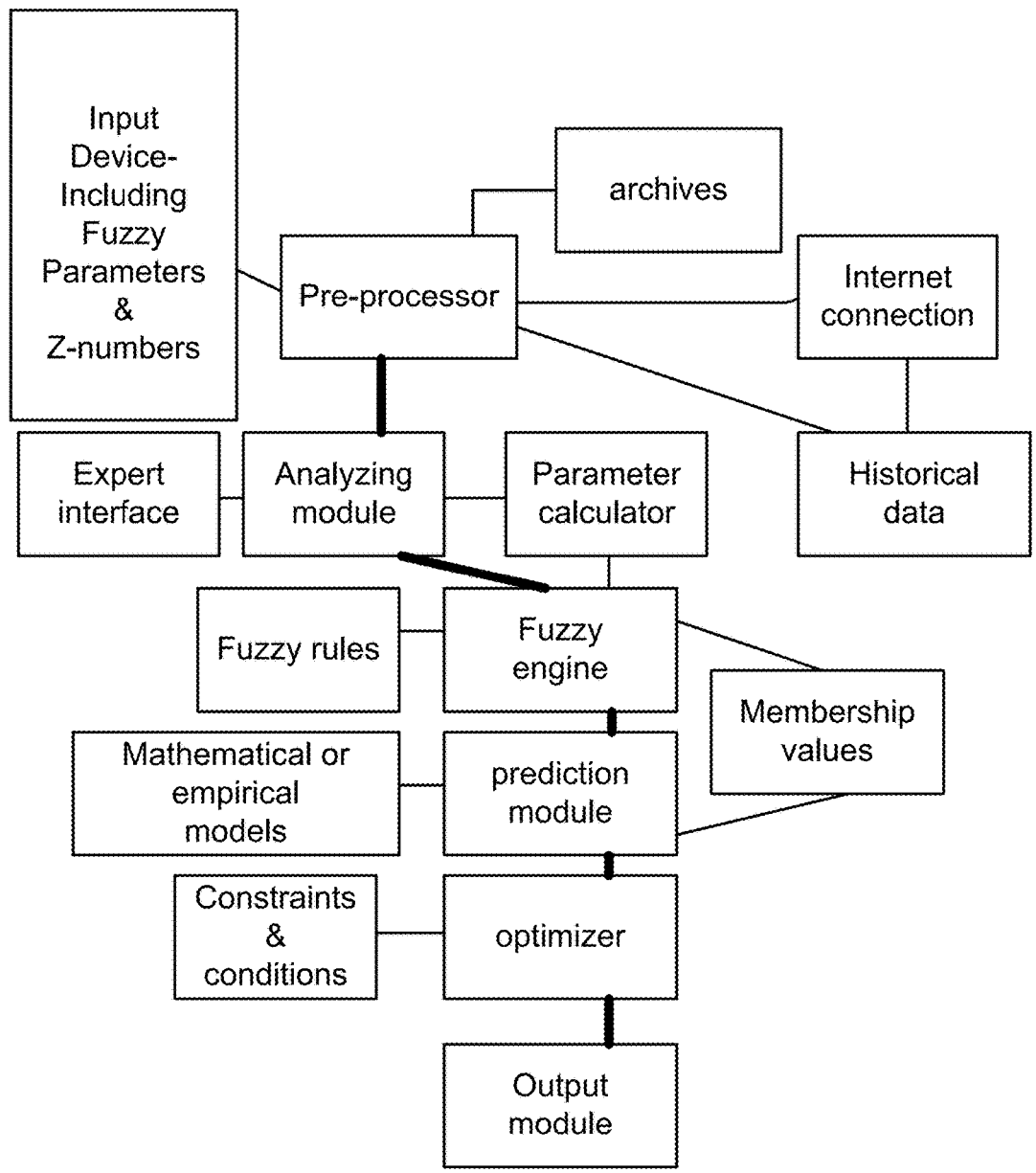

FIG. 96 is a system for prediction or optimization.

Figure 97:
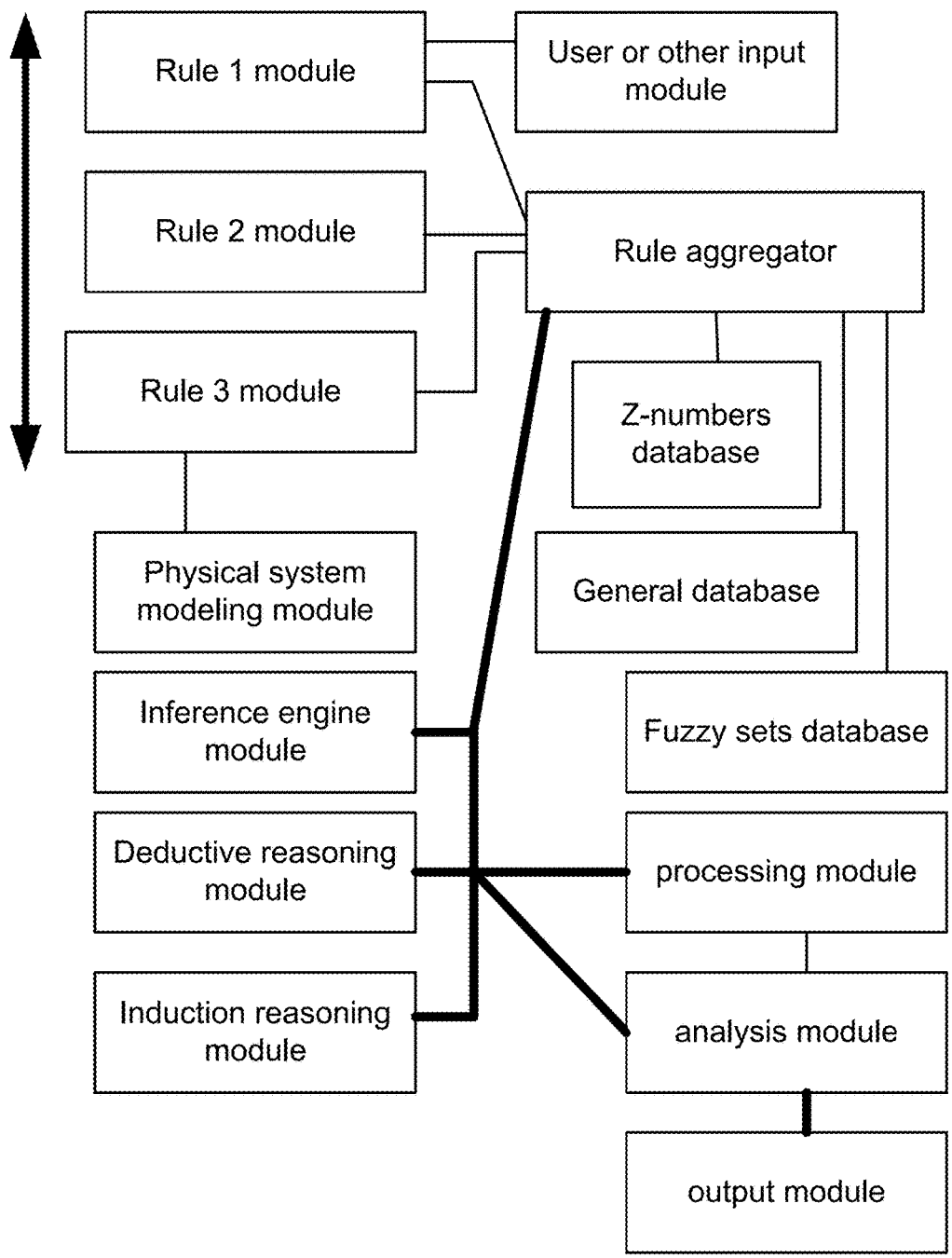

FIG. 97 is a system based on rules.

Figure 98:
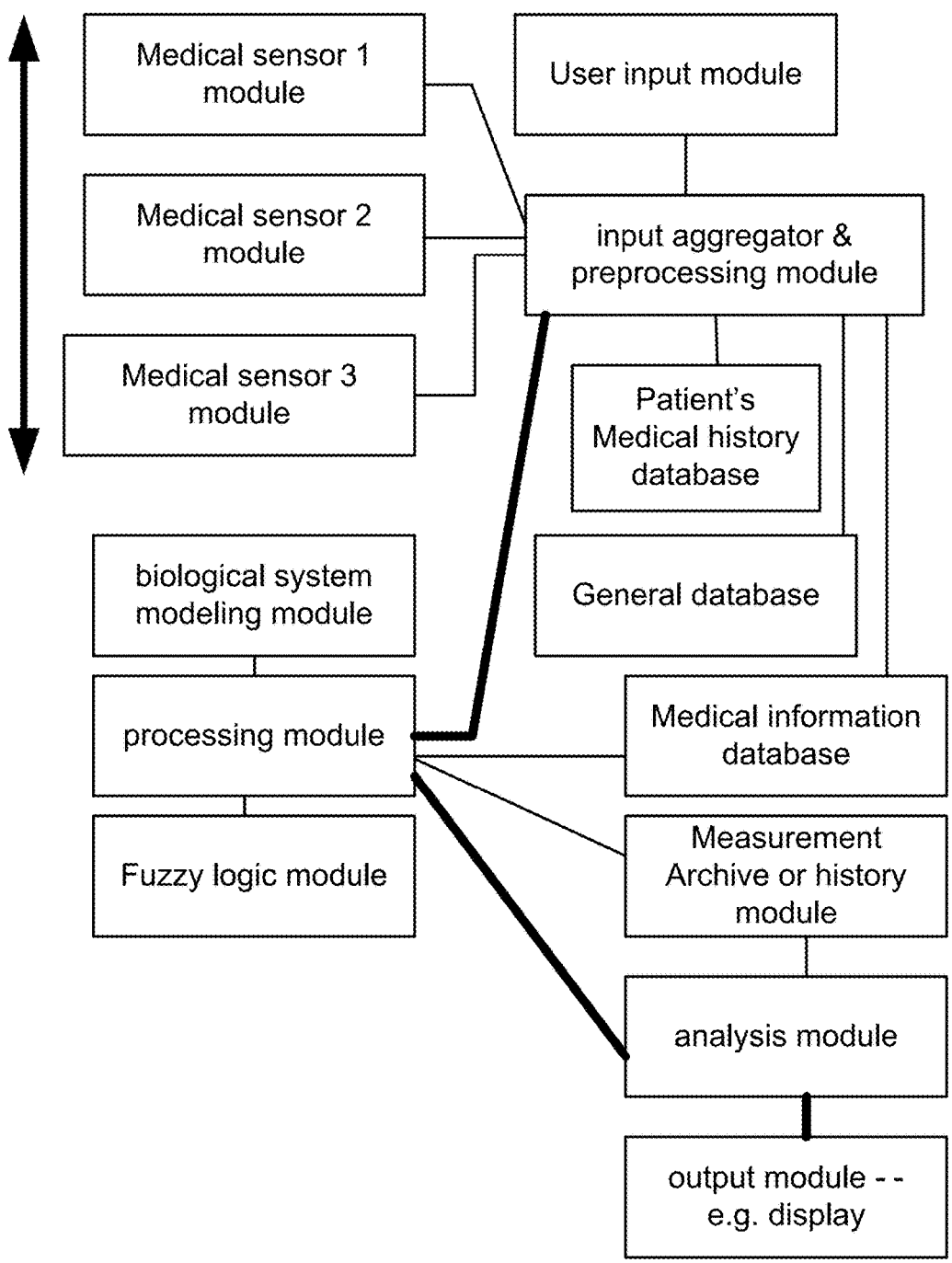

FIG. 98 is a system for a medical equipment.

Figure 99:
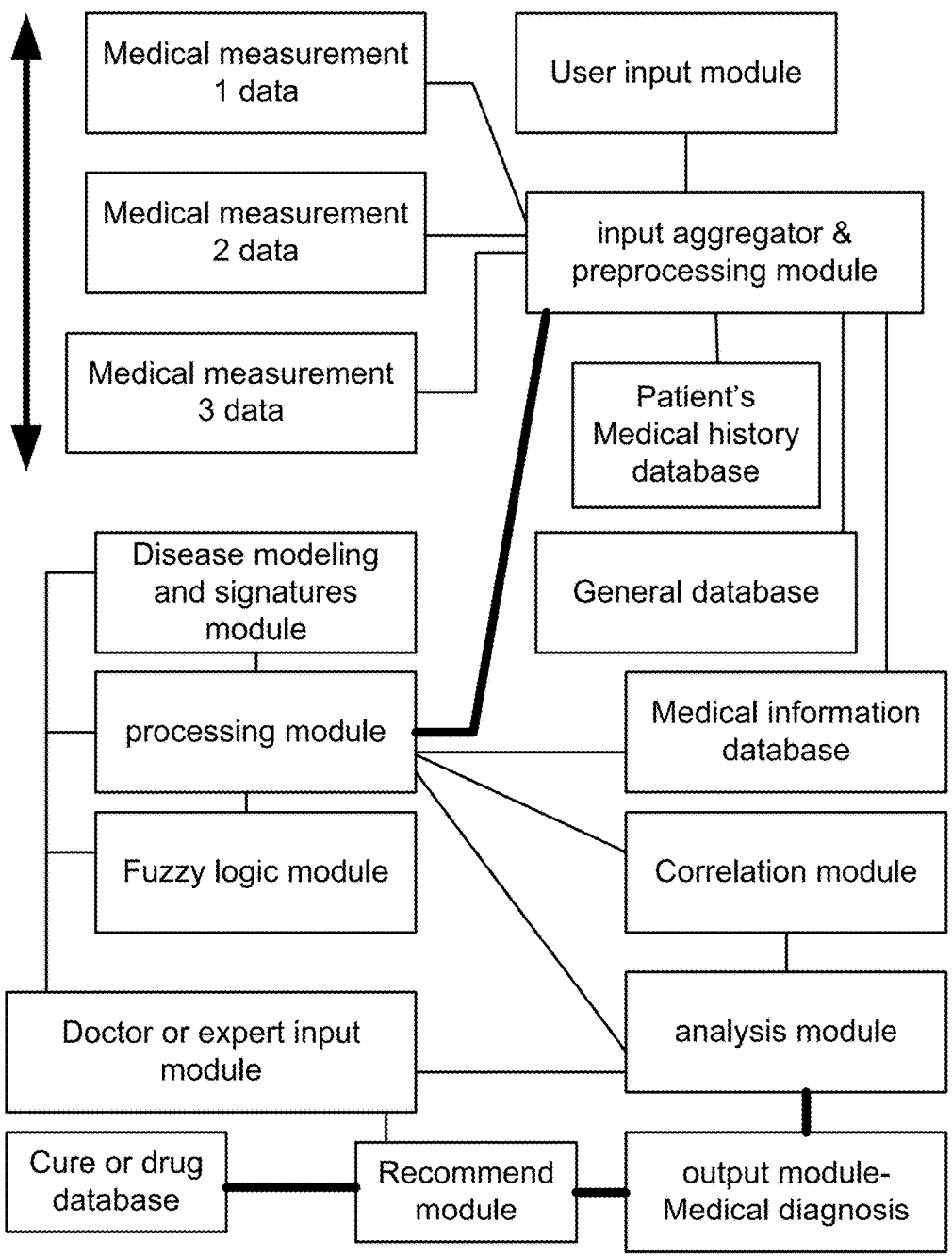

FIG. 99 is a system for medical diagnosis.

Figure 100:
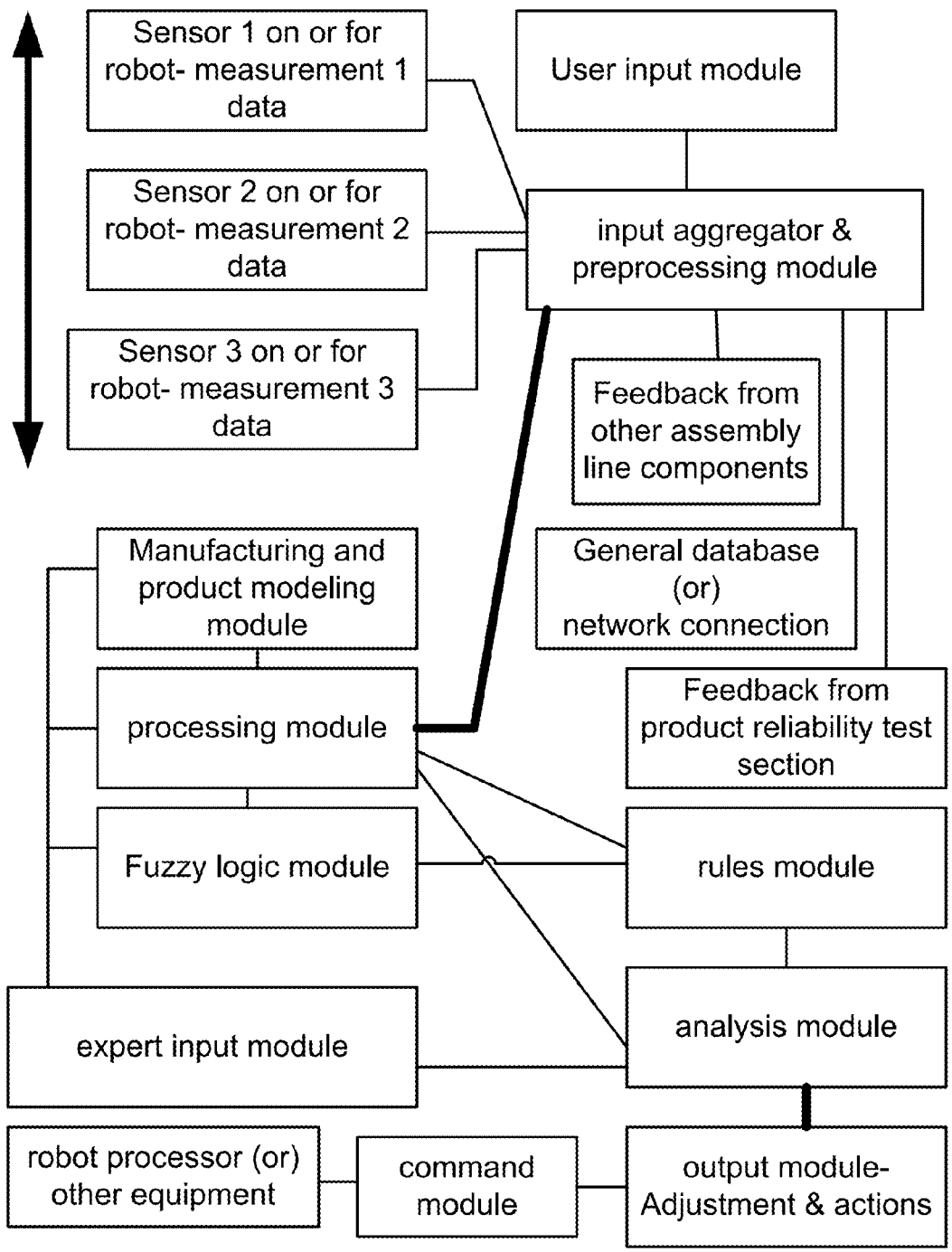

FIG. 100 is a system for a robot.

Figure 101:
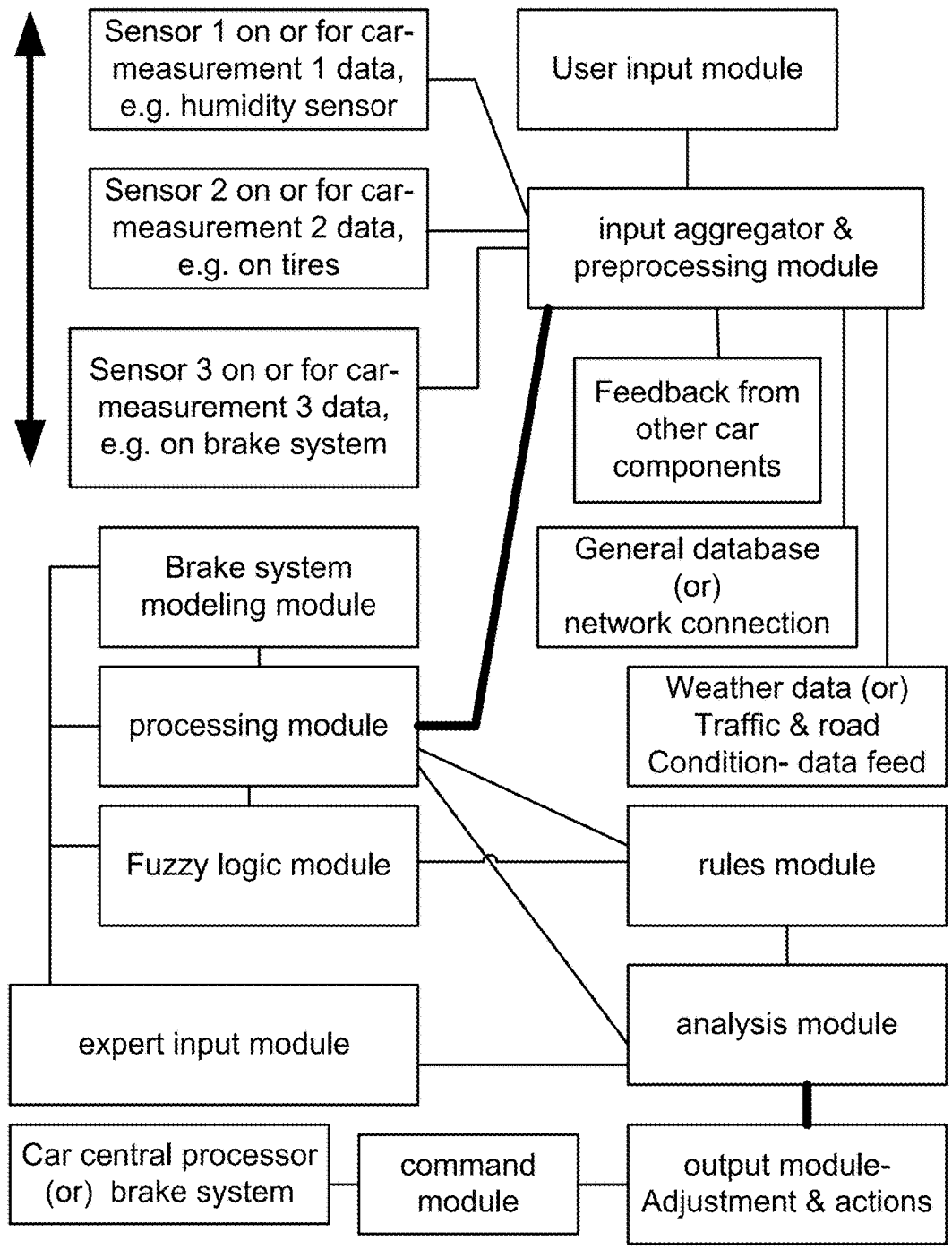

FIG. 101 is a system for a car.

Figure 102:
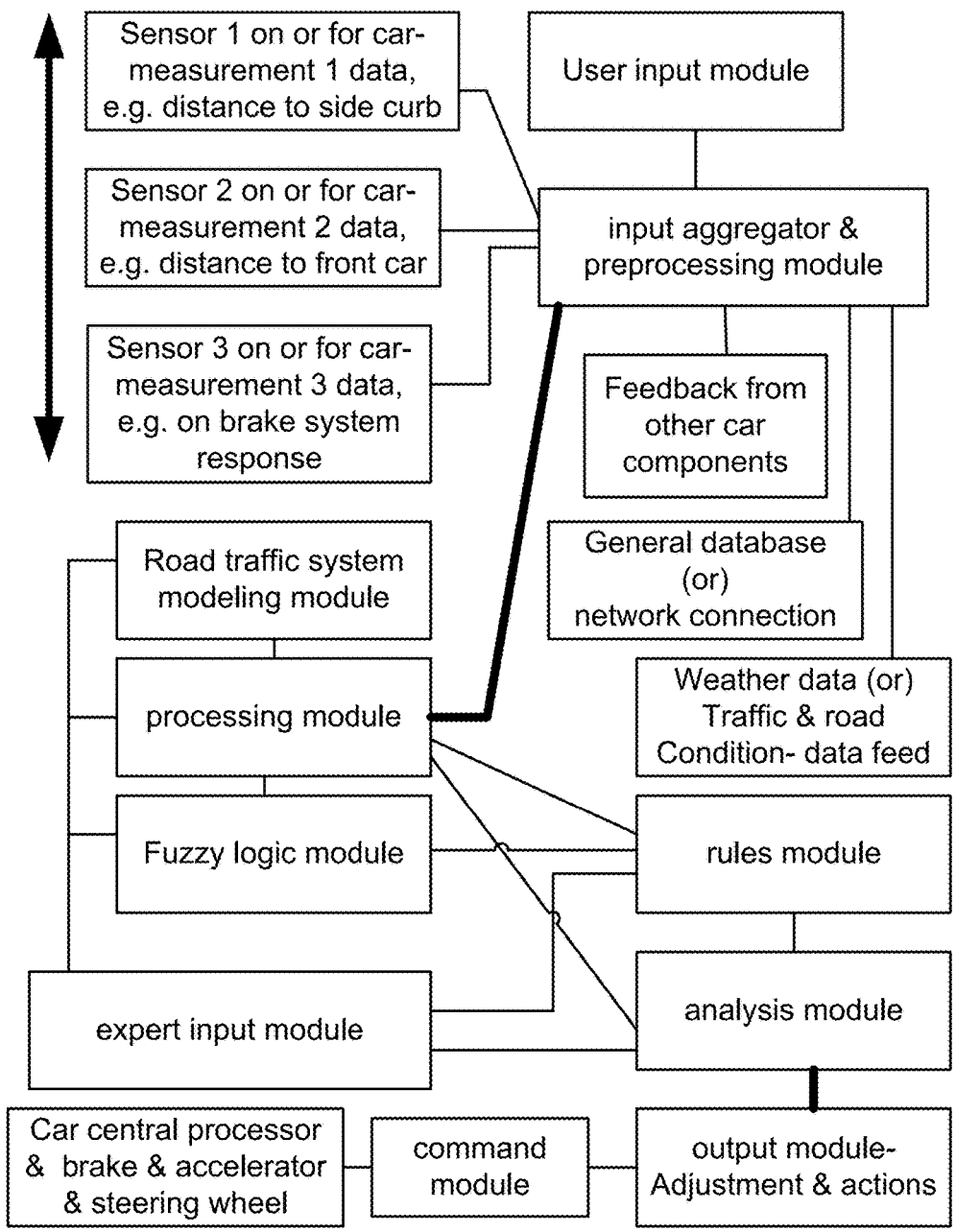

FIG. 102 is a system for an autonomous vehicle.

Figure 103:
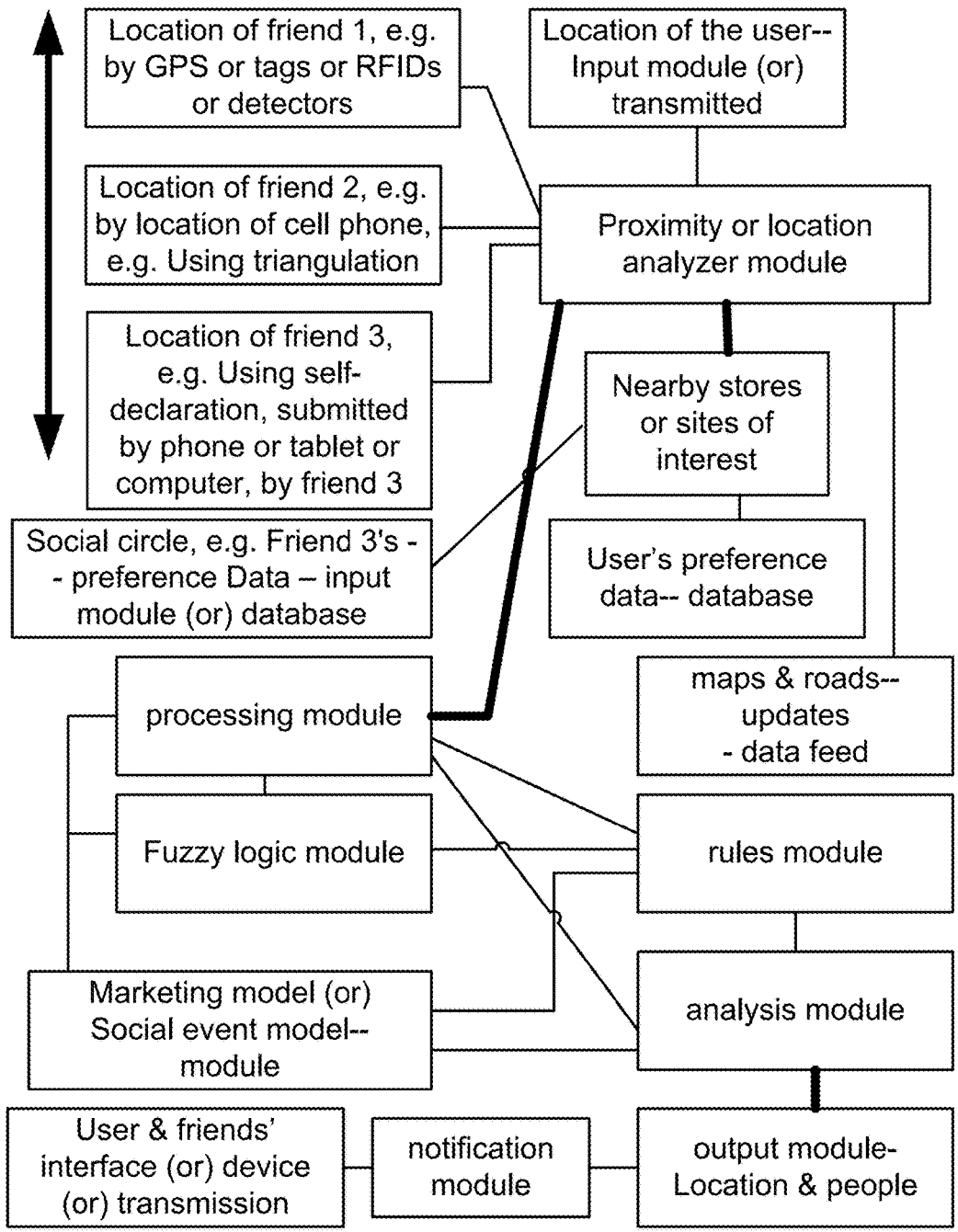

FIG. 103 is a system for marketing or social networks.

Figure 104:
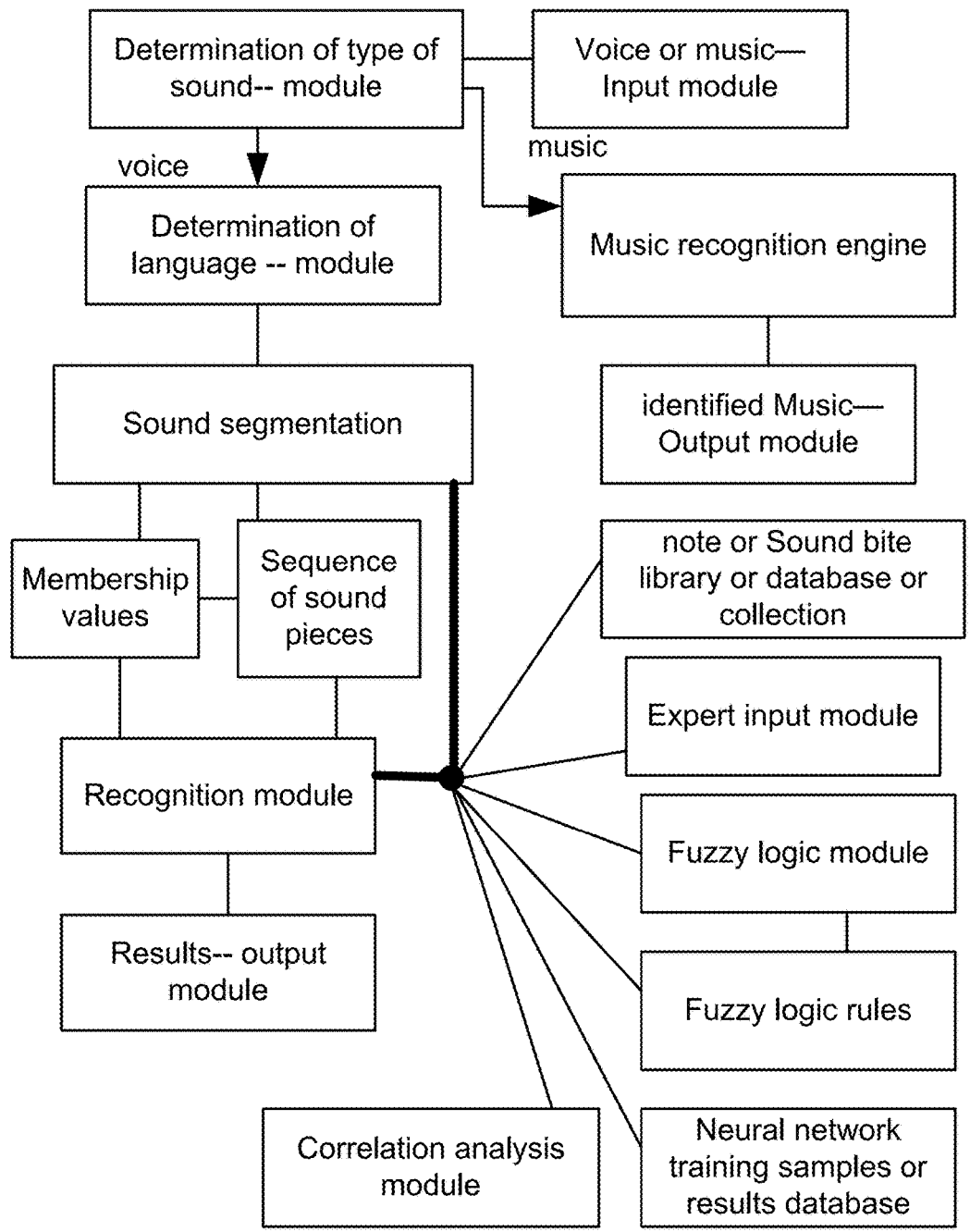

FIG. 104 is a system for sound recognition.

Figure 105:
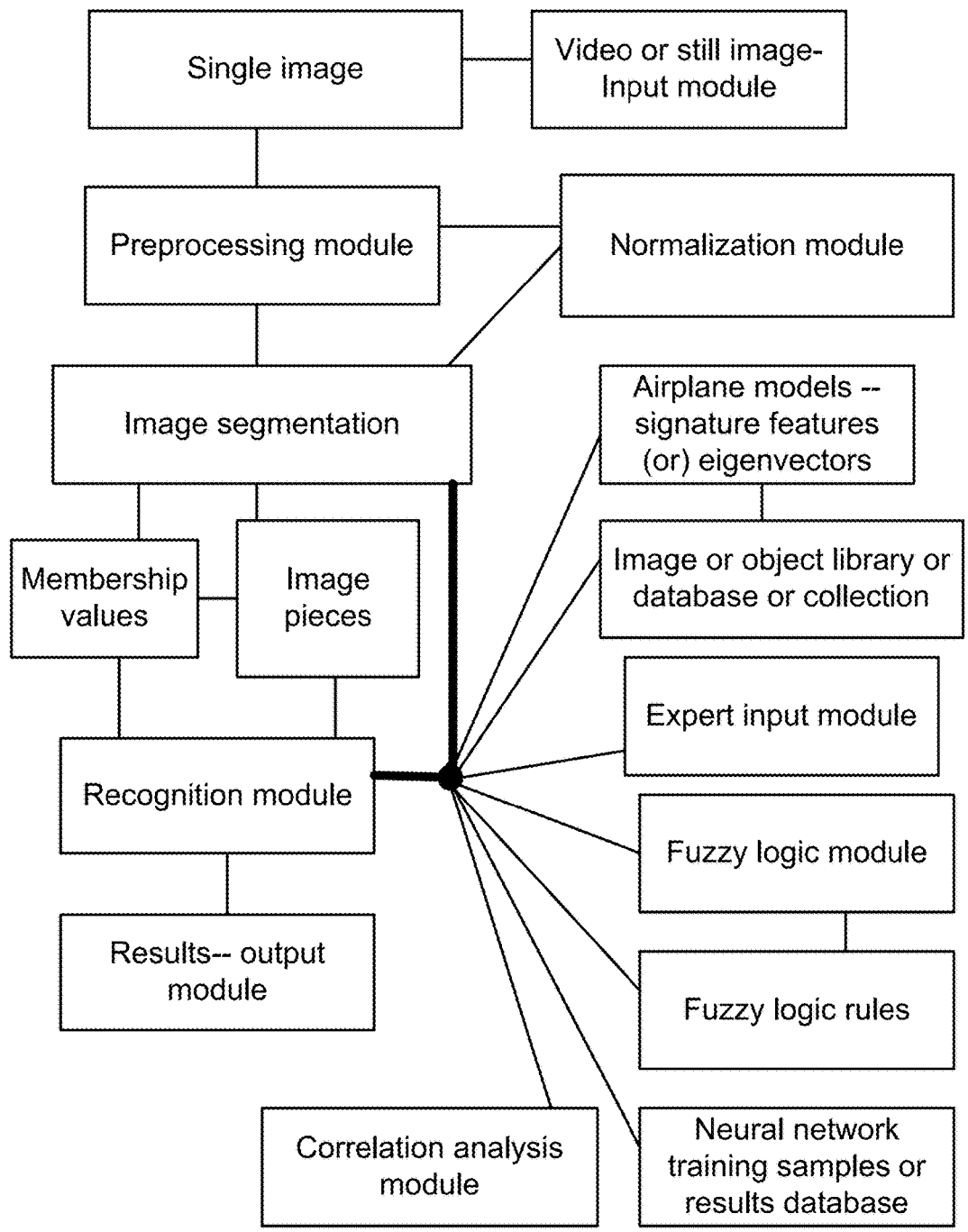

FIG. 105 is a system for airplane or target or object recognition.

Figure 106:
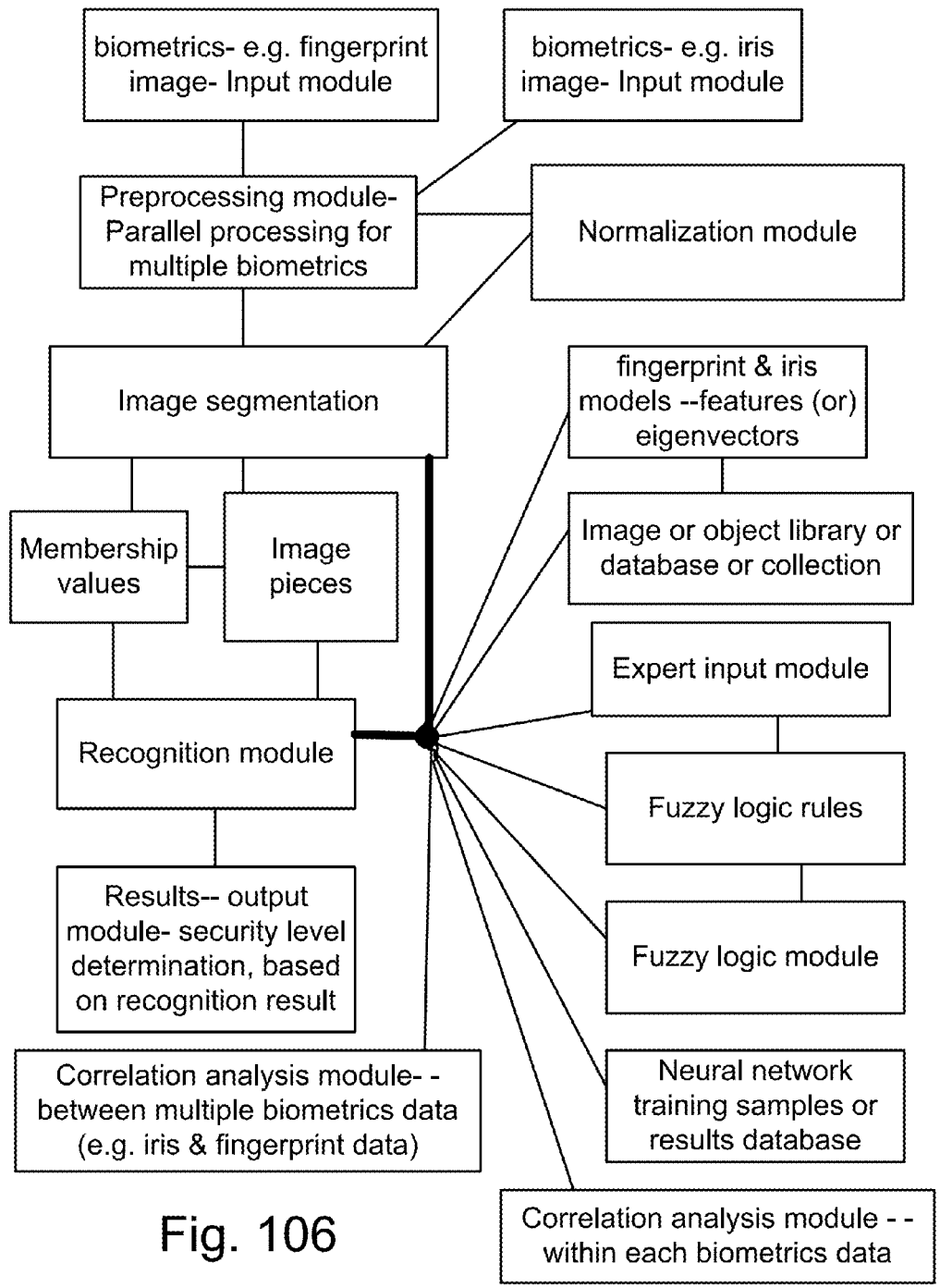

FIG. 106 is a system for biometrics and security.

Figure 107:
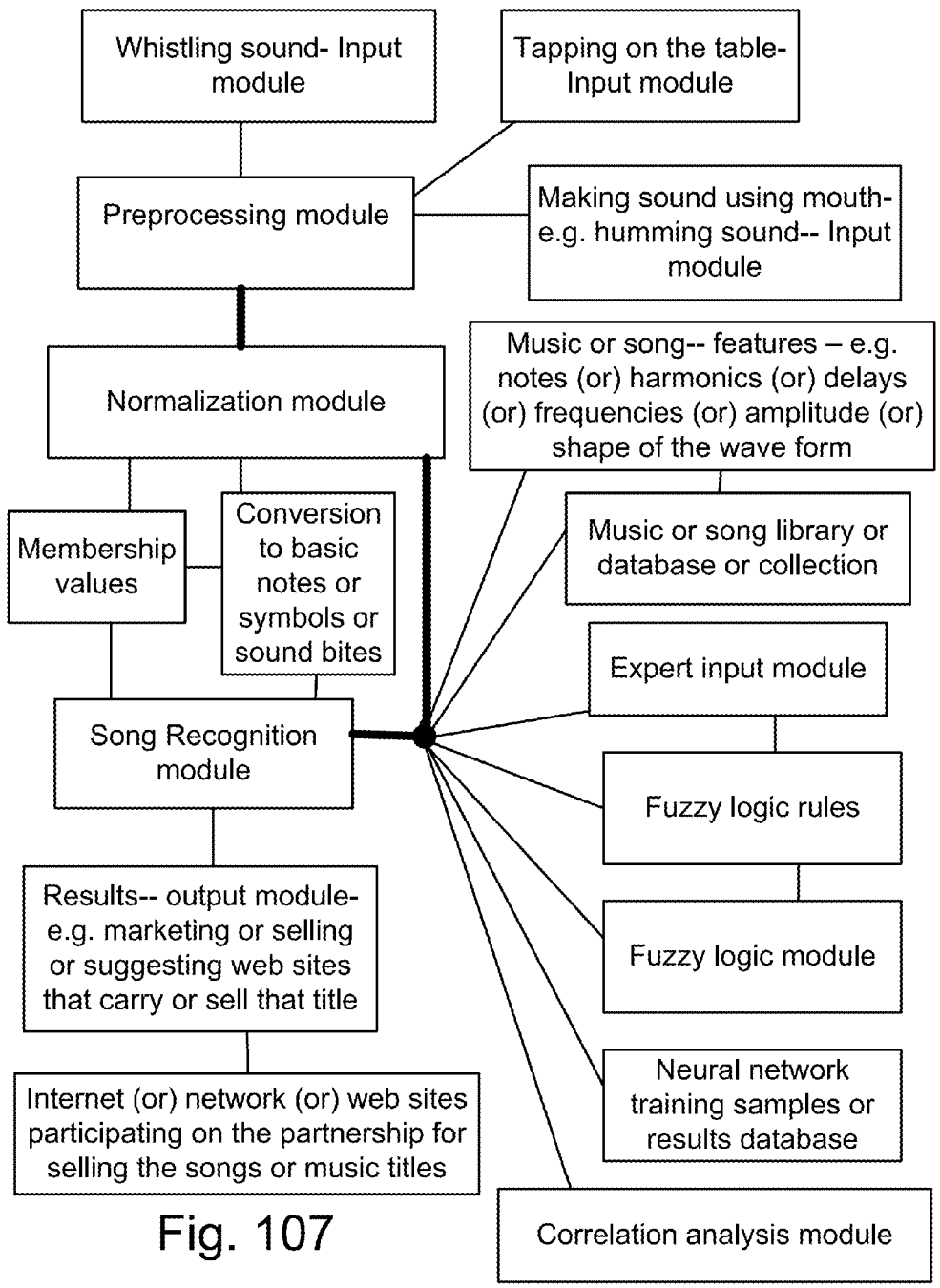

FIG. 107 is a system for sound or song recognition.

Figure 108:
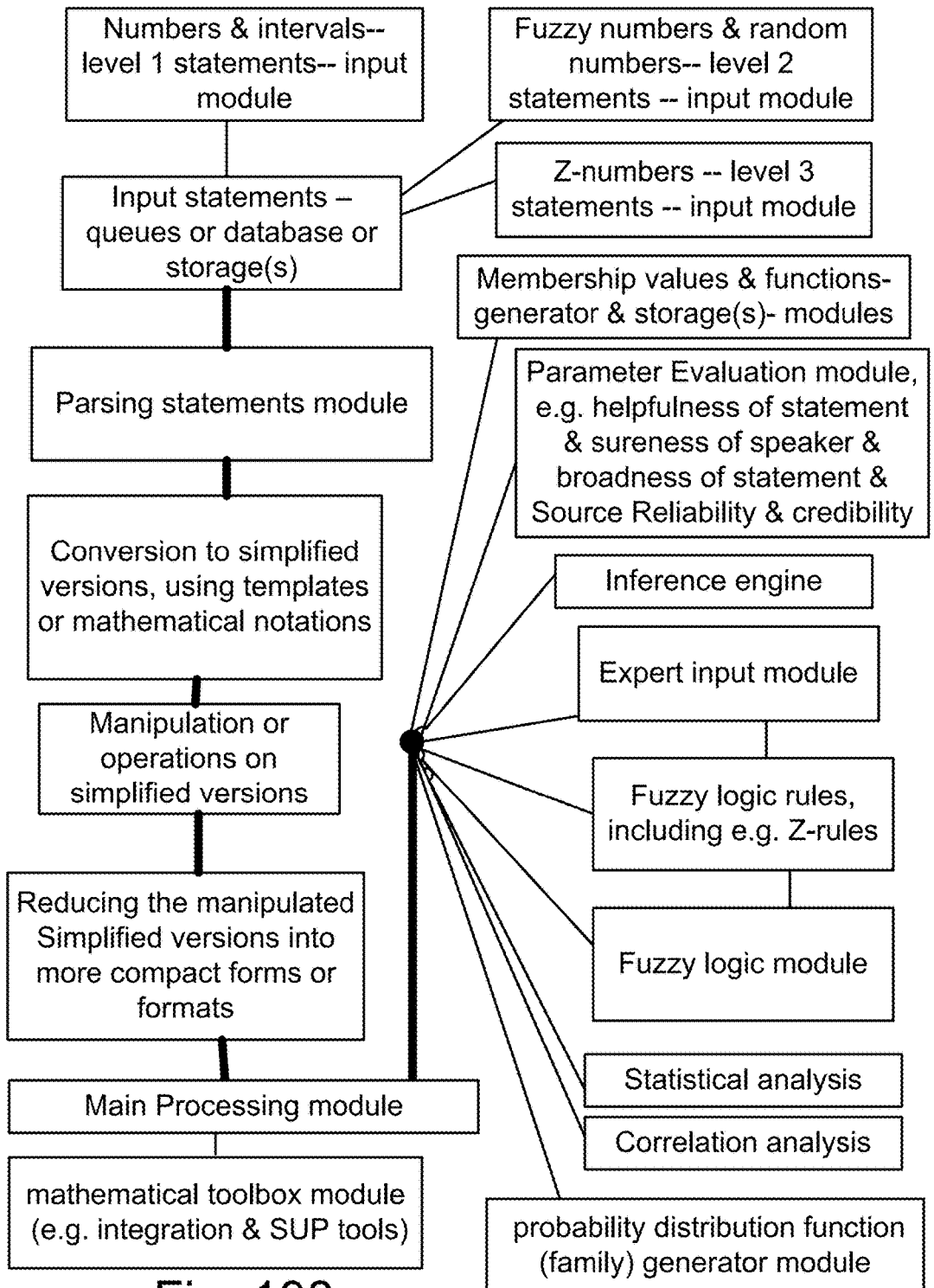

FIG. 108 is a system using Z-numbers.

Figure 109:
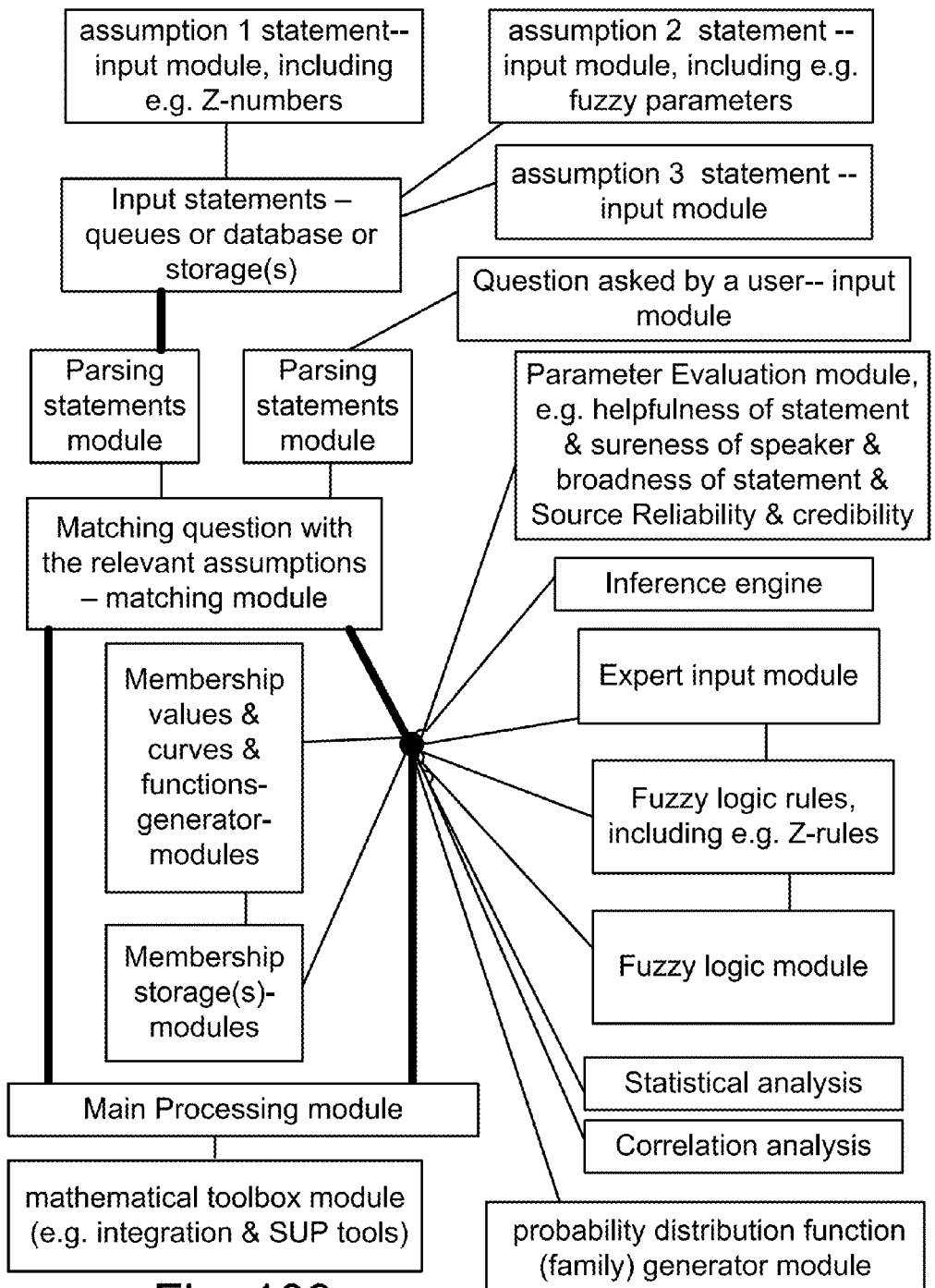

FIG. 109 is a system for a search engine or a question-answer system.

Figure 110:
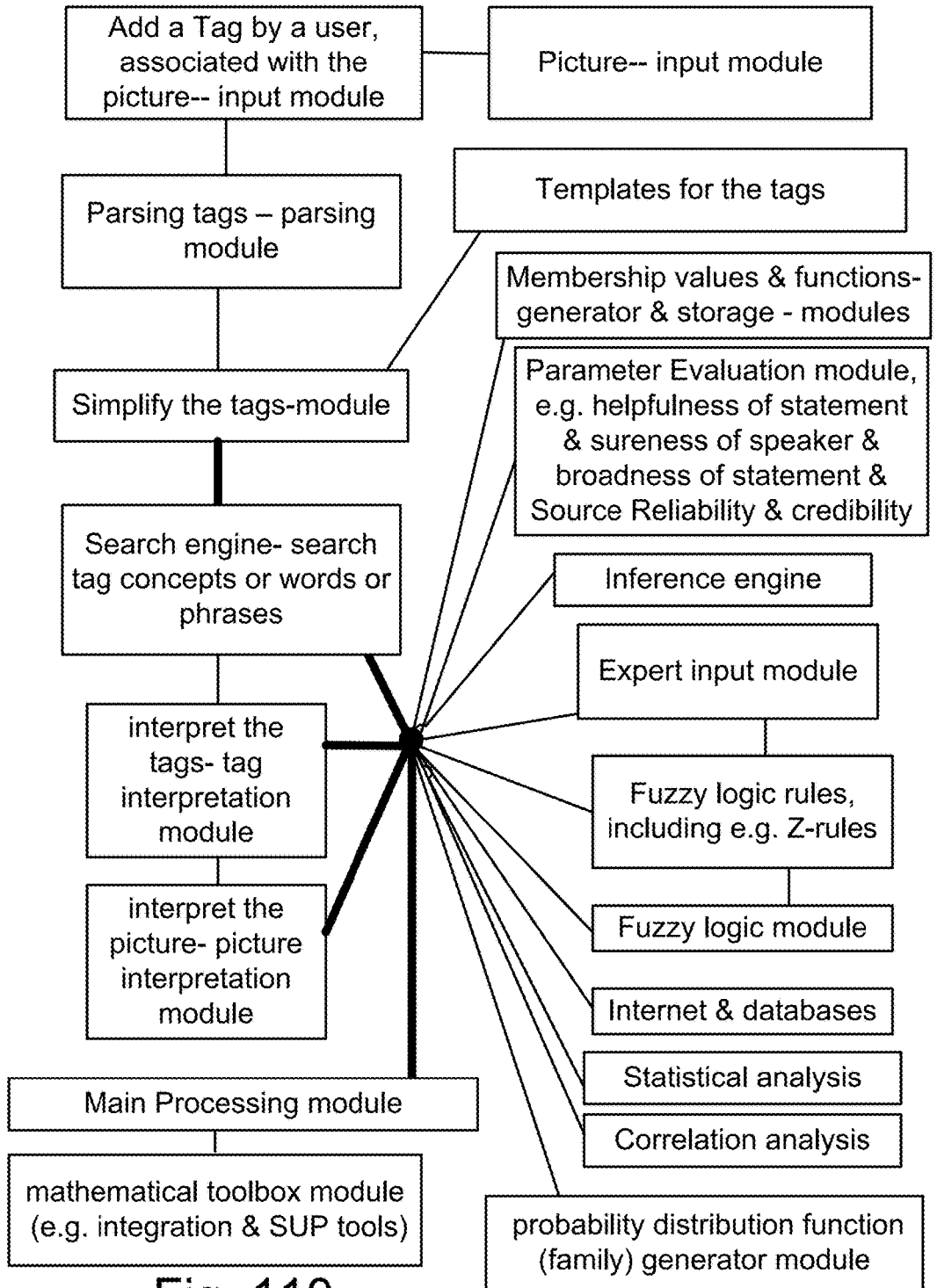

FIG. 110 is a system for a search engine.

Figure 111:
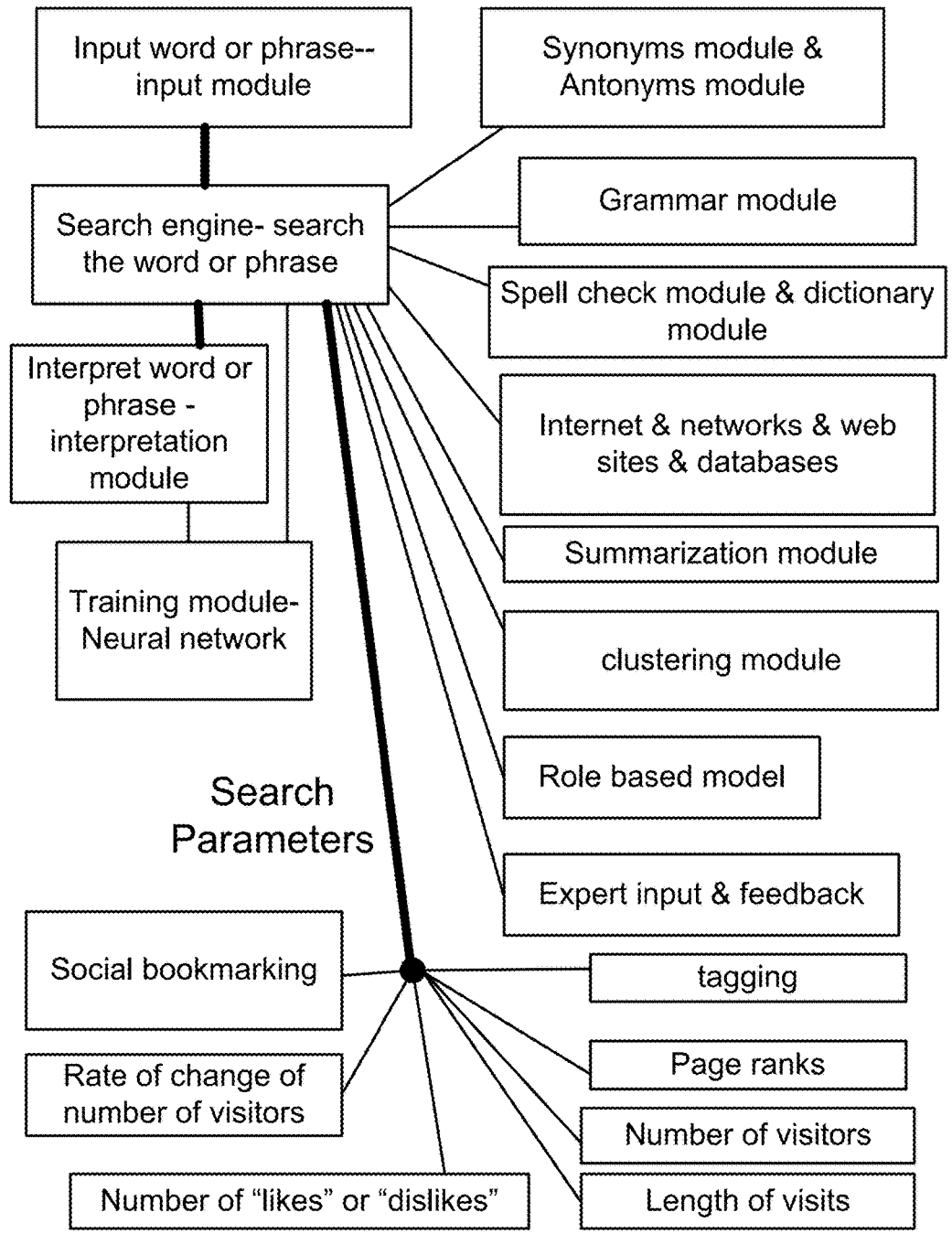

FIG. 111 is a system for a search engine.

Figure 112:
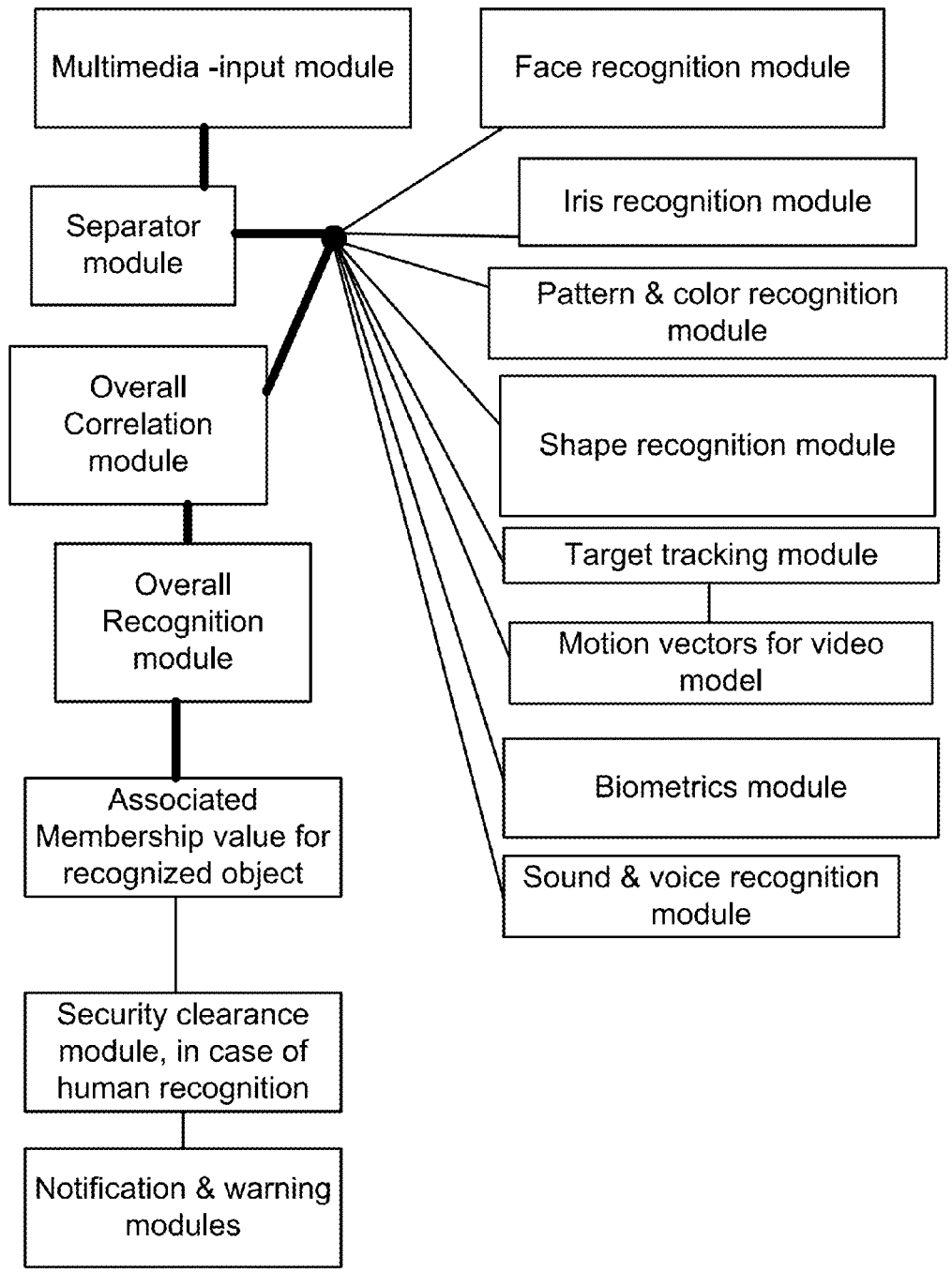

FIG. 112 is a system for the recognition and search engine.

Figure 113:
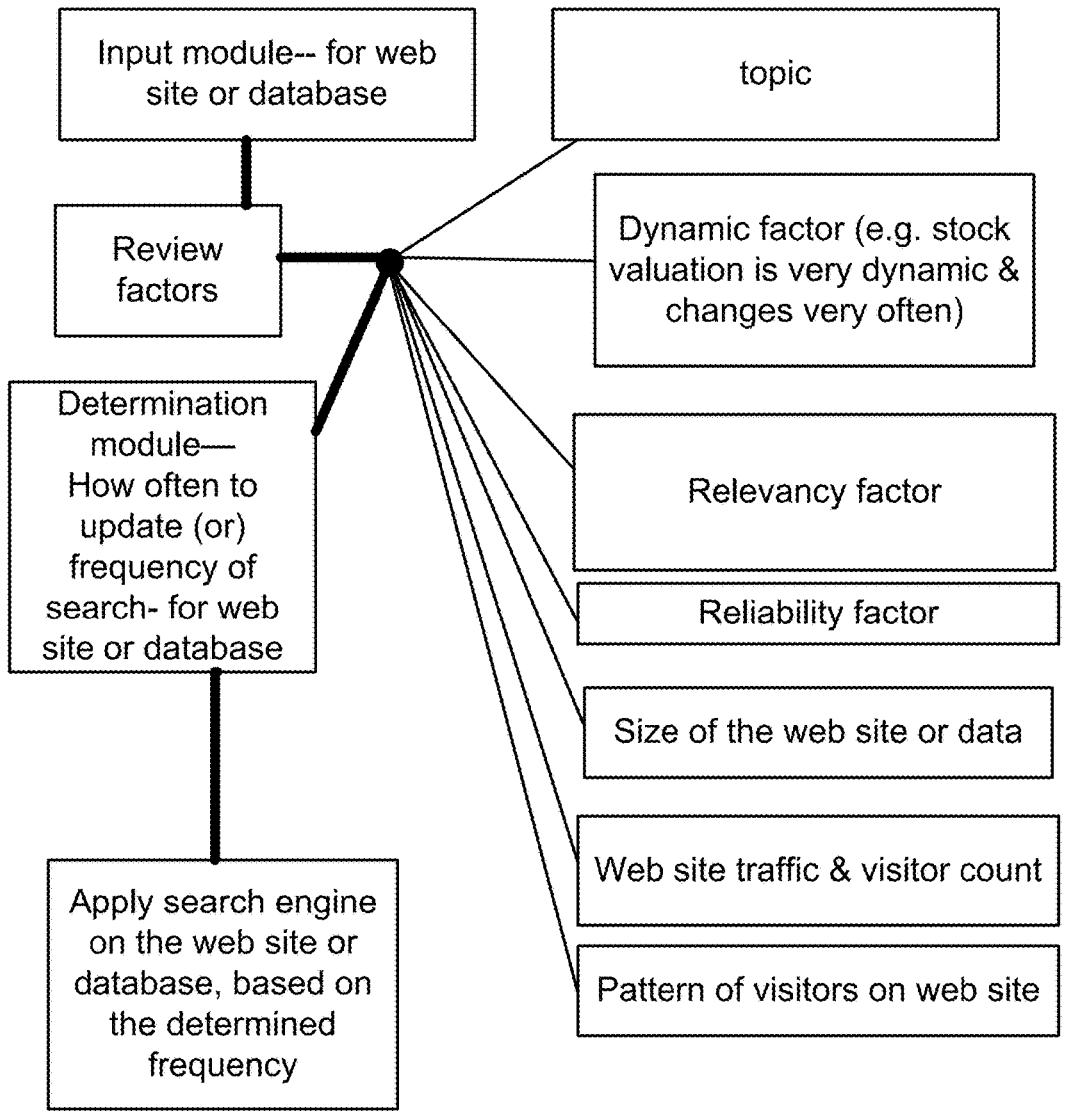

FIG. 113 is a system for a search engine.

Figure 114:
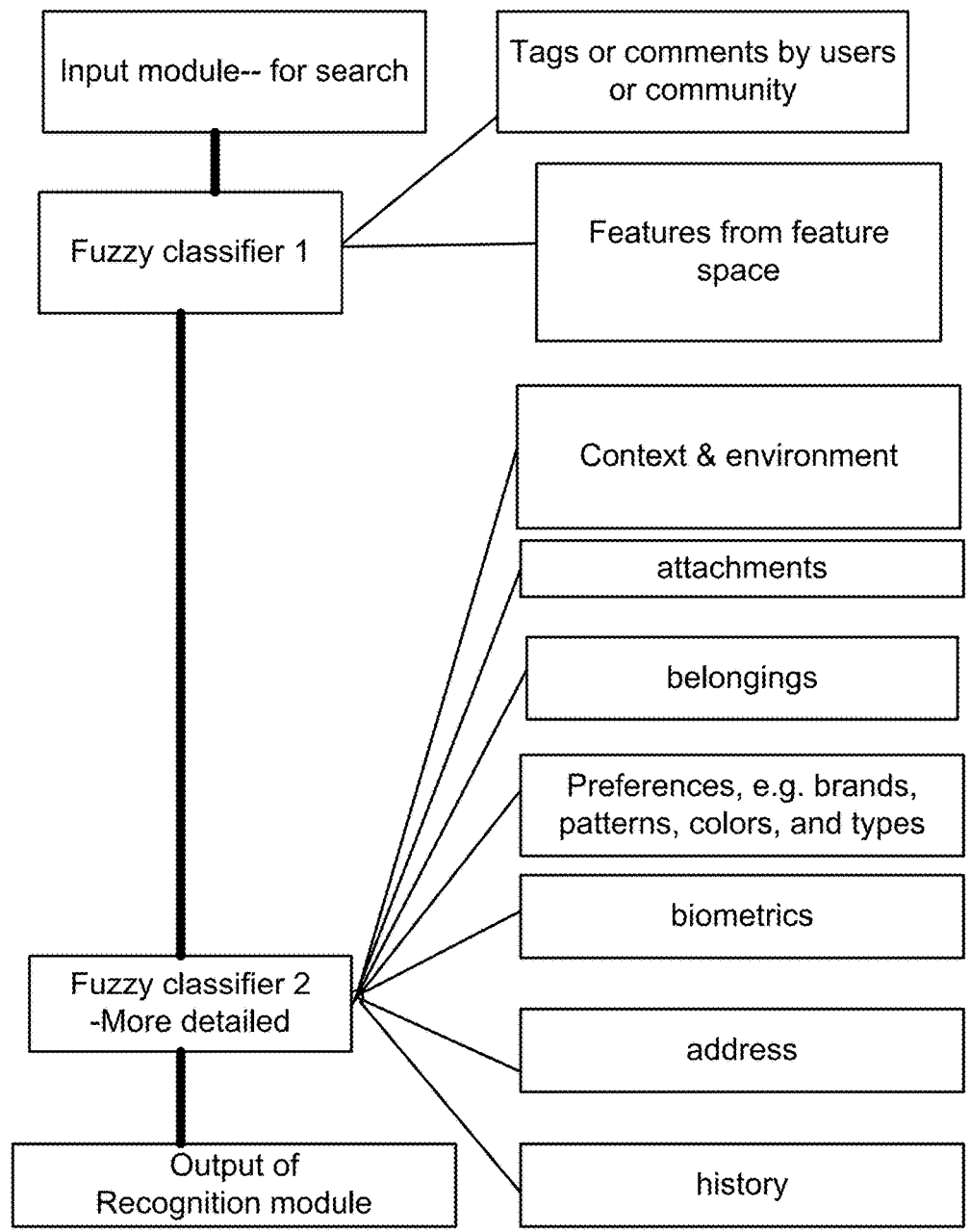

FIG. 114 is a system for the recognition and search engine.

Figure 115:
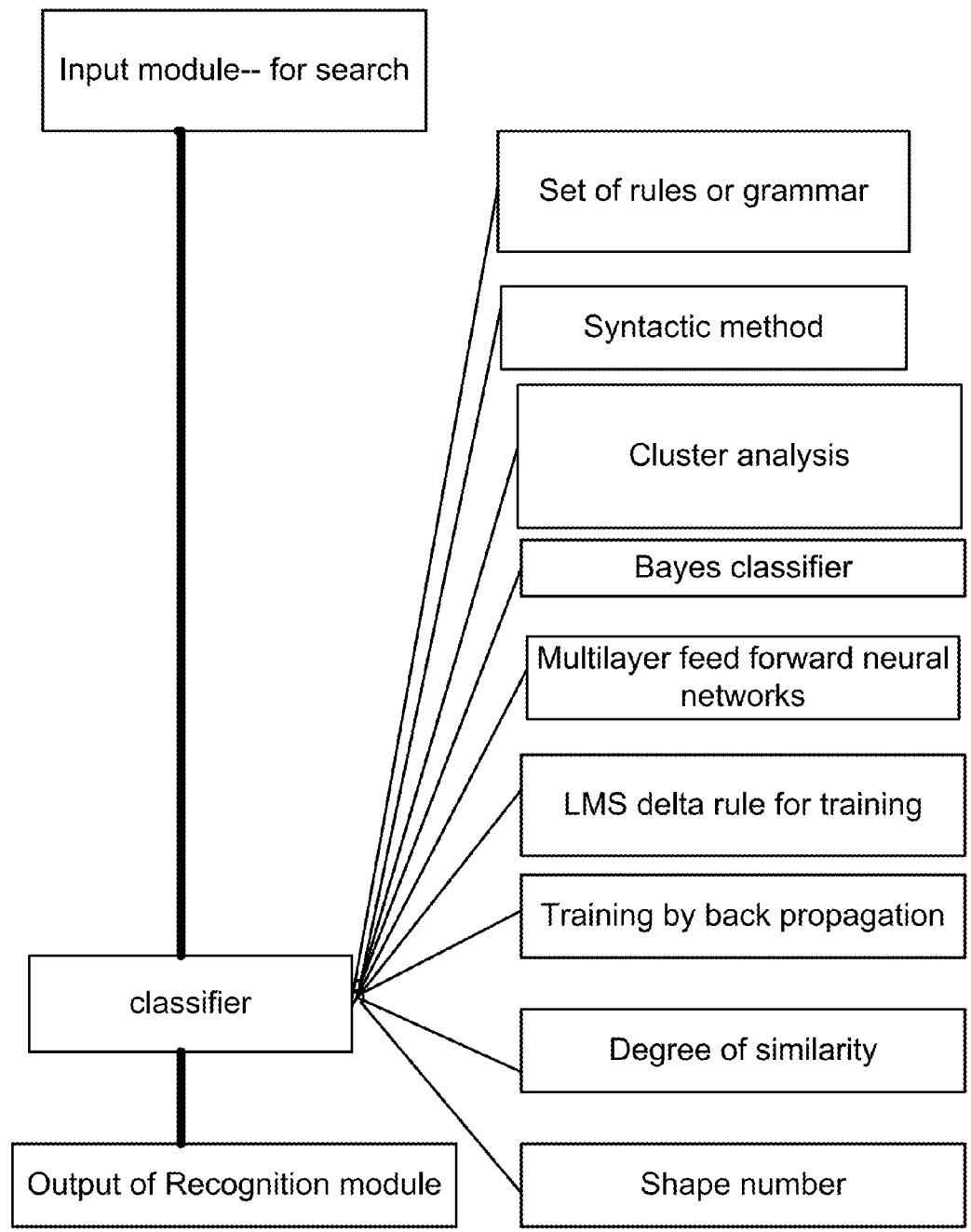

FIG. 115 is a system for the recognition and search engine.

Figure 116:
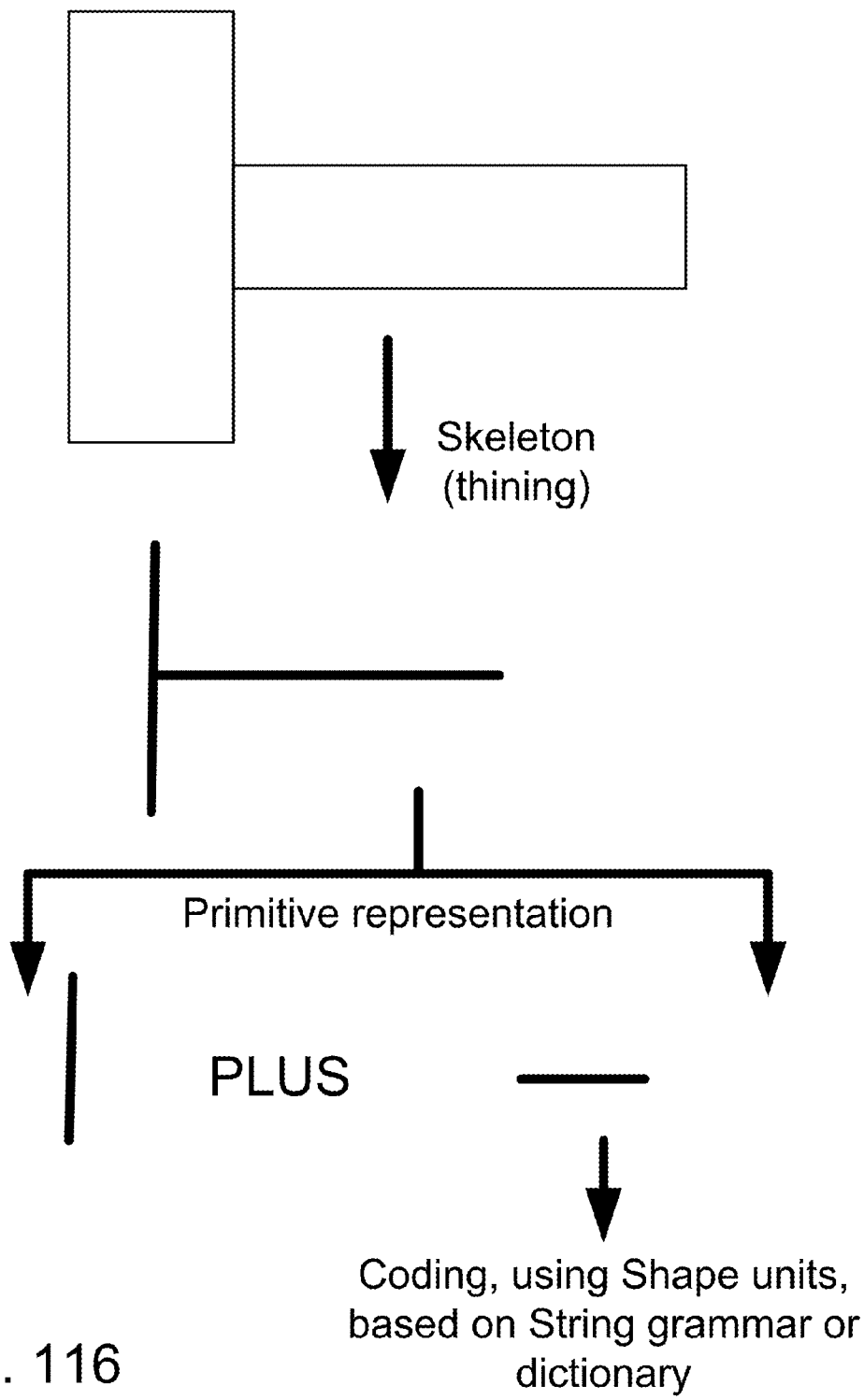

FIG. 116 is a method for the recognition engine.

Figure 117:
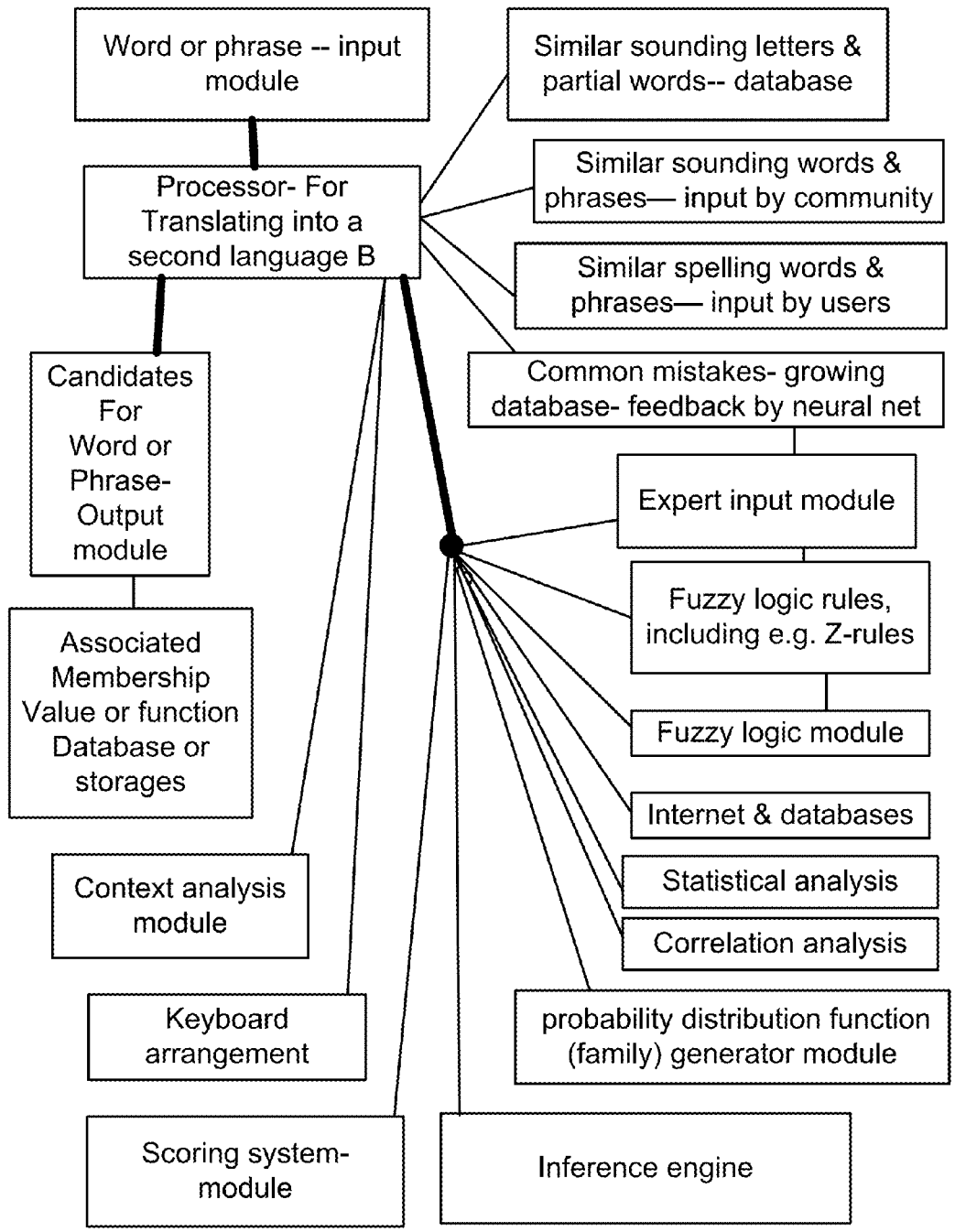

FIG. 117 is a system for the recognition or translation engine.

Figure 118:
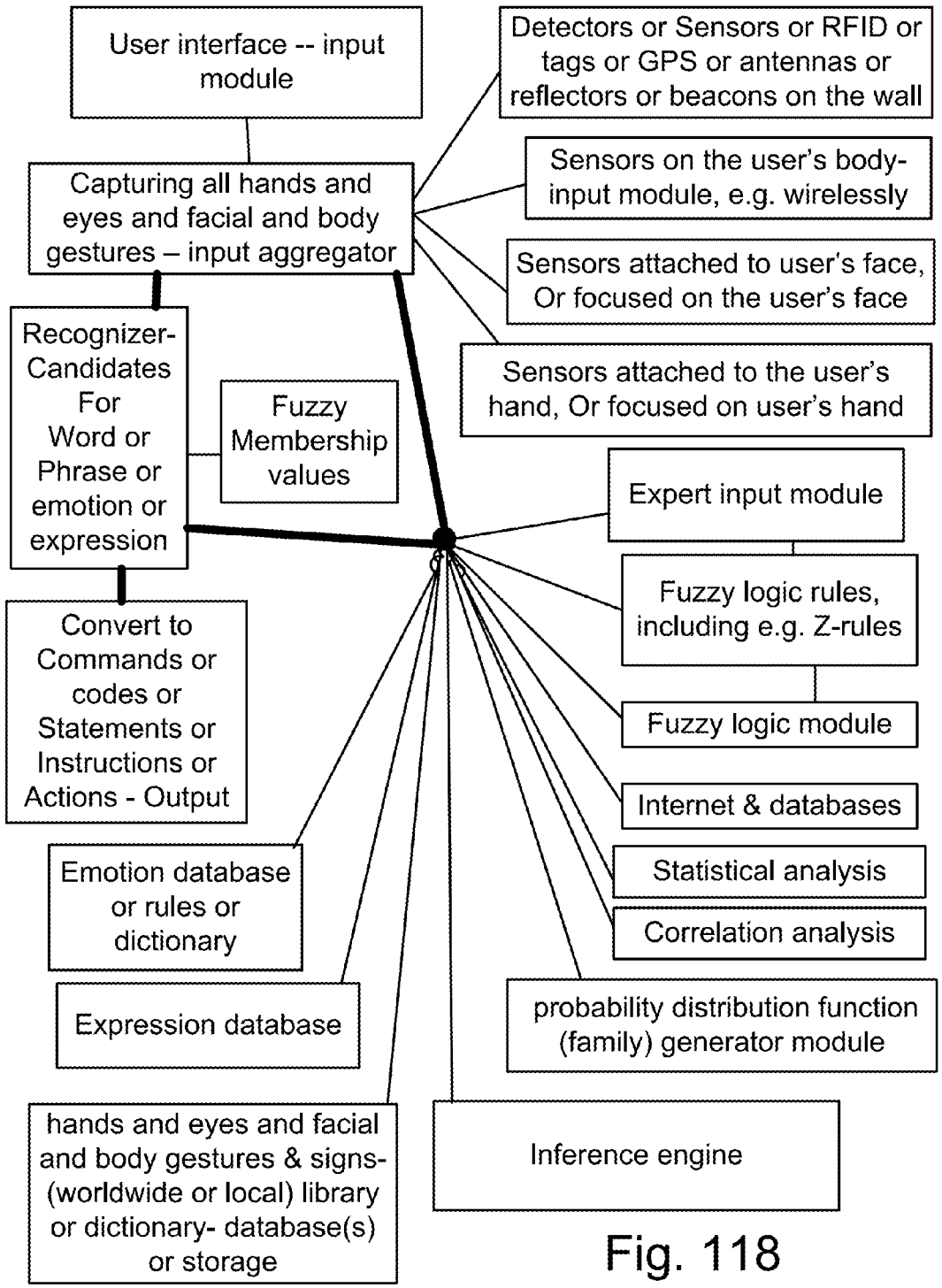

FIG. 118 is a system for the recognition engine for capturing body gestures or body parts' interpretations or emotions (such as cursing or happiness or anger or congratulations statement or success or wishing good luck or twisted eye brows or blinking with only one eye or thumbs up or thumbs down).

Figure 119:
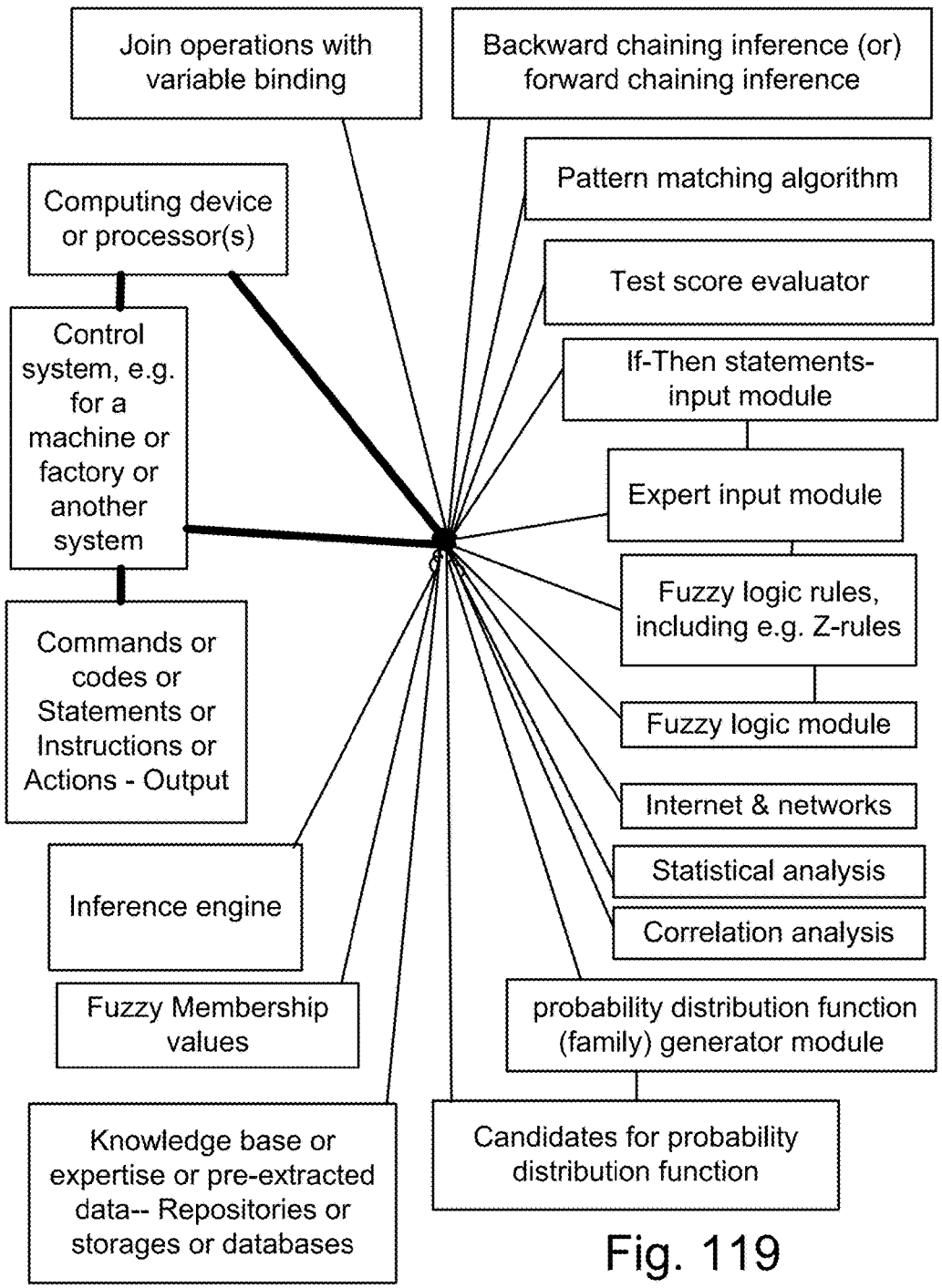

FIG. 119 is a system for Fuzzy Logic or Z-numbers.

Figure 120A:
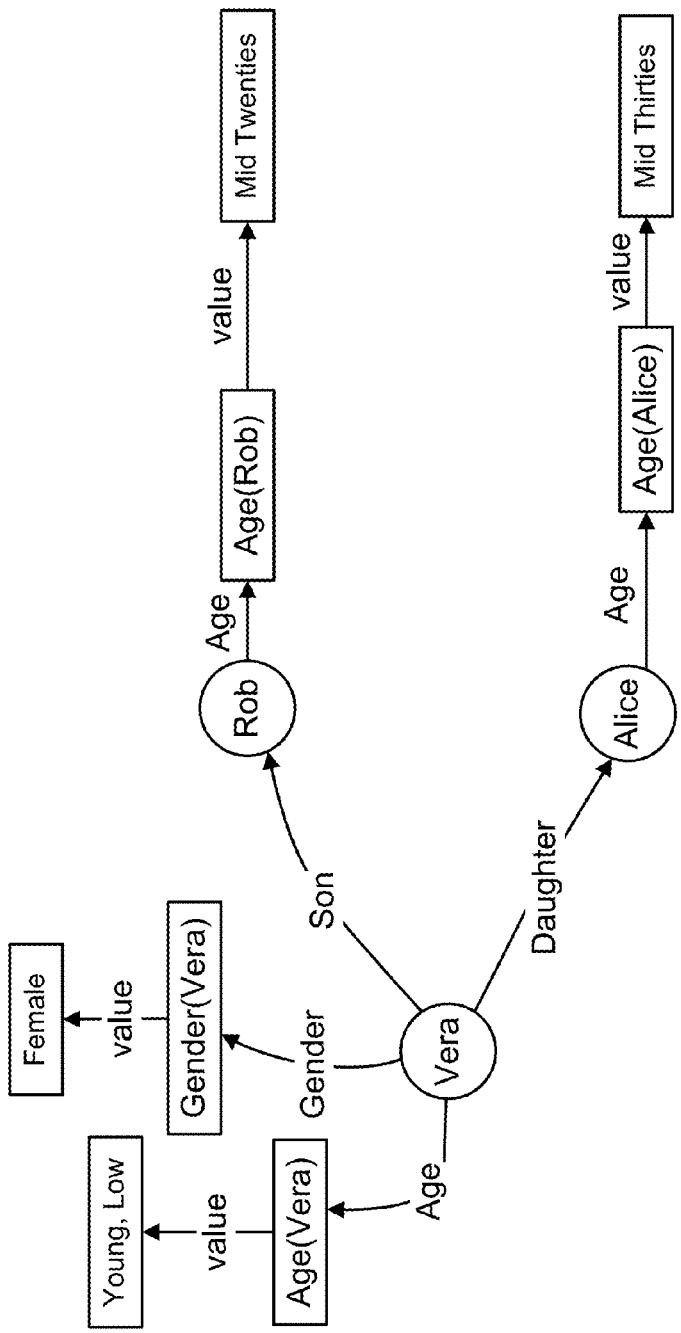
Figure 120B:
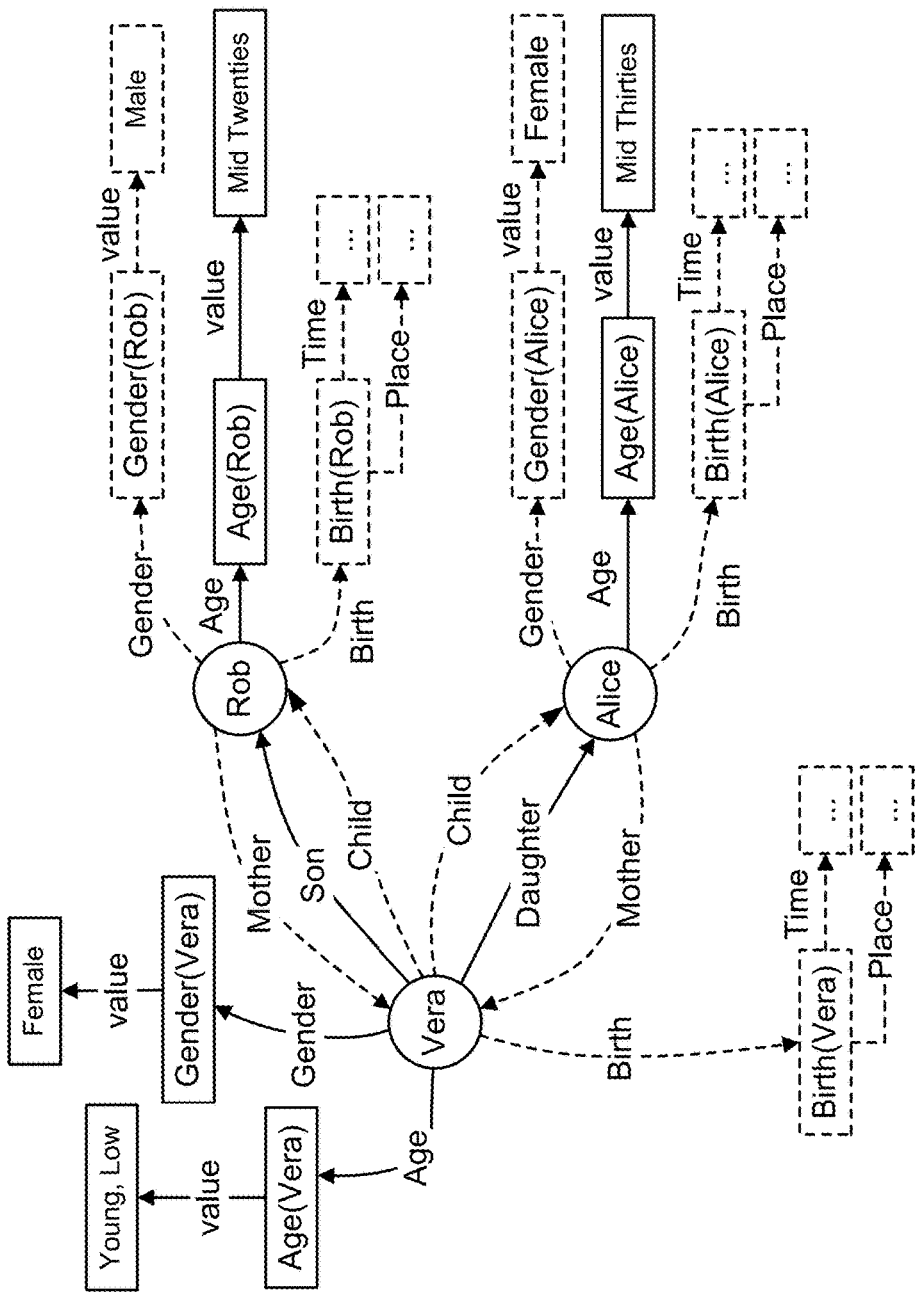

FIG. 120(a)-(b) show objects, attributes, and values in an example illustrating an embodiment.

Figure 120C:
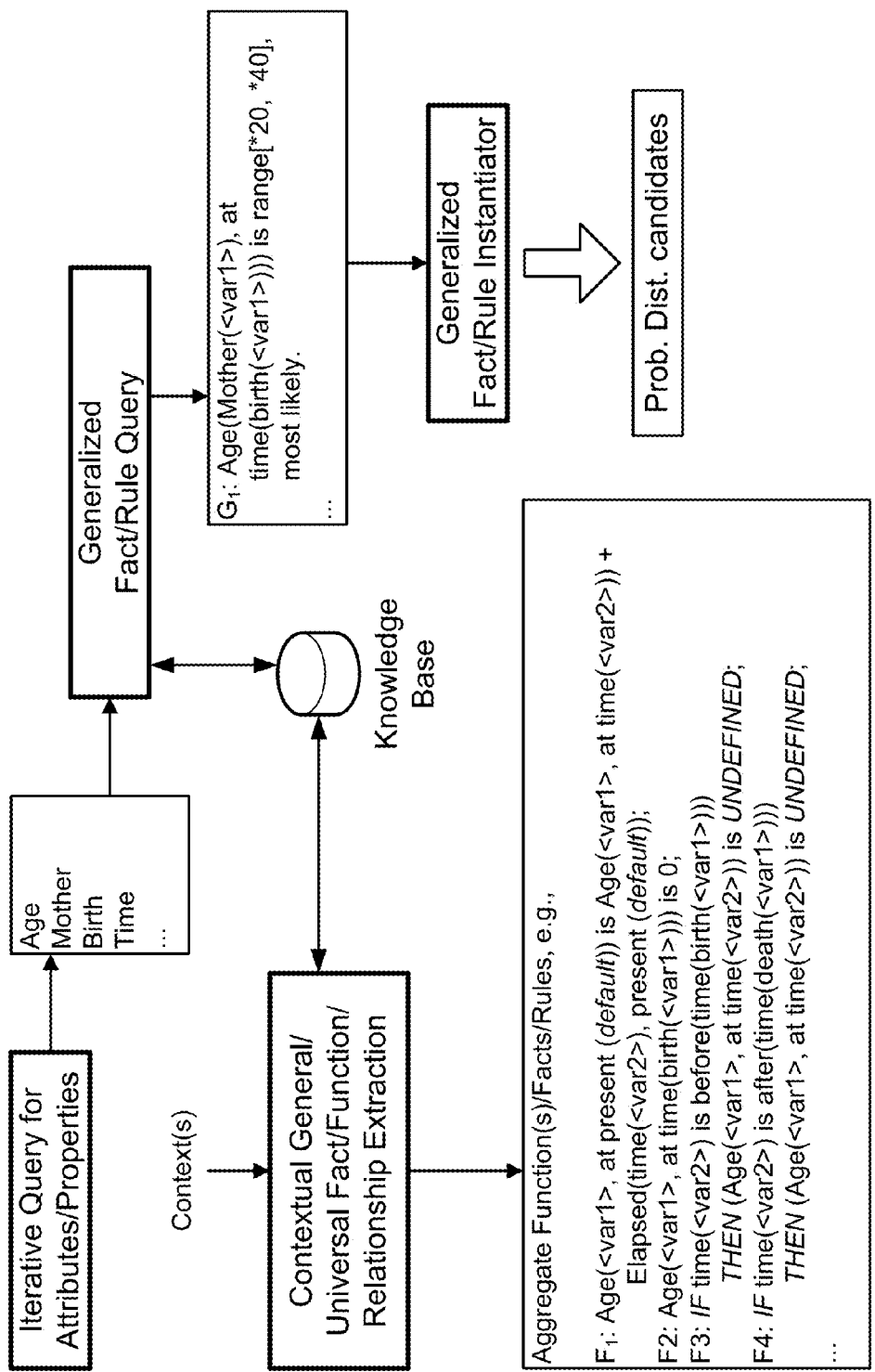

FIG. 120(c) shows querying based on attributes to extract generalized facts/rules/functions in an example illustrating an embodiment.

Figure 120D:
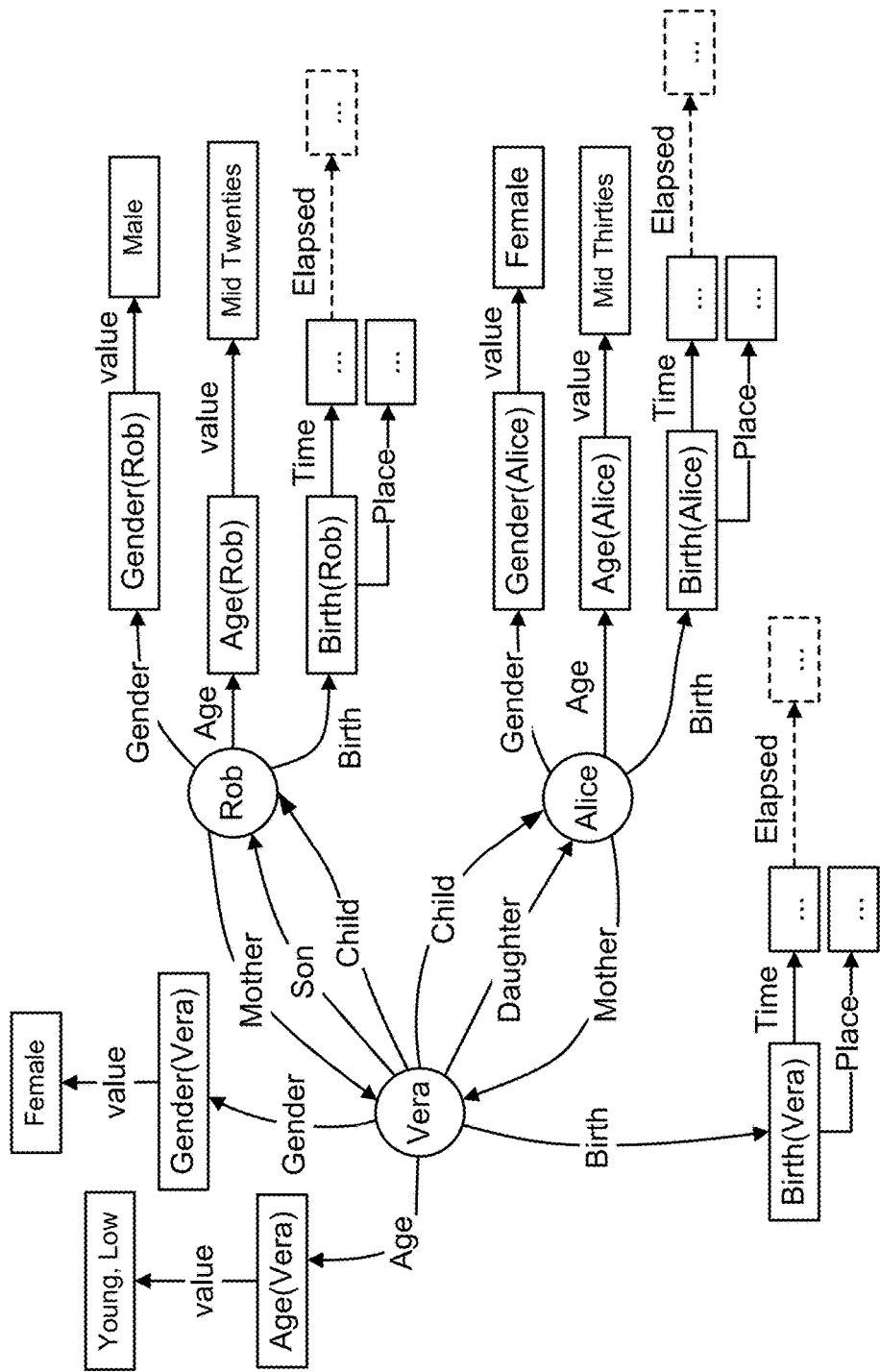
Figure 120E:
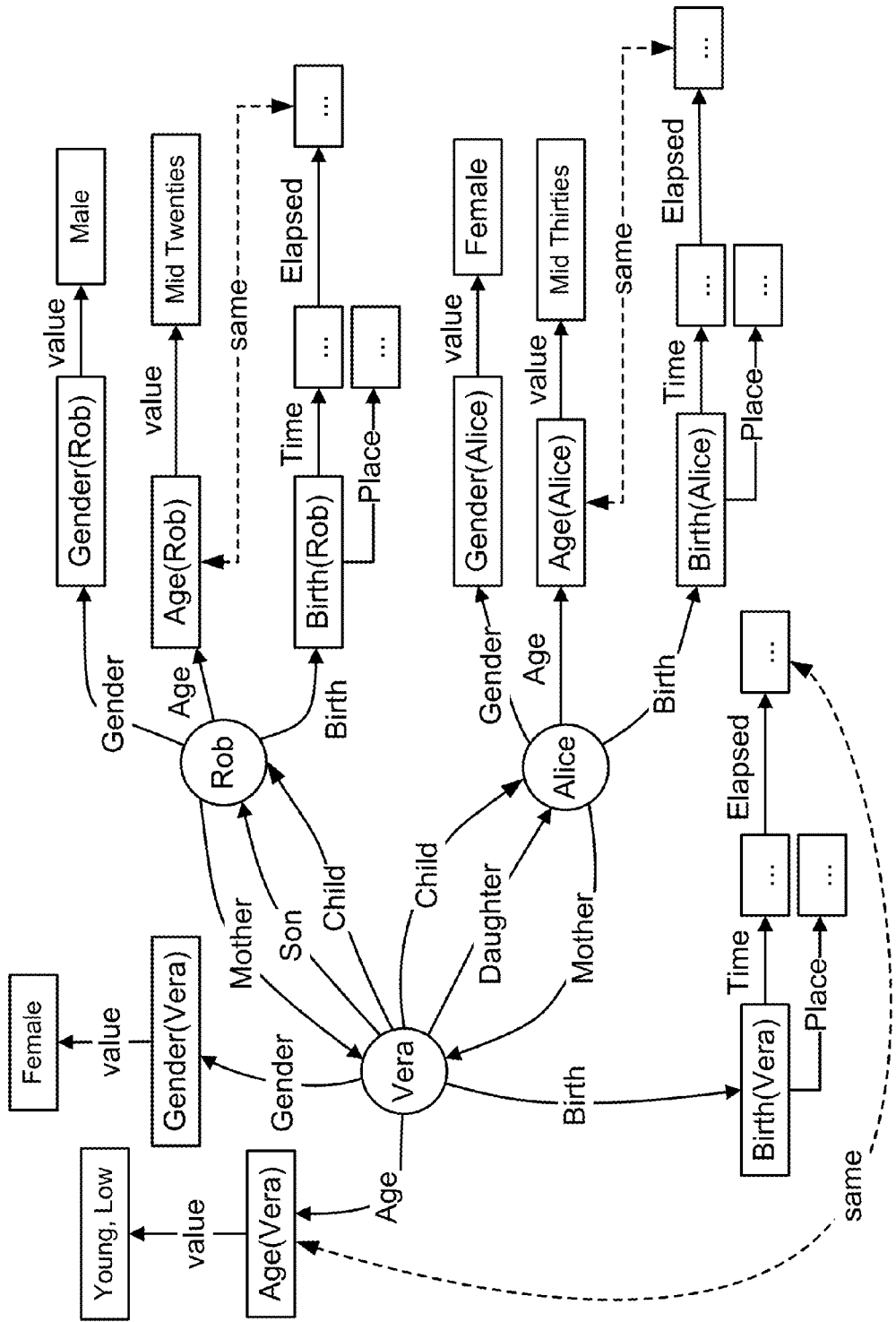

FIG. 120(d)-(e) show objects, attributes, and values in an example illustrating an embodiment.

Figure 120F:
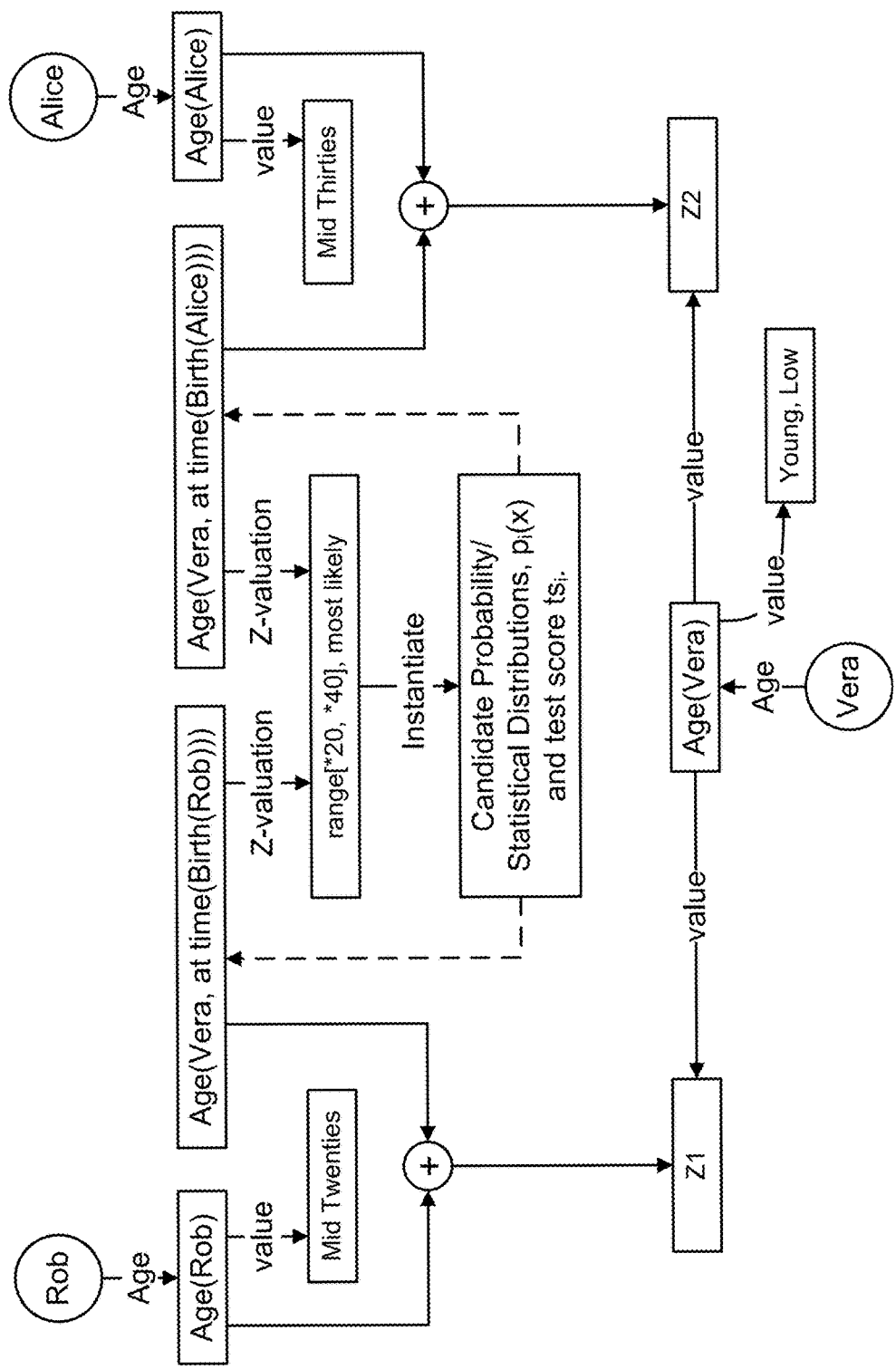

FIG. 120(f) shows Z-valuation of object/record based on candidate distributions in an example illustrating an embodiment.

Figure 120G:
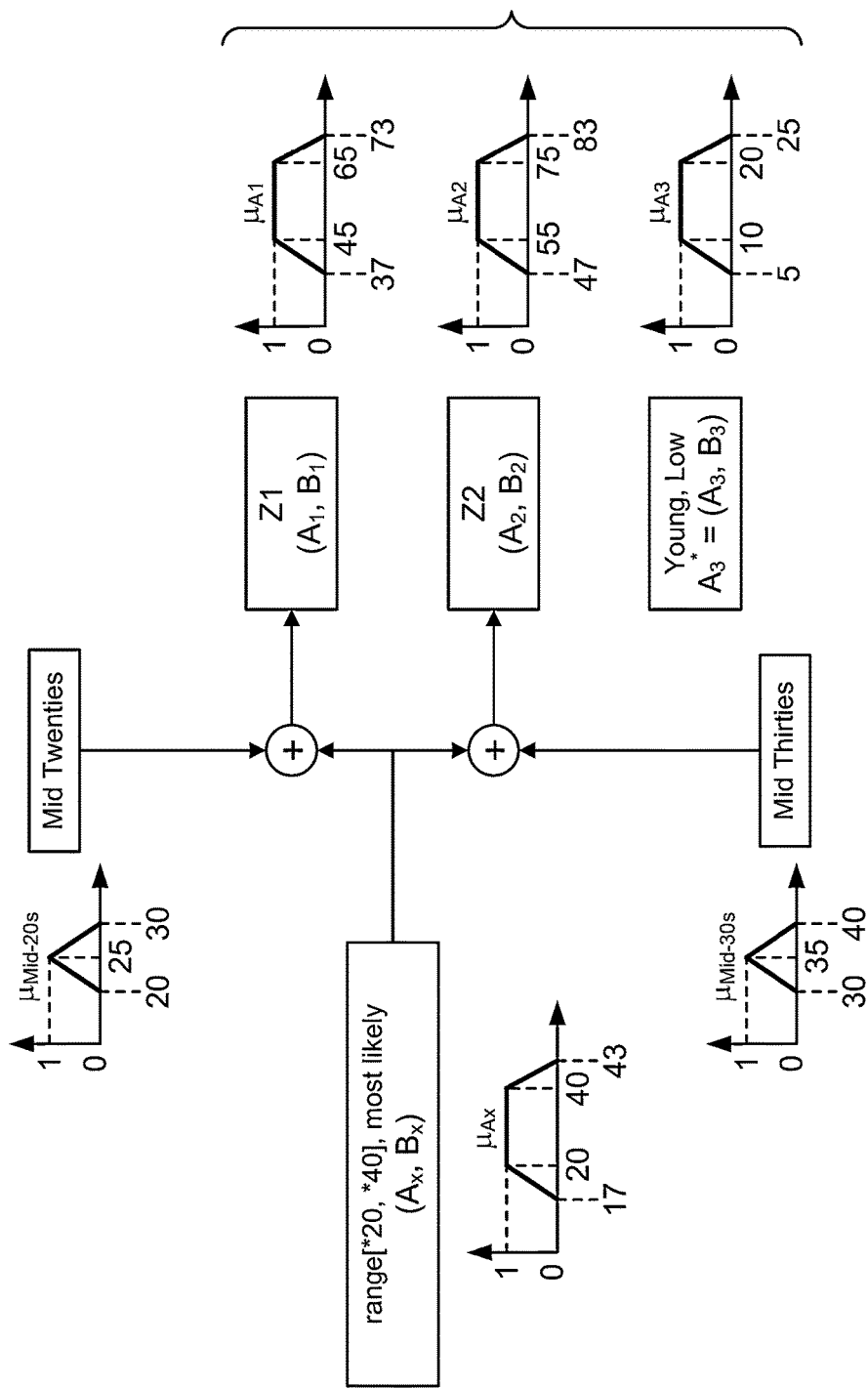

FIG. 120(g) shows memberships functions used in valuations related to an object/record in an example illustrating an embodiment.

Figure 120H:
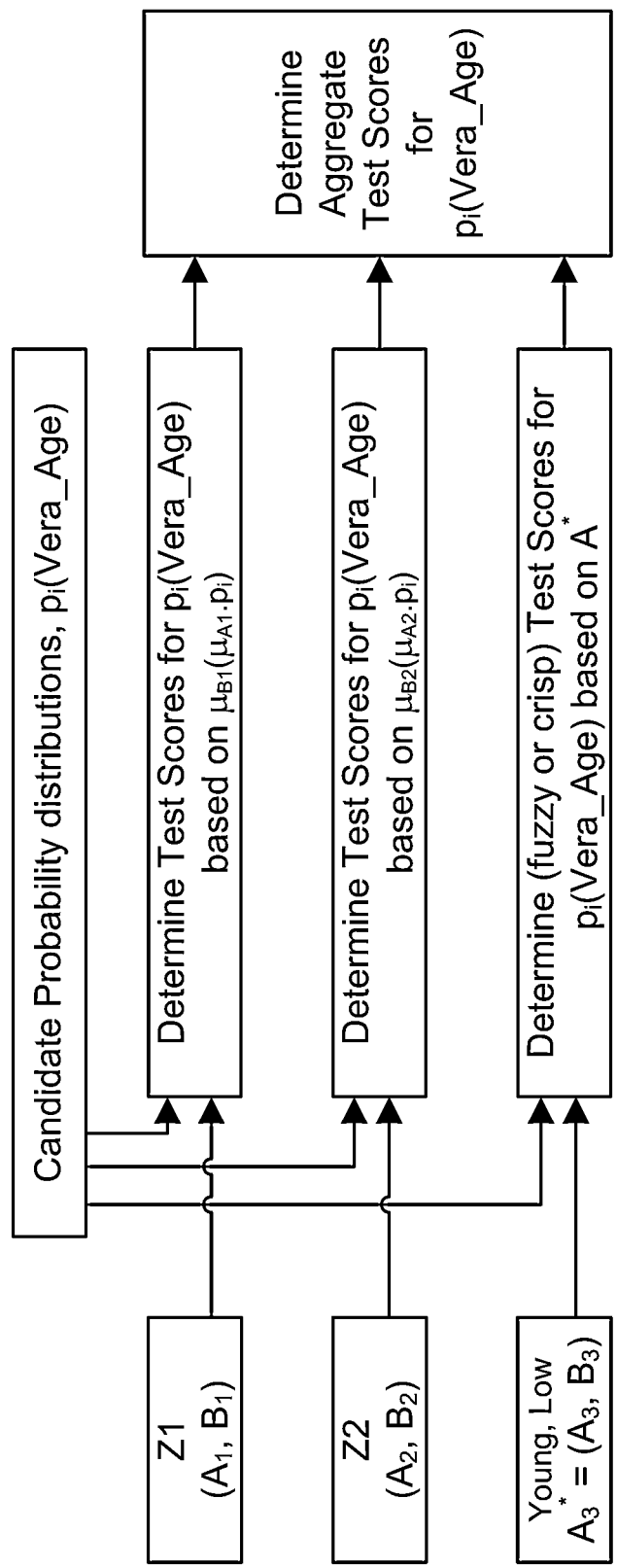

FIG. 120(h) shows the aggregations of test scores for candidate distributions in an example illustrating an embodiment.

Figure 121A:
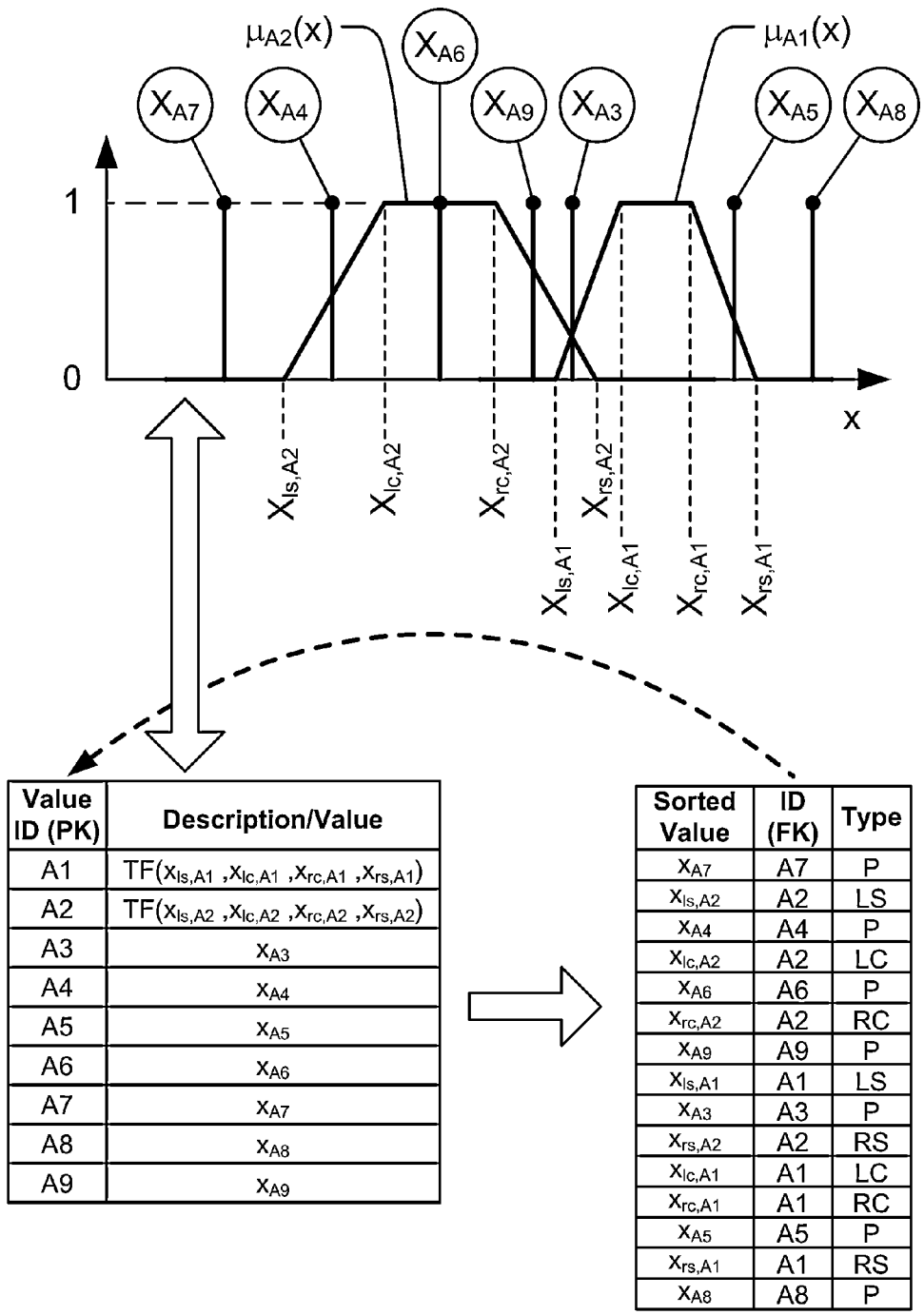

FIG. 121(a) shows ordering in a list containing fuzzy values in an example illustrating an embodiment.

Figure 121B:
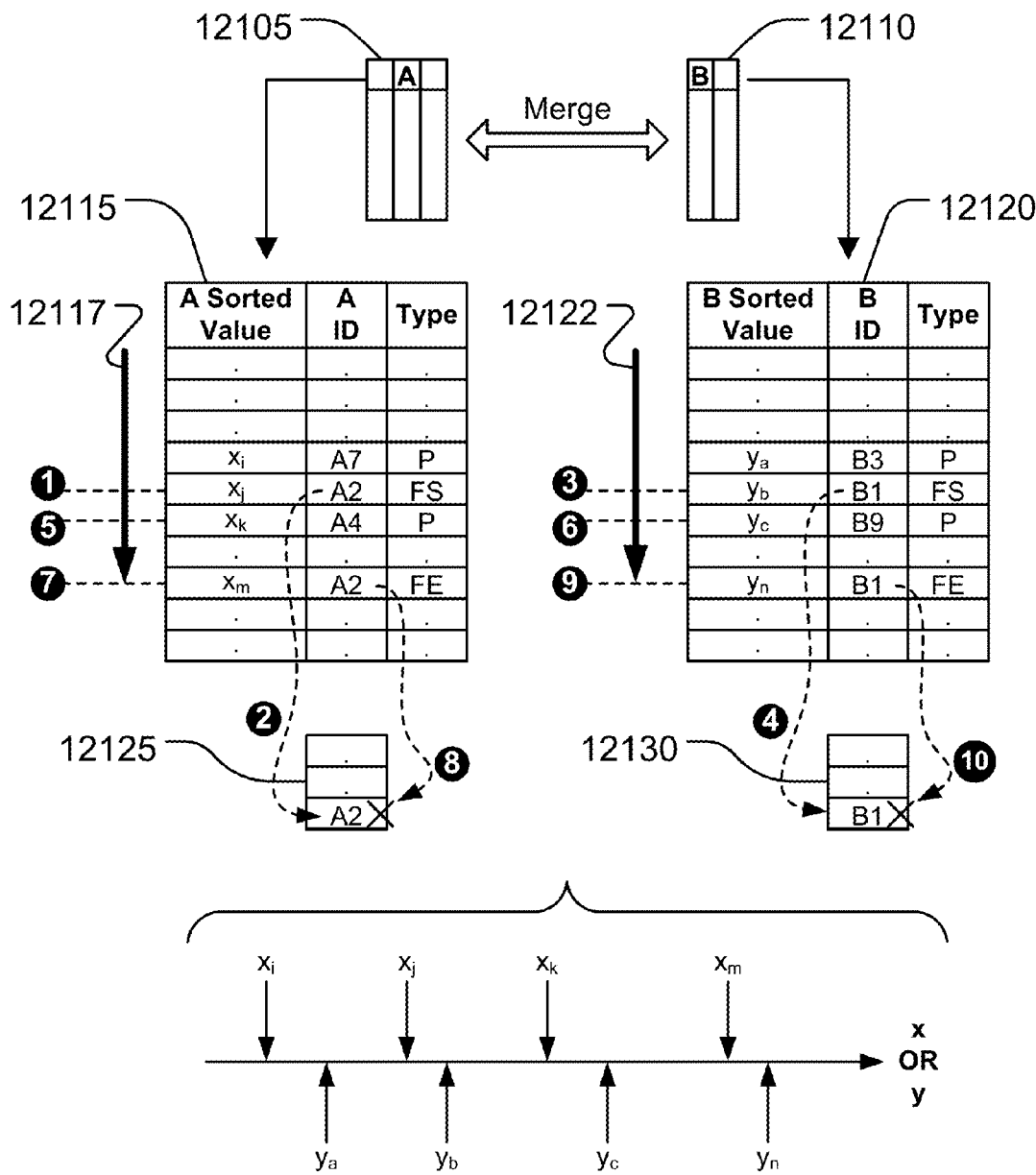

FIG. 121(b) shows use of sorted lists and auxiliary queues in joining lists on the value of common attributes in an example illustrating an embodiment.

Figure 122A:
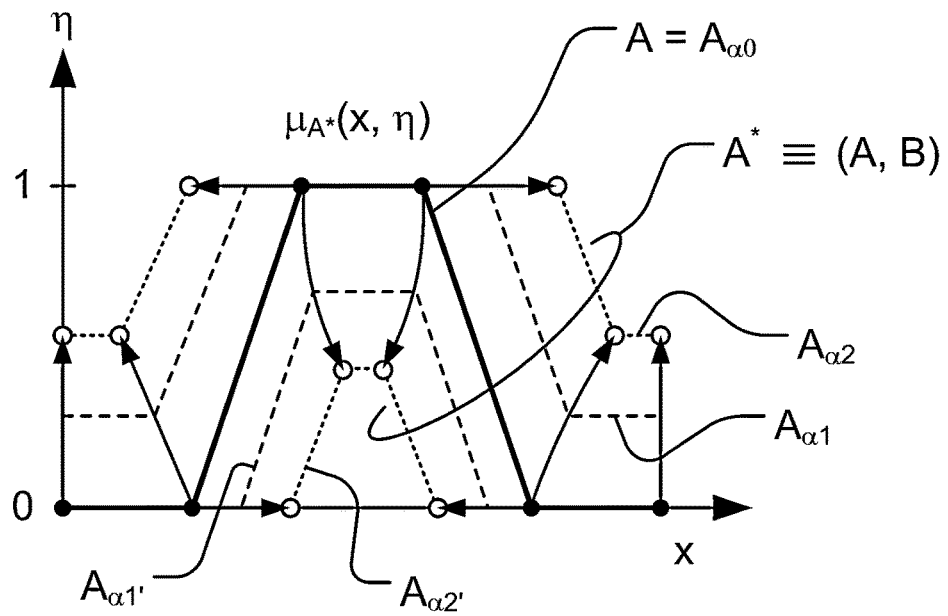
Figure 122B:
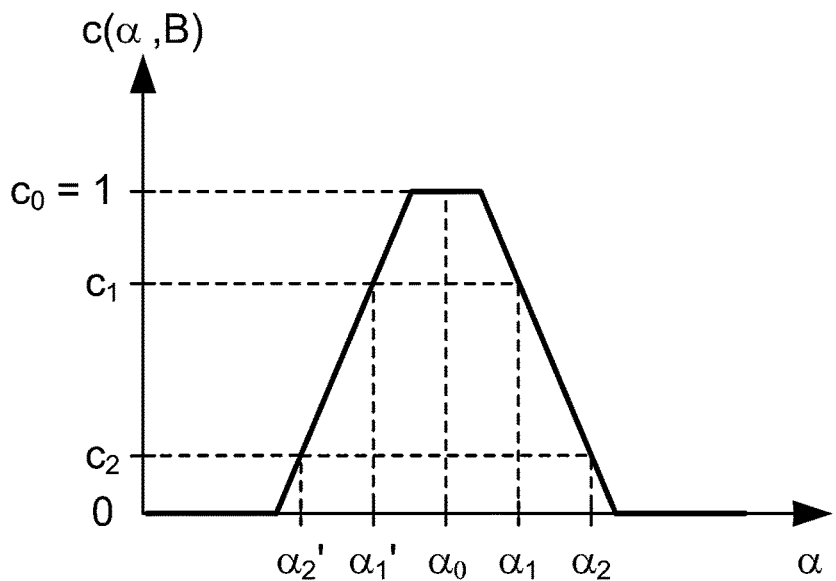

FIG. 122(a)-(b) show parametric fuzzy map and color/grey scale attribute in an example illustrating an embodiment.

Figure 123A:
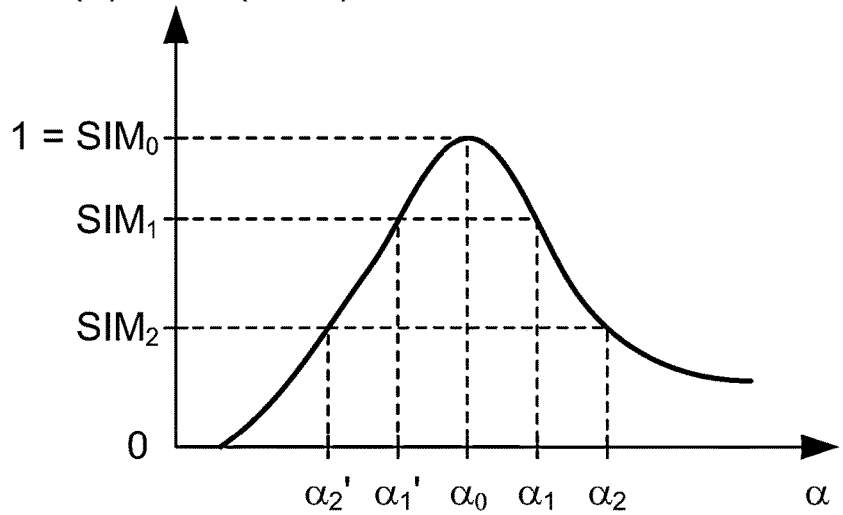
Figure 123B:
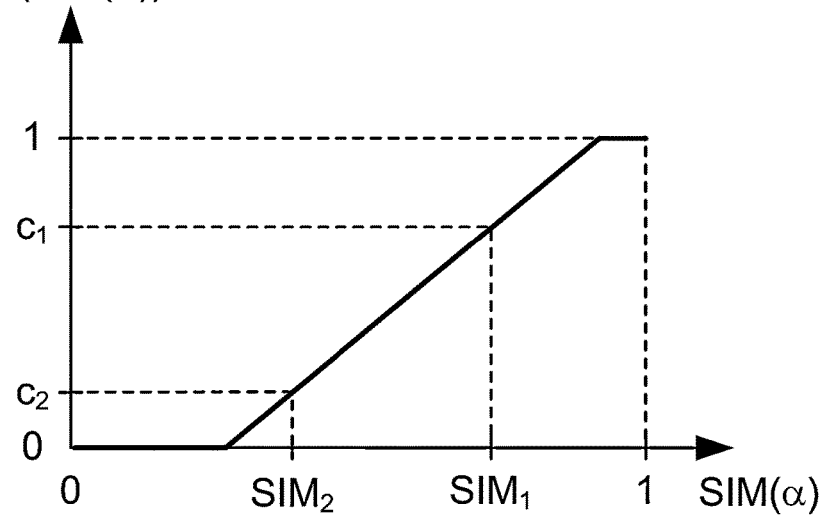

FIG. 123(a)-(b) show a relationship between similarity measure and fuzzy map parameter and precision attribute in an example illustrating an embodiment.

Figure 124A:
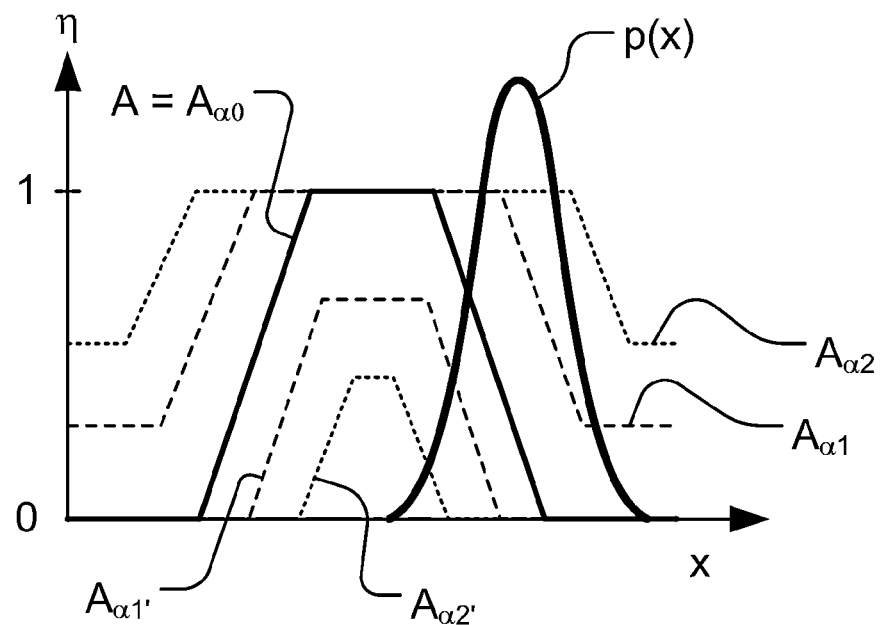
Figure 124B:
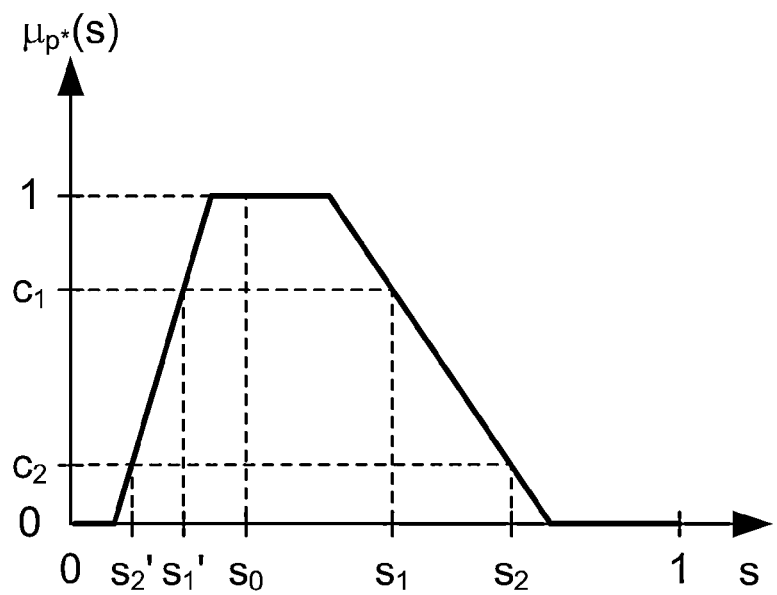

FIG. 124(a)-(b) show fuzzy map, probability distribution, and the related score in an example illustrating an embodiment.

Figure 125A:
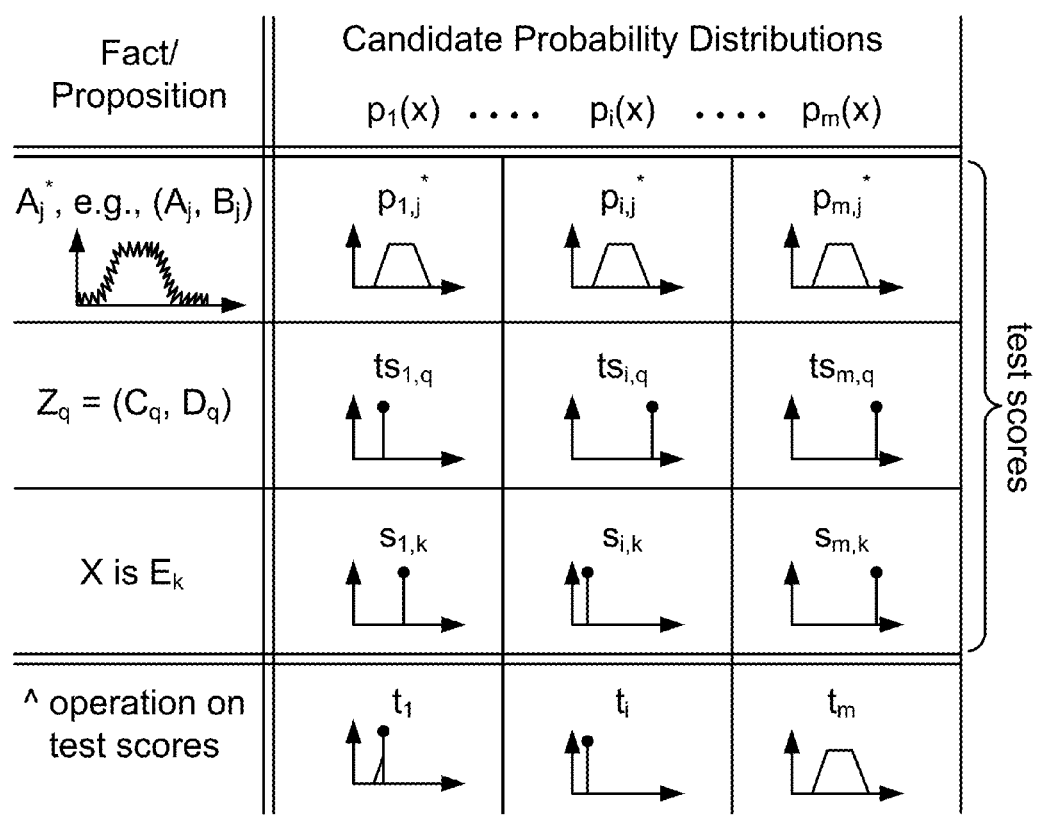

FIG. 125(a) shows crisp and fuzzy test scores for candidate probability distributions based on fuzzy map, Z-valuation, fuzzy restriction, and test score aggregation in an example illustrating an embodiment.

Figure 125B:
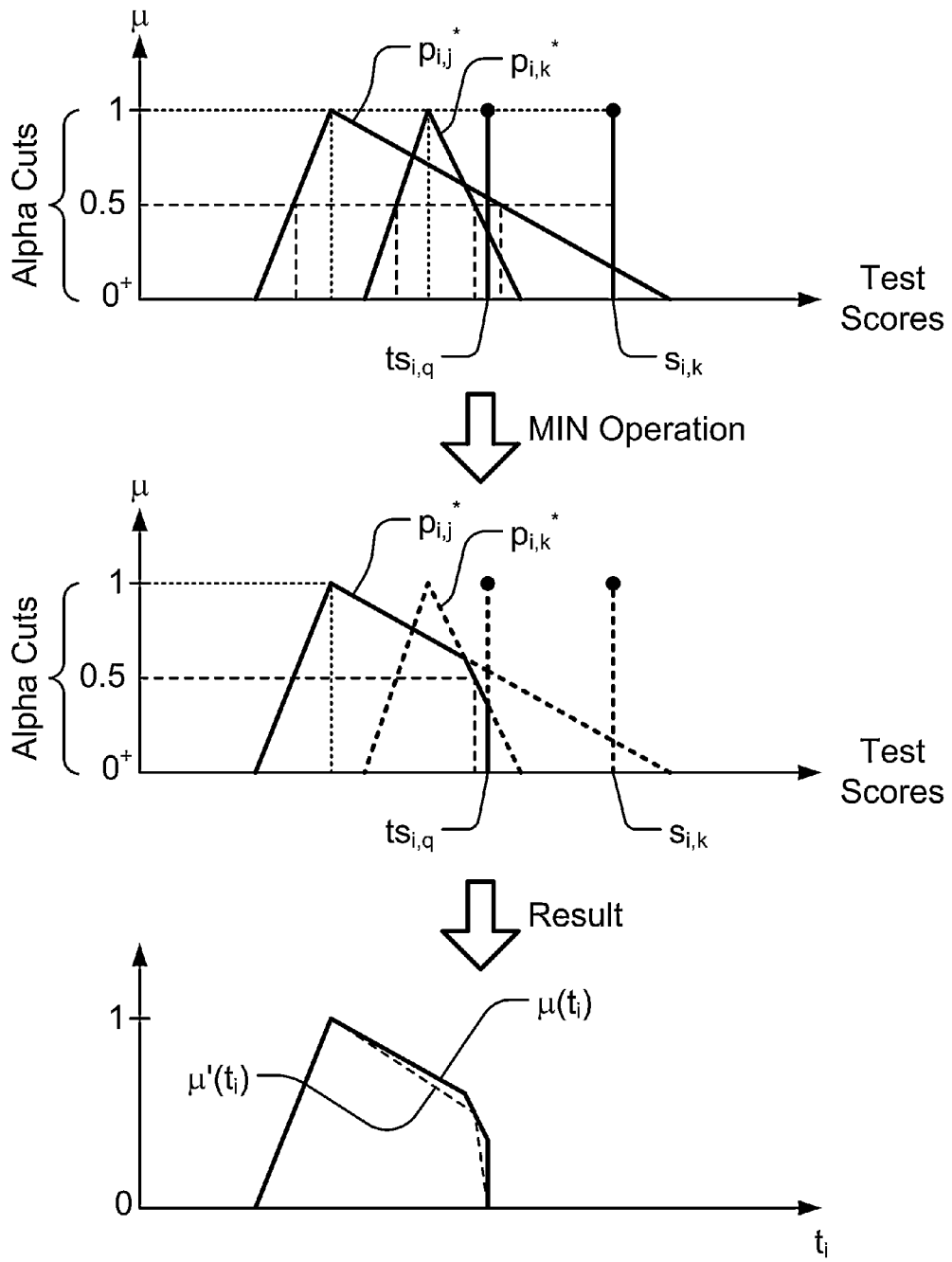

FIG. 125(b) shows MIN operation for test score aggregation via alpha-cuts of membership functions in an example illustrating an embodiment.

Figure 126:
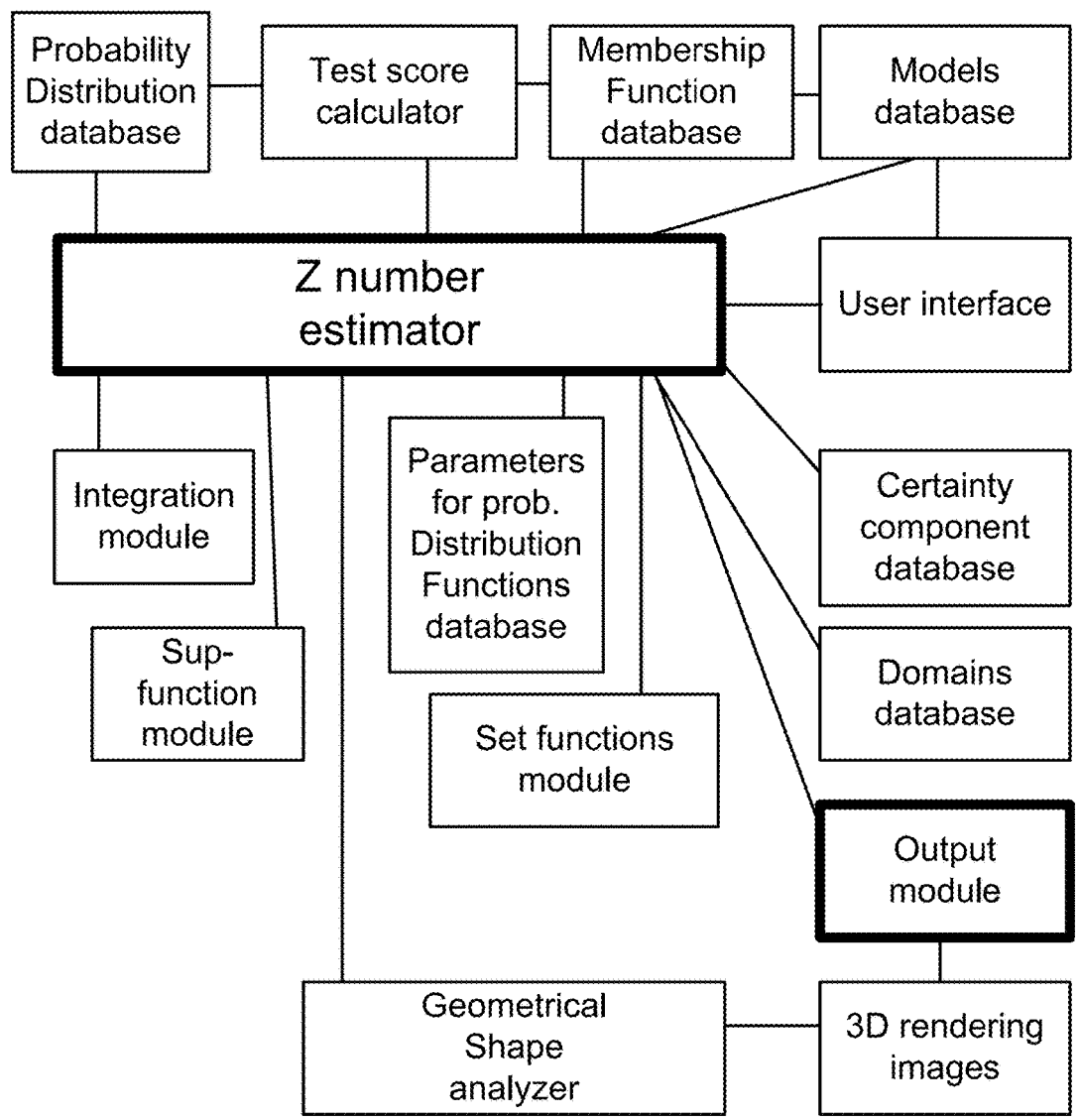

FIG. 126 shows one embodiment for the Z-number estimator or calculator device or system.

Figure 127:
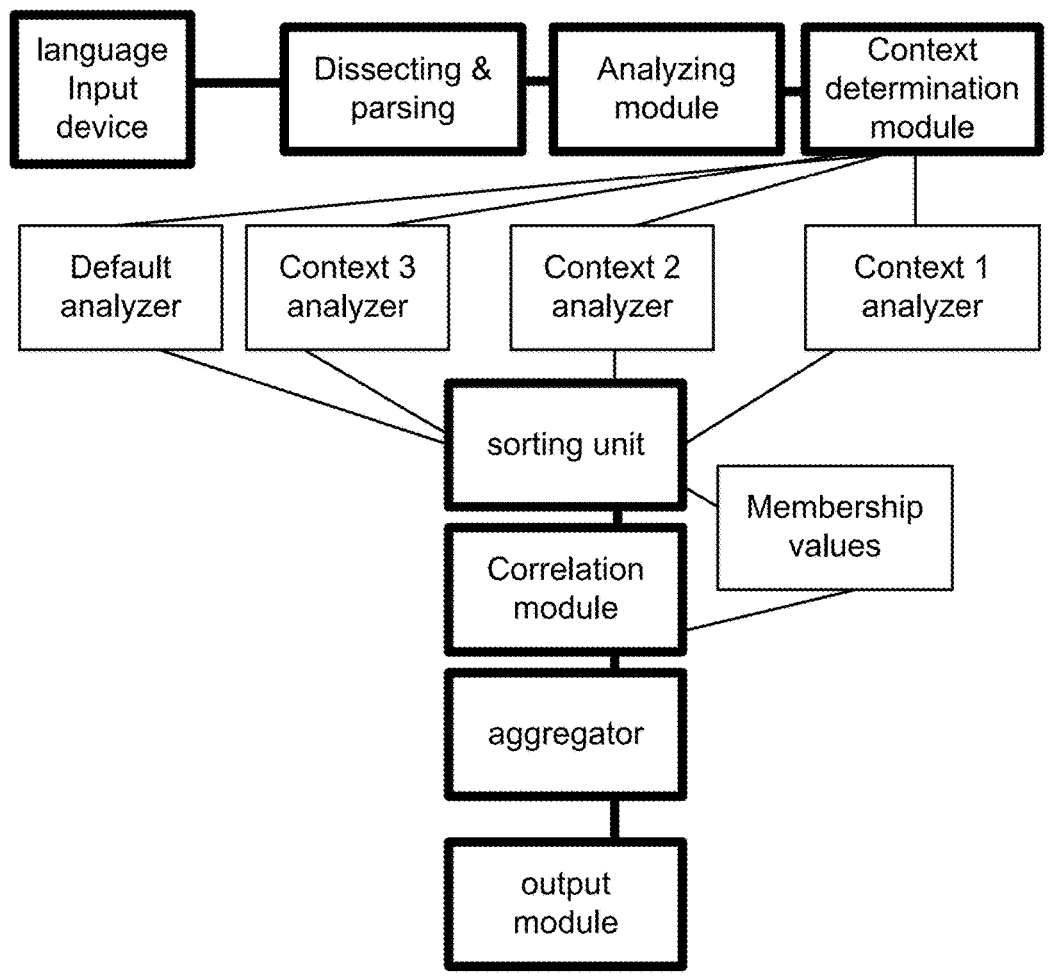

FIG. 127 shows one embodiment for context analyzer system.

Figure 128:
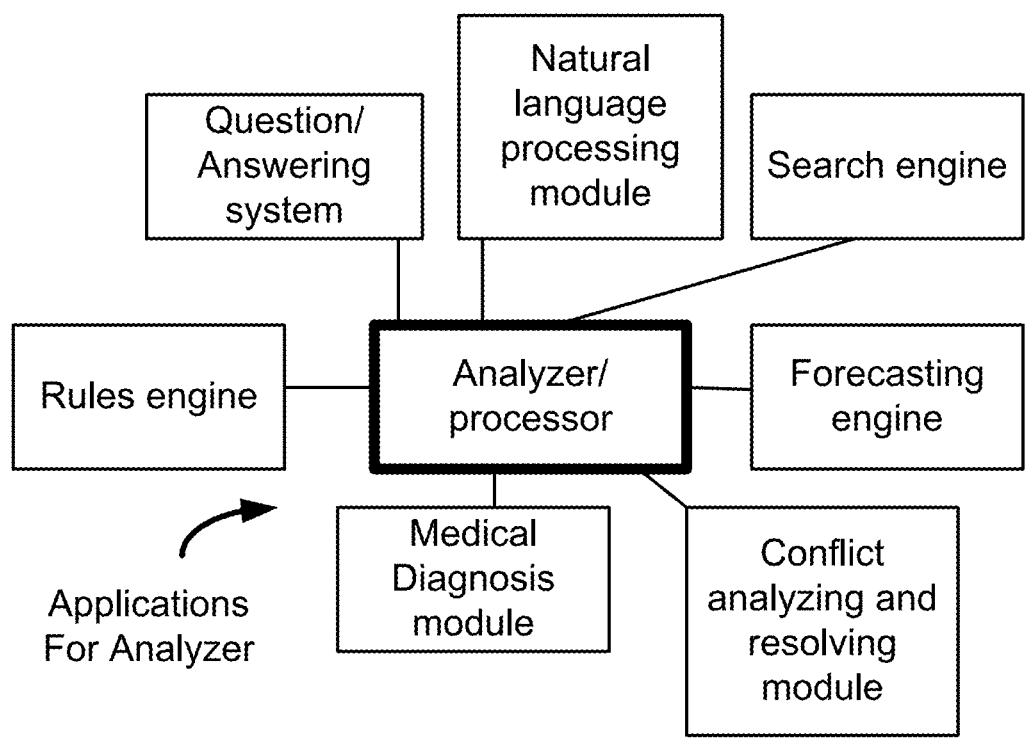

FIG. 128 shows one embodiment for analyzer system, with multiple applications.

Figure 129:
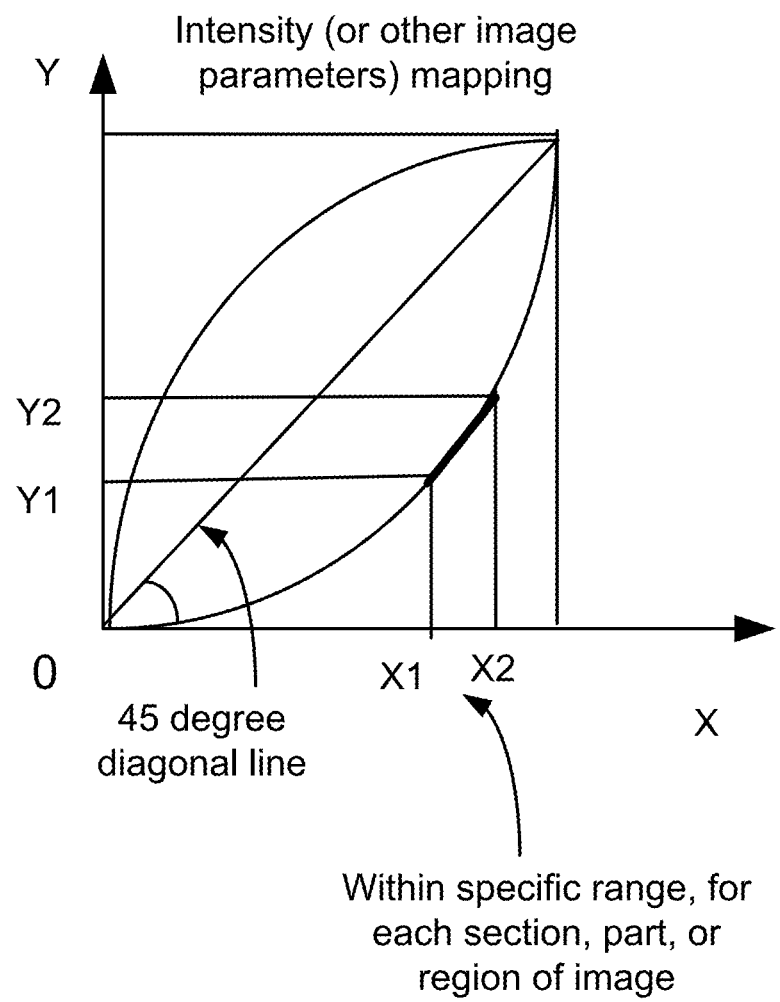

FIG. 129 shows one embodiment for intensity correction, editing, or mapping.

Figure 130:
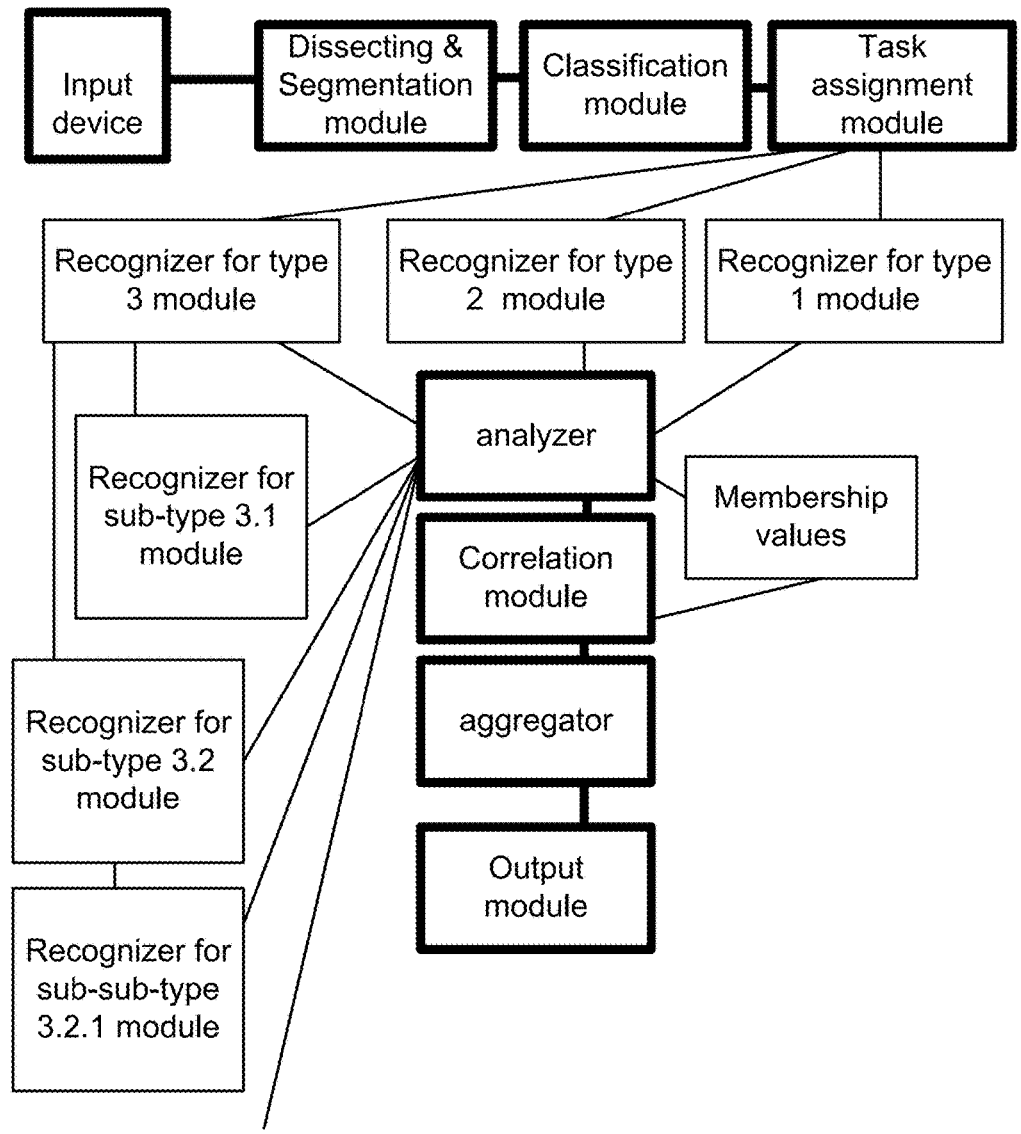

FIG. 130 shows one embodiment for multiple recognizers.

Figure 131:
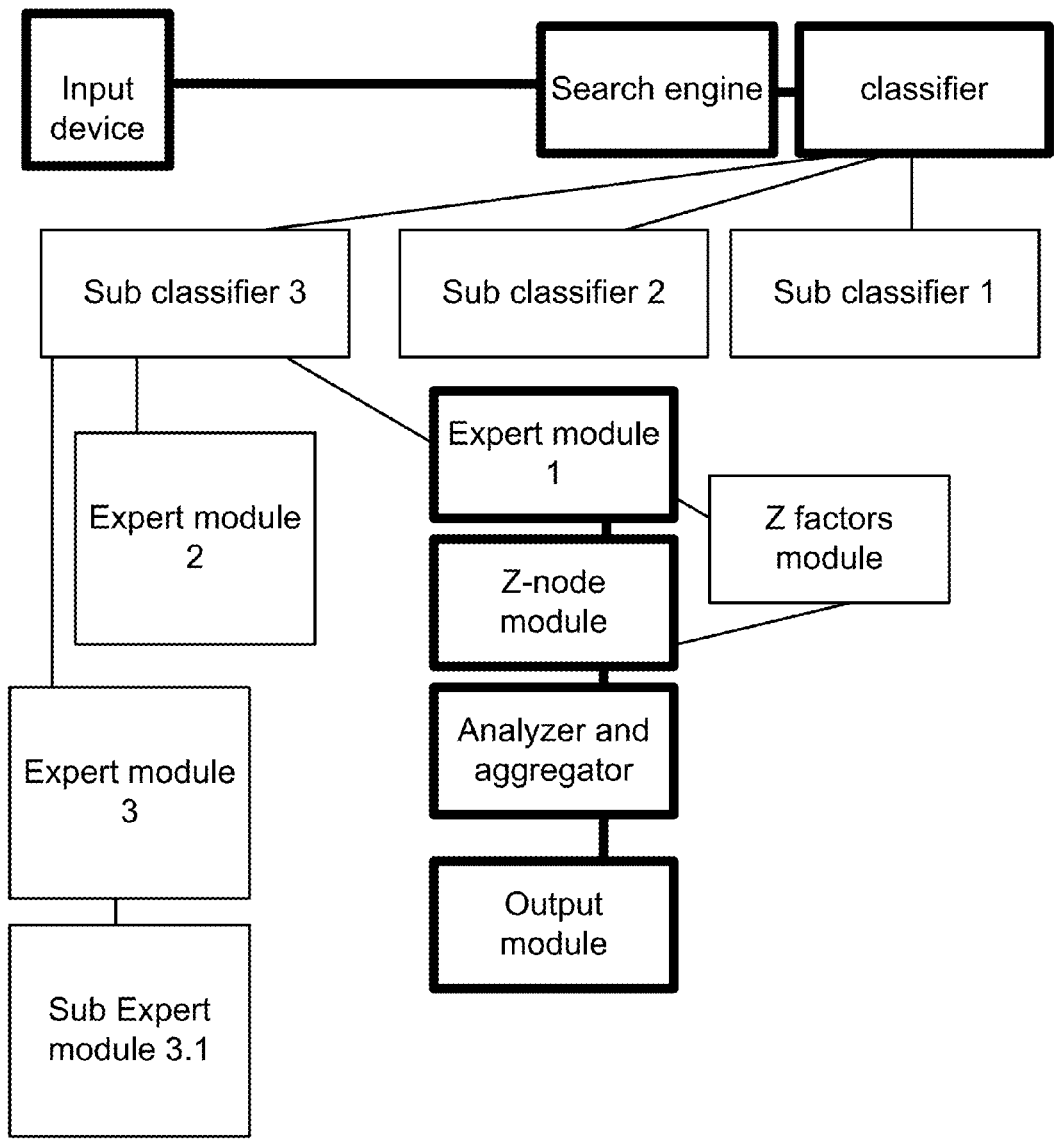

FIG. 131 shows one embodiment for multiple sub-classifiers and experts.

Figure 132:
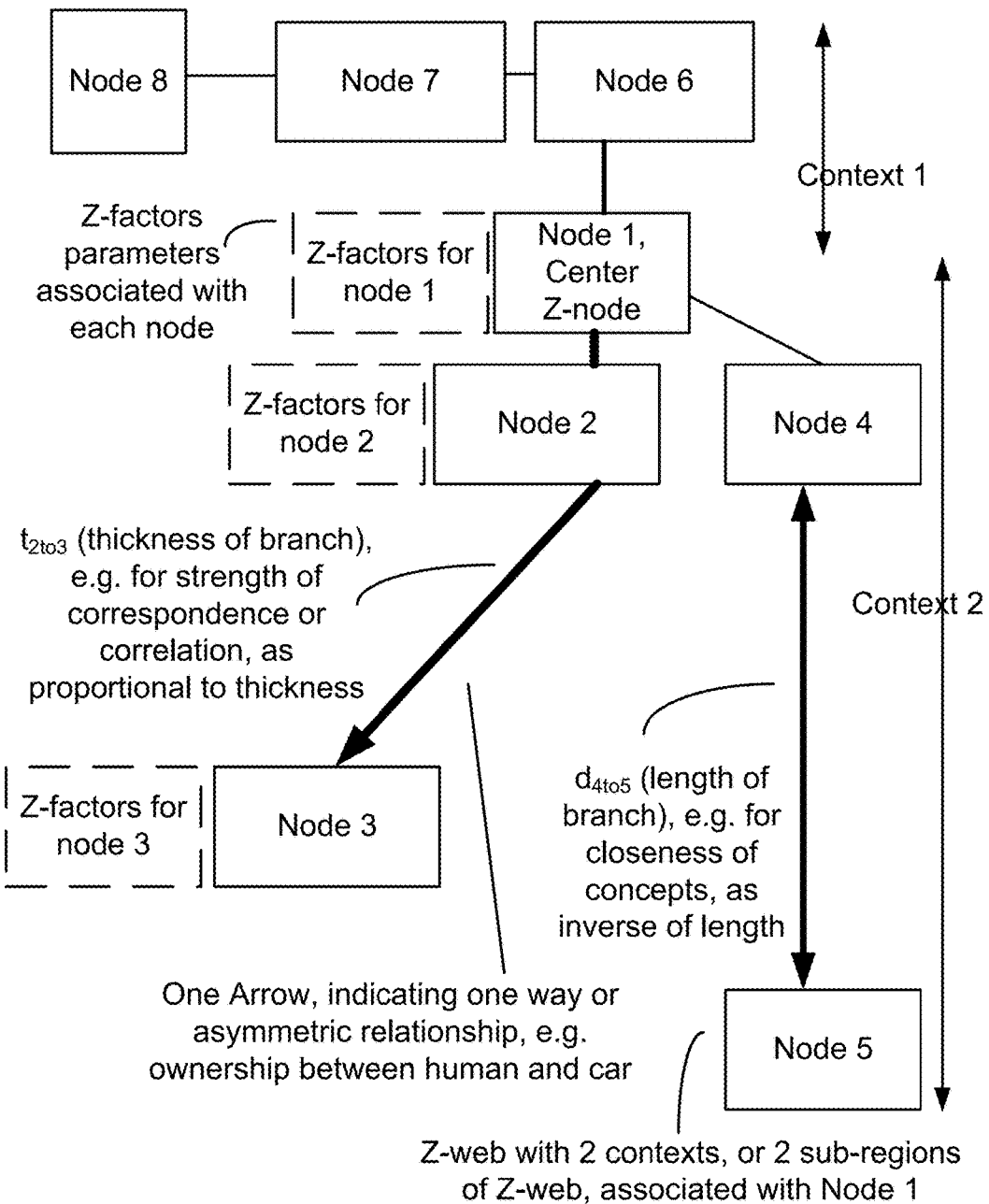

FIG. 132 shows one embodiment for Z-web, its components, and multiple contexts associated with it.

Figure 133:
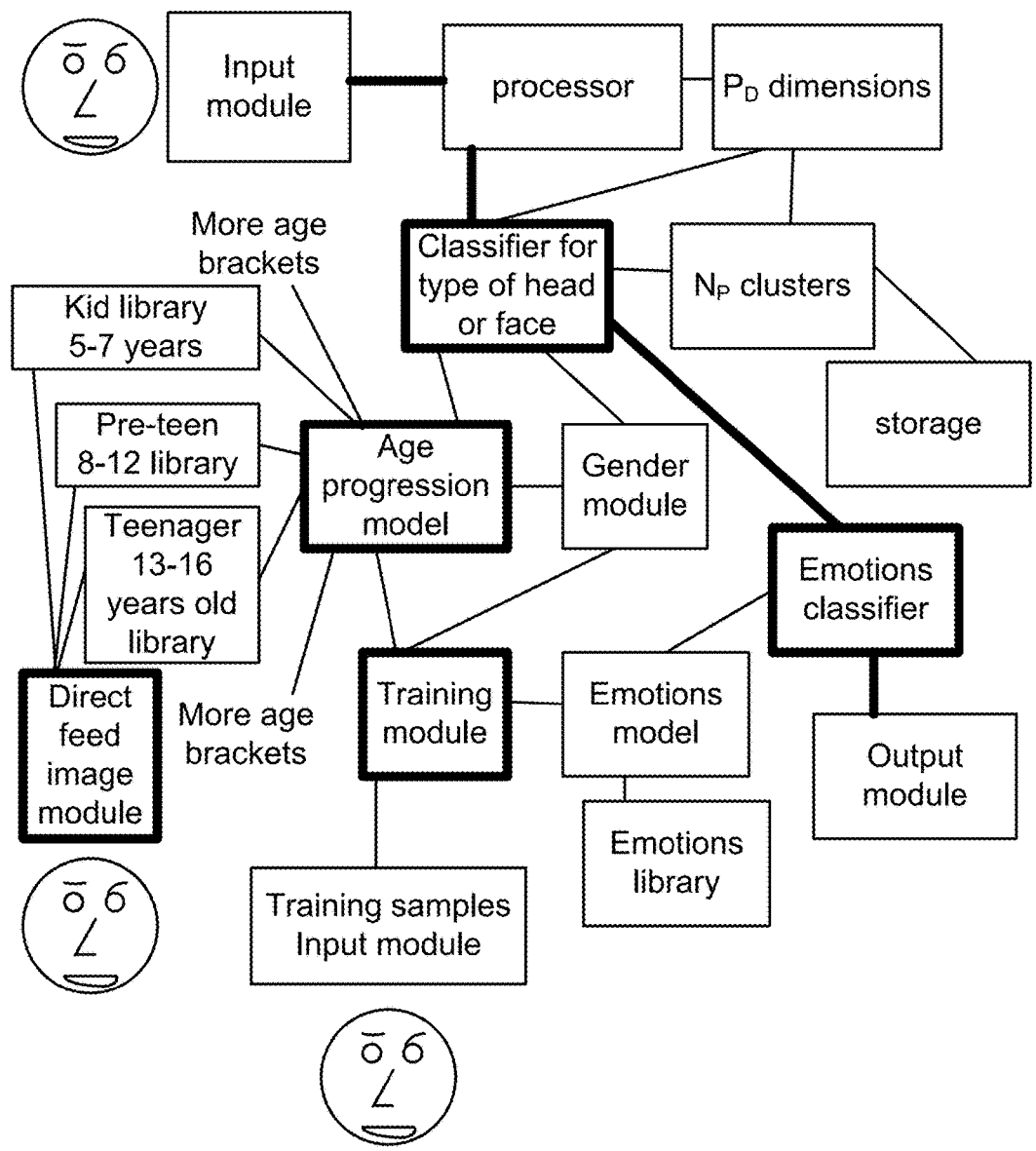

FIG. 133 shows one embodiment for classifier for head, face, and emotions.

Figure 134:
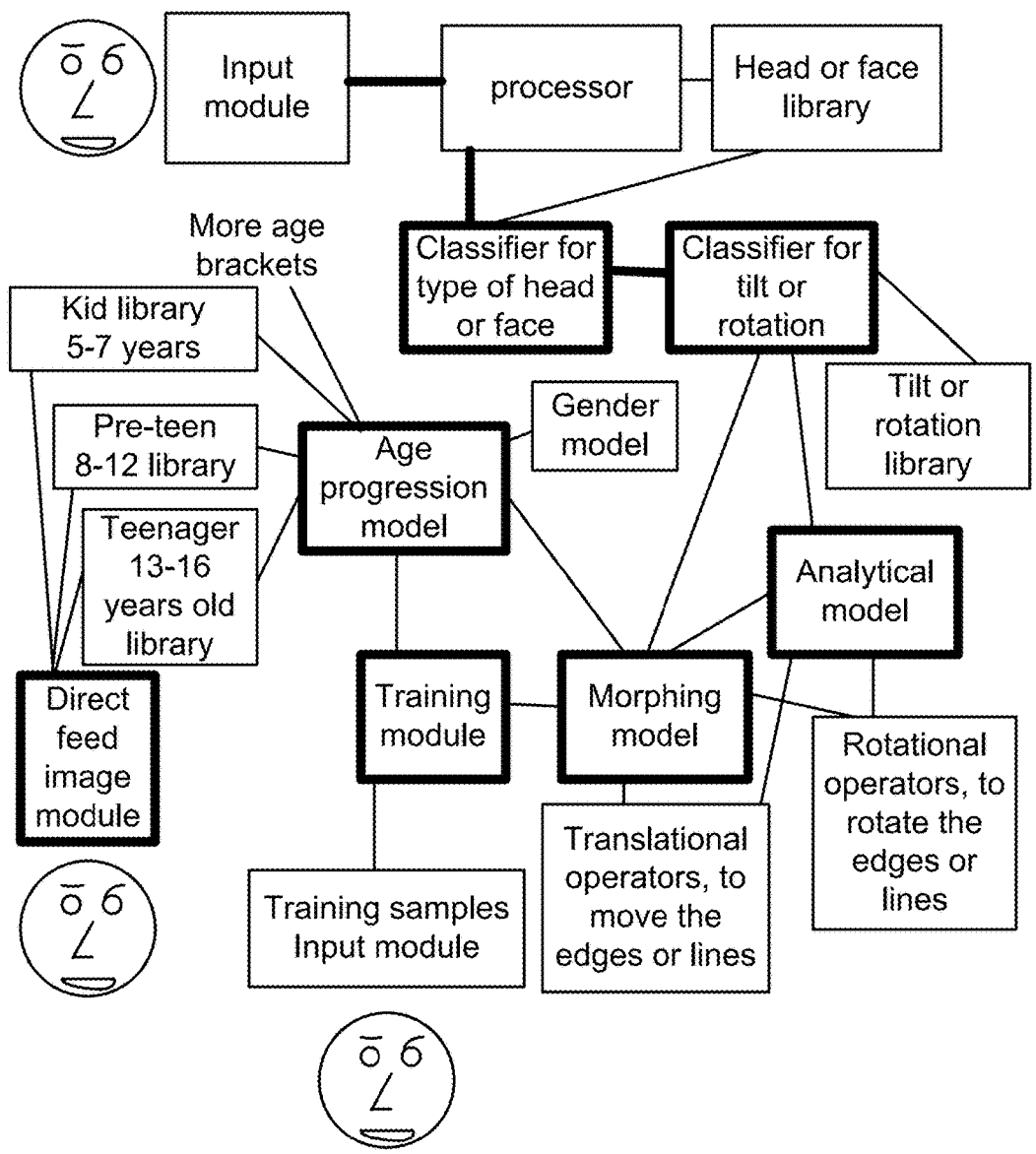

FIG. 134 shows one embodiment for classifier for head or face, with age and rotation parameters.

Figure 135:
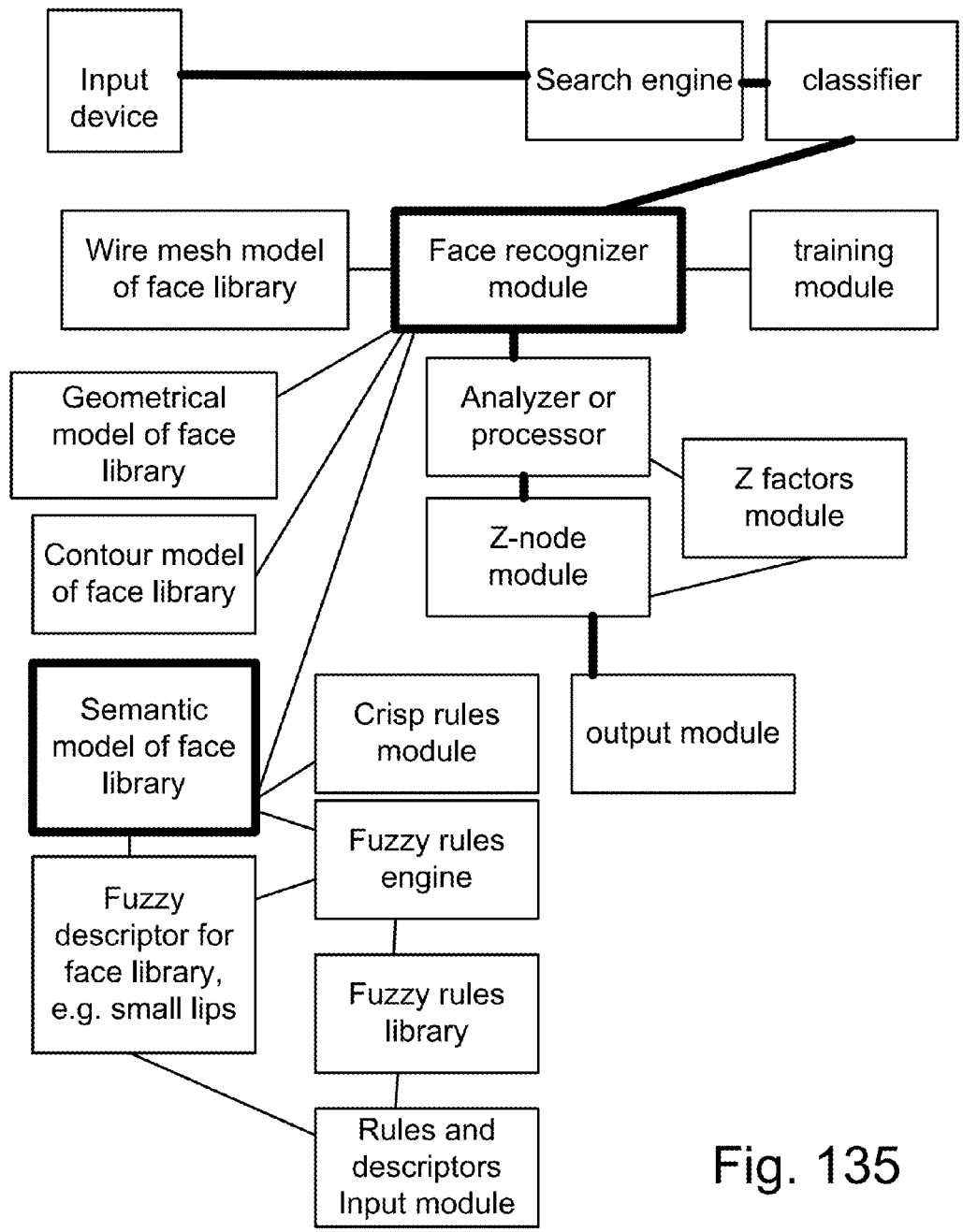

FIG. 135 shows one embodiment for face recognizer.

Figure 136:
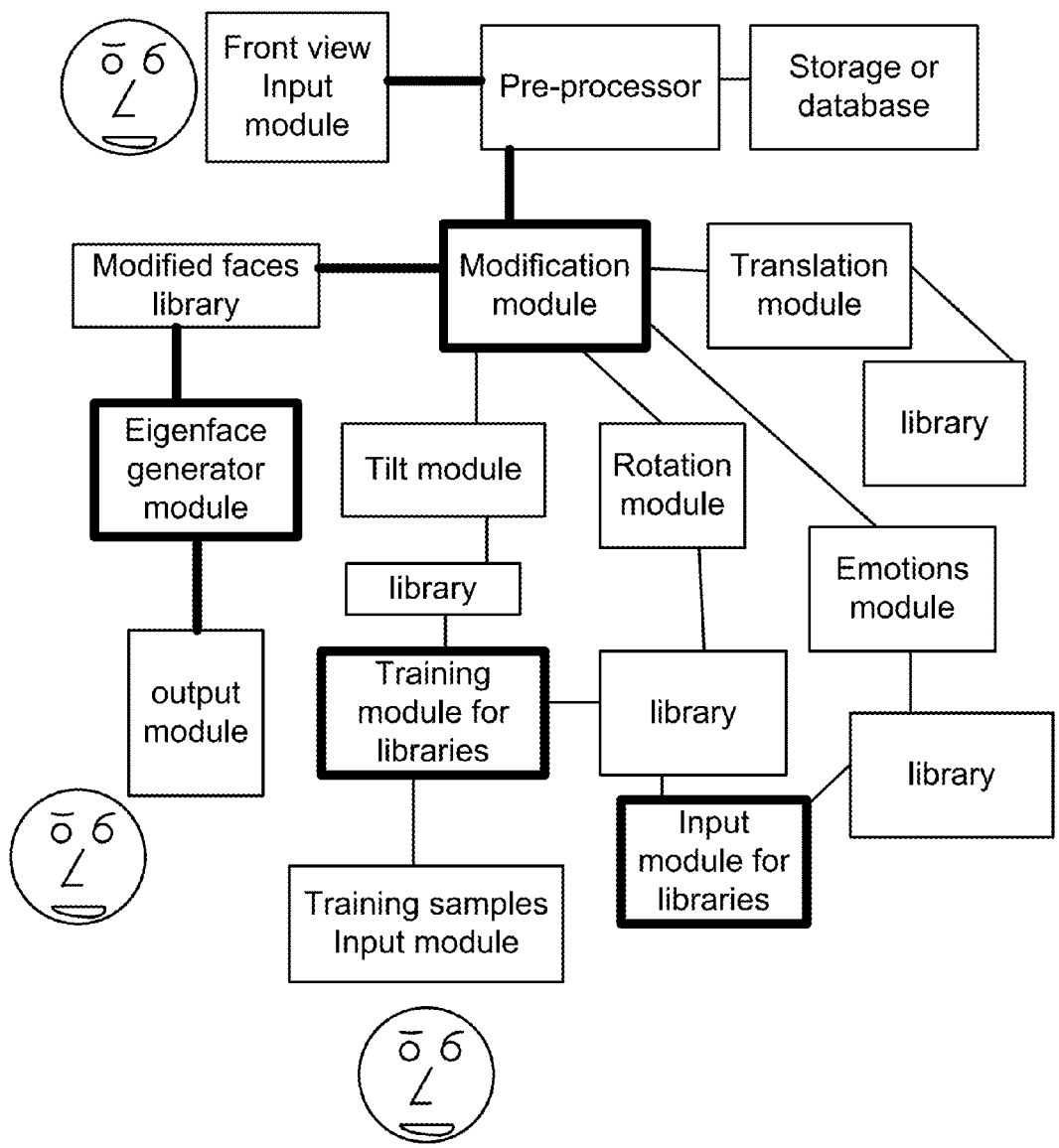

FIG. 136 shows one embodiment for modification module for faces and eigenface generator module.

Figure 137:
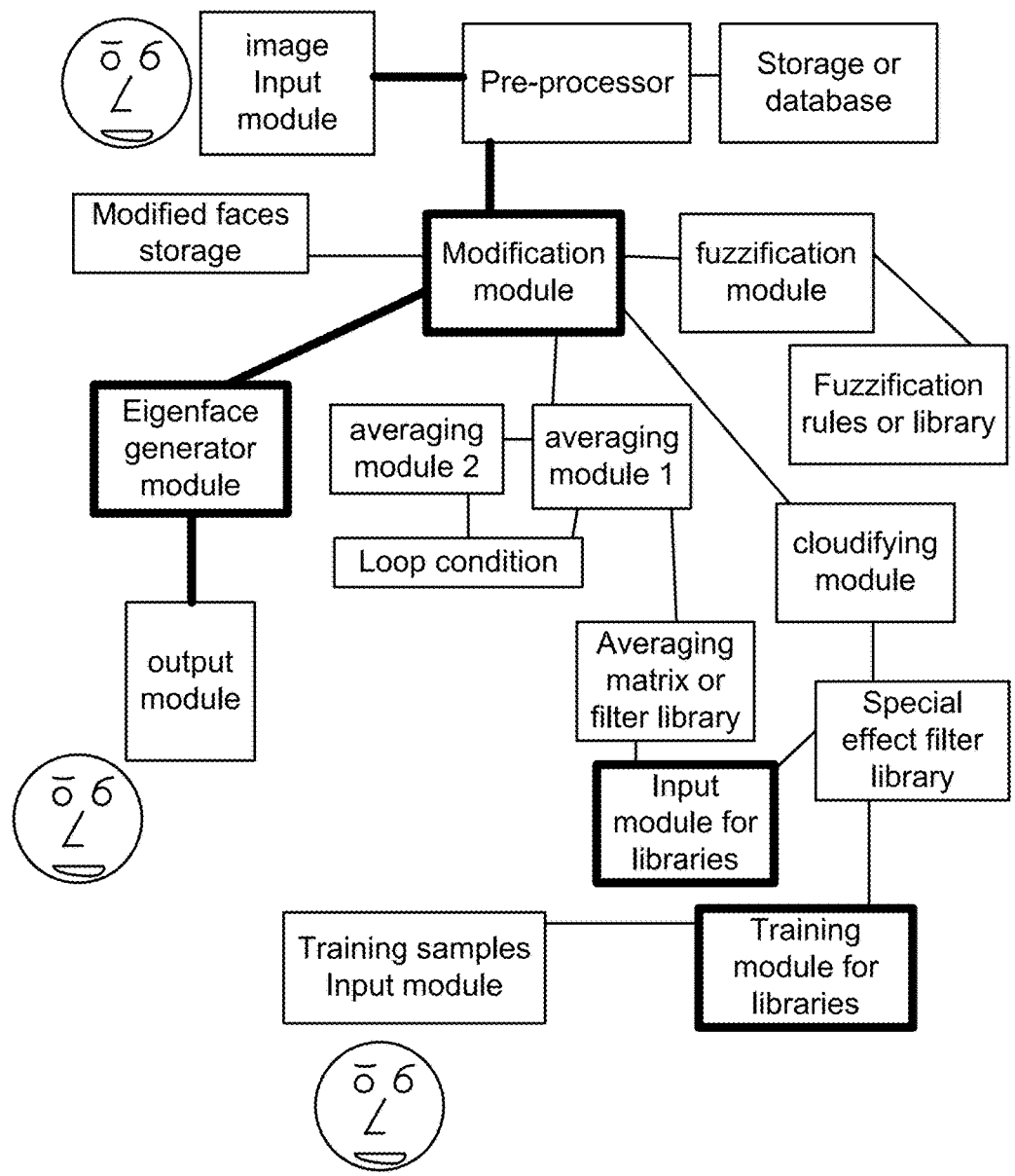

FIG. 137 shows one embodiment for modification module for faces and eigenface generator module.

Figure 138:
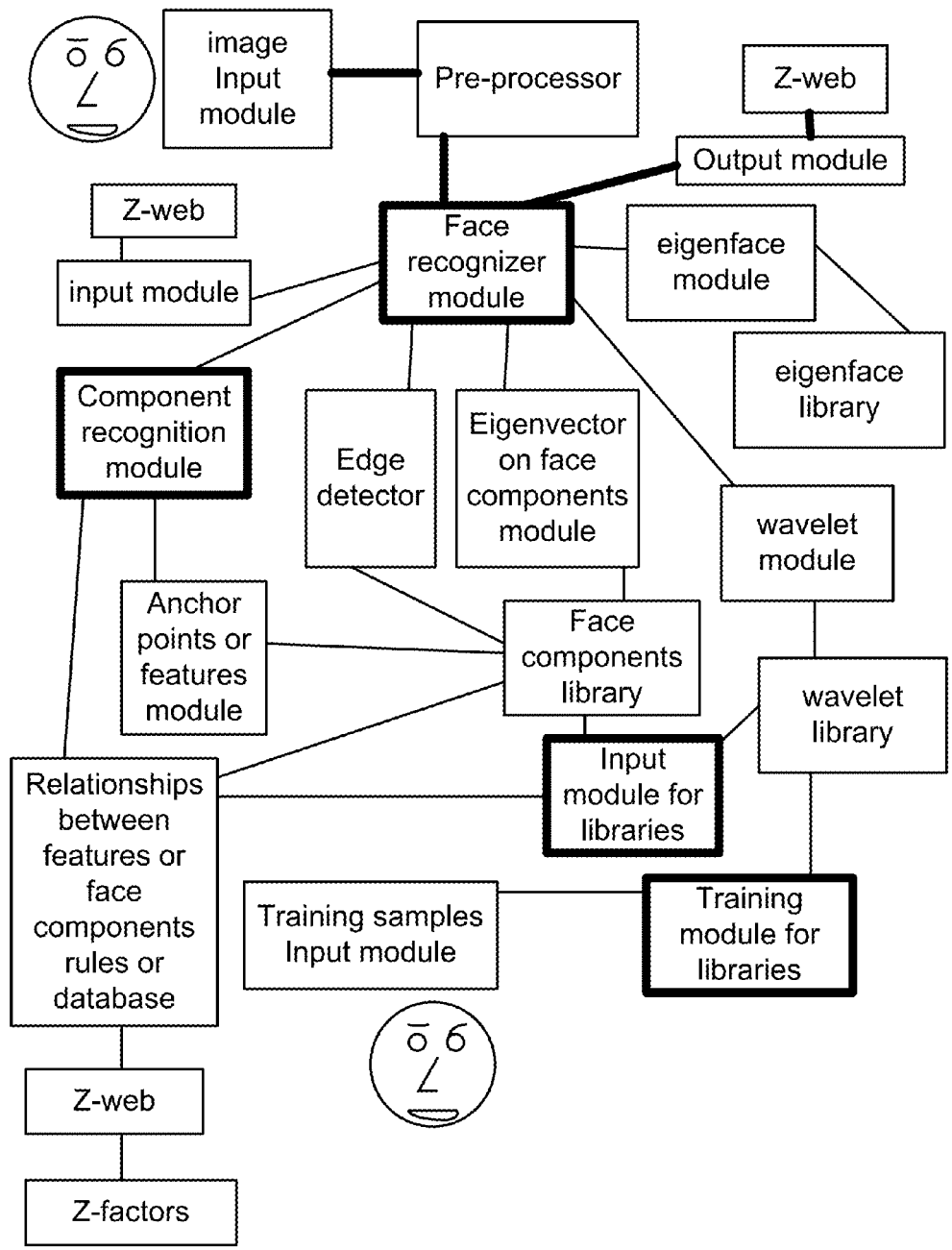

FIG. 138 shows one embodiment for face recognizer.

Figure 139:
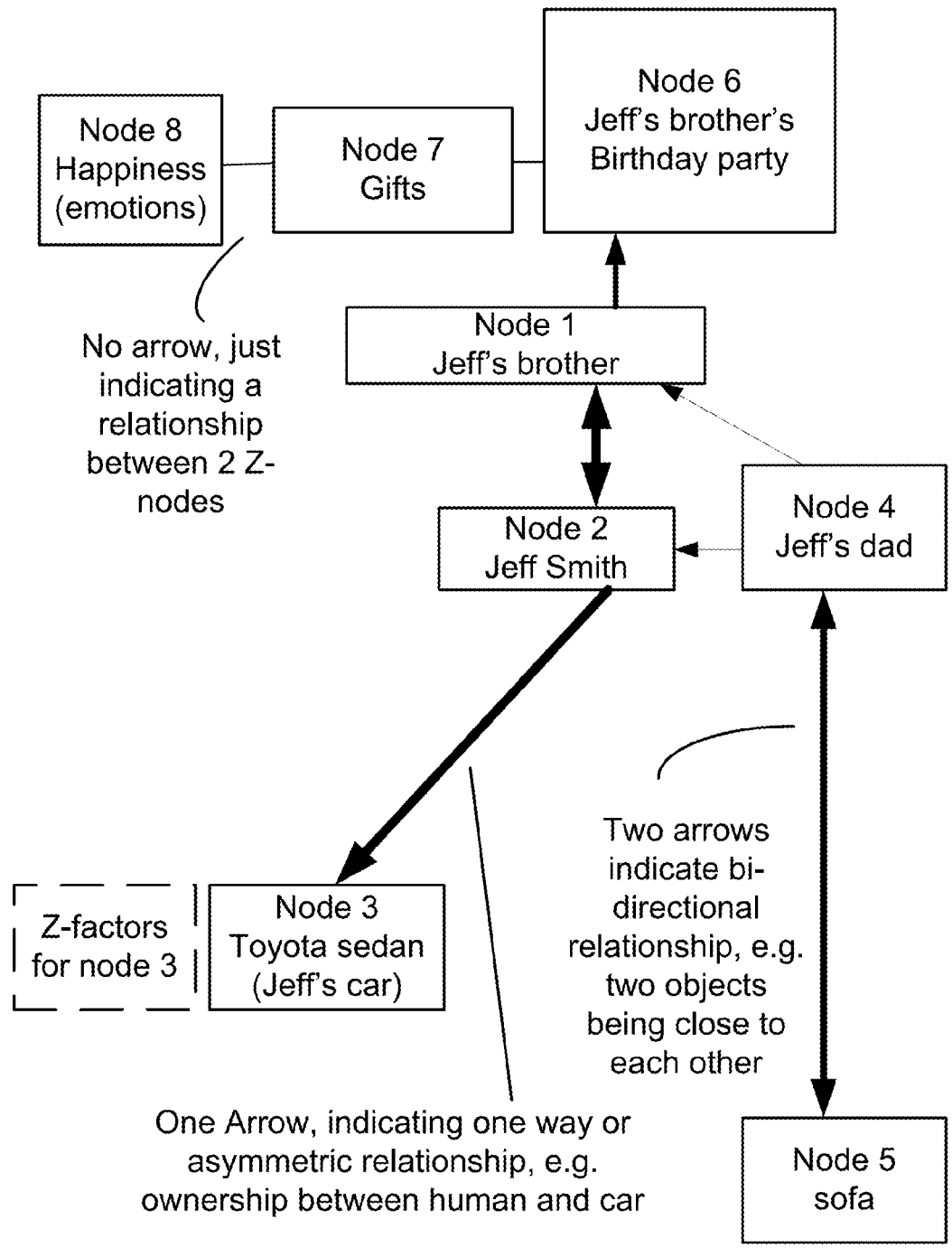

FIG. 139 shows one embodiment for Z-web.

Figure 140:
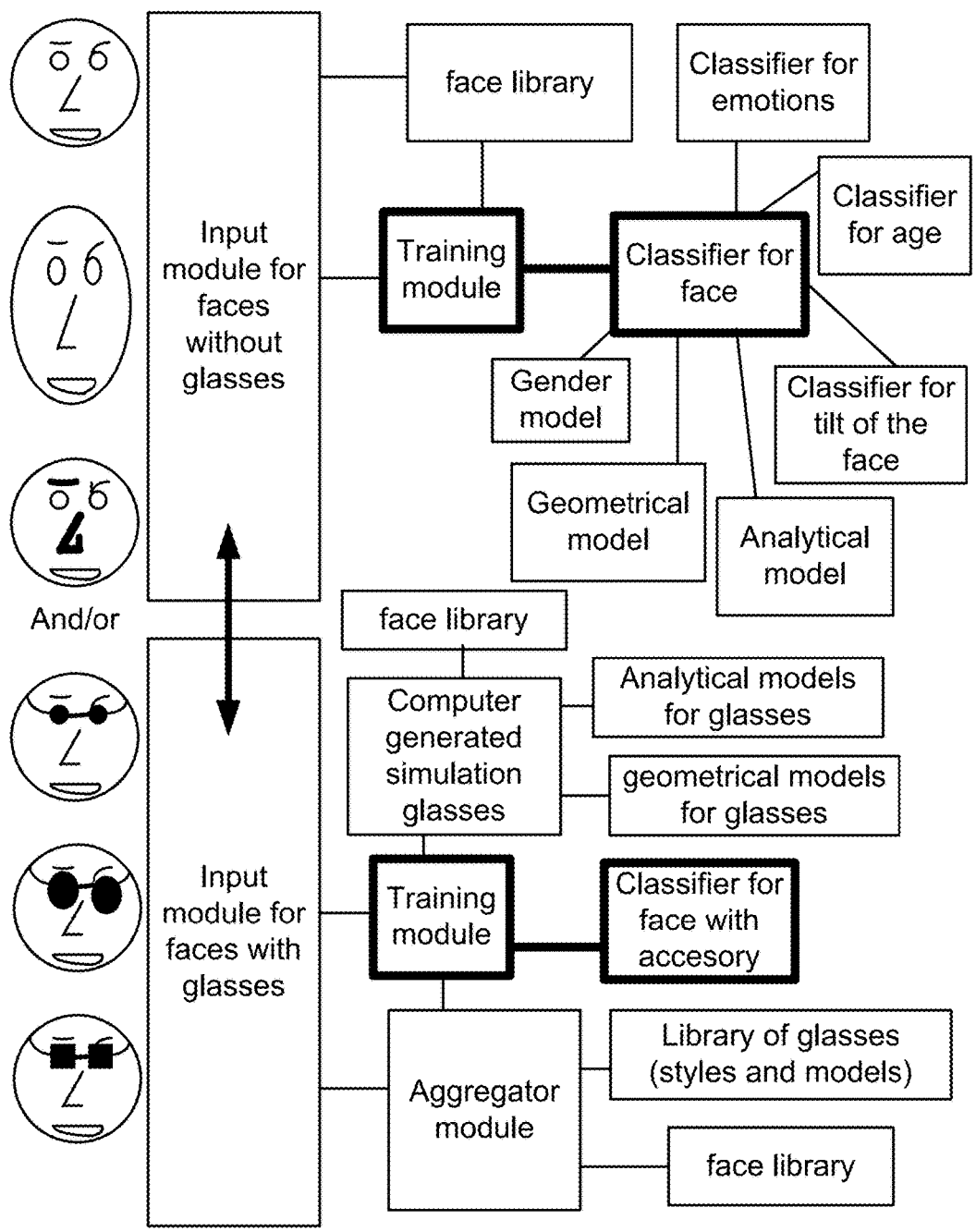

FIG. 140 shows one embodiment for classifier for accessories.

Figure 141:
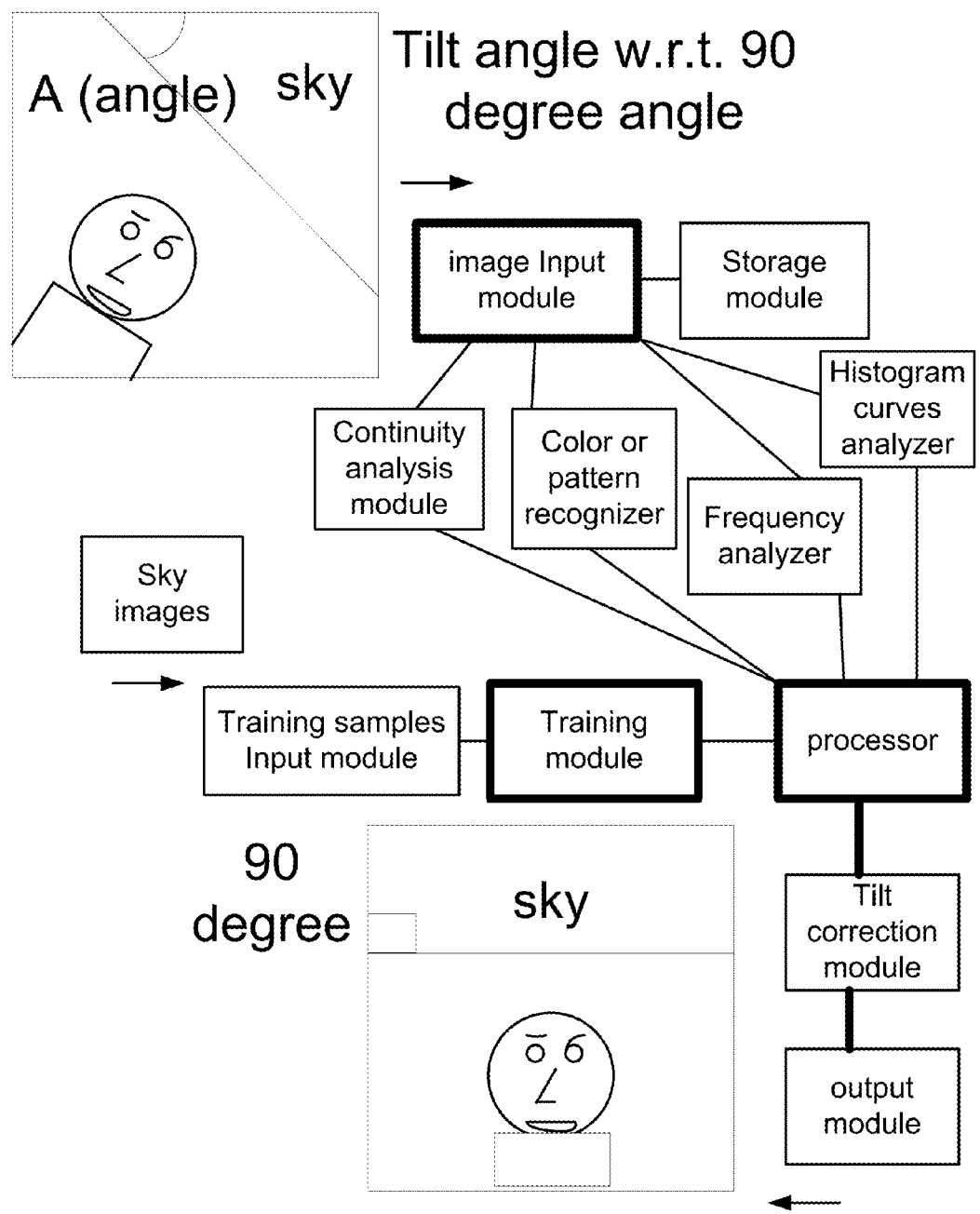

FIG. 141 shows one embodiment for tilt correction.

Figure 142:
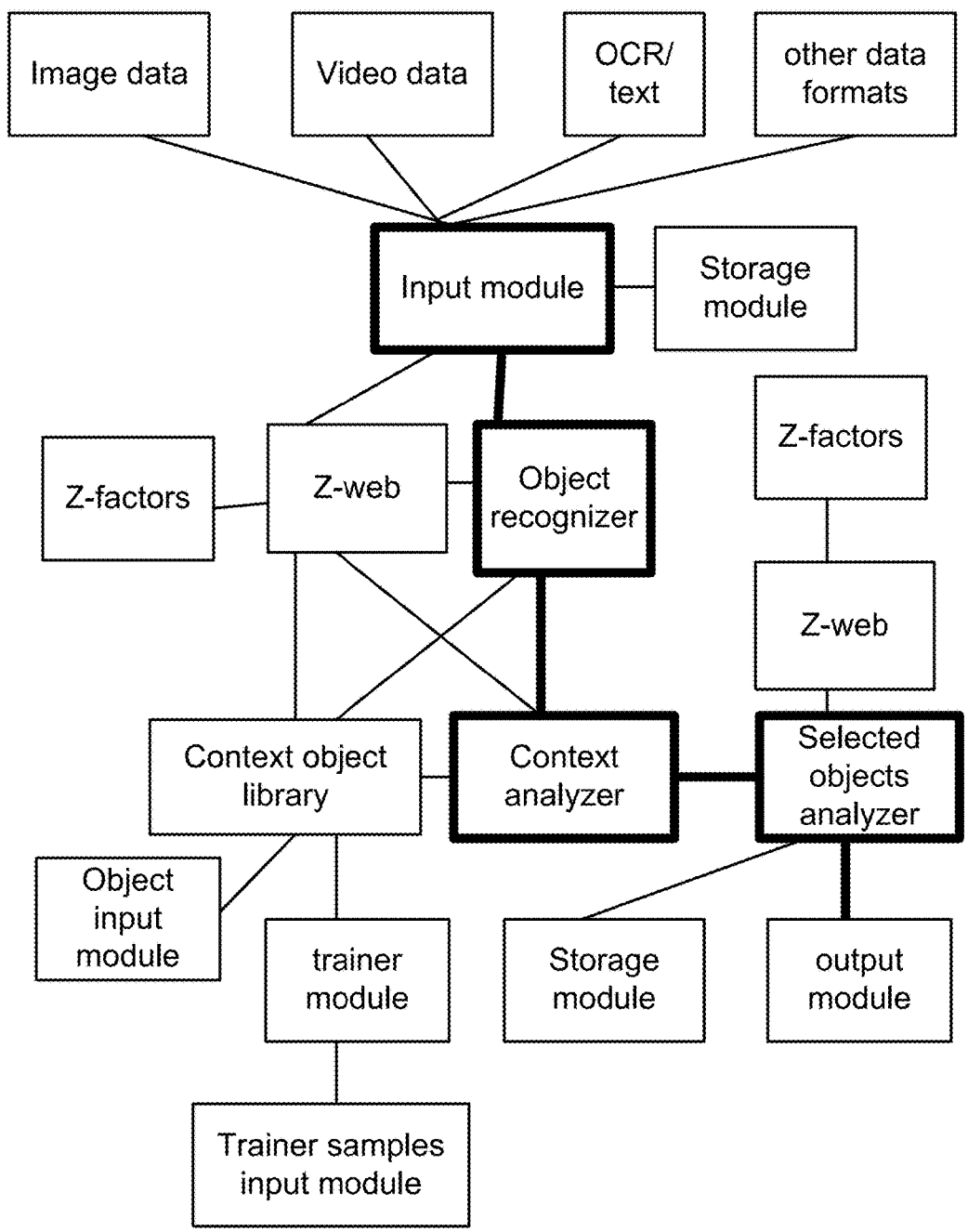

FIG. 142 shows one embodiment for context analyzer.

Figure 143:
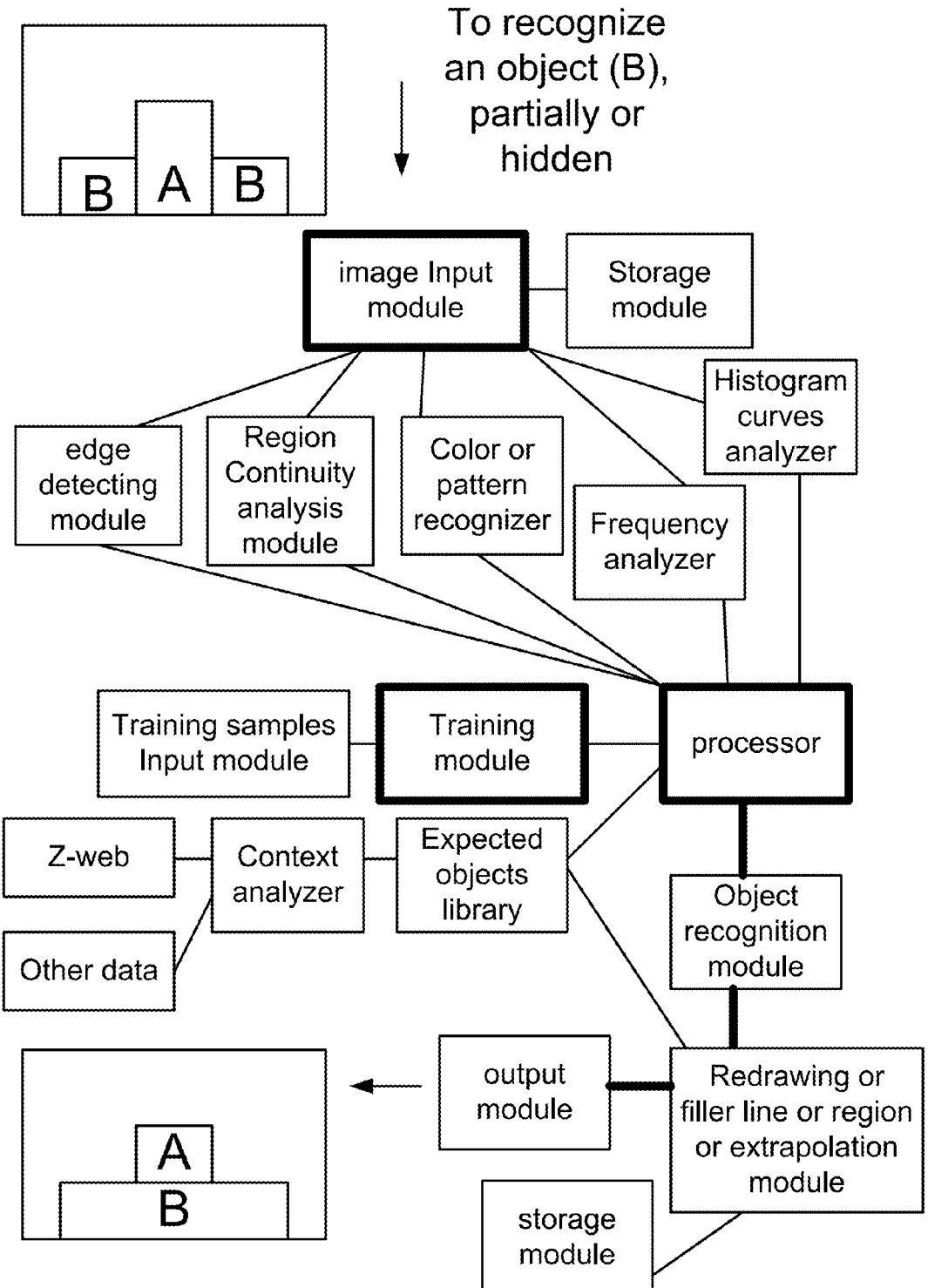

FIG. 143 shows one embodiment for recognizer for partially hidden objects.

Figure 144:
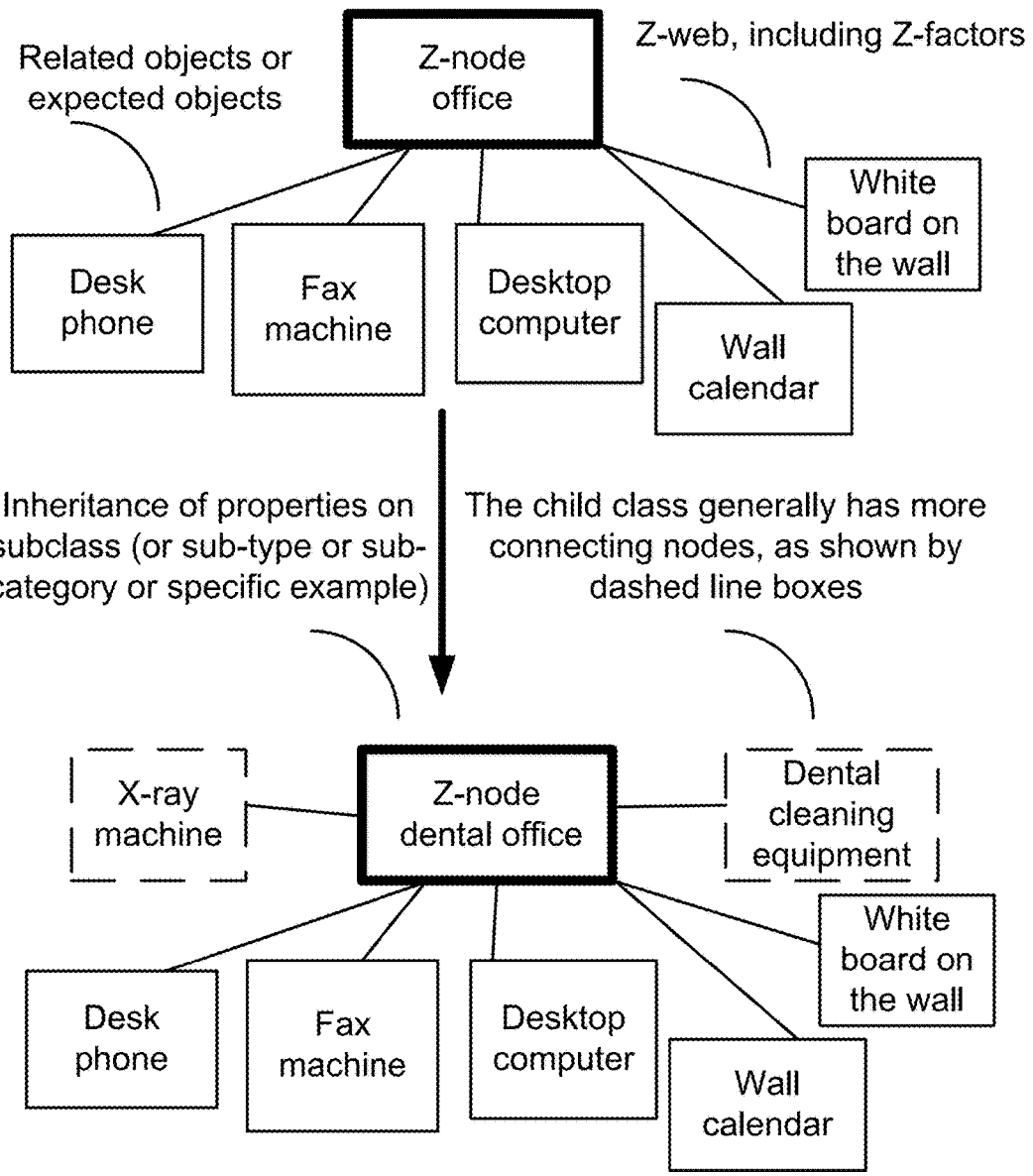

FIG. 144 shows one embodiment for Z-web.

Figure 145:
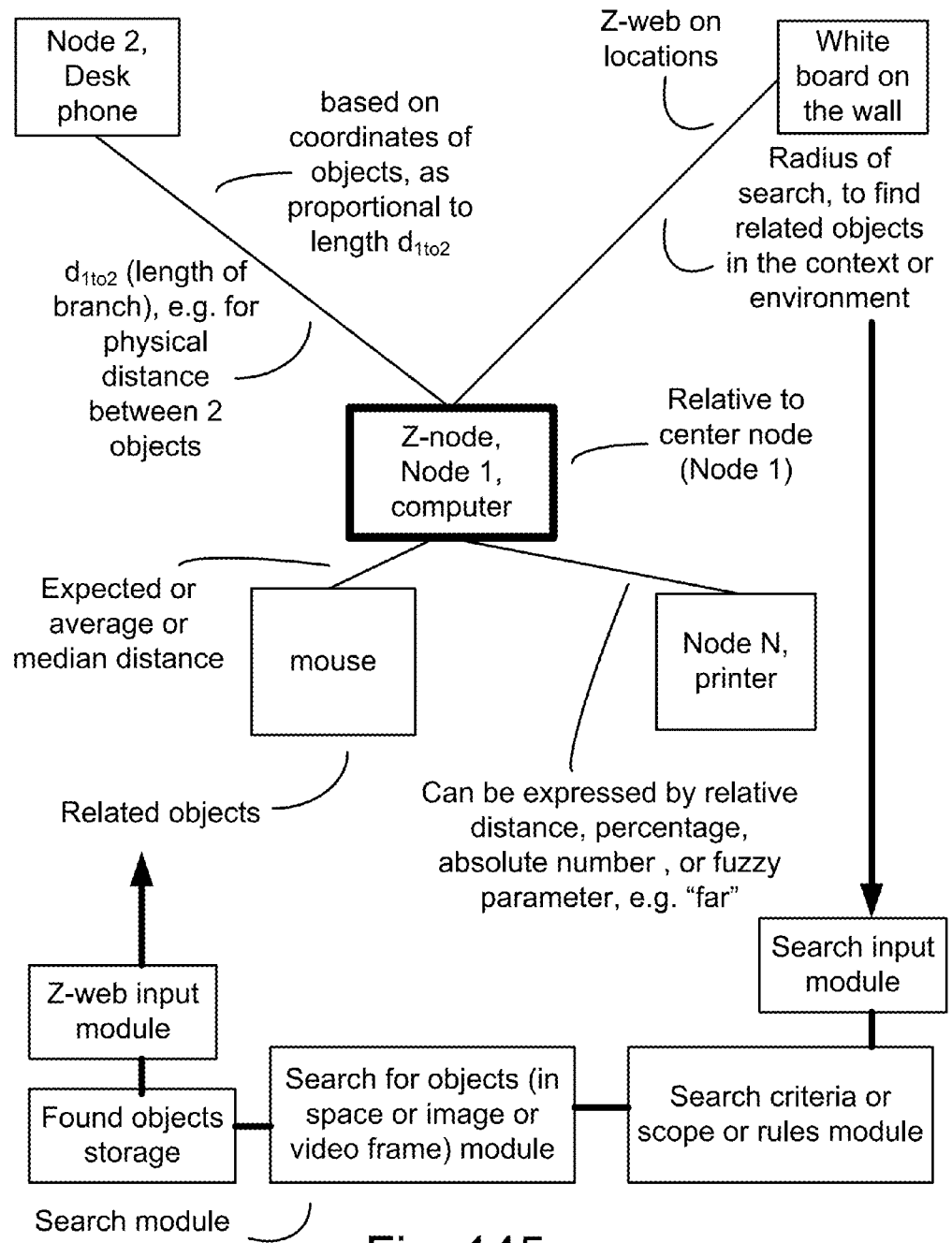

FIG. 145 shows one embodiment for Z-web.

Figure 146:
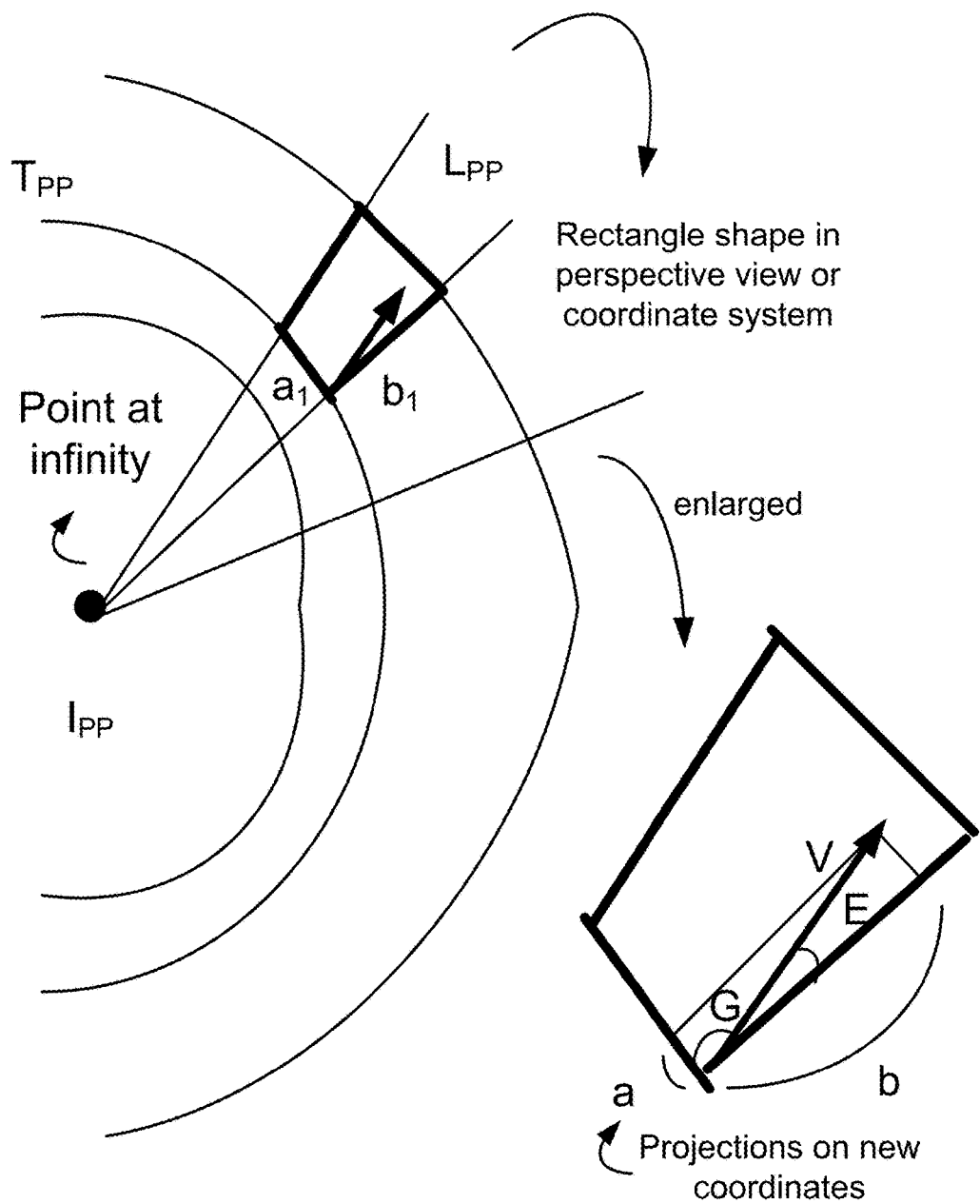

FIG. 146 shows one embodiment for perspective analysis.

Figure 147:
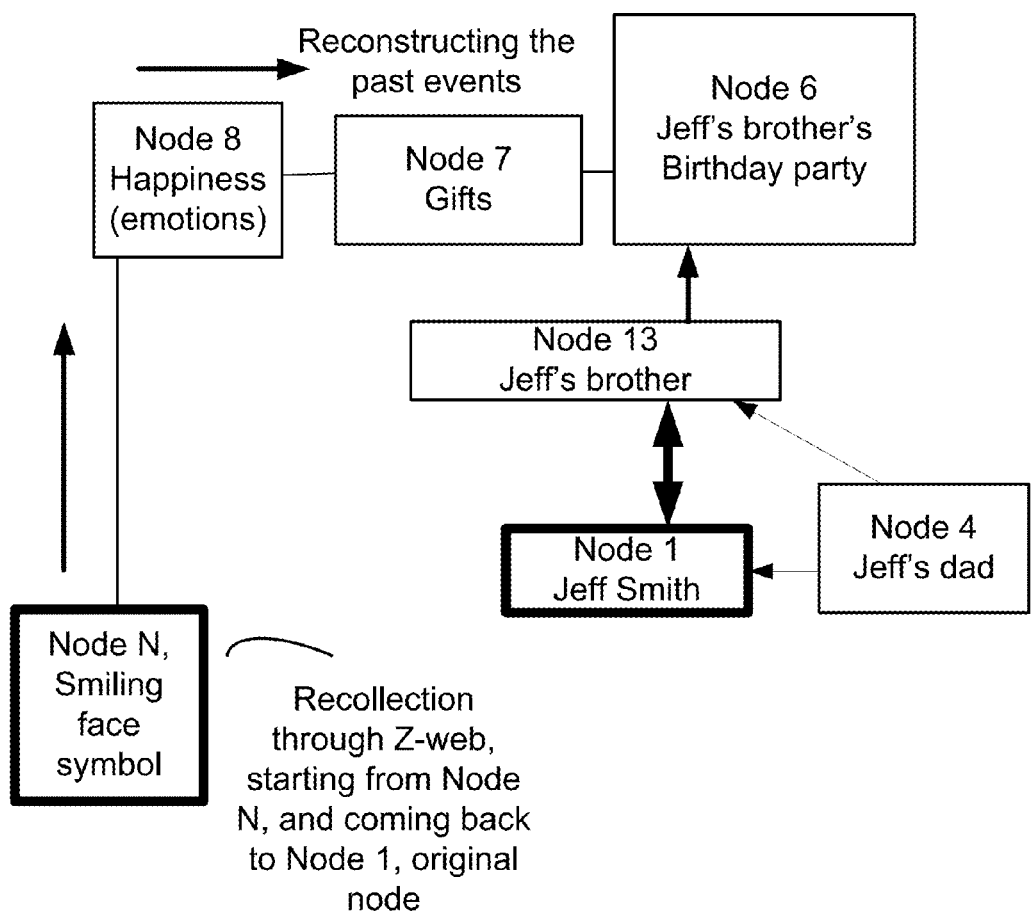

FIG. 147 shows one embodiment for Z-web, for recollection.

Figure 148:
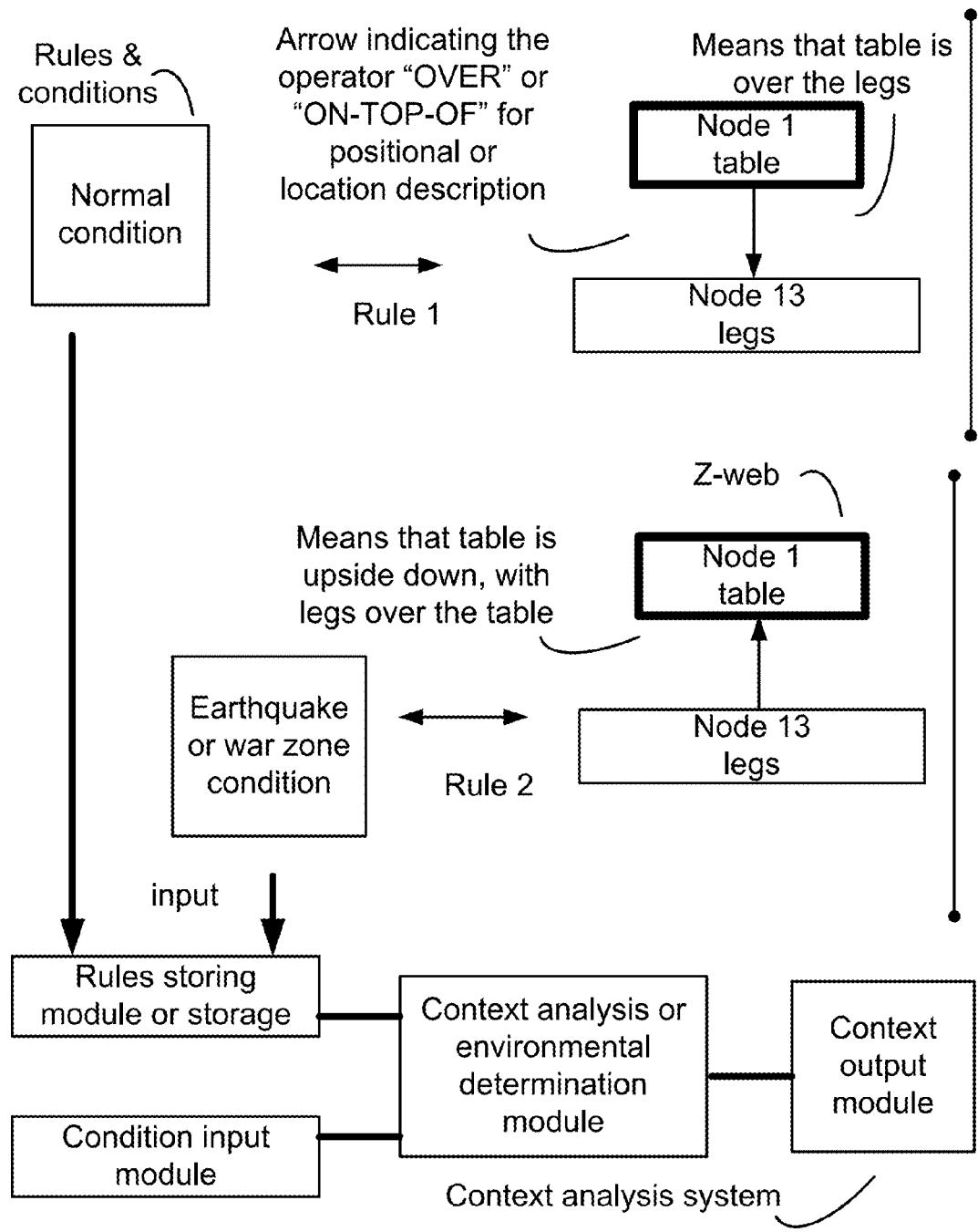

FIG. 148 shows one embodiment for Z-web and context analysis.

Figure 149:
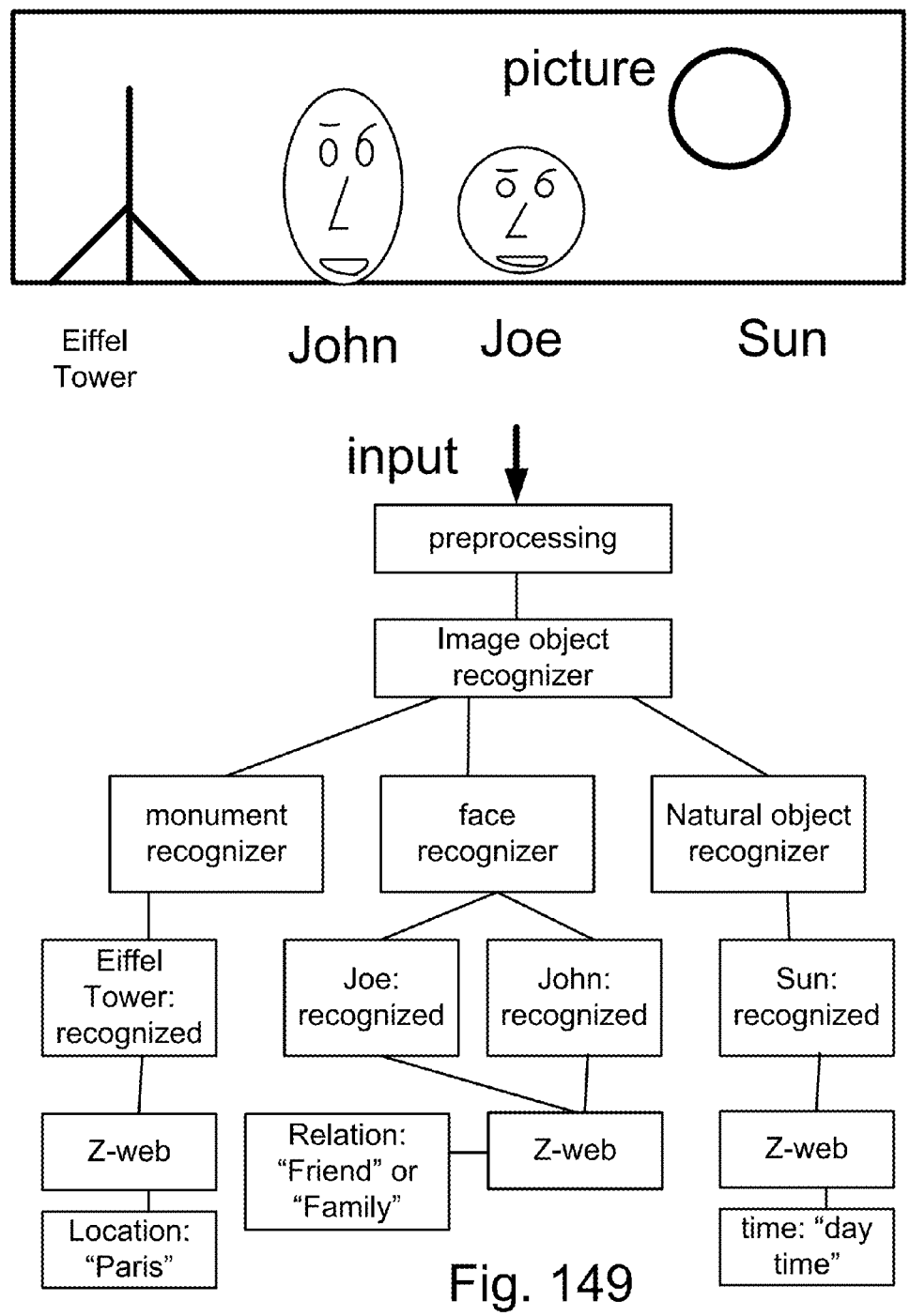

FIG. 149 shows one embodiment for feature and data extraction.

Figure 150:
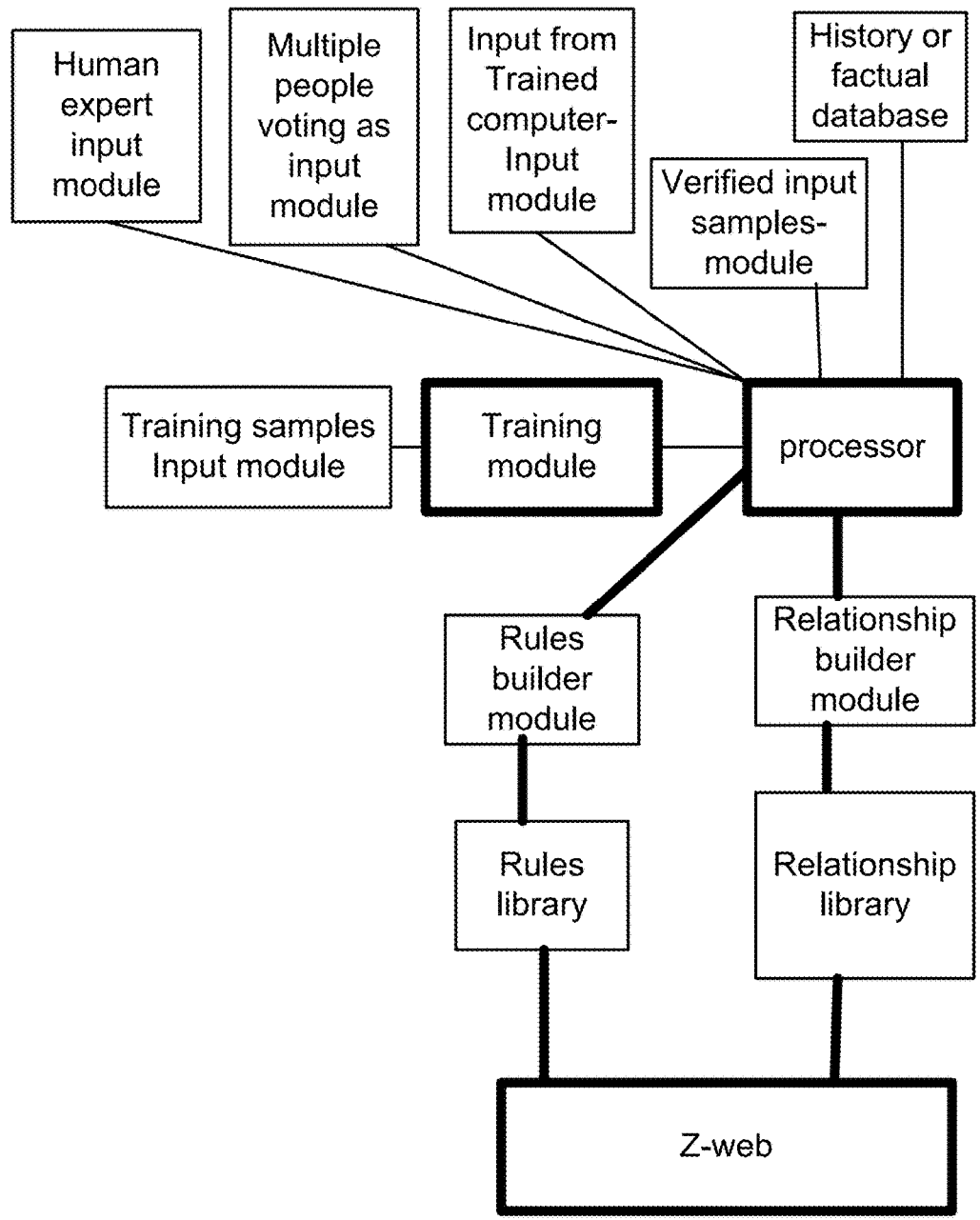

FIG. 150 shows one embodiment for Z-web processing.

Figure 151:
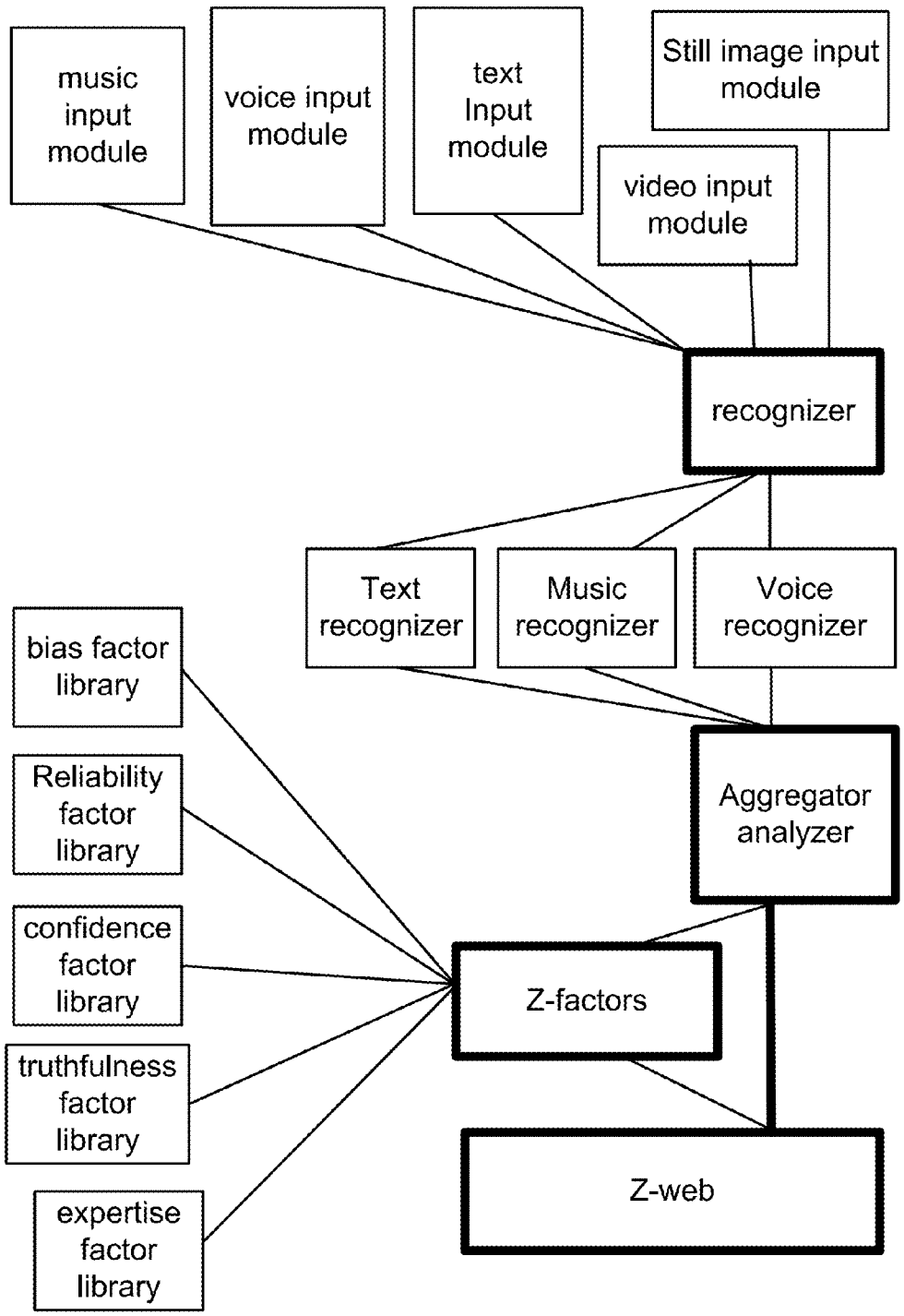

FIG. 151 shows one embodiment for Z-web and Z-factors.

Figure 152:
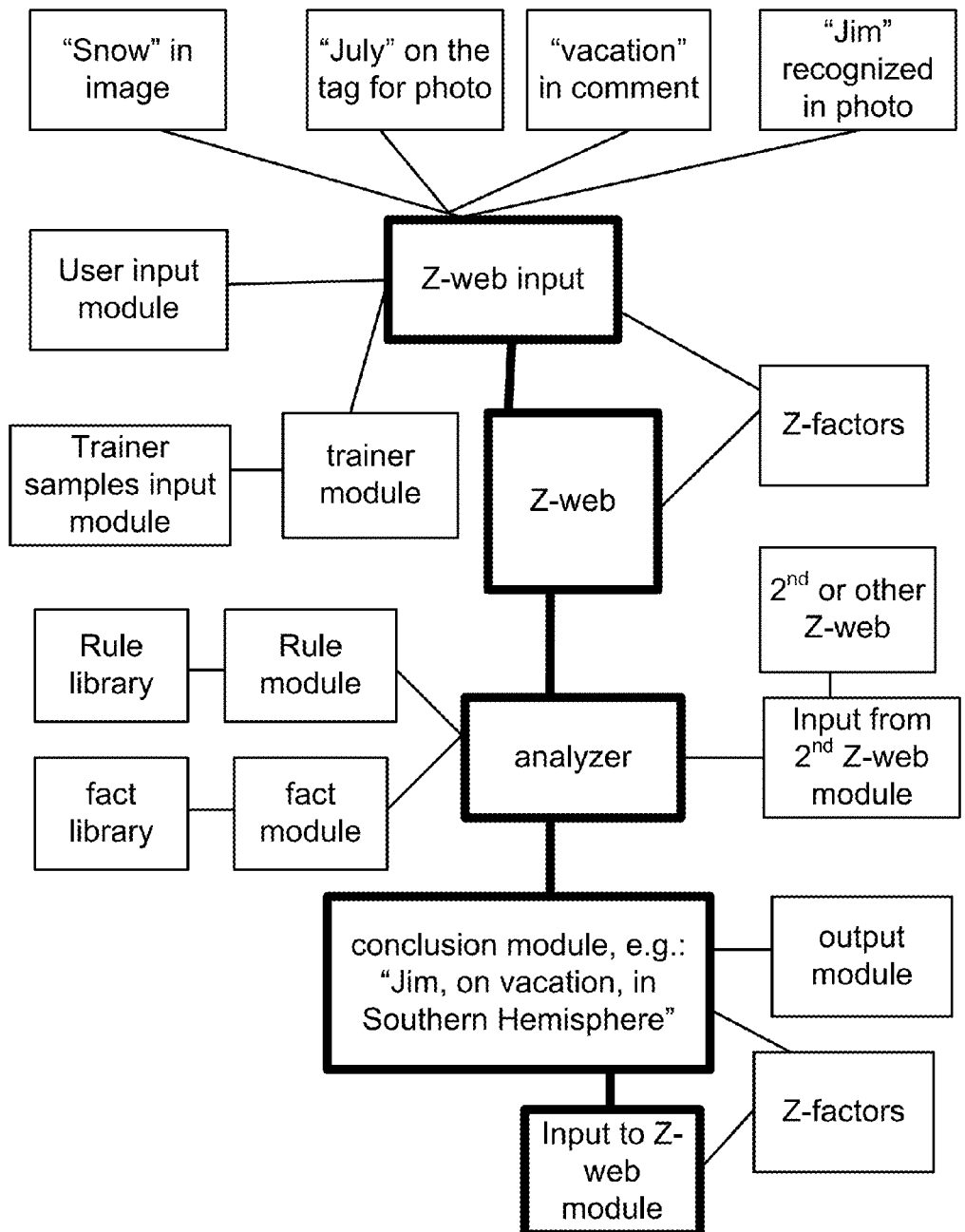

FIG. 152 shows one embodiment for Z-web analysis.

Figure 153:
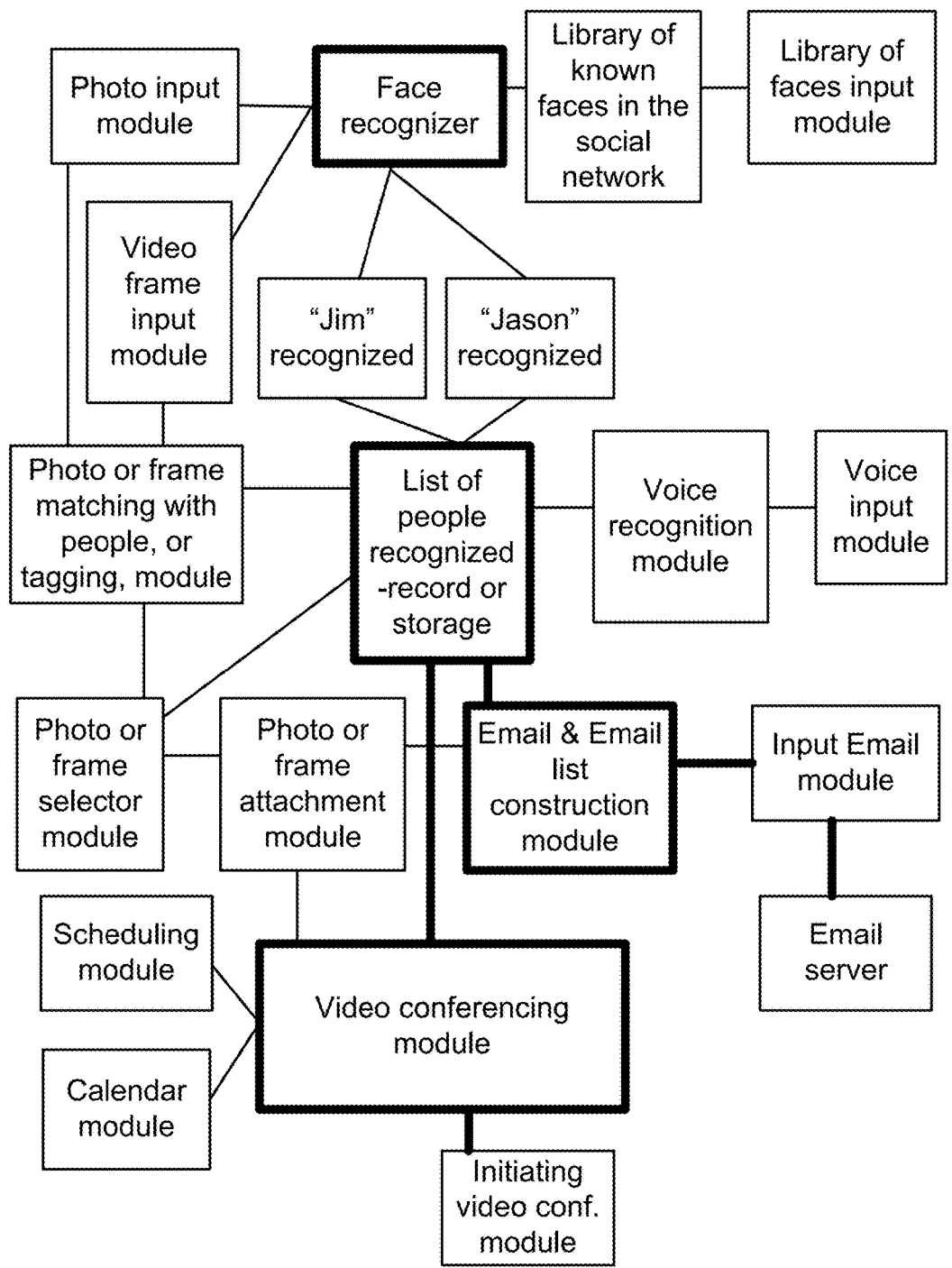

FIG. 153 shows one embodiment for face recognition integrated with email and video conferencing systems.

Figure 154:
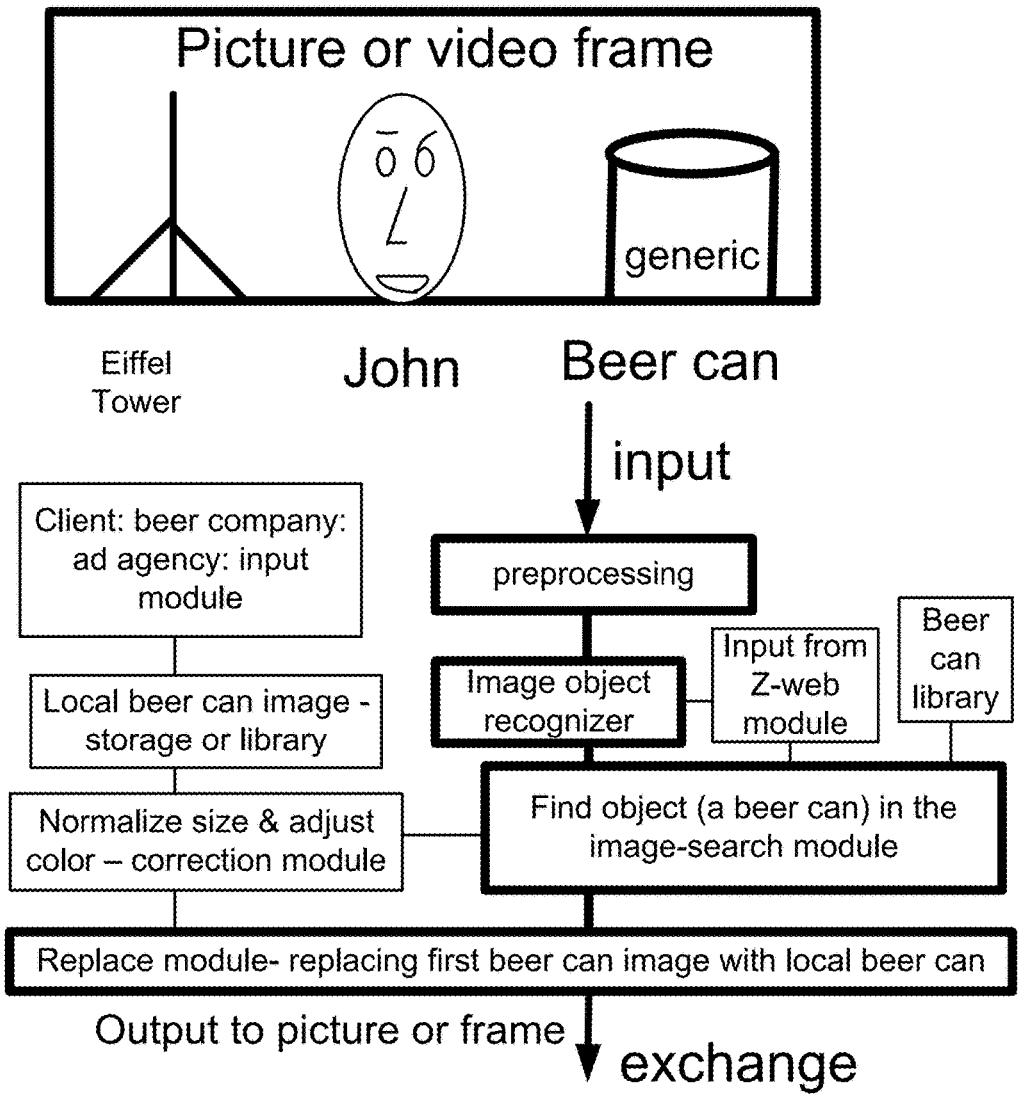
Figure 154:
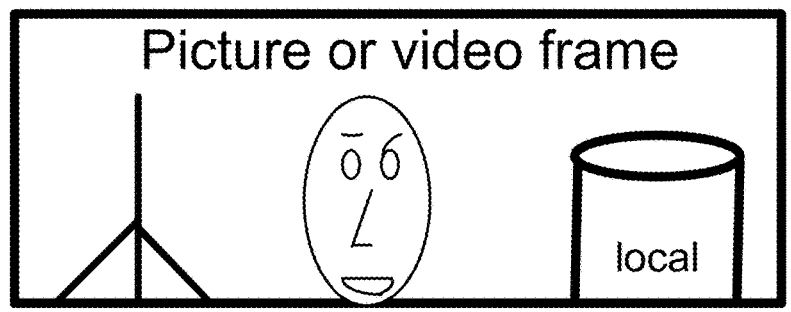

FIG. 154 shows one embodiment for editing image for advertising.

Figure 155:
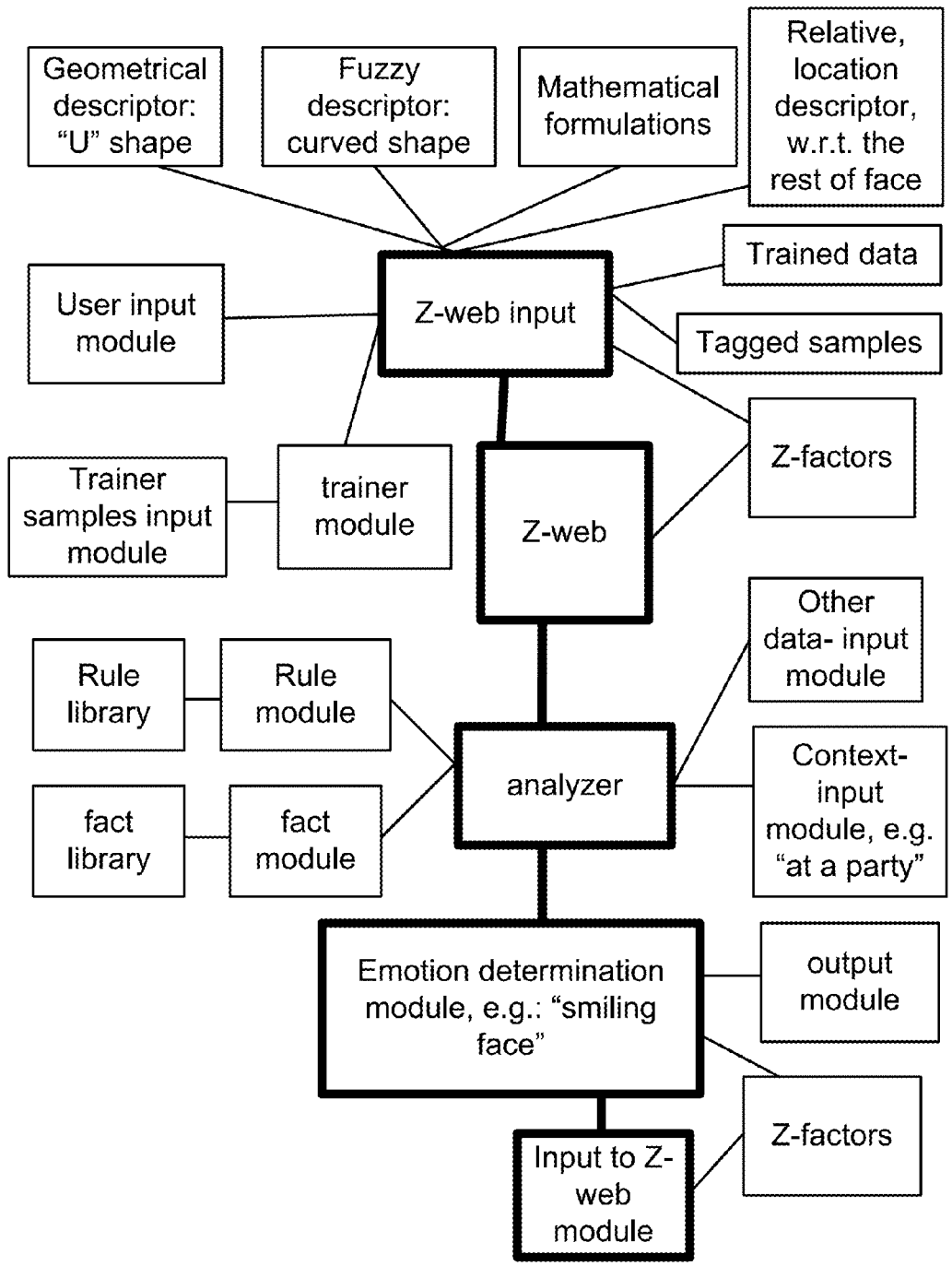

FIG. 155 shows one embodiment for Z-web and emotion determination.

Figure 156:
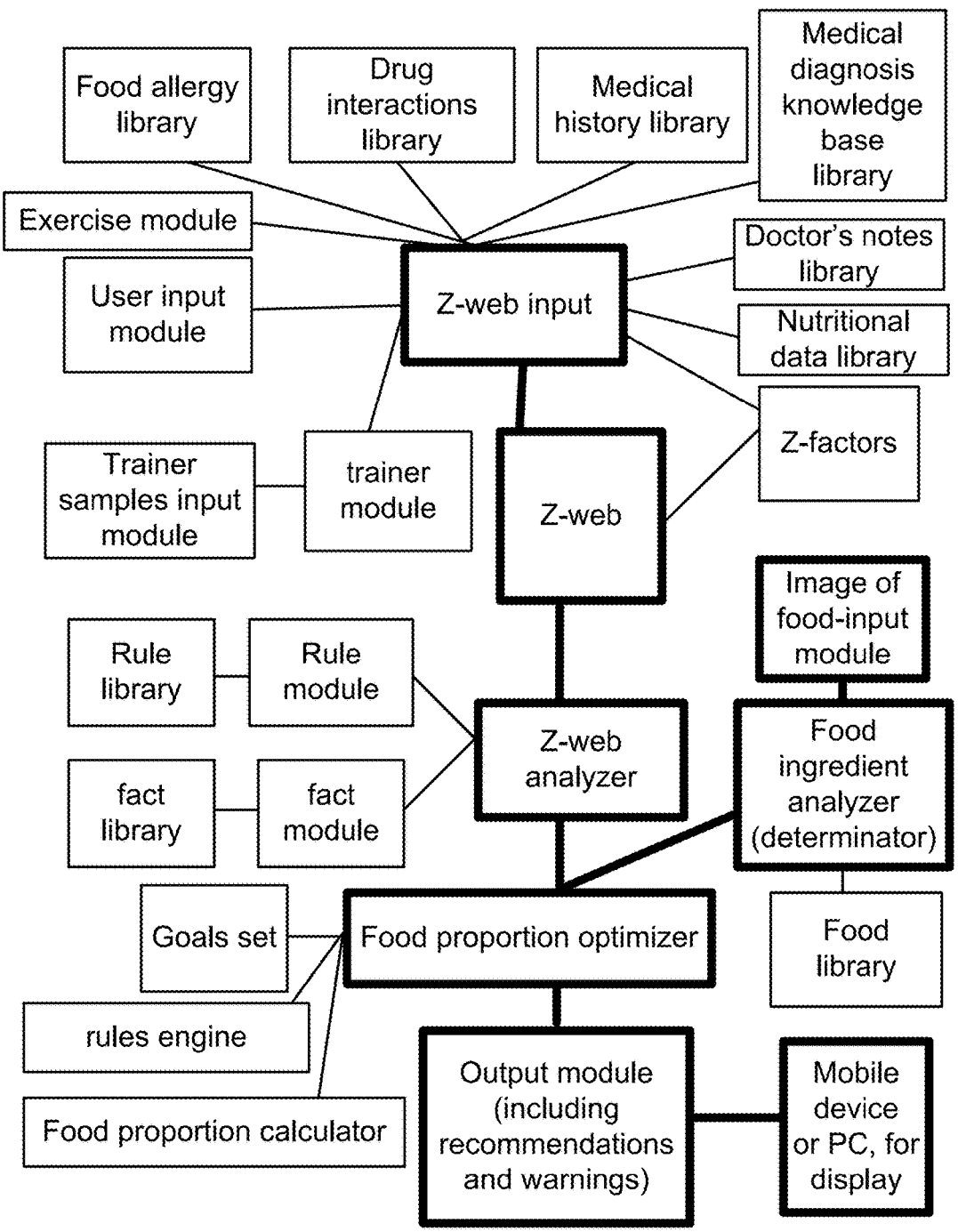

FIG. 156 shows one embodiment for Z-web and food or health analyzer.

Figure 157:
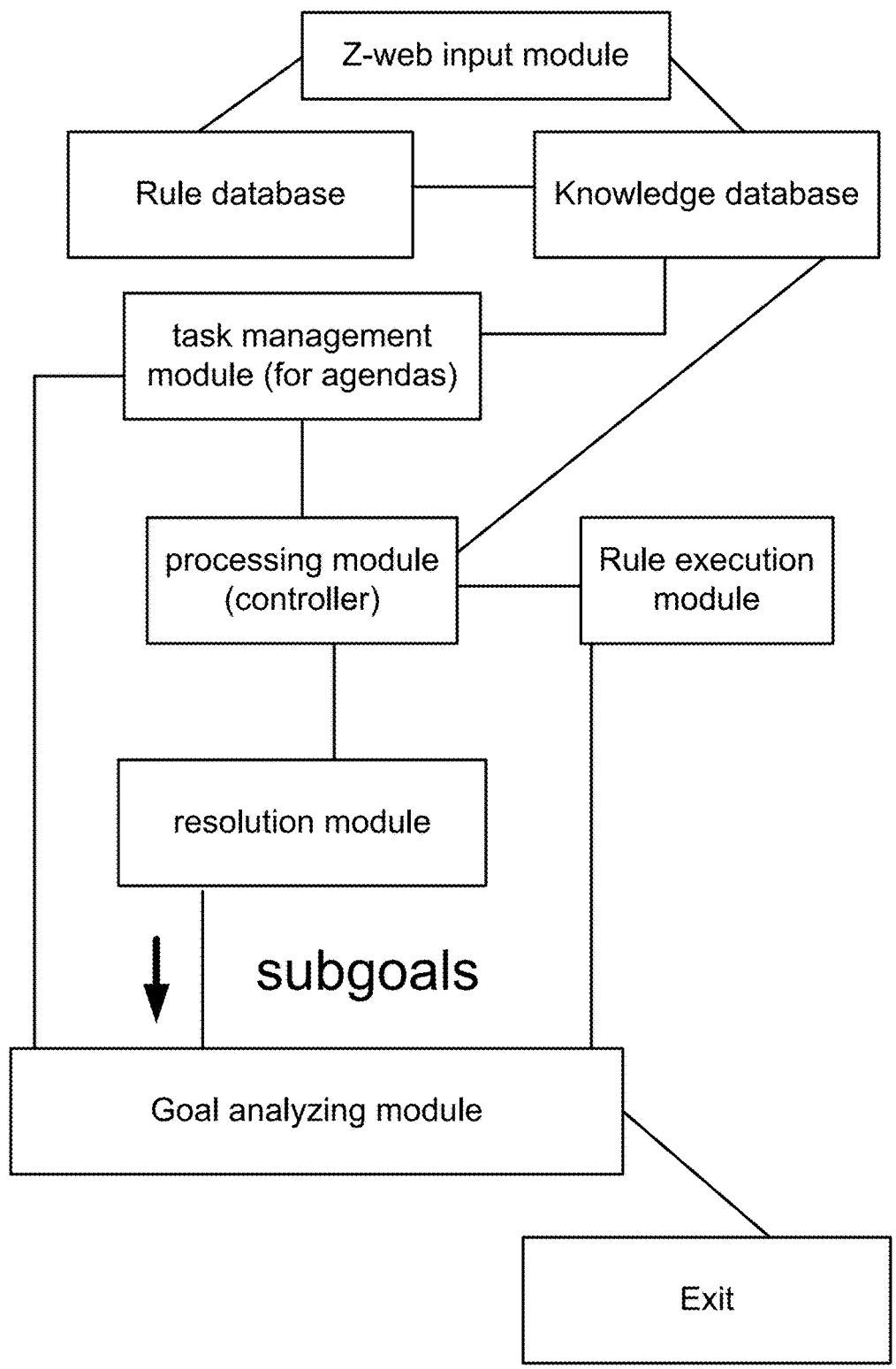

FIG. 157 shows one embodiment for a backward chaining inference engine.

Figure 158:
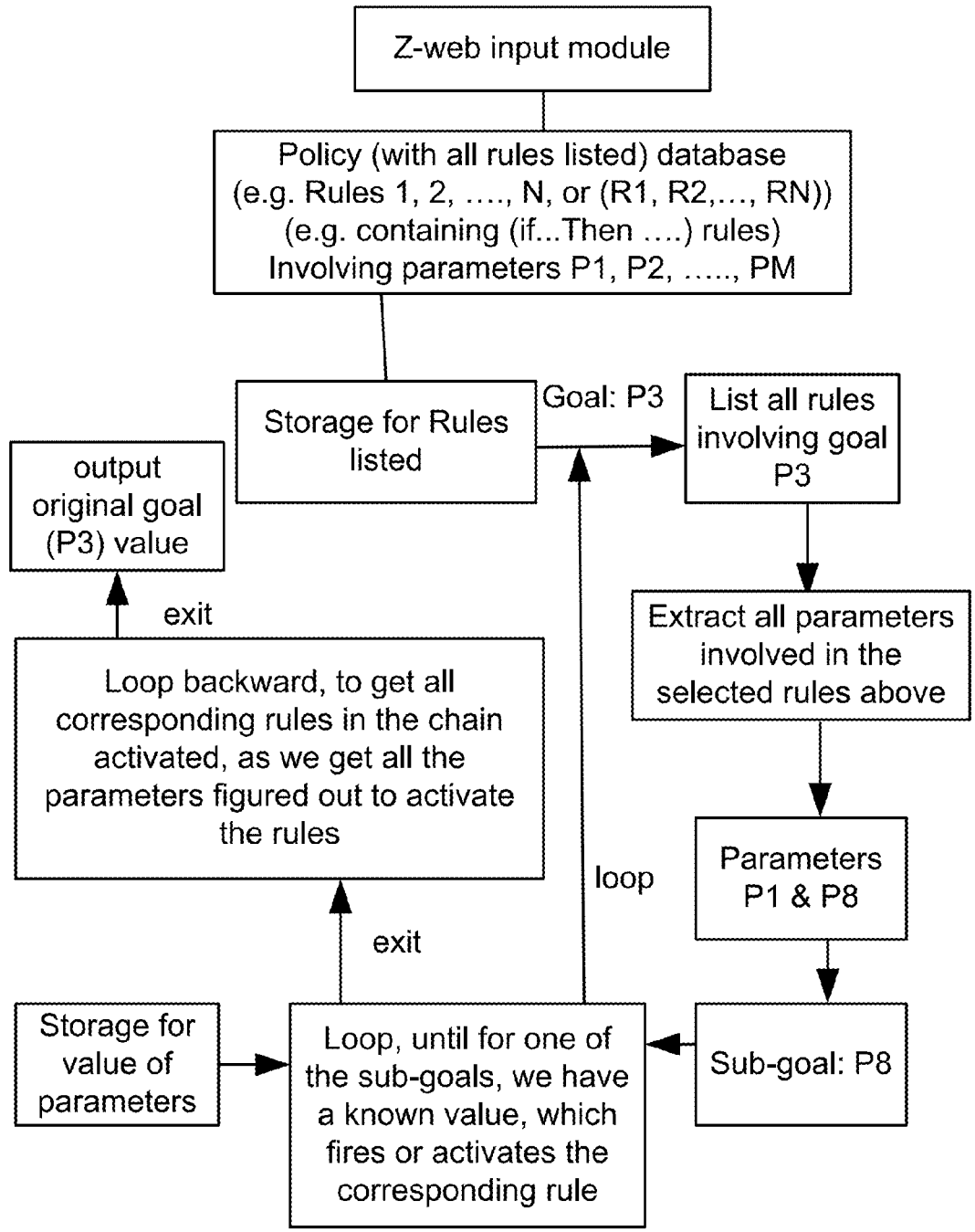

FIG. 158 shows one embodiment for a backward chaining flow chart.

Figure 159:
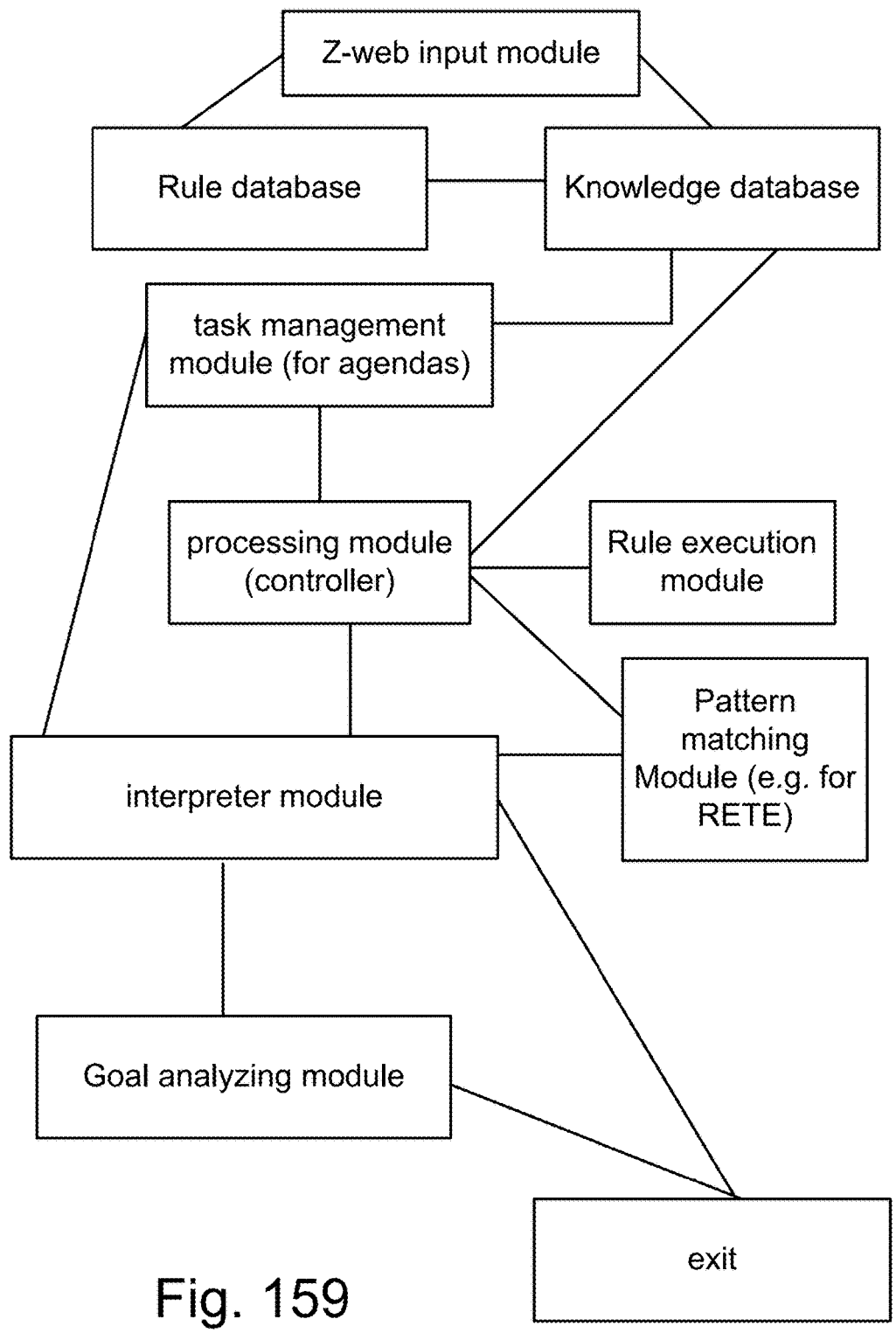

FIG. 159 shows one embodiment for a forward chaining inference engine.

Figure 160:
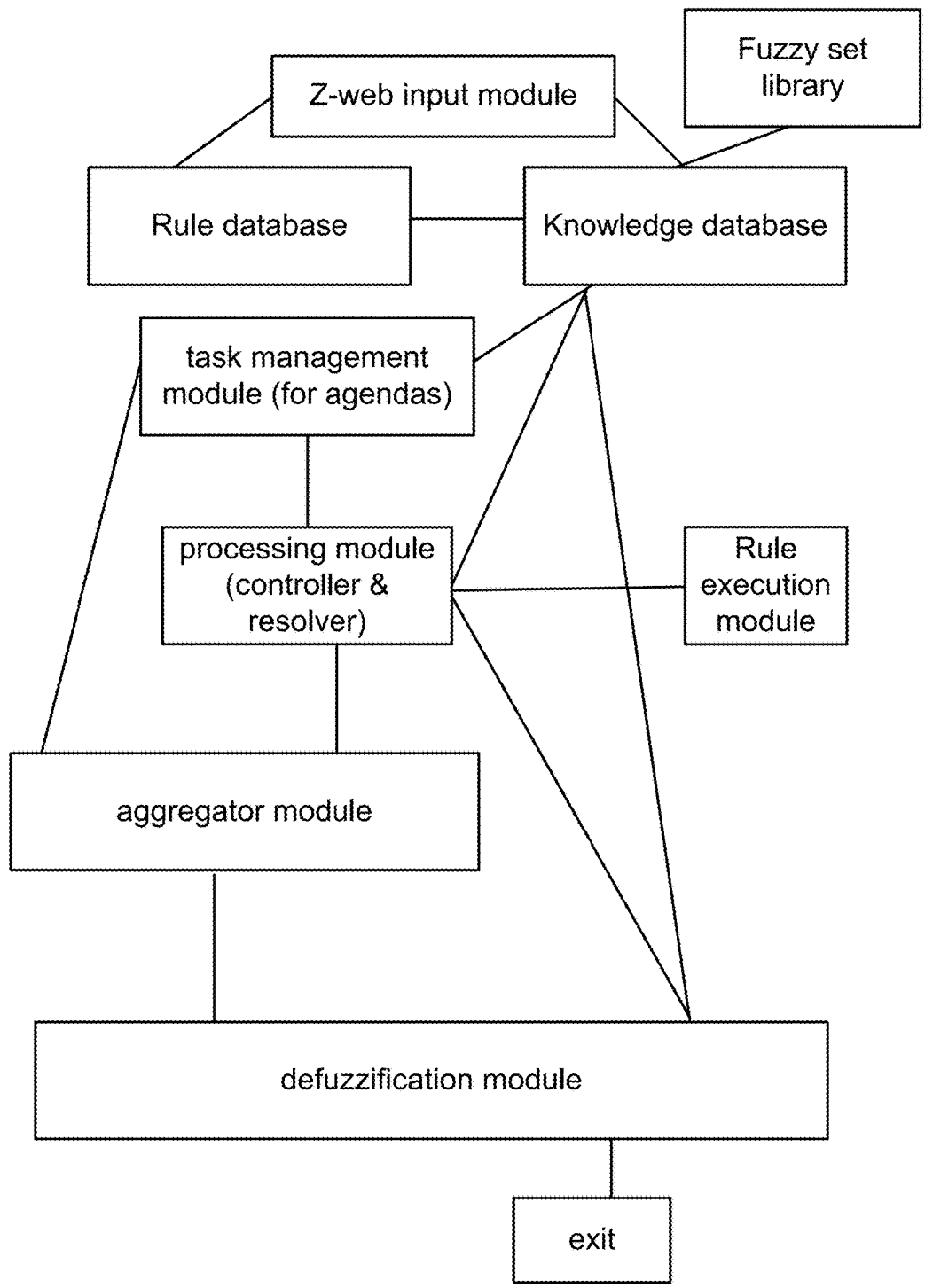

FIG. 160 shows one embodiment for a fuzzy reasoning inference engine.

Figure 161:
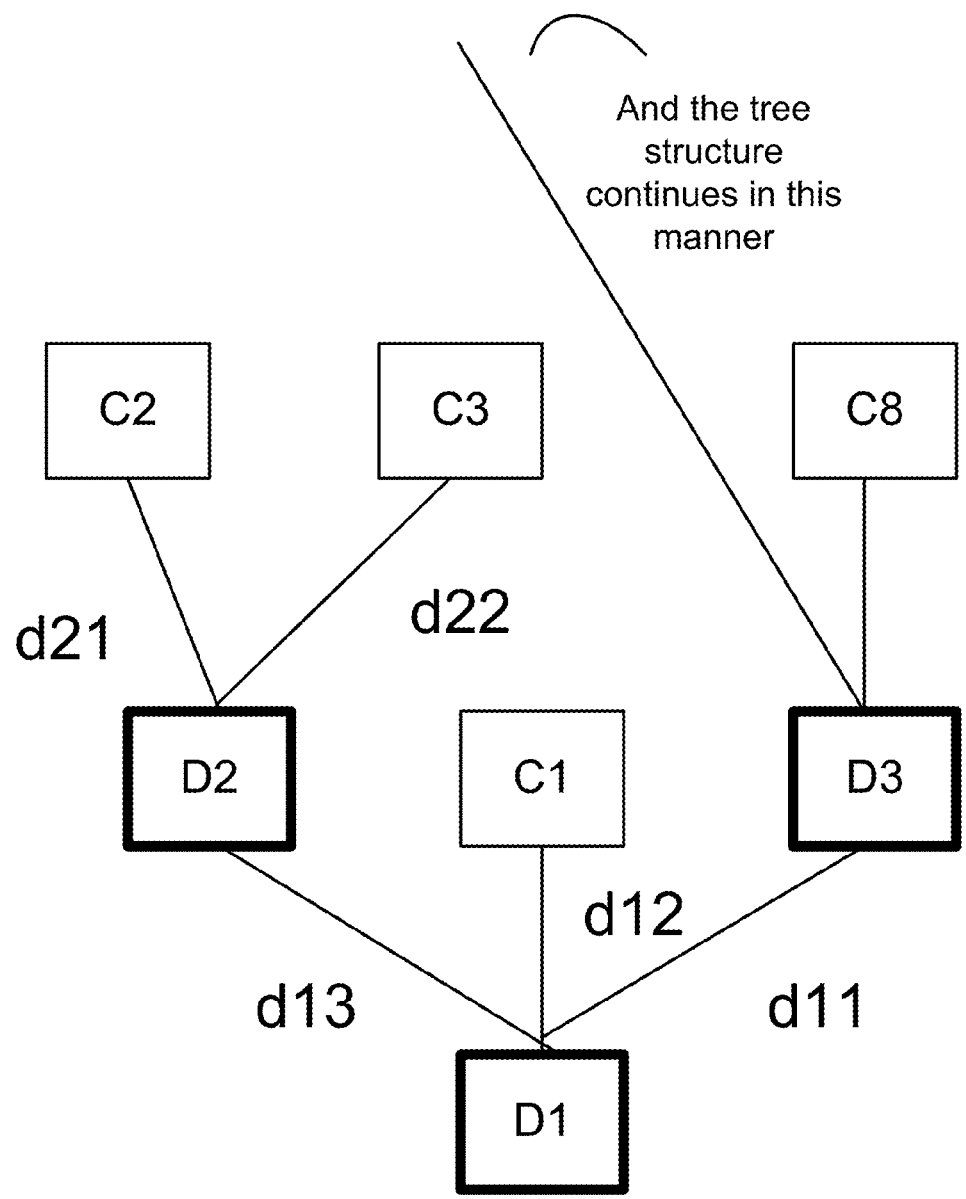

FIG. 161 shows one embodiment for a decision tree method or system.

Figure 162:
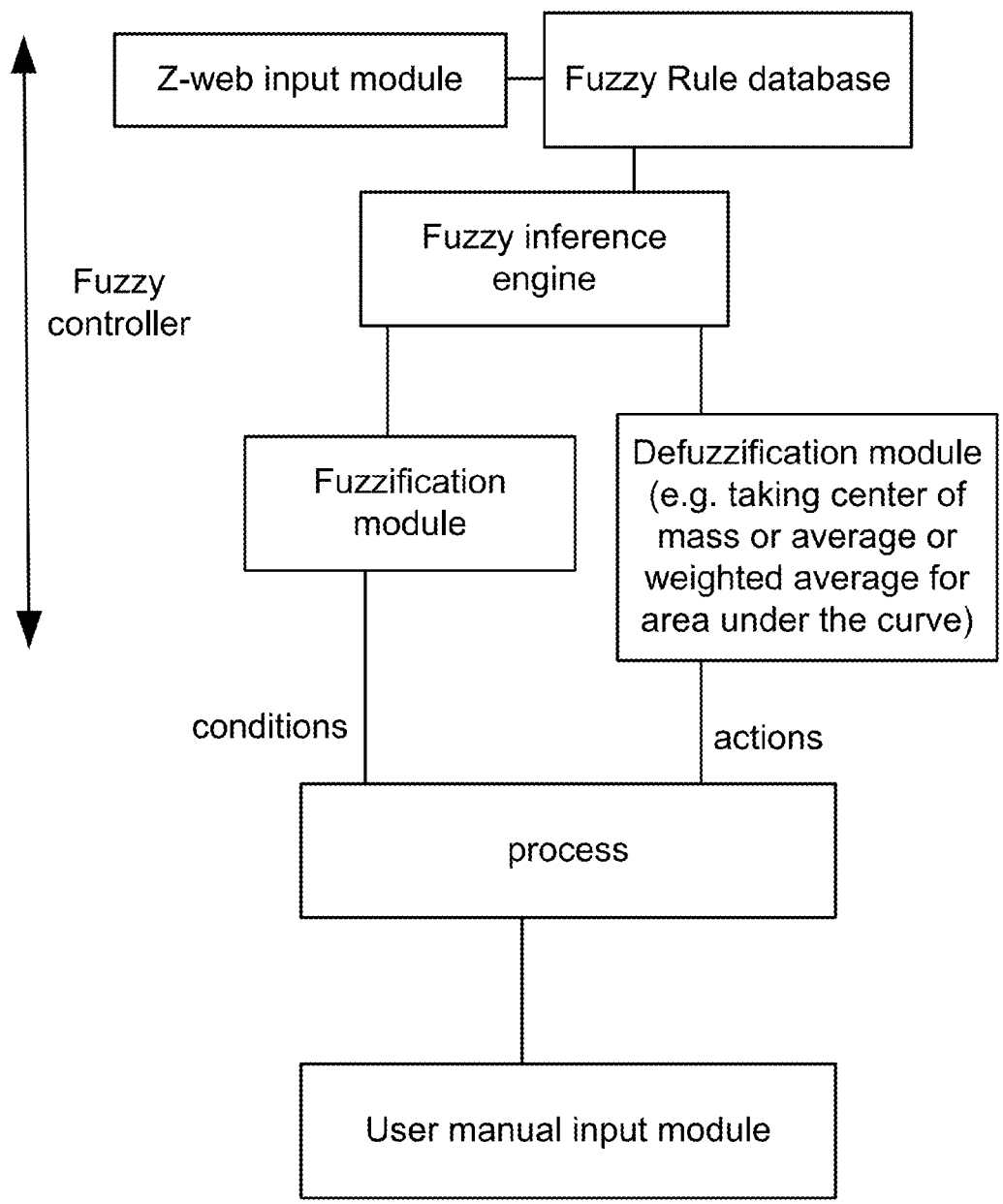

FIG. 162 shows one embodiment for a fuzzy controller.

Figure 163:
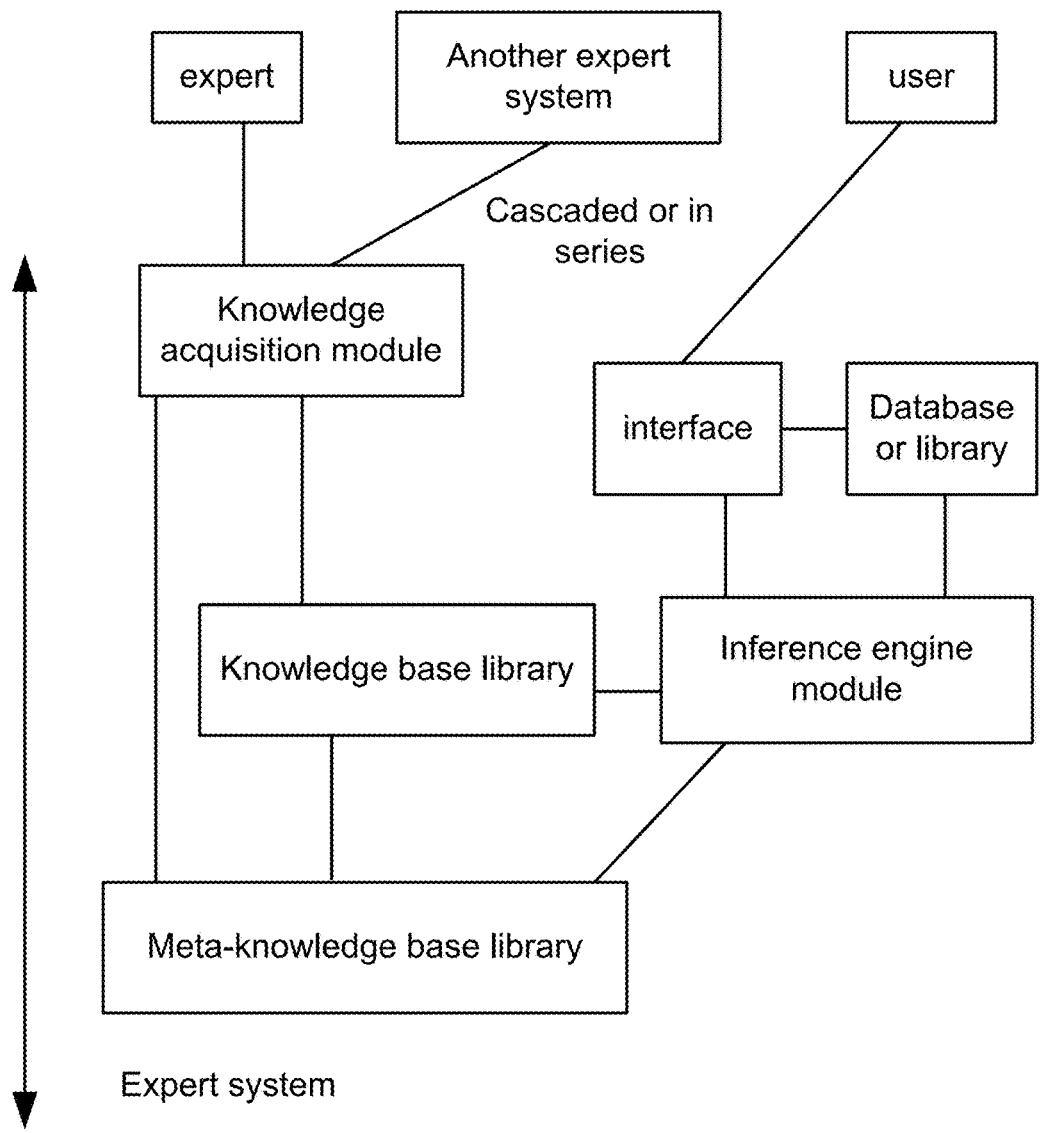

FIG. 163 shows one embodiment for an expert system.

Figure 164:
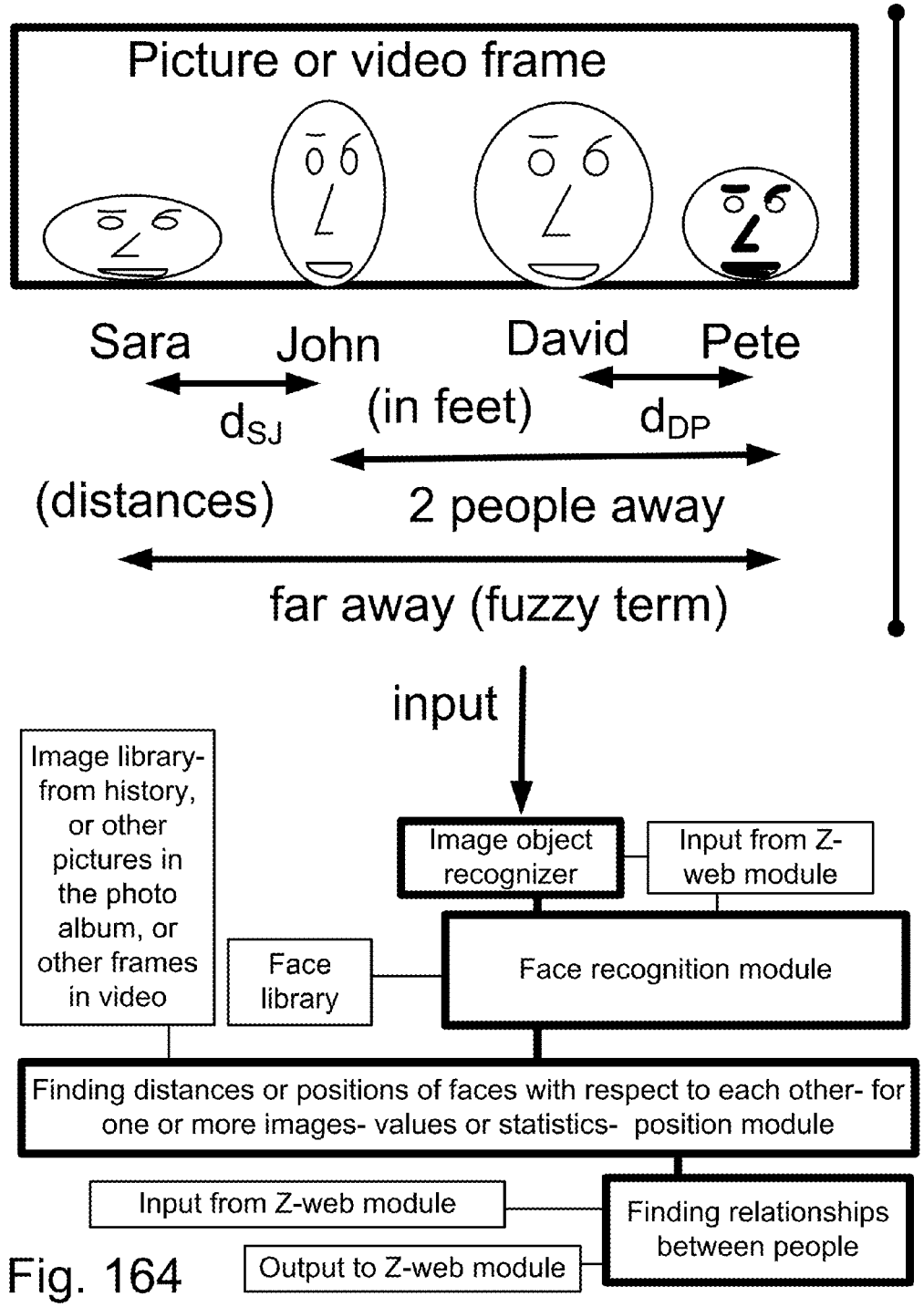

FIG. 164 shows one embodiment for determining relationship and distances in images.

Figure 165:
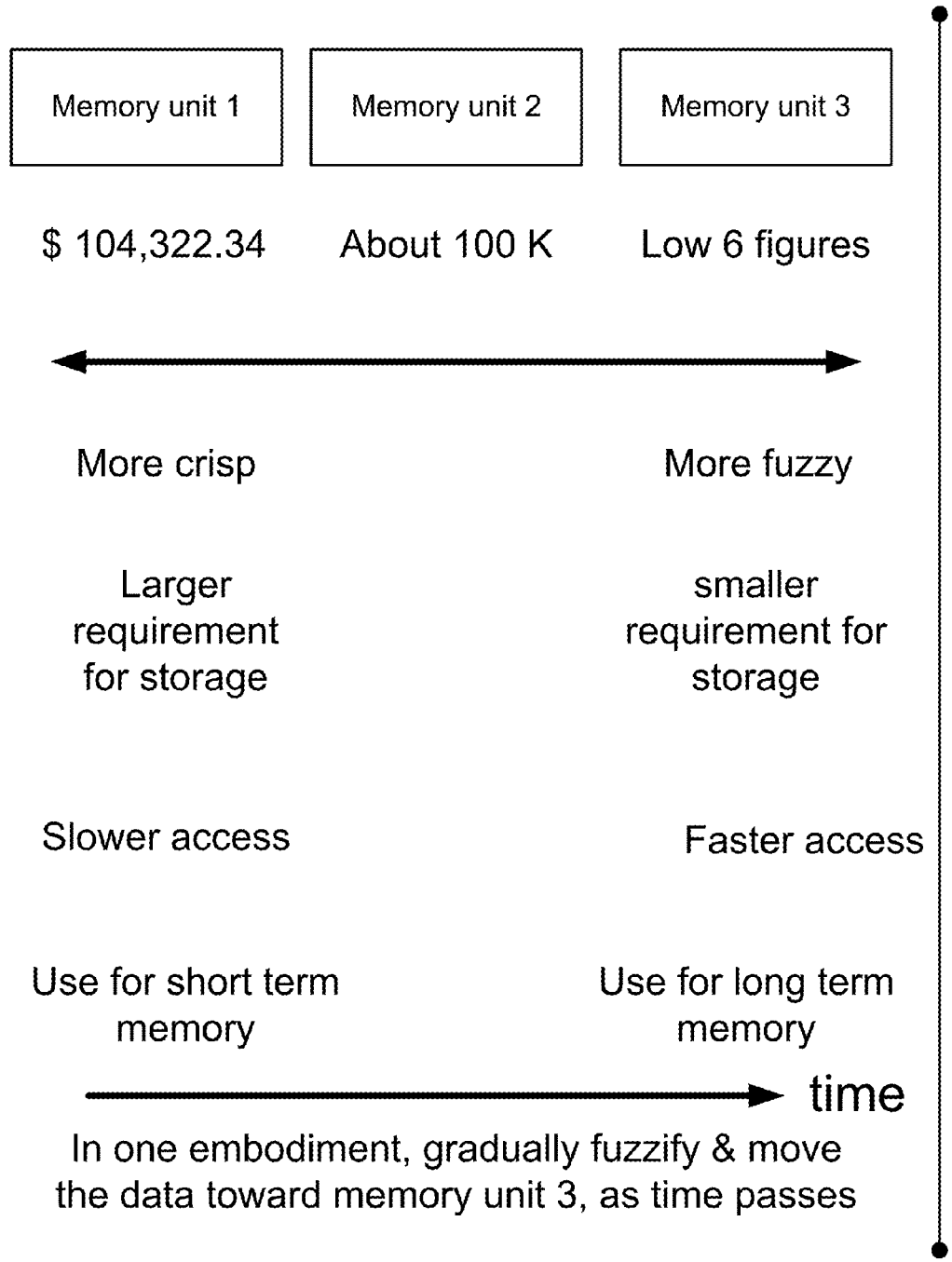

FIG. 165 shows one embodiment for multiple memory unit storage.

Figure 166:
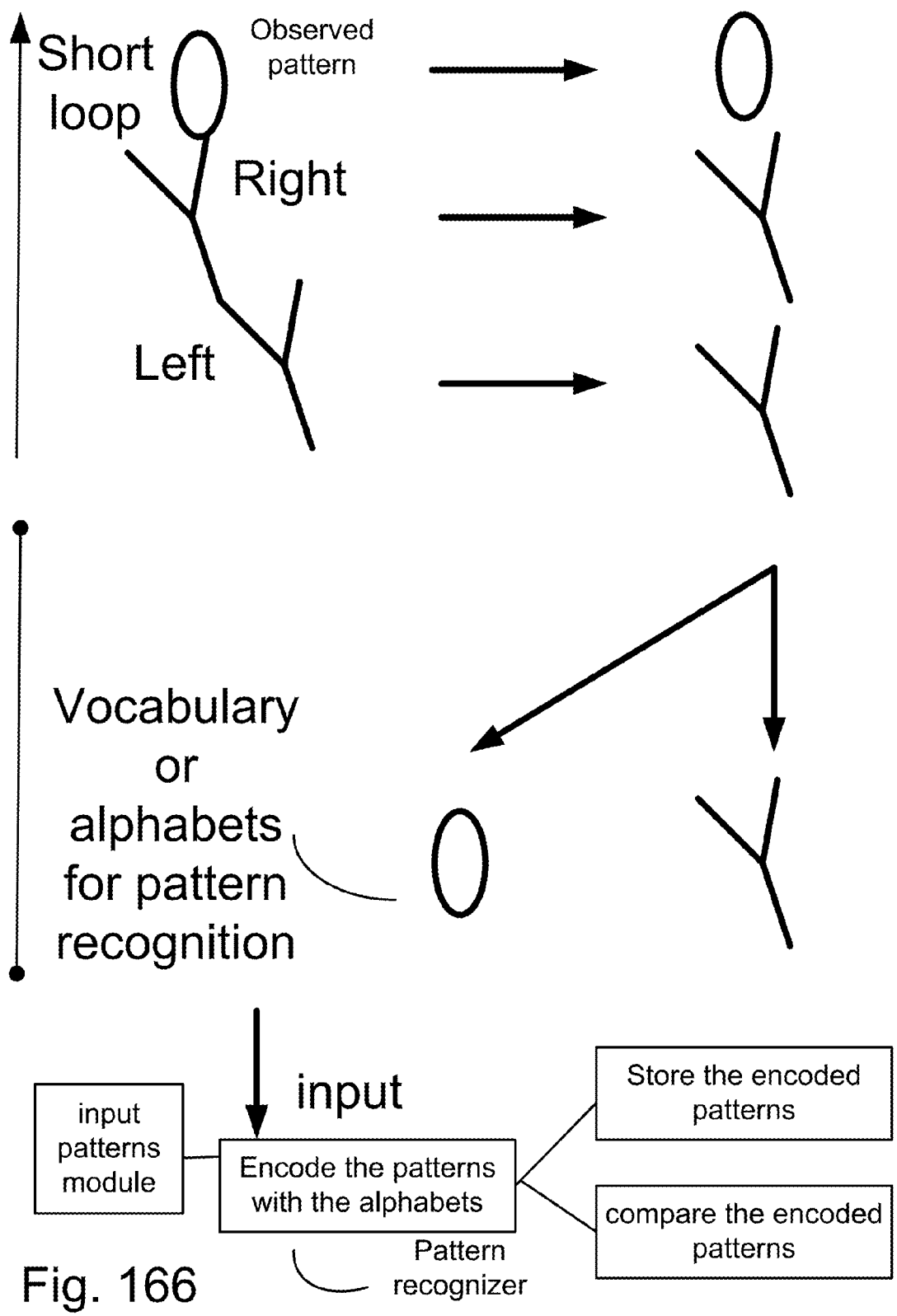

FIG. 166 shows one embodiment for pattern recognition.

Figure 167:
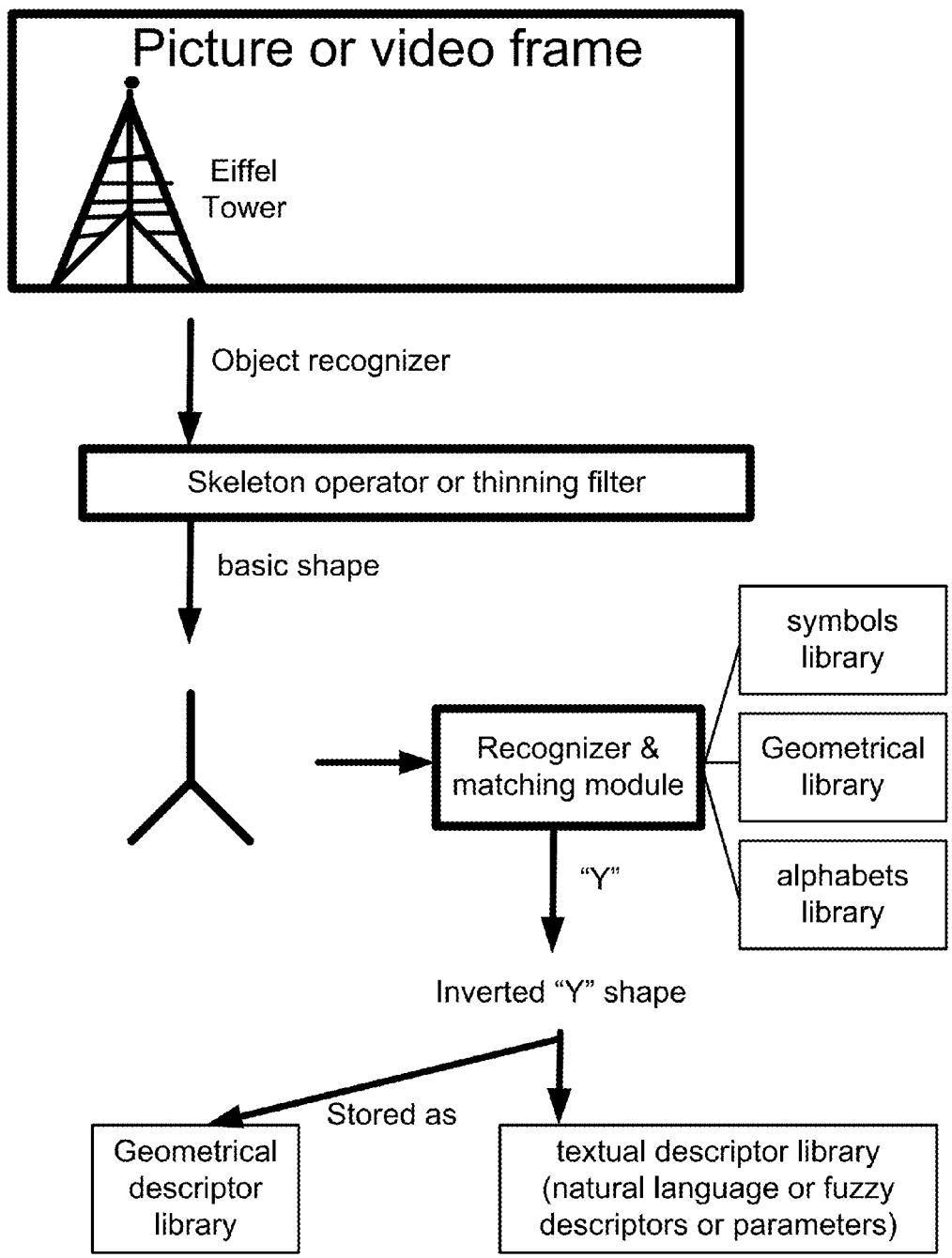

FIG. 167 shows one embodiment for recognition and storage.

Figure 168:
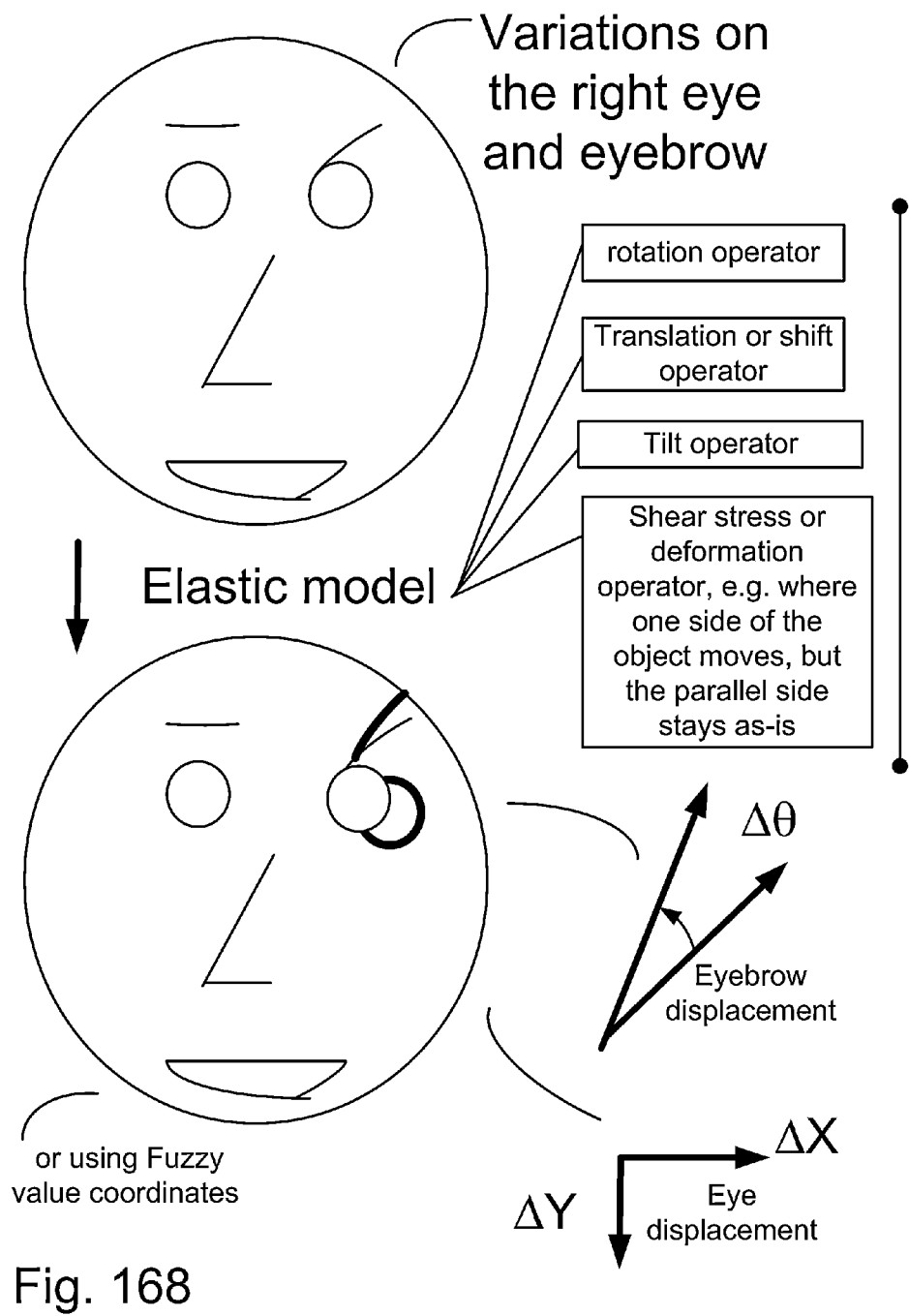

FIG. 168 shows one embodiment for elastic model.

Figure 169:
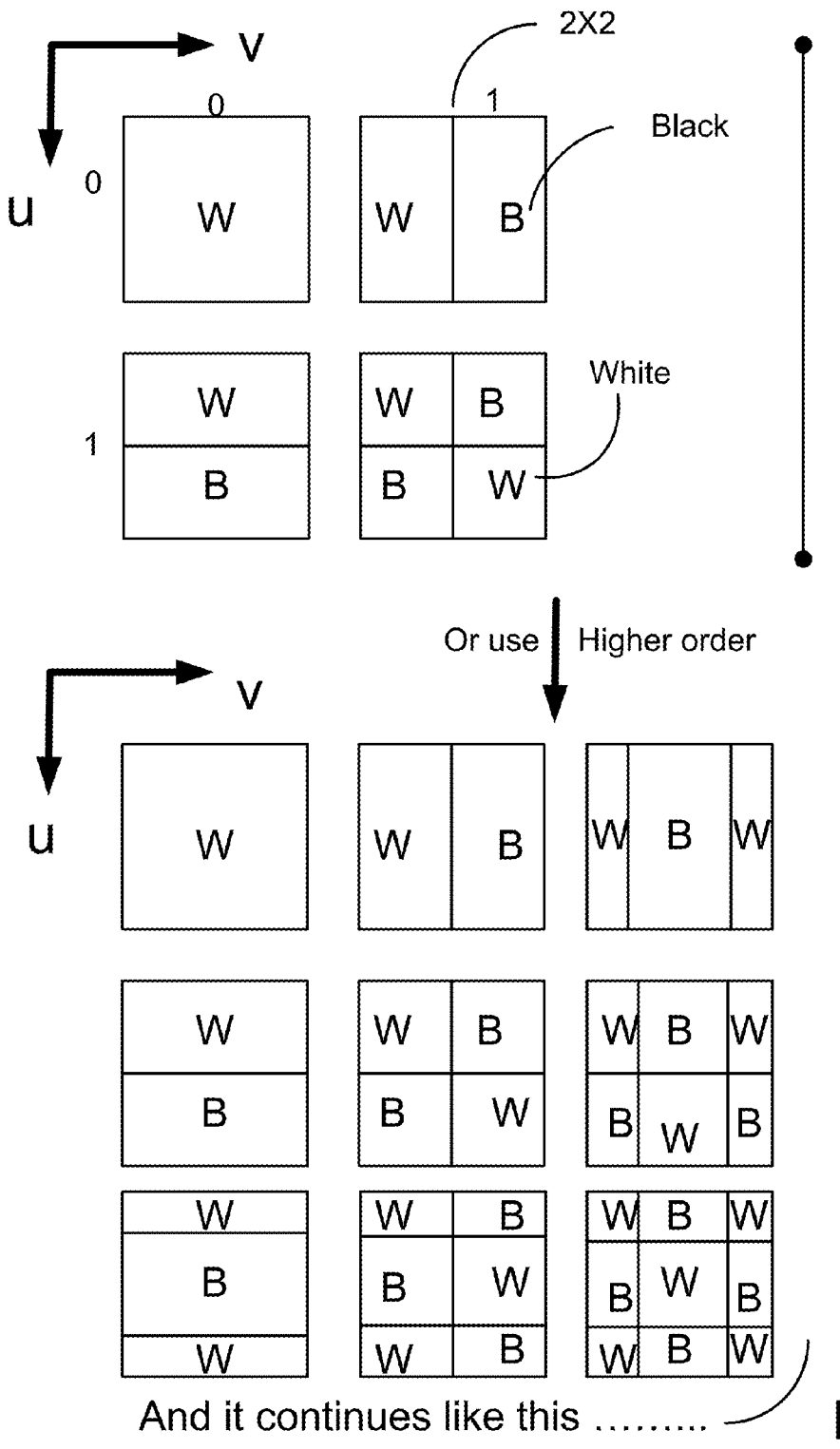

FIG. 169 shows one embodiment for set of basis functions or filters or eigenvectors.

Figure 170:
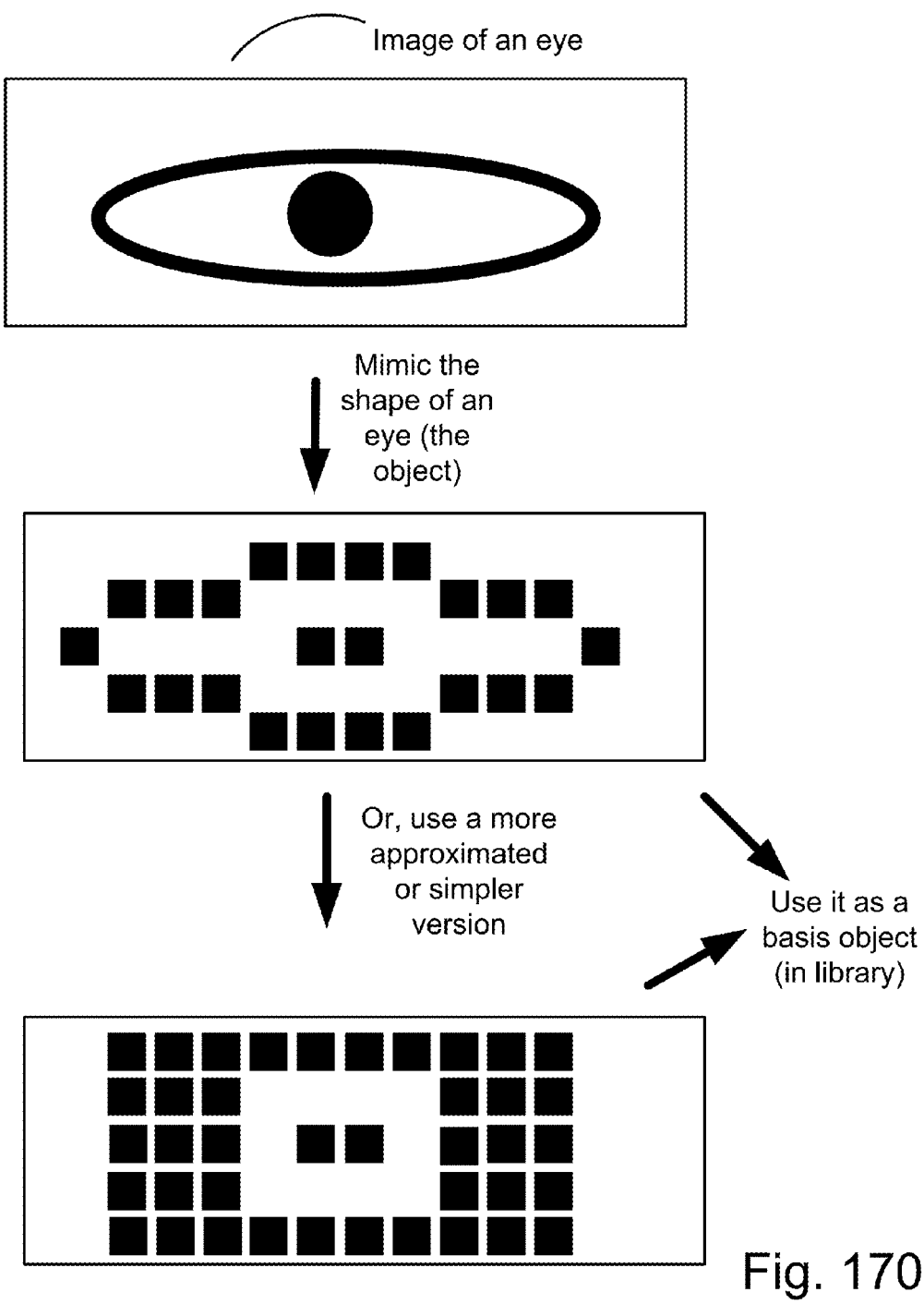

FIG. 170 shows one embodiment for an eye model for basis object.

Figure 171:
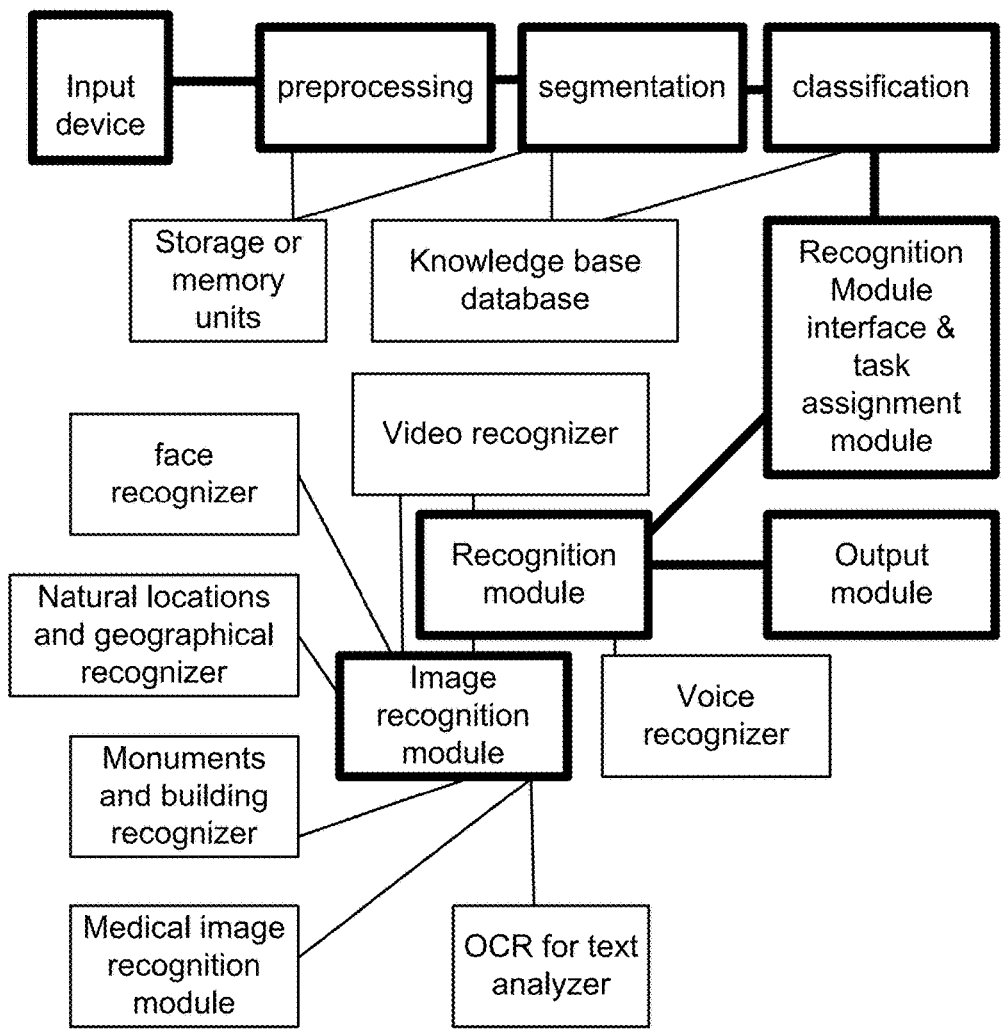

FIG. 171 shows one embodiment for a recognition system.

Figure 172:
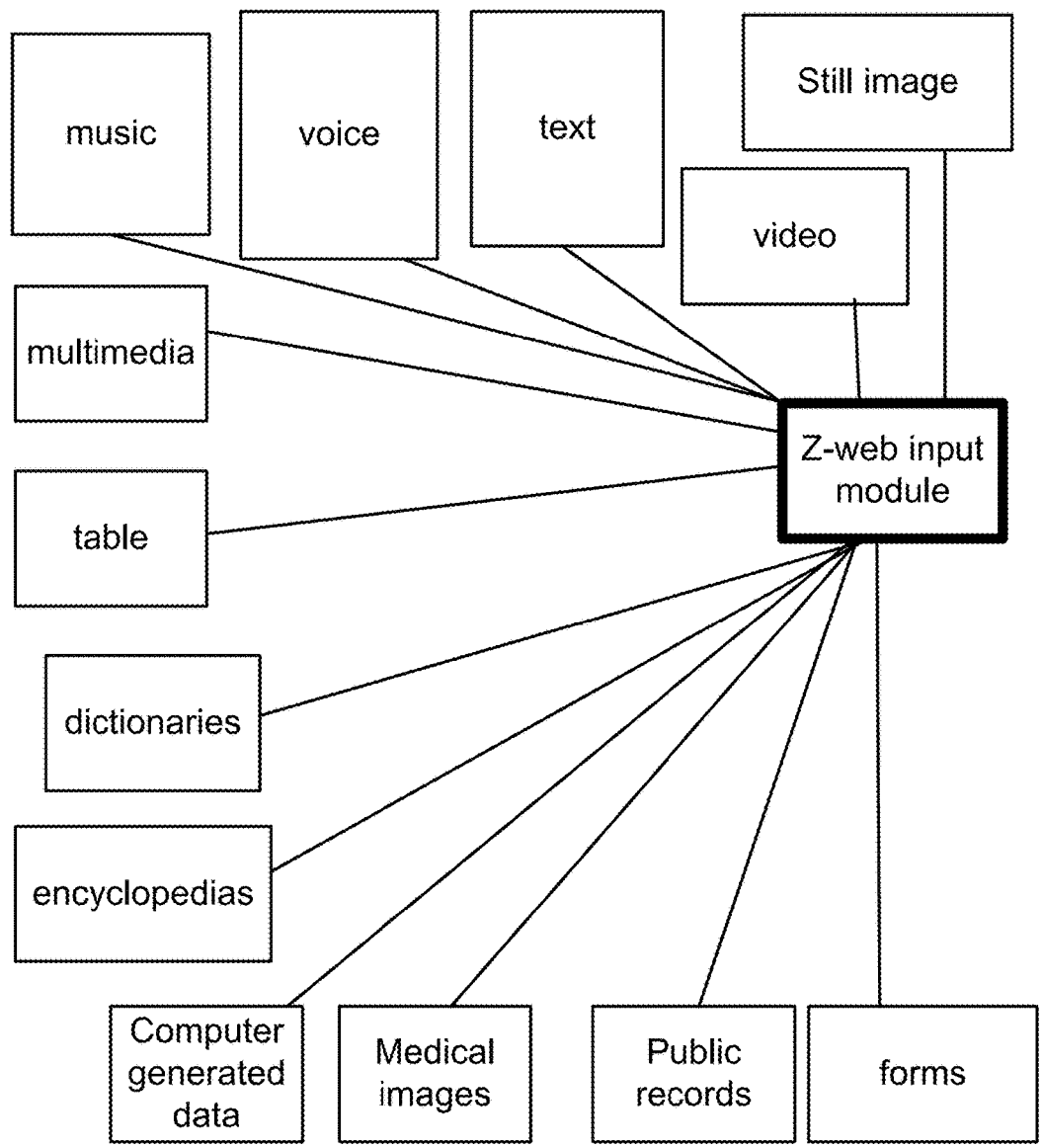

FIG. 172 shows one embodiment for a Z-web.

Figure 173:
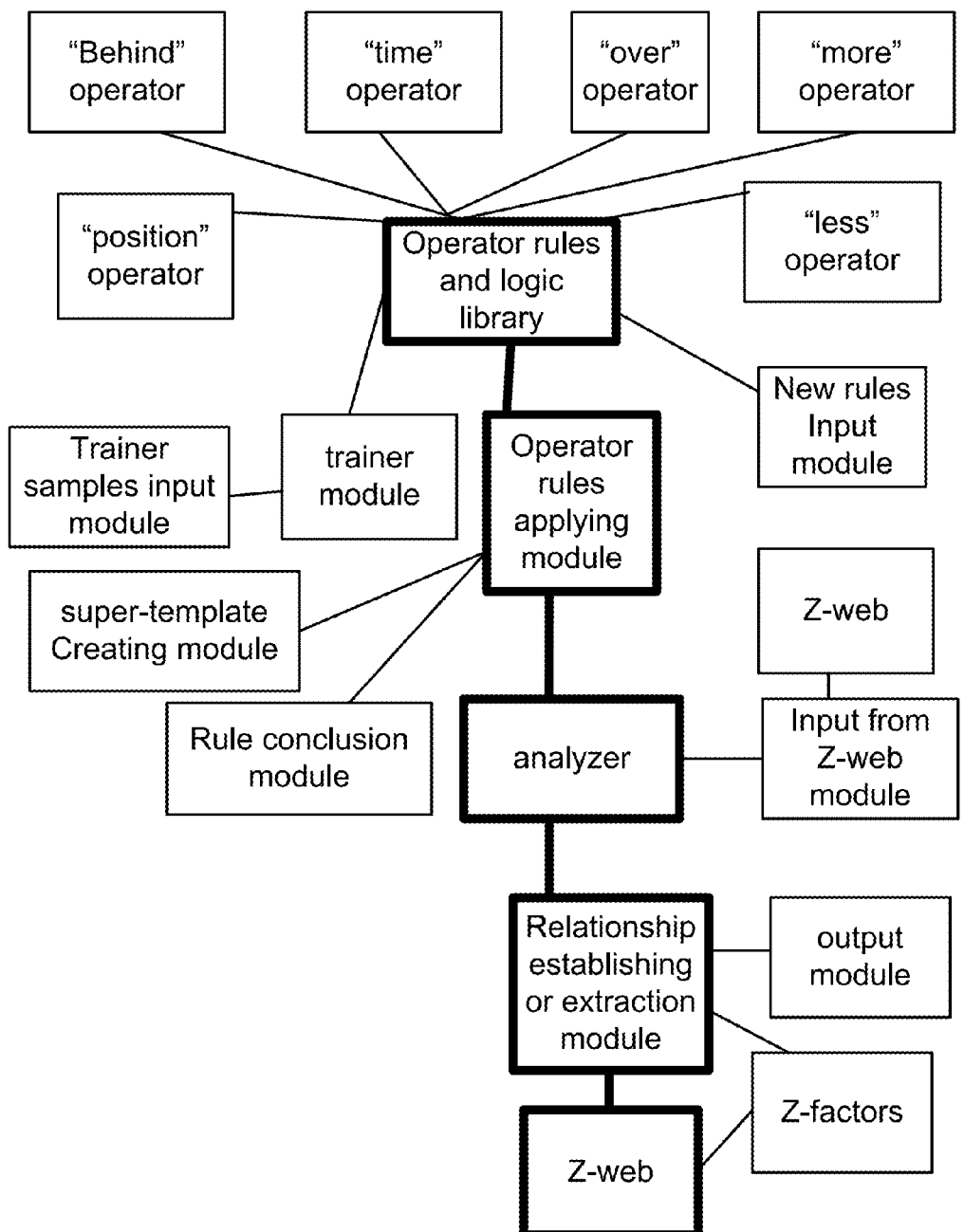

FIG. 173 shows one embodiment for a Z-web analysis.

Figure 174:
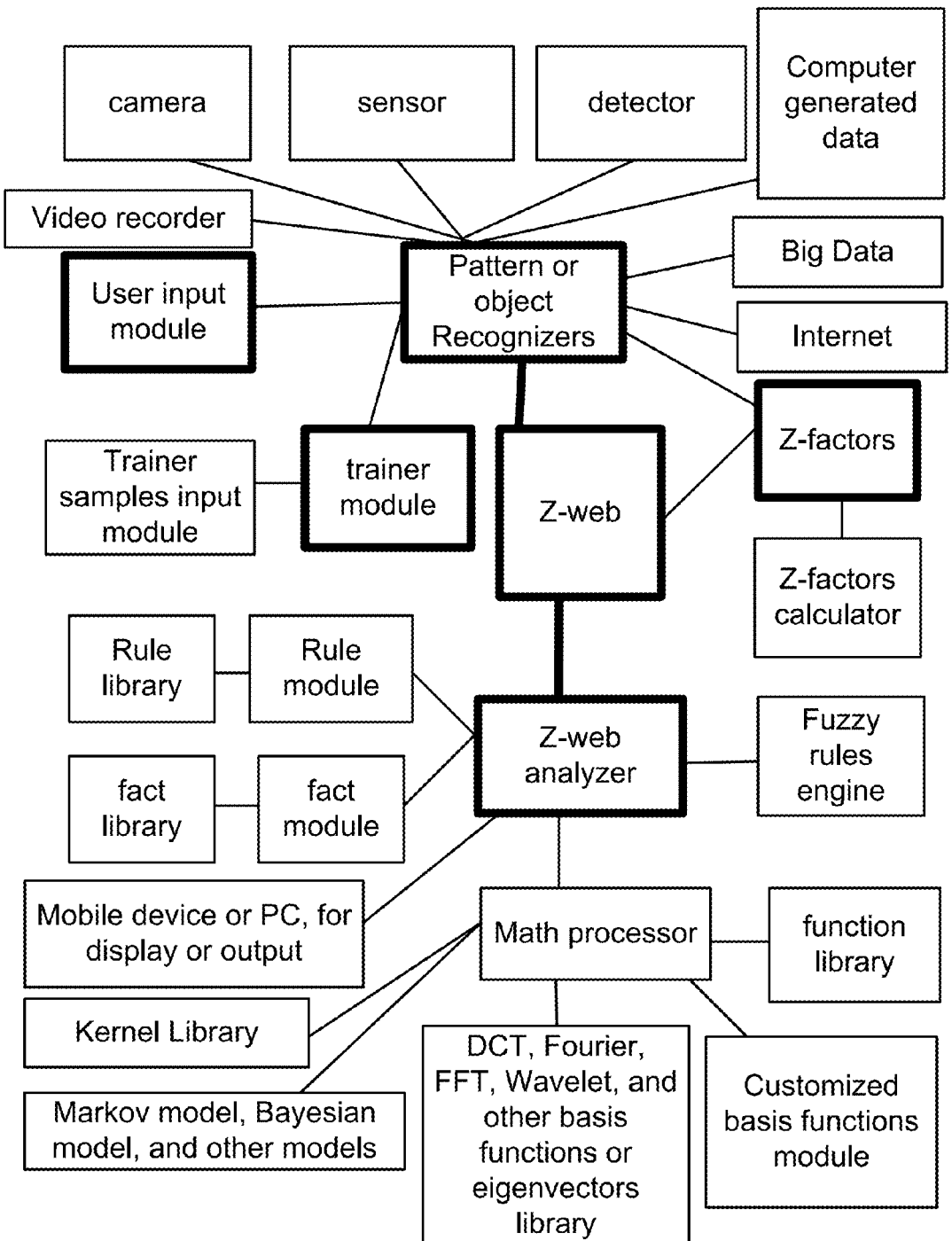

FIG. 174 shows one embodiment for a Z-web analysis.

Figure 175:
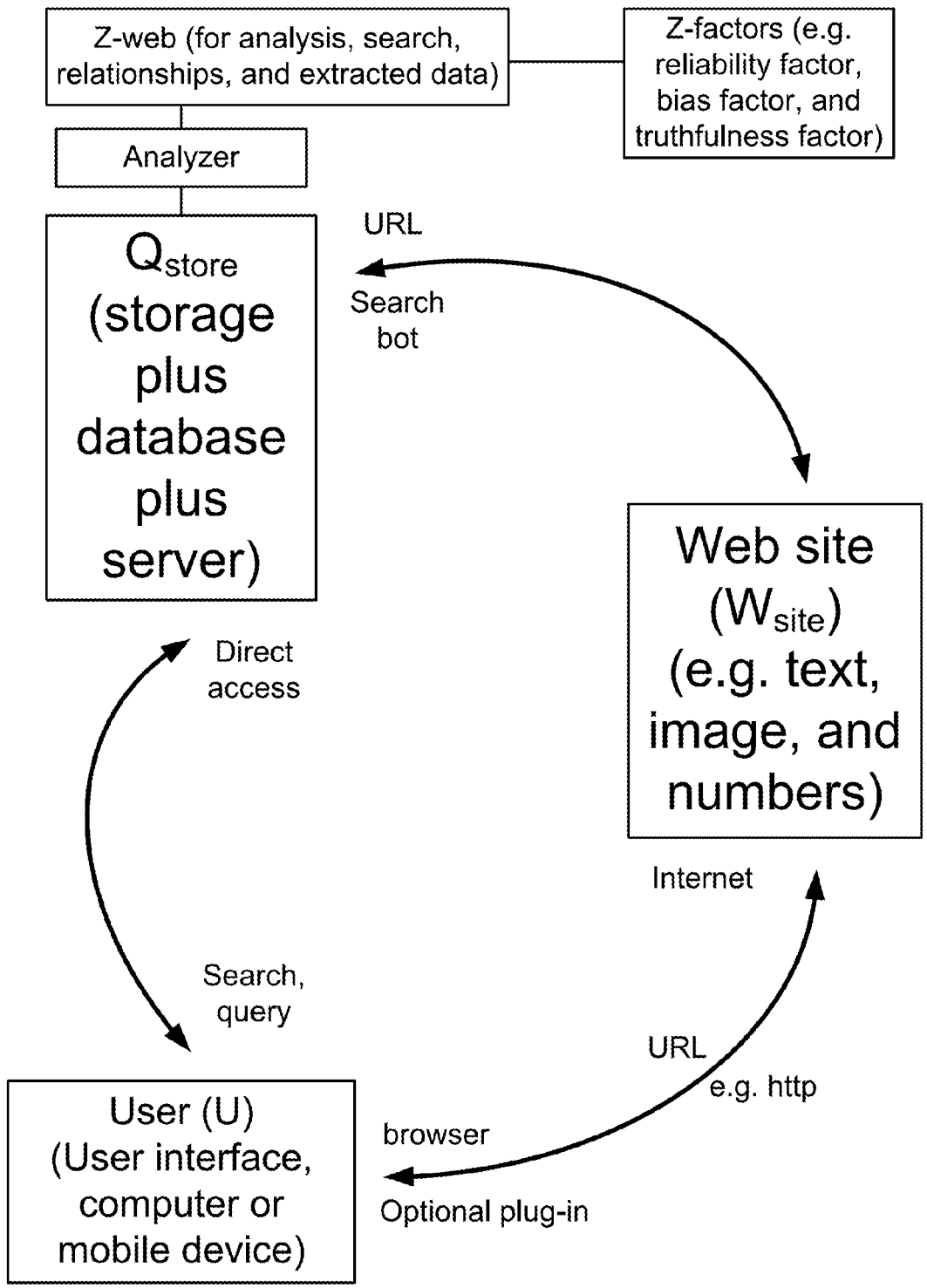

FIG. 175 shows one embodiment for a search engine.

Figure 176:
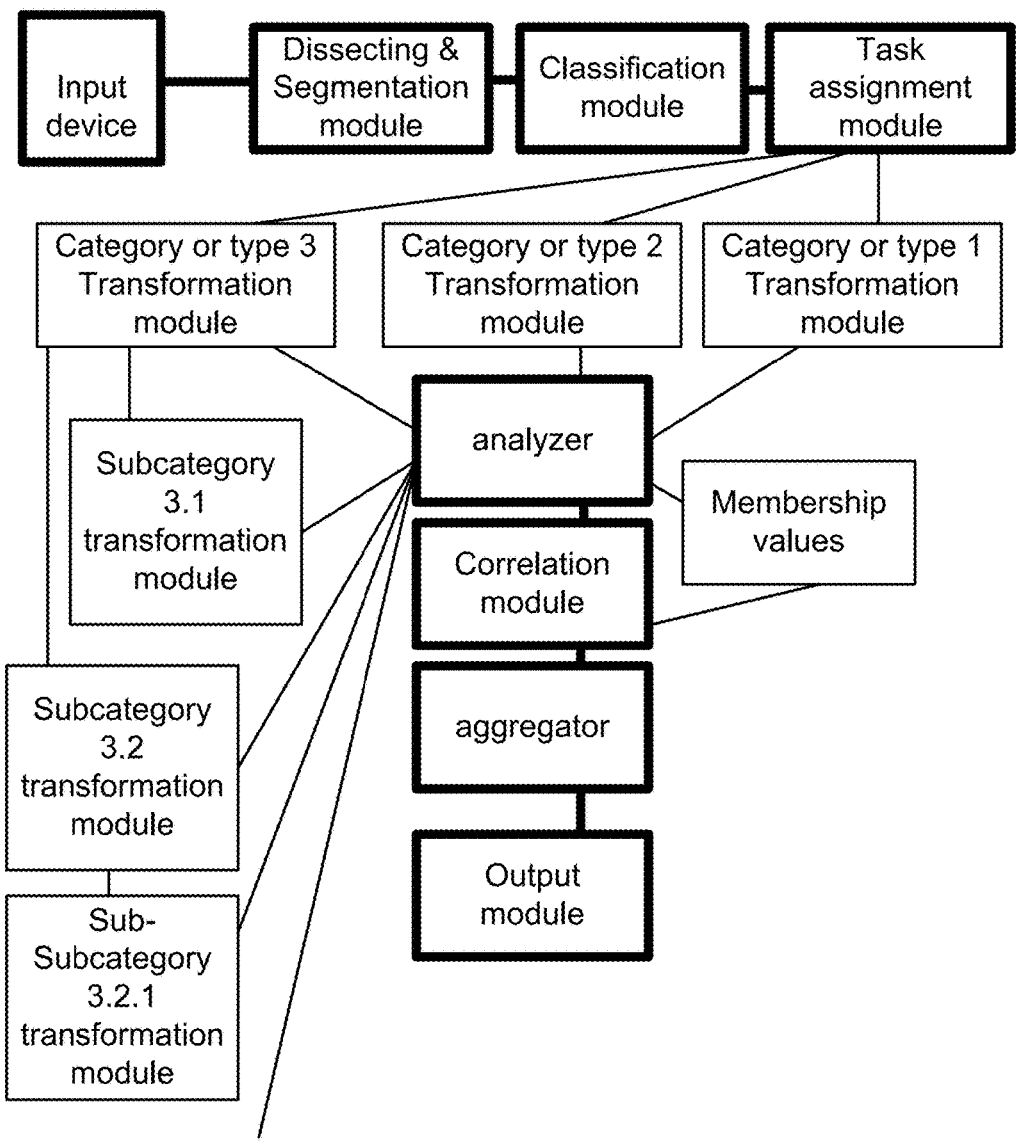

FIG. 176 shows one embodiment for multiple type transformation.

Figure 177:
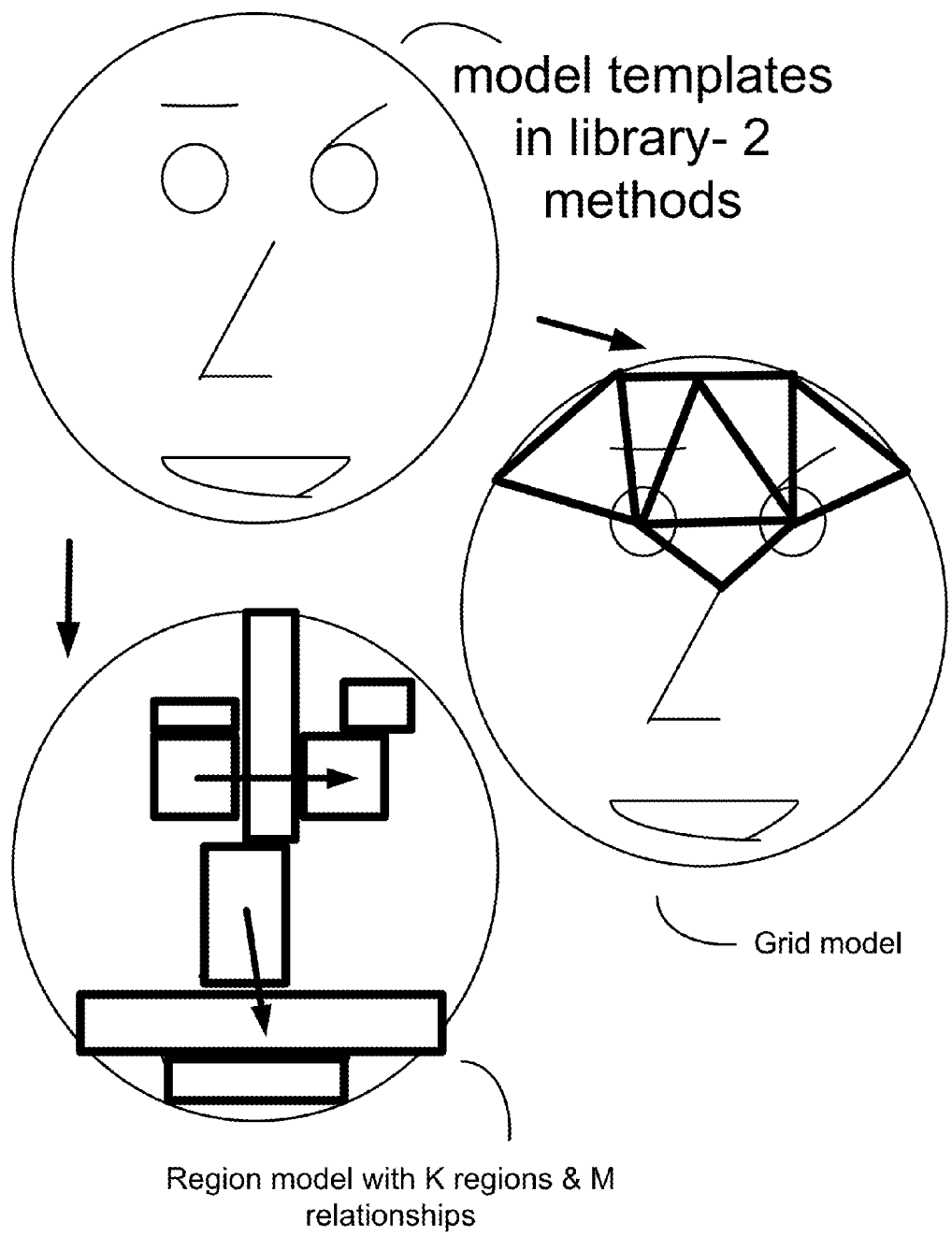

FIG. 177 shows one embodiment for 2 face models for analysis or storage.

Figure 178:
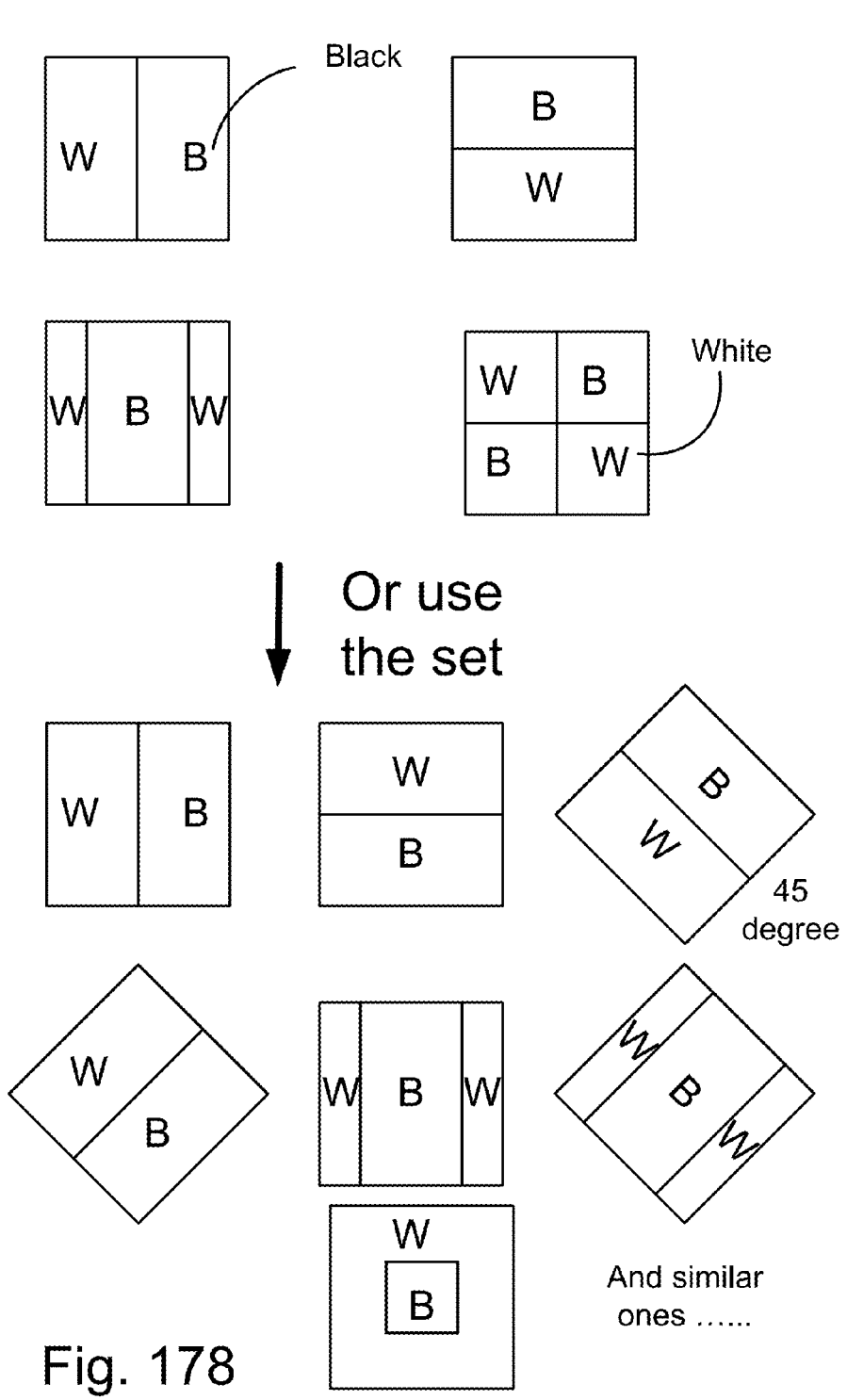

FIG. 178 shows one embodiment for set of basis functions.

Figure 179:
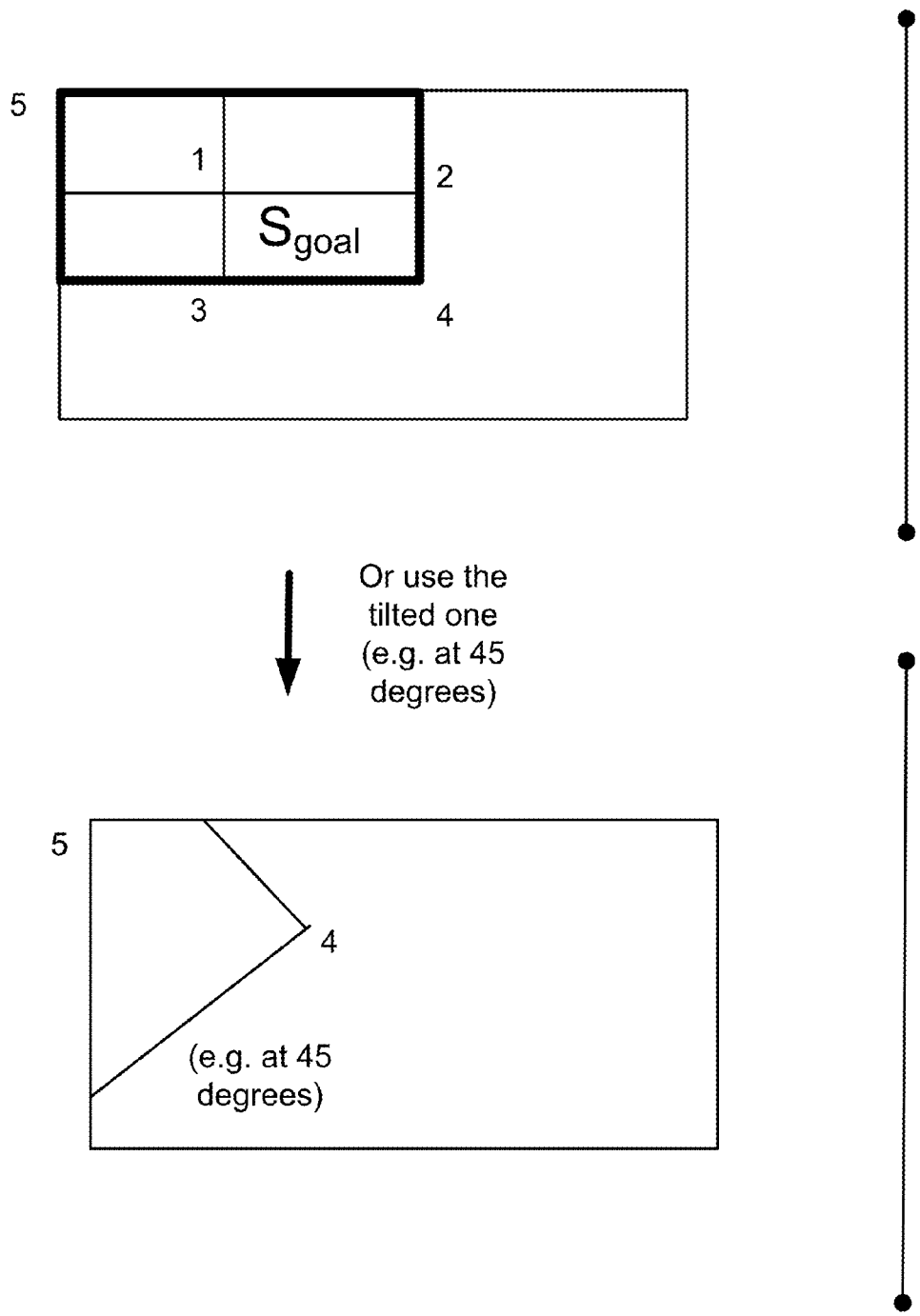

FIG. 179 shows one embodiment for windows for calculation of "integral image", for sum of pixels, for any given initial image, as an intermediate step for our process.

Figure 180:
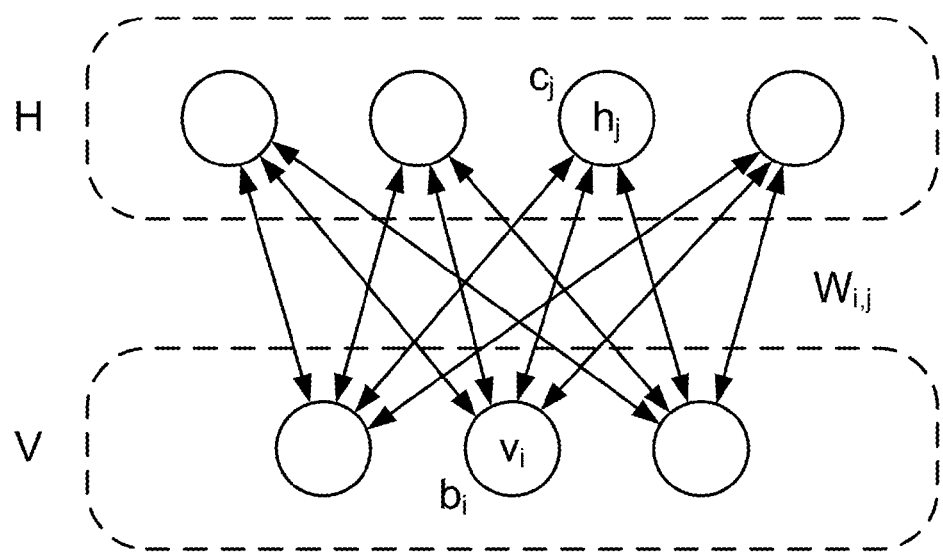

FIG. 180 shows one embodiment for an illustration of restricted Boltzmann machine.

Figure 181:
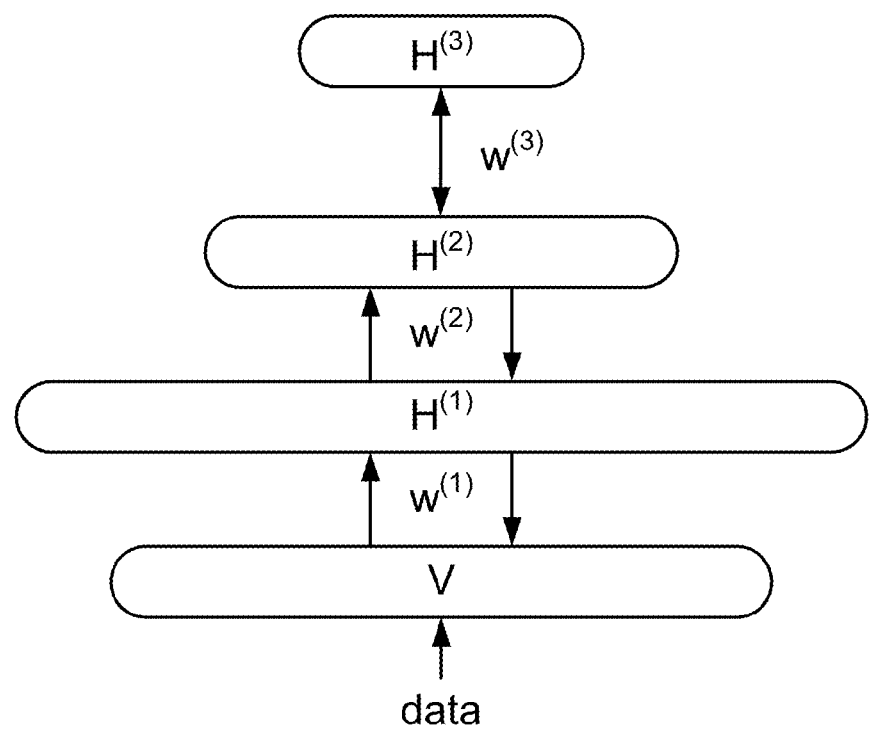

FIG. 181 shows one embodiment for three-level RBM.

Figure 182:
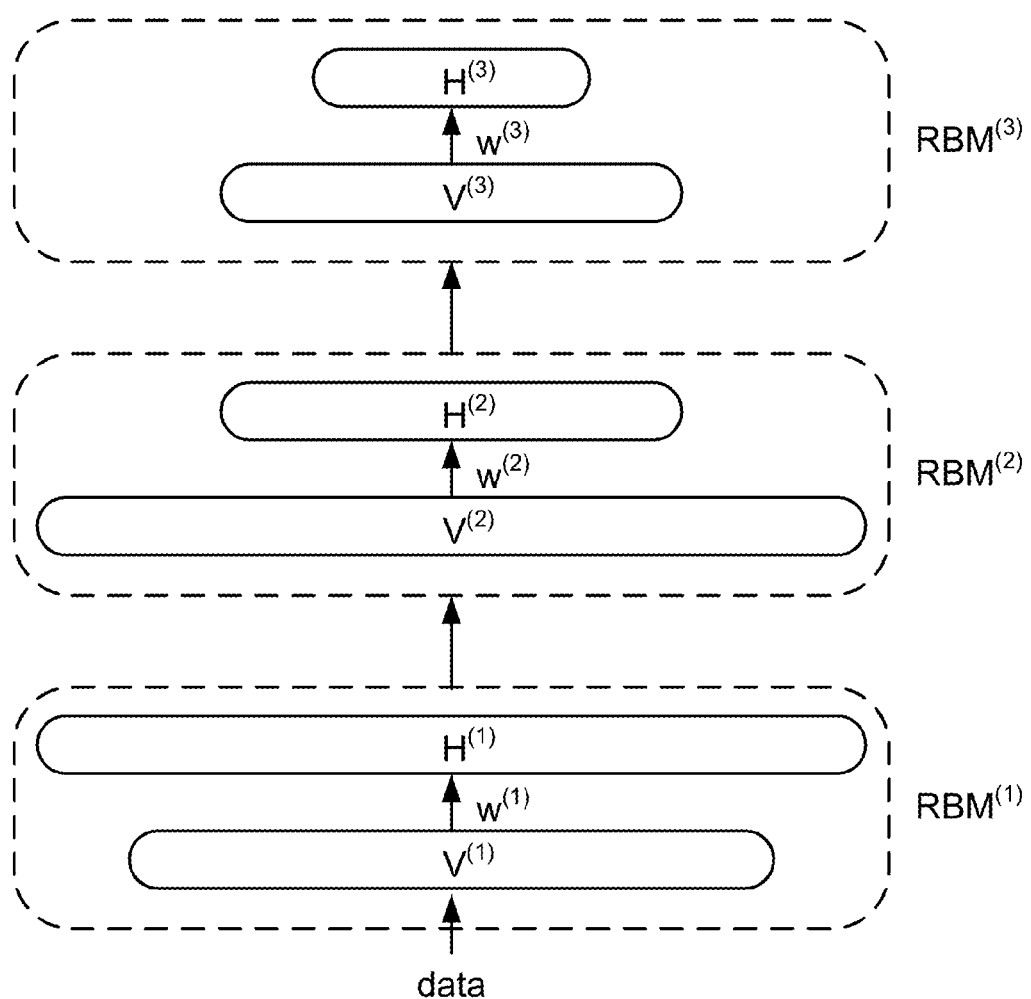

FIG. 182 shows one embodiment for stacked RBMs.

Figure 183:
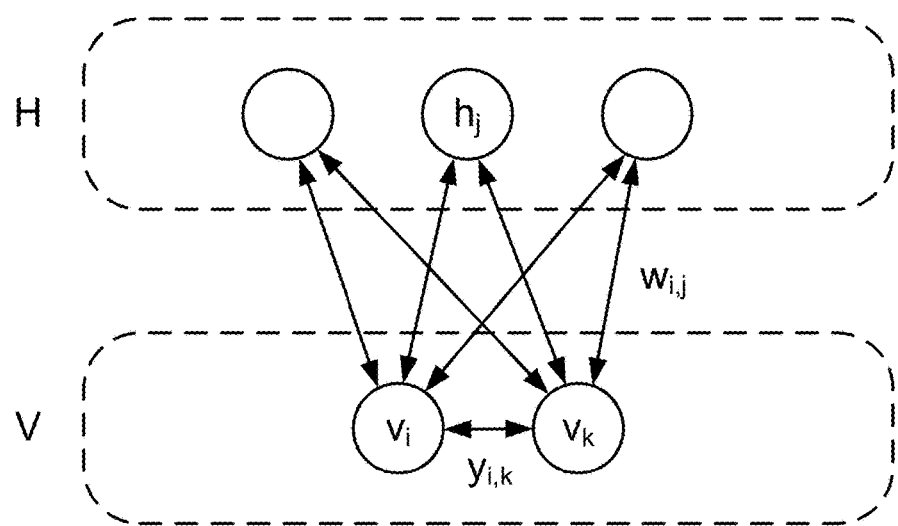

FIG. 183 shows one embodiment for added weights between visible units in an RBM.

Figure 184:
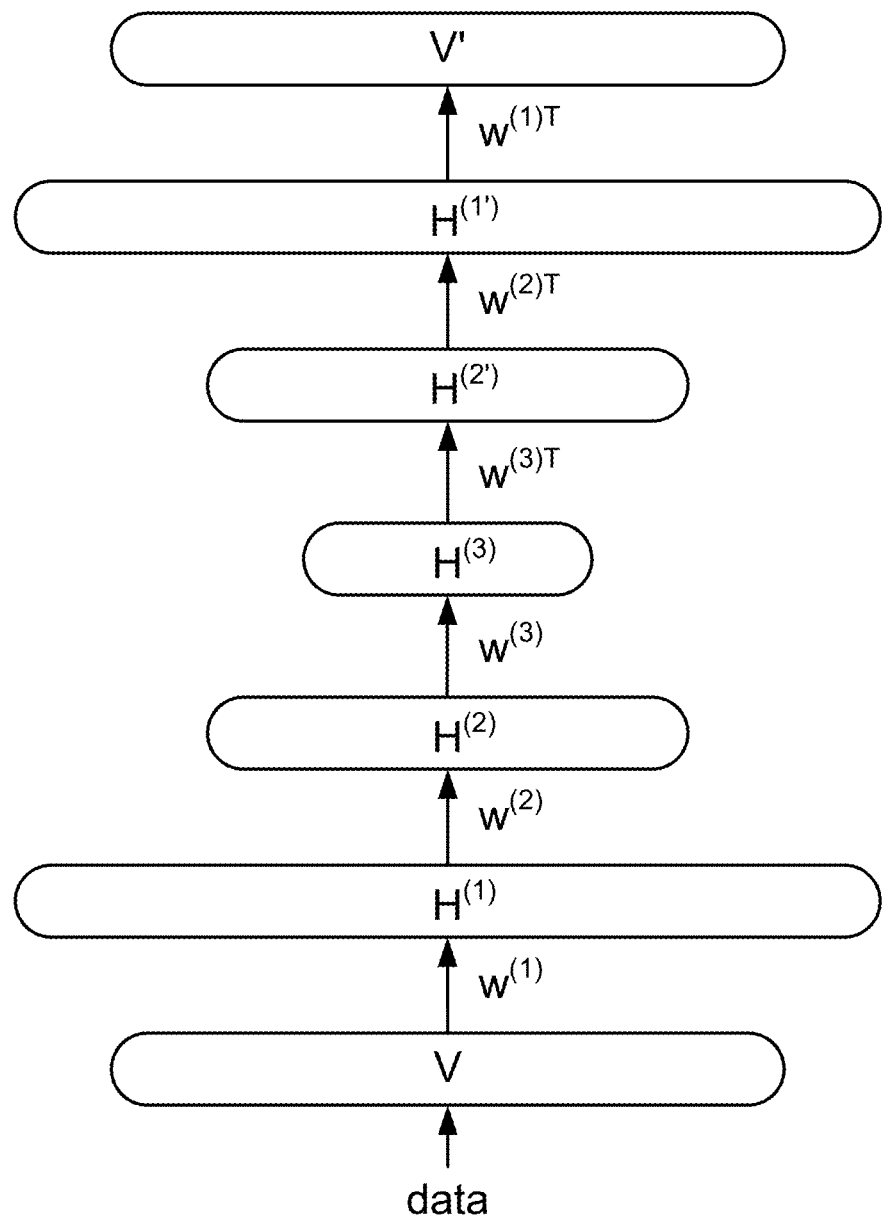

FIG. 184 shows one embodiment for a deep auto-encoder.

Figure 185:
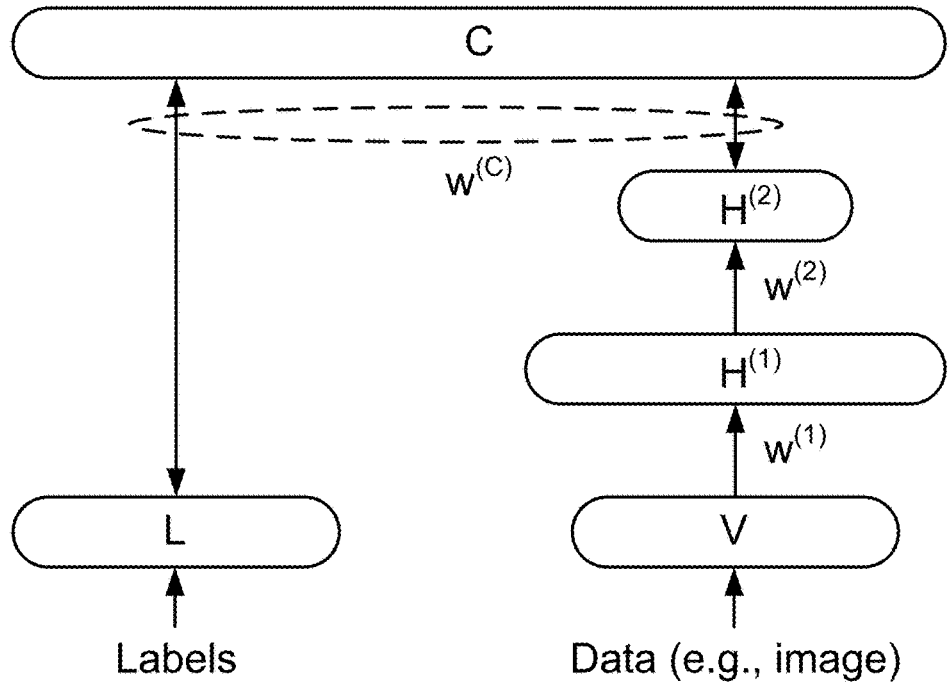

FIG. 185 shows one embodiment for correlation of labels with learned features.

Figure 186:
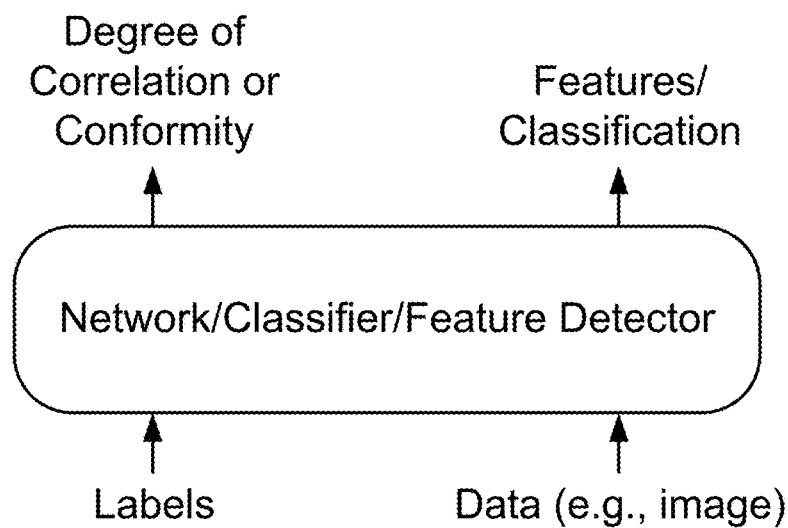

FIG. 186 shows one embodiment for degree of correlation or conformity from a network.

Figure 187:
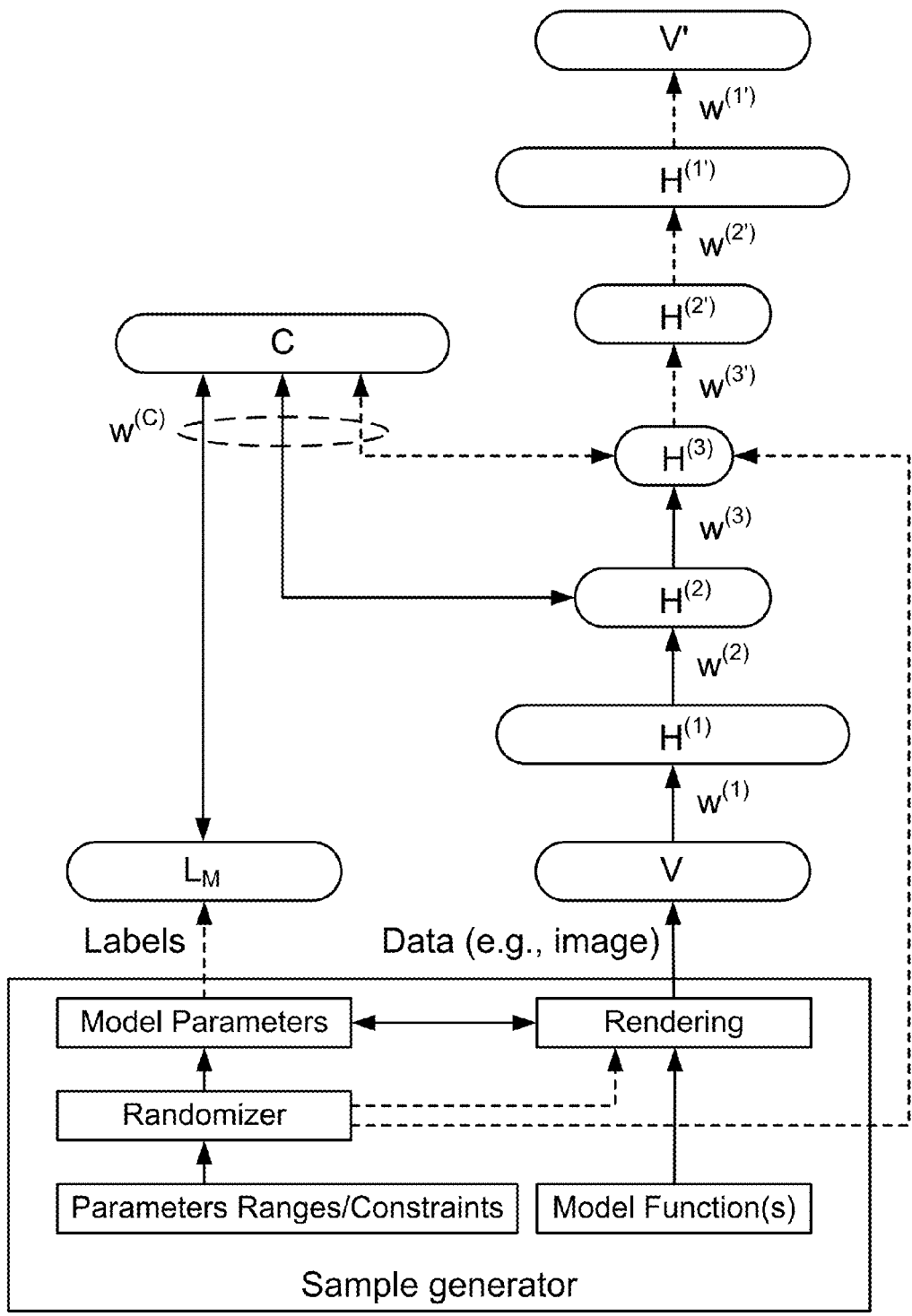
Figure 188:
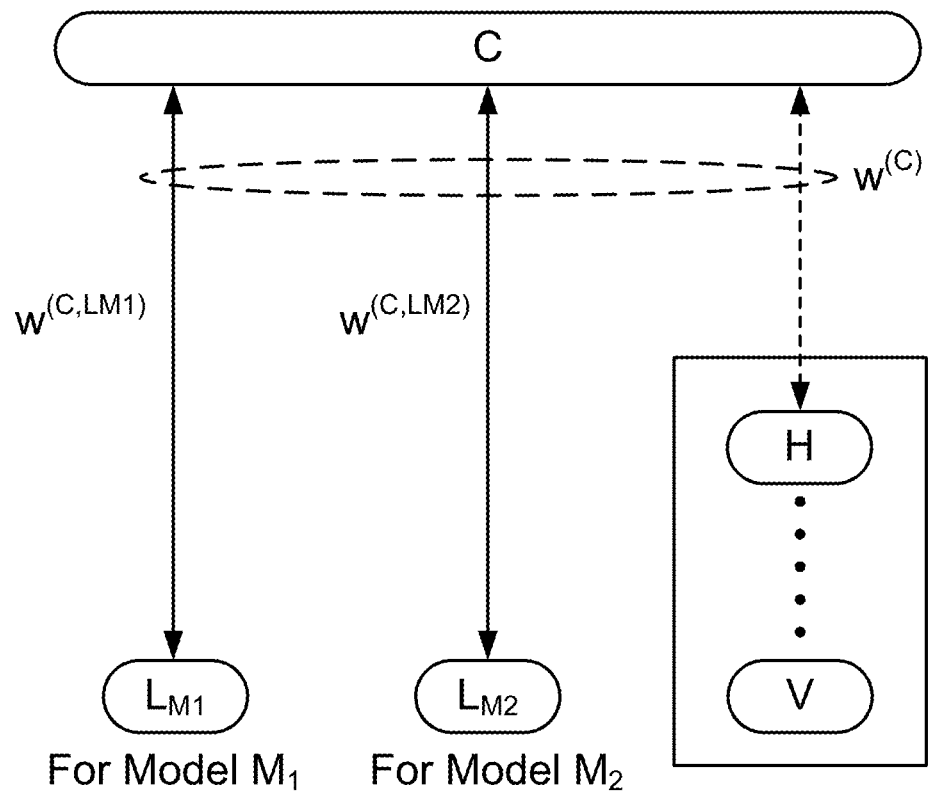

FIG. 187 shows one embodiment for sample/label generator from model, used for training FIG. 188 shows one embodiment for classifier with multiple label layers for different models.

Figure 189:
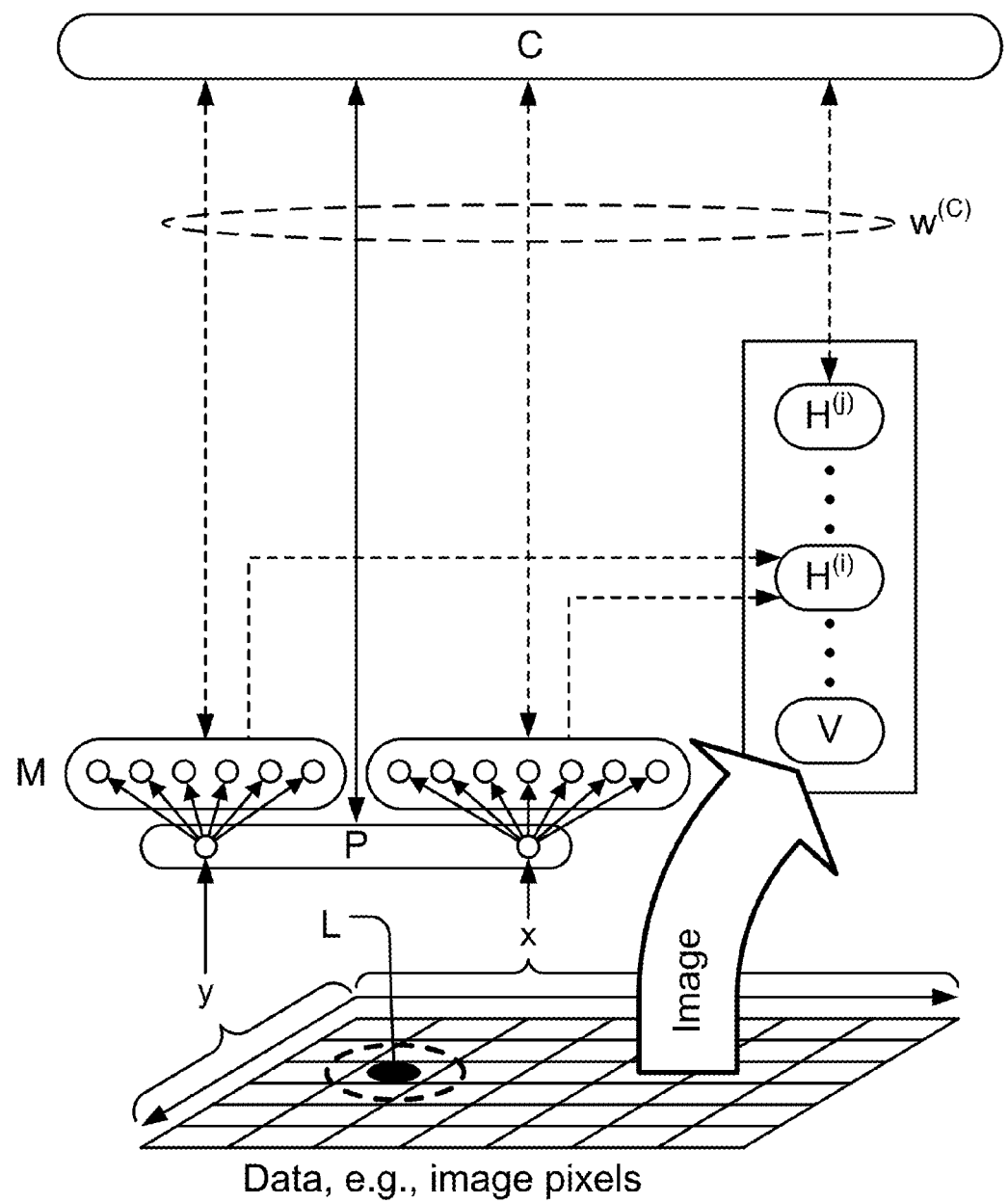

FIG. 189 shows one embodiment for correlation of position with features detected by the network.

Figure 190:
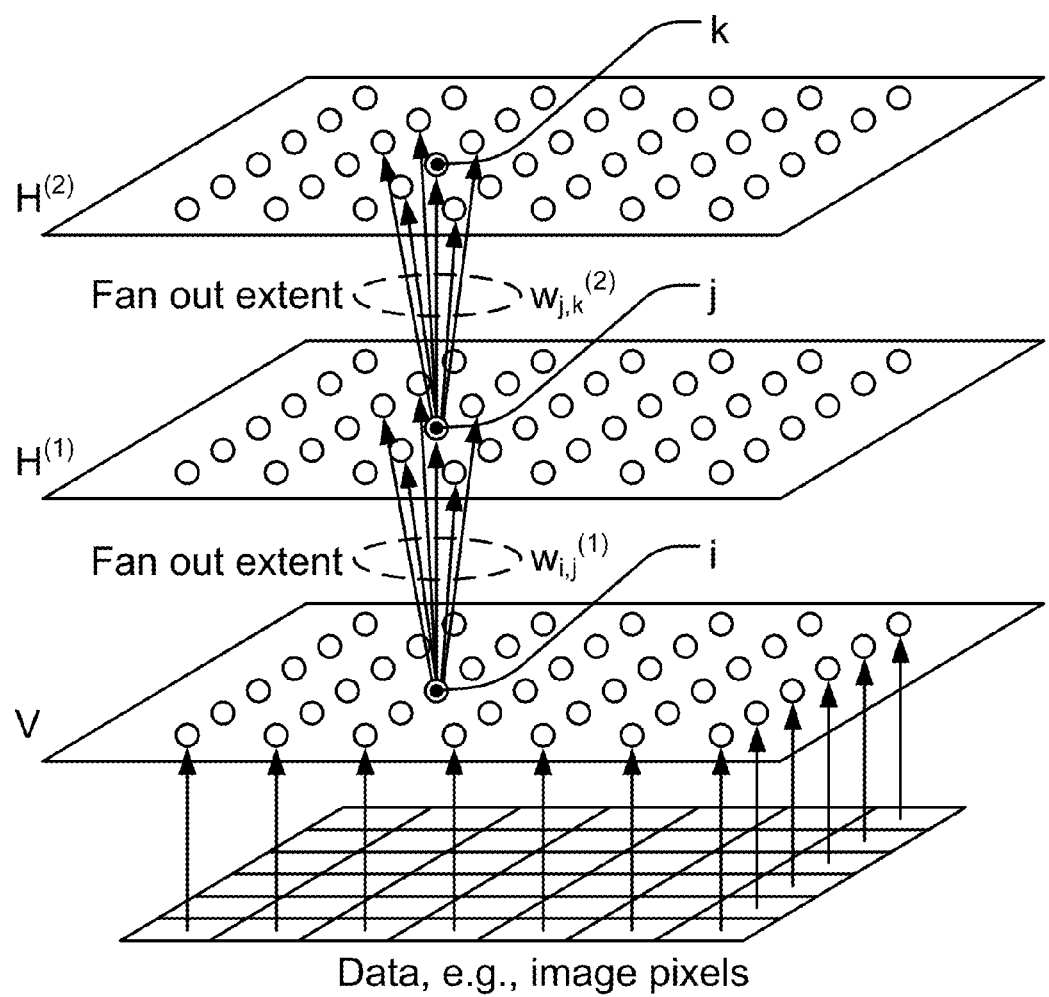

FIG. 190 shows one embodiment for inter-layer fan-out links.

Figure 191:
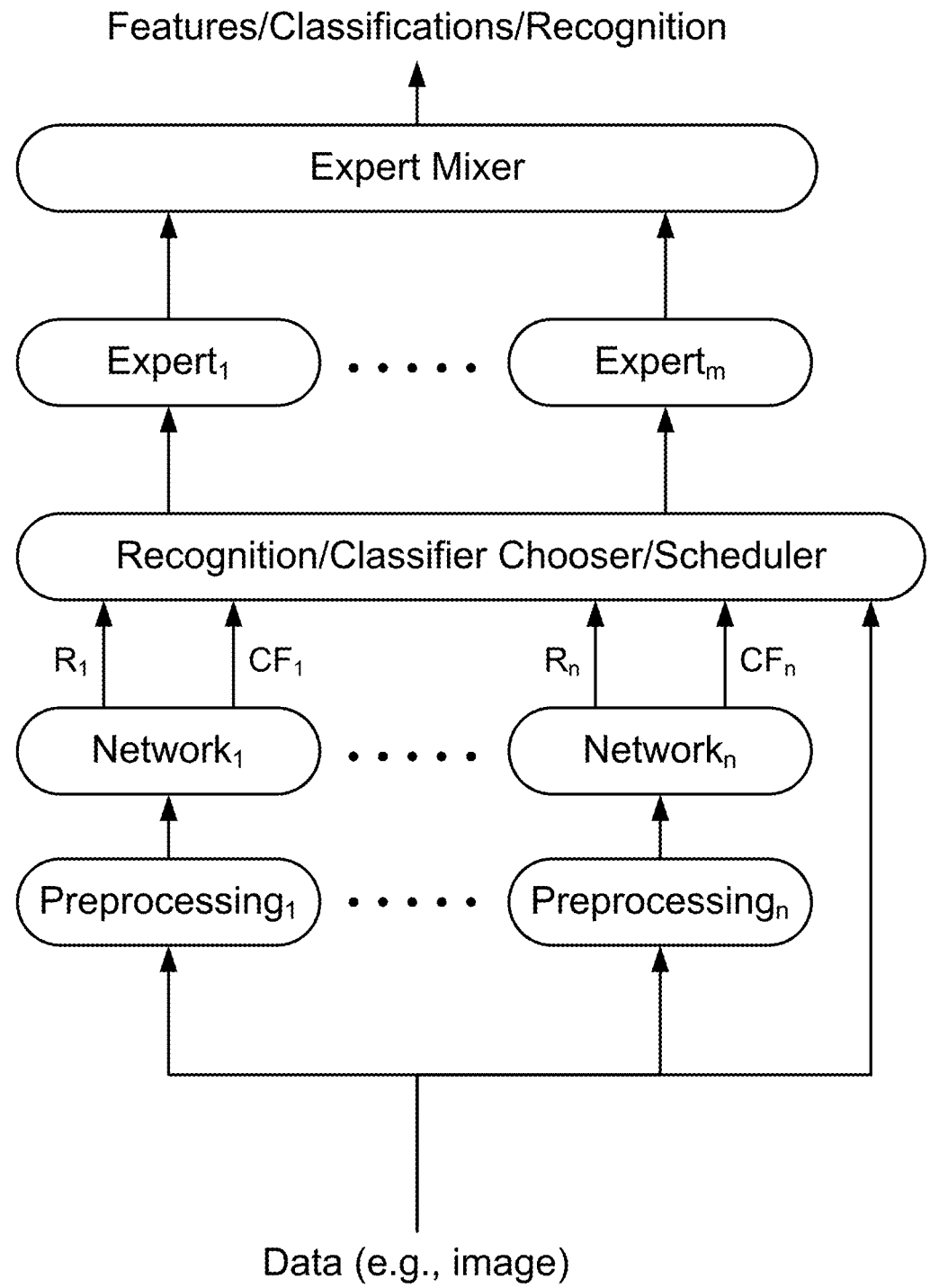

FIG. 191 shows one embodiment for selecting and mixing expert classifiers/feature detectors.

FIGS. 192 a-b show one embodiment for non-uniform segmentation of data.

Figure 193A:
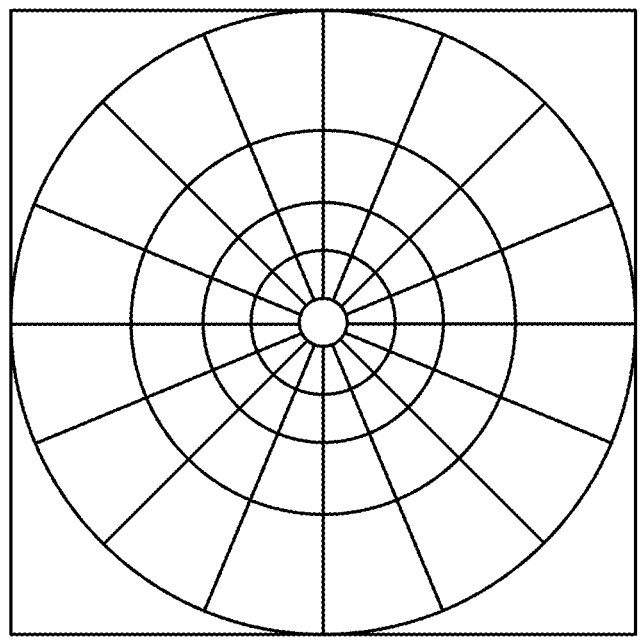
Figure 193B:
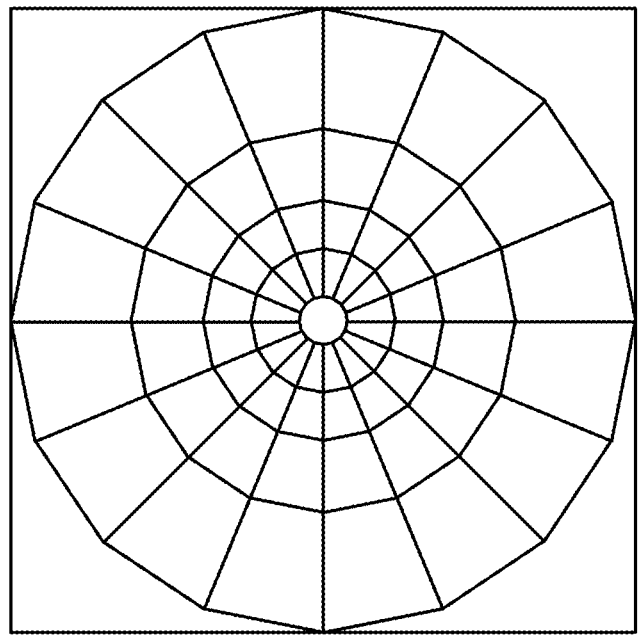

FIGS. 193 a-b show one embodiment for non-uniform radial segmentation of data.

Figure 194A:
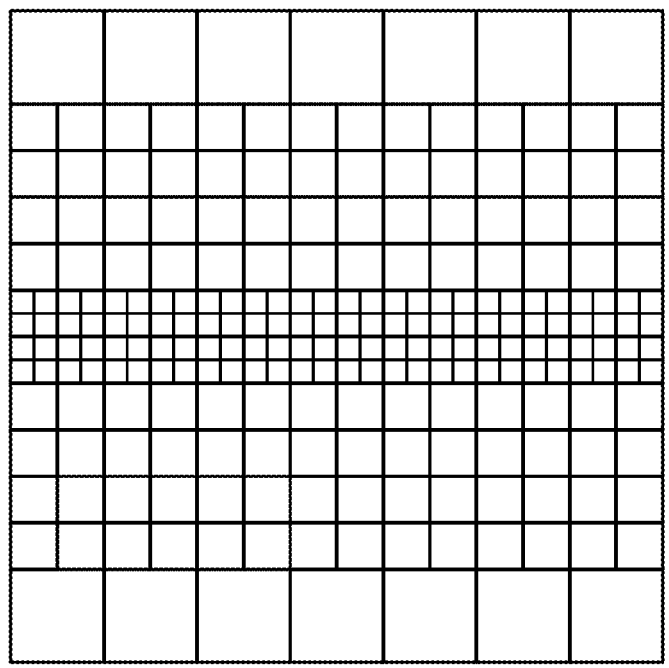
Figure 194B:
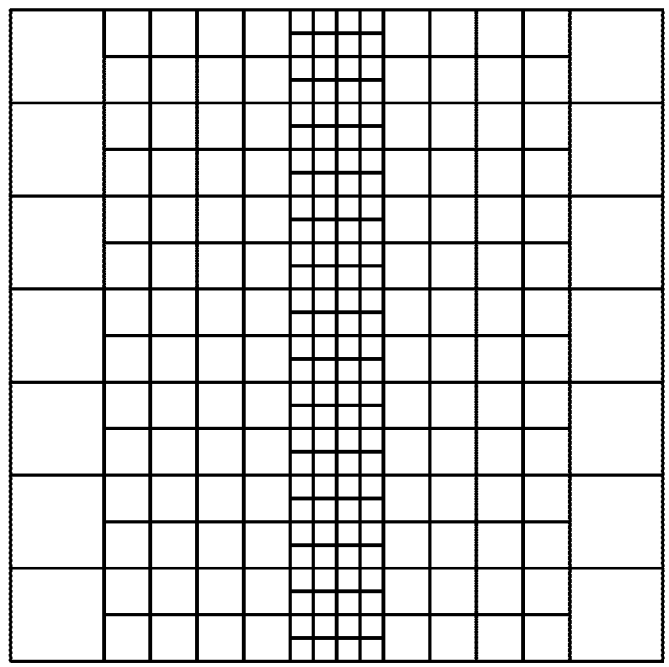

FIGS. 194 a-b show one embodiment for non-uniform segmentation in vertical and horizontal directions.

Figure 195A:
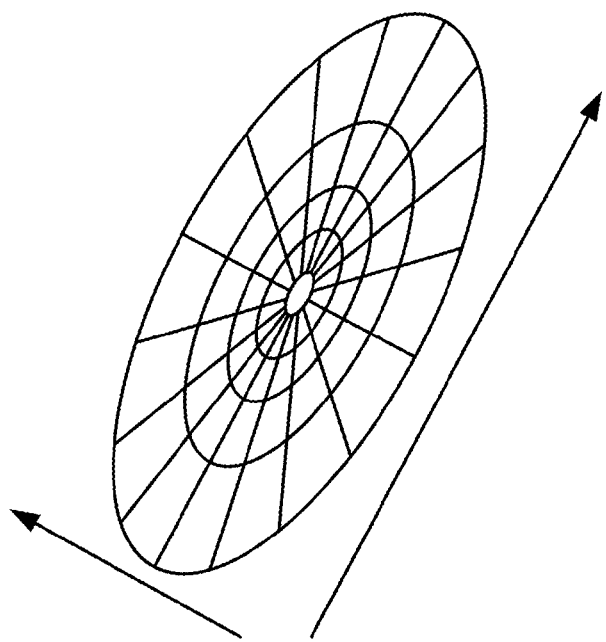
Figure 195B:
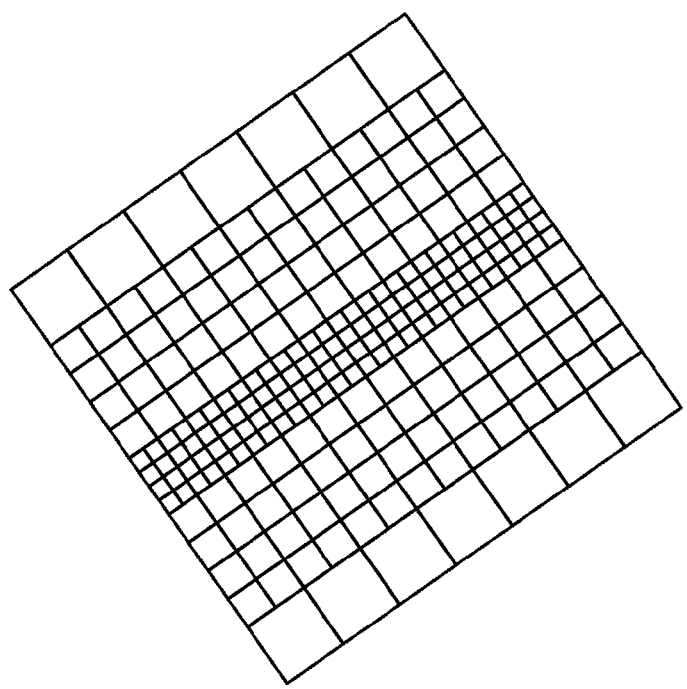

FIGS. 195 a-b show one embodiment for non-uniform transformed segmentation of data.

Figure 196:
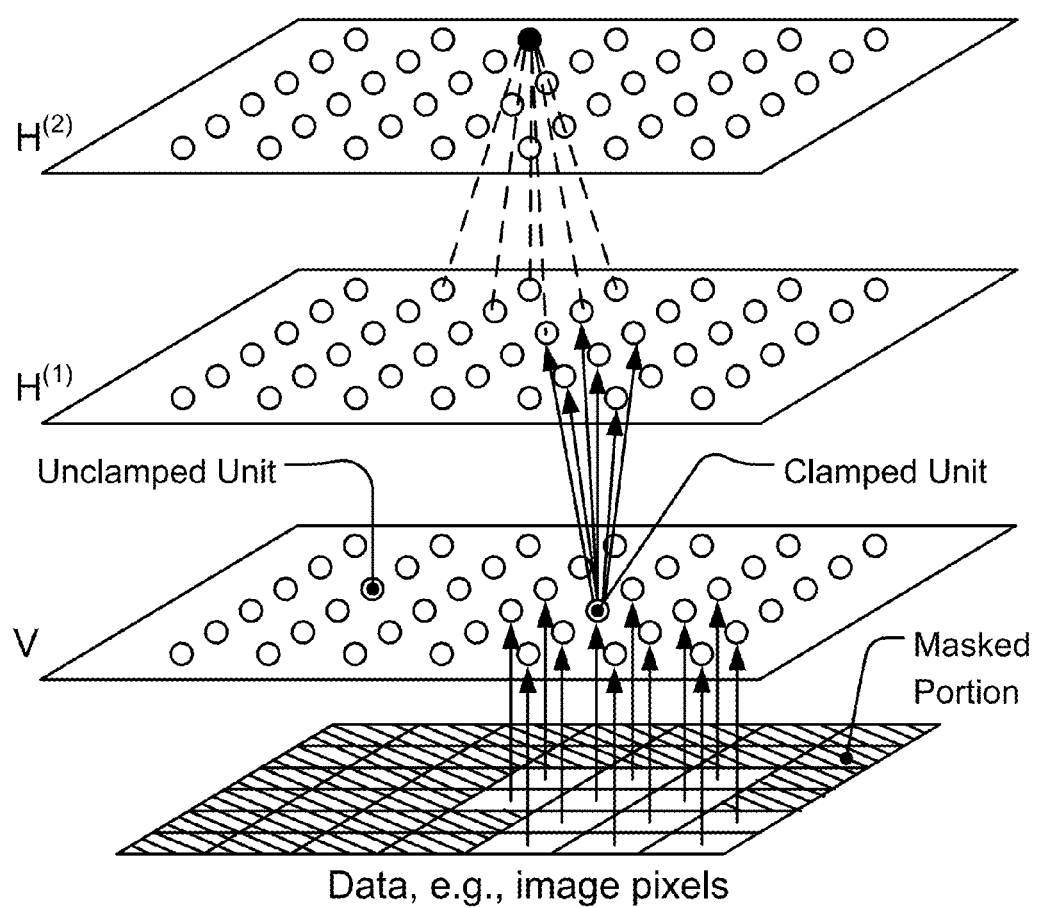

FIG. 196 shows one embodiment for clamping mask data to a network.

FIGS. 197 a, b, c show one embodiment for clamping thumbnail size data to network.

Figure 198:
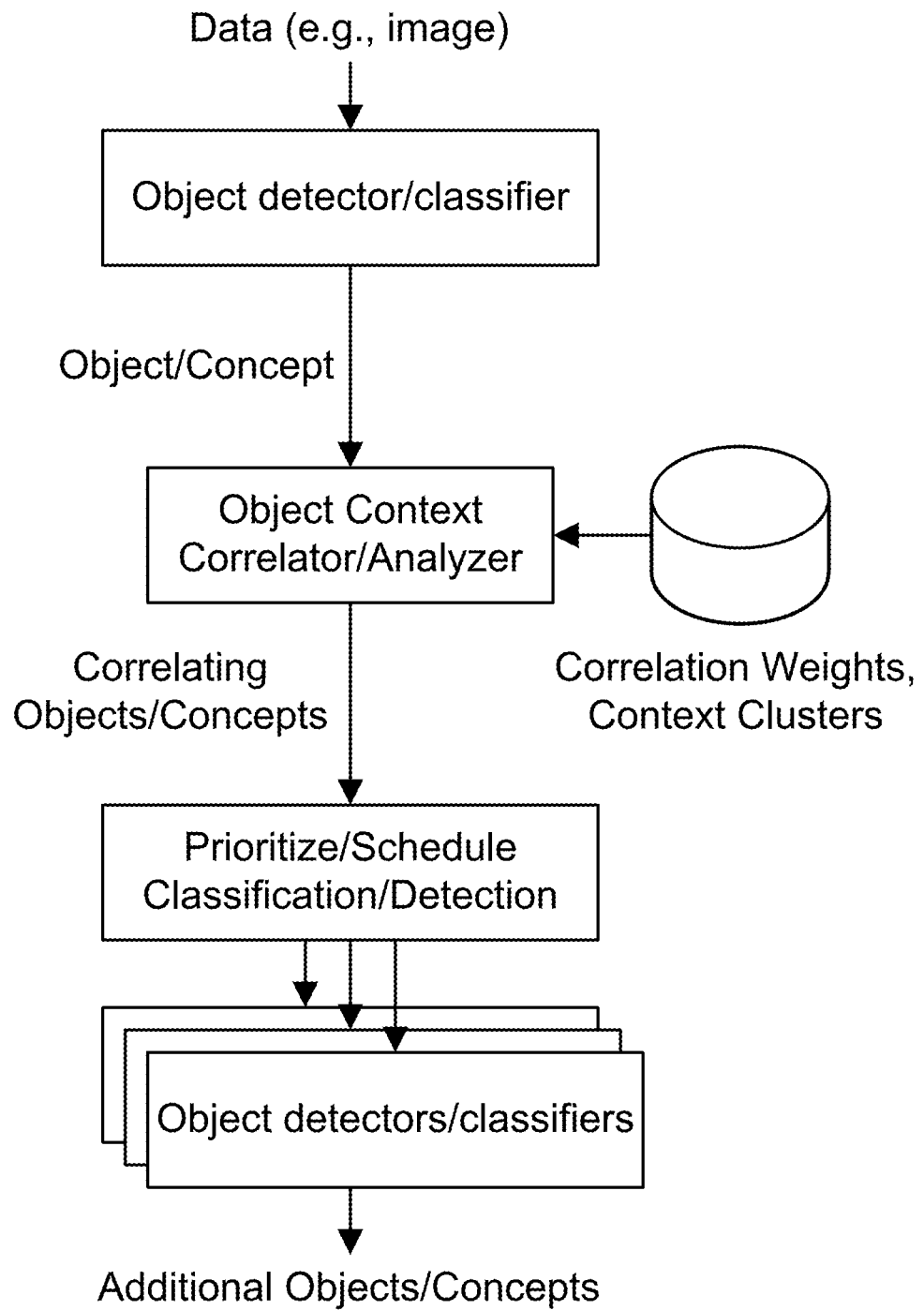

FIG. 198 shows one embodiment for search for correlating objects and concepts.

Figure 199A:
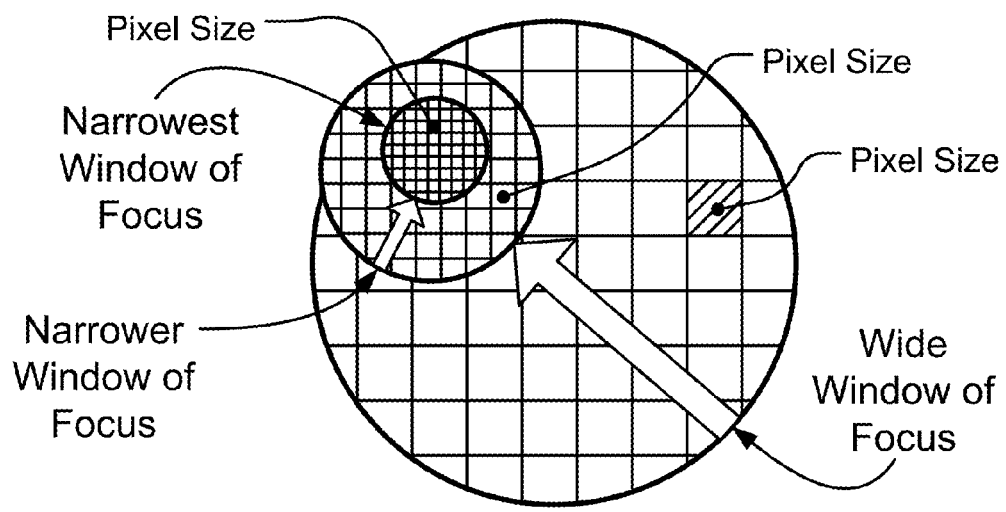
Figure 199B:
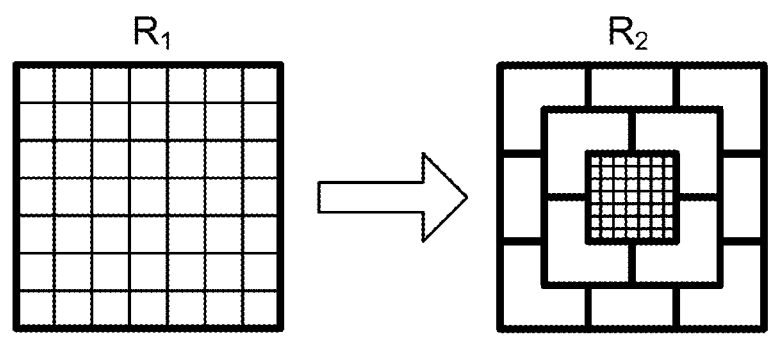

FIGS. 199 a-b show one embodiment for variable field of focus, with varying resolution.

Figure 200:
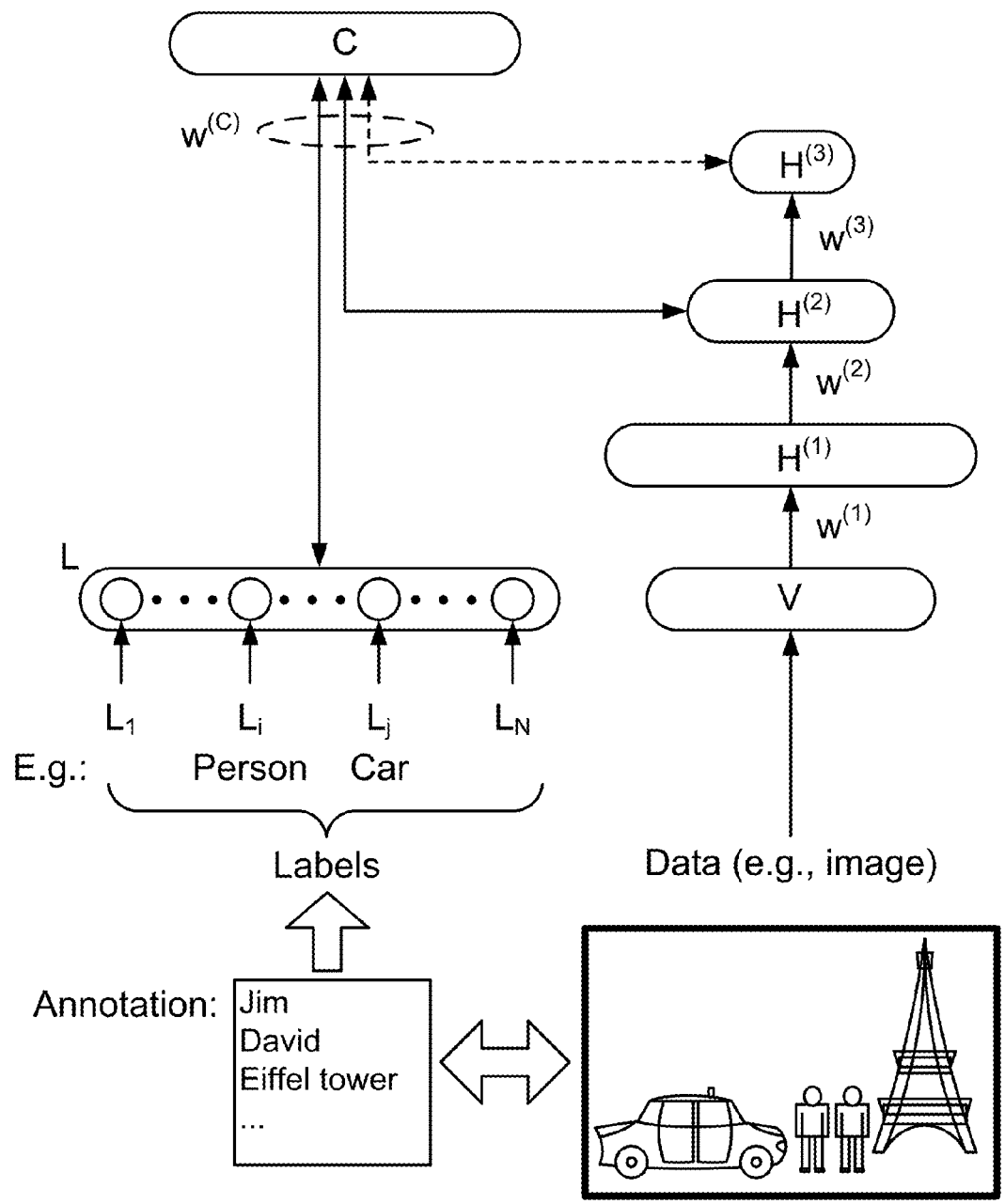

FIG. 200 shows one embodiment for learning via partially or mixed labeled training sets.

Figure 201:
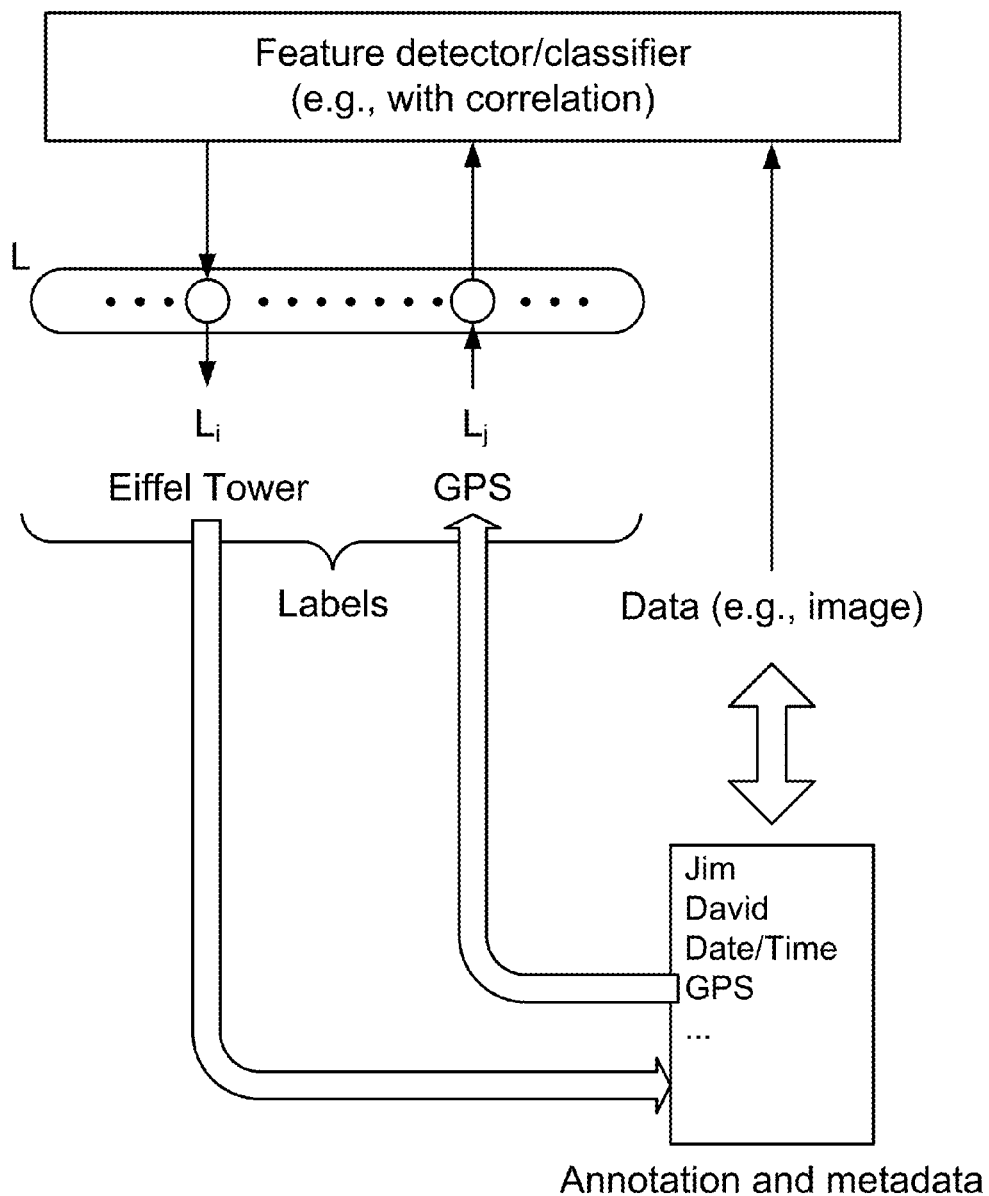

FIG. 201 shows one embodiment for learning correlations between labels for auto-annotation.

Figure 202:
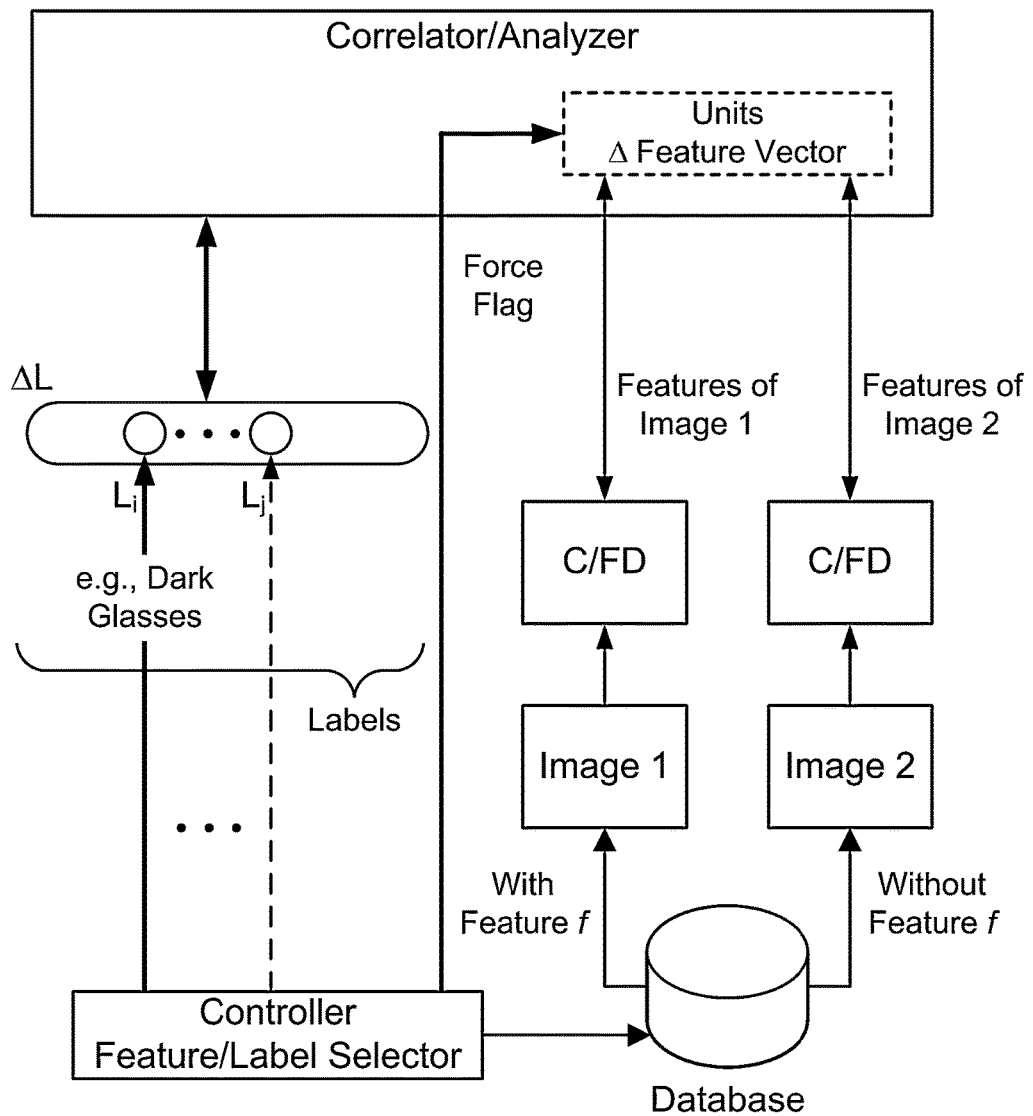

FIG. 202 shows one embodiment for correlation between blocking and blocked features, using labels.

Figure 203:
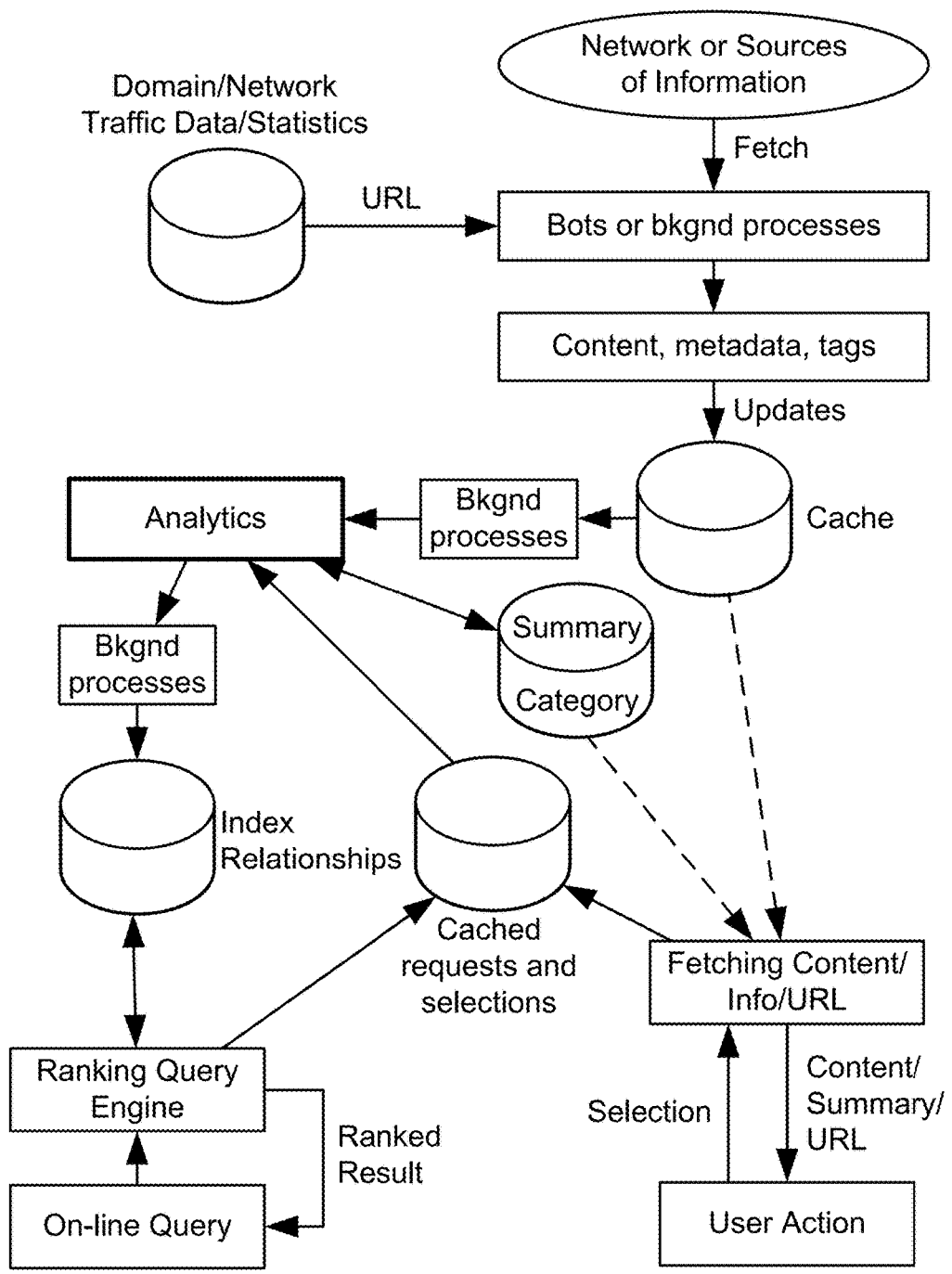

FIG. 203 shows one embodiment for indexing on search system.

FIGS. 204 a-b show one embodiment for (a) factored weights in higher order Boltzmann machine, and (b) CRBM for detection and learning from data series.

FIGS. 205 a, b, c show one embodiment for (a) variable frame size with CRBM, (b) mapping to a previous frame, and (c) mapping from a previous frame to a dynamic mean.

Figure 206:
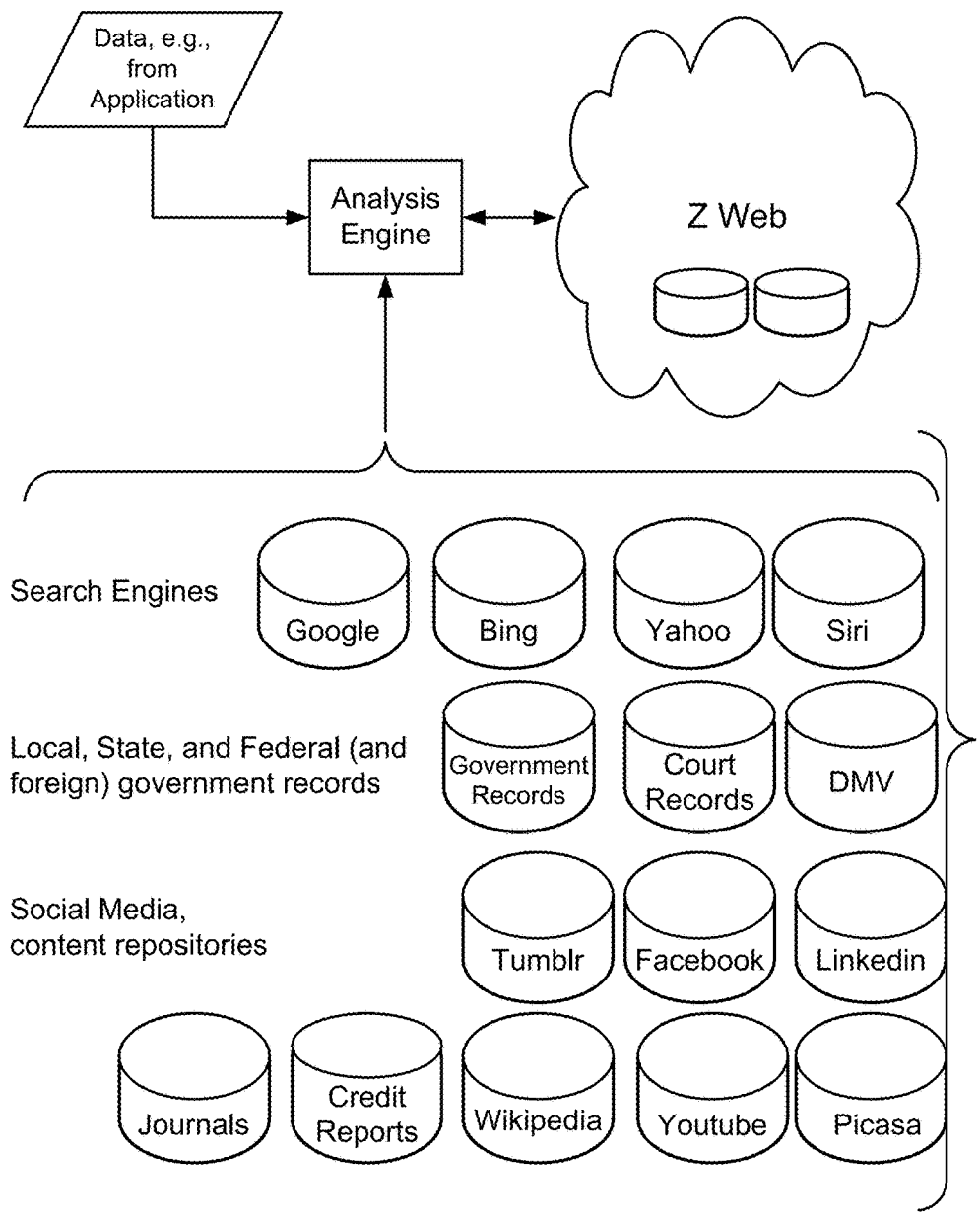

FIG. 206 shows an embodiment for Z web.

Figure 207:
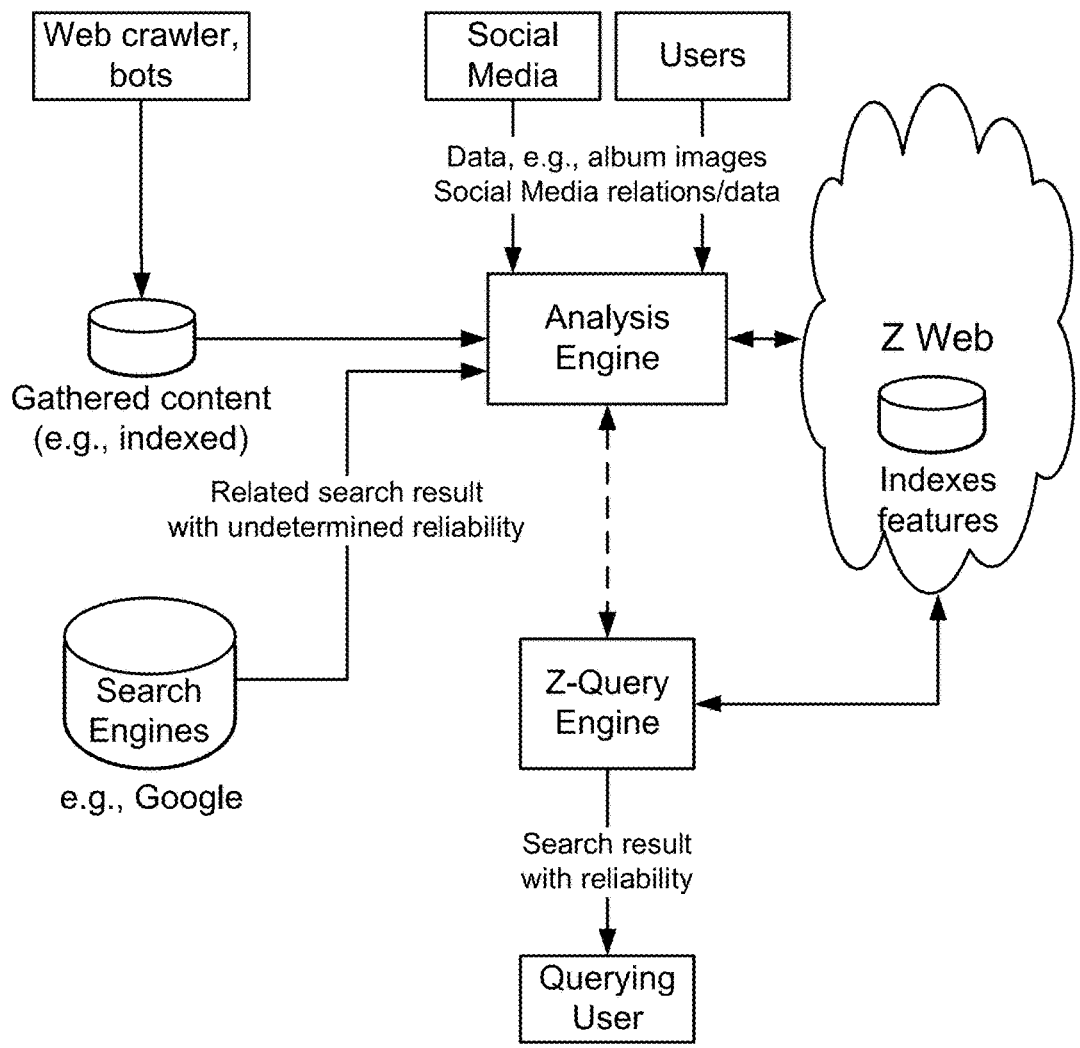

FIG. 207 shows an embodiment for Z web.

Figure 208:
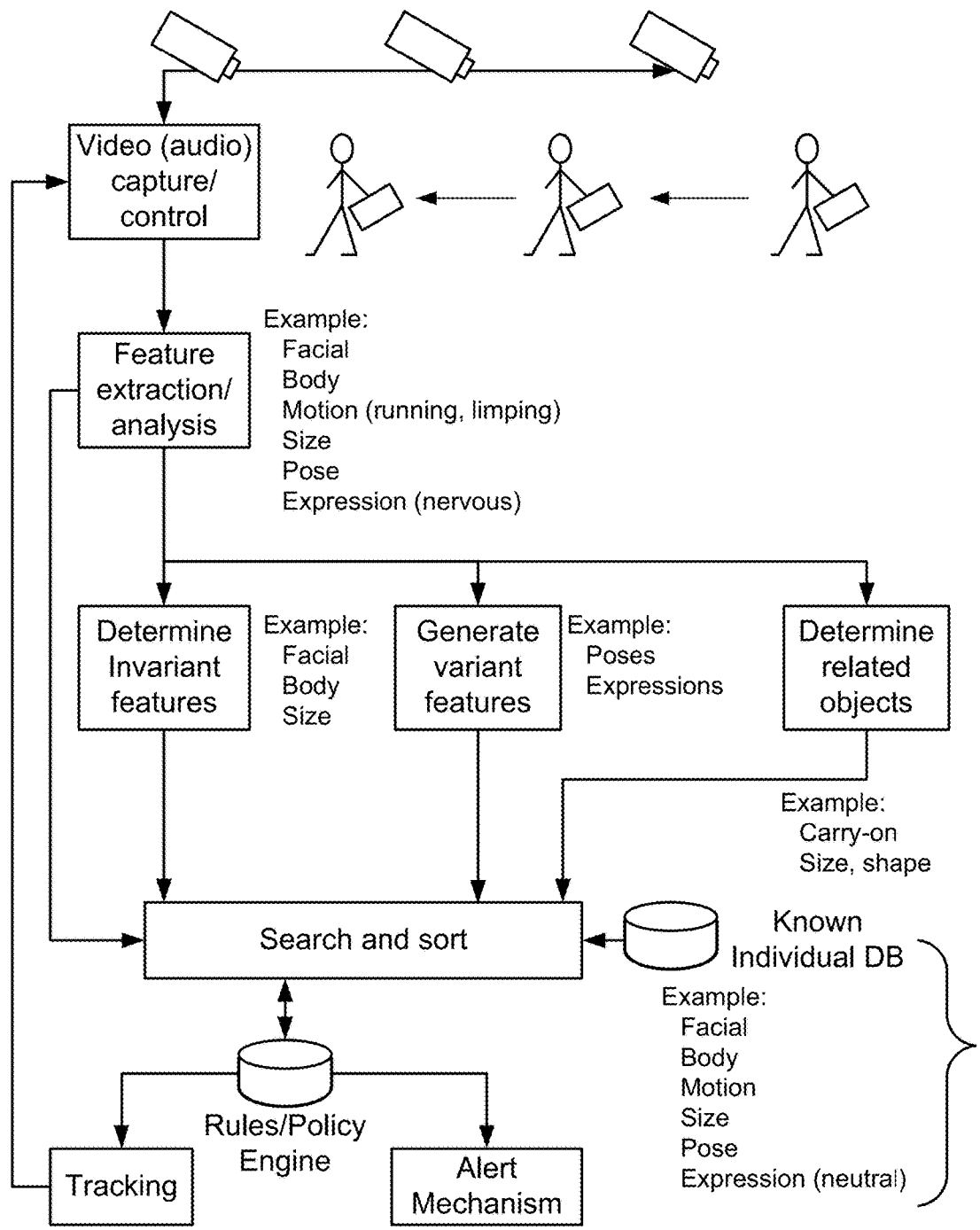

FIG. 208 shows an embodiment for video capture.

Figure 209:
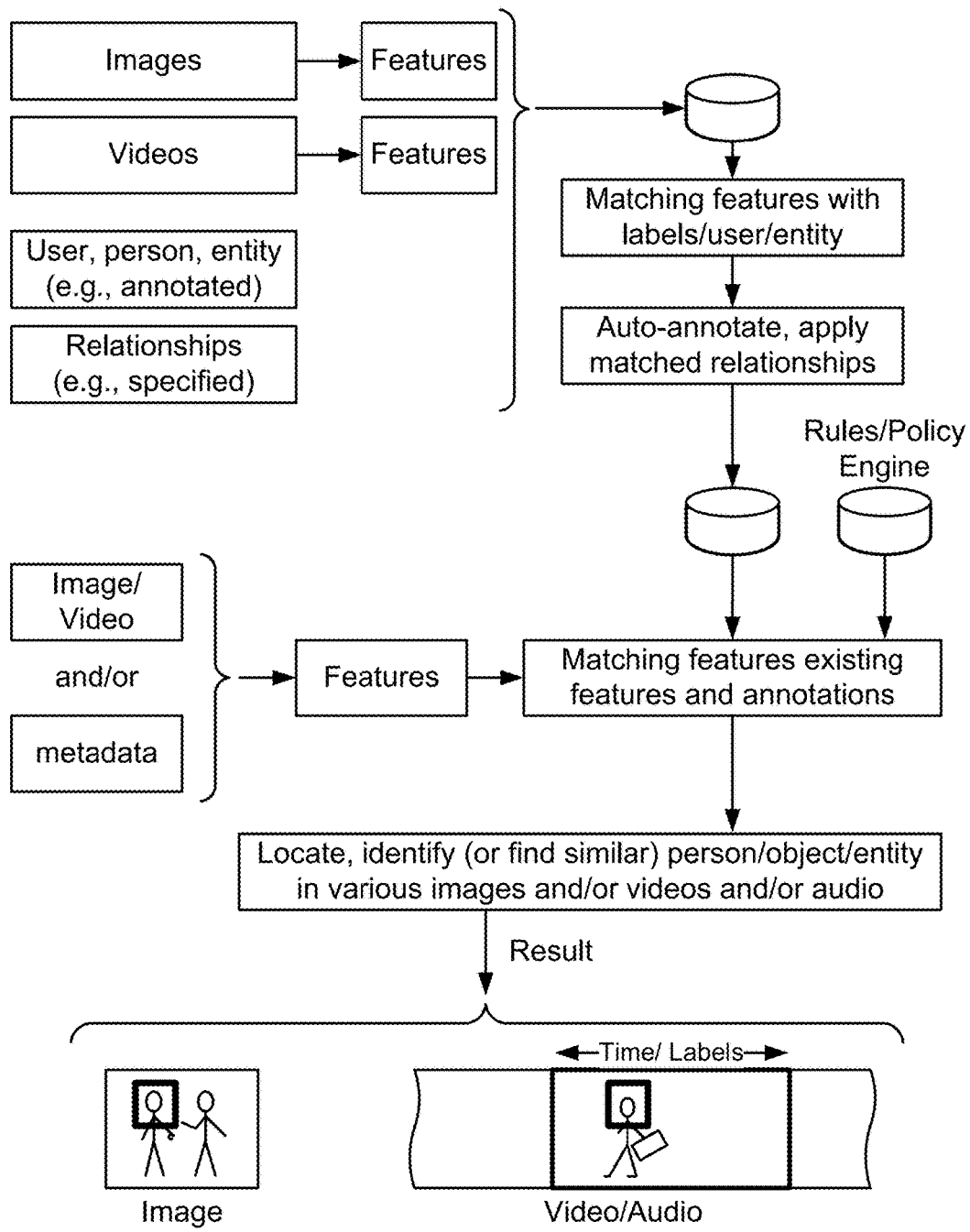

FIG. 209 shows an embodiment for video capture.

Figure 210:
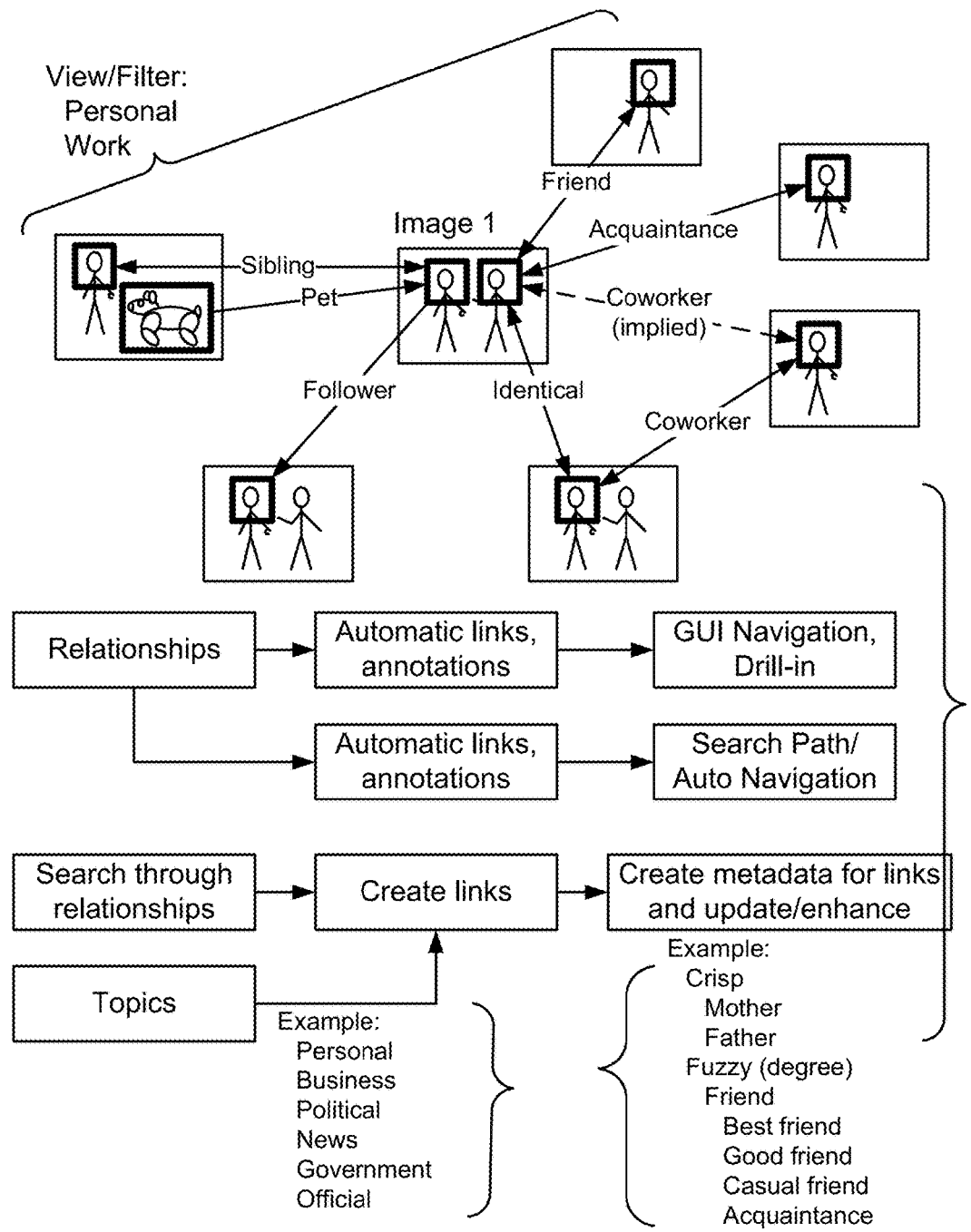

FIG. 210 shows an embodiment for image relations.

Figure 211:
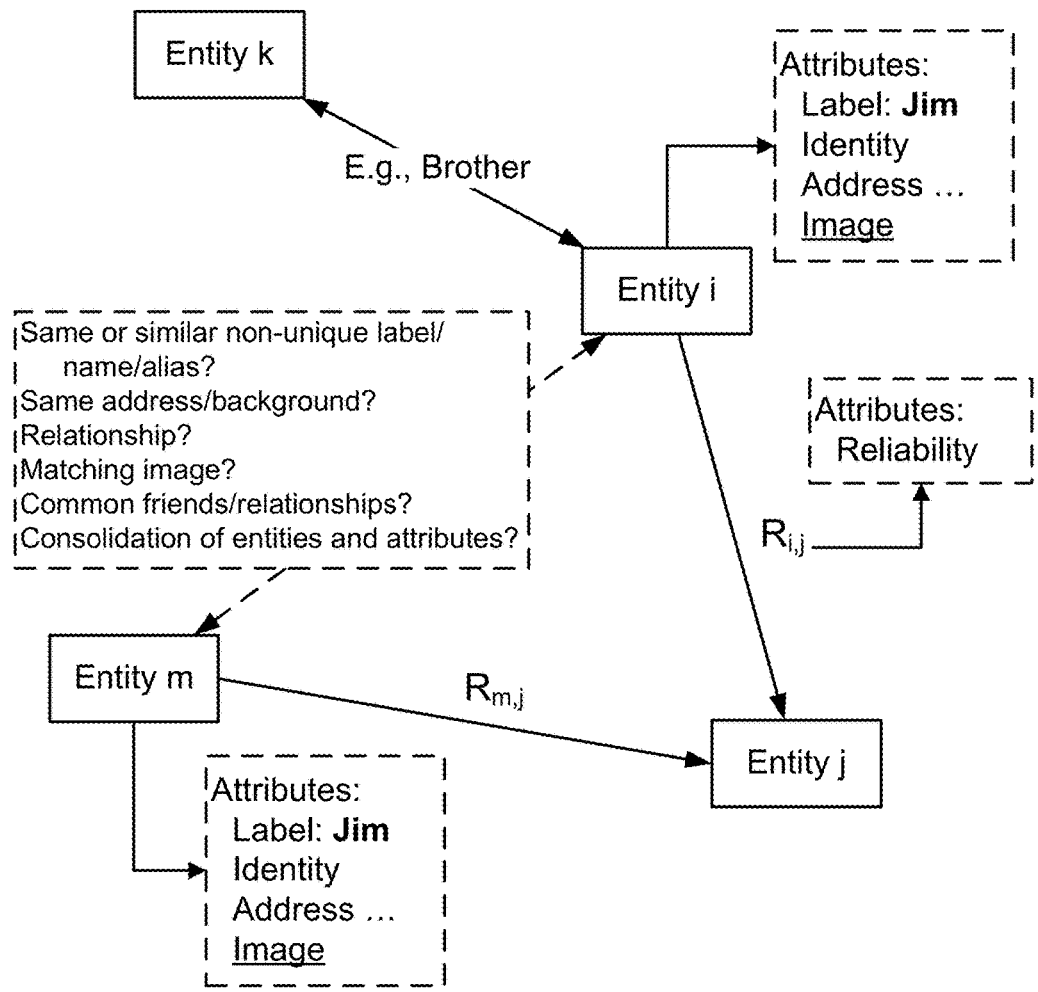

FIG. 211 shows an embodiment for entities.

Figure 212:
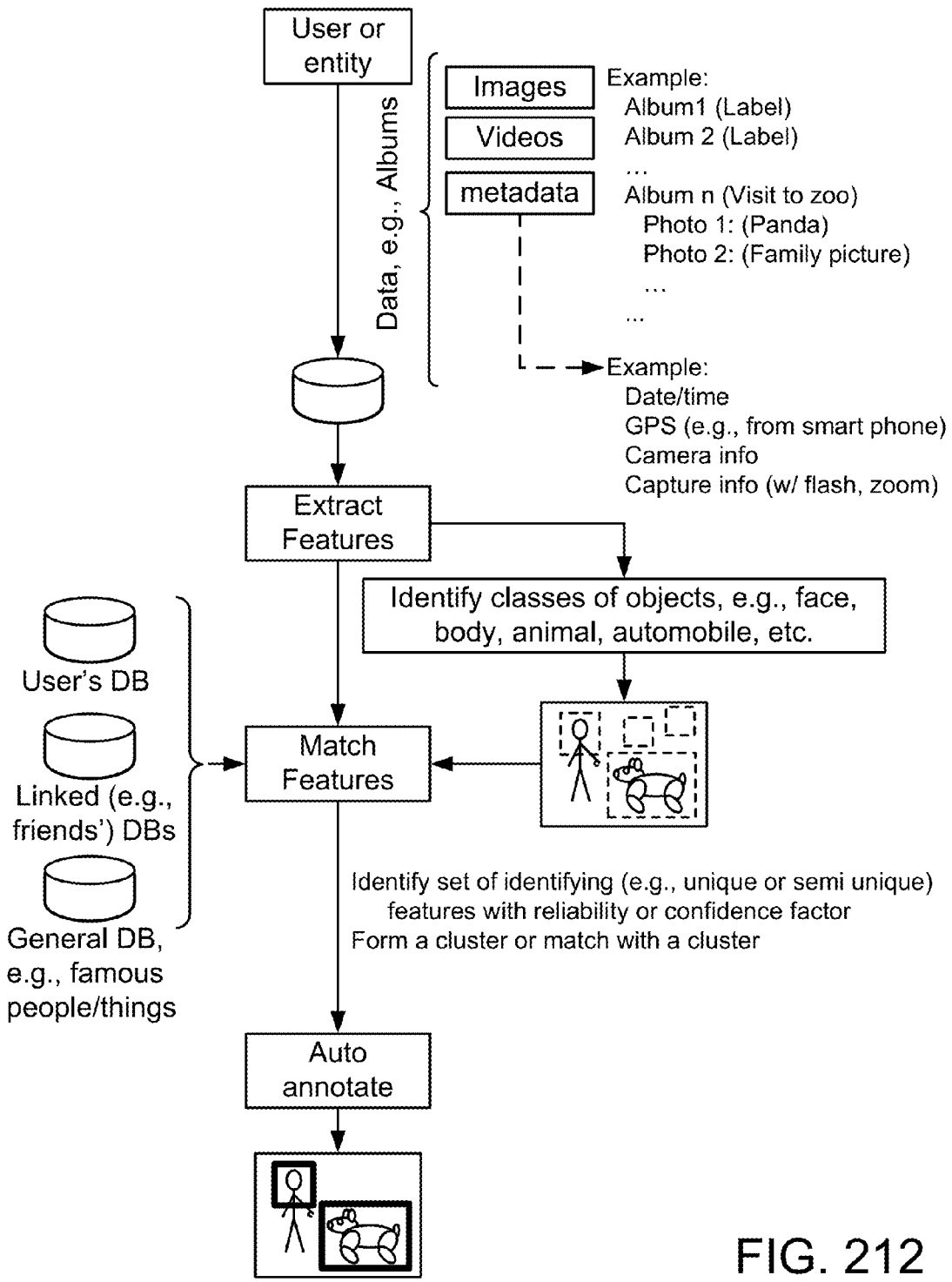

FIG. 212 shows an embodiment for matching.

Figure 213:
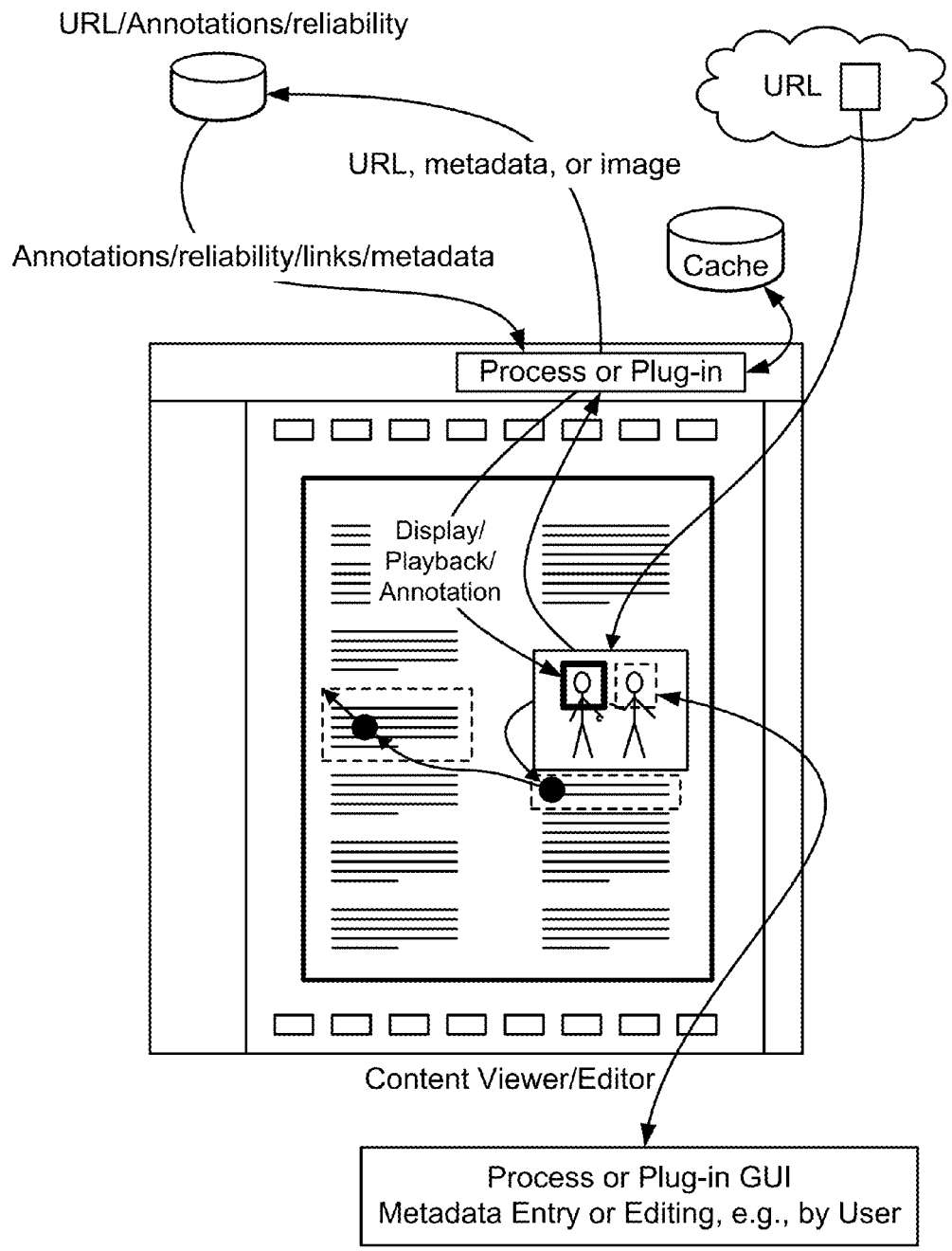

FIG. 213 shows an embodiment for URL and plug-in.

Figure 214:
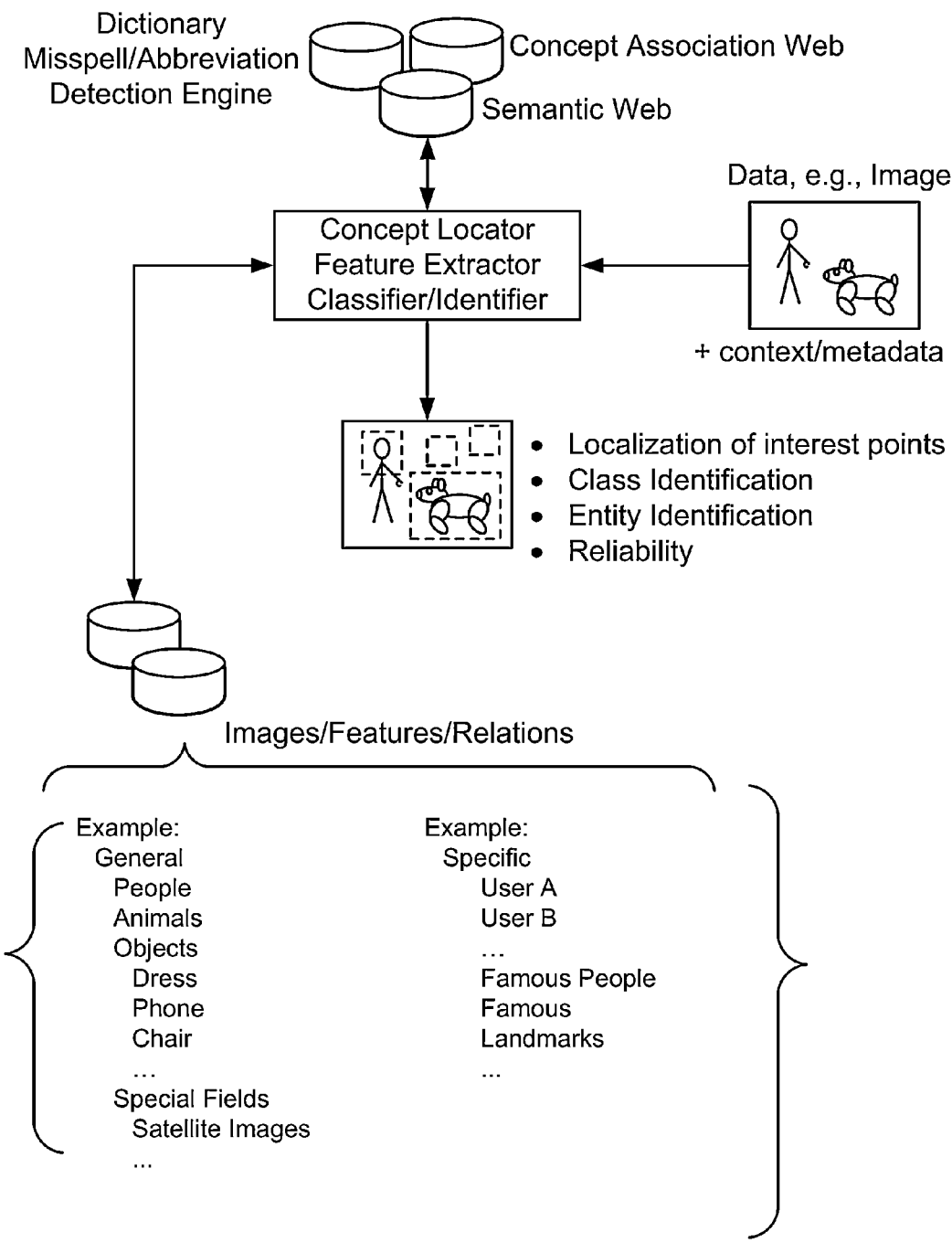

FIG. 214 shows an embodiment for image features.

Figure 215:
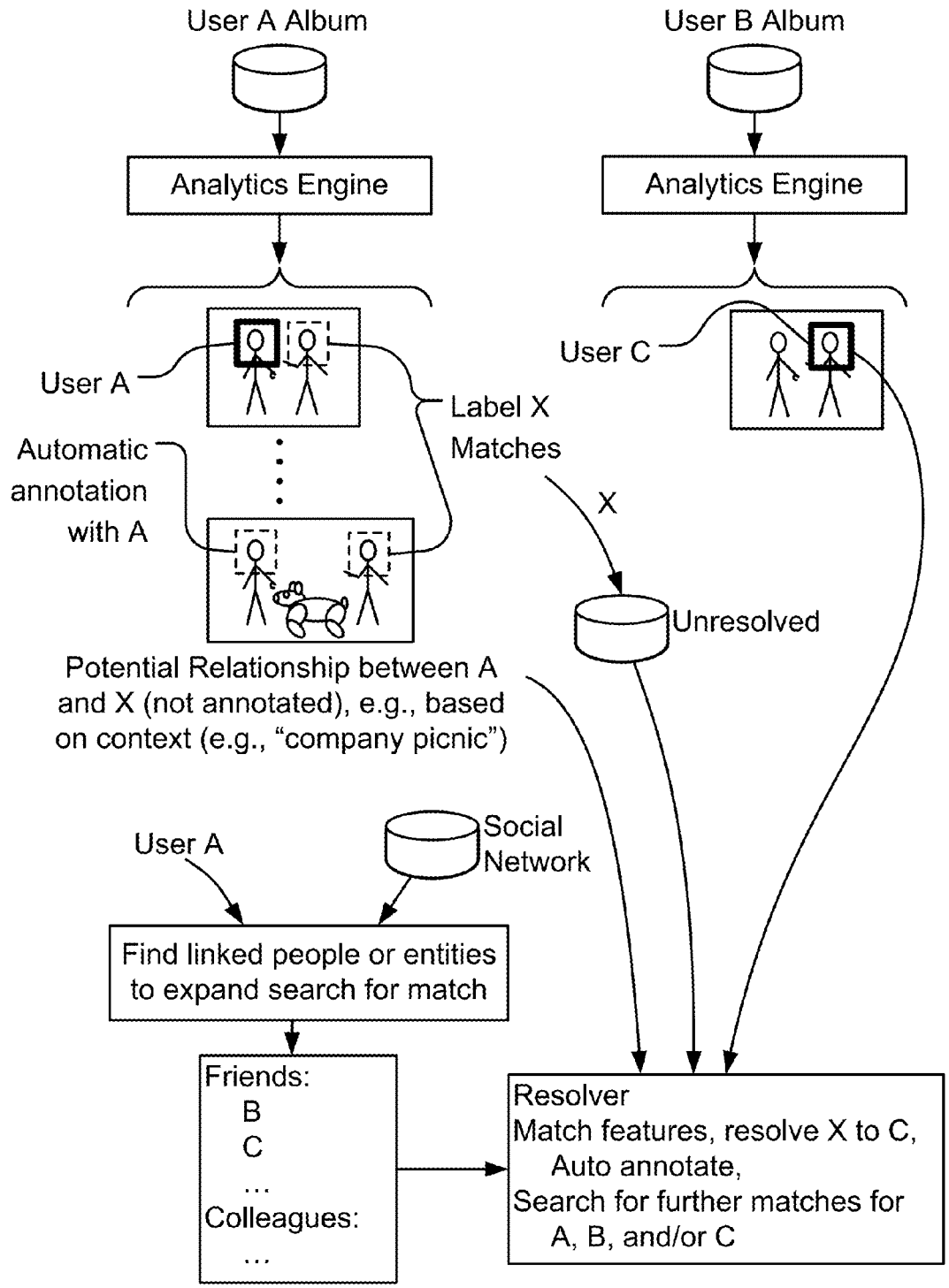

FIG. 215 shows an embodiment for analytics.

Figure 216:
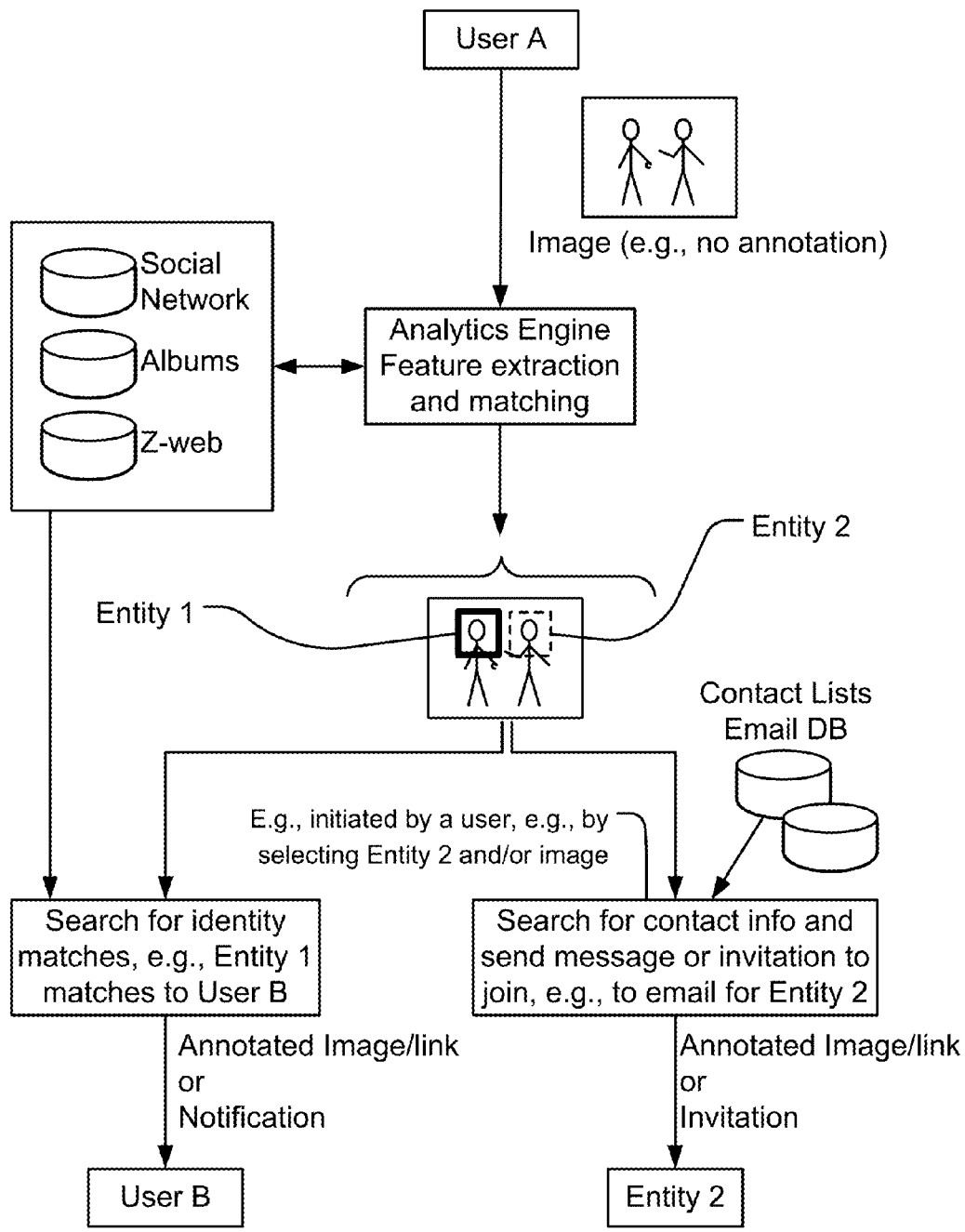

FIG. 216 shows an embodiment for analytics.

Figure 217:
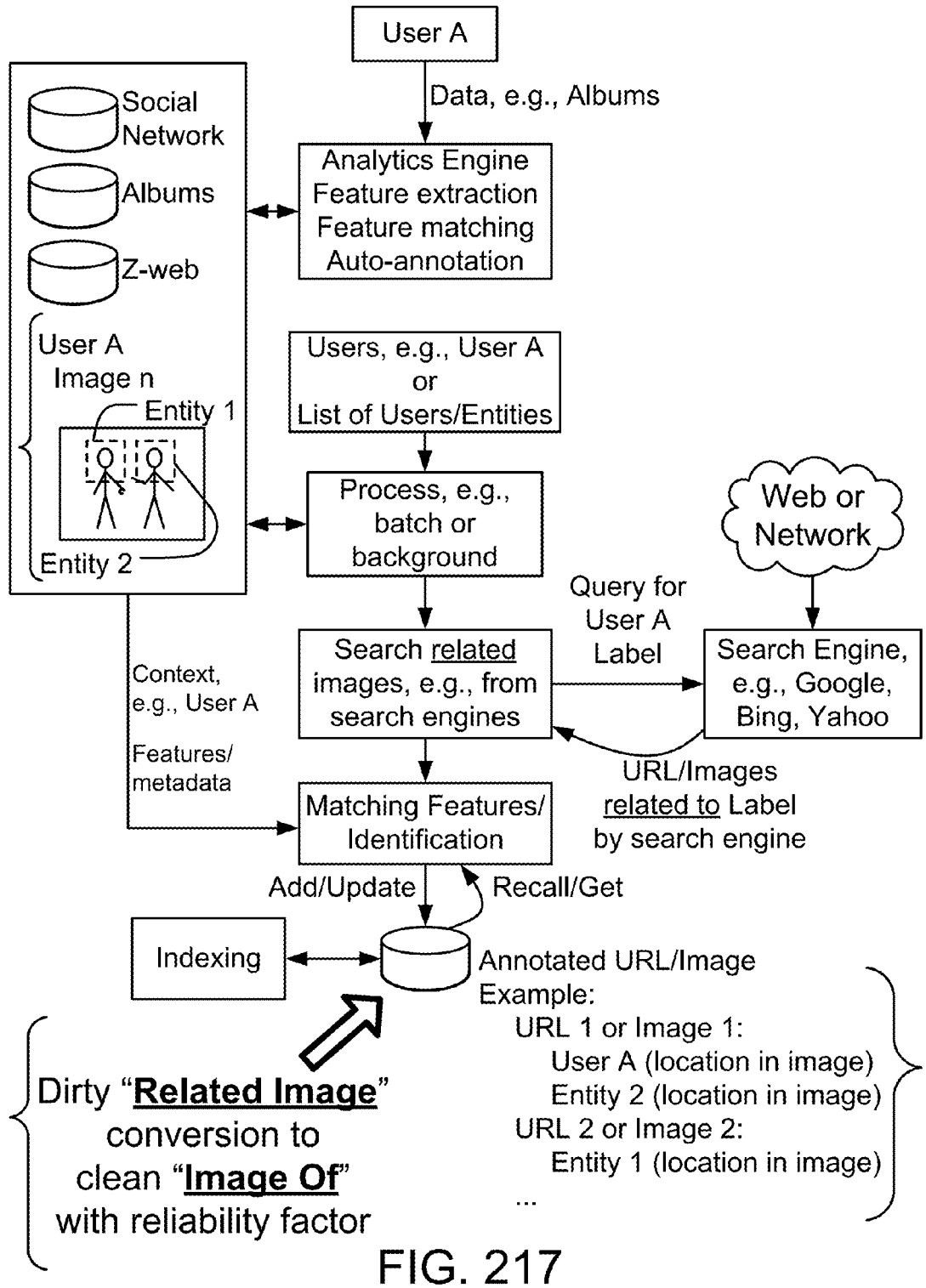

FIG. 217 shows an embodiment for analytics.

Figure 218:
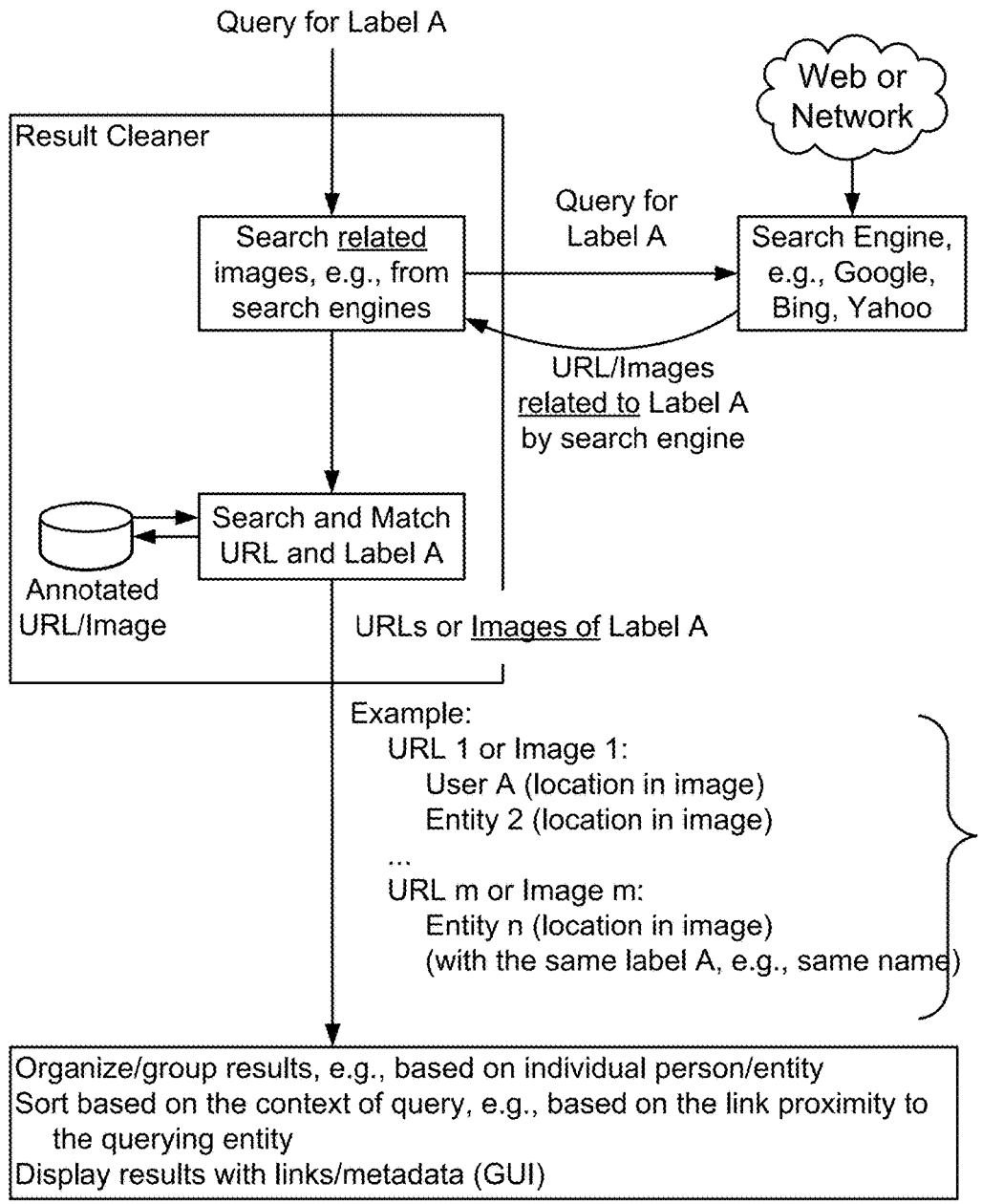

FIG. 218 shows an embodiment for search.

Figure 219:
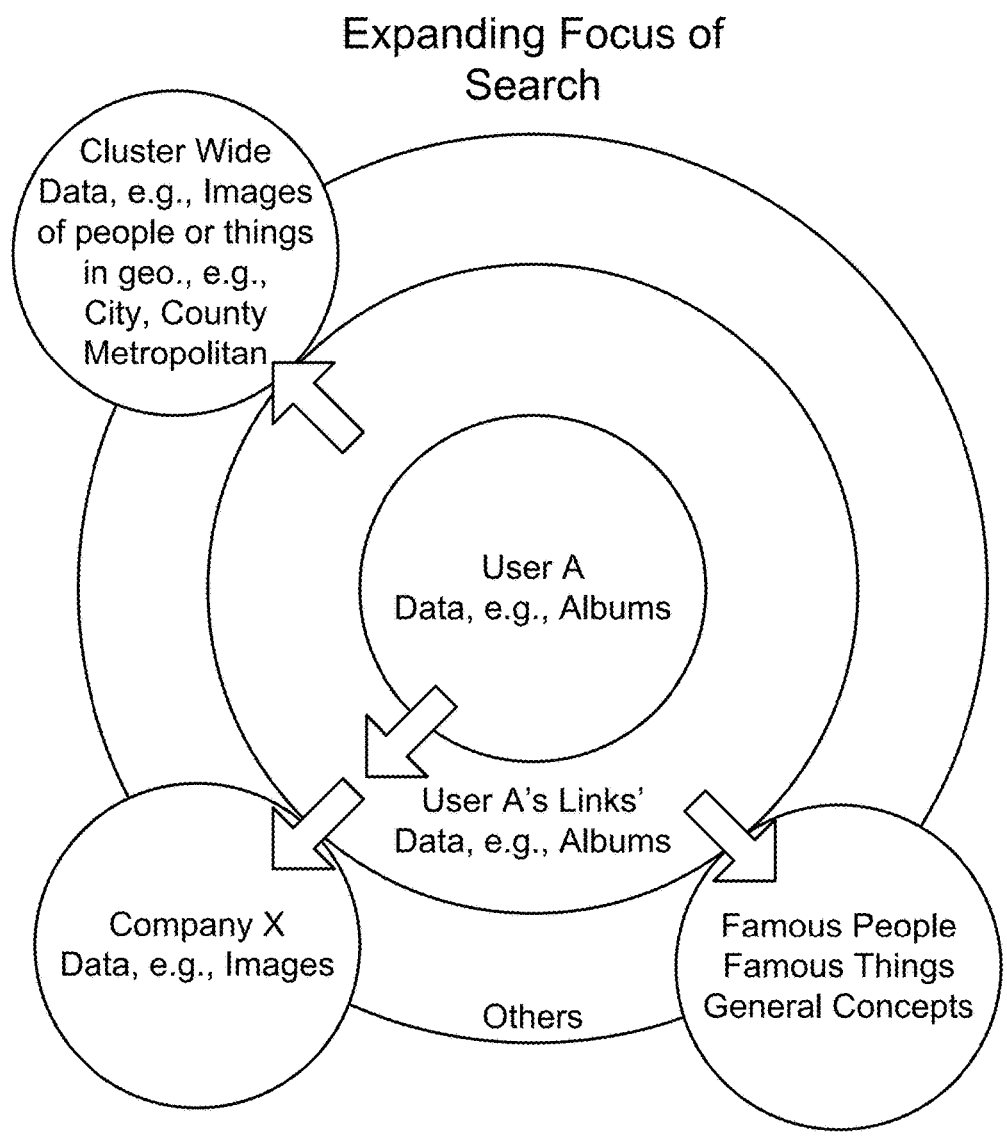

FIG. 219 shows an embodiment for search.

Figure 220:
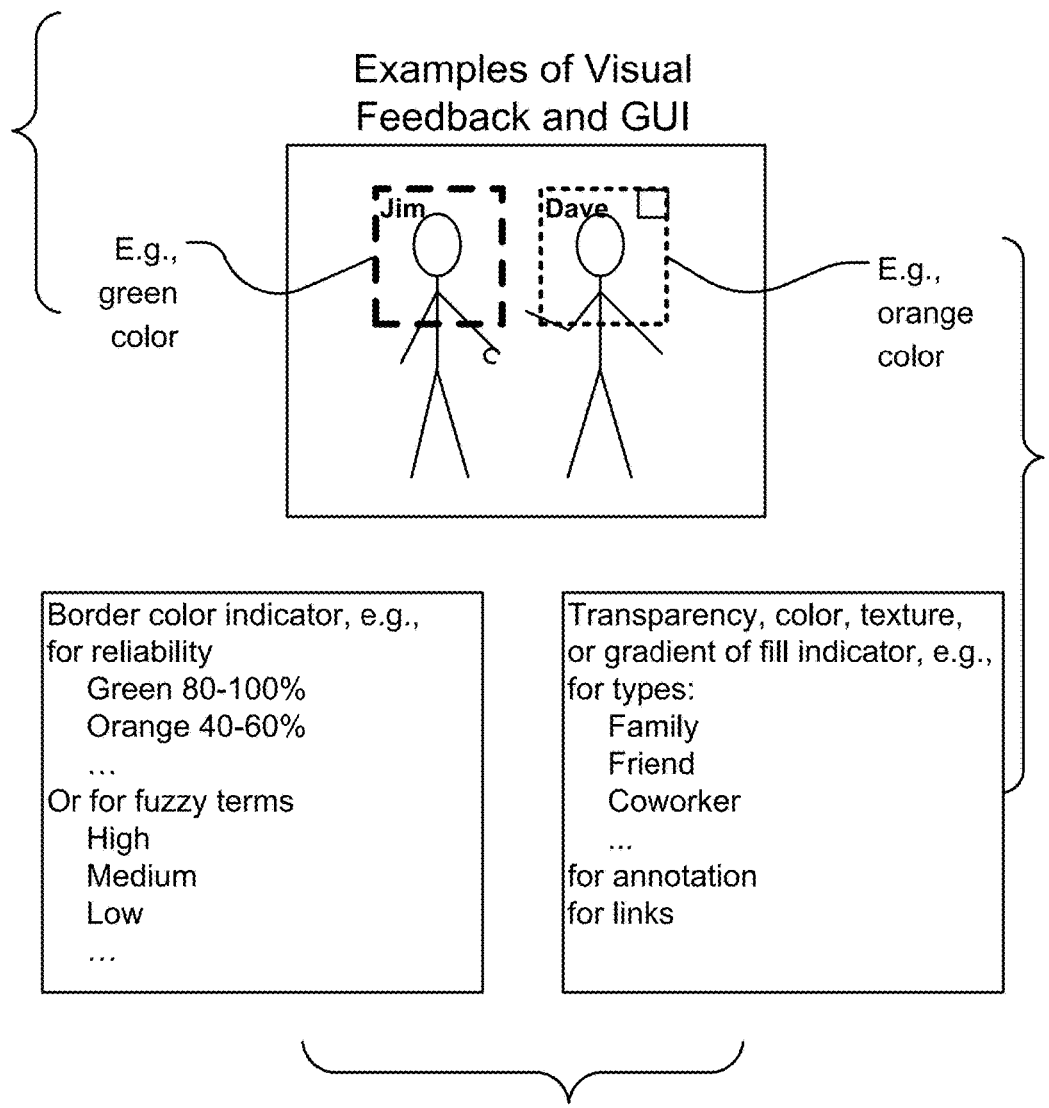

FIG. 220 shows an embodiment for image features.

Figure 221:
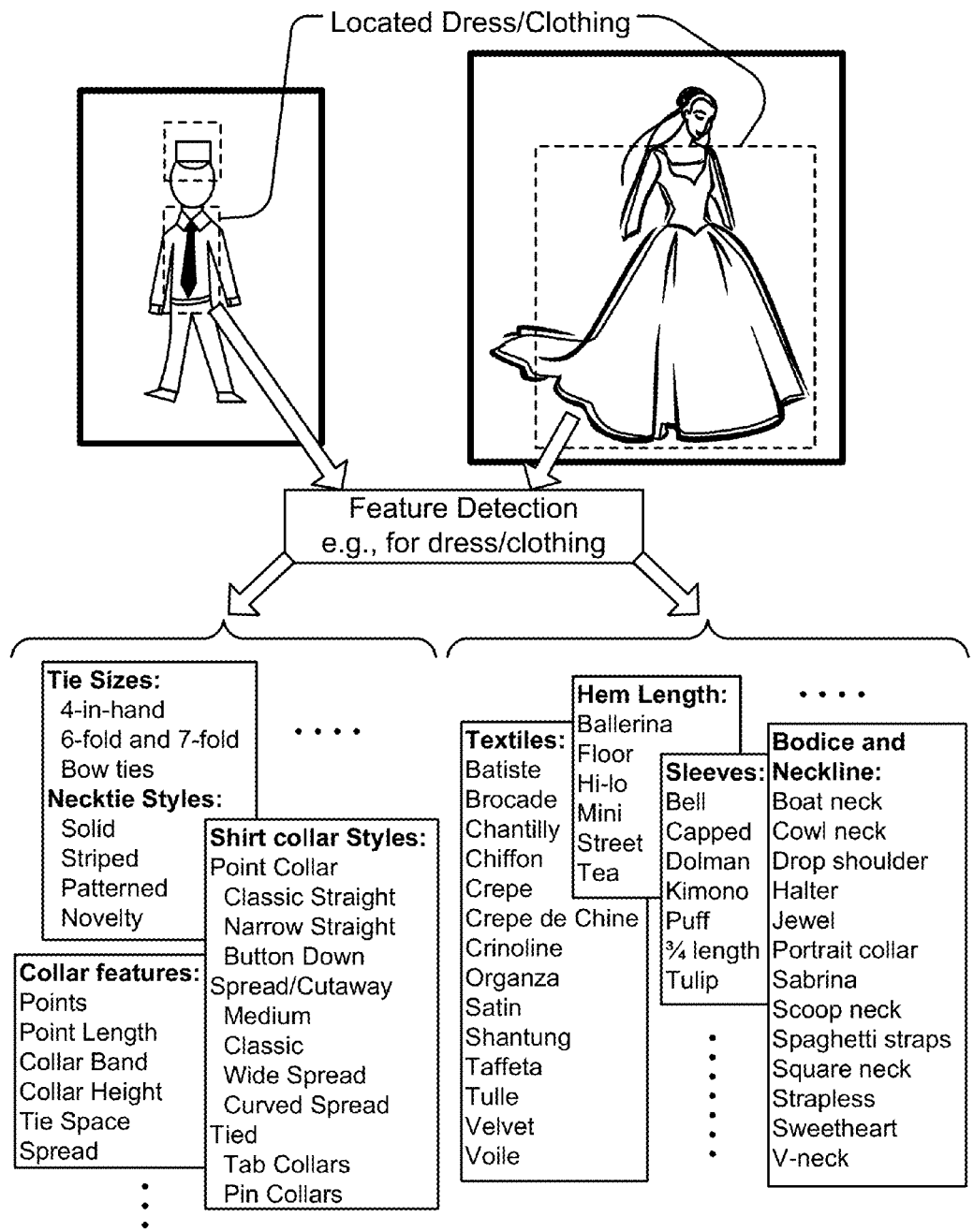

FIG. 221 shows an embodiment for image features.

Figure 222:
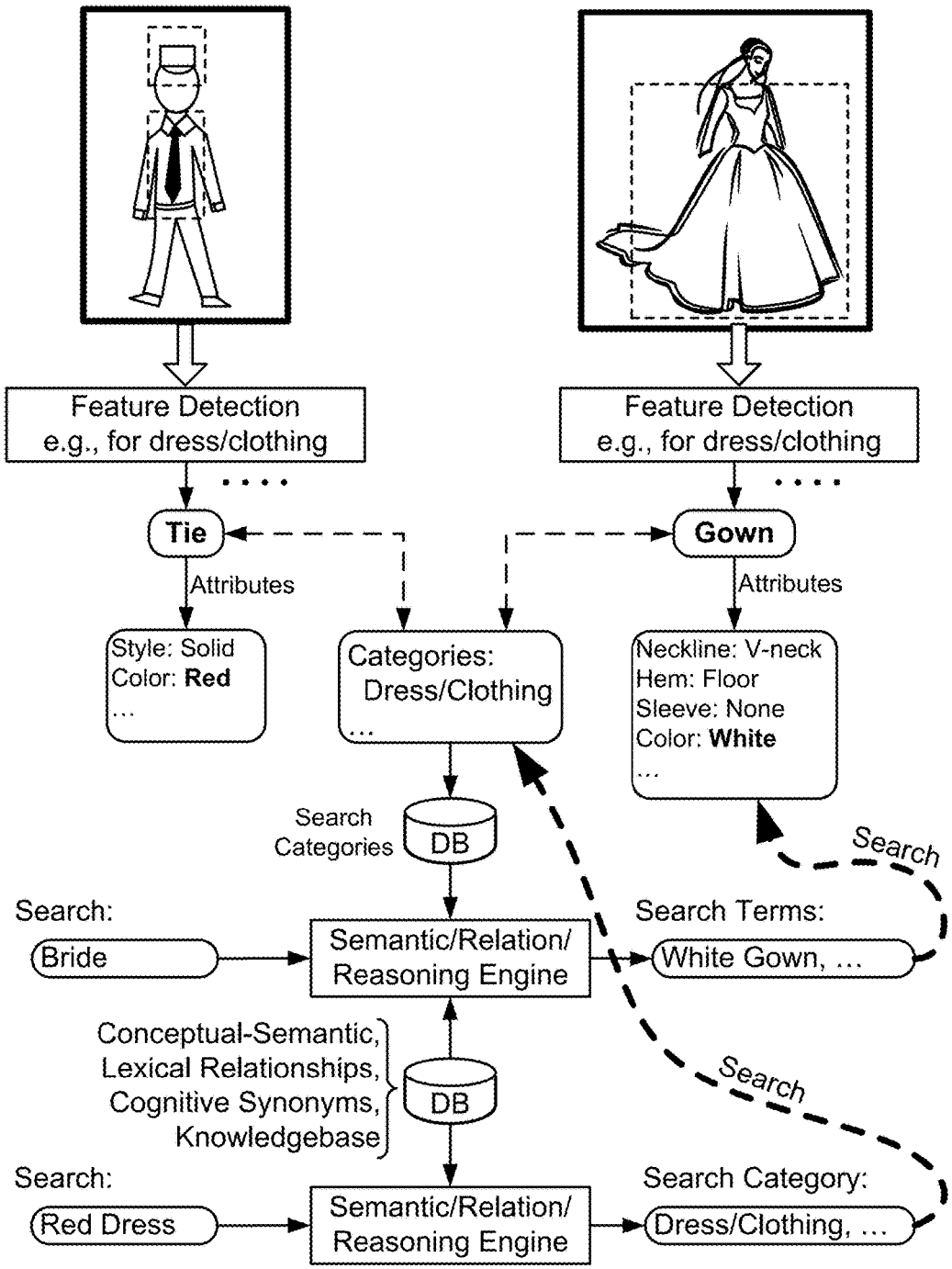

FIG. 222 shows an embodiment for image features.

Figure 223:
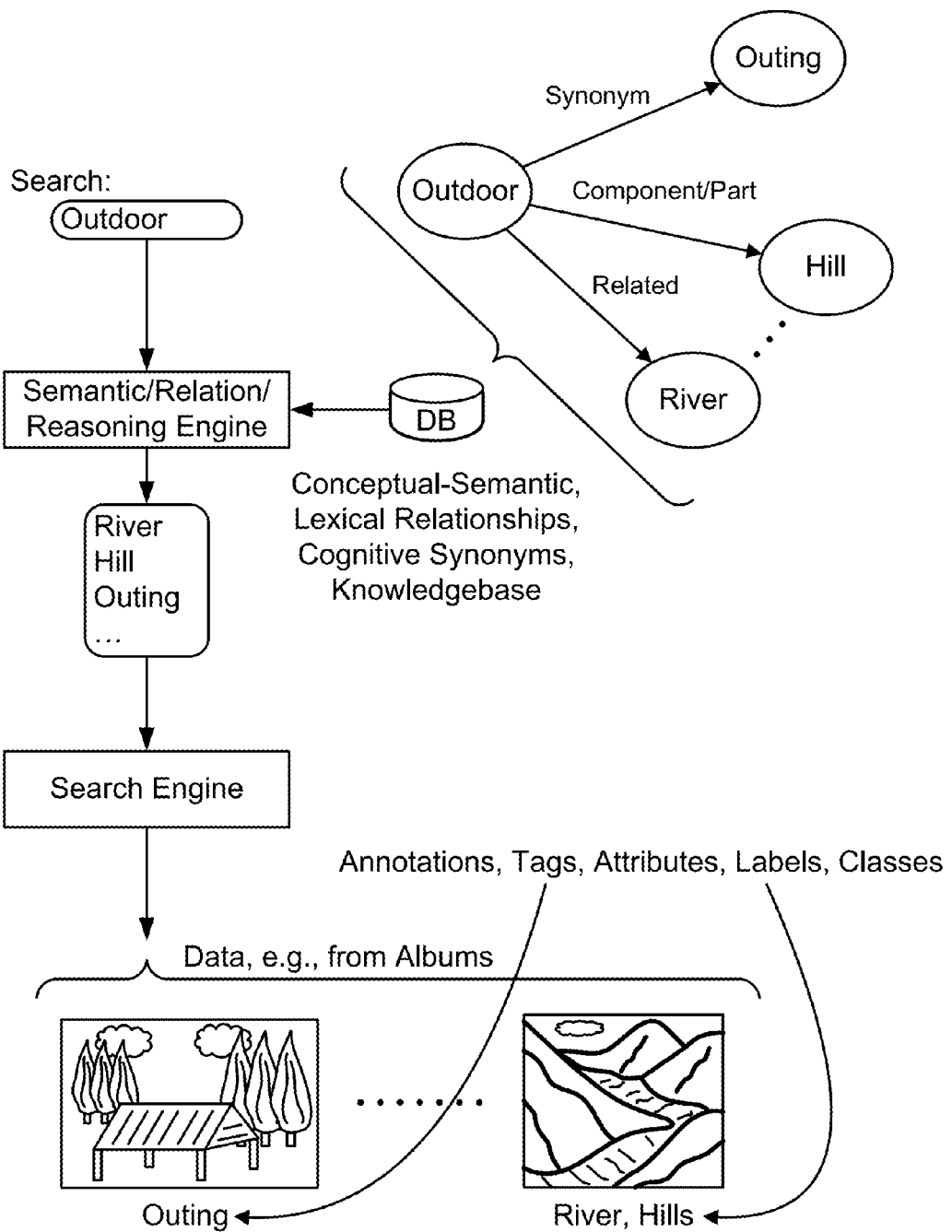

FIG. 223 shows an embodiment for image features.

Figure 224:
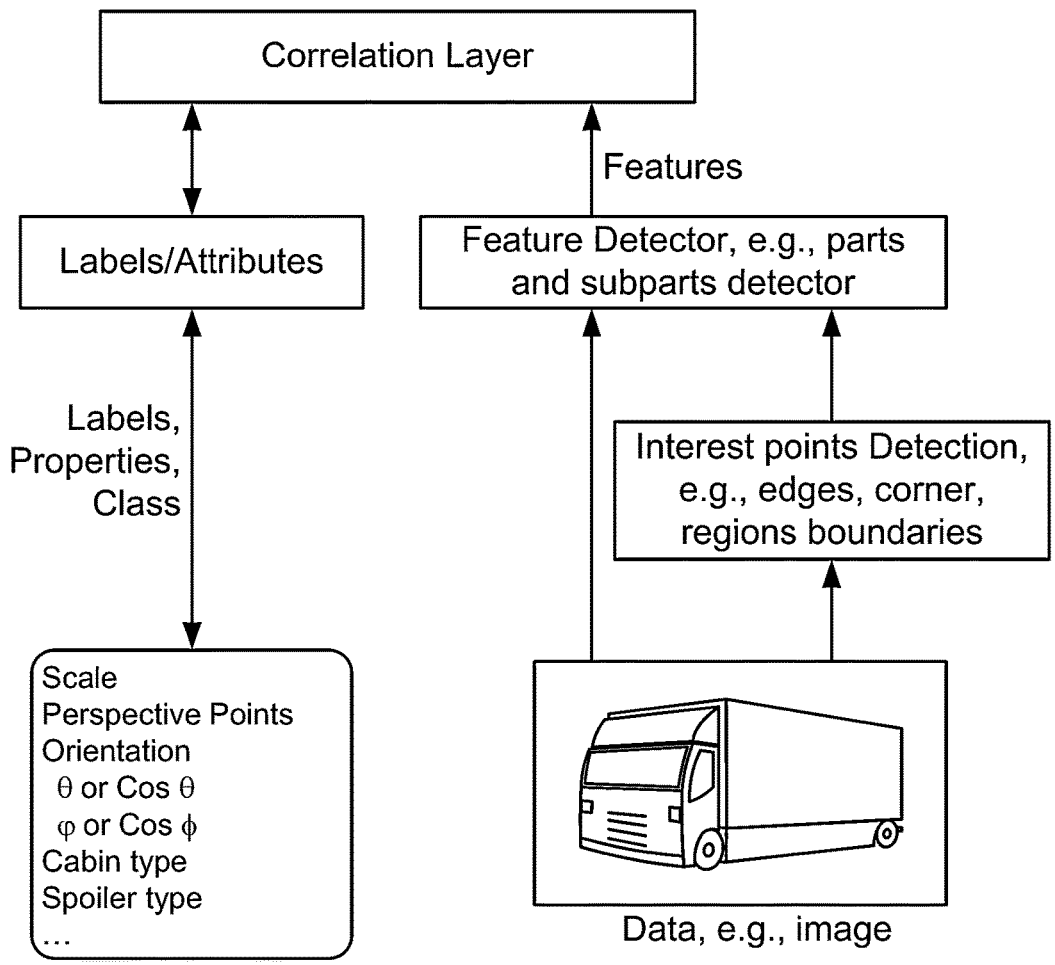

FIG. 224 shows an embodiment for correlation layer.

Figure 225A:
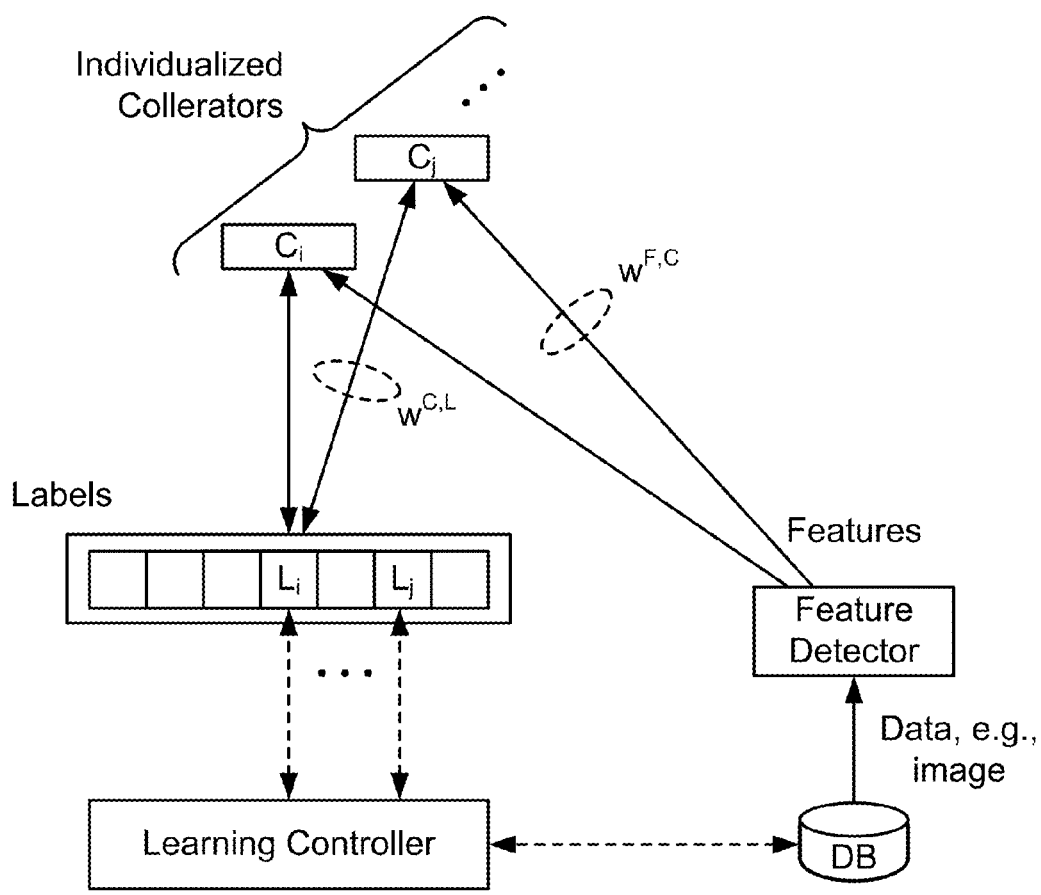
Figure 225B:
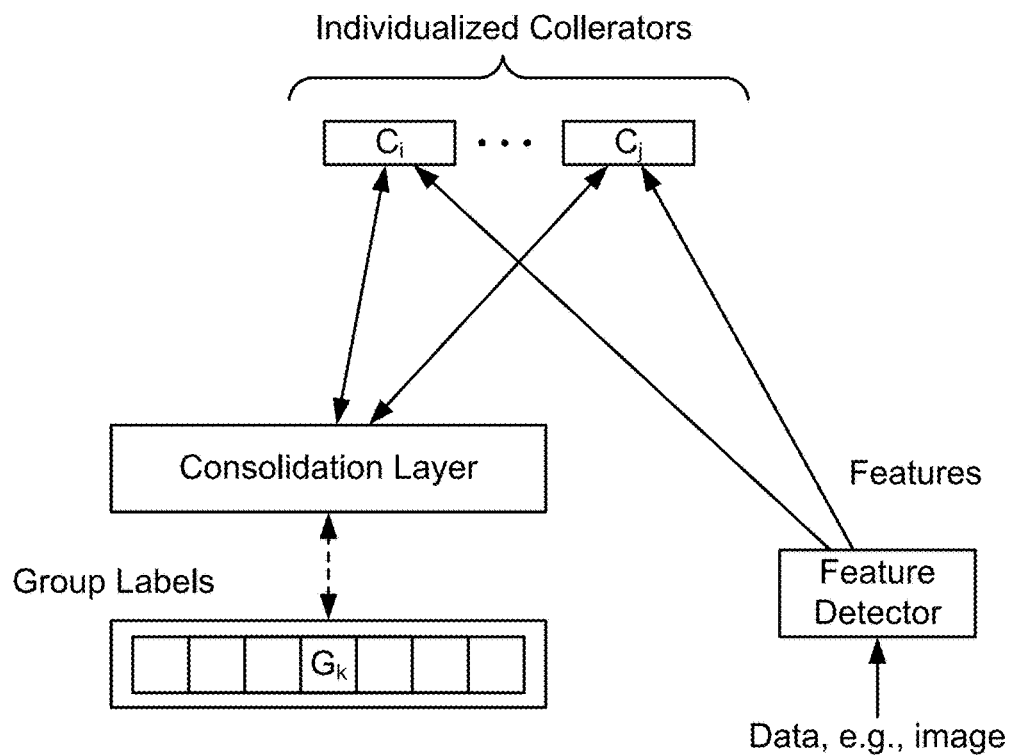

FIG. 225a-b show an embodiment for individualized correlators.

Figure 226:
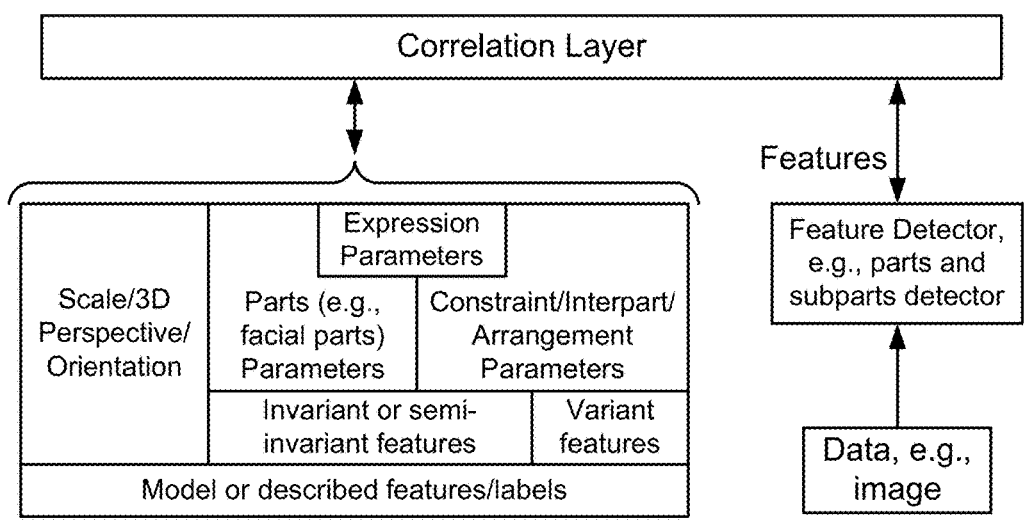

FIG. 226 shows an embodiment for correlation layer.

Figure 227:
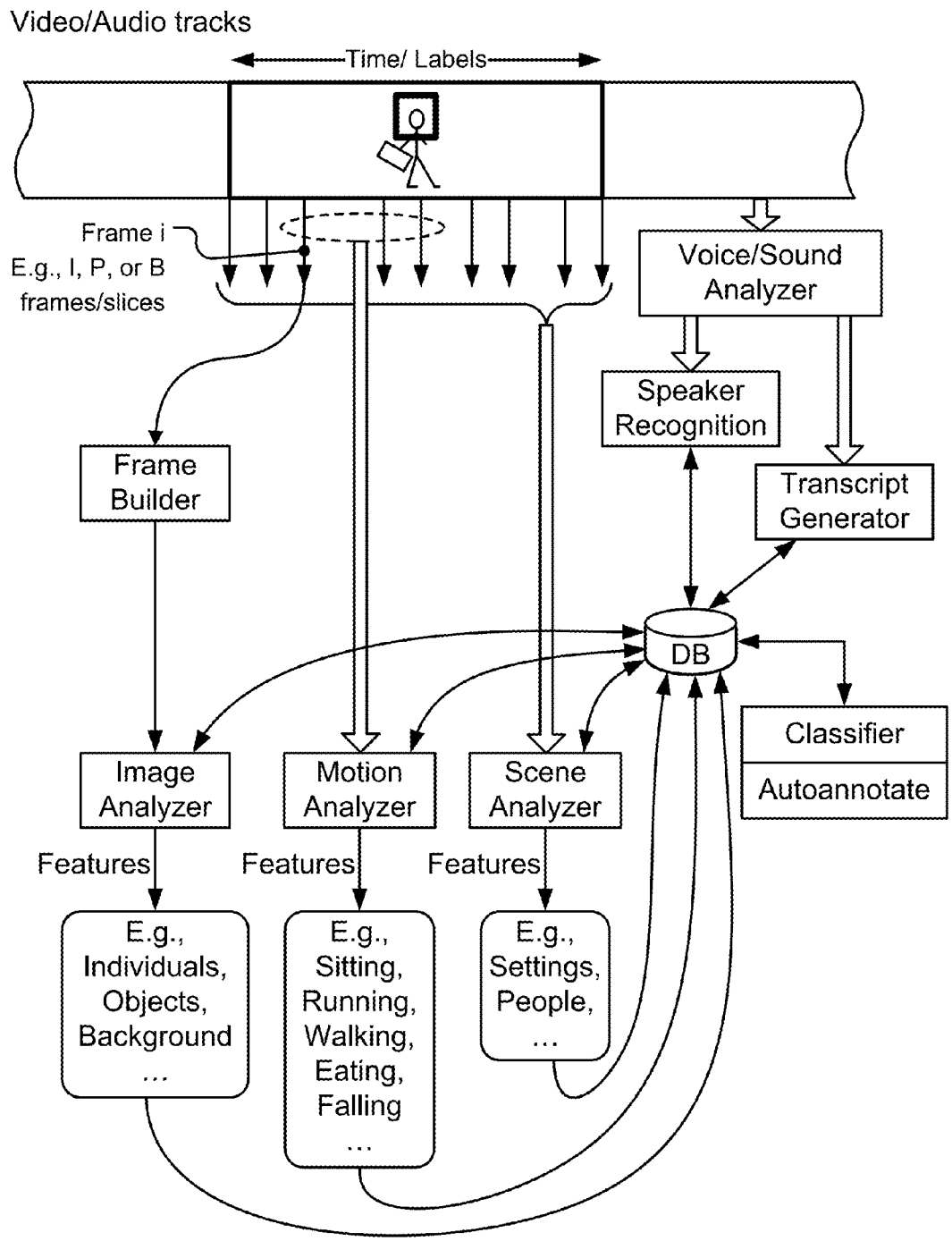

FIG. 227 shows an embodiment for video.

Figure 228:
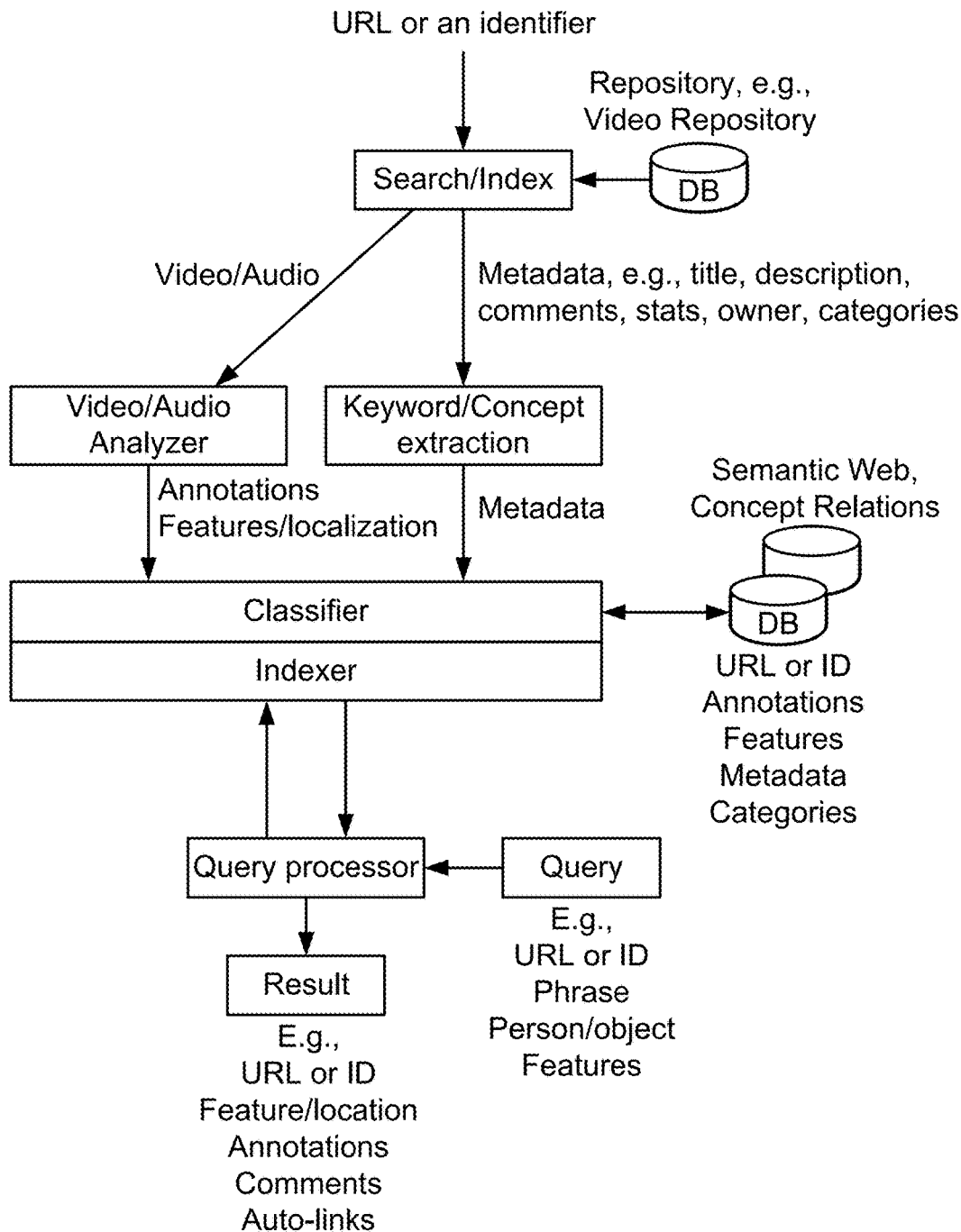

FIG. 228 shows an embodiment for video.

Figure 229:
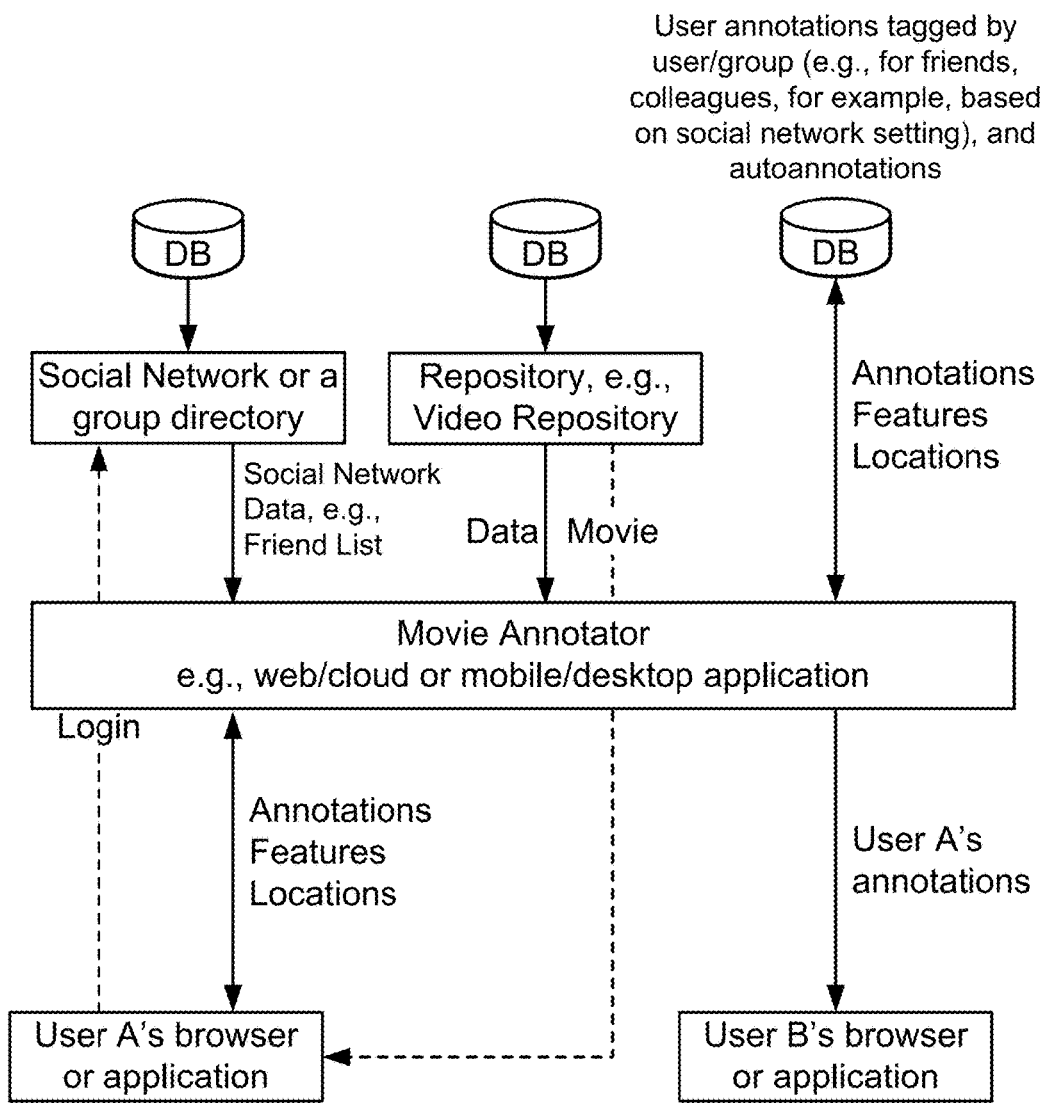

FIG. 229 shows an embodiment for movie.

Figure 230:
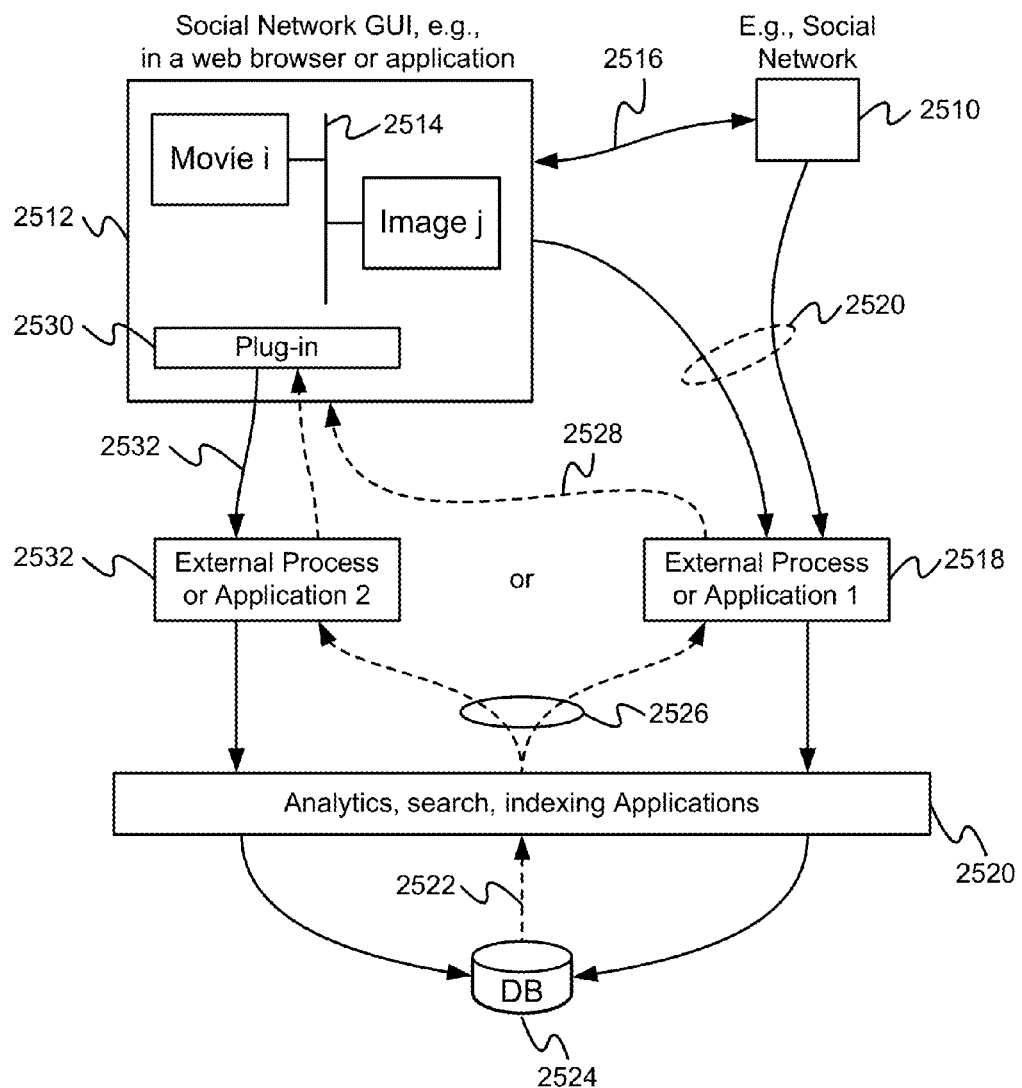

FIG. 230 shows an embodiment for social network.

Figure 231:
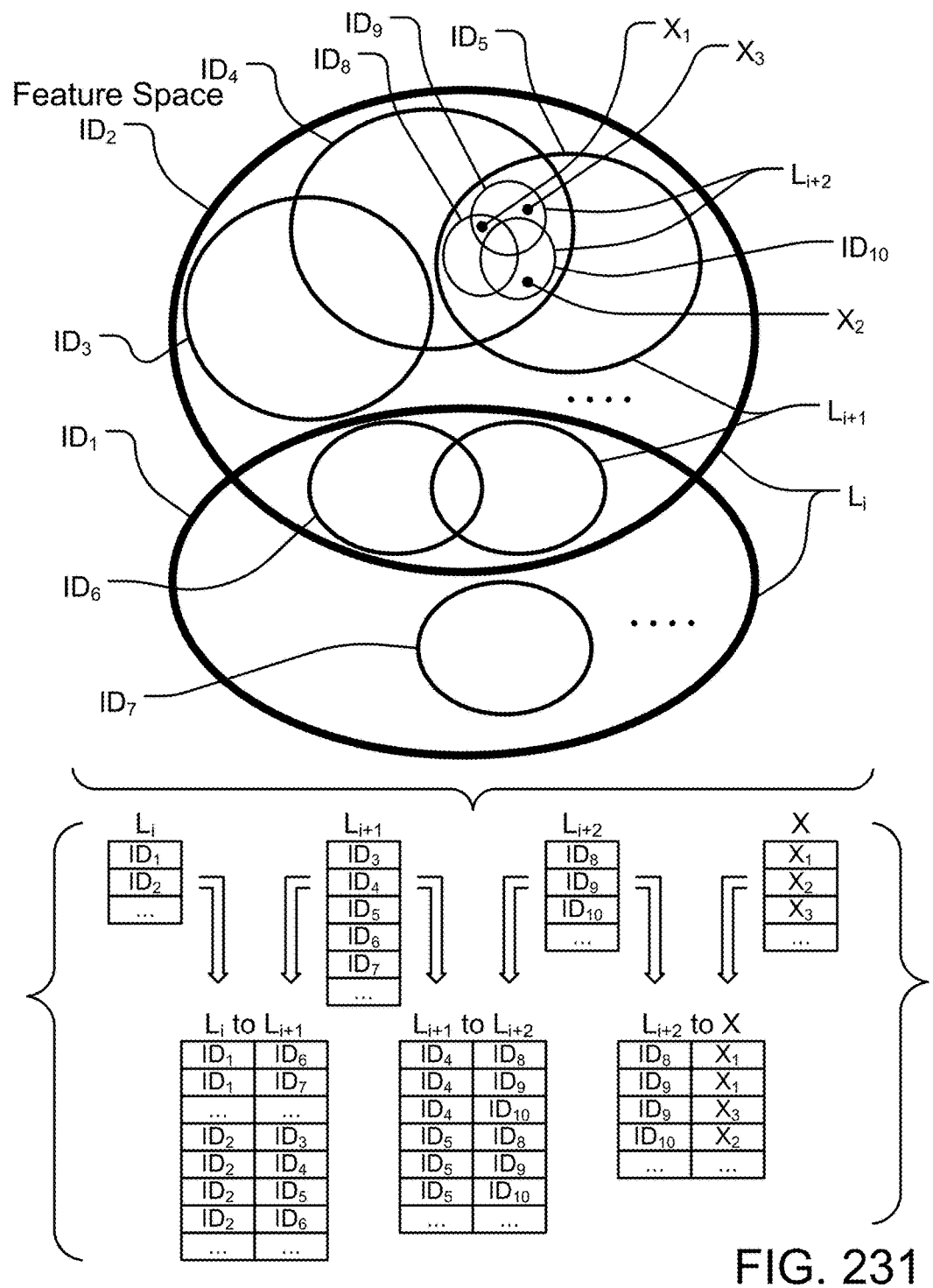

FIG. 231 shows an embodiment for feature space.

Figure 232:
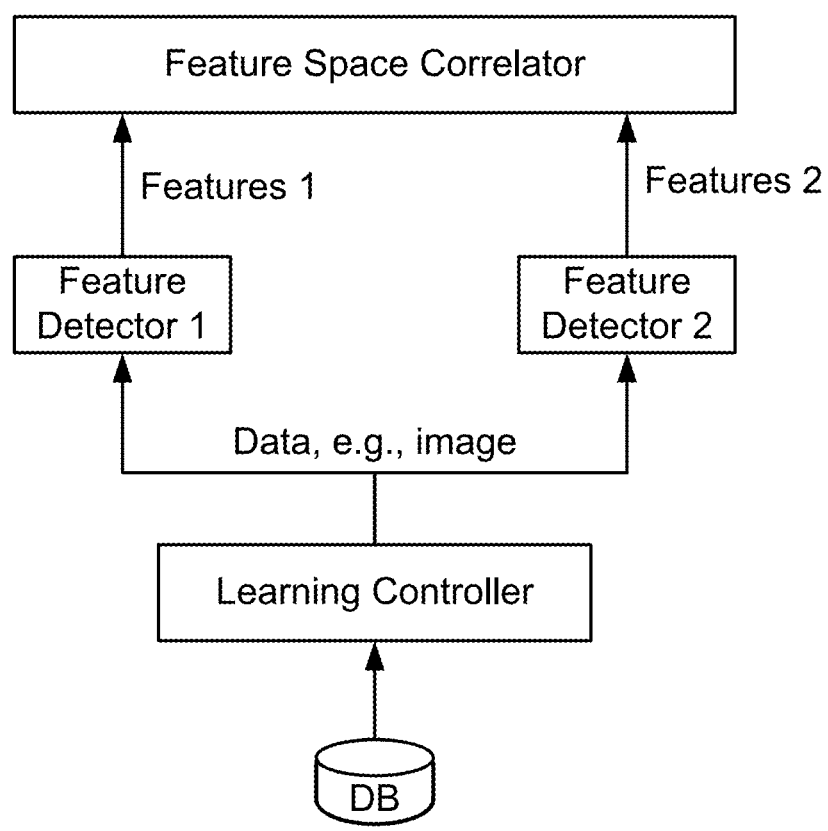

FIG. 232 shows an embodiment for correlator.

Figure 233:
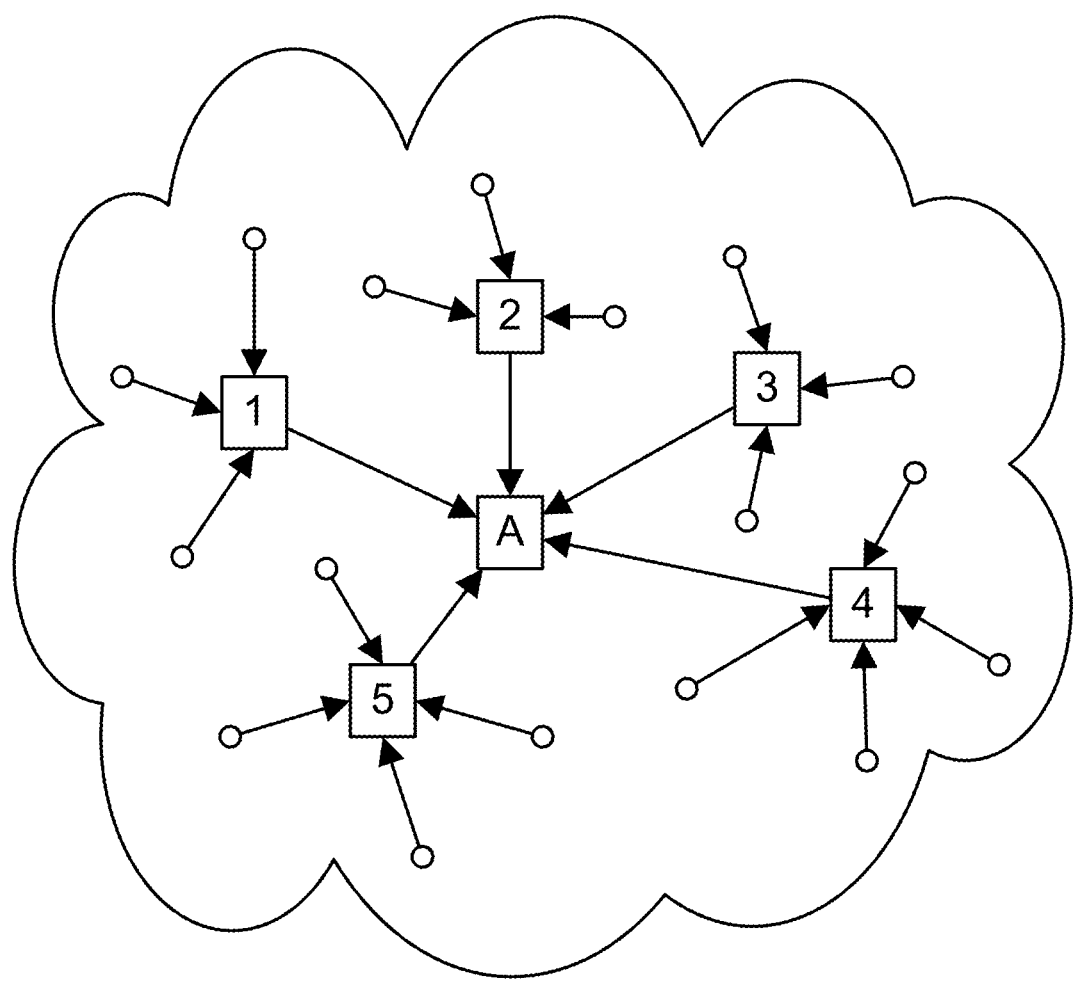

FIG. 233 shows an embodiment for relations.

Figure 234:
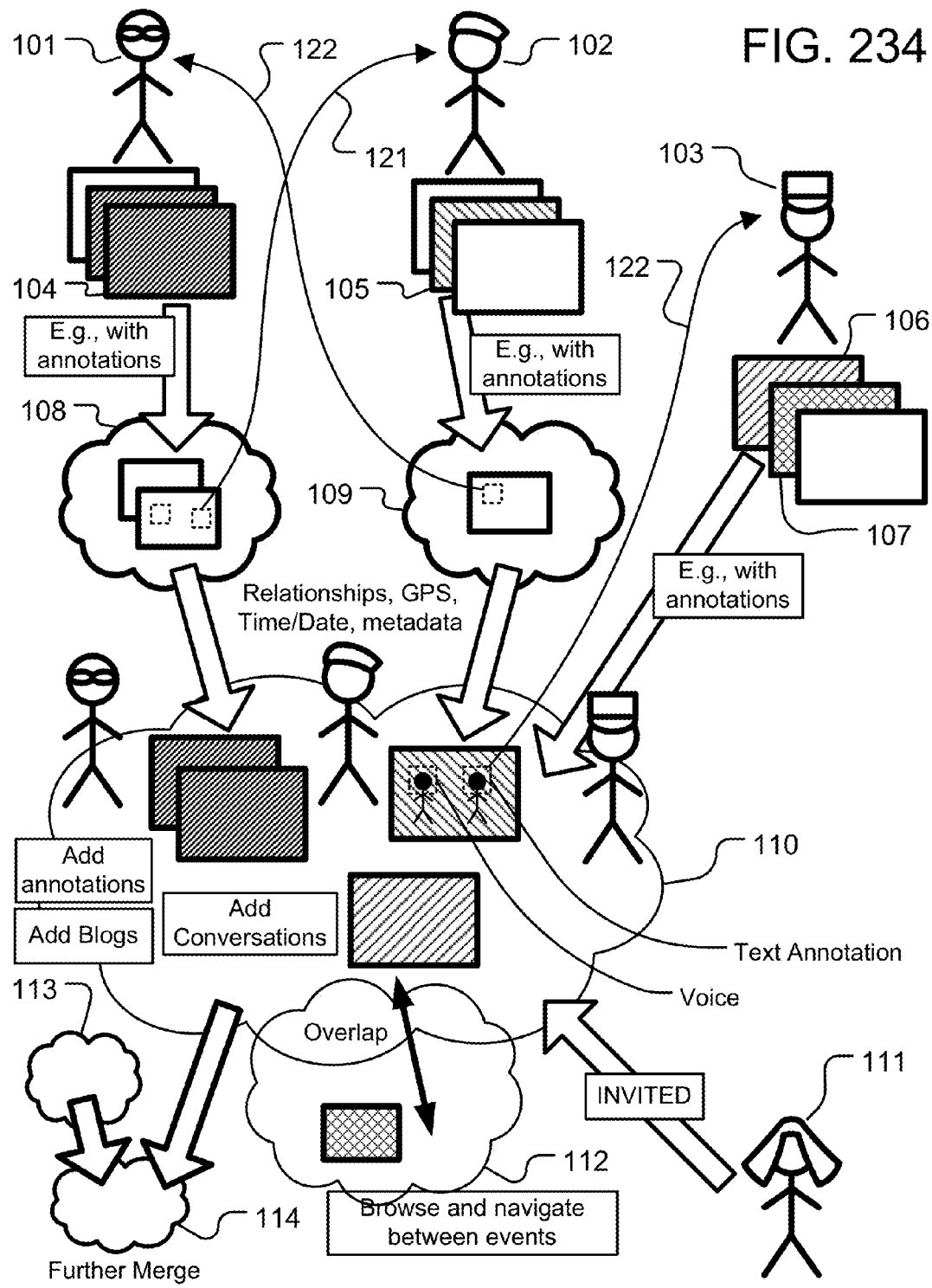

FIG. 234 shows an embodiment for events.

Figure 235:
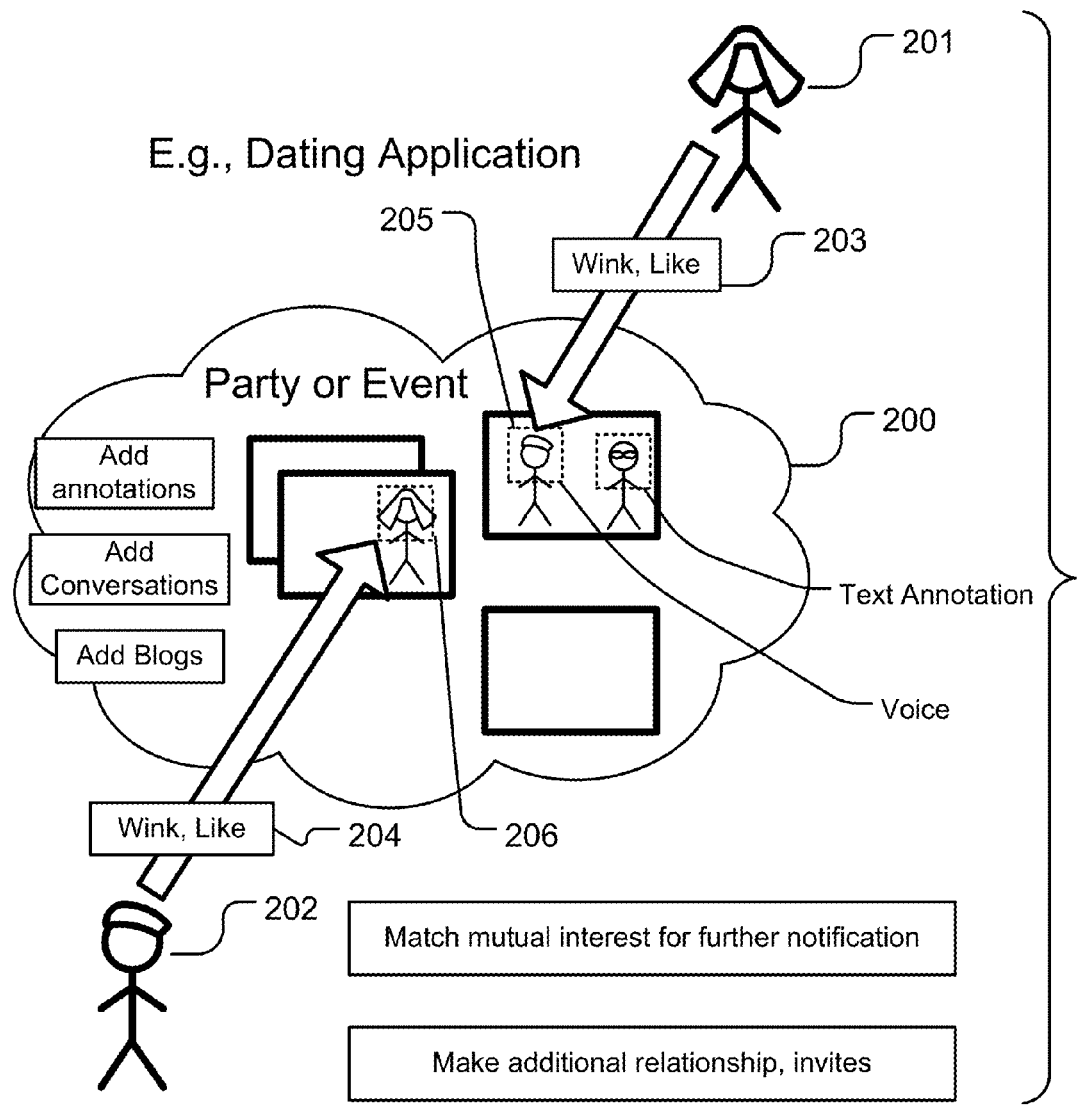

FIG. 235 shows an embodiment for dating.

Figure 236:
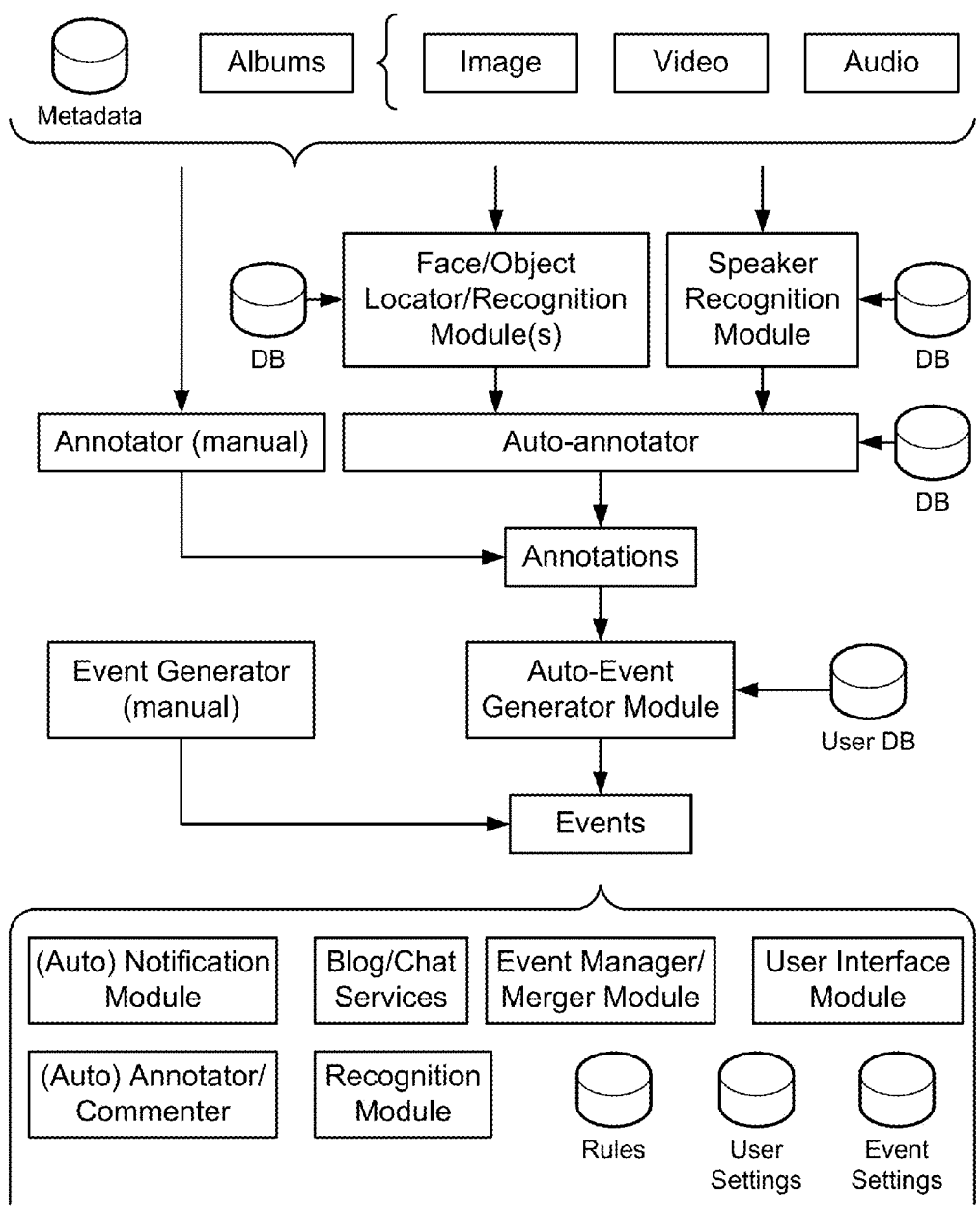

FIG. 236 shows an embodiment for annotation.

Figure 237:
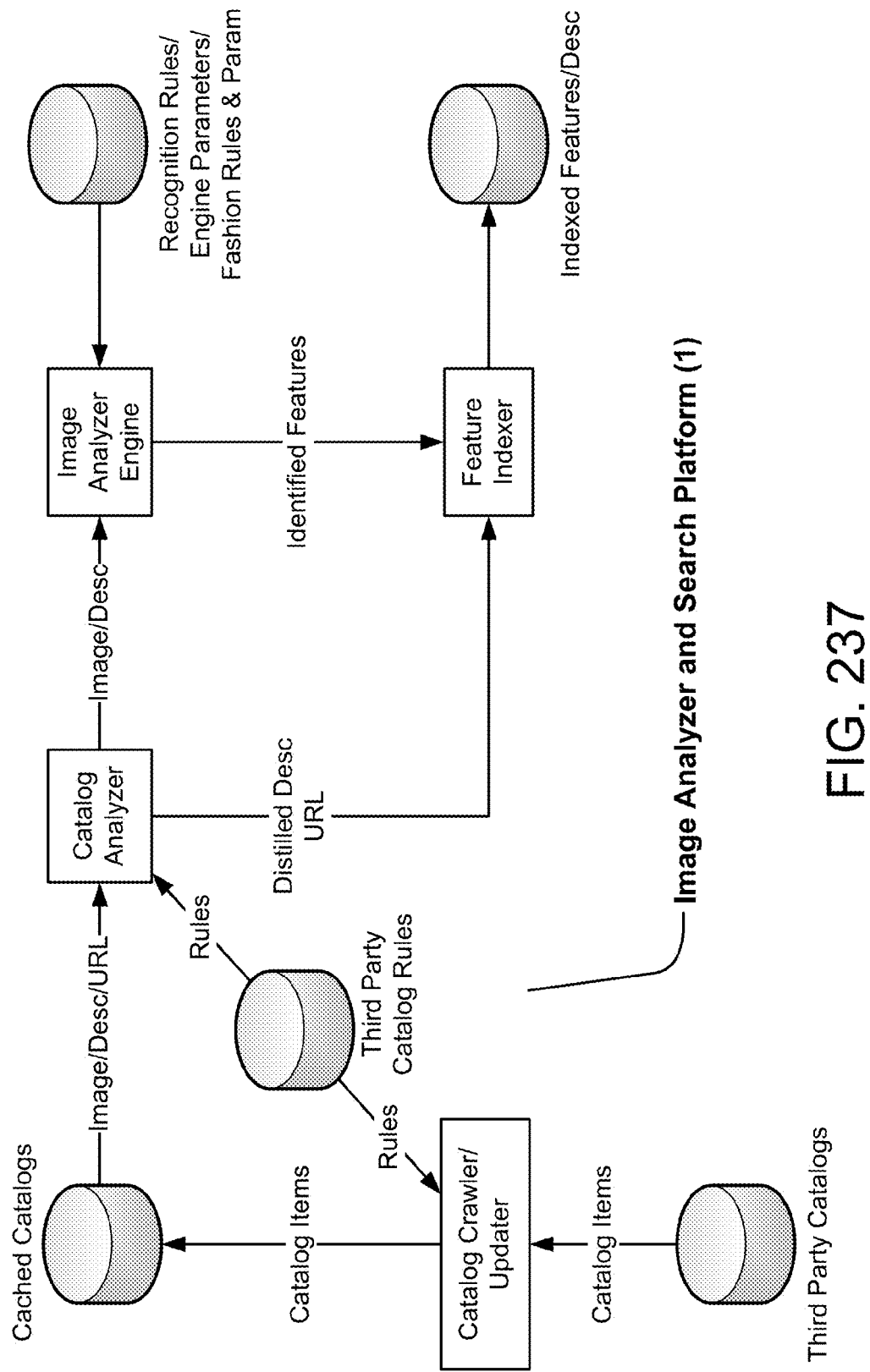

FIG. 237 shows an embodiment for catalog.

Figure 238:
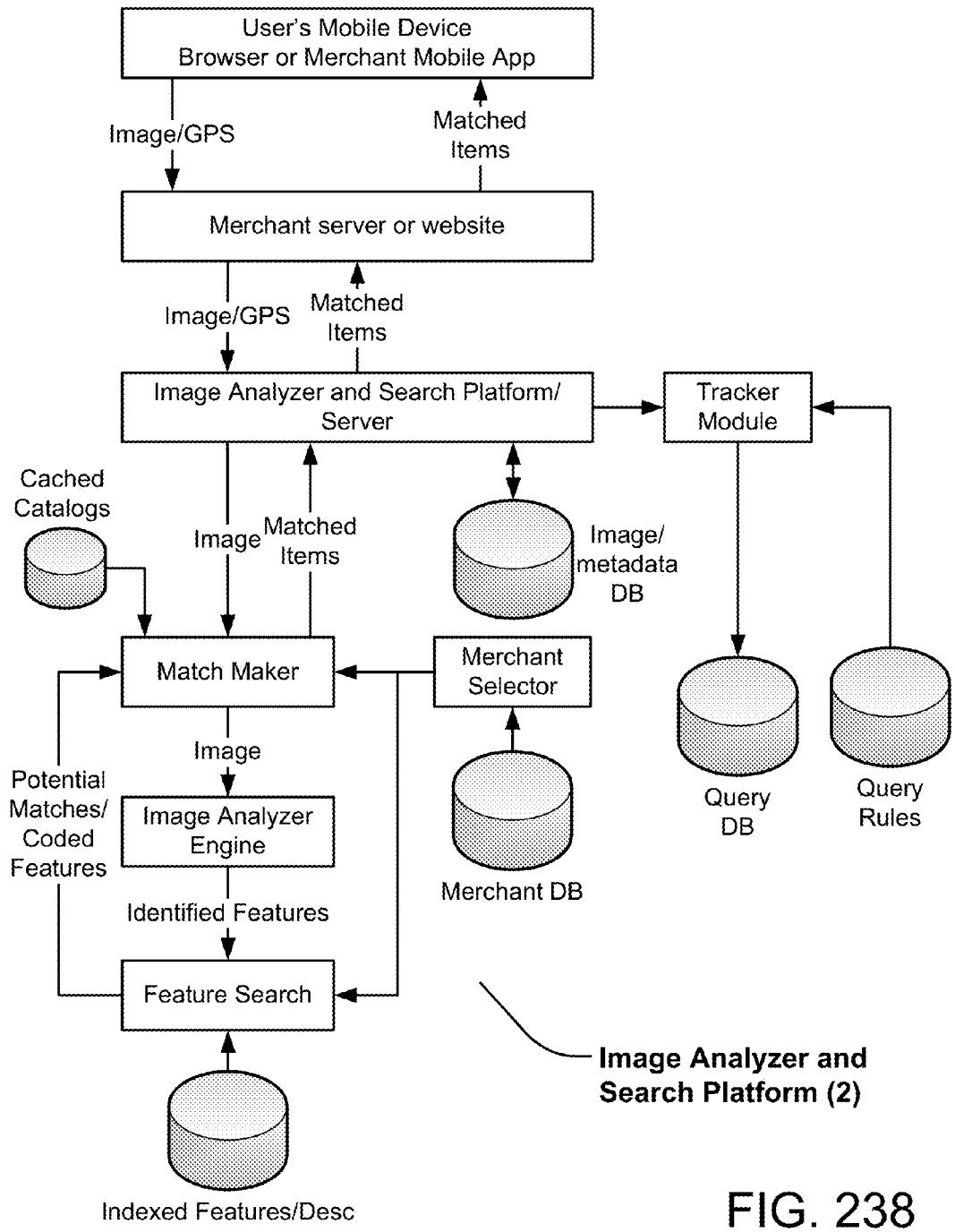

FIG. 238 shows an embodiment for image analyzer.

Figure 239:
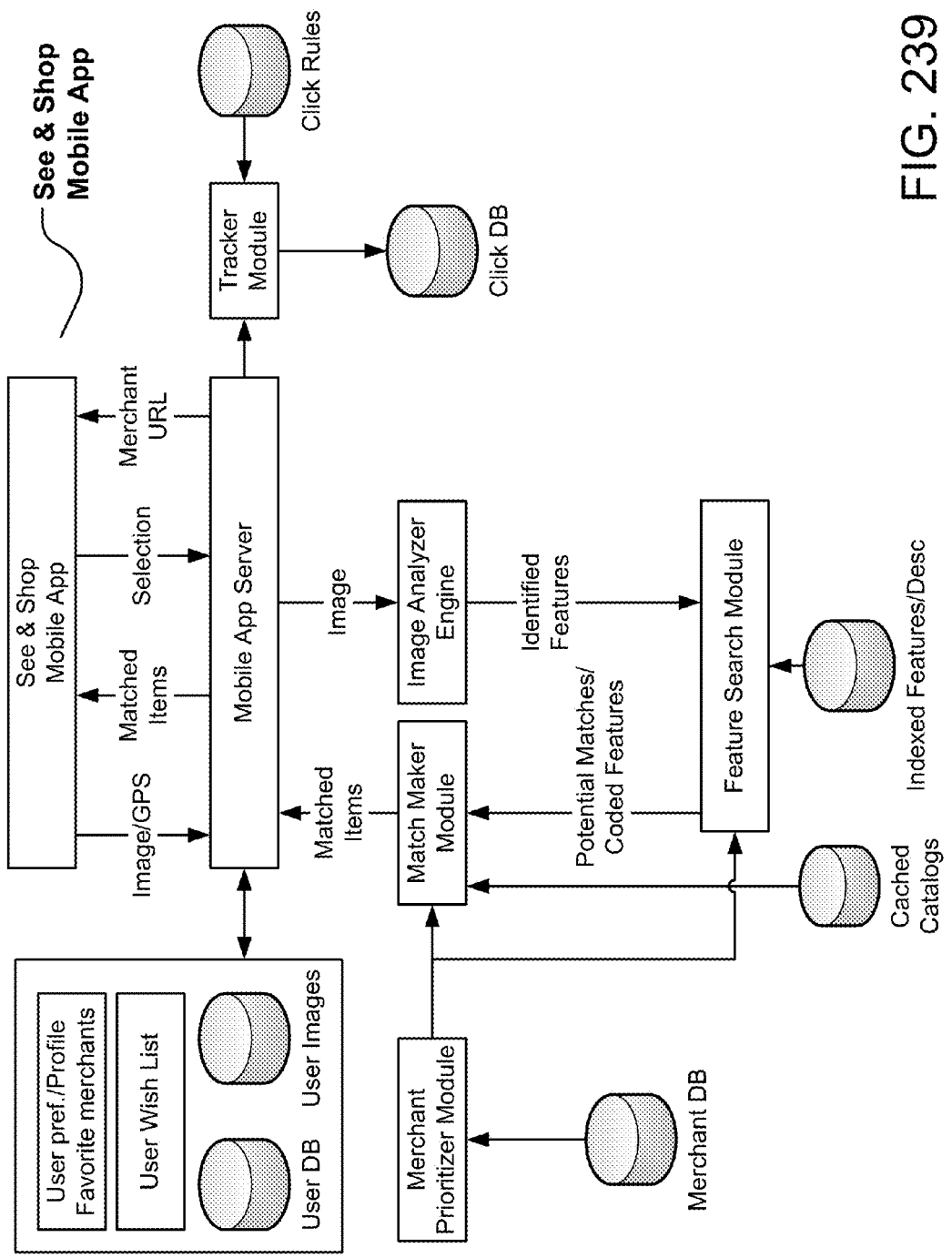

FIG. 239 shows an embodiment for "see and shop".

Figure 240:
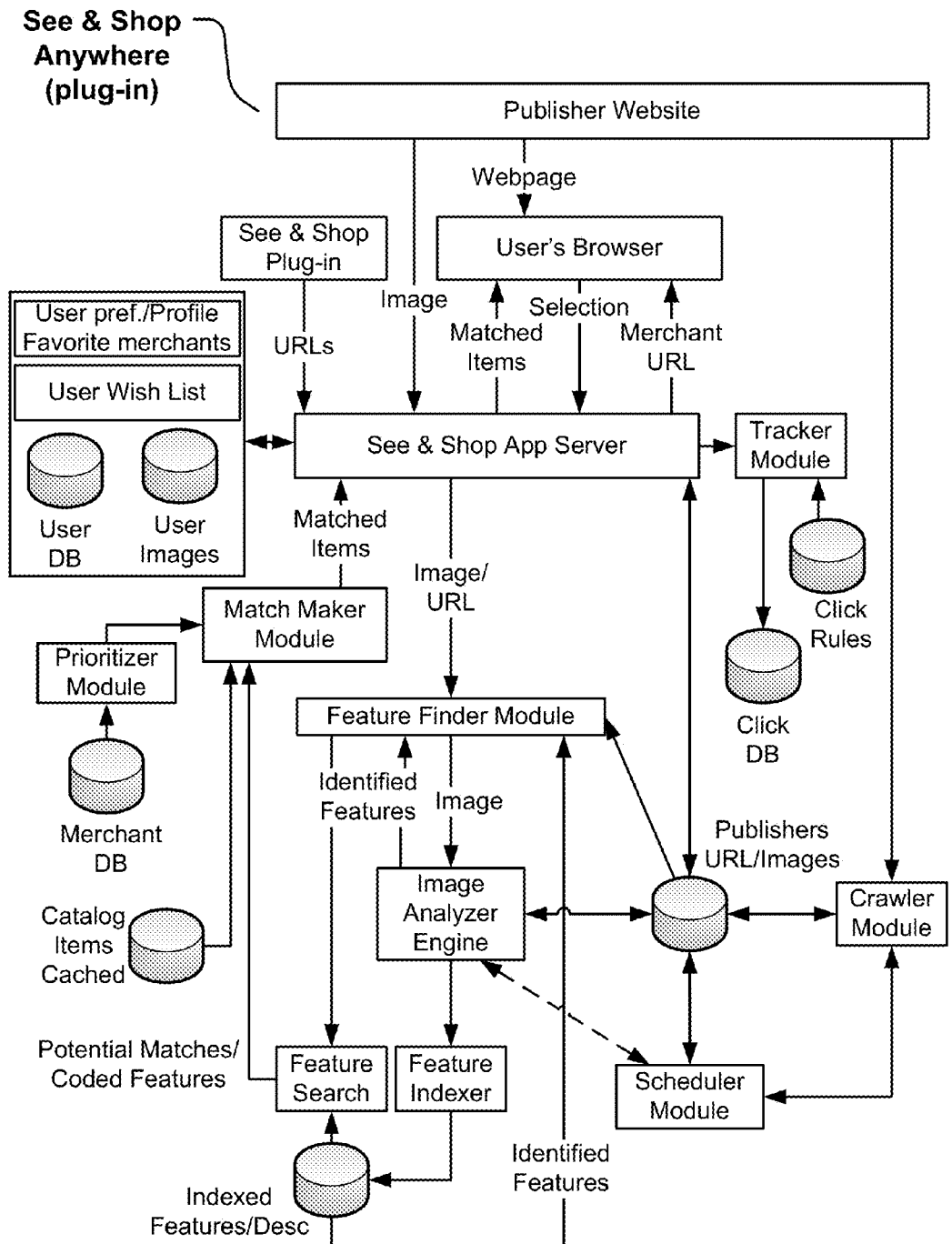

FIG. 240 shows an embodiment for "see and shop".

Figure 241:
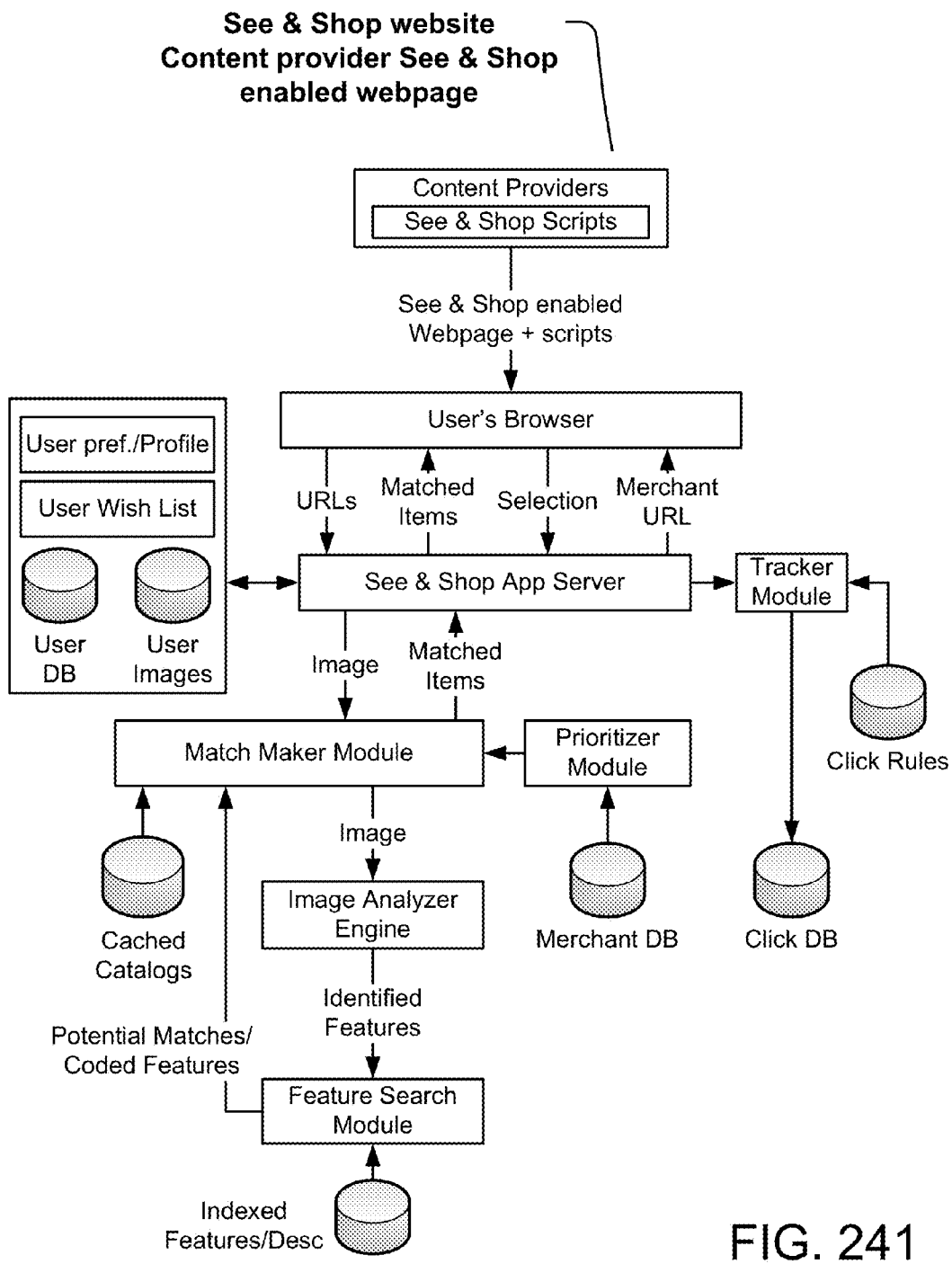

FIG. 241 shows an embodiment for "see and shop".

Figure 242:
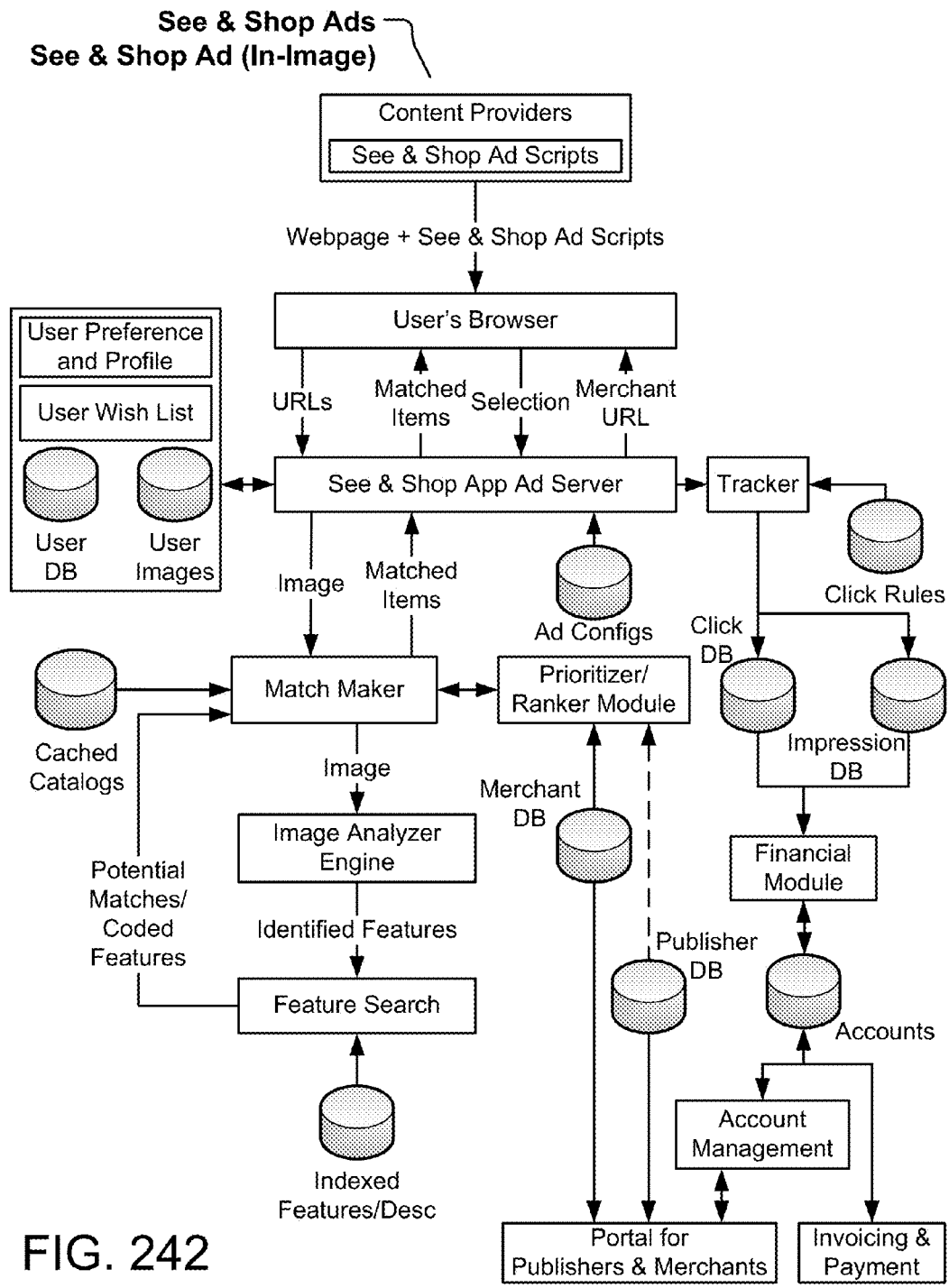

FIG. 242 shows an embodiment for "see and shop".

FIG. 243a-e show an embodiment for app and browser.

Figure 244:
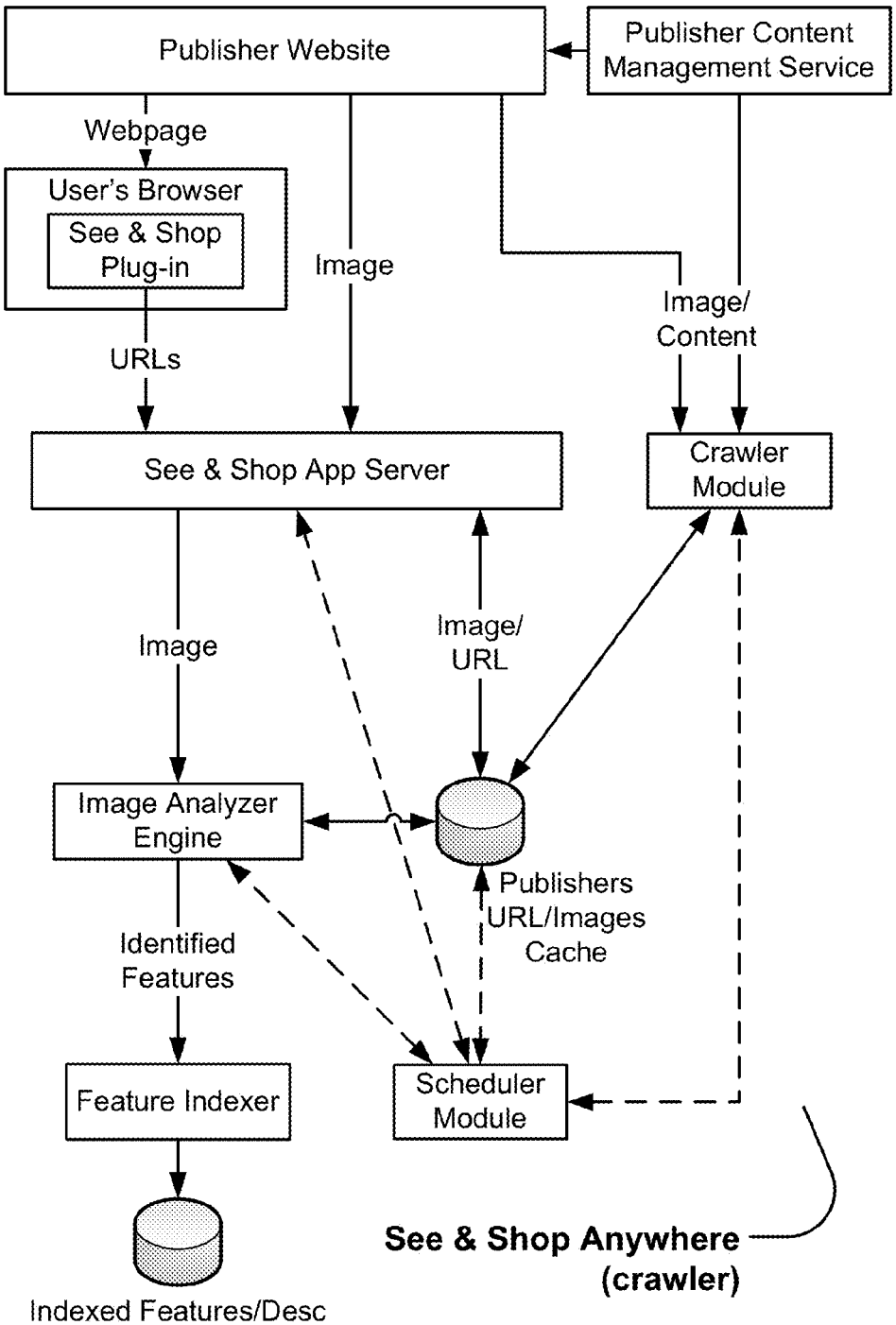

FIG. 244 shows an embodiment for "see and shop".

Figure 245:
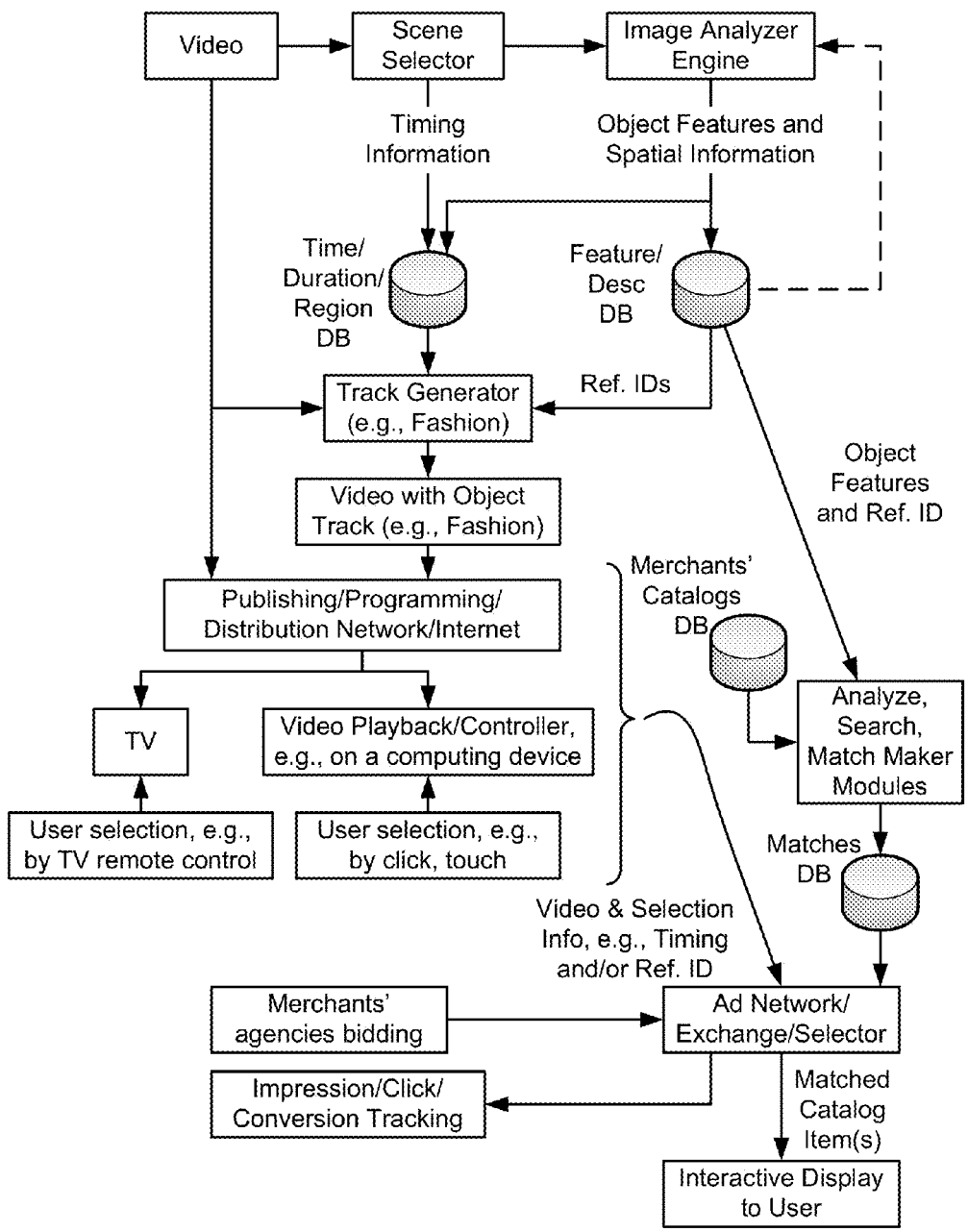

FIG. 245 shows an embodiment for image analyzer.

Figure 246:
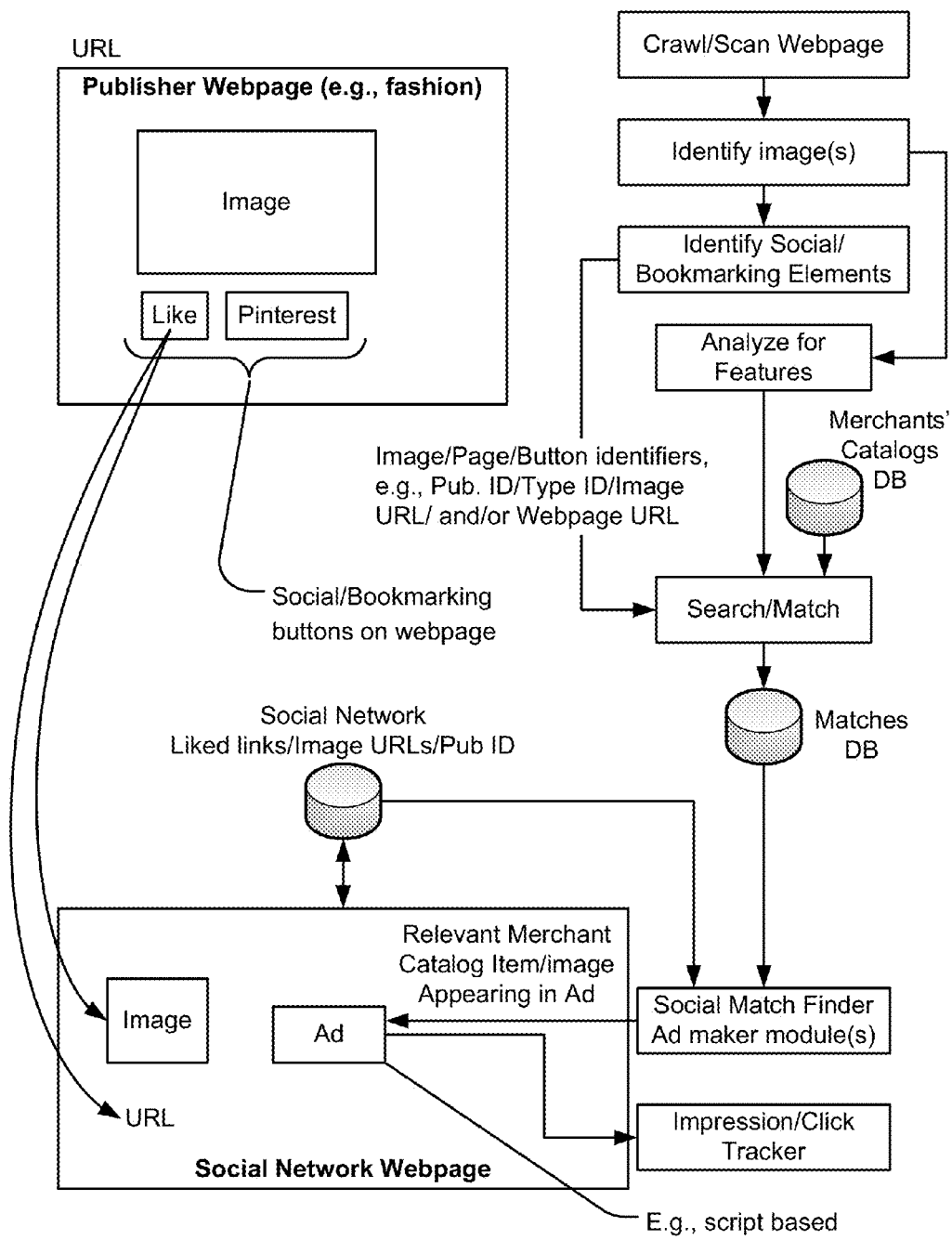

FIG. 246 shows an embodiment for image analyzer.

Figure 247:
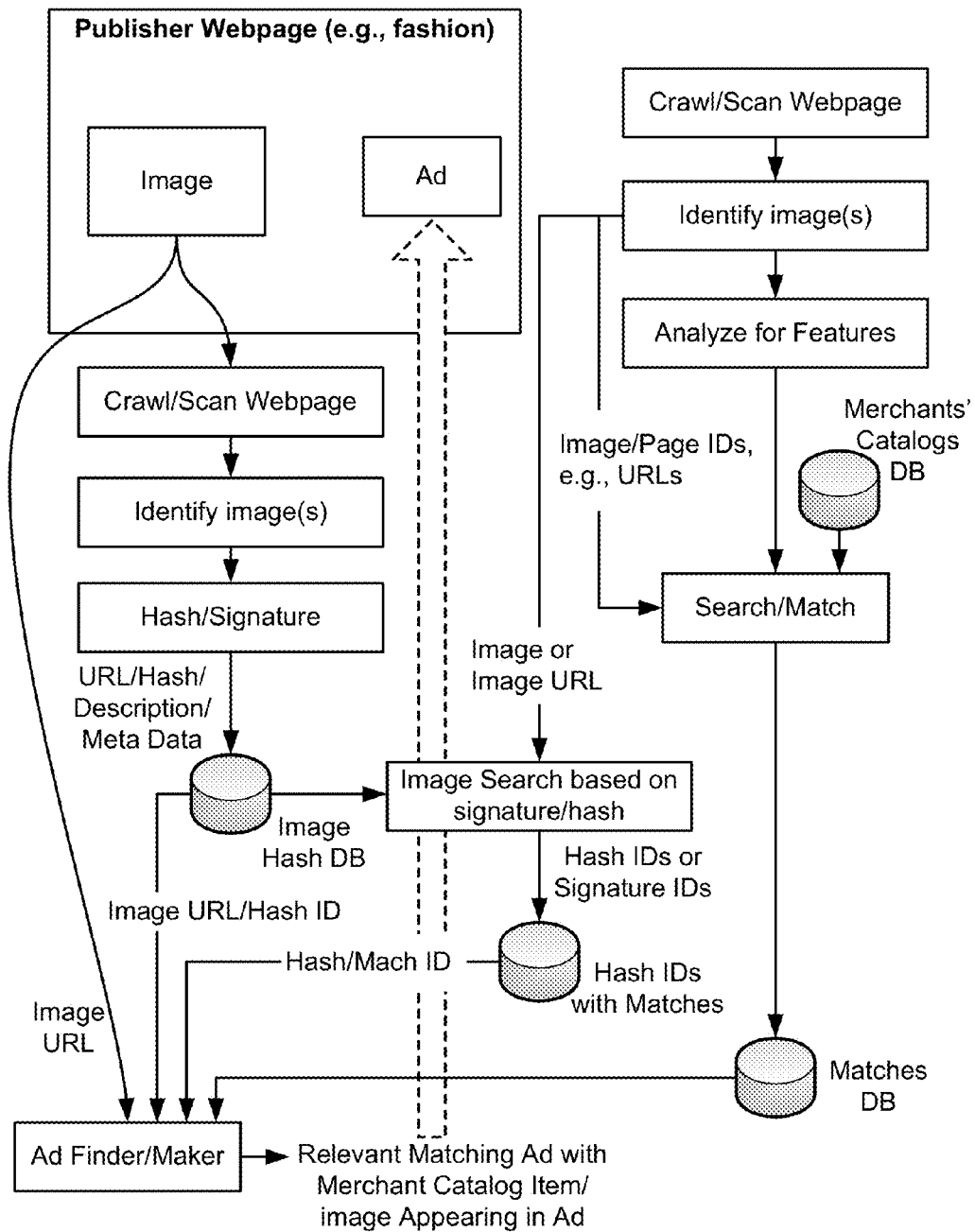

FIG. 247 shows an embodiment for image analyzer.

Figure 248:
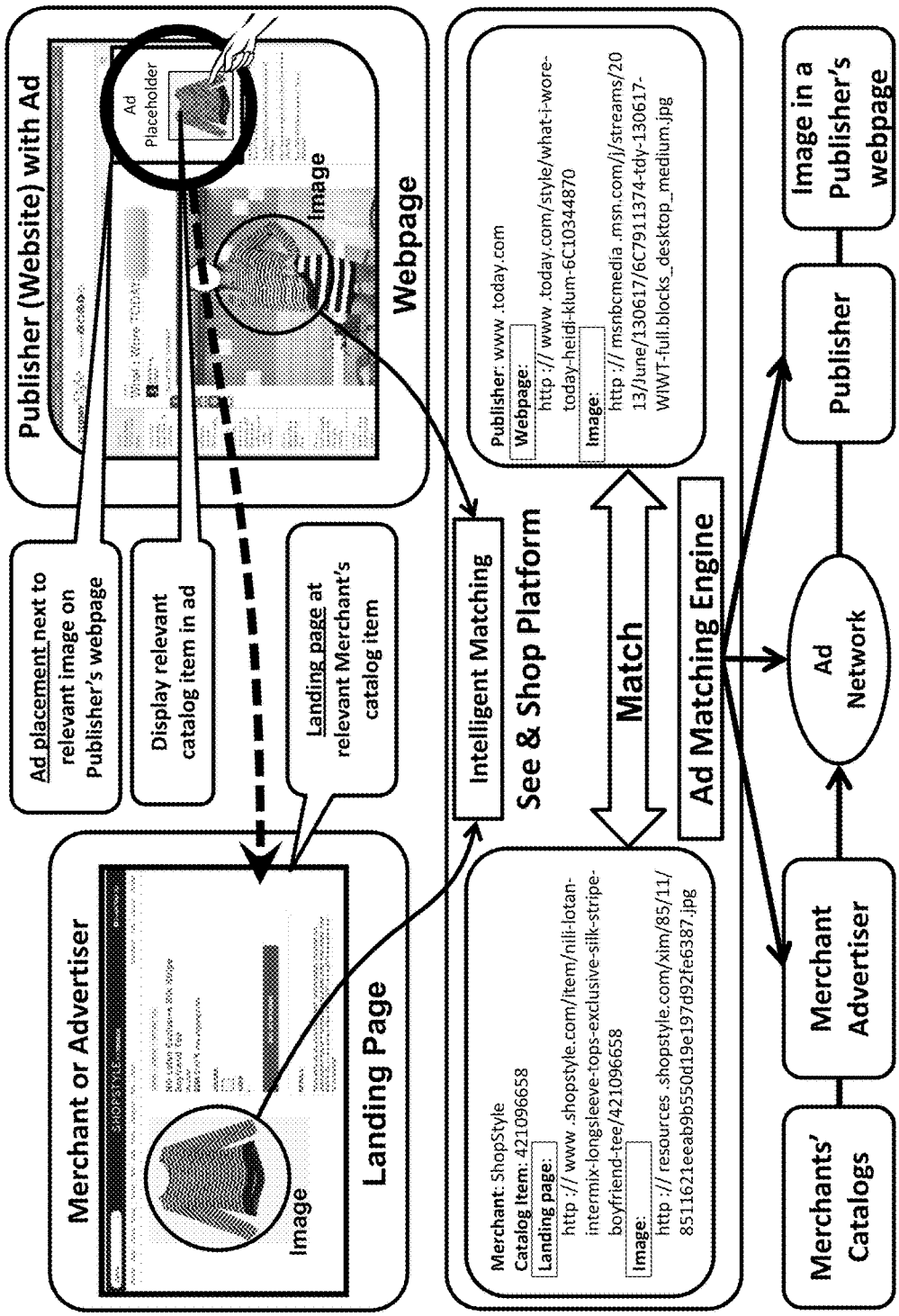

FIG. 248 shows an embodiment for image network.

Figure 249:
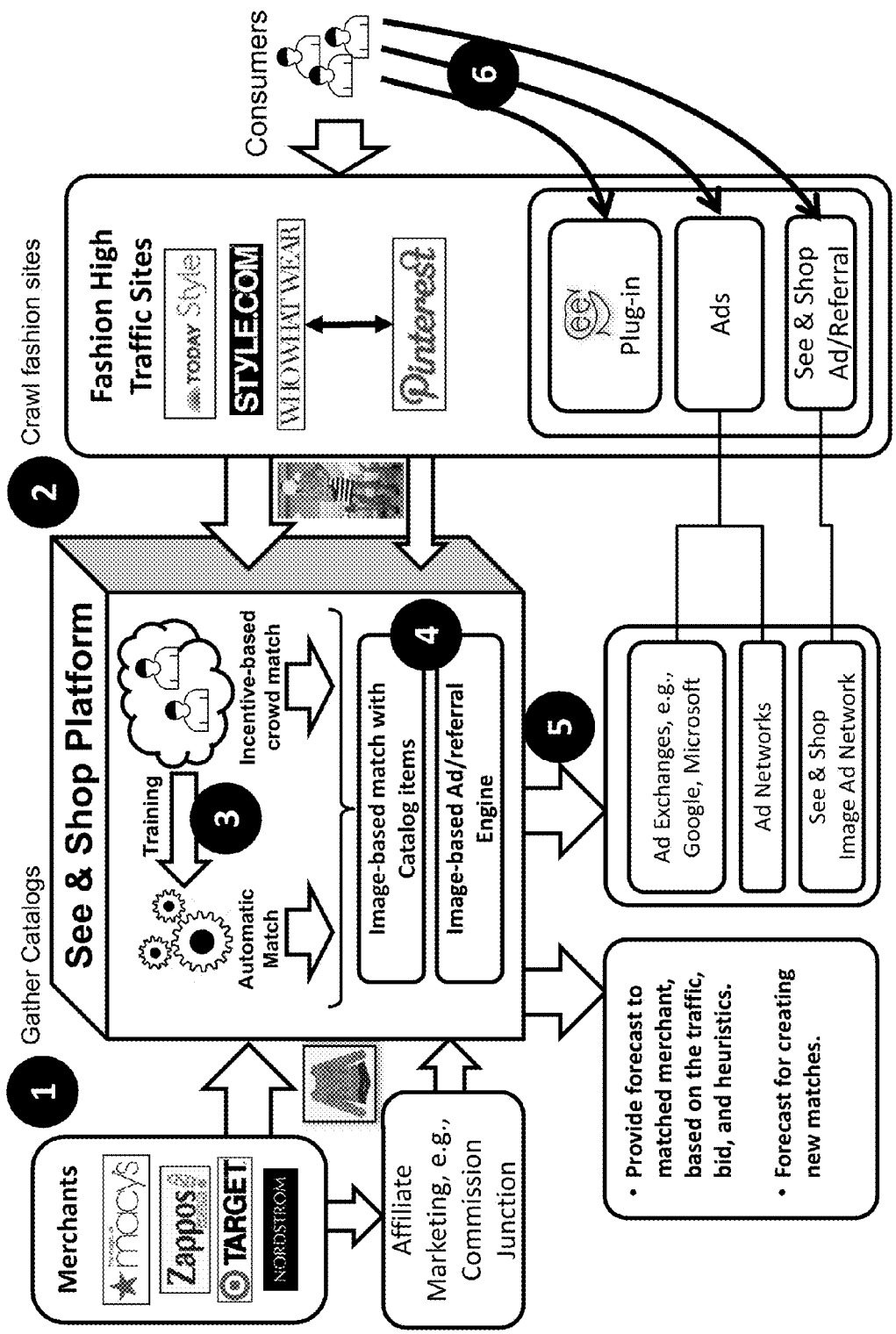

FIG. 249 shows an embodiment for "see and shop".

Figure 250:
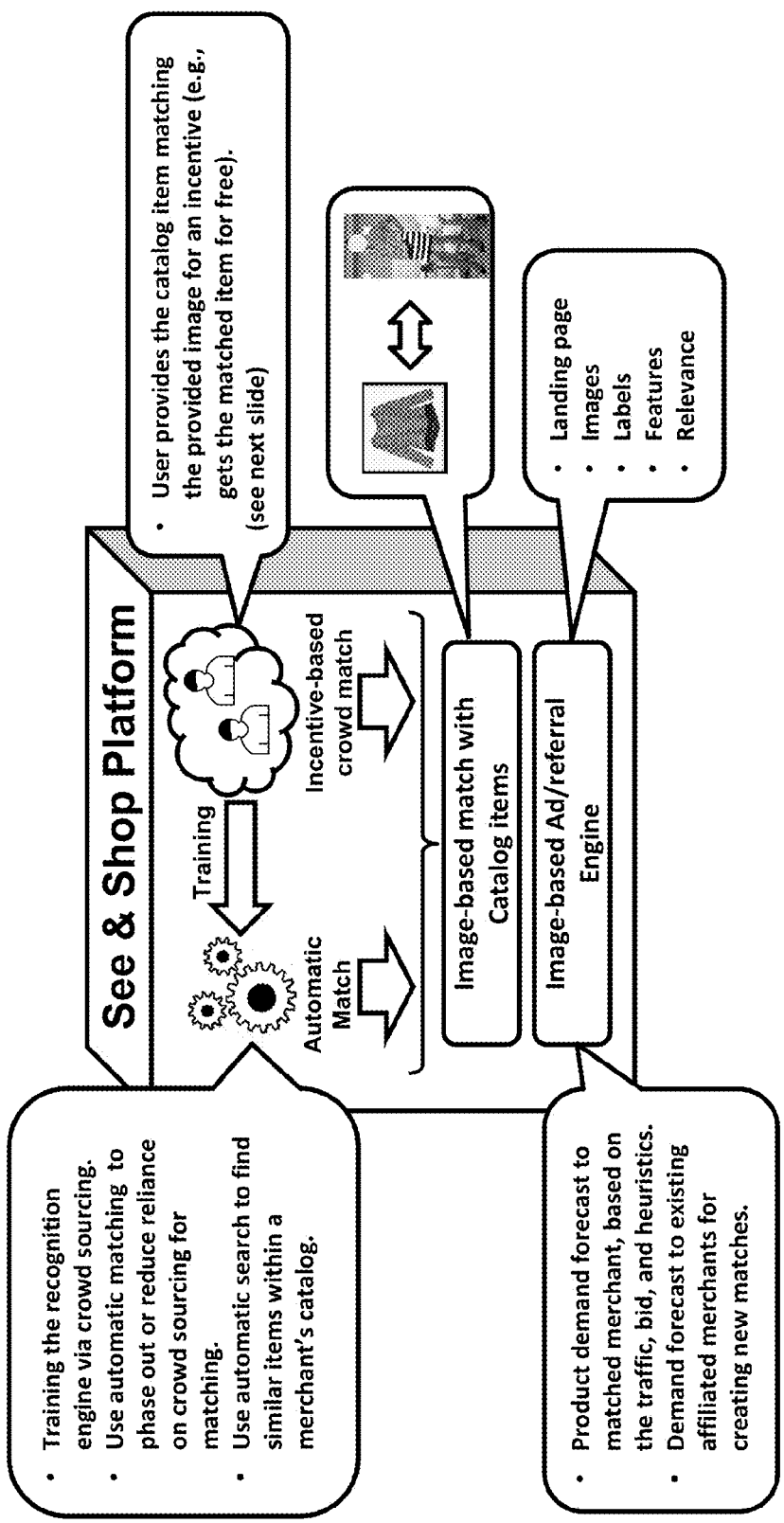

FIG. 250 shows an embodiment for "see and shop".

Figure 251:
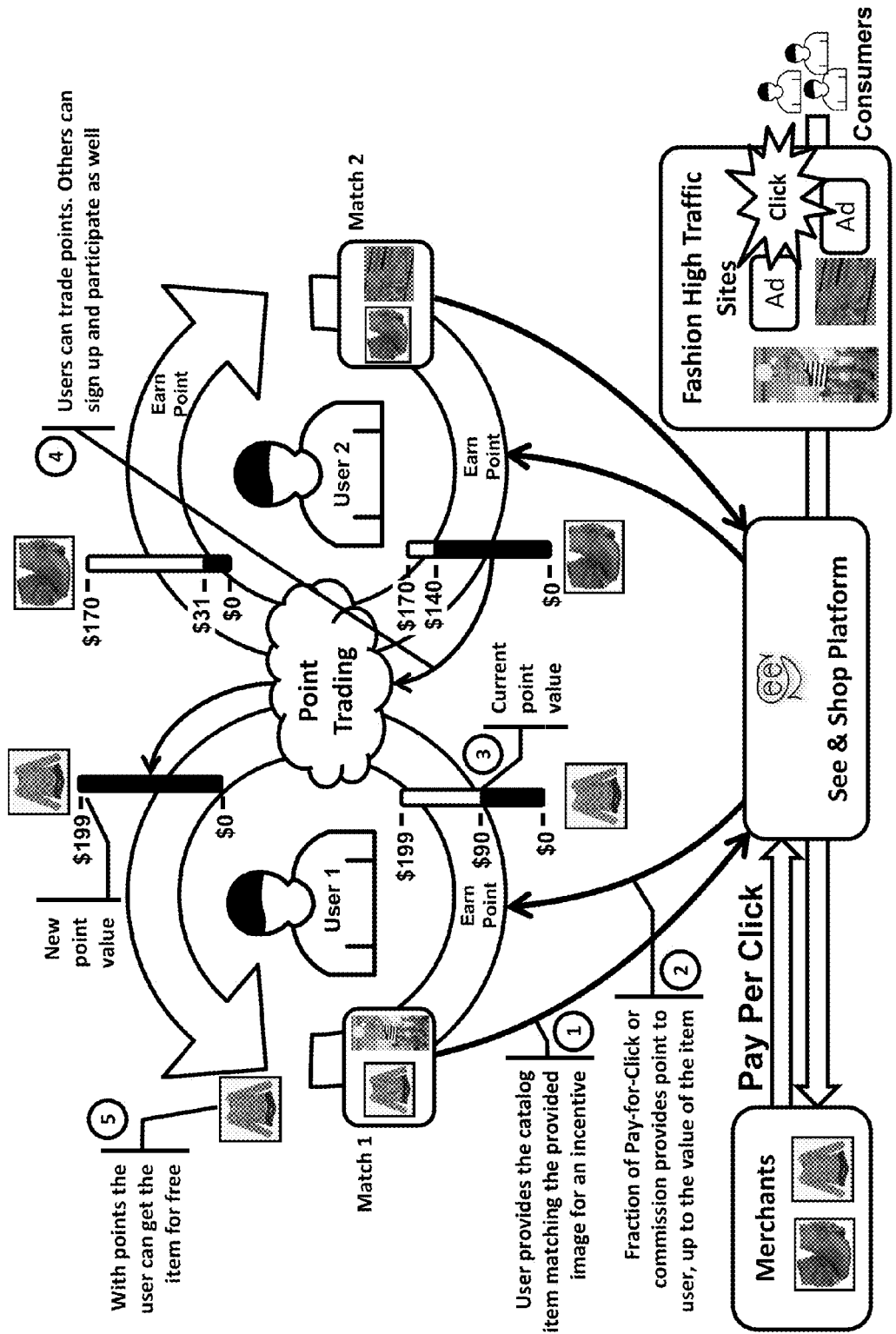

FIG. 251 shows an embodiment for "see and shop".

Figure 252:
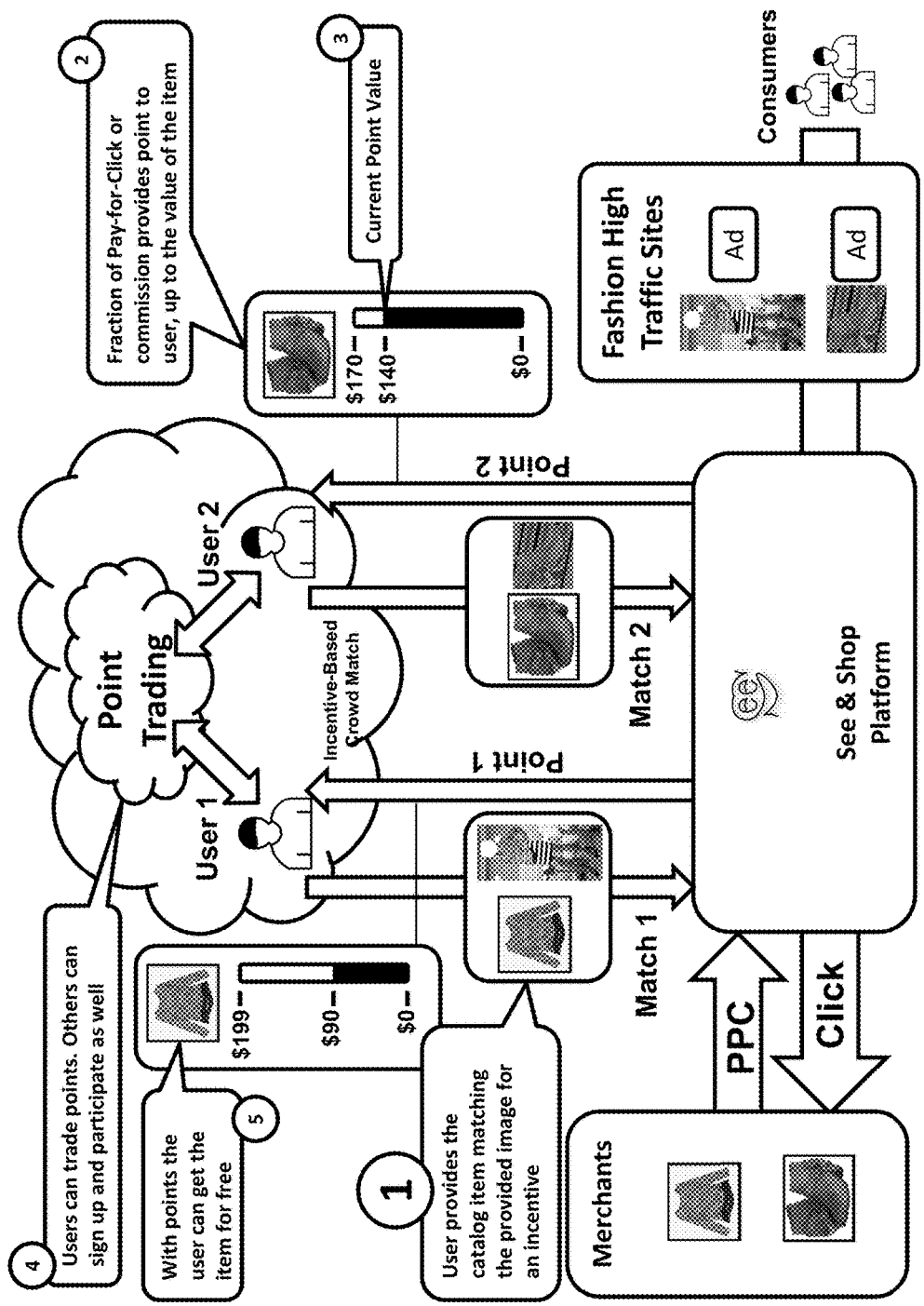

FIG. 252 shows an embodiment for "see and shop".

Figure 253:
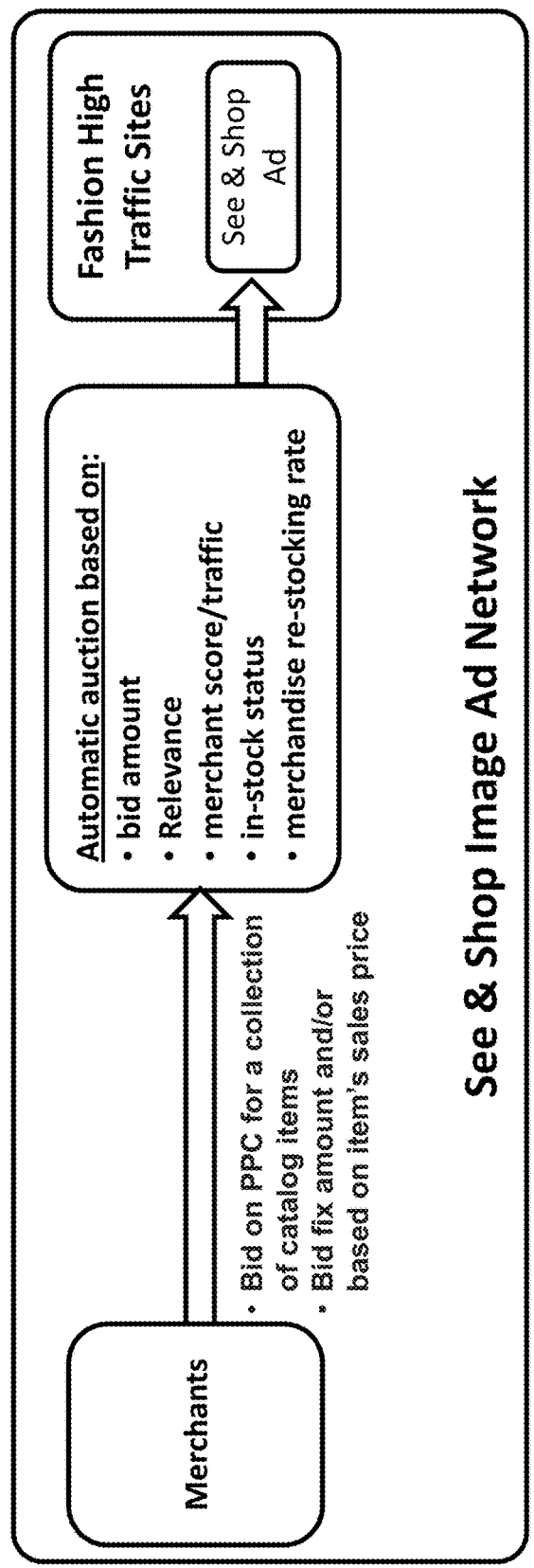

FIG. 253 shows an embodiment for "see and shop".

Figure 254:
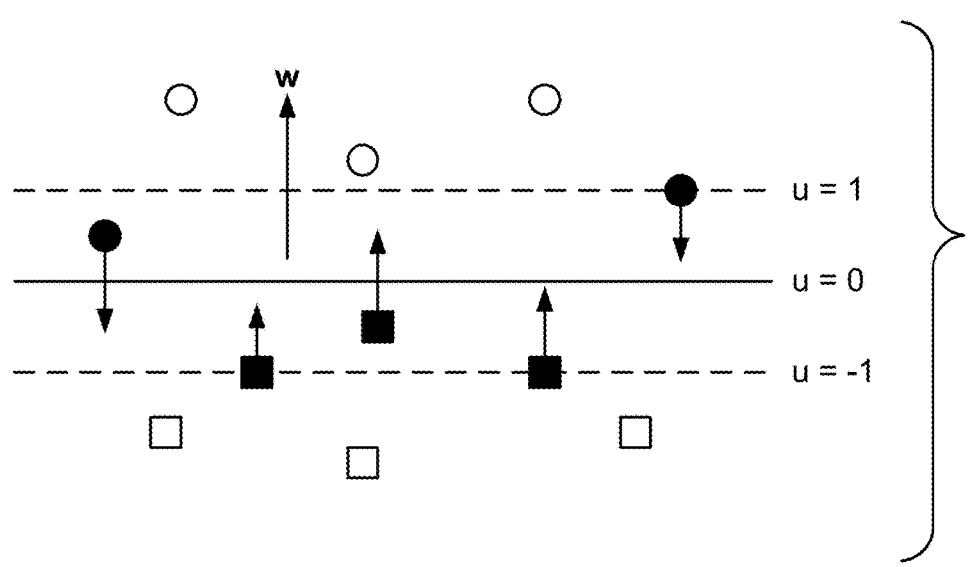

FIG. 254 shows an embodiment for leverage model of data points at the margin.

Figure 255:
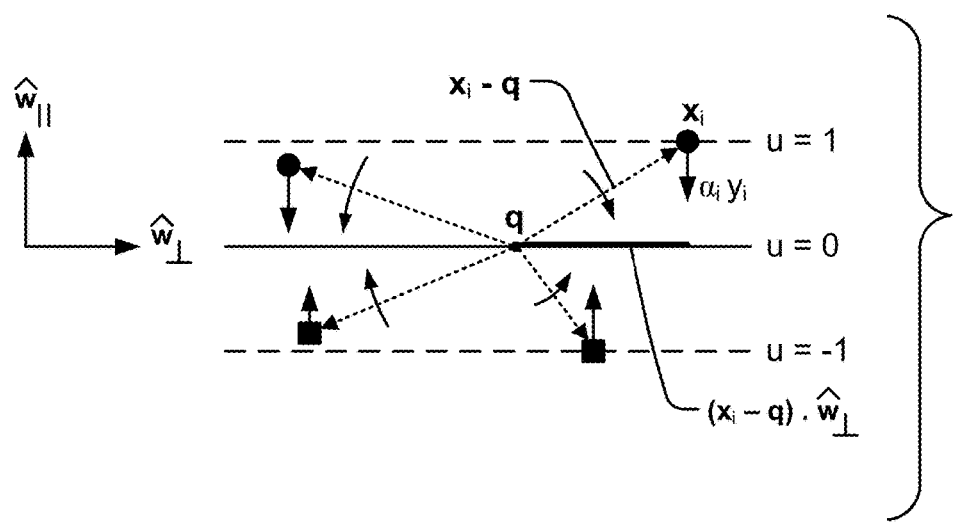

FIG. 255 shows an embodiment for balancing torques at pivot point q with leverage projected on $\hat{w}_\perp$.

Figure 256:
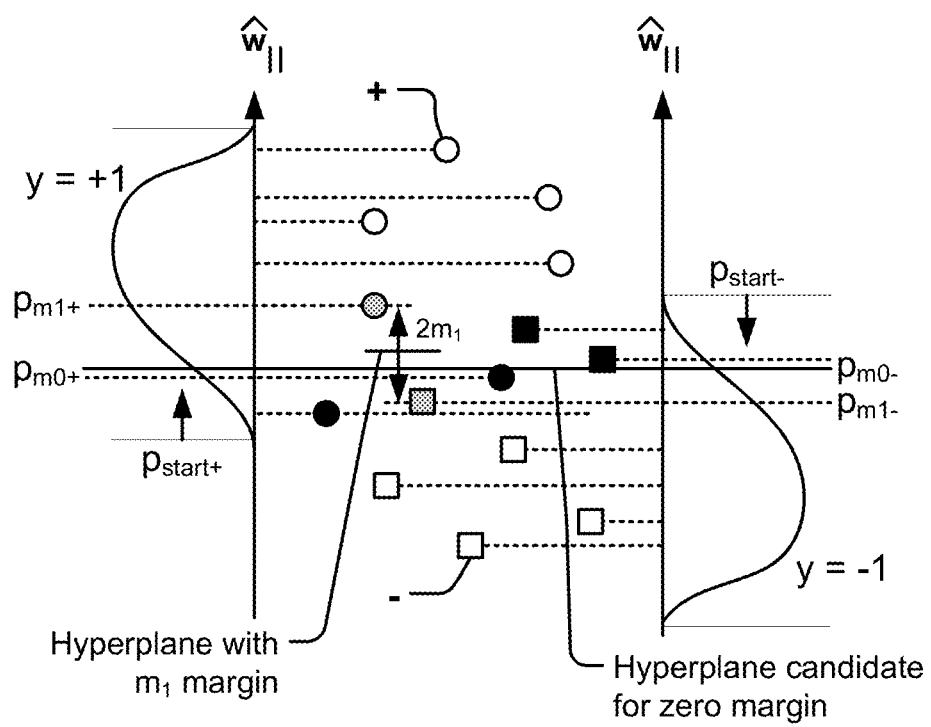

FIG. 256 shows an embodiment for projection of $x_i$ on $\hat{w}_\parallel$.

Figure 257:
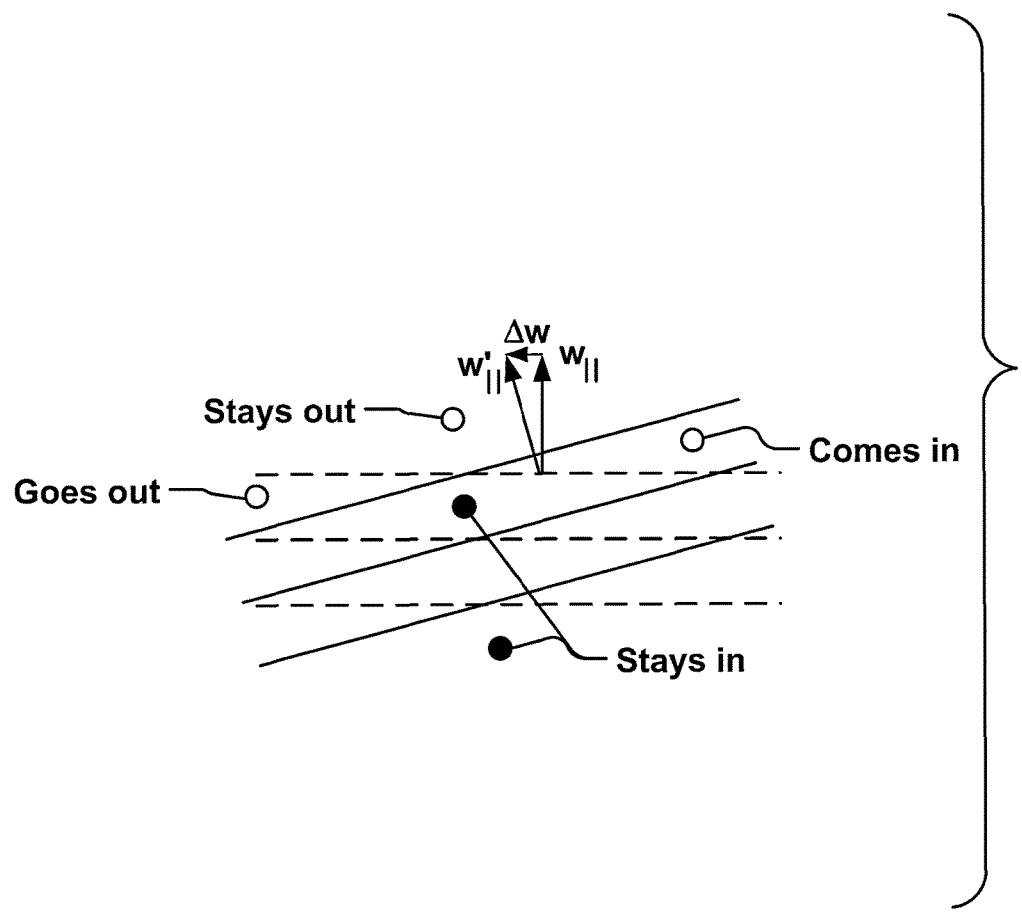

FIG. 257 shows an embodiment for tilt in $\hat{w}_\parallel$.

Figure 258:
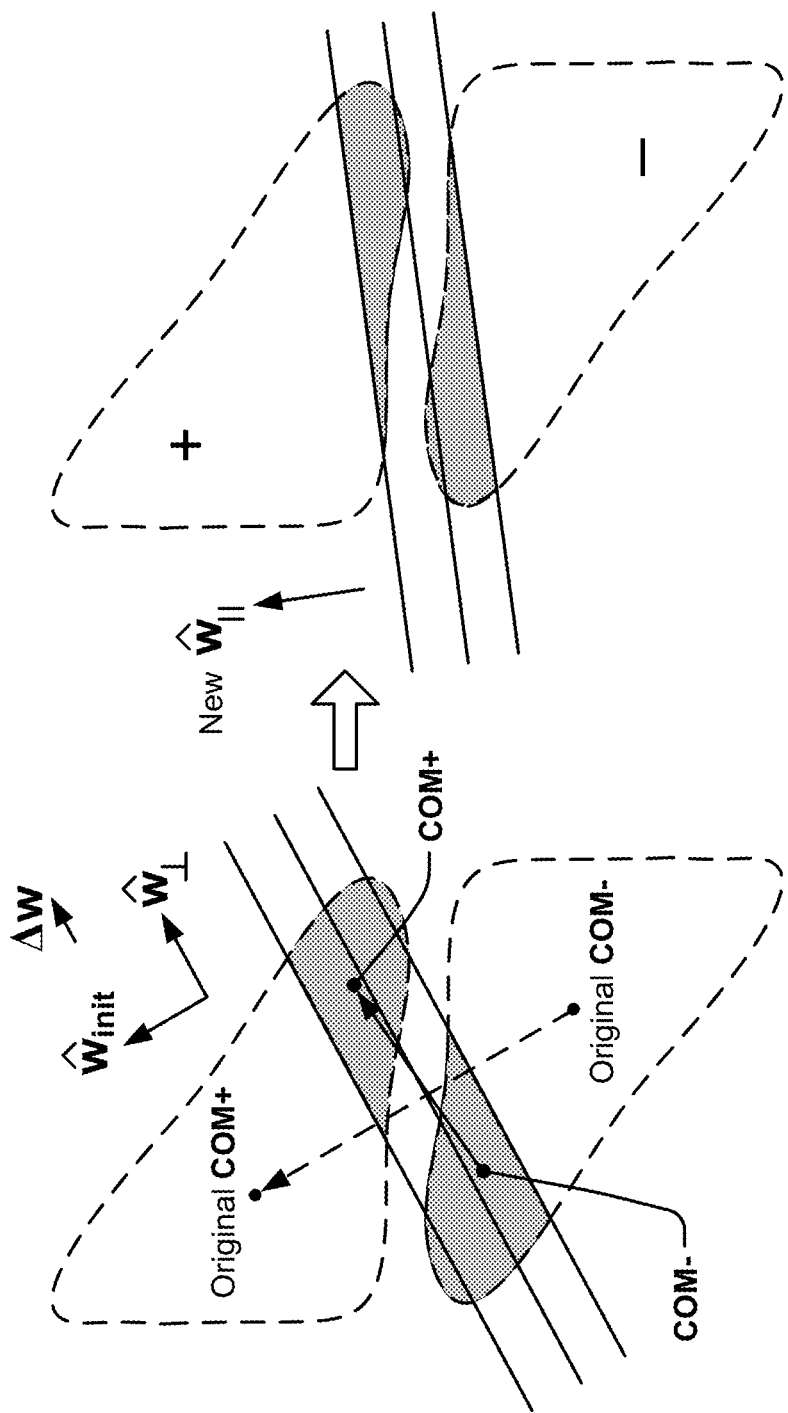

FIG. 258 shows an embodiment for reduction of slack error by tilting $\hat{w}_\parallel$ based on center of masses of data points that violate the margin (shown in darker color).

Figure 259:
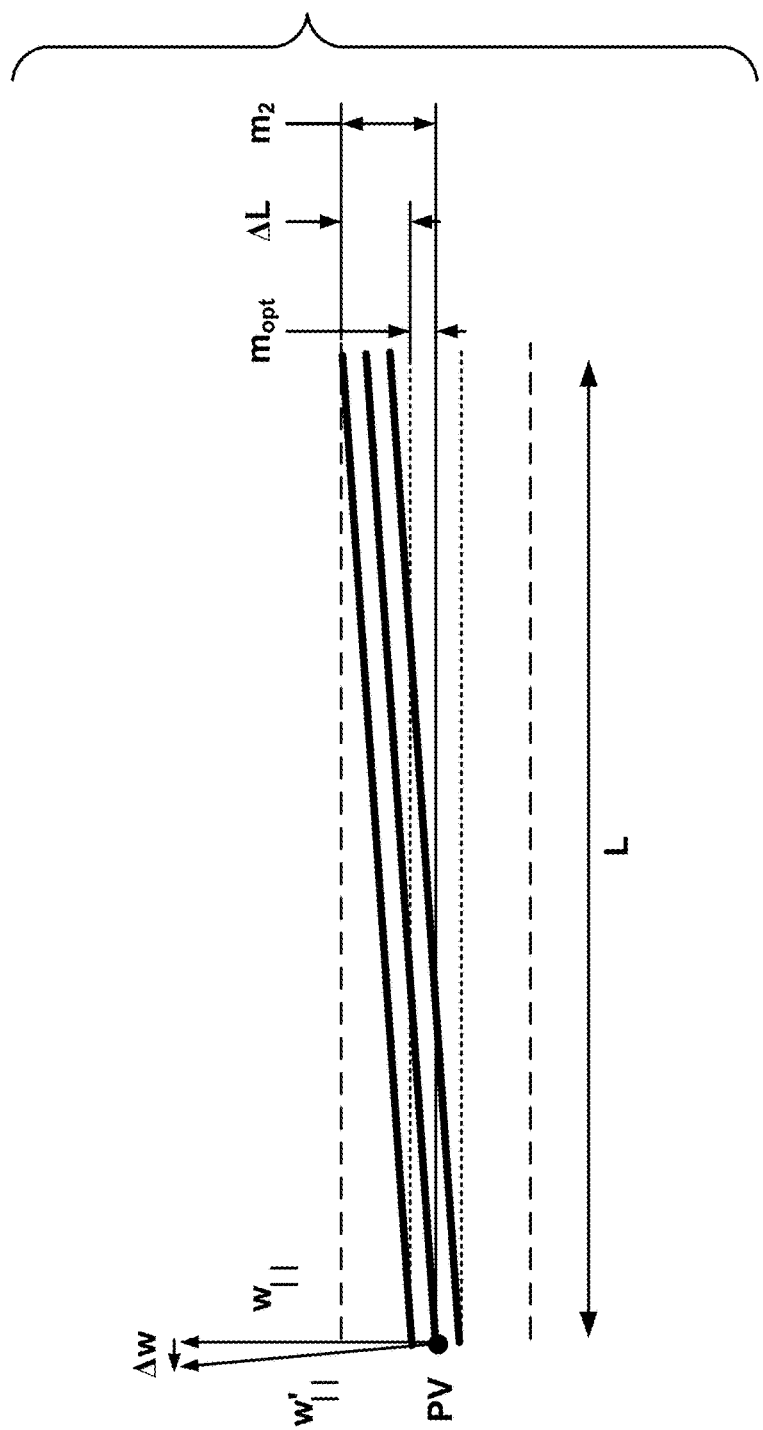

FIG. 259 shows an embodiment for limiting the tilt based on data obtained in projection scan along $\hat{w}_\parallel$.

Figure 260:
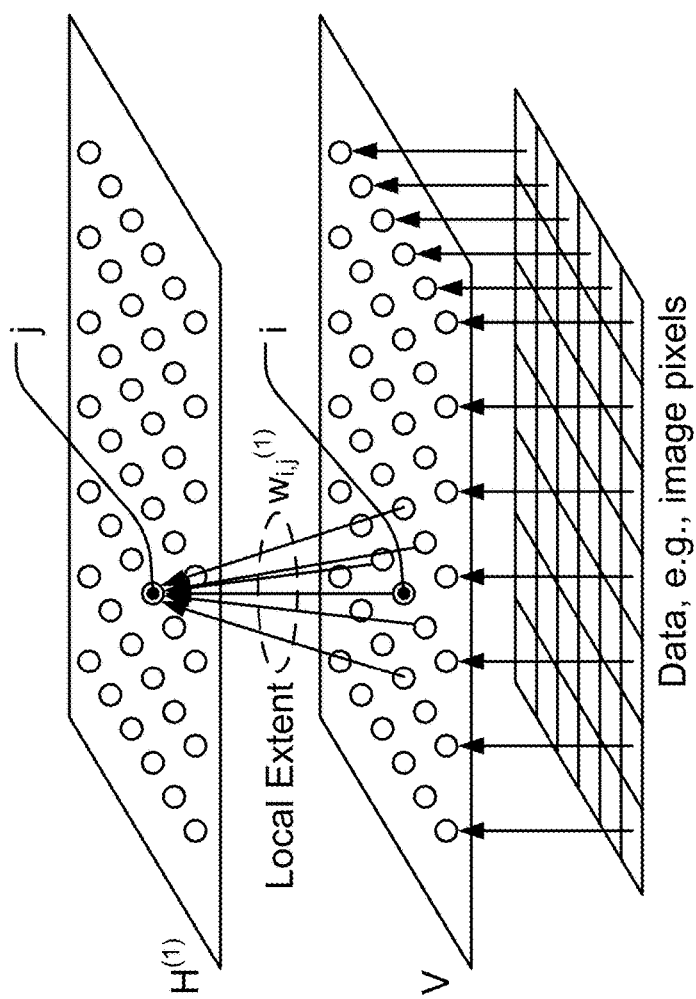

FIG. 260 shows an embodiment for image analysis.

Figure 261:
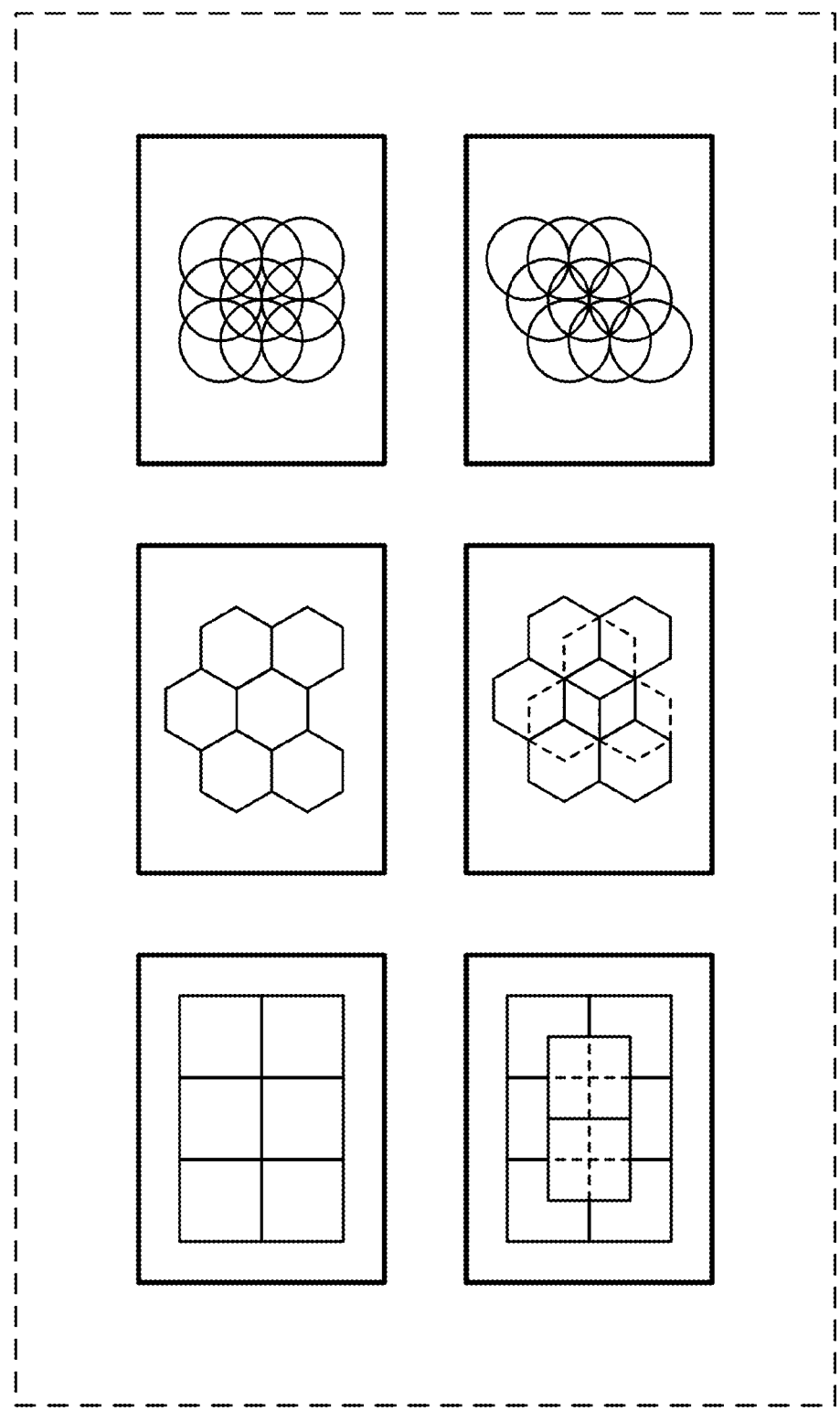

FIG. 261 shows an embodiment for different configurations.

Figure 262:
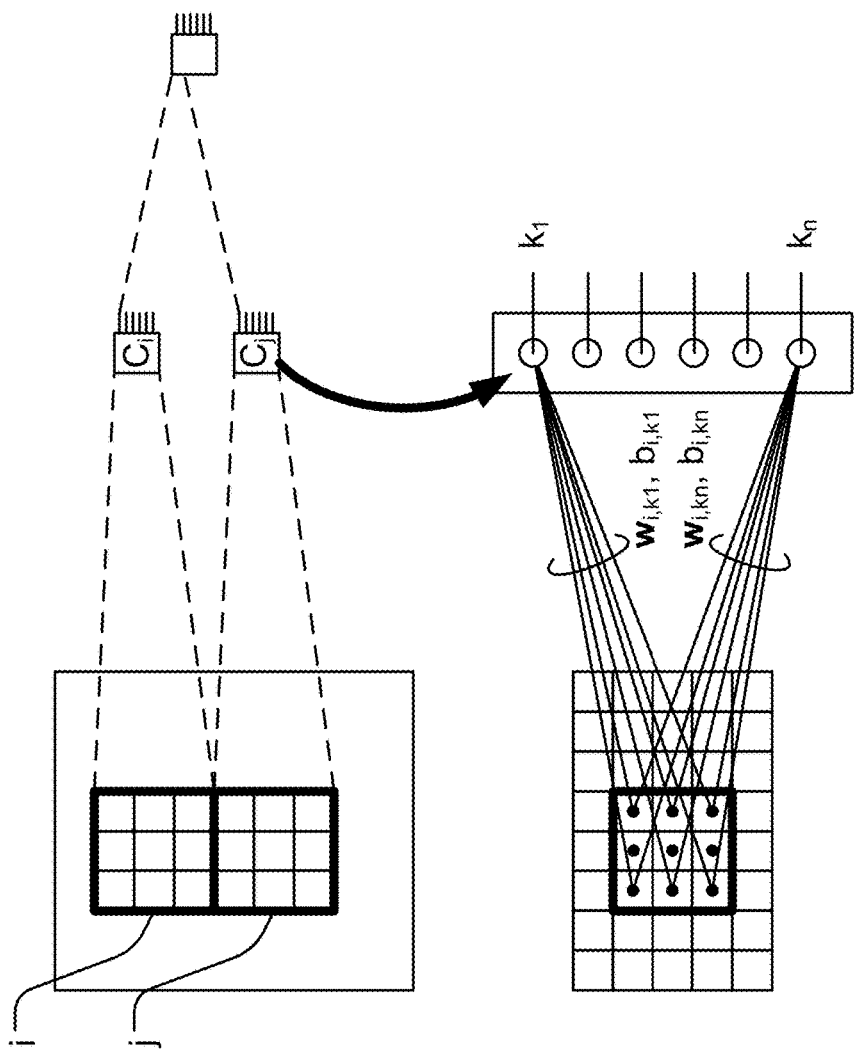

FIG. 262 shows an embodiment for image analysis.

Figure 263:
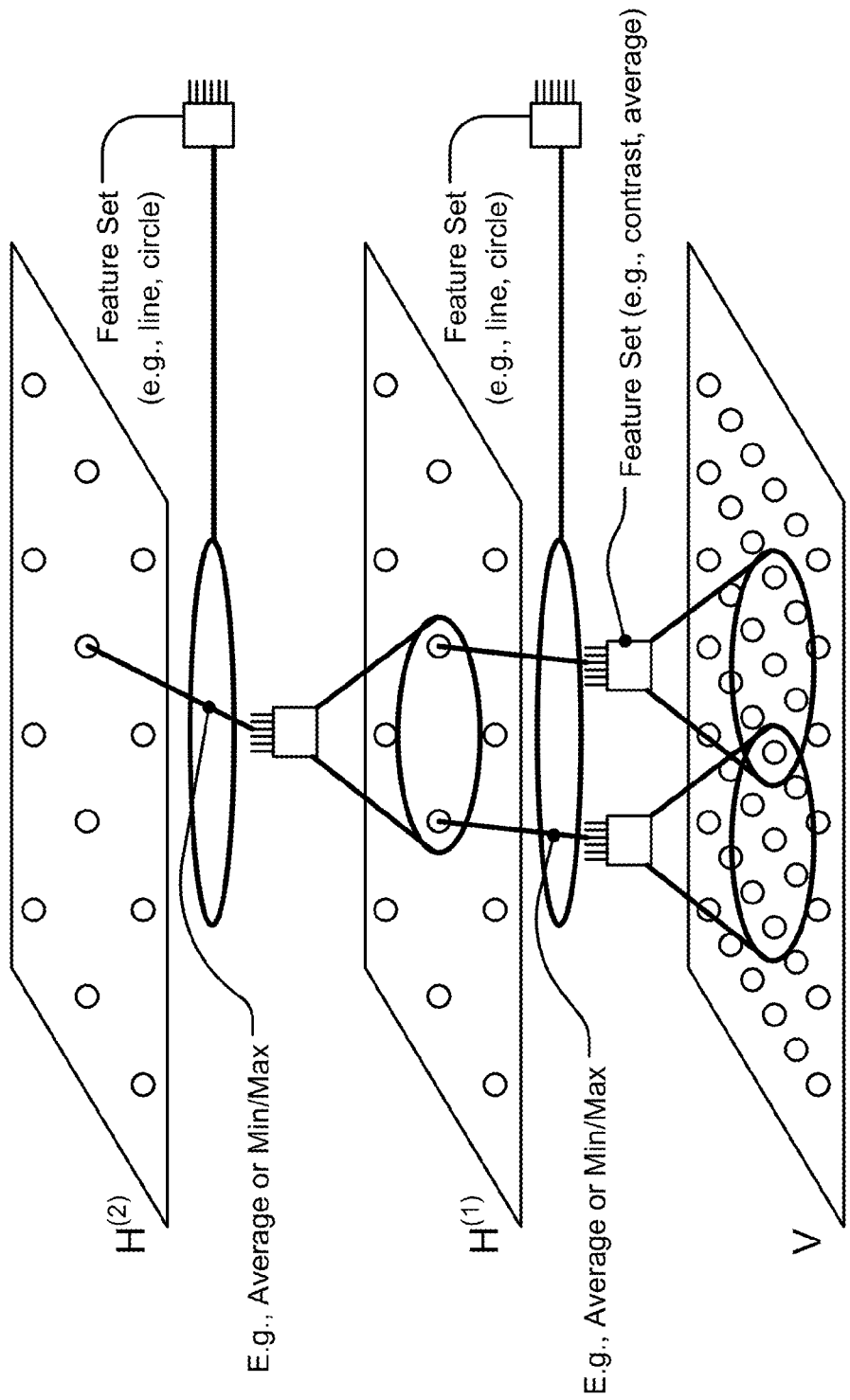

FIG. 263 shows an embodiment for image analysis.

Figure 264:
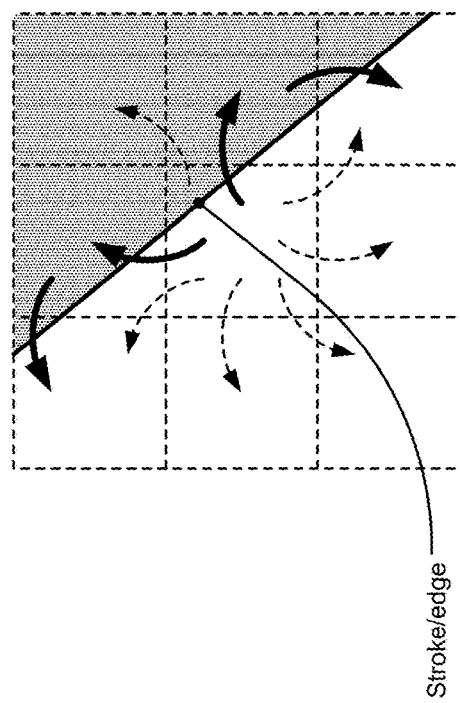

FIG. 264 shows an embodiment for image analysis.

Figure 265:
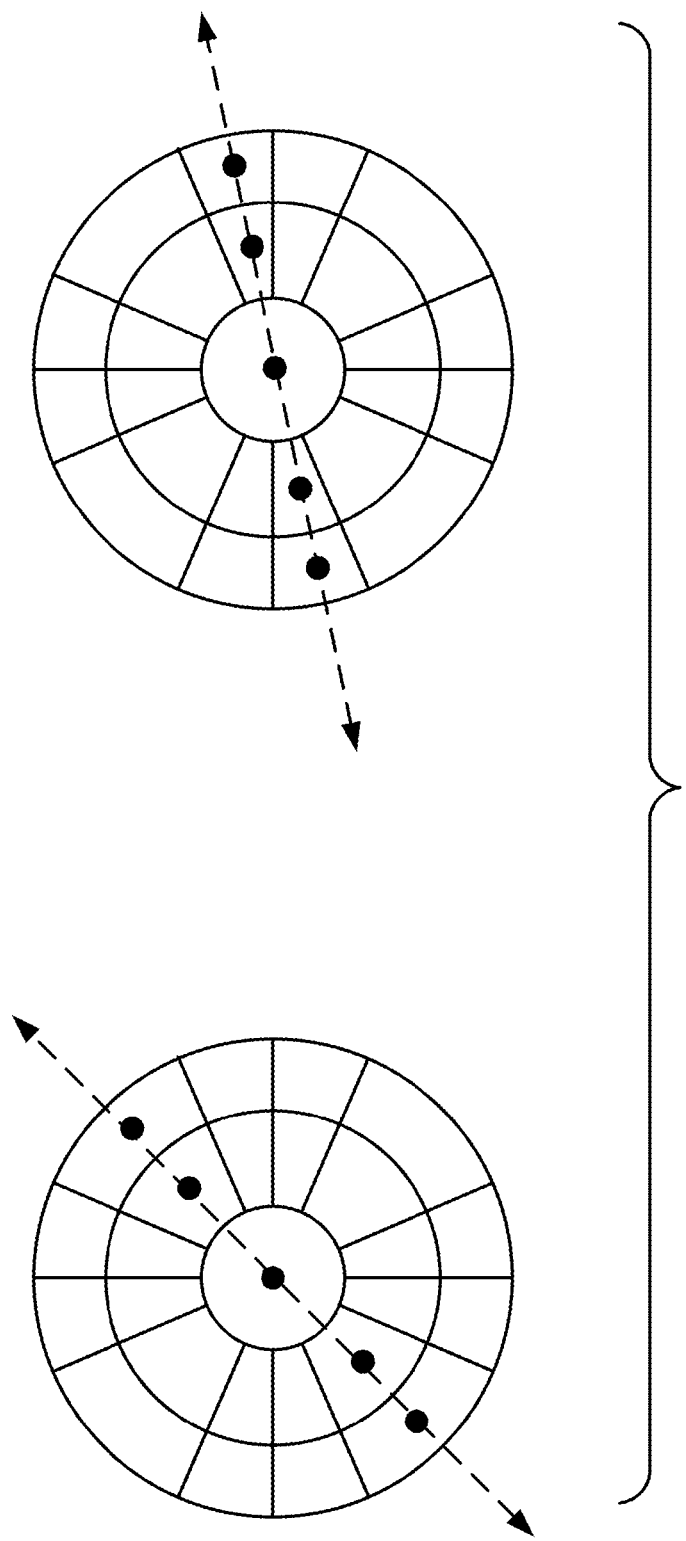

FIG. 265 shows an embodiment for image analysis.

Figure 266:
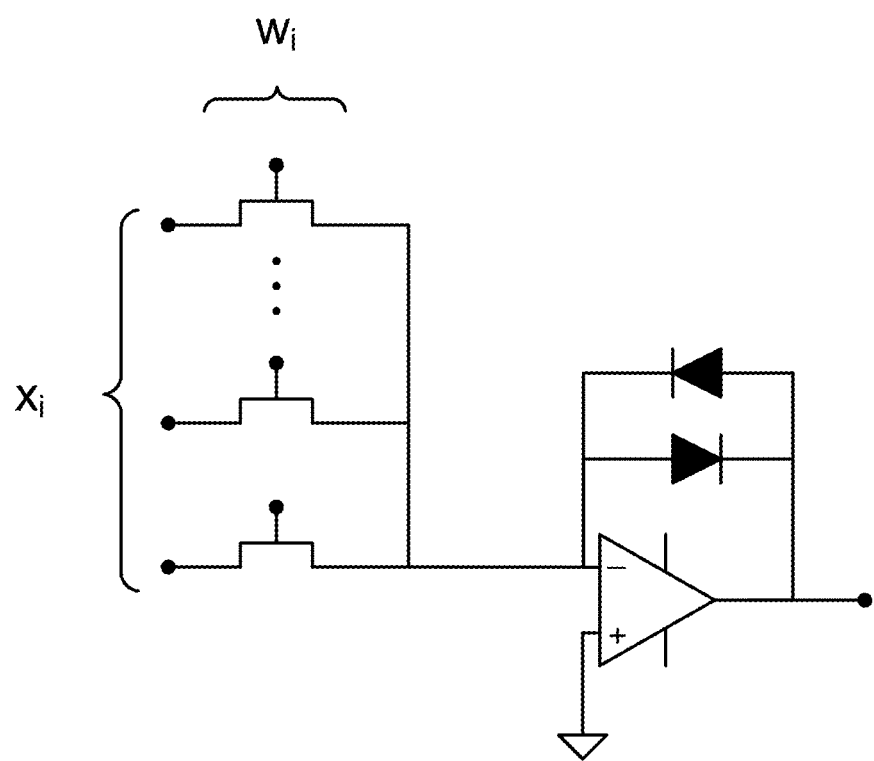

FIG. 266 shows an embodiment for circuit implementation.

Figure 267:
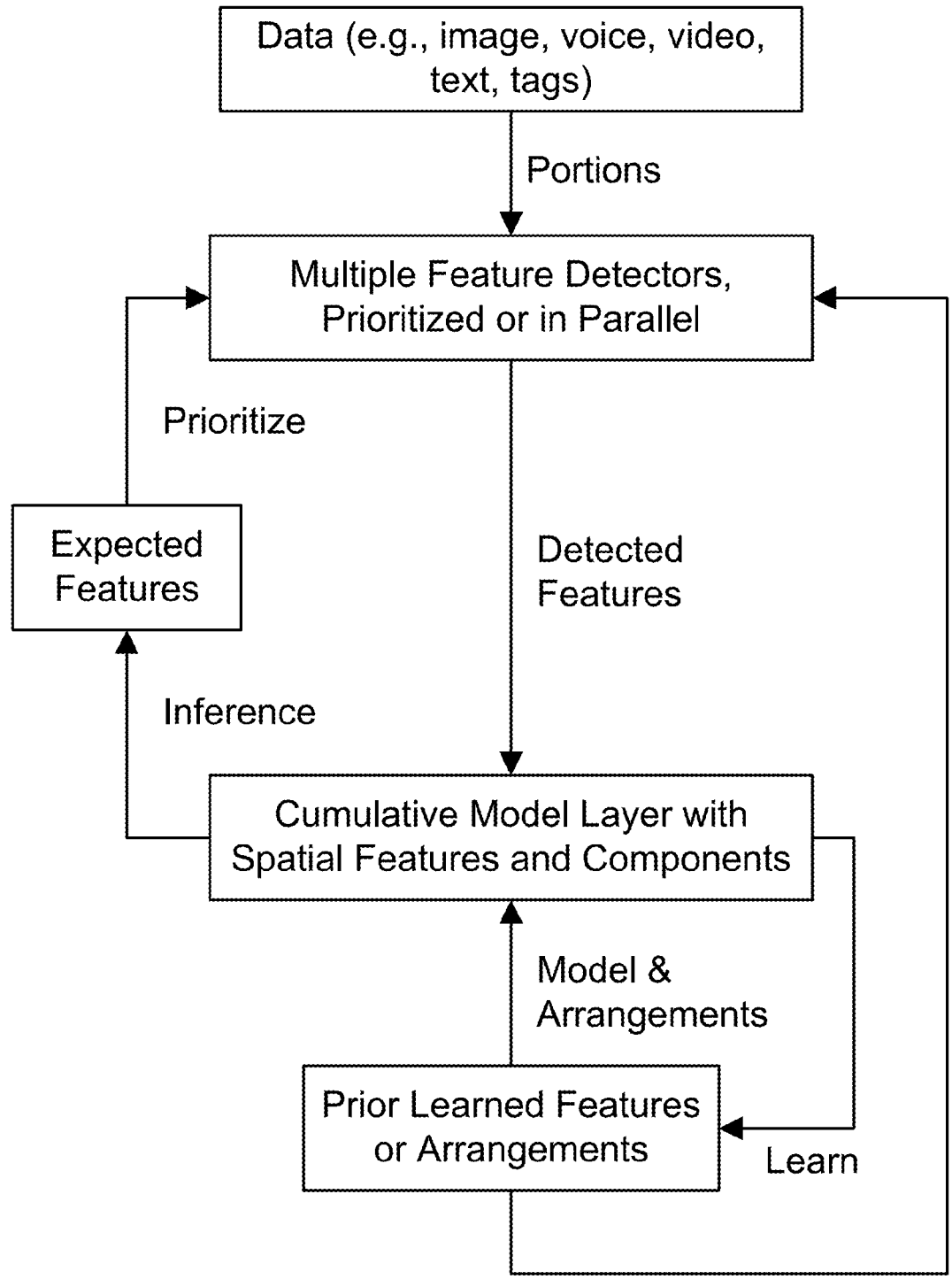

FIG. 267 shows an embodiment for feature detection.

DETAILED DESCRIPTION OF THE EMBODIMENTS

Z-Numbers:

A Z-number is an ordered pair of fuzzy numbers, (A,B). For simplicity, in one embodiment, A and B are assumed to be trapezoidal fuzzy numbers. A Z-number is associated with a real-valued uncertain variable, X, with the first component, A, playing the role of a fuzzy restriction, R(X), on the values which X can take, written as X is A, where A is a fuzzy set. What should be noted is that, strictly speaking, the concept of a restriction has greater generality than the concept of a constraint. A probability distribution is a restriction but is not a constraint (see L. A. Zadeh, Calculus of fuzzy restrictions, In: L. A. Zadeh, K. S. Fu, K. Tanaka, and M. Shimura (Eds.), Fuzzy sets and Their Applications to Cognitive and Decision Processes, Academic Press, New York, 1975, pp. 1-39). A restriction may be viewed as a generalized constraint (see L. A. Zadeh, Generalized theory of uncertainty (GTU)—principal concepts and ideas, Computational Statistics & Data Analysis 51, (2006) 15-46). In this embodiment only, the terms restriction and constraint are used interchangeably.

The restriction

R(X): X is A, is referred to as a possibilistic restriction (constraint), with A playing the role of the possibility distribution of X. More specifically, R(X): X is A→Poss(X=u)=$\mu_A$(u)

where $\mu_A$ is the membership function of A, and u is a generic value of X. $\mu_A$ may be viewed as a constraint which is associated with R(X), meaning that $\mu_A$(u) is the degree to which u satisfies the constraint.

When X is a random variable, the probability distribution of X plays the role of a probabilistic restriction on X. A probabilistic restriction is expressed as:

R(X): X isp p where p is the probability density function of X. In this case,

R(X): X isp p→Prob(u≤X≤u+du)=p(u)du

Note. Generally, the term "restriction" applies to X is R. Occasionally, "restriction" applies to R. Context serves to disambiguate the meaning of "restriction."

The ordered triple (X,A,B) is referred to as a Z-valuation. A Z-valuation is equivalent to an assignment statement, X is (A,B). X is an uncertain variable if A is not a singleton. In a related way, uncertain computation is a system of computation in which the objects of computation are not values of variables but restrictions on values of variables. In this embodiment/section, unless stated to the contrary, X is assumed to be a random variable. For convenience, A is referred to as a value of X, with the understanding that, strictly speaking, A is not a value of X but a restriction on the values which X can take. The second component, B, is referred to as certainty. Certainty concept is related to other concepts, such as sureness, confidence, reliability, strength of belief, probability, possibility, etc. However, there are some differences between these concepts.

In one embodiment, when X is a random variable, certainty may be equated to probability. Informally, B may be interpreted as a response to the question: How sure are you that X is A? Typically, A and B are perception-based and are described in a natural language. Example: (about 45 minutes, usually.) A collection of Z-valuations is referred to as Z-information. It should be noted that much of everyday reasoning and decision-making is based, in effect, on Z-information. For purposes of computation, when A and B are described in a natural language, the meaning of A and B is precisiated (graduated) through association with membership functions, $\mu_A$ and $\mu_B$, respectively, FIG. 1.

The membership function of A, $\mu_A$, may be elicited by asking a succession of questions of the form: To what degree does the number, a, fit your perception of A? Example: To what degree does 50 minutes fit your perception of about 45 minutes? The same applies to B. The fuzzy set, A, may be interpreted as the possibility distribution of X. The concept of a Z-number may be generalized in various ways. In particular, X may be assumed to take values in $R^n$, in which case A is a Cartesian product of fuzzy numbers. Simple examples of Z-valuations are:

(anticipated budget deficit, close to 2 million dollars, very likely)
(population of Spain, about 45 million, quite sure)
(degree of Robert's honesty, very high, absolutely)
(degree of Robert's honesty, high, not sure)
(travel time by car from Berkeley to San Francisco, about 30 minutes, usually)
(price of oil in the near future, significantly over 100 dollars/barrel, very likely)

It is important to note that many propositions in a natural language are expressible as Z-valuations. Example: The proposition, p, p: Usually, it takes Robert about an hour to get home from work,
is expressible as a Z-valuation:
(Robert's travel time from office to home, about one hour, usually)

If X is a random variable, then X is A represents a fuzzy event in R, the real line. The probability of this event, p, may be expressed as (see L. A. Zadeh, Probability measures of fuzzy events, Journal of Mathematical Analysis and Applications 23 (2), (1968) 421-427.):

$$p = \int_R \mu_A(u) p_X(u) du,$$

where $p_X$ is the underlying (hidden) probability density of X. In effect, the Z-valuation (X,A,B) may be viewed as a restriction (generalized constraint) on X defined by:
Prob(X is A) is B.

What should be underscored is that in a Z-number, (A,B), the underlying probability distribution, $p_X$, is not known. What is known is a restriction on $p_X$ which may be expressed as:

$$\int_R \mu_A(u) p_X(u) du \text{ is } B$$

Note: In this embodiment only, the term "probability distribution" is not used in its strict technical sense.

In effect, a Z-number may be viewed as a summary of $p_X$. It is important to note that in everyday decision-making, most decisions are based on summaries of information. Viewing a Z-number as a summary is consistent with this reality. In applications to decision analysis, a basic problem which arises relates to ranking of Z-numbers. Example: Is (approximately 100, likely) greater than (approximately 90, very likely)? Is this a meaningful question? We are going to address these questions below.

An immediate consequence of the relation between $p_X$ and B is the following. If Z=(A,B) then Z'=(A',1−B), where A' is the complement of A and Z' plays the role of the complement of Z. 1−B is the antonym of B (see, e.g., E. Trillas, C. Moraga, S. Guadarrama, S. Cubillo and E. Castiñeira, Computing with Antonyms, In: M. Nikravesh, J. Kacprzyk and L. A. Zadeh (Eds.), Forging New Frontiers: Fuzzy Pioneers I, Studies in Fuzziness and Soft Computing Vol 217, Springer-Verlag, Berlin Heidelberg 2007, pp. 133-153.).

An important qualitative attribute of a Z-number is informativeness. Generally, but not always, a Z-number is informative if its value has high specificity, that is, is tightly constrained (see, for example, R. R. Yager, On measures of specificity, In: O. Kaynak, L. A. Zadeh, B. Turksen, I. J. Rudas (Eds.), Computational Intelligence: Soft Computing and Fuzzy-Neuro Integration with Applications, Springer-Verlag, Berlin, 1998, pp. 94-113.), and its certainty is high. Informativeness is a desideratum when a Z-number is a basis for a decision. It is important to know that if the informativeness of a Z-number is sufficient to serve as a basis for an intelligent decision.

The concept of a Z-number is after the concept of a fuzzy granule (see, for example, L. A. Zadeh, Fuzzy sets and information granularity, In: M. Gupta, R. Ragade, R. Yager (Eds.), Advances in Fuzzy Set Theory and Applications, North-Holland Publishing Co., Amsterdam, 1979, pp. 3-18. Also, see L. A. Zadeh, Possibility theory and soft data analysis, In: L. Cobb, R. M. Thrall (Eds.), Mathematical Frontiers of the Social and Policy Sciences, Westview Press, Boulder, Colo., 1981, pp. 69-129. Also, see L. A. Zadeh, Generalized theory of uncertainty (GTU)—principal concepts and ideas, Computational Statistics & Data Analysis 51, (2006) 15-46.). It should be noted that the concept of a Z-number is much more general than the concept of confidence interval in probability theory. There are some links between the concept of a Z-number, the concept of a fuzzy random number and the concept of a fuzzy random variable (see, e.g., J. J. Buckley, J. J. Leonard, Chapter 4: Random fuzzy numbers and vectors, In: Monte Carlo Methods in Fuzzy Optimization, Studies in Fuzziness and Soft Computing 222, Springer-Verlag, Heidelberg, Germany, 2008. Also, see A. Kaufman, M. M. Gupta, Introduction to Fuzzy Arithmetic: Theory and Applications, Van Nostrand Reinhold Company, New York, 1985. Also, see C. V. Negoita, D. A. Ralescu, Applications of Fuzzy Sets to Systems Analysis, Wiley, New York, 1975.).

A concept which is closely related to the concept of a Z-number is the concept of a $Z^+$-number. Basically, a $Z^+$-number, $Z^+$, is a combination of a fuzzy number, A, and a random number, R, written as an ordered pair $Z^+=(A,R)$.

In this pair, A plays the same role as it does in a Z-number, and R is the probability distribution of a random number. Equivalently, R may be viewed as the underlying probability distribution of X in the Z-valuation (X,A,B). Alternatively, a $Z^+$-number may be expressed as $(A,p_X)$ or $(\mu_A,p_X)$, where $\mu_A$ is the membership function of A. A $Z^+$-valuation is expressed as $(X,A,p_X)$ or, equivalently, as $(X,\mu_A,p_X)$, where $p_X$ is the probability distribution (density) of X. A $Z^+$-number is associated with what is referred to as a bimodal distribution, that is, a distribution which combines the possibility and probability distributions of X. Informally, these distributions are compatible if the centroids of $\mu_A$ and $p_X$ are coincident, that is, $$\int_R u \cdot p_X(u) \cdot du = \frac{\int_R u \cdot \mu_A(u) \cdot du}{\int_R \mu_A(u) \cdot du}$$

The scalar product of $\mu_A$ and $p_X$, $\mu_A \cdot p_X$, is the probability measure, $P_A$, of A. More concretely, $$\mu_A \cdot p_X = P_A$$
$$= \int_R \mu_A(u) p_X(u) du$$

It is this relation that links the concept of a Z-number to that of a $Z^+$-number. More concretely, $Z(A,B) = Z^+(A, \mu_A \cdot p_X \text{ is } B)$ What should be underscored is that in the case of a Z-number what is known is not $p_X$ but a restriction on $p_X$ expressed as: $\mu_A \cdot p_X$ is B. By definition, a $Z^+$-number carries more information than a Z-number. This is the reason why it is labeled a $Z^+$-number. Computation with $Z^+$-numbers is a portal to computation with Z-numbers.

The concept of a bimodal distribution is of interest in its own right. Let X be a real-valued variable taking values in U. For our purposes, it is convenient to assume that U is a finite set, $U=\{u_1, \ldots, u_n\}$. We can associate with X a possibility distribution, $\mu$, and a probability distribution, p, expressed as:

$\mu = \mu_1/u_1 + \ldots + \mu_n/u_n$ $p = p_1 \backslash u_1 + \ldots + p_n \backslash u_n$ in which $\mu_i/u_i$ means that $\mu_i$, i=1, ... n, is the possibility that $X=u_i$. Similarly, $p_i \backslash u_i$ means that $p_i$ is the probability that $X=u_i$.

The possibility distribution, $\mu$, may be combined with the probability distribution, p, through what is referred to as confluence. More concretely, $\mu:p = (\mu_1,p_1)/u_1 + \ldots + (\mu_n,p_n)/u_n$ As was noted earlier, the scalar product, expressed as $\mu \cdot p$, is the probability measure of A. In terms of the bimodal distribution, the $Z^+$-valuation and the Z-valuation associated with X may be expressed as:

$(X,A,p_X)$ $(X,A,B)$, $\mu_A \cdot p_X$ is B, respectively, with the understanding that B is a possibilistic restriction on $\mu_A \cdot p_X$.

Both Z and $Z^+$ may be viewed as restrictions on the values which X may take, written as: X is Z and X is $Z^+$ respectively. Viewing Z and $Z^+$ as restrictions on X adds important concepts to representation of information and characterization of dependencies. In this connection, what should be noted is that the concept of a fuzzy if-then rule plays a pivotal role in most applications of fuzzy logic. What follows is a very brief discussion of what are referred to as Z-rules—if-then rules in which the antecedents and/or consequents involve Z-numbers or $Z^+$-numbers.

A basic fuzzy if-then rule may be expressed as: if X is A then Y is B, where A and B are fuzzy numbers. The meaning of such a rule is defined as:

if X is A then Y is B $\rightarrow$ (X,Y) is A$\times$B where A$\times$B is the Cartesian product of A and B. It is convenient to express a generalization of the basic if-then rule to Z-numbers in terms of Z-valuations. More concretely, if $(X, A_X, B_X)$ then $(Y, A_Y, B_Y)$ Examples:

if (anticipated budget deficit, about two million dollars, very likely) then (reduction in staff, about ten percent, very likely)

if (degree of Robert's honesty, high, not sure) then (offer a position, not, sure)

if (X, small) then (Y, large, usually.)

An important question relates to the meaning of Z-rules and $Z^+$-rules. The meaning of a $Z^+$-rule may be expressed as:

if $(X,A_X,p_X)$ then $(Y, A_Y, p_Y) \rightarrow (X,Y)$ is $(A_X \times A_Y, p_X p_Y)$ where $A_X \times A_Y$ is the Cartesian product $A_X$ and $A_Y$ Z-rules have the important applications in decision analysis and modeling of complex systems, especially in the realm of economics (for example, stock market and specific stocks) and medicine (e.g. diagnosis and analysis).

A problem which plays a key role in many applications of fuzzy logic, especially in the realm of fuzzy control, is that of interpolation. More concretely, the problem of interpolation may be formulated as follows. Consider a collection of fuzzy if-then rules of the form:

if X is $A_i$ then Y is $B_i$, i=1, ... , n where the $A_i$ and $B_i$ are fuzzy sets with specified membership functions. If X is A, where A is not one of the $A_i$, then what is the restriction on Y?

The problem of interpolation may be generalized in various ways. A generalization to Z-numbers may be described as follows. Consider a collection Z-rules of the form:

if X is $A_i$ then usually (Y is $B_i$), i=1, ... , n where the $A_i$ and $B_i$ are fuzzy sets. Let A be a fuzzy set which is not one of the $A_i$. What is the restriction on Y expressed as a Z-number? An answer to this question would add a useful formalism to the analysis of complex systems and decision processes.

Representation of Z-numbers can be facilitated through the use of what is called a Z-mouse. Basically, a Z-mouse is a visual means of entry and retrieval of fuzzy data.

Figure 2A:
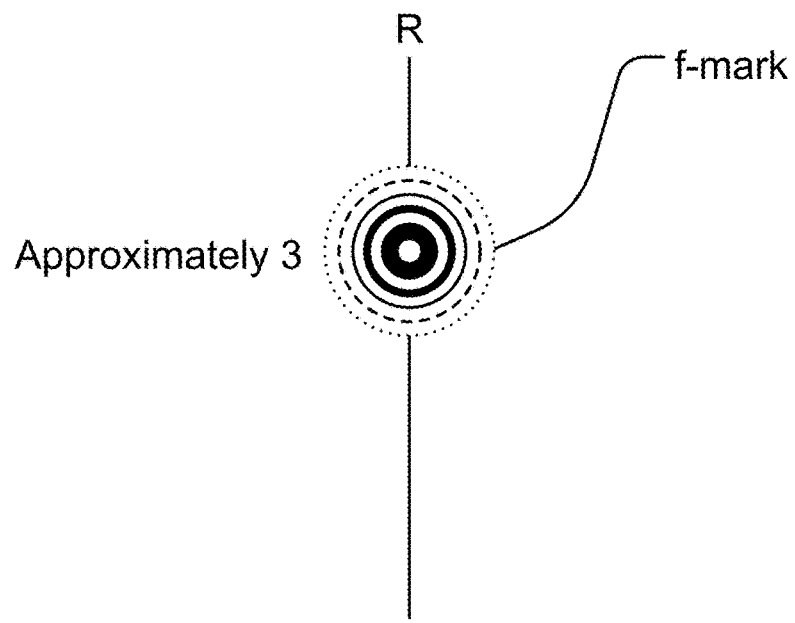
FIG. 2(a) shows f-mark of approximately 3.

The cursor of a Z-mouse is a circular fuzzy mark, called an f-mark, with a trapezoidal distribution of light intensity. This distribution is interpreted as a trapezoidal membership function of a fuzzy set. The parameters of the trapezoid are controlled by the user. A fuzzy number such as "approximately 3" is represented as an f-mark on a scale, with 3 being the centroid of the f-mark (FIG. 2a). The size of the f-mark is a measure of the user's uncertainty about the value of the number. As was noted already, the Z-mouse interprets an f-mark as the membership function of a trapezoidal fuzzy set. This membership function serves as an object of computation. A Z-mouse can be used to draw curves and plot functions.

A key idea which underlies the concept of a Z-mouse is that visual interpretation of uncertainty is much more natural than its description in natural language or as a membership function of a fuzzy set. This idea is closely related to the remarkable human capability to precisiate (graduate) perceptions, that is, to associate perceptions with degrees. As an illustration, if I am asked "What is the probability that Obama will be reelected?" I would find it easy to put an f-mark on a scale from 0 to 1. Similarly, I could put an f-mark on a scale from 0 to 1 if I were asked to indicate the degree to which I like my job. It is of interest to note that a Z-mouse could be used as an informative means of polling, making it possible to indicate one's strength of feeling about an issue. Conventional polling techniques do not assess strength of feeling.

Figure 2B:
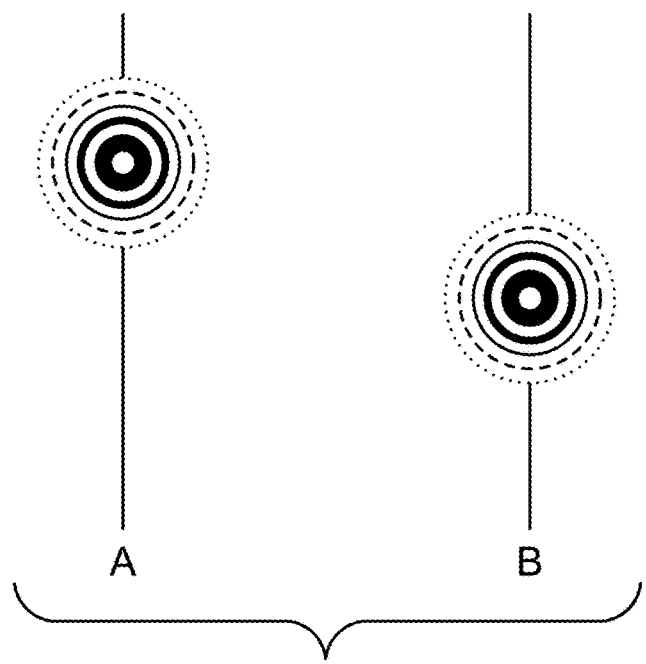
FIG. 2(b) shows f-mark of a Z-number.

Using a Z-mouse, a Z-number is represented as two f-marks on two different scales (FIG. 2b). The trapezoidal fuzzy sets which are associated with the f-marks serve as objects of computation.

Computation with Z-Numbers:

What is meant by computation with Z-numbers? Here is a simple example. Suppose that I intend to drive from Berkeley to San Jose via Palo Alto. The perception-based information which I have may be expressed as Z-valuations: (travel time from Berkeley to Palo Alto, about an hour, usually) and (travel time from Palo Alto to San Jose, about twenty-five minutes, usually.) How long will it take me to drive from Berkeley to San Jose? In this case, we are dealing with the sum of two Z-numbers (about an hour, usually) and (about twenty-five minutes, usually.) Another example: What is the square root of (A,B)? Computation with Z-numbers falls within the province of Computing with Words (CW or CWW). Example: What is the square root of a Z-number?

Computation with $Z^+$-numbers is much simpler than computation with Z-numbers. Assume that * is a binary operation whose operands are $Z^+$-numbers, $Z^+_X=(A_X,R_X)$ and $Z^+_Y=(A_Y,R_Y)$. By definition, $$Z^+_X * Z^+_Y = (A_X * A_Y, R_X * R_Y)$$

with the understanding that the meaning of * in $R_X*R_Y$ is not the same as the meaning of * in $A_X*A_Y$. In this expression, the operands of * in $A_X*A_Y$ are fuzzy numbers; the operands of * in $R_X*R_Y$ are probability distributions.

Example: Assume that * is sum. In this case, $A_X+A_Y$ is defined by:

$$\mu_{(A_X+A_Y)}(v)=\sup_u(\mu_{A_X}(u) \wedge \mu_{A_Y}(v-u)), \wedge =\min$$

Similarly, assuming that $R_X$ and $R_Y$ are independent, the probability density function of $R_X*R_Y$ is the convolution, $\circ$, of the probability density functions of $R_X$ and $R_Y$. Denoting these probability density functions as $p_{R_X}$ and $p_{R_Y}$, respectively, we have:

$$p_{R_X+R_Y}(v) = \int_R p_{R_X}(u)p_{R_Y}(v-u)du$$

Thus, $$Z^+_X+Z^+_Y=(A_X+A_Y,p_{R_X} \circ p_{R_Y})$$

It should be noted that the assumption that $R_X$ and $R_Y$ are independent implies worst case analysis.

More generally, to compute $Z_X*Z_Y$ what is needed is the extension principle of fuzzy logic (see, e.g., L. A. Zadeh, Probability measures of fuzzy events, Journal of Mathematical Analysis and Applications 23 (2), (1968) 421-427.). Basically, the extension principle is a rule for evaluating a function when what are known are not the values of arguments but restrictions on the values of arguments. In other words, the rule involves evaluation of the value of a function under less than complete information about the values of arguments.

Note. Originally, the term "extension principle" was employed to describe a rule which serves to extend the domain of definition of a function from numbers to fuzzy numbers. In this disclosure, the term "extension principle" has a more general meaning which is stated in terms of restrictions. What should be noted is that, more generally, incompleteness of information about the values of arguments applies also to incompleteness of information about functions, in particular, about functions which are described as collections of if-then rules.

There are many versions of the extension principle. A basic version was given in the article: (L. A. Zadeh, Fuzzy sets, Information and Control 8, (1965) 338-353.). In this version, the extension principle may be described as:

$$Y = f(X)$$

$$\frac{R(X): X \text{ is } A \text{ (constraint on } u \text{ is } \mu_A(u))}{R(Y): \mu_Y(v) = \sup_u \mu_A(u) \ (f(A) = R(Y))}$$

subject to $$v = f(u)$$

where A is a fuzzy set, $\mu_A$ is the membership function of A, $\mu_Y$ is the membership function of Y, and u and v are generic values of X and Y, respectively.

A discrete version of this rule is:

$$Y = f(X)$$

$$\frac{R(X): X \text{ is } (\mu_1/u_1 + \ldots + \mu_n/u_n)}{R(Y): \mu_Y(v) = \sup_{u_1,\ldots,u_n} \mu_i}$$

subject to $$v = f(u_i)$$

In a more general version, we have $$Y = f(X)$$

$$\frac{R(X): g(X) \text{ is } A \text{ (constraint on } u \text{ is } \mu_A(g(u)))}{R(Y): \mu_Y(v) = \sup_u \mu_A(g(u))}$$

subject to $$v = f(u)$$

For a function with two arguments, the extension principle reads:

$Z = f(X, Y)$ $$\frac{R(X): g(X) \text{ is } A \text{ (constraint on } u \text{ is } \mu_A(g(u)))}{R(Y): h(Y) \text{ is } B \text{ (constraint on } u \text{ is } \mu_B(h(u)))}$$
$$R(Z): \mu_Z(w) = \sup_{u,v}(\mu_X(g(u)) \wedge \mu_Y(h(v))), \quad \wedge = \min$$

subject to $v = f(u)$

In application to probabilistic restrictions, the extension principle leads to results which coincide with standard results which relate to functions of probability distributions. Specifically, for discrete probability distributions, we have:

$Y = f(X)$ $$\frac{R(X): X \text{ isp } p, \quad p = p_1 \backslash u_1 + \ldots p_n \backslash u_n}{R(Y): p_Y(v) = \sum_i p_i \ (f(p) = R(Y))}$$

subject to $v = f(u_i)$

For functions with two arguments, we have:

$Z = f(X, Y)$ $R(X): X \text{ isp } p, p = p_1 \backslash u_1 + \ldots p_m \backslash u_m$ $$\frac{R(Y): Y \text{ isp } q, q = q_1 \backslash v_1 + \ldots q_n \backslash v_n}{R(Z): p_Z(w) = \sum_{i,j} p_i q_j \ (f(p,q) = R(Z))}$$

subject to $v = f(u_i, v_j)$

For the case where the restrictions are $Z^+$-numbers, the extension principle reads:

$Z = f(X, Y)$ $R(X): X \text{ is } (A_X, p_X)$ $$\frac{R(Y): Y \text{ is } (A_Y, p_Y)}{R(Z): Z \text{ is } (f(A_X, A_Y), f(p_X, p_Y))}$$

It is this version of the extension principle that is the basis for computation with Z-numbers. Now, one may want to know if $f(p_X, p_Y)$ is compatible with $f(A_X, A_Y)$.

Turning to computation with Z-numbers, assume for simplicity that *=sum. Assume that $Z_X=(A_X, B_X)$ and $Z_Y=(A_Y, B_Y)$. Our problem is to compute the sum $Z=X+Y$. Assume that the associated Z-valuations are $(X, A_X, B_X)$, $(Y, A_Y, B_Y)$ and $(Z, A_Z, B_Z)$.

The first step involves computation of $p_Z$. To begin with, let us assume that $p_X$ and $p_Y$ are known, and let us proceed as we did in computing the sum of $Z^+$-numbers. Then $p_Z = p_X \circ p_Y$ or more concretely, $$p_Z(v) = \int_R p_X(u) p_Y(v-u) du$$

In the case of Z-numbers what we know are not $p_X$ and $p_Y$ but restrictions on $p_X$ and $p_Y$ $$\int_R \mu_{A_X}(u) p_X(u) du \text{ is } B_X$$

$$\int_R \mu_{A_Y}(u) p_Y(u) du \text{ is } B_Y$$

In terms of the membership functions of $B_X$ and $B_Y$, these restrictions may be expressed as:

$$\mu_{B_X}\left(\int_R \mu_{A_X}(u) p_X(u) du\right)$$

$$\mu_{B_Y}\left(\int_R \mu_{A_Y}(u) p_Y(u) du\right)$$

Additional restrictions on $p_X$ and $p_Y$ are:

$$\int_R p_X(u) du = 1$$

$$\int_R p_Y(u) du = 1$$

$$\int_R u p_X(u) du = \frac{\int_R u \mu_{A_X}(u) du}{\int_R \mu_{A_X}(u) du} \quad \text{(compatibility)}$$

$$\int_R u p_Y(u) du = \frac{\int_R u \mu_{A_Y}(u) du}{\int_R \mu_{A_Y}(u) du} \quad \text{(compatibility)}$$

Applying the extension principle, the membership function of $p_Z$ may be expressed as:

$$\mu_{p_Z}(p_Z) = \sup_{p_X, p_Y}\left(\mu_{B_X}\left(\int_R \mu_{A_X}(u) p_X(u) du\right) \wedge \mu_{B_Y}\left(\int_R \mu_{A_Y}(u) p_Y(u) du\right)\right)$$

subject to $p_Z = p_X \circ p_Y$ $$\int_R p_X(u) du = 1$$

$$\int_R p_Y(u) du = 1$$

$p_Z = p_X \circ p_Y$ $$\int_R u p_X(u)du = \frac{\int_R u\mu_{A_X}(u)du}{\int_R \mu_{A_X}(u)du}$$

$$\int_R u p_Y(u)du = \frac{\int_R u\mu_{A_Y}(u)du}{\int_R \mu_{A_Y}(u)du}$$

In this case, the combined restriction on the arguments is expressed as a conjunction of their restrictions, with ∧ interpreted as min. In effect, application of the extension principle reduces computation of $p_Z$ to a problem in functional optimization. What is important to note is that the solution is not a value of $p_Z$ but a restriction on the values of $p_Z$, consistent with the restrictions on $p_X$ and $p_Y$.

At this point it is helpful to pause and summarize where we stand. Proceeding as if we are dealing with $Z^+$-numbers, we arrive at an expression for $p_Z$ as a function of $p_X$ and $p_Y$. Using this expression and applying the extension principle we can compute the restriction on $p_Z$ which is induced by the restrictions on $p_X$ and $p_Y$. The allowed values of $p_Z$ consist of those values of $p_z$ which are consistent with the given information, with the understanding that consistency is a matter of degree.

The second step involves computation of the probability of the fuzzy event, Z is $A_Z$, given $p_Z$. As was noted earlier, in fuzzy logic the probability measure of the fuzzy event X is A, where A is a fuzzy set and X is a random variable with probability density $p_X$, is defined as:

$$\int_R \mu_A(u)p_X(u)du$$

Using this expression, the probability measure of $A_Z$ may be expressed as:

$$B_Z = \int_R \mu_{A_Z}(u)p_Z(u)du,$$

where $\mu_{A_Z}(u) = \sup_v(\mu_{A_X}(v) \wedge \mu_{A_Y}(u-v))$

It should be noted that $B_Z$ is a number when $p_Z$ is a known probability density function. Since what we know about $p_Z$ is its possibility distribution, $\mu_{p_Z}(p_Z)$, $B_Z$ is a fuzzy set with membership function $\mu_{B_Z}$. Applying the extension principle, we arrive at an expression for $\mu_{B_Z}$. More specifically, $\mu_{B_Z}(w) = \sup_{p_Z}\mu_{p_Z}(p_Z)$ subject to $w = \int_R \mu_{A_Z}(u)p_X(u)du$ where $\mu_{p_Z}(p_Z)$ is the result of the first step. In principle, this completes computation of the sum of Z-numbers, $Z_X$ and $Z_Y$.

In a similar way, we can compute various functions of Z-numbers. The basic idea which underlies these computations may be summarized as follows. Suppose that our problem is that of computing $f(Z_X,Z_Y)$, where $Z_X$ and $Z_Y$ are Z-numbers, $Z_X=(A_X,B_X)$ and $Z_Y=(A_Y,B_Y)$, respectively, and $f(Z_X,Z_Y)=(A_Z,B_Z)$. We begin by assuming that the underlying probability distributions $p_X$ and $p_Y$ are known. This assumption reduces the computation of $f(Z_X,Z_Y)$ to computation of $f(Z_X^+,Z_Y^+)$, which can be carried out through the use of the version of the extension principle which applies to restrictions which are $Z^+$-numbers. At this point, we recognize that what we know are not $p_X$ and $p_Y$ but restrictions on $p_X$ and $p_Y$. Applying the version of the extension principle which relates to probabilistic restrictions, we are led to $f(Z_X,Z_Y)$. We can compute the restriction, $B_Z$, of the scalar product of $f(A_X,A_y)$ and $f(p_X,p_Y)$. Since $A_Z=f(A_X,A_Y)$, computation of $B_Z$ completes the computation of $f(Z_X,Z_Y)$.

It is helpful to express the summary as a version of the extension principle. More concretely, we can write:

$Z = f(X, Y)$ $X$ is $(A_X, B_X)$ (restriction on $X$)

$Y$ is $(A_Y, B_Y)$ (restriction on $Y$)

$$\frac{Z \text{ is } (A_Z, B_Z) \text{ (induced restriction on } Z\text{)}}{A_Z = f(A_X, Y_X) \begin{pmatrix} \text{application of extension} \\ \text{principle for fuzzy numbers} \end{pmatrix}}$$

$B_Z = \mu_{A_Z} \cdot f(p_X, p_Y)$ where $p_X$ and $p_Y$ are constrained by:

$\int_R \mu_{A_X}(u)p_X(u)du$ is $B_X$ $\int_R \mu_{A_Y}(u)p_Y(u)du$ is $B_Y$

In terms of the membership functions of $B_X$ and $B_Y$, these restrictions may be expressed as:

$\mu_{B_X}\left(\int_R \mu_{A_X}(u)p_X(u)du\right)$ $\mu_{B_Y}\left(\int_R \mu_{A_Y}(u)p_Y(u)du\right)$ Additional restrictions on $p_X$ and $p_Y$ are:

$\int_R p_X(u)du = 1$ $\int_R p_Y(u)du = 1$ $\int_R u p_X(u)du = \frac{\int_R u\mu_{A_X}(u)du}{\int_R \mu_{A_X}(u)du}$ (compatibility)

$\int_R u p_Y(u)du = \frac{\int_R u\mu_{A_Y}(u)du}{\int_R \mu_{A_Y}(u)du}$ (compatibility)

Consequently, in agreement with earlier results we can write:

$$\mu_{P_Z}(p_Z) = \sup_{p_X, p_Y}\left(\mu_{B_X}\left(\int_R \mu_{A_X}(u)p_X(u)du\right) \wedge \mu_{B_Y}\left(\int_R \mu_{A_Y}(u)p_Y(u)du\right)\right)$$

subject to $$p_Z = p_X \circ p_Y$$

$$\int_R p_X(u)du = 1$$

$$\int_R p_Y(u)du = 1$$

$$\int_R up_X(u)du = \frac{\int_R u\mu_{A_X}(u)du}{\int_R \mu_{A_X}(u)du}$$

$$\int_R up_Y(u)du = \frac{\int_R u\mu_{A_Y}(u)du}{\int_R \mu_{A_Y}(u)du}$$

What is important to keep in mind is that A and B are, for the most part, perception-based and hence intrinsically imprecise. Imprecision of A and B may be exploited by making simplifying assumptions about A and B—assumptions that are aimed at reduction of complexity of computation with Z-numbers and increasing the informativeness of results of computation. Two examples of such assumptions are sketched in the following.

Briefly, a realistic simplifying assumption is that $p_X$ and $p_Y$ are parametric distributions, in particular, Gaussian distributions with parameters $m_X$, $\sigma_X^2$ and $m_Y$, $\sigma_Y^2$, respectively. Compatibility conditions fix the values of $m_X$ and $m_Y$. Consequently, if $b_X$ and $b_Y$ are numerical measures of certainty, then $b_X$ and $b_Y$ determine $p_X$ and $p_Y$, respectively. Thus, the assumption that we know $b_X$ and $b_Y$ is equivalent to the assumption that we know $p_X$ and $p_Y$. Employing the rules governing computation of functions of $Z^+$-numbers, we can compute $B_Z$ as a function of $b_X$ and $b_Y$. At this point, we recognize that $B_X$ and $B_Y$ are restrictions on $b_X$ and $b_Y$, respectively. Employment of a general version of the extension principle leads to $B_Z$ and completes the process of computation. This may well be a very effective way of computing with Z-numbers. It should be noted that a Gaussian distribution may be viewed as a very special version of a Z-number.

Figure 3:
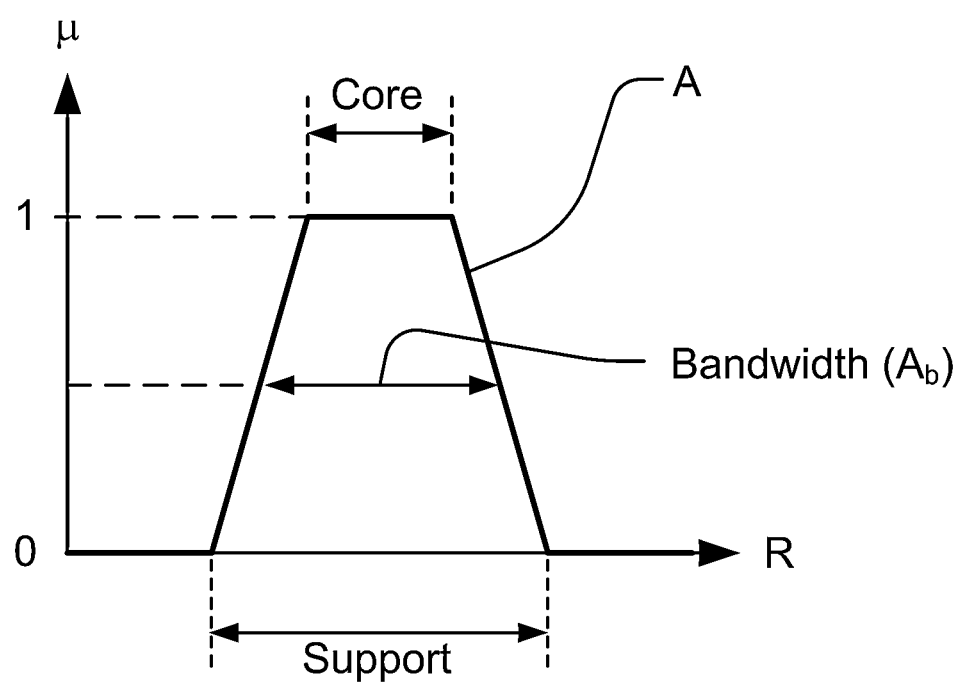
FIG. 3 shows interval-valued approximation to a trapezoidal fuzzy set.

Another effective way of exploiting the imprecision of A and B involves approximation of the trapezoidal membership function of A by an interval-valued membership function, $A^b$, where $A^b$ is the bandwidth of A (FIG. 3). Since A is a crisp set, we can write:

$$(A_X^b, B_X) * (A_Y^b, B_Y) = (A_X^b * A_Y^b, B_X \times B_Y)$$

where $B_X \times B_Y$ is the product of the fuzzy numbers $B_X$ and $B_Y$. Validity of this expression depends on how well an interval-valued membership function approximates to a trapezoidal membership function.

Clearly, the issue of reliability of information is of pivotal importance in planning, decision-making, formulation of algorithms and management of information. There are many important directions which are explored, especially in the realm of calculi of Z-rules and their application to decision analysis and modeling of complex systems.

Computation with Z-numbers may be viewed as a generalization of computation with numbers, intervals, fuzzy numbers and random numbers. More concretely, the levels of generality are: computation with numbers (ground level 1); computation with intervals (level 1); computation with fuzzy numbers (level 2); computation with random numbers (level 2); and computation with Z-numbers (level 3). The higher the level of generality, the greater is the capability to construct realistic models of real-world systems, especially in the realms of economics, decision analysis, risk assessment, planning, analysis of causality and biomedicine.

It should be noted that many numbers, especially in fields such as economics and decision analysis are in reality Z-numbers, but they are not currently treated as such because it is much simpler to compute with numbers than with Z-numbers. Basically, the concept of a Z-number is a step toward formalization of the remarkable human capability to make rational decisions in an environment of imprecision and uncertainty. FIG. 108 is an example of such a system described above.

Analysis Methods Using Probability Distributions with Z-Number

We discussed the probability measure of a fuzzy set A in Rx based on a hidden probability distribution $p_X$, is determined as $$p_X \cdot \mu_A = \int_R \mu_A(u)p_X(u)du.$$

In evaluation of Z number, this probability measure is restricted by a fuzzy set B, with the restriction determined by $$\mu_B\left(\int_R \mu_A(u)p_X(u)du\right).$$

Figure 10A:
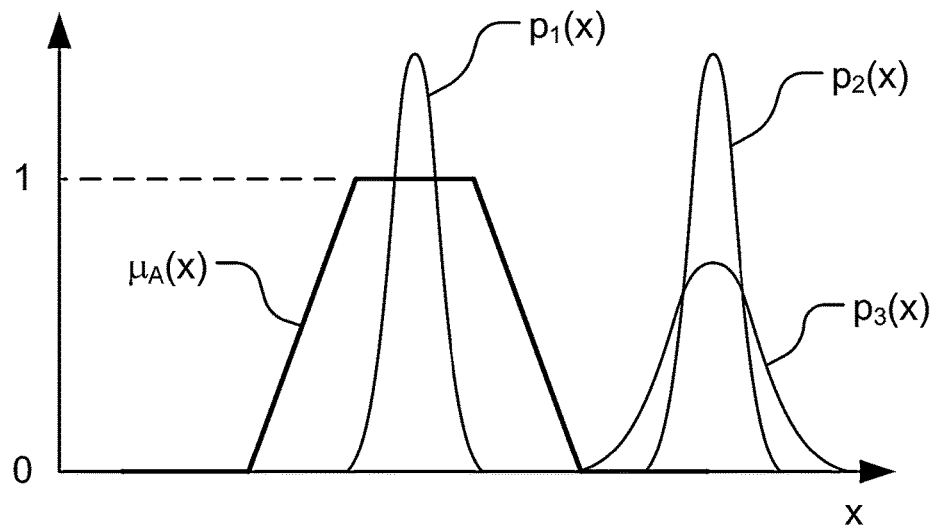
FIGS. 10(a)-(b) depict various types of normal distribution with respect to a membership function, in one embodiment.
Figure 10B:
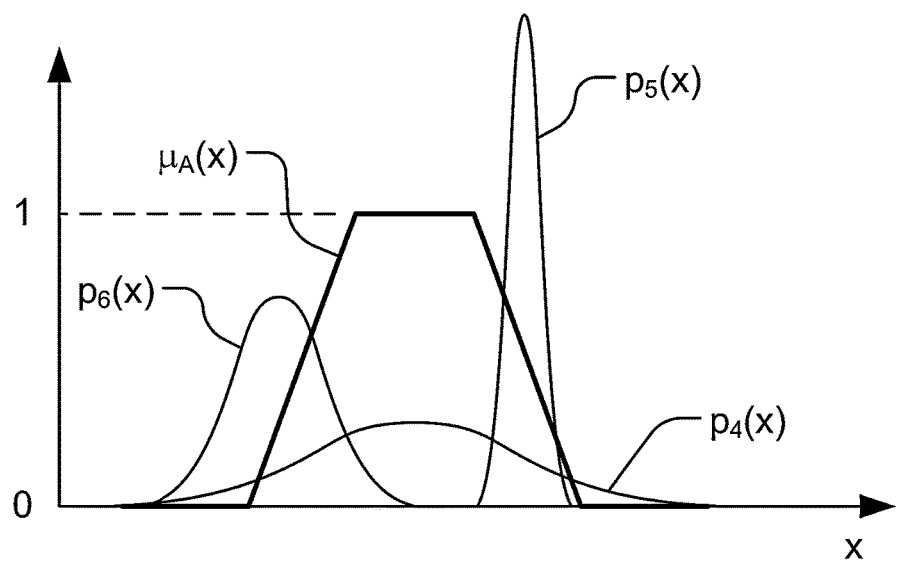
Figure 10C:
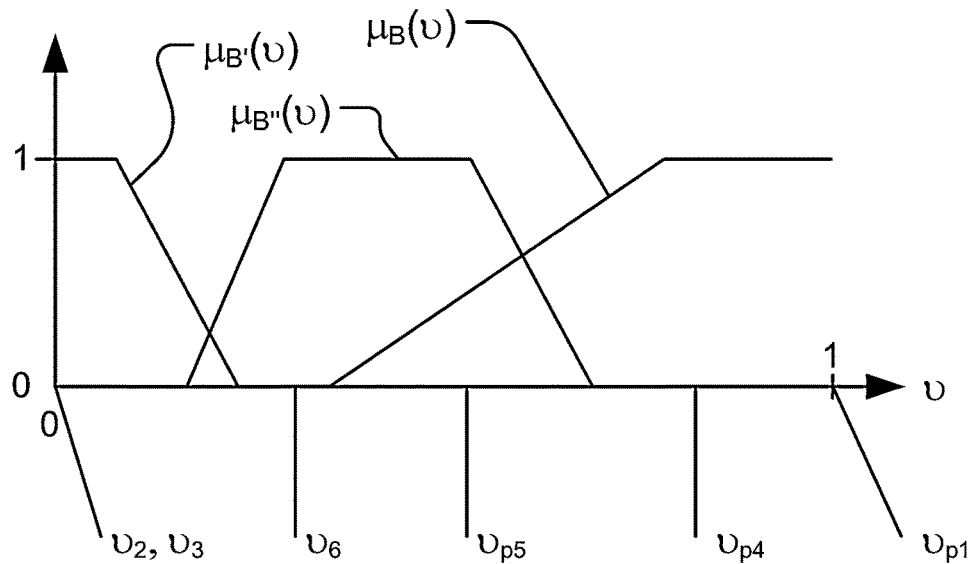
FIGS. 10(c)-(d) depict various probability measures and their corresponding restrictions, in one embodiment.

The restriction is then implied on the probability distribution. In an example shown in FIGS. 10(a)-(b), of a trapezoid like membership function for A is depicted to several candidate probability distributions to illustrate the probability measure, in each case. Note that in this example, a Gaussian distribution is used for illustration purposes, but depending on the context, various types of distributions may be used. A category of distribution, e.g., $p_1(x)$ and $p_4(x)$, is concentric with A (or have same or similar center of mass). For a category such as $p_1(x)$, the confinement is at the core of A, and therefore, the corresponding probability measure of A, $v_{p1}$, is 1. (see FIG. 10(c)). Conversely, a category of distribution with little or no overlap with A, e.g., $p_2(x)$ and $p_3(x)$, have a corresponding probability measure of 0 (i.e., $v_{p2}$ and $v_{p3}$). The other categories resulting in probability measure (0, 1), include those such as $p_4(x)$, $p_5(x)$, and $p_6(x)$. As mentioned above, $p_4(x)$ is concentric with A, but it has large enough variance to exceed core of A, resulting probability measure ($v_{p4}$) of less than 1. $p_5(x)$ resembles a delta probability distribution (i.e., with sharply defined location), which essentially picks covered values of $\mu_A(x)$ as the probability measure. When placed at the fuzzy edge of A, it results in probability measure, $v_{p5}$, in (0, 1) range depending on $\mu_A(x)$. Such a distribution, for example, is useful for testing purposes. $p_6(x)$ demonstrates a category that encompasses portions of support or core of A, resulting in a probability measure ($v_{p4}$) in (0, 1). Unlike $p_5(x)$, $p_6(x)$ is not tied to A's core, providing a flexibility to adjust its variance and location to span various probability measures for A. Turning to FIG. 10(c), category of distributions resulting in probability measures in (0, 1) are of particular interest, as they sample and span the restriction membership function $\mu_B(v)$, where $v=\int_R \mu_A(u)p_X(u)du$. FIG. 10(c), also shows three types of restriction denoted by B, B', and B". Restriction B with high membership values for higher measures of probability of A, (e.g., for $v_{p1}$ and $v_{p4}$) demonstrates restrictions such as "very sure" or "very likely". These in turn tend to restrict the probability distributions to those such as $p_1(x)$, $p_4(x)$, which present strong coverage of A, to relative exclusion of other categories such as $p_2(x)$, $p_3(x)$. In such a case, the informativeness of Z number (A, B), turns on the preciseness of both A and B, i.e., the more precise A and B are, the more restricted $p_x$ can be. On the other hand, restriction B' with high membership values for low measures of probability of A, (e.g., for $v_{p2}$ and $v_{p3}$) demonstrates restrictions such as "very seldom" or "highly unlikely". Such restrictions tend to reject distributions such as $p_1(x)$ or $p_4(x)$, in favor of those showing less or no overlap with A. Therefore, if A has a wide and imprecise nature, such a Z number would actually appear to be informative, as the possible distributions are restricted to cover those more precise regions in R corresponding to not A. Thus, in such a case, the informativeness of Z number (A, B), turns on the preciseness of both not A and B. Similarly, restriction B" with high membership values for medium measures of probability of A, (e.g., for $v_{p5}$ and $v_{p6}$ or even $v_{p4}$), demonstrates restrictions such as "often" and "possible". These tend to restrict the distributions to those over-encompassing A (such as $p_4(x)$) or those encompassing or located at the fuzzy edges of A (such as $p_6(x)$ and $p_5(x)$).

Figure 10D:
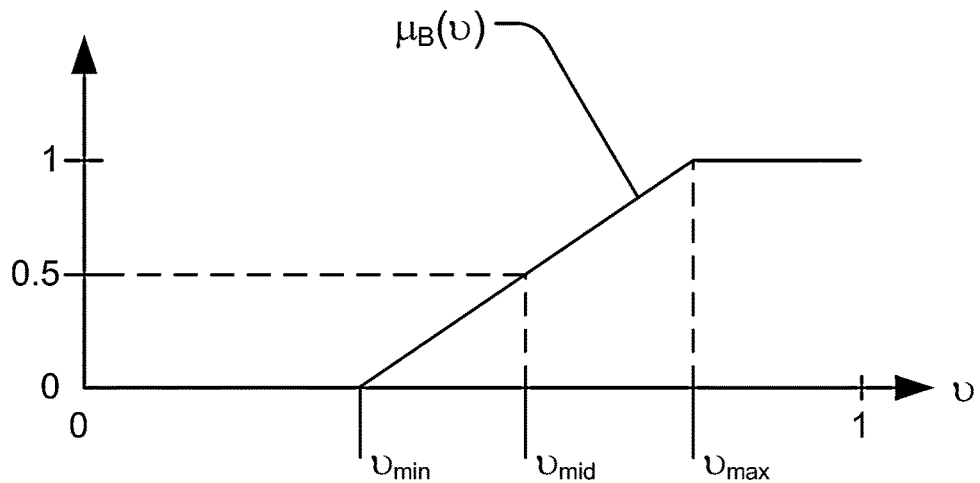

In one embodiment, as depicted for example in FIG. 10(d), the particular probability measures (e.g., $v_{min}$, $v_{mid}$ and $v_{max}$) defined by restriction B are determined, such as midpoint or corner points of membership function $\mu_B(v)$. In one embodiment, probability measures (v) corresponding to multiple cuts of $\mu_B(v)$ at (e.g., predefined levels) are determined. In one embodiment, these particular probability measures (v) for a fuzzy set ($A_x$) of a given variable X are used to determine the corresponding probability measures ($\omega$) for a fuzzy set ($A_y$) on variable Y through a method such as extension principle. This targeted approach will reduce the amount of computation resources (memory and time) needed to determine restriction $B_y$ on probability measure of $A_y$.

Figure 11A:
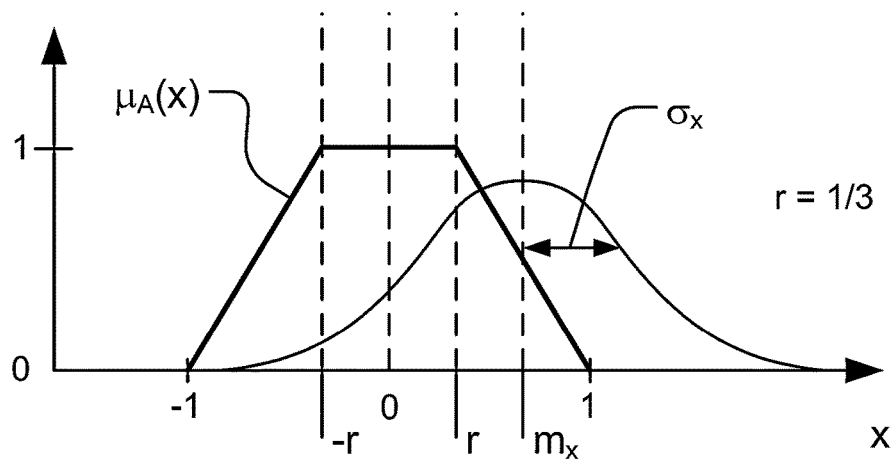
FIG. 11(a) depicts a parametric membership function with respect to a parametric normal distribution, in one embodiment.

In one embodiment, a particular class/template/type of probability distribution is selected to extend the restriction on $p_X$ onto restriction on $p_X$'s parameters. For example, in one embodiment, a normal or Gaussian distribution is taken for $p_X$ (as shown in FIG. 11(a)) with two parameters, mean and standard deviation, ($m_x$, $\sigma_x$), representing the distribution. In one embodiment, the typical or standard-shape membership functions (e.g., triangular, trapezoid, one-sided sloped step-up, one-sided sloped step-down, etc.) are normalized or taken in their normalized form to determine the probability measure against various parameters of the probability distributions (used in the same normalized domain as the fuzzy set). For example, FIG. 11(a) depicts a symmetric trapezoid membership function $\mu_A(x)$, normalized (and shifted) so that its support extends from −1 to 1 and its core at membership value of 1 (extending from −r to r, with respect to its support). In one embodiment, the normalization makes X a dimensionless quantity. The probability distribution, e.g., $N(m_x, \sigma_x)$, is used in the same normalized scale as A. (Note that, to denormalize the distribution, the shift and scaling is used to determine denormalized $m_x$ while the scaling is used inversely to determine denormalized $\sigma_x$.) In such normalized scale, the probability measure is determined, e.g., by:

$$p_X \cdot \mu_X = \int_R p_X(u) \cdot \mu_X(u) du$$

$$= \int_{-1}^{-r} p_X(u) \cdot \mu_X(u) du + \int_{-r}^{r} p_X(u) \cdot \mu_X(u) du + \int_{r}^{1} p_X(u) \cdot \mu_X(u) du$$

$$= \frac{1}{1-r} \int_{-1}^{1} p_X(u) du - \frac{r}{1-r} \int_{-r}^{r} p_X(u) du + \frac{1}{1-r} \int_{-1}^{1} p_X(u) u du -$$

$$\frac{r}{1-r} \int_{-r}^{r} p_X(u) u du$$

For $p_X$ as $N(m_x, \sigma_x)$, the above probability measure of A, is reduced to expression with erf and exp terms with $m_x$, $\sigma_x$ and r. In one embodiment, the probability measures are pre-determined/calculated/tabulated for various values of $m_x$, $\sigma_x$ and r. Note that any denormalization on X does not affect the probability measure, while a denormalization in $\mu_A(x)$ (i.e., maximum membership value) scales the probability measure.

Figure 11B:
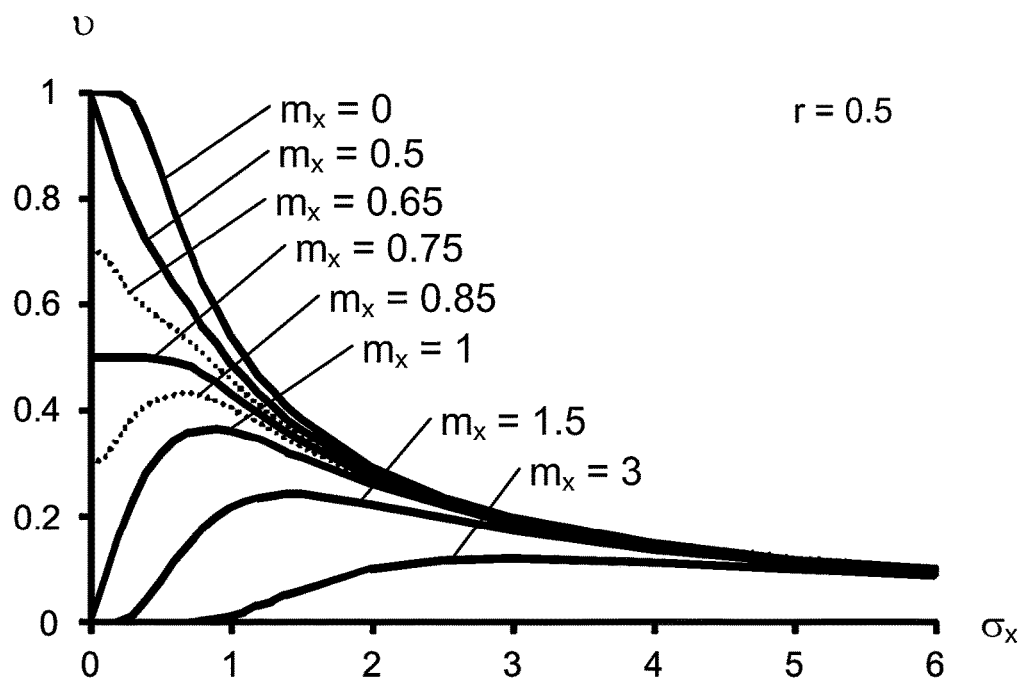
FIGS. 11(b)-(e) depict the probability measures for various values of probability distribution parameters, in one embodiment.
Figure 11C:
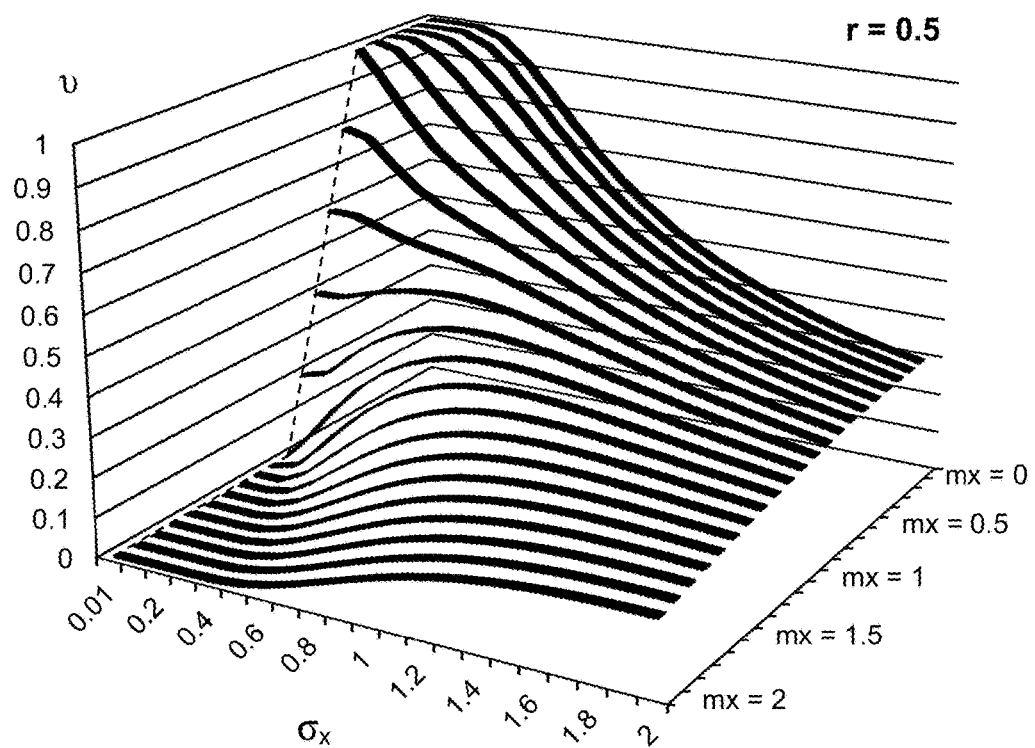
Figure 11D:
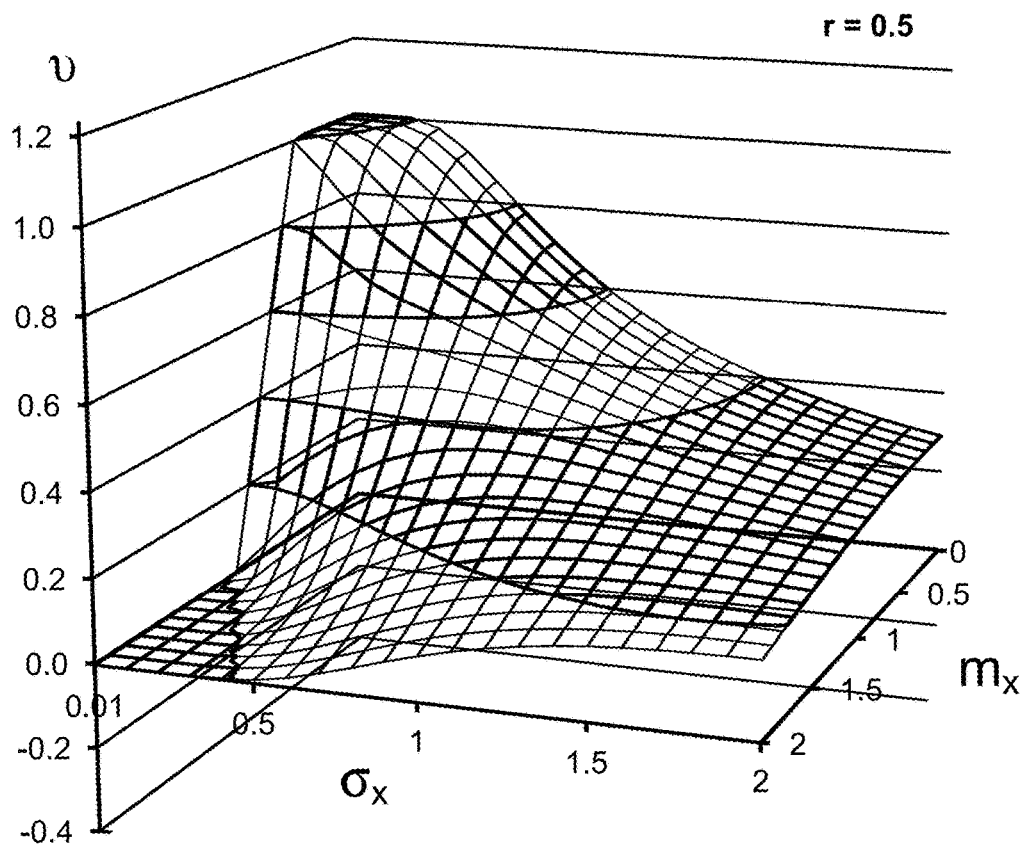
Figure 11E:
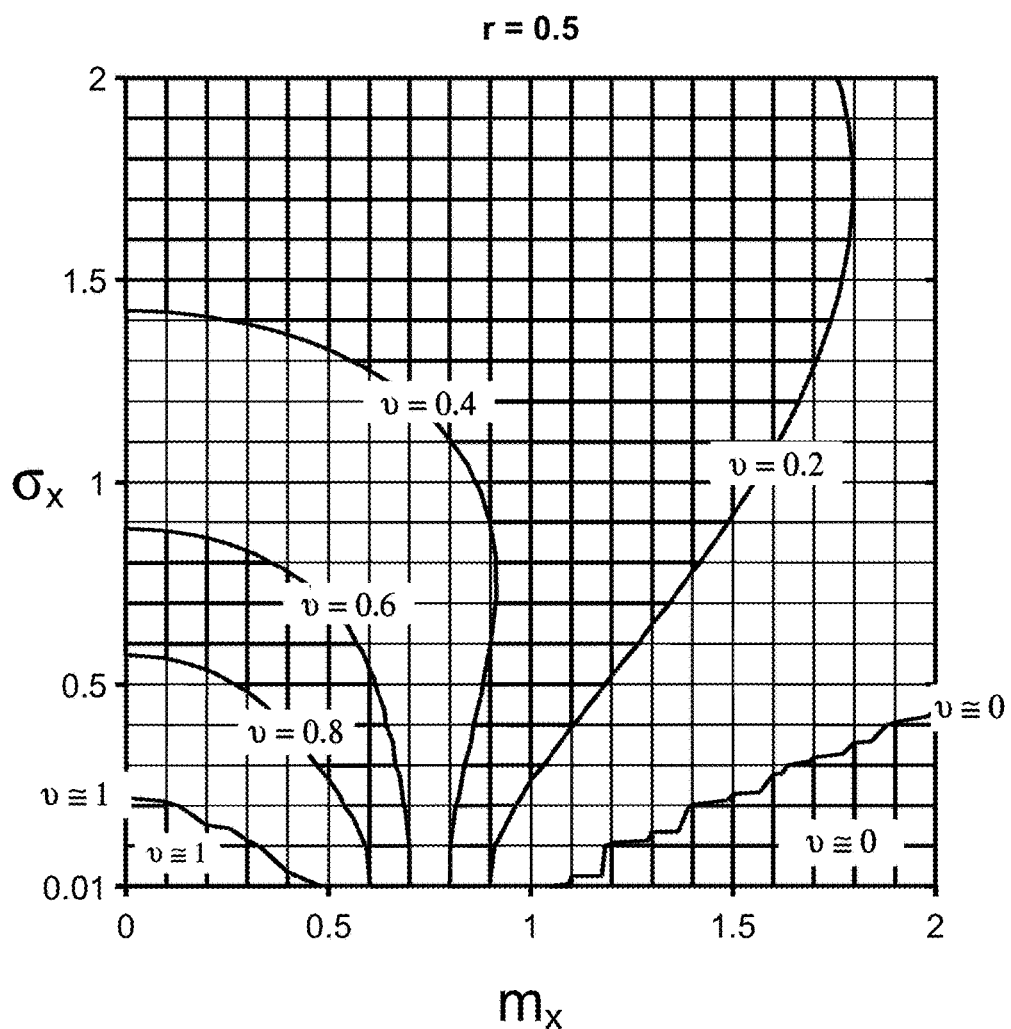
Figure 11F:
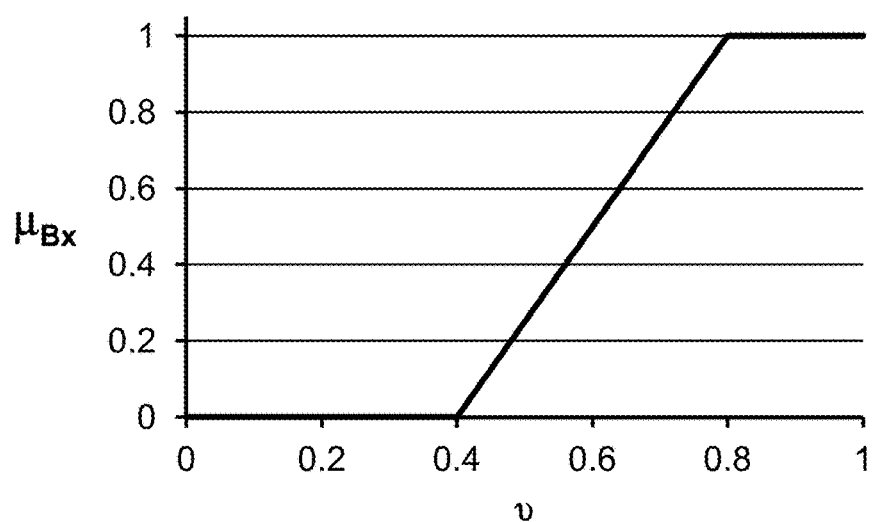
FIG. 11(f) depicts the restriction on probability measure, in one embodiment.
Figure 11G:
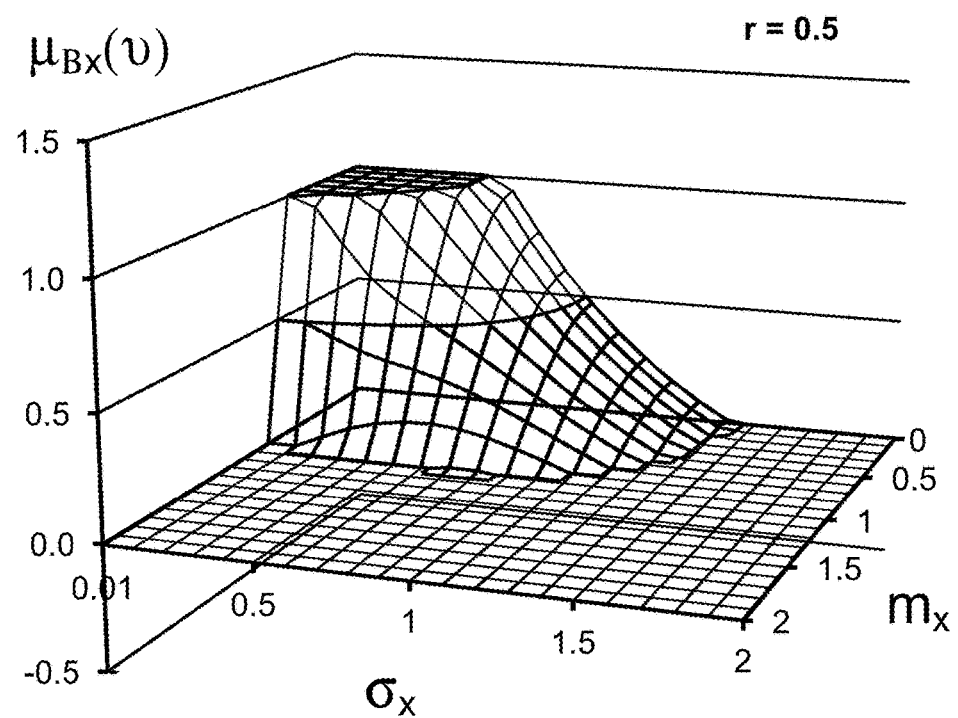
FIGS. 11(g)-(h) depict the restriction imposed on various values of probability distribution parameters, in one embodiment.
Figure 11H:
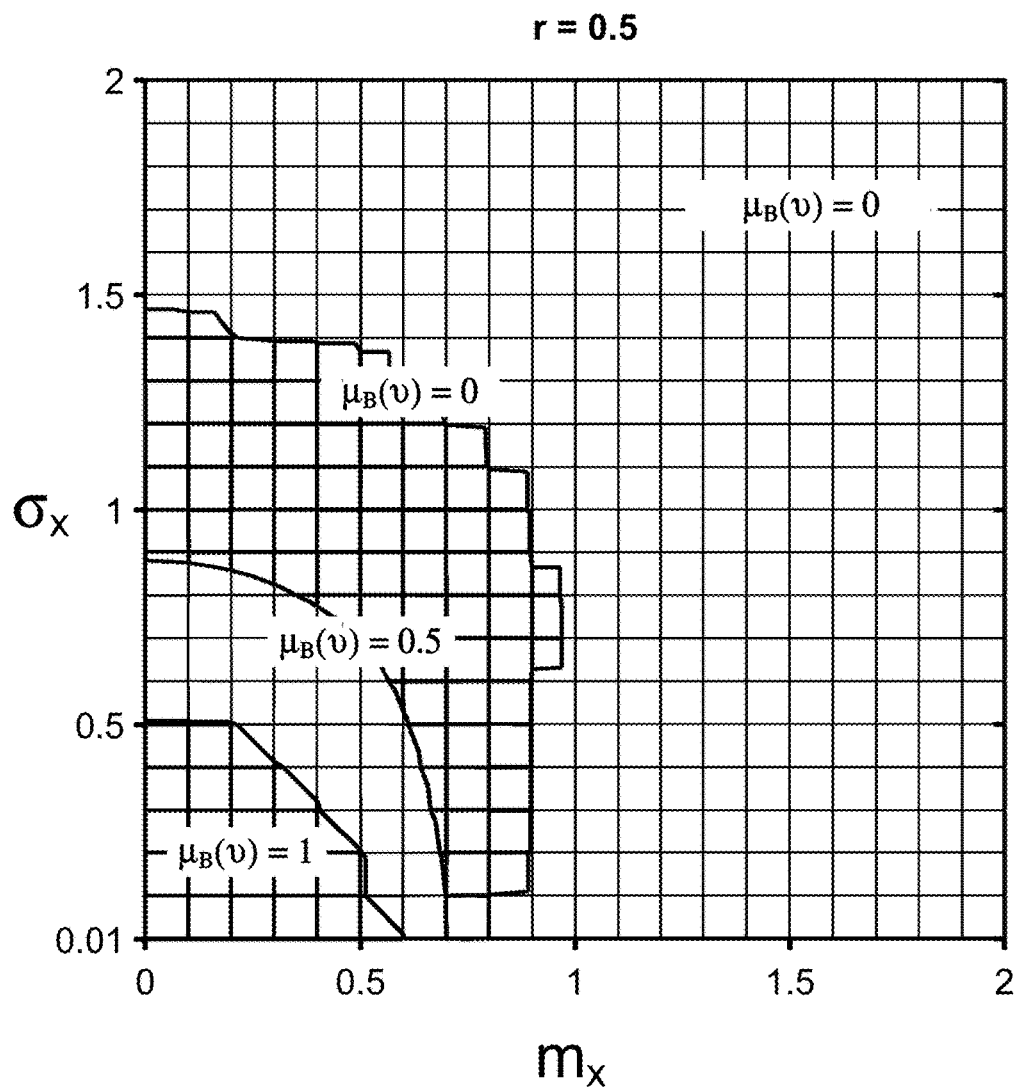

In one embodiment, $(p_X \cdot \mu_X)$ (here denoted as v) is determined and/or stored in a model database, for various $p_X$. For example, v is depicted versus $\sigma_x$ in FIG. 11(b), for various $m_x$ (from 0, to 3), based on a trapezoid $\mu_X$ with r=0.5. At low values of $\sigma_x$, $p_X$ resembles a delta function picking up values of $\mu_X$ evaluated at $m_x$. For example, FIG. 11(c), plot of v depicts the trace of $\mu_X$ (as dotted line) at low $\sigma_x$. As shown on FIGS. 11(b)-(c), at high values of $\sigma_x$, v drops is less sensitive to $m_x$ due to increased width of $p_X$. In one embodiment, various $p_X$ may be determined for a target value of v. For example, as depicted in FIG. 11(d), the contour lines of v are illustrated at ~0, 0.2, 0.4, 0.6, 0.8, and ~1. Similarly, FIG. 11(e) depicts various contour lines for v. In one embodiment, involving Z-valuation (X, $A_x$, $B_x$), $\mu_{Bx}$ is used to restrict the probability measure v $(=p_X \cdot \mu_{Ax})$. For example, as depicted in FIG. 11(f), $\mu_{Bx}$ is a step up membership function with ramp from $v_{min}$ and $v_{max}$ (see FIG. 10(d)) of 0.4 and 0.8. Applying the restriction to $v(p_X)$ or $v(m_x, \sigma_x)$, the restriction, $\mu_{Bx}(v)$, may be extended to a candidate $p_X$ or ($m_x$, $\sigma_x$), as depicted in FIG. 11(g). A contour map of $\mu_{Bx}(m_x, \sigma_x)$ is for example depicted in FIG. 11(h). In this example, the contour lines of $\mu_{Bx}$ are shown for $\mu_{Bx}$ of 1, 0.5, and 0, which based on membership function of $\mu_{Bx}(v)$ (see FIG. 11(f)), correspond to v values of 0.8, 0.6, and 0.4, respectively. As illustrated, these contour lines coincide from FIGS. 11(e) and (h).

In one embodiment, based on $\mu_{Bx}(v)$, for various v's (e.g., $v_{min}$, $v_{mid}$, and/or $v_{max}$), close $p_X$'s or ($m_x$, $\sigma_x$)'s candidate are determined, e.g., by tracking/determining the contour lines, via (mesh) interpolation using test (or random) $p_X$'s or ($m_x$, $\sigma_x$) (e.g., by using a root finding method such as Secant method). In one embodiment, these subsets of $p_X$'s or ($m_x$, $\sigma_x$) reduce the computation resources needed to apply the restriction on other variables or probability distributions.

For example, in a setting where Y=F(X), Z-valuation (X, $A_x$, $B_y$) may be extended to (Y, $A_y$, $B_y$) through restrictions on $p_Y$. In one embodiment, where $A_y$ is determined via extension principle using F(X) and $A_x$, $B_y$ is determined by finding the restrictions on probability measure of $A_y$. In one embodiment, F(X) is monotonic, i.e., X=$F^{-1}$(Y) is unique.

$$p_Y(y) \cdot dy = p_X(x) \cdot \delta_{XY} \cdot dx p_Y(y)$$

or $$p_Y(y) = p_X(x) \cdot \delta_{XY} \cdot \left(\frac{dy}{dx}\right)^{-1}$$
$$= p_X(x) \cdot \delta_{XY} \cdot (F'(x))^{-1}$$
$$= p_X(x) \cdot \delta_{XY} \cdot \text{abs}(F'(x))^{-1}$$

where $\delta_{xy}$ is (+1) if F(X) is (monotonically) increasing and it is (−1) if F(X) is decreasing.

The extension principle also provides that, $\mu_{Ax}(x)$ is $\mu_{Ay}(y)$, where y=F(x). Therefore, the probability measure of $A_y$, denoted as ω ($=p_Y \cdot \mu_{Ay}$), becomes the same as υ, for the same px or ($m_x$, $\sigma_x$), as shown below:

$$\omega = p_Y \cdot \mu_{A_y}$$
$$= \int_{y_{min}}^{y_{max}} p_Y(y) \cdot \mu_{A_y}(y) \cdot dy$$
$$= \int_{F^{-1}(y_{min})}^{F^{-1}(y_{max})} p_Y(y) \cdot \mu_{A_y}(y) \cdot \left(\frac{dy}{dx}\right) \cdot dx$$
$$= \int_{F^{-1}(y_{min})}^{F^{-1}(y_{max})} p_Y(y) \cdot \mu_{A_x}(x) \cdot \left(\frac{dy}{dx}\right) \cdot dx$$
$$= \int_{F^{-1}(y_{min})}^{F^{-1}(y_{max})} p_X(x) \cdot \delta_{XY} \cdot (F'(x))^{-1} \cdot \mu_{A_x}(x) \cdot \left(\frac{dy}{dx}\right) \cdot dx$$
$$= \int_{x_{min}}^{x_{max}} p_X(x) \cdot \mu_{A_x}(x) \cdot dx$$
$$= v$$

Therefore, $\mu_{By}(\omega)$ becomes identical to $\mu_{Bx}(\upsilon)$ (for any candidate $p_X$), when F(X) is monotonic and $A_y$ is determined via extension principle from $A_x$ and F(X). This result does not hold when F(X) is not monotonic, but it may be used as first order approximation, in one embodiment. For example, for non-monotonic F(X), still assuming $A_y$ is determined via extension principle from $A_x$ and F(X):

$$\mu_{A_y}(y) = \sup_{\forall x'} \mu_{A_x}(x')$$

where $x' \in \{\text{solutions of } F^{-1}(y)\}$

Suppose in Y domain, there are N piecewise monotonic regions of F(X). Therefore, there are up to N number of x's as solutions to $F^{-1}(y)$, denoted by a set $\{x_1, \ldots, x_i, \ldots, x_N\}$. An event occurring in Y domain, may occur at any of $\{x_i\}$, therefore $$p_Y(y) = \sum_{i=1}^{N} \frac{p_X(x_i)}{F'(x_i) \cdot \delta_{XY,i}} = \sum_{i=1}^{N} \frac{p_X(x,i)}{\text{abs}(F'(x_i))}$$

where $\delta_{xy,i}$ indicates, as before, whether $i^{th}$ monotonic region of F(X) is increasing or decreasing.

In an embodiment, ω is determined by:

$$\omega = p_Y \cdot \mu_{A_y}$$
$$= \int_{y_{min}}^{y_{max}} p_Y(y) \cdot \mu_{A_y}(y) \cdot dy$$
$$= \sum_{i=1}^{N} \int_{y_{min}}^{y_{max}} \sup_{\forall x'} \mu_{A_x}(x') \cdot \frac{p_X(x_i) \cdot dx}{F'(x_i) \cdot \delta_{XY,i}} \cdot \frac{dy}{dx}$$

where $x' \in \{x_i\}$.

Therefore, $$\omega = \sum_{i=1}^{N} \int_{x_{min,i}}^{x_{max,i}} \sup_{\forall x'} \mu_{A_x}(x') \cdot p_X(x_i) \cdot dx$$

Thus, ω≥υ, for a given $p_X$, because:

$$\omega = \sum_{i=1}^{N} \int_{x_{min,i}}^{x_{max,i}} \sup_{\forall x'} \mu_{A_x}(x') \cdot p_X(x_i) \cdot dx$$
$$\geq \sum_{i=1}^{N} \int_{x_{min,i}}^{x_{max,i}} \mu_{A_x}(x_i) \cdot p_X(x_i) \cdot dx$$
$$= \int_{x_{min}}^{x_{max}} \mu_{A_x}(x_i) \cdot p_X(x_i) \cdot dx$$
$$= v$$

In one embodiment, where, e.g., due to relative symmetry in F(X) and $\mu_{Ax}(x)$, $\mu_{Ax}(x)$ is the same for $\forall x' \in \{x_i\}$, then ω=υ, because $\mu_{A_y}(y) = \sup_{\forall x'} \mu_{A_x}(x') = \mu_{A_x}(x_i)$ for any $x_i$.

Likewise, in one embodiment, where $\mu_{Ax}(x)$ is zero or negligible in a region (e.g., for N=2), then ω=υ, as the contribution to ω comes from the dominant monotonic region of F(X).

In one embodiment, deviation of ω from υ is estimated/determined by determining difference between $\sup_{\forall x'} \mu_{A_x}(x')$ and various $\mu_{A_x}(x_i)$'s.

In one embodiment, where $\mu_{Ay}(y)$ is provided via a proposition (instead of being determined via extension principle through F(X) and $A_x$), $\mu_{A'y}(y)$ is determined (via extension principle) and compared to $\mu_{Ay}(y)$. If there is a match, then ω is estimated using υ, e.g., as described above.

Figure 11I:
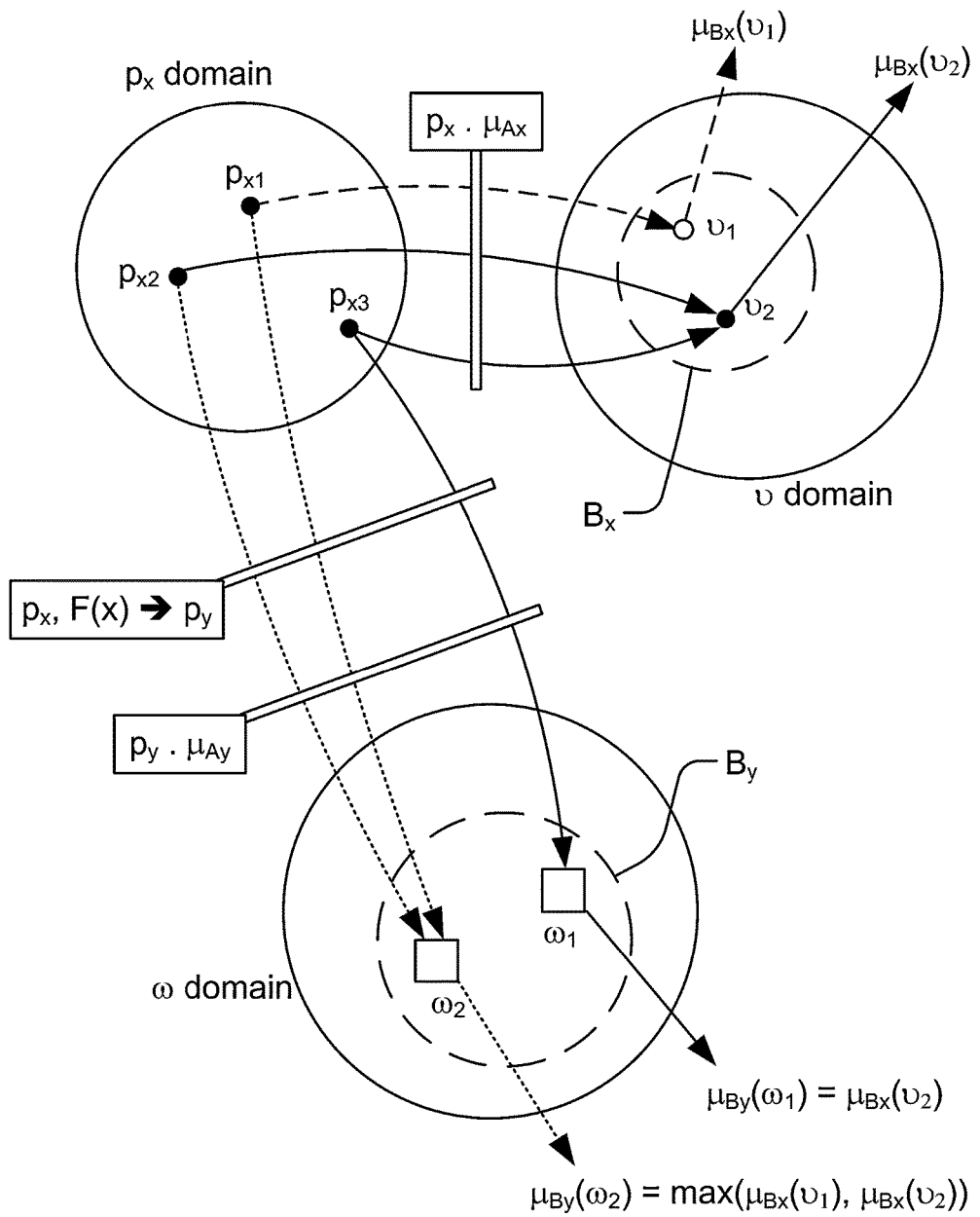
FIG. 11(i) depicts the restriction relationships between the probability measures, in one embodiment.

In one embodiment, as for example depicted in FIG. 11(i), $\mu_{By}(\omega)$ is determined by a series of mapping, aggregation and maximization between $p_X$, υ, and ω domains.

One embodiment, for example, uses the concepts above for prediction of stock market, parameters related to economy, or other applications. Consider the following example:

Example 1

We are given this information (for anticipation and prediction): There probability that the price of oil next month is significantly over 100 dollars/barrel is not small.

Assume that the ticket price for an airline from Washington D.C. to New York is in the form of (Y=F(X)=$a_1 \cdot X + a_2$), where X is the next month's estimated price of oil (in dollars/barrel) and Y is the ticket price (in dollars). For this example, further assume that $a_1$=1.5 and $a_2$=150, i.e., Y=1.5X+150. Then, we have the following questions:

$q_1$: What is the Price of the Ticket from Washington D.C. to New York?

Figure 12A:
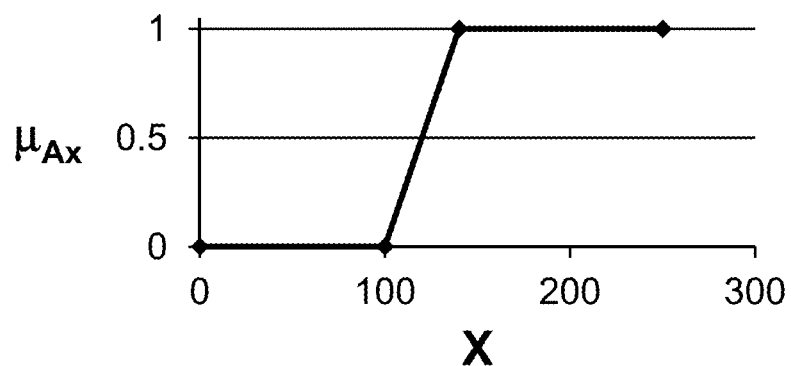
FIG. 12(a) depicts a membership function, in one embodiment.
Figure 12B:
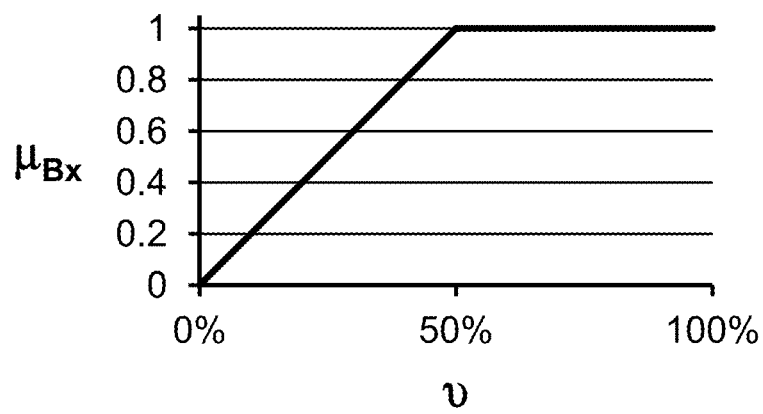
FIG. 12(b) depicts a restriction on probability measure, in one embodiment.
Figure 12C:
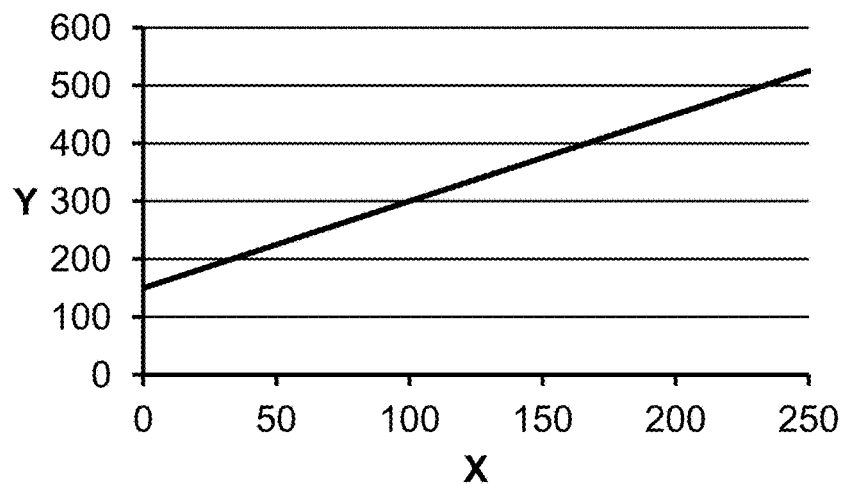
FIG. 12(c) depicts a functional dependence, in one embodiment.
Figure 12D:
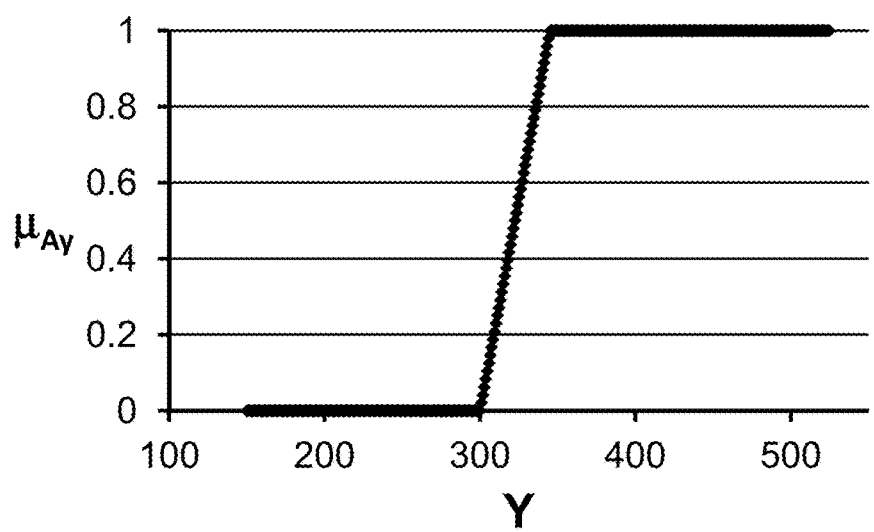
FIG. 12(d) depicts a membership function, in one embodiment.

X represents (the price of oil the next month), $A_x$ is (significantly over 100 dollars/barrel) and $B_x$ is (not small). Then, $(X, A_x, B_x)$ is a Z-valuation restricting the probability of (X) the price of oil the next month. In this example, as depicted in FIG. 12(a), significantly over is represented by a step-up membership function membership function, $\mu_{Ax}$, with a fuzzy edge from 100 to 130. Also, as depicted in FIG. 12(b), not small is represented by a ramp-up membership function membership function, $\mu_{Bx}(\upsilon)$, with the ramp edge at $\upsilon$ from 0 to 50%. Note that $\upsilon$ is the probability measure of $A_x$. The answer to $q_1$, also represented in a Z-valuation, is (Y, $A_y$, $B_y$), where Y represents the price of the ticket, $A_y$ represents a fuzzy set in Y, and $B_y$ represents the certainty of Z-valuation for the answer. Here both $A_y$ and $B_y$ are being sought by $q_1$. In one embodiment, an X domain is created from [0, 250], a form of Normal Distribution, $N(m_x, \sigma_x)$, is assumed for $p_X(u)$ (where u is a value in X domain). A set of candidate $p_X$ are setup by setting a range for $m_x$, e.g., [40,200], and a range for $\sigma_x$, e.g., [0, 30]. Note that value of zero for $\sigma_x$, signifies delta function which is estimated by a very small value, such as 0.01 (in this case). In one embodiment, the range of $(m_x, \sigma_x)$ is chosen so that they cover various categories of distributions with respect to $\mu_{Ax}$, as discussed previously. For example, maximum $\sigma_x$ is determined, in one embodiment, as a factor (e.g., between 1 to 3) times the maximum ramp width of $\mu_{Ax}$. In this example, maximum $\sigma_x$ is taken as (1 times) ramp width of $\mu_{Ax}$ of 30 (=130–100). In one embodiment, $m_x$ range is determined with respect to $\mu_{Ax}$ (e.g., beginning of the ramp, at 100) and maximum $\sigma_x$ (e.g., 30). For example, $m_x$ range is taken to cover a factor of $\sigma_x$ (e.g., 2 to 3) from ramp (e.g., bottom at 100 and top at 130). In one embodiment, the range of X domain is also taken to encompass $m_x$ range by a factor of $\sigma_x$ (e.g., 2 to 3) at either extreme (e.g., if valid in the context of X). In one embodiment, as shown in FIG. 12(c), X range/values are used to find the corresponding Y values based on F(X). Given that $q_1$ looks for $A_y$ as part of the answer, one embodiment uses extension principle determine the membership function of $A_y$ in Y, $\mu_{Ay}$. In one embodiment, $\mu_{Ay}$ is determined by determining the corresponding Y values for X values which identify $\mu_{Ax}$ (e.g., X values of ramp location or trapezoid corners). In such an embodiment, when F(X) is monotonic in the range of X domain, for $X=x_0$, the corresponding $y_0$ are $\mu_{Ay}$ are determined as: $y_0=F(x_0)$ and $\mu_{Ay}(y_0)=\mu_{Ax}(x_0)$. In one embodiment, where multiple values of X exist for $F^{-1}(y)$, $\mu_{Ay}(y)=\sup(\mu_{Ax}(x'))$ for all x' in X domain where $y_0=F(x')$. In one embodiment, $\mu_{Ay}(y)$ is determined at every y corresponding to every x in X domain. In one embodiment, the range of resulting Y values is determined (e.g., min and max of values). For example, the range of Y is [150, 525]. In one embodiment, $\mu_{Ay}(y)$ is determined as an envelope in Y domain covering points $(F(x'), \mu_{Ax}(x'))$ for all x' in X domain. The envelope then represents sup $(\mu_{Ax}(x'))$. In one embodiment, Y domain is divided in bins (for example of equal size). For various x values, e.g., $x_1$ and $x_2$, where values of F(x) fall in the same bin, maximum $\mu_{Ax}(x)$ for those x's are attributed to the bin. In one embodiment, y values signifying the bins are used for determining the probability measures of $A_y$. In one embodiment, the original y values corresponding to the set of x values used in X domain are used to determine probability measures of $A_y$. In such an embodiment, for example, the maximum corresponding $\mu_{Ax}$ attributed to the bin is also attributed to such y values. For example, as depicted in FIG. 12(d), $\mu_{Ay}$ is calculated for corresponding y values.

In one embodiment, the probability measure of $A_x$, (i.e., $\upsilon$), is determined by dot product of $p_X$ and $\mu_{Ax}$. In one embodiment, $p_X$ is evaluated at x values in X domain (e.g., against a set of points between $x_{min}$ and $x_{max}$). Similarly, $\mu_{Ax}$ is determined at the data set $\{x_i\}$ in X domain (or at significant, e.g., corner points of $\mu_{Ax}$). In one embodiment, the dot product is determined by evaluating $$\upsilon_{p_x} = \Sigma_i p_X(x_i) \cdot \mu_{A_x}(x_i)$$

Figure 12E:
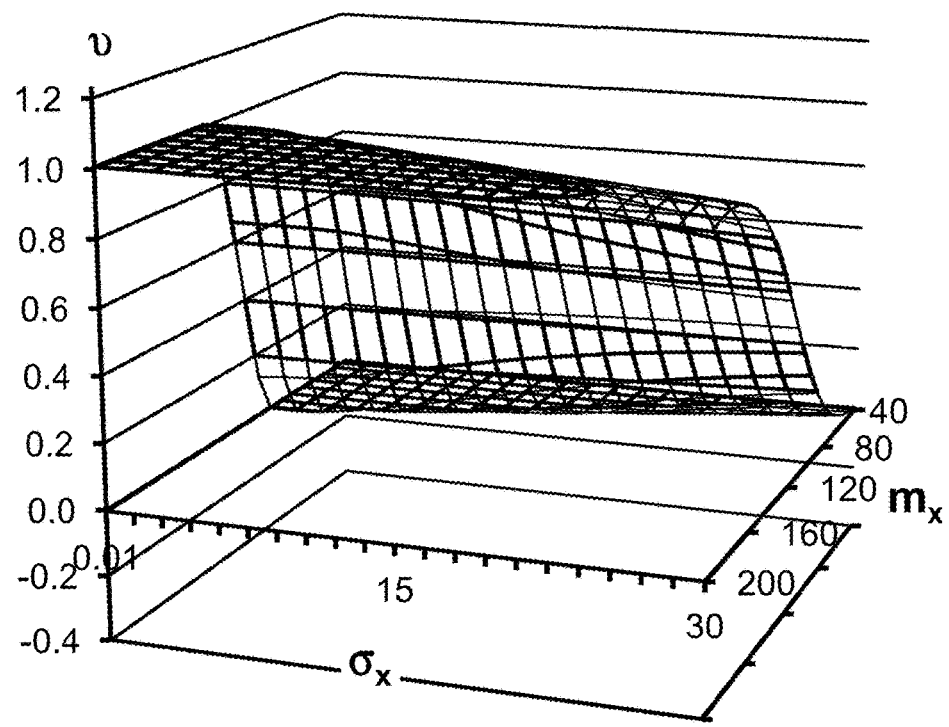
FIGS. 12(e)-(h) depict the probability measures for various values of probability distribution parameters, in one embodiment.
Figure 12F:
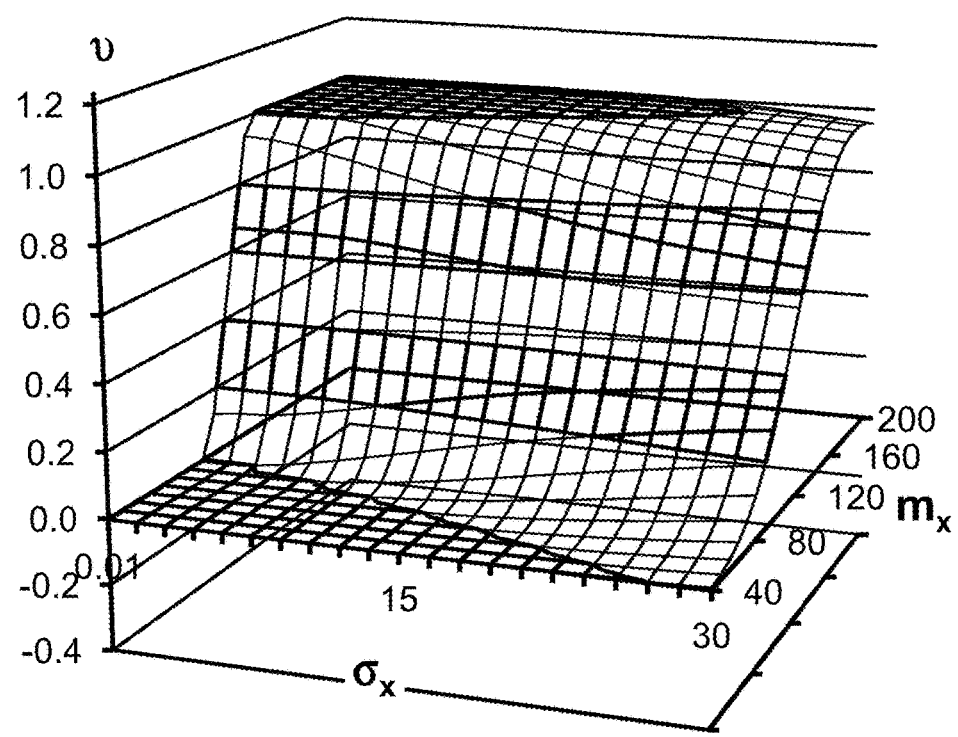
Figure 12G:
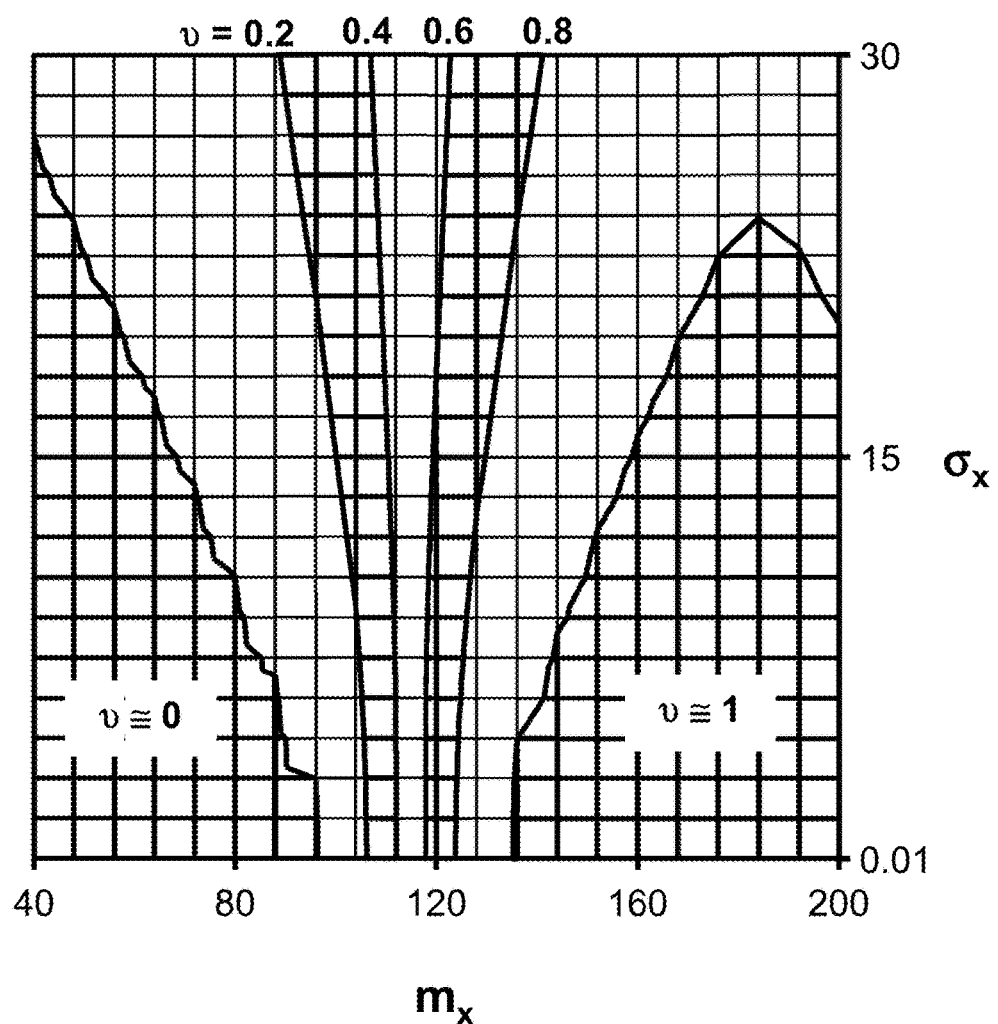
Figure 12H:
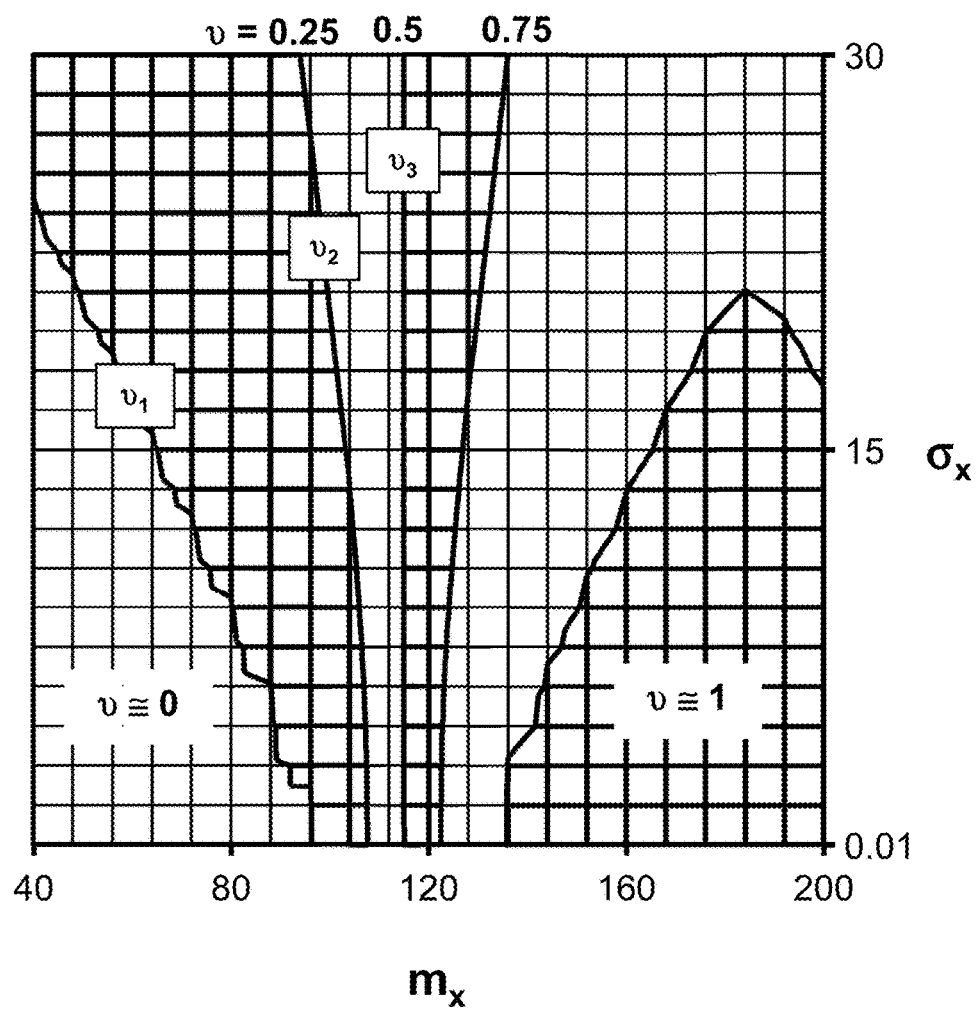

In one embodiment, $\upsilon$ is determined via piecewise evaluation (e.g., using exp and erf functions when $p_X$ is Gaussian). In one embodiment, $\upsilon$ is determined for various candidates for $p_X$. For example, taking $p_X$ as $N(m_x, \sigma_x)$ as described above, $\upsilon$ is determined for various $(m_x, \sigma_x)$ combination, as depicted in FIGS. 12(e)-(f). The contour maps of $\upsilon$ versus $(m_x, \sigma_x)$ is depicted in FIGS. 12(g)-(h). As depicted in these figures, at low $\sigma_x$ (delta function limit of $p_X$), $\upsilon(m_x, \sigma_x)$ becomes $\mu_{Ax}(m_x)$. At higher, $\sigma_x$ smoothing effect takes over for intermediate values of $\upsilon$.

Figure 12I:
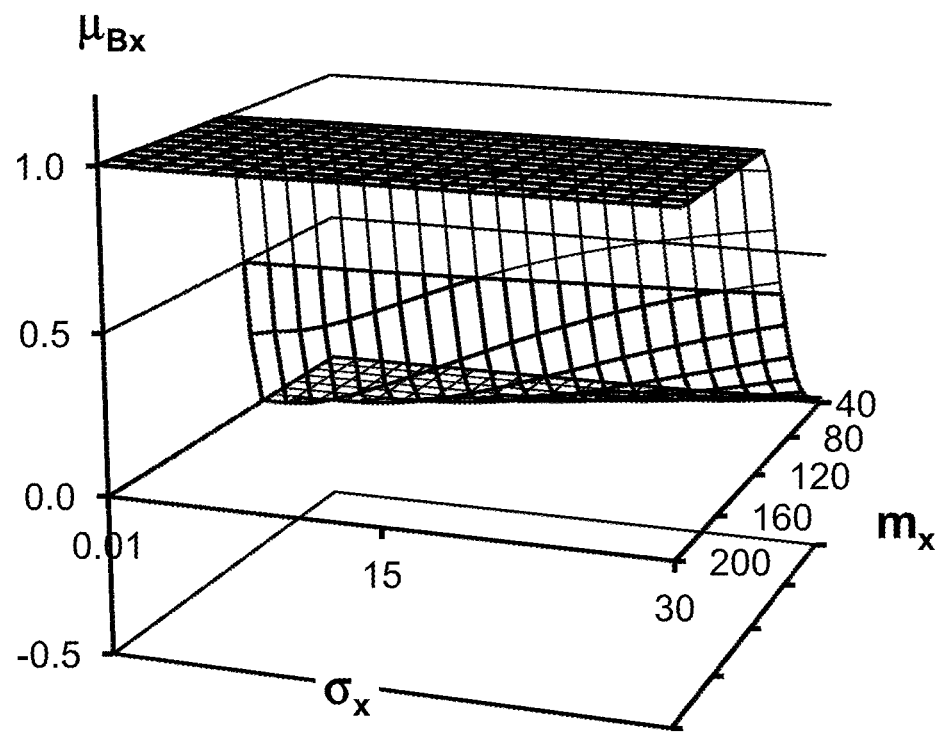
FIGS. 12(i)-(j) depict the restriction imposed on various values of probability distribution parameters, in one embodiment.
Figure 12J:
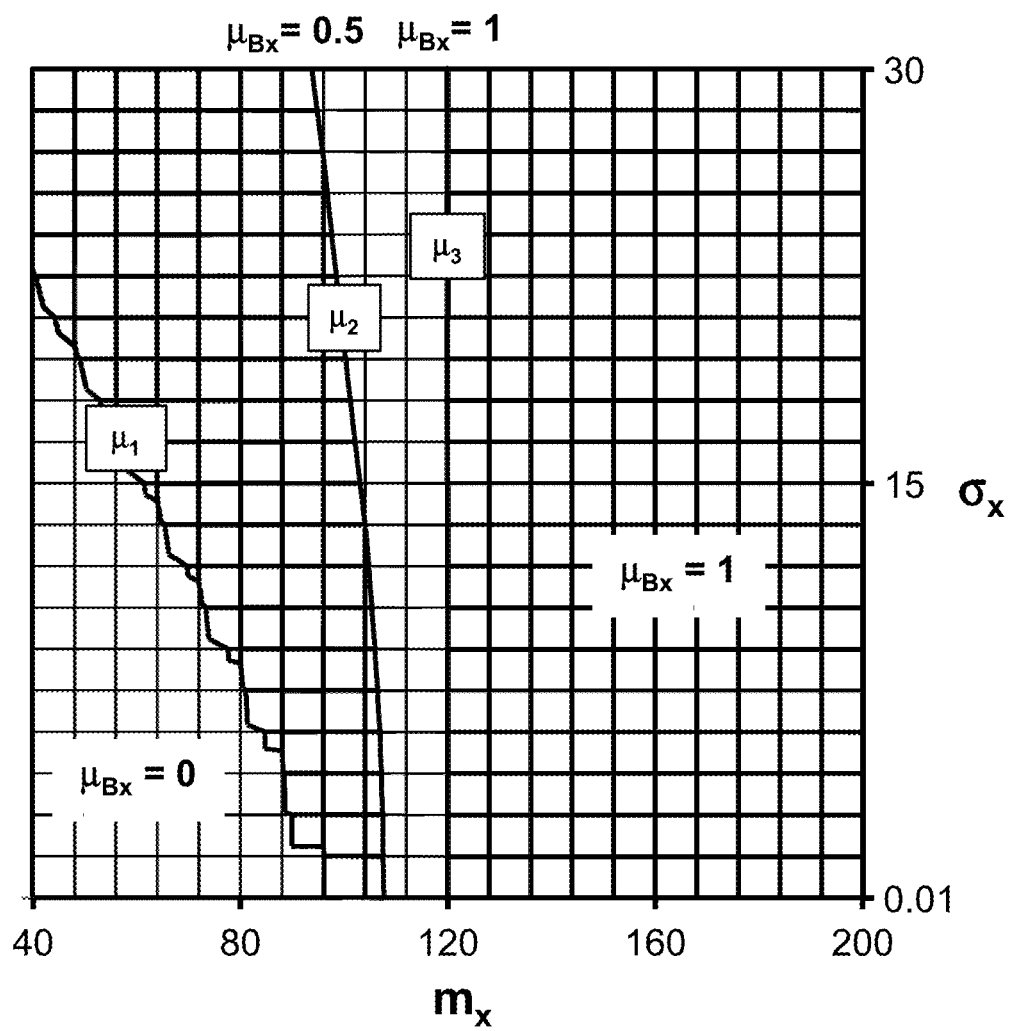

Given restriction not small, $B_X$, in one embodiment, the test score for each candidate $p_X$ is evaluated, by evaluating the truth value of its corresponding probability measure of $A_x$, $\upsilon$, in $\mu_{Bx}(\upsilon)$. In one embodiment, the assignment of test score is used for $p_X$ candidates corresponding to a particular set of $\upsilon$ values (e.g., those used to define $\mu_{Bx}(\upsilon)$ such as the ramp location or trapezoid corners). In such an embodiment, bins are associated with such particular $\upsilon$'s to determine $p_X$ candidates with corresponding $\upsilon$ values within a bin. Those candidates, are for example, identified by those $(m_x, \sigma_x)$ at or near particular contour lines of interest (e.g., marked as $\upsilon_1$, $\upsilon_2$, and $\upsilon_3$ at $\upsilon$ values of 0, 0.25 and 0.5, on FIG. 12(h), indicating the beginning, middle, and end of the ramp for $B_x$ as shown in FIG. 12(b)). FIG. 12(i) depicts, for example, the test score for a given $(m_x, \sigma_x)$ by evaluating the corresponding $\upsilon(m_x, \sigma_x)$ against $\mu_{Bx}(\upsilon)$. FIG. 12(j) depicts, for example, depicts a contour map of $\mu_{Bx}(\upsilon(m_x, \sigma_x))$ on $(m_x, \sigma_x)$ domain. For example, $\mu_1$, $\mu_2$, and $\mu_3$ at $\mu$ values of 0, 0.5, and 1 marked on the contour map correspond to $\upsilon$ contours for $\upsilon_1$, $\upsilon_2$, and $\upsilon_3$.

In one embodiment, the probability measure of $A_y$, (i.e., $\omega$), is determined by dot product of $p_Y$ and $\mu_{Ay}$. In one embodiment, $p_Y$ is determined via application of extension principal. In one embodiment, $p_X$'s for points in $\{x_i\}$ in X domain are attributed to their corresponding points $\{y_i\}$ in Y domain. Such an embodiment accommodates having multiple $y_i$'s have the same value (or belong to the same bin in Y domain). Alternatively, or additionally, in one embodiment, bins are setup in Y domain to determine $p_Y$ for each bin by summing over corresponding $p_i$'s (from X domain) where $F(x_i)$ is within the Y-bin. In such an embodiment, $\omega$, for example, is determined by taking $p_Y$ and $\mu_{Ay}$ dot product in Y domain over Y bins. However, in one embodiment, $p_Y$ and $\mu_{Ay}$ dot product is essentially determined in X domain, for example by:

$$\omega_{p_x} = \Sigma_i p_X(x_i) \cdot \mu_{A_y}(y_i)$$

Figure 12K:
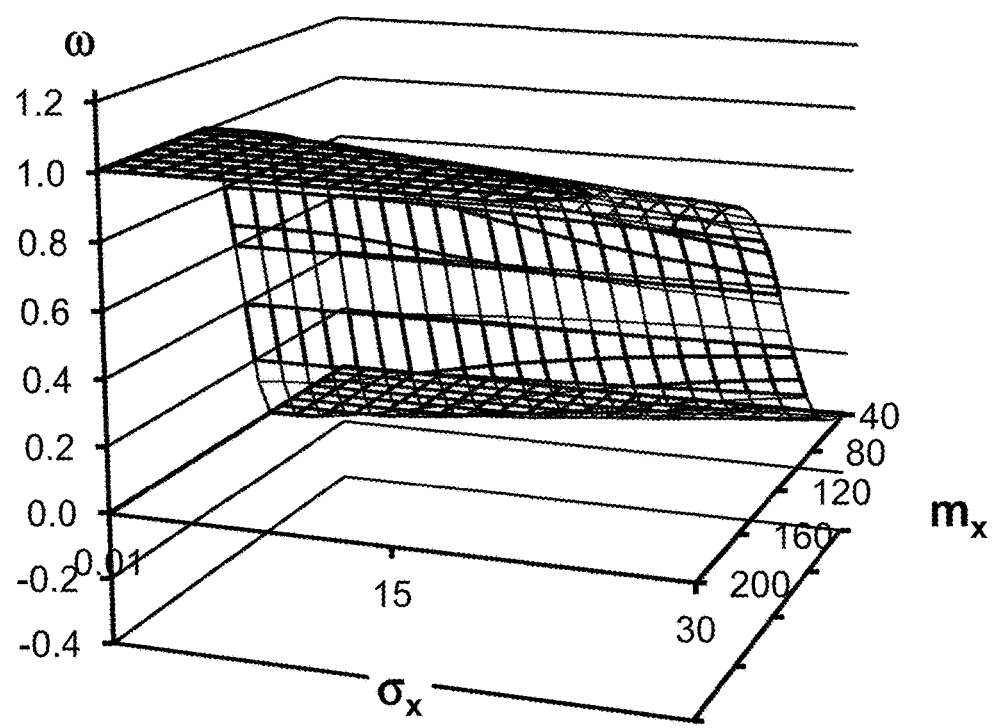
Figure 12I:
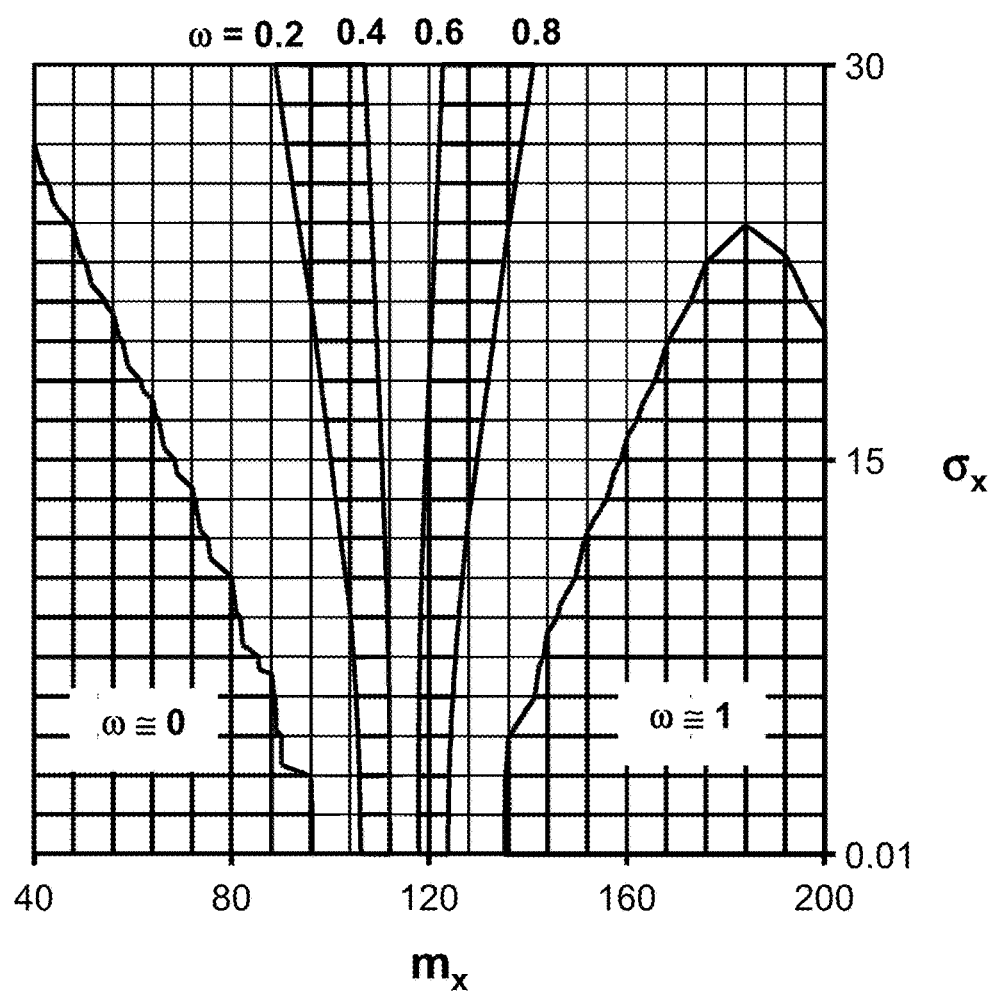

In one embodiment, $\omega$ is determined via piecewise evaluation. In one embodiment, $\omega$ is determined for various candidates for $p_X$. For example, taking $p_X$ as $N(m_x, \sigma_x)$ as described above, $\omega$ is determined for various $(m_x, \sigma_x)$ combination, as depicted in FIGS. 12(k)-(l). These contour maps of $\omega$ are identical to those of $\upsilon$ versus $(m_x, \sigma_x)$ (depicted in FIGS. 12(e) and (g)), as expected, since F(X), in this example, is monotonic (as explained previously).

Figure 12M:
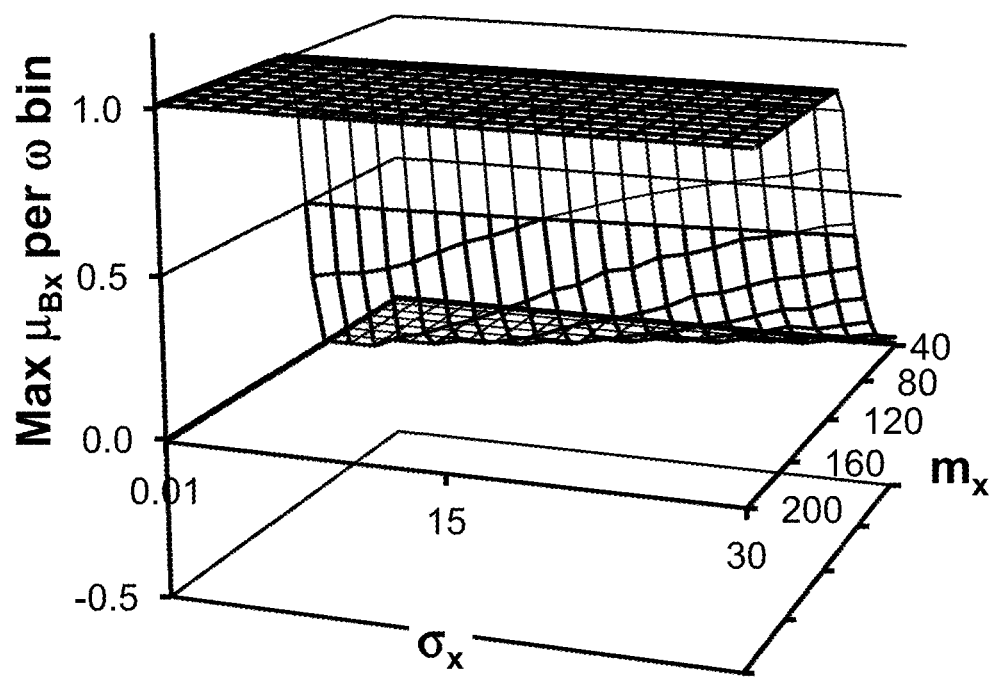
FIGS. 12(m)-(n) depict the restriction (per ω bin) imposed on various values of probability distribution parameters, in one embodiment.
Figure 12N:
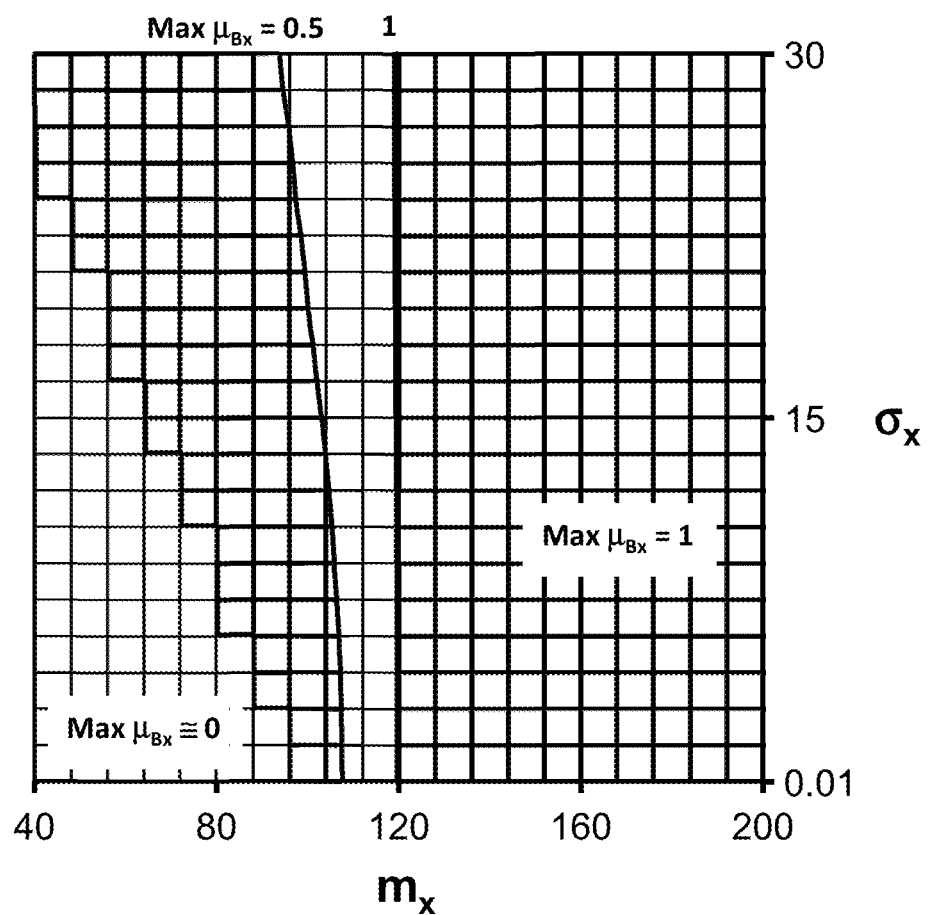
Figure 12O:
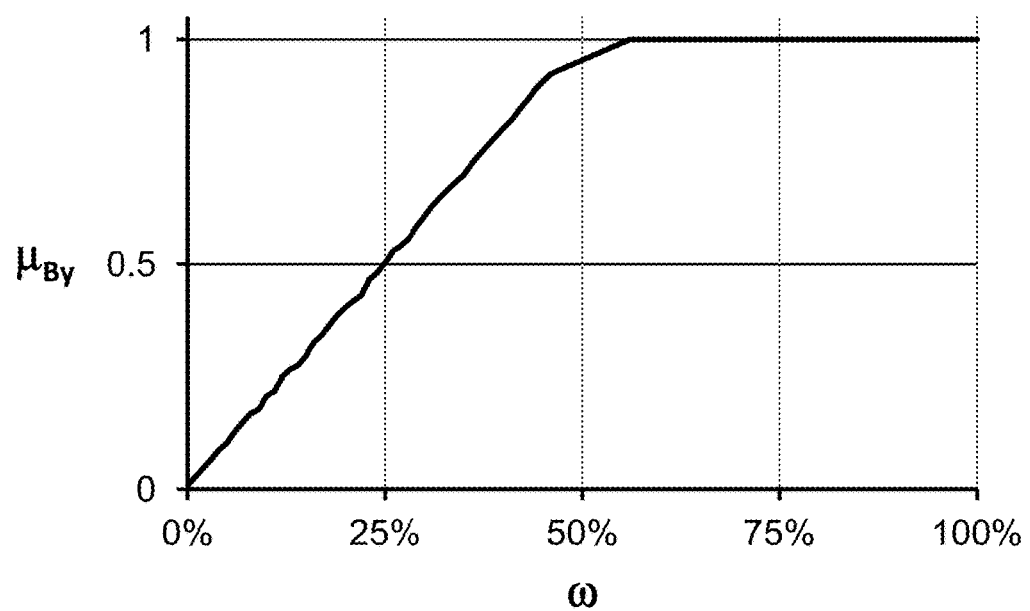
FIG. 12(o) depicts a restriction on probability measure, in one embodiment.

In one embodiment, to obtain the relationship between $\omega$ and restriction test scores from $B_x$, to determine $B_y$, bins are setup in $\omega$ domain (e.g., between $\omega_{min}$ and $\omega_{max}$, or in [0, 1]

range). In one embodiment, the size/number of bin(s) in ω is adjustable or adaptive to accommodate regions in ω domain where $(m_x, \sigma_x)$ mapping is scarce, sparse or absent. In one embodiment, for each $(m_x, \sigma_x)$, the calculated $\omega(m_x, \sigma_x)$, is mapped to a bin in ω domain. In such an embodiment, each $(m_x, \sigma_x)$ becomes associated to a ω bin (e.g., identified by an ID or index). Multiple $(m_x, \sigma_x)$ may map to the same ω bin. In one embodiment, through this association with the same ω bin, the maximum $\mu_{Bx}(\upsilon(m_x, \sigma_x))$ for $(m_x, \sigma_x)$'s associated with the same ω bin is determined. For example, FIG. 12(m)-(n) depict the contour maps of Max $\mu_{Bx}(\upsilon(m_x, \sigma_x))$ for various $(m_x, \sigma_x)$. In one embodiment, maximum $\mu_{Bx}(\upsilon(m_x, \sigma_x))$ is associated to the ω bin of the corresponding $(m_x, \sigma_x)$'s. In one embodiment, unique set of ω bins is determined that are associated with at least one $(m_x, \sigma_x)$. Associated maximum $\mu_{Bx}(\upsilon(m_x, \sigma_x))$ is determined per ω value representing the corresponding ω bin. In one embodiment, this maximum $\mu_{Bx}(\upsilon(m_x, \sigma_x))$ per ω is provided as the result for $\mu_{By}(\omega)$. For example, FIG. 12(o) depicts $\mu_{By}(\omega)$ for this example, which very closely resembles $\mu_{Bx}(\upsilon)$, as expected, because F(X) is a monotonic, as explained previously.

Therefore, in this example, assuming that $\mu_{Ay}(y)$ (ramping up from 300 to 345) indicates somewhat higher than 300, and that $\mu_{By}(\omega)$ maps to more than medium (i.e., not small) (in this context), then the answer to $q_1$ becomes: The probability of the price of the ticket being somewhat higher than 300 is more than medium.

q2: What is the Probability that the Price of the Ticket (from Washington D.C. to New York) is not Low?

Figure 13A:
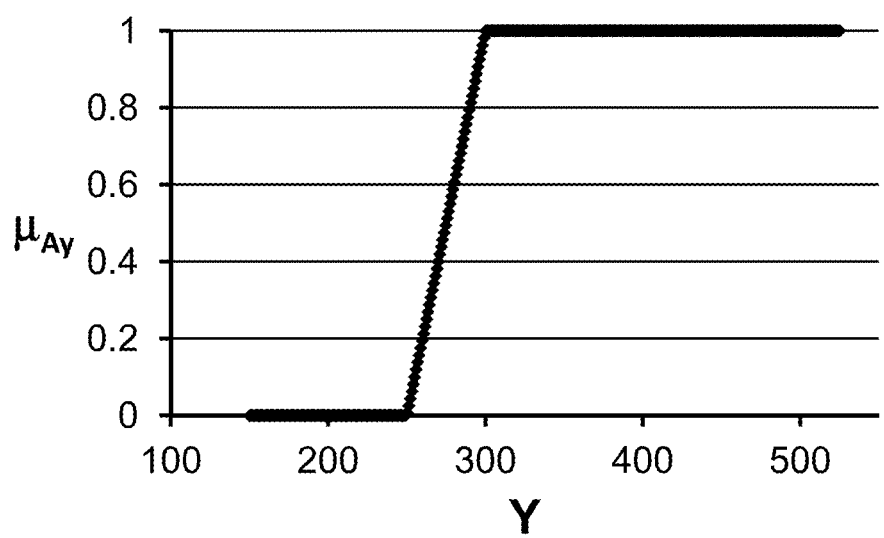
FIG. 13(a) depicts a membership function, in one embodiment.

In this question, Y still presents the price of the ticket; however, $A_y$ is already specified by $q_2$ as not low in this context. Parsing the question, Prob(Y is $A_y$) or $B_y$ in Z-valuation of (Y, $A_y$, $B_y$) is the output. In one embodiment, the knowledge database is searched to precisiate the meaning of not low in the context of Y. In one embodiment, in parsing $q_2$, not is recognized as the modifier of a fuzzy set low in context of Y. In one embodiment, the knowledgebase is used to determined, for example low is a step down fuzzy set with its ramp located between 250 and 300. In one embodiment, the modifiers are used to convert the membership functions per truth system(s) used by the module. For example, FIG. 13(a) depicts $\mu_{Ay}(y)$ for not low. In one embodiment, $\mu_{Ay}$ is determined for every y in $\{y_i\}$ where $y_i=F(x_i)$. In one embodiment, $\mu_{Ay}$ is determined via a piecewise evaluation/ lookup from $\mu_{Ay}$.

Figure 13B:
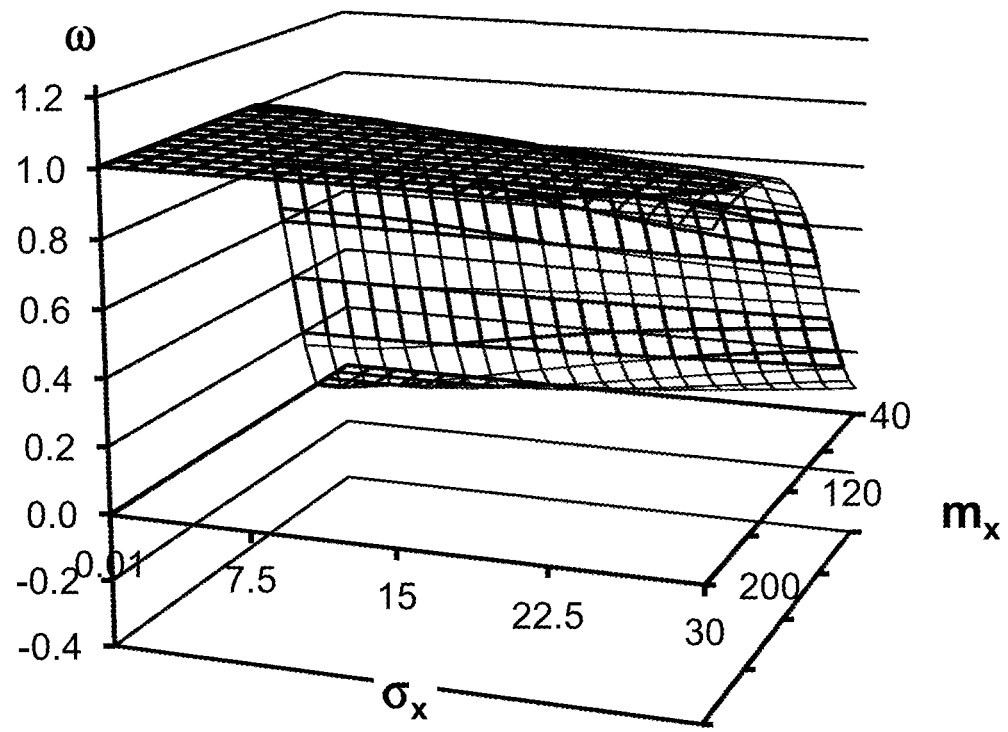
FIGS. 13(b)-(c) depict the probability measures for various values of probability distribution parameters, in one embodiment.
Figure 13C:
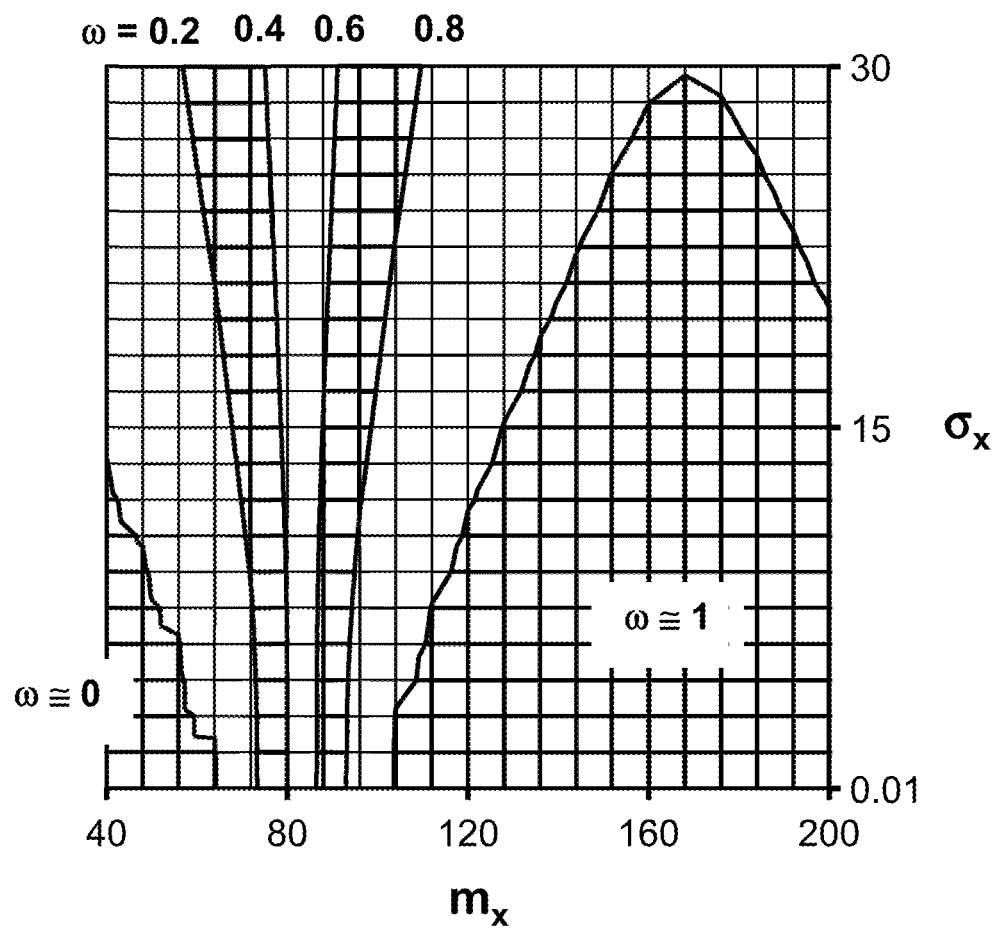
Figure 13D:
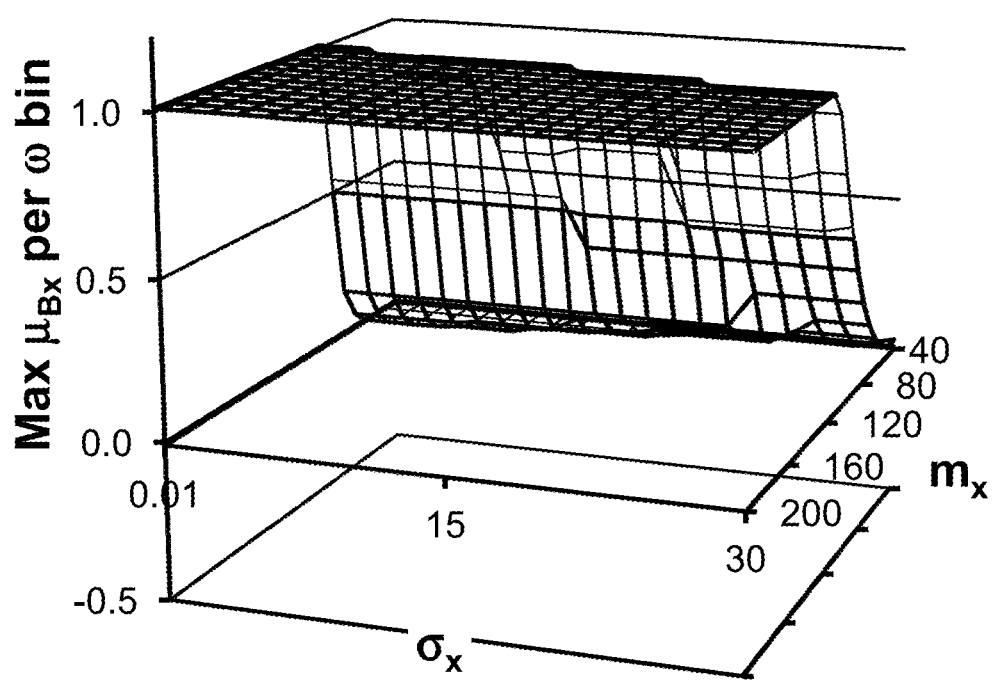
FIGS. 13(d)-(e) depict the restriction (per ω bin) imposed on various values of probability distribution parameters, in one embodiment.
Figure 13E:
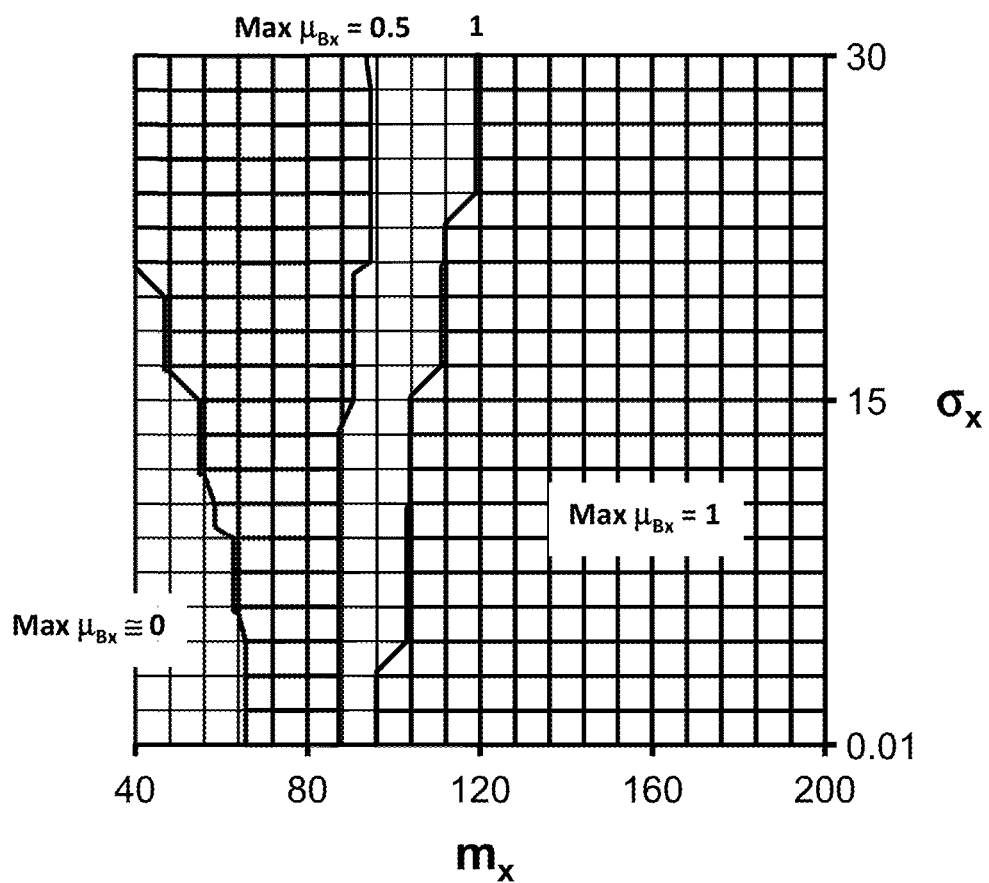

In one embodiment, the association of $(x_i, y_i)$ is used to attribute $p_X$ values to $(x_i, y_i)$. Comparing with $q_1$, in one embodiment, $\upsilon$ and $\mu_{Ax}$ are reused or determined similarly. For example, FIGS. 12(a)-(c) and 12(e)-(j) are applicable to $q_2$, as in this example, $\mu_{Ax}$ (FIG. 12(a)), $\mu_{Bx}$ (FIG. 12(b)), and F(X) (FIG. 12(c)) are still the same; $\upsilon$ determination/ calculation (FIGS. 12(e)-(h)) is still applied the same; and $\mu_{Bx}$ is applied similarly to $\upsilon$, in order to map $\mu_{Bx}$ to candidate $p_X$'s (FIGS. 12(i)-(j)). However, given $\mu_{Ay}$ is provided via by $q_2$ (instead of, e.g., an extension principle via $\mu_{Ax}$), the corresponding probability measures, ω, is expected to be different. For example, FIGS. 13(b)-(c) depict ω (as dot product of $\mu_{Ay}$ and $p_Y$) per various candidate distribution, i.e., $(m_x, \sigma_x)$. Compared to ω in $q_1$ (FIGS. 12(k)-(l)), the contours appear to be shifted to lower values of $m_x$, because the shift in the fuzzy edge of $\mu_{Ay}$ (from $q_1$ to $q_2$) toward lower ticket prices, causes similar shift in ω contours in this example, as F(X) is monotonic and increasing. At any rate, contours of ω and $\upsilon$ are no longer collocated on $(m_x, \sigma_x)$ given $A_y$ was not obtained through application of the extension principle to F(X) and $A_x$. The maximum $\mu_{Bx}(\upsilon(m_x, \sigma_x))$, for example obtained via application of ω bins, is depicted in FIGS. 13(d)-(e). In one embodiment, through association with ω bins, the corresponding $B_y$ is determined obtaining $\mu_{Bx}(\upsilon(m_x, \sigma_x))$ per ω, as shown for example in FIG. 13(f). One embodiment, varies the number/size of ω bins to compensate the scarcity of distribution candidate to provide the maximum $\mu_{Bx}(\upsilon(m_x, \sigma_x))$ at a particular ω bin. For example, ω bin factor of 5 was applied to obtain the results depicted in FIGS. 13(d)-(f), i.e., the number of bins was reduced from 101 to 20, while the bin size was increased from 0.01 to 0.0526. With ω bin factor of 1, the result for $\mu_{Bx}(\omega)$ are depicted in FIG. 13(g). In one embodiment, the ω bin factor is varied within a range (e.g., 1 to 20) to reduce the number of quick changes (or high frequency content) in the resulting $B_y$ membership function, beyond a threshold. In one embodiment, ω bins are determined for which there appear to be inadequate candidate distribution (e.g., based on quick drops in the membership function of $B_y$). For such ω values, a set of probability distributions, i.e., $(m_x, \sigma_x)$'s, are determined (e.g., those at or close to the corresponding ω contours). Then, more finely distributed parameters/distributions are used to increase the varied candidates contributing to maximum levels of $\mu_{By}(\omega)$. In one embodiment, an adaptive process is used to select various size ω bins for various ω values. In one embodiment, an envelope-forming or fitting process or module, e.g., with an adjustable smoothing parameter or minimum-piece-length parameter, is used to determine one or more envelopes (e.g., having a convex shape) connecting/covering the maximum points of resulting $\mu_{By}(\omega)$, as for example depicted as dotted line in FIG. 13(g).

In one embodiment, the resulting $\mu_{By}(\omega)$ is provided to other modules that take membership function as input (e.g., a fuzzy rule engine) or store in a knowledge data store. In one embodiment, the resulting $\mu_{By}(\omega)$ (e.g., in FIG. 13(f)) is compared with templates or knowledge base to determine the natural language counterpart for $B_y$. In one embodiment, the knowledge base, for example, includes various models of membership function (e.g., in [0, 1] vs. [0, 1] range or a subset of it) to find the best fit. In one embodiment, fuzzy logic rules (including rules for and, or, not, etc.) are used to generate more models. In one embodiment, fuzzy modifiers (e.g., very, somewhat, more or less, more than, less than, sort of slightly, etc.) are used to construct modified models. In one embodiment, the best fit is determined by a combination of models from the knowledge base. One embodiment uses adjustable parameter to indicate and control the complexity of combinations of models for fitting $B_y$.

Figure 13F:
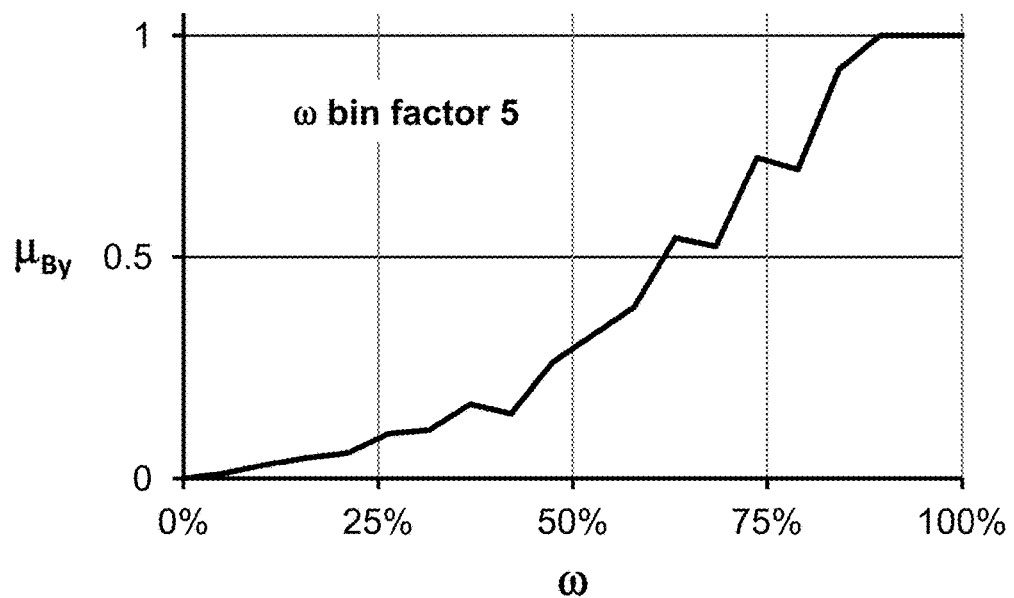
FIGS. 13(f)-(g) depict a restriction on probability measure, in one embodiment.
Figure 13G:
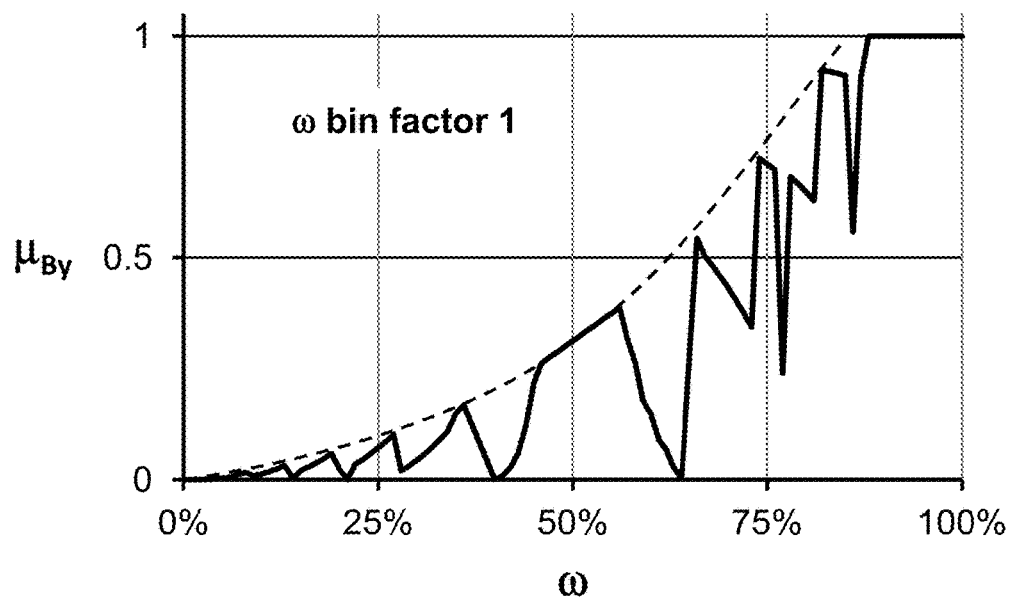

In one embodiment, $\mu_{By}(\omega)$ (e.g., in FIG. 13(f)) is determined to map to very probable. Therefore, the answer to $q_2$ becomes: The price of the ticket is very probably not low.

q3: What is the Probability that the Price of the Ticket (from Washington D.C. to New York) is High?

Figure 14A:
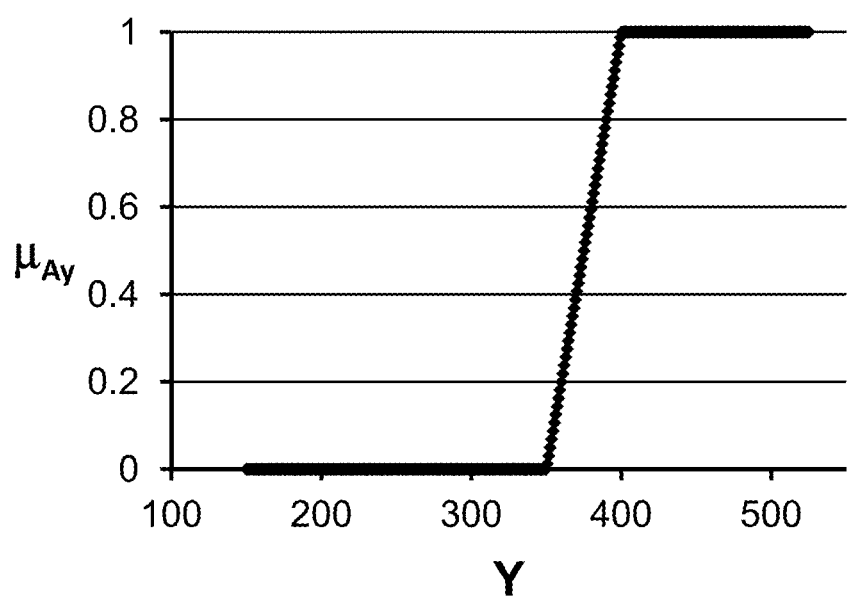
FIG. 14(a) depicts a membership function, in one embodiment.
Figure 14B:
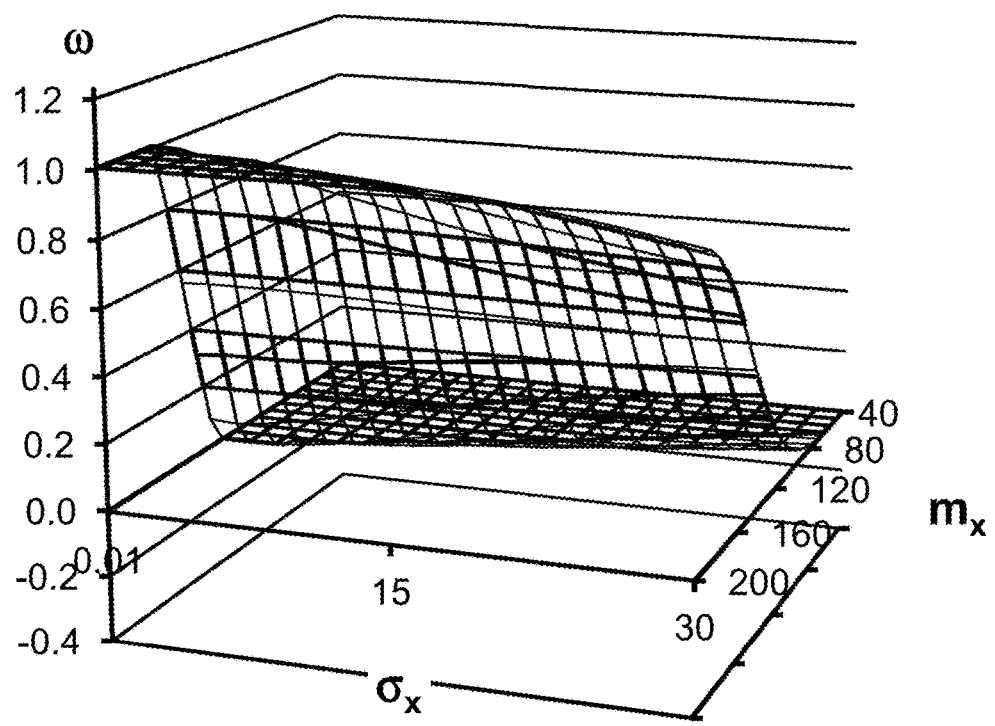
FIGS. 14(b)-(c) depict the probability measures for various values of probability distribution parameters, in one embodiment.
Figure 14C:
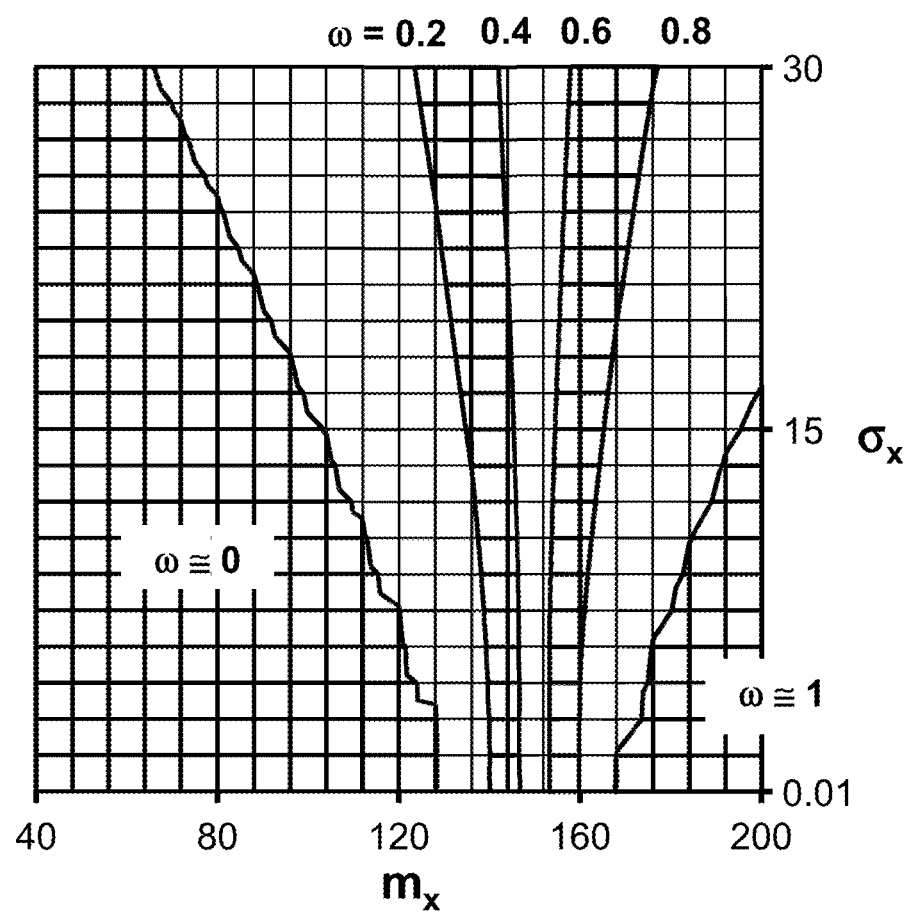
Figure 14D:
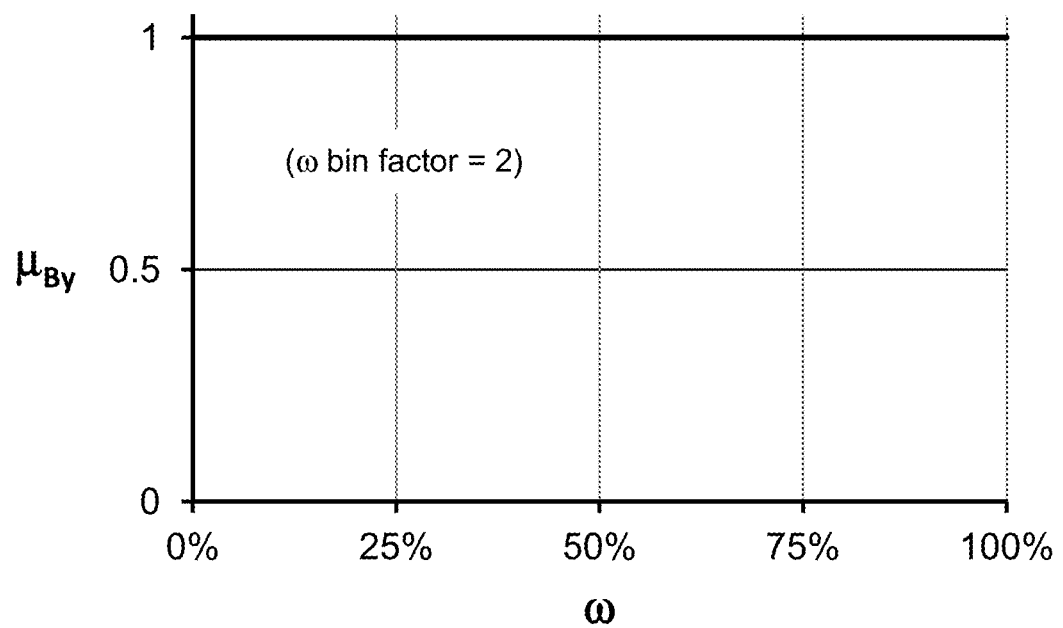
FIG. 14(d) depicts a restriction on probability measure, in one embodiment.

As in $q_2$, $q_3$ presents $A_y$ as high. In one embodiment, within the context, $\mu_{Ay}$ is given, for example, as ramp located at 350 (with a width of 50), as depicted in FIG. 14(a). Probability measure of $\mu_{Ay}$ (i.e., ω) is determined as above. 14(b)-(c) depict ω contour maps, and indicate the shifting of the contour lines to higher $m_x$ values (in the reverse direction compared to the scenario of $q_2$). However, comparing with the contour map of $\mu_{Bx}$ in FIG. 12(j), it is evident that at $\sigma_x$ of 120 (contour marked as $\mu_3$), $\mu_{Bx}$ is 1, while in such a region, all potential values of ω are covered (from 0 to 1) as shown in 14(c). Therefore, all values of ω's are definitely possible (i.e., not restricted by application of $A_y$). The resulting $\mu_{By}$ is depicted in 14(d), indicating 1 for all possible values with the counterpart natural language term anything.

Therefore, in this example, the answer to $q_3$ is: The probability of the price of the ticket being high can be anything.

FIG. 109 is an example of a system described above.

Fuzzy Control with Z-Number

As mentioned previously, an extension of a fuzzy control system that uses fuzzy rules can employ Z-numbers a either or both antecedent and consequent portion of IF THEN fuzzy rule. Regularly, in executing a fuzzy rule, such as (IF X is A THEN Y is B), the value of variable X used in antecedent, is determined (e.g., from an Input or from defuzzification result of other relevant rules) to be $x_0$. In one embodiment, the truth value of the antecedent is evaluated given the knowledge base (e.g., $X=x_0$) as the truth value of how (X is A) is satisfied, i.e., $\mu_A(x_0)$. The truth value of the antecedent (assuming more than a threshold to trigger the consequent) is then applied to the truth value of the consequent, e.g., by clipping or scaling the membership function of B by $\mu_A(x_0)$. Firing of fuzzy rules involving the same variable at the consequent yields a superimposed membership function for Y. Then, a crisp value for Y is determined by defuzzification of Y's resulting membership function, e.g., via taking a center of mass or based on maximum membership value (e.g., in Mamdani's inference method), or a defuzzied value for Y is determined by a weighted average of the centroids from consequents of the fuzzy rules based on their corresponding truth values of their antecedents (e.g., in Sugeno fuzzy inference method).

In one embodiment, where the antecedent involves a Z-number, e.g., as in the following fuzzy rule:

IF (X is Z) THEN (Y is C), where $Z=(A_X, B_X)$ and X is a random variable, the truth value of the antecedent (X is Z) is determined by how well its imposed restriction is satisfied based on the knowledge base. For example, if the probability or statistical distribution of X is $p_X$, the antecedent is imposing a restriction on this probability distribution as illustrated earlier as:

$$\mu_{B_X}\left(\int_R \mu_{A_X}(u)p_X(u)du\right)$$

where u is a real value parameter in X domain. In one embodiment, the probability distribution of X, $p_X$, is used to evaluate the truth value of the antecedent, by evaluating how well the restriction on the probability distribution is met. In one embodiment, an approximation for $p_X$ is used to determine the antecedent's truth value. Denoting $p_{Xi}$ as an estimate or an input probability distribution for X, the antecedent truth value is determined as:

$$\mu_{B_X}\left(\int_R \mu_{A_X}(u)p_{Xi}(u)du\right)$$

An embodiment, e.g., in a fuzzy control system or module, uses multiple values of u to estimate $p_X$. In one embodiment, the values of u are discrete or made to be discrete through bins representing ranges of u, in order to count or track the bin population representing the probability distribution of X. For example, at $bin_i$, $p_X$ is estimated as:

$$p_X|_{bin_i} \approx \frac{1}{\Delta u_i} \cdot \frac{Count_i}{\sum_j Count_j}$$

where $\Delta u_i$ and $Count_i$ are the width and population of $i^{th}$ bin. This way, a running count of population of bins is tracked as more sample data is received.

In one embodiment, Z-number appears as the consequent of a fuzzy rule, e.g.,

IF (Y is C) THEN (X is Z), where $Z=(A_X, B_X)$ and X is a random variable.

As other fuzzy rules, when the rule is executed, the truth value of the antecedent (i.e., $\mu_C(y_0)$, where $y_0$ is a value for Y, that is input to the rule) is applied to the restriction imposed by the consequent. The restriction imposed by the consequent is, e.g., on the probability distribution of X, which is the variable used in the consequent. Given the antecedent's truth value of $T_{ant}$ (between 0 and 1), in one embodiment, the contribution of the rule on the restriction of $p_X$ is represented by $\mu_{B_X}(\int_R \mu_{A_X}(u) \cdot p_X(u) \cdot du)$ clipped or scaled by $T_{ant}$ In one embodiment, Z-number appears in an antecedent of a fuzzy rule, but instead of the quantity restricted (e.g., $p_X$), other indirect knowledge base information may be available. For example, in the following fuzzy rule:

IF (X is Z) THEN (Y is C), where $Z=(A_X, B_X)$ and X is a random variable, suppose from input or other rules, it is given that (X is D), where D is a fuzzy set in X domain. In one approach, the hidden candidates of $p_X$ (denoted by index i) are given test scores based on the knowledge base, and such test scores are used to evaluate the truth value of the antecedent. For example, the truth value of the antecedent is determined by:

$$T_{ant} = \sup_{\forall i} (ts_i \wedge ts_i')$$

where $$ts_i = \int_R \mu_D(u)p_i(u)du$$

$$ts_i' = \mu_{B_X}\left(\int_R \mu_{A_X}(u)p_i(u)du\right)$$

In one embodiment, various model(s) of probability distribution is employed (based on default or other knowledge base) to parameterize $\forall i$. For example, a model of normal distribution may be assumed for $p_X$ candidates, and the corresponding parameters will be the peak location and width of the distribution. Depending on the context, other distributions (e.g., Poisson distribution) are used. For example, in "Bus usually arrives about every 10 minutes", where X is bus arrival time, $A_X$ is about 10 minutes, and $B_X$ is usually, a model of probability distribution for bus arrival time may be taken as a Poisson distribution with parameter $\tau$:

$$p_i(u) = \frac{u}{\tau_i} \cdot e^{\frac{-u}{\tau_i}}$$

Then, the antecedent truth value is determined by $$T_{ant} = \sup_{\forall \tau_i} (ts_i \wedge ts_i')$$

In one embodiment, the truth value of the antecedent in a fuzzy rule with Z-number, e.g., IF (X is Z) THEN (Y is C), where $Z=(A_X, B_X)$ and X is a random variable, is determined by imposing the assumption that the probability distribution $p_X$ is compatible with the knowledge base possibility restriction (e.g., (X is D)). Then, a candidate for $p_X$ may be constructed per $\mu_D$. For example, by taking a normalized shape of possibility distribution:

$$p_X(u) = \frac{\mu_D(u)}{\int_R \mu_D(u')\,du'}$$

In one embodiment, the compatibility assumption is used with a model of distribution (e.g., based on default or knowledge base). For example, assuming a model of normal distribution is selected, the candidate probability distribution is determined as follows:

$$p_X(u) = \frac{1}{\sqrt{2\pi}\cdot r \cdot D_{width}} \cdot e^{-\frac{(u-D_{cent})^2}{2\cdot r^2 \cdot D_{width}^2}}$$

where $D_{width}$ and $D_{cent}$ are the width and centroid location of (e.g., a trapezoid) fuzzy set D, and r is a constant (e.g., $1/\sqrt{12} \approx 0.3$) or an adjustable parameter.

In one embodiment, the truth value of the antecedent in a fuzzy rule with Z-number, e.g., IF (X is Z) THEN (Y is C), where $Z=(A_X, B_X)$ and X is a random variable, is determined by simplifying the $\forall i$ examination in $$T_{ant} = \sup_{\forall \tau_i} (ts_i \wedge ts_i')$$

by taking a candidate for $p_X$ based on a model of probability distribution which would be compatible with fuzzy set B. Then, the antecedent truth value is determined based on such compatible probability distribution $p_o$, as $T_{ant} = ts_o \wedge ts_o'$ In one embodiment, such optimized probability distribution is determined based on the knowledge base (e.g., X is D). For example, when the model distribution is a normal distribution, in one embodiment, the center position (parameter) of the distribution is set at the centroid position of the fuzzy set D, while the variance of the probability distribution is set based on the width of fuzzy set D.

In one embodiment, an input proposition in form of Z-valuation, e.g., $(X, A_X, B_Y)$ or (X is Z) where $Z=(A_X, B_Y)$ and X is a random variable, is used to evaluate an antecedent of a fuzzy rule, e.g., IF (X is C) THEN (Y is D), where C and D are fuzzy sets in X and Y domains, respectively. In one embodiment, candidates of $p_X$ (denoted by index i) are given test scores based on the knowledge base, and such test scores are used to evaluate the truth value of the antecedent. For example, in one embodiment, the truth value of the antecedent is determined by:

$$T_{ant} = \sup_{\wedge i} (ts_i \wedge ts_i')$$

where $$ts_i = \int_R \mu_C(u) p_i(u)\,du$$

$$ts_i' = \mu_{B_X}\left(\int_R \mu_{A_X}(u) p_i(u)\,du\right)$$

Example 2

In one embodiment, a fuzzy rules database includes these two rules involving Z-valuation (e.g., for a rule-based analysis/engine). Rule 1: If the price of oil is significantly over 100 dollars/barrel, the stock of an oil company would most likely increase by more than about 10 percent. Rule 2: If the sales volume is high, the stock of an oil company would probably increase a lot. There is also this input information: The price of oil is at 120 dollars/barrel; the sales volume is at $20B; and the executive incentive bonus is a function of the company's stock price. The query or output sought is:

q4: What is the Likelihood of High Executive Incentive Bonuses?

In one embodiment, the rules engine/module evaluates the truth value of the rules' antecedents, e.g., after the precisiation of meaning for various fuzzy terms. For example, the truth value of Rule 1's antecedent, the price of oil is significantly over 100 dollars/barrel is evaluated by taking the membership function evaluation of 120 (per information input) in fuzzy set significantly over 100 dollars/barrel (see, e.g., FIG. 12(a)). Therefore, this antecedent truth value ($t_1$) becomes, in this example, 0.67. Similarly, the truth value of Rule 2's antecedent, the sales volume is high, is evaluated by using (e.g., contextual) membership function $\mu_{High}$ for value $20B. Let's assume the antecedent truth value ($t_2$) is determined to be 0.8, in this example. In firing the Rules, the truth values of antecedents are imposed on those of consequents. Rule 1's consequent, is a Z-valuation (X, $A_1$, $B_1$) where X represents the change in stock, $A_1$ represents more than about +10 percent, and B1 represents most likely. Rule 2's consequent, is a Z-valuation (X, $A_2$, $B_2$) where $A_2$ represents a lot, and B1 represents probably. The consequent terms impose restriction on $p_X$, therefore, the truth values of the consequent (i.e., restriction on $p_X$) is determined by triggering of the Rules. In one embodiment, the restrictions are combined, e.g., via correlation minimum and Min/Max inference or correlation product and additive inference. In one embodiment, a model of $p_X$, e.g., $N(m_x, \sigma_x)$, is used to apply the restriction on $p_X$ to restrictions on parameters of the distributions (e.g., $(m_x, \sigma_x)$). In one embodiment, the range of X domain is taken from the knowledge base. In one embodiment X domain range(s) is determined from characteristics of $A_1$ and/or $A_2$. In one embodiment, a consolidated range(s) is determined in X domain. One or more sets of X values are used to evaluate $p_X(m_x, \sigma_x)$, $\mu_{A1}$, and $\mu_{A2}$. In one embodiment, probability measures $\upsilon_1$ and $\upsilon_2$ for $A_1$ and $A_2$, respectively, are determined for candidate $p_X$'s, e.g., for various $(m_x, \sigma_x)$. The possibility measures of $\upsilon_1$ and $\upsilon_2$ in $B_1$ and $B_2$ are determined by evaluating $\mu_{B1}(\upsilon_1)$ and $\mu_{B2}(\upsilon_2)$, e.g., for various $(m_x, \sigma_x)$. These possibility measures are test scores imposed on the probability distribution candidate for X (e.g., identified by $(m_x, \sigma_x)$) via the consequents of the triggered rules. Therefore, in one embodiment, the fuzzy rule control system uses the restrictions on candidate distributions. For example, in a control system employing correlation minimum and Min/Max inference, the restriction on $p_X(m_x, \sigma_x)$ is determined as follows, e.g., for various $(m_x, \sigma_x)$:

$$\mu_{P_x}(m_x, \sigma_x) = \max_{\forall j} \left(\min(\mu_{B_j}(v_j(m_x, \sigma_x)), t_j)\right)$$

where j is an index for triggered fuzzy rule (in this example, from 1 to 2).

As an example, in a control system employing correlation product and additive inference, the restriction on $p_X(m_x, \sigma_x)$ is determined as follows, e.g., for various $(m_x, \sigma_x)$:

$$\mu_{P_x}(m_x, \sigma_x) = \min\left(\sum_{\forall j} \mu_{B_j}(v_j(m_x, \sigma_x)) \cdot t_j, 1\right)$$

In one embodiment, $\mu_{P_x}(m_x, \sigma_x)$ is the basis for determining answer to $q_4$. For example, $q_4$ is reduced to Z-valuation $(Y, A_y, B_y)$, where Y represents executive incentive bonuses, $A_y$ represents high, $B_y$ represents restriction on Prob(Y is $A_y$). The knowledge database, in one embodiment, provides the functional dependence (G) of executive incentive bonuses (Y) on the stock price (SP), and therefore on X, i.e., the change in stock, via the current stock price (CSP). For example:

$$Y = G(SP) = G(CSP + X) = F(X)$$

In one embodiment, as in the previous examples, ω, probability measure of $A_y$ is determined for various $p_X$ (i.e., $(m_x, \sigma_x)$) candidates. In one embodiment, maximum $\mu_{px}(m_x, \sigma_x)$ for ω (or ω bin) is determined, and applied as membership function of $\mu_{B_y}(\omega)$. In another word, in this example, the output of rules engine provides the restriction on $p_X$ (or its parameters) similar to previous examples, and this output is used to determine restriction on a probability measure in Y.

Example 3

In one embodiment, e.g., in a car engine diagnosis, the following natural language rule "Usually, when engine makes rattling slapping sound, and it gets significantly louder or faster when revving the engine, the timing chain is loose." is converted to a protoform, such as:

IF
$\left(\left(\begin{array}{c} \text{type(sound(engine)) is } RattlingSlapping \\ \text{AND} \\ \text{(level(sound(revved.engine)), level(sound(engine)))} \\ \text{is significantlylouder} \\ \text{OR} \\ \text{(rhythm(sound(revved.engine)), rhythm(sound(engine)))} \\ \text{is significantlyfaster} \\ (Prob\{\text{(tension}(TimingChain)\text{ is loose)}\}\text{ is usually)}. \end{array}\right)\right)$
THEN In one embodiment, a user, e.g., an expert, specifies the membership of a particular engine sound via a user interface, e.g., the user specifies that the truth value of the engine sound being Rattling-Slapping is 70%. In one embodiment, the user specifies such truth value as a fuzzy set, e.g., high, medium, very high. In one embodiment, a Z-mouse is used to specify the fuzzy values (i.e., membership function) of various attribute(s) of the sound (e.g., loudness, rhythm, pitch/squeakiness). The Z-mouse is for example provided through a user interface on a computing device or other controls such as sliding/knob type controls, to control the position and size of an f-mark.

In one embodiment, the engine sound is received by a sound recognition module, e.g., via a microphone input. In one embodiment, the loudness (e.g., average or peak or tonal) of the engine sound is determined, e.g., by a sound meter (analog or digital) or module. In one embodiment, the rhythm is determined via the frequency of the loudness, or using the frequency spectrum of the received sound (e.g., the separation of the peaks in the frequency domain corresponds to the period of (impulse) train making up the rhythm of the engine sound). In one embodiment, the values of these parameters are made fuzzy via evaluating the corresponding membership functions (of e.g., engine sound level) for evaluating the truth value of the predicate in fuzzy rule. In one embodiment, the fuzzy rule is rewritten to use more precision, e.g., if readily available. For example, in one embodiment, level(sound(revved.engine)) and level(sound (revved.engine)) take on measured values.

Figure 15A:
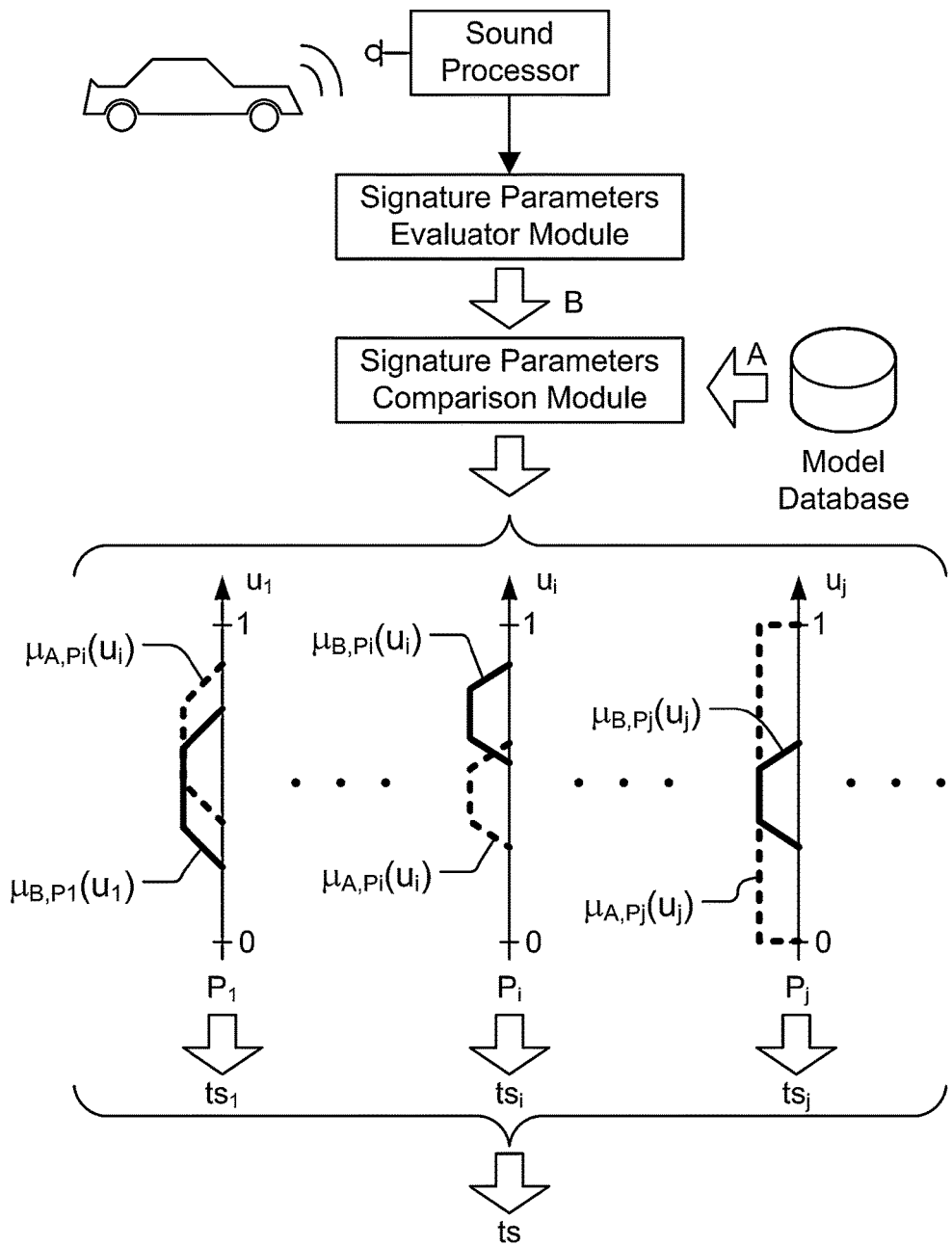
FIG. 15(a) depicts determination of a test score in a diagnostic system/rules engine, in one embodiment.

In one embodiment, as for example depicted in FIG. 15(a), the type of engine sound is determined automatically, by determining a set of (e.g., fuzzy) signature parameters (e.g., tonal or pattern). In one embodiment, various relevant fuzzy sets (e.g., RattlingSlapping) are expressed via veristic distribution restriction on signature parameters. In one embodiment, the truth value of the predicate is determined via comparison with the truth values of the fuzzy parameters. For example:

$$ts = \min_{\forall i}(ts_i)$$

$$= \min_{\forall i}\left(\max_{\forall u_i}(\mu_{A,P_i}(u_i) \wedge \mu_{B,P_i}(u_i))\right)$$

where i is an index identifying the ith signature parameter $P_i$. $u_i$ is a generic truth value parameter in [0, 1]. $ts_i$ is the test score contribution from comparison of A and B against $P_i$. $\mu_{A,P_i}$ and $\mu_{B,P_i}$ are fuzzy values of the A and B with respect to signature parameter $P_i$. For example, A represents RattlingSlapping; B represents the engine sound; ts represents the truth value of the engine sound being RattlingSlapping; and $ts_i$ represents a possibility test score match of A and B with respect to the signature (fuzzy) parameter $P_i$, for example determined, by comparison of A's and B's truth degree in $P_i$. In one embodiment, the comparison with respect to $P_i$ is determined by:

$$ts_i = \max_{\forall u_i}(\mu_{A,P_i}(u_i) \wedge \mu_{B,P_i}(u_i))$$

For example, as depicted in FIG. 15(a), $ts_1$ is 1 as $\mu_{A,P1}$ and $\mu_{B,P1}$ overlap in $u_1$ where both are 1; and $ts_2$ is less than 1 (e.g., say 0.4) as $\mu_{A,P2}$ and $\mu_{B,P2}$ overlap in $u_2$ at their fuzzy edges. In one embodiment, as shown above, ts is determined by minimum of individual $ts_i$'s. In one embodiment, ts is determined via averaging, or weighted ($w_i$) averaging:

$$ts = \operatorname*{ave}_{\forall i}(ts_i)$$

or $$\frac{\sum_i w_k \cdot ts_i}{\sum_k w_k}$$

In one embodiment, where not all signature parameters are used, relevant, or available for A, then a subset of those signature parameters that are used, relevant, or available for A is used to determine ts, e.g., by limiting taking minimum or averaging operations based on those signature parameters. For example, $$ts = \min_{\forall i} (ts_i)$$

Subject to $P_i \in$ {relevant signature parameters to $A$}

In such an embodiment, the relevant signature parameters for A are identified, for example, via a query in the model or knowledge database.

In one embodiment, for example, when minimum of $ts_i$'s are used to determine ts, the irrelevancy of a signature parameter with respect to A may be expressed as a truth membership function of 1 for all possibilities. For example, as depicted in FIG. 15(a), $\mu_{A,Pj}$ is flat (=1) for all $u_j$'s, and therefore, $ts_j$ is 1 (assuming maximum of $\mu_{B,Pj}$ is 1 at some $u_j$). Thus, in this case, the contribution of $ts_j$ in is effectively disappears.

Figure 15B:
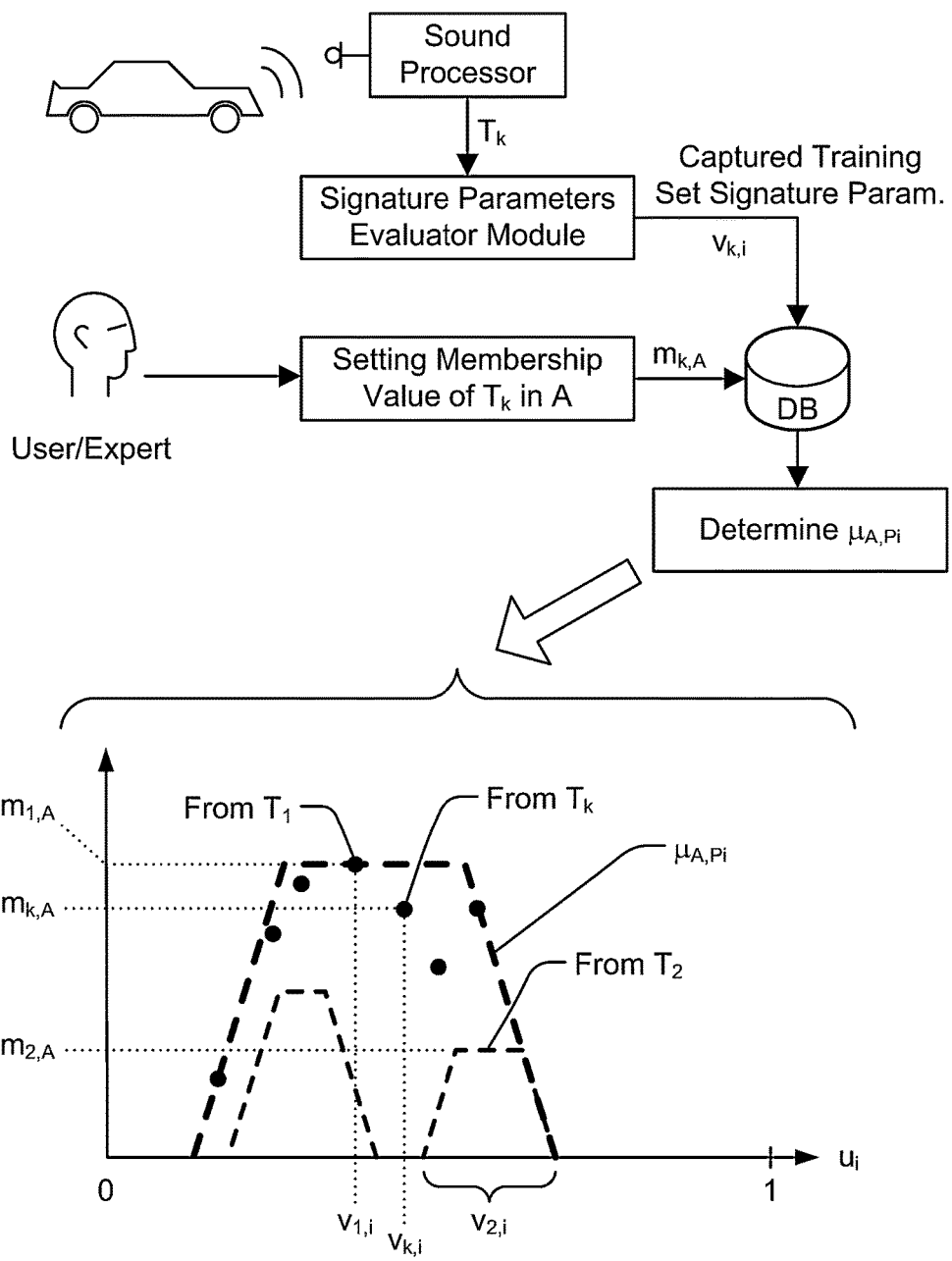
FIG. 15(b) depicts use of training set in a diagnostic system/rules engine, in one embodiment.

In one embodiment, $\mu_{A,Pi}$ is determined through empirical methods, user settings, or training sets. For example, in one embodiment, N training set engine sounds (denoted as $T_k$ with k from 1 to N) are used to determine $\mu_{A,Pi}$. In one embodiment, the truth values for the training element $T_k$ with respect to signature parameters are determined (e.g., as a crisp number, range, or a fuzzy set). For example, as depicted in FIG. 15(b), the truth value of the training element $T_k$ in signature parameter $P_i$, is determined (denoted as $\upsilon_{k,i}$), for example through an expert assignment, rule evaluation, or functional/analytical assessment. In one embodiment, the membership value of $T_k$ in A is (denoted as $m_{k,A}$) determined, e.g., by user/expert, expert system, or via analytical methods. $m_{k,A}$ may have crisp or fuzzy value. In one embodiment, the contribution of $T_k$ to $\mu_{A,Pi}$ is determined similar to the execution of the consequent of a fuzzy rule, e.g., the contribution of $\upsilon_{k,i}$ is scaled or clipped by $m_{k,A}$ as depicted in FIG. 15(b). For example, as depicted, the truth value of $T_1$ in $P_i$ is a crisp value $\upsilon_{1,i}$, and the truth value of $T_1$ in A is $m_{1,A}$. Thus, the contribution of $T_1$ to $\mu_{A,Pi}$ appears as a dot at $(\upsilon_{1,i}, m_{1,A})$. Another example is the contribution of $T_2$ to $\mu_{A,Pi}$ where the truth value of $T_2$ in $P_i$ is a fuzzy value $\upsilon_{2,i}$, and the truth value of $T_2$ in A is $m_{2,A}$. Thus, the contribution of $T_2$ to $\mu_{A,Pi}$ appears as a clipped or scaled membership function as depicted in FIG. 15(b). In one embodiment, $\mu_{A,Pi}$ is determined as the envelope (e.g., convex) covering the contributions of $T_k$'s to $\mu_{A,Pi}$, for example as depicted in FIG. 15(b). In one example, truth value bins are set up in $u_i$ to determined the maximum contribution from various $T_k$'s for a given $u_i$ (bin) to determined $\mu_{A,Pi}$.

In one embodiment, user/expert assigns verity membership values for $T_k$ in A.

In one embodiment, a module is used to determine correlation between the various type sounds and the corresponding engine diagnosis (by for example experts). In one embodiment, the correlation is made between the signature parameters of the sound and the diagnosis (e.g., in for of fuzzy graphs or fuzzy rules). In one embodiment, a typical and highly frequent type of sound may be identified as the signature parameter (e.g., RattlingSlapping may be taken as a signature parameter itself). Therefore, in one embodiment, the creation of new signature parameters may be governed by fuzzy rules (e.g., involving configurable fuzzy concepts as "typical" for similarity and "frequent"). In one embodiment, the reliability and consistency of the rules are enhanced by allowing the training or feedback adjust $\mu_{A,Pi}$.

In one embodiment, such diagnosis is used an autonomous system, e.g., in self-healing or self-repair, or through other systems/subsystems/components.

In one embodiment provides music recognition via similar analysis of its signature parameters and comparison against those from a music library/database. In one embodiment, the categories of music (e.g., classic, rock, etc) may be used as fuzzy concept A in this example.

q5: What is the Probability of Loose Timing Chain, when the Engine Sound is a Loud "Tick, Tick, Tack, Tack" and it Gets Worse when Revving the Engine?

In one embodiment, as shown by $q_5$, the specification of an input to the system is not in form of the actual sound engine (e.g., wave form or digitized audio), but a fuzzy description of the sound. A conversion process evaluates the fuzzy description to find or construct a sound/attributes (e.g., in the data store) which may be further processed by the rules. For example, in one embodiment, within the context, the module interprets fuzzy descriptions "Tick" and "Tack" as a tonal variation of abrupt sound. In one embodiment, the sequence of such descriptions is interpreted as the pattern of such sounds. With these attributes, in one embodiment, signature parameters are determined, and as described above, the test score related to whether "Tick, Tick, Tack, Tack" is RattlingSlapping is determined. The evaluation of the fuzzy rule predicate provides the test score for the limiting truth score for the consequent, which is a restriction on the probability of loose timing chain.

In one embodiment, e.g., in music recognition, similar fuzzy description of music is used to determine/search/find the candidates from the music library (or metadata) with best match(es) and/or rankings. When such a description accompanies other proposition(s), e.g., a user input that "the music is classical", it would place further restrictions to narrow down the candidates, e.g., by automatic combinations of the fuzzy restrictions, as mentioned in this disclosure or via evaluation of fuzzy rules in a rules engine.

Example 4

In this example, suppose these input propositions to system: $p_1$: the weather is seldom cold or mild. $p_2$: Statistically, the number of people showing up for an outdoor swimming pool event is given by function having a peak of 100 at 90° F., where X is the weather temperature:

$$Y = F(X) = \max\left(100 \times \left(1 - \text{abs}\left(\frac{X - 90° \text{ F.}}{25° \text{ F.}}\right)\right), 0\right)$$

q6: How Many People Will Show Up at the Swimming Event?

Figure 16A:
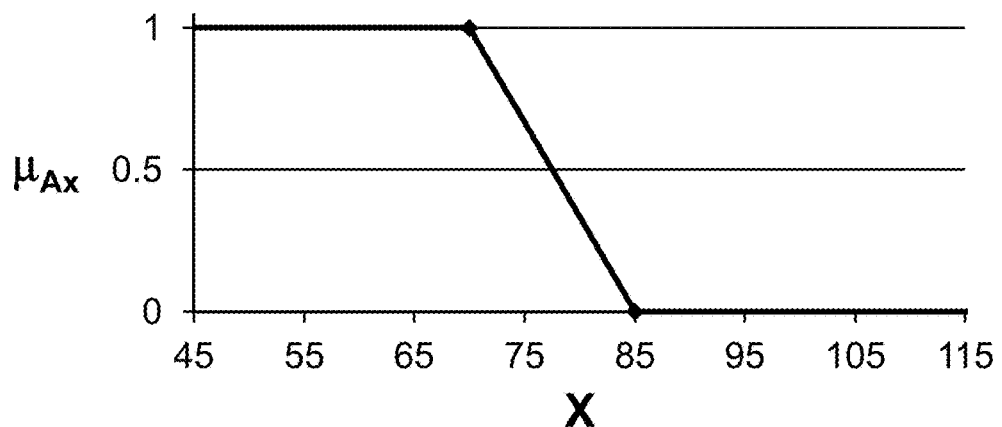
FIG. 16(a) depicts a membership function, in one embodiment.
Figure 16B:
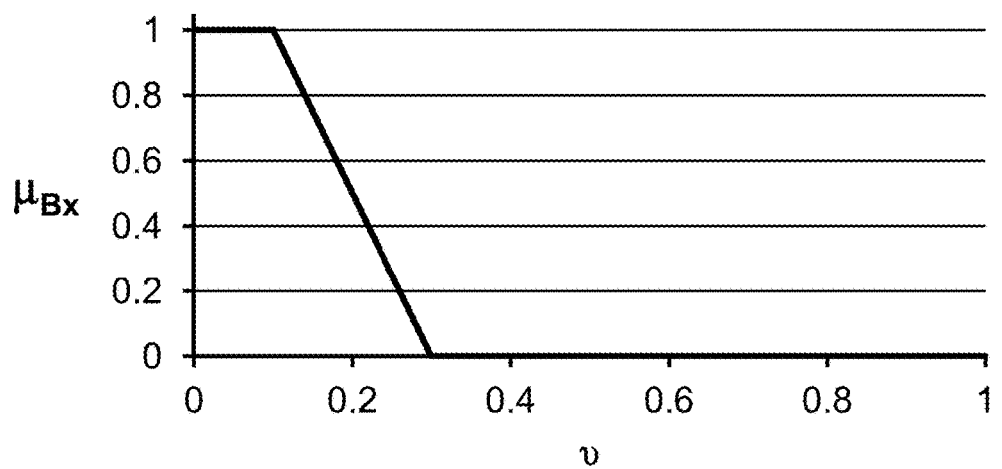
FIG. 16(b) depicts a restriction on probability measure, in one embodiment.

In one embodiment, the precisiation of input proposition is in Z-valuation $(X, A_x, B_x)$, where $A_x$ is cold or mild and $B_x$ is seldom. For example, as depicted in FIG. 16(a), $\mu_{A_y}$ is depicted as a step-down membership function with ramp from 70° F. to 85° F., representing the fuzzy edge of mild on the high side, and as depicted in FIG. 16(b), $\mu_{A_y}$ is depicted as a step-down membership function with ramp from 10% to 30%, representing seldom.

Figure 16C:
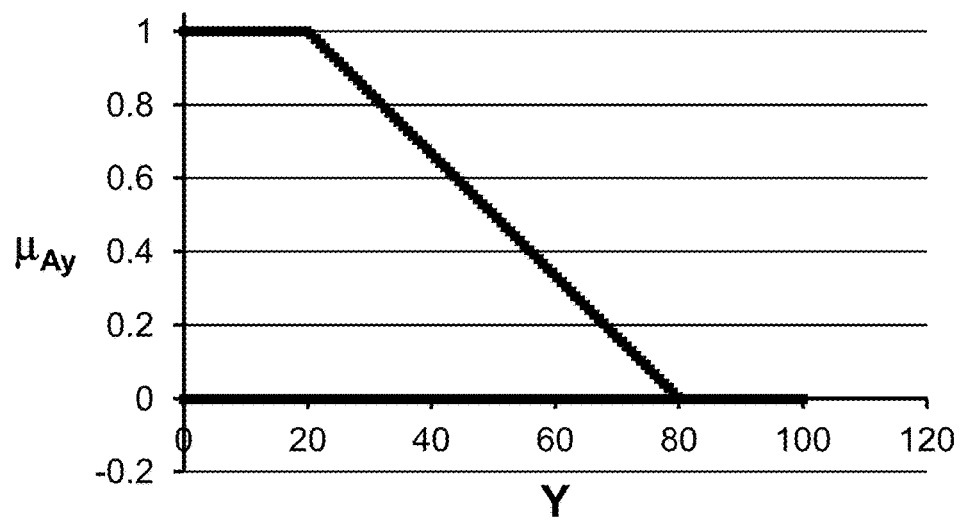
FIG. 16(c) depicts membership function tracing using a functional dependence, in one embodiment.
Figure 16D:
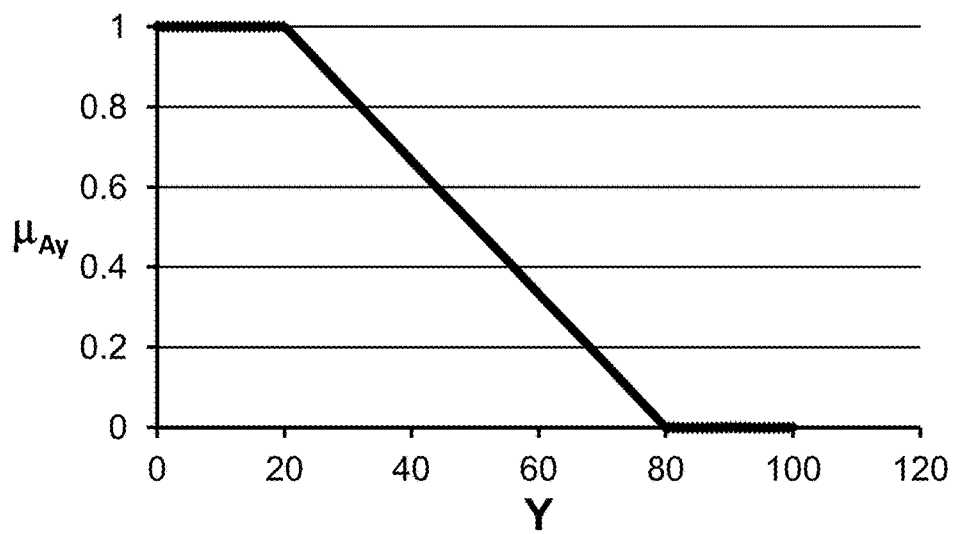
FIG. 16(d) depicts membership function determined using extension principle for functional dependence, in one embodiment.
Figure 16E:
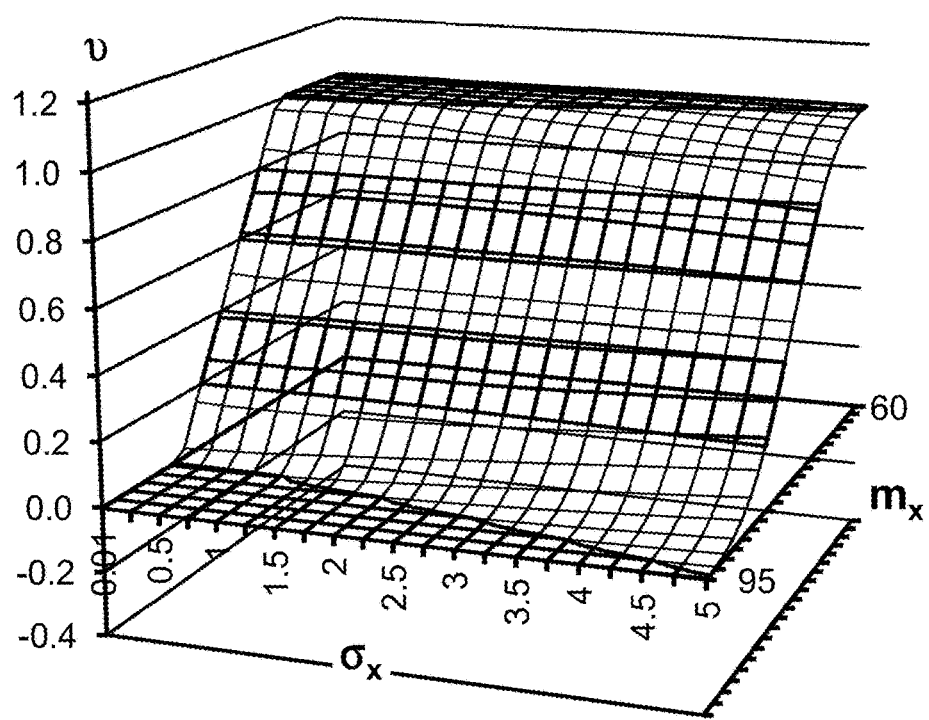
FIGS. 16(e)-(f) depict the probability measures for various values of probability distribution parameters, in one embodiment.
Figure 16F:
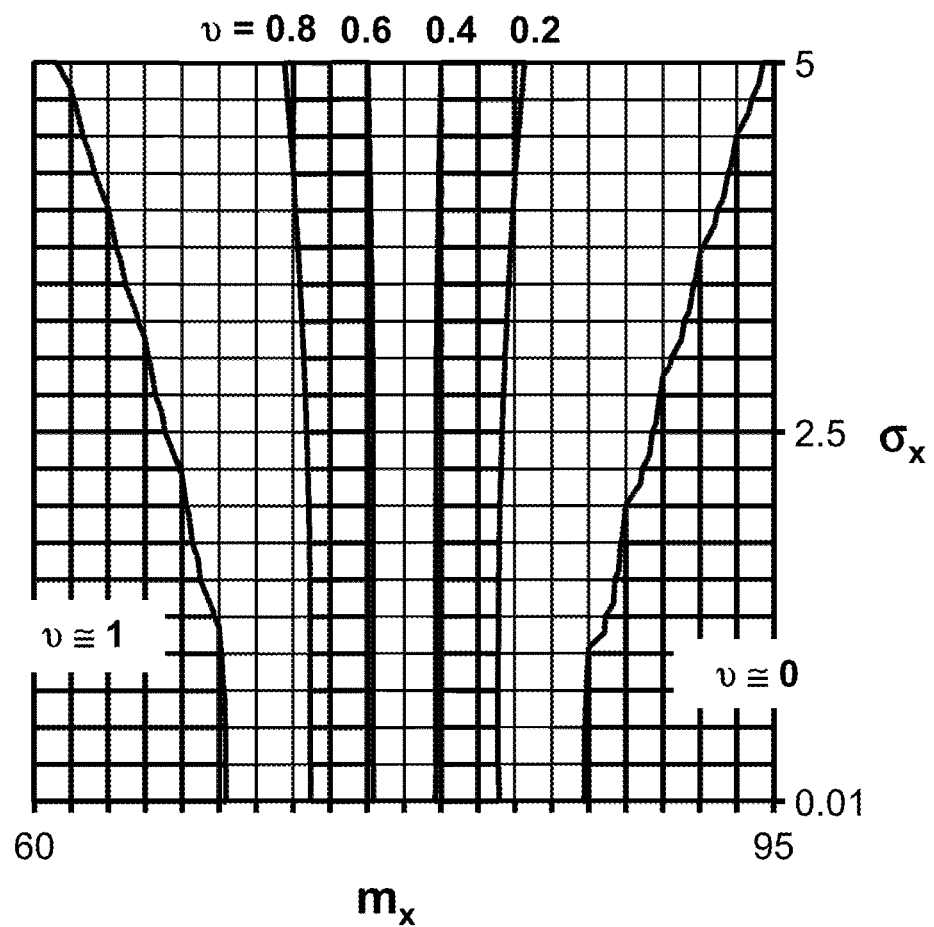
Figure 16G:
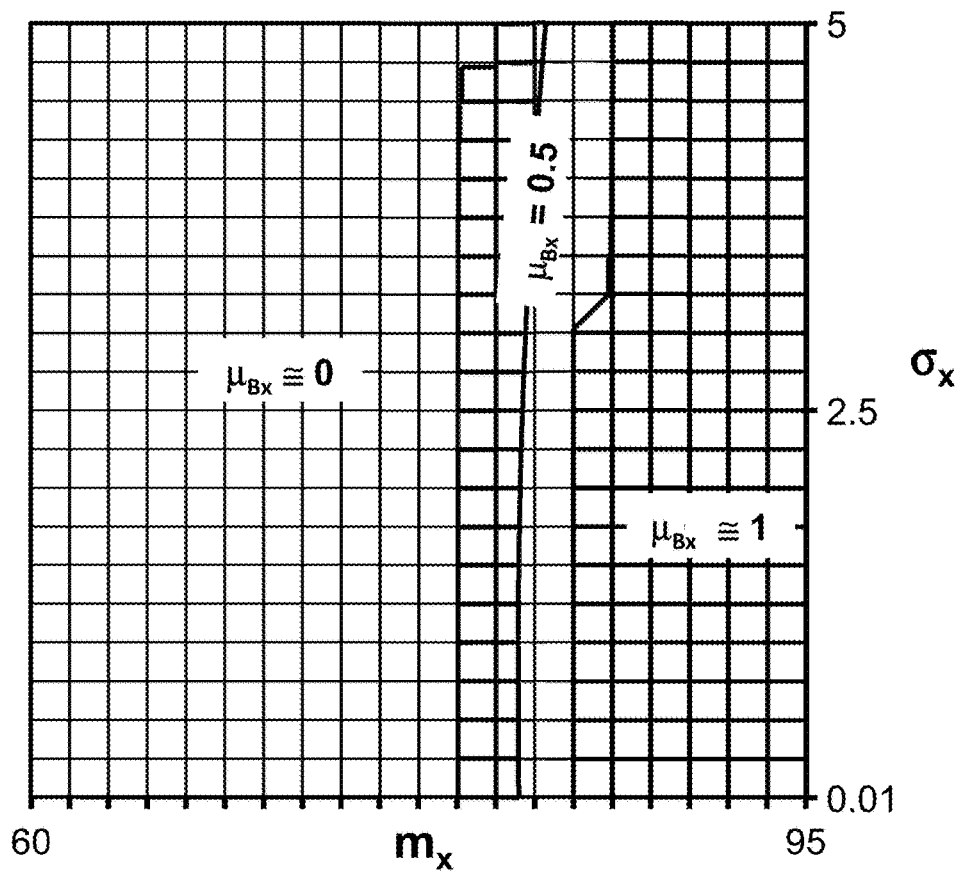
FIG. 16(g) depicts the restriction imposed on various values of probability distribution parameters, in one embodiment.
Figure 16H:
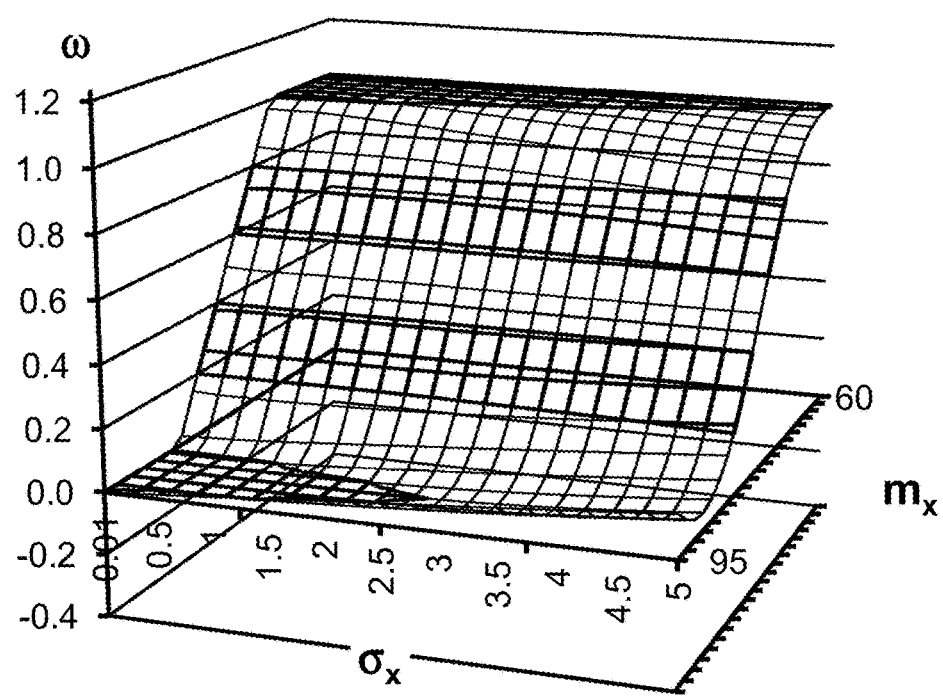
FIGS. 16(h)-(i) depict the probability measures for various values of probability distribution parameters, in one embodiment.
Figure 16I:
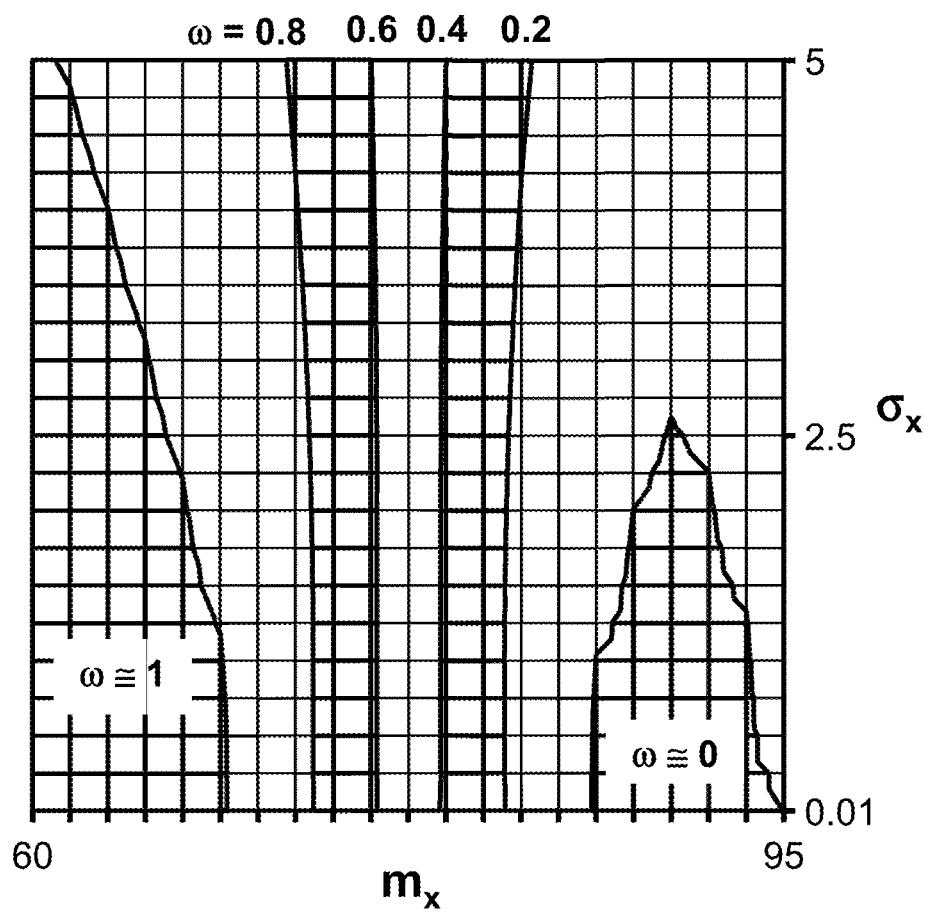
Figure 16J:
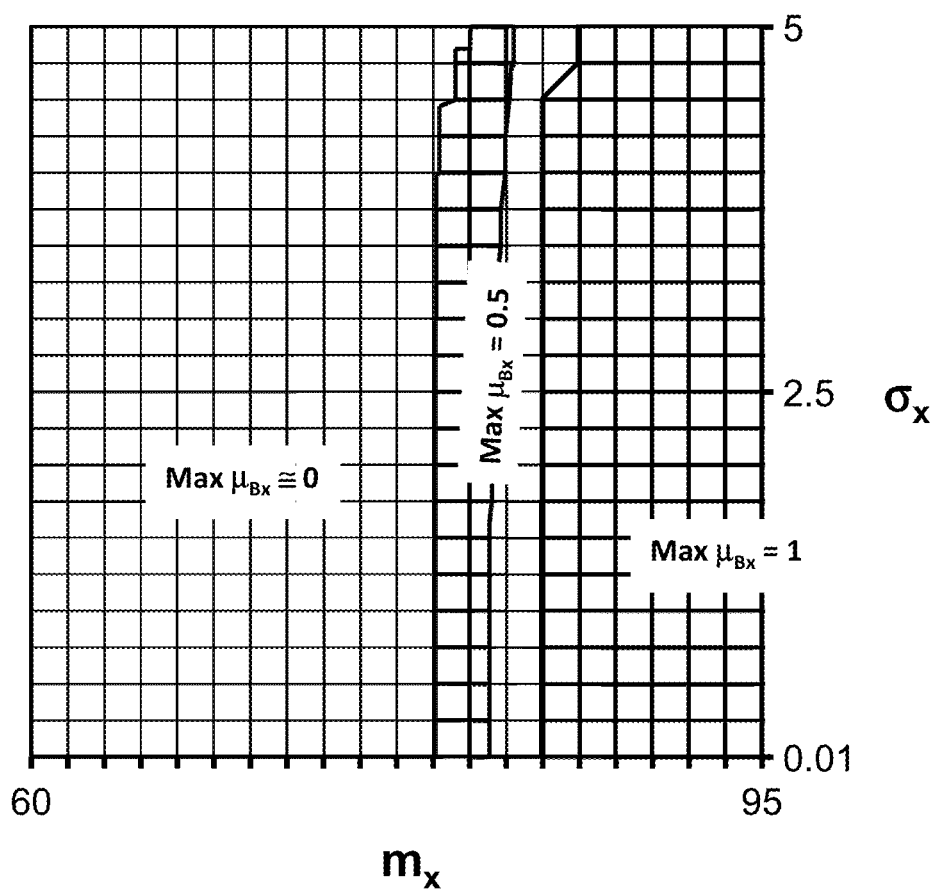
FIG. 16(j) depicts the restriction (per ω bin) imposed on various values of probability distribution parameters, in one embodiment.
Figure 16K:
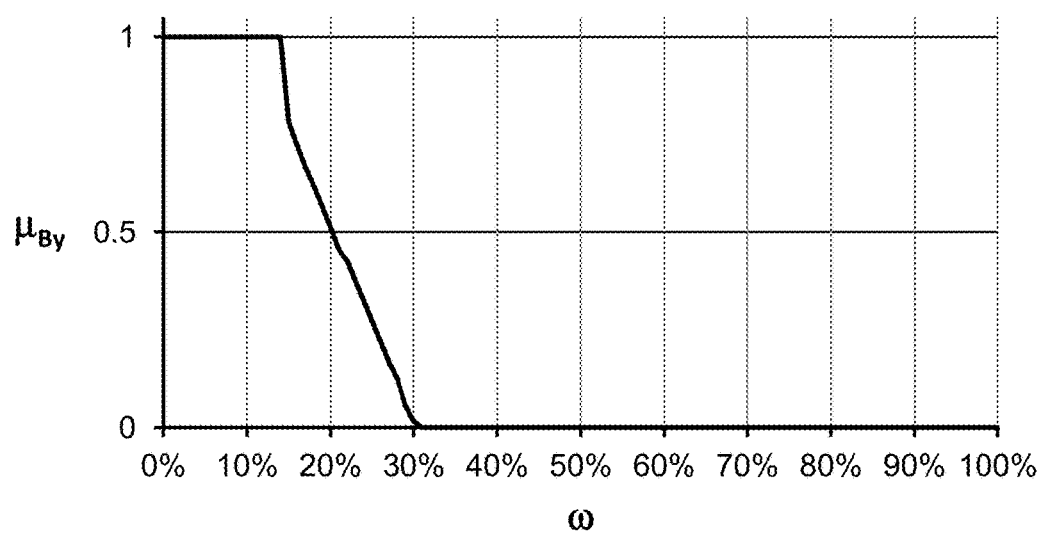
FIG. 16(k) depicts a restriction on probability measure, in one embodiment.

In one embodiment, the parsing of $q_6$ results in an answer in form of Z-valuation, $(Y, A_y, B_y)$ form, where Y is the number of people showing up for an outdoor swimming pool event. In one embodiment, as described in this disclosure, a candidate $\mu_{A_y}$ is determined using F(X) and $\mu_{A_x}$ via extension principle. For example, as depicted in FIG. 16(c), $\mu_{A_y}$ (without taking maximum possibility) is determined for X ranging from 45° F. to 120° F. Given non-monotonic nature of F(X) in this example, same Y (or bin) maps to multiple X's with different membership function values, as depicted in FIG. 16(c). The resulting $\mu_{A_y}$, by maximizing membership function in a Y (bin) is depicted in FIG. 16(d). For example, in one embodiment, this $\mu_{A_y}$ maps to quite significantly less than 80, based on the knowledge database, context, and models. In one embodiment, for example, a probability Gaussian distribution is selected for $p_X$, $N(m_x, \sigma_x)$, with $m_x$ selected in [60, 95] and $\sigma_x$ selected in (0, 5]. In one embodiment, the corresponding probability measure of $A_x$ (denoted as υ) is determined for various candidate $p_X$'s. For example, FIGS. 16(e)-(f) show υ (and its contours) for various ($m_x$, $\sigma_x$). As described in this disclosure, the test score based on $\mu_{B_x}$ for various ($m_x$, $\sigma_x$) is determined as depicted in FIG. 16(g). As described in this disclosure, the probability measure of $A_y$ (denoted as ω) is determined for various υ's or $p_X$'s. For example, as depicted in FIGS. 16(h)-(i), ω contours are shown for various values of ($m_x$, $\sigma_x$). As described in this disclosure, the maximum $\mu_{B_x}$ per ω (bin) is determined, for example as depicted in FIG. 16(j). In one embodiment, $\mu_{B_y}$ is determined as described in this disclosure, and is depicted in FIG. 16(k). In one embodiment, comparison of the resulting $\mu_{B_y}$ to the model database indicates that $B_y$ maps to more or less seldom. In one embodiment, the answer to $q_6$ is provided as: More or less seldom, the number of people showing up for an outdoor swimming pool event, is quite significantly less than 80.

q7: What are the Odds that the Weather is Hot?

Figure 17A:
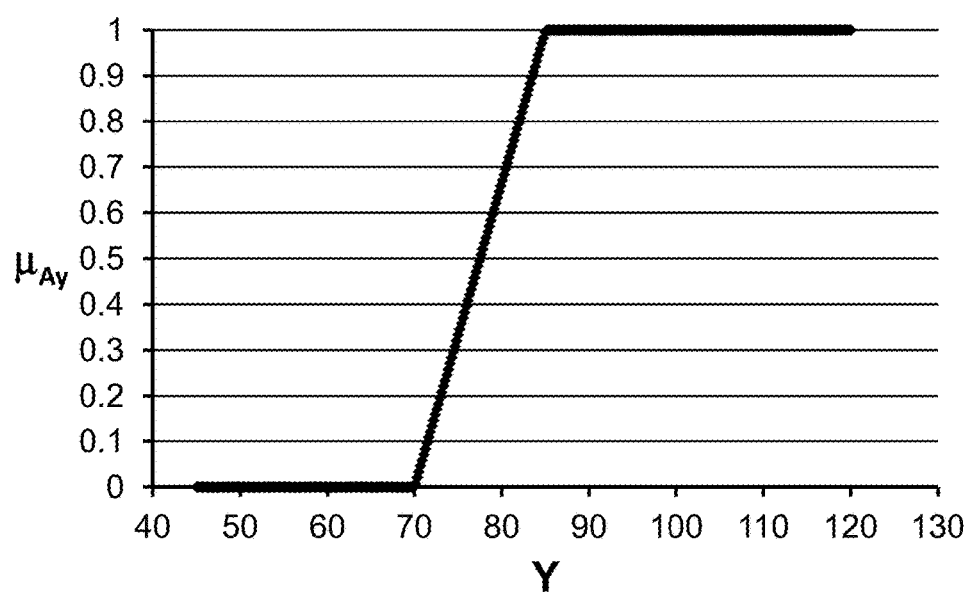
FIG. 17(a) depicts a membership function, in one embodiment.
Figure 17B:
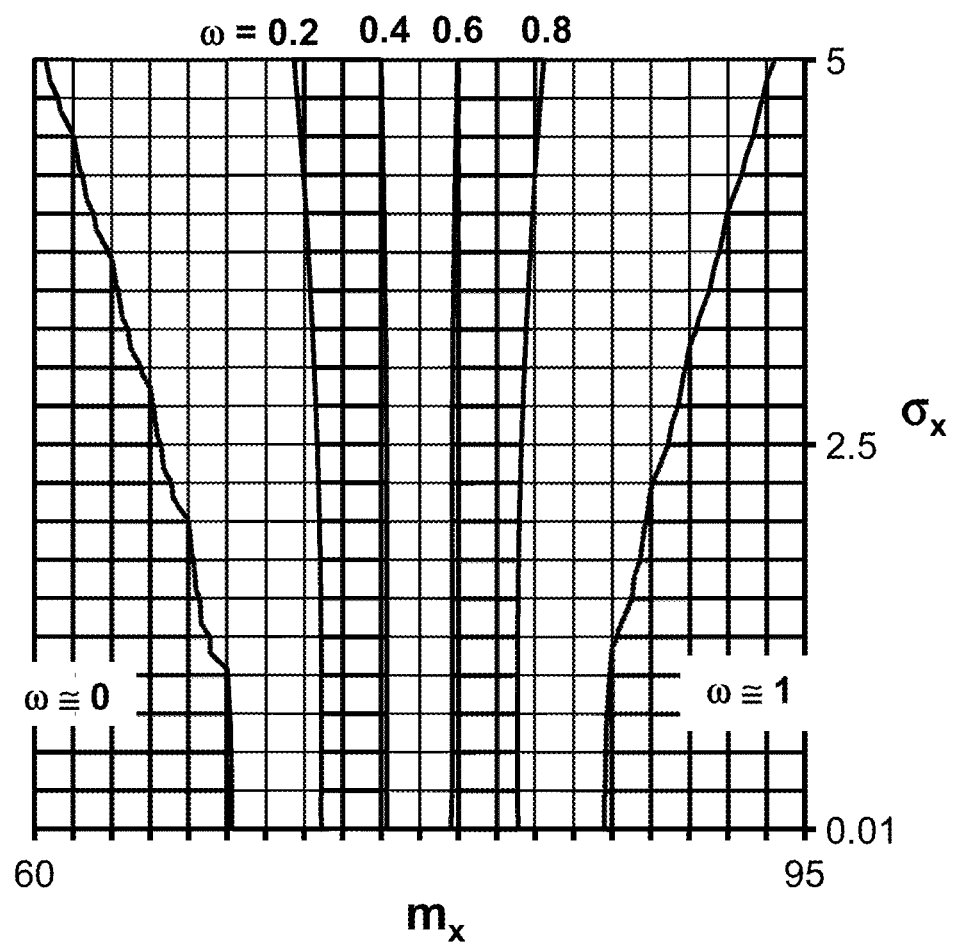
FIG. 17(b) depicts the probability measures for various values of probability distribution parameters, in one embodiment.
Figure 17C:
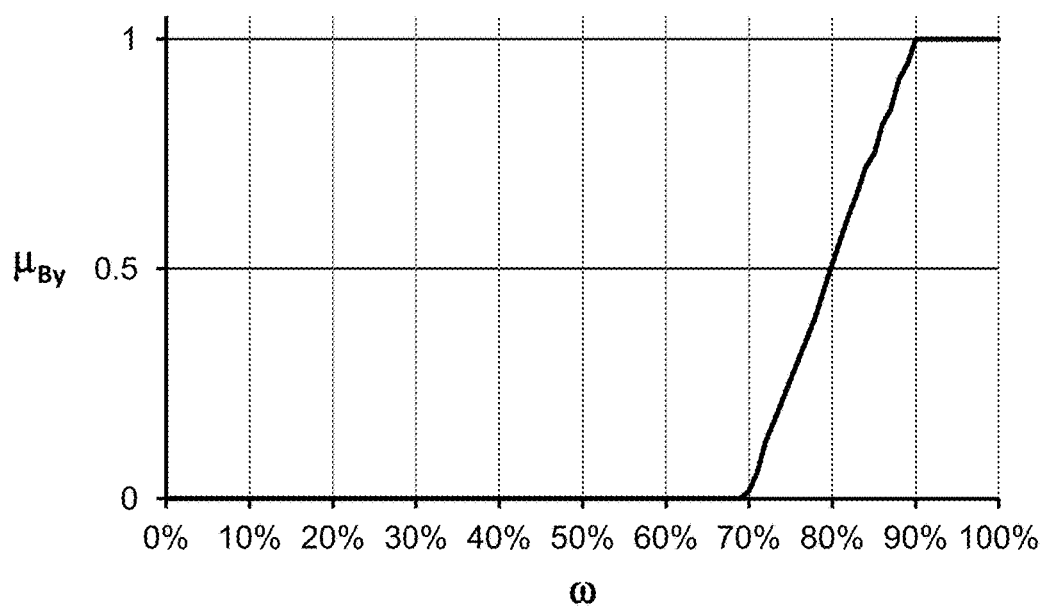
FIG. 17(c) depicts a restriction on probability measure, in one embodiment.

In one embodiment, the answer is in a Z-valuation Y, $A_y$, $B_y$) form, where Y is temperature (same as X, i.e., Y=F(X)=X). $q_6$ provides $A_y$ as hot, as for example depicted in FIG. 17(a). As described in this disclosure, in one embodiment, the probability measure of $A_y$ is determined (e.g., see FIG. 17(b)), and $\mu_{B_y}$ is determined (e.g., see FIG. 17(c)). In one embodiment, this $\mu_{B_y}$ is mapped to usually (or anti-seldom), and the answer is determined as: the weather temperature is usually hot.

q8: What are the Odds that More than about 50 People Show Up?

Figure 18A:
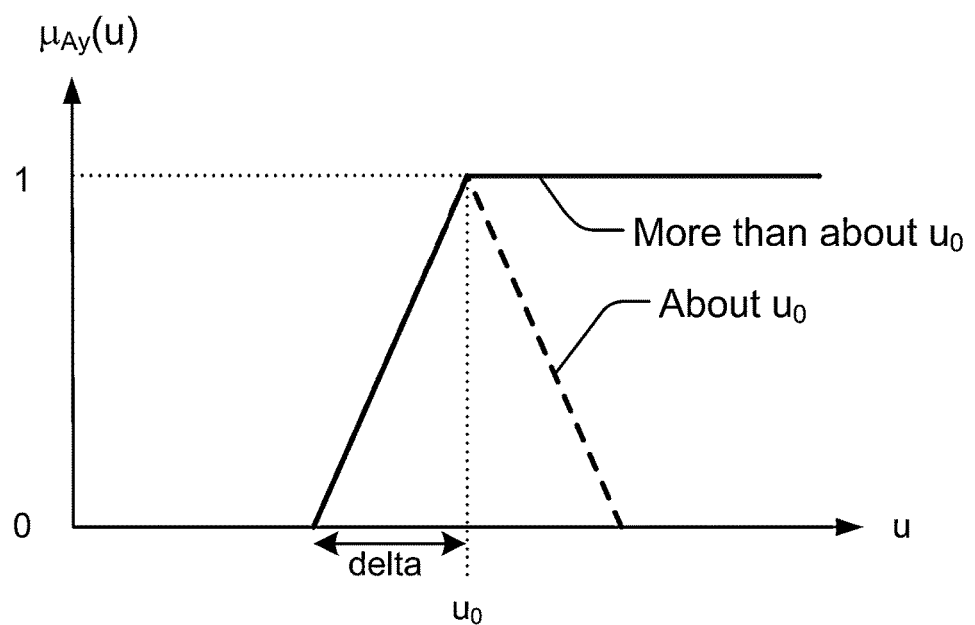
FIG. 18(a) depicts the determination of a membership function, in one embodiment.
Figure 18B:
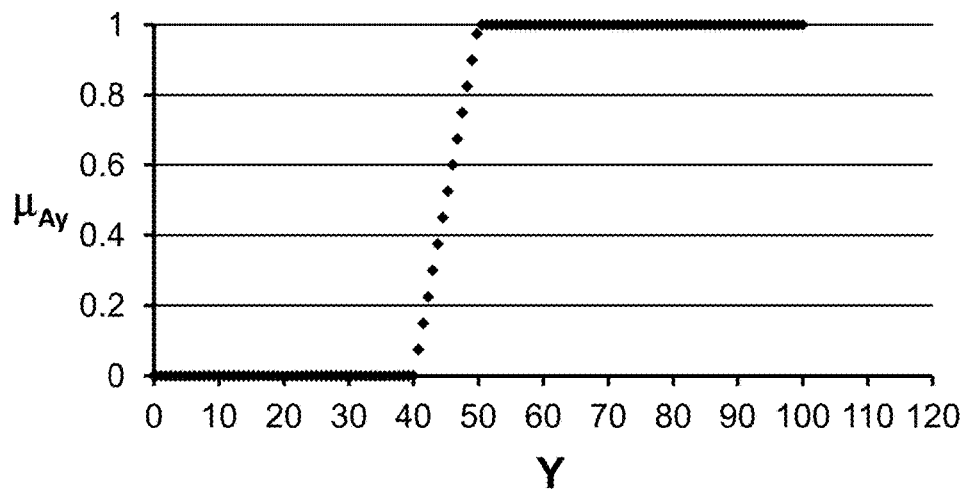
FIG. 18(b) depicts a membership function, in one embodiment.
Figure 18C:
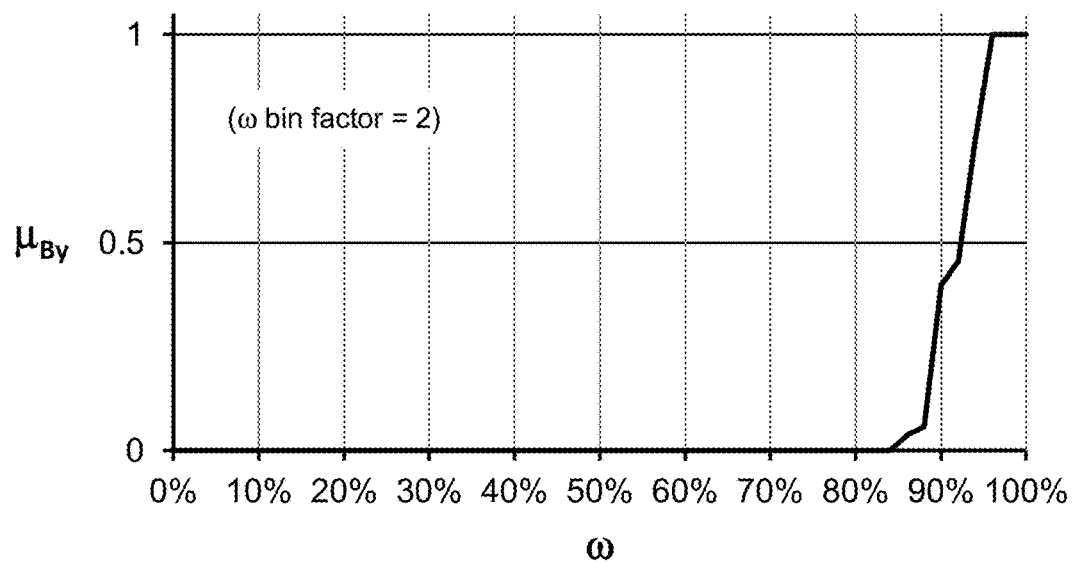
FIG. 18(c) depicts a restriction on probability measure, in one embodiment.

In one embodiment, the answer is in a Z-valuation Y, $A_y$, $B_y$) form, where Y is again the number of people showing up for an outdoor swimming pool event, and $A_y$ is more than about 50. In one embodiment, $\mu_{A_y}$ is determined from $q_8$, e.g., by using the model database and fuzzy logic rules for modifiers within the context and domain of Y, for example, as depicted in FIG. 18(a). In one embodiment, $\mu_{A_y}$ is determined to be a step-up membership function with a ramp from 40 to 50 (delta=10), as depicted from FIG. 18(b). Similar to above, $B_y$ is determined, as for example depicted in FIG. 18(c). Then, in one embodiment, the answer becomes: Almost certainly, the number of people showing up for an outdoor swimming pool event, is more than about 50. Or the odds of the number of people showing up for an outdoor swimming pool event, being more than about 50 is more than about 95%.

q9: What are the Odds that More than about 65 People Show Up?

Figure 19A:
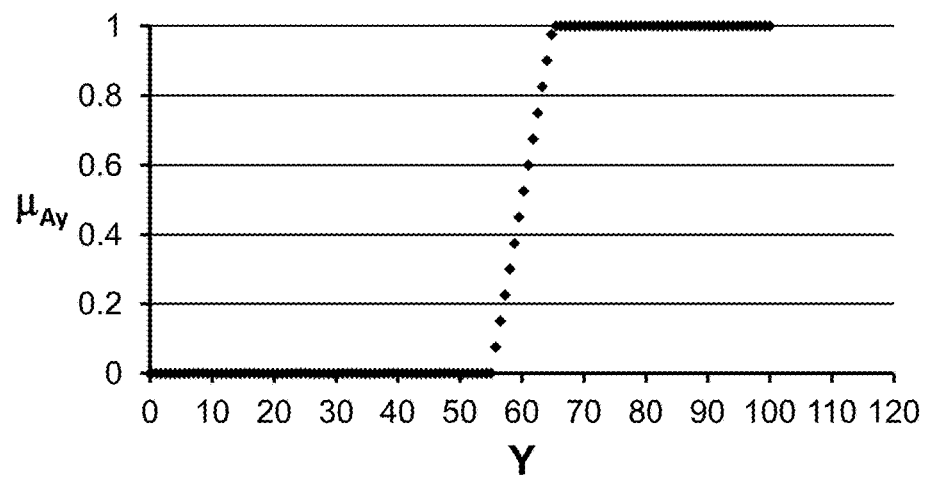
FIG. 19(a) depicts a membership function, in one embodiment.
Figure 19B:
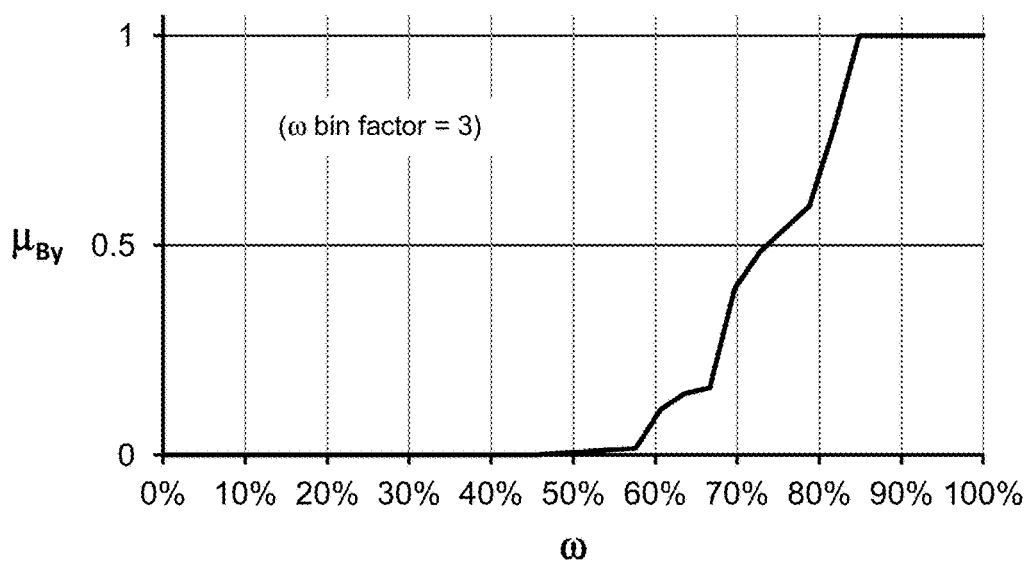
FIG. 19(b) depicts a restriction on probability measure, in one embodiment.

In one embodiment, similarly to above, $\mu_{A_y}$ is determined to be a step up membership function with a ramp from 55 to 65, as depicted in FIG. 19(a). Similarly, $B_y$ is determined, as for example depicted in FIG. 19(b). Then, in one embodiment, the answer becomes: Usually, the number of people showing up for an outdoor swimming pool event, is more than about 65. Or the odds of the number of people showing up for an outdoor swimming pool event, being more than about 65 is more than about 85%.

q10: What are the Odds that about 30 People Show Up?

Figure 20A:
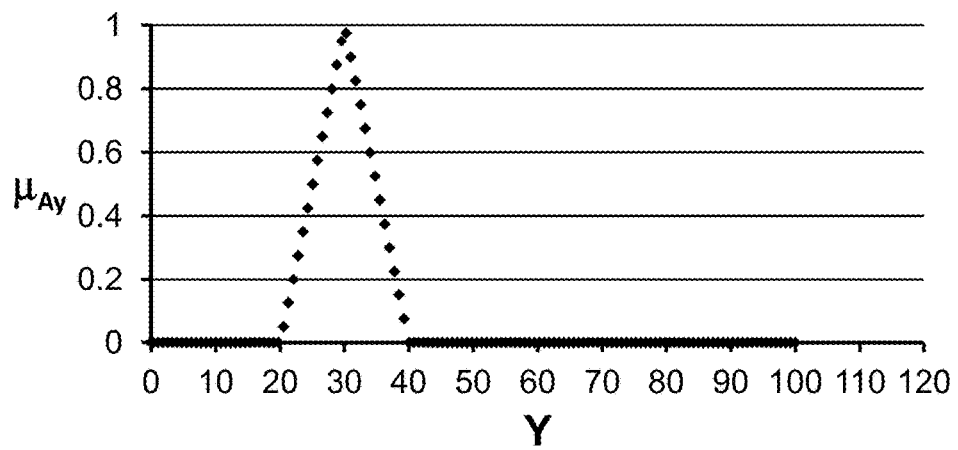
FIG. 20(a) depicts a membership function, in one embodiment.
Figure 20B:
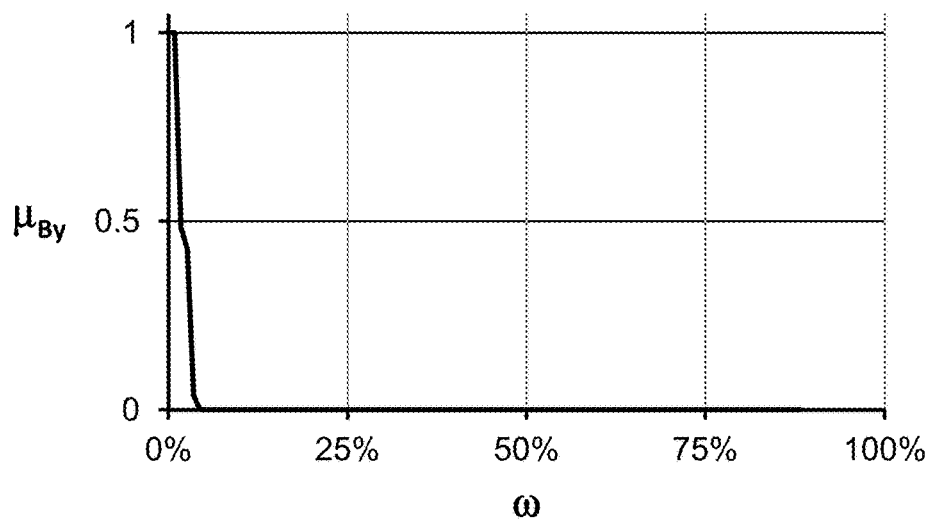
FIG. 20(b) depicts a restriction on probability measure, in one embodiment.

In one embodiment, similarly to above, $\mu_{A_y}$ is determined to be a triangular membership function with a base from ramp from 20 to 40, as depicted in FIG. 20(a). Similarly, $B_y$ is determined, as for example depicted in FIG. 20(b). Then, in one embodiment, the answer becomes: The number of people showing up for an outdoor swimming pool event, is almost never about 30.

Confidence Approach on Membership Function

As mentioned earlier, in the Z-valuation (X, A, B), a restriction on X (e.g., assuming X is a random variable), in one embodiment, is imposed via a restriction on its probability distribution $p_X$, to the degree that the probability measure of A, defined as $$p = \int_R \mu_A(u) p_X(u) du,$$

satisfies the restriction that (Prob(X is A) is B). In such a case, $p_X$ is the underlying (hidden) probability density of X. In one embodiment, this approach takes a view that such Z-valuation is based on an objective evaluation against the probability distribution $p_X$. In the following, we consider the view that B does not necessarily impose a restriction on $p_X$, but on A itself. For example, B can be viewed as the confidence level on the speaker of the proposition. For example, while there may be absolutely no confidence on the propositions generated out of a random fortune teller machine, some of the propositions themselves may in fact be true or highly probable. In such a case, the confidence level imposed on the propositions have more to do with confidence in the source of the propositions rather than restriction on the probability distributions related to the random variables associated with the content of the propositions. In another example, take the proposition "Fred's height is medium height, but I am not too sure (because I don't recall too well)." In one embodiment, we take such proposition (as a matter of degree) to allow Fred's height to be medium-high or medium low. In essence, the restriction from B, in this approach, is imposed not necessarily on $p_X$, but on imprecision of A itself. In one embodiment, this approach provides a method to deal with seemingly conflicting propositions, for example by discounting the confidence levels on such propositions (or, for example, on the speakers of those propositions), as opposed to imposing conflicting restrictions on $p_X$.

Figure 21A:
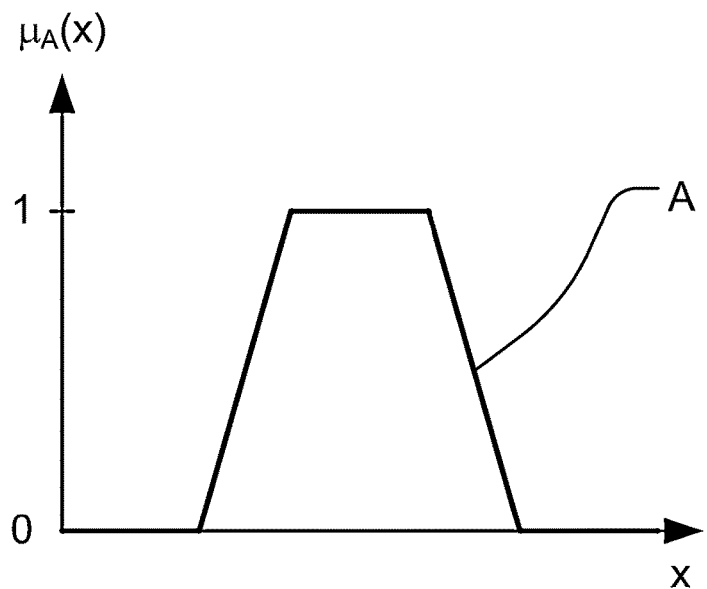
FIGS. 21(a)-(b) depict a membership function and a fuzzy map, in one embodiment.
Figure 21B:
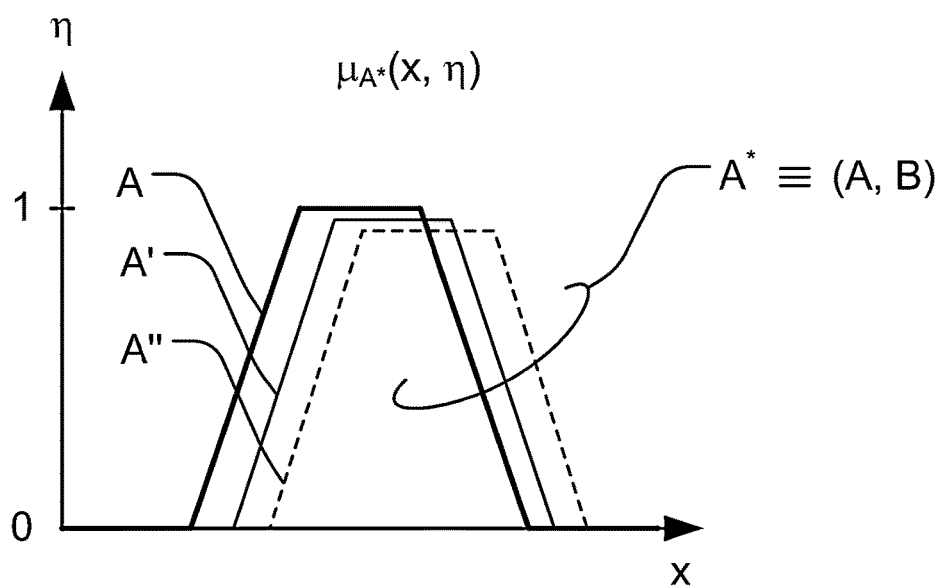

As shown in FIG. 21(a), (X is A) is graphically depicted by possibility distribution $\mu_A(x)$. (A, B) in this context allows for possibilities of other membership functions, such as A' or A", as depicted in FIG. 21(b), to various degrees, depending on the confidence level imposed by B. The fuzzy set of such membership functions are denoted as A*. In another words, whereas in (X is A) the membership degree of x is denoted by $\mu_A(x)$, in (A, B), the value of membership function of x is not a singleton, but a fuzzy value itself. The possibility of such membership value is denoted by $\mu_{A*}(x, \eta)$. This would indicate the possibility degree that the value of membership function of x be η. In this approach, a single crisp trace indicating membership function of X in FIG. 21(a) turns into a two dimensional fuzzy map in FIG. 21(b), where a point in (x, η) plane is associated with a membership function $\mu_{A*}(x,\eta)$. An example of such map can be visualized in one embodiment, as color (or grayscale graduation) mapping in which high possibility (for membership values) areas (e.g., a pixel or range in (x,η) plane), are associated with (for example) darker color, and low possibility (for membership values) areas are associated with (for example) lighter color. In one extreme where there is no imprecision associated with the proposition (X is A), such map results in a crisp trace, as for example shown in FIG. 21(a).

Figure 22A:
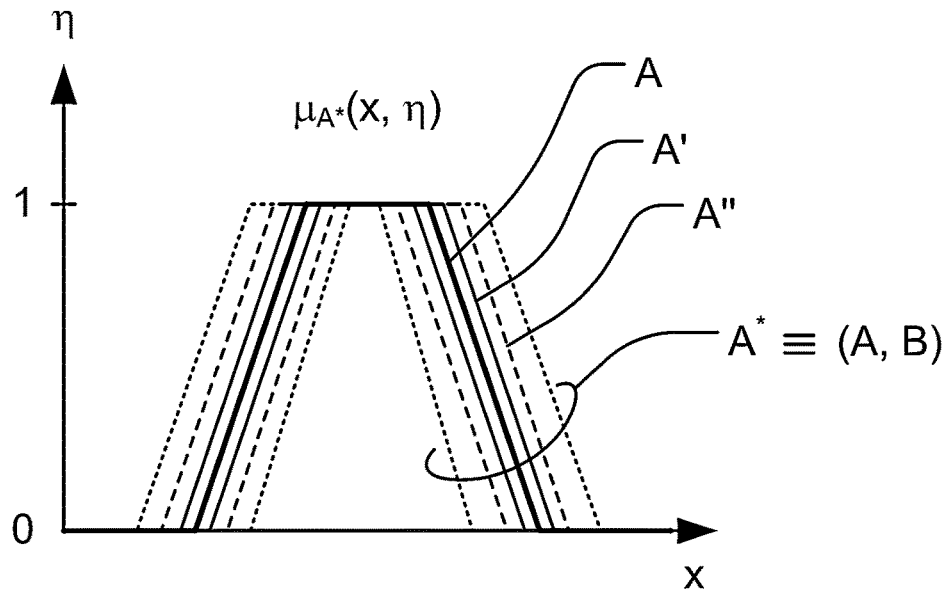
FIGS. 22(a)-(b) depict various types of fuzzy map, in one embodiment.
Figure 22B:
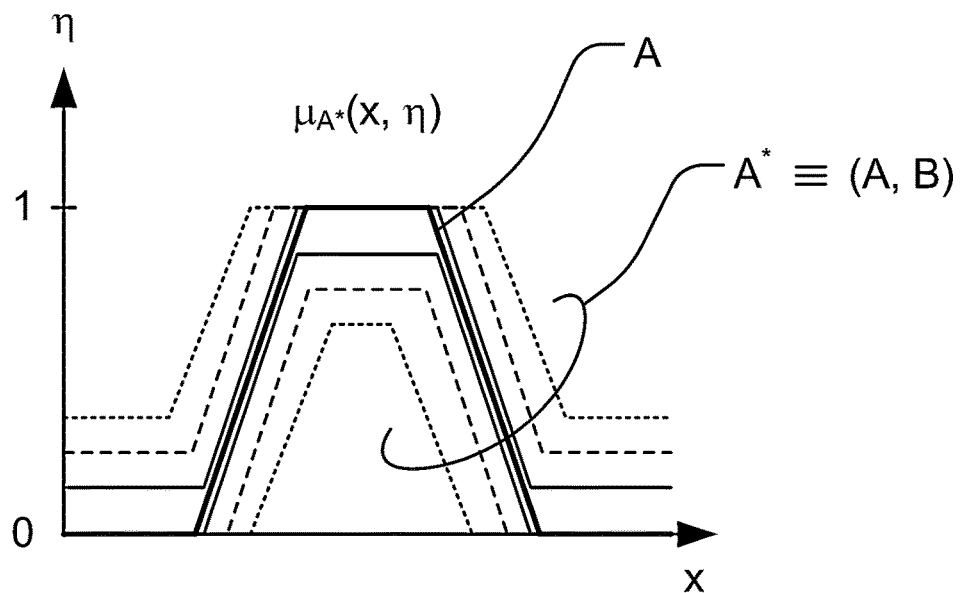

In one embodiment, as depicted for example in FIG. 22(a), the effect of B in (A, B) is to fuzzy the shape of membership function of X in A, primarily by making the sides of the membership function fuzzy (for example, compared to flat high/low portions). For example, such fuzziness is primarily performed laterally in (x,η) plane. In one embodiment, as for example depicted in FIG. 22(b), (A, B) is presented with a fuzzy map primarily carried out vertically in (x,η) plane. In one embodiment, the map may contain bands of similar color(s) (or grayscale) indicating regions having similar possibility of membership functions of x.

In one embodiment, the possibility map of membership function of x associated with A* may be determined by superimposing all possible membership functions of x with their corresponding membership degree (or test score) in A* on (x, η) plane, for example, by taking the supreme test score (or membership degree in A*) of such potential membership functions for each point in (x, η) plane.

Figure 23:
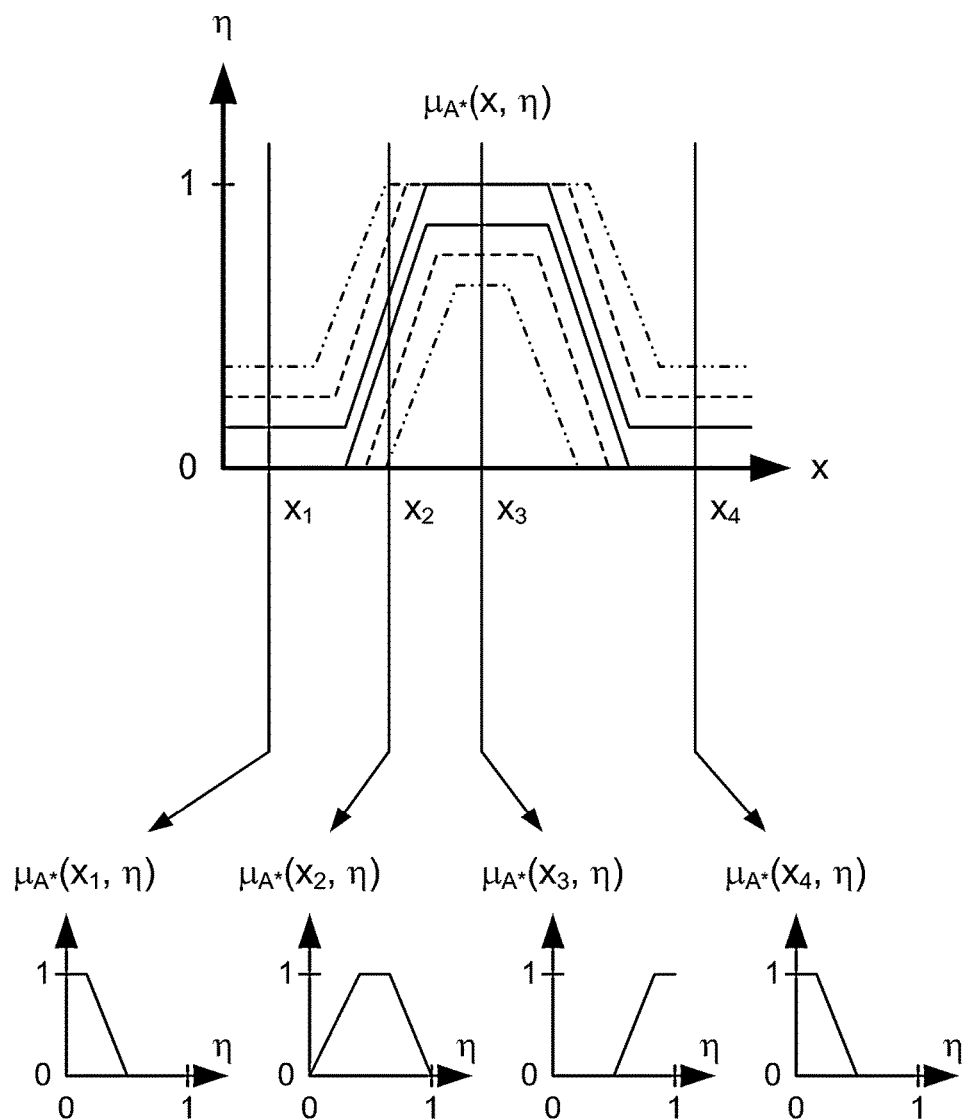
FIG. 23 depicts various cross sections of a fuzzy map, in one embodiment.

As depicted in FIG. 23, the cross sections of the fuzzy map in (x, η) plane, for example, at various X values $X_1$, $X_2$, $X_3$, and $X_4$, show a membership function for η for each cross section. In general, the shape of membership function of η for each X value, depends on X and B (affecting the degree of fuzziness and imprecision), i.e., the membership function of η for a given X (e.g., $X_0$) takes the value of $\mu_A*(X_0, \eta)$.

Figure 24:
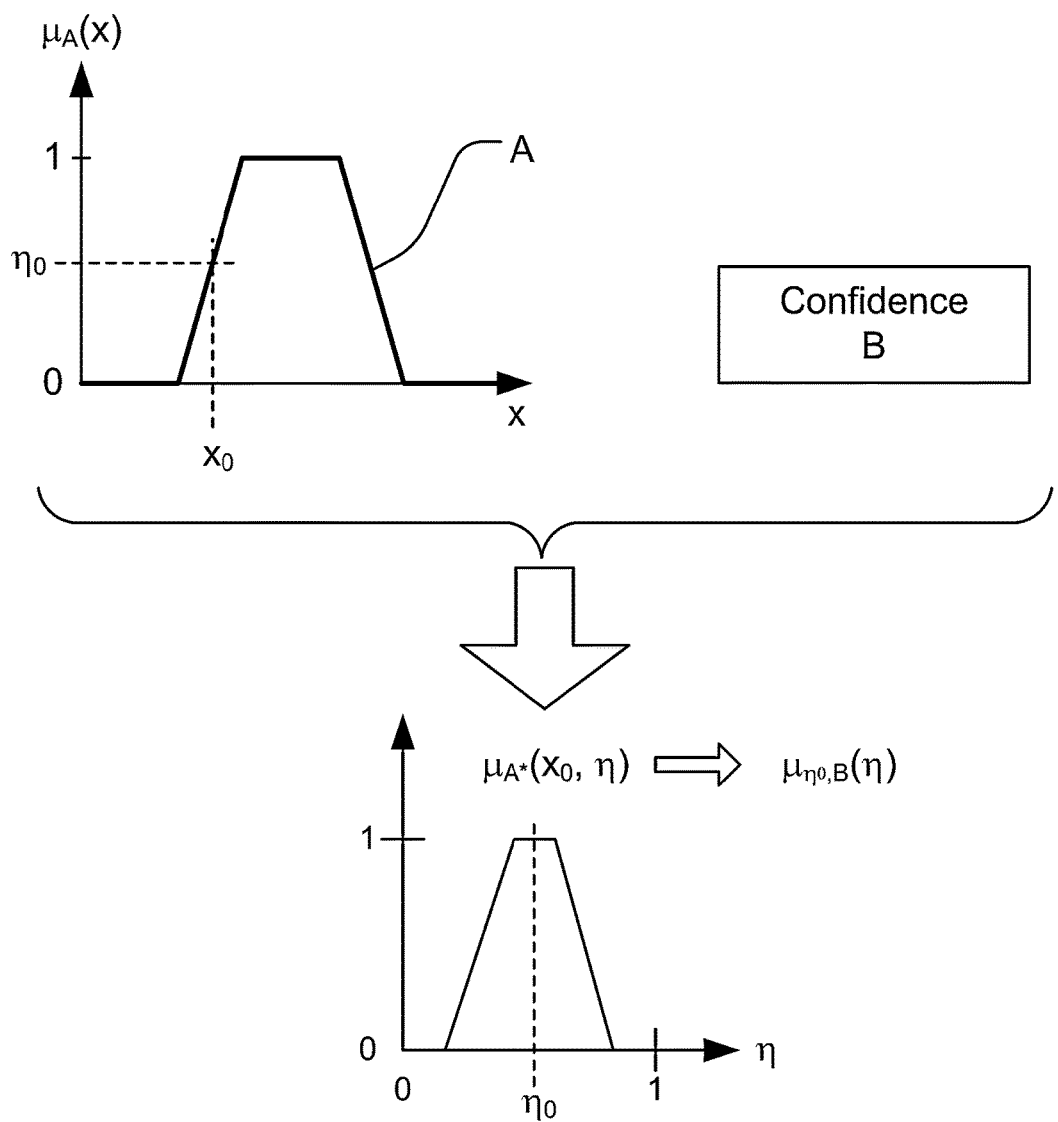
FIG. 24 depicts an application of uncertainty to a membership function, in one embodiment.

In one embodiment, as for example depicted in FIG. 24, the membership function of η, $\mu_{A*}(X_0, \eta)$, for X value of $X_0$, revolves around $\eta_0$, which is the value of membership function of X in A at $X_0$ (i.e., $\eta_0 = \mu_A(X_0)$). In one embodiment, the shape of $\mu_{A*}(X_0, \eta)$ depends on B and $X_0$. In one embodiment, the shape of $\mu_{A*}(X_0, \eta)$ depends on B and $\eta_0$. In such an embodiment, for two values of X, e.g., $X_1$ and $X_4$ (for example, as depicted in FIG. 23), where $\mu_A(X)$ is the same for both values, $\mu_{A*}(X_1, \eta)$ and $\mu_{A*}(X_2, \eta)$ also have the same shape. In such an embodiment, $\mu_{A*}(X_0, \eta)$ may be expressed as $\mu_{\eta 0, B}(\eta)$, indicating its dependence on B and $\eta_0$.

Figure 25:
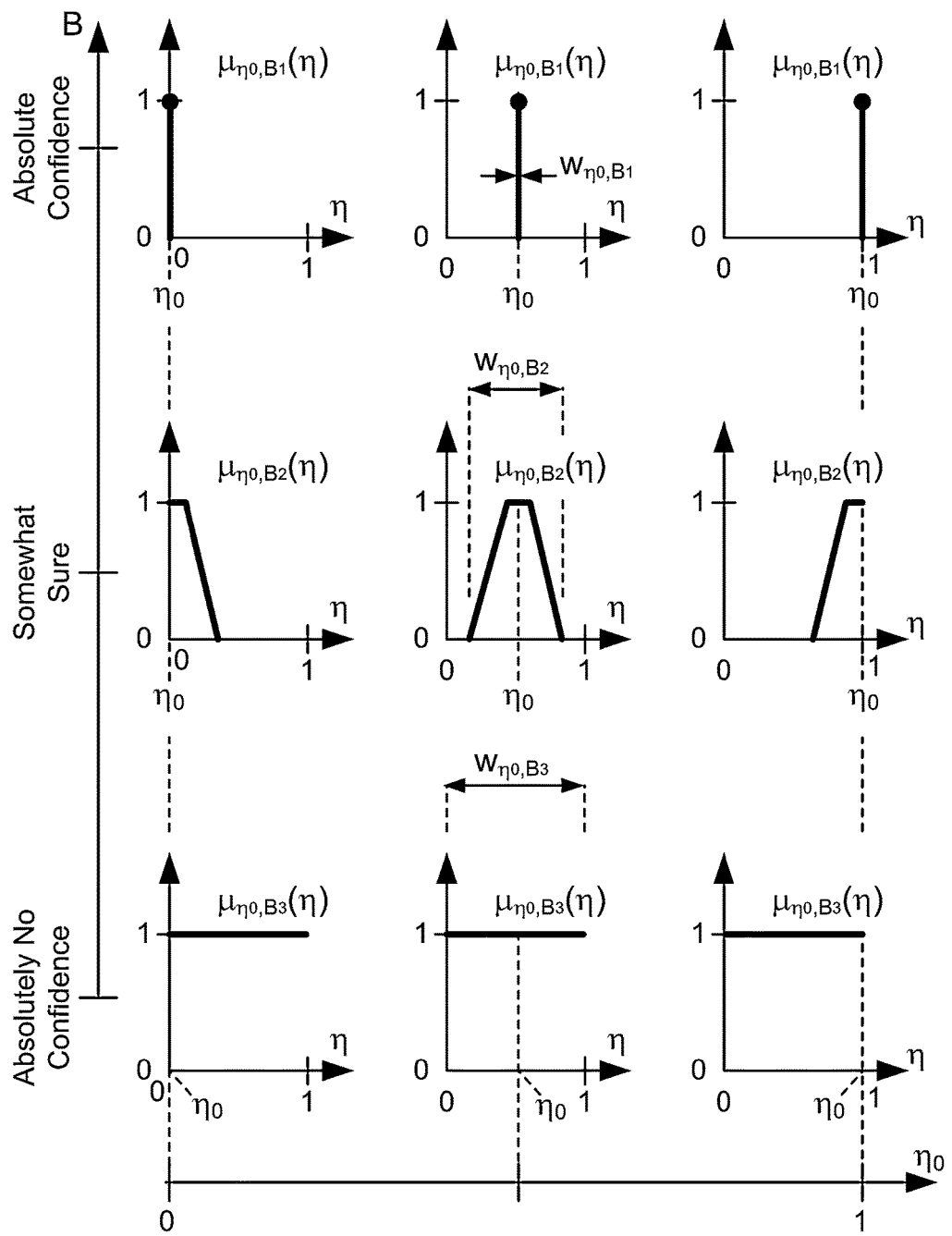
FIG. 25 depicts various cross sections of a fuzzy map at various levels of uncertainty, in one embodiment.

In one embodiment, as depicted for example in FIG. 25, $\mu_{\eta 0, B}(\eta)$ is depicted for various B's and $\eta_0$. For example, at high confidence levels (e.g., Absolute Confidence, $B_1$), the membership function of η, $\mu_{\eta 0, B}(\eta)$, is narrow ($W_{\eta 0, B1}$) precise function with membership value of 1 at $\eta_0$. In such a case, $\mu_A*(X, \eta)$ would resemble the crisp trace of $\mu_A(X)$ (as depicted in FIG. 21(a)). At a medium confidence level (e.g., "Somewhat Sure", $B_2$), $\mu_{\eta 0, B}(\eta)$ is a membership function of η revolving around $\eta_0$. In one embodiment, the imprecision measure of $\mu_{\eta 0, B}(\eta)$, (e.g., $W_{\eta 0, B2}$), is increased by reduction in level of confidence B. For example, when B represent very little or no confidence at all (e.g., "Absolutely No Confidence", $B_3$), there is no confidence on the membership function of X (e.g., at $X_0$), and such membership function value η, may take any value (from 0 to 1), yielding flat profile for $\mu_{\eta 0, B}(\eta)$. In one embodiment, this flat profile has value of 1. In one embodiment, this flat profile is independent of $\eta_0$. In one embodiment, reduction in confidence level in B, works to increase the imprecision measure of $\mu_{\eta 0, B}(\eta)$, (e.g., $W_{\eta 0, B3}$), to encompass whole range of η. In such a case, the color (or grayscale) map $\mu_{A*}(X, \eta)$ would become a block of all (or mostly) black areas, indicating that any membership value is possible for a given values of X. Then in such an embodiment, "X is A, with absolutely no confidence" will put no restriction on X.

Figure 26A:
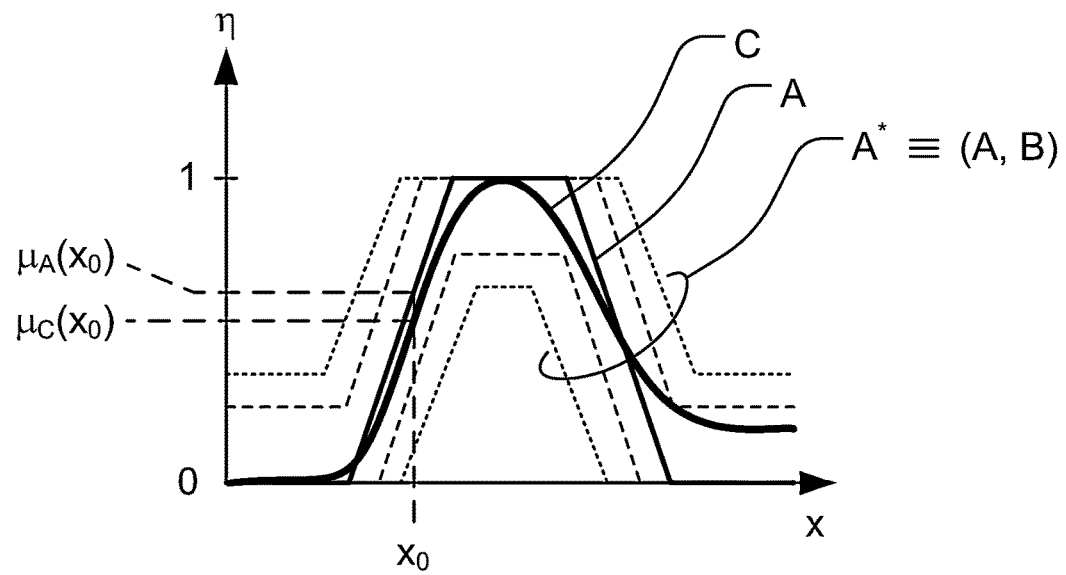
FIG. 26(a) depicts coverage of fuzzy map and a membership function, in one embodiment.
Figure 26B:
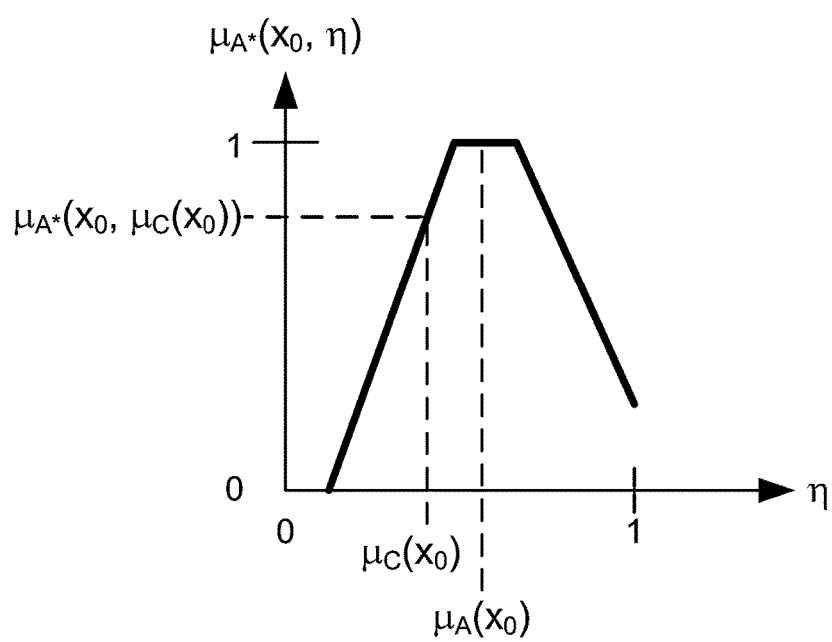
FIG. 26(b) depicts coverage of fuzzy map and a membership function at a cross section of fuzzy map, in one embodiment.

In one embodiment, as depicted in FIG. 26(a), "X is C" is evaluated against (A, B). Membership function of X in C is depicted as thick line (denoted as $\mu_C(X)$). In one embodiment, the degree in which C is consistent with (or satisfies restriction due) A* is determined by coverage of $\mu_{A*}(X, \eta)$ mapping on C. As an example, at $X=X_0$, the membership function of X in C has the value of $\mu_C(X_0)$. As depicted in FIG. 26(b), the possibility of such value in $\mu_{A*}(X, \eta)$ map is evaluated as $\mu_{A*}(X_0, \mu_C(X_0))$. In one embodiment, this is the degree in which C satisfies or is consistent with A* at $X_0$.

In one embodiment, as depicted in FIG. 26(b), $\mu_{A*}(X_0, \mu_C(X_0))$ is determined by determining the membership function of η for a given X (i.e., $X_0$). In one embodiment, the membership function of η, i.e., $\mu_{A*}(X_0, \eta)$, is determined based on $\mu_A(X_0)$ and B (as for example shown in FIGS. 24 and 25).

In one embodiment, the consistency of "X is C" against (A, B) is evaluated based on the degree in which C satisfies or is consistent with A* at various values of X. In one embodiment, the lowest value of such degree is taken as the degree in which C satisfies (A, B):

$\mu_{A*}(C) = \min_{\text{Over all } x \text{ in } R}(\mu_{A*}(x, \mu_C(x)))$

In one embodiment, with $\mu_{A*}(X_0, \eta)$ expressed as $\mu_{\eta 0, B}(\eta)$, where $\eta_0$ is $\mu_A(X_0)$, $\mu_{A*}(C) = \min_{\text{Over all } x \text{ in } R}(\mu_{\mu_A(x), B}(\mu_C(x)))$ In one embodiment, the consistency of "X is C" against (A, B) is evaluated based on the degree in which C overall satisfies or is consistent with A* by taking an average or a weighted average of the consistency of C with A* over all X:

$$\mu_A*(C) = \frac{1}{N} \int_{\text{Over all } x \text{ in } R} \mu_{A*}(x, \mu_C(x)) \cdot W(x) \cdot dx$$

where N is a normalization factor and W(x) is a weight factor. In one embodiment, W(x) is one for all X. In one embodiment, W(x) is a function of $\mu_A(X)$. In one embodiment, W(x) is high for low or high membership values of $\mu_A(X)$, and it is low for intermediate values of $\mu_A(X)$. The normalization factor is then:

$$N = \int_{\text{Over all } x \text{ in } R} W(x) \cdot dx$$

The above relationships may be expressed in sigma form instead of integral if X is a discrete type variable.

Figure 27:
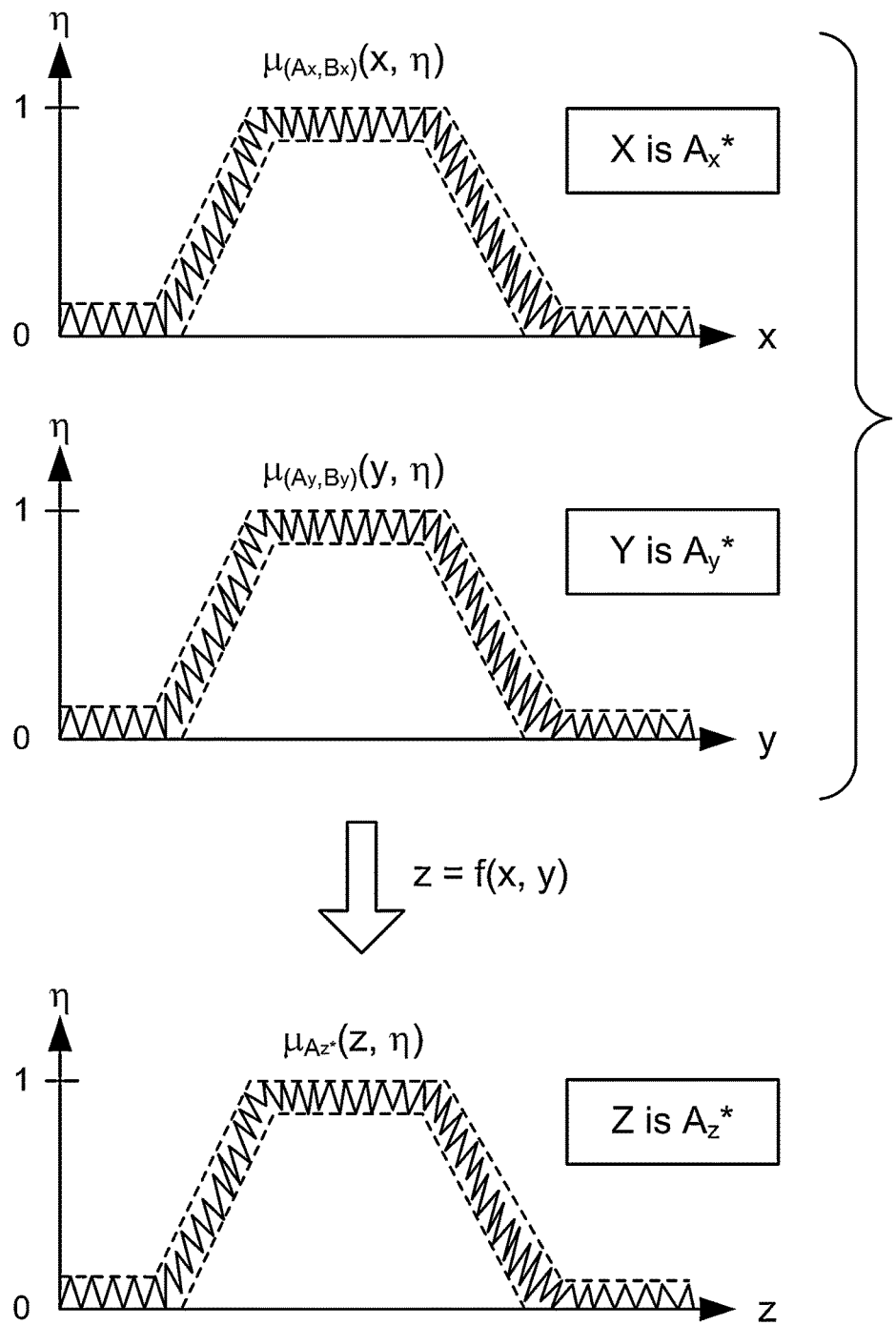
FIGS. 27 and 28(a) depict application of extension principle to fuzzy maps in functional dependence, in one embodiment.
Figure 28A:
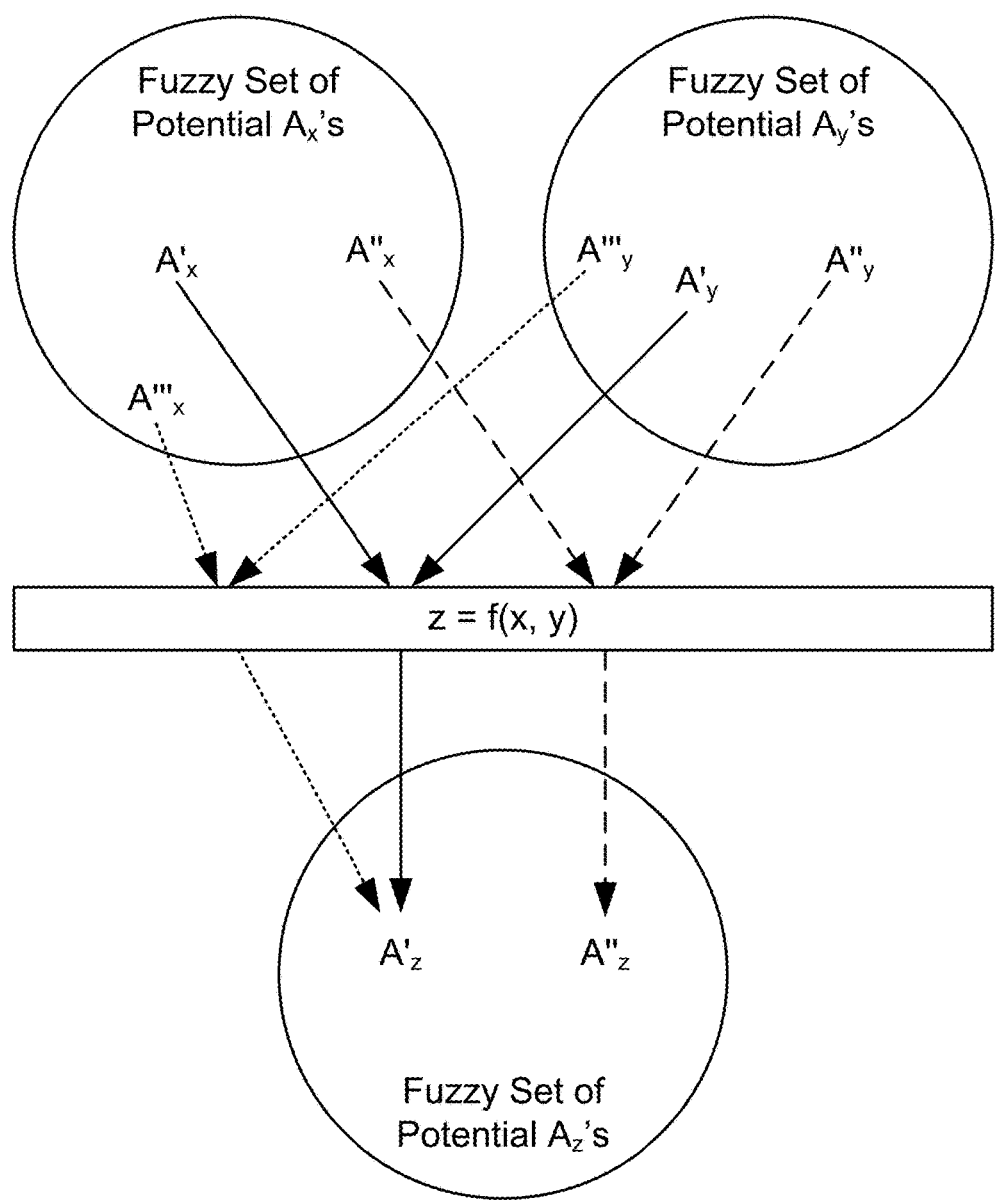

In one embodiment, as depicted in FIG. 27, two or more propositions are given, such as $(A_x, B_x)$ and $(A_y, B_y)$. A shorthand presentation of those propositions would be "X is $A_x$*" and "Y is $A_y$*", respectively. Given, a functional relation, such as $Z=f(X, Y)$, in one embodiment, a fuzzy membership function for Z is determined, as depicted for example in FIG. 27. In one embodiment, as depicted in FIG. 28(a), fuzzy set $A_x$* has one or more possible membership functions in X, e.g., $A'_x$, $A''_x$, and $A'''_x$, and fuzzy set $A_y*$ has one or more possible membership functions in Y, e.g., $A'_y$, $A''_y$, and $A'''_y$. In general, applying the functional relationship $f(X,Y)$, a possible membership function in Z may be obtained for each pair of membership functions in X and Y (e.g., $A''_x$ and $A''_y$). In one embodiment, the test score associated with the resulting membership function in Z (e.g., $A''_z$) is associated with the scores or membership values of $A''_x$ and $A''_y$ in $A_x*$ and $A_y*$, respectively:

$$ts(A_Z'') = \mu_{A_X*}(A_X'') \wedge \mu_{A_Y*}(A_Y'')$$

In one embodiment, multiple pairs of membership functions in X and Y may map to the same membership function in Z. For example as depicted in FIG. 28(a), ($A'_x$ and $A'_y$) and ($A'''_x$ and $A'''_y$) map to $A'_z$. In such an embodiment, the test score may be determined by:

$$ts(A_Z') = \sup_{\forall A_X', A_Y'} \mu_{A_X^*}(A_X') \bigwedge \mu_{A_Y^*}(A_Y')$$

subject to the possibility distribution of X and Y being $A'_x$ and $A'_y$, respectively, and $Z=f(X,Y)$, map to a possibility distribution of Z as $A'_z$.

Therefore, in an embodiment, possible membership functions of X and Y, belonging to fuzzy sets $A_x*$ and $A_y*$, are used to determine the corresponding membership functions of Z, with their degrees of membership in $A_z*$ determined via extension principle (from the degrees of membership of the possible membership functions of X and Y in fuzzy sets $A_x*$ and $A_y*$, respectively).

In one embodiment, the set of resulting membership functions of Z (e.g., $A'_z$) with their corresponding test score (e.g., $ts(A'_z)$) are used to setup a fuzzy map ($A_z*$) describing the membership function of Z:

$$\mu_{A_Z^*}(z, \eta) = \sup_{\forall A_Z'}\left(ts(A_Z')\right)$$

subject to $$\eta = \mu_{A_Z'}(z)$$

Figure 28B:
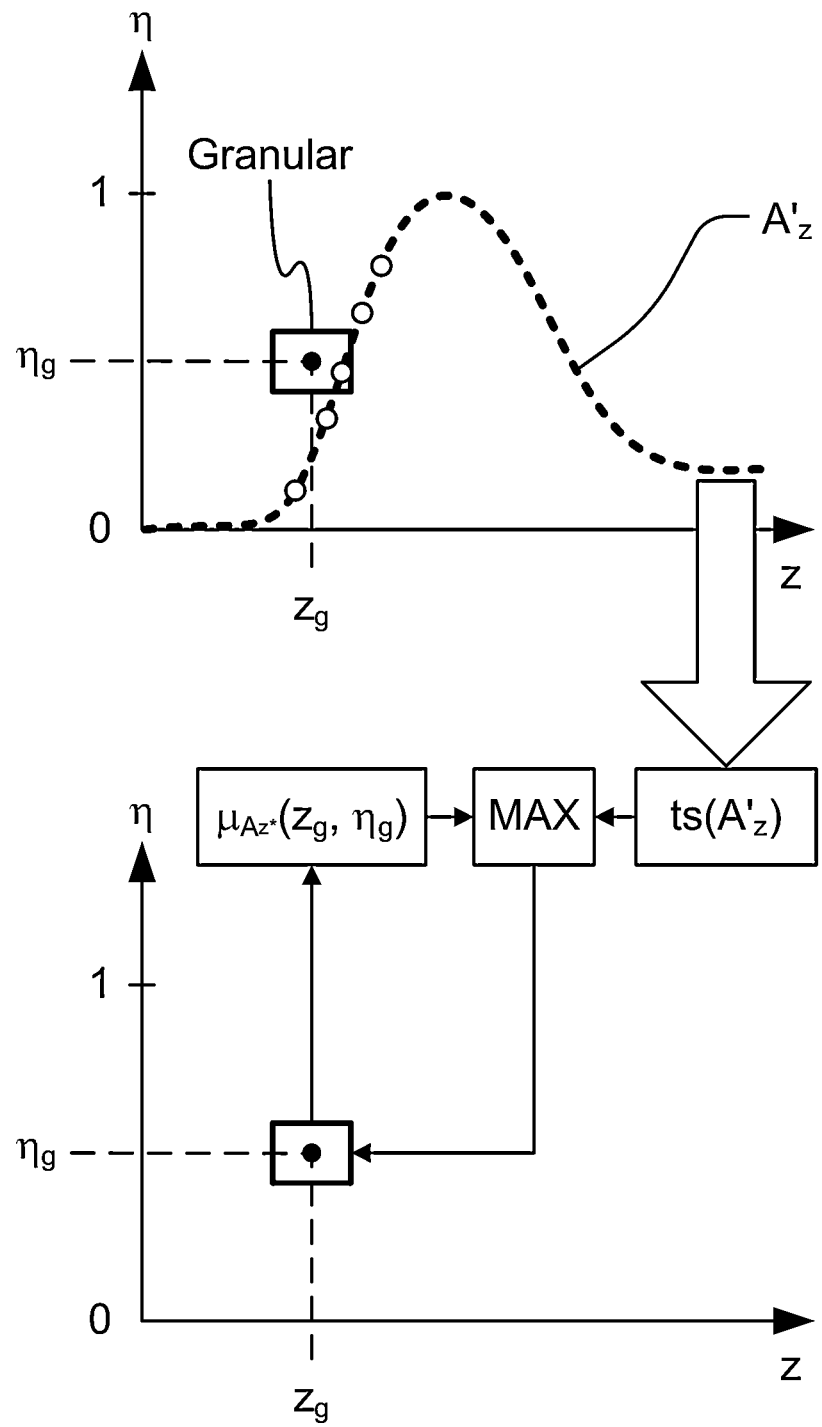
FIG. 28(b) depicts the determination of fuzzy map, in one embodiment.

In another words, in one embodiment, for all possible $A'_z$ passing through point (z, η), the maximum corresponding test score is used to assign the fuzzy membership value of $A_z*$ for that point. In one embodiment, $A'_x$ and $A'_y$ candidates are iteratively used to determine the corresponding $A'_z$. Then, a corresponding test score for $A'_z$ is determined based on membership values of $A'_x$ and $A'_y$ candidates in $A_x*$ and $A_y*$, respectively. To drive the mapping $A_z*$, in one embodiment, (z, η) plane is granulized into segments (e.g., pixels or granules). In one embodiment, as depicted in FIG. 28(b), each granularized segment of (z, η) plane is represented by a point ($z_g$, $\eta_g$), for example, a corner or a midpoint of the granularized segment. Then, $\mu_{A'_z}$ is evaluated at various granularized segments (e.g., by evaluating it at the representative point $z_g$, and determining $\eta_g$ as the granular containing $\mu_{A'_z}(z_g)$, and assigning $ts(A'_z)$ to $\mu_{A_z*}(z_g, \eta_g)$ if $ts(A'_z)$ larger than the current value of $\mu_{A_z*}(z_g, \eta_g)$. In one embodiment, at the conclusion of the iteration, $\mu_{A_z*}(z_g, \eta_g)$ estimates $\mu_{A_z*}(z, \eta)$. In one embodiment, $A'_z$ is presented by a discrete set of points or ranges in (z, η) (as for example depicted in FIG. 28(b) by circles on $A'_z$ trace) and for each point/ranges, the corresponding ($z_g$, $\eta_g$) granular is determined, and the test score contribution is imported, e.g., if larger than ($z_g$, $\eta_g$) granular's current test score. In one embodiment, various size pixel or granular (e.g., both big and fine pixels) are used to monitor and evaluate the limits on iterations through candidate $A'_z$. In one embodiment, test scores are used as color (gray) scale assignment to each pixel/granular overriding a lower assigned test score to the granular.

In one embodiment, instead of taking the approach from candidate membership functions from X and Y domain to arrive at resulting membership function at Z domain, candidates are taken from X and Y domain themselves to arrive at Z domain directly. Where the membership functions in X and Y are crisp (e.g., $A_x$ and $A_y$), the resulting membership function in Z has the following form:

$$\mu_{A_Z}(z) = \sup_{\forall x', y'} (\mu_{A_X}(x') \wedge \mu_{A_Y}(y'))$$

Subject to $z = f(x', y')$

When the membership functions in X and Y are themselves fuzzy (e.g., $A_x*$ and $A_y*$), the resulting map in Z domain, in one embodiment, is expressed as:

$$\mu_{A_Z^*}(z, \eta) = \sup_{\forall x', y'}\left(\sup_{\forall \eta', \eta''} \mu_{A_X^*}(x', \eta') \bigwedge \mu_{A_Y^*}(y', \eta'')\right)$$

Subject to $$\eta = \eta' \wedge \eta''$$

$$z = f(x', y')$$

Or alternatively expressed as:

$$\mu_{A_Z^*}(z, \eta) = \sup_{\forall \eta', \eta''}\left(\sup_{\forall x', y'} \mu_{A_X^*}(x', \eta') \bigwedge \mu_{A_Y^*}(y', \eta'')\right)$$

$$= \sup_{\forall x', y', \eta', \eta''} \mu_{A_X^*}(x', \eta') \bigwedge \mu_{A_Y^*}(y', \eta'')$$

Subject to $$\eta = \eta' \wedge \eta''$$

$$z = f(x', y')$$

Figure 28C:
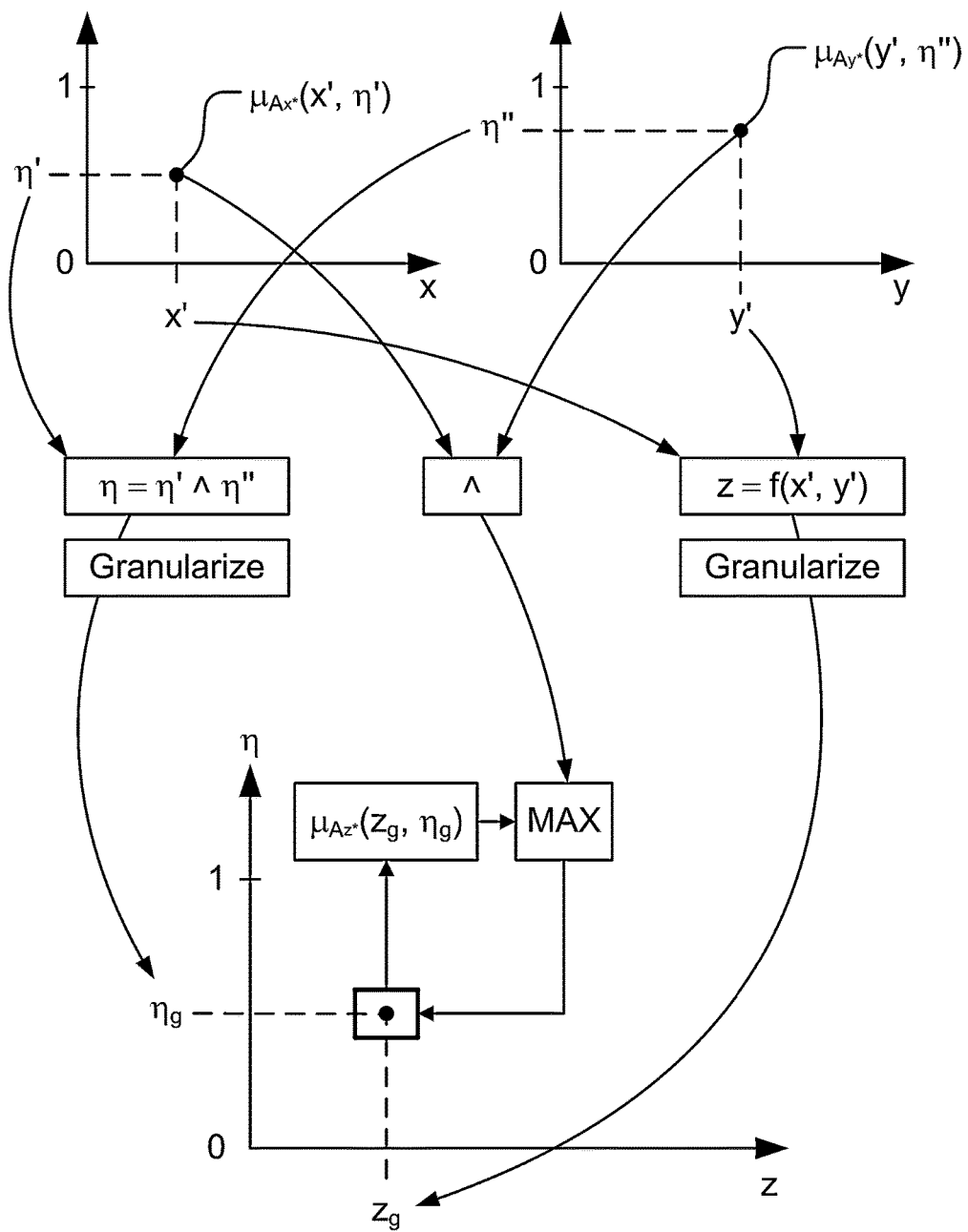
FIG. 28(c) depicts the determination of fuzzy map, in one embodiment.

In one embodiment, fuzzy maps in X and Y domains are scanned, and $\mu_{A_z*}(z, \eta)$ is determined by granularizing (z, η) to ($z_g$, $\eta_g$) as described above and illustrated in FIG. 28(c).

In one embodiment, the fuzzy map is derived based on candidate fuzzy sets in X and Y (each having same color/grayscale along its trace, e.g., based on color/grayscale contour of fuzzy maps $A_x*$ or $A_y*$) and/or using alpha-cut approach in membership functions of candidate fuzzy sets from $A_x*$ and/or $A_y*$ (e.g., explained in this disclosure) to derive candidate fuzzy sets and their associated color/grayscale representing $A_z*$ in Z.

Figure 29:
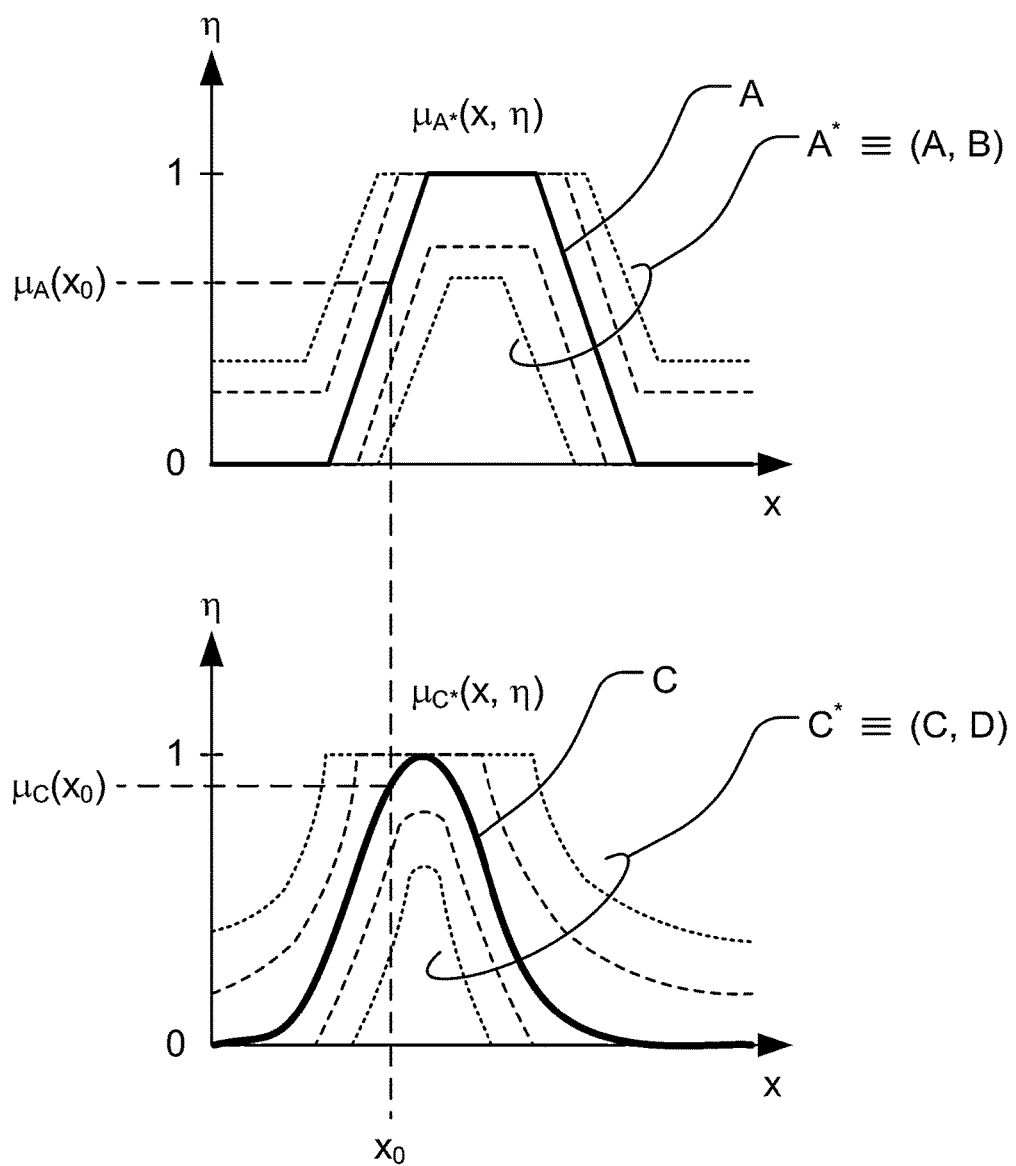
FIG. 29 depicts the determination parameters of fuzzy map, e.g., close fit and coverage, in one embodiment.

In one embodiment, a derived fuzzy map, such as $A_z*$ mentioned above, is used to test consistency against a candidate $A_z$. Above, a method to derive the test score for such consistency was provided. In one embodiment, a fuzzy map based on such a candidate $A_z$ is used to determine the consistency of a pair ($A_z$, $B_z$) against a derived map $A_z*$. In one embodiment, the confidence level $B_z$ is determined so that ($A_z$, $B_z$) is a representative approximation of derived map $A_z^*$. As depicted in FIG. 29 (which is using X instead of Z variable), in one embodiment, starting with a derived map $A_x^*$ (or calculated map from (A, B)), a candidate membership function of X in fuzzy set C is made fuzzy by D, to form another fuzzy map $C^*$. In one embodiment, the consistency of $C^*$ against $A^*$ is determined. In one embodiment, D or a restriction on D is determined to make $C^*$ consistent with $A^*$. In one embodiment, D or a restriction on D is determined to make $C^*$ consistent with or cover $A^*$, while maintaining higher level of confidence for D.

In one embodiment, the fuzzy maps are compared for consistency over (x and $\eta$), e.g., by comparing color/gray scale at corresponding points/granular. In one embodiment, weight is assigned to such comparison where the color/gray scale difference or the possibility of such membership value in each map is large. In one embodiment, the test score comparison between fuzzy maps is determined by point-wise coverage (e.g., with weight). In one embodiment, a threshold or a fuzzy rule is used to get point-wise coverage degree through summation or integration over map or portion of the map (e.g., where $A^*$ is above a threshold).

In one embodiment, as for example depicted in FIG. 29, a candidate fuzzy set C is used with a parametric certainty measure D (e.g., $D=D(\alpha)$). In one embodiment, a model of (C, D) is used with various values of $\alpha$ to test the coverage over (A, B). In one embodiment, an optimization is used to optimize or select among various (e.g., candidate) C's by minimizing uncertainty level/values with respect to $\alpha$. In one embodiment, coverage test score of $C^*$ over $A^*$ is treated as a constraint in an optimization engine, while coverage test score of $A^*$ over $C^*$ is used as an objective function.

Figure 30:
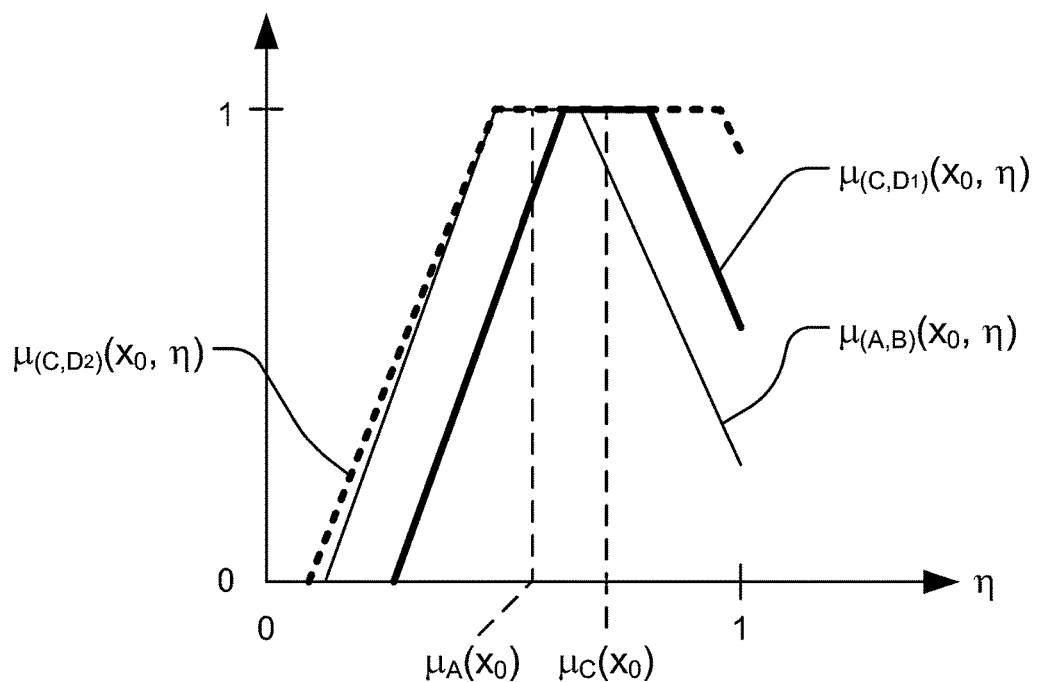
FIGS. 30 and 31 depict application of uncertainty variation to fuzzy maps and use of parametric uncertainty, in one embodiment.
Figure 31:
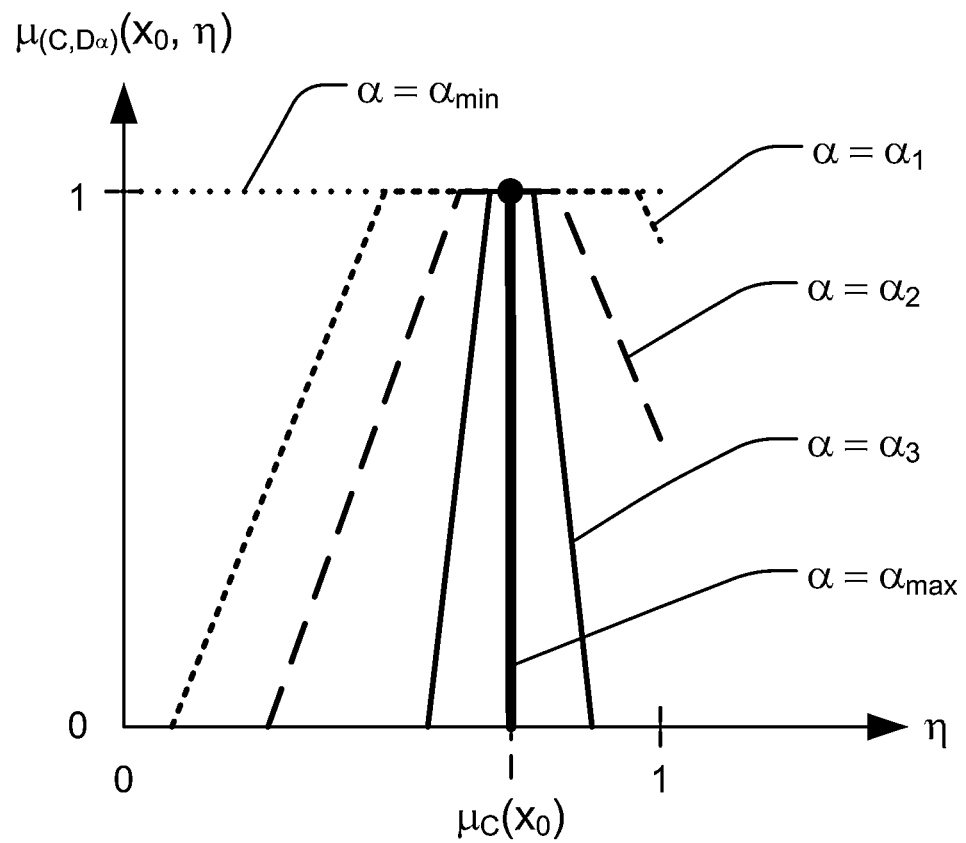
Figure 32:
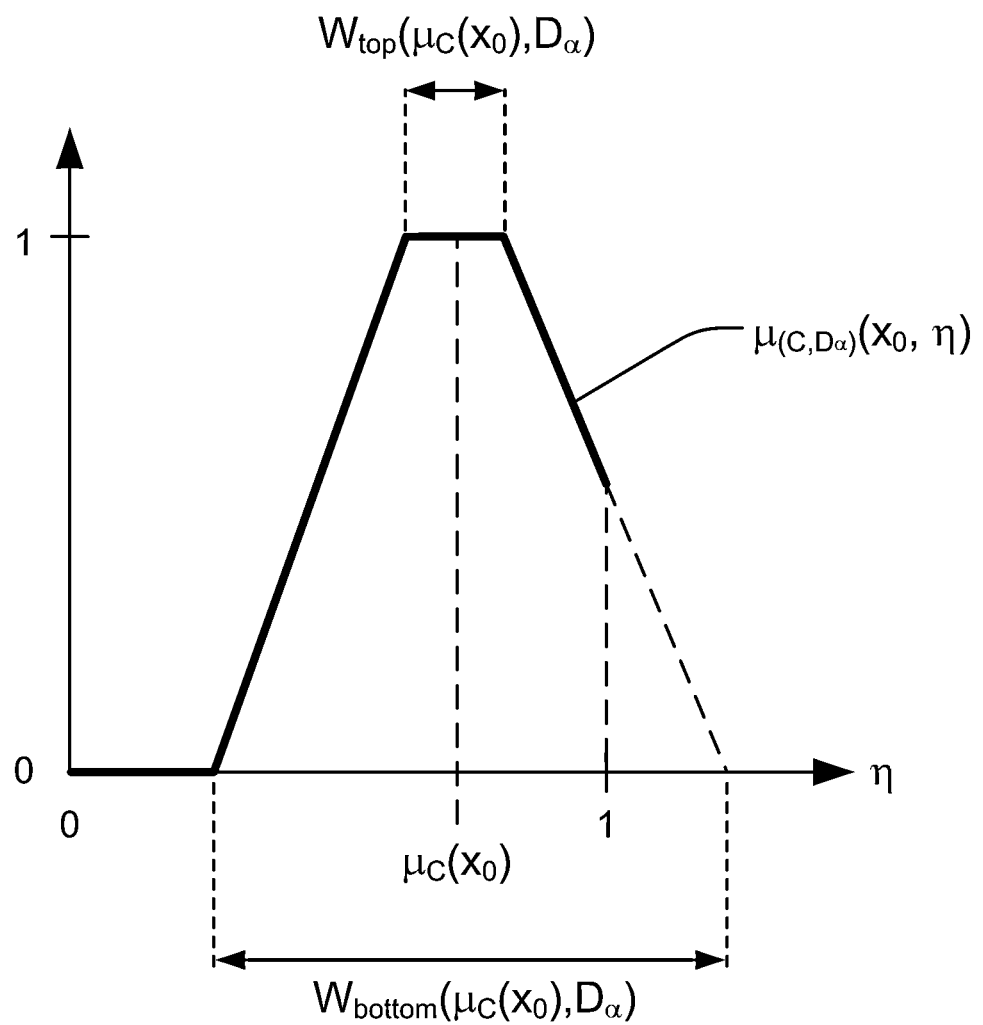
FIG. 32 depicts use of parametric uncertainty, in one embodiment.

In one embodiment, as depicted in FIG. 30, by varying D (e.g., by increasing uncertainty) from $D_1$ to $D_2$, the fuzzy map (at $x_0$ cross section) of $\mu_{(C, D2)}(x_0, \eta)$ (shown in dotted line) widens from $\mu_{(C, D1)}(x_0, \eta)$ (shown in solid thick line), to cover the fuzzy map of $\mu_{(A, B)}(x_0, \eta)$. In one embodiment, as shown in FIG. 30, when $\mu_C(x_0)$ does not coincide with $\mu_A(x_0)$, it would take larger degree of uncertainty (e.g., from $D_1$ to $D_2$) to cover the fuzzy map. In one embodiment, as for example depicted in FIG. 31, D is parameterized (e.g., by a indicating the level of certainty of D). The variation of the cross section of the fuzzy map $\mu_{(C, D\alpha)}(x_0, \eta)$, in one embodiment, is illustrated in FIG. 31, for various values of $\alpha$ (from $\alpha_{max}$ to $\alpha_{min}$). For example, in one embodiment, $\mu_{(C,D\alpha)}(x_0,\eta)$ reduces to $\mu_C(x_0)$ at $\alpha_{max}$ while it becomes flat 1 at $\alpha_{min}$ (implying any membership function is possible at $x_0$). For example, in one embodiment, the core and support of fuzzy map cross section $\mu_{(C,D\alpha)}(x_0,\eta)$ is determined based on parameter $\alpha$, using for example the model database and the context. For example, in one embodiment, as depicted in FIG. 32, the width of core and support of the fuzzy map cross section $\mu_{(C,D\alpha)}(x_0,\eta)$ and how they get clipped at limits of 0 and 1, are determined by $D_\alpha$ and $\mu_C(x_0)$. In such an embodiment, two values of x having the same $\mu_C(x)$ values will result in the same fuzzy map cross section as shown for example in FIG. 32.

Figure 33A:
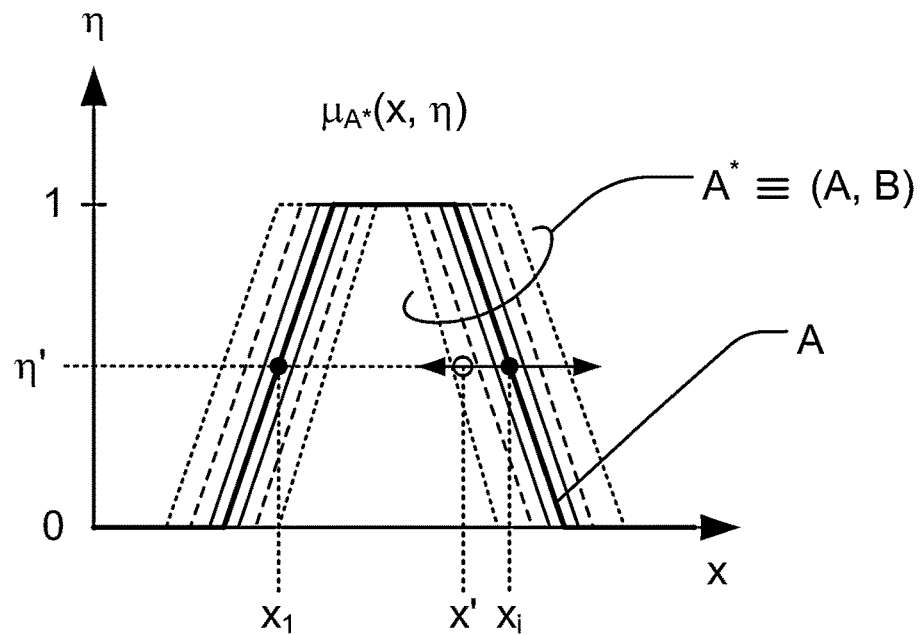
FIGS. 33(a)-(b) depict laterally/horizontally fuzzied map, in one embodiment.
Figure 33B:
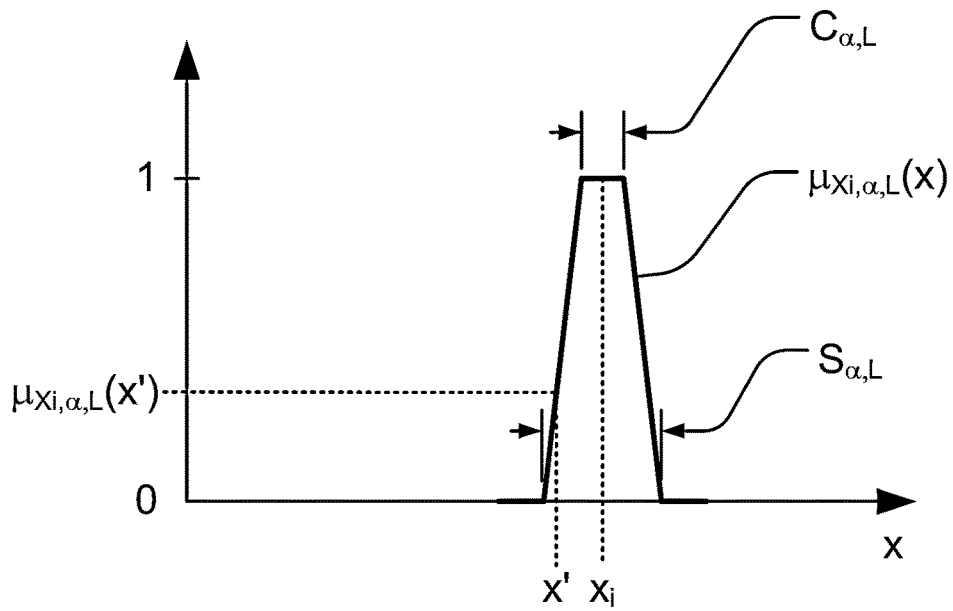

In one embodiment, as depicted in FIG. 22(a), a fuzzy map $A^*$ is constructed by lateral fuzziness of A by an amount determined by B. In one embodiment, as depicted in FIG. 33(a), the possibility of membership value at (x', $\eta$'), denoted by $\mu_{A^*}(x', \eta')$ is determined by the location of the set of x values denoted by $\{x_i\}$ where $\mu_A(x_i)$ is $\eta$'. For example, as depicted in FIG. 33(a), $x_1$ and $x_i$ belong to this set as they have the same membership function value (i.e., $\eta$') in A. In one embodiment, $\mu_{A^*}(x', \eta')$ is determined by the location of $\{x_i\}$ and B. In one embodiment, the characteristics of B is made parametric, e.g., $B=B(\alpha)$, where $\alpha$ (e.g., [0, 1]) represents the degree of sureness or certainty of B. In one embodiment, $\mu_{A^*}(x', \eta')$ is determined by the contributions from each x in $\{x_i\}$. In one embodiment, the contribution of possibility of membership value to $\mu_{A^*}(x', \eta')$ from $x_i$ is determined by a model (e.g., trapezoid or triangular) based on $x_i$ and B (or $\alpha$). In one embodiment, as depicted in FIG. 33(b), the contribution of $x_i$ is represented by a fuzzy set (denoted $\mu_{xi,\alpha,L}(x)$), where L is a characteristics obtained from or dependent on the context of X domain (or A). For example, as depicted in FIG. 33(b), the trapezoid model around $x_i$, has a core and support (denoted as $C_{\alpha,L}$ and $S_{\alpha,L}$, respectively) which are dependent on the characteristic length (in X domain) and severity of $\alpha$. Given $\alpha$ and $x_i$, $\mu_{xi,\alpha,L}(x)$ is constructed or determined and the contribution at x' is determined $\mu_{xi,\alpha,L}(x')$, as depicted in FIG. 33(b). Therefore, in one embodiment, the fuzzy map is determined as:

$$\mu_{A^*}(x', \eta') = \sup_{\forall x_i \in \{x_k | \eta' = \mu_A(x_k)\}} (\mu_{x_i,\alpha,L}(x'))$$

In one embodiment, $C_{\alpha,L}$ and $S_{\alpha,L}$ are further dependant on $x_i$ or $\mu_A(x_i)$.

Figure 34:
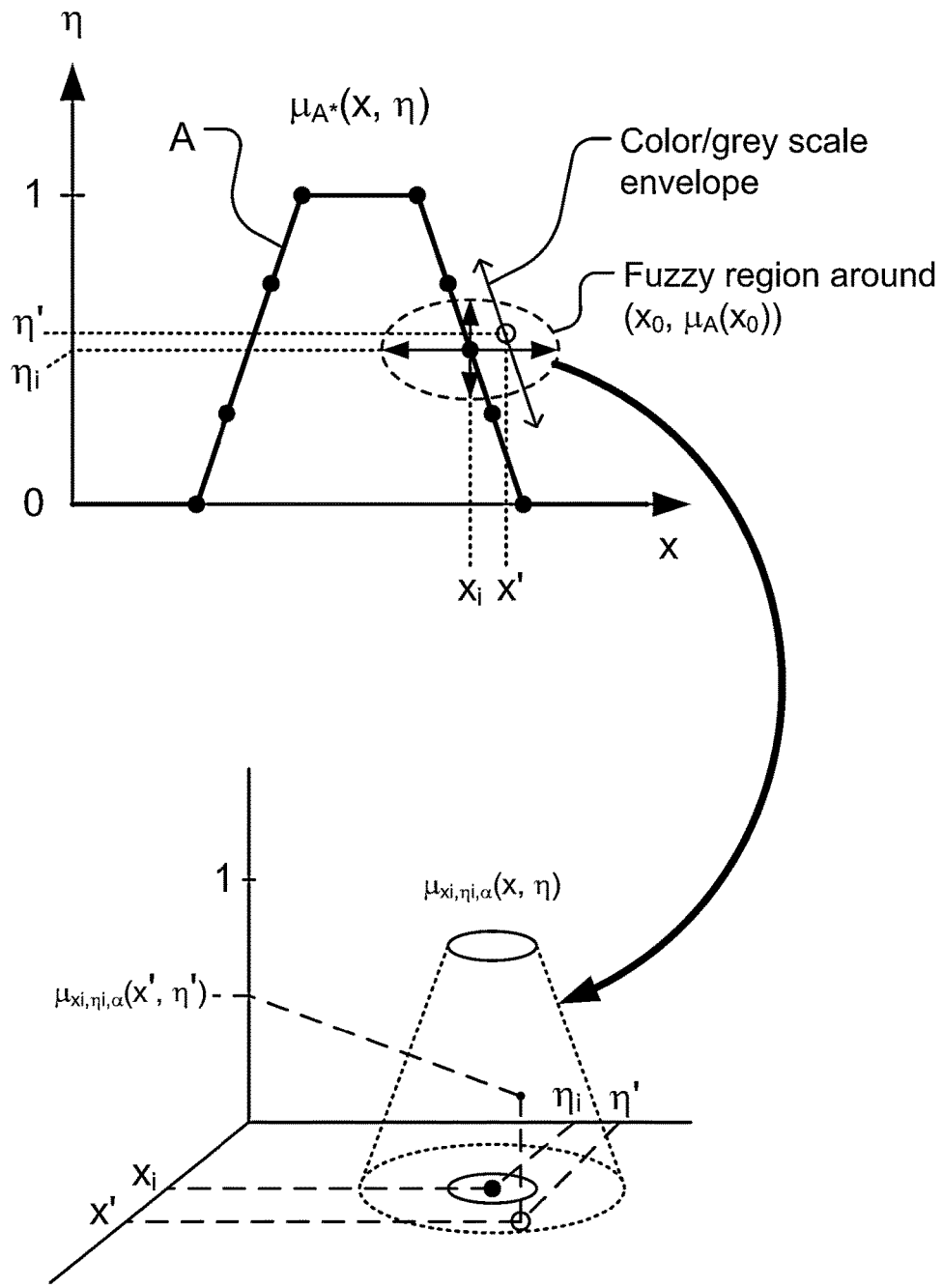
FIG. 34 depicts laterally and vertically fuzzied map, in one embodiment.

In one embodiment, a fuzzy map $A^*$ is constructed by both lateral and vertical fuzziness of A by an amount determined by B. In one embodiment, for example as depicted in FIG. 34, a fuzzy region around a set of points, e.g., $(x_i, \mu_A(x_i))$ on trace of $\mu_A(x)$, is used to determine $\mu_{A^*}(x', \eta')$. In one embodiment, such a fuzzy region describes a color/grey scale region about $(x_i, \mu_A(x_i))$ based on the certainty level of B. In one embodiment, B is parameterized, e.g., $B=B(\alpha)$, and value of $\alpha$ is used to determine the extent of the fuzzy region denoted by $(\mu_{xi,\eta i,\alpha}(x, \eta))$ for a given point $(x_i, \eta_i)$ on trace of $\mu_A(x)$. In one embodiment, $\mu_{A^*}(x', \eta')$ is determined as follows:

$$\mu_{A^*}(x', \eta') = \sup_{\forall (x_i,\eta_i) \text{ subject to } \eta_i = \mu_A(x_i)} (\mu_{x_i,\eta_i,\alpha}(x', \eta'))$$

In one embodiment, the fuzzy region $\mu_{xi,\eta i,\alpha}(x, \eta)$ is selected to decouple $(x, \eta)$ into vertical and horizontal fuzzy components, e.g.:

$$\mu_{x_i,\eta_i,\alpha}(x',\eta') = \mu_{Lat,x_i,\eta_i,\alpha}(x') \wedge \mu_{Ver,x_i,\eta_i,\alpha}(\eta')$$

In one embodiment, the above test is limited to set of signature points (e.g., defining the corners of $\mu_{Ax}$, or certain pre-defined values of $\eta$). In such an embodiment, color/grey scale contours (e.g., convex) are determined to envelope neighboring (x', $\eta$') points having the same assigned $\mu_{A^*}(x', \eta')$ value. The envelopes are then assigned the common color/grey scale value of $\mu_{A^*}(x', \eta')$. In one embodiment, these envelops of contours define $\mu_{A^*}(x, \eta)$.

Example 5

In one embodiment, a fuzzy rules engine employs a fuzzy rule with $A^*$ at its antecedent. E.g.:

IF (X is $A^*$) THEN (Y is C), where $A^*=(A_X, B_Y)$.

Figure 35A:
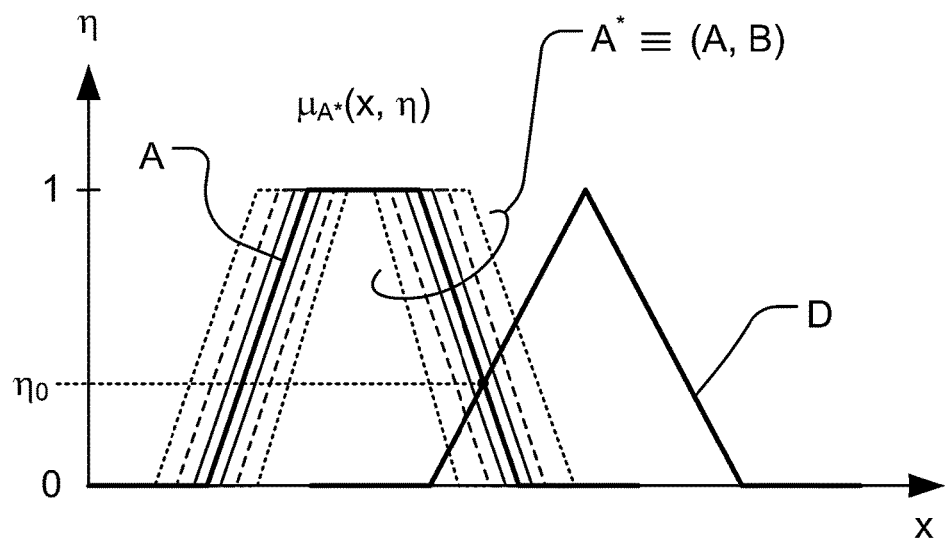
FIG. 35(a)-(d) depict determination of a truth value in predicate of a fuzzy rule involving a fuzzy map, in one embodiment.
Figure 35B:
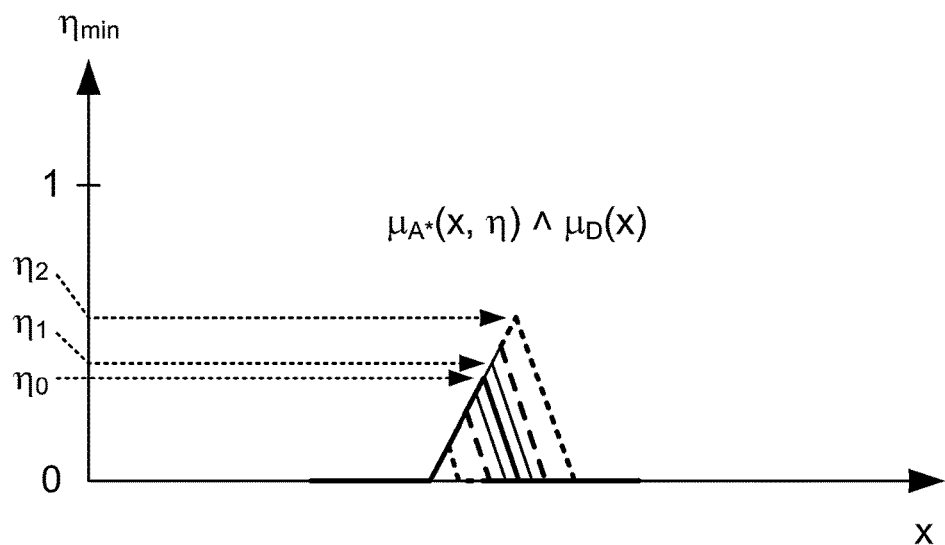
Figure 35C:
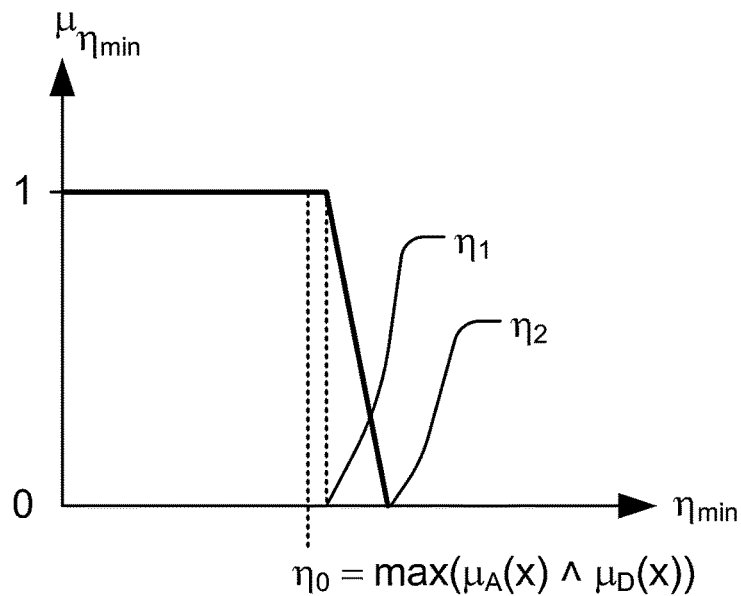

In one embodiment, an input proposition, e.g., X is D, is used to evaluate the truth value ($T_{ant}$) of the rule's antecedent. In one embodiment, $T_{ant}$ is determined based on the coverage of $A^*$ against D, such as a test score. In one embodiment, $T_{ant}$ is determined from $(\mu_{A*} \wedge \mu_D)$, as illustrated in FIGS. 35(a)-(d). As depicted in FIG. 35(a), $\max(\mu_A \wedge \mu_D)$ occurs at $\eta_0$. To determine $(\mu_{A*} \wedge \mu_D)$, in one embodiment, at various x values, such as x', possible $\eta$ values (in [0, 1]) and $\mu_D(x')$ are compared for minimum (with the result denoted as $\eta_{min}$). In one embodiment, this result is given the weight of $\max((\mu_{A*}(x', \eta) \wedge \mu_D(x'))$ subject to $\min(\eta, \mu_D(x'))=\eta_{min}$. This result/weight is a fuzzy map in (x, $\eta_{min}$) domain, as for example depicted in FIG. 35(b), representing $(\mu_{A*} \wedge \mu_D)$. In one embodiment, $\max(\mu_{A*} \wedge \mu_D)$ is used as the truth value of the antecedent. Note that in special case of extreme sureness for $B_x$, $T_{ant}$ is $\eta_0$ (or $\max(\mu_A \wedge \mu_D)$). In one embodiment, based on $(\mu_{A*} \wedge \mu_D)$, for various $\eta_{min}$ values, their corresponding degree of possibility (denoted as $\mu_{\eta min}$) are determined, as depicted for example in FIG. 35(c). For special case of $(\mu_A \wedge \mu_D)$, such $\mu_{\eta min}$ possibility becomes a crisp set with an edge at $\eta_0$. However, due to $(\mu_{A*} \wedge \mu_D)$ fuzzy map, the edge of $\mu_{\eta min}$ is fuzzy (ramping at $\eta_1$ to $\eta_2$) and also extended to higher values (i.e., $\eta_2$ instead of $\eta_0$, if for example, the core of A* fuzziness has non-zero width). In one embodiment, $T_{ant}$ is determined by taking maximum of $\eta_{min}$, as for example depicted in FIG. 35(d). In this example, the maximum $\eta_{min}$ has a possibility distribution (denoted as $\mu_{max(\eta min)}$) starting up at $\eta_1$ and ramping down at $\eta_2$.

Figure 35D:
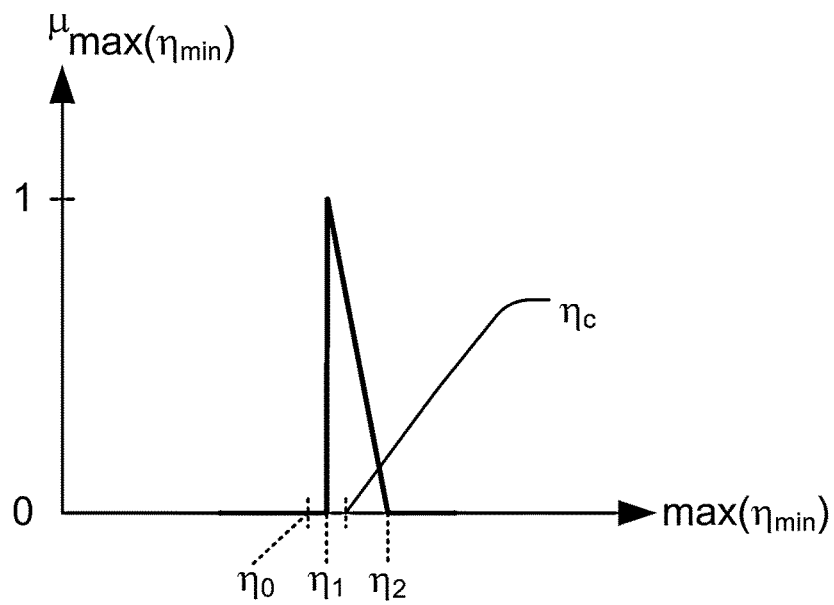

In one embodiment, a centroid location of $\mu_{max(\eta min)}$ (depicted as $\eta_c$ in FIG. 35(d)) is taken as $T_{ant}$. In one embodiment, a defuzzied value of $\mu_{max(\eta min)}$ (e.g., $\eta_1$) is taken as $T_{ant}$. In one embodiment, the fuzzy set $\mu_{max(\eta min)}$ is used directly to impact the truth value of the consequent, e.g., by fuzzy clipping of fuzzy scaling of the consequent's corresponding membership function.

Generalization of Some of the Concepts (a) Apparent Confidence of a Speaker

For example, let's start from the following statement: "Event A is very rare". Let's consider the following situation: Person B (a source of information, or the speaker, or the writer) says: "Event A is very rare, and I am sure about it". In this example, the word "rare" signifies the statistical frequency of the event A happening. "Being sure about the statement above" indicates the "apparent" confidence of the speaker (person B). In this case, the degree of the "apparent confidence of the speaker" is high. Please note that this is just the "apparent" confidence of the speaker, and it may not be the "real" confidence of the speaker, due to the parameters mentioned below, such as speaker's truthfulness (which can make the apparent confidence different from the real confidence of the speaker).

In one model, the degree of the apparent confidence of the speaker is set between 0 and 1, as a normalized axis (or scale), for example, corresponding to zero (minimum) apparent confidence of the speaker level and maximum apparent confidence of the speaker level, respectively.

Please note that sometimes, the speaker only says "Event A is very rare.", and he does not mention "and I think it is true." in his statement. However, a listener may conclude that the speaker meant to say that "Event A is very rare, and I think it is true.", which may be understood from the context of the statement by the speaker.

(b) Speaker's Truthfulness

In one embodiment, person B (the speaker) might have a bias or bad faith, or may be a liar (e.g. for the statement "Event A is very rare."). For example, he may lie very often, or he may lie often only on a specific subject or in a specific context. Or, we may have a history of lies coming from person B (as a source of information). In all of these cases, the person B "intentionally" twists his own belief, when he expresses his statement verbally or in writing. Of course, if his own belief is false (in the first place), the end result (his twisted statement) may become valid or partially valid, anyway. Thus, for any speaker who is biased, has a bad faith, or is a liar, the degree of the "speaker's truthfulness" is low. The degree of the "speaker's truthfulness" is usually hidden or unknown to the listener or reader.

In one model, the degree of the truthfulness of the speaker is set between 0 and 1, as a normalized axis (or scale), for example, corresponding to zero (minimum) and maximum truthfulness of the speaker levels, respectively. For example, 0 and 1 correspond to the always-"liar" and always-"not-liar" speakers, respectively.

Please note that the "truthfulness of a statement" is different from the "truthfulness of a speaker".

(c) Expertise of the Speaker

Another factor is the degree of expertise or knowledge of a person about a subject (or how well a person can analyze the data received on a given subject, or how well a person can express the ideas and conclusions to others using the right language and phrases). For example, if the event A is about astronomy and the speaker has low or no knowledge about astronomy, then the "degree of expertise of the speaker" (or source of information) is low. In one model, the degree of the expertise of the speaker is set between 0 and 1, or 0 to 100 percent, as a normalized axis (or scale), for example, corresponding to zero (minimum) and maximum expertise levels, respectively.

(d) Perception of the Speaker

Another factor is the degree of "perception of the speaker" about an event or subject. For example, a person with a weak eye sight (and without eyeglasses) cannot be a good witness for a visual observation of an event from a far distance, for example as a witness in a court. In one model, the degree of the perception of the speaker is set between 0 and 1, as a normalized axis (or scale), for example, corresponding to zero (minimum) and maximum levels, respectively.

(e) Trustworthiness of a Speaker

Now, here is a new parameter, the "trustworthiness of a speaker", which depends on at least the 4 factors mentioned above:

1—the degree of the "apparent confidence of the speaker"
2—the degree of the "speaker's truthfulness"
3—the degree of "expertise of the speaker"
4—the degree of "perception of the speaker"

Figure 43:
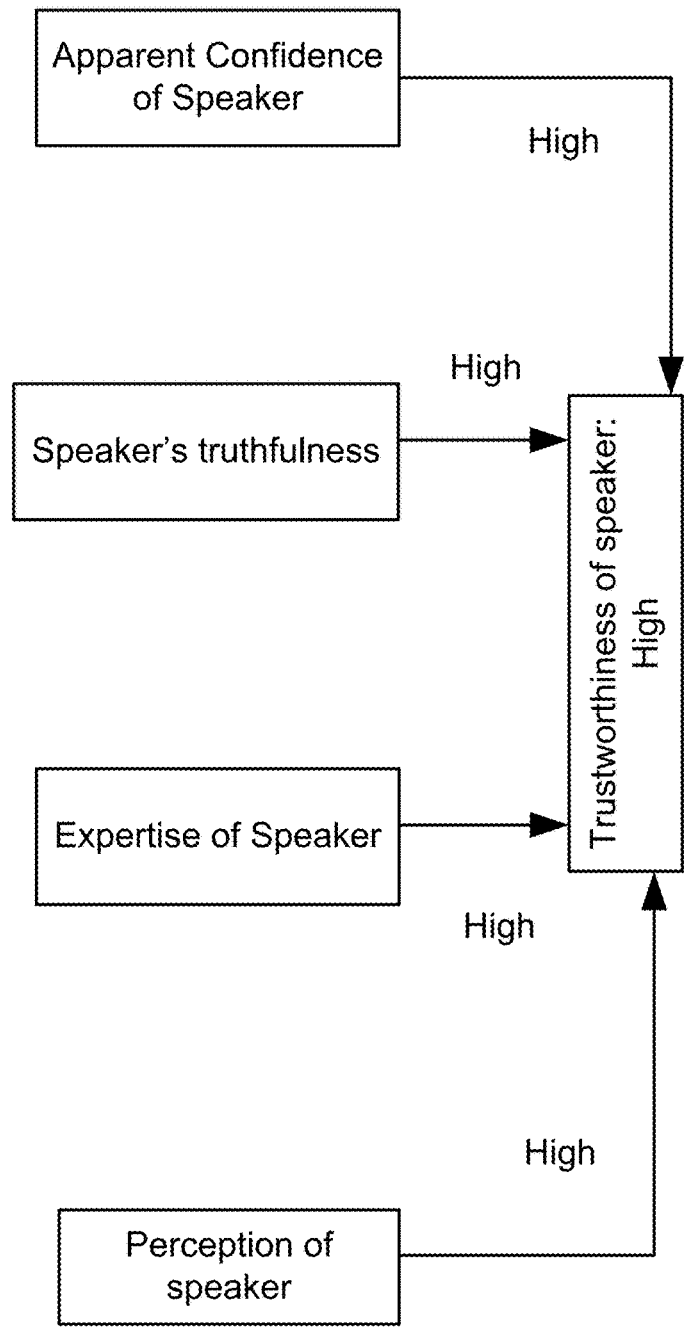
FIG. 43 shows a case in which the trustworthiness of a speaker is high (or the speaker is "trustworthy").

For example, as shown in FIG. 43, the trustworthiness of a speaker is high (or the speaker is "trustworthy"), if:

1—the degree of the "apparent confidence of the speaker" is high &
2—the degree of the "speaker's truthfulness" is high &
3—the degree of "expertise of the speaker" is high &
4—the degree of "perception of the speaker" is high In one model, the degree of the "trustworthiness" of a speaker is set between 0 and 1, as a normalized axis (or scale), for example, corresponding to zero (or minimum) and maximum trustworthiness levels, respectively.

Please note that, in some situations, the "apparent confidence of the speaker" may become dependent or intertwined on the statement itself or one of the other parameters mentioned above, e.g. the "perception of the speaker".

(f) Sureness of a Speaker

Similarly, here is another parameter, the "sureness" of a speaker, which depends on at least the 4 factors mentioned above:

1—the degree of the "apparent confidence of the speaker"
2—the degree of the "speaker's truthfulness"

3—the degree of "expertise of the speaker"

4—the degree of "perception of the speaker"

Figure 44:
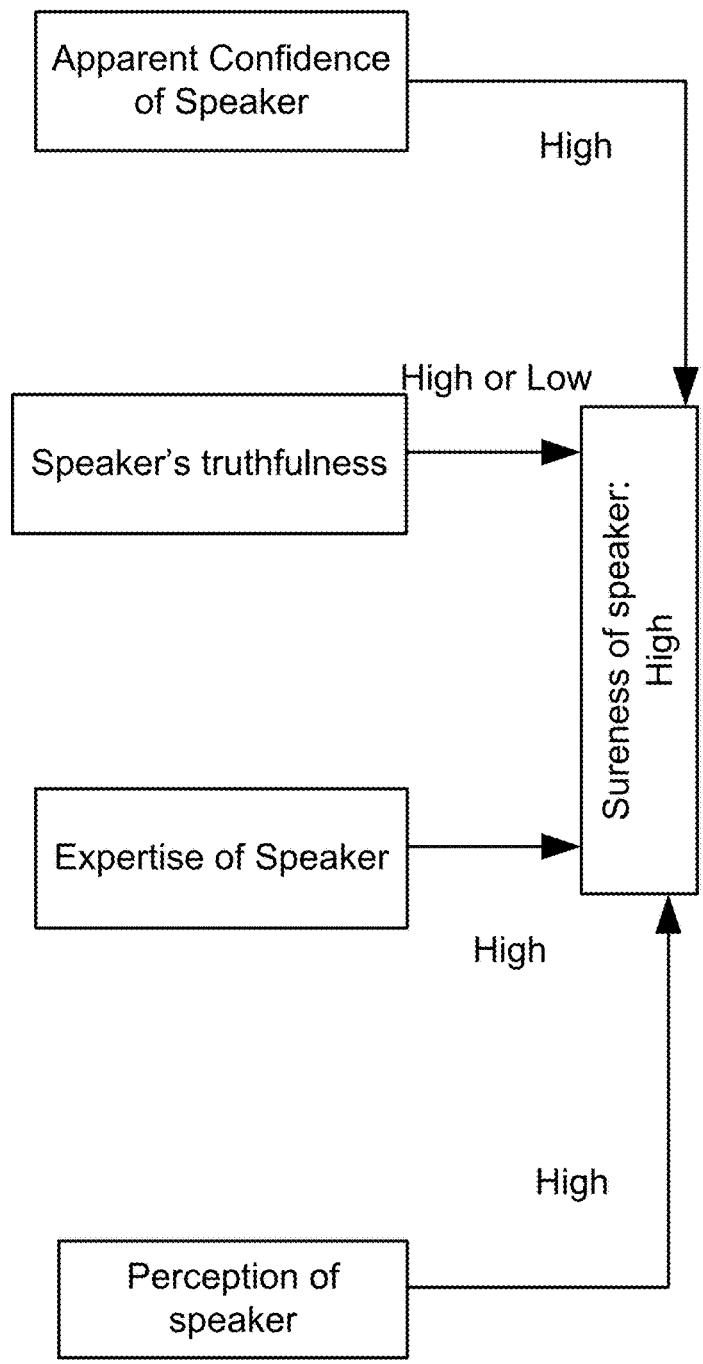
FIG. 44 shows a case in which the "sureness" of a speaker of a statement is high.

For example, as shown in FIG. 44, the "sureness" of a speaker of a statement is high, if:

1—the degree of the "apparent confidence of the speaker" is high &

2—the degree of the "speaker's truthfulness" is either high or low (but not medium) (i.e. when speaker's truthfulness is close to either 1 or 0, but away from 0.5) &

3—the degree of "expertise of the speaker" is high &

4—the degree of "perception of the speaker" is high

In one model, the degree of the "sureness of a speaker" of a statement is set between 0 and 1, as a normalized axis (or scale), for example, corresponding to zero (or minimum) and maximum sureness levels, respectively.

Please note that in our definitions here, there is a difference between the "sureness" and "trustworthiness" (of a speaker). For example, a speaker may have low trustworthiness, but has a high sureness. For example, for an always-liar speaker (i.e. when the speaker's degree of truthfulness is 0), the speaker has a low trustworthiness (for the listener), but has a high level of sureness. That is, for an always-liar speaker (i.e. not "trustworthy"), the conclusion from a statement becomes the reverse of the original statement, which means that the speaker has a high level of sureness (for the listener). For example, for an always-liar speaker, the statement "Event A is very rare" results in the following conclusion for the listener: "Event A is not very rare". That is, once the listener knows (or has the knowledge) that the speaker is an always-liar speaker, the listener can still "count on" the "reverse" of the statement given by the speaker (with a high degree of "sureness").

In another example, for a speaker that "sometimes lies" (i.e. a "sometimes-liar", with the speaker's degree of truthfulness around 0.5), the "sureness" about the speaker is low.

(g) Broadness of a Statement

Now, let's look at another factor, "the degree of the broadness of the statement", with some examples. For example, in response to the question that "What is the color of the table?", the statement "The color of the table may be green, blue, or red." has higher degree of broadness than that of the statement "The color of the table is green.", with respect to the information about the color of the table.

For example, in response to the question that "When does the meeting start today?", the statement "The meeting may start in the next few hours." has higher degree of broadness than that of the statement "The meeting starts at 10 am.", with respect to the information about the starting time of the meeting.

In one model, the degree of the "broadness" of a statement is set between 0 and 1, as a normalized axis (or scale), for example, corresponding to zero (or minimum) and maximum (or 100 percent) broadness levels, respectively.

(h) Helpfulness of a Statement

Now, let's look at another parameter, the degree of "helpfulness" (for a statement (for a listener or reader)), which depends on at least the following 2 parameters:

1—the degree of the "sureness of the speaker" of the statement

2—the degree of "broadness of the statement"

The degree of "helpfulness of a statement" is one measure of the information of a statement (for a listener or reader or the recipient of information), which is very contextual (e.g. dependent on the question asked).

Figure 45:
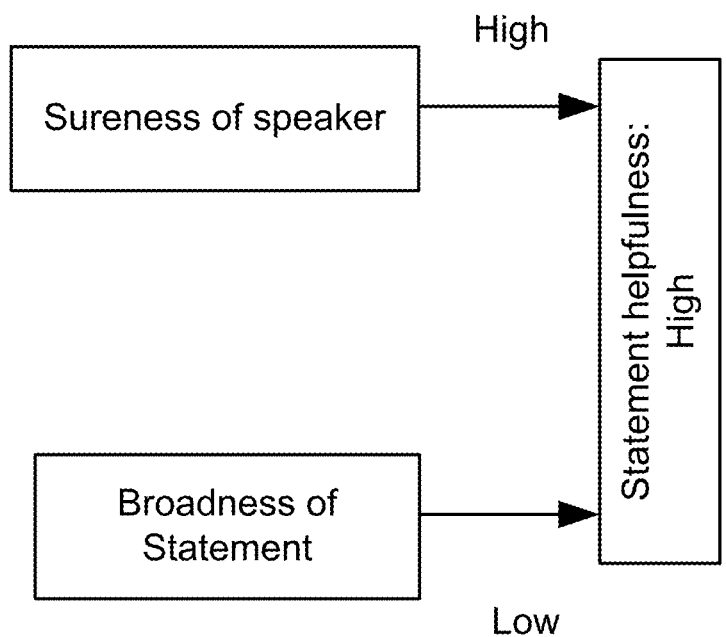
FIG. 45 shows a case in which the degree of "helpfulness" for a statement (or information or data) is high (or the statement is "helpful").

For example, as shown in FIG. 45, the degree of "helpfulness" for a statement (or information or data) is high (or the statement is "helpful"), if:

1—the degree of the "sureness of the speaker" of the statement is high &

2—the degree of the "broadness of the statement" is low (i.e. the statement is very "specific").

In one model, the degree of the "helpfulness" of a statement is set between 0 and 1, as a normalized axis (or scale), for example, corresponding to zero (or minimum) and maximum helpfulness levels, respectively. The degree of the "helpfulness" of a statement or information (I) is denoted by function H(I).

Please note that all the parameters above (e.g. the degree of the helpfulness) can also be expressed by percentages between 0 to 100 percent (or by any other scale, instead of scale of 0 to 1, respectively). The parameters above (e.g. the degree of the helpfulness) can be expressed by Fuzzy representations, as well.

Applications

The parameters above are useful for situations that one gets input or information from one or more sources, and one wants to evaluate, filter, sort, rank, data-mine, validate, score, combine, find and remove or isolate contradictions, conclude, simplify, find and delete or isolate redundancies, criticize, analyze, summarize, or highlight a collection of multiple information pieces or data, from multiple sources with various levels of reliability, credibility, reputation, weight, risk, risk-to-benefit ratio, scoring, statistics, or past performance.

For example, these parameters are useful for editors of an article (such as Wikipedia, with various writers with various levels of credibility, knowledge, and bias), search engines in a database or on Internet (with information coming various sources, with different levels of confidence or credibility), economy or stock market prediction (based on different parameter inputs or opinions of different analysts, and various political, natural, and economical events), background check for security for people (based on multiple inputs from various sources and people, each with different credibility and security risk), medical doctors' opinions or diagnosis (based on doctors with various expertise and experience, information from various articles and books, and data from various measurements and equipment), booking flights and hotel online (with information from various web sites and travel agents, each with different reliability and confidence), an auction web site (with different seller's credibility, reliability, history, and scoring by other users), customize and purchase a computer online (with different pricing and seller's credibility, reliability, history, and scoring by other users), customer feedback (with various credibility), voting on an issue (with various bias), data mining (from various sources with different credibility and weight), and news gathering (from multiple sources of news, on TV or Internet, with various reliability and weight).

Figure 46:
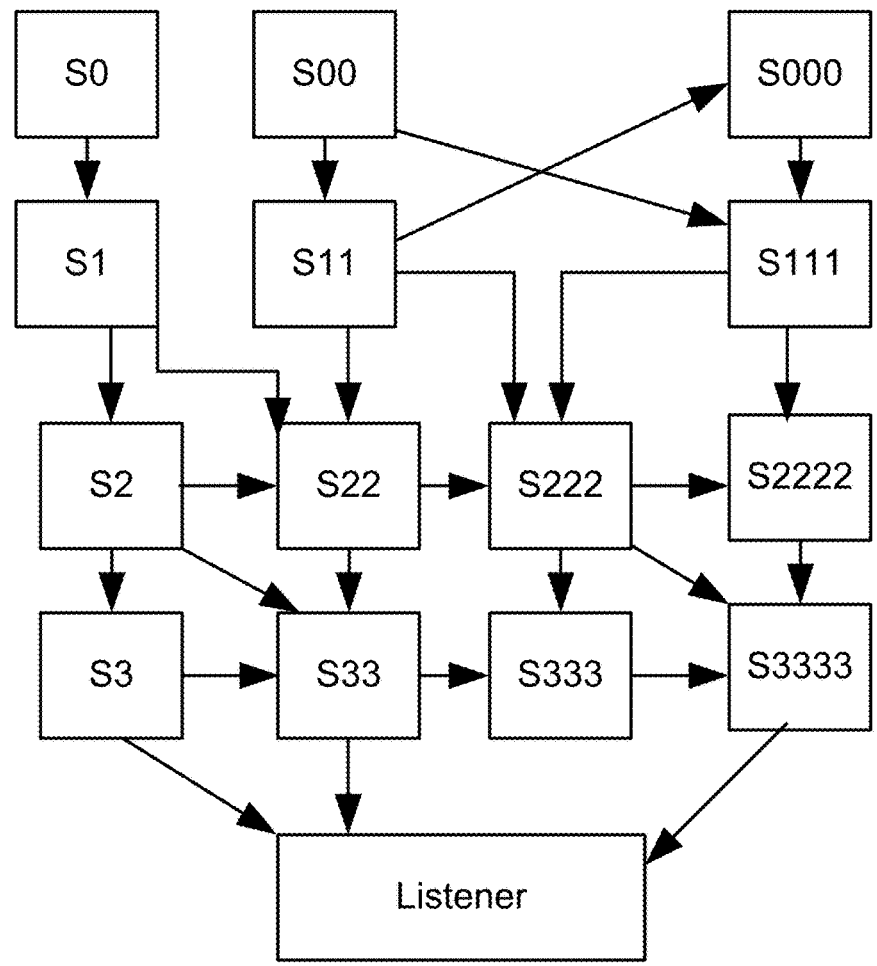
FIG. 46 shows a listener which or who listens to multiple sources of information or data, cascaded or chained together, supplying information to each other.

In one embodiment, an information source (S) may get its input or information from one or more other sources. In one embodiment, there is a network of other sources, connected in parallel or in series, or in combinations or mixtures of other sources in different configurations. In one embodiment, the information source S0 supplies some information to another information source S1, in a cascade of sources (with each source acting as a node in the structure), e.g. in a tree, pyramid, or hierarchical configuration (with many branches interconnected), where a listener gathers all the information from different sources and analyzes them to make a conclusion from all the information received, as shown in FIG. 46, as an example. The listener itself (in turn) can be a source of information for others (not shown in FIG. 46).

Thus, the overall reliability and the overall credibility of the system (or other parameters describing the system) depends on (is a function of) the components, or the chain of sources in the relevant branch(es), going back to the source(s) of information. That is, for the overall reliability, R, we have:

$$R = \text{Function}(R_{S0}, R_{S1}, \ldots, R_{Sm}),$$

for m sources in the chain, starting from S0.

In one embodiment, for a source of information, when it comes through a cascade or chain of sources, the weakest link dominates the result. For example, the most unreliable link or source determines or dominates the overall reliability. In one embodiment, this can be modeled based on the MINIMUM function for reliability values for multiple sources. In one embodiment, this can be based on the AND function between the values. In one embodiment, this can be based on the additions on inverse values, e.g.:

$$(1/R) = (1/R_1) + (1/R_2) + \ldots + (1/R_N)$$

(with R as the overall reliability, and $R_N$ as the reliability for source N)

In one embodiment, the sources are independent sources. In one embodiment, the sources are dependent sources (dependent on each other).

One of the advantages of the fuzzy analysis mentioned here in this disclosure is that the system can handle contradictory and duplicative information, to sort them out and make a conclusion from various inputs.

In one embodiment, the information can go through a source as a conduit, only (with no changes made on the received information by the source, itself). In another embodiment, the information can be generated, analyzed, and/or modified by the source, based on all the inputs to the source, and/or based on the source's own knowledge base (or database) and processor (or CPU, controller, analyzing module, computer, or microprocessor, to analyze, edit, modify, convert, mix, combine, conclude, summarize, or process the data).

In one embodiment, the source of information has time-dependent parameters. For example, the credibility or reliability of the source changes over time (with respect to a specific subject or all subjects). Or, the bias of the source may change for a specific topic or subject, as the time passes. For example, a news blog, newspaper, radio show, radio host, TV show, TV news, or Internet source may have a predetermined bias or tendency toward a specific party, political idea, social agenda, or economic agenda, which may change due to the new management, owner, or host.

Search Engines and Question-Answering Systems

Part of this section is a part of a paper by one of our inventors on the subject of search engines, titled "From search engines to question answering systems", appeared in "Fuzzy logic and semantic web", edited by Elie Sanchez, 2006, Elsevier B. V. publisher, Chapter 9, pages 163-210.

For one embodiment, for search engines or question-answering systems, one of the main goals is the deduction capability—the capability to synthesize an answer to a query by drawing on bodies of information which reside in various parts of the knowledge base. By definition, a question-answering system, or Q/A system for short, is a system which has deduction capability. The first obstacle is world knowledge—the knowledge which humans acquire through experience, communication and education. Simple examples are: "Icy roads are slippery," "Princeton usually means Princeton University," "Paris is the capital of France," and "There are no honest politicians." World knowledge plays a central role in search, assessment of relevance and deduction.

The problem with world knowledge is that much of it is perception-based. Perceptions—and especially perceptions of probabilities—are intrinsically imprecise, reflecting the fact that human sensory organs, and ultimately the brain, have a bounded ability to resolve detail and store information. Imprecision of perceptions stands in the way of using conventional techniques—techniques which are based on bivalent logic and probability theory—to deal with perception-based information. A further complication is that much of world knowledge is negative knowledge in the sense that it relates to what is impossible and/or non-existent. For example, "A person cannot have two fathers," and "Netherlands has no mountains."

The second obstacle centers on the concept of relevance. There is an extensive literature on relevance, and every search engine deals with relevance in its own way, some at a high level of sophistication. There are two kinds of relevance: (a) question relevance and (b) topic relevance. Both are matters of degree. For example, on a very basic level, if the question is q: Number of cars in California? and the available information is p: Population of California is 37,000,000, then what is the degree of relevance of p to q? Another example: To what degree is a paper entitled "A New Approach to Natural Language Understanding" of relevance to the topic of machine translation.

Basically, there are two ways of approaching assessment of relevance: (a) semantic; and (b) statistical. To illustrate, in the number of cars example, relevance of p to q is a matter of semantics and world knowledge. In existing search engines, relevance is largely a matter of statistics, involving counts of links and words, with little if any consideration of semantics. Assessment of semantic relevance presents difficult problems whose solutions lie beyond the reach of bivalent logic and probability theory. What should be noted is that assessment of topic relevance is more amendable to the use of statistical techniques, which explains why existing search engines are much better at assessment of topic relevance than question relevance.

The third obstacle is deduction from perception-based information. As a basic example, assume that the question is q: What is the average height of Swedes?, and the available information is p: Most adult Swedes are tall. Another example is: Usually Robert returns from work at about 6 pm. What is the probability that Robert is home at about 6:15 pm? Neither bivalent logic nor probability theory provide effective tools for dealing with problems of this type. The difficulty is centered on deduction from premises which are both uncertain and imprecise.

Underlying the problems of world knowledge, relevance, and deduction is a very basic problem—the problem of natural language understanding. Much of world knowledge and web knowledge is expressed in a natural language. A natural language is basically a system for describing perceptions. Since perceptions are intrinsically imprecise, so are natural languages, especially in the realm of semantics.

A prerequisite to mechanization of question-answering is mechanization of natural language understanding, and a prerequisite to mechanization of natural language understanding is precisiation of meaning of concepts and proposition drawn from a natural language. To deal effectively with world knowledge, relevance, deduction and precisiation, new tools are needed. The principal new tools are:

Precisiated Natural Language (PNL); Protoform Theory (PFT); and the Generalized Theory of Uncertainty (GTU). These tools are drawn from fuzzy logic—a logic in which everything is, or is allowed to be, a matter of degree.

The centerpiece of new tools is the concept of a generalized constraint. The importance of the concept of a generalized constraint derives from the fact that in PNL and GTU it serves as a basis for generalizing the universally accepted view that information is statistical in nature. More specifically, the point of departure in PNL and GTU is the fundamental premise that, in general, information is representable as a system of generalized constraints, with statistical information constituting a special case. Thus, much more general view of information is needed to deal effectively with world knowledge, relevance, deduction, precisiation and related problems. Therefore, a quantum jump in search engine IQ cannot be achieved through the use of methods based on bivalent logic and probability theory.

Deduction capability is a very important capability which the current search engines generally have not fully developed, yet. What should be noted, however, is that there are many widely used special purpose Q/A systems which have limited deduction capability. Examples of such systems are driving direction systems, reservation systems, diagnostic systems and specialized expert systems, especially in the domain of medicine.

It is of historical interest to note that question-answering systems were an object of considerable attention in the early seventies. The literature abounded with papers dealing with them. Interest in question-answering systems dwindled in the early eighties, when it became obvious that AI was not advanced enough to provide the needed tools and technology. In recent years, significant progress toward enhancement of web intelligence has been achieved through the use of concepts and techniques related to the Semantic Web, OWL, CYC and other approaches. But such approaches, based on bivalent logic and probability theory, cannot do the job. The reason, which is not widely recognized as yet, is that bivalent logic and bivalent-logic-based probability theory have intrinsic limitations. To circumvent these limitations what are needed are new tools based on fuzzy logic and fuzzy-logic-based probability theory. What distinguishes fuzzy logic from standard logical systems is that in fuzzy logic everything is, or is allowed to be graduated, that is, be a matter of degree. Furthermore, in fuzzy logic everything is allowed to be granulated, with a granule being a clump of values drawn together by indistinguishability, similarity or proximity. It is these fundamental features of fuzzy logic that give it a far greater power to deal with problems related to web intelligence than standard tools based on bivalent logic and probability theory. An analogy to this is: In general, a valid model of a nonlinear system cannot be constructed through the use of linear components.

There are three major obstacles to upgrading a search engine to a question-answering system: (a) the problem of world knowledge; (b) the problem of relevance; and (c) the underlying problem of mechanization of natural language understanding and, in particular, the basic problem of precisiation of meaning Since the issues to be discussed are not restricted to web-related problems, our discussion will be general in nature.

The Problem of World Knowledge

World knowledge is the knowledge which humans acquire through experience, education and communication. Simple examples are:

Few professors are rich
There are no honest politicians
It is not likely to rain in San Francisco in midsummer
Most adult Swedes are tall
There are no mountains in Holland
Usually Princeton means Princeton University
Paris is the capital of France
In Europe, the child-bearing age ranges from about sixteen to about forty-two The problem with world knowledge is that much of it is perception-based. Examples:

Most adult Swedes are tall
Most adult Swedes are much taller than most adult Italians
Usually a large house costs more than a small house
There are no honest politicians Perception-based knowledge is intrinsically imprecise, reflecting the bounded ability of sensory organs, and ultimately the brain, to resolve detail and store information. More specifically, perception-based knowledge is f-granular in the sense that (a) the boundaries of perceived classes are unsharp (fuzzy); and (b) the values of perceived attributes are imprecise (fuzzy). Bivalent-logic-based approaches provide no methods for deduction from perception-based knowledge. For example, given the datum: Most adult Swedes are tall, existing bivalent-logic-based methods cannot be employed to come up with valid answers to the questions q1: How many adult Swedes are short; and q2: What is the average height of adult Swedes?

The Problem of Relevance

The importance of the concept of relevance is hard to exaggerate. Relevance is central to search. Indeed, the initial success of Google is due, in large measure, to its simple but ingenious page ranking algorithm for assessment of relevance. Despite its importance, there are no satisfactory definitions of relevance in the literature.

In fact, it may be argued that, as in the case of world knowledge, the concept of relevance is much too complex to lend itself to treatment within the limited conceptual framework of bivalent logic and bivalent-logic-based probability theory. An immediate problem is that relevance is not a bivalent concept. Relevance is a matter of degree, that is, it is a fuzzy concept. To define fuzzy concepts, what is needed is the conceptual structure of fuzzy logic. As was stated earlier, in fuzzy logic everything is, or is allowed to be, a matter of degree.

For concreteness, it is convenient to define a relevance function, $R(q/p)$, as a function in which the first argument, $q$, is a question or a topic; the second argument, $p$, is a proposition, topic, document, web page or a collection of such objects; and R is the degree to which p is relevant to q. When q is a question, computation of $R(q/p)$ involves an assessment of the degree of relevance of p to q, with p playing the role of question-relevant information. For example, if q: What is the number of cars in California, and p: Population of California is 37 million, then p is question-relevant to q in the sense that p constrains, albeit imprecisely, the number of cars in California. The constraint is a function of world knowledge.

If q is a topic, e.g., q: Ontology, then a document entitled p: What is ontology?, is of obvious relevance to q, i.e., p is topic-relevant. The problem in both cases is that of assessment of degree of relevance. Basically, what we need is a method of computing the degree of relevance based on the meaning of q and p, that is, we need semantic relevance. Existing search engines have a very limited capability to deal with semantic relevance. Instead, what they use is what may be called statistical relevance. In statistical relevance, what is used is, in the main, statistics of links and counts of words. Performance of statistical methods of assessment of relevance is unreliable.

A major source of difficulty in assessment of relevance relates to non-compositionality of the relevance function. More specifically, assume that we have a question, q, and two propositions p and r. Can the value of R(q/p, r) be composed from the values of R(q/p) and R(q/r)? The answer, in general, is: No. As a simple, not web-related, example, suppose that q: How old is Vera; p: Vera's age is the same as Irene's; r: Irene is 65. In this case, R(q/p)=0; R(q/r)=0 and yet R(q/p, r)=1. What this implies is that, in general, relevance cannot be assessed in isolation. This suggests a need for differentiation between relevance and what may be called i-relevance, that is, relevance in isolation. In other words, a proposition, p, is i-relevant if it is relevant by itself, and it is i-irrelevant if it is not of relevance by itself, but might be relevant in combination with other propositions.

The Problem of Precisiation of Meaning—a Prerequisite to Mechanization of Natural Language Understanding Much of world knowledge and web knowledge is expressed in a natural language. This is why issues relating to natural language understanding and natural language reasoning are of direct relevance to search and, even more so, to question-answering.

Humans have no difficulty in understanding natural language, but machines have many. One basic problem is that of imprecision of meaning A human can understand an instruction such as "Take a few steps," but a machine cannot. To execute this instruction, a machine needs a precisiation of "few." Precisiation of propositions drawn from a natural language is the province of PNL (Precisiated Natural Language). A forerunner of PNL is PRUF. In PNL, precisiation is interpreted as meaning precisiation, rather than value precisiation. A proposition is precisiated through translation into the Generalized Constraint Language (GCL). An element of GCL which precisiates p is referred to as a precisiand of p, GC(p), with GC(p) representing a generalized constraint. A precisiand may be viewed as a model of meaning A concept which plays a key role in precisiation is cointension, with intension used in its usual logical sense as attribute-based meaning Thus, p and q are cointensive if the meaning of p is a close approximation to that of q. In this sense, a precisiand, GC(p), is valid if GC(p) is cointensive with p. The concept of cointensive precisiation has an important implication for validity of definitions of concepts. More specifically, if C is a concept and Def(C) is its definition, then for Def(C) to be a valid definition, Def(C) must be cointensive with C (see FIG. 4, regarding cointension: degree of goodness of fit of the intension of definiens to the intension of definiendum).

The concept of cointensive definition leads to an important conclusion: In general, a cointensive definition of a fuzzy concept cannot be formulated within the conceptual structure of bivalent logic and bivalent-logic-based probability theory.

Figure 5:
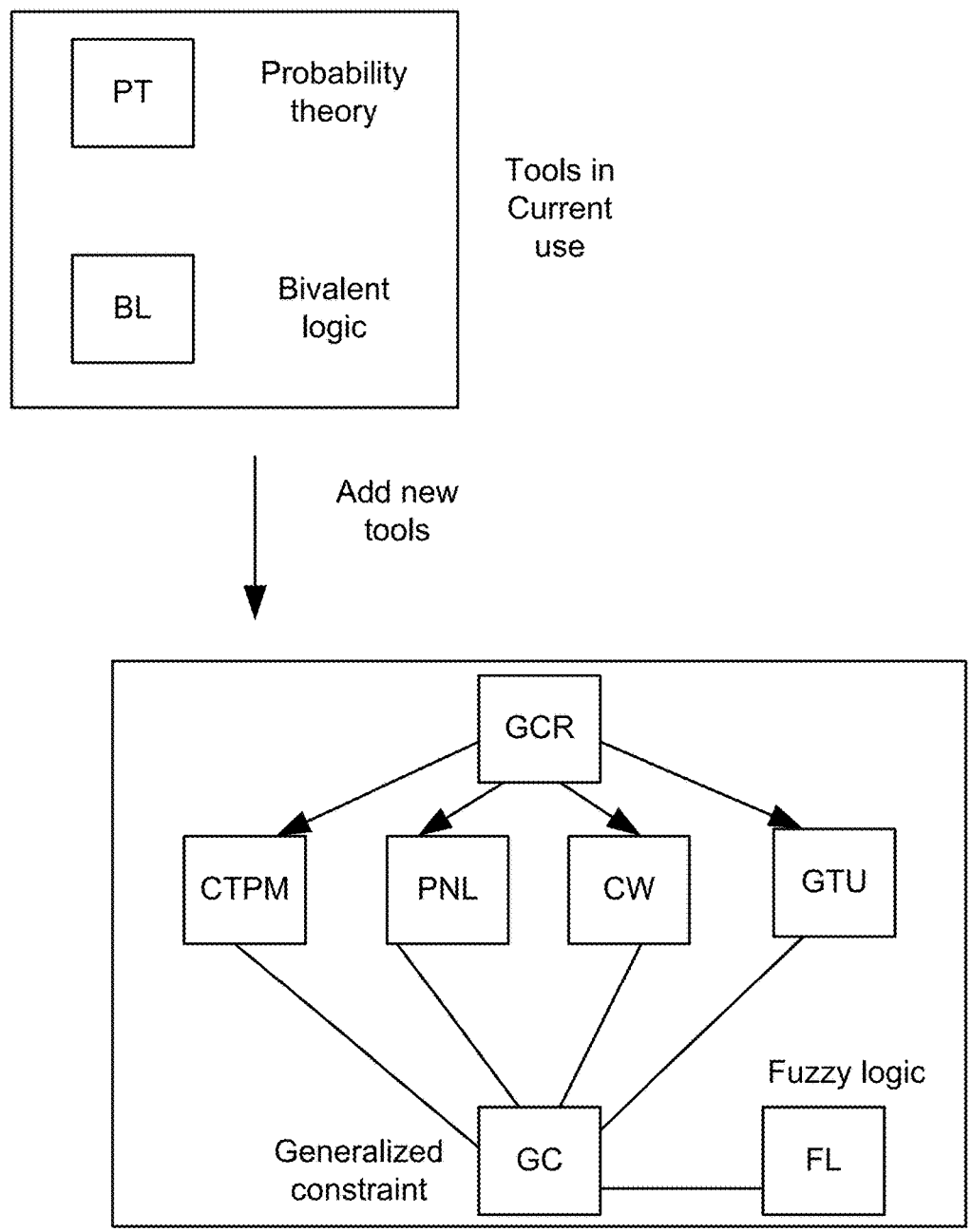
FIG. 5 shows structure of the new tools.

See FIG. 5, regarding structure of the new tools:
PT: standard bivalent-logic-based probability theory
CTPM: Computational Theory of Precisiation of Meaning
PNL: Precisiated Natural Language
CW: Computing with Words
GTU: Generalized Theory of Uncertainty
GCR: Theory of Generalized-Constraint-Based Reasoning The Concept of a Generalized Constraint Constraints are ubiquitous. A typical constraint is an expression of the form X∈C, where X is the constrained variable and C is the set of values which X is allowed to take. A typical constraint is hard (inelastic) in the sense that if u is a value of X then u satisfies the constraint if and only if u∈C.

The problem with hard constraints is that most real-world constraints are not hard, meaning that most real-world constraints have some degree of elasticity. For example, the constraints "check-out time is 1 pm," and "speed limit is 100 km/h," are, in reality, not hard. How can such constraints be defined? The concept of a generalized constraint is motivated by questions of this kind Real-world constraints may assume a variety of forms. They may be simple in appearance and yet have a complex structure. Reflecting this reality, a generalized constraint, GC, is defined as an expression of the form.

GC: X isr R, where X is the constrained variable; R is a constraining relation which, in general, is nonbivalent; and r is an indexing variable which identifies the modality of the constraint, that is, its semantics. R will be referred to as a granular value of X.

The constrained variable, X, may assume a variety of forms. In particular,

X is an n-ary variable, $X=(X_1, \ldots, X_n)$
X is a proposition, e.g., X=Leslie is tall
X is a function
X is a function of another variable, X=f(Y)
X is conditioned on another variable, X/Y
X has a structure, e.g., X=Location(Residence(Carol))
X is a group variable. In this case, there is a group, G[A]; with each member of the group, $Name_i$, i=1, ..., n, associated with an attribute-value, $A_i$. $A_i$ may be vector-valued. Symbolically:
G[A]: $Name_1/A_1 + \ldots + Name_n/A_n$.
Basically, G[A] is a relation.
X is a generalized constraint, X=Y isr R.

A generalized constraint, GC, is associated with a test-score function, ts(u) which associates with each object, u, to which the constraint is applicable, the degree to which u satisfies the constraint. Usually, ts(u) is a point in the unit interval. However, if necessary, the test-score may be a vector, an element of a semi-ring, an element of a lattice or, more generally, an element of a partially ordered set, or a bimodal distribution. The test-score function defines the semantics of the constraint with which it is associated.

The constraining relation, R, is, or is allowed to be, non-bivalent (fuzzy). The principal modalities of generalized constraints are summarized in the following.

Principal Modalities of Generalized Constraints
    (a) Possibilistic (r=blank)
    X is R
    with R playing the role of the possibility distribution of X. For example:
    X is [a, b]
    means that [a, b] is the set of possible values of X. Another example:
    X is small.
    In this case, the fuzzy set labeled small is the possibility distribution of X. If $\mu_{small}$ is the membership function of small, then the semantics of "X is small" is defined by
    Poss $\{X=u\}=\mu_{small}(u)$
    where u is a generic value of X.
    (b) Probabilistic (r=p)
    X isp R,
    with R playing the role of the probability distribution of X. For example:

X isp N(m, σ2) means that X is a normally distributed random variable with mean m and variance $\sigma^2$.

If X is a random variable which takes values in a finite set $\{u_1, \ldots, u_n\}$ with respective probabilities $p_1, \ldots, p_n$, then X may be expressed symbolically as X isp $(p_1\backslash u_1 + \ldots + p_n\backslash u_n)$, with the semantics Prob$(X=u_i)=p_i$, (i=1, ..., n).

What is important to note is that in the Generalized Theory of Uncertainty (GTU), a probabilistic constraint is viewed as an instance of a generalized constraint.

When X is a generalized constraint, the expression

X isp R is interpreted as a probability qualification of X, with R being the probability of X. For example:

(X is small) isp likely, where small is a fuzzy subset of the real line, means that the probability of the fuzzy event {X is small} is likely. More specifically, if X takes values in the interval [a, b] and g is the probability density function of X, then the probability of the fuzzy event "X is small" may be expressed as the following integral, taken between a and b interval:

$$Prob(X \text{ is small}) = \int_{between\ a\ and\ b} (\mu_{small}(u))g(u)\,du$$

Hence:

$$ts(g) = \mu_{likely}\left(\int_{between\ a\ and\ b} (\mu_{small}(u))g(u)\,du\right)$$

This expression for the test-score function defines the semantics of probability qualification of a possibilistic constraint.

(c) Veristic (r=v)

X isv R, where R plays the role of a verity (truth) distribution of X. In particular, if X takes values in a finite set $\{u_1, \ldots, u_n\}$ with respective verity (truth) values $t_1, \ldots, t_n$, then X may be expressed as X isv $(t_1|u_1 + \ldots + t_n|u_n)$, meaning that Ver$(X=u_i)=t_i$, i=1, ..., n.

For example, if Robert is half German, quarter French and quarter Italian, then

Ethnicity(Robert) isv (0.5|German+0.25|French+0.25|Italian).

When X is a generalized constraint, the expression

X isv R is interpreted as verity (truth) qualification of X. For example, (X is small) isv very.true, should be interpreted as "It is very true that X is small." The semantics of truth qualification is defined this way.

Figure 37:
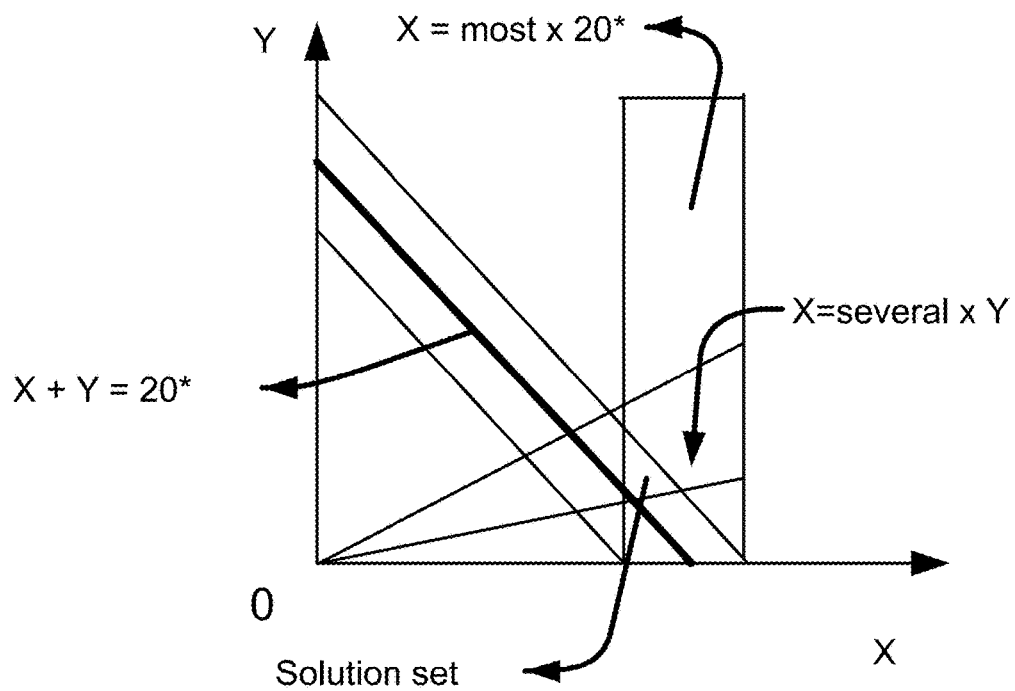
FIG. 37 shows an application of fuzzy integer programming, which specifies a region of intersections or overlaps, as the solution region.

Ver(X is R) is t→X is $\mu_R^{-1}(t)$, where $\mu_R^{-1}$ is inverse of the membership function of R and t is a fuzzy truth value which is a subset of [0, 1], as shown in FIG. 37.

Note. There are two classes of fuzzy sets: (a) possibilistic, and (b) veristic. In the case of a possibilistic fuzzy set, the grade of membership is the degree of possibility. In the case of a veristic fuzzy set, the grade of membership is the degree of verity (truth). Unless stated to the contrary, a fuzzy set is assumed to be possibilistic.

(d) Usuality (r=u)

X isu R.

The usuality constraint presupposes that X is a random variable, and that probability of the event {X isu R} is usually, where usually plays the role of a fuzzy probability which is a fuzzy number. For example:

X isu small means that "usually X is small" or, equivalently,

Prob {X is small} is usually.

In this expression, small may be interpreted as the usual value of X. The concept of a usual value has the potential of playing a significant role in decision analysis, since it is more informative than the concept of expected value.

(e) Random-set (r=rs)

In

X isrs R,

X is a fuzzy-set-valued random variable and R is a fuzzy random set.

(f) Fuzzy-graph (r=fg)

In

Figure 38:
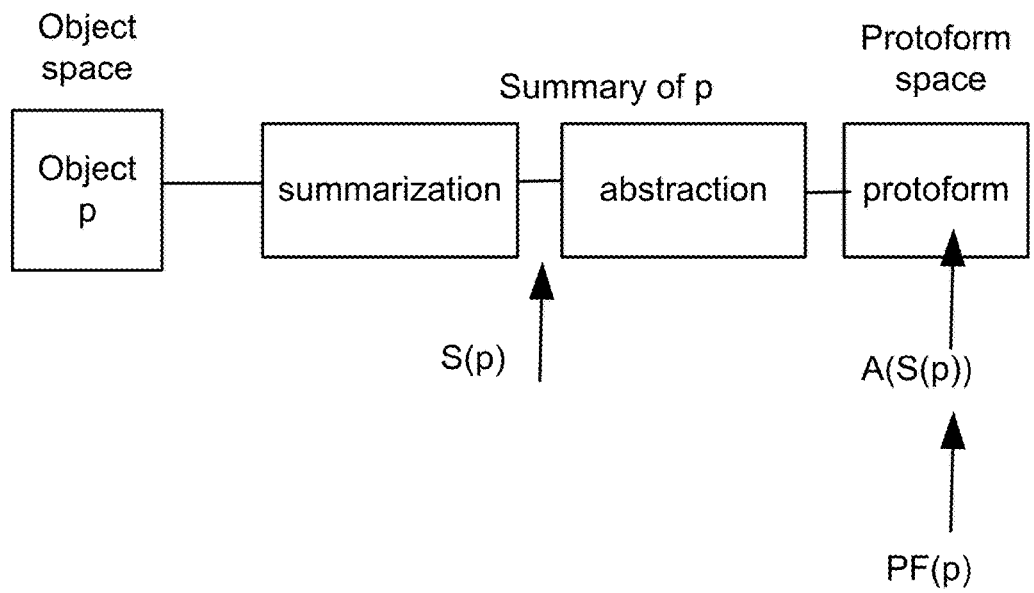
FIG. 38 shows the definition of protoform of p.

X isfg R,

X is a function, f, and R is a fuzzy graph which constrains f (see FIG. 38). A fuzzy graph is a disjunction of Cartesian granules expressed as $$R = A_1 \times B_1 + \ldots + A_n \times B_n,$$

where the $A_i$ and $B_i$, i=1, ..., n, are fuzzy subsets of the real line, and x is the Cartesian product. A fuzzy graph is frequently described as a collection of fuzzy if-then rules.

R: if X is $A_1$ then Y is $B_1$, i=1, ..., n.

The concept of a fuzzy-graph constraint plays an important role in applications of fuzzy logic.

(g) Bimodal (r=bm)

In the bimodal constraint,

X isbm R,

R is a bimodal distribution of the form

R: $\Sigma_i$ Pi\Ai, i=1, ..., n, which means that Prob(X is Ai) is Pi.

To clarify the meaning of a bimodal distribution, it is expedient to start with an example. I am considering buying Ford stock. I ask my stockbroker, "What is your perception of the near-term prospects for Ford stock?" He tells me, "A moderate decline is very likely; a steep decline is unlikely; and a moderate gain is not likely." My question is: What is the probability of a large gain?

Information provided by my stock broker may be represented as a collection of ordered pairs:

Price: ((unlikely, steep.decline), (very.likely, moderate.decline), (not.likely, moderate.gain)).

In this collection, the second element of an ordered pair is a fuzzy event or, generally, a possibility distribution, and the first element is a fuzzy probability. The expression for Price is an example of a bimodal distribution.

The importance of the concept of a bimodal distribution derives from the fact that in the context of human-centric systems, most probability distributions are bimodal. Bimodal distributions can assume a variety of forms. The principal types are Type 1, Type 2 and Type 3. Type 1, 2 and 3 bimodal distributions have a common framework but differ in important detail. A bimodal distribution may be viewed as an important generalization of standard probability distribution. For this reason, bimodal distributions of Type 1, 2, 3 are discussed in greater detail in the following.

Type 1 (default): X is a random variable taking values in U

A1, ..., An, A are events (fuzzy sets)

pi=Prob(X is Ai), Prob(X is Ai) is Pi, i=1, ..., n, $\Sigma_i$ pi is unconstrained BD: bimodal distribution: ((P1,A1), ..., (Pn,An))

or, equivalently,

X isbm (P1\A1+ . . . +Pn\An)

Now, what is the probability, p, of A? In general, this probability is fuzzy-set-valued.

A special case of bimodal distribution of Type 1 is the basic bimodal distribution (BBD). In BBD, X is a real-valued random variable, and X and P are granular. (See FIG. 6, regarding basic bimodal distribution.)

Type 2 (fuzzy random set): X is a fuzzy-set-valued random variable with values
A1, . . . , An (fuzzy sets)
pi=Prob(X=Ai), Prob(X is Ai) is Pi, i=1, . . . , n
BD: X isrs (P1\A1+ . . . +Pn\An)
$\Sigma_i$ Pi=1,
where the Pi are granular probabilities.

Now, what is the probability, P, of A? P is not definable. What are definable are (a) the expected value of the conditional possibility of A given BD, and (b) the expected value of the conditional necessity of A given BD.

Type 3 (Dempster-Shafer): X is a random variable taking values X1, . . . , Xn with probabilities p1, . . . , pn.
Xi is a random variable taking values in Ai, i=1, . . . , n
Probability distribution of Xi in Ai, i=1, . . . , n, is not specified.

Now, what is the probability, p, that X is in A? Because probability distributions of the Xi in the Ai are not specified, p is interval-valued. What is important to note is that the concepts of upper and lower probabilities break down when the Ai are fuzzy sets.

Note: In applying Dempster-Shafer theory, it is important to check on whether the data fit Type 3 model. In many cases, the correct model is Type 1 rather than Type 3.

The importance of bimodal distributions derives from the fact that in many realistic settings a bimodal distribution is the best approximation to our state of knowledge. An example is assessment of degree of relevance, since relevance is generally not well defined. If I am asked to assess the degree of relevance of a book on knowledge representation to summarization, my state of knowledge about the book may not be sufficient to justify an answer such as 0.7. A better approximation to my state of knowledge may be "likely to be high." Such an answer is an instance of a bimodal distribution.

(h) Group (r=g)
In
X isg R,
X is a group variable, G[A], and R is a group constraint on G[A]. More specifically, if X is a group variable of the form
G[A]: $Name_1$/A1+ . . . +$Name_n$/An
or
G[A]: $\Sigma_i$ $Name_i$/Ai, for short, i=1, . . . , n,
then R is a constraint on the Ai. To illustrate, if we have a group of n Swedes, with $Name_i$ being the name of i-th Swede, and Ai being the height of $Name_i$, then the proposition "most Swedes are tall," is a constraint on the Ai which may be expressed as:

(1/n)$\Sigma$Count(tall.Swedes) is most
or, more explicitly,
(1/n)($\mu_{tall}(A_1)$+ . . . +$\mu_{tall}(A_n)$) is most,
where most is a fuzzy quantifier which is interpreted as a fuzzy number.

Operations on Generalized Constraints

There are many ways in which generalized constraints may be operated on. The basic operations—expressed in symbolic form—are the following.

(a) Conjunction
X isr R
Y iss S
(X, Y) ist T
EXAMPLE (possibilistic constraints)
X is R
Y is S
(X, Y) is R×S
where × is the Cartesian product.
EXAMPLE (probabilistic/possibilistic)
X isp R
(X, Y) is S
(X, Y) isrs T In this example, if S is a fuzzy relation then T is a fuzzy random set. What is involved in this example is a conjunction of a probabilistic constraint and a possibilistic constraint. This type of probabilistic/possibilistic constraint plays a key role in the Dempster-Shafer theory of evidence, and in its extension to fuzzy sets and fuzzy probabilities.

EXAMPLE (possibilistic/probabilistic)
X is R
(X, Y) isp S
Y/X isp T

This example, which is a dual of the proceeding example, is an instance of conditioning.

(b) Projection (possibilistic)
(X, Y) is R
X is S
where X takes values in U={u}; Y takes values in V={v}; and the projection
S=$Proj_X$ R,
is defined as $\mu_S(u)=\mu_{Proj\,X\,R}(u)=\max_v \mu_R(u,v)$, where $\mu_R$ and $\mu_S$ are the membership functions of R and S, respectively.

(c) Projection (probabilistic)
(X, Y) isp R
X isp S
where X and Y are real-valued random variables, and R and S are the probability distributions of (X, Y) and X, respectively. The probability density function of S, $p_S$, is related to that of R, $p_R$, by the familiar equation $p_S(u)=\int p_R(u,v)dv$ with the integral taken over the real line.

(d) Propagation
f(X) isr R
g(X) iss S
where f and g are functions or functionals.
EXAMPLE (possibilistic constraints)
f(X) is R
g(X) is S
where R and S are fuzzy sets. In terms of the membership function of R, the membership function of S is given by the solution of the variational problem $\mu_S(v)=\sup_u(\mu_R f(u))$ subject to $v=g(u)$.

Note. The constraint propagation rule described in this example is the well-known extension principle of fuzzy logic. Basically, this principle provides a way of computing the possibilistic constraint on g(X) given a possibilistic constraint on f(X).

Figure 7:
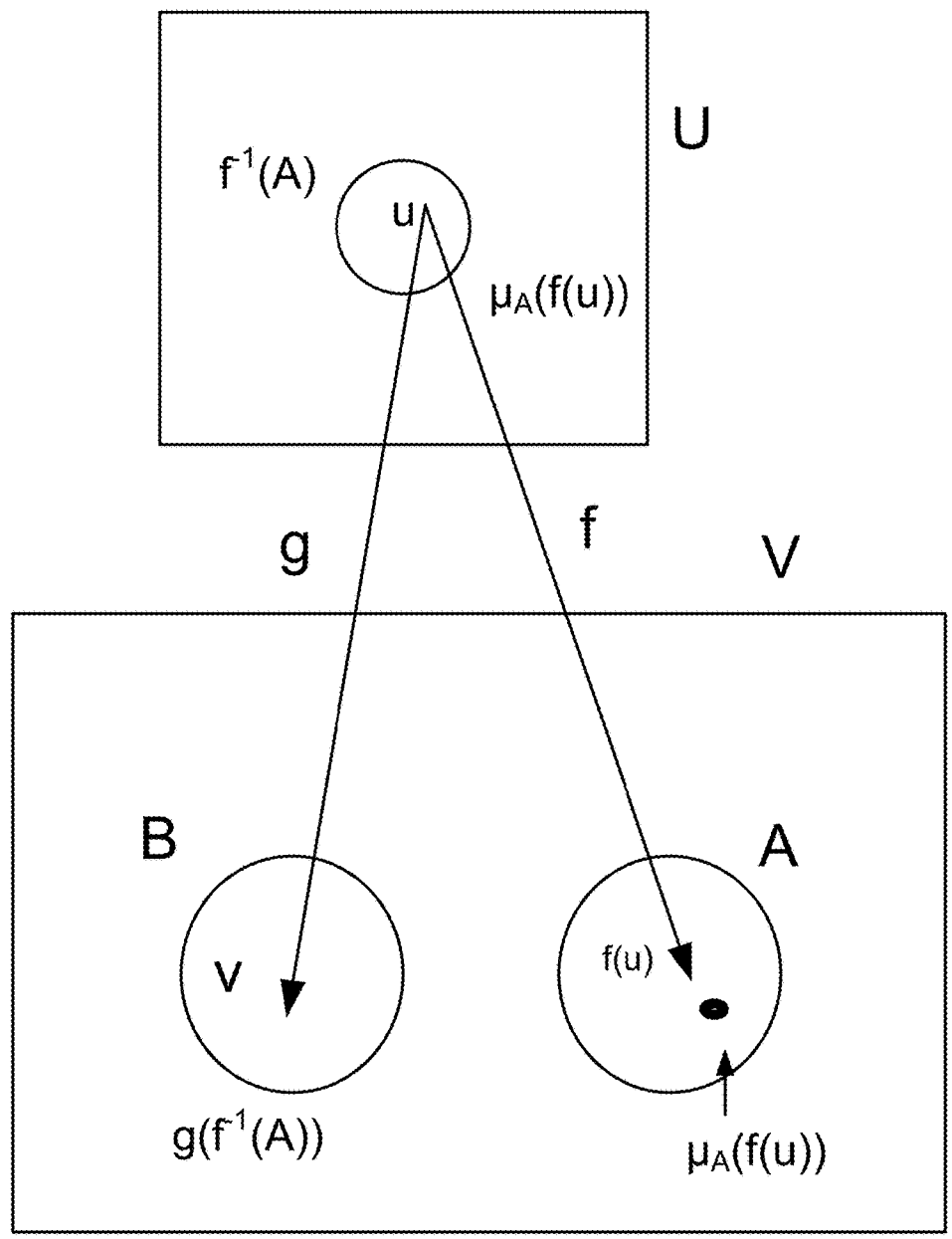
FIG. 7 shows the extension principle.

See FIG. 7, regarding extension principle:
f(X) is A g(X) is B $$\mu_S(v) = \sup_u(\mu_A(f(u)))$$

subject to $$v = g(u).$$

Primary Constraints, Composite Constraints and Standard Constraints

Among the principal generalized constraints there are three that play the role of primary generalized constraints. They are:

Possibilistic constraint: X is R
Probabilistic constraint: X isp R
and
Veristic constraint: X isv R A special case of primary constraints is what may be called standard constraints: bivalent possibilistic, probabilistic and bivalent veristic. Standard constraints form the basis for the conceptual framework of bivalent logic and probability theory. A generalized constraint, GC, is composite if it can be generated from other generalized constraints through conjunction, and/or projection, and/or constraint propagation, and/or qualification and/or possibly other operations. For example, a random-set constraint may be viewed as a conjunction of a probabilistic constraint and either a possibilistic or veristic constraint. The Dempster-Shafer theory of evidence is, in effect, a theory of possibilistic random-set constraints. The derivation graph of a composite constraint defines how it can be derived from primary constraints.

The three primary constraints—possibilistic, probabilistic and veristic—are closely related to a concept which has a position of centrality in human cognition—the concept of partiality. In the sense used here, partial means: a matter of degree or, more or less equivalently, fuzzy. In this sense, almost all human concepts are partial (fuzzy). Familiar examples of fuzzy concepts are: knowledge, understanding, friendship, love, beauty, intelligence, belief, causality, relevance, honesty, mountain and, most important, truth, likelihood and possibility. Is a specified concept, C, fuzzy? A simple test is: If C can be hedged, then it is fuzzy. For example, in the case of relevance, we can say: very relevant, quite relevant, slightly relevant, etc. Consequently, relevance is a fuzzy concept.

The three primary constraints may be likened to the three primary colors: red, blue and green. In terms of this analogy, existing theories of uncertainty may be viewed as theories of different mixtures of primary constraints. For example, the Dempster-Shafer theory of evidence is a theory of a mixture of probabilistic and possibilistic constraints. The Generalized Theory of Uncertainty (GTU) embraces all possible mixtures. In this sense the conceptual structure of GTU accommodates most, and perhaps all, of the existing theories of uncertainty.

The Generalized Constraint Language and Standard Constraint Language

A concept which has a position of centrality in PNL is that of Generalized Constraint Language (GCL). Informally, GCL is the set of all generalized constraints together with the rules governing syntax, semantics and generation. Simple examples of elements of GCL are:

((X, Y) isp A) ∧ (X is B)
(X isp A) ∧ ((X, Y) isv B)
$Proj_Y((X \text{ is } A) \wedge ((X, Y) \text{ isp } B))$,
where ∧ is conjunction.

A very simple example of a semantic rule is:
(X is A) ∧ (Y is B) → Poss(X=u, Y=v) = $\mu_A(u) \wedge \mu_B(v)$,
where u and v are generic values of X, Y, and μA and μB are the membership functions of A and B, respectively.

In principle, GCL is an infinite set. However, in most applications only a small subset of GCL is likely to be needed.

In PNL, the set of all standard constraints together with the rules governing syntax, semantics and generation constitute the Standard Constraint Language (SCL). SCL is a subset of GCL.

The Concept of Cointensive Precisiation

As was pointed out already, much of world knowledge and web knowledge is expressed in a natural language. For this reason, mechanization of natural language understanding is of direct relevance to enhancement of web intelligence. In recent years, considerable progress has been made in areas of computational linguistics which relate to mechanization of natural language understanding. But what is widely unrecognized is that there is a fundamental limitation to what can be achieved through the use of commonly-employed methods of meaning representation. The aim of what follows is, first, to highlight this limitation and, second, to present ways of removing it.

To understand the nature of the limitation, two facts have to be considered. First, as was pointed out earlier, a natural language, NL, is basically a system for describing perceptions; and second, perceptions are intrinsically imprecise, reflecting the bounded ability of human sensory organs, and ultimately the brain, to resolve detail and store information. A direct consequence of imprecision of perceptions is semantic imprecision of natural languages. Semantic imprecision of natural languages is not a problem for humans, but is a major problem for machines.

To clarify the issue, let p be a proposition, concept, question or command. For p to be understood by a machine, it must be precisiated, that is, expressed in a mathematically well-defined language. A precisiated form of p, Pre(p), will be referred to as a precisiand of p and will be denoted as p*. The object of precisiation, p, will be referred to us precisiend.

To precisiate p we can employ a number of meaning-representation languages, e.g., Prolog, predicate logic, semantic networks, conceptual graphs, LISP, SQL, etc. The commonly-used meaning-representation languages are bivalent, i.e., are based on bivalent logic. Are we moving in the right direction when we employ such languages for mechanization of natural language understanding? The answer is: No. The reason relates to an important issue which we have not addressed: cointension of p*, with intension used in its logical sense as attribute-based meaning. More specifically, cointension is a measure of the goodness of fit of the intension of a precisiand, p*, to the intended intension of precisiend, p. Thus, cointension is a desideratum of precisiation. What this implies is that mechanization of natural language understanding requires more than precisiation—it requires cointensive precisiation. Note that definition is a form of precisiation. In plain words, a definition is cointensive if its meaning is a good fit to the intended meaning of the definiendum.

Here is where the fundamental limitation which was alluded to earlier comes into view. In a natural language, NL, most p's are fuzzy, that is, are in one way or another, a matter of degree. Simple examples: propositions "most Swedes are tall" and "overeating causes obesity;" concepts "mountain" and "honest;" question "is Albert honest?" and command "take a few steps."

Employment of commonly-used meaning-representation languages to precisiate a fuzzy p leads to a bivalent (crisp) precisiand p*. The problem is that, in general, a bivalent p* is not cointensive. As a simple illustration, consider the concept of recession. The standard definition of recession is: A period of general economic decline; specifically, a decline in GDP for two or more consecutive quarters. Similarly, a definition of bear market is: We classify a bear market as a 30 percent decline after 50 days, or a 13 percent decline after 145 days. (Robert Shuster, Ned Davis Research.) Clearly, neither definition is cointensive.

Another example is the classical definition of stability. Consider a ball of diameter D which is placed on an open bottle whose mouth is of diameter d. If D is somewhat larger than d, the configuration is stable: Obviously, as D increases, the configuration becomes less and less stable. But, according to Lyapounov's bivalent definition of stability, the configuration is stable for all values of D greater than d. This contradiction is characteristic of crisp definitions of fuzzy concepts—a well-known example of which is the Greek sorites (heap) paradox.

The magnitude of the problem becomes apparent when we consider that many concepts in scientific theories are fuzzy, but are defined and treated as if they are crisp. This is particularly true in fields in which the concepts which are defined are descriptions of perceptions. To remove the fundamental limitation, bivalence must be abandoned. Furthermore, new concepts, ideas and tools must be developed and deployed to deal with the issues of cointensive precisiation, definability and deduction. The principal tools are Precisiated Natural Language (PNL); Protoform Theory (PFT); and the Generalized Theory of Uncertainty (GTU). These tools form the core of what may be called the Computational Theory of Precisiation of Meaning (CTPM). The centerpiece of CTPM is the concept of a generalized constraint.

The concept of a generalized constraint plays a key role in CTPM by providing a basis for precisiation of meaning More specifically, if p is a proposition or a concept, its precisiand, Pre(p), is represented as a generalized constraint, GC. Thus, Pre(p)=GC. In this sense, the concept of a generalized constraint may be viewed as a bridge from natural languages to mathematics.

Figure 8:
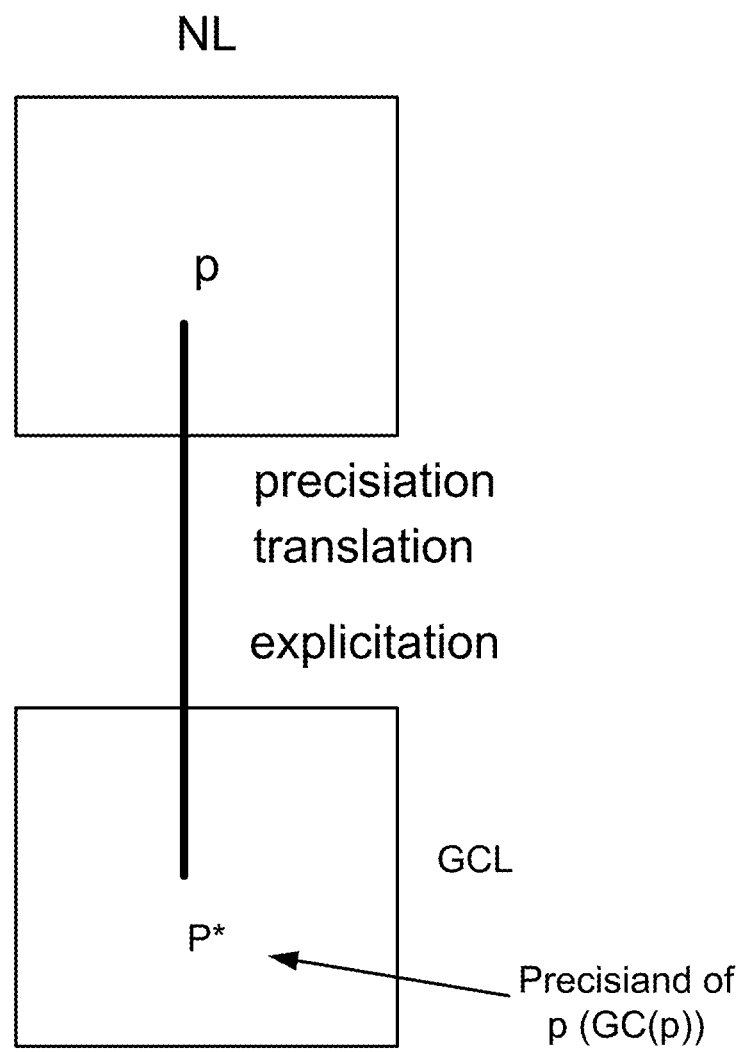
FIG. 8 shows precisiation, translation into GCL.

See FIG. 8, regarding precisiation=translation into GCL:
Annotated translation:
p→X/A isr R/B←GC(p)

Representing precisiands of p as elements of GCL is the pivotal idea in CTPM. Each precisiand is associated with the degree to which it is cointensive with p. Given p, the problem is that of finding those precisiands which are cointensive, that is, have a high degree of cointension. If p is a fuzzy proposition or concept, then in general there are no cointensive precisiands in SCL.

In CTPM, a refinement of the concept of precisiation is needed. First, a differentiation is made between v-precision (precision in value) and m-precision (precision in meaning) For example, proposition p: X is 5, is both v-precise and m-precise; p: X is between 5 and 7, is v-imprecise and m-precise; and p: X is small, is both v-imprecise and m-imprecise; however, p can be m-precisiated by defining small as a fuzzy set or a probability distribution. A perception is v-imprecise and its description is m-imprecise. PNL makes it possible to m-precisiate descriptions of perceptions.

Granulation of a variable, e.g., representing the values of age as young, middle-aged and old, may be viewed as a form of v-imprecisiation. Granulation plays an important role in human cognition by serving as a means of (a) exploiting a tolerance for imprecision through omission of irrelevant information; (b) lowering precision and thereby lowering cost; and (c) facilitating understanding and articulation. In fuzzy logic, granulation is m-precisiated through the use of the concept of a linguistic variable. Further refinement of the concept of precisiation relates to two modalities of m-precisiation: (a) human-oriented, denoted as mh-precisiation; and (b) machine-oriented, denoted as mm-precisiation. Unless stated to the contrary, in CTPM, precisiation should be understood as mm-precisiation. (See FIG. 9, regarding modalities of m-precisiation.)

Figure 36A:
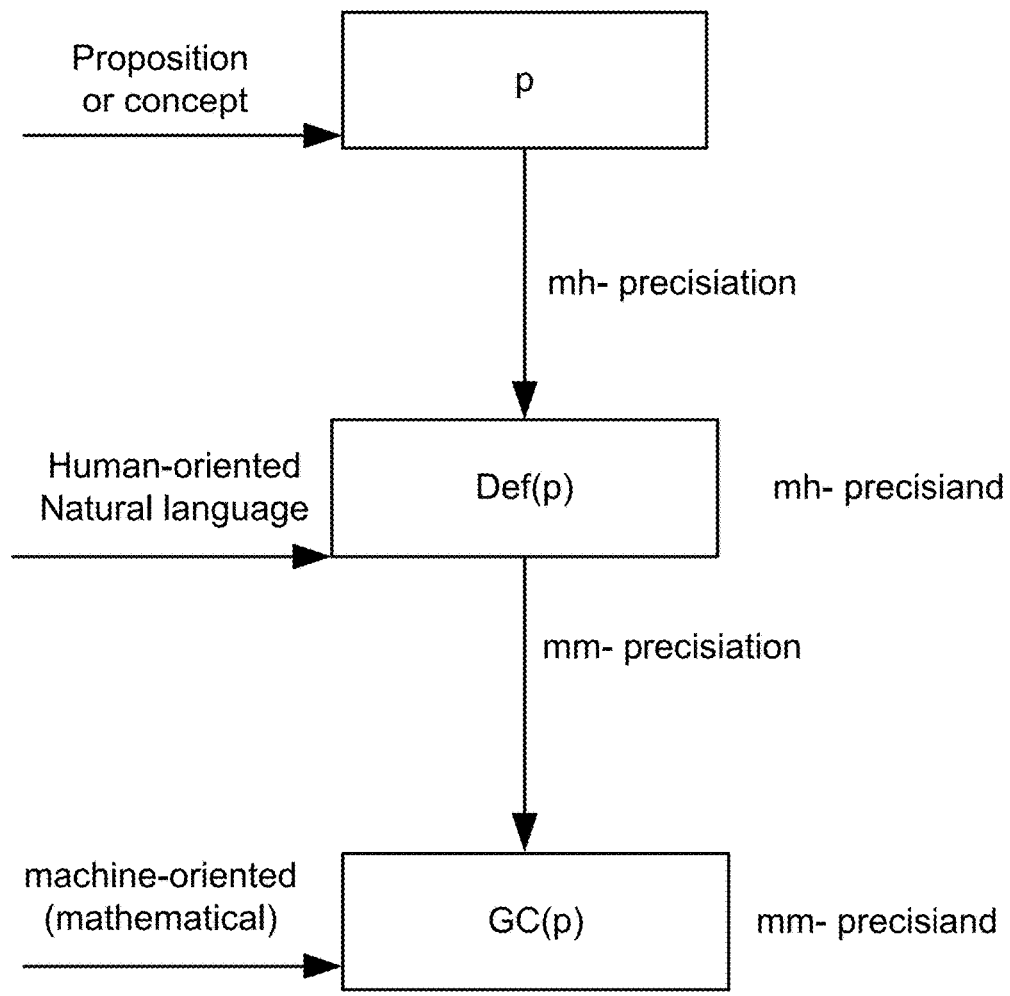
FIG. 36(a) shows bimodal lexicon (PNL).

In a bimodal dictionary or lexicon, the first entry, p, is a concept or proposition; the second entry, p*, is mh-precisiand of p; and the third entry is mm-precisiand of p. To illustrate, the entries for recession might read: mh-precisiand—a period of general economic decline; and mm-precisiand—a decline in GDP for two or more consecutive quarters. (See FIG. 36(a), regarding bimodal lexicon (PNL).)

There is a simple analogy which helps to understand the meaning of cointensive precisiation. Specifically, a proposition, p, is analogous to a system, S; precisiation is analogous to modelization; a precisiand, expressed as a generalized constraint, GC(p), is analogous to a model, M(S), of S; test-score function is analogous to input-output relation; cointensive precisiand is analogous to well-fitting model; GCL is analogous to the class of all fuzzy-logic-based systems; and SCL is analogous to the subclass of all bivalent-logic-based systems. To say that, in general, a cointensive definition of a fuzzy concept cannot be formulated within the conceptual structure of bivalent logic and probability theory, is similar to saying that, in general, a linear system cannot be a well-fitting model of a nonlinear system.

Figure 36B:
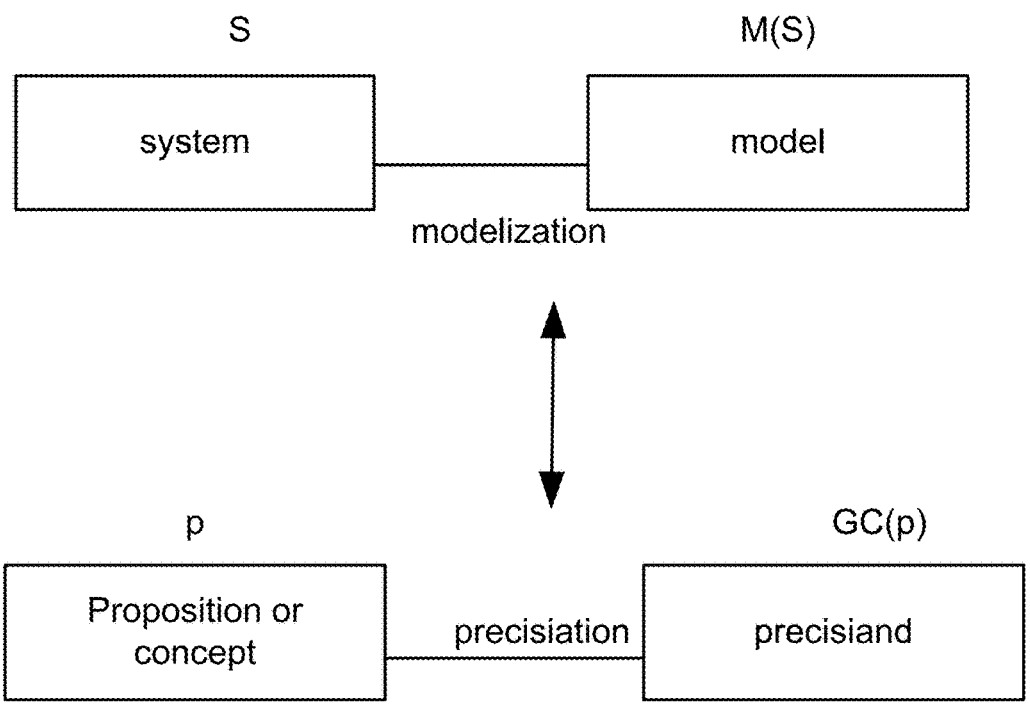
FIG. 36(b) shows analogy between precisiation and modelization.

See FIG. 36(b), regarding analogy between precisiation and modelization:
input-output relation→intension
degree of match between M(S) and S→cointension Ramifications of the concept of cointensive precisiation extend well beyond mechanization of natural language understanding. A broader basic issue is validity of definitions in scientific theories, especially in the realms of human-oriented fields such as law, economics, medicine, psychology and linguistics. More specifically, the concept of cointensive precisiation calls into question the validity of many of the existing definitions of basic concepts—among them the concepts of causality, relevance, independence, stability, complexity, and optimality.

Translation of p into GCL is made more transparent though annotation. To illustrate,
(a) p: Monika is young→X/Age(Monika) is R/young
(b) p: It is likely that Monika is young→Prob(X/Age(Monika) is R/young) is S/likely Note: Example (b) is an instance of probability qualification.

More concretely, let g(u) be the probability density function of the random variable, Age(Monika). Then, with reference to our earlier discussion of probability qualification, we have:

$$Prob(\text{Age(Monika) is young}) \text{ is likely} \rightarrow \int_0^{100} g(u)\mu_{young}(u)\,du$$

is likely, or, in annotated form, $$GC(g) = X \Big/ \int_0^{100} g(u)\mu_{young}(u)\,du,$$

is R/likely.

The test-score of this constraint on g is given by $$ts(g) = \mu_{likely}\!\left(\int_0^{100} g(u)\mu_{young}(u)\,du\right)$$

(c) p: Most Swedes are tall

Following (b), let h(u) be the count density function of Swedes, meaning that h(u) du=fraction of Swedes whose height lies in the interval [u, u+du]. Assume that height of Swedes lies in the interval [a, b]. Then, fraction of tall Swedes:

$$\int_a^b h(u)\mu_{tall}(u)\,du,$$

is most.

Interpreting this relation as a generalized constraint on h, the test-score may be expressed as:

$$ts(h) = \mu_{most}\!\left(\int_0^h h(u)\mu_{tall}(u)\,du\right)$$

In summary, precisiation of "Most Swedes are tall" may be expressed as the generalized constraint.

$$\text{Most Swedes are tall} \to GC(h) = \mu_{most}\!\left(\int_a^b h(u)\mu_{tall}(u)\,du\right)$$

An important application of the concept of precisiation relates to precisiation of propositions of the form "X is approximately a," where a is a real number. How can "approximately a," or *a (for short), be precisiated? In other words, how can the uncertainty associated with the value of X which is described as *a, be defined precisely? There is a hierarchy of ways in which this can be done. The simplest is to define *a as a. This mode of precisiation will be referred to as singular precisiation, or s-precisiation, for short. s-precisiation is employed very widely, especially in probabilistic computations in which an imprecise probability, *a, is computed with as if it were an exact number, a.

The other ways will be referred to as granular precisiation, or g-precisiation, for short. In g-precisiation, *a is treated as a granule. What we see is that various modes of precisiating *a are instances of the generalized constraint. The concept of precisiation has an inverse—the concept of imprecisiation, which involves replacing a with *a, with the understanding that *a is not unique. Imprecisiation has a negative connotation. In fact, imprecisiation serves an important purpose. More specifically, consider a proposition p of the form p: X is V, where X is a variable and V is its value. X may assume a variety of forms. In particular, X may be a real-valued variable, an n-ary variable, a function or a relation. The value, V, is v-precise if it is singular, that is, V is a singleton. V is v-imprecise if it is granular. In this framework, v-imprecisiation may be interpreted as a transition from singular to granular value of V.

v-imprecisiation is forced (necessary) when the value of V is not known precisely. v-imprecisiation is deliberate (optional) if there is no need for V to be known precisely. In this case, what may be called v-imprecisiation principle comes into play.

v-imprecisiation principle: Precision carries a cost. If there is a tolerance for imprecision, exploit it by employing v-imprecisiation to achieve lower cost, robustness, tractability, decision-relevance and higher level of confidence.

A word about confidence: If V is uncertain, the confidence in p, Con(p), may be defined as the probability that p is true. Generally, v-imprecisiation of V serves to increase Con(p). For example, Con(Carol is young)>Con(Carol is 23). Thus, as a rule, confidence increases when specificity decreases.

An important example is granulation. In fuzzy logic, granulation may be interpreted as v-imprecisiation followed by mm-precisiation. In this perspective, the concept of granulation—in combination with the associated concept of a linguistic variable—may be viewed as one of the major contributions of fuzzy logic.

A basic problem which relates to imprecisiation is the following. Assume for simplicity that we have two linear equations involving real-valued coefficients and real-valued variables:

$$a_{11}X + a_{12}Y = b_1,$$

$$a_{21}X + a_{22}Y = b_2.$$

Solutions of these equations read, $$X = ((a_{22}b_1 - a_{12}b_2)/(a_{11}a_{22} - a_{12}a_{21})),$$

$$Y = ((a_{11}b_2 - a_{21}b_1)/(a_{11}a_{22} - a_{12}a_{21})).$$

Now suppose that we imprecisiate the coefficients, replacing, $a_{ij}$ with $*a_{ij}$, i, j=1, 2, and replacing $b_i$ with $*b_i$, i=1, 2. How can we solve these equations when imprecisiated coefficients are defined as generalized constraints?

There is no general answer to this question. Assuming that all coefficients are defined in the same way, the method of solution will depend on the modality of the constraint. For example, if the coefficients are interval-valued, the problem falls within the province of interval analysis. If the coefficients are fuzzy-interval-valued, the problem falls within the province of the theory of relational equations. And if the coefficients are real-valued random variables, we are dealing with the problem of solution of stochastic equations.

One complication is the following. If (a) we solve the original equations, as we have done above; (b) imprecisiate the coefficients in the solution; and (c) employ the extension principle to complete X and Y, will we obtain solutions of imprecisiated equations? The answer, in general, is: No.

Nevertheless, when we are faced with a problem which we do not know how to solve correctly, we proceed as if the answer is: Yes. This common practice may be described as Precisiation/Imprecisiation Principle which is defined in the following.

Precisiation/Imprecisiation Principle (P/I Principle)

Informally, let f be a function or a functional. Y=f(X), where X and Y are assumed to be imprecise, Pr(X) and Pr(Y) are precisiations of X and Y, and *Pr(X) and *Pr(Y) are imprecisiations of Pr(X) and Pr(Y), respectively. In symbolic form, the P/I principle may be expressed as $$f(X)^* = *f(Pr(X)),$$

where *= denotes "approximately equal," and *f is imprecisiation of f. In words, to compute f(X) when X is imprecise, (a) precisiate X, (b) compute f(Pr(X)); and (c) imprecisiate f(Pr(X)). Then, usually, *f(Pr(X)) will be approximately equal to f(X). An underlying assumption is that approximations are commensurate in the sense that the closer Pr(X) is to X, the closer f(Pr(X)) is to f(X). This assumption is related to the concept of gradual rules of Dubois and Prade.

As an example, suppose that X is a real-valued function; f is the operation of differentiation, and *X is the fuzzy graph of X. Then, using the P/I principle, *f(X) is obtained. It should be underscored that imprecisiation is an imprecise concept.

Use of the P/I principle underlies many computations in science, engineering, economics and other fields. In particular, as was alluded to earlier, this applies to many computations in probability theory which involve imprecise probabilities. It should be emphasized that the P/I principle is neither normative (prescriptive) nor precise; it merely describes imprecisely what is common practice—without suggesting that common practice is correct.

Precisiation of Propositions

In preceding discussion, we focused our attention on precisiation of propositions of the special form "X is *a." In the following, we shall consider precisiation in a more general setting. In this setting, the concept of precisiation in PNL opens the door to a wide-ranging enlargement of the role of natural languages in scientific theories, especially in fields such as economics, law and decision analysis.

Within CTPM, precisiation of propositions—and the related issues of precisiation of questions, commands and concepts—falls within the province of PNL. As was stated earlier, the point of departure in PNL is representation of a precisiand of a proposition, p, as a generalized constraint.

p→X isr R.

To illustrate precisiation of propositions and questions, it will be useful to consider some examples.

(a) The Robert example:
p: Usually Robert returns from work at about 6 pm.
Q: What is the probability that Robert is home at about 6:15 pm?
Precisiation of p may be expressed as
p: Prob(Time(Return(Robert))) is *6:00 pm) is usually
where "usually" is a fuzzy probability.
Assuming that Robert stays home after returning from work, precisiation of q may be expressed as
q: Prob(Time(Return(Robert))) is ≤∘6:15 pm) is A?
where ∘ is the operation of composition, and A is a fuzzy probability.

(b) The balls-in-box problem:
p1: A box contains about 20 black and white balls
p2: Most are black
p3: There are several times as many black balls as white balls
q1: What is the number of white balls?
q2: What is the probability that a ball drawn at random is white?

Let X be the number of black balls and let Y be the number of white balls. Then, in precisiated form, the statement of the problem may be expressed as:
For the data, we have:
p1: (X+Y) is *20
p2: X is most×*20
p3: X is several×Y, And, for the questions, we have:
q1: Y is ?A
q2: Y/*20 is ?B,
where Y/*20 is the granular probability that a ball drawn at random is white.

Solution of these equations reduces to an application of fuzzy integer programming. (See FIG. 37, which specifies a region of intersections or overlaps, corresponding to pairs of X and Y coordinates, which provide solutions for our questions, related to the values for Y.)

(c) The tall Swedes problem:
p: Most Swedes are tall.
Q: What is the average height of Swedes?
Q: How many Swedes are short?
As was shown earlier,
p:

$$\text{Most Swedes are tall} \rightarrow \int_a^b h(u)\mu_{tall}(u)du,$$

is most, where h is the count density function.
Precisiations of q1 and q2 may be expressed as $$q1: \int_a^b uh(u)\,du, \text{ is } ?A,$$

where A is a fuzzy number which represents the average height of Swedes, and $$q2: \int_a^b h(u)\mu_{short}(u)du, \text{ is } ?B,$$

where $\mu_{short}$ is the membership function of short, and B is the fraction of short Swedes.

(d) The partial existence problem:
X is a real number. I am uncertain about the value of X. What I know about X is:
p1: X is much larger than approximately a,
p2: X is much smaller than approximately b,
where a and b are real numbers, with a<b.
What is the value of X?
In this case, precisiations of data may be expressed as
p1: X is much.larger ∘ *a
p2: X is much.smaller ∘ *b,
where ∘ is the operation of composition. Precisiation of the question is:
q: X is ?A,
where A is a fuzzy number. The solution is immediate:
X is (much.larger ∘ *a ∧ much.smaller ∘ *b),
when ∧ is min or a t-norm. In this instance, depending on a and b, X may exist to a degree.

These examples point to an important aspect of precisiation. Specifically, to precisiate p, we have to precisiate or, equivalently, calibrate its lexical constituents. For example, in the case of "Most Swedes are tall," we have to calibrate "most" and "tall." Likewise, in the case of the Robert example, we have to calibrate "about 6:00 pm," "about 6:15 pm" and "usually." In effect, we are composing the meaning of p from the meaning of its constituents. This process is in the spirit of Frege's principle of compositionality, Montague grammar and the semantics of programming languages.

In probability theory, for example, independence of events is a bivalent concept. But, in reality, independence is a matter of degree, i.e., is a fuzzy concept. PNL, used as a definition language, makes it possible, more realistically, to define independence and other bivalent concepts in probability theory as fuzzy concepts. For this purpose, when PNL is used as a definition language, a concept is first defined in a natural language and then its definition is precisiated through the use of PNL.

The Concept of a Protoform

Viewed in a broader perspective, what should be noted is that precisiation of meaning is not the ultimate goal—it is an intermediate goal. Once precisiation of meaning is achieved, the next goal is that of deduction from decision-relevant information. The ultimate goal is decision.

Figure 39:
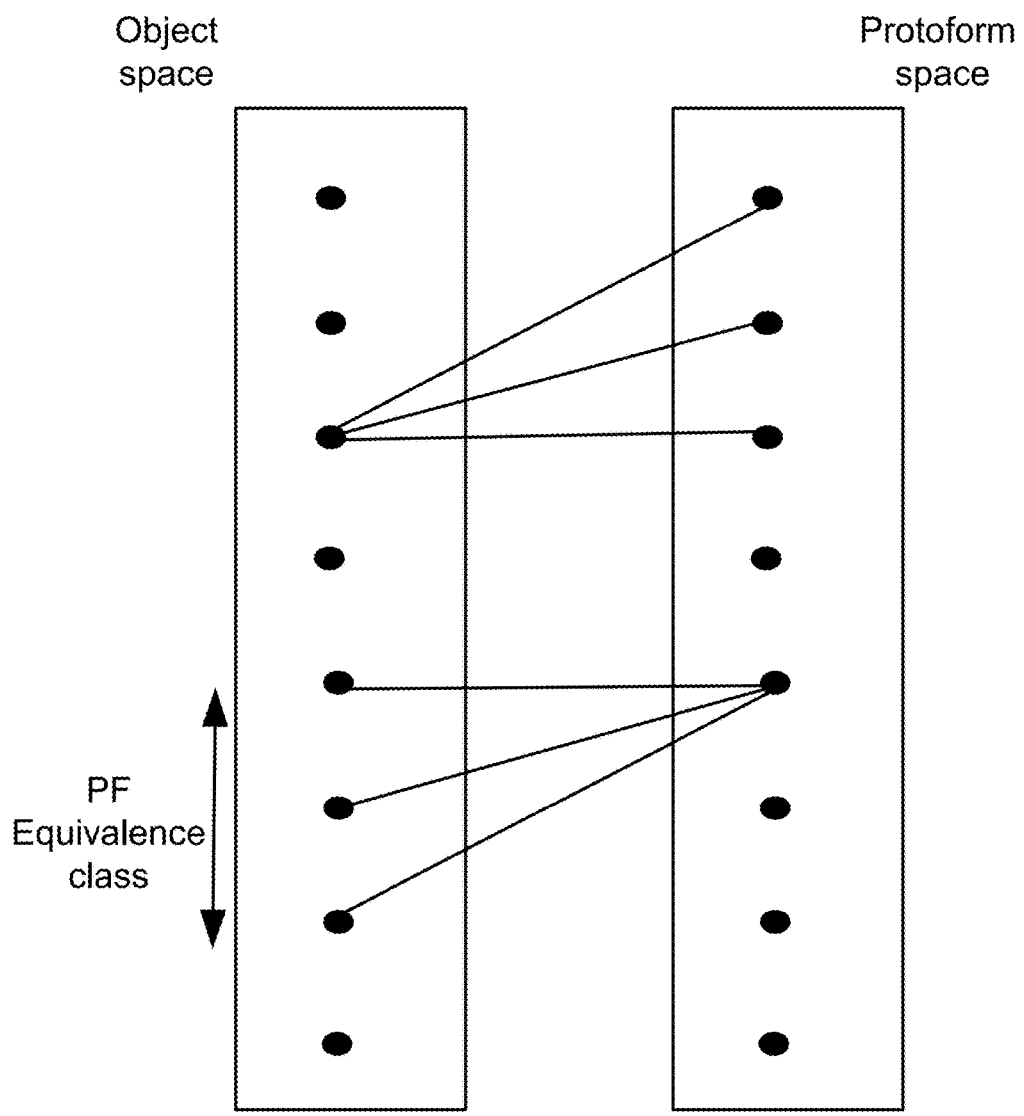
FIG. 39 shows protoforms and PF-equivalence.

In CTPM, a concept which plays a key role in deduction is that of a protoform—an abbreviation for prototypical form. Informally, a protoform of an object is its abstracted summary. More specifically, a protoform is a symbolic expression which defines the deep semantic structure of an object such as a proposition, question, command, concept, scenario, or a system of such objects. In the following, our attention will be focused on protoforms of propositions, with PF(p) denoting a protoform of p. Abstraction has levels, just as summarization does. For this reason, an object may have a multiplicity of protoforms. Conversely, many objects may have the same protoform. Such objects are said to be protoform-equivalent, or PF-equivalent, for short. The set of protoforms of all precisiable propositions in NL, together with rules which govern propagation of generalized constraints, constitute what is called the Protoform Language (PFL). (See FIG. 38, regarding definition of protoform of p, with S(p), summary of p, and PF(p), abstracted summary of p, deep structure of p.) (See also FIG. 39, regarding protoforms and PF-equivalence. Note that at a given level of abstraction and summarization, objects p and q are PF-equivalent, if PF(p)=PF(q).)

EXAMPLES

Monika is young→Age(Monika) is young→A(B) is C, where Age refers to A, Monika to B (as instantiation), and Young to C (as abstraction).

Monika is much younger than Pat→(A(B), A(C)) is R, where Age refers to A, Monika to B, Pat to C, and "much younger" to R.

distance between New York and Boston is about 200 mi→A(B,C) is R, where Distance refers to A, New York to B, Boston to C, and "about 200 miles" to D.

usually Robert returns from work at about 6 pm→Prob {A is B} is C, where "Time(Robert.returns.from.work)" refers to A, "about 6 pm" to B, and Usually to C.

Carol lives in a small city near San Francisco→A(B(C)) is (D and E), where "small city" refers to E, "city near SF" to D, Carol to C, Residence to B, and Location to A.

most Swedes are tall→1/nΣCount(G[A] is R) is Q, where Most refers to Q, Swedes to G, tall to R, and Height to A.

Figure 40:
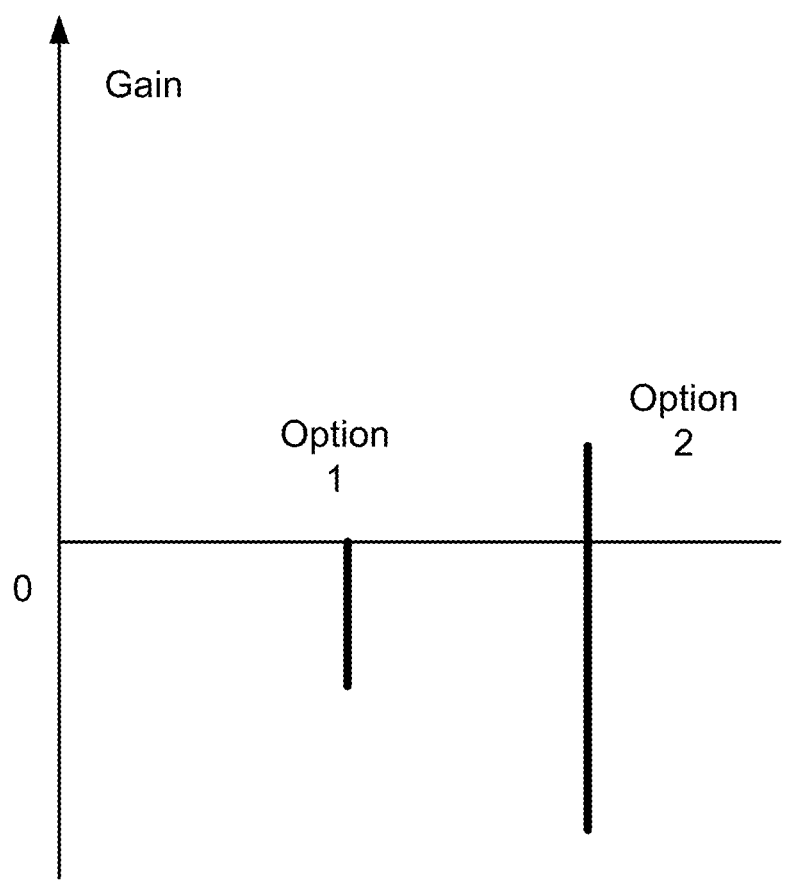
FIG. 40 shows a gain diagram for a situation where (as an example) Alan has severe back pain, with respect to the two options available to Alan.

Another example: Alan has severe back pain. He goes to see a doctor. The doctor tells him that there are two options: (1) do nothing; and (2) do surgery. In the case of surgery, there are two possibilities: (a) surgery is successful, in which case, Alan will be pain free; and (b) surgery is not successful, in which case Alan will be paralyzed from the neck down. (See FIG. 40)

Protoformal Deduction

The rules of deduction in CTPM are, basically, the rules which govern constraint propagation. In CTPM, such rules reside in the Deduction Database (DDB). The Deduction Database comprises a collection of agent-controlled modules and submodules, each of which contains rules drawn from various fields and various modalities of generalized constraints. A typical rule has a symbolic part, which is expressed in terms of protoforms; and a computational part which defines the computation that has to be carried out to arrive at a conclusion.

Figure 41:
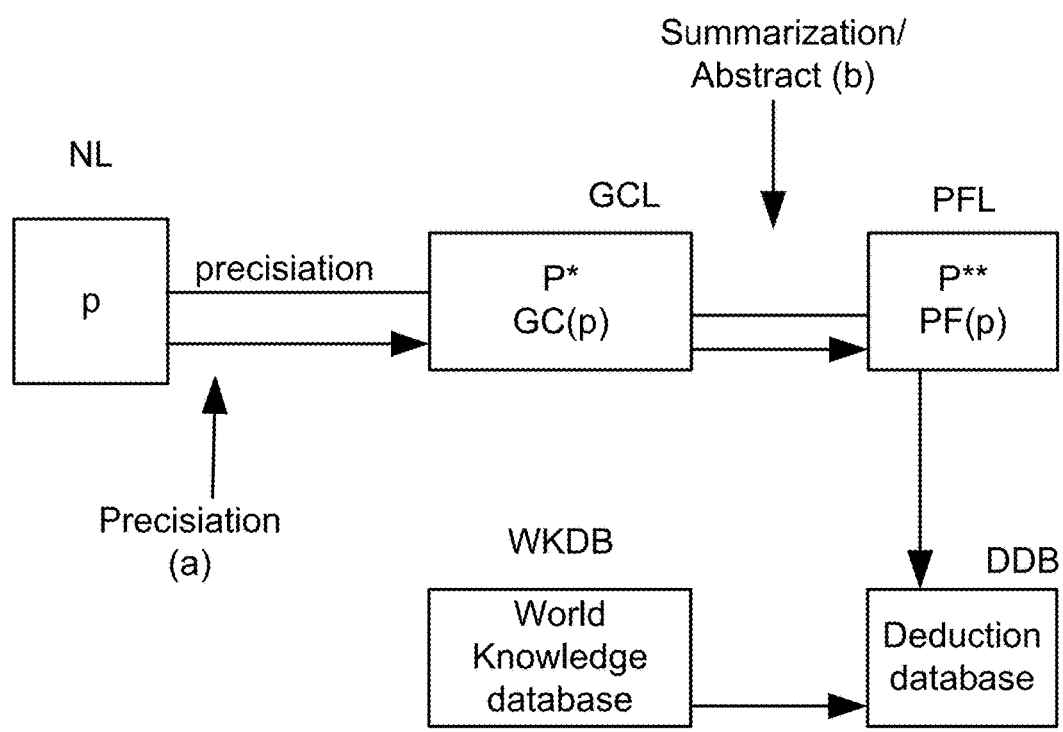
FIG. 41 shows the basic structure of PNL.

See FIG. 41, regarding basic structure of PNL:

In PNL, deduction=generalized constraint propagation

PFL: Protoform Language

DDB: deduction database=collection of protoformal rules governing generalized constraint propagation WKDB: World Knowledge Database (PNL-based)

Figure 42:
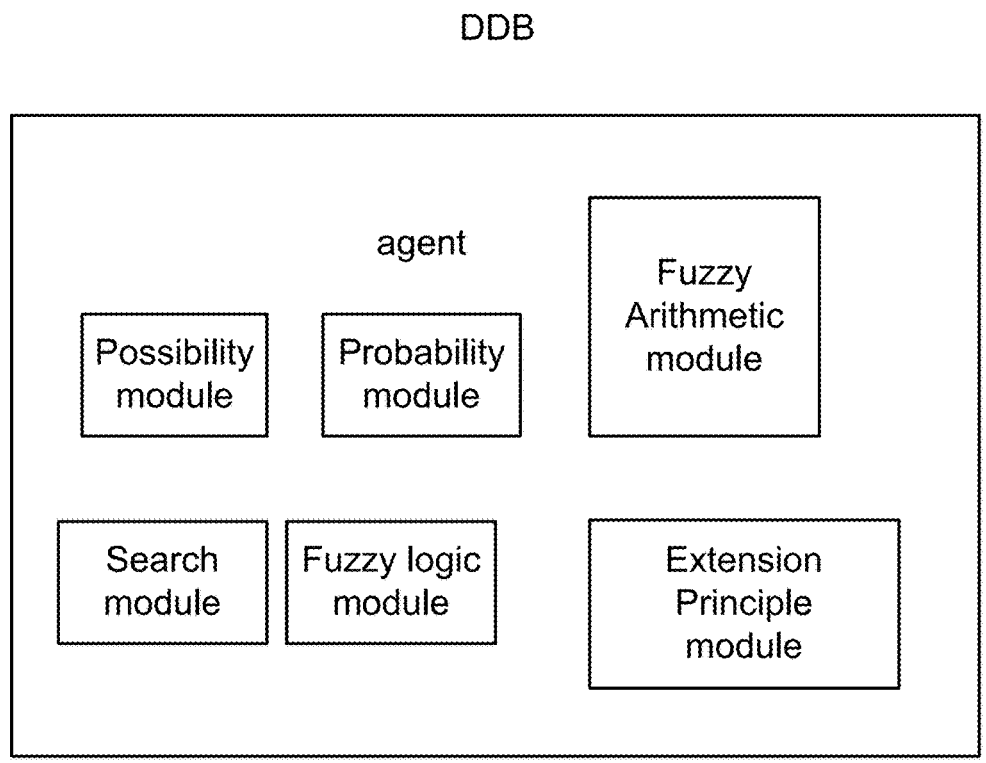
FIG. 42 shows the structure of deduction database, DDB.

See also FIG. 42, regarding structure of deduction database, DDB.

(a) Computational rule of inference:

For symbolic part, we have:

X is A (X, Y) is B

Y is C

For computational part, we have:

$$\mu_C(v) = \max_u(\mu_A(u) \wedge \mu_B(u,v))$$

(b) Intersection/product syllogism:

For symbolic part, we have:

Q1 A's are B's

Q2 (A&B)'s are C's

Q3 A's are (B&C)'s

For computational part, we have:

$$Q3 = Q1 * Q2$$

where Q1 and Q2 are fuzzy quantifiers; A,B,C are fuzzy sets; * is product in fuzzy arithmetic.

(c) Basic extension principle:

For symbolic part, we have:

X is A f(X) is B

For computational part, we have:

$$\mu_B(v) = \sup_u(\mu_A(u))$$

subject to $$v = f(u)$$

g is a given function or functional; A and B are fuzzy sets.

(d) Extension principle:

This is the principal rule governing possibilistic constraint propagation.

For symbolic part, we have:

f(X) is A g(X) is B

For computational part, we have:

$$\mu_B(v) = \sup_u(\mu_B(f(u)))$$

subject to $$v = g(u)$$

Note. The extension principle is a primary deduction rule in the sense that many other deduction rules are derivable from the extension principle. An example is the following rule.

(e) Basic probability rule:
For symbolic part, we have:
Prob(X is A) is B
Prob(X is C) is D
For computational part, we have:

$$\mu_D(v) = \sup_r \left( \mu_B \left( \int_U \mu_A(u) r(u) du \right) \right)$$

subject to $$v = \int_U \mu_C(u) r(u) du,$$

$$\int_U r(u) du = 1.$$

X is a real-valued random variable; A, B, C, and D are fuzzy sets: r is the probability density of X; and U={u}. To derive this rule, we note that $$Prob(X \text{ is } A) \text{ is } B \rightarrow \int_U r(u) \mu_A(u) du \text{ is } B$$

$$Prob(X \text{ is } C) \text{ is } D \rightarrow \int_U r(u) \mu_C(u) du \text{ is } D$$

which are generalized constraints of the form
f(r) is B
g(r) is D.
Applying the extension principle to these expressions, we obtain the expression for D which appears in the basic probability rule.
(f) Bimodal interpolation rule:
The bimodal interpolation rule is a rule which resides in the Probability module of DDB. The symbolic and computational parts of this rule are:
Symbolic parts:
Prob(X is Ai) is Pi
Prob(X is A) is Q
where i=1, . . . , n
Computational parts:

$$\mu_Q(v) = \sup_r \left( \mu_{P1} \left( \int_U \mu_{A1}(u) r(u) du \right) \wedge \ldots \wedge \mu_{Pn} \left( \int_U \mu_{An}(u) r(u) du \right) \right)$$

subject to $$v = \int_U \mu_A(u) r(u) du$$

$$\int_U r(u) du = 1$$

In this rule, X is a real-valued random variable; r is the probability density of X; and U is the domain of X.
Note: The probability rule is a special case of the bimodal interpolation rule.
What is the expected value, E(X), of a bimodal distribution? The answer follows through application of the extension principle:

$$\mu_{E(X)}(v) = \sup_r \left( \mu_{P1} \left( \int_U \mu_{A1}(u) r(u) du \right) \wedge \ldots \wedge \mu_{Pn} \left( \int_U \mu_{An}(u) r(u) du \right) \right)$$

subject to

-continued $$v = \int_U u r(u) du$$

$$\int_U r(u) du = 1$$

Note. E(X) is a fuzzy subset of U.
(g) Fuzzy-graph interpolation rule:
This rule is the most widely used rule in applications of fuzzy logic. We have a function, Y=f(X), which is represented as a fuzzy graph. The question is: What is the value of Y when X is A? The $A_i$, $B_i$ and A are fuzzy sets.
Symbolic part is:
X is A
Y=f(X)
f(X) isfg $\Sigma_i A_i \times B_i$
Y is C
Computational part is:

$$C = \Sigma_i m_i \wedge B_i,$$

where $m_i$ is the degree to which A matches $A_i$ $$m_i = \sup_u (\mu_A(u) \wedge \mu_{Ai}(u)),$$

i=1, . . . , n.
When A is a singleton, this rule reduces to
X=a
Y=f(X)
f(X) isfg $\Sigma_i A_i \times B_i$
i=1, . . . , n.

$$Y = \Sigma_i \mu_{Ai}(a) \wedge B.$$

In this form, the fuzzy-graph interpolation rule coincides with the Mamdani rule—a rule which is widely used in control and related applications.
In the foregoing, we have summarized some of the basic rules in DDB which govern generalized constraint propagation. A few examples of such rules are the following.
(a) Probabilistic extension principle:
f(X) isp A
g(X) isr ?B
(b) Usuality-qualified extension principle:
f(X) isu A
g(X) isr ?B
(c) Usuality-qualified fuzzy-graph interpolation rule:
X is A
Y=f(X)
f(X) isfg E, if X is $A_i$ then Y isu $B_i$
Y isr ?B
(d) Bimodal extension principle:
X isbm $\Sigma_i Pi\backslash Ai$
Y=f(X)
Y isr ?B
(e) Bimodal, binary extension principle:
X isr R
Y iss S
Z=f (X,Y)
Z ist T
In the instance, bimodality means that X and Y have different modalities, and binary means that f is a function of two variables. An interesting special case is one in which X is R and Y isp S.
The deduction rules which were briefly described in the foregoing are intended to serve as examples:
(a) The Robert example:
p: Usually Robert returns from work at about 6:00 pm. What is the probability that Robert is home at about 6:15 pm?

First, we find the protoforms of the data and the query.
Usually Robert returns from work at about 6:00 pm
Prob(Time(Return(Robert)) is *6:00 pm) is usually
which in annotated form reads
Prob(X/Time(Return(Robert)) is A/*6:00 pm) is B/usually
Likewise, for the query, we have
Prob(Time(Return(Robert)) is ≤∘*6:15 pm) is ?D
which in annotated form reads
Prob(X/Time(Return(Robert)) is C/≤∘*6:15 pm) is D/usually Searching the Deduction Database, we find that the basic probability rule matches the protoforms of the data and the query
Prob(X is A) is B
Prob(X is C) is D
where $$\mu_D(v) = \sup_g \left( \mu_B \left( \int_U \mu_A(u) g(u) du \right) \right)$$

subject to $$v = \int_U \mu_C(u) g(u) du$$

$$\int_U g(u) du = 1$$

Instantiating A, B, C, and D, we obtain the answer to the query:
Probability that Robert is home at about 6:15 pm is D, where:

$$\mu_D(v) = \sup_g \left( \mu_{usually} \left( \int_U \mu_{*6:00\ pm}(u) g(u) du \right) \right)$$

subject to $$v = \int_U \mu_{\leq \circ *6:15\ pm}(u) g(u) du$$

and $$\int_U g(u) du = 1$$

(b) The tall Swedes problem:
We start with the data
p: Most Swedes are tall.
Assume that the queries are:
q1: How many Swedes are not tall
q2: How many are short
q3: What is the average height of Swedes
In our earlier discussion of this example, we found that p translates into a generalized constraint on the count density function, h. Thus:

$$p \to \int_a^b h(u) \mu_{tall}(u) du,$$

is most

Precisiations of q1, q2 and q3 may be expressed as $$q1: \to \int_a^b h(u) \mu_{not.tall}(u) du$$

$$q2: \to \int_a^b h(u) \mu_{short}(u) du$$

$$q3: \to \int_a^b u h(u) du.$$

Considering q1, we note that $$\mu_{not.tall}(u) = 1 - \mu_{tall}(u).$$

Consequently $$q1: \to 1 - \int_a^b h(u) \mu_{tall}(u) du$$

which may be rewritten as
q2→1−most
where 1−most plays the role of the antonym of most.
Considering q2, we have to compute $$A: \int_a^b h(u) \mu_{short}(u) du$$

given that $$\left( \int_a^b h(u) \mu_{tall}(u) du \right) \text{ is most.}$$

Applying the extension principle, we arrive at the desired answer to the query:

$$\mu_A(v) = \sup \left( \mu_{most} \left( \int_a^b \mu_{tall}(u) h(u) du \right) \right)$$

subject to $$v = \int_a^b \mu_{short}(u) h(u) du$$

and $$\int_a^b h(u) du = 1.$$

Likewise, for q3 we have as the answer $$\mu_A(v) = \sup_u \left( \mu_{most} \left( \int_a^b \mu_{tall}(u) h(u) du \right) \right)$$

subject to $$v = \int_a^b u h(u) du$$

and $$\int_a^b h(u) du = 1.$$

As an illustration of application of protoformal deduction to an instance of this example, consider:
p: Most Swedes are tall
q: How many Swedes are short?

We start with the protoforms of p and q (see earlier example):
Most Swedes are tall→1/n ΣCount(G[A is R]) is Q
?T Swedes are short→1/n ΣCount(G[A is S]) is T,
where $$G[A]=\Sigma_i Name_i/A_i, \ i=1, \ldots, n.$$

An applicable deduction rule in symbolic form is:
1/n ΣCount(G[A is R]) is Q
1/n ΣCount(G[A is S]) is T
The computational part of the rule is expressed as
1/n $\Sigma_i \mu_R(A_i)$ is Q
1/n $\Sigma_i \mu_S(A_i)$ is T
where $$\mu_T(v)=\sup_{A_i,\ldots,A_n} \mu_Q(\Sigma_i \mu_R(A_i))$$

subject to $$v=\Sigma_i \mu_S(A_i).$$

What we see is that computation of the answer to the query, q, reduces to the solution of a variational problem, as it does in the earlier discussion of this example in which protoformal deduction was not employed.

The foregoing examples are merely elementary instances of reasoning through the use of generalized constraint propagation. What should be noted is that the chains of reasoning in these examples are very short. More generally, what is important to recognize is that shortness of chains of reasoning is an intrinsic characteristic of reasoning processes which take place in an environment of substantive imprecision and uncertainty. What this implies is that, in such environments, a conclusion arrived at the end of a long chain of reasoning is likely to be vacuous or of questionable validity.

Deduction (Extension) Principle

Underlying almost all examples involving computation of an answer to a question, is a basic principle which may be referred to as the Deduction Principle. This principle is closely related to the extension principle of fuzzy logic.

Assume that we have a database, D, and database variables X1, . . . , Xn, with $u_i$ being a generic value of $X_i$, (i=1, . . . , n).

Suppose that q is a given question and that the answer to q, Ans(q), is a function of the $u_i$.

$$Ans(q)=g(u_1, \ldots, u_n), u=(u_1, \ldots, u_n).$$

I do not know the exact values of the My information about the $u_i$, I(u1, . . . , un), is a generalized constraint on the $u_i$. The constraint is defined by its test-score function $$ts(u)=f(u_1, \ldots, u_n).$$

At this point, the problem is that of constraint propagation from ts(u) to g(u). Employing the extension principle, we are led to the membership function of the answer to q. More specifically, $$\mu_{Ans(q)}(v)=\sup_u(ts(u))$$

subject to $$v=g(u)$$

This, in brief, is the substance of the Deduction Principle.

As a simple illustration, let us consider an example that was discussed earlier. Suppose that q: What is the average height of Swedes. Assume that D consists of information about the heights of a population of Swedes, Swede$_1$, . . . , Swede$_n$, with height of i-th Swede being $h_i$, i=1, . . . , n. Thus, average height may be expressed as $$Ave(h)=(1/n)(h_1+ \ldots +h_n).$$

Now, I do not know the $h_i$. What I am given is the datum d: Most Swedes are tall. This datum constrains the $h_i$. The test-score of this constraint is $$ts(h)=\mu_{most}((1/n)(\Sigma_i \mu_{tall}(h_i))),$$

$$h=(h_1, \ldots, h_n).$$

The generalized constraint on the $h_i$ induces a generalized constraint on Ave(h). Thus:

$$\mu_{Ave(h)}(v)=\sup(\mu_{most}((1/n)(\Sigma_i \mu_{tall}(h_i)))),$$

$h=(h_1, \ldots, h_n)$, subject to:

$$v=((1/n)(\Sigma_i h_i)).$$

More Search Engine Examples:

Let's consider a search engine query in which a person age is desired. For example, the question is: "What is the age of Mary?" or "How old is Mary?" or "What is Mary's age?"

Templates

This question can be scanned or parsed, to extract its components, as (for example) in the following shorthand notation or format: "Mary/Age?" The parsing is done using many templates for recognition of the pattern or grammar for a specific language (e.g. American English), dialect, topic (e.g. political topic), or method and type of speech (e.g. written, as opposed to spoken information or question). The templates are stored and designed by linguists or experts, in special databases beforehand, to be able to dissect the sentences into its components automatically later on, and extract the relevant and important words and information. The degree of matching to a specific template (e.g. for English grammar), to find (for example) the subject and the verb in the sentence, is done by fuzzy membership function and other fuzzy concepts described elsewhere in this disclosure.

One example for the template is that the symbol "?" at the end of an English sentence "usually" indicates a "question" type sentence. (The concept of "usually" (or similar concepts) is addressed elsewhere in this disclosure.)

For question-type sentences, one can have the following template (as a simple example) for the question "How old is Mary?":

(how old?/verb (to be)/noun (person's name))

That simplifies to: (how old?/person's name)

Or, equivalently, one can get this template: (age?/person's name)

Or, equivalently, one can get this template: (Mary K. Jones/human/Age?)

For a regular sentence of "Mary is 40 years old.", we will have the following template, as an example: (Noun (person's name)/verb (to be)/number/years/age)

Using the keywords or flag words (e.g. the usage of verb "is"), that simplifies to: (person's age/number/years)

Or, equivalently, one can get this template: (Mary K. Jones/Age/40/years)

Or, equivalently, one can get this template: (Mary K. Jones/Age/40 years)

Obviously, many other choices of templates and grammar also work here, as long as there is consistency and brevity in the definitions and templates, to reduce the size and get the common features for batch processing, faster search, faster data extraction, better data presentation, and more efficient data storage. The good thing about templates is that it makes the translation between different human languages (or translation between speech and computer commands) much easier, as they tend to carry only pure necessary (bare bone) information, without extra words, in a predetermined order or format, for fast and efficient access, search, and comparison.

Removal of Ambiguities

First of all, there is an ambiguity as which Mary we are talking about. If the prior conversation or context of the conversation makes it clear that we are talking about a specific Mary or person, e.g. "Mary Jones", then the search does not have to get the age of all people with that name or nickname that it can find, and the search will be limited (in scope) to the age of Mary Jones, only. Of course, if there are more than one persons with the name of "Mary Jones", one has to search for other identifiers or distinguishing parameters, such as her middle name, middle initial, age, social security number, address, father's name, husband's name, neighbor's name, friend's name, graduation date from high school, name of high school, nickname, pictures, tags on pictures, voice sample, fingerprint chart, other biometrics, or employee ID number, to remove the ambiguity, if possible.

Another information from context or background base knowledge is that Mary is a human, and not the name of a pet or doll, in which case the search would be diverted to another domain of age determination (e.g. for pets or dolls). Now, let's assume, for this example, that the context of the conversation or background knowledge (database) dictates or indicates that Mary is the name of a person, and furthermore, we are talking about Mary K. Jones, specifically. Thus, the question becomes: "Mary K. Jones/human/Age?"

In addition, for humans, one can distinguish male names from female names for majority of the names, stored in corresponding female and male (or human) name databases. Thus, we will have the following question: "Mary K. Jones/human/female/Age?" This is such a common question that we have a template in our template database for this type of questions: "human/female/Age?" or "human/Age?" Let's now consider the template "human/female/Age?" for this example. For our question template "human/female/Age?", we will have relevant data and relevant questions, associated with such a template, designed or input previously by humans, community users, search engine company, or the computer (automatically, based on the prior results and training or learning from the past associations in similar situations or relationships), into the template relational database(s).

The relevancy and reliability of sources of information (or information itself) are discussed elsewhere in this invention disclosure, using fuzzy systems (and Z-numbers). So, we will not repeat those formulations here again.

Relevant Questions

The examples of relevant questions are shown below. These are linked to the template "human/female/Age?", by linguists, or machine/computers trained for this purpose, using neural networks and fuzzy logic system combination, forming relational databases, that grows in size by experience and time/training, manually, automatically, or both.

"What is the age of the person's kid(s)?" or "What is the age of the person's oldest kid?" (Because, usually, one has kids within some age range. For female humans (in today's standard) (living in US), for non-adopted kids, mother's age is usually in the range of 18 to 45 years old, with a membership function that is not flat, more or less in trapezoidal shape. Thus, the oldest kid's age is a very relevant question or piece of information.)

"What year did the person graduate from high school (or college)?" (Because people in US normally graduate from high school around the ages of 17-19, with a corresponding membership function.)

"When did the person buy a house (or his or her first house)?" (Because a female person in US (or at different regions of US, or in certain city, or within a certain income bracket or job classification) buys her first house at a certain age, say, for example, around the ages 25-35, with a corresponding membership function.)

"How old is the person's best friend?" (Because, "generally", each person is about the same age as her/his best friend, with a corresponding membership function.) (Please note that the concept of "generally" (or similar concepts) is addressed elsewhere in this disclosure.)

"How old is the person's pet?" (Because, usually, one's pet is younger than himself or herself, with a corresponding membership function.)

"How old are the person's parents?" (Because, usually, one is younger than his or her parents by about 20 to 45 years, with a corresponding membership function.)

Combining all the questions above (and their answers or similar information), one can get a good estimate of the person's age, using fuzzy concepts shown in this disclosure. In addition, using a relevance scoring system, one can filter and find all or most relevant questions. Each relevant question can in turn refer to another relevant question or information, as a cascade and chain, bringing or suggesting more questions and information for the user. The history of the user or history of the users or history of similar or same question(s) can be stored in some relational databases with relevance scoring, for future filtering and usage, based on a threshold. The system is adaptive and dynamic, as well as having learning/training mode, because as the time passes, with more experience and history, the database gets more accurate and larger in size, to fit or find the questions or relevant information better and faster.

Similarly, for answers or information available, one can find relevant information, using a membership function for relevance degree. Some examples for answers or information are:

"The age of Mary K. Jones's oldest child (or kid) is 15."
"Mary K. Jones graduated from high school in 1989."
"Mary K. Jones bought her first house in about 1996."
"Mary K. Jones's best friend is most likely 35 years old."
"Mary K. Jones's dog is roughly 10 years old."
"Mary K. Jones's mother is about 70 years old."

Sometimes, one gets the age of Mary K. Jones indirectly, through the information about her best friend's parent's age, which typically has less relevance and less credibility, in the chain of connected information. However, in this disclosure, we have shown the tools to treat and analyze/process all of those situations and information, with different degrees of relevance and credibility, using fuzzy concepts, such as membership functions for corresponding parameters.

Note that to search information and questions, one can use the following templates for the following sentences, as examples:

"Mary K. Jones's dog is roughly 10 years old." is converted to the template: (person/person's pet/pet's age/roughly/10 years), which is stored in relational databases, which can be queried, compared, aggregated, edited, combined, re-named, indexed, or re-ordered.

"How old is the person's pet?" is converted to the template: (person/person's pet/pet's age?), which is stored in relational database(s) or template storage.

Figure 64:
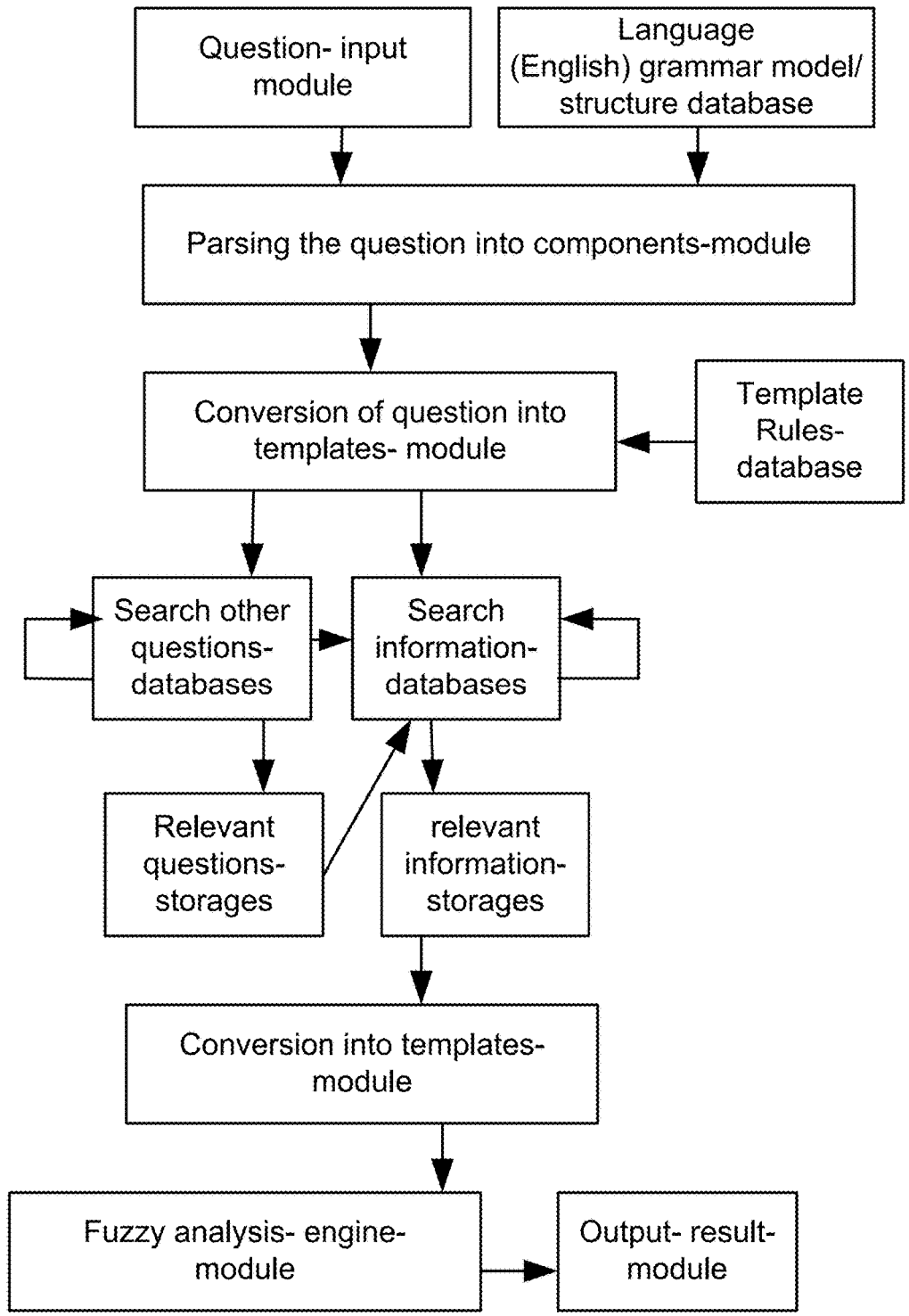
FIG. 64 is a system for the search engine.

FIG. 64 is a system for the search engine explained above. The fuzzy analysis engine is used to find Mary's age from all the received information. The scores, thresholds, and membership functions are used in the fuzzy analysis engine, as explained elsewhere in this disclosure.

Another example for the search engine is an inquiry about Mary's house: "How much is the price of Mary's house?" To analyze this question, a process and system similar to the one given above is followed. However, in this case, in addition, we have some predetermined templates for links to relevant web sites or government information repositories. For example, for price of the house, the average price of the houses (the trend) for US, city, region, county, and specific street or neighborhood become relevant, as well as, inflation, housing indices reported by Wall Street Journal or the US Government (e.g. the new permits issued for the last quarter or the current inventory of the new or old houses), and the size and details of Mary's house (such as the number of floors, number of garages, number of bedrooms, age of the house, and square feet of the land and living area), plus the recent real estate activities in the same area for similar size houses (from real estate repositories or county records for recent transactions). The prior sale prices of Mary's house, if any, with corresponding dates, are also relevant information.

Therefore, one needs some indices and data from newspapers, US Government, local government, county records, and real estate databases. These data are usually directly or indirectly available for search engines (assuming they are not protected by password or only available on subscription basis, which may need human intervention and input). The indirect ones may require proper question or another relevant data (or intermediary information) to link with the final answer. Thus, at the beginning, the people experts in economy and real estate are needed to design and set the links and relationships (or mathematics formulas and fuzzy rules or relationships between different parameters), as the initialization step. However, if similar concepts already exist in the rules and patterns or templates, the machines can initialize the new search links and populate the relationships, automatically, without any human intervention or input. The updates for the links or feedbacks can be done periodically by humans or users, or automatically by machines, e.g. by feedback from the history using a learning machine (e.g. using neural networks, trained to update the links or improve them, gradually, based on prior scores and past performances).

Figure 66:
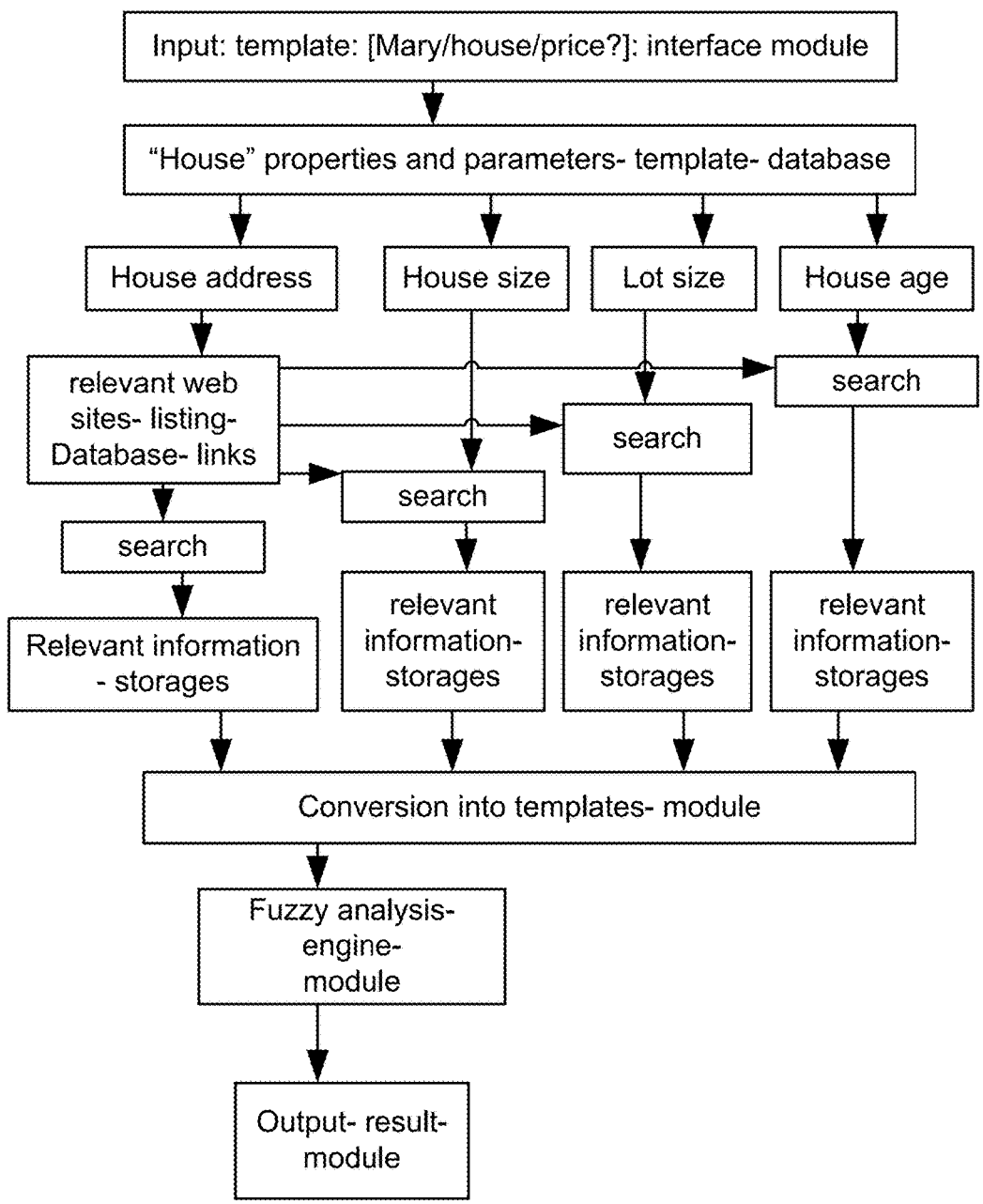
FIG. 66 is a system for the search engine.

In the above example, the most important piece of information is probably the address of the house. A system for this example is shown in FIG. 66 (with the template (Mary/house/price?), which is a question about the price of Mary's house). So, after finding which Mary we are talking about, we need to find the address of the house, or remove the ambiguities as much as possible, to narrow down the possibilities for the addresses, which can be expressed by the membership functions, e.g. in discrete mode, as a discrete function. Most databases and data mentioned above are expressed in terms of the house address and zip code, as shown in FIG. 66, where the search for the parameter "address" is helping the searches related to the other parameters, e.g. as an intermediate parameter to get to the other parameters.

Figure 65:
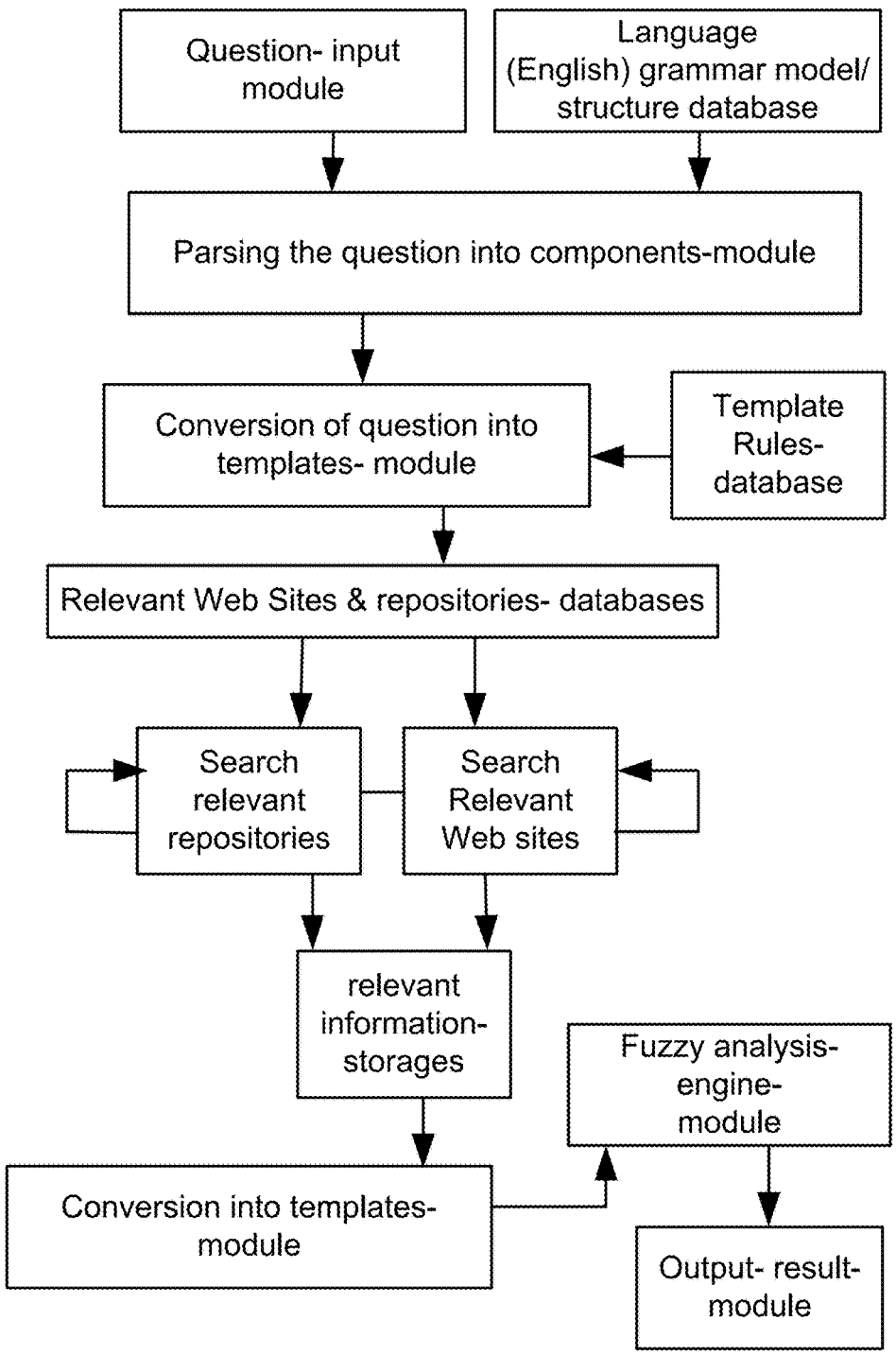
FIG. 65 is a system for the search engine.

So, after finding the address(es), the search engine is focused on any relevant information related to the found address, especially targeting the focused web sites and predetermined repositories that probably contain relevant and reliable information, as mentioned above. In case of multiple addresses, if we cannot resolve the real address among the multiple possible addresses (or if Mary may actually own multiple houses), we end up having a list of (multiple) possible addresses and their corresponding prices, with some certainty (or confidence) value or membership function, associated with each found address (and its corresponding price). The additional system components in this example are captured in FIG. 65 (in addition to our teachings of FIG. 64).

Another example for the search engine is an inquiry about the price of a car: "How much is the price of a low mileage 1991 Ford Mustang?" or "How much does a 1991 Ford Mustang (in a good condition) worth?" To analyze this question, a process and system similar to the one given above is followed. However, in this case, in addition, we have some predetermined templates for links to relevant web sites or commercial (or standard) information repositories, such as E-Bay web site, auction web sites, used car dealers, car advertisement or newspapers' web sites, car collectors' web sites, car magazines' web sites, reliable car blogs, car experts' web sites, or Blue Book values for cars.

In addition, the mileage on the car, car condition, and details of the car are also relevant. In this case, we know that the car has a low mileage (or is in good condition), which is a fuzzy statement, with its corresponding membership values and function regarding mileage (and/or condition) of the car. The fuzzy analysis is discussed elsewhere in this disclosure. We do not know the exact details of the car, for example, the options or extra features on the car. Thus, we probably get a range of values for the car (to include various options or features).

Updating Information

History and the results of the same or similar questions asked or searched earlier by others can be stored by the search engine company (or others) on different repositories for fast retrieval or updates. Some questions have answers which are time-dependent, such as the value of a dollar with respect to Euro's, which changes every day or every hour. Some answers do not change that much (or not at all). For example, the capital of France is Paris, and it probably does not change very often or very soon. Or, (2+2) is always 4 (in conventional mathematics). So, one can separate these questions into at least 7 categories (which is a fuzzy concept by itself, with assigned percentages being approximate fuzzy ranges of numbers, as well). It can also be defined as a crisp range. One example is:

Things that never change. (about 0%)
Things that rarely change. (about 1-10 percent)
Things that seldom change. (about 10-25 percent)
Things that sometimes change. (about 25-75 percent)
Things that often change. (about 75-90 percent)
Things that usually change. (about 90-99 percent)
Things that always change. (about 100 percent)

Figure 67:
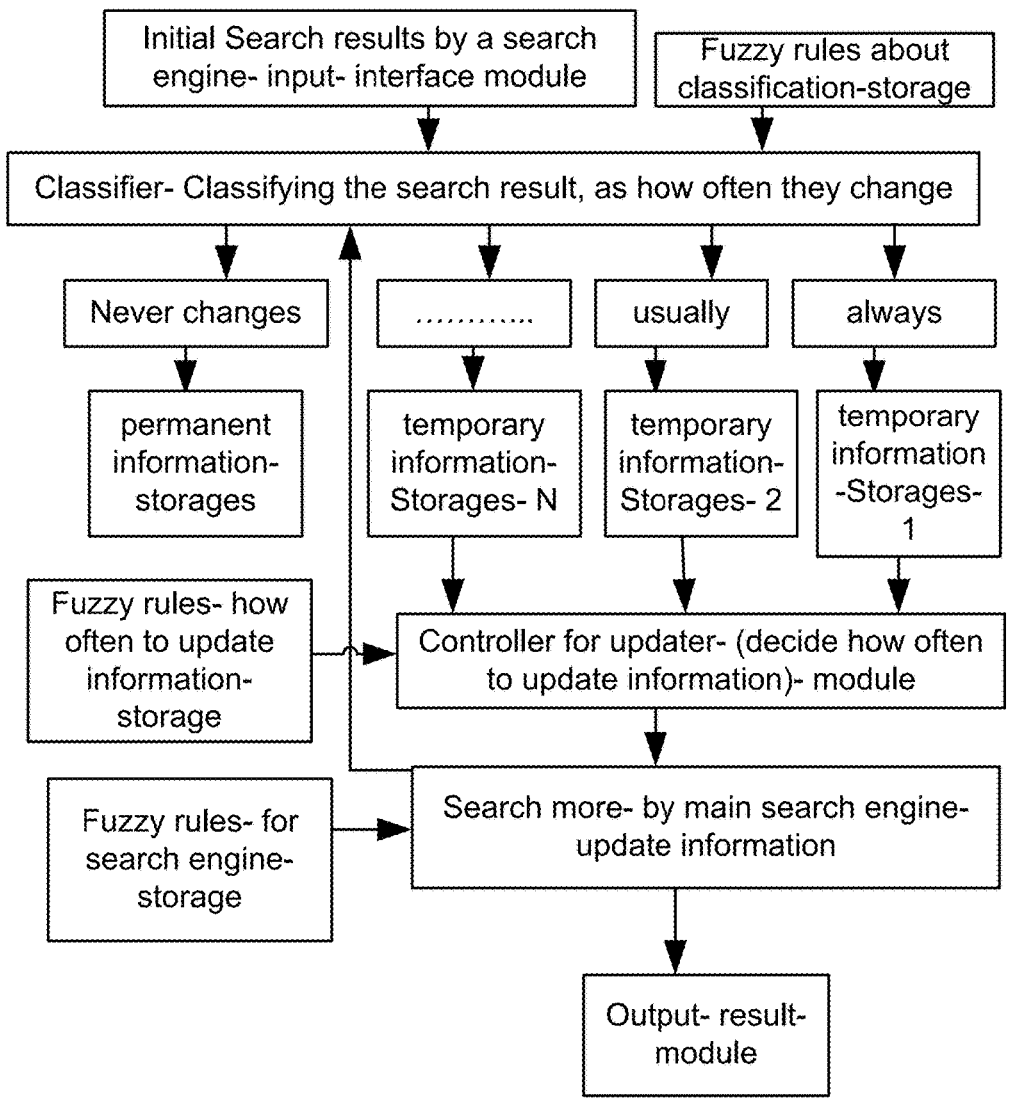
FIG. 67 is a system for the search engine.

The classification above is shown in system of FIG. 67, using a classifier module with fuzzy rules, and then updating (and looping back) the information and the assignment of the storages (to put the new data into different repositories, if applicable), for faster future search and access. In the figure, we have N temporary storage classes and one permanent storage class, based on how often they are changing, based on the corresponding fuzzy rules and predictions. The N temporary storage classes have different access time and delays (and different priorities for access), based on how often they are changing or accessed. For example, generally, temporary storages of class-1-type in the figure have the fastest access, search, and retrieval times (if all other things being equal).

For example, in one embodiment, one can store the corresponding history and past answers in repositories which have different purposes, such as "long term repository" or "daily repository". The "daily repository" is updated on a daily basis or very often. In addition, an unreliable otherwise "long term" answer (with low score or low membership value, in terms of reliability) will still be stored in a "daily repository", because it should probably be changed or updated soon. Thus, fuzzy concepts determine where we put or access the prior results or history of prior searches. In addition, generally, all things being equal, a "daily repository" has a faster access or update time, because it is used more often by the search engine, as the short term repository or database.

Figure 84:
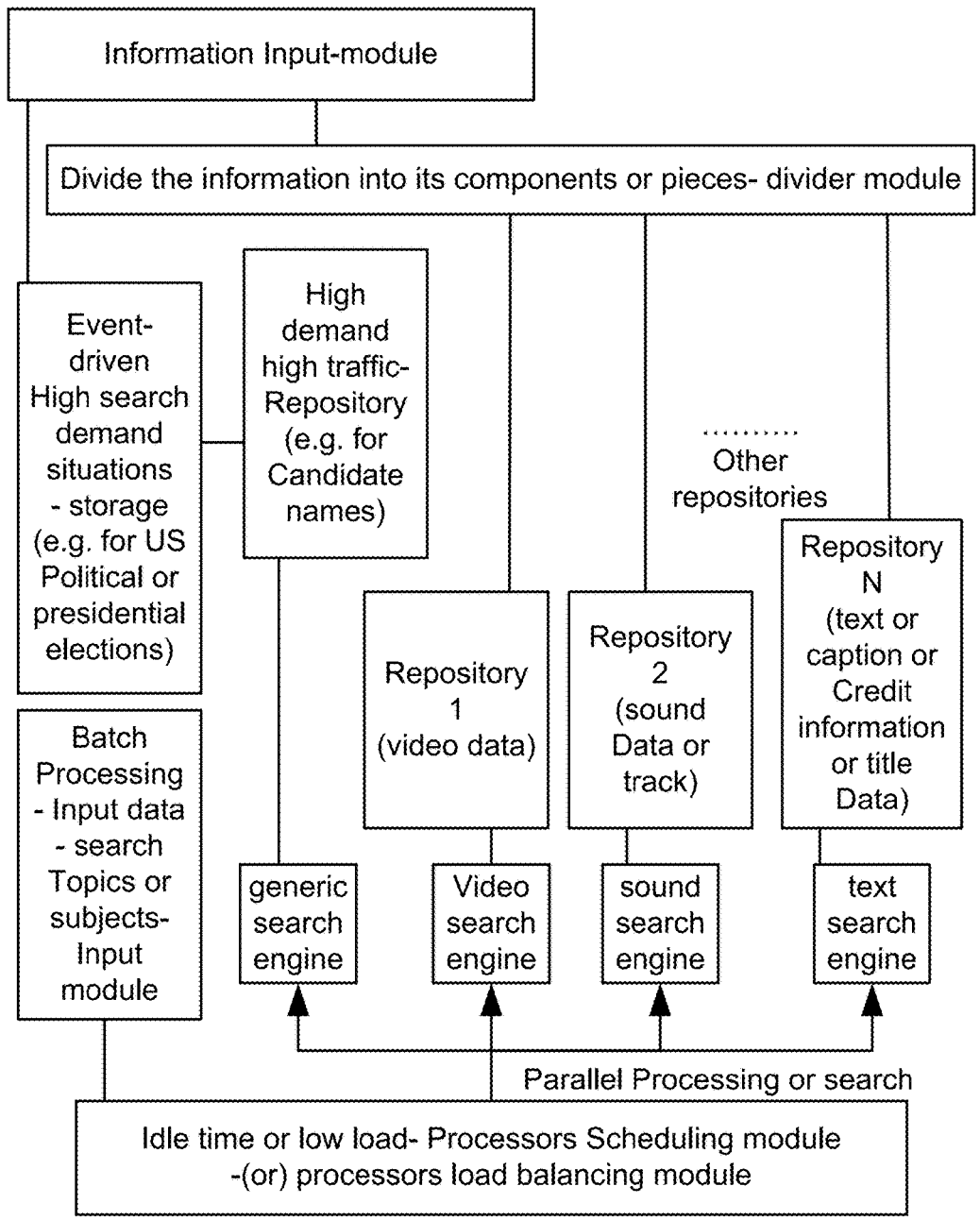

In addition, as an off-line mode, one can do batch processing in advance on future anticipated searches that are common or possible, based on some "possibility" degree (which is fuzzy value by itself), to store the information in repositories for future fast access, without too much (or not at all) processing delay. The repositories are classified based on topics they carry information for (on a fuzzy set basis). See FIG. 84 for a diagram of such system.

Also, there are some dynamic assignment and updates as to where information is stored (or be restored), for faster access, because some topics or subjects may become very much searched for in a specific period of time or on a temporary basis (e.g. political candidates' names are generally searched very often just before the elections, and the search will go down drastically right after the election). The predictor engine (which predicts or stores such trends or patterns) and assignor engine or module (which assigns or re-assigns the storage location) periodically re-evaluate and re-assign the repository locations for various subjects and topics, to be more efficient, for search and access the data. The prediction, assignment, and topics themselves are all based on fuzzy concepts and fuzzy sets. See FIG. 84 for a diagram of such system.

Furthermore, some repositories are assigned as intermediary repository, as a hierarchical structure or tree configuration, to access certain data faster. Alternatively, the data can be split up and stored in pieces for faster search or access, in a distributed fashion, due to the size of the files or the purpose of the files. For example, title, text, video, and sound related to a movie can be split and stored separately, in separate databases, servers, or repositories, where just the titles are stored in a specific server for fast access and search (by title only). Then, after the title searches are complete (with low overhead) and a specific title is selected, the pieces or components of the movie can be retrieved from various locations. For some applications, this increases the efficiency of the search engine. The classification of purposes or tasks to assign various repositories (by itself) is a fuzzy concept, with fuzzy set(s) and membership function(s). (These were addressed elsewhere in this disclosure.) See FIG. 84 for a diagram of such system.

In one embodiment, to answer the question "What is the price of Mary's house?", one tries to start from "Mary" and get to "her (Mary's) house price". But, one does not know at the beginning that which subjects are relevant and how relevant they are. For example, is the price of her car relevant? Or, is the price of her dad's house relevant information? Or, is the address of her dad's house relevant information? What is the relevancy and to what degree? Is there any general rule or relationship connecting the 2 concepts? Is there any specific rule or relationship (just for Mary) connecting the 2 concepts? If so, what is the rule or relationship connecting the 2 concepts? Should we search for the other concepts and at what length or at what expense? Now, we address the above questions.

The computational expense is generally in terms of search time and computing expenses, e.g. using total CPU power by many servers or a server farm (e.g. using the unit FLOPS (or flops or flop/s) for floating-point operations per second, as a measure of a computer's performance), to justify or gauge how far we should search for a concept, as a fuzzy limit or threshold, to stop or limit the searches. Generally, the more relevant the subject (which is a fuzzy parameter by itself), the more computational expense or time is justified, allowed, or allocated for searching that subject or topic (i.e. the threshold for how long we can search for that subject is higher).

The relevance is generally not known at the beginning. So, the system guesses the best it can, and if during the search steps is proven otherwise, the relevance factor is re-adjusted accordingly (going up and down, based on the observations, performances, and satisfaction of the goals or scores, on the first search cycle). For example, the system may guess a few subjects that may be somewhat relevant to Mary's house price, but it is not sure about them. Based on the specific initial knowledge base from Mary and the general knowledge base from the Universe (all other available data), the system prioritizes those guesses and assigns some scores to those possible subjects (so that the relative or absolute computational times are determined and limited for those subjects or topics), using fuzzy rules for relevance scoring, described elsewhere in this disclosure.

Let's assume for this example that "the address of Mary's dad's house" is set as relevant (with a high degree of relevance, which is a fuzzy parameter). Then, the system tries to step forward from both sides to reach each other. This approach is similar to digging a tunnel in a big mountain, from both sides of the mountain, but without the exact GPS information, trying to get to the other side, simultaneously digging and stepping forward from both sides, using the best guesses and knowledge available for the best direction for digging (which is the same as guessing the relevance of the next step or subject, and choosing the most relevant subject(s), in the chain of relevancy, as accurate as possible, with the current knowledge we have so far, to minimize the computational power needed to get to the result (to the other side of the tunnel)). For example, now, we have "the address of Mary's dad's house", and from that, we want to get to "Mary's house price". In the next step, if we assume that "Mary's house address" is relevant to the context of this problem, then we have the following situation:

We now have "Mary's house address", and from that, we want to get to "the address of Mary's dad's house". Now, we look at the rules in our universe of rules storage, and we find that there is a strong correlation (which is another fuzzy parameter) between the address of a person and her parents, in terms of street address proximity, neighborhood, city, or zip code. So, we now can connect the two sides. That is, we can connect "Mary's house address" with "the address of Mary's dad's house". That is, from the address of her dad, we can choose the best address(es) for her house, from all possible choices so far, that "fits the best" with her dad's address (with a higher correlation factor). So, we can narrow down or pinpoint her address(es) (or choices of her addresses).

In addition, if we are dealing with 2 or more topics or subjects simultaneously, we can get to her address from 2 or more directions, adding more confidence to the final result (of her address). For example, using "her income" to get to "her address", in addition to the above, we will probably get more confidence on her address, at the end.

Figure 68:
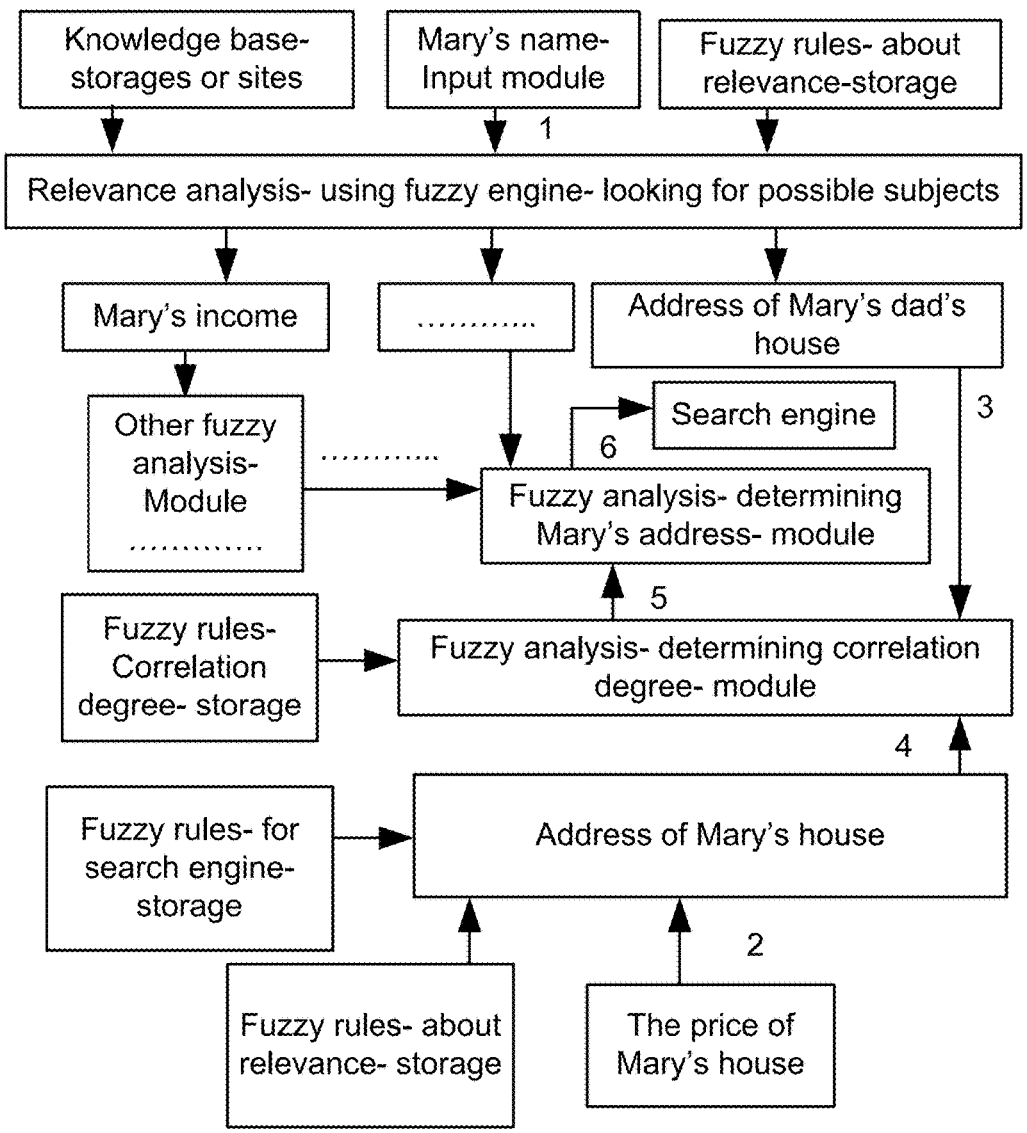
FIG. 68 is a system for the search engine.

The system described above is shown in FIG. 68, with numbers 1, 2, 3, and 4 indicating the sequence of steps of getting the 2 sides (i.e. the subjects "Mary's name" and "the price of Mary's house") approaching each other gradually, by finding the relevant information in-between in the next step, by using fuzzy analysis. Of course, in some other examples, we may need more steps in-between to connect the 2 sides together (which translates to more computing expense and power). The "Mary's income" also helps to find or ascertain the right address for Mary's home (number 5 in FIG. 68). Then, the final result for Mary's home address is fed into the search engine again, to find the price of her house (as her address is the most relevant information for indicating her house value) (number 6 in FIG. 68). Then, the result of the search engine would be the value of her house.

Figure 69:
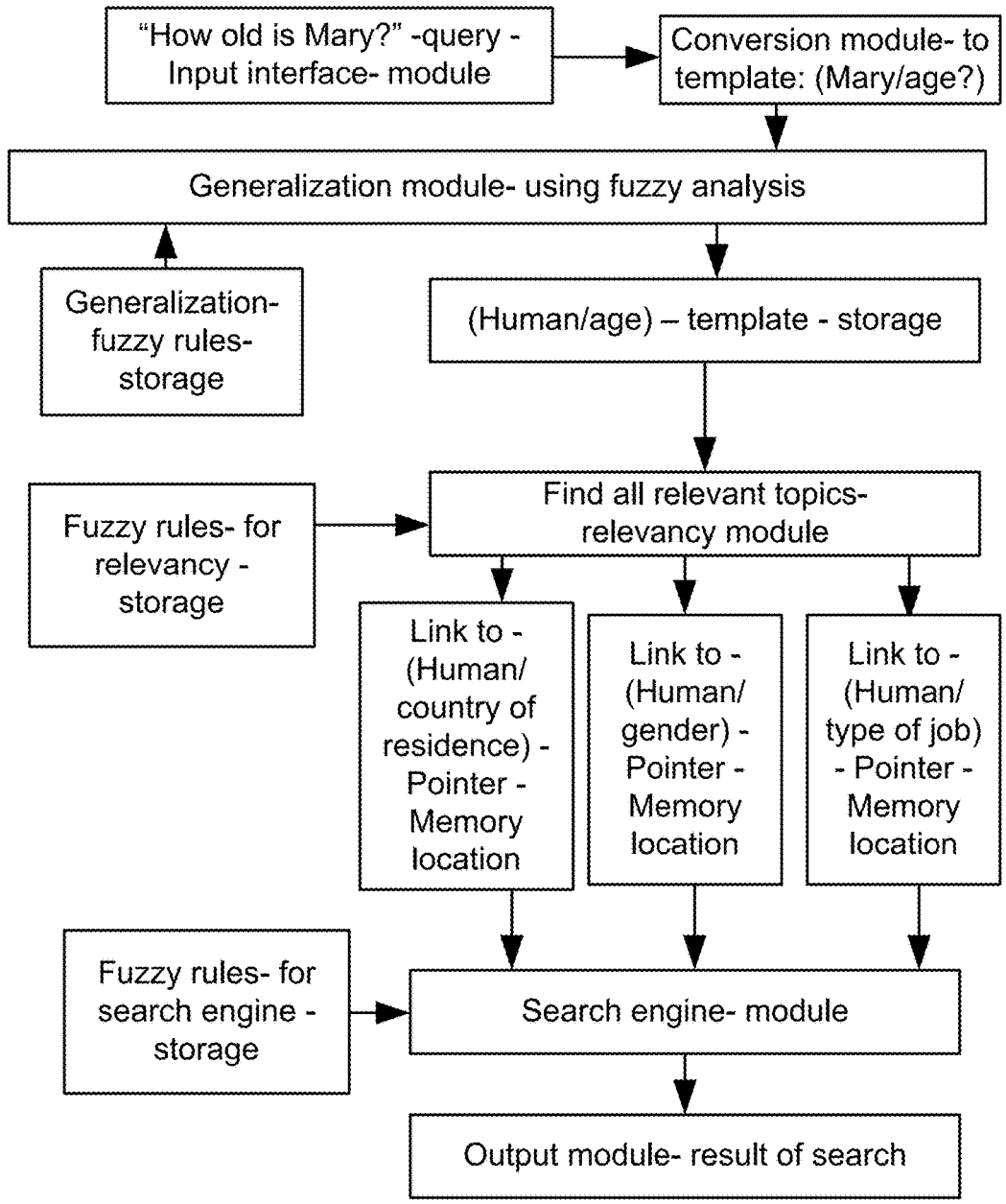
FIG. 69 is a system for the search engine.

In one embodiment, to answer the question "How old is Mary?", we are looking for relevant answers (or information, subjects, or topics) and relevant questions. If the relevant information is not readily obvious or available, we can generalize and expand the scope of the topics, to try to fish or search for new topics under the larger new scope. For example, here, we have: (Mary/age?), which can be generalized to a larger scope as: (human/age?), which (in turn) relates to (human/country of residence) & (human/gender) & (human/type of job). Therefore, we have increased our choices of relevant topics or subjects to: "country of residence", "gender", and "type of job", which were not obvious at the beginning of the analysis. Thus, we can follow those leads, for topics for the search engine, to find the possible ages (or range of ages) for Mary. This is shown in FIG. 69, where topic generalization is used to increase the scope, to find leads to better topics for the next cycle of search engine, to have a more accurate search result for the original topic or query.

Figure 83:
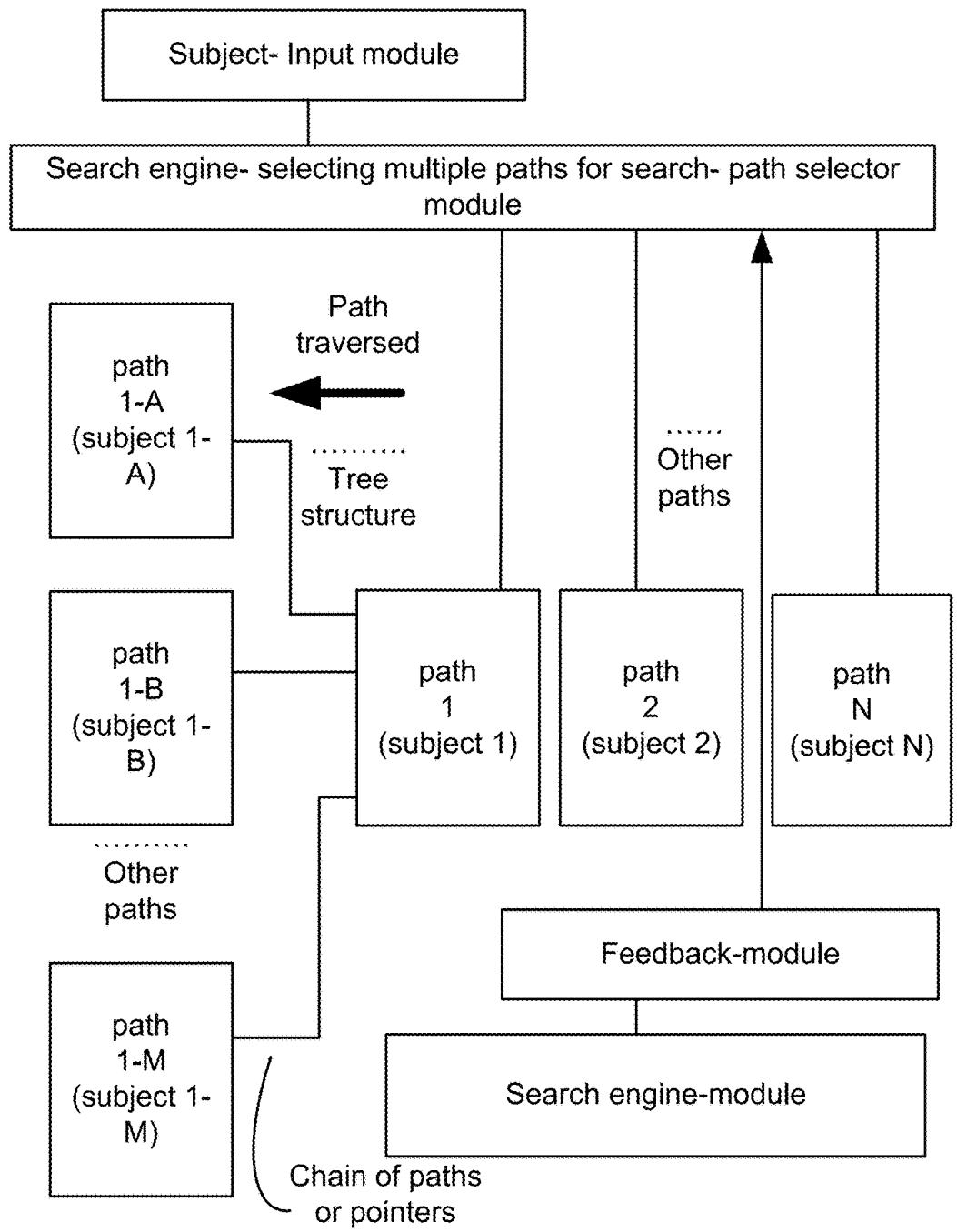
FIG. 83 is a system for the search engine.

In one embodiment, one gets to the answer(s) by following multiple paths, starting from the question template, working toward the possible answer(s). In one embodiment, users can give feedback or score answers or paths traversed, for better future path selections. See FIG. 83 for a diagram of such system.

Figure 82:
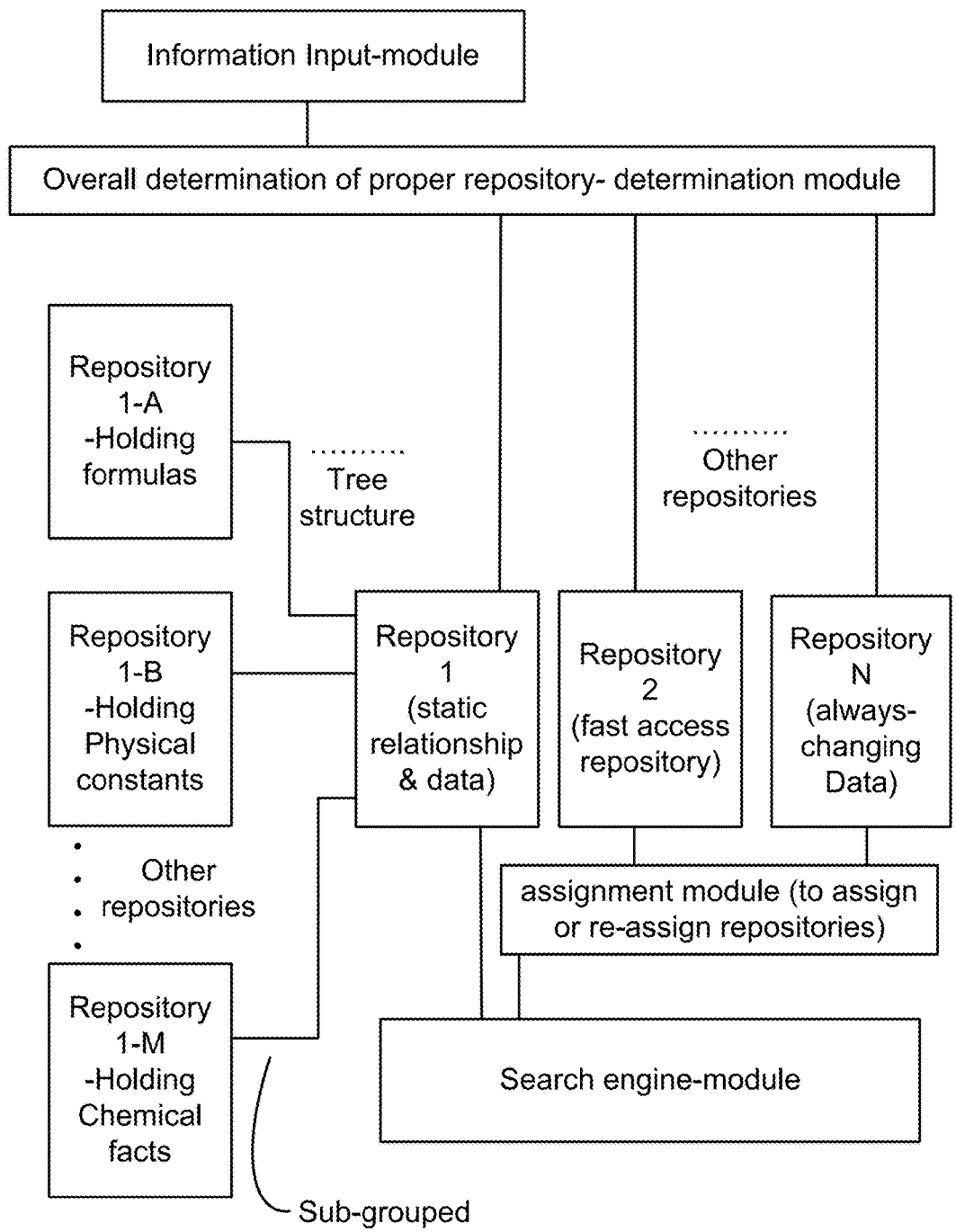
FIG. 82 is a system for the search engine.

In one embodiment, the relationships stay the same, but the inputs may constantly change, resulting in a dynamic (constantly-changing) output. For example, Gross Domestic Product (GDP) of a country and the population of a country (the inputs) constantly change. So, GDP per capita (the output) also constantly changes, but the relationship between GDP, population of the country, and GDP per capita of the country (the relationship between inputs and output) never changes. Therefore, the relationships or parameters that remain constant are stored in different repositories (compared to those of the dynamic parameters), and are accessed without any updating or verification in the future. For example, the formula for GDP per capita is always the same, for the same country or other countries, and it does not have to be updated or reviewed again, making access to that parameter or relationship much faster and less costly for the search engine. The most common or most used parameters, relationships, definitions, or topics are stored in separate repositories, which are grouped and sub-grouped in different classes and categories according to their topics, in a tree-structure or hierarchical form, for faster and easier access by the search engine. In one embodiment, the grouping is done based on fuzzy definitions and sets/subsets. See FIG. 82 for a diagram of such system.

Figure 81:
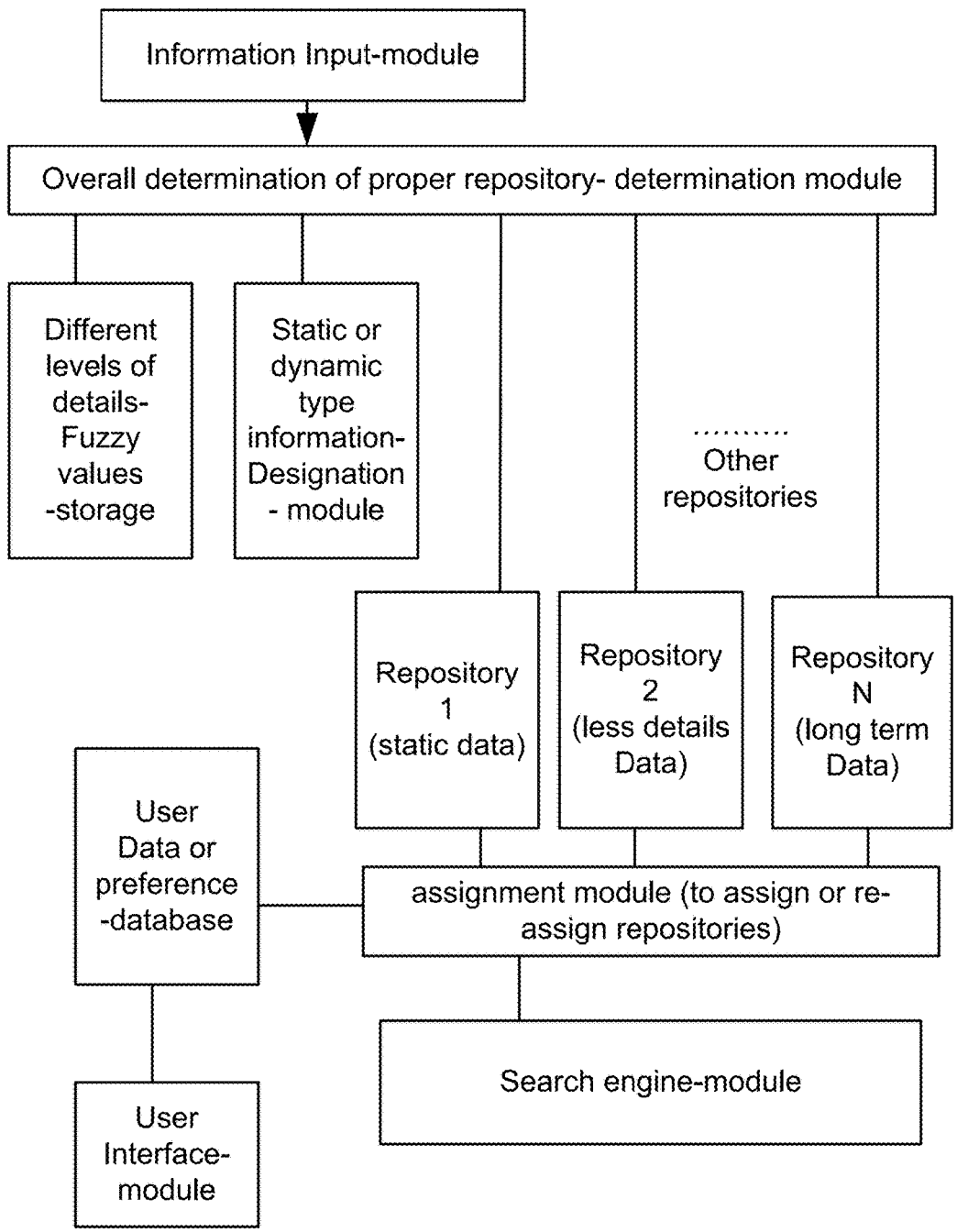
FIG. 81 is a system for the search engine.

In one embodiment, the same information may have various representations with different levels of details: $L_1$, $L_2, \ldots L_N$, where $L_1 < L_2 < \ldots < L_N$, in term of "level of details". So, we can store them in different repositories, available for different searches. Search and access to $L_1$ is much faster than those of $L_N$ (which carries more details). Based on the application, if it is determined that there is no need for details of $L_N$, one can choose a version with lower amount of details, such as $L_1$ or $L_2$. An example for this situation is when an image or picture is stored at different resolutions (with different sizes) at different repositories. Or, another example is when a table (or spreadsheet or database) is stored, with various sections or columns are hidden or disabled (and not stored), so that different versions of the table (with different sizes and details) are stored in different locations or repositories, and each version of the table may fit or serve different types of user, application, need, search, or query. The level of details can be expressed (by the user) as a fuzzy parameter, for the original file or data. See FIG. 81 for a diagram of such system.

In one embodiment, there are 2 types of information (static and dynamic) which yield the same result(s). For example, for Mary's age, one can store the information as "39 years old" (dynamic information, which changes every year). Or alternatively, one can store that same information as her exact birth date, as an equivalent data, which is always static (not changing). The second method or type (static information) is more useful for the future referrals. For example, once the today's date is known, the birth date is always useful (and complete information) to calculate the age of a person, whereas the age number or value (from an unknown number of years ago) (by itself) is much less useful (and less complete, to calculate the age of the person). Thus, one can store the static information separate from the dynamic information, as they are accessed differently, with different priorities, access frequencies, and degree of "usefulness" (which can be expressed by fuzzy concepts), to optimize the search engine, especially for future searches on similar topics. See FIG. 81 for a diagram of such system.

Familiar or Famous Names or Titles

Figure 80:
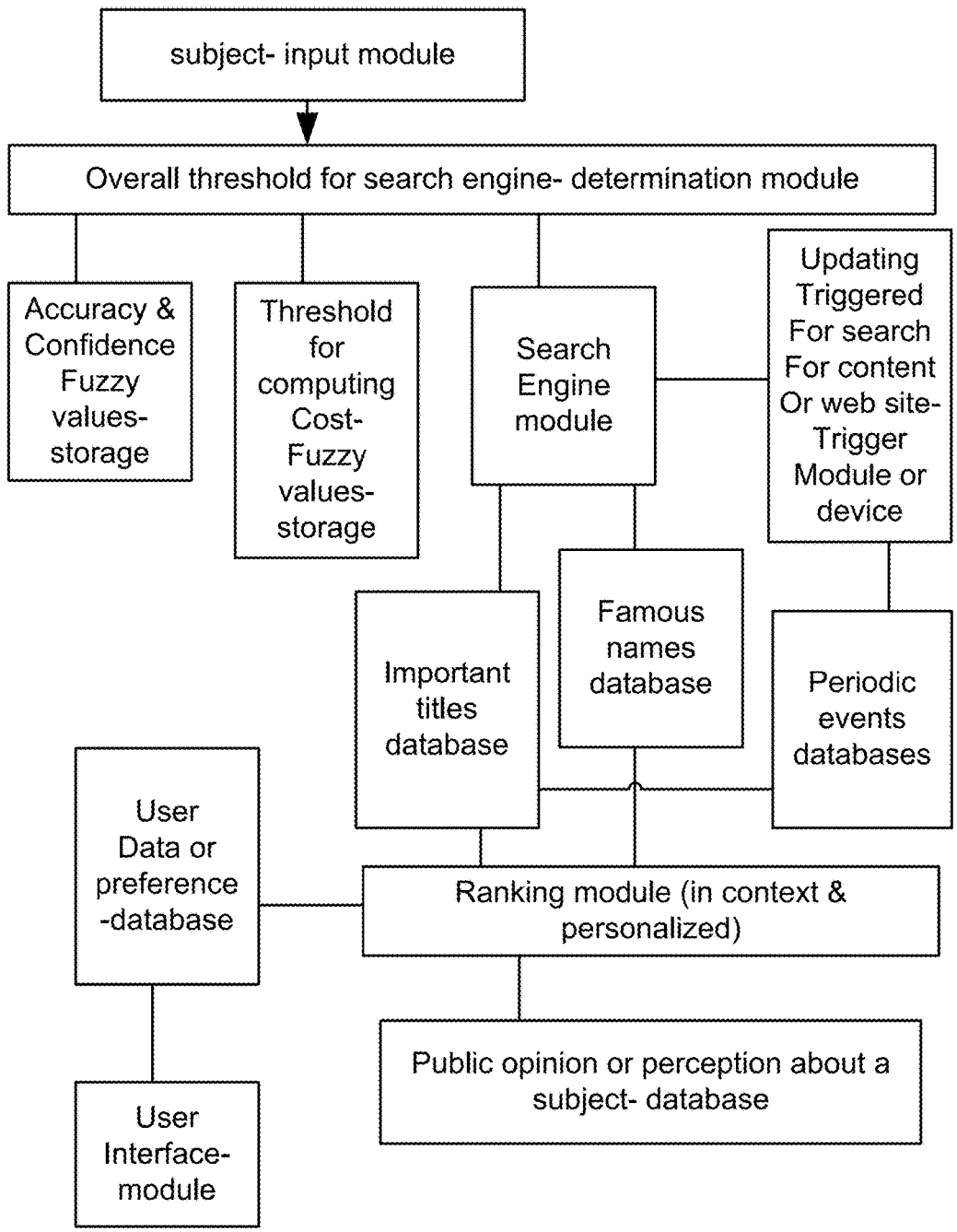
FIG. 80 is a system for the search engine.

In one embodiment, famous names and titles are stored and indexed or ranked separately, for fast and efficient access, e.g. Eiffel Tower, Clinton (referring to the former US President Clinton), Paris (referring to Paris, France), or The US President. There are 2 types of famous names and titles. The first type has a single choice only, with no ambiguity (e.g. Eiffel Tower), but the second type has more than 1 choices, with some degree of ambiguity (or membership value). For example, we have more than one city in the world called Paris, and Paris is also the name of a person, as well as the name of a Las Vegas hotel and casino. However, "Paris" by itself (without any context) most likely means "Paris, the capital city in France", as our first choice. Other choices can be ranked as a list (with some membership value), but the ranking can be changed based on the context, e.g. prior sentences, history, background, speaker, audience, or the location of the conversation. In addition, in one embodiment, the $1^{st}$ and $2^{nd}$ types are separately stored and listed, to streamline the process, for more efficient search engine access. See FIG. 80 for a diagram of such system.

In one embodiment, some titles are placeholders, e.g. The President of the United States, which is expected to have possibly different values every few years, which should be checked and updated, according to that time periodicity, e.g. every 4 years, starting from an election year in US. This means that some repositories are tagged and treated that way, for optimum performance, e.g. more accuracy and less frequency of updating of the data (or less required computing power or expense). See FIG. 80 for a diagram of such system.

In one embodiment, there are the accuracy factor and reliability factor involved in the search engine, in addition to the cost factor for computing power (used so far, for the search engine). That is, there is a threshold as to how much accuracy we need for the result (which could be a fuzzy parameter itself). As an example, we may need to find (and search for) the diameter of the planet Earth to 10 km accuracy (rather than 100 km accuracy). Thus, we generally have to do more search to get that much confidence or accuracy (with enough reliability) (i.e. for 10 km accuracy (rather than 100 km accuracy)). Another example is to find the value of real number "e" to 5 decimal point accuracy (rather than, for example, 2 decimal point accuracy). There is also a threshold as to how much computing time or money we want to spend on this search, which means that how bad we want the answer, and how long we are willing to (or allowed to) spend on this search. Thus, accuracy, reliability, confidence, and cost are some of the factors that determine the scope and depth of each search. All of these factors can be expressed as the fuzzy concepts, as explained elsewhere in this disclosure. See FIG. 80 for a diagram of such system.

Figure 79:
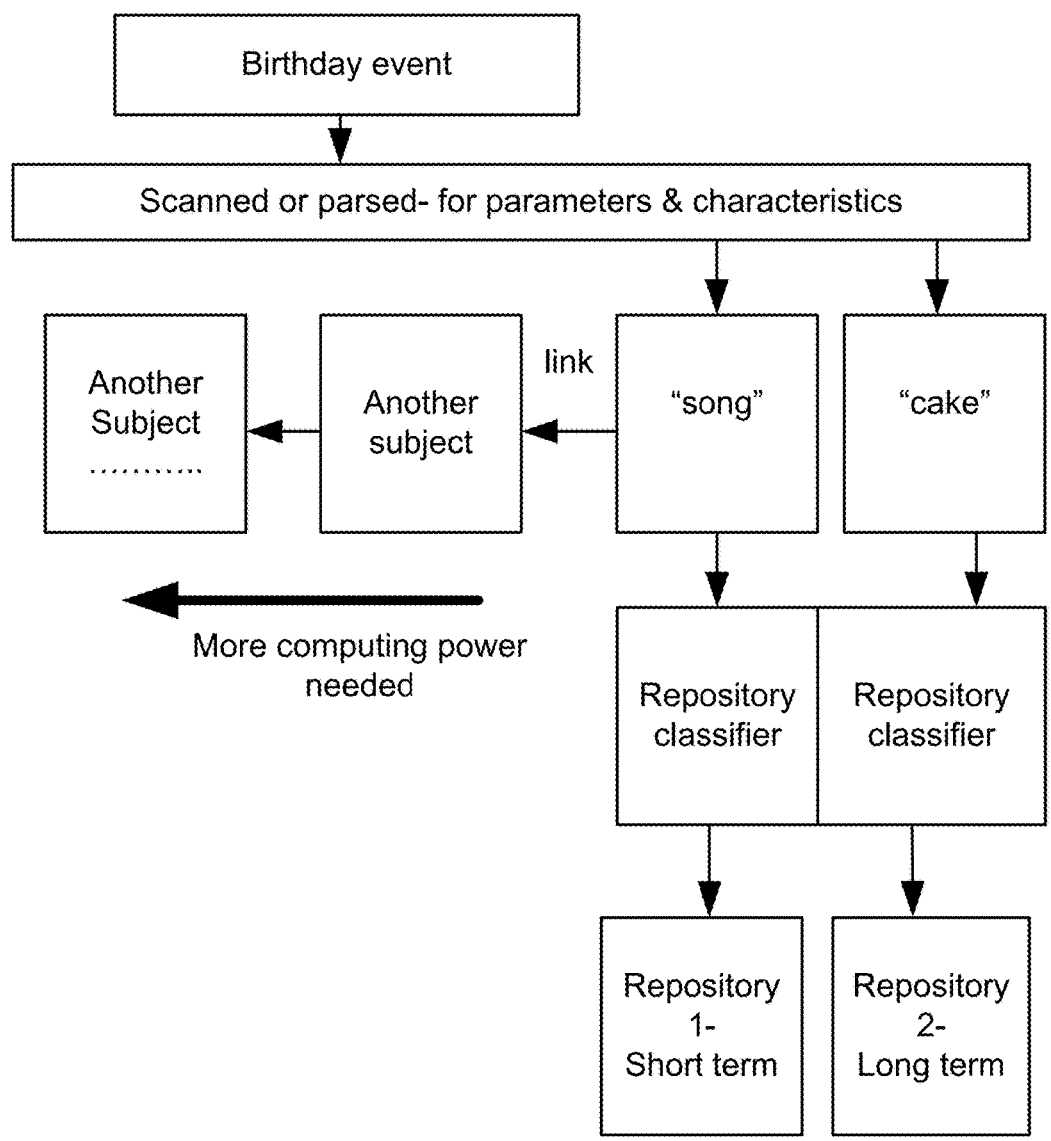
FIG. 79 is a system for the search engine.

In one embodiment, storing the prior results or calculations (or intermediate results), especially when they are requested multiple times or very often by other users or the same user, increases the efficiency of searching same or similar terms or topics in the future, similar to the way humans gain experience, learn, and store information, for future recollection. The storage and recollection of the prior information is done in multiple steps. First, the information is scanned or parsed (e.g. a birthday event for a person) for its parameters and characteristics (e.g. cake shape, cake taste, birthday song, colorful hat, friends present, and gifts received). Then, it is tagged or indexed based on those parameters and characteristics (e.g. song, cake, taste, shape, hat, gift, friend, human, and food). Then, it is stored based on the tags or indexes in proper repositories. There are multiple classes of repositories, e.g. in terms of short-term and long-term, e.g. for frequency of access or access speed for retrieval (or access speed for editing and updating information already stored). So, there is a processor or controller which makes that classification (which can be fuzzy, as well), for proper storage. See FIG. 79 for a diagram of such system.

Figure 78:
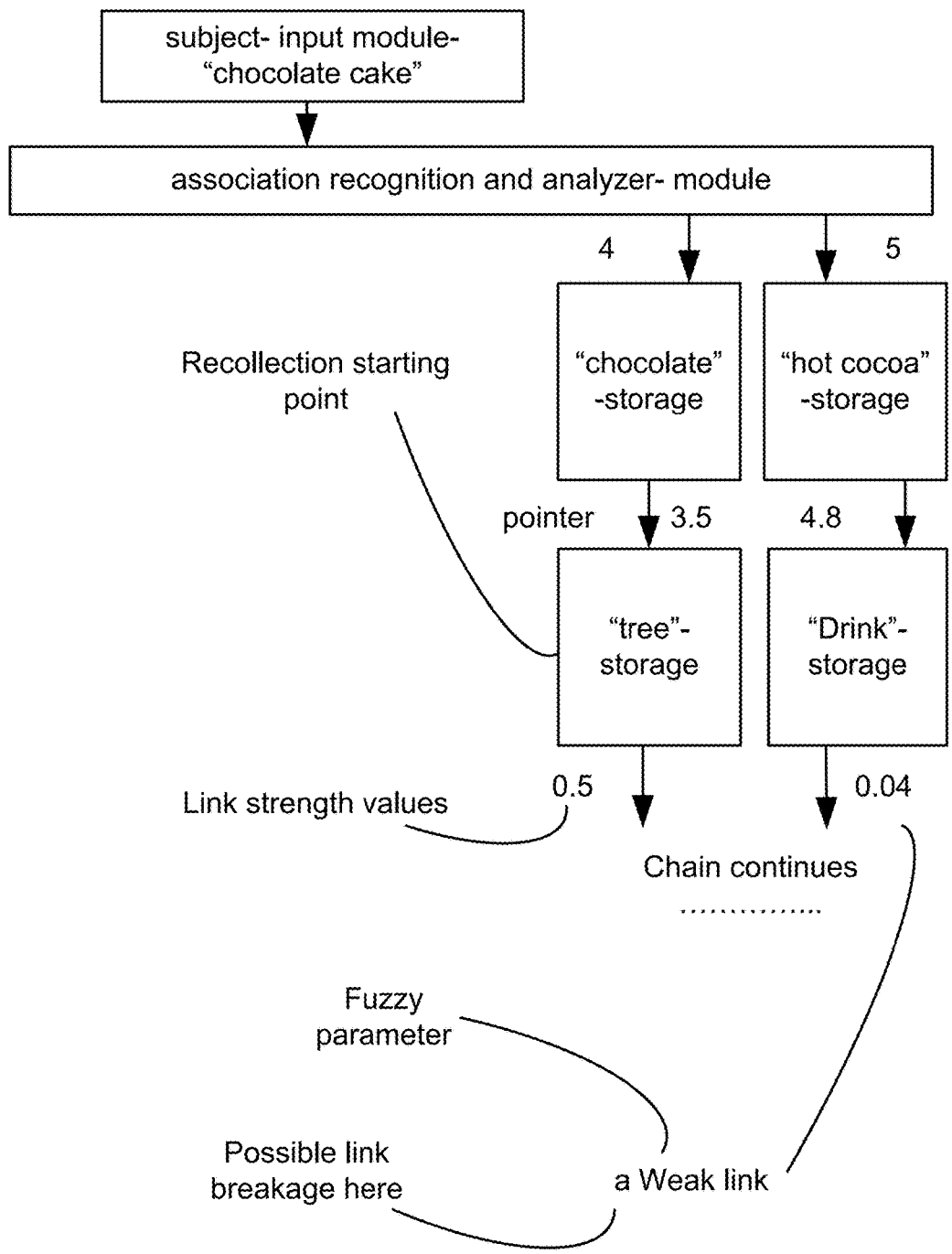
FIG. 78 is a system for the search engine.

Then, there is an association tag or pointer that points the subject to another similar subject (e.g. with a similarity degree, being expressed as a fuzzy concept, as well). For example, the taste of the cake (being a chocolate cake) is a reminder of the other subjects or topics, e.g. "chocolate" or "hot cocoa". Thus, it would point to "chocolate" or "hot cocoa", or both, with a pointer(s). In one embodiment, the association pointers can point to other subject pointers, as N cascaded or chain of pointers in series (or combination of series and parallel configurations), where N is an integer bigger or equal to one. In one embodiment, the links in the chain have different (non-uniform) strength, indicating the different degrees of associations between pair of chained subjects. In one embodiment, the association is among M subjects, where M is bigger than 2, e.g. 3 subjects, which are all related to each other. See FIG. 78 for a diagram of such system.

In one embodiment, the association can be with an event, such as "cake dropping on the curtain". Thus, it points to the subject "curtain" or "stain" (which in turn points to "circular marking" and "circle"). One way for recollection is to store the links or end of the links (or pointers or pointed subjects), and follow the chain or link backward or forward to get the result from either sides, or even start from the middle of the chain and continue in one direction, to recover or find the original subject. So, each subject can trigger another one through the chain sequence. See FIG. 78 for a diagram of such system.

In one embodiment, for long term storage, one puts the information or chain of associations as a whole (or broken into some components or parts, or even sampled e.g. every other subject in the chain, to store less data, as a lossy storage, to save storage space) into long term repositories (for not-frequent access or not-in-near-future access). Note that for the recollection of the broken data or lossy storages, one requires some computing power to reconstruct the lost links later on (by associating pointers), to reassemble the jigsaw puzzle, as the original chain. See FIG. 78 for a diagram of such system.

In one embodiment, when parsing sentences using our methods described here in this disclosure, to search for a more accurate meaning, among possible meanings, especially in a specific context, we can narrow down the choices or targets, as a whole sentence, because the possibility of adjacent two or more words to have a coherent meaning or consistent interpretation eliminates most of the initial individual possibilities for a single word, when presented as a sequence of words in a specific order (or chain of pointers between words).

Note that a human brain carries information and memories as encoded patterns of neural firings.

In one embodiment, the system (of our invention) stores the information for our search engine in the distributed memory repositories. In one embodiment, the links or pointers between subjects get deleted, by the system, if the pointers or links are not used for a long time, to recycle the released memory, as available, for future use. For example, periodically, the system checks for unused links that are idle for a long time (a fuzzy variable), to release the memory location (and break the link or pointer), if applicable.

Figure 71:
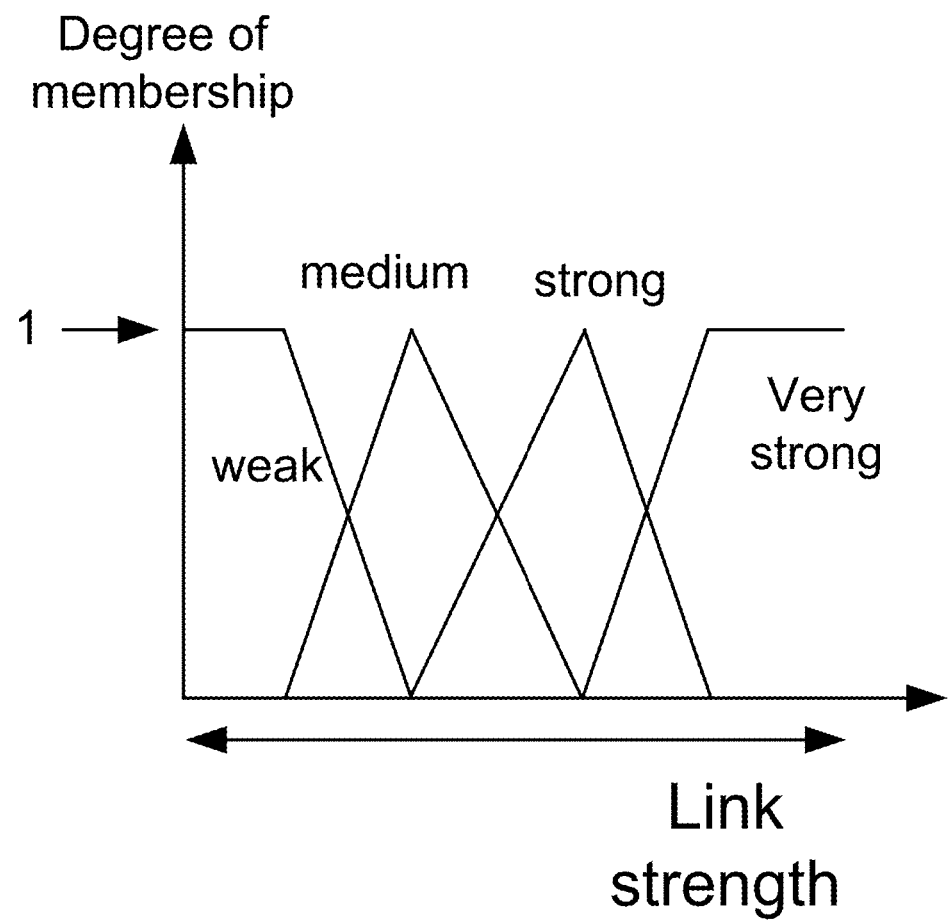
FIG. 71 shows a variable strength link between two subjects, which can also be expressed in the fuzzy domain, e.g. as: very strong link, strong link, medium link, and weak link, for link strength membership function.

In one embodiment, the links or pointers between subjects have various weights. That is, the links are not uniform in strength. Or, the link between two subjects is not binary (e.g. "linked" or "not-linked"). For example, the link strength can be expressed as a real number between 0 and 1. The higher the value of the link strength, the more correlation exists (or more correspondence) between the two subjects. Variable strength link between two subjects can also be expressed in the fuzzy domain, e.g. as: very strong link, strong link, medium link, and weak link, as shown in FIG. 71, for link strength membership function. The value of link strength helps the search engine follows the right direction (or link or pointer), in terms of finding the best solution or answer.

Figure 77:
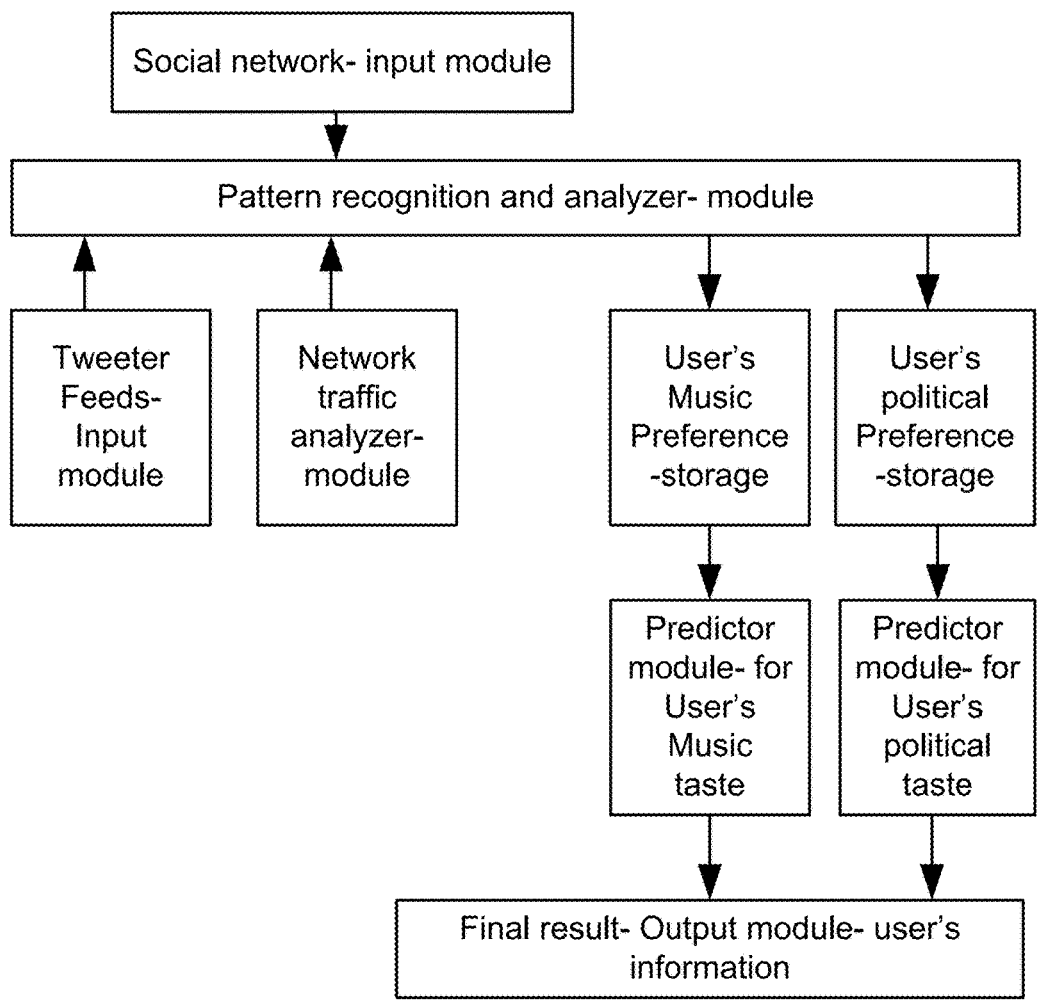
FIG. 77 is a system for the search engine.

In one embodiment, social network sites provide feedback of the users and connectivity between users as an indication of the trend or pattern of society, groups, or individuals, with respect to different subjects, such as taste in music, marketing directions, or political opinions. Thus, they are good databases for data mining. Tweeted subjects (on Tweeter feed traffic monitoring module) can also be studied and classified to find patterns and extract data, for marketing and political purposes, e.g. as to who may become the next president of the United States, e.g. by counting or getting the frequency of a name or subject at a specific time. See FIG. 77 for a diagram of such system.

Figure 76:
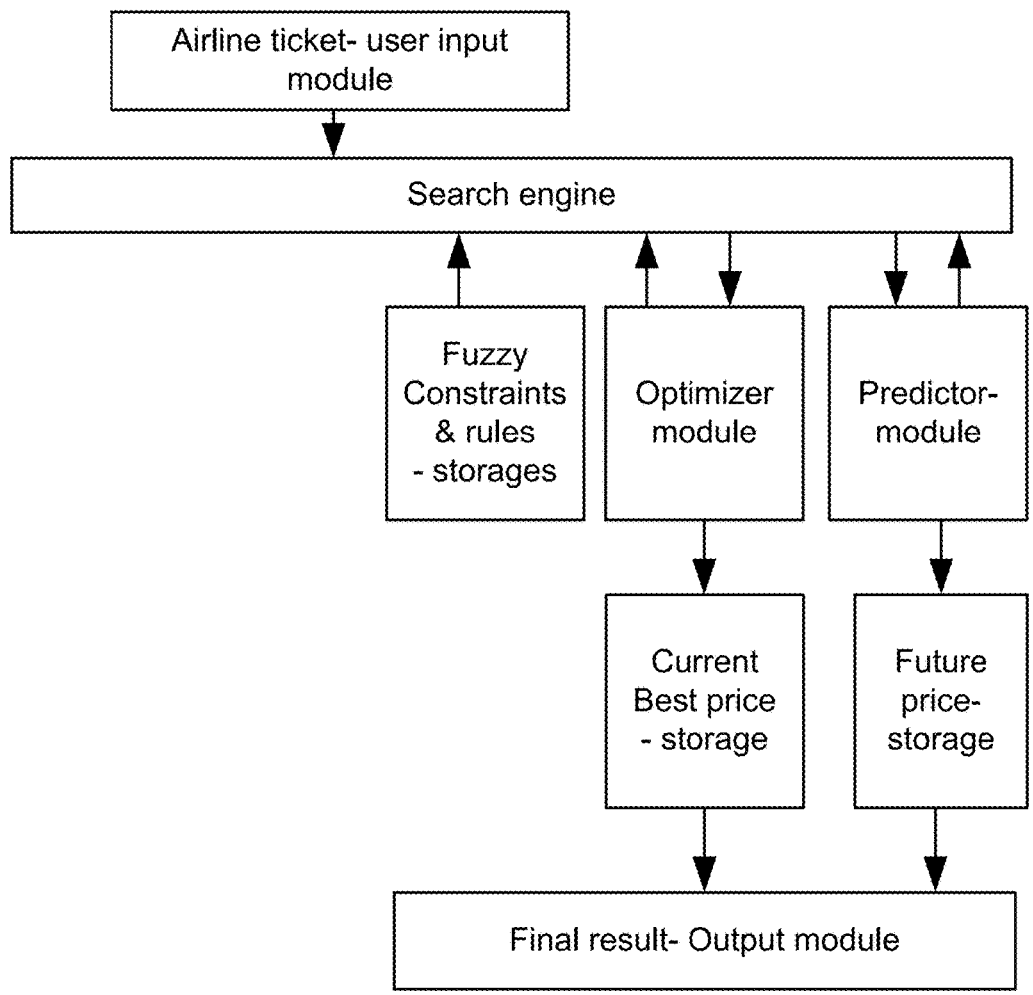
FIG. 76 is a system for the search engine.

In one embodiment, one can use the search engine to predict the price of airline ticket for next vacation for next month, or find the current best price or option available (or best travel plan), considering the travel constraints or rules that we impose. In one embodiment, the search engine can also be used to find the best route to drive home from airport, considering the rules and conditions, with traffic constraints or how much gas we have, to minimize the driving time (as an example). In one embodiment, the price of a company's stock or average group of stocks is predicted for next month, or the best stock value is distinguished, among many companies, based on the rules and constraints about their products and the industry, using fuzzy analysis, explained elsewhere in this disclosure. See FIG. 76 for a diagram of such system.

Figure 75:
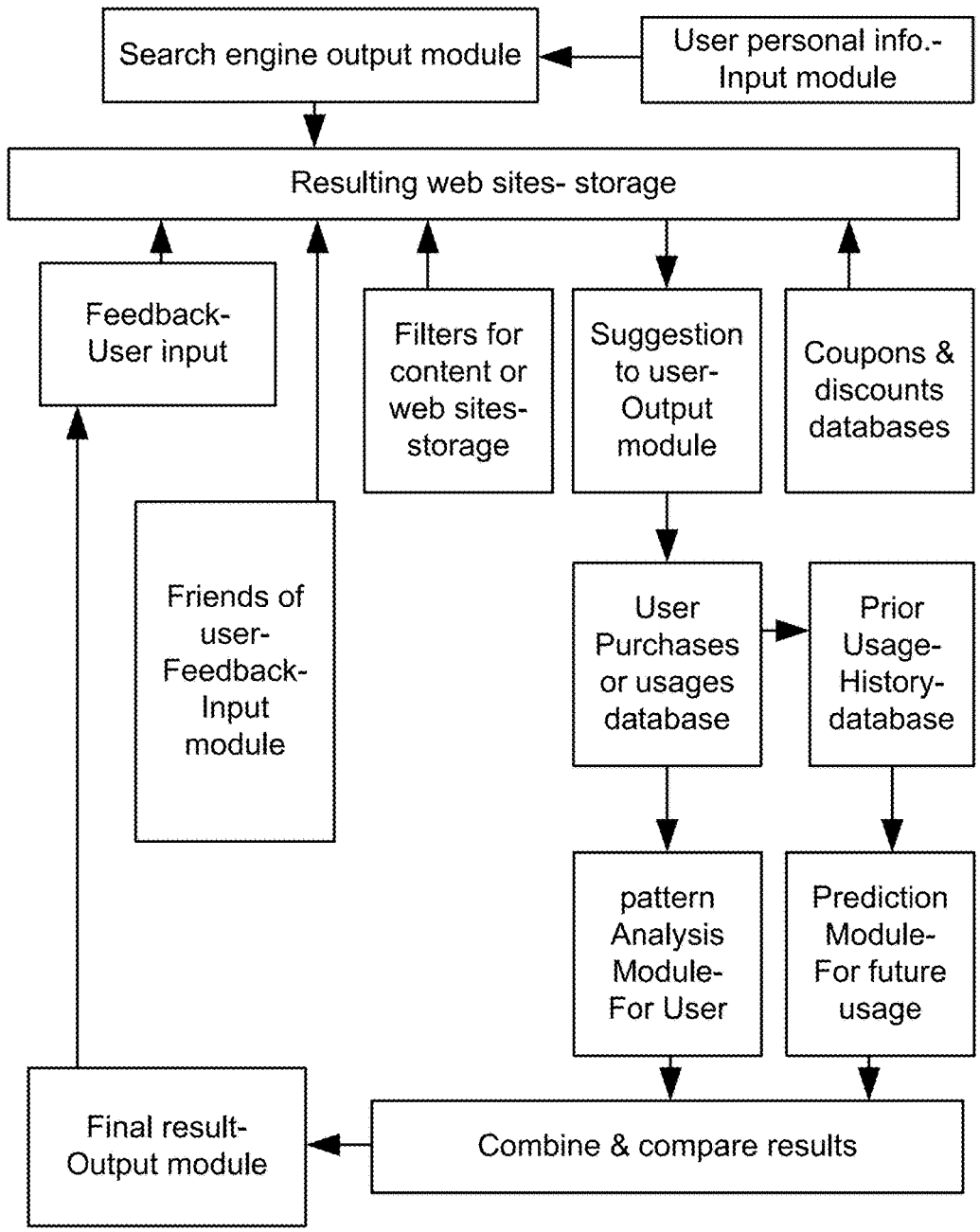
FIG. 75 is a system for the search engine.

In one embodiment, the search engine displays the source of the information for the user, e.g. "Wall Street Journal", as the added value for the search result, which accompanies the credibility of the source, e.g. as a fuzzy parameter. In one embodiment, the search engine focuses on web sites to return personalized results, based on previous browsing habits of the user. In one embodiment, the user inputs personal information to customize the search results or help the search engine go to the right or more relevant direction, with respect to the user's preferences, taste, or parameters. For example, knowing that the user lives in San Francisco or vicinity area (in California, USA) (as her resident address, as one input by the user, through the user interface module), the search for "football team" yields "The San Francisco 49ers" (which is a professional American football team based in San Francisco, Calif.), and this result has a higher ranking or score than another American football team in another city, and this result also has a higher ranking or score than a soccer team in San Francisco, Calif. (because "football" (generally, in US) refers to the "American football", not "soccer"). This means that the meanings of the words are clarified and set based on the context and background information, e.g. user's information or preferences, such as address, zip code, ethnicity, religious, weight, height, age, gender, job, income, political affiliations, college degree, food preferences, health information, marriage status, type of car, or the like. See FIG. 75 for a diagram of such system.

Similarly, in one embodiment, the prior queries help customize the search result for future queries. Other factors can be how many times or how often a user (for example) searches for food or nutritional facts, and how long the users spend on a web site related to the food. This interest in food-related subjects makes "food" a more relevant subject for that user for future, to be a factor for relevance determination of other subjects in the search. In one embodiment, the user allows that the search engine tracks her usage and habits or patterns, from the user-input module, e.g. through the menu on screen, for privacy level settings, which can also be another fuzzy parameter. See FIG. 75 for a diagram of such system.

In one embodiment, the search engine tracks the music, books, movies, and videos that the user downloads, buys, rents, listens, watches, or looks at. In one embodiment, the search engine tracks the user's emails and the patterns related to the emails or SMS, e.g. the recipients, how often sent, what time of day sent or received, any attachments to the email, what type of attachments to the email (type of file, e.g. JPEG or PDF), size of the file of the attachment or the email, or the like. All of the above parameters indicating the degrees or quality can also be expressed as fuzzy parameters. In one embodiment, the search engine has a user-interface or GUI (graphical user interface) for the user inputs, with scaling or sliding bars, knobs, or selectors. See FIG. 75 for a diagram of such system.

In one embodiment, the search engine connects to the modules for controlling ads, coupons, discounts, gifts, or filters for web sites (e.g. filters deleting specific web sites for children, from the search results). In one embodiment, the search engine rewards the user on points for discounts for purchases or coupons, in exchange for giving up some privacy, for personal information input by the user. In one embodiment, the search engine is self-customized engine or module that can be embedded on a web site. In one embodiment, the search engine helps the ads targeting a user, based on personal information, such as birth date, e.g. for gift suggestions, or statistics or biometric-driven, such as user's height or user's household's income percentage, with respect to those of national average or median. See FIG. 75 for a diagram of such system.

Figure 74:
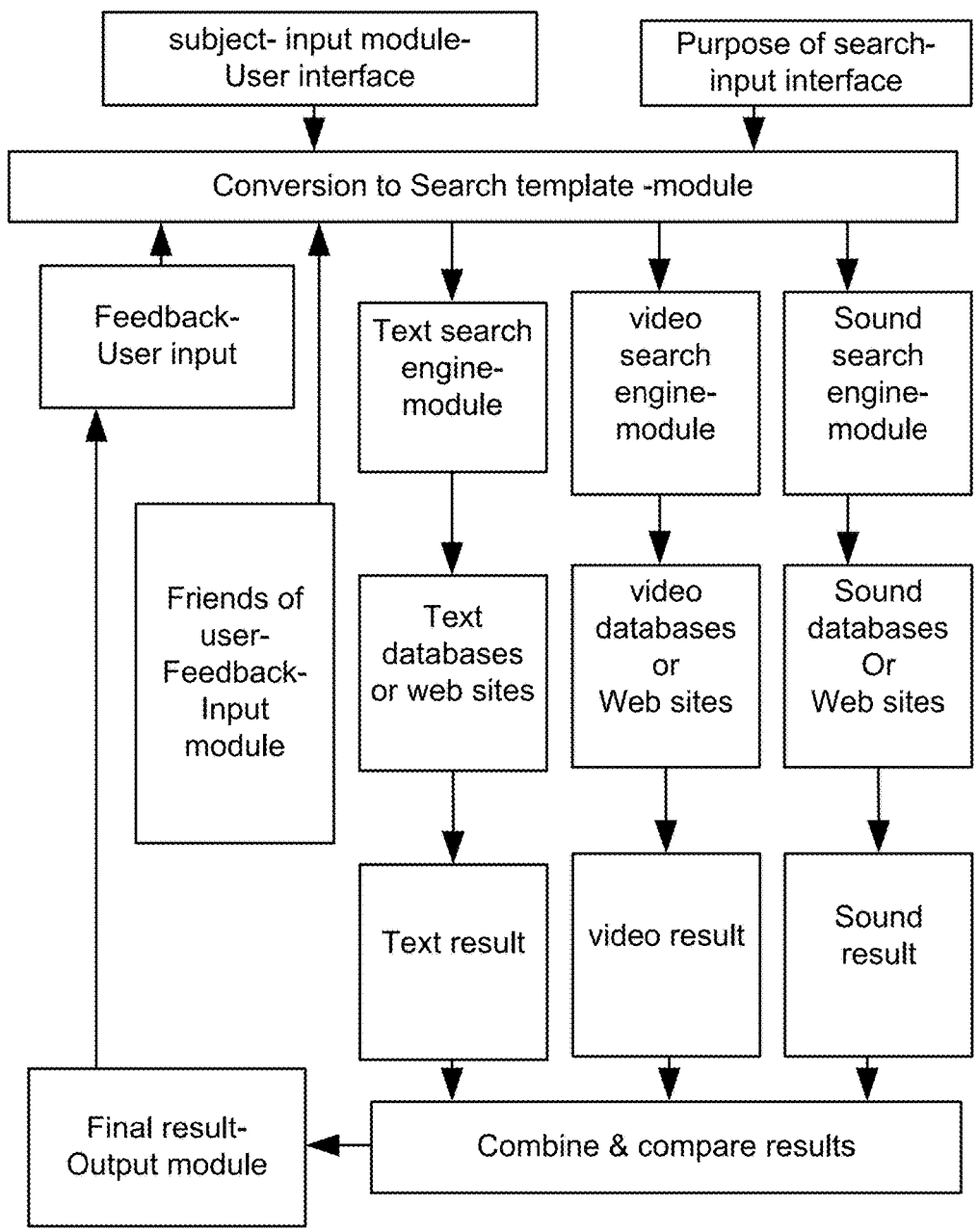
FIG. 74 is a system for the search engine.

In one embodiment, the user specifies her purpose of the search, e.g. medical, business, personal, or the like. For example, searching for a hotel yields different results for a business trip (near convention center or downtown), versus for a vacation trip (near the beach or amusement park). In addition, for example, specifying the accompanying persons can modify the search results. For example, having kids with the user during a vacation trip tilts or focuses the search results toward the vacations, hotels, or cruises that are tailored to families and kids (family-friendly or oriented), whose information can be extracted from the tags or scores supplied by the hotel itself or its web site, e.g. meta-tags or metadata, or from the tags or scores supplied by other users, or from the text comments or feedback by other users about their experiences with that hotel. See FIG. 74 for a diagram of such system.

In one embodiment, the user asks a question, and the search engine first determines the language of the question (e.g. by parsing the sentence or question), or the user herself supplies the information about the language, e.g. French. The search can be focused on web sites in French language (e.g. using the metadata or flags from the web site), or search any web site, depending on the user's or default settings for the search engine. In one embodiment, the search is on one or more of the following formats (and the search results are also in one or more of the following formats): text, web sites, links, emails, video, images, line drawings, paintings, satellite images, camera images, pictures, human pictures, music, blogs, HTML, PDF, sound, multimedia, movies, databases, spread sheets, structured data, slides, or the like (or a combination of the above), per user's setting or default. See FIG. 74 for a diagram of such system.

In one embodiment, the search engine is queryless, i.e. with no questions at all, but the search engine provides or suggests some subjects or topics automatically, sua sponte, based on the history and user's preferences or prior user's feedback. In one embodiment, the tagging, scoring, and feedback can also come from friends, social network, other users, similar users, club members, or co-workers, e.g. using bookmarks, links, and shared searches, presented, displayed, or forwarded to others. In one embodiment, there is a biometrics or security module associated with the circle of friends or social network, to protect the shared information, against unauthorized or free access or hacking. See FIG. 74 for a diagram of such system.

Figure 73:
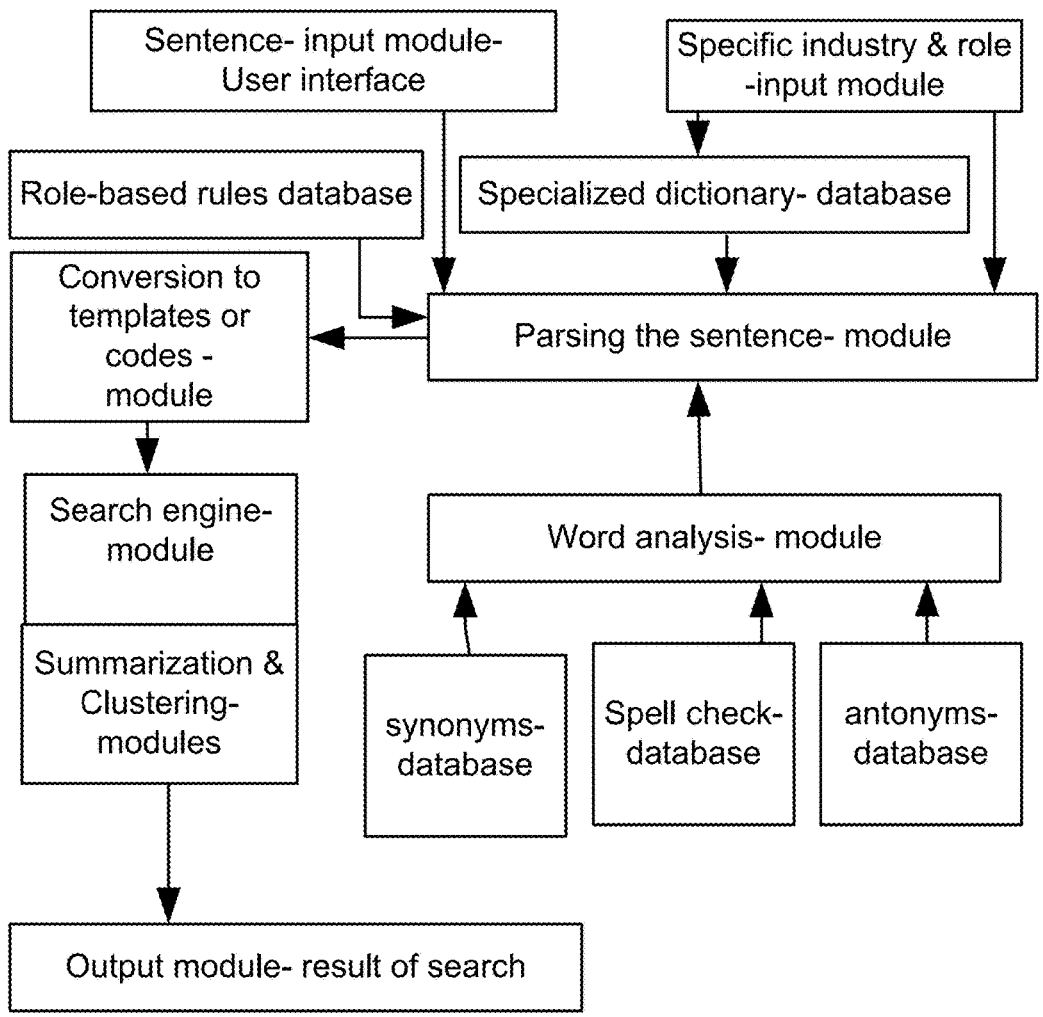
FIG. 73 is a system for the search engine.

In one embodiment, the search engine and corresponding natural language parsing and processing are tailored toward the specific application or industry, e.g. telecommunication, stock trading, economy, medical diagnosis, IP (intellectual property), patent, or claim analysis or valuation, company valuation, medical knowledge, and the like. For example, a lot of abbreviations and words have very specific meanings in a specific technology, context, or industry, which may be very different in other contexts or environments, causing uncertainty or misleading search results or language construction or interpretations. For example, "IP" means "Internet protocol" in telecom industry, but it means "intellectual property" in patent-related businesses. To minimize those negative effects, the user specifies the industry from the beginning. The modules can be trained for various industries, and they can be separately sold or accessed as a service for specific industry. See FIG. 73 for a diagram of such system.

Figure 72:
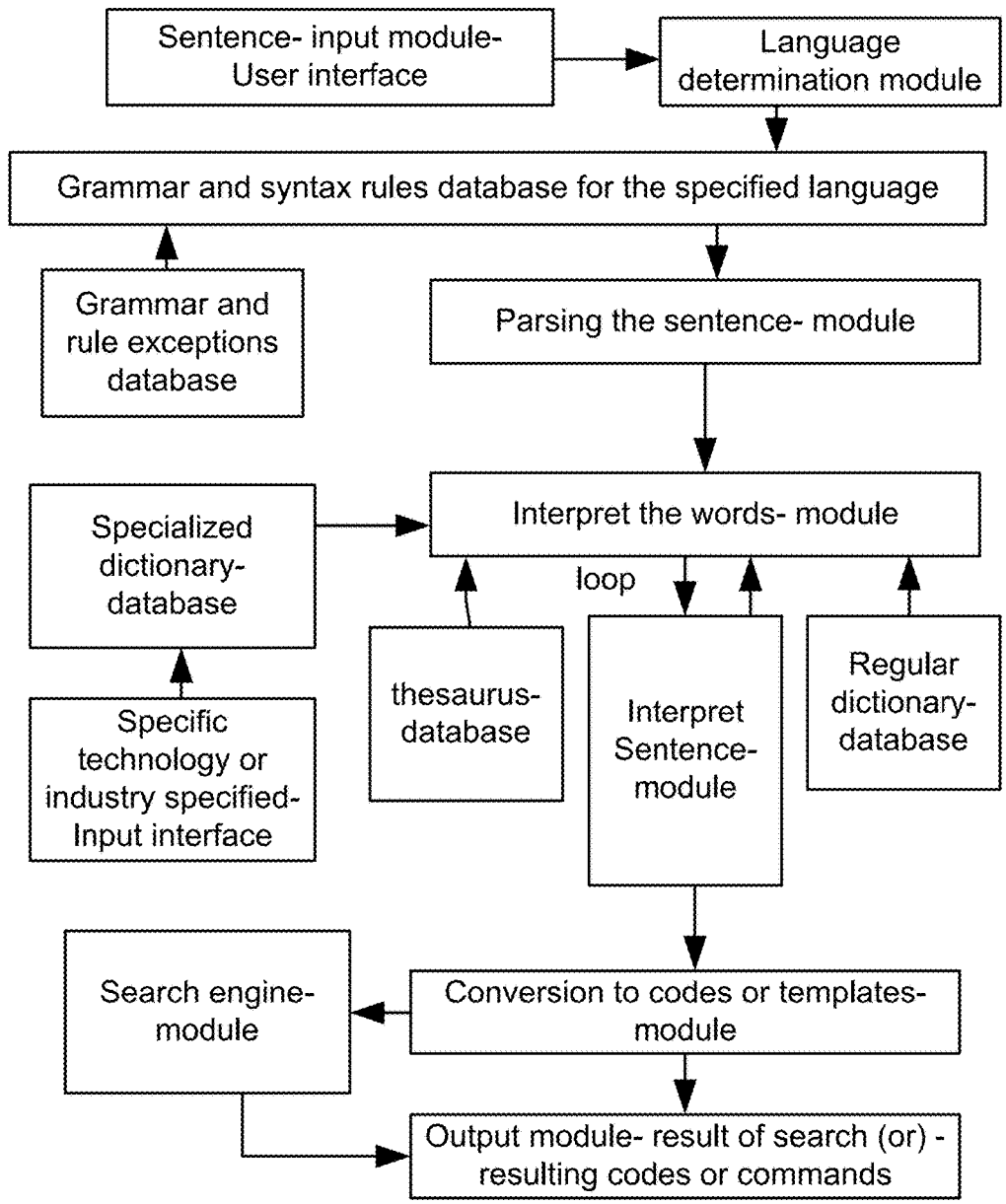
FIG. 72 is a system for the search engine.

In one embodiment, using common rules for grammar and syntax for a specific language for sentence structure (and corresponding exceptions to those rules), the search engine parses and dissects the sentence (as explained elsewhere in this disclosure) and applies dictionaries (in different categories, such as medical dictionaries) and thesaurus (or phrase books or glossaries or idiom or phrase or dialect listings) to find or interpret the meaning of the words, phrases, and sentences, e.g. to convert them into codes, templates, abbreviations, machine codes, instructions, text, printout, voice, sound, translation, script, or computer commands, to process further, if needed. See FIG. 72 for a diagram of such system.

In one embodiment, the synonyms module, spell check module, antonyms module, and variation or equivalent word module are all part of a search engine, to help find similar words and concepts, or parse the sentences. In one embodiment, for analytics, the search engine includes summarization module and clustering module, to group the data in sets for systematic analysis, such as based on N-dimensional feature space for components of a word or phrase, based on all the possibilities for basic components, partial words, or letters in a given language (as a dictionary for all possible basic word components in a given language, with all connecting possibilities with other neighboring components, which is held in a database(s) or relational databases, and can be updated and improved by users periodically as feedback, or by machine or processor, automatically, with a training module, such as a neural network). FIG. 111 is an example of a system described above.

In one embodiment, social bookmarking, tagging, page ranks, number of visitors per month, number of unique visitors per month, number of repeat visitors per month, number of new visitors per month, frequency and length of visits for a given web site or web page, number of "likes" or "dislikes" feedback for a site or topic from users, and number of links actually requested or existing for a web site, as absolute or relative numbers, or as a rate of change (first derivative) of the parameter, are all parts of the search engine analytics, for finding the more relevant search results, with respect to a specific user or general public users. In one embodiment, tagging and user comments are done as an annotation to search results, as an extra layer. In one embodiment, what other people, users, or friends have done is displayed or suggested to the user, e.g. actions performed or web sites visited or items purchased. FIG. 111 is an example of a system described above.

In one embodiment, a search is personalized or customized using the position or role of a person in an organization, e.g. CEO of a company, with her parameters pre-set as a generic CEO, and can be further defined based on specific personality of the CEO, by herself, in such a way that a new CEO does not have to change the pre-set generic or basic part of the profile, making the transitions much smoother for a new CEO. The role-based model can be combined with the concept of inherency, so that a class of roles or positions can be defined categorically (only once, in a very efficient way), and then, subclasses may have extra features, conditions, or constraints on top of those of the corresponding class. FIG. 111 is an example of a system described above.

In one embodiment, live search is conducted using human experts as helpers, to guide the searches in a general direction by input phrases or feedbacks, in a limited scope, interactively with machine or computer. This is useful for a new field, in which not much information is accumulated in the databases, and most of the information is in the head of the human experts at this early stage. In addition, the user base and number of queries are manageable (small enough) with a few experts on line. This is not scalable or cost effective for large user base or databases, with too many queries to handle by human interventions. FIG. 111 is an example of a system described above.

Pattern Recognition

In one embodiment, the images are searched for specific color or patterns or shapes, e.g. for houses or clothing, to match a target or find one similar to a target, based on the features defined in feature space, such as stripes patterns, color red, circles, dot patterns, trapezoid shape, or the like, as a pattern recognition module, looking for degree of similarity, e.g. as a fuzzy parameter, for real estate agents to search databases and sell houses or for department stores or store web sites to sell clothing to potential customers. This is also useful for analyzing and classifying Facebook® and photo album sites, e.g. for face or iris recognition, e.g. to identify, track, or classify people or objects. This is also useful for the security purposes on Internet or by cameras at the airports or buildings. FIG. 112 is an example of a system described above.

In one embodiment, the video is searched, using still images, motion vectors, and difference frames, e.g. to find a car or face in the video, to find the speed of the car from the location of the car in different frames, or to recognize a person in the video, using face, iris, or eye recognition (or other biometrics), or target tracking objects in video frames to get other identification parameters or features from the video. This is also useful for analyzing and classifying YouTube or movie repositories or music videos, e.g. to find or track people, subjects, objects, topics, or songs. FIG. 112 is an example of a system described above.

In one embodiment, the video track and sound track from a movie can be separately analyzed, for various sound and video recognitions, such as spotting some sound signatures or sequence of notes, indicating an event or music, or using voice or speaker recognition (as explained elsewhere in this disclosure), to find or recognize a person and tag or classify the track or movie. In one embodiment, the recognition engines or search engines from different tracks are combined or compared with each other, to get a better result, with more confidence, faster. FIG. 112 is an example of a system described above.

In one embodiment, the maps or road maps are scanned and analyzed to get (for example) geographical or residential information, for civilian or military purposes, e.g. for market search or business intelligence gathering. Markings, captions, scales, symbols, and names on the maps are recognized by OCR or pattern recognition module, to interpret the maps and find people and locations of interest. For satellite images, the objects have to be recognized, first (by object or pattern recognition module), as what they are, and then they can be categorized or classified (by tags or flags), with comments, text, or identifiers superimposed or attached to the image file. Object recognition with possibility of choices is expressed in fuzzy system, with membership values, e.g. recognizing an object as a bus or truck in a satellite image.

In one embodiment, Wikipedia and other encyclopedia or informational sites are referred to by the search engine for search on the topics they carry. In one embodiment, the search engine categorizes as how often a web site should be reviewed or searched based on how often it gets updated (in average), how relevant is the web site for our topic of search, and how reliable is the source of the web site. For example, the more often it gets updated and the more relevant and reliable the web site, the more often the search engine would check the web site for updates and new information, to search and extract data. In one embodiment, the search engine tracks and analyzes the web site traffic, for patterns and information about the web site, including for the web site reliability analysis. FIG. 113 is an example of a system described above.

In one embodiment, all the units of weight, length, and the like, with the corresponding conversion factors are stored in a database, for example, to convert "meter" to "foot", for unit of length. The physical constants and physical, chemical, or mathematical formulas or facts (e.g. as relationships or numbers), such as speed of light or formula for velocity in terms of distance and time, are also stored in corresponding databases or tables, for easy and fast access for the search engine, e.g. with a hierarchical indexing structure or relational database(s). Alternatively, the search engine can refer to reliable web sites with similar information, for search and extraction of data.

In one embodiment, the components (such as text, video, and sound track in a movie data) are separated and searched separately, on an optimized and dedicated search engine for that format of data. See FIG. 84 for such a system. In one embodiment, all the components are searched using the same (or generic) search engine (not optimized for any specific data format). In one embodiment, the results of all components are combined to make a better overall result. In one embodiment, the results for each component are reported separately. In one embodiment, the processors are processing the results in parallel. In one embodiment, the processors are processing the results in series.

In one embodiment, the system uses the tags or comments written by various users, or searches and parses those comments to dissect or convert them to the individual tags. (The example or method of parsing of a sentence or phrase is given in another part of the current disclosure.) This way, the collection of knowledge or intelligence of many users and people are combined to find a better or faster match(es) for the search. One example is the pictures tagged by the users, which are searchable in different databases, to find a correspondences or likelihood of relationship between one name and multiple pictures. FIG. 114 is an example of a system described above.

On the first cycle, the fuzzy classifier module or device classifies or separates different pictures into clusters or groups in N-dimensional feature space. For example, it uses facial features and parameters or biometrics, e.g. the approximate length of the nose, or ratio of width of the nose to length of the nose (as a dimensionless number or normalized parameter), or other features related to iris or eye recognition. This corresponds to multiple individuals having the same exact or similar name. Please note that "similar name" is a fuzzy concept, by itself, with its own membership function value. FIG. 114 is an example of a system described above.

On the second cycle, it further distinguishes between or finds pictures of the same person in different ages or in different forms or settings (such as with dark eyeglasses, or wearing fake or real beard or mustache, or wearing scarf), which as the first filtering pass or cycle, it may look or get classified as a different person. One way to find the right person is the use of biometrics parameters, such as eye and nose, that "usually" do not change by age "that much" for the same person. Please note that "usually" and "that much" are also fuzzy parameters and concepts, by themselves. The other way is the correspondence of the date that the picture was tagged or posted, which may correspond to the date of the original picture, or equivalently, to the age of the person in the picture (or the year the picture was originally taken or captured). The other way is the comments or text or tags by the users that accompany the pictures, which collectively give probability or correlation for the identification of such person. The other way is the correspondence of the item of clothing (or attached objects, external items, context, environment, or surrounding), e.g. wearing the same or "similar" shirt or neck tie in 2 different pictures. Note that "similar" is another fuzzy parameter here. FIG. 114 is an example of a system described above.

Even, more general is the correspondence of the preferences or characteristics of the person, as a collection or set of parameters. For example, for a person living near the beach in Florida (e.g. a Miami Beach address as residential address), the system expects higher probability of casual dressing, bathing suit, sun glasses, and tropical trees appearing in the picture. So, those features appearing in a picture (e.g. casual dressing, bathing suit, sun glasses, and tropical trees) favors or increases the probability of a person with Miami zip code or address (or a person on vacation near beach), for identification purposes of a person in a picture, instead of a person with an Alaska address (or a person with no travel habits or history in tropical or beach areas). FIG. 114 is an example of a system described above.

Another example is that if a lady has many pictures with a red dress (or striped T-shirt or particular hat or design or designer or signature or pattern or style or brand or trademark or logo or symbol, e.g. a Polo shirt with its logo on it), the system can assume that the person has a lot of red dresses or prefer the color red for dress or shoes or car. Or, the red color preference is obtained from the user herself or her friends' input, as preference or history files (or based on a detective work file, by a third party, or by a software agent searching all over Internet for a person's personal data, or by marketing databases from a Macy's department store, based on past behavior or purchases, as her file history). Thus, if a person is sitting in a red car or wearing red shoes, in a picture or a video, it has a higher probability to be the person in question, based on her past or characteristic files, for identification or recognition purposes, e.g. for searching through Internet or databases to find all pictures or videos related to a name or a person. FIG. 114 is an example of a system described above.

The recognition of a pattern, color, person, face, logo, and text, including OCR (optical character recognition), is generally done by dissecting the image or video into pieces and components (including motion vectors for video, to track the objects, between the frames, as the difference between the neighboring frames) to find features or objects, and from the parameters associated with those features and objects, e.g. geometrical lengths or ratios or angles, the system finds or guesses the identity of those features or objects, based on some certainty factor or membership value (which is a fuzzy parameter). For an object with images captured from multiple angles, the data can be more useful, as it gives the information on 3-D (dimensional) object or depth, for better recognition.

Figure 85:
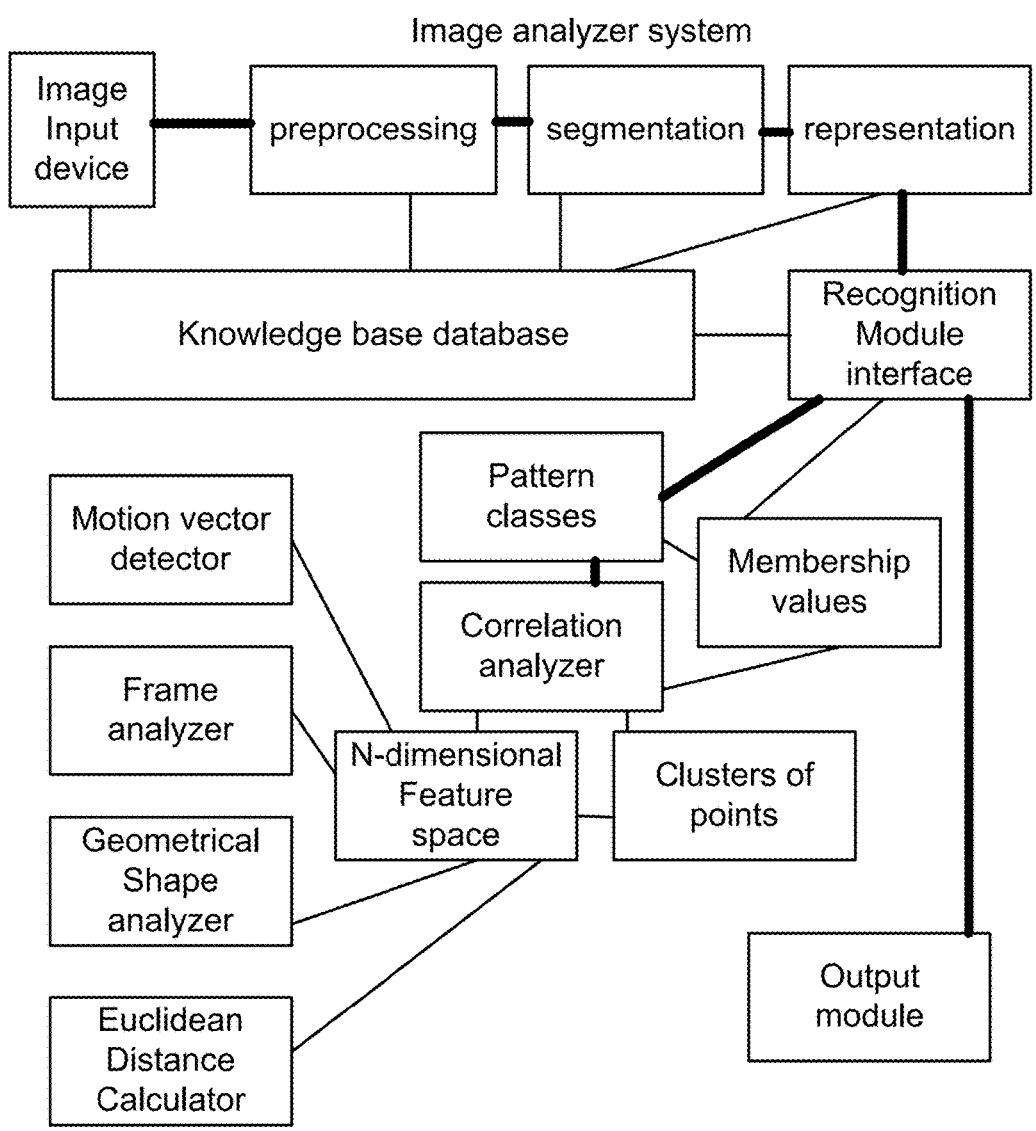

For a pattern recognition module, we have an image analyzing system, e.g. as shown in FIG. 85, with image acquisition and preprocessing modules, followed by segmentation module and description module, and ended with interpretation and recognition modules, with all modules interacting with the knowledge base databases. To recognize pattern or pattern class, using features or descriptors, based on pattern vectors, strings, or trees, the system measures the parameters (e.g. length of nose, ratio of iris width to the nose length, or angle between two curves or strikes in a letter of handwriting or signature, e.g. using the pixels of an image), and plots them as points in the N-dimensional feature space. Clusters of points around or close to letter "a" specification and parameters, as an example, are recognized as potential candidates for letter "a". For example, a letter may be recognized as 0.80 "a" and 0.05 "e". This can be expressed as membership values, as well, which is a fuzzy parameter.

In one embodiment, a decision or discriminant function (an N-dimensional pattern vector) is used, to find the pattern class memberships and the fuzzy decision boundaries between different classes. For matching, in one embodiment, the system uses a minimum distance classifier, with each pattern class being represented by a prototype or mean vector, $\overline{P}$:

$$\overline{P} = (1/N)\Sigma \overline{X}_i$$

where N is the number of pattern vectors, and $\overline{X}$ is a pattern vector.

Then, the Euclidean distance to determine the closeness is determined as, D:

$$D = \|\overline{X}_i - \overline{P}\|$$

where $\|\overline{K}\| = (\overline{K}^T \overline{K})^{0.5}$ (It is the Euclidean Norm.)

The matching can be done by correlation, C, as well, between A and B, in another embodiment:

$$C(x,y) = \Sigma_g \Sigma_h A(g,h) B(g-x, h-y)$$

The correlation function may be normalized for amplitude, using correlation coefficient (e.g. for changes in size or rotation).

In one embodiment, an optimum statistical classifier is used. In one embodiment, a Bayes classifier is used, to minimize the total average loss (due to incorrect decisions), e.g. for the ones used for Gaussian pattern classes. In one embodiment, a perceptron for 2-pattern classes is used. In one embodiment, the least mean square (LMS) delta rule for training perceptrons is used, to minimize the error between the actual response and the desired response (for the training purposes). FIG. 115 is an example of a system described above.

In one embodiment, a multi-layer feed-forward neural network is used. In one embodiment, the training is done by back propagation, using the total squared error between the actual responses and desired responses for the nodes in the output layer. In one embodiment, the decision surfaces consisting of intersecting hyperplanes are implemented using a 3-layer network. FIG. 115 is an example of a system described above.

In one embodiment, for pattern recognition, the system uses the structural methods, to find the structural and geometrical relationship for a pattern shape, using a degree of similarity, which is associated with a membership value, which is a fuzzy parameter. In one embodiment, a shape number is defined for the degree of similarity. In one embodiment, a four-directional chain code is used to describe the shape. The distance between 2 shapes is expressed as the inverse of their degree of similarity. So, for the identical shapes, the distance between the shapes is zero, and their degree of similarity is infinite. In one embodiment, for shapes, the system uses similarity tree and similarity matrix to evaluate the degree of similarity, which can be expressed as a membership function, which is a fuzzy parameter. FIG. 115 is an example of a system described above.

In one embodiment, for shapes, the region boundaries is coded as strings, with the number of symbols matching as an indication of the degree of similarity. In one embodiment, for shapes, polygonal approximations are used to define different object classes. In one embodiment, a syntactic method is used to recognize the patterns. The system uses a set of pattern primitives, a set of rules (grammar) for their interconnections, and a recognizer with the structure defined by the grammar. The regions and objects are expressed based on strings, using primitive elements. The grammar is a set of rules of syntax, which governs the generation of sentences from the symbols of the alphabets. The set of sentences produces a language, which represents pattern classes. FIG. 115 is an example of a system described above.

In one embodiment, we represent the string grammar as a 4-tuple, (A, B, C, D), for the strings, with e.g. A, B, C, and D representing non-terminals (a set of variables), terminals (a set of constants), the starting symbol, and a set of rules, respectively. Then, objects or shapes can be expressed mathematically, by first conversion into its skeleton (using image processing on pixel level, for example, to thin down the image to get the line structure shape), followed by primitive representation (for example, basic structure or geometrical shapes, from database, to replace the skeleton), followed by structure generated by regular string grammar (to resemble the original shape, region, or figure). String recognizers can be represented using nodes and arrow connectors between the nodes in a graphical manner, similar to a state diagram. FIG. 116 is an example of a system described above.

In one embodiment, the string grammar can be extended or generalized into the tree grammar, for syntactic recognition of the trees, using a 5-tuple, (A, B, C, D, E), with E representing a ranking function to represent the number of direct descendants of a node with a label which is terminal in the grammar. Again, objects or shapes can be expressed mathematically, by first conversion into its skeleton (using image processing on pixel level, for example, to thin down the image to get the line structure shape), followed by primitive representation, using a tree grammar, to resemble the original shape, region, or figure. Selection of the primitives in this case is based on the membership values, and thus, it is a fuzzy parameter.

For recognition, the system deals with various knowledge base databases: procedural knowledge (e.g. for selection of parameters and procedures), visual knowledge (e.g. angle of illumination, producing shadow and other visual effects), and world knowledge (for relationships between objects, e.g. in an image of a car, the system expects to find or detect one or more tires under the car, if it is visible in that perspective), which sets the expectation in an image for higher validation, consistency, and accuracy. For example, for the world knowledge, the fact that "Cars usually have 4 tires." can be expressed as follows:

[OWNERSHIP (car, tire, 4), USUALLY]

Or, it can be rewritten as:

OWNERSHIP (car, tire, at least 1)

Or, it can be expressed as: ("For all" cars, "there exists" one tire):

OWNERSHIP ($\forall$ car, $\exists$ tire)

These statements can be combined with others using logical or relationship operators, e.g. AND, OR, NOT, XOR, and IF-THEN statement (rules). Using the rules and relations, the system performs inference or deduction, using an inference module or deduction engine or device. The term USUALLY adds the Z-number to the statement of the world knowledge. Thus, if the system detects an oval or circular object in the image under the body of the car structure image object, then that may be a tire of the car. The tire detection can be expressed based on membership values, which is a fuzzy parameter.

In one embodiment, semantic networks are used, with nodes representing objects and the arrows representing the relationships between the objects. For example, for the example given above regarding "a car having a tire", one node is CAR, and the second node is TIRE, with an arrow connecting the node CAR to the node TIRE, representing OWNERSHIP relationship between the 2 nodes.

Figure 86:
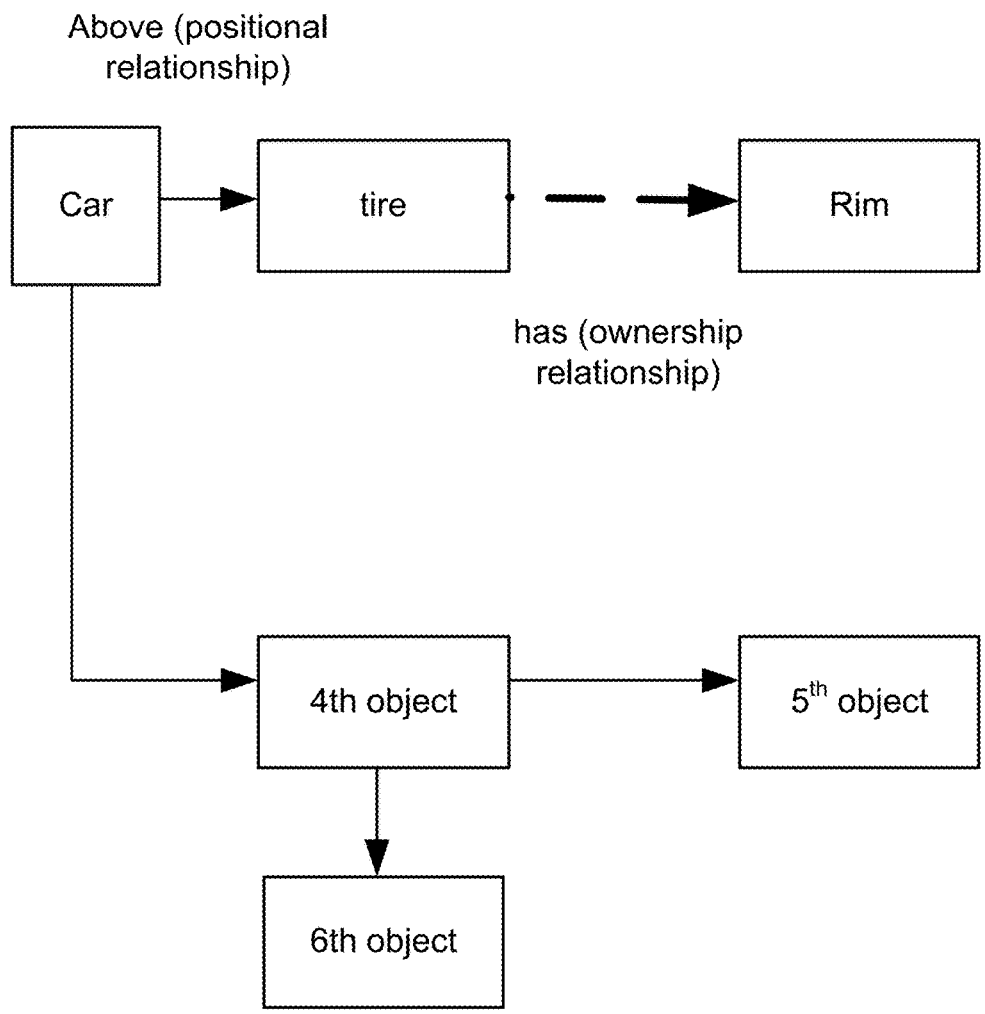

Another example is the application of the position of two objects with respect to each other. For example, for a statement of "a car located above a tire", one node is CAR, and the second node is TIRE, with an arrow connecting the node CAR to the node TIRE, representing ABOVE (positional) relationship between the 2 nodes, representing the 2 objects CAR and TIRE. The knowledge of the possibility of the existence and position of a tire in the image of a car helps the identification of the objects in the image (more accurately and faster). In addition, if the system is given another fact or statement that "A tire has a star-shaped rim.", then if a star-shaped object is detected in the middle of the object of TIRE in the car image, then that star-shaped object may be the rim for the tire of the car. FIG. 86 shows such an example. Thus, the relationship between the objects can be cascaded and expanded this way, so that the detection of the objects gets easier or better, especially if one object is detected already, or if the detection of the first object has to be confirmed or verified by other objects in the image.

The above example also works for facial features, e.g. for iris, face, or identity of a person recognition, in which there is a relationship between relative size and position of different components of eye or face of a human. The above example also works for spelling or word recognition (e.g. OCR) and voice recognition, in which there is a relationship between different sounds or letters that make up a word or sentence, for a given grammar and language, e.g. American English, in terms of sequence of the letters that make up a word or phrase or written sentence, or sequence of sound bites or tones or notes or frequencies that make up a speech or voice or spoken sentence. So, for all of the above, the relationship or relative position of one object or feature with respect to another is known, which helps the detection and recognition (or verification and confirmation) of all features and patterns in the image or in any other media.

In one example, if the comment or tag for a picture refers to "The last $4^{th}$ of July with Clinton in the office". After dissecting, parsing, and analyzing the statement (as described elsewhere in this disclosure), for a user in the United States of America (context-specific for the user), the phrases "$4^{th}$ of July" and "Clinton in the office" is probably a reference to "the former President Bill Clinton, of the United States of America" (based on the correlation of the words or concepts, or combination of the words, or order of the words in a phrase). The last $4^{th}$ of July of President Bill Clinton's presidency (from the historical facts and databases, available to the search engine) is Jul. 4, 2000. Thus, the picture is tagged by a statement which refers to the date of Jul. 4, 2000. Having a date associated with a picture or piece of data usually helps to find the owner of the picture or identity of the objects in the picture or things associated with the picture (based on correlation, association, or probability), e.g. the identity of the person(s) in the picture. Note that the dates associated with a picture may generally be multi-valued, fuzzy, a range, or approximation date(s). FIG. 110 is an example of a system described above.

Figure 87:
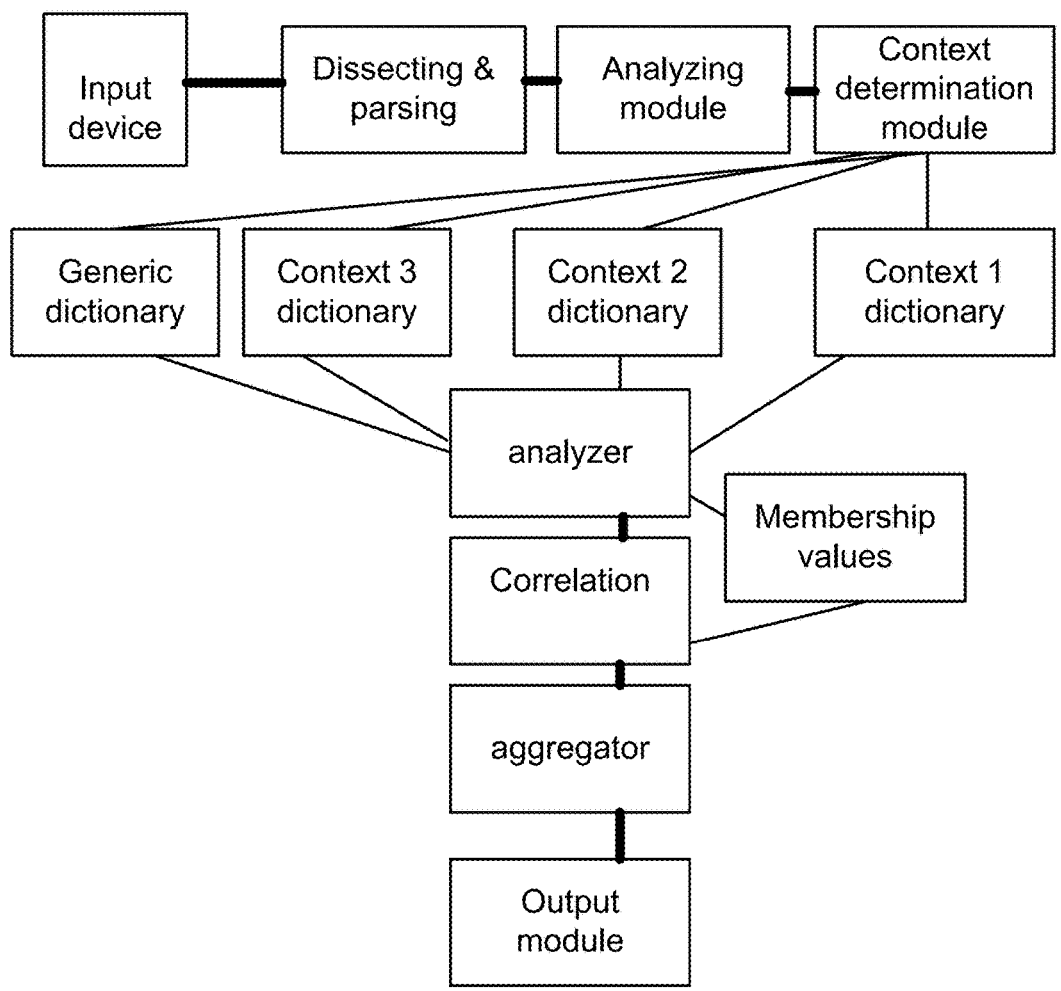

Note that in the example above, "Clinton" (extracted from the sentence and distinguished as a possible given name or family name) is already stored in a database for the famous names or people, with the following ranking order: (1) President Bill Clinton (as the more probable candidate); (2) Secretary of State Hillary Clinton; and so on. If there is no other supporting information available, the system tries the choices from the highest to the lowest. For the first choice (President Clinton), the "office" refers to the "White House" or "presidency". In fact, the generic or common words in a language may have a specific meaning or different meaning, once it gets associated with another word, concept, context, or environment (e.g. politics, versus medical field). Thus, once a context is set or determined (such as politics or politicians), the specific database(s) for that specific context is activated or referred to, instead of the general or generic databases, to find the more exact or better meaning of the words or phrases. This is shown in FIG. 87, as an example.

In an example, one name is very similar to another name in spelling or sound. Thus, during typing or conversion from sound to the text, the spelling may come out differently. In addition, names in different scripts such as Arabic, Persian, or Chinese may end up differently during conversion to the English or Latin script or alphabets. This uncertainty of the sound or spelling is captured in a database for a variation of a name or word, as possible candidates with different membership values, which is a fuzzy parameter. The database can be filled up and corrected by the users in a community of users. Another way is to have candidates for a partial word or sound, e.g. as the most common mistakes or errors, e.g. to find the final word with the correlation analysis, e.g. based on the scoring the combinations, and maximizing the score of the combination for all candidates. In an example, the partial word candidates are stored separately. FIG. 117 is an example of a system described above.

One example of the common mistakes is from the proximity of the letters on the typical keyboard, e.g. Qwerty keyboard, e.g. with R and T in the close proximity, making it likely for a person to type R, instead of T, e.g. typing RANK, instead of TANK (or typing TTANK, instead of TANK). In the cases that the mistaken word has a meaning, the mistake cannot be found by the spell check alone, and it can only be found through context analysis, e.g. for the phrase "water tank on the roof", it would be understood by the system that the phrase "water rank on the roof" is just a typo or misspell, because the second phrase does not have a proper meaning FIG. 117 is an example of a system described above.

Figure 88:
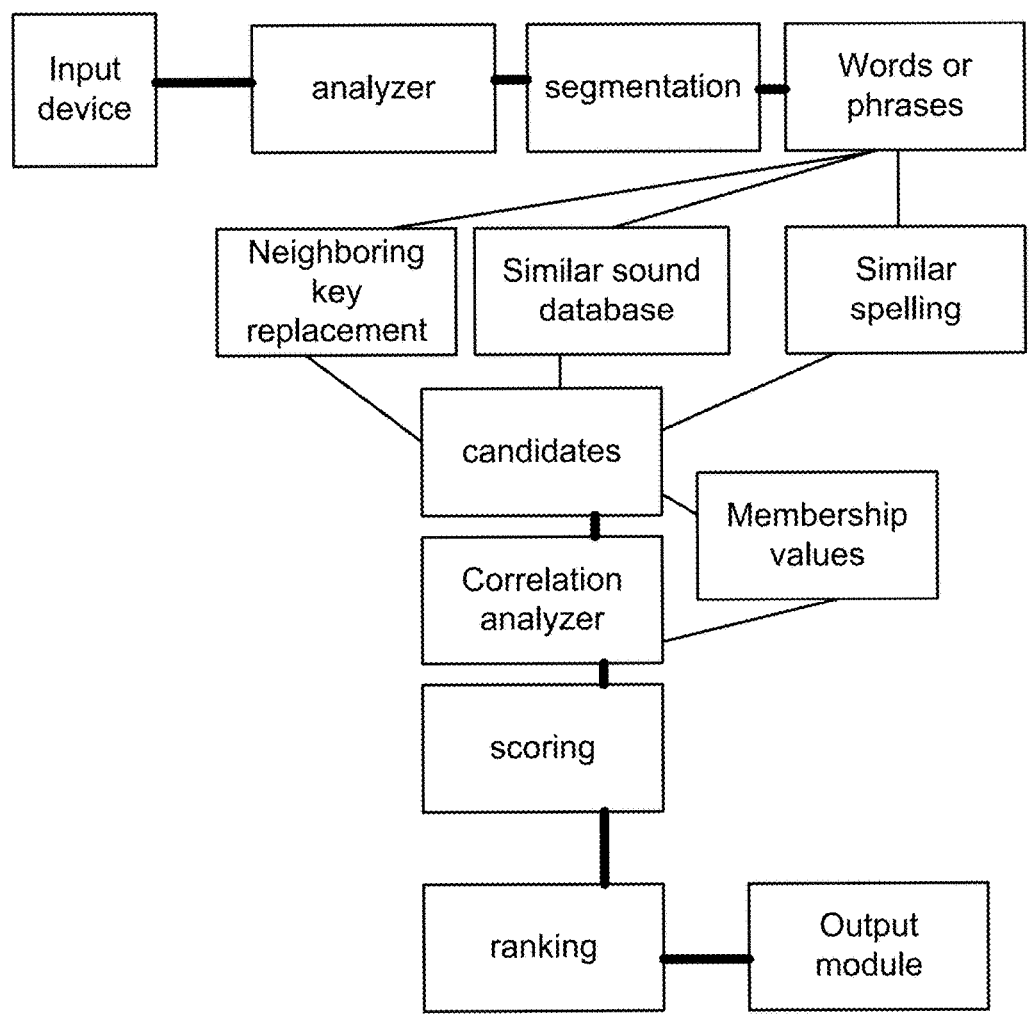

Once the flag is raised about the improper meaning or misspell in the recognition system, one of the tests that the system does is to try and test similar words or phrases with similar sound or spelling, e.g. testing neighboring keys on the keyboard for possible mistakes, by replacing them in the suspected word, to see if any of the results has a proper meaning. Then, the system ranks the results, and it marks the result that has the highest score in the context of the phrase or sentence, for possible candidate for the original (correct)

word. FIG. 88 shows an example of such system. The databases of similar spellings and sounds are routinely updated by the feedback from the users' community or group or by the administrator.

To analyze a phrase or sentence, in one embodiment, the system looks at adjectives or related words, e.g. "water tank". For example, for "tank", when used as a word equivalent to a "container" (which can be extracted from the context, from neighboring words or paragraphs), it logically can hold some objects, especially fluids, e.g. gas, liquid, water, nitrogen, and liquid nitrogen. Thus, one can combine them this way, as a template:

[FLUID+tank]

Or:

[tank of+FLUID]

One can store these templates (and any exception to the templates) in multiple databases, which can be categorized and separated based on their topics and usages, in a hierarchical or tree or pyramid structure, with inherency property, e.g. parent nodes and children nodes.

This can be done with adjectives, as well, for example, "big" in the phrase "big tank", which is expressed as a template:

[ADJECTIVE+tank]

Now, when we are scanning the sentences or phrases, we are using (searching for) the stored or pre-recorded templates in databases or storages, to find the patterns mandated by a template. Once a template is found (to match the pattern of a given sentence or phrase), the system can understand the meaning of that section of the text, phrase, or sentence. Then, it can understand the meaning of the whole sentence or phrase through the combinations or series of templates that construct those phrases and sentences (for a given language, based on the collection of the grammar templates (along with their exceptions or special usages)).

For another example of "a tank on the roof", the system will have the following template:

[tank+roof+RELATIONSHIP]

Or:

[tank+roof+POSITION WITH RESPECT TO THE OTHER OBJECT]

Or:

[tank+roof+on]

Again, the above templates are categorized and stored accordingly, in various (e.g. tagged) hierarchical storages, files, and databases, for future use by the search engine, to dissect, recognize the patterns and templates, and understand the meaning of the sentence or phrase.

In one embodiment, the range of numbers or values or approximate values or measurement accuracies (e.g. length of the table=(5 meter±2 centimeter)) are expressed based on fuzzy values. In one embodiment, the dimensions in the image (for recognition purposes) are based on approximation, based on fuzzy values.

In one embodiment, the relationships and templates are based on fuzzy terms, with membership values. In one embodiment, the relationships and templates (or grammar) are based on Z-numbers, with terms such as "USUALLY", expressing concepts such as certainty for the relationships, templates, and grammar.

Multi-Step Recognition

Figure 89:
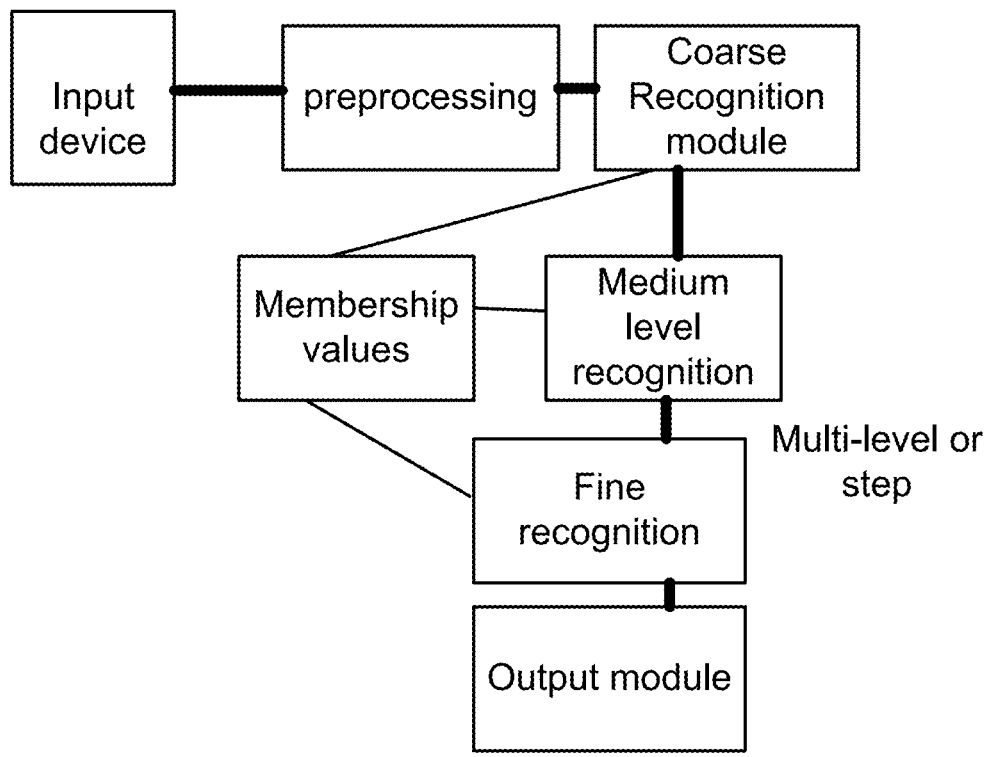

In one embodiment, the recognition (such as image recognition) is done in multiple steps. For example, for signature recognition, in one embodiment, first, we have a coarse recognition. Then, if the first step of the recognition shows a match possibility, then the system performs the second step of medium recognition. Then, if the second step of the recognition shows a match possibility, then the system performs the third step of fine recognition. Then, if the third step of the recognition shows a match possibility, then the system indicates a match, with corresponding membership value, which is a fuzzy concept. This is a much more efficient method of recognition for most samples and environments (instead of a one-step recognition method). See FIG. 89 for such a system.

Figure 90:
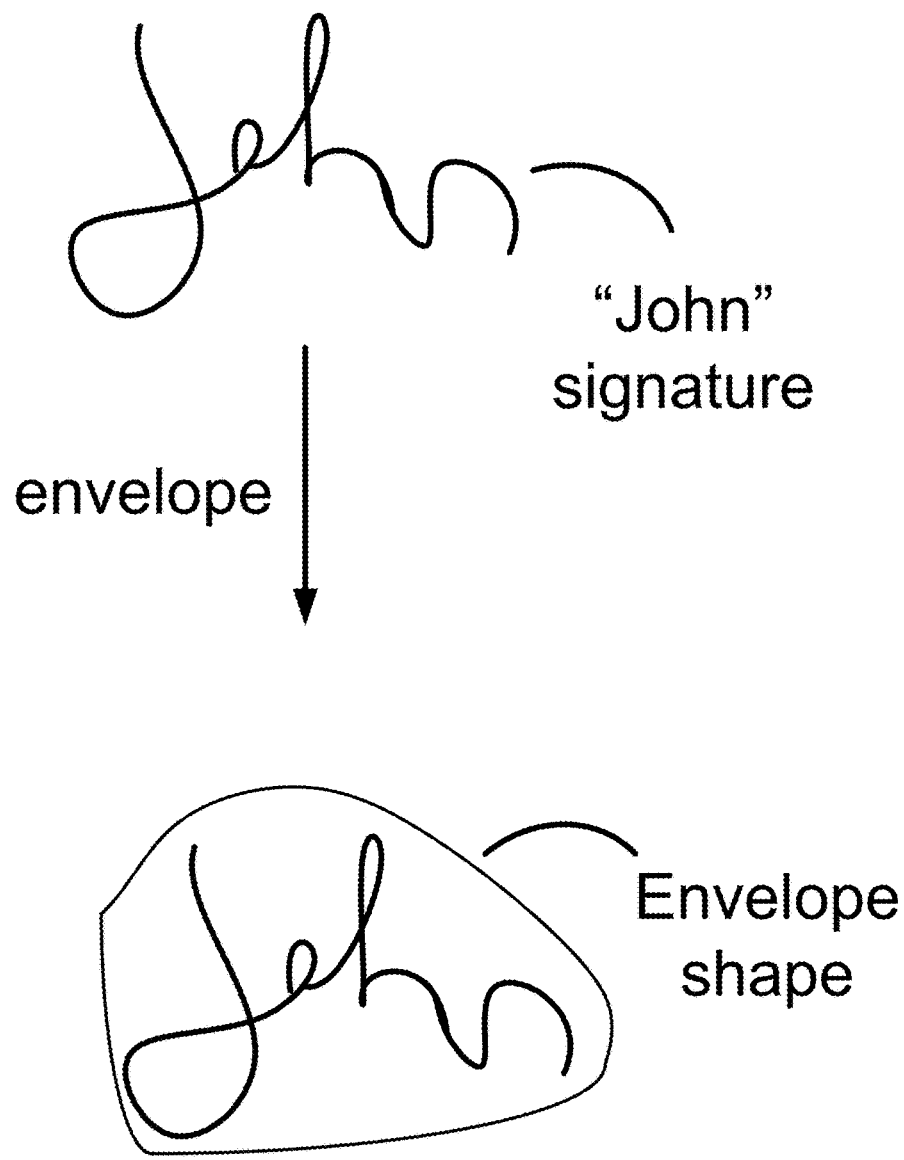
Figure 91:
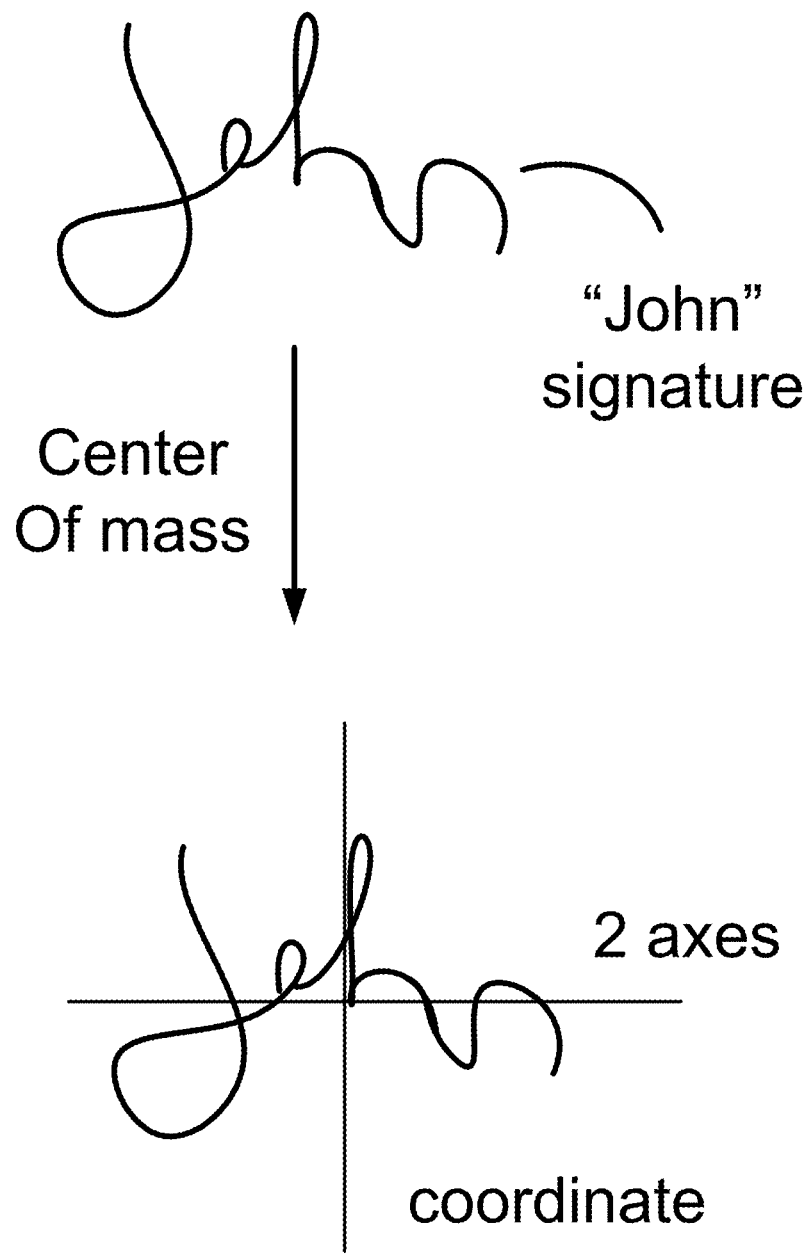

For example, for the signature recognition, the first step is the envelop analysis, which is the step of finding the general shape of the signature, and doing the first comparison, to obtain a first degree of match, which is a coarse analysis, as shown in FIG. 90. Then, the second step, the medium recognition, is to find the center of mass for the signature, based on the pixel values and pixel density on the image, to use a weighted average of the pixels, to calculate the center of the mass (coordinate) for the signature (as an object), denoted as ($X_c$, $Y_c$), on both X-Y axes, for horizontal and vertical axes, for 2-dimensional image coordinates, with X and Y coordinates (as shown in FIG. 91):

$$X_c=(\Sigma_i K_i X_i)/(N(\Sigma_i K_i))$$

where $K_i$ is the weight, value, or intensity for the pixel or image element, and N is an integer denoting the number of pixels, with i as a running variable (an integer, for the summation).

Similarly, for the Y coordinate, we have:

$$Y_c=(\Sigma_i K_i Y_i)/(N(\Sigma_i K_i))$$

Figure 92:
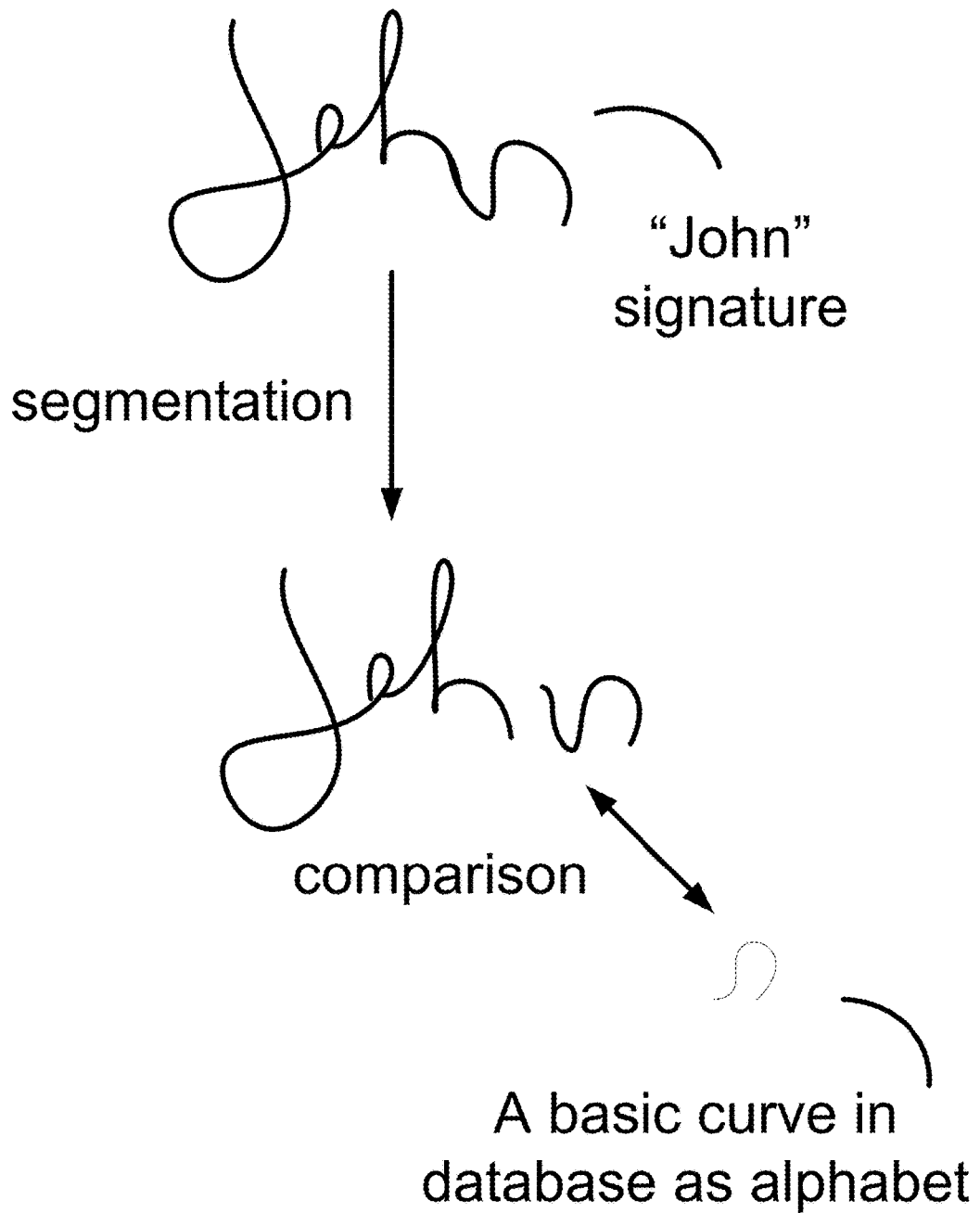

This is followed by a second comparison, to obtain a second degree of match, which is a medium degree analysis. Then, the third step, the fine recognition, is to find and compare all pieces of curves and concave and convex shapes in the signature, and map them to an alphabet or dictionary of all typical pieces of curves (cusps or arcs in various shapes, with various angles, ratios, and lengths, and various number of curve or line crossings or loops) and concave and convex shapes (stored in a databases or storage), to convert them in the new language of codes or symbols whose sequence resembles the signature form and shape (as shown in FIG. 92), as much as possible, with corresponding membership values for matching degrees, which is a fuzzy parameter. Once two shapes are in the symbolic or coded form, the comparison and degree of similarity can be done mathematically, based on the number of symbolic matches and degree of symbolic matches.

In one embodiment, a statement describes an event or object, such as a signature's shape, with a qualification of e.g. USUALLY, in the statement, which is a Z-number parameter. Thus, a signature is expressed based on the Z-number.

Context

The context, for example, can be tagged by the user, or voted by community, or based on history, habit of the user, use of other words, keywords as a flag, or proximity of the words, or any combination of the above. The context (as an attribute) is also a fuzzy parameter, with membership values. One method of measuring the context (C) is based on the word or letter distance (e.g. number of words or letters or paragraphs or pages or chapters or minutes or seconds, as physical distance in between 2 specific words or as the temporal distance or frequency or period between the usage of 2 specific words), or D, which can be expressed, for example, as:

$$C=1/D$$

This means that the closer or shorter the distance, the higher the degree of context or related concept between 2 words or phrases or concepts. Or, in general, it can be written as some dimensionless numbers:

$$C=(K_1/D)+K_2$$

where $K_1$ and $K_2$ are some constants or coefficients.
Or, in another embodiment, we have:

$$C=\exp(-D/D_0)$$

where $D_0$ is some constant or coefficient.

In one embodiment, one adds a constant $D_1$ to the equation above:

$$C=\exp(-D/D_0)+D_1$$

The context helps us understand that, for example, the word TANK in an article about military budget (as context) refers to a military hardware with engine (that moves on the ground during the war or military exercise). However, in a plumbing magazine, the word TANK refers to a water or fluid tank, as a container. The frequency counter or histogram (e.g. how many times the word MILITARY appears in the article or magazine) and other similar parameters are attached or tagged to the article or file, as a property or attribute.

Contrast

In one embodiment, the recognition is based on the parameters representing contrast. For example, in an image, a black line in a drawing is detected based on the contrast between neighboring pixels, e.g. black pixels on a line in a white background. For example, the contrast is described as the difference between intensities or grey scale values or values from 2 neighboring pixels, image units, or data units (e.g. in a sequence of data) (or any other form similar to that):

$$\text{Contrast}=\Delta X/X=((X_2-X_1)/((X_2+X_1)/2))$$

Thus, the system analyzes the contrast, as a method of the detection of patterns and features, for recognition of objects or features, e.g. face recognition or voice recognition, which uses pixel intensity contrast or sound frequency (and amplitude) contrast, respectively.

In one embodiment, the search engine works on music or sound or speech or talking pieces or notes, to find or match or compare, for taped e-books, text-to-voice conversions, people's speech, notes, music, sound effects, sound sources, ring tones, movie's music, or the like, e.g. to find a specific corresponding music title or movie title, by just humming or whistling the sound (or imitate the music or notes by mouth, or tapping or beating the table with hand), as the input. The output is all the similar sounds or sequence of notes that resemble the input, extracted and searched from Internet or a music or sound repository. See FIG. 107 for such a system, with a conversion or normalization of a music piece to a sound bite, based on a dictionary or library, e.g. a piece such as "BE-BE-BA-BO------BE-BE-BA-BO", with each of BE, BA, and BO representing a sound unit or symbol or alphabet or note or frequency or pitch in the dictionary, and each "-" representing a unit of time or time delay or pause between different notes or sound pieces or sound units.

In one embodiment, the text or speech has content with more than one language. Thus, it has to be distinguished and separated into pieces, first, before it can be further processed for each language separately, as described elsewhere in this disclosure. FIG. 118 is an example of a system described above.

Body Language, Expressions, or Emotions

In one embodiment, the patterns or sequences of sign language or hand movements or eye or lip or facial or foot or body expressions can be recognized, for emotion recognition or translated or converted to text expressions. In one embodiment, the sensors or tags are attached to the body of the user (e.g. the hand of a user), to record movements and positions of a hand with respect to multiple fixed points or coordinates (with beacons or detectors or signal sources) in the room, so that the movements can be recorded and then later interpreted as emotions (e.g. anger) or expressions, such as sentences, data, commands, sequence of information, or signal, e.g. to be converted to text or voice or computer code or instructions, for a person or computer to receive. FIG. 118 is an example of a system described above.

For example, this can be used for hands-free navigation of an aircraft by a pilot, using commands, translated based on her body or facial movements or gestures or shapes, e.g. capturing position of facial features, tracking the features, and speed of movements, based on the typical templates of a face or a hand, in a database, to interpret hand signals (e.g. position of fingers with respect to each other, e.g. to indicate that "The package was received.") or facial definitions or expressions or signals (e.g. position or angle of nose, lips, eye lid, eye, and eye brows, e.g. indicating anger or smile), or based on templates from a specific user for hand or facial gestures. The commands or codes or transcripts or instructions can be fed into a computer or device for a specific action or result. The pattern recognition (described elsewhere in this disclosure) is used to find or interpret the hand or facial signals or data. The interpretations may be not-definite and has a membership value, which is a fuzzy parameter. FIG. 118 is an example of a system described above.

In one embodiment, the search is done on multimedia or movies or videos, with text, tags, and sound track associated with it, which can correlate each findings or recognitions from different components of the multimedia, for more accurate overall combined recognition process. In one embodiment, if a piece of a video or the whole video is repeated, similar, or exact copy, to save the storage space (e.g. for video archiving or referencing purposes), depending on the degree of similarity and degree of importance of the video for the user, which are fuzzy parameters, the system may eliminate full or partial data from the video storage(s). For example, for a video with the subject classified as "not-important", a second video with the same exact data can be deleted, by the policy enforcer module or device, as there is no need for a backup data, based on the pre-set policy in a database, with thresholds and fuzzy parameters or rules, as explained elsewhere in this disclosure.

This method can be used, for example, for minimizing the size of repository needed for video storage web sites (e.g. YouTube.com), or similarly, for emails or attachments carrying the same or similar content or information, e.g. to open up space and delete the duplicative data or files, on a computer or hard drive or server or memory device(s), for faster data management or faster search through that data.

More Embodiments

Rules Engine, Filter/Test and Join Networks

An embodiment implements a rules engine based using Z-valuation or fuzzy maps. In one embodiment, a set of rules are analyzed and the constituents of the antecedent part of the rules are determined, in order to determine pattern in the antecedent parts among rules. This approach helps dealing with many rules in a system where similar antecedent parts appear within different rules. In this approach, the redundancy in evaluating antecedent parts is eliminated/reduced and the temporal issues and inconsistent evaluations of the same parts in different rules are prevented. In one embodiment, a pattern network nodes based on rules' antecedents is setup, e.g., by filtering the variable attributes used in rules' antecedents. In one embodiment, multiple fact patterns satisfy/trigger/fire the same rule. In one embodiment, the facts or propositions are propagated through a pattern network, and a link or a copy of the fact/proposition (or a part thereof) is associated to a pattern node (or added to an associated list/table) along with a truth value indicating how well the fact satisfies the pattern/test/filter associated with the pattern node. For example, if a pattern associated with a pattern node is (X is A) and the fact propagated is (X is B), then the truth value is determined, for example, based on max-min approach (i.e., maximum, for all x, of minimum of $\mu_A(x)$ and $\mu_B(x)$). In one embodiment, a join network comprises of join nodes based on antecedents of rules to determine the fact patterns satisfying the antecedents. In one embodiment, the list of facts/working memory from pattern network nodes are joined with other lists of facts/working memory from nodes of pattern network of join network, in order to build up the antecedent or parts of antecedent of each rule, at each node of join network. In one embodiment, the joining is performed via a binding variable in both lists being joined. In one embodiment, the truth value associated with the joined record is determined by the truth values of the joining records and the type of the join. For example, in a conjunctive join the truth value of the joined record is determined as minimum of the truth values of the joining records. In one embodiment, the truth value associated with the joined record is also based on the binding variable matching from records of the lists being joined. For example, in one embodiment, where the binding variable has a fuzzy value in one or both lists, the threshold for binding records from the lists (e.g., in equality test of binding variable) or associated truth value based on the binding is determined based on a max-min approach. For example, if the binding variable has fuzzy values A and B in two lists being joined, then the threshold or binding truth value is determined by maximum, for all x, of minimum of $\mu_A(x)$ and $\mu_B(x)$. For example, if the binding variable has fuzzy values A and crisp value b in two lists being joined, then the threshold or binding truth value is similarly determined as $\mu_A(b)$.

To illustrate an embodiment, suppose the following example of facts provided to the rules engine or inference engine.

Rob is Vera's son.
Alice is Vera's daughter.
Vera is a woman.
Rob's age is mid twenties.
Alice's age is mid thirties.
Alice is young (with low confidence in accuracy of speaker).
Also, suppose there is a rule indicating:
If a woman is middle-age then <some consequent>.

The facts are presented in a protoform and relationships are setup (e.g., in database or linked memory), as for example, depicted in FIG. 120(*a*):

Son(Vera) is Rob.
Daughter(Vera) is Alice.
Gender(Vera) is female.
Age(Rob) is *25.
Age(Alice) is *35.

With the rule antecedent being:
(Age(<var1>) is middle-age) and (Gender(<var1>) is female).

In one embodiment, based on the existing attributes and relationships (e.g., age, son, daughter) other attributes and relationships are extracted from an attribute/relationship database based on context and existing attributes. For example, a reciprocity relationship is queried and results are used to expand the relationship between the objects or records. For example, relationships "son" and "daughter" result in the reciprocal relationships "parent" or "mother" or "father" (depending the gender of the parent). In one embodiment, the reciprocal relationships per object/record relationship is further filtered based on the existing attributes of the object/records. For example, reciprocal relationship "father" is filtered, while reciprocal relationship "mother" is kept, based on the value of the gender attribute of object/record "Vera" where the queried relationships "son" and "daughter" are based. In one embodiment, consequential attributes are determined, e.g., by querying an attribute/relationship database. For example, the consequential attribute query of "son" (to "Rob") results in consequential attribute for "Gender" with value of "male" to object/record "Rob". Similarly, the consequential attribute query for "daughter" (to "Alice") results in consequential attribute of "Gender" with value of "female" to object/record "Alice".

In one embodiment, synonym/liked attributes are queried, and the results are instantiated as supplemental relationships between the objects/records. For example, a query for "son" or "daughter" results in relationship "child", and in an embodiment, a supplemental "child" relationship between the records "Vera" and "Alice" is instantiated. Similarly, in one embodiment, "parent" relationship from between "Rob" (or "Alice") to "Vera" is instantiated (not shown in figures), based on equivalence/superset to the corresponding "mother" relationship/attribute.

In one embodiment, additional relationships (e.g., "brother" and "sister" between "Alice" and "Rob" (not depicted in figures)), are determined from knowledge base, by matching a set of related object/attributes to a set of general rule(s) for expanding relations/attributes. For example, in one embodiment, the following rules in knowledge base IF parent(<var1>) EQUAL parent(<var2>)
THEN Bi_Direction_Relation(<var1>, <var2>, Sibling);
IF Sibling(<var1>, <var2>) AND Gender((<var1>) is Male
THEN Relation_To(<var2>, <var1>, Brother);
IF Sibling(<var1>, <var2>) AND Gender((<var1>) is Female
THEN Relation_To(<var2>, <var1>, Sister);

when binding with object/records "Alice" and "Rob", results in bi-directional Sibling attribute/relationship between "Rob" and "Alice", directional "Sister" and "Brother" attribute/relationship and/or protoforms.

In one embodiment, parallel/suggestive attributes are queried, e.g., from an attribute/relationship database. For example, a parallel/suggestive query for "Age" attribute, results in attribute "Birth". In one embodiment, a template set of attributes/relationship is determined based on the result of such query. For example, along with attribute/event "Birth", other related attributes, e.g., "Time" and "Place" related to "Birth" are returned as set/template for application and instantiation. For example, such template is applied to objects/records "Vera", "Rob", and "Alice", e.g., based on their existing attribute "Age". In one embodiment, the instantiation of template results in separate records and relationships for each instance. A template may include a class level attribute with instantiation at the class level. In one embodiment, the expanded attributes/relationships are supplemented to the relationships and records, e.g., in database. In one embodiment, a protoform of the existing attributes/relationships are instantiated and/or linked to the objects/records, as for example, depicted in FIG. 120(b) (in dotted lines):

Mother(Rob) is Vera.
Mother(Alice) is Vera.
Child(Vera) is Rob.
Child(Vera) is Alice.
Gender(Rob) is male.
Gender(Alice) is female.

In one embodiment, placeholder objects/records or protoform fragments are instantiated, e.g.: Birth(Alice), Time(Birth(Alice)), Place(Birth(Alice)), Birth(Rob), Time(Birth(Rob)), Place(Birth(Rob)), Birth(Vera), Time(Birth(Vera)), and Place(Birth(Vera)). In one embodiment, such fragments or placeholder/records/objects are used to further discover relationships and potential joins.

In one embodiment, a query (e.g., an iterative query) is made to expand the facts and related rules from the knowledgebase. For example, a query into the attributes and records results in the following attributes (as depicted in FIG. 120(c)): "Age", "Mother", "Birth", "Time", etc. In one embodiment, a query using the attributes in a knowledgebase (e.g., database) results in related (e.g., via tags or relevance factors) general facts or relationship, e.g., in Z-valuation form. For example, as depicted in FIG. 120(c), a general fact is returned indicating "Most likely, the age of mothers when giving birth is between about twenty to about forty years old." Or in a protoform, such statement/fact may appear as:

G1: Age(Mother(<var1>), at time(birth(<var1>))) is range[*20, *40], most likely.

In this example, <var1> is indicative of instantiation point or join potential.

In one embodiment, as for example depicted in FIG. 120(c), a query (e.g., contextual) is made in a knowledge base, e.g., to extract general relationship used to extend the existing facts and relationship and/or provide relationships (e.g., aggregate functions) between related entities or classes of objects/record types. For example, as depicted in FIG. 120(c), the following facts/functions/rules resulted from query:

F1: Age(<var1>, at present (DEFAULT)) is Age(<var1>, at time(<var2>))+Elapsed(time(<var2>), present (DEFAULT));
F2: Age(<var1>, at time(birth(<var1>))) is 0;
F3: IF time(<var2>) is before(time(birth(<var1>))) THEN (Age(<var1>, at time(<var2>)) is UNDEFINED;
F4: IF time(<var2>) is after(time(death(<var1>))) THEN (Age(<var1>, at time(<var2>)) is UNDEFINED;

In one embodiment, the contextual facts/functions are provided as template/set to supplement via instantiation and/or used in bind/join operation. In one embodiment, such instantiation further extends the attributes related to records/objects, as for example depicted in FIG. 120(d) in dotted lines, expanding "Elapsed" attribute/function on "Time" attribute, i.e., on "Time(Birth(Vera))", "Time(Birth(Rob))", and "Time(Birth(Alice))".

In one embodiment, to efficiently match the facts and rules, a network (e.g., linked) of objects/attributes/filters and a network of join lists are setup. For example, based on the protoform and attributes list of objects/working memory elements are determined and associated with such attributes or protoforms. For example, protoform "Age(Mother (<var1>))" in G1 has a potential match with "Rob" or "Alice" when binding to <var1>, where as "Time(Birth(<var1>))" has potential match with "Rob", "Alice", or "Vera", based on existing records/objects. Joining based on the common value, i.e., by enforcing the consistency of <var1> (e.g., via a database join operation with WHERE clause of JOIN or SELECT statement), results in joining on records "Rob" and "Alice". In one embodiment, the instantiations of general facts/functions result in additional elements or attributes (e.g., as described above for "Elapse"), in a backward chaining method. For example, in one embodiment, the following function/record/relationship is instantiated, based on F1, via binding of <var1> with "Vera" (having an attribute "Age") and binding of <var2> with "Birth(Rob)" event/record (having an attribute "time"):

Age(Vera) is Age(Vera, at time(Birth(Rob)))+Elapsed(time(Birth(Rob)));

Similarly, the following is instantiated, in an example:

Age(Vera) is Age(Vera, at time(Birth(Alice)))+Elapsed(time(Birth(Alice)));

In one embodiment, an instantiation results in further supplement of attributes for objects/records, e.g., by scanning the form of the template with binding values and linking to the existing object if it already exists (e.g., Age(Vera)) or instantiating additional attribute/object if not existing (e.g., Elapsed(time(Birth(Rob))) or Elapsed(time(Birth(Alice)))) as for example, depicted in FIG. 120(d) (in dotted lines).

In one embodiment, the instantiation of the general facts or functions result in further facts that act as functions or facts bridging or aggregating other facts. For example, instantiation of G1, based in binding <var1> with "Rob" and "Alice" due to matching/filtering protoforms ("Age (Mother( ))" and "time(birth( ))") and joining the result consistent with <var1>, results in:

Age(Mother(Rob), at time(birth(Rob))) is range[*20, *40], most likely.
Age(Mother(Alice), at time(birth(Alice))) is range[*20, *40], most likely.

In one embodiment, protoforms are resolved based on one-to-one or many-to-one type relationships. For example, Mother(Rob) is resolved to Vera or refers to the same record/object. Similarly, Mother(Alice) is resolved to Vera:

Age(Vera, at time(birth(Rob))) is range[*20, *40], most likely.
Age(Vera, at time(birth(Alice))) is range[*20, *40], most likely.

Note that the instantiation of F1 results in additional combinations when joining the list based on common attributes/protoforms. For example, binding of <var1> with "Vera", "Alice", and "Rob" (having an attribute "Age") and binding of <var2> with "Birth(Vera)", "Birth(Alice)", and "Birth(Rob)" event/record (having an attribute "time"), creates 9 Cartesian combinations (two mentioned above), e.g.:

Age(Vera) is Age(Vera, at time(Birth(Vera)))+Elapsed(time(Birth(Vera));
Age(Vera) is Age(Vera, at time(Birth(Alice)))+Elapsed(time(Birth(Alice));
Age(Vera) is Age(Vera, at time(Birth(Rob)))+Elapsed(time(Birth(Rob));
Age(Alice) is Age(Alice, at time(Birth(Vera)))+Elapsed(time(Birth(Vera));
Age(Alice) is Age(Alice, at time(Birth(Alice)))+Elapsed(time(Birth(Alice));
Age(Alice) is Age(Alice, at time(Birth(Rob)))+Elapsed(time(Birth(Rob));

Age(Rob) is Age(Rob, at time(Birth(Vera)))+Elapsed (time(Birth(Vera));

Age(Rob) is Age(Rob, at time(Birth(Alice)))+Elapsed (time(Birth(Alice));

Age(Rob) is Age(Rob, at time(Birth(Rob)))+Elapsed (time(Birth(Rob));

In one embodiment, the instantiation of other general facts/rules is used to simplify or evaluate the other facts or relations, e.g., by evaluating or substituting the prototype fragments. For example, instantiating F2 by binding <var1> with "Vera", "Alice", and "Rob" (having an attributes "Age" and "time(birth( ))") results in the followings:

Age(Vera, at time(birth(Vera))) is 0;
Age(Alice, at time(birth(Alice))) is 0;
Age(Rob, at time(birth(Rob))) is 0;

In one embodiment, the relationships are partially or iteratively evaluated, e.g., by simplifying the protoforms by substitution or by creating relationships. For example, based on instantiation of F2, several of F1 instances become:

Age(Vera) is Elapsed(time(Birth(Vera));
Age(Alice) is Elapsed(time(Birth(Alice));
Age(Rob) is Elapsed(time(Birth(Rob));

In an embodiment, additional relationships/attributes are made between records/objects based on the evaluations. For example, as depicted in FIG. 120(*e*) in dotted lines, "identity"/"same" type relationship is made between Elapsed (time(Birth(Rob)) and Age(Rob) records/objects.

In one embodiment, such simplification is done at the template/class/general functions/rule level. For example, in one embodiment, general facts are joined via binding variables having common attributes. For example, general facts F1 and F2 are joined based on F1:<var2> and F2:birth (<var1>) both having "time( )" attribute, resulting in a general fact that:

F1': Age(<var1>, at present (default)) is Elapsed(time (birth(<var1>)), present (default));

In one embodiment, additional general facts are derived based on other facts via a background process. In one embodiment, the additional facts are tested against specific test scenarios for scoring and validations. In one embodiment, additional facts are promoted/tagged as general facts after a validation process and/or passing a validation threshold.

In one embodiment, the instantiation of other general facts/rules is used to filter and trim inapplicable combinations. For example, the instantiation of F3 with binding of <var1> with "Vera", "Alice", and "Rob" (having an attribute "time(birth( ))") and binding of <var2> with "Birth(Vera)", "Birth(Alice)", and "Birth(Rob)" event/record (having an attribute "time"), creates 9 Cartesian combinations, including, e.g., "Birth(Vera)" for <var2> and "Rob" for <var1>:

IF time(Birth(Vera)) is before(time(birth(Rob)))
THEN (Age(Rob, at time(Birth(Vera))) is UNDEFINED;

For example, further evaluation (e.g., in a subsequent cycle or during a instantiation of a general fact by feeding the instance through a filter/test network) of this instance (e.g., using other generalized facts/functions), trims and nullifies the following G1 instance:

Age(Rob) is Age(Rob, at time(Birth(Vera)))+Elapsed (time(Birth(Vera));

given that Age(Rob, at time(Birth(Vera))) is evaluated as UNDEFINED.

Other instances of F1, for example, are further simplified/ substituted or used to build further relationships (based on other instantiations of F1), e.g.:

Age(Vera) is Age(Vera, at time(Birth(Alice)))+Age(Alice);
Age(Vera) is Age(Vera, at time(Birth(Rob)))+Age (Rob);

In one embodiment, a candidate generalized fact is generated (e.g., in protoform) based on instantiated/modified facts, e.g., by resolving multiple object references to the same object. For example, in one embodiment, from the above statements, one or more of the following candidate generalized facts are obtained:

Age(<var1>) is Age(<var1>, at time(Birth (child<var1>)))+Age(child<var1>);
Age(mother(<var1>)) is Age(mother(<var1>), at time (Birth(<var1>)))+Age (<var1>);

In one embodiment, as for example depicted in FIG. 120(*f*), the valuation of Age(Vera, at time(Birth(Alice))) and Age(Vera, at time(Birth(Alice))) objects/records is of Z-valuation type. An instantiation of such valuation, in one embodiment, sets up a candidate probability or statistical distributions, $p_i(x)$ and their corresponding test scores $ts_i$. In one embodiment, additional valuations for Age(Vera) is obtained by further valuations of matching instantiated facts/aggregate functions/rules. For example, Age(Vera), in one embodiment, is given two more valuations, Z1 and Z2, based on valuation of above instantiated/simplified statements/aggregate functions. In one embodiment, an aggregate valuation of an object/record (e.g., Age(Vera)) is obtained by further aggregating its multiple valuation (e.g., Z1, Z2, and (Young, Low)). For example, as depicted in FIG. 120(*g*), Z1 is obtained by adding Z-valuation (range[*20, *40], most likely) and (mid twenties), and Z2 is obtained by adding Z-valuation (range[*20, *40], most likely) and (mid thirties). In one embodiment, the membership functions of various fuzzy sets/values are determined using knowledge base (e.g., by querying contextual tables/database with records identifying fuzzy sets and modifiers (e.g., "mid-twenties", "mid-thirties", "young", "about", etc) and their corresponding attributes such as their membership functions, e.g., in a piecewise format). As depicted for example in FIG. 120(*g*), Z1 ($A_1$, $B_1$) has a membership function for $A_1$, obtained, for example, via extension principle or alpha-cuts from the membership functions of $\mu_{Mid\text{-}20s}$ and $\mu_{Ax}$ (where Ax denotes the fuzzy range [*20, *40]). Similarly, in Z2 ($A_2$, $B_2$), a membership function for $A_2$ is determined, in one embodiment, from $\mu_{Mid\text{-}30s}$ and $\mu_{Ax}$, as depicted in FIG. 120(*g*). In one embodiment, the valuation of (Young, Low) is of a fuzzy map $A_3$*, given the Low confidence level, e.g., applies to the speaker's confidence/reliability. In one embodiment, the probability distribution test scores are imposed from $B_x$ to $B_1$ and $B_2$, for example, $B_1$ and $B_2$ take on the value of $B_x$.

In one embodiment, multiple valuation of a record/object (e.g., Age(Vera)) is aggregated by aggregating test scores related to the valuations. (For example, see more detail in section Scoring with Fuzzy Map and FIGS. 125(*a*)-(*b*)). In one embodiment, as for example depicted in FIG. 120(*h*), multiple valuations for a record/object (e.g., Z1, Z2, and A3* (valuations of Age(Vera))) are used to determine (an aggregate) test scores or restriction (membership function) for (candidate) probability distribution of the variable representing the record/object (e.g., Vera_Age).

In one embodiment, a set of candidate probability/statistical distribution is instantiated per object/record having Z-valuation, e.g., Age(Vera, at time(Birth(Rob))) and Age (Vera, at time(Birth(Alice))) both valued to (range[*20, *40], most likely), are associated each to a set of probability/ statistical distribution candidates. In one embodiment, a set of test scores are associated/instantiated per object/record having Z-valuation. In one embodiment, the candidate probability distributions are scored based on facts/rules/functions related to a specific record/object with the resulting test scores associated to the specific corresponding record/object. In one embodiment, the candidate probability distributions are shared by same Z-valuations, while the corresponding test scores are associated to specific records/objects based on the facts/rules/functions related to those specific records/objects. For example, in applying the following fact/function Age (<var1>) is Age(mother(<var1>))−Age(mother (<var1>), at time(Birth(<var1>)));

to "Rob" and "Alice" by binding to <var1>, aggregate functions affecting Age(Rob) and Age(Alice) are obtained, for example:

Age (Rob) is Age(Vera)−Age(Vera, at time(Birth(Rob)));
Age (Alice) is Age(Vera)−Age(Vera, at time(Birth(Alice)));

For example, in one embodiment, a set of probability distribution candidates are set up for variable representing Age (Rob), and test scores are determined, for example, via Z-valuations imposed via Age(Vera, at time(Birth(Rob))) (i.e., range[*20, *40], most likely). Such test scores alone are expected to be the same as those for a set of probability distribution candidates set up for variable representing Age (Alice). However, the application of other facts to the scoring of the probability distributions, in one embodiment, results in different scoring (aggregate) per record/object/variable. For example, facts (Age(Rob) is min-twenties) and (Age(Alice) is mid-thirties) produce different scores for the same set of probability distributions ($p_i$), i.e., ($p_i \cdot \mu_{Mid-20s}$) score is in general different from ($p_i \cdot \mu_{Mid-30s}$) score. In one embodiment, the resulting aggregate test scores associated with the candidate probability distributions of the same Z-valuations are different and are associated with specific records/objects (e.g., Age(Rob) and Age(Alice)).

In one embodiment, as mentioned above, supplemental facts (specific or general) are determined by applying a template for equivalent transformation (e.g., including substitutions) to recognized protoforms. For example, in one embodiment, querying form (A is B+C) in a knowledge database results in a set of equivalent templates including (B is A−C) or (C is A−B). Applying the equivalent forms, for example, by parsing and substitution or reference to objects, generates and expands the facts base or aggregate function sets.

Join Operation

In one embodiment, the joining of the lists is optimized by using the ordering or indexing on the lists. In one embodiment, the crisp and fuzzy values of X in a list are ordered based on partial ordering $\mathcal{R} \langle, \preceq \rangle$, e.g., based on alpha cuts and interval comparison. In one embodiment, as shown in FIG. 121(a), values of attribute A (column) in a list includes one or more of crisp and/or fuzzy numbers. In one embodiment, the values are identified via an identifier (e.g., a unique ID such as a primary key (PK)) as depicted in FIG. 121(a), for example, as $A_1, \ldots, A_9$. In one embodiment, the ID is a hash key or a sequential counter or an internal counter/ID, e.g., assigned by a database management system (DBMS). In this example, as depicted in FIG. 121(a), TF($x_{ls,A1}, x_{lc,A1}, x_{rc,A1}, x_{rs,A1}$) represents a trapezoid fuzzy set defined by the left (l) and right (r) of its support (s), and core (c) on x-axis, for fuzzy set identified by $A_1$. Similarly, $x_{A3}$ is a value identified by $A_3$ for column/attribute A in the list. In one embodiment, as for example depicted in FIG. 121(a), an index or a sorted list is setup by sorting x values of the crisp number/intervals and corner points of fuzzy sets (e.g., the support and/or core locations). In one embodiment, the sorted list includes a type attribute to indicate the type of the sorted record, e.g., precise value (P), left-support (LS), right-core (RC), etc. as depicted in FIG. 121(a). In one embodiment, the sorted list has a column/attribute identifying the record ID of the main list, e.g., as a foreign key (FK). In one embodiment, alpha cuts (e.g., at membership function values of $0^+$, 0.5, and 1) are used to get the intervals of the fuzzy sets (e.g., A1 and A2) at those cuts. In one embodiment, the x values of such intervals are sorted in the sorted list. In one embodiment, the type for such x values is indicated as alpha cut and/by its alpha cut level/indicator, e.g., as an attribute in the sorted list. In one embodiment, left/right points of the cut interval is identified by an attribute, e.g., in the sorted list. In above example, S (support) and C (core) are indicators for special case of alpha cuts at $0^+$ and 1. In various embodiments, the indicators may be in one or more attributes/columns and in various forms (such as characters/numbers).

In one embodiment, as for example depicted in FIG. 121(b), two or more lists/tables (e.g., 12105 and 12110) are joined on one or more attributes/variables (e.g., joining on attribute A from 12105 and attribute B from 12110). In one embodiment, a sorted list/index on attribute A (12115) and a sorted list/index on attribute B (12120) are used to make joining the lists more efficient by avoiding full table scan of for one attribute for every record of the other attribute. In this example, the x values (e.g., $x_i$, $x_j$, $x_k$, and $x_m$) and y values (e.g., $y_a$, $y_b$, $y_c$, and $y_n$) are in same variable domain in which the lists are being joined. To illustration purposes, as depicted in FIG. 121(b), let's assume the following order in x and y values: $x_i < y_a < x_j < y_b < x_k < y_c < x_m < y_n$. In one embodiment, as for example depicted in FIG. 121(b), the sorted lists/indexes include or are associated with one or more attributes indicating the identification of the records in original list (e.g., $A_7$, $A_2$, $A_4$, $A_2$, $B_3$, $B_1$, $B_9$, and $B_1$) and/or the type of x or y values (e.g., P for precise, FS for fuzzy start or support start, FE for fuzzy end or support end). In one embodiment, the sorted lists or indexes are scanned together, e.g., using a running counters (12117 and 12122) (e.g., in ascending direction), instead of performing a full Cartesian product search between the records. Assume for example, the counters are at some point advancing from $x_i$ from 12115 and $y_a$ from 12120. In one embodiment, an index for which the current value is smaller is advanced, i.e., given for example $x_i < y_a$, index/counter 12117 is advanced to $x_j$ (shown by annotation 1 in FIG. 121(b)). In one embodiment, when an index counter moves to a record indicating a fuzzy value/set association (e.g., FS for fuzzy start), the potential joins may be forthcoming from the other list as other index(es)/counter(s) advance. In one embodiment, the record is marked or an attribute (e.g., the identifier and/or its sorted value) or a copy of the record is moved into an auxiliary queue/list/table (e.g., 12125) associated with the original (e.g., 12105) or sorted list (e.g., 12115) as shown by annotation 2 in FIG. 121(b). In one embodiment, the join based on fuzzy $A_2$ starting at $x_j$ and crisp $B_3$ at $y_a$ (currently pointed by index/counter 12122) is tested. If, as in this example, $x_j$ is more than $y_a$, there is no join possibility (i.e., based on equality join). In one embodiment, $A_2$ is tested against records in an auxiliary queue/list/table (e.g., 12130) associated with other list (12110 or 12120) for potential join(s). In one embodiment, after testing potential joins with items of auxiliary list, index/counter is advanced, e.g., counter/index (12122) is advanced to $y_c$ associated with start of fuzzy set $B_3$, given that $y_a < x_j$ (as shown by annotation 3 in FIG. 121(b)). Likewise, in one embodiment, $B_1$ and/or its associated value(s) are marked or moved into an auxiliary queue/list/table (e.g., 12130), as shown by annotation 4 in FIG. 121(b). In one embodiment, the record pointed by the advancing index/counter (e.g., $B_1$) is tested against other crisp values (pointed by other index/counters) and items (fuzzy set/value related records) in auxiliary queue/list/table (e.g., 12125) associated with other list. In one embodiment, $B_1$ is tested for join potential against $A_2$, e.g., identified via auxiliary queue/list/table 12125. Assuming for example $x_j < y_b$, the index/counter 12117 is advanced to $x_k$ associated with $A_4$ (e.g., a precise or crisp value), as shown by annotation 5 in FIG. 121(b). Likewise, the record pointed by the advancing index/counter (e.g., $A_4$) is tested for potential join with other crisp value(s) (pointed by other index/counters) and items (fuzzy set/value related records, e.g., $B_1$) in auxiliary queue/list/table (e.g., 12130) associated with other list. Similarly, since for example $y_b < x_k$, index/counter 12122 is advanced to $B_9$ having a crisp value $y_c$, as shown by annotation 6 in FIG. 121(b). In one embodiment, $y_c$, the value of $B_9$, is tested for join with $x_k$ (i.e., crisp value of $A_2$ (currently pointed by index/counter 12117)) and fuzzy set/value $A_2$ currently in auxiliary queue/list/table 12125. As depicted in this example by annotation 7 in FIG. 121(b), index/counter 12117 advances to value $x_m$ associated with the end (of support) of fuzzy set/value $A_2$ (e.g., type FE indicates fuzzy end). In one embodiment, upon such event, as for example depicted by annotation 8 in FIG. 121(b), the record/item associated with $A_2$ is marked (e.g., as non-pending) or removed from the associated auxiliary queue/list/table (e.g., 12125). In one embodiment, such record is marked/tagged for later removal upon the value pointed to by other index/counter surpasses $x_m$. This allows finding other potential joins if other forthcoming value(s) pointed to by 12122, for example, falls between $x_j$ and $x_m$ (or support of $A_2$). For example, when index/counter 12122 advances to $y_n$ associated with the start of fuzzy set/value $B_1$ (as shown by annotation 9 in FIG. 121(b)), in one embodiment, auxiliary queue/list/table (e.g., 12125) is scanned and items marked for removal (e.g., $A_2$) are removed having fuzzy ending value(s) (e.g., $x_m$) less than current value ($y_n$) pointed to by the advancing index/counter 12122. In this example, since the type associated with $y_n$ is also a fuzzy ending type (for fuzzy set/value $B_1$), in one embodiment, the record associated with $B_1$ in the associated auxiliary queue/list/table 12130, is similarly marked/tagged for removal, as shown by annotation 10 in FIG. 121(b).

In one embodiment, tagging/marking (e.g., for removal) is done via codes and/or attributes associated with items in auxiliary queue/list/table. In one embodiment, several steps are taken in batch mode or at page level, for example, to enhance speed or the database performance. In one embodiment, a positive testing for join is followed by inserting the joined record (from two lists) in a joining list/table or a result set.

In various embodiments, various methods to join lists/tables based on variable taking fuzzy values are used. The resulting joined record, in one embodiment, includes a score relating to the joining values (fuzzy or crisp). For example, when determining the score for joining record associated with $A_2$ from 12105 to $B_1$ from 12110, the test score for the join (or threshold) is for example, determined by max-min approach, i.e., $$TS_{join(A_2,B_1)} = \sup_{\forall x}(\mu_{A_2}(x) \wedge \mu_{B_1}(x))$$

In one embodiment, the join test score is used to affect the overall truth value or test score for the joined record, e.g.:

$$TS_{joined\ record} = TS_{A_2} \wedge TS_{B_1} \wedge TS_{join(A_2,B_1)}$$

Scoring with Fuzzy Map

In one embodiment, a fuzzy map A* (e.g., as depicted in FIG. 122(a)) is modeled as a set of membership functions (e.g., in a piecewise fashion). In one embodiment, a membership function, e.g., $\mu_A(x)$ is modeled by its corner points (e.g., shown as black dots in FIG. 122(a)). In one embodiment, $\mu_A(x)$ is modeled as a set of points $(x, \eta)$ indicating corners in the piecewise membership function. In one embodiment, a fuzzy map (A, B), is represented by a (discrete or continuous) set of membership functions (e.g., denoted by $\{A_\alpha\}$), where, in one embodiment, $\alpha$ is a parameter controlling the position of the corner points of the membership function in the set. For example, as depicted in FIG. 122(a), for $\alpha$ values of $\alpha_2'$, $\alpha_1'$, $\alpha_1$, and $\alpha_2$, the corresponding piecewise membership functions are denoted as $A_{\alpha_2'}$, $A_{\alpha_1'}$, $A_{\alpha_1}$, and $A_{\alpha_2}$. In one embodiment, an $A_\alpha$, is described by a set of corner points $\{(x_{i,\alpha}, \eta_{i,\alpha})\}$, e.g., as depicted by white dots on $A_{\alpha_2}$ in FIG. 122(a). In this example, for $\alpha_0$, $A_{\alpha_0}$ is A. In one embodiment, each $(x, \eta)$ point on $A_\alpha$, corresponds to the same value or color/grayscale in A*, i.e.

$$\text{For } \forall x, \alpha : \mu_{A^*}(x, \mu_{A_\alpha}(x)) = c_{\alpha,B}$$

where c is the possibility degree (or color/grayscale) of the value of membership function. For example, as depicted in FIG. 122(b), for various values of $\alpha$, the color/grayscale measure of the fuzzy map is indicated by $c(\alpha,B)$. In one embodiment, the uncertainty measure B affects the shape of $c(\alpha,B)$. For example, the more uncertain B is, the wider $c(\alpha,B)$ becomes. In this example, the color associated with $A_{\alpha_2'}$ and $A_{\alpha_2}$, is denoted by $c_2$ corresponding to $\alpha$ values of $\alpha_2'$ and $\alpha_2$, respectively. In this example, color $c_0$ (or 1) is associated with $\alpha_0$.

In one embodiment, a similarity measure between A and $A_\alpha$ is used as the basis for color/grayscale distribution with B. For example, in one embodiment as depicted in FIG. 123(a), a similarity measure is used between two fuzzy set (based on a similarity approach, e.g., Jaccard similarity coefficient, geometric distance and Hausdorff metrics, or union and intersection operations, the maximum difference, and the difference and sum of membership grades). In one embodiment, for example, the following similarity measure is used:

$$SIM(A, A_\alpha) = \frac{\|A \cap A_\alpha\|}{\|A \cup A_\alpha\|} = \frac{\int \min(\mu_A(x), \mu_{A_\alpha}(x)) \cdot dx}{\int \max(\mu_A(x), \mu_{A_\alpha}(x)) \cdot dx}$$

In one embodiment, such similarity measure is based with the certainty measure B to determine the possibility measure (i.e., the color or grayscale) for $A_\alpha$. For example, in an embodiment, as depicted in FIG. 123(b), the color or grayscale is determined as the value of the membership function of B at $SIM(\alpha)$, i.e., $$c_{\alpha,B} = \mu_B(SIM(A, A_\alpha))$$

In one embodiment, certainty measure B is expressed as a crisp percentage $B_c$ (as opposed to a fuzzy value). In an embodiment, a fuzzy set $B_f$ is setup based on $B_c$, e.g., as depicted in FIG. 123(b) with its core and support based on $B_c$, in order to provide a graduated scale to assign color/grayscale value to various $A_\alpha$'s.

In one embodiment, a non-commutative function of (A, $A_\alpha$) is used to determine a similarity measure. In one embodiment, a different similarity function is used for $\alpha'$ (e.g., $<\alpha_0$) than $\alpha$ (e.g., $>\alpha_0$). In one embodiment, a different color/grayscale assignment is used for $\alpha'$ (e.g., $<\alpha_0$) than $\alpha$ (e.g., $>\alpha_0$). In one embodiment, for example, increasing $\alpha$ ($>\alpha_0$) results in $A_\alpha$ allowing more possibilities, i.e., $\mu_{A\alpha}(x) \geq \mu_A(x)$ for all x, and decreasing $\alpha$ ($<\alpha_0$) results in $A_\alpha$ allowing less possibilities, i.e., $\mu_{A\alpha}(x) \leq \mu_A(x)$ for all x.

In one embodiment, when a fuzzy map, e.g., A*, is used in a calculation, a set $\{A_\alpha\}$ with corresponding color set $c(\alpha,B)$ is used to determine the result of the calculation. In one embodiment, multiple values of $\alpha$'s are used to model A*. In one embodiment, values of $\alpha$ span the shape of $c(\alpha,B)$. In one embodiment, a predefined number of $\alpha$'s are used to form set $\{A_\alpha\}$. In one embodiment, the values of $\alpha$'s corresponding to the significant points of $c(\alpha,B)$ are used to form set $\{A_\alpha\}$. For example, in such an embodiment, the corner points of $c(\alpha,B)$ (depicted in FIG. 122(b)) are used determine set $\{A_\alpha\}$. In one embodiment, predefined colors (e.g., c=1 and 0.5) are used to determine (the corresponding $\alpha$'s and hence) set $\{A_\alpha\}$.

In one embodiment, a fuzzy probability measure (p*) of fuzzy map A*, given probability distribution p(x), is determined using set $\{A_\alpha\}$, as follows:

$$p^* \equiv p_x \cdot \mu_{A^*}$$
$$\mu_{p^*}(s) = \sup_{\forall \alpha} c(\alpha, B)$$

subject to:

$$s = \int p(x) \cdot \mu_{A_\alpha}(x) \cdot dx$$

where $\mu_{p^*}$ is the membership function of the fuzzy probability measure p*. In another words, s indicates the possible probability measures of $A_\alpha$, and the color associated with $A_\alpha$ is associated to s as the measure of this possibility (or rather maximum color for various $A_\alpha$'s resulting in the same probability measure s is associated with s) indicating the membership function of p* in s domain.

For example, as depicted in FIG. 124(a), a probability distribution p(x) in x domain is used to determine the probability measure for various $A_\alpha$'s. For example, for $\alpha$ values $\alpha_2'$, $\alpha_1'$, $\alpha_1$, and $\alpha_2$, the probability measures for (e.g., piecewise membership functions of) $A_{\alpha2'}$, $A_{\alpha1'}$, $A_{\alpha0}$, $A_{\alpha1}$, and $A_{\alpha2}$ are determined and denoted as $s_2'$, $s_1'$, $s_0$, $s_1$, and $s_2$, respectively, as depicted in FIG. 124(b). The corresponding color/grayscale (sup c) is determined as the measure of the possibility of the probability measure value of s, as depicted in FIG. 124(b). Whereas the probability measure of A (according to p(x)) is a crisp value $s_0$, the probability measure of (A,B) is a fuzzy value p*.

In one embodiment, a test score is associated with a proposition or fact (e.g., in form of X is A). In one embodiment, this test score is based on a probability measure of A based on a probability distribution in X. In one embodiment, a fuzzy test score is associated with a proposition or fact (e.g., in form of X is A*), where the test score is based on a fuzzy probability measure of A* and a probability distribution in X. In one embodiment, multiple candidate probability distributions are used to determine test scores associated with each candidate probability distribution per one or more facts or propositions. In one embodiment, an aggregate test score is determined per candidate probability distribution based on associated test scores based on multiple facts or propositions. For example, as depicted in FIG. 125(a), in one embodiment, multiple facts/propositions are used to determined test scores for one or more candidate probability distribution, e.g., $p_i(x)$ in X domain. In one embodiment, one or more propositions are in form of fuzzy map A* (e.g., ($A_j$, $B_j$)). As described in this disclosure, a fuzzy test score, $p_{i,j}^*$, associated with the probability distribution $p_i(x)$ is determined based on fuzzy map A* (e.g., ($A_j$, $B_j$)). In one embodiment, one or more propositions are in form of Z-valuation, e.g., X is $Z_q$ (or (X, $C_q$, $D_q$)). As described in this disclosure, such Z valuation imposes a restriction (or test score $ts_{i,q}$) on a candidate probability distribution $p_i(x)$, e.g., in form of value of membership function of $D_q$ for probability measure of $C_q$. In one embodiment, such a test score is a crisp value in [0, 1] range. As depicted in FIG. 125(a), test score $ts_{i,q}$ is shown as a sharp/crisp value between [0, 1] with a membership value (crisp) of 1. In one embodiment, one or more propositions are in form of fuzzy restriction, e.g., X is $E_k$, where $E_k$ is a fuzzy set in X domain. As described in this disclosure (as depicted in FIG. 125(a)), a score ($s_{i,k}$) is associated to a probability distribution $p_i(x)$, e.g., in form of a probability measure of $E_k$ based on $p_i(x)$. In one embodiment, various test scores (crisp and/or fuzzy) associated with a probability distribution $p_i(x)$ are aggregated by, for example, MIN or $\wedge$ operation. For example, MIN operation is used between fuzzy sets/numbers and crisp numbers to determined an aggregate test score ($t_i$) associated with a probability distribution $p_i(x)$.

$$t_i = (\ldots \wedge p_{i,j}^* \wedge \ldots \wedge ts_{i,q} \wedge \ldots \wedge s_{i,k} \wedge \ldots)$$

In one embodiment, $\wedge$ operation takes the minimum of all the crisp test scores such as $ts_{i,q}$ and $s_{i,k}$. In one embodiment, the $\wedge$ operation with fuzzy set/numbers (e.g., $p_{i,j}^*$) uses extension principle. In one embodiment, the $\wedge$ operation with fuzzy set/numbers (e.g., $p_{i,j}^*$) uses alpha-cut approach to determine a minimum fuzzy set. In one embodiment, a crisp number is modeled as a discrete impulse having a membership function of one, e.g., as depicted in FIG. 125(a), for $s_{i,k}$. In one embodiment, for example, a set of alpha cuts (e.g., at predefined values of 0+, 0.5, and 1) are used to determine the alpha cut intervals in various fuzzy sets/values and crisp numbers, as depicted in FIG. 125(b). In one embodiment, piecewise corner points in fuzzy sets/values are used to determine MIN. For example, FIG. 125(b) depicts the MIN operation on two fuzzy sets $p_{i,j}^*$ and $p_{i,k}^*$ and two crisp numbers $ts_{i,q}$ and $s_{i,k}$. The result of MIN operation, in the example, as depicted in FIG. 125(b), is a fuzzy set with a membership function denoted as $\mu(t_i)$ (shown in solid line). An approximate result based on alpha cuts at 0+, 0.5, and 1, is a fuzzy set denoted as $\mu'(t_i)$ (shown in dash line in FIG. 125(b)). In one embodiment, a centroid or peak of $\mu(t_i)$ or $\mu'(t_i)$ is used as a test score associated with $p_i(x)$. In one embodiment, $\mu(t_i)$ or $\mu'(t_i)$ is used in a subsequent operation as the test score associated with $p_i(x)$.

Note that usage of "MIN" and "min" are context dependant. For example, in above "MIN" is used to indicate hierarchy/order between two or more fuzzy values/sets, such as "small", "medium", and "large". "min" has been used to indicate the minimum of two values, such as the membership functions values at a given x, e.g., $\min(\mu_A(x), \mu_B(x))$ for all x, for example, to indicate the membership function of (A∩B).

More Examples

Now, we look at some more examples:

In one embodiment, we have a method for fuzzy logic control, in which an input module receives a precisiated proposition associated with a protoform. A fuzzy logic inference engine evaluates a first fuzzy logic rule from the fuzzy logic rule repository. The fuzzy logic inference engine is in or loaded on or executed on or implemented in a computing device, which comprises one or more of following: computer, processor device, integrated circuit, microprocessor, or server. The fuzzy logic rule repository comprises one or more fuzzy logic rules. The fuzzy logic rule comprises an antecedent part and a consequent part. The precisiated proposition comprises a Z-valuation, which is in a form of ordered triple (X, A, B), representing a statement assignment of X to a pair (A, B), where X represents a variable, A is a fuzzy logic set in domain of X, and B is a fuzzy logic set representing a certainty indicator of X being possiblistically restricted by the fuzzy logic set A. FIG. 119 is an example of a system described above.

The evaluating step comprises a test score evaluation module assigning a first test score to a candidate probability distribution for X based on the Z-valuation. The candidate probability distribution belongs to a set of candidate probability distributions. The test score evaluation module assigns a second test score to the antecedent part based on the antecedent part, set of candidate probability distributions, and the first test score. The fuzzy logic inference engine determines whether the antecedent part is satisfied beyond a threshold, based on the second test score. FIG. 119 is an example of a system described above.

In one embodiment, we have the precisiated proposition comprising a Z-valuation. In one embodiment, we have the consequent part comprising a Z-valuation. The fuzzy logic inference engine determines whether the antecedent part is satisfied beyond a threshold. The system correlates the consequent part with a first truth value based on the antecedent part. The system assigns a first test score to a candidate probability distribution for X based on the Z-valuation. The candidate probability distribution belongs to a set of candidate probability distributions. The correlating step uses the first truth value and the first test score. The fuzzy logic inference engine aggregates a possibilistic restriction on the candidate probability distribution, based on the correlated consequent part. FIG. 119 is an example of a system described above.

In one embodiment, we have all parts of the system comprising a Z-valuation. In one embodiment, we have the fuzzy logic rule repository comprising one or more databases, tables, or codes (e.g. as instructions or executables). In one embodiment, the set of candidate probability distributions is generated dynamically, obtained from a database, or input from an interface, e.g. by a user. In one embodiment, the set of candidate probability distributions is based on one or more parameters associated to a model of probability distribution function, e.g. a family of class of probability distribution functions. In one embodiment, the fuzzy logic inference engine uses backward chaining inference or forward chaining inference. In one embodiment, the fuzzy logic inference engine uses a pattern matching algorithm in a forward chaining inference. In one embodiment, the fuzzy logic inference engine performs one or more join operations with variable binding. FIG. 119 is an example of a system described above.

In one embodiment, the system comprises a rule execution or a rule firing manager, an agenda or task manager, a knowledge base database or storage, a parallel rule execution module, device, or subsystem, a goal analyzing module or device, a resolving module or device, a deffuzification module or device, an aggregation module or device, a correlation module or device, and/or a join network. In one embodiment, the fuzzy logic inference engine comprises the test score evaluation module. In one embodiment, the fuzzy logic inference engine is separate or different from the test score evaluation module. FIG. 119 is an example of a system described above.

Specific Applications

Figure 94:
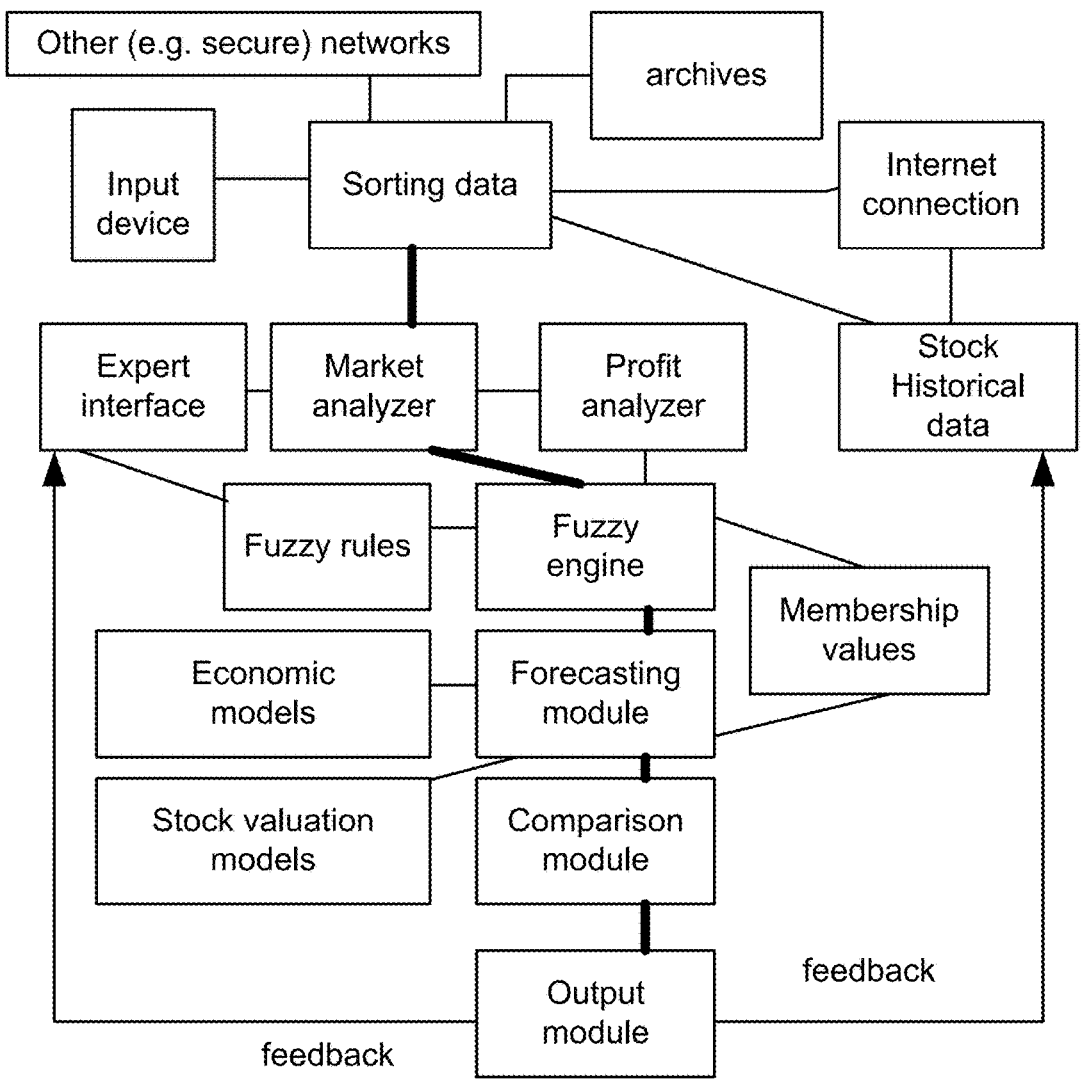
Figure 95:
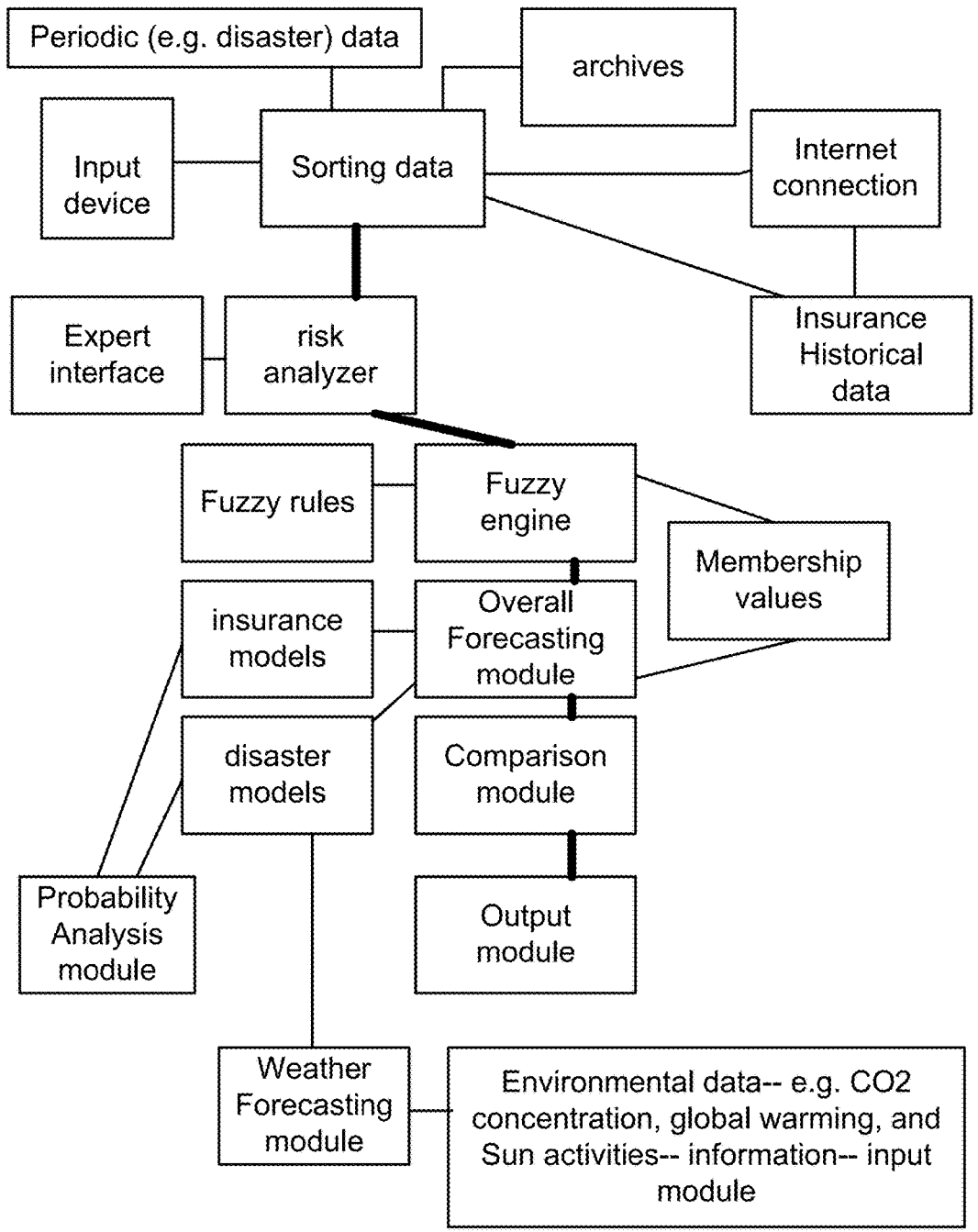

In different embodiments, the system is designed for the different applications, such as:
 (a) economics and stock market or decision analysis (see FIG. 94),
 (b) risk assessment and insurance (see FIG. 95),
 (c) prediction or anticipation (see FIG. 96),
 (d) rule-based characterization of imprecise functions and relations (see FIG. 97),
 (e) biomedicine and medical diagnosis (see FIG. 99, e.g. for tele-medicine and remote diagnosis),
 (f) medical equipment and measurements (see FIG. 98, e.g. for measuring blood pressure or X-ray analysis),
 (g) robotics (see FIG. 100, e.g. on a factory floor for an assembly line),
 (h) automobile (see FIG. 101, e.g. measuring environmental parameters, to adjust braking system in different driving conditions),
 (i) control systems and autonomous systems (see FIG. 102, e.g. for driving a car autonomously, without a driver),
 (j) searching for objects, search engines, and data mining (see FIG. 103, e.g. for searching to find friends in the vicinity of the user (or the store), for social networking, event planning, or marketing purposes),
 (k) speaker or voice recognition (see FIG. 104, for an example of a voice recognition system),
 (l) pattern or target recognition (e.g. airplane recognition or detection, or tracking in video frames, with signature or main features for an airplane) (see FIG. 105),
 (m) security and biometrics (see FIG. 106),
 (n) translation between languages (For example, one can use multiple systems for interpretation as shown as a part of FIG. 72, with one system per language, feeding each other, as a cascade, to translate between languages.).

In one embodiment, the system does the translation between 2 languages, however, there is not a one-to-one mapping or relationship between 2 words or phrases in the 2 languages. Thus, the system uses the context to find the proper meaning, and for the second language (to which it is translated), the system carries the real meaning as an attachment to the word. For example, for the second language, for the translated part, we have:

[Tank, CONTAINER]

where TANK is the translation in English, and CONTAINER is the real concept behind the word TANK, to remove the ambiguity in the translation (as the word TANK has at least 2 meanings in the American English language).

Surveys

In one embodiment, the system collects data through voting, survey, on-line, on-paper, using experts, using psychologists, using linguists, collecting opinions, with question on multiple choices with degree of agreement e.g. between 0 to 100, telephone surveys, computer surveys, online surveys, using social networks, using databases, government surveys, random surveys, statistical analysis, population specific surveys, target specific surveys, market surveys, using market reports, using census data, using agents on Internet, using robots, using search engines, or using neural networks as trainers, in order to get membership values, meaning of words or phrases in a language, region, dialect, profession, city, country, or population, language dynamics and evolvement, new words or usage of words, new technical words or Hollywood words or slangs, find the rate of changes in meanings, convergence or divergence of words or concepts or usages, define or extract membership curves and functions, reliability, credibility degree or value, information value, trustworthiness of the speaker or source, or any fuzzy parameter or Z-number concept, e.g. those defined or used in this disclosure.

This is a time-dependent exercise and concept, and it must be updated, as needed, or regularly, depending on the degree of dynamics of the vocabulary or dictionary or slangs or culture or industry or concept or immigration or changes in population mix, which are fuzzy values by themselves. The results of surveys and opinions of people, users, experts, section of population, and other data are stored in databases for future use, for example, for definition or values for Fuzzy membership functions or Z-number interpretations and applications.

In one embodiment, the system handles multiple Z-valuations or numbers. In one embodiment, the system does the reasoning step and/or summarization step with Z-valuations or numbers.

In one embodiment, please note that there are two types of IF-THEN statements. For the first type, at the THEN part, we set a value for a variable. Thus, if the IF section is partially satisfied, based on a membership value, then the value of the variable can be clipped or scaled down (e.g. as a ratio) based on (e.g. proportional to) the membership value. For the second type, at the THEN part, we have an action, e.g. to turn off the light switch for an equipment, which is a binary decision. In this case, if the IF section is partially satisfied, based on a membership value, then we have a threshold(s) (or ranges of values), for which for the values above or below the threshold, to activate or fire the THEN part, e.g. turn off the light switch for an equipment. The threshold can be expressed based on an absolute value, a relative value, a range, a Z-number, or a fuzzy value. Examples of threshold are 0.1, 0.5, 10 percent, 10 percent of average, 10 percent of maximum value, open/close range of real numbers (0, 0.5], 10 Kg (i.e. kilograms, for mass measurement), "usually 10 years", or "about 10 years".

Please note that since our method of computation is the closest to the human thinking and speech, it would be the most efficient way of instructing the machines to do a function based on the user's voice command (after parsing the speech, for speech recognition, and conversion to text, commands, templates, or computer codes, based on predefined and dynamic/adjustable grammar or rules).

Control systems, e.g. with multiple (If . . . Then . . . ) rules, can be used for efficient washing machines (consuming less water and detergent, based on level of dirt and type of clothing), braking system for train or cars (for optimum braking), air-conditioning system (better control of the temperature in the room, with less waste in energy), cameras or copy machines (for better image color adjustment or contrast adjustment or ink concentration), car fuel injection systems (for better air and fuel supply, for different engine environments and performances), parallel parking or autonomous driving cars (for optimum performances), robots in a factory assembly floor (with variations on objects received, on the manufacturing steps, for optimum correctional procedures), self-diagnosis and self-repair robots (for best possible diagnosis, to fix itself), system-of-systems (e.g. a colony of swimming robots acting together for a common task, e.g. finding an object in or under water, for proper target recognition or classification and proper feedback to each other, to guide other robots to proper areas of the ocean floor, to avoid duplicative work and effort by other robots in the colony), or any operation of complex machinery in a complex environment for optimum results. (The rules are discussed elsewhere in this disclosure.)

Figure 60:
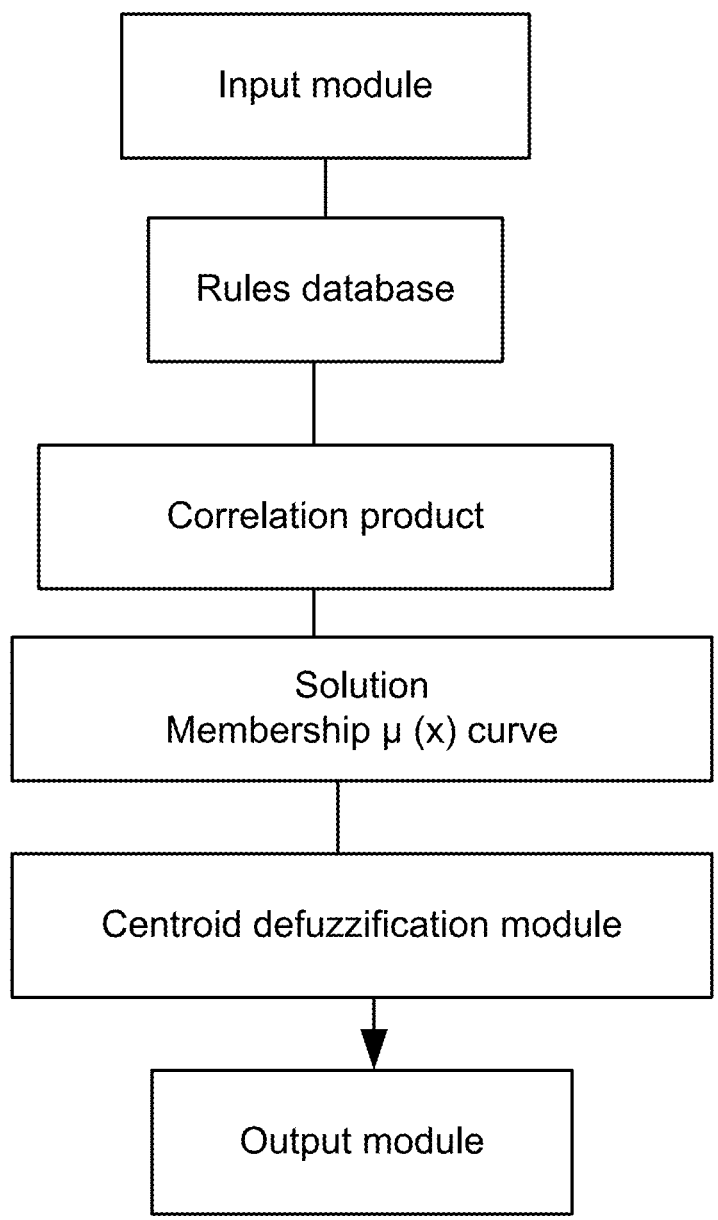
FIG. 60 shows a fuzzy system, with multiple (If . . . Then . . . ) rules.

FIG. 60 shows a fuzzy system, with multiple (If . . . Then . . . ) rules. There are 2 different main approaches for analysis and processing of the resulting membership function curves: (1) One method is to trim resulting membership function curve at the specific value of the membership function, as the upper allowed value. (2) The second method is to scale down the original membership function curve by a factor equal to the specific value of the membership function (which is a real number between 0 and 1), as the upper allowed value. Either way, the maximum allowed membership function is generally reduced from 1, in the final membership function curve.

In one embodiment, one uses composite maximum for the defuzzification step. In another embodiment, one uses composite moments (for the area under the curve, or the center of mass) for the defuzzification step.

Figure 57:
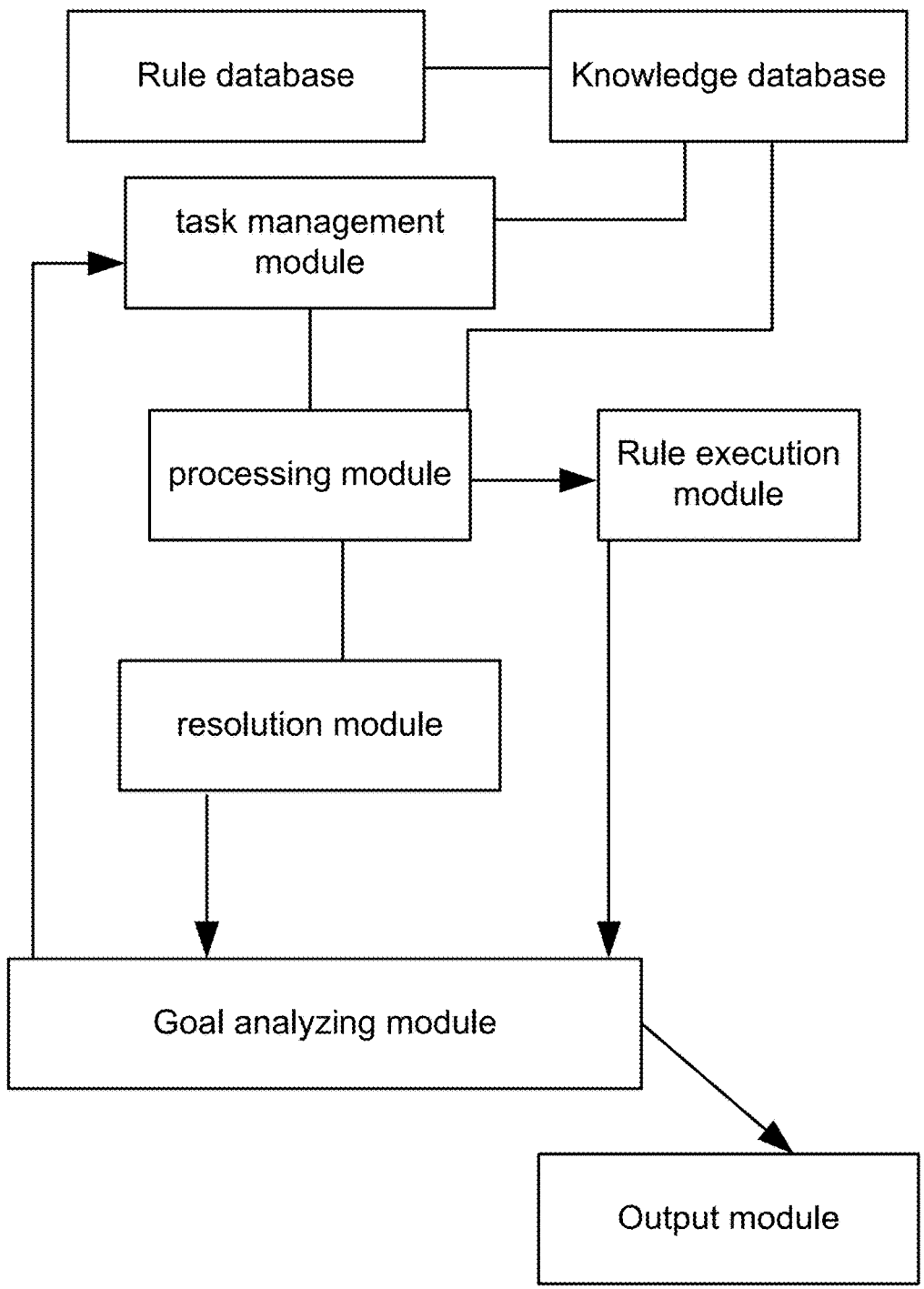
FIG. 57 shows a backward chaining inference engine.
Figure 58:
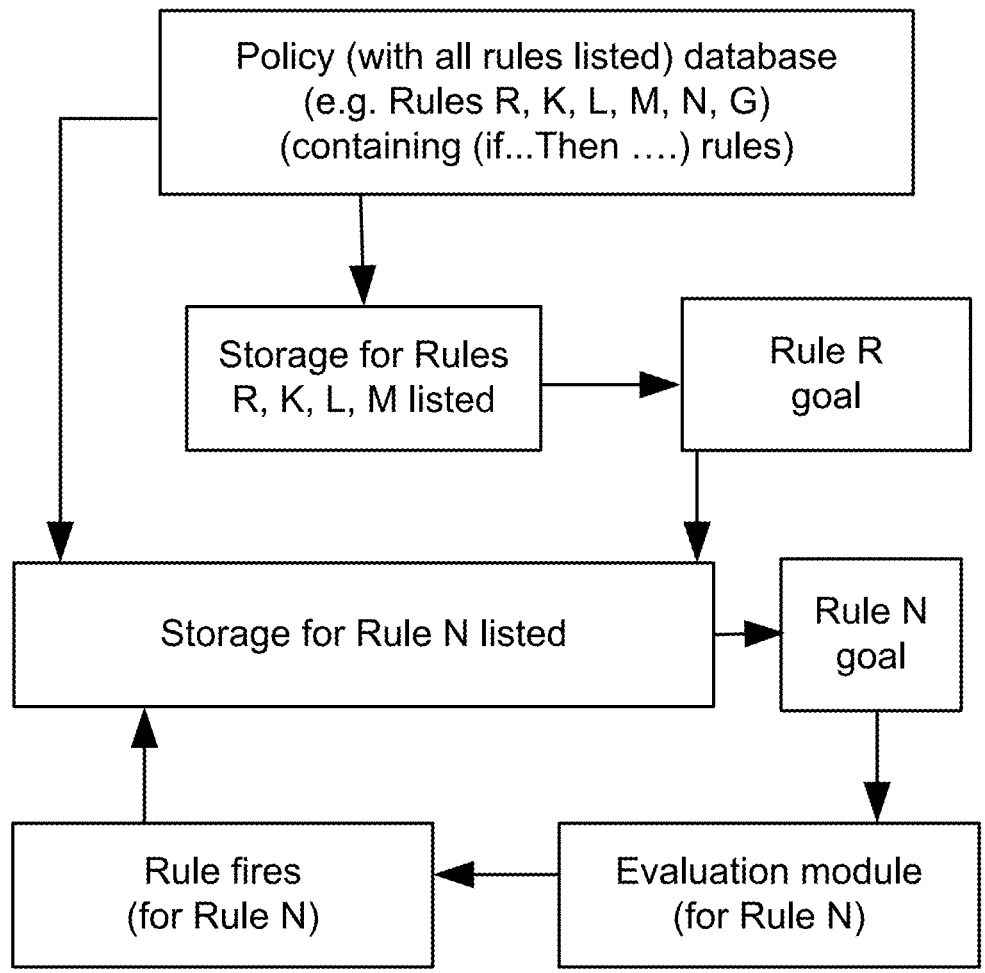
FIG. 58 shows a procedure on a system for finding the value of a goal, to fire (or trigger or execute) a rule (based on that value) (e.g. for Rule N, from a policy containing Rules R, K, L, M, N, and G).

For backward chaining inference engine, one can use a system as shown in FIG. 57, with a processor (or controlling) module, knowledge base, rule storage, and a task manager. FIG. 58 shows a procedure on a system for finding the value of a goal, to fire (or trigger or execute) a rule (based on that value) (e.g. for Rule N, from a policy containing Rules R, K, L, M, N, and G).

Figure 59:
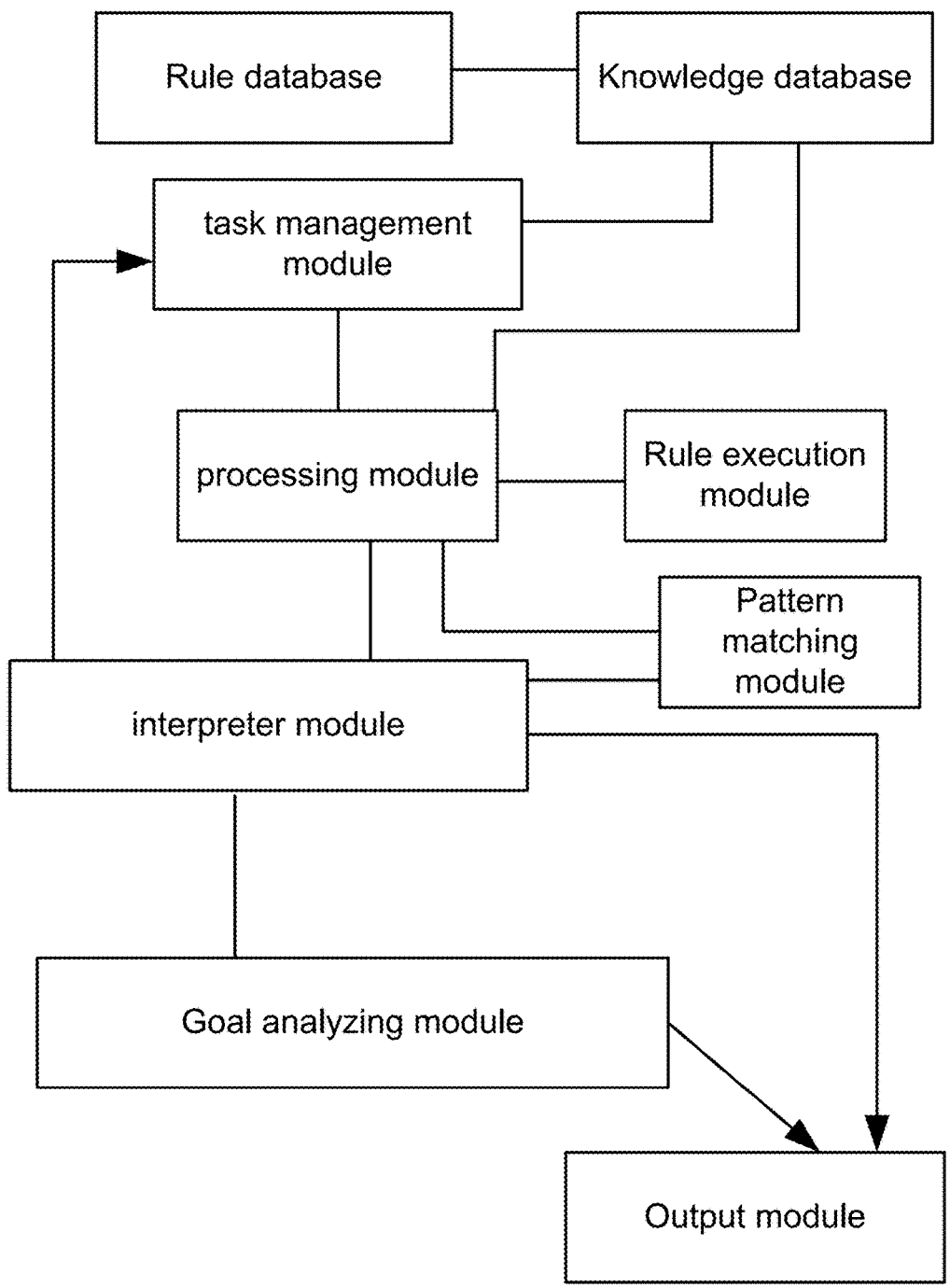
FIG. 59 shows a forward chaining inference engine (system), with a pattern matching engine that matches the current data state against the predicate of each rule, to find the ones that should be executed (or fired).

FIG. 59 shows a forward chaining inference engine (system), with a pattern matching engine that matches the current data state against the predicate of each rule, to find the ones that should be executed (or fired). Pattern matching module is connected to both processing (or controlling) module and interpreter module, to find the rules and also to change the association threads that find each candidate node for next loop (cycle).

Figure 50:
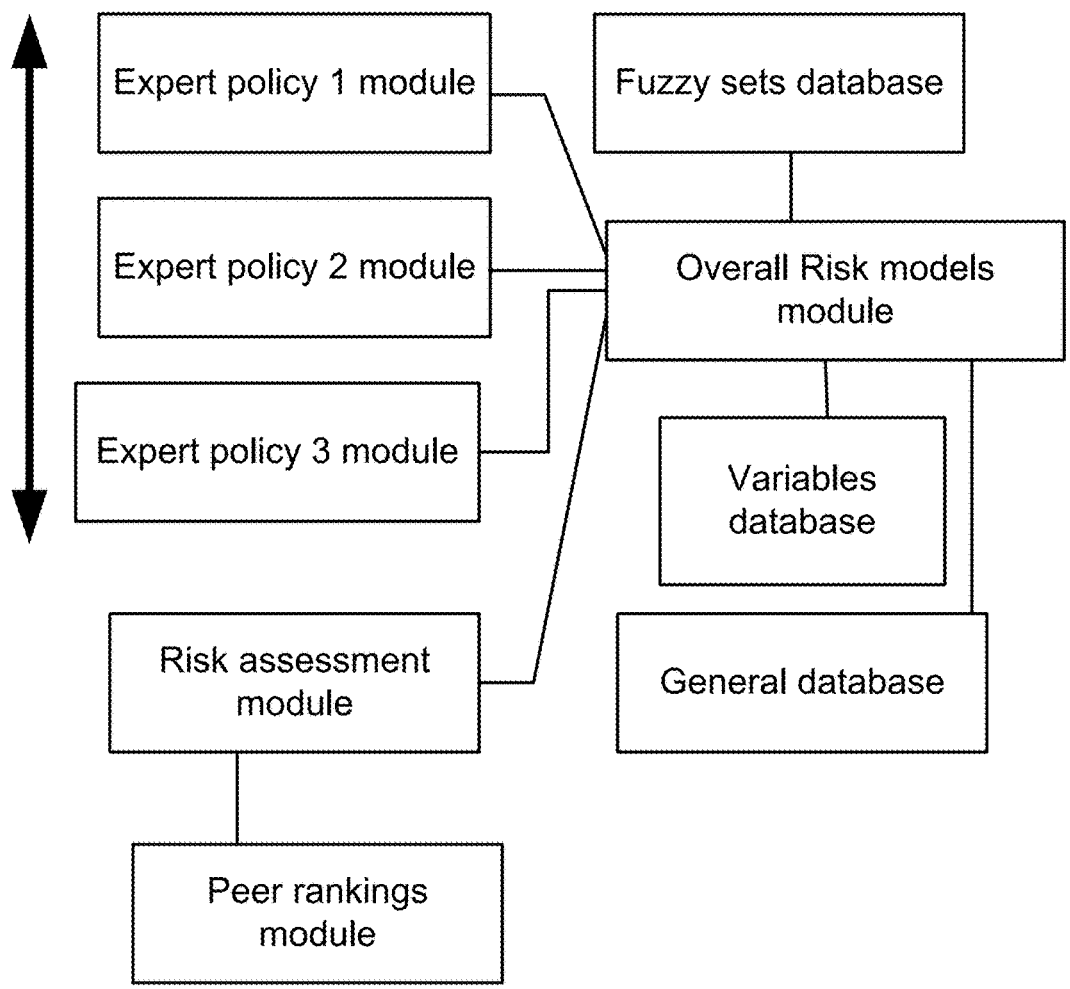
FIG. 50 shows a system for combining multiple fuzzy models.

As mentioned above, fuzzy reasoning systems can gather knowledge from multiple sources (experts), e.g. conflicting, collaborating, and cooperating experts. In a conventional system, one can use a weighted (biased) average technique, to assign weights on different advisors or sources of information. In the fuzzy system, one can use an adaptive peer ranking parameter (with peer ranking amplification), while firing rules in the fuzzy investment model, and with combination through weighted output averaging, or with combination through fuzzy set aggregation (i.e. combined intelligence). To combine multiple fuzzy models, one uses a system such as the one shown in FIG. 50.

Figure 51:
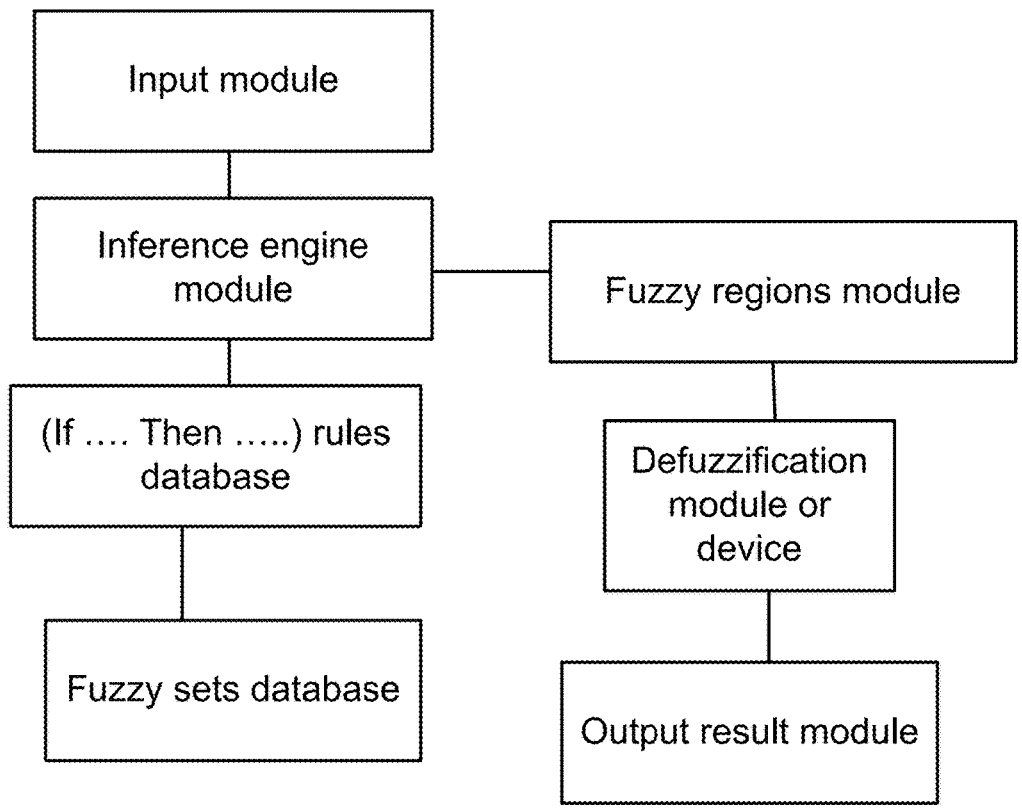
FIG. 51 shows a feed-forward fuzzy system.
Figure 52:
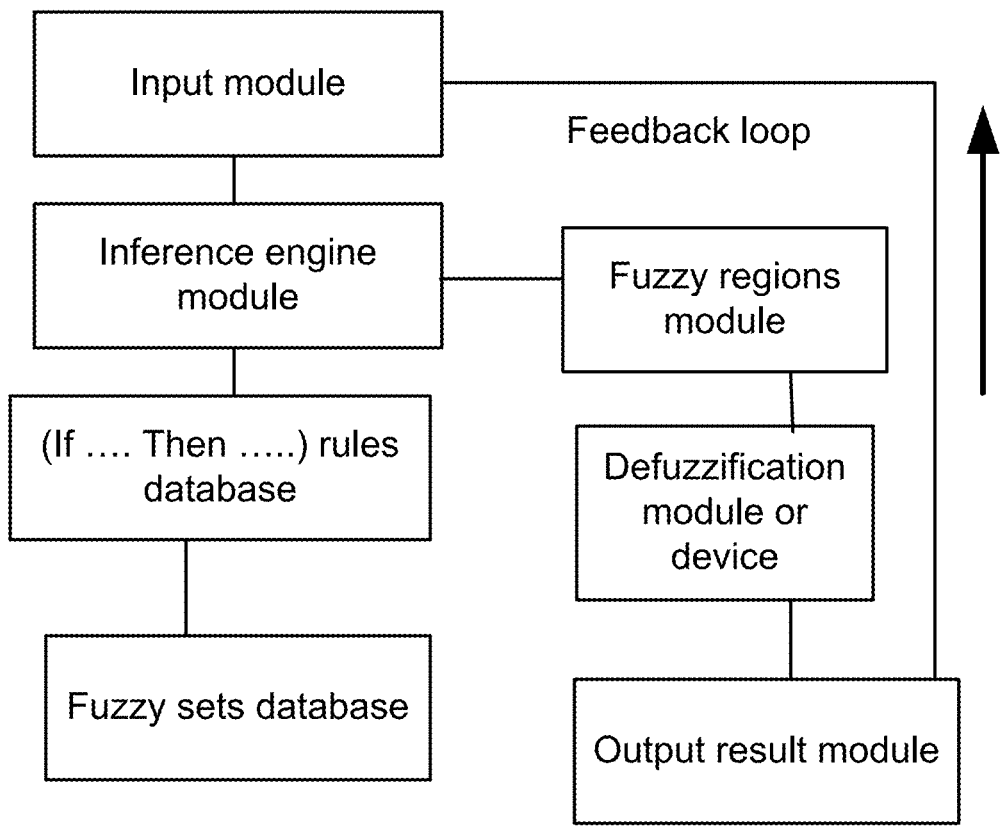
FIG. 52 shows a fuzzy feedback system, performing at different periods.
Figure 53:
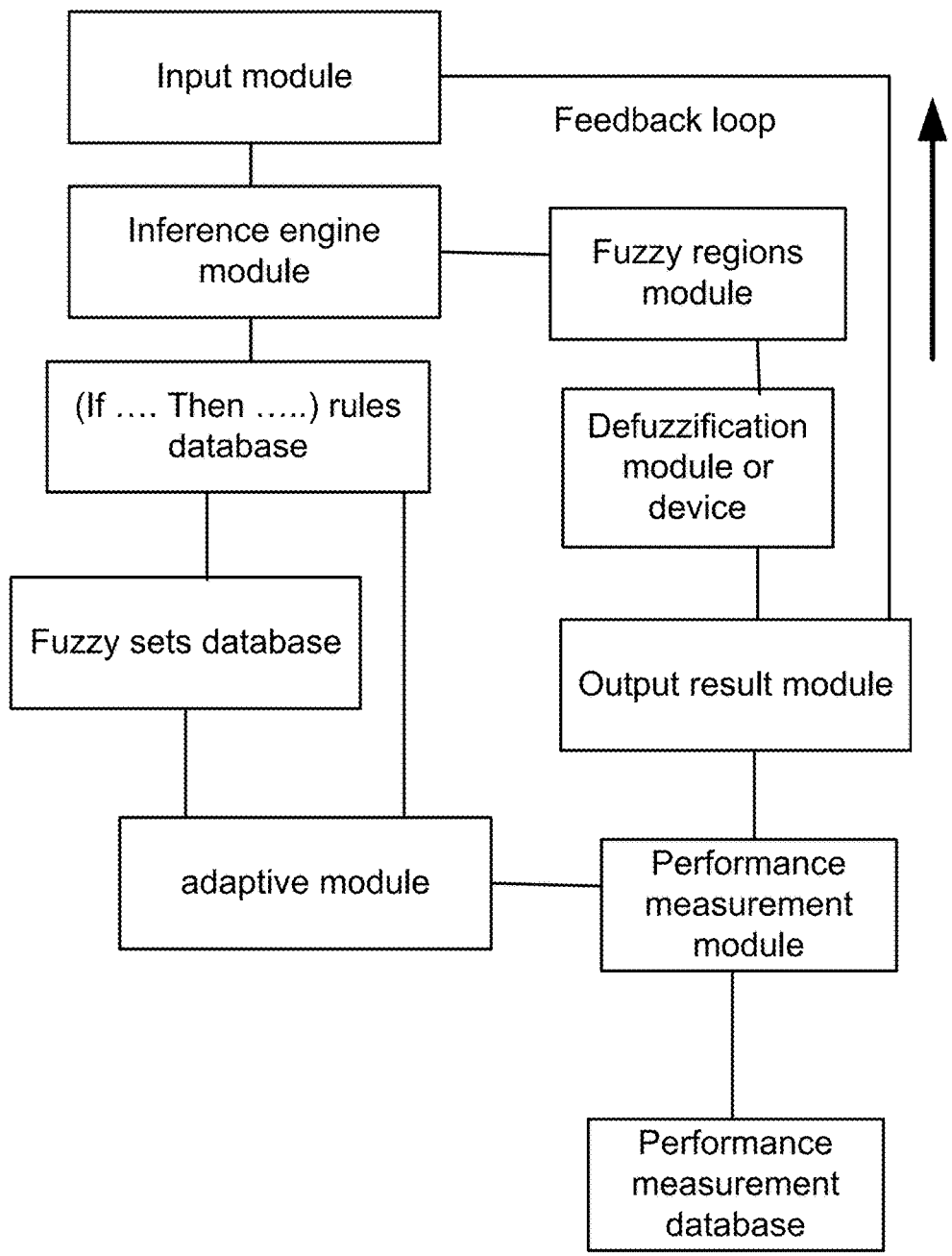
FIG. 53 shows an adaptive fuzzy system.

FIG. 51 shows a feed-forward fuzzy system. FIG. 52 shows a fuzzy feedback system, performing at different periods. FIG. 53 shows an adaptive fuzzy system, in which an objective function is measured against, to change the parameters of the model. A training algorithm such as "If . . . Then . . . " rules can be used, or fuzzy system rules are generated from the data. (The new rules are generated or modified.)

Figure 54:
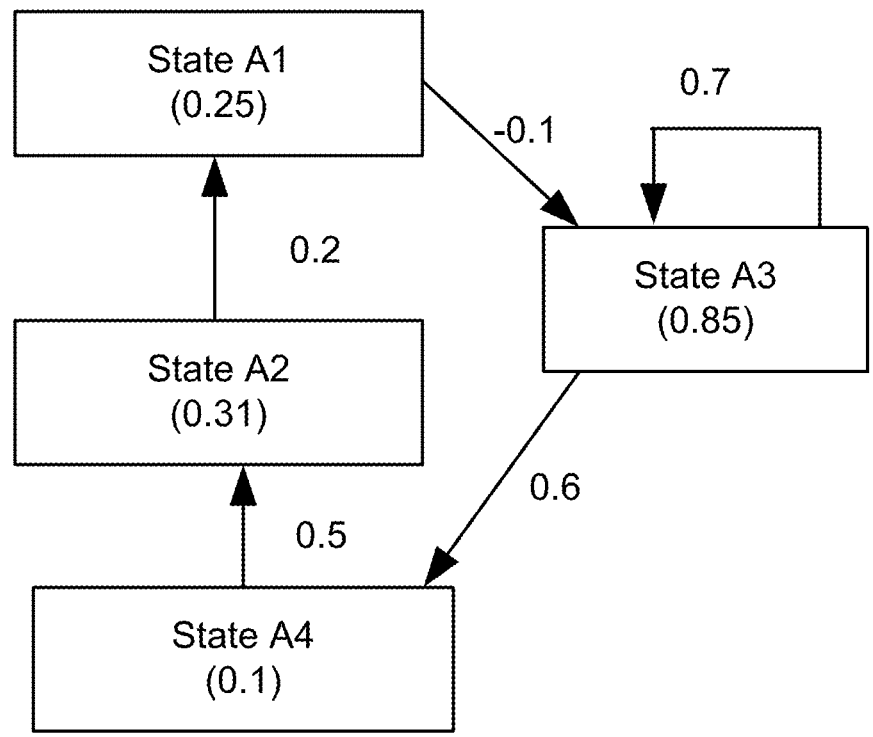
FIG. 54 shows a fuzzy cognitive map.
Figure 55:
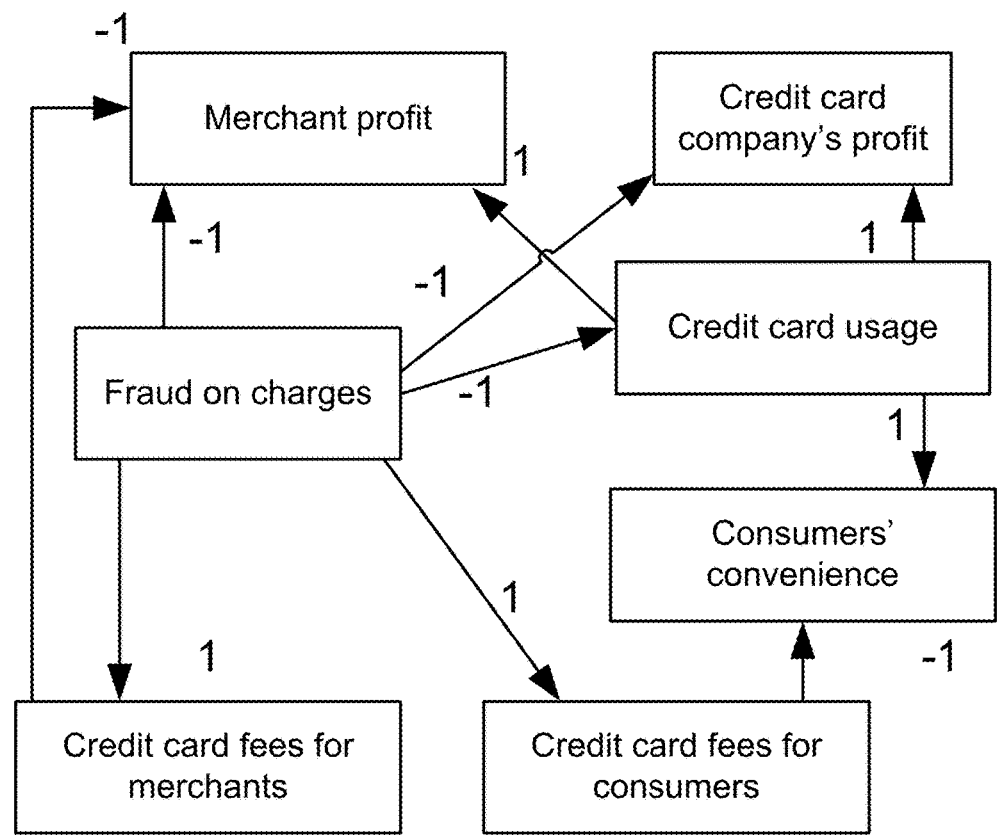
FIG. 55 is an example of the fuzzy cognitive map for the credit card fraud relationships.

A fuzzy cognitive map (FCM) for causal flow can be used for adaptive and feedback systems, to model: if $A_i$ then $A_j$ to $B_{ij}$, where the nodes are concepts (e.g. $A_i$ and $A_j$) and $B_{ij}$ represents the degree of strength of the connection between $A_i$ and $A_j$. To activate each concept, there is an activation threshold required (as the minimum strength required). This diagram can represent complex relationships (e.g. one concept increases or decreases the likelihood of another concept). A fuzzy cognitive map is shown in FIG. 54, with $B_{ij}$ displayed near the arrows and activation thresholds displayed inside the rectangles (representing each state). A special function is used to combine fuzzy rule weights. FIG. 55 is an example of the fuzzy cognitive map for the credit card fraud relationships, indicating positive or negative effects of one parameter on another, using 1 or −1 values, respectively (with the direction of the arrow).

For an M-state fuzzy cognitive map, we generally need an M×M matrix for the representation of all the relationships. So, if we get N opinions from N different experts, as N fuzzy cognitive maps, we can combine all N fuzzy cognitive maps using Σ (summation) operation on all corresponding matrix entries (L). Then, if each expert has a different level of expertise or reliability (as peer or user ranking, or an assigned weight, $w_j$, for j=1, . . . , N), then we will have:

$$L = \Sigma_j (w_j L_j)$$

Figure 56:
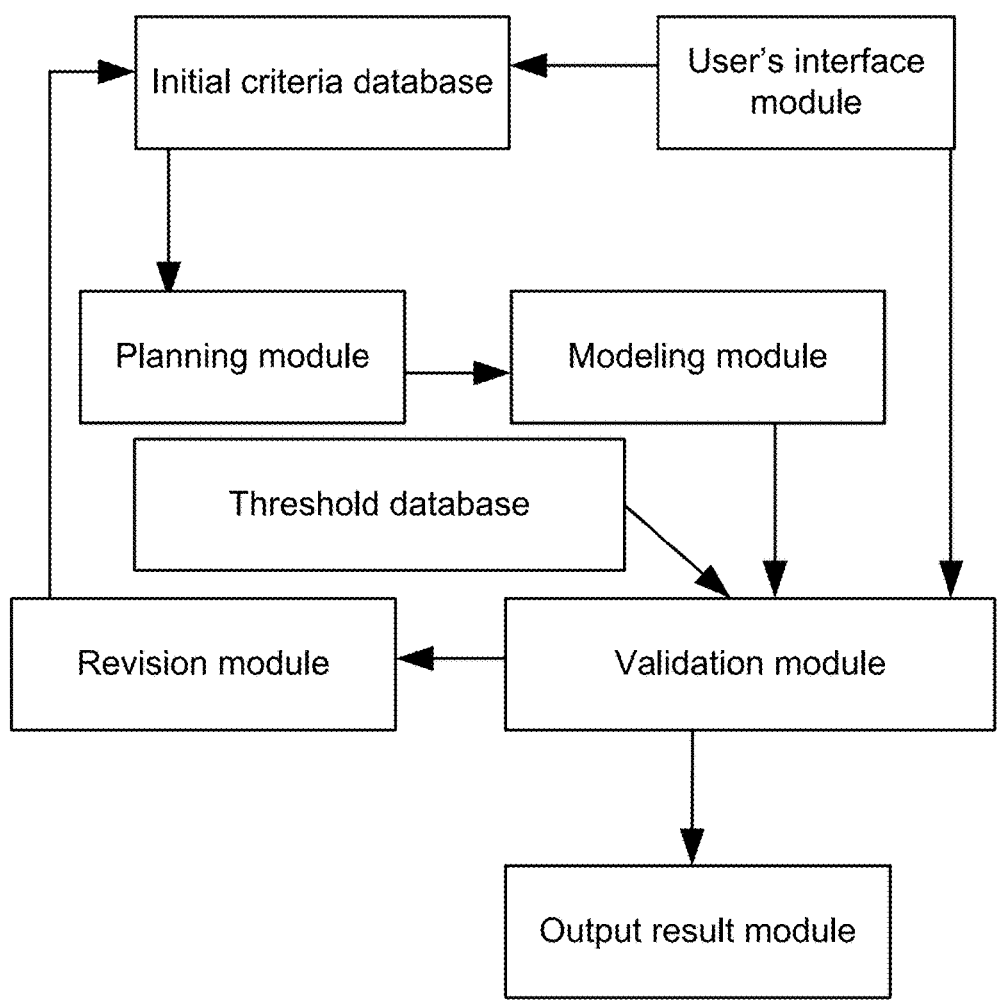
FIG. 56 shows how to build a fuzzy model, going through iterations, to validate a model, based on some thresholds or conditions.

To build a fuzzy model, one can go through iterations, as shown in FIG. 56, to validate a model, based on some thresholds or conditions.

Figure 49:
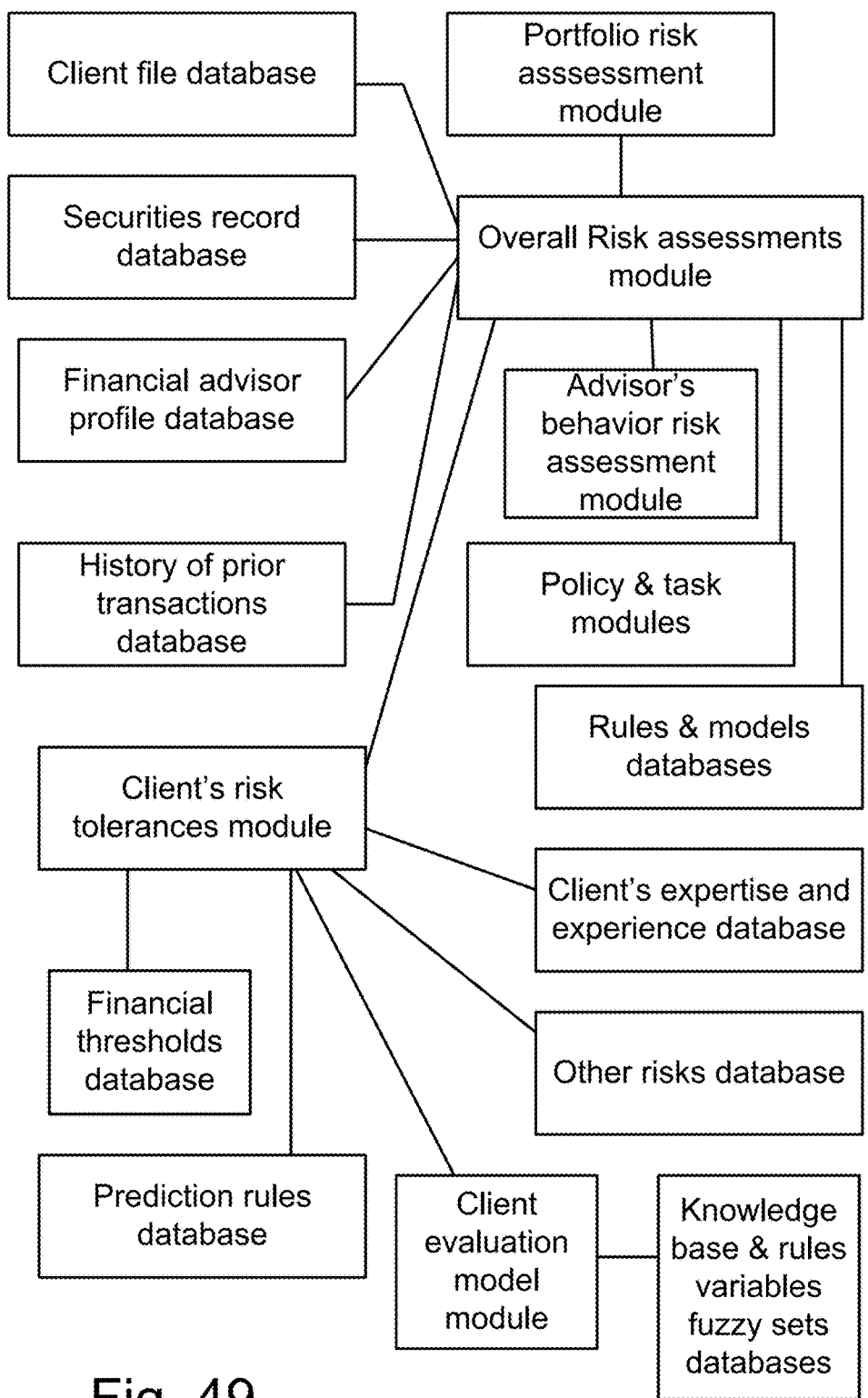
FIG. 49 shows a financial management system, relating policy, rules, fuzzy sets, and hedges (e.g. high risk, medium risk, or low risk).

For investment portfolio management for a client, one can have a financial management system as shown in FIG. 49, relating policy, rules, fuzzy sets, and hedges (e.g. high risk, medium risk, or low risk).

Figure 47:
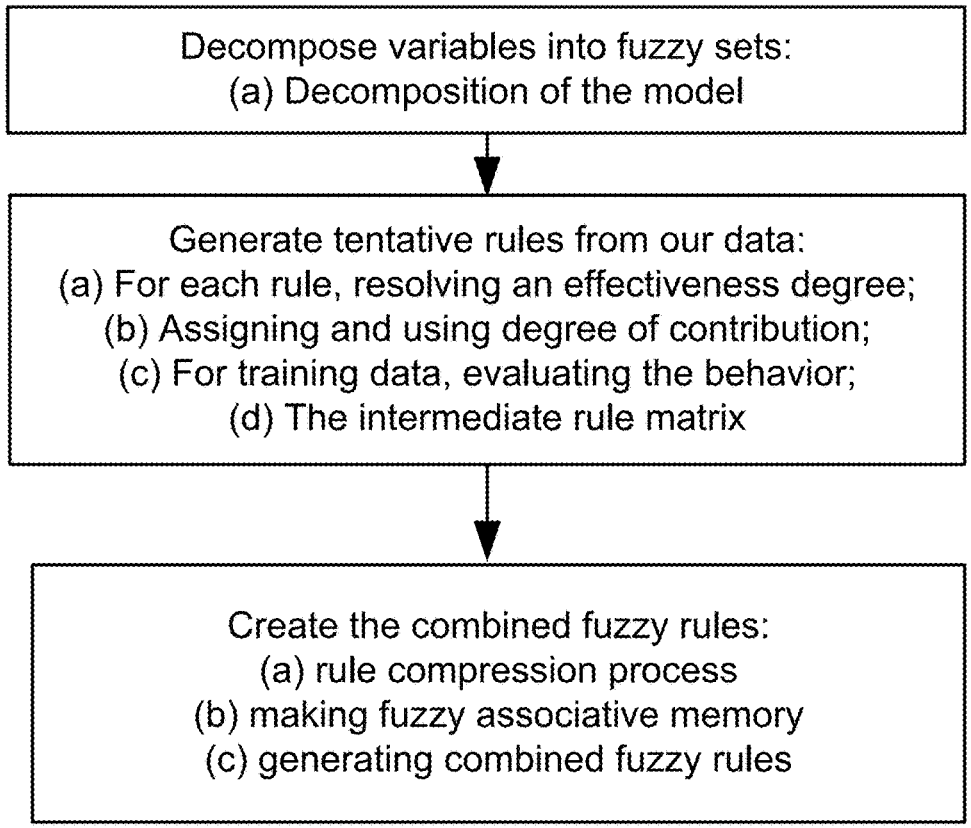
FIG. 47 shows a method employing fuzzy rules.
Figure 48:
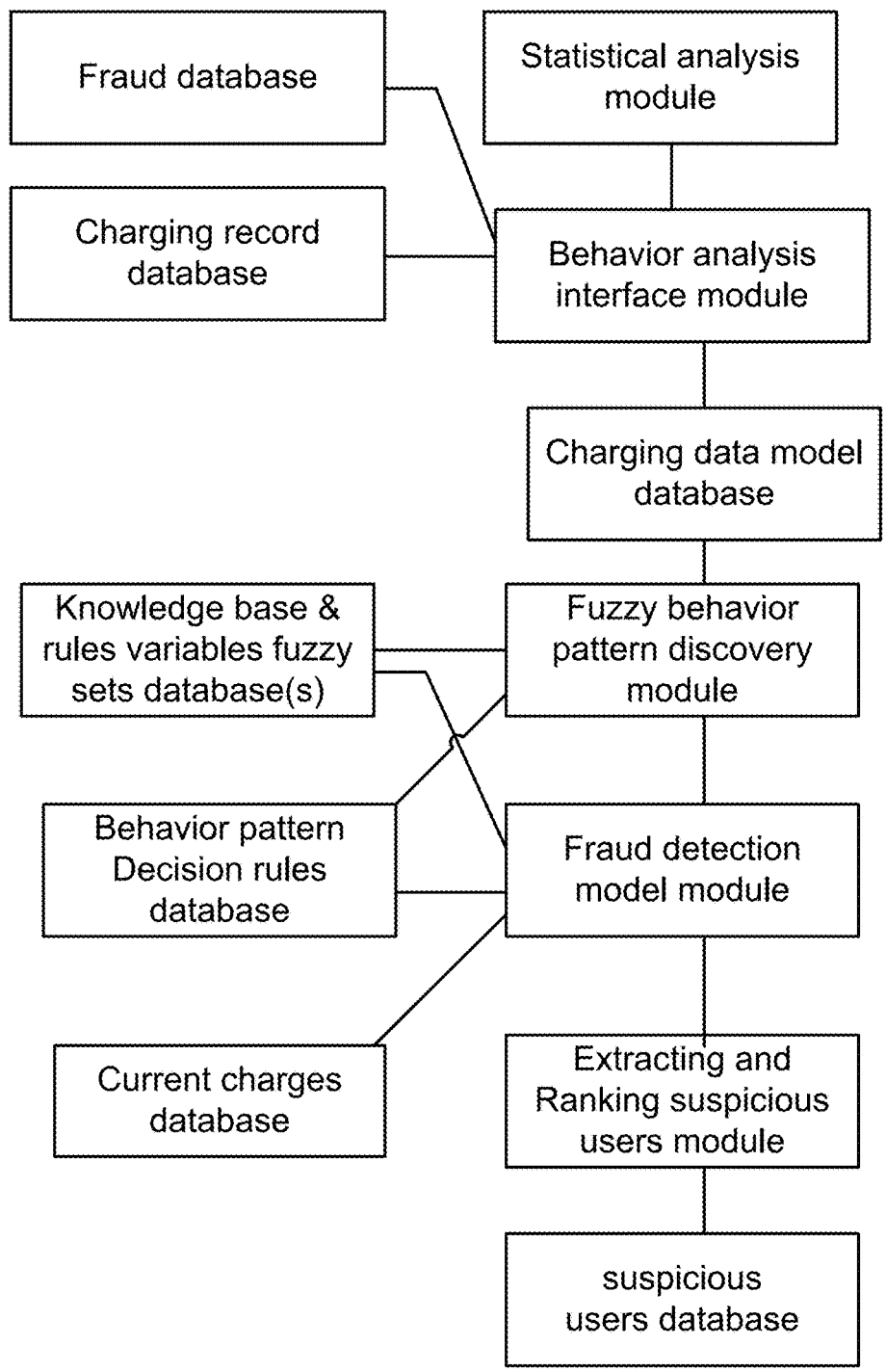
FIG. 48 shows a system for credit card fraud detection.

For knowledge mining and rule discovery, one can use Wang-Mendel rule discovery method, to partition input-output spaces into fuzzy regions, then generate fuzzy rules from training data, apply discriminant filter to rules, and create a combined fuzzy associative memory (FAM), which is a matrix (based on the inputs). A method is shown in FIG. 47. This can be used in health care claim (e.g. Medicare) and credit card processing fraud detections, as a knowledge mining technique. A system is shown in FIG. 48, for credit card fraud detection.

With the teachings mentioned above, in one embodiment, one can ask about "the top ten biggest companies" (which may change every year) or "top ten tallest mountains in the world" (which does not change every year), and get an answer by the search engine. See, for example, FIG. 109, for such a system.

The search engine can accumulate data from FACEBOOK or YOUTUBE or social sites or government sites or others on idle times, and store them for future searches in the databases, with classes and sub-classes, for faster retrieval, when needed. That also helps to find or distinguish people with the same exact name, build their profiles, and focus advertisement or marketing products, based on their preferences or past history or behaviors.

Please note that for the teachings above, a function y=f(x) as a graph, but without a known formula, can always be approximated by fuzzy graph, as piecewise approximation on the graph, which makes that relationship fuzzy. Then, one can solve based on the fuzzy graph, instead.

For systems that need load balancing, such as server farms for a search engine company or power generators in a electric grid for a country (which have different down times, delays, redundancies, supplies, demands, growths, expenses, new sources, or the like), the system can work in optimum conditions, or adjust fast, using the fuzzy rules and constraints for the system (as explained elsewhere in this disclosure), e.g. for emergency conditions and procedures, to reduce (for example) the blackout time for the consumers in the power grid in various parts of the country, or e.g. speed up the search engine in all parts of the world (by reducing the demand pressure on some areas, and increasing utilization percentages on idle or under-utilized areas of the server farms, to spread out the computing power in an optimized way), using the fuzzy parameters (such as the utilization factor which has a membership value between 0 and 1), as explained elsewhere in this disclosure.

Figure 61:
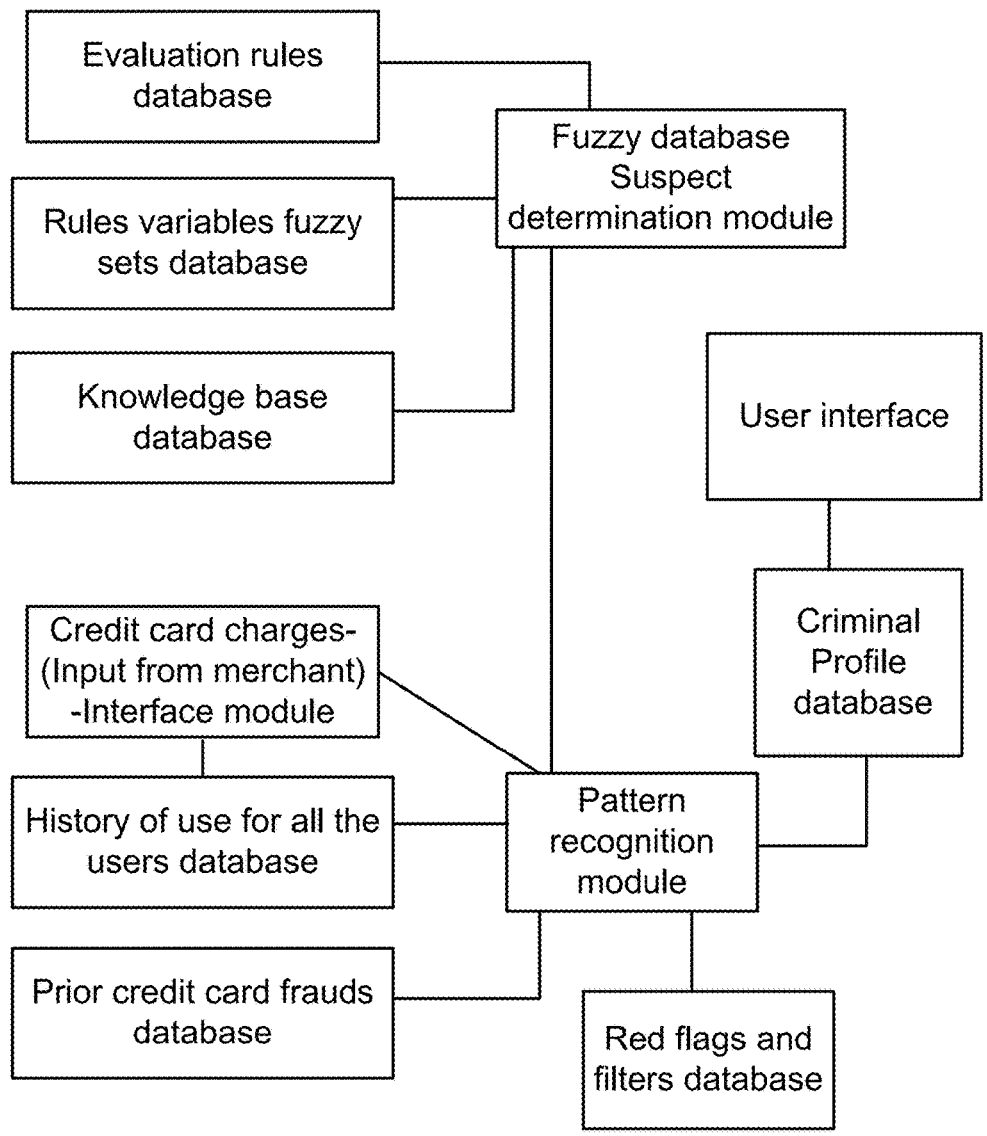
FIG. 61 shows a system for credit card fraud detection, using a fuzzy SQL suspect determination module, in which fuzzy predicates are used in relational database queries.

For databases, the database entries can generally be ordered and compared, with respect to one or more fuzzy rules, to index and sort or extract (or query) some useful information from the database(s), resulting in a listing or an ordered table. For example, FIG. 61 shows a system for credit card fraud detection, using a fuzzy SQL suspect determination module, in which fuzzy predicates are used in relational database queries. The fuzzy queries in relational database environment result in better fraud detection (because they fit better in real life situations). In one embodiment, the fuzzy database management process involves using fuzzy indexes, scanning database row, determining column membership grades, storing row locations and membership grades, and sorting the stored rows in descending membership order.

Figure 93:
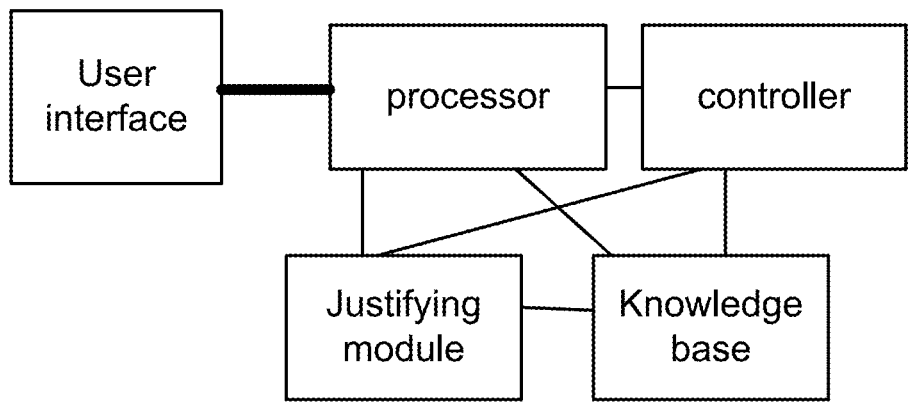

For one embodiment, FIG. 93 shows an expert system, which can be integrated or combined with any of the systems taught in this disclosure.

Figure 62:
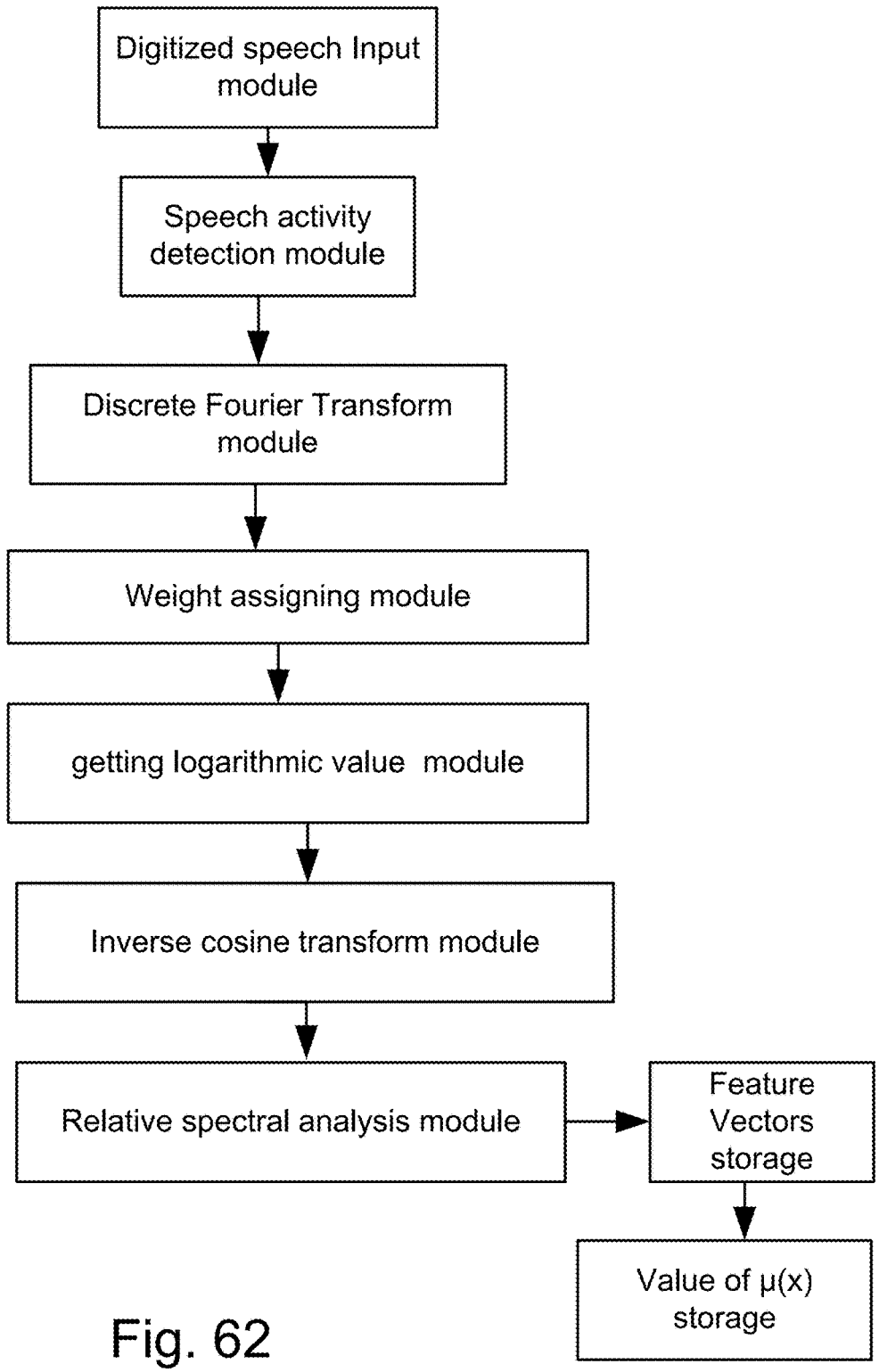
FIG. 62 shows a method of conversion of the digitized speech into feature vectors.
Figure 63:
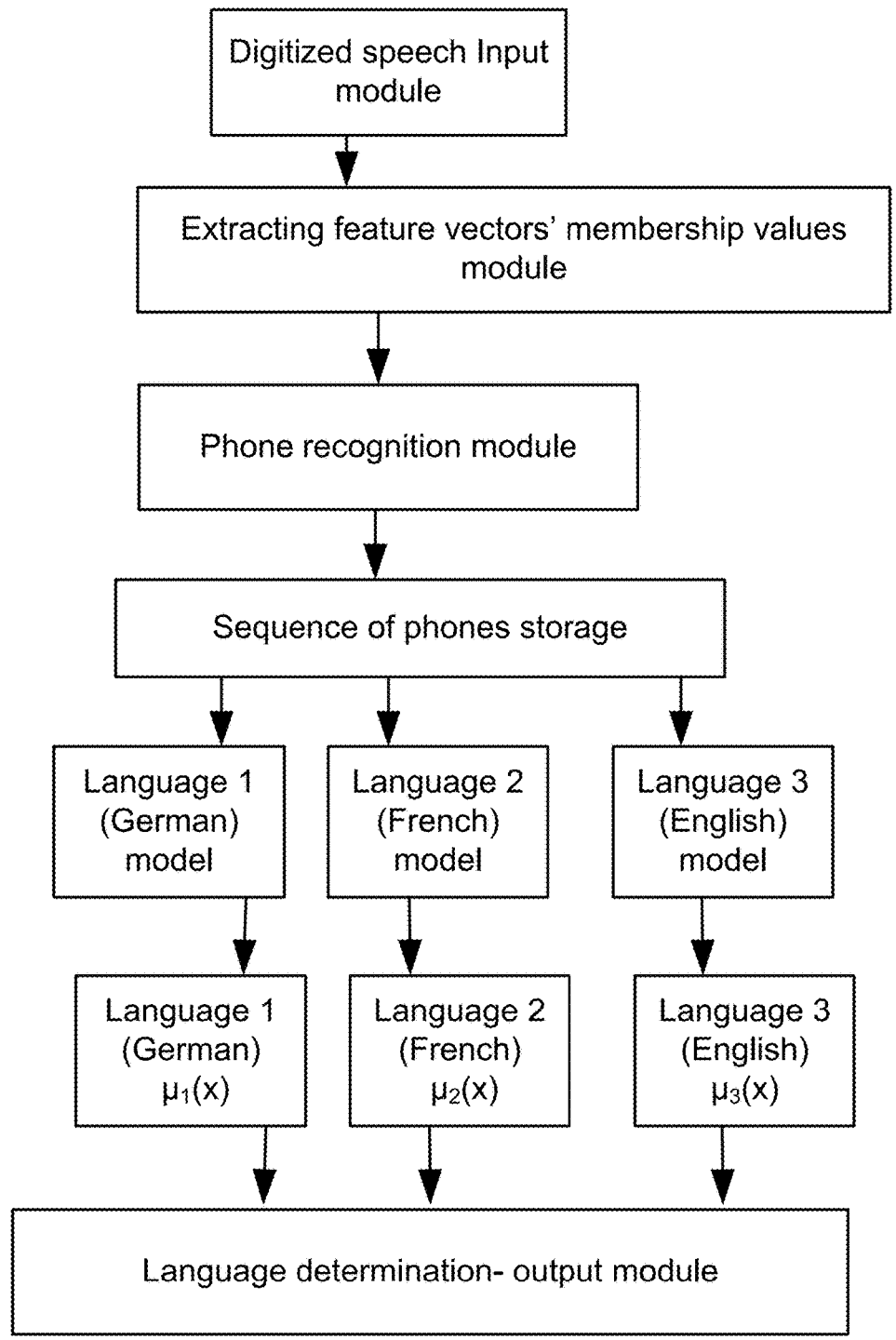
FIG. 63 shows a system for language recognition or determination, with various membership values for each language (e.g. English, French, and German).

The teachings above can be used for speech recognition, as well. For example, FIG. 62 shows a method of conversion of the digitized speech into feature vectors (for example, suggested by S. B. Davis and P. Mermelstein). In our case, the feature vectors are not the exact matches, and the matching (or contribution) is based on (expressed as) the value of membership function for the corresponding feature vector. FIG. 63 shows a system for language recognition or determination, with various membership values for each language (e.g. English, French, and German). The feature vectors can also be used for speaker recognition (e.g. male-female identity, or a specific person's identity, from pre-recorded samples in a database from various people). This can be used for the verification of the identity of a specific user, or to find the possible owner of a specific speech among many users.

Feature vectors can be used for speech recognition, as well, which can be done after the language is determined. In this case, one tries to match the phones or words with a large database of dictionary of all possible words or phones or sequence of phones in a specific language, pre-recorded and categorized. Again, the membership function values are used to find the possible words, via the possible sequence of phones which make up those words, phrases, or sentences. In one embodiment, the sequence of phones is compared to a chain of pointers connecting database phones, in a predetermined database, for all possible combinations of phones, resulting in all possible words, phrases, or sentences, especially the most common ones in a language, to give a possibility of each candidate word or phrase, to rank and select one or more of them for further processing, depending on some threshold(s), which can be a fuzzy parameter itself. In one embodiment, the sequences of phones are mapped to the words in a relational database, which can be updated by the user frequently, or gets trained to recognize the words (with an accompanied neural network system) for a specific user(s).

The similar teachings can be applied to the OCR (optical character recognition) of typed text or handwriting or signature. The text can be broken down in units of letters, pieces of words or letters, or feature vectors (as a basis for a fuzzy set, corresponding to an N-dimensional feature space), and gets compared with those in a database with variations on style or in handwriting, to find the possible targets, with various membership values.

This can be applied to any pattern recognition system or method, such as image mining or recognition on a large number of images (for example, for satellite or radar or laser or stereo or 3D (3-dimensional) imaging), e.g. using a knowledge-based database, with metadata attached or annotated to each image, identifying the source, parameters, or details of the image, e.g. as keywords or indices (which can also be used for database query). This can be used as a user-trainable search tool, employing a neural network module, with scoring functions using examples and counterexamples histograms. For example, in a bin (or partition) where there are more counterexamples than the number of examples, the resulting score is negative. These can be used for the recognition of (for example) trucks, cars, people, structures, and buildings in the images, with membership values associated with each target recognition. Each stored object or class of objects in the database (of all possible objects) has a signature (or one or more specific features, in an N-dimensional feature space, such as the length of the object, the angle between two lines, or the ratio of the length-to-width of the object), which can be matched to (or compared with) a target, with a corresponding membership value for each feature. This can be used for biometrics and security applications, as well, such as face recognition, iris recognition, hand recognition, or fingerprint recognition (e.g. with feature vectors defined from the curved pieces on fingerprints).

There are 2 major types of fuzzy inference systems: Mamdani-type (using the center of mass of the aggregation result) and Sugeno-type, both of which can be used in the systems of the current invention.

In one embodiment, the fuzzy system is used for trip planning or scheduling and its optimization in a trip or daily work. For example, the time for traffic delays and time for leaving the office, plus the threshold time for catching an air plane, are all expressed as fuzzy parameters, as discussed and analyzed elsewhere in this disclosure.

In one embodiment, when we have many systems, one feeding another one, we may want to keep the result of one in fuzzy form (as fuzzy region(s)), e.g. without applying the centroid defuzzification step. This way, the information does not get lost, when it feeds into another system, and it is also convertible to the human's natural language, based on the combination of predetermined templates and their corresponding hedges, stored beforehand in some database (for comparison and conclusion or conversion).

Context Dependant

Please note that the concept of "tall" (as an example) is both speaker-dependent and audience-dependent. For example, the same person giving lectures in Holland (having very tall population, in general) and Indonesia means differently, when talking with the audience of different population (having different size and height) in different countries, regarding various concepts, such as "being tall". This is also time-dependent. For example, if a person is giving lecture in the year 1700 AD (or talk about people living a few hundred years ago), in comparison to today (when people are generally taller), the concept of "being tall" is different for those situations. For some embodiments, the membership function and values are time-dependant. In addition, for some embodiments, the element of time is a part of the context analysis.

General Teaching & Variations

Figure 70:
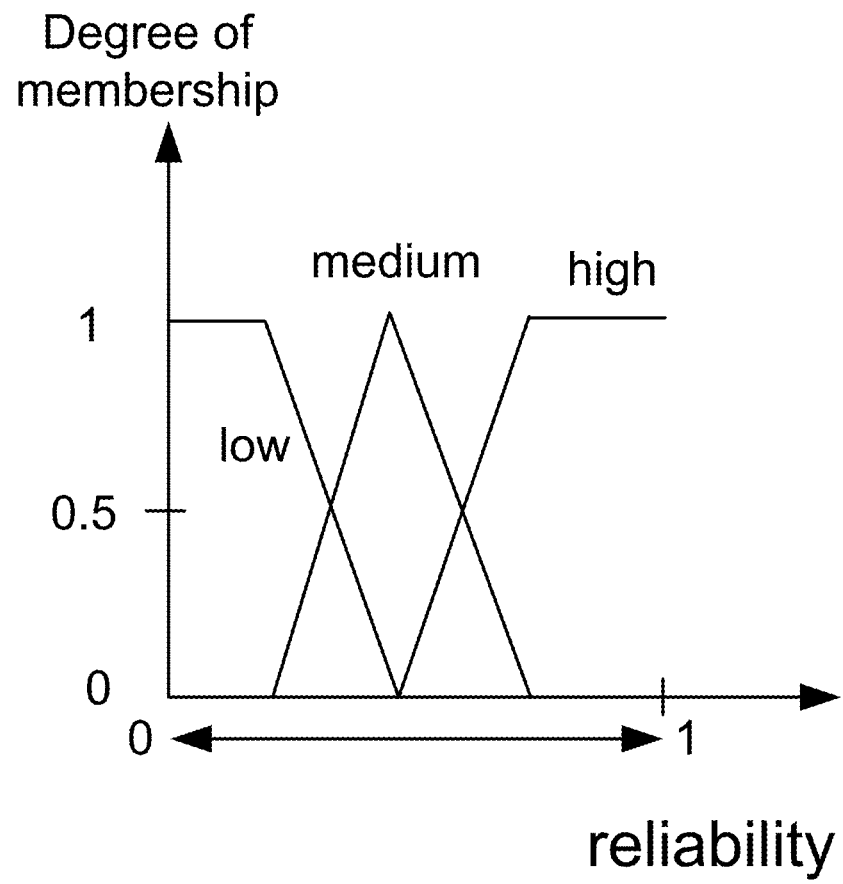
FIG. 70 shows the range of reliability factor or parameter, with 3 designations of Low, Medium, and High.

In one embodiment, the sum of the values of membership functions (corresponding to any point on the horizontal axis) is exactly 1. See FIG. 70 for an example, for the range of reliability factor or parameter, with 3 designations of Low, Medium, and High.

Please note that for all of our teachings here, different truth-value systems (e.g. those suggested by or known as Lukasiewicz, Godel, Product, and Zadeh), for definitions of e.g. T-norm operation, T-co-norm, and negation, can be used. For example, the symbol ∧ means AND, "minimum", or PRODUCT, for various truth-value systems. We can be consistent on one definition throughout the calculations and analysis (from the beginning to the end), or alternatively, mix the definitions (i.e. use various definitions for the same operation, from various truth-value systems) for various steps of the analysis. Either way, it is covered in our teachings here, for this patent application.

For all the systems taught here, one can use a microprocessor, processor, computer, computing device, controller, CPU, central processing module, processing unit, or controlling unit, to calculate, analyze, convert, and process the data, and it can store the information on a disk, hard drive, memory unit, storage unit, ROM, RAM, optical disc, magnetic unit, memory module, database, flash drive, removable drive, server, PC, RAID, tape, or the like. The information can be processed serially or in parallel. The communication between different units, devices, or modules are done by wire, cable, fiber optics, wirelessly, WiFi, Bluetooth, through network, Internet, copper interconnect, antenna, satellite dish, or the like.

Any variations of the teachings here are also intended to be covered by this patent application.

More Embodiments

Here, we introduce Z-webs, including Z-factors and Z-nodes, for the understanding of relationships between objects, subjects, abstract ideas, concepts, or the like, including face, car, images, people, emotions, mood, text, natural language, voice, music, video, locations, formulas, facts, historical data, landmarks, personalities, ownership, family, friends, love, happiness, social behavior, voting behavior, and the like, to be used for many applications in our life, including on the search engine, analytics, Big Data processing, natural language processing, economy forecasting, face recognition, dealing with reliability and certainty, medical diagnosis, pattern recognition, object recognition, biometrics, security analysis, risk analysis, fraud detection, satellite image analysis, machine generated data analysis, machine learning, training samples, extracting data or patterns (from the video, images, and the like), editing video or images, and the like. Z-factors include reliability factor, confidence factor, expertise factor, bias factor, and the like, which is associated with each Z-node in the Z-web.

Approximate Z-Number Evaluation:

In this section, we present a method for approximate evaluation of Z-Numbers, using category sets of probability distributions corresponding to similar certainty measures. All the figures are displayed in Appendix 1, as color images. This is also (partially) the subject of a paper (pages 476-483 of the conf. proceedings) and presentation given at an international Fuzzy conf. in Baku, Azerbaijan, on Dec. 3-5, 2012 ("The $2^{nd}$ World Conference on Soft Computing"), by the inventors. Appendix 1 is a copy of the paper at the Baku Conf. Appendix 3 is a copy of the VU graph PowerPoint presentation at the Baku Conf. Appendix 2 is a copy of the handwritten notes, in addition to the teachings of Appendices 1 and 3. All the Appendices 1-3 are the teachings of the current inventors, in support of the current disclosure, and are incorporated herein.

A Z-Number is denoted as an ordered pair (A,B), where A and B are fuzzy numbers (typically perception-based and described in natural language), in order to describe the level of certainty or reliability of a fuzzy restriction of a real-valued uncertain variable X in Z-valuation (X,A,B). (See L. A. Zadeh, "A note on Z-numbers," Inform. Sciences, vol 181, pp. 2923-2932, March 2011.) For example, the proposition "the price of ticket is usually high", may be expressed as a Z-valuation (price or ticket, high, usually). In Z-valuation, the certainty component B describes the reliability of the possibilistic restriction, R, for the random variable X, where $$R(X): X \text{ is } A \quad (1)$$

with the reliability restriction given by $$\text{Prob}(X \text{ is } A) \text{ is } B \quad (2)$$

In another words, the certainty component B, restricts the probability measure of A, denoted by v, $$v = \text{Prob}(X \text{ is } A) = \int_X \mu_A(x) \cdot p_x(x) \cdot dx \quad (3)$$

where $\mu_A(x)$ is the membership function of x in fuzzy set A on X domain, and $p_X$ is the probability distribution of X. Therefore, the certainty component B indirectly restricts the possibilities of various (candidate) hidden probability distributions of X by: (eq. 4 below)

$$\mu_B(v) = \mu_B\left(\int_X \mu_A(x) \cdot p_x(x) \cdot dx\right),$$

where $\mu_B(v)$ is the membership function of the probability measure v in fuzzy set B.

Here, we show a method to approximate Z-valuation, based on categories (sets) of $p_X$'s with similar probability measures (or resulting in similar certainty measure), as an approach to reuse predetermined calculations of probability measures. First, we demonstrate an example of Z-valuation without such approach, and then, we present an approximate approach to Z-valuation via categorical sets of probability distributions.

A. Z-Valuation: Basics

Figure 1:
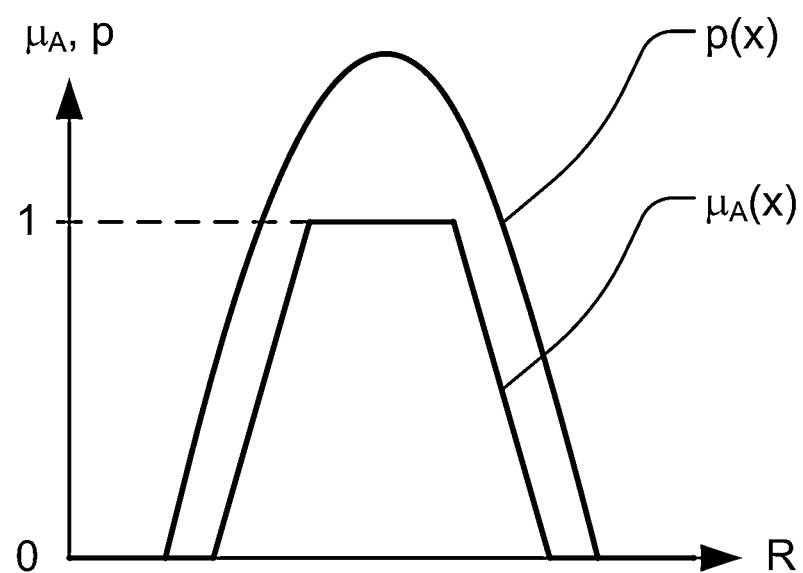
FIG. 1 shows membership function of A and probability density function of X.

The Z-valuation uses the mapping of the test scores given by (4) to each of hidden probability distribution candidates of X (See L. A. Zadeh, "A note on Z-numbers," Inform. Sciences, vol 181, pp. 2923-2932, March 2011. See also R. Yager, "On Z-valuations using Zadeh's Z-numbers," Int. J. Intell. Syst., Vol. 27, Issue 3, pp. 259-278, March 2012.), collectively referred to as $$\text{Prob. Distrib. Candidates} = \{p_i\}, \quad (5)$$

where i numerates different candidates. Fig. 1 of Appendix 1 conceptually illustrates the mapping, where each $p_i$ is first mapped to a probability measure of A, $v_i$, and then mapped to a test score determined by B, where $$v_i = \mu_A p_i = \int_X \mu_A(x) \cdot p_i(x) \cdot dx, \quad (6)$$

and $$ts_i = \mu_B(v_i) \quad (7)$$

Note that the dot symbol in $(\mu_A \cdot p_i)$ in (6) is used as shorthand for the probability measure. Fig. 1 of Appendix 1 shows the test score mapping to hidden probability distribution candidates $p_i$ in X, for Z-valuation (X,A,B).

Via the extension principle, the application of the restriction (test scores) on $p_{x,i}(x)$ (i.e., probability distribution candidates in X domain) to other entities is illustrated. For example, the restriction on $p_{x,i}(x)$ can be extended to the possibilistic restriction on the corresponding probability distributions, $p_{y,i}(y)$, in Y domain, where $$Y = f(X).$$

In such a case, the restrictions can further be extended to the probability measures, $w_i$, of a fuzzy set $A_y$ in Y domain, based on $p_{y,i}(y)$. The aggregation of the best test scores for $w_i$ would determine the certainty component $B_Y$ in Z-valuation $(Y, A_Y, B_Y)$, based on the original Z-valuation $(X, A_X, B_X)$, as indicated in Fig. 2 of Appendix 1, which illustrates the extension of test scores to Y domain. Fig. 2 of Appendix 1 is a test score mapping from X domain to Y domain and aggregation of test scores on probability measures, w, for Z-valuation $(Y, A_Y, B_Y)$.

For simplicity, as shown in Fig. 2 of Appendix 1, three probability distribution candidates in X domain, $p_{x,1}$, $p_{x,2}$, and $p_{x,3}$, are assigned test scores $ts_1$ and $ts_2$, via certainty restriction on probability measures $v_1$ and $v_2$ (with $p_{x,2}$ and $p_{x,3}$, having the same probability measure $v_2$ for $A_X$). By applying f(X) to each probability distribution candidate in X domain, we can obtain a corresponding probability distribution in Y domain, denoted as $p_{y,i}$, which can be used to compute the corresponding probability measure of $A_Y$ (assume given), denoted as $w_i$. In this example, $p_{y,1}$ and $p_{y,2}$ (mapped from $p_{x,1}$ and $p_{x,2}$) result in the same probability measure $w_2$ (or aggregated w bin), while $p_{y,3}$ (mapped from $p_{x,3}$) maps into $w_1$. In this simple example, the aggregation of the best test scores for $p_{y,i}$, denoted as $ts(p_{y,i})$, in w domain (e.g., in each w bin) would result in the following membership function for $B_Y$:

$$\mu_{B_Y}(w_1) = ts_2$$

$$\mu_{B_Y}(w_2) = \max(ts_1, ts_2).$$

In other words, in this scenario, $$\mu_{B_Y}(w) = \sup_{\forall p_{y,i}} ts(p_{y,i}) \quad (8)$$

subject to $$w = \mu_{A_Y} \cdot p_{y,i}.$$

In case of single variable dependency Y=f(X), the probability measure w can be evaluated by unpacking the probability distribution in Y as illustrated by (9) and transforming the integration over X domain as shown in (10), without explicitly evaluating $p_{y,i}$:

$$w_i = \mu_{A_Y} \cdot p_{y,i} \quad (9)$$

$$= \int_Y \mu_{A_Y}(y) \cdot p_{y,i}(y) \cdot dy$$

$$= \int_Y \mu_{A_Y}(y) \cdot \sum_j \frac{p_{x,i}(x_j)}{|f'(x_j)|} \cdot dy$$

where j denotes the consecutive monotonic ranges of f(X) in X domain, and $x_j$ is the solution for $f^{-1}(y)$, if any, within the monotonic range j, for a given y. This takes into account that the probability $(p_{y,i} \cdot dy)$ for an event within the infinitesimal interval of [y, y+dy] in Y domain, is the summation of the infinitesimal probabilities from various infinitesimal intervals $[x_j+dx_j]$ (if applicable) in X domain, where for each j:

$$dy=f'(x_j) \cdot dx_j$$

Therefore, with repacking the integration (9) in X domain over the consecutive monotonic ranges of f(X), we obtain:

$$w_i = \int_X \mu_{A_Y}(f(x)) \cdot p_{x,i}(x) \cdot dx \qquad (10)$$

Furthermore, if f(X) is monotonic (i.e., $f^{-1}(y)$ has only one solution in X, if any) AND $\mu_{A_Y}$ is obtained from $\mu_{A_X}$ via the extension principle by applying f(X) to $A_X$, then $w_i$ is guaranteed to be equal to $\upsilon_i$ for all candidate probability distributions $p_{x,i}$, because $\mu_{A_Y}(y)=\mu_{A_X}(x)$ for $\forall y=f(x)$ in such a case. This also means that in such a case, $B_Y$ becomes equal to $B_X$, and no additional computation would be necessary.

B. Z-Valuation: Example

To illustrate an example of Z-valuation, assume the following is given:

$$X=(A_X,B_X),$$

$$Y=f(X)=(X+2)^2, \text{ and}$$

$$A_Y.$$

Figure 4:
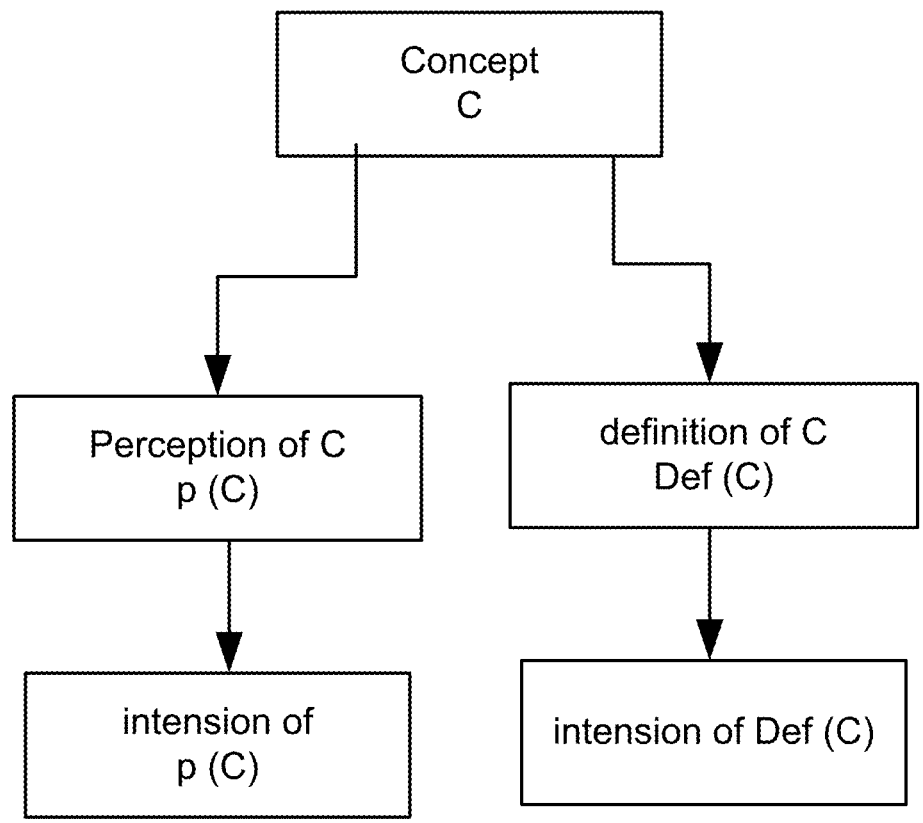
FIG. 4 shows cointension, the degree of goodness of fit of the intension of definiens to the intension of definiendum.
Figure 6:
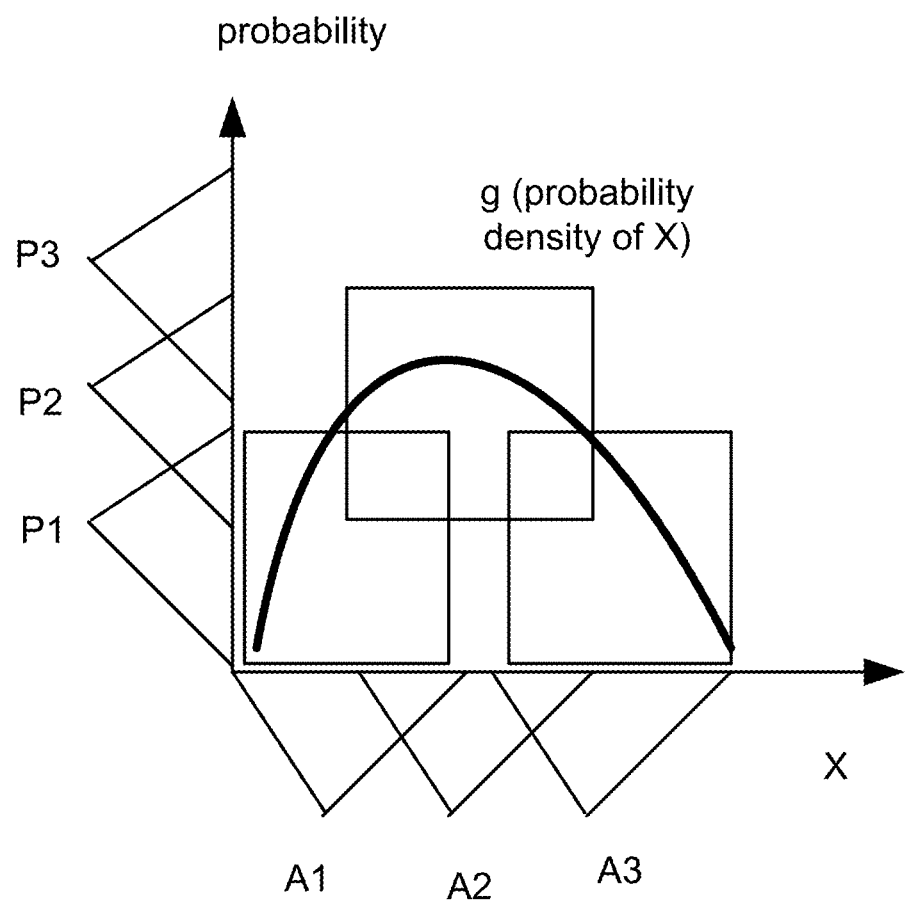
FIG. 6 shows basic bimodal distribution.

The goal is to determine the certainty value $B_Y$ for the proposition that (Y is $A_Y$), i.e., the Z-valuation $(Y,A_Y,B_Y)$. For purpose of this example, assume Figs. 3, 4, and 5 of Appendix 1 depict the membership functions for $A_X$, $B_X$, and $A_Y$, respectively. The function f(X) is also depicted in Fig. 6 of Appendix 1. Fig. 3 of Appendix 1 is the membership function of $A_X$, e.g., "X is around zero". Fig. 4 of Appendix 1 is the membership function of $B_X$, e.g., "Likely". Fig. 5 of Appendix 1 is the membership function of $A_Y$, e.g., "Y is about nine". Fig. 6 of Appendix 1 is a diagram depicting f(X).

Figure 9:
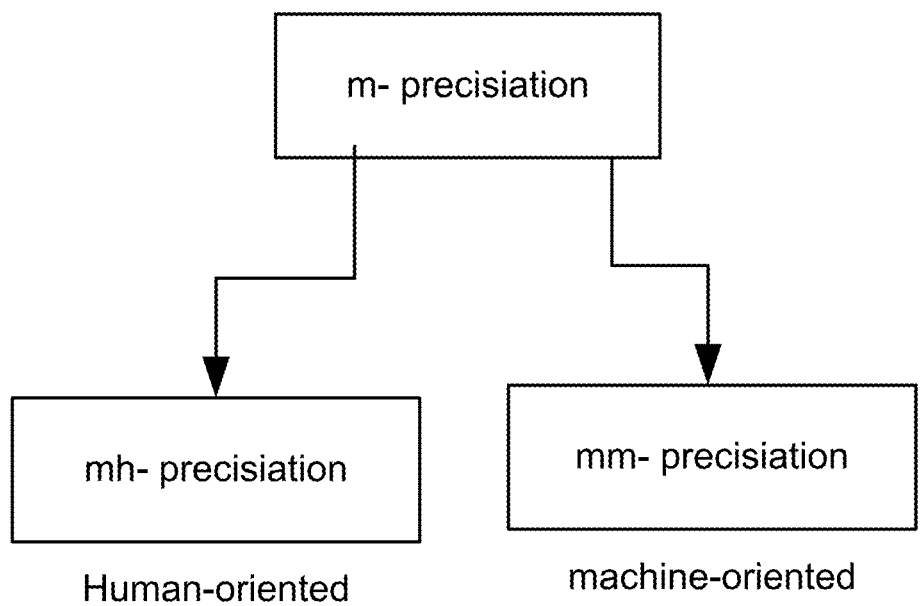
FIG. 9 shows the modalities of m-precisiation.

In this example, the set of candidate probability distribution for X was constructed using Normal distributions with mean $(m_x)$ ranging from −2 to 2 and standard deviation $(\sigma_x)$ ranging from $0^+$ (close to Dirac delta function) to 1.2. Figs. 7 and 8 of Appendix 1 depict the probability measure of $A_X$, denoted as v, based on (3) and each of these probability distribution candidates represented by a point on $(m_x, \sigma_x)$ plane. These also illustrate the contour maps of constant probability measures. Figs. 9 and 10 of Appendix 1 depict the test scores (denoted as ts) for each probability distribution candidate, based on the application of certainty component $B_X$ to each probability measure, v, via (4). Given that $B_X$ imposes a test score on each v, the probability distribution candidates that form a contour (on $(m_x, \sigma_x)$ plane) for constant v, also form a contour for the corresponding test score. However, given that a range of v values may result in the same test score (e.g., for v less than 0.5 or above 0.75, in this example), some test score contours on $(m_x, \sigma_x)$ plane collapse to flat ranges (e.g., for test scores 0 and 1, in this example), as depicted on Figs. 9 and 10 of Appendix 1.

By applying (10), we can then determine the probability measure of $A_Y$ (in Y domain), denoted as w, based on the probability distribution candidates in X domain (i.e., bypassing the direct calculation of the corresponding probability distributions in Y domain). The probability measure w is depicted in Figs. 11 and 12 of Appendix 1 for each probability distribution candidate in $(m_X, \sigma_X)$ plane.

Given that each probability distribution candidate is associated with a possibility restriction test score (as shown for example in Fig. 10 of Appendix 1), such test score can be applied and correlated with the probability measure w (shown for example in Fig. 12 of Appendix 1). A given w (or a w bin) may be associated with multiple test scores as indicated by contours of constant w or regions of very close or similar w in Fig. 12 of Appendix 1.

Therefore, to assign a final test score to a given w (or w bin) based on (8), we can determine the maximum test score for all w's associated with the given w bin.

The result of an intermediate step for determining the maximum test score for correlated w's (i.e., falling in the same w bin) is illustrated in Fig. 13 of Appendix 1, on the $(m_x, \sigma_x)$ plane (for illustrative comparison with Fig. 11 of Appendix 1).

The resulting maximum test score associated with a given w bin defines the membership function of w (or a value of w representing the w bin) in $B_Y$, as depicted for this example in Fig. 14 of Appendix 1. As shown in Figs. 11 and 13 of Appendix 1, where w is high, the maximum associated test score is low, resulting in $B_Y$ which represents "significantly less than 25%" for this example. Fig. 7 of Appendix 1 is the probability measure of $A_X$, v, per each (Normal) probability distribution candidate represented by $(m_x, \sigma_x)$. Fig. 8 of Appendix 1 is the contours of the probability measure of $A_X$, v, per each (Normal) probability distribution candidate represented by $(m_x, \sigma_x)$. Fig. 9 of Appendix 1 is the test score based on certainty measure $B_X$ for each (Normal) probability distribution candidate represented by $(m_x, \sigma_x)$. Fig. 10 of Appendix 1 is the test score based on certainty measure $B_X$ for each (Normal) probability distribution candidate represented by $(m_x, \sigma_x)$. Fig. 11 of Appendix 1 is the probability measure of $A_Y$, w, per each probability distribution (Normal) candidate represented by $(m_x, \sigma_x)$.

Fig. 12 of Appendix 1 is the contours of the probability measure of $A_Y$, w, per each probability distribution (Normal) candidate represented by $(m_x, \sigma_x)$. Fig. 13 of Appendix 1 is the maximum test score for a w-bin associated with each probability distribution (Normal) candidate represented by $(m_x, \sigma_x)$. Fig. 14 of Appendix 1 is the maximum test scores for w-bins defining the membership function of w in fuzzy set $B_Y$, e.g., "significantly less than 25%".

II. Z-Valuation Using Granular Category Sets

A. Predetermined Category Sets: Test Scores, Probability Measures, and Probability Distributions The probability measure of $A_X$, denoted as v, may be predetermined and reused, given that the integration in (3) may be normalized based on the general shape of the membership function of $A_X$ and the class/parameters of probability distribution candidates. In normalized form, for example, a category of normalized membership function may be defined as symmetric trapezoid with its support at interval [−1,1] with a single parameter, β, indicating the ratio of its core to its support (as shown in Fig. 15 of Appendix 1). Examples of classes of probability distribution are Normal distribution and Poisson distribution, with their corresponding parameters normalized with respect to normalized $A_X$. For example, for Normal distribution, the parameters $(m_x, \sigma_x)$ may be normalized with respect to half width of the support having the origin of the normalized coordinate translated to cross zero at the center of the support.

Furthermore, we may reduce the level and complexity of computation in approximating the Z-valuation by using a granular approach. For example, for a category of normalized $A_X$ (e.g., symmetric trapezoid with β of about 0.5, as shown in Fig. 15 of Appendix 1), we may predetermine relations/mapping (or a set of inference rules) between (fuzzy or crisp) subset of probability distribution candidates (of a given class such as Normal or Poisson distribution) and (fuzzy or crisp) subsets of probability measures, v's (as for example shown in Fig. 16 of Appendix 1).

Let $V_j$ denote a category/set of probability measures of $A_X$ (e.g., probability measure "High"), where j numerates such categories in v domain. Each $V_j$ corresponds to a range or (fuzzy or crisp) subset of probability distribution candidates, denoted by $C_j$ whose $p_i$ members are defined via the following membership function: (eq. 11, below)

$$\mu_{C_j}(p_i) = \mu_{V_j}(\mu_A \cdot p_i) = \mu_{V_j}\left(\int_X \mu_A(x) \cdot p_i(x) \cdot dx\right),$$

Therefore according to (11), we may predetermine $C_j$ via a similar method of applying test scores to the probability distribution candidates, $p_i$, (as for example shown in Fig. 9 of Appendix 1), by replacing $B_X$ with $V_j$. For example, the categories of probability measure $W_{Low}$ and $V_{High}$ (shown in Figs. 17 and 18 of Appendix 1, respectively), correspond to the (category) fuzzy sets of probability distribution candidates, denotes as $C_{Low}$ and $C_{High}$ (with labels used in place of j), with a membership function depicted in Figs. 19 and 20 of Appendix 1, respectively.

Furthermore, the certainty levels (test scores) may also be made into granular (fuzzy or crisp) sets $TS_k$, e.g., in order to reduce the complexity of calculation during the aggregation process of Z-valuation. Index k numerates these test score category sets. Fig. 16 of Appendix 1 may also serve as an example of such categorization (with test score replacing v).

In one approach, the certainty component $B_x$ is granularly decomposed or mapped (or approximately expressed) via pairs of probability measure and test score category sets, i.e., $(V_j, TS_k)$'s, as for example demonstrated in Fig. 21 of Appendix 1. In one approach, each relation pair may be further associated with a $weight_{j,k}$ that indicates the degree of mapping of $B_X$ among the pairs (e.g., when $TS_k$ is a predefined set). For example:

$$weight_{j,k} = \sup_{v \in [0,1]} \left(\mu_{V_j}(v) \wedge \mu_{TS_k}(\mu_{B_X}(v))\right).$$

In one scenario, the decomposition of $B_X$ may be expressed as series of tuples in the form $(V_j, TS_k, weight_{j,k})$ or simply as a matrix with $weight_{j,k}$ as its elements. Given the correspondence between $C_j$ and $V_j$, the granular test score sets $TS_k$'s are also associated with granular probability distribution candidate sets, $C_j$'s (with the same $weight_{j,k}$).

In another approach, a non-categorical test score (e.g., a fuzzy or crisp set) $TS_j$ is determined for each $V_j$ (and $C_j$), e.g., by using extension principle, based on mapping via $B_X$:

$$\mu_{TS_j}(ts) = \sup_{v' \in [0,1]}(\mu_{V_j}(v')), \quad (12)$$

subject to: $ts = \mu_{B_X}(v')$.

Fig. 15 of Appendix 1 is a membership function parameter β (ratio of core to support), which adjusts the symmetric trapezoid shape from triangular with (β=0) to crisp with (β=1). Fig. 16 of Appendix 1 shows examples of various granular (fuzzy) sets of probability measures. Fig. 17 of Appendix 1 is membership function of v in $V_{Low}$. Fig. 18 of Appendix 1 is membership function of v in $V_{High}$. Fig. 19 of Appendix 1 is membership function of $p_i$ in $C_{Low}$ (with $p_i$ represented by its parameters ($m_x$, $\sigma_x$)). Fig. 20 of Appendix 1 is membership function of $p_i$ in $C_{High}$ (with $p_i$ represented by its parameters ($m_x$, $\sigma_x$)). Fig. 21 of Appendix 1 is an example of granularizing/mapping of $B_x$, via $(V_j, TS_k)$ pairs.

B. Computation and Aggregation Via Normalized Categories

One advantage of reusing the predetermined normalized categories is the reduction in number of calculations, such as the integration or summation in determining probability measures per individual probability distribution candidates in X domain or their corresponding probability distributions in Y domain, per (4) and (8). In addition, instead of propagating the test scores via an individual probability distribution candidate, the extension of the test scores may be done at a more granular level of the probability distribution candidate subsets, $C_j$, which are typically far fewer in number than the individual probability distribution candidates. However, the aggregation of test scores for Z-valuation, e.g., for $(Y, A_Y, B_Y)$, will involve additional overlap determination involving various normalized category sets, as described below.

The normalization of symmetrical trapezoid membership function $A_Y$, e.g., "Y is about nine," as shown in Fig. 5 of Appendix 1, involves shifting the origin by −9 and scaling the width by 0.5 (in Y domain) in order to match the position and width of the support to the normalized template depicted in Fig. 15 of Appendix 1 (with β=0 determined as the ratio of the core to support). Note that such normalization (translation and scaling) also impacts the location and scaling of associated $p_y$'s (e.g., mean and standard deviation) in order to preserve the probability measure of $A_Y$ per (8).

Note that the predetermined categorical subset of probability distributions in Y domain, denoted as $C_{Y,j}$, that is associated with $V_j$, may be distinct from the corresponding one in X domain, denoted as $C_{X,j}$, e.g., due to parameters such as β (or the class of the membership, such as trapezoid or ramp). For example, Fig. 22 of Appendix 1 illustrates the membership function of $C_{Y,High}$, for normalized $A_Y$ (β=0), for comparison with $C_{X,High}$, depicted in Fig. 20 of Appendix 1, for the same values of normalized probability distribution parameters. Fig. 22 of Appendix 1 is membership function of $p_y$ in $C_{Y,High}$ (with $p_y$ represented by its parameters ($m_y$, $\sigma_y$)).

i) Mapping in X Domain

In one approach to estimate (10), we may determine (or approximate) $\mu_{A_Y}(f(x))$ in X domain as for example depicted in Fig. 23 of Appendix 1, labeled $\mu_{A_{Y \to X}}(x)$. Then, we may proceed with mapping and normalization of the membership function to one or more normalized categories of membership functions (e.g., a symmetric trapezoid shape with (β=0)). Fig. 23 of Appendix 1 is membership function $\mu_{A_{Y \to X}}(x)$. In such an approach, the normalization effects on Ax and $A_{Y \to X}$ are combined into a transformation operation, T, (e.g., translation and scaling) used to also transform the normalized probability distribution parameters (e.g., mean and standard deviation). Thus, T also transforms the predetermined subsets of probability distribution candidates, $C_{X,j}$, to $C_{X,j}^T$, e.g., via the extension principle, as follows:

$$\mu_{C_{X,j}^T}(p_{X,i}^T) = \sup_{\forall p_{X,i}} \mu_{C_{X,j}}(p_{X,i}), \quad (13)$$

subject to $$p_{X,i}^T = T(p_{X,i}),$$

where $p_{X,i}^T$ represents the transformed probability distribution candidate (in X domain) from $p_{X,i}$.

Since in our example, $\mu_{Ax}$ (depicted in Fig. 3 of Appendix 1) is already in a normalized form, we focus on the transformation due normalization of $\mu_{A_{Y \to X}}(x)$. Note that in Fig. 11 of Appendix 1, the outline of probability measure w for ($\sigma_X$=0+) is the same as the membership function $\mu_{A_{Y \to X}}(x)$ prior to the normalization, as depicted in Fig. 23 of Appendix 1. To normalize $\mu_{A_{Y \to X}}(x)$, the membership function must be scaled by factor of about 3, denoted by s, and translated by the amount of −3 (or −1 before scaling), denoted by t. The ordered translation and scaling operations, denoted by $T_t$ and $T_s$ respectively, define the transformation operation which also transforms a probability distribution (13) by scaling and translating its parameters, for example:

$$p_{X,i}{}^T = T(p_{X,i}) = T_t \cdot T_s \cdot p_{X,i},$$

with $$T_s \cdot p_{X,i} = T_s(m_{X,i}, \sigma_{X,i}) = (s \cdot m_{X,i}, s \cdot \sigma_{X,i}),$$

$$T_t \cdot p_{X,i} = T_t(m_{X,i}, \sigma_{X,i}) = (m_{X,i} + t, \sigma_{X,i}). \quad (14)$$

Once normalized, $\mu_{A_{Y \to X}}(x)$ is associated with a predetermined subset(s) of normalized probability distributions, $C_{Y,j}$'s (e.g., as shown in Figs. 22, 24 and 25 of Appendix 1 for j as "High," "Med," and "Med-Low" (or "ML"), respectively). To associate $C_{Y,j}$ with the test score value(s) (e.g., $TS_{X,n}$) assigned to $C_{X,n}$ (shown for example in Fig. 20 of Appendix 1 with n as "High"), the relative position and scaling of $C_{Y,j}$ and $C_{X,n}$ are adjusted by transforming $C_{X,n}$ to $C_{X,n}{}^T$ per (13), to determine the intersection between $C_{X,n}{}^T$ and $C_{Y,j}$, for example by:

$$I_{j,n} = \sup_{\forall p_{X,i}{}^T}(\mu_{C_{X,n}{}^T}(p_{X,i}{}^T) \wedge \mu_{C_{Y,j}}(p_{X,i}{}^T)), \quad (15)$$

where $I_{j,n}$ describes a grade for overlap between $C_{X,n}{}^T$ and $C_{Y,j}$. Fig. 26 of Appendix 1 schematically illustrates the (fuzzy) intersection of $C_{X,n}{}^T$ and $C_{Y,j}$, with n being "High" and j being "ML", based on the predetermined category sets $C_{X,high}$ and $C_{Y,ML}$ from Figs. 20 and 25 of Appendix 1, respectively. Fig. 24 of Appendix 1 is membership function $C_{Y,Med}$. Fig. 25 of Appendix 1 is membership function $C_{Y,ML}$. Fig. 26 of Appendix 1 is illustrating the fuzzy intersection of $C_{Y,j}$ and $C^T_{X,n}$, where $C^T_{X,n}$ is transformed from $C_{X,n}$ via scaling and translation. For the predetermined category sets $C_{Y,j}$ and $C_{X,n}$, $C_{Y,ML}$ and $C_{X,High}$ are used from Figs. 25 and 20 of Appendix 1.

For example, as shown in Fig. 26 of Appendix 1, $C_{X,High}{}^T$ overlaps $C_{Y,ML}$ (to a degree), while it may not intersect $C_{Y,Med}$ (which is depicted in Fig. 24 of Appendix 1). If $I_{j,n}$ exceeds an (optional) overlap threshold value, then we may apply the category test score $TS_k$ associated with $C_{X,n}$, to $C_{Y,j}$. Note that the association with $TS_k$ was determined based on $B_X$, e.g., through mapping of $\mu_{Bx}$ to the relation pairs $(V_{X,n}, TS_{X,k})$. This means that the category set of probability measures $V_{Y,j}$ associated with $C_{Y,j}$ may get associated with category test score $TS_{X,k}$, as well. In general, $V_{X,n}$ and $V_{Y,j}$ may be sets of probability measures belonging to the same family of sets (i.e., without X or Y dependencies). The steps from $B_X$ to approximating $B_Y$ is conceptually summarized as:

$$\left. \begin{array}{l} B_X \xrightarrow{map} (V_{X,n}, TS_{X,k}) \\ B_X \to C_{X,n} \xrightarrow{T} C^T_{X,n} \\ A_Y \xrightarrow{f} A_{Y \to X} \to C_{Y,j} \end{array} \right\} \to I_{j,n} \right\} \to (V_{Y,j}, TS_{X,k}) \xrightarrow{approx.} B_Y.$$

The determination of the test scores for $V_{Y,j}$ may be implemented via a set of fuzzy rules linking $C_{X,n}$ and $C_{Y,j}$. For example, the antecedent of each rule is triggered if the corresponding $I_{j,n}$ is above an overlap threshold, and the consequent of the rule assigns $TS_{X,k}$'s (or an aggregate of $TS_{X,k}$'s based on weight$_{n,k}$ for a given n) to a variable $SC_{Y,j}$. A simpler test score assignment rule may use a non-categorical test score $TS_{X,n}$ which is determined for each $V_{X,n}$, e.g., via (12), based on the mapping through $B_X$:

Rule$_{j,n}$: if $(I_{j,n})$ then $(SC_{Y,j}$ is $TS_{X,n})$ \quad (16)

However, in correlation/aggregation of assigned (fuzzy) test scores to variable $SC_{Y,j}$, we must consider the maximization of test score required by (8). For example, in aggregating the rules for $SC_{Y,j}$, we may use α-cuts to determine an aggregated (fuzzy) result, denoted as $AGSC_{Y,j}$, as follows: (Eq. 17 below)

$$AGSC_{Y,j} = \mathrm{MAX}_n(\mathrm{Correl}(I_{j,n}, TS_{X,n}))$$

where Correl($I_{j,n}, TS_n$) modifies the membership function of $TS_{X,n}$ by correlating it with the factor $I_{j,n}$, e.g., via scaling or truncation. Membership function of $B_Y$ is then approximated by a series of fuzzy relations ($V_{Y,j}, AGSC_{Y,j}$).

For a given w (probability measure of $A_Y$), $\mu_{BY}(\omega)$ may be approximated as a fuzzy number (or a defuzzified value), by further aggregation using fuzzy relations ($V_{Y,j}, AGSC_{Y,j}$), e.g.: (Eq. 18 below)

$$\mu_{BY}(w, ts) = \sup_j (\mu_{V_{Y,j}}(w) \wedge \mu_{AGSC_{Y,j}}(ts)).$$

ii) Overlap Approximation

An approach to approximate or render the overlap (15) between the category sets, such as $C_{X,n}$, may use α-cuts to present each crisp α-cuts of predetermined category set as a set of points in (m,σ) space. These sets of points may be modeled efficiently, e.g., based on graphical models, optimized for fast transformation and intersection operations. For example, the models that use peripheral description for the α-cuts allow robust and efficient determination of intersection and avoid the need to transform all the points within the set individually, in order to reduce the computation involved in (13).

iii) Estimation Using Contour Approach

In addition to predetermining $C_{X,n}$, based on $V_{X,n}$, for a normalized set $A_X$, we can predetermine various α-cuts of probability measures (e.g., depicted as contours of constant v in Figs. 7 and 8 of Appendix 1) or various α-cuts of associated test scores (e.g., depicted as contours of constant test scores, ts, in Figs. 9 and 10 of Appendix 1) for a set of predefined (e.g., most frequently used) $B_X$ components. These α-cuts that represent sets of probability distribution candidates in (m,σ) space (already associated with specific test scores) may be transformed per (13) and intersected with $C_{Y,j}$ in extending their test scores to $V_{Y,j}$. In essence, this is similar to the previous analysis except $V_{X,n}$ and $TS_{X,n}$ become singleton, and $C_{X,n}$ becomes a crisp set, while $C_{Y,j}$ and $V_{Y,j}$ are predetermined (crisp or fuzzy) set.

Another approach uses (e.g., piecewise) representation of $B_X$ (not predefined) where based on inspection or description, key values of v associated with key values of test scores may readily be ascertained (e.g., based on α-cuts), resulting in a set of $(v_i, ts_i)$ pairs. Then, the predetermine α-cuts of probability measures (e.g., depicted as contours of constant v in Figs. 7 and 8 of Appendix 1) are used to interpolate the contours of constant $ts_i$'s in (m,σ) space, based on the corresponding $v_i$ values. Again, these crisp contours of constant (crisp) $ts_i$'s, may be transformed and intersected with $C_{Y,j}$ to extend the test scores to $V_{Y,j}$ for estimating $B_Y$.

For quick estimation of $B_Y$ in an alternate approach, the predetermined α-cuts (i.e., w's) of probability measures for normalized $A_Y$ may be used (similar to those shown in Figs. 7 and 8 of Appendix 1 based on $A_X$), in essence, turning $V_{Y,j}$ to a singleton and $C_{Y,j}$ to a crisp set (contour) for carrying out the intersect determination. The estimates for $\mu_{BY}(w)$ may be determined via interpolation between the aggregated test score results obtained those w values associated with the α-cuts.

In one embodiment, for Z-number analysis, for probability distributions analysis, the predetermined categories of hidden probability distribution candidates and normalized Fuzzy membership functions facilitate the pre-calculation of probability measures and their associated reliability measures in Z evaluation or as Z-factors, for fast determination of the reliability levels of new propositions or conclusions. This approach opens the door to the extension of the reliability measures (e.g., via extension principle) to new propositions, based on graphical analysis of contours (α-cuts) of similar probability measures in the domain of parameters representing the probability distribution candidates. Basically, we will use the transformation and mapping of categorical set of the probability distribution candidates (represented as regions or α-cut contours) for extension of the reliability measures. This way, as we pre-calculate and store the shapes and results in our library or database for future use (as templates), the new analysis on any new data can be much faster, because we can readily match it with one of the templates, whose results are already calculated and stored, for immediate use.

Now, let's look at Appendix 2. In one embodiment, referring to the top Fig. and derivation on page 1 of Appendix 2, we have different values of $v_{\alpha,n}$, based on various α-cuts (with (ts=α)). Then, we match against category (singleton) $v_s$ (see the bottom Fig. on page 1 of Appendix 2). Then, on Fig. and derivation on page 2 of our Appendix 2, we get a series of the curves. We use the predetermined contours $C_{s,m}$ of probability measures $v_{s,m}$. Note that $(v_{s,m}=p_i \cdot \mu_{AX}^{normalized})$. Note that $p_i$'s define the contour(s) for $v_{s,m}$ (or regions of $p_i$'s) defining region(s) for $v_{s,m}$ (such as 0 or 1), to interpolate and determine contours (or regions) of constant $v_{\alpha,n}$'s, denoted by $C_{\alpha,m}$. These $C_{\alpha,m}$'s are associated with test scores set by α, i.e. (ts=α) for $C_{\alpha,m}$.

Then, on Fig. and derivation on page 3 of our Appendix 2, we transform or do other manipulations, according to extension rules (e.g. on normalized) for $\mu_{AY}$:

$$C_{\alpha,m}^T = T(C_{\alpha,m})$$

While maintaining the test score for $C_{\alpha,m}^T$ (as α).

Based on categories of $w_{s,j}$ (similar to $v_{s,n}$ except for w), probability measure of $A_Y$ in Y-domain, where $w_{s,j}$ are singletons (predefined), have corresponding contours (or regions) $C_{s,j}$ (see the figure on the bottom of page 3 of our Appendix 2). Then, we find the intercepts between $C_{\alpha,m}^T$ and $C_{s,j}$, if any, i.e. $I_{\alpha,m,j}$.

Then, on Fig. and derivation on page 4 of our Appendix 2, based on the intercepts, we find the best test score for a given $C_{s,j}$ extended from $C_{\alpha,m}^T$, e.g.:

$$ts_{s,j} = \sup_{\forall \alpha'} \alpha'$$

where $I_{\alpha'',m,j}$ exists.

(i.e., the best test score from intercept points to a given $C_{s,j}$.)

Now, we associate $ts_{s,j}$ to $w_{s,j}$ to construct $(\mu_{BY}(\omega))$, and interpolate for other w (see the figure on the bottom of page 4 of our Appendix 2). Since $ts_{i,j}$'s source is α, $ts_{s,j}$'s appear as α-cuts in $\mu_{BY}$, as well.

Then, on derivation on page 5 of our Appendix 2, we have: Where the scenario involves e.g. z=f(x,y), instead of y=f(x) (where the solution may be worked out in the X-domain), we can still use contours (or regions) of specific test scores (e.g. based on α-cuts), and contours determined by interpolation of predefined or predetermined probability measure contours or regions. The manipulation, e.g. $(p_z=p_x Op_y)$, can be implemented based on contours or regions of constant test scores (for X or Y), instead of individual $p_{x,i}$ and $p_{y,i}$, to reduce the number of combinations and calculation. The test scores can be extracted from X, Y domains to Z domain (in this example) and maximized based on the intercept points in $p_z$ domain with predetermined contours of probability measures of (normalized) $A_Z$, to again calculate $\mu_{BZ}$.

FIG. 126 is a system for Z-number estimation and calculation, with all related modules and components shown in the Figure, with a processor or computing unit in the middle for controlling all the operations and commands (Z-number estimator).

Thus, in summary, the above section provides the methods for approximation or calculation or manipulation of Z-numbers, and related concepts. Now, we explain other components of our inventions, below.

Thumbnail Transformation

In one embodiment, the input data (e.g., image) is pre-processed. For example, the image is transformed into a smaller thumbnail that preserve the high level nature of the image content, while not necessarily preserving its unique characteristics. This may be achieved, for example, by down sampling or aggregation of neighboring pixels. Other methods may include reduction of the variable space by consolidating the colors into intensity (e.g., gray scale) and/or reducing the number of bits representing color or intensity. Such a transformation is denoted as thumbnail.

A thumbnail includes less resolution and data, and hence, it contains less overall detailed features. The purpose is to simplify the task of dealing with many pixels while still managing to detect the high level features associated with the images (or other type of data). For example, using a thumbnail, a recognition module quickly identifies the presence of a head or face (while not intended to necessarily determine the identity of the person or object).

One embodiment uses a preliminary search to detect main features in a thumbnail data/image for fast computation. In one embodiment, the limitation may be on the number of pixels on the visual layer (via preprocessing). In one embodiment, the limitation is imposed on the detection/classifier network (e.g., on hidden layers) itself. For example, the main features are learned and isolated (e.g., by units or neurons of higher hidden layers) or learned by targeted attempt (e.g., by keeping all other weights and letting the weight on certain units change when learning a certain feature.)

Feature Detection and Learning

In one embodiment, for example where labeled training samples may be difficult to prepare or scarce, the training is done with unlabeled samples to learn the features from the sample details. For example, a restricted Boltzmann machine (RBM) may be used to successively learn the features one layer at a time.

A Boltzmann machine refers to a type of stochastic recurrent neural network, where the probability of the state is based on an energy function defined based on the weights/biases associated with the units and the state of such units. In a Boltzmann machine, some units are denoted visible where the state may be set/clamped or observed and others may be hidden (e.g., those used for determining features). In the Restricted Boltzmann machine (RBM), the weights between hidden units within the same layer are eliminated to simplify the learning process. The learning process tends modifies the weights and biases so that the energy state associated with the samples learned are lowered and the probability of such states is increased. In one embodiment, the state of hidden layers are presented by a stochastic binary variable (e.g., in [0, 1] range) based on a sigmoid such as logistic function. In one embodiment, the energy function is given as $$E = -\sum_{i,j} v_i \cdot h_j \cdot w_{i,j} - \sum_i v_i \cdot b_i - \sum_j h_j \cdot c_j$$

where $v_i$ and $h_j$ denote the state of the $i^{th}$ visible unit and the $j^{th}$ hidden unit (as for example depicted in FIG. 180), respectively, and $b_i$ and $c_j$ are bias or threshold associated to such units, respectively. $w_{i,j}$ is an undirected weight or connection strength linking such units. Per Boltzmann machine, the probability of the state $\alpha$ (for a given set of H and V states of the units) depends on the weights (including bias values) and the state of H and V:

$$P(\alpha) = P(V, H) = \frac{e^{\frac{-E_\alpha}{T}}}{\sum_\beta e^{\frac{-E_\beta}{T}}}$$

where $E_\alpha$ is the energy associated with state $\alpha$; T denotes the "Temperature" of the system; the denominator denotes the "partition function", Z; and $\beta$ denotes any state of the system. Since the energy of a state is proportional to negative log probability of the state, the probability that a binary stochastic unit j is at state 1 (or ON) in such RBM becomes the following logistic function:

$$p_{j \text{ is ON}} = \frac{1}{1 + e^{\frac{-\Delta E_j}{T}}}$$

where T controls relative width of the above logistic function, and $\Delta E_j$ (for example for a hidden unit) is given by:

$$\Delta E_j = \sum_i v_i \cdot w_{i,j} + c_j$$

Note that in an embodiment with T is set to zero, the stochastic nature of the binary units becomes deterministic, i.e., taking the value sigmoid function (zero or one), as in Hopfield Network.

In one embodiment, the training attempts to reduce the Kullback-Leibler divergence, G, between the distributions of V states based on the training sets and based on thermal equilibrium of the Boltzmann machine, by modifying weights and biases, e.g., via a gradient decent over G with respect to a given weight or bias. The aim of training is to determine weights/biases such that the training samples have high probability. In maximizing the average probability of a state V, P(V), with respect to weights, we have $$\left\langle \frac{\partial \log P(V)}{\partial w_{i,j}} \right\rangle_{data} = \langle v_i h_j \rangle_{data} - \langle v_i h_j \rangle_{model}$$

where the average over the data means average over the training data (i.e., when V units sample from the training sets and are clamped to a training sample while hidden units are updated repeatedly to reach equilibrium distribution), and the average over model means the average from Boltzmann machine sampling from its equilibrium distribution (at a given T). In one embodiment, learning algorithm uses a small learning rate with the above to perform gradient decent. Similarly, the following can be used in learning bias $c_j$:

$$\left\langle \frac{\partial \log P(V)}{\partial c_j} \right\rangle_{data} = \langle h_j \rangle_{data} - \langle h_j \rangle_{model}$$

In one embodiment, where the weights are absent between the hidden units, the updating of the hidden states, H, is done in parallel as the hidden units are conditionally independent for a given set of visible states, V. In one embodiment, sampling from model involves one or more iterations alternating between updating (in parallel) hidden and visible layers based on each other. In one embodiment, sampling for the model is substituted with sampling from reconstruction, which updates the hidden units (for example, in parallel) using the visible units clamped to a training set, then updates the visible units (e.g., in parallel) to get a reconstruction from the features in the hidden layers, followed by updating the hidden units based on the reconstruction. This approach approximates the gradient decent of contrastive divergence in an efficient and fast manner. In RBM learning, contrastive divergence can be used instead of maximum likelihood learning which is expensive. In one embodiment, T is lowered from a higher initial value to make low cost (energy) states more probable than high cost states, while the higher initial value of T allows for reaching and sampling equilibrium states quicker. In one embodiment, the stochastic nature of binary units allows escaping from local minima. In one embodiment, during the reconstruction, a subset of visible units are clamped to input data to reconstruct other visible units from the features including those affected or derived (e.g., stochastically) from the input data. The training in such a conditional Boltzmann machine tends to maximize the log probability of the observed visual units (now taken as output in reconstruction), given the input data.

In one embodiment, other non-binary discrete stochastic units may be used. In one embodiment, continuous value units may be used. In one embodiment, mean filed units are used having their state (in the range of [0, 1]) determined by the total input (e.g., a logistic function) and a noise (e.g., as a Gaussian). In one embodiment, other stochastic functions/distributions (e.g., binomial and Poisson) are used for the units. In one embodiment, where continuous data (including semi-continuous data with many levels as opposed to few discrete levels) is used for state of the visible units, the sampling from a probability distribution (e.g., Gaussian with a given variance, with the mean determined by the other signal and weights) keeps the stochastic nature, while making the signal in visible unit continuous (as opposed to discrete). The hidden layers may stay binary (stochastic). In one embodiment, stochastic visible units use continuous signal (e.g., in [0, 1] range) based on other signals and weights and a probability distribution (e.g., logistic function) for sampling or updating its signal.

In one embodiment, following the training of one RBM, another hidden layer is added on top which employs the lower RBM's hidden layer as input to determine higher level features, and the training is done one layer at the time. For example, FIG. 181 illustrates 3 level RBM with 3 hidden layers $H^{(1)}$, $H^{(2)}$, and $H^{(3)}$. In one embodiment, in training the weights ($w^{(3)}$) for additional hidden layer ($H^{(3)}$), the weights for the trained lower layers are fixed. The fixed weights are used to pass data from bottom up to higher layer and to reconstruct from top down based on higher order features. In one embodiment, as for example depicted in FIG. 182, RBMs are stack on top of each other and training is done one layer at the time from bottom up. In one embodiment, the visible units have continuous value state (e.g., logistic units). In one embodiment, in training a higher level RBM (e.g., $RBM^{(3)}$), signals in its corresponding visible units (e.g., $V^{(3)}$) are set to the probability values associated with the corresponding hidden units (e.g., $H^{(2)}$) of the previous RBM, while the hidden units ($H^{(2)}$) themselves are binary stochastic units. In one embodiment, the top hidden layer (e.g., $H^{(3)}$) has continuous stochastic value, e.g., based on Gaussian probability distribution (e.g., with unit variance) having a mean based on the weights (e.g., $w^{(3)}$) and signals from its corresponding visible units, $V^{(3)}$ (e.g., logistic units). In one embodiment, the top hidden layer includes a relatively low number of units (e.g., for representing the high level features as low dimensional codes). In one embodiment, hidden units use continuous variables for to represent their features/dimensions, e.g., to facilitate classification based on high level features from the top hidden level (e.g., via training one or more correlation layers, or other methods such as SVM). In one embodiment, layer by layer training creates proper features detection in the hidden layers to enhance the back-propagation in discrimination. This allows for fine tuning by local search, e.g., via contrastive wake-sleep approach for better generation. In one embodiment, few labeled samples are used to fine tune the classification boundaries after the features have already been determined primarily based on the unlabeled data features.

In one embodiment, weights ($y_{i,k}$) are introduced in the visible layer while training the weights ($w_{i,j}$) between the visible layer and the hidden layer (e.g., as depicted in FIG. 183). In one embodiment, this approach is also used for higher level RBMs by introducing weights between hidden units of the lower RBM while training the weights for the higher RBM. In this sense, the RBM becomes a semi-restricted Boltzmann machine. In one embodiment, a gradient decent approach for modifying the weights follows the following update contrastive divergence method:

$$\Delta w_{i,j} = \epsilon \cdot (\langle v_i h_j \rangle^0 - \langle v_i h_j \rangle^1)$$

$$\Delta y_{i,k} = \epsilon' \cdot (\langle v_i v_k \rangle^0 - \langle v_i v_k \rangle^1)$$

where superscript 0 indicates the correlation after the initial update of hidden layer after clamping the training sample to the visual units, and superscript 1 indicates the correlation after the hidden layer is updated next time by the reconstruction at the visual layer. In one embodiment, to get to the reconstruction in the visible layer, the visible units are updated one or more times (e.g., iteratively in parallel) based on the current weights, the updated hidden units, and the state of the visible units (from the initial or prior iteration). In one embodiment, the update activity involves stochastic sampling from the probability distribution (e.g., logistic function). Note that $\epsilon$ and $\epsilon'$ correspond to the learning rate. In one embodiment, the hidden units are updated multiple times before the correlations are used to determine changes in weight. In one embodiment, visible units with continuous value state (e.g., mean field units) are updated in parallel based on the total input to the unit (e.g., based on a logistic function).

In one embodiment, intra-layer weights are introduced during the training of a higher hidden layer in order to establish tighter relationships among inter-layer units (e.g., neighboring visible units corresponding to neighboring pixels in an image/data). This enforces constraint during generation. In an embodiment, this facilitates the generation of the parts of a larger recognized object that would not fit each other due to loose relationships between corresponding sub-features. In one embodiment, more features (e.g., redundant) are used to tighten the relationships. In one embodiment, the interrelations between the features (e.g., constraints or rules) are used to limit the choices (i.e., placement of parts), and the placement of one feature helps determine the placement of the other features based on the interrelationship between those features.

In one embodiment, as for example depicted in FIG. 184, an autoencoder, e.g., a deep autoencoder, is provided by stacking further hidden layers, in reverse order with respect to the lower layer, having the same size and the same corresponding interlayer weights as their corresponding lower layers. While the lower half layers (including the coding layer $H^{(3)}$) act as a decoder, the added top layers act as encoder to produce similar data in V' (output) based on the features learned/captured at the coding layer. The added weights in FIG. 184 are depicted with superscript T to indicate that these weights (initially) are represented by the transpose matrix representing the corresponding weights in the lower layers. In one embodiment, the weights of the autoencoder is fine tuned, e.g., by using a back propagation method based on gradient decent. Since the initial weights of autoencoder were determined by a greedy pre-training of lower RBMs, the back propagation will be efficient. In one embodiment, during the back propagation fine tuning, the stochastic binary units are assumed to be deterministic continuous value units adopting the probability value as their state value, to carry out the back propagation. In one embodiment, the objective function (error function) to optimize in back propagation, is the cross entropy error, $E_s$, between the data (e.g., image pixel intensity in V layer) and the reconstruction (e.g., the corresponding pixel intensities in V' output), for a given sample:

$$E_s = -\sum_i (v_i \cdot \log v_i' + (1 - v_i) \cdot \log(1 - v_i'))$$

where $v_i$ and $v_i'$ are the state of the $i^{th}$ units (or intensity of the image at given pixel corresponding to unit i) associated with V and V', respectively. In one embodiment, for the same number of parameters, deep autoencoders tend to produce less generalization errors compared to shallow ones.

In one embodiment, the dimensionality of the data is reduced via the coding presentation at the coding layer (e.g., $H^{(3)}$) having few units compared to the number of units in V.

In one embodiment, a noise signal is introduced in the top hidden layer units (e.g., $H^{(3)}$) during training (but the same for the corresponding training data sample used in V layer) to adjust the weights resulting in more bimodal probabilities in order to make the system more resilient against the noise in the data.

In one embodiment, the features of the training samples are learned, e.g., via an unsupervised learning algorithm (e.g., by greedy learning by RBMs). Then, the features are correlated or associated with labels from a subset of training sample, as for example depicted in FIG. 185. Labels are clamped to a set of units (in L layer) during the training, while data (e.g., image pixels) are clamped to the V units. An RBM is added on top to learn the correlation or association between the data features and the labels. During the training, L layer and one or more hidden layers (e.g., $H^{(2)}$) provide data to C layer (which may be an RBM, as well). Labels may be binary, multi-valued discrete, or continuous. Similarly the weights (e.g., $W^{(C)}$) and biases related to the added layer are learned by feeding labels and corresponding Data at L and V layers, respectively.

Once the association between the labels and Data is learned, in one embodiment, data is input to V layer, and its corresponding label is ascertained at L layer, by having the units in C layer drive the units in L layer. In one embodiment, data samples corresponding to a label may be constructed by clamping unit(s) in L layer to derive units in C Layer, and followed by a top-down reconstruction in V layer. In one embodiment, a subset of units in V layer are clamped to input (e.g., to input a partial image or a portion of image) and the state of one or more labels are set in L layer by clamping to environment. Then, the other unclamped V units are used to determine the state of the other V units (given the clamped visible and label units), deterministically or stochastically (e.g., through iteration). In one embodiment, a larger image may be recovered from partial data (e.g., partial image) through reconstruction.

Reliability Measure

In one embodiment, the strength of the correlation between data and label or conformity of data to the system (e.g., a trained system) may be determined based on the energy of states given the clamped data (and label). In one embodiment, the strength of correlation or conformity is based on relative probability of various states. For example, the energy difference of two states in Boltzmann machine (in equilibrium) is proportional to the log of the ratio of their probabilities. In one embodiment, the relative strength of the correlation or conformity is based on the relative probability of two states. In one embodiment, a baseline for the probability of training samples is established during and/or after training. In one embodiment, the strength of correlation or conformity indicates how well the state(s) representing the data (and label) fit into the energy landscape of the system. In one embodiment, as depicted in FIG. 186, the strength of correlation or conformity of a dataset (including any associated label) is used to determine Z-factor associated with the associated features and/or classification of the data from the network.

In one embodiment, the quality of the search is evaluated based one or more approaches including for example, the probability, e.g., the total energy of RBM, or the difference between the regenerated data/image and the input, the frequency the recognized labels change while anchoring the visible units/neurons to the input/image.

Learning Based on Models

In one embodiment, the learning is achieved through simulation using a data (and label) sample generation based on one or more models. In one embodiment, a network trained based on model(s) is used to recognize and classify actual data which may not have been seen before. In one embodiment, the system is trained to infer the potential model(s) itself by recognizing the (e.g., observed) data conforming to a particular model and its associated labels/parameters.

In one embodiment, as for example depicted in FIG. 187, a sample generator is used to provide data (e.g., images) for training. A rendering unit renders the data according to one or more models (e.g., functional, tabular, and/or heuristic) and the corresponding model parameters governing the instantiation of the model by the rendering unit. In one embodiment, at least a subset of model parameters are generated stochastically (or via a deterministic sequential algorithm) by a randomizer unit, which for example, uses applicable probability model(s) and/or model rules to generate the subset of model parameters within given ranges or constraints. In one embodiment, the training of the network (e.g., a deep belief network based on Boltzmann machines) is done repeatedly generating training data samples via the sample generator to feed to the V layer of a network being trained. In one embodiment, the training is done one hidden layer at the time (e.g., until $H^{(3)}$). In one embodiment, the training of hidden layers is done unsupervised (i.e., without supplying labeled training samples). In one embodiment, an autoencoder is setup (e.g., as shown in FIG. 187) and fine tuned using back propagation. In one embodiment, a correlation or associative layer is added to learn the correlation between the features of the data and the labels ($L_M$), where the labels are supplied by the sample generator (along with the rendered data). In one embodiment, for example as depicted in FIG. 188, multiple $L_M$ layers (e.g., in parallel) are used to represent various classes of (e.g., independent) models. In one embodiment, the relevant weights between C layer and an $L_M$ layer are fixed for one class of model(s) while training another class of model(s) through the same C layer. In one embodiment, the cross correlation between two models is determined, via cross correlation (e.g., through layer C) between the labels associates with both models. For example, by a subset of labels from $L_{M1}$ layer is clamped and sampled generated from top-down reconstruction from layer C to layer LM2 are used to determine such cross correlation. In one embodiment, states on layer C are stochastically run to derive the reconstruction in both $L_{M1}$ and $L_{M2}$ layers for determining a correlation between the reconstructions samples. In one embodiment, the units in layer C are derived (e.g., through inference) from V layer (by inputting data), and labels are reconstructed in layers $L_{M1}$ and $L_{M2}$. In one embodiment, the levels of conformity or correlation of data supplied to V units (or a subset of V units) with models(s) are obtained for each model based on relative probabilities and energy of states. In comparing on model to another, the weights associated with one model are not used in determining energy or probability associated with the other model (for such comparison).

In one embodiment, noise is incorporated into the rendering in order to make the network more resilient to noise. In one embodiment, a stochastic noise (e.g., Gaussian) is applied to the rendering, e.g., in illumination, intensity, texture, color, contrast, saturation, edges, scale, angles, perspective, projection, skew, rotation, or twist, across or for portion(s) of the image. In one embodiment, noise is added to a hidden layer in a reproducible manner, i.e., for a given data sample (or for a given model parameters), in order to adjust the weight to result in a more modal range of activities to increase tolerance for noise.

In one embodiment, elastic distortions (as well as affine transformations) are used to expand the size and variety of the training set, e.g., when the training set is produced from a model (such as a rendered data/image) or when the data/image is provided separately as part of a training set. In one embodiment, such a distortion is parameterized and rendered by the rendering unit. One embodiment used both affine (e.g., translation, scaling, reflection, rotation, homothety, shear mapping, and squeeze mapping) and distorting type transformations. In one embodiment, various transformations are rendered to generate training dataset to let the system learn features that are transformation invariant. In one embodiment, a shape model is generated with various parameters, such as various textures, colors, sizes and orientations, to let the system learn the invariant features such as the relative positions of the sub features of the modeled shape. In one embodiment, orthogonal matrixes, for example, are used to perform rotation and reflection transformation for rendering the image or on the provided data sample.

In one embodiment, the features of a high level model (with parameters) are learned by a system (such as RBM) through training (e.g., unsupervised). For example, in one embodiment, a 3D model generates various 2D images at different poses (including position, orientation, and scale) and expressions/emotions (or illumination), and the system would learn correlation between the images and their features (derived from the model). Then, the model parameters (and their probabilities) may be obtained for an image.

In one embodiment, various samples are generated/rendered from a 3D model, by varying relative location and angle of the viewer and the model object (e.g., polar coordinates (r, θ, φ)). These variation span various poses (based on θ and φ) and scaling (based on r), using other perspective parameters (e.g., derived from camera/viewer's view span).

In one embodiment, a 3D model rendering mapped to 2D images is based on the normal vectors at a given point of the 3D model, illumination parameters (e.g., location of light(s) and intensity), and reflectivity and texture model of the surface. In one embodiment, the location/presence of rigid points from the model improves the accuracy. In one embodiment, PIE (pose, illumination, expression) variations are used to generate training data/images (e.g., by rendering in 2D).

In one embodiment, multiple models can be learned in combination. E.g., the model for generating of texture of surfaces or colors can be learned in conjunction with a 3D model of head or body. In rendering a 3D model, the texture model may be incorporated to provide textures and colors for the rendered images used for training. The correlation between the model parameters and the rendered images is learned via training. In one embodiment, noise is added to prevent over fitting and regularize the weights to better generalize when used with out of sample data/images.

In one embodiment, getting a low level of conformity of a data/image (for example based in a conformity measure such as energy error or probabilities) with a trained system (e.g., based on a model) causes the data to be marked/tagged or included in a set of data to be recognized/classified by other expert systems/networks.

In one embodiment, the model comprises of rules governing the parameters, structure, and relationships between various components and sub-components of the model. In one embodiment, the rules engine is iteratively executed to generate sample data for training, by using a rules engine.

In one embodiment, the model includes a databases of background and foreground objects (with parameters) or images. In one embodiment, various data samples are created with various background and foreground models to train the system recognize high level features of foreground and background (e.g., wide uniform horizontal bands or regions of color/intensity). In one embodiment, generic labels are used to train the correlation between the labels and the features of the background or foreground scenes.

Correlating of Features and Locations of Interest within the Data (e.g., Image)

In one embodiment, a location within the image is specified by a continuous value (e.g., in range of [0, 1] to indicate/identify the location or pixel along a direction (e.g., x or y direction) in the data/image) or a multi-discrete value (e.g., indicating/identifying a range of locations or pixels along a direction in the date/image). In one embodiment, as for example depicted in FIG. 189, a position L in the data (e.g., a pixel map), is represented by its (x, y) coordinate. In one embodiment, x or y may be fuzzy numbers (e.g., with membership functions such as triangular, trapezoidal, rectangular, or singular). In one embodiment, the state of a unit (e.g., neurons) is represented by fuzzy values. In one embodiment, information such as coordinates, width, height, orientation, type of shape, are presented by units in a parameter layer P. In one embodiment, M layer(s) are used to provide/approximate the membership function value of a parameter, such as coordinate of allocation. The units in M represent the values (or range of values) that a parameter may take. In one embodiment, a unit in M layer corresponds to a pixel (or a range of pixels) along a direction (e.g., x axis) within the image. In one embodiment, one or more units (e.g., continuous valued) in M layer are set to represent the membership function over the pixels (or range of pixels), for example in x axis, corresponding to the corresponding fuzzy parameter in P layer that, for example, represents the x coordinate of L. In one embodiment, units in M layer are used to train association of, for example, a location on the image and the features of the image. In one embodiment, weighted link are made from P or M units to a correlation layer C for training the association. In one embodiment, weighted links from M layer are made to hidden layers to associate parameters to features of the image. In one embodiment, M layer(s) includes a unit for every pixel (or a range of pixels) on the image, e.g., full coverage to specify any shape (or blob) in M layer for association with the image.

In one embodiment, where inter-layer links between units are not fully connected, the connection from M layers to units in lower hidden layer(s) are substantially arranged to spatially resemble or correspond to M units' corresponding pixels (or range of pixels) in the image viewed via V layer. In such a case, the links from V layer to higher hidden layers are also limited in number of connectivity, and for example, the few links follow a fan out pattern from a 2D layout of V layer to next hidden layer.

In one embodiment, blobs (of fuzzy blobs) are provided on M layer for association with the image during training Fuzzy blob, for example, may have fractional membership function value at the blob's edge. In an embodiment, the membership function value in range of [0, 1] is represented by a logistic function in a unit.

In one embodiment, the location, area, or focus of interest is provided on M layer with the corresponding training sample in V layer, to train the correlation. In one embodiment, the representation of the focus of interest may be a (fuzzy or crisp) border or a region specified parametrically or per pixel.

In one embodiment, with a training sample having multiple focuses of interest, the training may be performed by submitting the same data (image) with individual focus of interests during the training. In one embodiment, the stochastic nature of C layer will cause reconstruction of focus of interest in M or P layers, given an input image (or a portion of image) in V layer. For example, in training face recognition, images including one or more faces are supplied to V layer while their corresponding focuses of interest (e.g., the location/size of the face) are supplied to M or P layers, to train the correlation. In one embodiment, the various focuses of interest are iteratively constructed in M or P layer by clamping data (e.g., an image) in V to, for example, derive stochastically the corresponding focuses of interest from C layer. In one embodiment, the reconstructed parameters are output in M or P layers based on their corresponding probability.

In one embodiment, the correlation of image/data to its locations of interest is performed during training by implementing a representation of such locations on a layer of units laid out to correspond to the image/data (e.g., by linking such units to a hidden layer above V layer). In one embodiment, the position parameters (e.g., location, width/height, type, orientation) and the coverage parameters (border type, fill type, fuzzy/crisp) are used to render representation of the location(s) of interest on the representation units, e.g., by using a value in range of [0, 1]. In one embodiment, the fuzzy type rendering helps avoid making false correlations with other irrelevant features in the image/data, by representing the features of the location of interest as coarse. Fill type rendering identifies a blob where the location of interest is in the image, so that if the features of the interest are in the middle of the location, the training would catch the correlation.

Limiting Number of Weights Based on 2D Fan Out Layout

In one embodiment, as for example depicted in FIG. 190, the extent of the inter-layer connections are limited for the lower layers (e.g., $H^{(1)}$ and/or $H^{(2)}$). In one embodiment, the number of inter-layer connections between the lower layers is substantially less than that of fully connected ones. For example, if the (average) number of fan out links per unit, f, is significantly smaller than the number of units in the higher layer, the number of inter-layer connections (or weights) are significantly reduced compared to the fully connected scheme. This scheme helps reduce the complexity of the structure, reduces the over fitting, and enhances generalization. Conversely, the number of fan out links (top-down, e.g., from $H^{(1)}$ to V units) are also limiting a until in the higher layer to relatively few units at the lower unit. Therefore, in one embodiment, for example, the number of fan out links from a unit in $H^{(1)}$ to V units may be about 3 to 10 pixel wide.

In one embodiment, there are multiple type of units in a hidden layer (e.g., $H^{(1)}$), with each type corresponding to different number (or range of number) of links to its lower layer units. In one embodiment, for example, type 1 units have about $f_1$ links (e.g., about 3-10 links), type 1 units have about $f_2$ links (e.g., about 20-30 links), and type 3 are fully connect. In one embodiment, there are more number of units (e.g., in $H^{(1)}$ layer) which have less number of connections to the lower layer units (e.g., in V layer), i.e., most units in $H^{(1)}$ have few connections to V layer units and few units in $H^{(1)}$ are fully connected to units in V layer.

Training with Samples of Varying Reliability

In one embodiment, a measure of reliability of training samples may be provided with the sample data. In one embodiment, a default value for the reliability is assumed if not provided for a particular sample.

In one embodiment, an error function (to be minimized by training) defined over the training sample space (e.g., in a batch processing of an epoch) accounts for data sample reliability by including sample reliability factor as a weight in the contribution of the data sample to the batch error function, e.g., in the summation of the errors contributed from individual data samples.

In one embodiment, for example, a stochastic approach is used (instead of full epoch batch) to sample one (or several) training data sample(s) while optimizing the sample error function, and the sample error function is weighted by the reliability factor of the data sample. In one embodiment, the learning rate (e.g., the factor associated with the step to take in modifying the weights during the training) is modified based on the reliability weight for a given data sample used during the learning (e.g., in stochastic sampling of the data samples).

In one embodiment, some key data samples may be marked as the key representative samples. In one embodiment, an elevated weight is assigned to such samples during the training, e.g., to simulate the training with multiple instances of such training sample.

Preprocessing Prior to Classification and Training

In one embodiment, one or more types of preprocessing is performed on the data (e.g., used for training or recognition) to focus on certain aspects of the data (e.g., image) in order to make the training and classification more efficient. In one embodiment, the preprocessing makes certain features to become more pronounced and easier to distinguish by the network (during and after training) For example, a filter such as Sabel filter is used in the preprocessing of an image to detect the line edges before feeding as training set for an RBM. In one embodiment, the preprocessing reduces features that may be less relevant in detection of pose and greatly simplify an initial step of choosing a more relevant expert system to further classify the image. In one embodiment, the preprocessing may actually introduce artifacts into the preprocessed image, e.g., a shadow on a face, may result in an edge across the face after an edge detector filter. In one embodiment, as for example depicted in FIG. 191, multiple preprocessing (e.g., edge detection, edge sharpening, contrast enhancement, intensity conversion (e.g., non-linear mapping), cosine transformation, and histogram) are performed, for example, in parallel, and the preprocessed image is fed into various networks, classifiers, or feature detectors for detection of classification(s) and feature(s) (e.g., denoted by $CF_1$ and $CF_n$). In one embodiment, the classification and/or feature detection is associated with one or more measures of reliability factor (e.g., denoted as $R_1$ and $R_n$). Based on the features/classes detected (and their corresponding reliability factors), in one embodiment, further feature detection or classification (e.g., more detailed detection/classification, expert system, or sub-classification used for example for identity recognition) are identified, chosen, and/or scheduled to be performed. In one embodiment, the outcome of further feature analysis/detection or classification are consolidated/mixed based on the reliability of the results (e.g., from classifiers or expert modules) as well as the reliability of parameter extraction based on the model (e.g., a front pose and side view images of a person's head present the aspects of facial features with different reliability due the image projection from 3D to 2D, as well as hidden/blocked features).

In one embodiment, the reliability of an expert module is trained by correlating the features indicating the domain of the expert module with the error encountered by the expert module.

Fuzzy Valued Feature/Label Output

In one embodiment, multiple units are used to present various labels corresponding to a class of object. In one embodiment, feature detection system is used to train document classification based on learned (e.g., unsupervised) features corresponding to documents based on terms contained in the document (such as statistics of several hundred or several thousand common words). In one embodiment, latent semantic analysis (LSA) is used to provide the correlation between the terms or documents based on document-term matrix, and decomposition using orthogonal matrices and a low dimensional diagonal matrix (to a low dimensional space), e.g., by using single value decomposition technique (SVD). In one embodiment, RBMs are used for learning features, e.g., by limiting to top hidden layer to low number of units (dimensions/features). In one embodiment, the similarity between documents is determined by comparing (e.g., by cosine similarity) of their features. In one embodiment, the features (e.g., continuous valued) are correlated/associated with provided labels/classification (e.g., in supervised training) For example, in one embodiment, the labels indicate the type of document, such as legal, historical, fiction, scientific, business, manufacturing, technical, etc. In one embodiment, the layers are supplied to label units and correlation/association is learned via a correlation layer, e.g., by using an RBM and using the features learned from unsupervised training. In one embodiment, more than one label may be provided during the training of a sample (e.g., a document). In one embodiment, the labels are binary (e.g., indicating whether the document is "technical" or not). In one embodiment, the labels are continuous valued (or multi-valued), e.g., having values in range [0, 1], to indicate the degree in which the document is classified by a label (or the membership function of the document in the label's class). In one embodiment, upon training the correlation/association, given an input data (e.g., a document), the reconstruction of labels (as output via, for example, correlation layer), presents the classification of the document based on those labels. In one embodiment, one or more labels are identified in the output, indicating that the document is determined to belong to both classes/types. In one embodiment, the output (multi-valued or continuous) indicates the degree in which the document is determined to be of the class/type. In one embodiment, the values output at the labels are thresholded (or further discretized) to simplify the presentation and further usage. For example, in one embodiment, an output less than 15% is zeroed, or an output more than 85% is turned to 100%.

In one embodiment, the membership function values presented by the output values in label units are consolidated to form a fuzzy number. For example, in one embodiment, the labels reconstructed from a handwriting recognition sample, show the membership function values in classes "1", "7", and "2". In one embodiment, the labels for expression (e.g., facial) can be represented by fuzzy concept, e.g., smiling, laughing, sad, angry, scared, nervous, sleepy, apprehensive, surprised, and tired. And each label may have a degree of membership (e.g., degree of smiling compared to neutral) for a sample data, used for training. The labels may also be correlated based on the training data.

In one embodiment, various labels (i.e., their membership degrees) get correlated/associated with the features (e.g., at the top hidden layer of RBM or deep belief network) via training through a correlation layer.

Adding New Features

In one embodiment, an already trained (e.g., unsupervised) feature detector (e.g., RBMs or a deep belief network) is used to provide additional feature(s). In one embodiment, one or more units are added at the top hidden layer. In one embodiment, the weights/biases related to the units already at the top (e.g., hidden) layer are fixed/frozen, and training (e.g., unsupervised) is performed to adjust the weights/biases related to the added units. In one embodiment, the added units represent a set of sub features that help enhance the reconstruction from top-down direction. In one embodiment, regularization techniques (e.g., limiting the weight amounts or weight decay techniques) or verification techniques (e.g., testing using reserved test datasets) are used to maintain or monitor generalization. In one embodiment, training samples with and without the features are provided to adjust the weights of the added units. In one embodiment, back propagation is used for fine tuning of the weights/biases. In one embodiment, the added units and the previous units are used to make association and/or correlation with labeled samples, e.g., during the supervised training In one embodiment, an expert classifier/detector is trained predominantly from one class to detect the distinguishing features of data within the class. In one embodiment, a set of feature nodes/units/neurons are added, e.g., to the top hidden layer of RBMs, for training to detect features of an additional class (for new expert). In one embodiment, the original expert classifier/detector is trained for a different class of objects (or expertise) to detect/determine the new features at the added units at the top layer. In one embodiment, the related weights/biases for the existing units at the top layer are fixed (i.e., prevented from changing) while training for the additional class. In one embodiment, redundant features (units) are eliminated (for example from the top layer) based on their strong correlation between those from the existing expert and the additional expert. In one embodiment, correlations between top redundant units are determined based on sampling from the data in the visible layer. In one embodiment, the correlation or covariance between top redundant units (e.g., at layer $H^{(3)}$) are determined based on their biases and weights to the lower layer units.

In one embodiment, additional units are provided in lower hidden layers (e.g., layer $H^{(2)}$) to allow more flexibility to handle more complex feature sets in a class of data/images. In one embodiment, the redundancy of such units are determined by strong correlation between the stochastic probability associated with such units, e.g., based on the value of logistic function of the total input to the unit. In one embodiment, in eliminating a unit due to redundancy, the weights linking the remaining unit to other units (e.g., in a higher layer) are updated by consolidating (e.g., algebraically) the corresponding weights from the existing and redundant units, in order to maintain the same total input to the top layer linked unit.

Focus of Interest with Variable Resolution

Figure 192A:
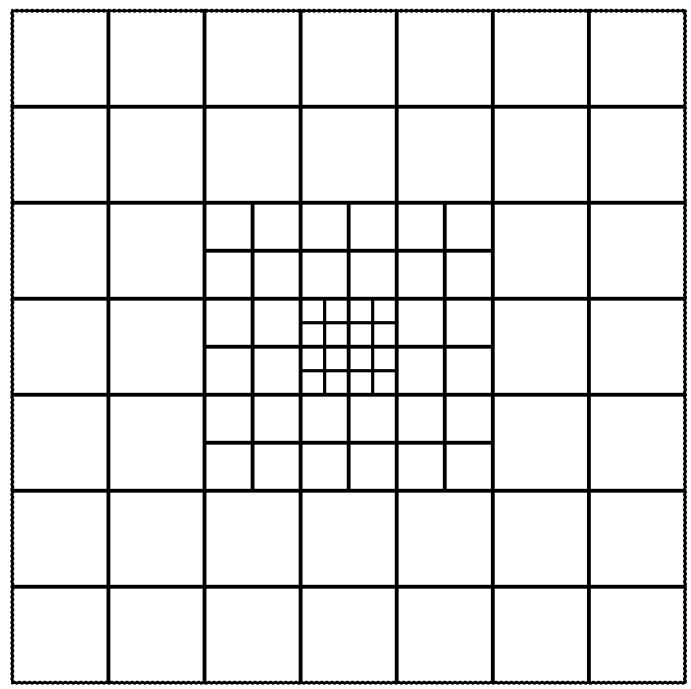
Figure 192B:
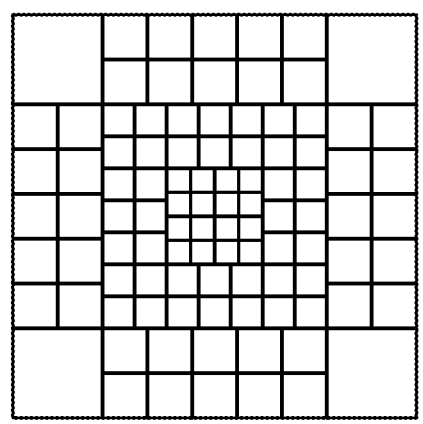

In one embodiment, as for example depicted in FIGS. 192(a)-(b), the data (e.g., image) is laid out using a set of non-uniform sections, with smaller size (higher resolution) sections at the center of the image, and larger (low resolution) sections further way from the center. For example, as shown in FIG. 192(a), the sections are rectangular (or squared) forming square bands with increasing size. In one embodiment, the consecutive segment sizes are multiple (e.g., 2) of the next smaller size (as for example depicted in FIG. 192(*a*)). In one embodiment, as depicted in FIG. 192(*b*), multiple segment sizes may be used in various bands around the center, for example, in diagonal positions compared to the center. In one embodiment, the relative size of the segments may be a rational number (fraction), as for example depicted in FIG. 192(*b*).

In one embodiment, as for example depicted in FIGS. 193(*a*)-(*b*), some of the segments are radially distributed from the center, having similar sizes but different orientation. In one embodiment, the segment radial boundaries are approximated by an arc (e.g., of a circle), as for example depicted in FIG. 193(*a*). In one embodiment, the segment boundaries are defined by a polygon, as for example depicted in FIG. 193(*b*).

In one embodiment, the resolution/size of segments varies in vertical or horizontal direction, as for example depicted in FIGS. 194(*a*)-(*b*), respectively.

In one embodiment, as for example depicted in FIGS. 195(*a*)-(*b*), the segment layout follows a transformation(s) such as rotation, skew, perspective, scaling, or even distorting type transformation. In one embodiment, the details in an image is recognized (or trained) by mapping the image (or portion of the image) in such a transformed segment layout.

In one embodiment, features of an object (e.g., pose including rotation) is determined, and based on such features, features of sub-objects of other objects depicted in an image are extracted by preprocessing (e.g., mapping) a portion of an image into a segmented layout with variable resolution. Then, the mapped image (or portion thereof) is provided to a classifier or feature recognition system to determine the features from the mapped image. For example, in an embodiment, a frame depicted in an image is identified (e.g., a frame of a picture or a frame corresponding to a side of a building or a container). In one embodiment, based on the perspective/skew/projection of the frame (or other indicators), the image or a portion of image is mapped to a segmented layout for input to a network for further feature detection or classification.

In one embodiment, mapping of an image to a segment is done by averaging the intensity/color of the pixels falling into the segment. In one embodiment, summary information from the enclosed pixels of the image is attributed to the segment (e.g., texture, variance of intensity/color).

In one embodiment, a recognition/classification network or module (e.g., a deep belief network or RBMs) is trained using a variable segment layout associated with its visible/input layer. In one embodiment, an image is mapped to a variable segment layout before inputting to a recognition/classification network or module (e.g., for training or for recognition).

In one embodiment, an expert module uses/selects a variable segment layout to use based on other features of data/image determined by other recognition module. For example, a text recognition module may use a layout such as those, for example, depicted in FIGS. 194(*a*)-(*b*) and 195(*b*).

Estimating/Predicting/Localizing the Focuses of Interests

In one embodiment, the locations of interest (e.g., the location of faces within an image) is determined by a scanning the image through a variable size window over an image at different location on the image, searching for example for particular features or signatures (e.g., head or face). In one embodiment, the locations of interest are determined, for example, by determining an enclosure (e.g., the smallest enclosure, such as rectangle or ellipse) around the object of interest, to localize the object within an image. In one embodiment, the type of object (e.g., face) and its location (including orientation, skew, etc.) and other parameters (e.g., pose or identity of the object) are extracted and associated with the image. Then, such image and the associated information are used to train a feature detector/classifier to learn or predict the focuses of interest, by correlating/associating the image features with the locations of interest. In one embodiment, the image and various positions of interest are iteratively inputted to the system during training. The stochastic nature of the correlation layer, stochastically reconstruct parameters associated with the location of interest as output, e.g., using an RBM.

In one embodiment, a feature recognizer/classifier uses a data/image to extract features from an initial location (e.g., from the center of the image through a window or through a variable segment mapping). In one embodiment, based in the features determined, a set of one or more focuses of interest is reconstructed from the correlation layer (e.g., iteratively and stochastically). Then, the image is used to extract additional features from those predicted locations, e.g., through a window or a variable segment mapping. For each exploring location, a set of a location of focuses of interest are further predicted. In one embodiment, such lists of focuses of interest are consolidated and checked against the locations already covered. In one embodiment, the process stops after a certain number of locations of interest explored (for a given type of image), a certain number of features found, predicted location of interests were exhausted, certain amount of resources (e.g., computing power expanded), or other rules.

Partial Image Training

In one embodiment, partial images, e.g., masked or blocked, are used for training a detection/classifier module. In one embodiment, image samples are prepared by masking out the portions omitted e.g., by hiding the portion of image using straight edges through the image. In one embodiment, a randomizer generated masking parameters (e.g., the location of the mask edge). In one embodiment, the rendering module applies the mask to the image before inputting the masked image to the recognition module. In one embodiment, the masked regions of the image are filled with random fill color or random texture/pattern.

In one embodiment, as for example depicted in FIG. 196, the masked image is mapped/associated with the visible layer of a recognition/classifier module only at the units corresponding to the unmasked portion of the image. In one embodiment, during the training of an RMB, the visible units corresponding to masked portion of the image remain unclamped (i.e., their state stochastically adopt a value based on other units while the other visible units are clamped to sample data).

In one embodiment, during the training, the weights/biases associated with unclamped V units are not allowed to change due to the learning step involving the training with the corresponding partial image. In one embodiment, the contributions to the error function related to the unclamped visible units are ignored in the training step using the corresponding partial image/data.

In one embodiment, in the partial image training, the weight/bias adjustments for a learning step is modified by scaling the learning rate for a given unit (e.g., a hidden unit in $H^{(1)}$ layer) with the ratio of the number of its links traceable to the clamped visible units and the number of its links traceable to any visible unit. In one embodiment, similar adjustment to the learning rate is made with respect to a higher level hidden unit (e.g., in layer $H^{(2)}$) by, for example, determining such ratio (indirectly) by tracing through layer $H^{(1)}$, or simply by estimating the ratio based on similar average ratio from the traceable units in $H^{(1)}$ layer. For higher hidden layers where each unit is quite likely traceable to every visible unit, the ratio is estimated as number of clamped visible units to number of visible units. In one embodiment, by tempering the learning rate, the impact of the partial image on the weights is tempered as well. I none embodiment, by limiting the adjustment of weights, the impact of learning from phantom or residual data/images from the unclamped is also reduced.

Learning Higher Details Iteratively

Figure 197A:
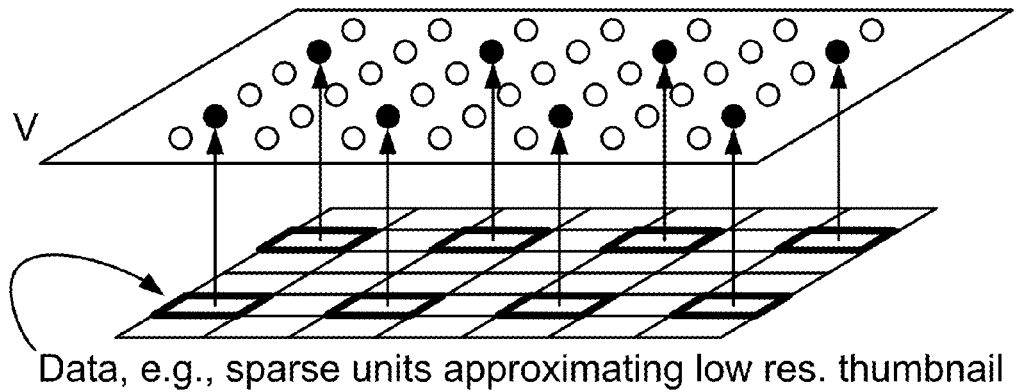

In one embodiment, an effective (approximate) thumbnail is input to a visible layer of a feature detector/classifier (during training or search) by blocking/masking the data from the original image, from being clamped to the corresponding units in the visible layer, except as to sparse visible units, as for example depicted in FIG. 197(a). For example, if the thumbnail has 8 times less resolution in both directions, then about 1 in 64 pixels from the data/image (i.e., 1 in 8 from each direction) is taken to approximate a thumbnail (e.g., without averaging with their neighboring pixels), and it is provided to the visible layer, e.g., to the corresponding unit that would have otherwise taken that pixel value when the V units are clamped with all of the data.

Figure 197B:
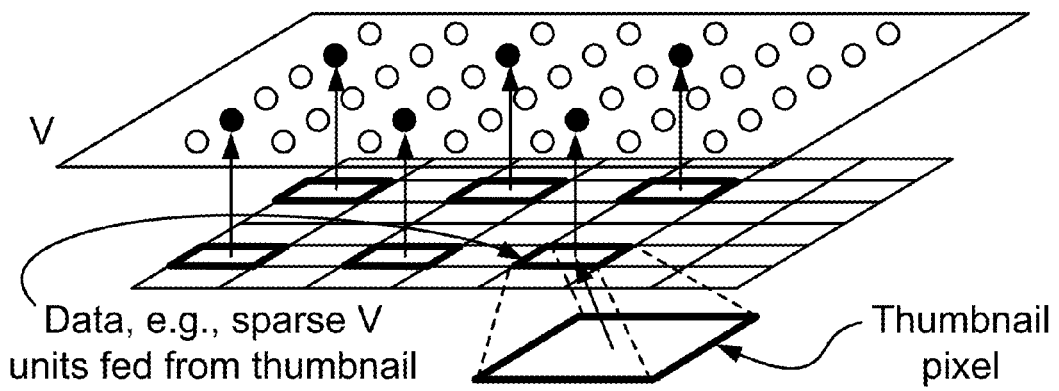

In one embodiment, the preprocessed thumbnail is applied to the visible layer, as for example depicted in FIG. 197(b), by clamping a thumbnail pixel value (e.g., obtained by averaging the data/image pixel values) to a corresponding (sparse) visible unit in V layer, according to the resolution reduction from the image/data to the thumbnail. For example, if the thumbnail has 8 times less resolution in both directions, then about 1 in 64 units in V layer are used to clamp to the corresponding thumbnail pixel values, e.g., by connecting 1 in 8 visible units in both directions.

Figure 197C:
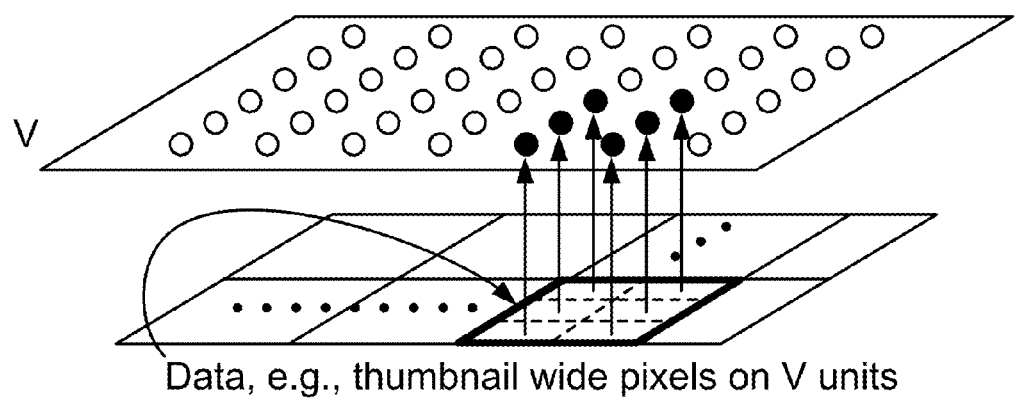

In one embodiment, the thumbnail pixel value is applied to multiple visible units, as for example depicted in FIG. 197(c), as if the thumbnail is expanded back to the image/data size with wide pixels covering multiple visible units. For example, if the thumbnail has 8 times less resolution in both directions, then each thumbnail pixel is clamped to about 64 units in V layer corresponding to image pixels, had the thumbnail were to expand to the image/data size.

In one embodiment, the learning of features is initially performed by using thumbnails. In one embodiment, e.g., as shown in FIGS. 197(a)-(b), the weights related to unclamped visible units not used to determine the error function and their related weights are not modified in the learning steps. In one embodiment, the learning of weights related to higher layers is performed using a learning rate, based on the number of traceable clamped visible units in V layer. In one embodiment, the second round of training uses higher resolution thumbnails, involving more visible units in the training. In one embodiment, during the second round of training, the learning rate for weights/biases related to the visible units involved in the first round of training starts lower than the learning rate for the visible units just used in the second round of training. In one embodiment, the learning rate is adjusted, so that before the end of the second round of training, the learning rate is substantially the same for all visible units involved in the second round of training In one embodiment, the stepwise learning of features from high level to more detailed takes advantage of the training weights established in earlier rounds of training Context Relationships In one embodiment, the datasets (e.g., images) include (or associated with) various objects or concepts (e.g., face, body, book, computer, chair, car, plane, road, and building). In one embodiment, classifiers are trained to detect high level signatures/features of various objects/concepts, e.g., by training the classifiers with (labeled) training data sets, including those with and without object features. Some data sets may include multiple objects or concepts, and therefore, the occurrences of the objects/concepts overlap. In one embodiment, a classifier may classify multiple objects/concepts. In one embodiment, the correlations between the objects/concepts are determined as the result of classification of various datasets. In one embodiment, a data-concept matrix is setup based on the classification of the data sets, and further analyzed, for example, by decomposition using orthogonal matrices and a (e.g., low dimensional) diagonal matrix (e.g., to a low dimensional space), e.g., by using single value decomposition technique (SVD). In one embodiment, this dimensional space represents various contexts (e.g., family, sitting, coworkers, house, office, city, outdoor, and landscape) that support or relate to various object/concepts. In one embodiment, each context represents/contributes a set of weights representing the relationships between object/concepts.

In one embodiment, upon detection or classification of a feature of an object/concept in a data/image, the distance of the data to one or more clusters representing various contexts is determined. In one embodiment, the clusters (or contexts) that support the data are determined. In one embodiment, a set of other concepts/objects are identified based on the correlation with the classified object/concept from the image. In one embodiment, the image/data is further explored, e.g., by other classifiers or feature/object detectors), selected based on the set of predicted/suggested concepts/objects. For example, in one embodiment, a face and a computer is detected in an image. Then, it is determined that such a data is consistent with several contexts (e.g., office and home) ranked in order of distance or consistency level to such clusters, or it is determined that such data is correlated to other objects such as keyboard, table, screen, room, etc., with various correlation strengths. In one embodiment, the classifiers or expert modules tuned for such objects are used to further detect the presence of such objects in the data.

In one embodiment, the contextual relationship between objects/concepts is used to further detect other objects/concept in data/image, by prioritizing and selecting the corresponding feature detectors/classifiers, as for example depicted in FIG. 198.

Object Detection in Layers

In one embodiment, an object/feature detector/classifier detects an object in a data/image. In one embodiment, the detected object may be part of or component of another object or detected for example based on the recognition of a partial image. In one embodiment, the structure of the object (e.g., the periphery, blob, coverage projection, or support regions) is determined based on localization of the object within the image (e.g., through reconstruction). In one embodiment, the potential objects/concepts in the image are determined, e.g., based on the context of the image or correlation with the context(s) of the detected object. In one embodiment, the visible structure of the object is removed from the image, e.g., as part of the objects in the image foreground. In one embodiment, e.g., with RBMs or deep belief networks, partial clamping of the input (visible) data is done for regions in the image not removed. Based on the context or correlation with other types of objects, corresponding detectors, e.g., RBMs or deep belief networks, are used to detect objects (which may be partially visible). In one embodiment, through reconstruction at the visible layer, the hidden/blocked portion of such objects is estimated/predicted. For example, this facilitates reconstructing background (if learned) or the rest of the face of a person (if learned). This approach can be executed continuously or iteratively to gather correlated collections of objects or their degree of possibilities based on the reliability factors. In one embodiment, more specific context may be derived based on each correlated (and for example expanding) collection of objects, and further information or proposition may be inferred (with a reliability factor) based on the image, by feeding the relationships and the reliability factors in a knowledge web.

In one embodiment, face recognition is performed on a partially blocked face in an image using a feature detector/classifier and database of known signature (vectors) associated with identified faces. In one embodiment, the comparison of detected features provides a matching probability measure between the partial image and a subset of those known in the database. In one embodiment, the reconstructed image at, for example, unclamped visible units representing the blocked portion, may provide full a face candidate for comparison with those images in the database.

In one embodiment, the consistency/reliability of a potential match with images/features (whether known or not) in a database is associated with the measure of uniqueness among the matches. The uniqueness measure indicates how uniquely the input image/feature is matched among the other images in the database.

In one embodiment, based on the context, there is a correlation between the hidden/blocked objects and the blocking object. For example, a dark glass covering a person's eye region has a strong correlation with the eyes. By training with the similar data/images with and without glasses, the correlation between the features of two data samples, given other common features may be established. In one embodiment, a data/image is searched by a trained feature detector/classifier. The features/labels indicating "wearing dark glasses" are activated based on previous training/correlation/association. In one embodiment, the region of dark glasses is identified (having correlation with the feature/label). In one embodiment, the value of feature/label is modified (e.g., forced off) by clamping the feature/label to the forced value. In one embodiment, such change/modification related to a feature/label is sent to a correlator/analyzer to determine the region on the data/image affected by the change, e.g., by reconstruction mechanism and comparison. In one embodiment, a threshold is used to limit the affected region on the image/data, e.g., based on relative changes in color, contrast, or intensity, size of region/sub-region. In one embodiment, the visible units corresponding to the thresholded region on the image/data are unclamped, while the other regions are kept clamped to the corresponding image/data pixel/portion. In one embodiment, a reconstruction in V layer, based on the forced value of the label/feature is used to recover one or more candidates for the blocked image within the unclamped visible units. In one embodiment, a two step process to uncover the blocked images, uses the rest of the (unblocked) image as prior condition in predicting a likely covered image, as opposed to a top-down pass to reconstruct the whole image which may create more variety in the visible layer. In one embodiment, multiple pass from bottom up (inference) and top-down (reconstruction) is performed to obtain more candidate or likely candidates under the constraint of clamping the visible layer to the unblocked portion of the image.

In one embodiment, the correlation between the blocked object (e.g., eyes) and the blocking object (e.g., dark glasses) is learned by sequential learning or by using two instances of the classifier/feature detector (denoted as "C/FD"), as for example depicted in FIG. 202. In one embodiment, a controller module selects a feature (or label) (such as "Dark Glasses") and supply it to the label layer (e.g., by clamping the corresponding label unit to the label value (e.g., in range of [0,1]). In one embodiment, the controller module provides the selection to a database (e.g., of images) to select a pair of images identical within the class of images but for the feature selected (e.g., two images of the same person with or without dark glasses, in similar pose and expression). The images are provided to the same (trained) classifier/feature detector (e.g., to two instances in parallel or using the same instance sequentially). The features of both images (and in particular the differences between their features) are correlated using a correlator/analyzer module (e.g., having unit/neurons) with the label/feature difference identified in the label layer (e.g., $L_i$). In one embodiment, the L layer represents the labels indicated the feature differences between the images (denoted by $\Delta L$). In one embodiment, more than one label is selected by the controller (indicating the differences between the features of the images selected from the database for training the correlation). In one embodiment, during the search process (i.e., for detecting objects in data/image), for uncovering the blocked feature (e.g., eyes region), a force flag selector is used to let the units representing the change in image features contribute to the state of the image features for top-down reconstruction of the image in the visible layer, while the controller maintains the corresponding label unit in $\Delta L$ layer to (e.g., stochastically) invoke the state of the units representing the change in image features. In one embodiment, the units are not separately set aside in the correlator/analyzer for determining the image feature difference/distance/vector between the two images. In one embodiment, the weights related to the units in the correlator/analyzer are trained to detect the feature differences by a stochastic or batch learning algorithm.

Measure of Scale in Context

In one embodiment, upon recognizing an object by a feature/object detector/classifier, the size of the detected object relative within the image and the relevant context(s) are used to correlate to size of other objects potentially in the image. In one embodiment, such estimates for the sizes of other objects are used to locate potential areas in the image and the sizes to search for such potential objects. In one embodiment, this approach facilitates discovery of other objects in the image more efficiently given the location and size of window for searching for such objects have higher probability to yield detection of such objects.

In one embodiment, one or more pose detection modules (e.g., based on edge detection or color region/shape) are used to determine the pose of a face within an image/data. The scaling determined from the pose detection(s) is used to make more efficient detailed feature detection, for example, by scaling the portion of image containing the pose based on the size in a preprocessing step prior to inputting the preprocessed image to an expert feature detector.

Variable Field of Focus with Limited Data/Pixel Points

In one embodiment, as for example depicted in FIG. 199(a), the recognition of object in data/image employs a wide window (e.g., rectangular, circular, elliptical) of focus on the image, but with a limited number of pixels (i.e., with low resolution). In one embodiment, the image within the window of focus is mapped to the specified number of pixel (e.g., in mapping/creating a thumbnail image). In one embodiment, the high level features and objects (or classes of objects, such as people and faces) are detected/located within this wide focus of the image. Then, in one embodiment, a narrower window of focus, containing similar number of pixels (i.e., higher resolution), is used to explore the object(s) located during the previous detection. In one embodiment, such process is done iteratively until reaching a maximum focus (or narrowest window of focus), maximum resolution of the original image, full identification of object, or satisfaction of a search criterion or constraint (e.g., based on a rule or policy). In one embodiment, with wide window of focus, small details, such as texture that require higher resolution, may not detected. In one embodiment, an expert feature detector/classifier is used with a narrower window of focus to efficiently determine features of an object in image/data, after the class of object is determined at a high level by a prior feature detector using a wider window of focus.

In one embodiment, a quick scan recognition approach is used, based on resolution level of the focus window. In one embodiment, at a given resolution level (e.g., $R_1$ or $R_2$, as for example depicted in FIG. 199(*b*)), a portion of image is picked based on (e.g., predefined) windows associated with the resolution level (e.g., 1 window for $R_1$, and 13 overlapping windows for $R_2$, as for example depicted in FIG. 199(*b*)). In one embodiment, a thumbnail or portion of the image at the picked window for the given resolution is prepared. A feature recognition/classifier is used to locate/recognize objects within the window (e.g., in the thumbnail). In one embodiment, if an object or a class of object is found in a resolution level (e.g., $R_2$), the search is continued for more objects of similar class in other windows at the same level of resolution. In one embodiment, if the detected object or class of object is not reliably matched/classified by the classifier/feature detector, then the search proceeds to the next higher resolution for more detailed recognition or for increasing the reliability of recognition/classification of the object, or to eliminate or reduce the potential for a false positive. In one embodiment, the approach for searching within the same resolution or gearing up to higher resolution is stopped upon reaching a resolution limit or a threshold for computing resources. In one embodiment, the determination of which window to pick next is based on an order associated with the context of the image. For example in a photo of standing people, the search proceeds horizontally to identify people (e.g., from faces). In one embodiment, the windows closer to the center of the image are ranked higher to be picked for search. In one embodiment, the next window to pick is determined based on the likelihood of finding features/objects within similar images (e.g., based on training)

In one embodiment, the sizes of the windows for a given resolution are the same (e.g., for a given context). In one embodiment, the sizes of the windows for a given resolution are different depending on the location within the image (e.g., based on the context).

In one embodiment, the location of the windows are picked, determined, or adjusted based on the location of the object(s) detected in another windows, the context, the proximity and relative positions of the objects and/or the scale/size of the objects.

Learning High Level Features by Limiting Learning Space

As mentioned in this specification, one approach to learn the high level (e.g., class of object such as presence of face, as opposed to for example the identity of the person based on detailed detection of facial features) is to detect the object/class of object based on a thumbnail (e.g., via pre-processing) of the data/image. In one embodiment, the training for a high level feature detection focuses on the structure of the neurons or units used in a classifier/feature detector. In one embodiment, the resulting feature units at top layer are limited to few features, while the training is used with data/images that may include thumbnail and high resolution data/images, including those with and without the targeted features. In one embodiment, a correlation layer is used to established the features correlation with labels by feeding the labels (e.g., via a label layer) to a correlation layer, or use a supervised training to train a classifier based on the labeled samples (e.g., using SVM).

Learning Via Partially Labeled or Mixed Labeled Training Set

In one embodiment, the labels for supervised training or for making association with object features (e.g., already trained in RBMs or deep belief networks), may not reflect all the applicable properties of the sample training set. For example, a data/image containing a person and a chair may only be labeled as person. In one embodiment, as for example shown in FIG. 200, a sample training data/image may depict two people (e.g., David and Jim, based on for example the annotation associated with the image), Eiffel tower (in the distance) and a taxi. The labels may be drawn from the annotations based on correlation/conversion to generic labels, such as Person and Car, through a semantic web or through a latent semantic analyzer. In one embodiment, the associated labels (whether drawn automatically or assigned manually) are fed to corresponding units in L (label) layer for training the association/correlation to the features learned by feature detectors/classifiers such as RBMs or deep belief networks. In an example, the annotation is missing "Taxi", and the label may not include the generic label "Car" or "Vehicle" (or even "Taxi"). In one embodiment, the unused labels associated with a training data is unclamped, and even though the relevant features (e.g., indicating a car in the image) exist, the correlation is not punished (i.e., skewed) for not having the correlation with the missing label. In another word, in one embodiment, the missing label is prevented to skew the correlation and mislead the learning as if the label was set incorrectly. In one embodiment, the unclamped labels do not contribute to the error function, and their related weights are prevented to change during the learning step (e.g., by setting the corresponding learning rate to zero for the related weights and biases). In one embodiment, the labels provided for the training are associated with corresponding reliability factors. In one embodiment, such reliability factors (e.g., in range of [0,1]) are used to scale the learning step related to weights and biases of such unit. In one embodiment, the state of unclamped label units are allowed to vary stochastically based on links form other units. In one embodiment, some labels are used as positive (e.g., with a reliability factor) indicators of the features to discriminate, and their absence are not used to indicate the absence of features. In one embodiment, the absence of some labels are used to indicate the absence of the feature from the data/image (e.g., with a reliability factor). In such a case, for example, the state of the corresponding label unit is clamped to indicate absence of feature.

In one embodiment, specific annotations that repeat often (e.g., "Eiffel Tower") (e.g., in a collection of images/data or a series of related images/data or within a large collection of data/images from various sources and various reliability) is taken as label for training association by adding an additional label unit (e.g., a binary unit) representing the added label.

In one embodiment, meta data such as the GPS data (or for example other accompanying metadata captured with images taken from mobile devices such as smart phones) are used as labels (e.g., continuous valued). In one embodiment, as for example depicted in FIG. 201, the correlation can also be established between the labels. For example, suppose an image/photo is missing the associated label "Eiffel Tower", but based on the correlation with the GPS data given the image/data, the label "Eiffel Tower" is reconstructed in the corresponding unclamped label unit when searching for the features of the photo/image by a feature detector/classifier. In one embodiment, the reconstructed label is imported into the annotations associated with the image/data with a relevant certainty factor (e.g., based on the correlation). In one embodiment, based on the reconstruction of the labels, relevant (e.g., expert) detectors/classifiers associated with such labels/concepts are used to further validate the match. In one embodiment, such recognition of labels (e.g., the identity of people) is extended to recognition of people in various images (e.g., with no annotation or partial annotation) in order to implement auto-annotation of the images, based on recognition/identification of individuals in other images. In one embodiment, the existing annotations associated with a data/image are compared with the constructed/predicted label for conflict or redundancy, based on the correlation between the terms of annotation. In one embodiment, a subset of annotations associated with a data/image is used (e.g., selected in random) to determine the reliability of their correlation to the image/data based on a feature detector/classifier. In one embodiment, potentially unreliable annotations (e.g., a subset) are determined based on low reliability of correlation of the image/data with corresponding labels. In one embodiment, the unreliable annotations are tagged as such (e.g., with reliability factor). In one embodiment, the reliability factor is associated/inferred to the annotator (e.g., a person) by contributing to the annotator's reliability of annotations for a given context.

Search and Indexing

FIG. 203 depicts an example of an embodiment for indexing and search. In one embodiment, a network and/or sources of information are used to fetch various content, tags, and metadata, via bots or background processes. A cache is updated with the changes in the information gathered. In one embodiment, the background processes use the information from the network traffic or domain name servers to fetch resources. Via background processing, analytics engines organize, categorize, recognize, and correlate various cached content, and an index/relationship database is updated to facilitate (e.g., a real time) online query. Upon such query, a ranking query engine uses the query to return ranked result using the index/relationship database. In one embodiment, the online query is cached and analyzed for patterns of queries and to facilitate ranking and caching. In one embodiment, the user selects a result of the query and the user selection is also cached to correlate with the query and/or the user by analytics engines. Content, summary, or URL related to the selection is fetched from caches and returned to the user.

In one embodiment, map reduce technique is used to handle "Big Data" processing across distributed file system and systems. The task, such as distributed search (among the machines) use small portion of the data (e.g., one chunk at the time) and provide the result to a central machine(s) for collection. An instance of search task/job keeps the information about the search and identifies the result accordingly, so the result may be available or extended time. The result may get updated and available for use in real time.

Facial Expressions and Emotions

In one embodiment, the weights on features that are affected largely by various emotional states or ranges are reduced in an attempt to distinguish the invariant features that would help identify an individual among a database of individuals associated with a set of features (e.g., invariant features). However, in one embodiment, the reduction of weight on the affected features will also impact (reduce) the distinctive features between individual labels.

In one embodiment, the expressions and emotional states are learned as features captured in the images. For example, in one embodiment, RBMs or deep belief networks regenerate or construct unseen images with new emotions, by setting the correlated label (for an emotion/expression) and letting the reconstruction provide an image in a visible layer.

Time Series and Video

In one embodiment, multiple images are compared together to detect or infer transformation, e.g., translation, rotation, scaling of objects or features between the images. In one embodiment, the frames (images) from a time series collection (e.g., a video segment) is used to extract different poses of an object (e.g., a person's head), different expressions (emotions). In one embodiment, speaker recognition module, based on the analysis of sound track of audio/video tracks, identifies/distinguishes speakers and associates those entities to time segments in the audio/video tracks. An image extractor module uses the time segments to extract potential images at different poses of that speaker from the video track (in synch with audio).

In one embodiment, the feature detector is trained on various poses and expressions with many unlabeled samples before training with labeled samples to make association of features with labels (e.g., pose parameters, expression parameters, emotion states/degrees).

Figure 204A:
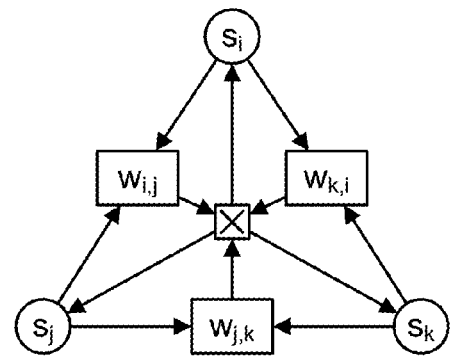

In one embodiment, the image transformation is modeled via a higher order Boltzmann machine, which links more than two units via a weight. A factored higher order Boltzmann machine reduces the complexity or the number of parameters (compared to non-factored version), where the weight (e.g., between 3 units i, j, and k) is factored into 3 mutual weights corresponding to each pair of units, in a multiplicative way: $(w_{i,j} \cdot w_{j,k} \cdot w_{k,i} \cdot s_i \cdot s_j \cdot s_k)$, as schematically shown in FIG. 204(a). In one embodiment, one signal, e.g., $s_k$, acts as a binary controller, i.e., when value of zero, the interaction between units i and j reverts to low order Boltzmann machine.

Figure 204B:
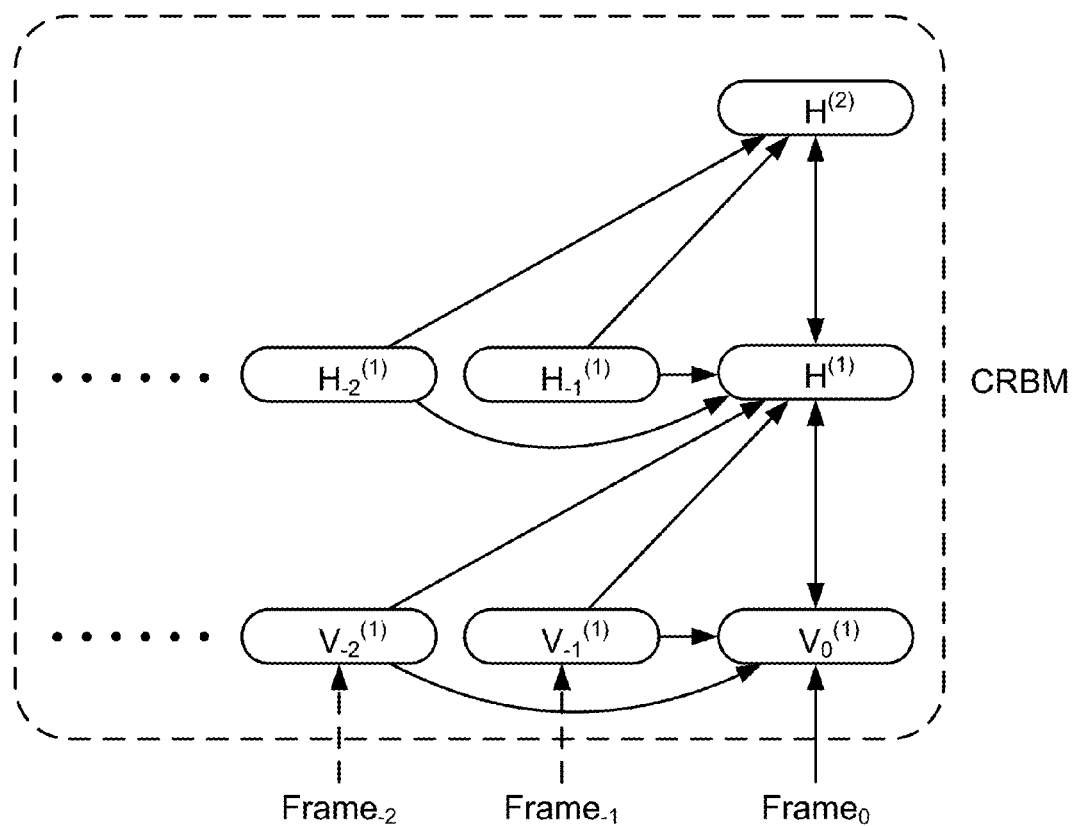

In one embodiment, as for example depicted in FIG. 204(b), short range temporal data (e.g., image) is modeled by providing a number of (e.g., consecutive) frames (e.g., 2 to 5 for large number of visible units per frame of data, or about 100 for few visible units, e.g., representing the parameters of motion instead of pixel images) from earlier times/series. In one embodiment, the data from these frames are provided to visible and hidden layers of RBM. CRBM denotes conditional RBM due to dependency of the hidden units on the previous states of visible units. In one embodiment, such a temporal module is stacked after training features on the lower layer. In one embodiment, the units representing previous frames are initialized (or their swapped) based on the units representing then current frames. In one embodiment, the same number of visible units (or hidden units) is used for each frame (representing current or previous frames). In one embodiment, the energy state of CRBM includes terms based on quadratic offset of the visible units' states from their corresponding dynamic mean (e.g., a linear combination of their previous states). In one embodiment, the bias for a hidden unit is based on its dynamic mean. In one embodiment, the weights for the linear combinations to get dynamic mean for a hidden or visible unit are autoregressive weights. In one embodiment, the contrastive divergence method is used in learning the weights and biases, by for example sampling the hidden units based on the visible units (current and previous), and reconstructing the visible units based on the sampled hidden units. The visible (or hidden units) corresponding to previous frames are not updated in this approach. In one embodiment, the hidden units are sampled based on logistic function. In one embodiment, the visible units are reconstructed using a Gaussian distribution (e.g., with unit variance) and a mean based on the weighted links from the hidden layer and the visible units' dynamic mean. In one embodiment, during the learning process, the learning rate in order of 0.001 is used for the weights between the visible and hidden layers. In one embodiment, during the learning process, the learning rate in order of 0.0001 is used for the autoregressive weights.

Figure 205A:
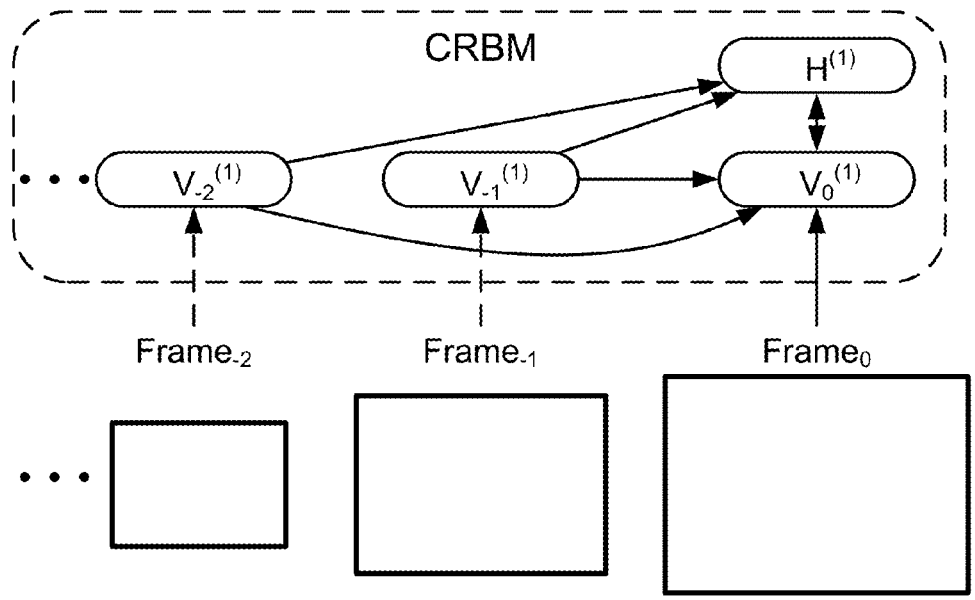
Figure 205B:
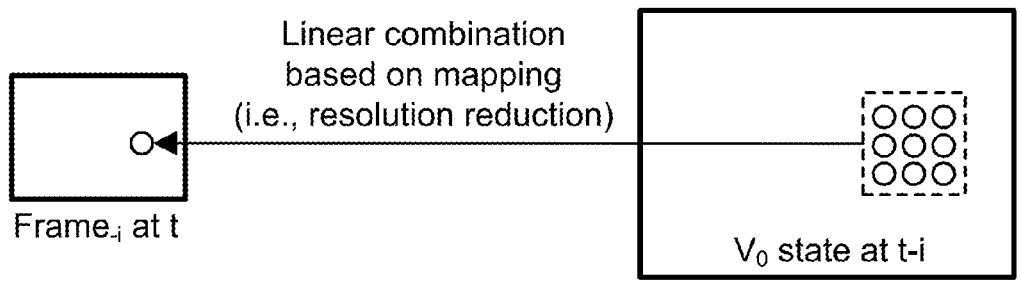
Figure 205C:
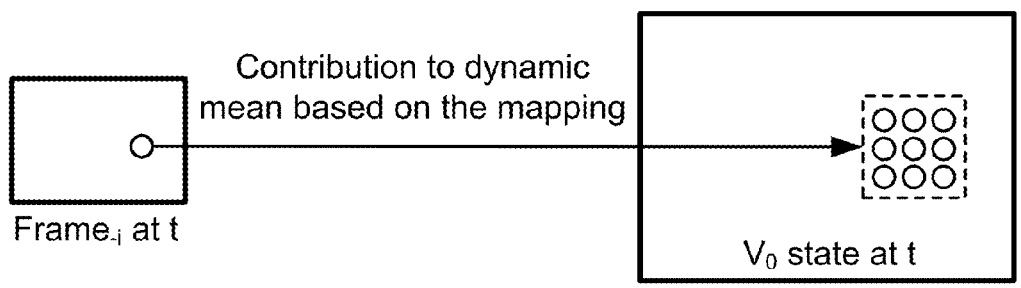

In one embodiment, as for example depicted in FIG. 205(a), the older frames use less number of visible units, e.g., by lowering the resolution/size of the frame as it gets older. In one embodiment, the longer lasting coarse features of motion are learned/detected based on the decreasing resolution for older frames. In one embodiment, the value/state of the visible units associated with previous frames are based on a linear combination (e.g., average) of the states of visible units from when the frame was current, as for example depicted in FIG. 205(b). In one embodiment, such linear combination is based on the reduction of resolution from the original frame to that of previous frame. For example, if a previous frame is 3 times smaller in each dimension compared to the original frame, then the state of a visible unit associated with the previous frame is based on (e.g., average of 3×3 visible units from the time the previous frame was current). Conversely, in one embodiment, fewer units from the previous frames contribute to the dynamic mean of the current units (in visible or hidden layers), as for example depicted in FIG. 205(c). In one embodiment, a snap shot of the visible units are taken for scaling according to resolution reduction for previous frames.

In one embodiment, the features recognized from previous analysis of the older frames are used with a predictive model such as Kalman filter to estimate the localization of the features in the current or upcoming frames. In one embodiment, for example based on such estimates/prediction, the analysis of frame (e.g., the current frame) is initially limited to a portion of the frame containing the estimated localization of the tracked features. In one embodiment, an area of focus of interest is used to analyze the portion of the data/image.

In one embodiment, stochastic sampling at hidden layers (e.g., based on an initial condition in visible layer) and the reconstruction in the visible layer reconstructs learned motion (in sequence), based on the learned weights, including autoregressive weights. In one embodiment, the learned (features) of the motion is correlated with a label via a correlation layer or other classifiers. In one embodiment, using one or more labels, the motion is reconstructed in sequence in visible layer via top-down regeneration. In one embodiment, a mix of motions are reconstructed based on a combination of labels (e.g., with varying degree).

In one embodiment, Long-short-term-memory (LSTM) which a recurrent type neural network is used to model the data in time series. In one embodiment, LSTM block includes sigmoid units (e.g., based on logistic function) to allow access to the block and control its functions (e.g., input, memorize, forget, and recall). It also uses product type units (with no weight) and summation units to direct the data through the block. In one embodiment, an LSTM module is trained via back propagation through time with iterative gradient decent algorithm.

Classifier and Complexities

In one embodiment, linear models, such as perceptron, linear regression, and/or logistic regression are used. For example, perceptron is used for classification, e.g., in or out, accept or deny, and is trained by perceptron learning algorithm including a pocket version. The linear regression is for example used to determine (continuous valued or real valued) amount, based on squared error function and pseudo-inverse algorithm. The logistic regression is used for example in determining probability, based on cross entropy error, using a gradient decent algorithm. Noise and error in input data makes the nature of the training data probabilistic. The VC (Vapnik-Chervonenkis) dimension for a Hypothesis set (i.e., he most points that can be shuttered by the hypothesis set) is related to hypothesis set's growth function, and in one embodiment, the VC inequality (in terms of growth function and number of training samples) provides a rule of experience for the number of points needed for training (e.g., >10×VC dimension). The VC inequality places an upper bound on the probability of the out-of-sample error (i.e., the generalization error) is within the in-sample error by a given error margin and a given number of in-sample (training) data. In one embodiment, a maximizing likelihood approach is used to select a hypothesis from the hypothesis set that results in maximum likelihood of getting the data given the hypothesis. In one embodiment, the learning with logistic regression uses a cross-entropy error $\log(1+\exp(-y_n W^T x_n))$ with $(x_n, y_n)$ representing the labeled data point and W is the weight matrix to be optimized. In one embodiment, the optimization uses a gradient decent approach by using variable size step (large to small). In one embodiment, the step size is proportional to the gradient which fixes learning rate (appearing as a multiplier for the learning step). One embodiment uses an adaptive learning rate. In one embodiment, the default learning rate is 0.1. In one embodiment, the number of iterations of epoch is limited to a maximum (early stopping), in order to avoid over fitting the noise/error and deteriorate generalization by increasing the out of sample error. In one embodiment, in order to tackle the problem of local minimum, the optimization starts at different initial values of weights (e.g., based on heuristic). In one embodiment, the "temperature" is used to escape local minimum, e.g., in RBM learning, the optimization starts at a high temperature, to allow escaping the local minimum. In one embodiment, a stochastic gradient decent is used by taking one data sample at the time, resulting in generally a simple, cheap, and random approach to optimization in comparison to batch optimization where all data sets are used in each step of optimization. In one embodiment, a binary search method is used to explore along the direction of error gradient. In one embodiment, a conjugate gradient is used to estimate the second order error from previous data points. In one embodiment, a multiclass classification is approached based on binary decision, i.e., 1 vs. all, 2 from the rest, etc. In one embodiment, non-linear transformation is used to optimize based on a feature in a transformed space. In one embodiment, the VC dimension of the neural network is approximately the number of weights and biases. In one embodiment, a regularization approach is used to kill some weights (e.g., in random) to enhance generalization (and reduce over fitting). In one embodiment, a genetic optimization is approach is used. In one embodiment, a regularization approach is used to limit the choice and ranges. In one embodiment, a validation is used to test the generalization, by dividing the sample data for fitting and cross comparing the error. In one embodiment, kernel methods are used for small labeled data and top features to model the classification. For example, one embodiment uses thousands of unlabeled training set with various orientations to learn features (including the orientation), and it uses few hundred labeled training sets to discriminate orientation (with regression for angle). In RBM training, the number of training cases may be less than number of weights as long as the number of pixels is much more than weights, because there are a lot of features that can be extracted from pixels. In one embodiment, the discriminative training (e.g., based on labels) quickly fits the data, and it is stopped quickly to avoid over fitting. In one embodiment, a weight decay technique is used to implement regularization in learning. In one embodiment, about 20% of the data samples are reserved for validation (and not training). In one embodiment, cross validation is used to conserve the number of data sample for fitting. In one embodiment, the probabilities indicating the certainty of inferences based on the correlated training sets are tracked, for example, to infer one pose from a different pose.

Feature Extraction:

In one embodiment, we note that people of same ethnicity or region (or members of the same species of animals) generally recognize each other better. For example, all tigers look the same to an average human, but tigers themselves can recognize each other very easily and efficiently. Or, a Middle Eastern person can distinguish other Middle Eastern people more accurately and efficiently, than what a Chinese person can, among the same set of people from the Middle Eastern origin (or the same set of pictures of people from the Middle Eastern origin), assuming that the Chinese person never lived among Middle Eastern people or lived in that region of the world.

The same is also true (for example) for the case of the identical triplets in humans, which can be distinguished easier by themselves. In addition, their parents can distinguish them easier than the rest of the general public can. The reason is that an average human can see a tiger as an animal with 4 legs and stripes, similar to a big domesticated cat, as the dominant features, however, the tigers see or focus on some other features or more details of stripes, to distinguish themselves or as they see themselves. Since a tiger's eyes and brain are trained by looking at a lot of other tigers for many years, their distinguishing features are all set accordingly, to focus and look for the right features or sub-features, to make the distinction. For example, they may look at the ratio of 2 lengths on 2 specific stripes, or width of a stripe near the nose, as the focused or re-focused features, to find or classify or distinguish the other tigers or objects or subjects. Such specific features may be transparent to the human eye and brain, as they do not know what to look for in a huge volume of information received by the eye or brain. It is also consistent with the fact that a zoo keeper (dealing with tigers for years) can distinguish them much easier than an average human, as the zoo keeper has seen many tigers, and thus, her brain and eyes are trained for those features and characteristics.

So, sub-sampling the input from all universe (for humans, for example), or $U_H$, is very critical for training purposes, to train appropriately, for a given task. Filtering or focusing or zooming in a few features ($F_F$), out of, e.g., billions of patterns or features available ($F_U$), on the sensory basis or recorded or obtained, when selected appropriately for the task at hand ($T_A$), reduces the training time and cost, and increases efficiency and accuracy of recognition and classification and appropriate response. Mathematically, we have:

$$T_A \rightarrow F_F$$

Wherein $F_F \subset F_U$

Wherein $U_H \rightarrow F_U$

Wherein "arrow" symbol indicates that the right hand side item is obtained from the left side item.

Large or Voluminous Input Data:

The same is true for an infant (e.g. 5-month old, at the early age) listening to all the noise and voices around herself, e.g., possibly spoken in English and French by bilingual parents or nanny, and the noise from highway outside in the background, as well as the very noisy and loud fan on the ceiling, or the voice of her grandfather and grandmother, with the TV announcer or anchor in the background shouting about a recent news or an advertisement about a car. She receives a large amount of voice and noise data by her ears (or internally from vibration on the ground or floor), but in the first few months, she gets all of the data with the same weight and importance. Overwhelmed by the large incoming data, she mostly ignores most of the input data, even the voices of her parents, that are supposed to be important to her well-being. After a while, though, she will understand that her parents' voice are more important than the noise of the cars outside or fan on the ceiling, even if they are very loud or louder. So, she will tune and filter or put more weights for those features or voices, as she gets trained on distinguishing between the voice, noise, music, warnings, background noise, dangerous signs or screech/scream, or angry tones. The same is true for vocabulary and grammar in a language.

It is the readjusting, reassigning, or rearranging the orders or weights or features, which focuses or re-focuses the learning subject on new or different features at the different stages of learning process, including distinguishing features or pattern recognitions. Thus, the learning process is dynamic and self-adjusting or adjusted by a trigger or test against a threshold or from an outside input. It evolves, as it gets more sophisticated, for more capabilities.

For example, in one embodiment, as the time passes, a subset of input features ($F_1(\ldots)$) are selected at a given time ($t_N$), compared to the previous time ($t_{N-1}$), until the subset becomes the same as the set itself from the previous time. Then, there is no need to sub-select anymore, to reduce the set of features. Thus, the optimization process stops at that point, and the final sub-set is selected and obtained. Mathematically, we have:

$$F_I(t_N) \subset F_I(t_{N-1})$$

For $\forall t_i$

Until we have: $F_I(t_M) \equiv F_I(t_{M-1})$

In machine learning, in one embodiment, we initially teach the machine the language or other things or subjects without any rule or grammar, just by training samples, and usually by sheer number of training samples. Then, on the second phase, we teach or input the machine some basic rules, e.g. Fuzzy rules or rules engine. Then, on the $3^{rd}$ phase, we train the machine with more training samples, simultaneous with more rules being input, to have some order to the training and samples, which is a very powerful way of learning rules and getting trained very efficiently.

In one embodiment, the machine learns one language (or concept) by training samples only. Then, we teach the $2^{nd}$ or $3^{rd}$ language by mapping and templates, based on the first language, especially with grammar or rules, for more efficient learning.

In one embodiment, the machine learns the OCR or recognition of the text based on strokes or basic curves which in combination make up the letters. For example, for letter "t", we have the shape "l" plus the shape "-", with their relative positions with respect to each other. So, we have 2 basic strokes in our dictionary, so far, namely, "l" and "-". Once we do this for all letters and marks on keyboard or in language, we get a lot of basic strokes in common in our dictionary, which we can re-use for others.

In one embodiment, the machine learns based upon the strokes, first. Then, it learns based on the shape of letters, e.g. "t". Then, it learns based on the words, e.g. "tall". Then, it learns based on the phrases, e.g. "tall building". So, in multiple stages, it graduates from basics to more complex structures, and reads phrase by phrase to understand the text, similar to an experienced human speed reader, who can read the articles in a specific subject of her specialty very fast, faster than an average person, in which she scans, reads, and understands the text by chunks bigger than simple letters or words.

In one embodiment, instead of the machine learning in different stages, the $1^{st}$ machine learns the strokes, and feeds to the $2^{nd}$ machine, which learns the letters, and feeds to the $3^{rd}$ machine, which learns the words, and feeds to the 4th machine, which learns the phrases, and so on.

In one embodiment, we have a neural network, with multiple hidden layers, each layer representing a more complex structure, for learning process, e.g. the first one for strokes, the second one for letters, the third one for words, the fourth one for phrases, and so on. In one embodiment, we have enough processing elements (PE) in each hidden layer for our learning machine, with artificial neural network (ANN) structure, so that it can accommodate a language with all its strokes, letters, words, and phrases. For example, for English language, for the second layer, we have 26 PEs, if we only deal with the 26 English letters of alphabet, and only with lower case, and only in one type and format, as our universe of possibilities, for recognition purposes. In one embodiment, with enough training and samples, with all the weights and PEs set, we set all the recognition for letter-level recognition in the language at the second hidden layer.

Data Segmentation or Classification, for Data Processing or Recognition:

In another word, in our daily life, we routinely receive a large amount of data, in which a first subset of that data may be useful for the first task, and a second subset of that data is useful for the second task (analysis, recognition, or distinction). So, for the first task, if we get rid of the rest of the original data that is not used, as useless data, to save storage space or increase recovery or retrieval speed, then, later, for the second task, we do not have the proper data for the second subset of the data, to complete the second task properly. However, if we have enough space to keep all or most of the original data, at least temporarily, to keep most or all of the second subset, or to keep all of the original data intact, then our second task can be accomplished successfully or relatively more successfully. One example is when we get voice data and image data from the same source at the same time, and the first task is to understand the voice data, and the second task is to understand the image data, which (in turn) comprises text images and pictures, which corresponds to subtask of text recognition (e.g. OCR) and subtask of picture recognition (e.g. face recognition). FIG. 171 is an example of such a system.

Data Segmentation or Classification, for Separate Optimization:

Another situation is when, for example, we have a compound image, which includes the combination of thin sharp line drawings and color photos. If one tries to optimize or improve the quality of one region or one type, e.g., the color photos, the other regions or types can be defocused or smudged, e.g. un-sharpening the lines, which destroys the crisp and sharpness or continuity of the thin line drawings, effectively destroying the black/white line drawings (or the text part) of the image. That is, we degrade the second part of the image, by improving the first part or section or type or region of the image.

Thus, we may want to classify and segment the original data, so that each part or section or type is optimized or improved separately, as the optimization is not universal for all parts of the image or data. For example, to read the text better/improve the text quality, the rest of the image (e.g. the color pictures) may get degraded at the same time. Thus, in one example, it is better to segment and classify first, and then do the optimization per region or type, or per task, as needed, e.g. to optimize the text only, and leave the rest of the image intact.

Separate optimizations with different degrees of optimization or filtering or transformation can be applied to different regions of an image, as shown in an example in FIGS. 129 and 176 (for the general system). So, for example, for intensity, for some part of the image, we emphasize, and in another part of the image, we deemphasize, to bring out some features for examination and recognition, optimized for that range of intensity. Thus, we map the intensity off-diagonal for a range, for different regions of image, as shown in FIG. 129. Then, we union all of the regions together to get the whole picture at the end. Or, alternatively, in one example, one can change everything along with the text optimization, altogether, which possibly degrades the other parts of the image, as the result. That is, the text is improved, at the expense of everything else in the image, e.g., for the situations which we do not care about the non-text data.

Optimization:

Note that the optimization is not universal. For example, we take a picture at night with a camera using a flash light, from a metal surface, with high reflection of light, which overwhelms the resulting image, with a big blob of high intensity light reflected and captured in the image, and the text underneath is not visible at all, at the first glance. However, if one plays with and adjusts contrast and intensity/other image parameters, at one point the text on the image from the metal surface becomes visible, of course, at the expense of the rest of the image (as it becomes degraded). That is, the optimization is usually localized and for specific purpose. That is, generally, the optimization is not universal, or not for all-purposes, or not for all types of data, or not for all regions of image.

Scope of Search:

In one embodiment, we start from task or goal, to limit or set the scope of search or result or filtering. Thus, the question (or task or goal or what we are asked for or looking for) ultimately determines how to optimize (or view or filter or twist or modify or convert or transform) the data or image. That is, the assigned task gives the proper context or scope, so that we can focus to search or filter or optimize for the corresponding answer or result. That is, there is no single answer or filtering for all tasks or goals. Each task demands and corresponds to its own filter or transformation or result. That is, the scope of the transformation or filtering is determined or limited by the task (or assigned goal at hand), itself. Another way to look at it is that once we define the "noise", as what the noise is in that context or environment, then we can define the filter that reduces that noise, which sets the goals or tasks for our optimization.

Relationship Possibilities:

Note that there are extremely large amount of relationship possibilities from a very limited finite set of data. For example, let's look at the tiger example again. The tigers may have only about 20 different stripes, as an example, as a finite and very limited set of data, e.g., expressed by a set of pixel data representing an image, e.g., with specific 256 color resolutions for each component of color RGB data and at 600×600 dpi pixel resolution in 2-D orthogonal axes/directions.

However, we can define much bigger number of relationships (e.g. hundreds of billions (although some are not independent of others, and can be derived from others)) between these 20 stripes, e.g. ratio between width and length of each stripe or between stripes, or angles or curvatures of each stripe or multiple stripes, as different combinations of ratios of these features, which by far dwarfs the number or size of the original data corresponding to 20 different stripes. However, from among all these ratios (e.g. billions), maybe, there are only a handful, say e.g., 3 stripes behind the nose and ear for each tiger, with their corresponding lengths or their ratios, that produce only 6 numbers, as an example, that are the determining parameters to distinguish any tiger in the set. So, only 6 numbers are needed for our recognition process. However, this is not readily apparent, when we look at the original 600×600 image, or when we look at the billions of calculated ratios or relationships or lengths.

Thus, one has to know what to look for, which is usually a subset of the original data or relationships or features, to make the recognition in the universe of the objects, to recognize all or most of the members of that universe. To zoom and focus on those 6 numbers (as an example), one can reduce the calculation and memory needed to do the task of the recognition, the same way a tiger recognizing her own family and siblings in a fast and efficient way, with much less analysis than an average human would do, to recognize the same tigers, if it is possible at all.

In one embodiment, we do not know what we are looking for, e.g. in a "big data" analytics. In those situations, we guess at some pattern or feature, as candidate(s), from our history or experience or library or other user's experience or using expert's opinion in other or similar situations, to test the hypothesis, to see if the first candidate yields anything in search or recognition. If not, then the system moves to the second candidate, and so on, to exhaust the list of candidates. If any candidate yields anything, then we continue the analysis on that candidate and follow that pattern or feature. In principal, we may end up using multiple candidates and find all the corresponding patterns or features.

The candidates can also be picked up randomly from our universe of possibilities or library, in some situations, e.g. where there is no preference in mind, or no experience or history on file. For example, for images received, we may want to see if we can find any face in the images, or find any text, or car, or any function with sinusoidal behavior (e.g. periodic), e.g. with intensity of pixels going up and down periodically, e.g. in a bar-code image with parallel stripes with some periodicity (T) or frequency (f).

Multiple Recognizers or Classifiers:

Let's look at the human/face recognizer engine or module or software. If a recognizer is trained for pictures or images of people from Middle East to distinguish among them (first module), and another one is trained from Chinese or oriental people or training samples or images (second module), then we do not want to re-train one module to change its weights, e.g. neural network weights, to convert or optimize first module to become second module. Thus, we want to keep both as-is, as each module is optimized on a subset of samples. So, in a first level, we figure out and sort based on the regions of the world, on a coarse and quick basis, and on the second level of analysis, we send the result(s) or images for analysis to the first module and the second module, and so on, which are optimized based on a subset or region of the world or population, to do an accurate recognition in that subset, only. This hierarchical model can expand to many layers, to go to subsets of a subset, for further analysis. So, in this embodiment, to be efficient, not all recognitions are done in one level or one recognizer or one neural network, as an example. See e.g. FIG. 130 for such a system.

In one embodiment, we use our search engine as multiple expert systems, e.g. it has a section for English language, a section for French language, a section for car engine, a section for food and wine, and the like. See e.g. FIG. 131 for such a system. By splitting the queries or searches according to classes or topics, and then splitting into subtopics and sub-subtopics and so on, we can get the context right, to go to the appropriate Z-web. For example, an abbreviation or word used in food industry has no meaning or different meaning than that of the car industry. So, for efficiency and for accuracy, we need to get the context or environment right as soon as possible, and classify and process accordingly.

FIG. 127 shows a system for context determination, with language input device, which feeds dissecting and parsing modules to get the components or parts of the sentence, which feeds the analyzing module (which e.g. may include memory units and processor units or CPU or computing module), which is connected to the context determination module, which is connected to the default analyzer module and multiple other context analyzer modules, each with different expertise or level of analysis or depth or subject matter (e.g. scientific expertise, or chemical expertise or knowledge), which are all connected to the sorting module, which is connected to both fuzzy membership values module (or alternatively, crisp scoring value or weight module) and correlation module (to sort and correlate the results), which is connected to the aggregator module to aggregate the results from above, which is connected to output module, e.g. printout or computer monitor or display or any graphic or table or list generator, for the user to use or see, or for other systems to use, e.g. as an input (e.g. without any human intervention or input or review).

In one embodiment, the context is hard to guess from one sentence ($S_{text}$). So, we usually need a large sampling or history or third entity input. However, in one example, Z-web itself can also help set the context right. For example, if we have 2 context candidates in mind to try, namely Context-1 and Context-2, then the corresponding Z-webs can be examined, namely Z-web-1 and Z-web-2, respectively. Then, if e.g. we have more nodes (or higher weights or reliability factors) related to our $S_{text}$ from Z-web-1 than that of Z-web-2, then we can conclude that between the two contexts, Z-web-1 or Context-1 is probably a more relevant context. So, between the 2 choices, we choose Context-1 as our context. See e.g. FIG. 132 for such a structure or system.

In one embodiment, we have multiple recognizers or classifiers, with different degrees of complexity (and overhead and cost and accuracy and depth analysis and focus). We cascade or chain them as from simple to more complex ones in series, one feeding the other, so that if the answer is NO for one level, it does not have to try the next level classifier any more, and stops the process at that point, with exit from the loop. If the answer is YES, then it tries the next level classifier, which goes more in depth, to find more about the object, or classify more specifically, based on the result of the previous classifier (which had a broader scope of inspection). For example, first, we find it is a text document, then, we will find out it is a book, and then, we will find out it is a novel. Obviously, if it were not a "text" determination at the first level of classification, we did not have to activate or feed it into the "book classifier" or "novel classifier" in the next steps, as they would have been useless, as their expertise or focus would not be needed at all. Thus, the system is more efficient and more compartmentalized and more expert-oriented and more depth analysis and deeper classification or recognition, now.

To combine classifiers, in one embodiment, for classifiers which only return the selected class or rejection, we can use the following methods to combine the classifiers: maximizing posterior probabilities, voting method, or Dempster-Shafer theory. To combine classifiers, in one embodiment, for classifiers which return a ranked list of classes or categories, we can use the following methods to combine the classifiers: Borda counts or logistic regression method. To combine classifiers, in one embodiment, for classifiers which return a ranked list of classes or categories, together with the classifiers which return a measurement associated with each class, we can use the following methods to combine the classifiers: weighted sum, ruled based, fuzzy integral model for classifier fusion, associative switch, or trained perceptron. To combine classifiers, in one embodiment, for all classifiers of any type, we can use the hierarchical decision making method. To combine classifiers, in one embodiment, we use and add the complementary classifier, to improve the performance of the combination. To combine classifiers, in one embodiment, we use unanimous voting or majority voting scheme for combination.

Classifiers:

In one embodiment, we have the nearest neighbor rule for training samples and the closest prototype, for assigning the corresponding class, to optimize the classification. In one embodiment, we get a binarized image. Then, it is thinned to get the skeleton image. Then, the system extracts a set of features to classify (as a separate class for recognition).

In one embodiment, we use a Markov chain-based classifier, with state transition probability depending only on the current state. For example, for Markov chain, we can represent an object with its boundaries or border or edge line, which is represented by a collection of points connected together using short straight lines, which can be represented by a chain of points, going from one to next, based on a direction and distance values, to set or get to the next point. So, starting from point one, we can complete the loop and find the boundaries or border of an object, and each point depends on the prior point in the chain, which is based on Markov model.

In one embodiment, for classification, we use "Fuzzy c-Means Clustering Method", with a fuzzy pseudopartition or fuzzy c-partition of our set (where c is the number of fuzzy classes in partition), in terms of cluster centers, and using inner product induced norm in our space (representing distances in that space). The performance metrics measures the weighted sum of distances between cluster centers and elements in those clusters. We want to minimize such a function. First, we choose an initial pseudopartition. Then, we calculate the c-cluster centers in the form of:

$$S_i = (\Sigma_k [P_i(x_k)]^n x_k) / (\Sigma_k [P_i(x_k)]^n)$$

for the initial pseudopartition and a specific n, wherein $\{P_1, P_2, \ldots, P_c\}$ represents a fuzzy pseudopartition, $x_k$ represents a set of given data, and $S_i$ represents the partition (with association being strong within clusters, but weak between clusters).

Then, we update the values, for (t+1) instance: If the distance measure $\|x_k - S_{i(t)}\|^2 > 0$, then we have:

$$P_i^{(t+1)}(x_k) = (\Sigma_j ((\|x_k - S_{i(t)}\|^2) / (\|x_k - S_{j(t)}\|^2))^{(1/n-1)})^{-1}$$

wherein j runs from 1 to c. If $\|x_k - S_{i(t)}\|^2 = 0$, then we have: $(\Sigma_i P_i^{(t+1)}(x_k) = 1)$, for ($i \in 1$). Otherwise, we have: $(P_i^{(t+1)}(x_k) = 0)$.

Then, we compare the values for instances t and (t+1). If the difference (or the distance in our space) is less than a predetermined threshold, then the system stops the process (and exits the loop). Otherwise, the system (or controller or processor) increases the counter t by 1, and repeats the loop again, as shown above (until it exits the loop at one point in the future).

In one embodiment, in the manipulation of Z-web, for any fuzzy clustering, we use the method detailed above, for clustering and recognition purposes.

In one embodiment, for pattern recognition or classification, we use clustering tree, e.g. with Euclidean distance or Hamming distance, or use Fuzzy Membership Roster Method. In one embodiment, for fuzzy pattern recognition, we use the degree of membership of an object to associate the object to a class or multiple classes (in contrast to the conventional or classical classification goal or method). That gives us more flexibility for classification. In one embodiment, we use a minimum threshold, for min. value for the membership, below which the membership is set to zero.

In one embodiment, we use fuzzy syntactic method for language(s) and its respective grammar, which governs the rules for string of symbols that makes up the language (or replaces the language or makes a template or encodes the language or summarizes the language). In one embodiment, we use fuzzy grammar, which is not crisp, and is based on overlap and partial relationship, with membership function or value expressing such a relationship, relaxing the strict requirement by crisp or conventional grammar, making it more compatible with natural language processing and human language. In one embodiment, we use multi-level hierarchical classification method, for class, subclass, and so on, at different levels.

Minimum Number of Objects Needed:

For the minimum number of objects needed for defining or describing a situation or relationship, let's look at one example. Let's assume a mother is teaching her new-born son how to speak English. If in that universe, there is no radio, TV, CD, or book available, and there is nobody else available to talk to them, then the distinction between "I" and "You" would be very hard for the son to understand, as he may think that "You" is his first name, at least at the beginning, because there is no third person to talk to, or other interactions with a third party, or a video to watch with a third person talking in it, that can set the meaning of "You" properly for the son. So, it would, at least initially, be very confusing for the son. So, for any given situation, one needs a minimum number of objects, or a "minimum" arrangement or setup, to define the situation properly and define the relationship between those objects properly.

Minimum Vocabulary Needed:

In addition, in a universe with 2 people only, there is no need to have a third person referral, e.g., "he", "she", "him", or "hers", in the language, because there is no use for it at all, and it may not make any sense to have an extra baggage or term or name or reference in the language for a non-existence concept or object. So, in one embodiment, we can reduce and simplify the minimum vocabulary set needed to operate or communicate in that universe, by eliminating the excess baggage or words or terms.

Age Progression Model for Pictures:

For all human races, genders, and face shapes, one finds $N_P$ clusters, based on $P_D$ dimensions or number of parameters extracted from each sample. For each type of face, from $N_P$ possible types, one defines or designs a set of $S_A$ age progression templates for different ages of the person, which can be morphed in a series, as the person gets old. This can be done analytical or mathematical based on coordinates and curves defined for each face. This can also be done by using a series of pictures from a real person at different ages, to fit the model, or for learning using a neural network, or use as template for that type of face. Of course, the larger the number of examples or number of people, $M_P$, the better the template will be for the fit. So, we need a lot of pictures of many people of different face shapes, at different ages. See e.g. FIG. 133 for such a system.

To be efficient, we use a subset of those images, as the ones from similar ages do not help any further. For example, the image of a person between 41 and 42 years of age does not generally change much. So, it is not much helpful to store both. But, image of a person, for every 6 months, between the ages 2-3, changes a lot, and so, it should be stored more often/frequent at younger ages, as an example. So, in a series of age progression images, one can mark the major changes as the main ages or images to keep, as a good sampling set or collection. So, we define the difference between 2 images, e.g. at pixel level, as difference between pixels, divided by the value of the original pixel, as the normalized value, to compare the relative changes in images at different ages, to find the largest jumps and changes at different ages.

So, we can find the major changes from real images. Alternatively, we can find the major changes based on prior knowledge from many thousands of images of other people, to categorize the age brackets, and find the break points, or alternatively, from medical database, indicating the expected changes for an average human, for various major changes in shape, height, face, or features, e.g. beard or hair loss, versus age brackets or break points in time axis, e.g. for the people from Middle East, as a subset of population, with expected values.

Note that if the scales or angles of view of the faces are not the same, in 2 images, then, before comparison, we have to adjust or normalize to one size or direction, so that we can compare them meaningfully. To adjust the size, one measures e.g. the length or width or diagonal of the face or nose, as the calibration metrics or normalization factor, to scale one with respect to the second one. To adjust the angle, one has to look at the symmetry or direction of the nose with respect to the oval of the face or position of ears or eyes, as an example, to estimate the direction and angle of rotation, to adjust the direction of the face, or normalize the direction. For angle adjustment, we use models we have for rotation of the face as templates, to morph one to the other direction. The models are based on $N_p$ possible types of the head or face in our database, described above, to get a better result. After rotation of the face, we compare it to the second image, which has about the same orientation. Then, it is a fair comparison. In one embodiment, all faces are turned to the same direction for comparisons, e.g. front view, only. See e.g. FIG. 134 for such a system.

In one embodiment, instead of rotating the image, we look for an image of the same person corresponding to the same rotated view or angle, from the same age category, if it is available in the database. Then, no rotation is needed, and less computation power is used.

To do the morphing from the first angle to the second angle, for the image of the face, we model the face or head as a mesh with contours, with points on it, as a template for each angle (or direction or view). Moving from one point from the first angle template to the next corresponding point on the second angle template is equivalent to moving the contours or meshes slightly around its current position. We choose the morphing in small increments for angles so that the differences are manageable by slight movements of contours or meshes. We can model the slight movements by vectors and translations and rotations of vectors, or a combination of them, in a series of instructions to morph properly, for piecewise regions of mesh or contour on the face.

Another way to do this vector modeling is by modeling and fitting a real picture or image of a person at different angles point by point (by coordinate in 3-D), then connecting the neighboring points to get contours, and from the series of contours get the mesh, modeling the face. Then, we have this repeated for different angles for the same person. Then, store the data for that person, representing one of the $N_P$ possible types, that corresponds to that type of head or face, in a database, for future referral and comparison.

During this process, for a given first point on the mesh, we find a corresponding second point on the template for a second angle or view. Then, on the coordinate of the 3-D model, with 3 components (x, y, z), we find how much the first point (x1, y1, z1) moved (to the second point (x2, y2, z2)), which is:

(x2−x1) in x-direction
(y2−y1) in y-direction
(z2−z1) in z-direction

We can repeat/get this calculated for multiple points, and then model all of those changes in coordinates in 3-D for those multiple points, using translation, scaling, and rotation, or a combination of the above. That would be our final recipe or series of instructions or steps for morphing process.

Please note that the translation is based on (x2−x1) in x-direction, (y2−y1) in y-direction, and (z2−z1) in z-direction. The scaling is based on (A x1) in x-direction, (B y1) in y-direction, and (C z1) in z-direction. The rotation is based on matrix of rotation, e.g. in 2-D expressed as a 2×2 matrix ($M_{2 \times 2}$), with the following 4 entries ($M_{ij}$), for a clockwise rotation by angle α on a 2-D plane, as one example:

$M_{11}$=cos α; $M_{12}$=−sin α; $M_{21}$=sin α; $M_{22}$=cos α

In one embodiment, we use 3 types of templates for face model in 3-D (dimensional) for face recognition, or after scanning the face (with a light, scanner, or by a 2D image or multiple 2-D images), or for storage, library, or comparison, alone or in combination: (1) wire mesh using thousands of points on the face, (2) contours of face for topography and geometry, e.g. cheek bone curves and structure, and (3) semantic model, which models the face based on the general semantics and description of the face, e.g. "big nose" or "small lips", which are Fuzzy descriptions, with corresponding library of descriptors and shapes, plus rules engine or database, defining those beforehand, so that we can store or reconstruct or combine Fuzzy features e.g. "big nose" and "small lips", and e.g. make up a face from descriptors later, or compare 2 faces just using descriptors without reconstructing the faces at all, which is very fast and cheap, for a Fuzzy match or closeness degree. In one embodiment, we use many small steps between Fuzzy descriptors on the scale or axis, to have differentiation between objects more easily and have a good coverage for all samples in the defined set or universe, e.g. for "height" property, we will have: "short", "very short", "very very short", "extremely short", "unbelievably short", and so on. See e.g. FIG. 135 for such a system.

The method of recognition mentioned above is helpful as one of the parameters for face recognition, or validation for identity of a person, using pictures of different years or ages, to find a person. Identity recognition, in turn, is a factor for determination of the relationships between objects and humans (or other subjects), and to build such a web of relationships or Z-web from all these determinations, like a tree structure, with nodes and branches, with strength of relationship and reliability of the determination e.g. symbolized with the thickness and inverse length of the branches (respectively), connecting the concepts as nodes, for example, for display purposes, for visual examination by the user (which we call Z-web).

In one embodiment, we have a picture, or multiple pictures of a same person, possibly from different angles, and then we feed that to the system, and then from library, based on shape comparison (e.g. features and parameters of the head in N-dimensional feature space), the system chooses the most possible type of head, out of say e.g. 105 types it has, to suggest that as a model. Once we have the model, we fit those one or more pictures into that model, and construct point by point or mesh structure or contour map of the face. The model has some parameters as variables, which can be adjusted in 3D using those 2D images as input, which gives elasticity to the form of the face and head in the 3D format, for minor adjustments to the 3D model in computer (which can be displayed for the user, as well, as an option). In addition, the same 3D model can be input to a 3D printer, or 2D rendering image printer, or laser induced bubble printer (in plastic or glass), to construct the same head in the solid format, e.g. in glass or plastic or polymer.

In one embodiment, we have e.g. front view of a person, e.g. in a picture or image. Then, we use slanting or some deforming lens or filter or translational transform(s) to change the shape of the face slightly, and store them as the basis for the rotating or moving head slightly, from the front view position (from its original position, with small perturbation or movements), in the library. So, we can use them as eigenfaces for frontal or near frontal sideway faces, for the future face modeling, face replacement, face recognition, face storage, as linear combination of eigenfaces, face approximation, efficient storing of faces, coding the face, and comparison of faces. See e.g. FIG. 136 for such a system.

In one embodiment, we have orthogonal or orthonormal eigenfaces as basis. In one embodiment, we have non-orthogonal or non-orthonormal eigenfaces as basis, e.g. some being as linear combination of others, which is less efficient for recognition (and being too redundant), but easier to generate the basis functions, due to less constraints on basis functions. In one embodiment, we obtain eigenfaces from thousands of samples, by cloudifying or fuzzifying or averaging pixels in large neighborhood regions for the samples, in the first step. Then, optionally, we can stop there, and use the result of the first step as our final answer, as eigenfaces. Or, we go one more step, in another embodiment, and we average the first step results together, to get even more "cloudy" images, as our final result, for our basis, for eigenfaces. Or, we go one more step, in a loop, recursively, in another embodiment, and we average the averages again, until it is cloudy enough or we reach N loop count, and we stop at that point, yielding our eigenfaces. Then, any given face is a linear combination of our eigenfaces. See e.g. FIG. 137 for such a system.

To remove redundant eigenfaces from our basis functions, e.g. to have an orthogonal set, we try or choose one eigenface, and if we can write it in terms of linear combination of others, then that chosen eigenface is redundant (and not needed) and can be removed from the set. In one embodiment, to make some image fuzzified, we can use fuzzy parameters, rather than crisp ones, or use dirty or oily lens for image, or use defocused lens or out-of-focus lens for images, as a filter or transformation or operator, to get the cloudy or average effect between pixels.

In one embodiment, for face recognition, or eyes or any other object, we have Sobel operator or filter or matrix or convolution, based on gradient or derivative, so that the operator finds the gradient of the image intensity at each pixel, e.g. the direction of the largest increase for pixel intensity (with the rate) or contrast, as an indication of abruptness of changes in the image, to find the edges or boundaries, to find the objects or recognize them. In one embodiment, other filter kernels, e.g. Scharr operators, can be used for edge detection or gradient analysis.

In one embodiment, for face recognition, we use edge detection or other object recognition methods to find eyes (or nose), first, as an anchor point or feature. Then, from the eyes' positions, we know relatively where other parts may be located, if it is a real face, based on expected values or distances based on face models in library, e.g. as a probability distribution or expected value or average value or median value, for distances. See e.g. FIG. 138 for such a system. Or, in one embodiment, based on the eyes' positions, we can normalize the face size or other components or the image, for faster comparison. In one embodiment, for face recognition, we find the edges, first. In one embodiment, for face recognition, we find the separate components, e.g. eyes and nose and mouth, first. In one embodiment, for face recognition, we find the whole face, as a whole, first, using e.g. eigenfaces. In one embodiment, we combine the 3 methods mentioned above, for different parts or components or stages of image or object or recognition process, for higher efficiency. In one embodiment, we generate the eigenfaces based on a large number of samples or pictures of many people, e.g. from front view or from side view, for different sets of corresponding eigenfaces, for front or side view, respectively, e.g. using averaging or weighted averaging on pictures, or using a training module.

Z-Web Representation and Manipulation:

The graphic representation of Z-web makes it easier to visually understand the strength of relationship and reliability factor, among other factors embedded in the Z-web, as explained in other parts of the current specification. The graphical representation also mirrors fuzzy parameters, as the human visual perception is not crisp, but it is fuzzy, similar to natural language processing and expression.

To get an object, one searches for nodes on the Z-web (e.g. using an index on a database or listing, using a query), and once the node is determined or found, the connectors and branches coming to or from that node are examined for determination of the reliability and other factors mentioned in this disclosure, from the numbers or sizes or dimensions associated with the connectors and branches, e.g. the thickness or length of the branch between 2 nodes. The "circle of influence" is based on (in different embodiments): the neighboring nodes, or N-th neighboring nodes, or nodes within radius $R_{node}$, centered at that original node, as a hyper-sphere, in the m-dimensional Z-web space, with m coordinates. The circle of influence gives us the guidance as to where and how far we should go for related nodes or concepts or objects, in the branches, to find other objects or recognize objects or find the reliabilities or confirm the objects. Sometimes, the influence of the circle of influence dies off gradually, and not abruptly, using a fuzzy parameter to model that behavior. In other embodiments, the influence of the circle of influence dies off abruptly, which is an easier model to handle and calculate for.

The user interface or GUI is based on a region or section of Z-web displayed in 3-dimensional or 2-dimensional space or coordinate, in one example. The storage of the Z-web is done in relational databases, in one example, to store node parameters and branch parameters and values, which can be fuzzy or crisp or based on natural language, e.g. "small", e.g., to describe the length of the branch.

To insert some nodes, in between 2 nodes, e.g., one can break the branch connecting the 2 nodes, and insert the piece or node in between, and add 2 new branches to the beginning and end of the added piece, to connect to the rest of the Z-web to expand the Z-web, if needed. The reverse process is applicable, for elimination of a node, if the concept or object is not applicable anymore (e.g. a species of an animal is extinct in year 2020, and the node relating or describing the current live species on planet Earth described in the Z-web has to be updated and eliminated).

Two (or more) Z-webs can be combined, as well. For example, if they do not have any common nodes, the combination is just the simple union of both, with not much adjustment. However, if they have some common nodes (e.g. object "animal" being present in both Z-webs, as a common node), the common nodes can be overlapped together, as a single node, and the branches for a common node can be added from one Z-web into another Z-web. After that, any other node or branch automatically follows the old connections they had from the original 2 Z-webs. However, in one embodiment, we make an adjustment on the values for nodes and branches for the overlapped common nodes to make them compatible. For example, all values can be normalized based on the value of one node on the first Z-web, with respect to the corresponding value of the same node on the second Z-web (mirror node), or ratio of those two values applied to all the values on the second Z-web, to "normalize" the second Z-web, with respect to the first Z-web, to make them compatible.

In one embodiment, we make the adjustment on the node, based on the reliability factor, or other factors mentioned in this disclosure. For example, the value of the first node on the first Z-web is changed towards (or changed to) its mirror node on the second Z-web, if the second Z-web has more reliability factor corresponding to that node. The change can be straight and exact assignment of the value of the mirror node, or can be gradual or partial adjustment towards that value, which could be a fuzzy concept by itself, for example, "almost the value of mirror node" or "90 percent of the value of mirror node".

In one embodiment, one party makes a first Z-web, and then combines it with N other parties producing N other Z-webs, as described above, to increase the knowledge base and relationship base, including reliability, credibility, truth value, and other factors mentioned elsewhere in this disclosure. This also takes care of the contradictions and inconsistent results, to fix or find anomalies or biases or other parameters described in this disclosure.

As time passes, the size of the super-Z-web increases, and its value grows, as more people or entities contribute to that super-Z-web, which includes more concepts and objects. If all branches associated with a node is broken, the node becomes irrelevant, and can be eliminated from the Z-web. If a node is accessed a lot, its "popularity" value goes up, making it harder to break the branches later. If a value is confirmed or approximately confirmed, in a fuzzy sense, then the reliability of that value increases.

The branches between nodes are not-directional, in one embodiment, so that the relationship is e.g. bi-directional or symmetric. For example, if object A is close to, or located close to, B, in terms of Euclidean distance or meter or length, then B is also close to A. Thus, relationship between A and B is symmetric in that respect. However, in another example, the relationship of "ownership" is not symmetric between a "car" and a "person", because a person owns a car, but not vice versa. Thus, "ownership" is a directional relationship or branch, between 2 nodes. See e.g. FIG. 139 for such a system.

In one embodiment, we have hunches or random guesses, or using guided templates, to follow some scenarios, to guess and validate some relationships between the objects. The rules are used for validation of the hunch or guess, e.g. using game theory. For example, one relationship between 2 people in a picture is father-son relationship, as a guess, which can be suggested and followed up to validate that guess, if it is true. If the parameters are non-crisp, then we use Fuzzy logic and sets and boundaries and values. If the assumption or guess ends up with contradiction, we back track, to invalidate the original assumption, and try another guess.

Of course, if later on, we have an input from social network (e.g. FACEBOOK® or LINKEDIN®) or family picture or family album web site or matching family names (or maiden name) or ancestry-type web site, that 2 people may be related, then we do not need to try the guess scheme, and the discovery goes much faster.

In one embodiment, to update a first object, which is based on one or more second object(s), the system tags the second object(s) or node(s) in the Z-web, so that if there is any changes on the second object (e.g. above a threshold, or any changes whatsoever), then as a trigger event, it would trigger the Z-web to ask the calculation module or the processor module to recalculate the first node and all its properties, including all its Z-factors, and optionally let the user know about the update event, for the user to extract data from the first node again, if desired. In one embodiment, it also propagates the update to the other nodes in the Z-web, or other related Z-webs. In one embodiment, this is used for incremental or small changes, or for fast update, or parallel updates in various regions of the Z-web (regionally or in small scale e.g. around one node only). In one embodiment, we have a Z-web with multiple nodes connected to each other, based on the relationships and functions, with different strengths or closeness for each branch connecting the nodes, each having its own Z-factor, including reliability factor and other factors discussed in this disclosure, with each node representing an object, concept, emotion, status, mood, mode, state, subject, number, human, animal, car, table, face, name, birth date, event, or the like.

Accessory Models:

Now, let's look at the accessory models for humans, animals, objects, faces, eyes, or other body parts, for image recognition. For example, for a human, the person may wear or carry a pair of glasses, hair piece, hat, beard (real or fake), moustache (grow or wear, fake or real, e.g. with different styles or sizes or forms or shapes), ski mask, eye patch, sun glasses, scarf, big loose rain coat, turtleneck clothing, body or face covers, umbrella, other accessories, and the like. These alter, modify, cover partially or fully, or hide the features (e.g. curvatures or contours or markers) of the body, face, human, or animal, in a way to make it harder or difficult to make proper or correct recognitions or classifications.

To overcome this problem, we can do multiple solutions. First method is to extrapolate or interpolate the regions, colors, texture, or lines in the image, to fill up the gaps or missing or covered part(s). There are multiple ways to do this. One is to filter or un-sharpen the image or lines to fill the small gaps. Another way is to distinguish the regions or open regions or connected regions, to copy the texture or color from one and paste and extend the patches or small copied regions into the neighboring connected regions, to fill up the gaps with correct color and texture, as much as possible.

Another method is to first add (for example) a pair of glasses to the picture of a specific/same person, by superimposing the picture/image of a pair of glasses on top of the person's face/person's image, and then to compare the resulting image to the images with pair of glasses, for proper recognition or verification for the face or person.

Another way is to compare only the visible parts with corresponding parts of the target images, to find the matches or degree of matches, and treat the invisible parts or hidden regions as "DONOT CARE" regions or "NEUTRAL" regions, which do not contribute to the match analysis.

Another way is to first use a template or generic face with glasses or a model with glasses or an accessory model (e.g. using real image of mannequin, or computer generated model or mesh or 3D surface, or averaging the normalized coordinates of thousands of images of the face), to modify or morph the first image, to compare the modified image to the second image, for match analysis and recognition.

Another way is to use neural networks for training purpose, with a large set of faces with eye glasses (for example), so that the neural network is trained (with weights set) to distinguish a person with glasses, or distinguish a specific person with glasses (e.g. with any style or type of glasses, or even when the person not wearing the glasses). In that case, a person with many types of glasses can be photographed for input to the training module, for training the neural network. See e.g. FIG. 140 for such a system.

In one embodiment, one can model different glasses as a 2-D (2-dimensional) object, and superimpose on the first image/picture. In one embodiment, one can model different glasses as a 3-D object, and superimpose on the first image/picture. The 3-D model is more computing power intensive, but has the advantage of better perspective and more realistic views from different angles. In general, any accessory on human, face, animal, automobile, or other objects can be modeled in 2-D or 3-D model, and stored in one or more databases, for usage, superimposing, editing, replacing, morphing, converting, or adding to the image or model of another object, e.g., human, face, animal, automobile, or other objects.

In one embodiment, one models different glasses separately and models different faces separately, and then superimpose them together. In one embodiment, one models different glasses and different faces together, as one object. In one embodiment, one models the objects using a real faces and real glasses (e.g. pictures or images from real objects), by classifying them, using many training samples, and having at least one of each classification stored for future referral. For example, if we have $N_f$ different types of faces and $N_g$ different types of glasses, then we will have ($N_f \cdot N_g$) different types of combination of faces and glasses. Similarly, for M objects, we will have ($N_1 N_2 \ldots N_M$) different types of combination of those M objects, stored in the database.

In one embodiment, one models the objects using a real faces and computer generated glasses types. In one embodiment, one models the objects using a computer generated face types and real glasses. In one embodiment, one models the objects using a computer generated face types and computer generated glasses types.

In one embodiment, the computer generated types are based on real images of real objects, as well, which are classified as different types by the computer, and an average or typical sample is stored as an example of that specific type in the database. In one embodiment, the storage of the example is either analytical, e.g. mathematical formulation of curves and meshes, to mimic the surfaces in 3-D, or brute force storage as a point-by-point storage of coordinates of data points, in 3-D (x, y, z) coordinates.

Features in Images (or Other Subjects) are Recognized in Different Orders:

Let's assume we are showing a picture of a red 2-door convertible Ford car to multiple recognizer units or modules. In the first order or step, they all may recognize the car in the image. Then, in the second order or step, they may recognize red color, or 2-door, or convertible, or Ford brand. Thus, based on the background or experience or training of the recognizer units or modules, the next step may be very different for the recognition process. Eventually, all or most of the features may be obtained by most or all the recognizer modules, but in very different orders. So, there is no universal classification or universal correctness in recognition or absolute classifier or single answer or single recognition method or formula or procedure. Having said that, however, one can still get to the same answer from different routes, e.g., saying or recognizing or resulting in: "a red 2-door convertible Ford car", or the combination of the following features:

CAR→
 +RED+(TWO-DOOR)+CONVERTIBLE+(FORD BRAND)

The principle mentioned above is applicable for any other recognition or any other subject or object, e.g. voice recognition or music recognition.

Recognition Method in an Image, for Background and Foreground:

First, for example, we find the background in the image, such as sky or water. That also determines the direction and angle or tilt adjustment for the image. See e.g. FIG. 141 for such a system. For example, the sky is usually on the top, and the horizon line, separating land/water/ocean and sky, is horizontally oriented, to correct the tilt of the image. For example, the sky is recognized by the specific color or range of colors or patterns (such as cloudy sky or bright sky), and/or the continuity of the region with minor or no features or variations (such as patches of clouds in the sky, or stars in the black or dark sky at night), or using histograms for pixel intensity and variations (or colors) (or peaks and valleys and plateaus and shapes) as signatures for sky (compared to trained samples or many stored in library or database), or using Fourier or DCT analysis (for frequency domain analysis and coefficients, for comparisons or signature or feature detection, for recognition).

In one example, once we know the background, all other objects blocking the background, e.g. ocean or sky, will be foreground objects, e.g. boat or airplane, located or positioned in the ocean or sky, respectively. The foreground objects can be recognized from the database of objects, using object recognition module or device, as boat or airplane, and tagged accordingly after recognition process. The recognition can be based on silhouette or shape or shadow or profile or boundaries of an object with respect to the samples of the database, as the percentage of match, between the normalized objects, for faster and better comparisons, using a vector or chain piecewise comparison, or pixel-by-pixel comparison for the silhouette or shape or shadow or profile or boundaries of an object.

In one example, we remove the foreground, and we end up with patches or regions of background objects. For example, once we distinguish a man on the foreground as foreground object, we can remove the man from the image (ending up with a blank region), and end up with the 2 pieces of sofa that the man was sitting on, on the left and right sides of the image. From the texture and color, or continuity of the border lines or extension/direction of the border lines, of the 2 sides, we recognize that they belong, or most likely belong, to the same object. So, we fill up the blank region behind the man's position in the image with the same texture or color from either or both sides of the image (or use an average or mixture of the texture or color from both sides of the image). So, now, we end up with a whole sofa, which is much easier to recognize as one piece, or single region object.

Also, the fact that we know we are in a home environment or context helps us to narrow down to about 200 objects, for example, in our database, related to possible objects in the house, or belong to a specific person living in Canada (based on the conventional furniture for that part of the world, e.g. a sofa, or e.g., knowing a specific person originally from Middle East, with big traditional pillows on the sofa, as possible choices to search or compare for, from the possible-choice-databases, available or compiled by us, beforehand). See e.g. FIG. 142 for such a system.

In one embodiment, we can recognize the two sides of sofa as a single object, i.e. sofa, without filling up the gap or blank region(s) with color or textual patches using copy/paste routine explained above for small unit regions or patches or tiles, which can be square, rectangle, circular, or non-geometrical shapes, repeated until the whole blank region is scanned or filled up or painted. For example, we extend the boundaries or border lines from both sides to connect or complete the whole sofa border line, or approximately find or complete the border line, to find the final shape of the sofa, to recognize the object as possible sofa. The approximate line can be connected and recognized as one single line, when the line is thickened with a thickness of 2 to 10 points, or more points, to produce a continuous line (thick jagged line). See e.g. FIG. 143 for such a system.

In one embodiment, we assign a value of "I DO NOT KNOW" to the invisible part of the sofa, in which we try to find the fitting objects based on the visible parts of the sofa, from our library of possible objects, common for a setting, with the condition that on the back (where it is hidden), it can be anything. So, we calculate the reliabilities based on this scenario, and we use fuzzy values to describe this, in one embodiment. In one embodiment, we use Z-web for this purpose, with all corresponding Z-factors.

Adjusting the Tilt or Orientation:

The orientation of an image, such as from horizon line, or water or ocean line far away, or tower in background, which indicate horizontal line or vertical line in the perspective view or expectation of humans, indicate how much an image should be rotated or tilted to get into the right orientation. For example, that normalizes the head or face of a human to be in the right angle or direction or orientation, to pre-process, before the actual recognition of the face or head by the face recognition module. That increases the accuracy of the recognition at the end, for the objects at the foreground.

To Find a Continuous Line:

To find a continuous line, one searches for the next point in the line, e.g. black pixel or dot or similar color pixel, in left, right, diagonal left up, up, down, diagonal left down, diagonal right up, and diagonal right down, i.e., in all eight neighboring directions or pixels, to find any match, which produces continuity in the line, point-by-point, to extend the line.

For small discontinuity e.g. due to bad image quality or a copied image by old copy machine multiple times, the bridge gap of 1-2 pixels can be forgiven or filled up. Thus, the search is beyond the immediate neighboring pixels, going e.g. to the $3^{rd}$ neighboring pixels, to find a match of pixel, to assume continuity for the line, and filling up the gaps with the same pixel or dot, to get a final continuous line. Or, one can defocus or widen the lines, using a filter to reduce the contrast for the edges, to bridge the gap of 1-2 pixels with filled pixels or dots, to get a final continuous line.

To find a narrow boundary or border, from the thick jagged line mentioned above, one can get the average coordinates or select the middle points of the thick jagged line, as the final fine boundary, which defines the object, e.g. sofa, very well, with sharp boundaries, for easier detection or recognition, versus the object with thick boundaries, which is harder to detect, when the small features are hidden or overshadowed by thickness of the line, itself.

Another way is to use skeleton or bare bone shape, to simplify the shapes fast and efficiently, as the first-cut/coarse search and comparison, from database of skeletons or shapes, to name the objects or tag them, which accompanies the objects as comments or tags data from now on, after tagging.

Another way to find or recognize a sofa is to use DONOT CARE or NEUTRAL region assignments for the blank region, for partial matching with test images as targets, to find the similarities between the object and targets based on the visible parts, and treating the invisible parts as having any values possible (or ignore them, as having no or negligible weights), for comparison or recognition purposes. The final match score or probability is only or mostly based on the visible parts, with respect to target or possible-object databases.

Use Images from Different Angles or Perspectives:

To model an object, from a 3-D perspective, one models the object using images taken by a real camera, from different angles. For example, for the recognition of a face or person, one looks at the face from multiple directions, e.g. from side view left, front view, half-side view right, and back side. Thus, we store the multiple views from different camera positions or angles, for the same person, for later recognition of the person, to find an exact match or a match between two or more of these snap shots or images (i.e. using limited numbers of images, as discrete sampling, for continuous matching positions, later on), as interpolation or extrapolation of one or more images, or some weighted average of them, or some average of them.

Use Computer Models of Objects:

Also, one can use a computer generated model for N possible shape of heads for men, women, and children at different ages, for various ethnicities and races, based on the images of shapes of head taken and input them to the model (e.g. artificially rendered or calculated or constructed by a computer), to cluster and classify all possible head shapes on the planet (where N is usually a manageable number, say, e.g. 100). So, starting from a 2-D image of a new person's face or side-view (person P), it can trigger or match approximately the image of one of those N shapes from the head shape library, and thus, call up the corresponding model for the selected head shape from the library or database.

Now, in one embodiment, we have a correction that can make the model more accurate. We change the parameters of the head on the model slightly, to match the image of the face or head for person P exactly, from the 2-D image, using manual adjustments, or computer control or automatic adjustment, e.g. fuzzy rule based adjustment, to morph one to another, so that the contours and/or points on the mesh representing the face or nose or head match exactly with the model. The morphing mechanism details are described elsewhere in this disclosure.

In one embodiment, we have a correction that uses two or more of those N shapes (say, e.g. T number of those N shapes) from the head shape library, and then combine them to get an approximate match, e.g. using a linear combination of them, or weighted average of them, or take an average of them. Then, in one embodiment, we have a further correction, similar to above, to change the parameters of the head on the model slightly, to match the image of the face or head for person P exactly, from the 2-D image, using manual adjustments, or computer control or automatic adjustment, e.g. fuzzy rule based adjustment, to morph one to another, so that the contours and/or points on the mesh representing the face or nose or head match exactly with the model. The morphing mechanism details are described elsewhere in this disclosure.

In one embodiment, we have some or all of the N shapes sub-divided into $Q_1$ to $Q_N$ shapes, respectively, as subcategories, for minor differences between head shapes. Then, we have better matches based on subcategories. However, the overhead for storage and computation is much higher, since we are dealing with much higher number of shapes now. That is, we have now: $(Q_1+Q_2+ \ldots +Q_N)$ shapes, rather than N shapes.

In one embodiment, we adjust the mesh or points or contours representing the face or head, as an example, using the parameters that change the coordinate of points, or change the formulas for curves or family of contours, in the computer model, and changing those parameters by a small percentage or small relative deviation. Then, we observe the result: If the difference (e.g. sum of square of differences, or sum of absolute value of the differences, as error function) on the match for all points or contours or meshes with respect to the model for the selected shape gets larger (gets worse), then we should change in the other direction or change other parameters. If the difference on the match for all points or contours or meshes with respect to the model for the selected shape gets smaller (gets better), then we are on the right track, and we can continue on the same direction, until we get worse off. Then, we stop at that point for that parameter. Then, we try other parameters, one by one, or in a batch, or bunch together, to optimize for complete match with the model. That is, we use a feedback to adjust the parameters, for complete match, as much as possible.

In one embodiment, to adjust the difference value mentioned above, we may be in a local minima region of the optimization curve for the difference value(s) function mentioned above, and small adjustments may get us only into a local minima. However, to get into an absolute minima of the optimization curve for the difference value(s) function mentioned above, one has to get out of the local minima region. To do so, we need a random adjustment on the parameter(s) or big adjustment on the parameter(s), to land in another part of the optimization curve for the difference value(s) function mentioned above. That will increase the chances of getting out of the trap of being in a local minima region for all optimization adjustments at all times.

Of course, even if we get to local minima, rather than absolute minima, for optimization, we still may have a good result for match process, to stop further search and optimization or adjustments, as mentioned above. That can be checked using a relative or absolute value as threshold, or an incremental improvement analysis, to stop beyond a threshold, for the optimization process, as optimization any further would not worth the cost of more computation power spent on such incremental improvements, if any.

Look for Expected Objects:

For example, in an office environment, one has a list associated with a typical office or law firm office or dental office, which are stored as possible objects in the office, in a web of related objects, or databases, related to an OFFICE or DENTAL OFFICE. So, an object behind a person in an office on the table may be a fax machine, which is a possible target candidate for examination and image recognition comparison, obtained from the corresponding list of related objects for the OFFICE. That increases the reliability, speed, focus, and accuracy of the recognition process.

One can also re-use the related objects from one into another one. For example, an "office" is superset of a "dental office", for most cases. Thus, all properties of "office" are a subset of (and included in) those of a "dental office", including e.g., related objects or expected objects or owned objects or property objects. That is, they inherit each other's properties automatically. See e.g. FIG. 144 for such a system.

Of course, in one embodiment, these concepts above are all fuzzy concepts and sets, with no hard or crisp boundaries, and with qualifications e.g. "for most cases" or "usually". Please see the discussions elsewhere in this disclosure, regarding the handling and processing of these concepts, values, and parameters.

OCR, as Textual Information, to Help Build the Relationship Web Between Objects:

In the next step, as one example, we look for a text as an object in the image, to recognize, for example, the brand, model number, and the type of the object, e.g. HP printer Model Number 100, written on the object, as text. So, we invoke an OCR (optical character recognition) module to read the text, to find and search for more relationships between the objects in the image. The text in the image can be vertical, slanted, wavy, morphed, or curved, as in a book in a bookshelf, or as in a newspaper on a table at an angle to the camera or frame of the picture or image, or as in a word written as a motto or slogan on a flying flag with the wind power behind it, or as a reflection of some big poster on the side the building or highway reflecting the text image on a wavy water or pool or pond nearby, or as a security word for user authentication (against sniffing search bots) with a slanted or twisted image of a text, usually with no meaning, on the screen or monitor of a computer.

List of manufacturer and model numbers or the like are also listed in separate files or databases for search and matching or recognition or validation, to further limit or focus or specify the identification of the object, such as printer or fax machine in the example above, using the OCR as a tool or as one of the linking methods between the objects.

On the related objects, e.g., once a computer is determined as an object in the image, we can expect a possible mouse or monitor (with some degrees of certainty corresponding to each device), or with some membership function or value associated with a fuzzy membership for mouse as an accessory to a computer, and hence, expecting a mouse as an expected object nearby in the image, and thus, look for it as a target object around a given computer, from a database or list of possible objects in the neighborhood.

The Distance or Size as a Factor:

In one embodiment, the distance to the object is also taken into account, for example, G meter or feet, for estimation, for proximity or location analysis, as the search radius and location estimator, e.g. based on the center of the object, e.g. based on the estimated scale of the object or picture, or relative to the size of the neighboring objects, or typical size of the objects. For example, the mouse's length is about 20 percent, or 20 plus/minus 5 percent, or exactly 20 percent, of a length of a laptop, or a specific laptop, or typical laptop, or an average laptop, or for a range of laptops, obtained from our database for relationships between the related objects, e.g. laptop and expected nearby possible mouse, with its corresponding membership value and reliability value and expectation value, relating the 2 objects, from A to B, as 2 nodes, in the network or web or relationships, e.g. for distances or sizes. Another example is the typical distance between a laptop and a mouse is 1-5 feet, for possible search location possibilities, for the center or the edge of the object, e.g. mouse. See e.g. FIG. 145 for such a system.

For some examples, for fuzzy ranges or fuzzy values for distances, we use unfocused or fuzzy lines or fuzzy geometry lines, with fuzzy distances and fuzzy endings and fuzzy thickness, for geometrical representation in Z-web. For some examples, for crisp ranges of distances (or uncertain distances with error values), we use dotted lines around the average value or around the minimum value, for geometrical representation in Z-web. For some examples, for geometrical representation in Z-web, we can draw spheres or circles, for radius of search of a target object, with respect to two or more given objects, and from their intersections of the regions or overlaps of areas, we can further pinpoint the location or distance of the target object.

Note that the size of the object is estimated or determined by comparing to relative size or distances of other objects in the image or video frame, as typical values in the library, or as a value we already know for a specific object, e.g. Fred Jackson's height is 6 feet. It can be based on Fuzzy parameters and values, as well, e.g. Fred Jackson is very tall. The perspective or depth in the image can be estimated using rectangular objects, such as table, having merging boundary lines for parallel sides, by extending the border lines to the back of the image, so that they cross at an imaginary perspective point $I_{PP}$ in the background of the image, which indicates the perspective for the image with a point located at infinity, very far away. Note that $I_{PP}$ can generally be more than one point or a line, representing infinity, or far away, in the image, at the horizon. Then, from that, the relative size or distances or angles can be obtained, using simple geometry relationships, e.g. mapping the distances or other lines as a projection on the imaginary lines connection to $I_{PP}$ (called $L_{PP}$), or as a projection on lines perpendicular to those $L_{PP}$ lines (called $T_{PP}$), which are generally curved or circular shaped lines or family of lines with the center at $I_{PP}$, in the perspective coordinate system of the image. For example, we divide the image into family of $L_{PP}$ and $T_{PP}$ lines (or curved lines), with some distance between each of 2 neighboring family members, to cover the image like a tilted "floor tile" scheme, and then for each dimension in the image, we try to do the comparison with the dimensions in the same neighborhood with known sizes, e.g. from known objects, e.g. we know that Mark is 6 ft tall, and that gives a reference size for objects in his neighborhood in the image.

See e.g. FIG. 146 for such a system. In one embodiment, from FIG. 146, we can get the length of an object, e.g. vector V (with real length $L_V$, and apparent length V), as follows:

$$b = V \cos(E)$$

$$a = V \cos(G)$$

Now, we want the ratios, to some known values or objects, e.g. as shown on the highlighted rectangle in FIG. 146, with apparent side lengths $a_1$ and $b_1$, and the real side lengths $a_{real}$ and $b_{real}$, respectively. Then, we have:

$$a_{calculated} = (a/a_1) a_{real}$$

$$b_{calculated} = (b/b_1) b_{real}$$

$$L_V = \sqrt{(a_{calculated}^2 + b_{calculated}^2)}$$

In another embodiment, note that for $T_{PP}$, we have to find the distances on the curved lines, e.g. a piece of a circle with a radius on $L_{PP}$, originating from $I_{PP}$, and ending at the point of interest (at the intersection of those specific $L_{PP}$ and $T_{PP}$).

In another embodiment, the projection of a line $S_{PP}$ with a length $G_{PP}$ on the $L_{PP}$ line is mathematically given as, $P_{PP}$:

$$P_{PP} = G_{PP} \cdot \cos(A_{PP})$$

Wherein $A_{PP}$ is the angle between that specific line $S_{PP}$ and a neighboring $L_{PP}$ line, to project on the $L_{PP}$ line. Once we have the projected lengths on those specific $L_{PP}$ and $T_{PP}$, we can compare that with other projected lengths from known objects with known sizes in that neighborhood, as projected on the same nearest specific $L_{PP}$ and $T_{PP}$, to get a relative distance or size, or ratio, to get the size of the unknown object (approximately).

In another embodiment, instead of using projection values, as shown above, one simply compares the size of the line piece from the unknown object with the size of the line piece from a known object, in the same neighborhood, to get the ratio, and then, get the size of the unknown object (estimated). Of course, the smaller the meshes associated with $L_{PP}$ and $T_{PP}$, on the image, the more accurate this estimate will be.

Note that in the general case, going from A to B may be not the same as, or reversible, with respect to going from B to A, e.g. between mouse and laptop as 2 related objects in the relationship web, with respect to the values of membership value and reliability value and expectation value. Thus, we can show that by two arrows going from A to B, and from B to A, with different strength or thickness or width or length or size, signifying the various valuations of membership value and reliability value and expectation value, in different directions. For example, in some embodiments, the expected value of finding a mouse in a specific region or radius or coordinate in the image (given a laptop is found nearby, as an assumption) is different from its reverse situation, i.e., it is different from the expected value of finding a laptop (given a mouse is found nearby, as an assumption). See e.g. FIGS. 147, 132, and 139 for such a system.

In FIG. 147, as an example, we show a recollection of past event using Z-web, as a memory storage function, with Z-factors, including the reliability factor. The Node N is a trigger node, and the events are reconstructed or relationships are traversed backward to Node 1, our original node.

In other embodiments, the two directions are reversible and have the same values for both directions, e.g. for membership value and reliability value and expectation value, between 2 objects, e.g. mouse and laptop.

Now, having specification or range of expectations, for possibilities and probabilities, for example, for distances and sizes, one can search more accurately for the secondary object, e.g. mouse, around a given laptop in the image, or in the universe around us, as the primary object. For example, given a distance between centers of 2 objects, as 0-5 feet, we can design a circle around the primary object, with that radius of 5 feet, to define a region for possible existence of the secondary object, e.g. mouse. That would reduce or limit the search time and criteria, or increase accuracy for a given time and computing power.

The radius can be defined in 2-D or in 3-D space in the image, depending on the fact that the second object has or may have any support for standing in space outside the planes defined by the first object, e.g. having a tripod or legs or support for a camera or mouse. In the 3-D space, it becomes a sphere, with radius R (instead of a circle or projected circle), which has a cross sectional projection or view on the image as an ellipse or oval or curved region, depending on the point of view or perspective view of the camera or image or user. The region defined by circle or sphere, or their projections on the 2-D original image under study, signifies the possible locations allowed for the center for the second object, e.g. for its coordinate(s) or center of mass or corner(s).

Position is also a factor for building relationships between objects, as for example, the 4 legs of a table, with respect to the table, which are usually presumed to be located and also attached at the bottom of the table (unless the table is reversed or broken, e.g. in a fight scene or war scene, as an example, depending on the context or history or assumptions, beforehand, which can change some relationships drastically, as in the case of the image of a war scene or hurricane scene disaster). The position or relative locations are defined using directions or distances, e.g. up, down, diagonal up, 45 degree up left, 5 ft, top, bottom, side, corner, and the like. Note that most of these concepts are fuzzy concepts, useful for membership values, e.g. side of a laptop, or corner of a laptop.

As mentioned above, the context is also very important. Given an image of a war scene or hurricane scene disaster, one may expect to find a table reversed or with broken legs, opposite or contrary to any normal expectation or relationship between normal objects in a normal environment. Thus, the relationship web is very different for those situations, with respect to normal situation. In addition, that is one way to confirm that an image is possibly from a war zone, based on tables with broken legs or houses with no roofs on the top. See e.g. FIG. 148 for such a system. This can go both ways. That is, from rules and conditions, we get the context. Or, from context and rules, we get the current condition of the object. The confirmation of assumptions is detailed below.

In one embodiment, when we look at a picture, we focus in the middle or at the main feature(s), first, as e.g. indicated by histogram or contrast map. Then, we look for other expected objects nearby, using the related objects list with associated probability and associated expected distance (relative or absolute values), which is part of Z-web. In one embodiment, once we find e.g. a face in the image, we can assume that most likely that other faces or other eyes or similar objects, if any, in that image, are in the same scale or distance or order of magnitude, which can adjust the scale or size of the basis functions, such as wavelets, to find the other eyes or faces in the image much faster, focusing or using only basis functions or filters within similar or same scale for basis functions or object size. In one embodiment, when scaling the basis functions, the lines or curves defining the basis function has the same thickness as that of the original. In one embodiment, when scaling the basis functions, the lines or curves defining the basis function get scaled linearly with respect to that of the original. In one embodiment, when scaling the basis functions, the lines or curves defining the basis function get scaled non-linearly with respect to that of the original, e.g. based on $\exp(x)$, $\log(x)$, or $x^2$.

Going Backward (and Testing or Verifying) on Assumptions:

As we get the input and build our web of relationships between objects or concepts or subjects, e.g. emotions, humans, and tables, we add reliability, truth, credibility, and consistency of the information, which can be addressed by Z-numbers or by fuzzy logic membership or other fuzzy concepts or other reliability calculations, also described in the U.S. Pat. No. 8,311,973, by Zadeh, which addresses Z-numbers and its applications, as well as other fuzzy concepts, plus the "trustworthiness of speaker", "sureness of speaker", and "statement helpfulness", with the analysis for cascaded or network of information sources ending up with a "listener", e.g. in FIGS. 43-46, 66, 68, 69, 78-80, 84-93, 104, and 120, plus other figures and corresponding text supporting the teachings. We also address some of these issues and solutions in the current disclosure.

Now, in one embodiment, let's start with multiple assumptions, $A_1$ to $A_N$, and from there, we can get some web connections for relationships between M objects, subjects, words, and concepts, e.g. emotions, humans, policeman, teacher, dog, and car, in this relationship web, as nodes on the network. All the relationships and assumptions have reliability, truth factor, confidence level, and credibility metrics (with their corresponding membership functions or values).

Now, in one embodiment, we start from a node and continue building the network, until we get to a point that inconsistency or contradiction flag is up, in terms of property of a node which gets contradictory results from different sides or routes. Then, we backtrack and clean up the route to the original assumption(s) or node(s) that may have caused this problem, to remove or change the assumption(s). We can change the assumptions one at a time, and see the results again, until "satisfied", which is also a fuzzy concept (for the degree of "satisfaction"). Or, for N being a very large number, we can change multiple assumptions at the same time, and observe the results, to adjust the assumptions in a feedback loop manner, or based on some fuzzy rules.

In one embodiment, for conditional relationships, or multiple choices, we can continue, until we get to a dead end or conflict, and then, backtrack to eliminate or adjust one or more choices, on the chain going backward, to correct or adjust some assumptions, choices, or conditions, on the way.

In one embodiment, using assumptions on human emotions, one can do behavioral analysis on individuals, or collectively on whole society, e.g. how the people feel or react on a bad news, such as earth quake, using e.g. the sad faces in images, or text analysis on expressed or typed words such as "Disaster!" in the email or texting message on phone. The collection of nodes in a Z-web can indicate that a person is very angry or sad at a given moment.

Of course, as the mood of a human changes, the corresponding Z-web changes accordingly, with new nodes, weights, reliability factors, and the like. So, the Z-web is a dynamic structure which is potentially time-dependent, with a corresponding characteristic time period ($T_{Char}$). For example, a geographical factual Z-web with many constant facts at its nodes has a large $T_{Char}$, because we do not need to update or change that Z-web very often, as most of their values stay the same for a long time (versus some Z-web related to e.g. the stock market, with fluctuations and variations on a daily or hourly basis, which requires daily updates, and thus, has a lower $T_{Char}$ value).

Optimization of Quality of Different Aspects of Image:

Consider the line on any line drawing image. The thicker the line, or the wider the tip of the pen used to draw the line, the less features are visible from the line drawings, as the small features are dominated or lost by the thickness of the line, itself. Sometimes, for some applications or situations, we want to increase the width of the lines or boundaries, for the sake of having continuous boundaries or borders between different objects, for better object recognitions or discriminating between neighboring objects, to figure out what is in the picture or image. However, for any image with small tiny features, that increase in the width of the lines or boundaries may cause problems of wiping out or hiding or losing the small features for the borders of objects or regions in the image, if those features are important for any other analysis. So, we have to figure out at the beginning that which one is more important, to preserve one or the other, i.e., in favor of one or the other. Or, we have to figure out at the beginning that to what degree this process should be done, in favor of one aspect, before damaging the other side/aspect.

So, (i) we classify the images at the beginning, and (ii) also see what kind of interest or information or query we need or want from the image(s). These 2 parameters determine how far we should optimize the image, for which aspect, and in the expense of what other aspect of the image. The compromise factor between different aspects of the image and optimization factor for each aspect of the image are also fuzzy parameters, and can be determined using a fuzzy rules engine or a fuzzy optimizer. The fuzzy rules engine or a fuzzy optimizer are explained here in this disclosure, as also explained in U.S. Pat. No. 8,311,973, by Zadeh.

One way to avoid this analysis or compromise is to make 2 copies of the same original image, and then optimize the first aspect on the first copy, and optimize the $2^{nd}$ aspect on the second copy, and then extract information from each image or copy separately for the $1^{st}$ aspect and the $2^{nd}$ aspect, from the $1^{st}$ image or copy and the $2^{nd}$ image or copy, respectively.

Another way is to make one analysis on the first aspect from the original image (that does not need much optimization or correction on the image), and then change the image to optimize the $2^{nd}$ aspect, for analysis of the $2^{nd}$ aspect, to extract more information about the second aspect. This way, we get somewhat good information about the $1^{st}$ aspect of the image, and excellent/large amount of information about the $2^{nd}$ aspect of the image. Yet, the overhead about computation power or storage of images is not as large as the previous solution, given above. So, it is a kind of middle ground compromise solution, good for some applications, which need some accuracy, but at lower cost for computation and analysis (or shorter turn-around time for analysis and results).

Window for Examination:

When looking at one image, for one embodiment, if the window for examination of the image is too wide, and we get one signal from all of the window, then we may get the average values from all regions of image contributing to the result. Then, in those situations, we may not get some of the features from the image. For example, if the features are based on sinusoidal function (sin(x)), with half of the time negative and half positive, in 2-D space of the image, then the average for all regions, containing a lot of the periods for the function (assuming small periodicity for such sin(x) function, i.e. small T, for this example), would be zero or near zero, for the total average. Thus, the behavior of sin(x) for the feature in the image is not detected at all, in this example.

Now, if the window of examination is too narrow, and the changes are negligible for consecutive windows, in absolute values or relative values, then the process is too slow or expensive for analysis, and we may also miss detecting some of the big scale behaviors in the image. Thus, the optimum window size depends on the periodicity ($T_F$) and size ($L_F$) of the features in the image, to have both efficiency and accuracy for the image analysis. So, at the beginning, we classify the image based on those parameters ($T_F$ and $L_F$), plus its complexity ($C_F$) and concentration of features ($M_F$) that we are looking for in the image. Then, the size of the window ($S_W$) is determined from all those parameters. Note that all these parameters can be expressed by e.g. real numbers (fuzzy or crisp values) or in terms of human natural language, e.g. "large window" (fuzzy values).

For example, we have $T_F$ as 2 features per 50 pixels or 2 features per $cm^2$ or 2 features per 5×5 pixel square or 2 features per cm of boundary. For example, we have $L_F$ as 50 pixel or 5 cm or 5.2 times bigger than size of the mouse of the computer or "bigger than size of mouse of the computer" (as fuzzy value).

For example, in one embodiment, we have complexity ($C_F$) defined as the number of gray scale used (out of 256, for example) (or available) in this particular image, or defined as number of color values used for components of RGB or CMYK system in the image, or defined as the number of intensity values used (out of Q total values available) for the image, or defined as the percentage of variations, in diagonal or horizontal axis, in the middle of image or passing the center of the image, in the intensity of pixels, plus the directions of those variations in the pixel intensity (which can be large or small positive or negative numbers or percentages or relative values), or expressing any of the above per square pixels or square cm or unit of area, or similar definition as a metrics for the complexity of an image.

For example, we have concentration of features ($M_F$) as number of features (or spikes or crosses or knots or curves or small squares (as examples)) per square pixels or square cm or unit of area, as examples, or when the features are confined on a line or curve or boundary, $M_F$ may also be expressed per pixel or cm or unit of length. For example, we have the size of the window ($S_W$) as 100 by 100 pixels, or 2 $cm^2$, or twice as big as the mouse of the computer in the image, or "very very large" (as fuzzy value), or 1 percent of the whole image, or "small square".

For example, in one application or embodiment, for small $T_F$ and small $L_F$, plus high complexity ($C_F$) and high concentration of features ($M_F$), the size of the window ($S_W$) is set to be small, e.g. 3×3 pixel (square).

In general, we have a function $F_W$, defining $S_W$ as dependent on parameters:

$$S_W = F_W(T_F, L_F, C_F, M_F)$$

Extracting Clues and Information from Images, to Determine Relationships:

From an image, picture, video, drawing, cartoon, caricature, sketch, or painting, one can guess or estimate or find relationships or find attributes or find the degrees for relationships or find connections between objects, subjects, humans, animals, plants, furniture, emotions (which can be used to predict e.g. social behavior, purchasing behavior, voting behavior, or rating system behavior), ownership, properties, characteristics, or the like, related to, for example, the following:

The age of the subject or person or animal, ethnicity of a person, relationships between subjects (in a picture or painting or image or video frame), picture setting (e.g. at office, official, military, family gathering, class reunion, primary school student picture, graduation from college, prom dance event, black tie event, Olympics medal ceremony, Oscar Academy Awards event/night, or karate class), family membership, happiness (or misery, despair, anger, emotion, or mood), closeness (friendship, or how close the subjects are to each other), intelligence of the person, sophistication of the person, gender of the person, style of the person, location of the picture, year (in which the picture was taken), political affiliation, country (in which the picture was taken), language of the location (in which the picture was taken), time of the day (in which the picture was taken), season or month, special occasion (New Year celebration at Times Square in NY City, Christmas, wedding, or carnival), special location (Disney Land, cruise trip, on the Moon, Grand Canyon, or near Eiffel Tower), temperature of air (in which the picture was taken), humidity (in which the picture was taken), time zone (in which the picture was taken), altitude or location on the planet Earth (in which the picture was taken), height (in which the picture was taken), depth (in which the picture was taken), or environment (e.g. cloudy, rainy, war zone, or foggy), as some examples, or the like. See e.g. FIG. 149 for such a system.

The correlation between objects, subjects, and concepts, at nodes in the relationship web or network, as the web grows and gets built up, with more relationships and larger number of nodes, brings more and more objects, subjects, and concepts together, and validates or verifies estimates, guess work, and possibilities, with more accuracy and higher confidence level.

The input to the web of relationships comes from many sources, e.g.: textual information, video, music, noise, voice, still images, pictures, sound bites, expressions, moods, emotions, tags, comments, recommendations, LIKEs on a web site, customer feedback, TWITTER®, FACEBOOK® entries, emails, blogs, votes, political opinions, surveys, summary of data, medical images, weather forecasts, historical data, geographical data, mathematical, physics, and chemical facts, historical monuments, famous quotations, books, slangs, Wikipedia, encyclopedia, dictionary, thesaurus, translation books, county land records, birth certificates, lectures, novels, science fiction, documentaries, history books, magazines, picture albums, databases, private network or storages, class notes, exam answers, dating sites, ancestry web sites, social media sites, petition documents, tax returns (if available), resumes, biographies, biometrics, gene or DNA sequence, medical data, medical history, medical knowledge, chemical formulas, mathematical relationships, physical constants, physical phenomenon, abstract concepts, architecture, psychology, philosophy, proof methodology, inductive reasoning, logic, calculus, hand written notes, scripts, computer program, codes, encrypted message, sign language, alphabet, Internet, search engine, opinion of famous people, opinion of friends, friend suggestions, social media votes or suggestions or opinions, court documents, dockets, or the like.

For example, to find the age of a person in a picture, the number of or concentration of wrinkles on the face or neck or skin can be counted or detected (as the older people tend to have more wrinkles, as an example), or based on the ratio of the size of the head to the rest of the body or height (as the average ratio or ratio changes for different ages, for most people, tabulated based on millions of samples in the database), or features of the face and their dimension ratios (as is different at different ages, within some range, for normal people, stored in the databases, which can be a crisp value or fuzzy parameter), or having bi-focal eye glasses (usually for older people), or having a hearing aid (usually for much older people), or having a bald head or receding hair line (usually for adult people, and usually male subjects), or having only one earring, nose ring, or tattoo (usually for younger people), or having 2 earrings (usually for female, above 10 year old, as an example), or having a tie or bow tie (usually adults in formal settings, and usually male subjects), or having a top hat (usually adults in formal settings, and usually male subjects), or having a baseball hat (usually kids or young adults, and mostly male subjects), or having a beard or moustache (usually 12 years or above, as an example, and almost all male subjects).

Please note that if we have other information about the culture or town or country or the date of the picture, we may be able to determine the age more accurately, for example, in 1960s, a lot of college students in certain countries wear tie in college, but it is not true for college students in US in year 2000. Another example is for Scottish culture or region, we know that Scottish men wear the skirt as tradition, which may tilt the possibility and probability and confidence and reliability of the decision or recognition or classification, one way or another, based on the subject having skirt on, in the picture or image. Thus, the culture and date of the picture and context and traditions and environment may all be influential and factors in the decision making Some of the features or criteria or tests mentioned above also apply to gender, as described above, e.g. having a moustache or beard on a person in the image or picture. However, if we know, e.g., that the date of the picture was Halloween, located in US, then the moustache may be fake or on a Halloween mask, or if the location is Universal Studio for a movie, from scene of the movie, then the moustache may be fake. So, again, the context and date of the picture are important to tilt the values or relationship strengths or possibilities or probabilities.

Also, most of the rules stated above are fuzzy rules, for relationships, for various objects and subjects or concepts, such as: "Having hearing aid in the ear, in the picture, usually infers that the subject (the person under evaluation, in the image) is probably an old person". First of all, "old" is a fuzzy value, and then "usually" plus "probably" can be handled by the Z-number mathematics and algorithms, as explained in this disclosure. In addition, fuzzy rules engine and related algorithms, e.g. backward chaining inference engine and the forward chaining inference engine (for handling a set of fuzzy rules for the relationships that we stated above, for determining the age of the person, as an example), are also explained in this disclosure.

Now, we have more information extracted from the images. For example, the picture setting may be at an office, with indicators such as tie and jackets or formal dresses, as well as desk, round table, water cooler, copy machine, cubicles, partitions, white board, calendar, deadlines on the board, tasks on the board (read by the OCR and understood by the natural language processor, as being tasks with dates in front of them, and possibly some arrows, with time line on horizontal axis), conference room, conference phone, employee award on the wall or on the desk, "men's room" indicated by word or by a "man" symbol on the door to the bath room, rack of coats or hangers, name tags on the desk or wall, room numbers on the door or wall, or the like.

One indicator may not have a high correlation coefficient to a setting, but a combination of multiple indicators has a much stronger correlation coefficient, e.g. some of the indicators mentioned above, with respect to the "office" setting. Also, one "fax machine" may be have a different correlation coefficient or relationship factor with respect to general office, or document processing office, versus dental or doctor office. So, same object in different environments or locations or contexts have different relationship factor, e.g. in day time setting versus night time setting.

To examine a setting, for example:
for official setting, we look for jackets and ties,
for military setting, look for guns and uniforms,
for family gathering, look for kids and grand parents or people at different ages,
for class reunion, look for people of the same age and banners stating a university or high school name, plus graduating date, e.g. 1977,
for primary school student picture, look for a lot of kids of about less than 12 years old,
for graduation from college, look for graduation gown and cap,
for prom dance event, look for prom dress and limousine,
for black tie event, look for black tie dress and jacket,
for Olympics medal ceremony, look for Olympics sign and medals around the neck,
for Oscar Academy Awards event/night, look for Oscar symbol or statue,
for Karate class, look for Karate belt and outfit, and the like.

These relationships come from expert humans, or many human voting or inputting, or from trained computer learning machine, or extracted from millions of relationships from a huge observation sampling or history file or database. See e.g. FIG. 150 for such a system.

Other examples are:
for family membership (look for hugging, kissing, how close people stand in a picture, smiling in a picture, casual dressing, vacation setting in the background, similar faces, similar clothing, at a dinner table at home setting),
for happiness (or misery, despair, anger, emotion, or mood) (look for the shape or expression or size or angle of mouth, face, eye brow, eye, color of face, or lines on the face, based on stick diagram defining laughing or other expressions or moods, or based on formulas defining those expressions, or based on curves defining those expressions, either analytically stored as curves or graphically stored as pixels, or based on thousands of faces stored from real people, tagged for expressions on their faces, for learning samples, as supervised learning),
for closeness (or friendship) (look for how close the subjects are to each other in the picture, as how many people are in between, or how tight they stand close to each other, or how hands hold each other and where they are located with respect to the body, which can be also trained with thousands of already tagged pictures by people or experts, as one way of doing it, or can be understood based on the relationships of objects, e.g. first person's hand ($H_1$) behind (or covered by, as function $C_B$) the second person's shoulder ($S_2$), indicating hugging, indicating closeness or friendship, or mathematically expressed as, when finding the objects and ordering of objects in the image: $C_B(H_1) \equiv S_2$) (Note that all objects in an image can be analyzed, to find which is front and which covers what, with mathematical relationships, as indicated above. Once part of the object, as expected, per our expectation (e.g. from shapes stored in a database for that name or object), is missing in the image, that is an indication (of most likely) that part of that object is behind another object, in that image),
for intelligence of the person or sophistication of the person (look for book in hand, standing near a library or concert hall or museum, degree near his title or name in text, titles on the door or email, his friends, his/her family members, her job, her SAT score, her GPA, her resume, her publications, or degrees in the frames on the wall or on desk),
for gender of the person (look for dress or clothing, hair cut, shoe, accessories, name, size or weight or height value or ratio, habits, title behind the name (such as "Mr."), favorite video game or movie or actress, and color of choices) (Note that these are still not deterministic at all, same as other parameters and indicators mentioned above. That is, sometimes, stereotypes and generalization are very misleading. However, using combination of all data and relationships and aggregating them using our analysis on our "Z-web" increase the accuracy and reliability of the recognition),
for style of the person (look for clothing or hair cut or shoe or glasses or wine choices or drink choices or car or watch),
for location of the picture (look for monuments or famous buildings or names or landmarks or emails indicating the locations of next vacation or tickets for airline or passport stamps),
for year (in which the picture was taken) (look for clothing style, text, objects in the background, such as cars or building, hair style, name of famous actors, name of movies on display, the president of the country, or tags or dates on the picture or image),
for political affiliation (look for tag on the car or bumper sticker or pictures on the wall or affiliations or clubs or friends or geographical area or job or title or essay in school or courses taken in college or food choices or vacation choices),
for country (in which the picture was taken) (look for landmarks, names, tags, signs, street names, architecture, pictures on wall, language on signs, people's faces, stores, cars, license tags, having snow on ground, type of trees, type of foods, politician names, national hero, famous athlete, famous singer or artist, or TV programs),
for language of the location (in which the picture was taken) (look for names, tags, signs, street names, architecture, language on signs, people's faces, stores, license tags, or TV programs),
for time of the day (in which the picture was taken), season or month, or special occasion (New Year celebration at Times Square in NY City, Christmas, wedding, or carnival) (look for Christmas tree, decorations, snow on ground, trees with no leaves or colorful leaves, big clock on the tower, position of Sun in sky, light or darkness, frozen lake, ice fishing, or winter sports), for special location (Disney Land, cruise trip, on the Moon, Grand Canyon, or near Eiffel Tower) (look for landmarks, text, or structures), for temperature of air (in which the picture was taken) (look for steam or fog, rain, snow, ice, people with bathing suit, beach, ice skating, snow man, sweat on face, Sun reflecting on a shiny metal object, thermometer, thermocouple, or weather channel on TV), for humidity (in which the picture was taken) (look for steam or fog, rain, snow, ice, sweat on face, mold, green and dense vegetation, or rusty cars in the street), for time zone (in which the picture was taken) (look for location landmarks, country, city, names, text, clock, region, marker on the map, flag of the country, or email time record), for altitude or location on the planet Earth (in which the picture was taken), height (in which the picture was taken), or depth (in which the picture was taken). (look for landmarks, signature characteristic, perspective view, or indicators of coordinates or locations, such as cloud in sky or fish in deep sea), or for environment (e.g. cloudy, rainy, war zone, or foggy), as some examples, or the like. (look for indicators or signatures, such as fog, cloud, wet street, tanks, soldiers, and ruins in a war zone).

In one embodiment, the information on the camera phones (on its memory, processor, or controller module), or on image (as text), or tagged as a header or file or comment to the image, e.g. GPS (location), date, lens data, focus information, and the like, are used for location of the picture, e.g. specific city and monument, or date, e.g. Jul. 4, 1999, 4:30 pm, or focal length, or estimate of distances in the image, or the like. These can be used for correlation with other objects and within themselves. Thus, we can input this information into our Z-web, as new nodes and Z-factors, e.g. for recognition purposes or reliability analysis.

Different Components of Recognizer:

The recognizer module has many sub-components, to do analysis on text, e.g. OCR, image (e.g. image recognizer), video (e.g. video analyzer), voice (e.g. voice analyzer), music, taste, numbers, patterns, texture, faces, names, records, tables, lists, "big data", and the like, as input modules, to gather, analyze, and aggregate, to find the relationships between objects and concepts, based on the reliability, confidence, truthfulness, probability, and possibility, as discussed elsewhere in this disclosure, to build the "web of relationships", which we call "Z-web", and to find or recognize or validate or confirm other or same objects or concepts or relationships. See e.g. FIG. 151 for such a system.

For constructing the Z-web, we can use various types of input, to build up relationships as described above, e.g., but not limited to: image, video, text, sound, voice, music, biometrics, table or list, tag, comment, metadata, multimedia or movie, link to information or web site, header, summary or abstract, record or database, listing, matrix, geometrical shapes, symmetrical shapes, patterns, symbols, abbreviations, encyclopedia or dictionary, personal data or preference, historical or geographical data, physical or chemical data, and/or mathematical facts, or the like. FIG. 172 is an example of such a system.

Adjusting Colors:

All colors look the same in a dark room, or in a picture with low light intensity, e.g. picture taken at night with no flash on the camera. So, in terms of recognition of a face, a normalization or adjustment is needed to convert the color or intensity of the pixels for a face in a dark image, to correct the color and intensity, toward the original normal color, toward real color, as a pre-processing, before recognizing the face, by face recognition module, to increase the accuracy of such recognition. The adjustment is based on the environment and background, so that color and intensity of pixels of the face is changed or corrected, such that the background becomes corrected to the normal or expected background, as if it were with/under enough light illumination.

Contrast Correction or Adjustment:

Let's assume that the intensity of a specific pixel $P_1$ is $I_1$. If $P_1$ is in the middle of patch of low intensity pixels $I_2$ (as the first environment), it (i.e. the apparent intensity, $I_{12}$) looks much brighter than to the average human eye, compared or with respect to the situation when $P_1$ is in the middle of patch or region of high intensity pixels $I_3$ (as the second environment), where $I_1$ looks darker, with low intensity (i.e. the apparent intensity, $I_{13}$), to the human eye. That is, the perception of intensity, for recognition, by human eye, is dependent on background or context or contrast to the surroundings. Mathematically, it means that, for intensity, for human perception:

$$I_{13} < I_{12}$$

Now, the machine (measuring the exact intensity) does not make such a mistake, and measures the exact intensity, regardless of contrast to the surroundings. So, to normalize the machine or real measurements with human perception, to adjust for such perception difference, one has to adjust for the ratio ($I_R$) of ($I_{13}/I_{12}$), between the given image in the first and the second environments (2 different environments). Thus, the number $I_R$ is our correction factor. So, starting from real intensity measurements, to go to the human domain or perception, one has to adjust the intensity by $I_R$ as our correction factor, to get the perception values or apparent values, relevant to the human perception. To go in the reverse direction, i.e. from human perception to the real intensity values or measurements, one does the correction or modification based on the inverse of value $I_R$ or ($1/I_R$). After the adjustment, or pre-processing, the face recognition or any recognition is performed, resulting in better accuracy and reliability for recognitions.

Searching and Extracting Information from the Images or Other Data, Using Z-Web:

In one embodiment, for pictures or images from the Internet, or other data, we find e.g. the web site by search bot or robot, and then extract the relevant information and tag them or put a summary of that image or web site or list the extracted information in a database or put the relationships and relevance and reliability factors (and other Z-factors mentioned above) into our Z-web or on our own server(s) or computer network or server farm (called $Q_{store}$ storage or module or computer or server). Now, a third party user can look at our Z-web, or other information mentioned above and stored on our $Q_{store}$, to use or extract or search or download those data, for a fee or for free, based on different business models, such as ad revenue on our web site.

Basically, in one embodiment, the data extracted and collected and aggregated by us for our Z-web or our $Q_{store}$, based on an image on a web site (as an example), is sitting as an extra layer on top of the web site, so that the user can access and get more information from the web site, through our Z-web or our $Q_{store}$. There are many ways to do this process. In one embodiment, the user U is at his PC (or mobile phone or device), with a browser, which goes to a web site $W_{site}$ and is interested in a data $D_{site}$ on $W_{site}$, e.g. an image or text data or tel. number. Since $W_{site}$ was previously scanned by search bot, and all the relevant information regarding $D_{site}$ was extracted, analyzed, and stored in our $Q_{store}$ (e.g. in a remote location), then the user U can manually go to $Q_{store}$ to get more information about $D_{site}$, as one embodiment. In one embodiment, the user automatically goes to $Q_{store}$ to get more information about $D_{site}$. In one embodiment, the user optionally goes to $Q_{store}$ to get more information about $D_{site}$.

In one embodiment, the information stored in $Q_{store}$ is also stored in $W_{site}$. In one embodiment, the information stored in $Q_{store}$ is instead stored in or moved to $W_{site}$, as an extra layer or shell or attachment or tag-along file. In one embodiment, the information stored in $Q_{store}$ is also stored in multiple places for easier or faster access, e.g. server farm or mirror server or backup server or redundant server, e.g. in another location. In one embodiment, the information stored in $Q_{store}$ has an expiration date, after which the information extracted from or related to $D_{site}$ is updated or re-extracted. In one embodiment, the network including $W_{site}$ is the Internet. In one embodiment, the network is a private network. In one embodiment, the user can e.g. do a search or query and look for some object on Internet, using a plug-in and a browser, to go to the web site $W_{site}$, and then from that web site, go to our database or Z-web or $Q_{store}$, to get the information extracted from the web site, automatically. Alternatively, the user can go directly to $Q_{store}$, using a plug-in and a browser, to get the information extracted from the target web site $W_{site}$.

In one embodiment, the process above is done with no plug-in. In one embodiment, the whole process is done automatically. In one embodiment, the whole process is done with the input from the user, or partially by user, or optionally chosen by user. In one embodiment, when the mouse is over an object or hover over it, the whole process is initiated automatically, e.g. a picture in a web site or name in a text is selected (e.g. by mouse or pointer or user's finger on touch screen, or on monitor or display or pad or input pad or device, or hovered over by finger or mouse without touching or touching, or by magnetic proximity or heat proximity from body, or capacitance changes or by electrical resistivity changes or pressure or piezoelectric changes, or RFID tag proximity, or image of finger recognition or fingerprint recognition or biometrics validation, or car key holder or ring proximity, or finger gesture or face gesture recognition, or finger stroke or sign recognition, or series of finger strokes pattern recognition). Then, the relevant information is obtained from $Q_{store}$ about that text or image, and automatically shown or presented to the user, which is very convenient and useful for the user on Internet or any private network.

In one embodiment, the web site $W_{site}$ can also request, generally or per usage, to have the information on $Q_{store}$ be also displayed on their web sites, or added or stored or tagged or linked or shown in their menus, based on another plug-in or code or predetermined arrangement with $Q_{store}$, for direct usage of their users or visitors. So, it would be a value added for them ($W_{site}$), for convenience of their users or visitors. Thus, it would be a source of income for the operator of the $Q_{store}$, as a service to $W_{site}$ or licensing the software or increased traffic for $W_{site}$, e.g. for ad money or income, to benefit the operator of $W_{site}$, e.g. as the client or customer for $Q_{store}$ operation, e.g. as its business model. In one embodiment, the information from $Q_{store}$ is supplied to the user directly, e.g. for mobile users or phone owners, per usage or per month or per subscription, for a separate business model or income source. In one embodiment, due to the value of the information from $Q_{store}$, the $Q_{store}$, itself, can have its own web site and direct visitors, for its own ad revenue, traffic, and referral income. In one embodiment, the web site includes text, image, tel. numbers, links, video, voice, music, and the like. See e.g. FIG. 175 for such a system, for one of the embodiments.

In one embodiment, an informational/graphical reader or renderer process (e.g., a web browser or a software application to view files or content such as a PDF reader or a word processor) runs on a device (e.g., a user device) that takes the content deliver from network (e.g., from a web server, file server, document or content server, web service, or an on-line application running on Cloud or distributed network of servers). In one embodiment, the reader/renderer process receives data (e.g., Z-web data for the annotation of an image identifying people on the image) related to a resource (e.g., the image) referenced or provided by the delivered content, based on (e.g., an automatic) query from the reader/renderer process (or a plug-in or another process running on the user device) to $Q_{Store}$ related to (e.g., identifying) the resource (e.g., by its URL, identification or location within content or document, and/or metadata such as date). In one embodiment, the reader/renderer process modifies/overrides/supplements the display/play back or presentation of the resource (e.g., on the user's device), by using the received data (e.g., from $Q_{Store}$) including the user interface interaction (e.g., by creating links and displaying annotations on the image). In one embodiment, further user interaction with the modified user interface based on the received data, invokes further queries to $Q_{Store}$ to fetch more data about the item selected (e.g., information about the person so annotated in the image). An embodiment makes the content (such as images) whether in web page or a document link to other knowledgebase entities by fetching the content in an automatic search (e.g., by bots or background processes), analyzing the content within a context and/or by using feature detectors/classifiers, importing the features of the content into Z-web, using the knowledgebase to automatically annotate the content and associate such annotation with the content (for a later search), e.g., via indexing.

In one embodiment, the network entity delivering the content does not include a reference to $Q_{Store}$ (e.g., resources, API, or query) embedded with its delivery content to the reader/renderer, and a query (e.g., automatic) is initiated be a process in the user's device (e.g., reader/renderer process) to fetch data related to the resources in the delivered content. In one embodiment, the network entity (e.g., a web site, $W_{site}$) has the content embedded with resources, API, query, or tags referencing $Q_{Store}$ and the renderer/reader uses such embedded resources to fetch data from $Q_{Store}$ or to display/playback the content (e.g., included the use of scripts such as Javascripts).

In one embodiment, the reader/renderer sends information to $Q_{Store}$ or a server, when for example, the user enters annotation on a resource such as a portion of the image. In one embodiment, the information is tagged with the user's ID (e.g., is logged in). In one embodiment, the sent information is queued for analyzer to incorporate into Z-web. In one embodiment, the plug-in provides the user interface to enter/edit annotations on the user's device. In one embodiment, a local service or process running on the user's device provide a local $Q_{Store}$ or Z-web on the user's device, e.g., giving local access to the user's auto-annotated photo albums, using other database (e.g., email or contact) to automatically build the relationship links between people appearing in the photos and appearing in the email to/cc lists. In one embodiment, the local $Q_{Store}$ or Z-web may be synchronized with those on the network (or Cloud). See e.g. FIG. 175 for such a system, for one of the embodiments.

Partial Matching:

In one of our embodiments, we have a partial matching on objects hidden or covered behind others, or partial understanding or recognition of patterns hidden or covered by other objects, or not fully visible for any other reason, such as bad or dirty or foggy lens on camera. We compare the partial pattern or image of the first object to the library of all possible objects in that setting or environment, for partial match, with assigned reliability, based on the estimated percentage of the visible part of the first object, to put or incorporate it in the Z-web, where the recognition is enhanced based on the multiple inputs from other sources to cross-verify and cross-recognize, as described elsewhere in this disclosure, even using partial recognitions with not full reliability, per object, or node on Z-web.

Here, we give an example for partial matching for image, but this method can be used for recognition or verification of text, sound piece, series of music notes, signature, fingerprint, face, or any other feature or object or pattern, that is partially lost, obscured, hidden, erased, or not detectable/visible.

In one example, we have the first object being partially-matching with n objects in our target library (e.g., $T_{O1}$, $T_{O2}, \ldots, T_{On}$), with different overall reliability factors, $R_{F1}$, $R_{F2}, \ldots, R_{Fn}$, respectively, for the full match. For example, part of the first object matches with part of n objects in our target library. For example, a "handle" (or an object which looks like a handle), as a part of the first object, may be a part of (a handle for) a kettle, as first target, or part of (a handle for) a bottle, as a second target. First, we determine how much the handle of the first object matches the handle of the kettle, and matches the handle of the bottle, and so on, as denoted by $M_{O1}, M_{O2}, \ldots, M_{On}$, respectively (for example, using matching or recognition confidence or score). Then, we determine the percentage of size or importance or contribution or dimension or ratio of a handle with respect to kettle, and with respect to bottle, and so on, as denoted by $P_{O1}, P_{O2}, \ldots, P_{On}$, respectively (for example, using the ratio of the sizes or dimensions or number of pixels).

Now, in one embodiment, the overall reliability factors, $R_{F1}, R_{F2}, \ldots, R_{Fn}$, for the full match, is based on $(P_{O1}M_{O1})$, $(P_{O2}M_{O2}), \ldots, (P_{On}M_{On})$, respectively. (In one embodiment, the relationship can be more general, i.e. as a function of those values ($F_f$), or written in terms of: $F_f(P_{O1}, M_{O1})$, $F_f(P_{O2}, M_{O2}), \ldots, F_f(P_{On}, M_{On})$, respectively.)

So, the maximum or optimum reliability factor corresponds to (as a Maximum function, for taking the Max values on multiple parameters):

Max$((P_{O1}M_{O1}), (P_{O2}M_{O2}), \ldots, (P_{On}M_{On}))$

Let's assume that the Max function above yields $(P_{Ok}M_{Ok})$, as the k-th term in the series above. That is:

Max$((P_{O1}M_{O1}), (P_{O2}M_{O2}), \ldots, (P_{On}M_{On}))=(P_{Ok}M_{Ok})$

Thus, the k-th object is the best target object for the full match.

Now, in addition, we can construct the relationships, to put all n objects in our target library into the Z-web, as described elsewhere in this disclosure, to find or recognize the best target object(s).

In one example, the problem is generally false positives, for recognition of target objects, but in one embodiment, with keeping track of reliability in our Z-web, we can tame that false positive rate to a reasonable quantity, making Z-web an extremely useful tool and technique for this type of situations.

Tags and Comments for Pictures and Images:

Picture annotation and caption is useful for recognition of people in the image, e.g. looking for phrases such as "from left to right", or "top row", to find location of faces or people in the image, and order them in rows or columns, and then call or label them as objects or persons $P_{R1}, P_{R2}, \ldots, P_{RN}$, as placeholders for names, and then compare them with the names coming after the flagged phrases such as "from left to right", to get names matched with placeholders $P_{R1}$, $P_{R2}, \ldots, P_{RN}$. For recognition of names and flagged or pre-designated phrases, we use OCR and then basic or full natural language processor module.

In one embodiment, we can simply look for specific words such as "left", as flagged words, and if successful, then look for specific phrases, such as "from left to right", as flagged phrases, from our library of flagged phrases and words, pre-recorded and stored, or dynamically adjusted and improved through time, without actually understanding the meaning of the full text and sentence, for fast picture analysis and matching names or tags or comments related to the pictures.

In one embodiment, we can ask the user or third party, e.g. friend or public, to tag names or objects, or as crowd-sourcing effort or by voting scheme, e.g. paid service or free, or they do it on their own, because e.g. the (assuming unbiased) people familiar with a person may be the best or most reliable people to tag the album or pictures of that person, as an example. In one embodiment, the indicators can be used for approval, confirmation, or increase of reliability factor, such as "Like" for a picture or comment on FACEBOOK®, as an indicator of approval by a friend or third party. In one embodiment, the voting or survey is used for measuring approvals. In one embodiment, the comments after a video or picture is used, e.g. as overall positive or negative, e.g. "Great picture!" indicates approval and conformation of a third party.

In one embodiment, the number of comments, number of views of a video, minutes watched for a video, length of comments, frequency of comments, date of recent comments, number of independent commentators, traffic of a web site, number of independent visitors to a site, number of followers on TWITTER® or other sites, number of connections, number of links, size of linked sites, quality of linked sites as rated by a third party, e.g. family-approved sites, number or size of advertisements or advertisers, marketing budget, income, revenue, number of cited references by other sites or parties, e.g. for a research paper or patent or case law, or the like, might be indications for approval or reliability of source e.g. news, e.g. CNN-TV channel.

In one embodiment, the system automatically tags the pictures, and in another embodiment, it asks the user for verification. In one embodiment, it searches for a person in the album and sort based on that person(s).

Images from Different Angles or Views:

For example, we take pictures of the Eiffel tower from different angles, for training purposes, and store them, e.g. from top view and side view or from underneath. Some of the views are not common, and thus, unfamiliar to average human or eye. For example, if a picture of the Eiffel tower is taken from an airplane from exactly the top, the shape from the top may look like a square inside a bigger square, which does not look the same as a regular tower at all (or our average expectation or view of the tower). Various views help the recognition of the tower or object, as they can correlate or refer to the same object, which increases the reliability factor of the recognition or the recognized object.

In one example, given a picture, which includes a square inside another bigger square, the picture may also resemble another $2^{nd}$ object, other than the Eiffel tower, in our library of the objects in the universe or at the specific location or city. Thus, other input information in the Z-web is used to increase the reliability of the data, and recognize the object, e.g. text or voice associated with the image.

In one example, given a picture, which includes a square inside another bigger square, one has to find the orientation of the image, from some templates in the library, or from thousands of training samples of many objects tagged versus direction and view by human or expert. The images in library can be real pictures or computer generated or drawn models, which compares shapes with each other, to find the best match, which indicates the view, e.g. "view from the top". Once the direction or perspective of the view is determined, we can store that information into Z-web, to integrate with the rest of the information about the tower or object.

Pixel Patterns, as Feature Vectors:

For an image, we define the square cells, e.g. 32×32 pixels or 8×8 pixels. Generally, each pixel has 8 neighbors, such as top-left, top-straight, and so on. We start from one neighbor and go around all neighbors, e.g. in the clockwise direction. We compare the center pixel with each neighbor. If the difference of the center value minus a neighbor value is above a threshold, e.g. 30 points in pixel value, or above a relative size, e.g. above 35 percent, then we put "1" for that position. Otherwise, we put "0" for that position.

In another embodiment, we can do this with bigger range of assignment, instead of assigning only 0 and 1. For example, we can use 0 to 3 (or 0 to 7 range), to classify for finer differences, for difference between the center pixel and the neighbor pixel. Of course, we have a bigger overhead in this case, for computation power needed and for storage.

In either case, we end up with a cell with a bunch of numbers assigned for each pixel. These numbers indicate the local pattern of differences between neighboring pixels. In another embodiment, we can represent those assigned numbers in binary format for easier comparisons, as comparing 0 and 1 per position in digit order is very simple, using e.g. XOR logical operation. Now, we can use a histogram for over the cell, for the frequency of each assigned number in the cell, as an indication of the frequency of that difference or pattern in the cell, and also in the whole image. In one embodiment, we can normalize the histogram, for comparison of different histograms, based on the average values or median values or based on the ratio to the maximum value, i.e. ending up with fractions less than 1 for all values, which is more computing intensive. The histogram for all cells is an indication of the pattern in the image or feature vector, e.g. bar code black and white lines, or patterns or checkered or striped shirt or tie or fabric.

Now, the support vector machine and other classification methods can be used to classify the patterns or recognize the patterns or textures, such as for face or fingerprint recognition. The face recognition, as an example, can have multiple target people for comparison in the database of faces. If the new face is matched with one of the faces in the database, nothing new is created in the database. Only, the new face is tagged along or referenced, e.g. with a pointer, with the matched face in the database, as the variation of the person's face already in the database. However, if there is no match, a new account is created for a new person. If there is no name yet available, we add it under NO NAME category, using generic names of NONAME1, NONAME2, NONAME3, and so on, until we find a name match later on, which replaces the placeholder in every instance. For example, "John Smith" replaces NONAME3 in our Z-web configuration. Placeholder is also useful in the Z-web for names with low reliability, as "John Smith" does not replace NONAME3 in our Z-web, in this example. Instead, it creates another node, as a property of NONAME3, as a new node connected to NONAME3 node, with the value of assigned "John Smith" for the new node.

In one embodiment, we classify the faces already in $N_{face}$ categories, e.g. 105 major types, based on regions of the world or shapes of faces, as a first level coarse classifier, so that the second level is a finer classifier to find a person. Or, if the number of faces in target database is huge, then we may need a third super-fine classifier, or even more levels of hierarchy for classifiers, feeding each other in multiple levels, for more efficient and faster classifications. In one embodiment, a human or expert or an already learned machine helps the training of a set.

Rule Templates Database:

In one embodiment, we have an image and we extract multiple objects from it, e.g. table and bottle, in which part of table is hidden or covered by bottle, which means table being behind bottle, referring to the positional situation of (from our position or relative location library): "bottle on the table", or in general, object A located on object B, or also, meaning that object A closer to camera position than object B, which are stored in our Z-web. Then, later on, one can search or query about the position of the objects and their relative locations, to extract these relationships. One advantage is that in Z-web, if object A is behind B, and B is behind C, then on the relational position between objects, one can conclude that A is probably behind C, for which such a template of rules are stored to support the Z-web, to help relate objects or simplify relationships, with the rule in a database of rules for Z-web, under category for positions of objects. Mathematically, the rule can be written as, where the function $B_E$ is the "Behind" function or operator:

If $[[B_E(B)=A] \& [B_E(C)=B]]$

Then $[B_E(C)=A]$

In general, the other logical relationships can be stored the same way in Rule Database engine (library), such as for "time", or "over", or "more", or "before", or "stronger", or the like. For example, for "time" operator, if time A is before time B, and time B is before C, then A is before C. This can also be written similar to "Behind" function, in mathematical form, for template, for Rule Database. If the template is very similar for time and space, one can use a single super-template, as generic template, for both situations, to reduce the number of templates and increase efficiency, in some embodiment. See e.g. FIG. 173 for such a system.

Rule database and templates can also have their own Z-web, relating the concepts, logic, relationships, and formulas, which can simplify the templates or get rid of the contradictions or inconsistencies. As an example, if we are not sure about a formula, we can store that as a rule in rule database, as a node with low reliability, which can be fixed, modified, or eliminated later on, on the rule database Z-web, which can be handled separately from our original Z-web structure. Alternatively, the 2 Z-webs can be combined as one super-Z-web, as explained elsewhere in this disclosure, with a common node being the object under study, such as "time".

Image Analysis:

In one embodiment, architectural building signature is an indication of a region or culture, e.g. mosque arches in the Middle East, or white buildings near beach on the cliff, as Mediterranean style near Greek islands. The databases of famous people, pictures, paintings, locations, historical buildings, monuments, books, authors, architecture of cities and locations, and the like are incorporated with our analytics engine. In one embodiment, using OCR, we can extract the name of the book on the bookshelf in the picture from the library or book store, or name of the store, or name of the street, or name of the person on the door, or name on the business card, to find the person, address, business, or taste, or correlate them together, as some examples.

In one embodiment, the facts may dictate some limitations in the universe of possibilities. For example, the "snow" in "July" may indicate that we are in the Southern Hemisphere (of planet Earth), or the picture was taken from such a location, limiting all possible locations on the planet for candidate for picture location. See e.g. FIG. 152 for such a system.

In one embodiment, travel guide is a good source of data for geography or history or facts. In one embodiment, the picture of an article either relates to the author or the subject of article. So, the face or person or author's name from caption or article or title or footnote should be extracted for comparison and classification or recognition of the picture or image. In one embodiment, the picture of an article in a web site is just an advertisement, i.e., nothing to do with the article itself. In that case, we have to figure out that it is an advertisement, from the caption or from subject matter or title or position on the web page or frequency of updates or functionality of the image. So, we have to partition the web page accordingly. In one embodiment, the GPS data or location data or time data or metadata, associated with a picture in a phone or camera, are used for data for Z-web for that picture.

In one embodiment, wax museum or movie setting is an indication of non-real people, even if the person looks like a famous people in the database. In one embodiment, a picture in a picture is analyzed, e.g. a picture in a movie or video frame, whereas the movie frame represents live humans in 3-D, but the picture frame on the table in the movie represents a 2-D image of a picture of a person, not a real person in the movie or video. Because to analyze the video, the 2-D image and the 3-D image may have different consequences and interpretations, e.g. as to who is related to who in the video. The 2-D picture frame on the table has specific signatures, e.g. it does not move around with respect to the other objects in the video, and has a constant coordinate.

In one embodiment, we have a database of famous people or US Presidents, e.g. George Washington, and database of famous places, e.g. Mount Vernon Estate, relating the two subjects or objects, as one being home of the other object. So, if we get a recognition of one object, automatically, the system looks for the other object in the vicinity, in terms of text or location or time or related objects or concepts, as expectation for other object(s) to be around. That also helps confirmation of validity of the recognition. That also helps building up reliability factors for the Z-web structure, and expanding the Z-web.

Street Scanners:

In one embodiment, we have satellite or aerial images from buildings and streets, and if a new building is shown in a new image from this year, compared to last year's photo, then we send the "street car 3-D photographer street scanner" back in that street, to scan the new building and scene, as an update (using multiple cameras from different angles and views, on the car, plus scanner, on a rotating table, with GPS or location determination module, plus calibration images or data, to adjust for coordinates and views, with redundancies on images or data, to glue pictures together seamlessly, and to correct the fringes in images or corners, or to correct mistakes in images or coordinates or 3D views). If no new feature or building is detected, no new update on street level for street view is needed for the city map on the computer or web site. So, we are looking for features or deltas or differences, with respect to last year's or previous picture(s). Thus, we compute the difference between 2 images, from this year compared to last year, e.g. using simple difference or subtraction of values, pixel by pixel.

In one embodiment, from the amount of the differences in images, the system determines how often or when next time the street scan is needed or proper, to be dispatched or scheduled, based on importance of the city map for the users, and being up-to-date as much as possible or to what degree, in terms of financial value for the users or advertisers or local businesses or city hall or tourists or residents. If they have a fleet of those scanning cars, then the schedule is set to optimize the usage of those cars in different neighborhoods or cities, so that they get the best value for the users, based on differences in images in terms of amount and its frequency, user base and value per city or neighborhood, cost of operation of those scanning cars, and distances between the neighborhoods, to get most coverage and value, with minimum cost or mileage on the cars, or smaller number of scanning cars used.

Camera Corrections:

In one embodiment, the lens of the camera is scratched or dirty (e.g. with dust on the lens or oily lens, diffracting the light) or defocused or otherwise foggy and degraded (e.g. as if the transformation of $F_{image}(x)$ is applied to each pixel). Then, the picture does not come out very well, and the recognition of murky objects in the image is very difficult and with a high error rate. So, we filter the image, first, as a pre-process, to focus the image, as the reverse of the lens problem, as a reverse transformation on the image, or $F_{image}^{-1}(x)$, applied to each pixel, to produce the corrected image. Then, we perform the recognition step, on the sharper or clearer objects or images, for improved recognition rate.

In one embodiment, for a camera taking pictures of an object, we have a family of transformations of $F_{image}(x)$ on the image or pixels, separately designed for each of these situations, to mimic the situation or effect on pixels or image: e.g. camera shaking, camera tripod shaking, object shaking, object moving in linear fashion, object rotating, blurred lens, dirty lens, scratched lens, oily lens, defocused lens (e.g. too far or too short for focal length), off-axis lens (e.g. astigmatism or refractive error of the lens), dust on the lens of camera, and the like, which are the common reasons for blurry or degraded or defocused pictures by a camera. All the family of transformations $F_{image}(x)$ are stored in a library or database, for future access. The transformations $F_{image}(x)$ are designed or derived based on the optics or physics of the lens or theoretical formulation or analytical or pure experimental or simulation or optics model or physical model or pure curve or pure listing or table or closed form formulation or equation or combination of the above or the like.

Then, for each of these transformations $F_{image}(x)$, we derive reverse transformation on the image, or $F_{image}^{-1}(x)$, applied to each pixel or image, analytically, experimentally, theoretically, in-closed-form, by mapping numbers, by table of numbers, by simulation, or the like. Since we may not know the cause of the problem, or even if there is any problem in the first place, in a given image, we try all or some of the family of reverse transformation ($F_{image}^{-1}(x)$)

on all images, or on blurry images with bad recognition rate, or only on one or few sample images, to see if the recognition (e.g. recognition rate or reliability, e.g. on some samples) is improved or the blurring is reduced (e.g. based on sharpness of lines or borders. If so, then we know what the problem was for the camera, and we use that specific reverse transformation for all images from that specific camera or lens. If there are 2 or more problems e.g. with the camera, then we need 2 or more (e.g. N) corresponding reverse transformations ($F_{1image}^{-1}(x)$, $F_{2image}^{-1}(x)$, $F_{3image}^{-1}(x), \ldots, F_{Nimage}^{-1}(x)$) on the images, applied to the images in the reverse order, to compensate for the problems e.g. with lens or camera. After the images are corrected, then the recognition steps are done, which yield improved results.

If we already know or guess what the problem(s) is, then we just try that corresponding specific reverse transformation $F_{Mimage}^{-1}(x)$, first. For the improvements, on recognition or blurring, we can have a threshold or rule or criteria or fuzzy rule or rule engine, to stop the process at that point, if we reach the threshold. The threshold can be fuzzy value, or crisp number, or percentage, or relative value or ratio, or absolute number, or the like, as the criteria for optimization.

Let's look at one example. For a defocused image with a defocused lens, we have a situation that e.g. the proper image is not formed on the plane of the film or photosensitive detector. Let's assume that the proper image would have been formed on an imaginary plane behind the current actual plane for the film or photosensitive detector or sensor. Let's also assume, from the geometry of the imaginary plane and the actual plane, the distance between those 2 planes produces e.g. approximately 2 pixel shift, on the actual data, for the current actual plane, because the optical beams or rays or photons hit the actual plane sooner than they should have, due to the defocusing effect of the lens. Thus, in this example, for a pixel (i, j) on the actual plane, to get the corrected value for the pixel, $V_C(i, j)$, based on the original pixel values, $V(i, j)$, we have approximately the following relationship, based on the neighboring pixel values, from 2 pixel away, e.g. in one embodiment, on each of the 4 directions, e.g. up, down, left, and right sides, having 4 component contributions, as the sum of all 4 contributions:

$$V_C(i,j)=V((i+2),(j+2))+V((i+2),(j-2))+V((i-2),(j+2))+V((i-2),(j-2))$$

To normalize, we get the average of 4 contributors above, by dividing by 4:

$$V_C(i,j)=[V((i+2),(j+2))+V((i+2),(j-2))+V((i-2),(j+2))+V((i-2),(j-2))]/4$$

Or, in another embodiment, we use 8 directions, including the diagonal directions, for neighboring pixels, with 8 component contributions. The method above for calculating the values can be applied to the intensity values, or each color component values, or each property value of pixel, e.g. RGB values or YMCK values or grayscale values. Now, we have the corrected values for pixels which correspond to the inverse transformation mentioned above.

The formulation above applies to all pixels in rows and columns, for all values of i and j. So, we have to scan the image. However, for pixels near the corner or boundaries, which do not have e.g. any neighboring pixel to the top or left, then we repeat the same value again for missing pixels, so that the formula above is still applicable. In summary, at the end, we can correct the image, to reduce or eliminate the defocusing effect, and then apply the recognition module on the corrected image for better recognition.

In one embodiment, we use convolution with a radial function, e.g. Gaussian function, with the variance of e.g. 2-4 pixels (or more), and move it around, to scan the whole image, to get the same effect as above.

Geometrical Analysis:

In one embodiment, homography and projective transformation can be used to compute camera rotation or translation, to account for a new point of view for a person or object, e.g. to match 2 views of the same face, from front and side, from 2 pictures, to match faces or recognize them.

In one embodiment, using filters for sharpening the edges as preprocessing, and then using contrast analyzer, between values of neighboring pixels, as their absolute or relative difference, versus a threshold or percentage, one can find the boundaries of objects (or using any other boundary analyzer). From the boundaries, one can find the corners of the objects, as their intersection of 2 boundary lines, or as the points in which the derivatives or slopes of boundary lines or curves change too much or abruptly or above some threshold. Corner points or boundaries are categorized as interesting points for the purpose of the feature extraction form the image, which collectively make up a feature vector in our feature space. Also, having all the corner points, the shape of the object can be found or named, from the geometrical shapes in the database.

Sorting & Analyzing Data:

In one embodiment, having "big data" coming in as input, we distinguish images in the first cut, very coarsely, e.g. text, medical images, satellite images, human faces, numbers, tables, computer codes, and the like, from their respective signatures and features, in training schemes or against databases already tagged. One example is text in different languages, as a sub-category, in later filtering or narrowing the class further, or typical street maps, which can be trained or learned using millions of samples, from that class or subclass. The learning machine generally works better with more training samples, as long as the samples are reliable (e.g. with high reliability factor, which can be extracted from their corresponding Z-web values).

In one embodiment, when analyzing a Big Data, the system comes up with or extracts some patterns or relationships at the beginning. Then, we store the patterns or relationships as templates for future use. As the time passes, the number of generated templates increases, increasing the value of the library of templates, and increasing the choices and possibilities for templates to fit in. Thus, at the end, we have some templates, from history, as educated guesses. For example, we can offer this as a service on the cloud, with all the templates generated so far, to analyze the data. In one embodiment, we export the templates from another system, into the first system, to add value to the template library. In one embodiment, our system buys or sells the templates from/to another system or source or entity. In one embodiment, the system uses the templates to analyze the data or extract information or data mine the data.

The examples of Big Data or data analytics are on the following data types: unstructured data, structured data, machine generated data, tables, listings, databases, collections, records, financial history, employment history, resume, business process logs, audit logs (file or database), packet data, industrial control system data, network state or status data, web proxy logs, system events, applications logs, click information (e.g. on Internet, web pages, buttons, menus, objects, figures, and the like), database logs, logging API, operating system status, information obtained from sensors or meters or detectors or cameras, web access or network access logs, texting records, SMS records, call records, TWITTER® records, configuration files, management API, message queue, operating system performances, data from control and data acquisition module, satellite images, input from airport cameras, movie scans, music scans, speech scans, text scans, medical images, library scans, database scans, or the like.

The analysis of the above data e.g. can be used for predicting customer behavior, finding correlations among sources, forecasting sales, catching fraud, finding computer security risks, processing sensor data, social network analysis, feedback analysis, emotion analysis, web click streams analysis, or the like.

Recognizing Objects for Various Applications:

In one embodiment, we identify people in the picture in album or by camera or video recorder, and automatically as default (unless chosen otherwise from the menu), email to all people involved or recognized through the album or from camera or from each picture, from their contact list, if desired, or to all in the event, or share through link or FACEBOOK®. The scope of distribution is set beforehand, for list of recipients. For example, if three people are in one picture, namely John, Amy, and Fred, then that picture is emailed to those 3 people, only. However, the next picture has e.g. 4 people in it, namely, Ted, John, Amy, and Fred, and the next picture goes to all 4 people, including Ted, and so on. The preferences are chosen beforehand for templates or single picture or batch processing, for all or subset of pictures or data or video.

For example, there are 2 people recognized, out of 10 people in the video, from our library. The other 8 people were not in our library or recognition was not successful. Then, a copy or link or track or frame number or pointer or position of the video or web site or storage for the video or specified frame of video is sent to the 2 friends that are recognized from the searched video. That can help for social networking sites and professional settings for a conference call between some co-workers, automating distribution of relevant data, including voice, text, video, or image, that include the name of specific people or image of the person or any related object to that person, found in that text or sound piece or video or image, to be sent to that person automatically. See e.g. FIG. 153 for such a system.

This can be used for example for copyright or trademark protections, in which the image including a person's copyright or trademark is sent automatically to the person for review, out of millions of web site pages scanned on the Internet, to find infringers or verify licensee payments, if any. Or, one can send the list of web sites using a specific logo or trademark or patent to a comparison module, to verify against the list of legitimate or paid or permitted licensees in its database, automatically, to approve or warn the related people, by email, pre-recorded voice message, texting, SMS, mail, vibration warning on the phone (e.g. specific vibration or cycle or sequence or variable magnitude or variable frequency), any communication means, or the like. So, it is a useful tool for sending information to relevant people, automatically, by email or tel. (via text, voice, or image) or any other communication means, once the object is recognized in the content under review, and the object is linked to an entity that subscribes to our services, such as friends or corporate legal department, for fee or for free, depending on the business model or purpose of the service.

For example, if I am interested in movies by director A, then any new or old movies found for her name can be automatically sent to me, even if the mention was on text or verbal (sound/voice) at the end of the movie, with no tags or comments. Of course, any tag or comment on the movie regarding that information makes it easier for such a process. Alternatively, those tags and comments can be verified based on the other data extracted from the video directly by Z-web engine, e.g. text or sound naming the director at the end of the movie. For those, we use OCR or voice recognition modules to recognize and convert information for comparisons.

The picture or sound albums or videos can be classified and archived this way, in a cross classification way, using a relational database, for relating e.g. objects, videos, and people together, in a final Z-web structure, and to be searched by the user later on, as a query, or question, about any subject, starting from one node and going to other nodes, even if the user does not know that the second node is related to the first node at the beginning. This is also a powerful search engine and archive, which is expandable by its knowledge base through expanding Z-web size and making more reliable and consistent and truthful branches and relationships on the Z-web, increasing the total value of the Z-web. For example, the same picture or video or voice speech may be referenced in multiple places for multiple reasons for multiple objects or nodes or branches, which can be queried or searched independently, through Z-web.

In one embodiment, we identify objects in the video or images for advertisement purposes, or for consumer purposes, to send ad notices or notify the potential buyers or notify new consumers or notify about new products or requested types of products or products of interest. The object in video, for example, has some relationship with the recipient of the email or communication or texting or notice or telephone call or fax or ring tone or the like, as a way of notification. For example, the relationship came from the Z-web, or the object was chosen by the user, or the class of objects was chosen by the user or third party or randomly by computer, through the menu or the user interface or GUI or tablet screen or tel. screen or by voice recognition command. So, the extracted object can be the subject of an ad, or suggested product, or put into a cart for purchase on web site, or sent to a reviewer, or stored in a database, or broadcasted to many people, or the like.

One can also search using a query for the album, e.g. using a text, to find an object. One example is to find out that, for the identified person in video, what kind of food or drink does he like? Those could be found through the other objects in frames (nearby) in video, e.g. on or near the person's desk or in his hand, holding the drink or bottle. Or, if somebody enters a textual or voice question for the system, as what kind of food or drink he likes? Then, we can use OCR or voice recognition or analysis to get the question, and then use word search or natural language processing or specific flags for key words, to get the meaning of the question, or approximate meaning of that. Then, we apply the method mentioned above, to answer the question(s) or find an approximate answer.

In one embodiment, we identify an object in the video or images, then we remove or edit it, or replace it with another object, e.g. for advertisement or localization purpose. For example, in different countries, different beer (local beer) is used in pictures or movies or ads, for better acceptance as a local favorite or for marketing and higher sales, by replacing one object on the table with another one from library for local objects, e.g. beer bottle, to be put on table, seamlessly and automatically. See e.g. FIG. 154 for such a system. However, we may need some adjustment on the background color and texture, if the size and shape of the beer bottles are not exactly the same, for the gaps that have no overlap between the 2 beer bottles. One correction is blurring or averaging or filtering the neighboring pixels around the gaps, or using the neighboring pixel color and texture, to extend inside the gap region(s), to cover the gaps with more or less same or similar color and texture nearby, as extrapolation and interpolation methods.

In one embodiment, we recognize a partial object ($1^{st}$ object), which is behind another object ($2^{nd}$ object), and for editing purposes, in the image or for movie (for all frames including that object), we bring the full image of the $1^{st}$ object in front of the $2^{nd}$ object, to block the $2^{nd}$ object partially, by the $1^{st}$ object, in effect reversing the order of the objects in the still image or video frames, in any order we wish. The image of the $1^{st}$ object is in our library of objects, which can be obtained from there. Then, the size or color or intensity is normalized to the one in the image, so that we do not feel any abrupt change in size or color or intensity, based on the ratio to the values in the neighboring pixels, or average in a region, or value of pixels near border lines or boundaries. For the perspective, if the $1^{st}$ object is tilted, then either we use the tilted version of the $1^{st}$ object from library (if available), or we morph the image of the $1^{st}$ object in the library slightly, based on translation, rotation, lens, or similar image transformation matrix, to look similar to the tilted image of the $1^{st}$ object, to be replaced, for editing purposes.

In one embodiment, we recognize faces in an album, and find the incorrect tagged ones, or edit and correct them automatically, with or without the user's or owner's permission or review, as multiple options in the software.

In one embodiment, we recognize faces in the album and insert it automatically in the phone display or screen, when the person calls in, to be displayed, with a specific ring-tone, or mentioning the person's name, in voice or text, to inform the receiver regarding the identity of the caller. In addition, the mute vibration mode can have different frequency of vibrations, set for different users or callers, so that they can be recognized by a mix of vibrations at single or multiple frequencies, or using notes or music style beats or vibrations, or using modulated waveforms as vibrations lasting a few seconds, for example.

In one embodiment, we recognize faces in the album and insert it automatically in the email, for sender or receiver, so that it would be easier to recognize the people in the email list, and fewer mistakes will happen for sending an email to unwanted or unintended people. The reverse can also be done. That is, we select pictures from the album, and the email list is generated automatically, from person's identity, which relates to the person's contact information, e.g. email addresses or telephone or fax numbers, which all can be part of the person's Z-web, as the related information to the person's node, represented by neighboring nodes.

Data Extraction, Including Emotions and Taste:

In one embodiment, the signature of the cell phone or ID number for camera relates the picture to the person who took the pictures or owner of the camera, which relates the picture to the friends of owner, which relates the picture to possible targets for people in the picture(s), for recognition. In one embodiment, the pictures from nature or mountain or cities relates to the taste or preference of the owner of the camera or cell phone camera, which relates her to the possible destinations for the next trip, which is helpful for marketing for travel agencies or local ads for products or services for those destinations, such as local rental car companies. In one embodiment, the pictures from a house in camera are used for extracting the taste of the owner of the camera, for the house setting and environment, such as in suburb or wooded area, for future house hunting for the new home buyer (camera owner), which is helpful to the real estate agents, for the preferences of the home buyer, for marketing or efficient house hunting.

In one embodiment, "smiling" in a picture is used to find emotions for the people in the picture or the situation in the image, such as celebration and birthday ceremony, as opposed to sad situations such as funerals. In one embodiment, smiling is recognized using the big library of smiling pictures of real people for comparison or training samples. In one embodiment, smiling is recognized as a symbolic (caricature) basic shape of the mouth versus the general shape of the face, in relation (or with respect) to each other. For example, smiling is defined as a curved mouth with both ends going upward, or a strike similar to a "U". That is, as long as we can distinguish such a relationship for the mouth with respect to the face, or such a general shape for the mouth, we can tag that as a smiling picture or person. This can be done for any emotions, such as angry, crying, shouting, and the like, for various contexts, for example, a sad situation, for example, for funeral, to relate the black dress and sad situation to family members in the picture or scene, for common loss of a family member, who is possibly the one of the few people missing in the scene or pictures, as extracted from the family tree or family album or family names tagged in the album or FACEBOOK® or similar social web sites, for all names in the whole family. See e.g. FIG. 155 for such a system. Thus, missing people in the picture has some significance, as well, when the universe of all people in the family is known, as a complete set. In one embodiment, we have a crisp set with well-defined boundaries and members, and in another embodiment, we have a fuzzy set, with fuzzy boundaries and fuzzy memberships and fuzzy members.

In one embodiment, the emotion is related to the character of the person, mood, intention, future action, state of mind, or psychology, e.g. one person being angry at some event may indicate his sad mood or his intention to spoil the event. These can be modeled through Z-web and Z-nodes.

Another example is when we have e.g. a total of 5 friends in the album for the trip or vacation to Miami Beach in 1995, which means that the universe of all buddies in that trip is 5 people, which is extracted as our system reviews all the pictures from that trip, with maximum 5 distinct faces recognized there, at the end of the evaluations. So, e.g., some pictures have 2 people and some have 4 people in them. For example, the missing person in a picture with e.g. 4 people in it might be the person who took that picture, and he might be the camera owner, as well, if most of the pictures are like that (i.e. him being missing from all or most of those pictures, in that camera).

In one embodiment, we find all objects in a picture and summarize them as data, templates, tags, comments, numbers, and the like, which can also be used for trainings for signatures or features of other images for future. In one example, we have about 5000 different objects in our library, for most often used objects in everyday life, such as shoe and door, which can be sub-classified for fast search and retrieval, such as office furniture. These objects are also represented in a Z-web, as related objects, e.g. computer and mouse.

In one embodiment, the type of beverage, wine, suit, car, fruit, clothing, cigar, and the like are also some examples of taste of a person. In one embodiment, when get some value for an object, then we instantiate all instants of the object with that value, e.g. object in a satellite image is a tank, or in a medical image is a cancer cell or tissue. Meanwhile, we can put a placeholder name for that object, until it is recognized.

In one embodiment, we do multiple steps hierarchy recognition, to get many images and analyze coarsely to put them in the right bins or classes (e.g. picture of people), as preprocessing, and then, go finer and finer analysis or filtering, to get into specific data, e.g. find or locate faces, and then face recognition. Another example is for recognition in different levels, e.g. starting from finding all radiology x-rays, then bone in image, then foot as the subject of the image, then broken foot as the property of the foot, or age or sex of the subject, from the parameters of the image, based on expected values in the medical databases, e.g. for our prior samples or training samples for neural networks.

In one embodiment, we have a face recognition based on the chunks or pieces of face, e.g. recognizing nose or lips, individually and with respect to each other, to confirm that they constitute a face, e.g. with respect to relative position or size. The parameters are all fuzzy parameters, in one embodiment. The relationship and relative position or size can be expressed through our Z-web, as a method of recognition of an object, with all its components, to first see that it is actually a face, and if so, whose face it belongs to, i.e. recognize the person in the next step. The shape and size of the components of a face or object are expressed in fuzzy relationships or fuzzy rules, in one embodiment. Or, it can be stored as a target object or training sample in a database or library or storage, for recognition, training, and comparison purposes.

In one embodiment, from a picture of food plate, the system extracts the objects and recognizes them, e.g. peanut, and from the library, the system gets all the nutritional facts, for proper diet for the user, per day, as accumulated and compared with the special or recommended regimen, for general or for a specific person or patient, to limit or warn the user or to recommend or remind a user, e.g. for deficiency of calcium or for allergy to an ingredient or for conflict between foods and drugs, stored in library for general knowledge and also on a separate database for a specific person, as customized, on her laptop or smart phone or mobile device. In one embodiment, such information is integrated into the routine for exercise for the same user, for scheduling and count and statistics and progress report. See e.g. FIG. 156 for such a system.

In one embodiment, for any picture that does not come out right (e.g. no smile, rotated head, or closed eyes), the system tags the pictures for review by the user, or in one embodiment, optionally, the system automatically deletes them from the photo album or frames, or exchanges them with the approved ones or good pictures or neighboring pictures or similar pictures, or leaves them as blank.

Cost of Search:

The cost of search in terms of computational power and delay time is a factor, as how far we want to go deep to get to other related nodes to find other related objects for more complete search, in our Z-web. For example, as one detects a computer mouse, then the system looks for a computer nearby, within the expected radius of proximity between 2 given objects, which is stored in a database or in a Z-web, as a parameter shared between computer and mouse nodes, as explained elsewhere in this disclosure. Thus, for a given computing power and time, one can estimate how deep and wide the search for related nodes is, and what and how many related objects can be obtained or analyzed.

The search or traversing the nodes can be directional or biased intentionally, for example, for one embodiment, for a geographical issue, one may expect more geographical or location related nodes. So, we follow the nodes that are more inclined or related to locations, such as "restaurant" or "coordinate values of a location on GPS or planet Earth". The selection of branch can be optimized, to go deeper in one branch versus another one, in a Z-web structure, to find related objects or nodes. With a parallel processor, the selection of multiple branches can be done simultaneously.

Another Way of Calculating "Z-Factors", Including Reliability Factor:

Please note the reliability factor can be calculated based on the other methods mentioned in this disclosure. This can be also calculated and addressed by Z-numbers or by fuzzy logic membership or other fuzzy concepts or other concepts, such as the "trustworthiness of speaker", "sureness of speaker", and "statement helpfulness", which deal with the source of information, where the information propagates through one or more sources to get to the listener or user, as the final destination, to analyze the information and its quality, including reliability factor, confidence factor, truth factor, bias factor, expertise factor, validity factor, expiration date (if any, to declare the information void after a certain date and time, such as stock market quotation), and the like (collectively called Z-factors, for factors used in Z-web).

For example, for reliability factor analysis, in another embodiment, we have e.g. for 3 nodes $N_1$, $N_2$, and $N_3$, where the information is moved from $N_1$, to $N_2$, and then to $N_3$, with reliability factors $R_{F1}$, $R_{F2}$, and $R_{F3}$, respectively. For example, assuming all being normalized to maximum the value of 1, then all $R_{F1}$, $R_{F2}$, and $R_{F3}$ are less than or equal to 1 (or it can be done in the percentage scale to the maximum value of 100). So, in one embodiment, we will have the total reliability factor $R_{FTotal}$ as the multiplication of all factors in the series of nodes:

$$R_{FTotal} = R_{F1} R_{F2} R_{F3}$$

In one embodiment, we will have the total reliability factor $R_{FTotal}$ as the intersection of all reliability factors in the series of nodes, or minimum of those values:

$$R_{FTotal} = \text{Min}(R_{F1}, R_{F2}, R_{F3})$$

In one embodiment, we will have each reliability factor is compared to a threshold, in the first case as being larger than a threshold to get a value of 1, and in the second case as being smaller than another threshold to get a value of 0, which makes the calculations simpler for calculations of formulas above for large number of nodes, because we end up with lots of 0 and 1 in the node factor assignments.

For parallel nodes situation (as opposed to series), we will have the corresponding formulation for the total reliability factor $R_{FTotal}$, for example, for 3 nodes ($N_1$, $N_2$, and $N_3$), going to a final $4^{th}$ node, $N_4$, as parallel inputs. If the information coming from all 3 nodes ($N_1$, $N_2$, and $N_3$) are not related, then they have no impact on each other in terms of reliability. However, if they are related to the same subject, then we will have, in one embodiment:

$$R_{FTotal} = R_{F1} + R_{F2} + R_{F3}$$

In one embodiment, we will have the total reliability factor $R_{FTotal}$ as the union of all reliability factors in the parallel configuration of nodes, or maximum of those values:

$$R_{FTotal} = \text{Max}(R_{F1}, R_{F2}, R_{F3})$$

Again, in one embodiment, we will have each reliability factor is compared to a threshold, in the first case as being larger than a threshold to get a value of 1, and in the second case as being smaller than another threshold to get a value of 0, which makes the calculations simpler for calculations of formulas above for large number of nodes, because we end up with lots of 0 and 1 in the node factor assignments.

If we are dealing with fuzzy numbers, then we can use the operators max, MAX, min, MIN, and sup, as commonly known in Fuzzy Logic, and e.g. as defined and shown by Fig. 4.6 and pages 111-112 of the book by Klir et al., "Fuzzy sets and fuzzy logic", published in 1995, by Prentice Hall. These are more general versions of Max and Min operations we mentioned above. Thus, the reliability factor will also be in Fuzzy domain and as a Fuzzy parameter, as an example.

All of these methods in this disclosure can also apply to other factors mentioned elsewhere in this disclosure, e.g. confidence factor, truth factor, bias factor, expertise factor, trust factor, validity factor, "trustworthiness of speaker", "sureness of speaker", "statement helpfulness", "expertise of speaker", "speaker's truthfulness", "perception of speaker (or source of information)", "apparent confidence of speaker", or "broadness of statement". The mathematics and vehicle to apply to Z-web nodes (also called "Z-node") or objects are the same for each of those factors (collectively called "Z-factors", for factors used in "Z-web"). The collection or aggregation of Z-web with all the associated factors mentioned above makes it the most reliable and most powerful search engine tool in the market, for data analytics or analysis of images, "big data", text, voice, moods, facial expressions, emotions, personality, character, characteristics, concepts, and the like. Of course, the bigger Z-web gets, the more valuable it becomes, with more nodes and factors and branches and other parameters, as mentioned above.

In one embodiment, "trustworthiness of speaker" ($A_{trust}$) depends on (as a function of, or Function(x)) at least 4 other factors (variables): "apparent confidence of speaker" ($A_{confidence}$), "speaker's truthfulness" ($A_{truth}$), "expertise of speaker" ($A_{expertise}$), and "perception of speaker (or source of information)" ($A_{perception}$) with each can be both fuzzy and crisp values, in different examples. In one embodiment, the "trustworthiness of speaker" is "high", only if all of its 4 factors are "high". So, mathematically, we have:

$$A_{trust} = \text{Function}(A_{confidence}, A_{truth}, A_{expertise}, A_{perception})$$

If we assign the value of 1 to "high" and 0 to "low", in one embodiment, then we can write this in a short form as, based on AND logical operation:

$$A_{trust} = (A_{confidence} \text{ AND } A_{truth} \text{ AND } A_{expertise} \text{ AND } A_{perception})$$

Or, in another presentation, in one embodiment, we can write it as, using intersection operator ($\wedge$):

$$A_{trust} = (A_{confidence} \wedge A_{truth} \wedge A_{expertise} \wedge A_{perception})$$

Or, in another presentation, in one embodiment, we can write it as, using minimum operators (e.g. min or MIN, as commonly known in Fuzzy Logic, and e.g. as defined and shown by Fig. 4.6 and pages 111-112 of the book by Klir et al., "Fuzzy sets and fuzzy logic", published in 1995, by Prentice Hall):

$$A_{trust} = \min(A_{confidence}, A_{truth}, A_{expertise}, A_{perception})$$

or $$A_{trust} = \text{MIN}(A_{confidence}, A_{truth}, A_{expertise}, A_{perception})$$

So, we can calculate or obtain $A_{trust}$ from its components or variables, based on fuzzy rules, set rules, logical operations, Venn diagram, or the like, for their respective domains of analysis.

Note that for any intersection operator or logical or fuzzy operations, mentioned here, we can use different logic domains and operations, e.g. Lukasiewicz logics, Bochvar logics, Kleene logics, Heyting logics, Reichenbach logics, or the like (see e.g. Table 8.4 of Klir et al. (on page 218 of the book mentioned above)). In addition, for the Generalized Modus Ponens, Generalized Modus Tollens, and Generalized Hypothetical Syllogisms, we can use the following conventions, as an example: Early Zadeh, Gaines-Rescher, Godel, Goguen, Kleene-Dienes, Lukasiewicz, Reichenbach, Willmott, Wu, or the like (see e.g. Tables 11.2, 11.3, and 11.4 of Klir et al. (on pages 315-317 of the book mentioned above)). In one embodiment, to be consistent, once we are using one logical domain, we have to stay in that domain for all operations.

In one embodiment, "sureness of speaker" ($A_{sureness}$) depends on at least 4 other factors: "apparent confidence of speaker", "speaker's truthfulness", "expertise of speaker", and "perception of speaker (or source of information)", with each can be both fuzzy and crisp values, in different examples. In one embodiment, the "sureness of speaker" is "high", only if "speaker's truthfulness" is either "high" or "low", and the other 3 factors are "high". So, mathematically, we have $A_{sureness}$ as a function of:

$$A_{sureness} = \text{Function}(A_{confidence}, A_{truth}, A_{expertise}, A_{perception})$$

If we assign the value of 1 to "high" and 0 to "low", in one embodiment, then we can write this in a short form as, based on AND and OR logical operations:

$$A_{sureness} = A_{confidence} \text{ AND } A_{expertise} \text{ AND } A_{perception} \text{ AND } (A_{truth} \text{ OR } \tilde{A}_{truth})$$

Wherein $\tilde{A}_{truth}$ is a logical complement to $A_{truth}$. In fuzzy logic, please note that, due to overlapping membership functions, ($A_{truth}$ OR $\tilde{A}_{truth}$) is not equivalent to 1.

Or, in another presentation, in one embodiment, we can write it as, using intersection operator ($\wedge$) and union operator ($\vee$):

$$A_{sureness} = A_{confidence} \wedge A_{expertise} \wedge A_{perception} \wedge (A_{truth} \vee \tilde{A}_{truth})$$

Or, in another presentation, in one embodiment, we can write it as, using minimum and maximum operators (e.g. max, MAX, min, MIN, and sup):

$$A_{sureness} = \min(A_{confidence}, A_{expertise}, A_{perception}, (\max(A_{truth}, \tilde{A}_{truth})))$$

or $$A_{sureness} = \text{MIN}(A_{confidence}, A_{expertise}, A_{perception}, (\text{MAX}(A_{truth}, \tilde{A}_{truth})))$$

Or, we can use any of the combinations of the similar operators, listed above. So, we can calculate or obtain $A_{sureness}$ from its components or variables, based on fuzzy rules, set rules, logical operations, Venn diagram, or the like, for their respective domains of analysis.

In one embodiment, "statement helpfulness" ($A_{helpfulness}$) depends on at least 2 other factors: "sureness of speaker" ($A_{sureness}$) and "broadness of statement" ($A_{broadness}$), with each can be both fuzzy and crisp values, in different examples. In one embodiment, the "statement helpfulness" is "high", only if "sureness of speaker" is "high" and "broadness of statement" is "low". In one embodiment, "statement helpfulness" indicates the parameter that is very useful for analysis of many pieces of data from multiple sources, such as Big Data or Internet. So, mathematically, we have $A_{helpfulness}$ as a function of:

$$A_{helpfulness} = \text{Function}(A_{sureness}, A_{broadness})$$

If we assign the value of 1 to "high" and 0 to "low", in one embodiment, then we can write this in a short form as, based on AND logical operation:

$$A_{helpfulness} = A_{sureness} \text{ AND } \tilde{A}_{broadness}$$

Wherein $\tilde{A}_{broadness}$ is a logical complement to $A_{broadness}$. In fuzzy logic, please note that, due to overlapping membership functions, ($A_{broadness}$ OR $\tilde{A}_{broadness}$) is not equivalent to 1.

Or, in another presentation, in one embodiment, we can write it as, using intersection operator ($\wedge$):

$$A_{helpfulness} = A_{sureness} \wedge \tilde{A}_{broadness}$$

Or, in another presentation, in one embodiment, we can write it as, using minimum and maximum operators (e.g. max, MAX, min, MIN, and sup):

$$A_{helpfulness} = \min(A_{sureness}, \tilde{A}_{broadness})$$

Or $$A_{helpfulness} = \text{MIN}(A_{sureness}, \tilde{A}_{broadness})$$

So, we can calculate or obtain $A_{helpfulness}$ from its components or variables, based on fuzzy rules, set rules, logical operations, Venn diagram, or the like, for their respective domains of analysis.

In one embodiment, the information comes from multiple sources or speakers (or originator or gatherer or reporter) and goes through more sources, and may get modified in there, based on the same parameters described above. Then, the information may get merged, edited, combined, aggregated, or modified by some sources, or otherwise, just goes through an intermediate source with no modifications, just as a conduit, with no effect on the data. Finally, one or more pieces of data reach a listener (or receiver or evaluator or user or computer or collector or public or third party entity), through those many possible routes (from one or more original sources of information). Then, the listener should gather all data, with all the factors mentioned above, from all sources and routes, and digest and evaluate, to make a conclusion from all of the above. Here, the Z-web is applied, because the whole propagation of data through all the nodes or sources can be modeled with the Z-web, from one part of the Z-web to another part or section or node of the Z-web, with all the reliability factors and other factors included in the Z-web. This is a very powerful tool for analytics e.g. for Big Data or Internet, with many sources of information, and many intermediate nodes, each having its own reliability, truthfulness, bias, expertise, addition, edit, and similar factors, e.g. as mentioned above, on the original data.

Of course, when we have a complex node structure for Z-web, we will have a multiple parallel and series situations, broken down as imaginary smaller units, which we can use the methods above or as explained elsewhere in this disclosure, to analyze for the Z-web. In addition to the above formulations, any similar formulations and combinations can also work in different embodiments. For example, the Z-factors can be based on tables, curves, formulas, analytical relationships, equations, Fuzzy rules, rules engine, conditional statements, or the like.

Processing & Mathematical Methods:

In one embodiment, root-mean-square error (RMSE) or ArcTan function (an inverse trigonometric function) can be used to reduce the effect of the large errors or dampen the big variations, because of their behaviors at large numbers.

In one embodiment, for optimization, the method of Lagrange multipliers is used for finding the local maxima and minima of a function subject to some constraints, which is equivalent to finding some optimum point on a surface, subject to a cross section of that surface, which is equivalent to tangent vectors of the 2 corresponding contour lines being parallel, which is equivalent to gradients of 2 functions (e.g. f(x,y) and g(x,y)) being parallel, subject to a constraint for g(x,y), e.g. being a constant value. So, we will have the following relationship for the gradients of the 2 functions (with the gradient being taken with respect to x and y (the 2 coordinate axes), and k representing a coefficient of proportionality):

$$\nabla f = -k \nabla g$$

We use this for any optimization, e.g. in our image processing method or recognition routines or image enhancements or optimization of one Z-factor in Z-web, subject to another Z-factor (as a constraint), e.g. reliability factor.

In one embodiment, for fuzzy system reasoning, for aggregation and implication techniques, e.g. we use Min/Max Aggregation method, in which we get the membership value from the $1^{st}$ curve or membership function, and trim the top of the $2^{nd}$ membership function or curve (as flat cut-off) with the first membership value (as the maximum value allowed on that $2^{nd}$ membership function or curve). In one embodiment, we use Additive Aggregation method, in which we get the membership value from the $1^{st}$ curve or membership function, and scale or normalize the $2^{nd}$ membership function or curve (usually reduce the peak height of the curve) based on the first membership value (as the maximum value or peak allowed on that $2^{nd}$ membership function or curve).

In one embodiment, for aggregating the correlated fuzzy sets, for the additive aggregation method, we can get the final membership value, $\mu_{final}$, based on the individual membership values, $\mu_1$ and $\mu_2$, as (where index i runs from 0 to n):

$$\mu_{final} = \forall_i \min((\mu_1 + \mu_2), 1)$$

In one embodiment, for aggregating the correlated fuzzy sets, for the Min-Max aggregation method, we can get the final membership value, based on the individual membership values, $\mu_1$ and $\mu_2$, as (where index i runs from 0 to n):

$$\mu_{final} = \forall_i \max(\mu_1, \mu_2)$$

Thus, we can aggregate and find the resultant membership functions. Then, if we have to defuzzify at one point, to get a crisp number for some applications, e.g. acting or not acting on some function, e.g. turn off the light, as a binary decision or output, then for that case, we get the center of mass coordinate, or the coordinate of where the membership curve bends (going down from its maximum value or plateau or flat region on the top), or the coordinate of the center of the highest plateau or flat region of the membership curve (if any), or any averaging or weighted averaging or the final membership curve, or any computation for the area under the membership curve to find a compromise value or middle point or median point or coordinate, or the like. However, if the crisp value is not needed, we keep the values as fuzzy values, stored or sent to the next step of the process, because when we defuzzify, e.g. to get a point or crisp value, we usually lose some information stored in the membership curve. So, we want to avoid that, if possible, or as much as possible.

In one embodiment, for fuzzy rules, e.g. rules engine, e.g. for control system applications, e.g. when we have a bunch of rules in terms of e.g. IF-THEN rules, or conditional statements, then we can apply the rules or policies based on fuzzy backward chaining, to resolve the rules backward, to fire or activate the rule(s), in our inference engine. Here, we start from a goal, and then find out which rules have that goal as output, and from those extracted rules, we find out what input parameter values we need to know to evaluate those extracted rules. Those input parameter value(s) now become our sub-goal(s), which is (are) similar to our goal above, which we repeat the same routine above again, recursively, until we get to an input value that we already know the value for, and we can plug in the value for that corresponding rule, as the input, to get the output (of that IF-THEN rule). Then, recursively, we use that output that we just got as the input of the previous rule(s), concerning that parameter, in our chain, to get the result or output of the previous rule(s). Then, we continue this recursively, until we get to our first goal at the top of the chain, in the beginning FIG. 157 shows a backward chaining inference engine. FIG. 158 shows a backward chaining flow chart.

In one embodiment, for fuzzy rules, we use forward chaining inference engine, to fire the rules in forward manner, as the input part of the rule has some available value, to trigger that rule, and instantiate some variables. So, we go through all rules that can be fired, until the list is exhausted. So, here, we do not require a goal. FIG. 159 shows a forward chaining inference engine. In one embodiment, we add a RETE algorithm to our method above, for better performance.

In one embodiment, based on both approaches mentioned above, to take advantage of our gathered knowledge in each step, we combine both methods, as an opportunistic forward firing, added to our backward chaining engine, for better performance. FIG. 160 shows a fuzzy reasoning inference engine. In one embodiment, all of the above are used as methods of handling data for our Z-web, with its corresponding Z-factors.

In one embodiment, we (i.e. our system or computer or processor or microprocessor or CPU or computing unit or the like) perform parallel processing for each signature for each object in the picture, to get the result faster, to extract and distinguish all objects in the image.

In one embodiment, we can combine our method with Adaptive Boosting, as a machine learning algorithm, designed by Yoav Freund and Robert Schapire, to improve the performance (AdaBoost algorithm). The subsequent classifiers are adjusted in favor of those instances misclassified by previous classifiers. In one embodiment, it is sensitive to noisy data and outliers. In one embodiment, it is less susceptible to the "overfitting" problem (which is a well-known problem in machine learning). The system generates and calls a new weak classifier in each cycle, with updated weights, based on the importance of examples in the data set. Then, repeatedly, the weights of incorrectly classified examples are increased, and those of correctly classified examples are decreased, to zoom in to the missed examples.

In one embodiment, we can combine our method with the following method, for classification, such as face recognition, to consider both the error and time for the final decision, based on sequential decision-making. When the false positive and false negative error rates are given to us, then we want the shortest average time to decision (number of measurements). We use a method called Wald's sequential probability ratio test (SPRT), or WaldBoost. We use both a priori ordered measurements and known joint probability density functions, for time and error rate tradeoff, with the joint probability density estimation using the optimal SPRT decision strategy, which has a good detection rate in a reasonable amount of time.

In one embodiment, we can combine our method with the c-means clustering algorithm, which produces input pattern groups with corresponding cluster centers. To learn fuzzy functions, one can use adaptive vector quantization (AVQ) (using unsupervised AVQ competitive learning) to estimate the local centroids (and covariance matrices) of clusters in the input-output space. From the resulting ellipsoid, one can derive the fuzzy rules (and fuzzy patches). In one embodiment, one can use the Kohonen self-organizing map (SOM), with unsupervised learning algorithm, to change weight vectors for a network (for modeling the features in training samples).

In one embodiment, for thresholding in image processing, we use a statistical decision theory, using statistical decision rules. In one embodiment, we use Otsu's thresholding technique, which uses discriminant analysis, which maximizes the class separation. In one embodiment, we use fuzzy threshold algorithm, using fuzzy membership functions (by the method suggested by Huang and Wang). In one embodiment, the selection is made using a fuzzy parameter, with entropy measure as the criteria function, to get the threshold for the optimal image. In one embodiment, we introduce a cost function. In one embodiment, we apply the multi-level thresholding. In one embodiment, we apply a model fitting method. In one embodiment, we apply the above to segment the document images, face, text, or the like. In one embodiment, we use the grey level histogram for thresholding and segmentation purpose. The histogram (and its peaks or its transition phases) is a good indicator of the multiple classes or clusters involved in the samples.

In one embodiment, we use a fuzzy rule based system to find the background in the image. For example, we have the following IF-THEN rule(s), using Z-numbers:

If, for a given pixel, the pixel's neighbors have small contrast and small variance with respect to the pixel, then the pixel is probably in the background of the image.

Otherwise, the pixel is the foreground, representing one or more objects in the image.

In one embodiment, for learning from samples or examples, we have the following steps: First, we fuzzify the input space. Then, using data, we produce fuzzy rules. Then, for each rule, we assign a degree, followed by the creation of the combined rule library. Finally, we use defuzzification to set the mapping.

In one embodiment, for recognition, we use decision tree method, with nodes and branches which can represent the rules. For example, we have: "If $D_1$ has a value of $d_{13}$, and $D_2$ has a value of $d_{21}$ (on the second level of branching out), then the class is $C_2$", as shown in FIG. 161. Note that "$D_j$" stands for a decision making node, and "$d_{jn}$" is one of the choices for that node (the n-th choice). "$C_i$" is the resulting class at the end of the last branch on that section of the tree, which classifies the object based on the rules stated on the decision tree, e.g. IF-THEN rule stated above, or a collection of such rules and branches and classes. By the way, the example above can be stated in another format, as well:

If $D_1(d_{13})$ is TRUE, and $D_2(d_{21})$ is TRUE,
Then the class is $C_2$.

In one embodiment, we assume the decision tree classifies the objects with the same proportion as the samples in our universe of objects, i.e. with the same probability. In one embodiment, if we look at the decision as a source of message, then we can relate that to the entropy formulation for the information (I) (with summation running on variable "j", and P denoting the probability):

$$I = -\Sigma_j P(a_j) \log(P(a_j))$$

In one embodiment, we use fuzzified decision rules based on membership functions, which have values between 0 and 1, which is sometimes modeled based on a linear slope or transition or line segment from 1 to 0, or vice versa.

In one embodiment, we use neural network on our Fuzzy system, in multiple different ways, e.g. using neural network to get the rules, or using neural network to do fuzzy logic inference, or using neural network to find and edit the membership functions or values for an object, or using neural network to construct a node combination structure based on fuzzy set connectives, e.g. union, intersection, and compensative connectives. In one embodiment, we use different aggregation operators to integrate membership values.

In one embodiment, we minimize the number of fuzzy rules, for efficiency, e.g. using rule pruning, rule combination, or rule elimination. In one embodiment, we eliminate the rules with low number of training samples or low reliability. In one embodiment, we use Karnaugh map to simplify the logic, including fuzzy rules. In one embodiment, we use data clustering to minimize fuzzy rules. In one embodiment, we use optimal defuzzification methods, e.g. using 2-layer neural network, or maximum matching, or centroid defuzzification, or maximum accumulated matching. These can be used e.g. for analyzing or recognition of maps, text, or handwriting.

In one embodiment, for learning machines, we use linear regression, least square, ridge regression, Widrow-Hoff algorithm, Support Vector Machines (SVM), Gaussian processes, Generalization technique (bounds on luckiness), or Kernel functions (to have a more general function for classification or cluster analysis), with SVM (and Kernel functions) at the center of our technique. Basically, in one embodiment, for the hyperplane separating the classes or clusters in the N-dimensional feature space, we want the largest distance from all neighboring points to the hyperplane, in average, as much as possible, as an optimization constraint. Or, in one embodiment, the separating hyperplane is defined as the plane that fits in between the growing neighboring points, as the growing neighboring points (from different clusters or classes) grow gradually in size or radius, as a point or sphere in the N-dimensional feature space, until there is no more room for their growth (and the growth stops at that point), with the separating hyperplane fitted in between the already-grown neighboring points (e.g. from the opposite clusters on two sides of the separating hyperplane).

In one embodiment, we use Vapnik's support vector machines (SVM) to classify the data or recognize the object. In one embodiment, in addition, we use kernels (e.g. using Gaussian processes or models) to be able to handle any shape of data distribution with respect to feature space, to transfer the space in such a way that the separation of classes or clusters becomes easier. In one embodiment, we use sparse kernel machines, maximum margin classifiers, multiclass SVMs, logistic regression method, multivariate linear regression, or relevance vector machines (RVM) (which is a variation of SVM with less limitations), for classification or recognition.

In one embodiment, for machine learning, the system starts with experiment generator describing the problem in hand. Then, the performance system (based on the history) feeds an analyzer, which provides the training examples to a generalizer module, which produces hypothesis for experiment generator, to complete the loop. In one embodiment, for machine learning, we use unsupervised learning or supervised learning or in combination, for different aspects of components of some data, e.g. in an image, with many objects in it, for each object recognition, using different technique.

In one embodiment, for designing the learning program, the system first determines the type of training experience, followed by identification of target function, followed by determination of representation of learned function, and followed by learning algorithm, to complete the design.

In one embodiment, based on "Occam's razor" statement, we prefer the simplest hypothesis that fits the data. For example, a 10 node decision tree that fits the data completely is preferred over a 1000 node decision tree that fits the data completely, as well (due to the fact that it is less statistical coincidence, and more chance to fit or generalize correctly to future data).

In one embodiment, for machine learning, we use neural networks, perceptrons, including gradient descent and delta rule, back propagation algorithm (including convergence and local minima problem), feedforward networks, hypothesis space search and inductive bias, with "Generalization" and "Overfitting" considerations, Q learning algorithm, or reinforcement learning, which all can be combined with our methods in this disclosure, as a complementary method, for improving the performance or efficiency.

In one embodiment, for classification, we may not be looking at enough dimensions for our feature space. So, randomly or based on historical data, the system guesses at the possible one or more extra dimensions to be added as new dimension(s) of feature space, and then tries to classify based on the new dimensions. If the result is better, based on separability of the clusters (or from their overlaps (which is generally an indication of not a good separation)), then we continue on that basis. Otherwise, we drop the new dimension from our space, and optionally, try another new dimension possibility, later on.

In one embodiment, for learning application, we use social collaborative filtering or adaptive lenses, to benefit from other people's experience, and to adapt to fluid language use for human language processing, which can be very dynamic these days, as new words or slangs or abbreviations enter a language in a fast pace, every year.

In one embodiment, for data fitting, we input data to adaptive system, which feeds into cost analysis module, with desired or goals input to cost analysis module, as well. Then, the cost analysis module feeds the error to training algorithm module, which feeds the changed parameters back to the adaptive system again, as a complete loop. In one embodiment, for linear models, we search for the performance surface with steepest descent, using gradients and LMS (least mean square) algorithm. In one embodiment, for pattern recognition, we use multilayer perceptrons with sigmoidal nonlinearities (functions), e.g. in (tan h(x)) or (1/(1+exp(−x))) forms. In one embodiment, for training networks, we use backpropagation method, to go backward to get the weights set, from the last layer, based on desired response and error backward. In one embodiment, to optimize, we derive energy function and surface, with attractor point on the minima of the surface, to analyze system state with respect to the attractor, which can be local or global minima (which we prefer to get into the global minima).

In one embodiment, to model the activity of a person in a computer, and learn from it for future simulation, based on learning from the actual real human action or activity measurements, we use cameras or sensors, e.g. attached to a person, to track the coordinates of parts of the person doing those activities, e.g. dancing (for doing different tasks, in real life). To get the 3D coordinates of those points, for the person, we put the sensors at her joints or major points on the body, e.g. position of knee, for a total of about e.g. 30-50 points on her body, to track all movements, based on the anchor points, and then interpolate the other points in between the anchor points. So, all the movements and series of movements are stored and fed into a learning machine, along with the tags naming the activities, for the machine learning those activities, to be able to generate those later, on its own, or mix the activities together. The mixing can be based on percentage or crisp number, or based on fuzzy parameter, e.g. "slightly" dancing (activity). Once the machine learns the specific activity or activities, it can be used for recognition of video, later on, for a person's activity in different frames.

In one embodiment, we use cameras, sensors, detectors, scanners, CPU, processor, color processor, color adjusting module, transformation image module, translation image module, rotation image module, tilting image module, memory units, storages, RAM, ROM, cloud computing, distributed storage, server farm, PC, user interface, GUI, FFT processor, DCT processor, Fourier analyzer, matrix manipulation processor, convolution operator processor, filters, comparators, subtractors, integration modules, neural nets, training sets, voice-to-text convertors, text-to-voice convertors, OCR, email system, fuzzifier, defuzzifier, center of mass determination module, rules engine, fuzzy rules engine, relational database, RETE, and the like, to implement the system and methods taught here in this disclosure. See e.g. FIG. 174 for such a system.

With our invention, as discussed in this disclosure, in one embodiment, we can use in or with any learning paradigms, e.g. supervised learning (which is very powerful and useful), unsupervised learning, semi-supervised learning, reinforcement learning (e.g. telling the machine if it is in the right track or not, using punishment or rewards, so that it can adjust based on an algorithm), active supervised learning (in which we query about the data, actively), active reinforcement learning, or online learning (in which we get the dataset in small chunks, due to storage or computation limitations, and process them gradually, as in Big Data or in Internet, with limited computing power or memory).

It also can be used in or with any learning theory, e.g. VC theory (including VC dimension and VC bound), Bias-Variance theory (for learning curve analysis), Complexity theory (for computational complexity, with asymptotic results, e.g. if we can do the task in polynomial time), or Bayesian theory (in terms of probability distribution and joint distribution, e.g. in handwriting or voice recognition).

It also can be used in or with any learning techniques, which are separated as models and methods. For models, we have algorithm, hypothesis, and test, e.g. linear transform (which is simple and at low cost), neural networks, SVM (e.g. with Kernel), nearest neighbors (which categorizes according to the nearest neighbors), RBF (or "radial basis function", which is a real-valued function, which depends on the distance from the origin, e.g. Gaussian form or multi-quadratic form), Gaussian processes (which is similar to Bayesian, with full probability distribution, related to random process, random function, and probability distribution over different functions, with distribution being jointly Gaussian), SVD (or "singular value decomposition", which e.g. matches 2 things, as a 2 set of factors, using 2 matrices), or graphical model (with target joint probability distribution, related to computation, graph algorithm, and simplifying the graph, to model the joint probability distribution).

For methods, we have high level entity that is superimposed on anything we use. For example, we have the regularization method, the validation method, the aggregation method, or the input processing method (e.g. for real data and practical considerations, e.g. to normalize or decorrelate).

For the aggregation method (also called ensemble learning, or boosting, or mixture of experts), we have a learning which tries to replicate the function independently (not jointly), and then combine and put them together later, e.g. combining different solutions, e.g. detecting eye and detecting nose, so that in combination, we can reliably detect the face later, which is useful for reliable computer vision applications with fast or real-time results. For the aggregation method, for regression or real number cases, we take an average or weighted average, and for classification or binary cases, we take a vote or weighted vote. For the aggregation method, we have 2 types: (a) After-the-fact situation (where we already have the solutions, and then we combine them), and (b) Before-the-fact situation (where we get solutions, with the view or intention or assumption to blend or combine them together later). For the aggregation method, as one example, we have the Boosting method, where we enforce the decorrelation (not by chance), e.g. by building one hypothesis at a time, for a good mixture, sequentially.

Fuzzy Database and Controller:

In one embodiment, for fuzzy databases or information retrieval, for COMPLEMENT, UNION, INTERSECTION, and JOIN, we use the operators commonly defined in fuzzy logic (e.g. see Klir et al. book, mentioned elsewhere in this disclosure, Table 8.3 page 215, Table 8.4 page 218, Formulas 8.3 pages 218-219, m(X) relationships defined on page 273, Tables on pages 309, 315-317, and FIG. 11.3 page 319), e.g. for the following operations (for the regular operations on the databases):

$\tilde{A}$ for COMPLEMENT $(A \vee B)$ for UNION $(A \wedge B)$ for INTERSECTION $(A \vee B)$ for JOIN For example, for combining the indexes after multiple scanning the database based on multiple criteria, we can use the operation JOIN on the index lists from multiple scans. For example, for search, we can have the following for house hunting or purchase for a buyer, based on the criteria of the houses in the market, in the real estate database:

Houses: [location: "Washington D.C.";

number of bedrooms: "usually preferred" "between 3 to 5";

price range: from "about 200,000" to "about 250000" US$;

structural quality: "at least good"]

The criteria for the statements above are based on fuzzy values, e.g. "from about 200,000 to about 250000" or "at least good". The criteria also include "usually preferred between 3 to 5", which is a Z-number. Thus, the search and query include fuzzy values and Z-numbers. Therefore, the fuzzy search in database is based on membership values between 0 and 1, e.g. for indexing the database based on any of the criteria with a fuzzy threshold, which produces fuzzy ranges (or index listing with fuzzy edges or boundaries). So, for example, if a house is found with a structural quality rated as "good", then it would satisfy that criteria (i.e. "at least good") with a membership value of e.g. 0.95 (which is a "high" membership value).

In one embodiment, we put a threshold for the membership values, e.g. a minimum low threshold to get rid of very low membership values as zero, or a high threshold to e.g. set very high values (such as 0.99) to 1, for ease of calculations. In one embodiment, we keep the membership values as real numbers, e.g. 0.95 and 0.3, e.g. limited to 1 or 2 decimal points. In one embodiment, we keep the membership values as fuzzy values, e.g. "high" membership value, in our index listings, which in some applications, is a preferred method, due to the higher speed of processing and low storage requirements, as the fuzzy classes for indexes can be manipulated faster (in some applications), compared to those of real numbers.

In one embodiment, we use the relevant documents (or relevancy factor for document, R), as a fuzzy parameter (which is also a Z-factor in our Z-web), for information retrieval. For example, for a given index terms X (which includes $x_i$) and relevant documents Y (which includes $y_i$), we define a fuzzy relationship G (also called Fuzzy Thesaurus) which expresses the degree of association of $x_i$ and $x_j$ (both belonging to X). We also have the grade of relevance for index term $x_i$ in the document $y_j$, or $R(x_i, y_j)$, as a membership value, set between 0 and 1.

In one embodiment, we find the membership value objectively or subjectively or both, for example, using author's tagging or commenting or indexing or summarizing or putting keywords or putting title, or using user or community for tagging, or using machine learned expert for tagging, or using algorithms (e.g. giving less weights to older documents, as less relevant), or using number of occurrences of a word, or finding and using the type of article or document, or the like, or all or any of the above in combinations.

Then for a fuzzy set for inquiry $S_{Inquiry}$, we define the "augmented inquiry" (augmented by associated index terms), $S_{AugInquiry}$, as (based on operator "o"):

$$S_{AugInquiry} = S_{Inquiry} \circ G$$

Which the operator "o" is defined as "max-min" composition, or:

$$S_{AugInquiry}(x_j) = \max \min_{xi}[S_{Inquiry}(x_i), G(x_i, x_j)]$$

Then, for the fuzzy set W for retrieved documents, we will have:

$$W = S_{AugInquiry} \circ R$$

Or, based on "max-min" composition:

$$W = \max \min[S_{AugInquiry}, R]$$

So, we have obtained the fuzzy set W for retrieved documents. Now, in one embodiment, all of these, including the retrieved documents and reliability factors and relevance factors and other Z-factors, are put into our Z-web. Please note that for fuzzy sets, each member of the set has a membership value or function.

In one embodiment, we use the same concept about fuzzy values and Z-numbers mentioned above on conditional statements or rules engine, e.g. for control systems or controllers to launch a spaceship based on multiple fuzzy rules. For example, for house buying, we have:

If for a house: [price range: from "about 200,000" to "about 250000" US$;
And structural quality: "at least good"]
Then Action:
"buy" the house In embodiment, we join the rules and results as an aggregate. In one embodiment, we use the conventional fuzzy rules engine. In one embodiment, if the result of THEN is an ACTION which is binary, then we have to defuzzify the result (to do the action or not to do the action). In one embodiment, if the result of THEN is a value, we can still remain in fuzzy domain, especially if the result of THEN feeds another system as an input (which can be a fuzzy value). The rules can be generated by expert human, or expert machine (with similar knowledge base or rules, or searching for exact answers in the universe or on Internet), or training neural network based on history or training samples.

FIG. 162 shows a typical fuzzy controller, and FIG. 163 shows a typical fuzzy expert system. In one embodiment, we have multiple experts, each for a separate task. In one embodiment, we have hierarchical experts to go more in depth in one task or analysis. In one embodiment, we associate each expert's result to a Z-factor in the Z-web, as the expertise factor, or also involving the reliability factor. In one embodiment, we have expert from a trained machine or neural network. In one embodiment, we have a human expert entering input in the system, through a user interface. In one embodiment, the expert systems are in parallel. In one embodiment, the expert systems are in series or cascaded or feeding each other. In one embodiment, the expert systems vote together for a decision. In one embodiment, the expert systems have different weights or veto power for voting for a decision. In one embodiment, the expert systems ORed (or ANDed or XORed or other logical operators) together for a decision.

Ordering or Processing Data, Files, and Z-Web:

In one embodiment, the system orders or processes our data, files, and Z-web, including updating the parameters and weights, including reliability factors for nodes, and also taking care of the queues, during low computation time periods or low loads or idle modes, to be more efficient. However, in one embodiment, instead of spending H hours in every P hours of time interval, to order or process our data, files, and Z-web, the system spends (H/n) hours, in every (P/n) hours of time interval. Thus, still, the ratio of ordering or processing period to the total period remains the same, as (H/P), but ordering or processing happens more often, with shorter periods or intervals. This way (i.e. more often, with shorter periods), the ordering or processing or updating the data, files, directories, queues, and Z-web becomes more efficient. So, the idle time or sleep time or slow time or recovery time or reboot time (for computer, processor, electronic device, tel., CPU, instruction processor, database arranging device, library ordering device, queue processor, waiting scheduler module for any processor or process, or any memory management module) is shorter, but more often, for higher efficiency of the process and more accuracy, in this example.

A Note about Bayesian Approach:

For situations and applications mentioned in this disclosure, one can also use or add Bayesian probability, Bayesian theory, and Bayesian inference (including prior and posterior discussions). However, one must be aware of the following important point and discussion.

In machine learning, we have a method of putting the brakes on fitting the noise (e.g. using hard and soft constraints), which is called "Regularization" method, which is well-known in the art.

Now, if we use the Bayesian approach, then we are actually applying a Regularization method to the system. There are at least 2 reasons for that: The first reason is that, by using the Bayesian approach, we assume that the summation of all probabilities is one, but for all samples in our situation may not be covering all situations, and thus, the total probability may be less than 1. The second reason is that, by using the Bayesian approach, we assume that we have related probabilities, which may not be true. Therefore, the Bayesian approach is actually a method of Regularization for the system. So, if one applies the Bayesian approach to the system, one has to be aware of the applied Regularization to the system.

More on Z-Web:

In one embodiment, we define unusual properties and usual properties for a given object, with associated probabilities and possibilities. In one embodiment, we define superclass, subclass, and class for a given object. In one embodiment, we define first order properties, 2nd order properties, . . . , and n-th order properties for a given object, e.g. height of a person as a first order, nose shape as a second order, and color of the eyes as the 3rd order. In one embodiment, we define default properties for a given object, so that they are applicable in the absence of any other data. In one embodiment, we define general knowledge and contextual knowledge, for specific situations. In one embodiment, having a large knowledge base and large training samples are very helpful for learning and recognition purposes.

In one embodiment, in Z-web, we find and isolate the irrelevant information, as the data with long period of no usage, or no or weak links to other nodes, to reduce the size of the Z-web, for efficiency. In one embodiment, in Z-web, we have a knowledge structure hierarchy, with nested information.

In one embodiment, in Z-web, to model a rich language, e.g. Persian, which has lots of poems and slangs with many philosophical or multiple or reversed meanings (or sarcastic language or idioms or proverbs or abbreviations or catch phrases), for natural language processing, to understand the meaning of the sentence or voice recording or text statement, one needs more dimensions and nodes with more branches and connections. So, translating from English to Persian, for word-by-word mapping, per node, we need much more branches and nodes connecting to each other. Thus, we need more complex Z-web constructed, after translation to Persian, to accommodate the extra complexity and various meanings of the translated language.

In one embodiment, Z-web also helps us understand the meaning of the proverbs and sarcastic language, as they refer to the related objects, in different contexts, based on different regions of the Z-web, initiating from the same node, with multiple meanings or interpretations. So, each region of the Z-web represents a context or environment, for a given node, in common. Thus, Z-web is a useful tool for natural language processing, as text or voice or any other form of communications. By the way, human natural language is generally based on Fuzzy logic and Fuzzy parameters, e.g. "big" or "usually" or "maybe" or "truth" or "relatively" or "soon".

In one embodiment, the fact that a specific person is uploading the picture, or tagging the picture, or owns the picture or album, is an indication that that person has some familiarity to the subjects or objects in the pictures, including the monuments and people. That assumption for relationship produces a link or branch between the nodes for those two objects in Z-web, which helps reliability and recognition of the faces, people, or objects, in those pictures or albums.

In one embodiment, to reconstruct an object or an event from memory, one object triggers another one or a chain of objects, which constructs the environment that happened before, using the Z-web nodes and branches, to follow the links. For example, I went to a gas station last Thursday, which was my birthday, and there was a gasoline leak and gasoline smell in the gas station. So, we input those data in the Z-web, as related objects, defining an event, as a memory unit for recollection of past events. Now, I smell some gasoline one week later in my garage. The trigger event is "smelling gasoline", which brings up the node "smelling gasoline" in my Z-web, which was populated before. Then, it links to other nodes, e.g., "gasoline leak", "gas station", "last Thursday", and "my birthday", in that order, to remember that I had a birthday last Thursday or recently. Then, it can branch out further to other nodes and past events.

Now, in one embodiment, if we remember an event from memory or Z-web, the weights for reliability for those nodes are increased, as reinforcement of the memory for a recent recall. In one embodiment, this increase in reliability values is a percentage of the original values (e.g. 10 percent increase), or an absolute value added to all original values. This way, the recalled events are getting stronger in reliability in the Z-web.

In one embodiment, we have other notes or data added for reminders to the past event, as extra nodes and connections added to the original Z-web (i.e. before recall or recollection). For example, we may add another related node that "last Thursday was also a Federal holiday". So, we connect that "last Thursday" node to the node "Federal Holiday", as an extra information or data (such as image, which can add a lot of other nodes from its own connections to the original Z-web), for future reference, to make the Z-web more complete and expansive and useful.

In one embodiment, we have a bunch of objects in the image or in an environment, and we are looking for an odd or surprising object, e.g. in a picture, in an airplane setting, there is a big snake in the airplane, which is very unusual in that setting. Now, we look at the Z-web corresponding to the "airplane", and all related objects around that node, but "snake" is not in any of them. So, we can conclude that having snake in an airplane is odd (or out of place or surprising or unexpected). Thus, Z-web can help us finding odd objects, with respect to other objects. That also indicates the probability of existence or position of an object, with respect to other objects, in one setting or environment. Having an unusual object in an environment is a feature by itself in that environment. For example, noticing a gun at the airport (with no uniform on the person holding the gun), in an image or video frame, in a security camera, is a red flag or feature, for further investigation, as it is an unusual object in that setting. So, it is a useful tool for analytics for counterterrorism and security purposes, or for analytics for "big data".

In one embodiment, we have a document, text, or object, and it is related to multiple other objects, with some reliability factor, truth factor, confidence factor, expertise factor, or the like (as described in details in this disclosure, and collectively called "Z-factors"). The Z-factors can be fuzzy or crisp values. The Z-factors are properties or characteristics of Z-nodes and Z-branches in the Z-web. The values of Z-factors can get propagated or calculated from one node to another in the Z-web, to evaluate the overall relationship between 2 nodes. When using the Fuzzy parameters in the Z-web, we can use the membership function or value to express the Z-factors. In addition, to express the context(s) for a node, we can use the membership function or value, to express how much the node belongs to that context or multiple contexts. Using the Z-web, we can classify the object, such as text or book or image, based on the related objects and Z-factors.

In one embodiment, when comparing 2 Z-webs, we can coincide the common nodes, if any, and then see how many related nodes connected to common node(s) are the same. For example, based on the percentages of matches, we can have a metrics for similarity of those Z-webs, with respect to one or more of the common nodes.

In one embodiment, the Z-web is used for finding a preference of a person, based on food, music, type of face he likes, and the like, through related nodes, so that it can be used for finding friends or dates or people of similar interest, or matching people or suggesting people, e.g. in the same area or store or street or neighborhood or school, by mobile phone or computer based software or a web site. The whole social network can also be mapped on to a Z-web, with friends on the nodes, connected together.

In one embodiment, since Z-number and Z-web deal with fuzzy and natural language (e.g. "about 4 pm" or "heavy traffic") and its reliability and other Z-factors (e.g. "usually", "maybe", or "not sure"), they can be used for the trip-planner and meeting schedule module or software, to optimize the schedule and resolve or minimize the conflicts. Each node can represent an event, where 2 nodes cannot have the same exact time, which means that the branches with conflicting time are broken or are weak branches, in the Z-web.

In one embodiment, crowd searching or group searching by multiple users helps improving the search results, and also builds up the Z-web at a faster pace, for the group, with respect to that of one individual user alone. In one embodiment, genealogy and ancestry type information are modeled on the Z-web, connecting people or families or objects together. In one embodiment, Z-web handles the vagueness in information, context, language, and logic, through application of Z-factors.

In one embodiment, while we gather information from a source, we keep track of the pieces, so that collectively the pieces can form a specific context at one point, which would be useful information for all pieces to have, at a later time. The pieces can get mapped to nodes of a Z-web, for storage and relationship presentation between the nodes. Thus, Z-web inherently can keep track of such context, as it evolves further in time.

In one embodiment, the Z-factors include factors for uncertainty, ambiguity, non-specificity, and discord, which can be associated with the Z-nodes or objects in the Z-web structure. In one embodiment, for linear regression or classification, the reliability factor of input values comes in, which is a Z-factor in our Z-web. In one embodiment, both the stochastic noise and deterministic noise are the properties of each node in Z-web. In one embodiment, exaggeration or bias or lie is a part of Z-factors, e.g. bias factor, which is associated with each node in Z-web. In one embodiment, all the properties of Z-web and Z-factors are expressed in terms of fuzzy parameters, or mix of fuzzy parameters and crisp parameters. In one embodiment, they are all crisp numbers or ranges or values.

In one embodiment, we have multiple documents, and from them, we get summary or abstract or title or key words or tag words or word phrases, which relate to topics, which relate to the context, using Z-web. In one embodiment, we use membership and fuzzy values for relationship between words to topics, and from topics to context. In one embodiment, we use tables or mapping tables to correspond the words to topics, and from topics to context.

In one embodiment, when training a learning machine, we may know a specific training sample is not good quality or good version or representative of the class or subclass, e.g. from an outside source, or another training machine, or from a human or machine expert, or from the samples being at the boundaries of the cluster for that class (i.e. neighboring and close by another cluster or class). In that case, we may give them less weight, or enter the other (good) training samples multiple times (to have more relative weight as training sample), or assign a separate value to the training samples for this extra information, e.g. reliability factor for training samples, which is a Z-factor, which is a part of the Z-web for training samples universe or domain.

Search for Text or Concept, Based on Fuzzy Memberships and Boundaries:

In one embodiment, to search through some articles or text, we have 3 types/levels of categorization or steps for search: (1) abstract/title/tag/keyword, then (2) summary, and then (3) specification or body of article (e.g. for a patent search engine). The owner of the article can do the first 2 steps above, beforehand, and store them along the main article or file. In one embodiment, to search for a word, we have multiple levels/steps: Level 1: pure word, extracted as a list; Level 2: connection of similar or related words; and Level 3: context of words. These methods can be done using crisp logic, or Fuzzy logic, or combination of both.

In one embodiment, to search for a topic or concept, since most concepts and natural language is Fuzzy in nature, we use the search based on Fuzzy sets and boundaries, with the topic belongs to or related to a class or another topic based on membership functions and membership values. So, the first item is related to the $2^{nd}$ item, with a membership value describing their relationship. To limit the computation to relevant results, one can set a lower bound for threshold, say, e.g. 0.1 for membership value, below which we can set the value to zero, effectively ignoring those values, as being practically non-contributing or non-relevant. For example, 0.05 value is set to zero, to reduce the amount of calculations or memory needed, for membership values and their manipulations.

In one embodiment, to search for a topic or concept, we use Fuzzy questions or queries, based on Fuzzy terms and language, and look into Z-web, based on Fuzzy parameters, to get a node and follow that node on different branches to get the related concepts or objects or answers. For example, a node is CAR, and the related nodes are PRICE, WHEELS, and HOOD. Another example is a node for AGE, and the related nodes are PERSON, STONE, and BUILDING. For example, the value of PRICE is "high", and the value of AGE is "old", which are all Fuzzy values.

In one embodiment, the system uses the queries or type of queries as a method of feedback to modify the weight or importance of the original data or the training samples in hand. That is, the queries indicate e.g. what majority of users are interested in or what is a hot topic today, which, by itself, is a feedback to the system, to adjust itself accordingly, as a collected, aggregated, statistical distribution, median, or average opinion or feedback or vote from the society, users, concerned citizens, or social network.

In one embodiment, we have a fuzzy database, in which we index and order the data or numbers, based on fuzzy values and thresholds, e.g. "small" or "big", rather than 2 and 200, as crisp values. For query, we have fuzzy query, which looks for entries based on fuzzy indexes or criteria, such as "much bigger than 100", to order the entries and filter or select entries or rows of data. For fuzzy criteria, we can use the membership functions and values of the objects.

To speed up the calculations, we can use centroid or center-of-mass of the regions under the curve, for expected values. Fuzzy query is the most natural way to access or relate to the humans, human thinking, human language, human reasoning, majority of Internet data, and natural language processing, e.g. one asks "What is the best company to invest in?", in which "the best" is a fuzzy concept and parameter, and "being good or best" is a contextual concept (depends on the context or environment) which can be handled with Z-webs, with originating 2 or more branches from the same node, each representing one context, as explained in this disclosure.

In one embodiment, for ambiguous context, the system asks the user, with extra questions to figure out the context or limit the context, e.g. if an abbreviation may refer to medical field and also to IT field, as context, then the system directly asks the user if she is interested in medical field or IT field context or discussion, to limit the context, from start.

In one embodiment, the relevance for a search engine is determined based on: term relationship, probability, proximity, vector space, user or link popularity, domain or server information, or the like. In one embodiment, we use the fuzzy searching, using the operators AND, OR, XOR, and the like, in fuzzy domain, to relate the words in the query together in the search, based on their respective membership functions and values, through the logical operators, e.g. search for: (image OR picture), as a search term.

In one embodiment, the information included and extracted from email (or texting or text or TWITTER® or SMS or the like) provides an indication of emotions for people, used for sentiment analysis and behavioral predictions, e.g. for fashion or political opinion or voting.

In one embodiment, the hierarchical model is used in fuzzy domain, using flexible hierarchical relationships, with no rigid structure, using the membership function and value to express the hierarchy relationship between 2 objects A and B in the structure, which has value between 0 and 1. In one embodiment, the hierarchical model is used for the ancestry relationships or family tree.

Editing Still Pictures or Frames in Video:

In one embodiment, multiple pictures of camera or an album on a web site are scanned for face recognition, and if during the scan, having focused on eye and eye brow and mouth and face, it turns out that the person in the picture is blinking or not smiling or closed eyes or otherwise having not a good gesture for the picture or tagged for any other reasons, then the system or controller removes that picture or frame of video from the video, album, or collection, automatically, as a default.

In one embodiment, the system asks from the user if the system should or the user desires to do so, or what to do, or gives an option to move away from set default, or gives an option to set default, or default set by service provider, or default set by manufacturer, or set by camera owner, e.g. using a menu of choices on screen or GUI or user-interface, e.g. to eliminate the picture or frame, or keep them as-is, or correct them with an exchange or substitute picture as supplied by the user, or as supplied by the system automatically from the rest of the album or collection, randomly, or based on similarity with the original picture, e.g. based on the people in the picture, e.g. using or replacing with another picture with the same exact same e.g. 4 people in the picture, or at least e.g. 3 out of 4 people (as a maximum number of matched people available in the album, if another 4-people combination picture is not available in the album), or same 4 people standing in the same order as the original picture e.g. from left to right, in terms of position in space or relative position in picture or relative to an object, such as waterfall, in the background, or relative to another person in the picture, e.g. 2 persons away from Fred, or on the left side of Fred, or about 5 ft away from Fred, or far away from Fred (which is a Fuzzy term, as a natural language spoken or thought by humans everyday). See e.g. FIG. 164 for such a system.

In one embodiment, for video situation or movie or multimedia case, the frame of videos are replaced or exchanged by simply interpolation or extrapolation from neighboring frames, or just simply replaced with one of the neighbors, or just simply replaced with the closest neighbor in terms of similarities of the 2 frames, e.g. in terms of motion vectors as a metrics for comparison, or in terms of object tracking as to how much it has changed from the last frame.

In one example, in one embodiment, for video situation, for video compression scheme, we have video I-frame (Intra-coded picture, fully specified, like a single static image), P-frames (predicted picture, or delta or difference to previous frame), and B-frames (Bi-predictive picture, or bi-directional from past and future, or differences from both sides/frames). Then, we use I, P, and B frames to get the missing frame, to be the best in terms of continuity to the human eyes or perception, or in one embodiment, just simply skip the frame, as it may not do much to the quality of the video anyway, or in one embodiment, blur or average or un-sharpen filter the pixels of the region of the frame that has the problem, e.g. the blinking eyes blurred out, so that it is not visible anymore.

Objects in Video or Movies:

Let's assume we have a series of frames in sequence. As soon as we find a big change in the scene (e.g. by comparing to the previous one, as percentage of changes in the new frame, or using motion vectors), we mark that frame as major delta or change, as a marker in the sequence. Then, for a sequence between 2 major deltas or changes or differences, we look for and extract all objects in the frames. For example, we find a red shirt in many of the frames of the $1^{st}$ sequence. In a couple of frames, we see and extract a logo or name brand, e.g. POLO written on the shirt. So, in those frames, we associate RED and POLO to the "shirt". So, we conclude that the red shirt is a POLO brand, for all sequence 1, even though we do not see or extract the brand or cannot verify that in all frames. The other neighboring sequences may also contain a red shirt, in which case, we can guess that it is also a POLO shirt, with a high probability or as one of the possibilities to investigate further.

In one embodiment, one can use a brand for ads or marketing, by editing, changing, or adding a brand or name or logo on a blank object, such as a shirt, in a sequence of frames, as explained elsewhere in this disclosure. In one embodiment, the system can select some of the frames or some of the directions of the view of the shirt, e.g. for adding the logo. Or, it can be done by a human user or expert. For example, the logo is appropriate to be added to the front of the shirt, as it is set in the library, not on the side or back of the shirt, for this particular brand. So, those frontal shirt views are selected and distinguished as a separate object, and the frames containing those frontal views are marked or flagged for addition of logo, later on, e.g. on the upper part of the shirt, as is described or specified in the library, by the manufacturer or expert or user. So, the proper frames are flagged, and only the shirts in those frames are edited, according to the library or rule collection or specifications.

Finding a brand or branding or re-branding has a lot of marketing and sales benefits. In addition, it will find the potential infringers or fake brand names, which copy or attach the brand name without permission or licensing, through image analysis on pictures or albums or on Internet web sites, using web search robots. One can use API (application programming interface), software development kit (SDK), metadata, tag, comment, or the like, for user interface or GUI or programming or specification of the objects.

For ads, once the user clicks on some object on screen, which is traceable, as an input device (such as screen of APPLE® IPHONE), the system can find what object is chosen by the user, based on extracted objects or based on the coordinate of the objects on screen, and send or connect or refer the user to the right or preferred or paid dealer or merchant(s), by email, web browser, give link, hyperlink, jump to address, fax, tel., mail, text message, or the like, with any communication means, to connect or inform or persuade or encourage the user to buy or at least learn about the object on the screen or image or video, for more sales, and to collect finder's fee, ad income, ad sharing, percentage income or revenue, partnership percentage, fees per click, traffic from ads, fees per links, fees per visit, fees per minute, fees per unique visitor, fees for actual purchases or transactions, fees for recommendations or feedback, fees for referrals, or the like, as a business model, to generate income for our system or web site.

In an embodiment, if the user puts the mouse or selector or menu option selection on an object on screen image or frame of a video, the system will understand what the user wants to select from its screen coordinate and location of the objects, and then the system gives all info, docs, specs, links, web sites, history, dictionary, encyclopedia, merchants, manufacturers, agents, characteristics, related objects, suggested objects, suggested similar or replacement or complementary objects by other users or bought by other users or reviewed or viewed by other users, from its library or databases or through its knowledge base or through its Z-web knowledge, starting from a node. In an embodiment, the user can automatically (using the system) send a TWITTER® or email or text or comment or SMS or vote or feedback or ask for opinion from all or close friends in her list or ask information about the object or express "LIKE" about the object or service or concept, based on the keywords or extracted descriptions of the object, e.g. car or TOYOTA.

In an embodiment, if the user selects an object, in an image (or frame), or the system selects an object for the user randomly, or from the list of the objects ordered in some fashion or reason (in the ordered list), then the system compares that object to the library, to figure out what type it is, e.g. tel. set, and then dig in more from other objects or attributes extracted from the image, e.g. brand name written or placed on the phone set as text or logo, e.g. APPLE, or the model number from its shape or size, versus rules and library information and Z-web, to figure out more details about that object, and build up Z-web even more.

In an embodiment, for marketing or sales purposes, the system uses sponsoring merchant's real or virtual store fronts on screen, to show 2D or 3D images of shelves and objects or services for sale or offer, for user to visit and select or review, to increase traffic and sales. This can be combined with the map of the city, for a virtual man walking in the 3D space of the city, visiting store-by-store, asking questions from store owner, robot, or other users, about the quality or spec of the object or service (on-line, by email, texting, SMS, IM, through dialog window, tel., or the like), meeting other people on-line in virtual store or street (e.g. setting a date or appointment to meet others on-line, for chat or common shopping experience or social networking or any other gathering), or the like.

In an embodiment, for marketing or sales purposes, at the store front, the objects or merchandise is shown in cartoonish or drawing format, or based on real pictures, on the screen, and the recognition or classification of the objects are done based on the teachings mentioned in this disclosure, through Z-web.

In an embodiment, for example, once we recognize a person with a red shirt in a video frame or in a vacation photo album for a specific date, then for any other person in that neighborhood of search in other frames or other photos, we can assume a person with the red shirt or same property is the same person, without checking his/her face, or minimally checking the face, for verification only. That speeds up the recognition process. In an embodiment, for example, we can assign a lower reliability factor value to the no-checking or minimally-checking face, mentioned above, which is a Z-factor in our Z-web, which can be improved by other neighboring nodes in our Z-web.

In an embodiment, for example, we can empirically or experimentally get the reliability factor value or other Z-factors for a set of recognition on e.g. some pictures, using a human or machine expert, to verify some or all of the samples e.g. after the recognition process, with the percentages recognized correctly, or membership values in fuzzy domain, as the metrics for the reliability factor values or parameters (or as scaling or normalization ratios for them). In an embodiment, for example, the same thing can be done for the bias factor or expertise factor, as other Z-factors, using people to tag or give opinion on the test samples, to show the bias or expertise and their degrees or values or fuzzy parameters, e.g. "highly expert" designation, e.g. for a human or machine.

Face Locating Module:

In one embodiment, we want to track, find, locate, or recognize faces in videos or frames or images. For a given type or class of face, we can get the histogram of colors of the face, obtained from our library, e.g. for faces or for histograms. Then, for a given picture, we define a window of examination, which can be scanned and shifted throughout the image, from one side or corner to the other side/corner, e.g. to the other diagonal side corner. In one example, the size of the window is 2×2, or 4×4, or 8×8, or 32×32, or 64×64, or the like (pixels). As the window moves and scans the image, we calculate the probability of the pixels belonging to histogram, for each instance of the window, per pixel within the window. Then, from the total probability per instance of window, we conclude which the most likely position or coordinate of a face in the image is, which corresponds to that specific window(s). In one embodiment, the total probability is defined as the sum of all probability values added, for pixels in that window. In one embodiment, the total probability is defined as the average or normalized value or median of all probabilities for pixels in that window. We compare the total probability versus some threshold, for such a determination, with binary decision or probability decision, as outcome.

In one embodiment, the threshold depends on the size of the window. In one embodiment, the threshold is obtained after scanning thousands or millions of faces, within some known or tagged training images or samples, with known histograms, for our basis or for comparison. In one embodiment, the threshold values are also stored in our libraries or databases, for various faces, images, and window sizes, beforehand. In one embodiment, the training is done by a neural network. In one embodiment, the threshold(s) is a Fuzzy parameter, and determination of a face is a Fuzzy determination, based on a Fuzzy set of faces. In one embodiment, the size of the window is chosen or set comparable with a typical size of a face in that scale in the image, or with respect to the average or estimated or expected size of the face of people in that scale of image. In one embodiment, from histograms and windows the potential for one or more positions or centers or regions for faces are obtained, which indicates how many faces are in the picture (and where in the picture, in terms of position or coordinate in the picture, e.g. in pixel values, in 2-D space, for picture frame axes).

In one embodiment, the threshold and histogram spectrum depend on the type of the faces, and so, the determination of existence of a face in an image depends on the type of the faces under examination. For example, if we are looking for a Chinese face signature, the signature is different with respect to that of a Middle Eastern face type or class signature, coming out of or extracted from the millions of samples from that type of face, beforehand, for calibration or learning or statistical analysis.

In one embodiment, the threshold and histogram are obtained from the size and direction of the faces, e.g. from millions of faces. The size of the face can be based on rectangle of (N×M) pixels. The direction of a face is e.g. frontal view, side view, half-way side view, and the like, which have different signatures, e.g. in terms of histogram shape and peaks. So, from this analysis, the size of the face and angle of view of the face are also determined.

In one embodiment, various histograms are generated and analyzed, e.g. for color (e.g. based on RGB or YMCK components), intensity, grey scale, frequency of any periodic function in image, wavelength of color, pattern in image, or the like. Of course, in general, the more histograms (including the data related to its general shape, position of peaks, and relative size of peaks), the better analysis for the image and better recognition or locating the face.

In one embodiment, various histograms are generated and analyzed for other kinds of images, such as sea or ocean pictures, or forest images, or outer space images, which have their own signatures and characteristics, e.g. to recognize forest images. Furthermore, the forest also has some subcomponents, e.g. trees or birds, with their own signatures and histograms, for locating or recognition purposes, e.g. to recognize trees (in the picture or painting or frame or video or image). Thus, generally, the method mentioned here can be used to find the types of images in a big scale, such as "big data" analysis, classification, or filtering, and also, it can be further used for a deeper analysis, to find objects in the images, such as trees or birds or animals in a forest setting. Therefore, face recognition is just an example, and the method is more comprehensive (and applicable to other objects, as well).

In one embodiment, for edge linking or boundary detection, we use local area processing, with magnitude and direction of the gradient vector, with respect to a threshold. In one embodiment, we use a global approach, using Hough Transform, by changing the parameter space, e.g. for a line equation, and then quantize the parameter plane (with a counter or accumulator), from which the edge linking for pixels is obtained. In one embodiment, we use region splitting and merging to connect and match similar regions, for segmentation purposes. In one embodiment, we use a chain code or vectors to express the boundaries. In one embodiment, we use histograms and similarity between its peaks and valleys (or its curve signatures or features), to classify the histograms, classify the objects, give a degree of similarity, or recognize the types or objects. In one embodiment, we use operations on regions of pixels, as sets (e.g. union or intersection or XOR), to merge or separate regions e.g. for continuity analysis for regions, e.g. for object recognition. In one embodiment, we use morphology operations, e.g. opening or closing operations or filters, for continuity analysis for regions or boundaries, e.g. for object recognition.

In one embodiment, we use pose, structural components, facial expression, image condition, or image orientation for the properties of an image of a face. In one embodiment, we use knowledge based (e.g. top-down method), template matching (e.g. predefined face templates or deformable templates), feature invariant (e.g. facial features, texture, skin color, or combination of multiple features, e.g. using color coordinates or histograms), feature based (e.g. bottom-up method), inductive learning (e.g. using decision trees, with positive and negative examples for face patterns), or appearance based technique (e.g. eigenface, distribution based, neural network, Bayes classifier (e.g. to estimate the joint probability of e.g. local appearance and position of patterns), Markov model (HMM, which relates to and depends on the probability of the prior state, for the chain of related events or objects, such as components of a face, e.g. eyes and nose, as related objects, with known or expected relationships or distances), SVM, or relative information), to recognize a face.

In one embodiment, we use knowledge based for human knowledge or rules e.g. for intensity distribution or difference values for regions of the face. In one embodiment, we use knowledge of the peaks in the profiles of horizontal and vertical scans e.g. for intensity or color values, to find a face. In one embodiment, we model a face as a plane with multiple oriented facial features, e.g. eyes and nose, using pairs of edges or short curves (as our basis or basic elements to build a face), starting with detecting interest points, then detecting boundaries or edges and linking them, and then testing the results with a statistical model, to verify.

In one embodiment, we use face and non-face clusters for estimation of density functions (using Gaussian functions) for patterns for face and non-face situations. In one embodiment, we use distribution based, with patterns grouped in multiple face and nonface clusters, with each cluster represented by a multidimensional Gaussian function (with a mean image and covariance matrix). In one embodiment, we use one of the distance metrics, e.g. Euclidean distance between 2 points in N-dimensional feature space, to find the distances between the input image and the prototype in library (in cluster), or use Mahalanobis distance between test pattern and cluster centroid or center of mass or average value (which includes the correlation of the data set (also related to Hotelling Transform used for multivariate statistical testing)). In one embodiment, we use Kohonen Self Organizing Map (SOM), e.g. for eigenfaces, with each prototype representing a center of a cluster. In one embodiment, we use information approach, with spatial property of the face and contextual constraints.

In one embodiment, we have a method for recognition of faces from a still image or video frame, in which the system receives a still image or video frame through an input interface. Then, it preprocesses the still image or video frame. Then, it recognizes a first class of image for the still image or video frame. Then, if the first class of image for the still image or video frame comprises face or human, then it sends the still image or video frame to a face recognizer module. The face recognizer module accesses a first basis function from a first library of basis functions, stored in a first basis function storage, corresponding to a first component of face, e.g. eyes. The face recognizer module accesses a second basis function from a second library of basis functions, stored in a second basis function storage, corresponding to a second component of face, e.g. nose. A computing processor applies the first basis function across the still image or video frame to detect the first component of face. The computing processor applies the second basis function across the still image or video frame to detect the second component of face. The computing processor accesses a relationship between the first component of face and the second component of face. Then, the system assigns a first Z-node and a second Z-node on a Z-web to represent the first component of face and the second component of face, respectively. Then, it assigns a first branch connecting the first node and the second node on the Z-web to represent the relationship between the first component of face and the second component of face.

Then, it assigns a Z-factor as a mathematical set of factors related to reliability, confidence, truth, expertise, bias, knowledge, usefulness, and relevance, or the like, for those objects. Then, it assigns a first Z-factor, a second Z-factor, and a third Z-factor to the first node, the second node, and the first branch, respectively. Then, the computing processor analyzes the first Z-factor, the second Z-factor, the said third Z-factor for the first node, the second node, and the first branch. Then, the computing processor detects one or more faces in the still image or video frame, with a fourth Z-factor, based on the above analysis step. Then, the computing processor compares the detected one or more faces with the fourth Z-factor against a library of faces, each with its own Z-factor, stored in a first face storage. If the detected one or more faces matches or corresponds to a first face in the library of faces, then it outputs the identity or identification number of the first face, as identification for the detected one or more faces from the still image or video frame, along with a fifth Z-factor corresponding to the matching or correspondence to the first face.

In one embodiment, in addition, it (i.e. the system) determines one or more contexts for the still image or video frame. In one embodiment, it (i.e. the system) determines a partial matching of an object. In one embodiment, it (i.e. the system) determines a match of an object partially shown in the still image or video frame. In one embodiment, it (i.e. the system) looks for a related object in vicinity of the first object in the still image or video frame, or in other related images or video frames, or looks for an expected object from a list of expected objects within a radius of search of the first object, looks for an expected object from the Z-web, with its corresponding nodes and Z-factors, with respect to a third node representing the first object. In one embodiment, it (i.e. the system) applies a rule for recognition, or a rule template for recognition. In one embodiment, it (i.e. the system) emails or communicates a file or data or recognized image or video to all or subset of people recognized in the still image or video frame, or video conferences among all people recognized in the still image or video frame, or coordinates calendar or meeting time among all people recognized in the still image or video frame, or sends notification or warning to all people recognized in the still image or video frame. In one embodiment, it (i.e. the system) edits, replaces, erases, covers, or exchanges one, some, or all people recognized in the still image or video frame. In one embodiment, it (i.e. the system) warns or notifies an authority or police about one, some, or all people recognized in the still image or video frame.

Compressing Text or Voice:

Sometimes, we have some text or voice recordings, e.g. some words, that rhyme together, e.g. "bank", "tank", and "sank", e.g. in a poem or in a sentence. Then, due to the pattern existing in the rhyme, one can reduce or compress the size of final data, and take advantage of redundancies or patterns existing in poems or rhymed phrases or sentences. For example, one can describe the pattern for the example given above as (which is a compressed version of the data, for more efficient storage or faster retrieval):

| ("b", "t", "s"} | + | " ank" |

The same thing can be done with notes, voices, music, or other modes of communications or data, which may have inherent patterns, to use redundancies for compression of data, to increase efficiency for storage or retrieval. The recognition of the pattern or comparison of data or building up the library or using training sets can also be done more efficiently, using the patterns or redundancies in data, in different levels, e.g. at word-level or at letter-level or at sentence-level, for the text. The redundancy or pattern also relates to the entropy of data (measure of disorder and unpredictability), which relates to the amount of information, and also, relates to the minimum storage needed to store the data.

Data Type:

Let's look at one example: Let's assume that we have two integer numbers: 86886668 and 86868668. The only difference between these series or combinations of digits is the position exchange of the following 2 digits: 86886668 versus 86868668. However, since the other digits located at the left side or right side of the difference digits are very similar to the difference digits (consisting of digits 8 and 6, only), the difference is not very visible to the human eye or perception. Thus, if the difference or feature is very similar to the background or environment, then the difference or feature is lost (for recognition or classification purposes). This may not be a big problem for a color photograph or picture from a family vacation in Italy, as the neighboring pixels or patterns or data can be mixed or exchanged or averaged, with not much problem for overall analysis or recognition of objects. However, this may be a major problem for cases dealing with numbers, such as integers, as the numbers may be very different in values, just e.g. by exchanging two digits, as shown in the example above.

Thus, depending on the data, as is the case with integers in this example, we may want to be more careful on the position and ordering of the pieces of data, such as position of digits in an integer value or data. Therefore, as the first filter or scan or pre-process, we want to separate the data in their format or usage or header or type, e.g. image, photograph, text, number, table, list of numbers, and the like, to treat the data accordingly in the next steps, e.g. separately and optimally, depending on its type. In this example, for integers, the window of examination for digits should be small, with focus on each digit, so that we do not miss or overlook or mix any digits, in the image under study.

Text Templates:

In one embodiment, we get statements or questions or sentences as inputs, and then we process them with respect to the templates in our library, based on grammar or other rules in language, to find the meaning of the sentence, or break it down or parse it to pieces for understanding the words and ultimately the sentence. For example, we have "Jim is 20 years old." as input. Then, we compare it with the template: [NAME+VERB+NUMBER+"years old"]. Of course, it may match multiple templates in our library, and all give the same meaning at the end to the user. The templates may have their own Z-web, so that we can get related templates for comparison and natural language processing. In one embodiment, the Z-web is based on Fuzzy nodes and Fuzzy reliabilities and Fuzzy boundaries and Fuzzy relationships and Fuzzy templates and Fuzzy definitions and Fuzzy sets and other Fuzzy parameters, including branch strength, length, and the like.

Since the system finds that VERB is a "to be" verb, namely, "is", the template is simplified as: [NAME+NUMBER+AGE], or [name/age/number], or [Jim/age/20]. The age attribute of Jim is stored in Z-web, next to JIM node, as a new node, or as an attribute or property of the original node, i.e. JIM node.

In one embodiment, many different inputs give the same result, namely, [Jim/age/20], at the end of analysis. For example, other inputs (with the same conclusion or result) are (using other similar templates):

Jim is a 20 year old kid.
Jim was born 20 years ago.
Age of Jim is 20 years old.
Jim is 20.
Jim is 20 years of age.
Jim is 20 years young.
Jim is twenty years old.

In one embodiment, the system instantiate the meaning based on the template. For example, at the time of the statement (e.g. year 2010), we set the age of Jim as being at 20 (as the set age for Jim), or in template form, we have e.g.: [2010/Jim/age/20], adding the time of the statement to the format of presentation of data, for completeness. Then, after 2 years, after the statement date, i.e. 2012, we add 2 years to the set age, namely, (20+2) or 22, as the current age for Jim, or in the template format: [(2010+x)/Jim/age/(20+x)], with (x=2), or [2012/Jim/age/22], wherein x represents the delta or difference in years. Also, see other parts of the current spec, for other methods for natural language processing and text parsing and understanding or converting sentences into templates or easy-process data formats.

Feature Space:

In one embodiment, when we have a "big data", we can define e.g. a few hundred parameters, $N_D$, for dimensions of the space characterizing such a data (related to components of such data). For example, for face recognition, for images containing faces, the parameters can be the length of the nose, width of the nose, ratio of the width to the length of the nose, and angle of the nose (with respect to the vertical plane in front of the face). As long as $N_D$ is large enough and comprehensive enough, we can analyze, sort, classify, or recognize such data, using $N_D$-dimensional feature space. Each instance of data is a point in the $N_D$-dimensional feature space. So, we can define the Cartesian distance between 2 points, in that space, as the measure of similarity (with each point representing a vector of $N_D$ dimensions). The closer the points, the more similar they are to each other. We can define the distance between points 1 and 2 as the conventional distance between 2 points in space, namely, the square root of the summation of square of all of the differences in coordinates of 2 points in different dimensions, or (wherein i (index) runs from 1 to $N_D$):

$$\sqrt{\Sigma_i (x_{i2} - x_{i1})^2}$$

Any other mathematical distance metrics used in the industry can be used for this analysis. We can also cluster similar points into same class or subclass in that space. Now, we can compare different instances of data very easily. For example, we can say one image is very similar to the $2^{nd}$ image, without even knowing what is in the image, per se, or what is in the text, specifically. The longer the data or document, the better statistical analysis one can do on the data, for classification.

In one embodiment, furthermore, for example, to cross between English and French textual data, for comparison, we can normalize one language to be comparable to the other language. For example, after normalization, a NOVEL or HISTORICAL or SCIENCE-FICTION category for books, as a class of textual data or books, from English language, has similar coordinates as those of the French language, making the comparison or classification between multiple languages possible. So, even if we do not know what the French book contains, we still can say it is a HISTORICAL book, by just looking at the normalized coordinates of the book, compared to those in English language, as being located in the same cluster or class in the feature space. This method is useful e.g. for email or image analysis, which is useful for security, summarization, e-discovery, medical data, marketing, prediction, pattern analysis, or the like.

Storage and Retrieval:

In one embodiment, for storage or retrieval of a data, we can use different versions of that data. For example, let's assume that somebody's (Jim's) salary is 104,322.34 US$ per year. Then, we can store that as "104,322.34", as a real number in the $1^{st}$ memory unit or module or storage or region or section, or as "about 100 K" in a $2^{nd}$ memory (as we classify that coarsely, or quantize that more coarsely, or fuzzify that value, or classify them in bigger bins or buckets, or classify them in less number of classes or types, or define bigger clusters to include multiple clusters), or as "low 6 figures" in a $3^{rd}$ memory, or as "average high salary" in the $4^{th}$ memory. The first memory is more accurate, but it has larger requirement for storage and slower retrieval time and slower search and query time. The $4^{th}$ memory, on the other extreme or spectrum, has smaller requirement for storage size and faster retrieval time and faster search and query time. The other memory units fall in between these two extremes or opposite performances (in the spectrum of performances or requirements or cost or constraints or usage or applications). Of course, we can expand the concept for n-th memory unit, as well, e.g. n=20 or 40. See e.g. FIG. 165 for such a system.

In one embodiment, based on the discussion above, the $4^{th}$ memory is better for long term storage or memory, and the $1^{st}$ memory is better for short term storage or memory, which can be erased and updated more often, e.g. when we are out of space or when we want to keep the size of the first memory low, for retrieval purposes, to focus on more urgent matters or data. So, the more fuzzified data is stored in the longer term memory. So, if the degree of fuzzification is shown as $F_{Fuzzy}$ and the degree of long term memory is expressed as $T_{memory}$, which both of them can be both fuzzy and crisp parameters, then, in one embodiment, we can say that $F_{Fuzzy}$ monotonically increases or decreases, as $T_{memory}$ increases or decreases, respectively. In one embodiment, we have $T_{memory}$ as a function of $F_{Fuzzy}$. In one embodiment, we can have those two parameters (values or degrees) as roughly proportional (linearly), or (with $K_{memory}$ as the coefficient of proportionality) (just as an example, and not limiting at all):

$$T_{memory} = K_{memory} F_{Fuzzy}$$

In one embodiment, we store the data in all 4 memory units. In one embodiment, we store the data in memory units 1-3, but not 4. In one embodiment, we store the data in memory units 2-4, but not 1. In one embodiment, we store the data in memory units 2-3, but not 1 and 4. In one embodiment, we store the data in one of the memory units, only. In one embodiment, we store the data in 2 of the memory units, only. In one embodiment, we store the data in 3 of the memory units, only, and so on. In one embodiment, we store the data in some (N) of the memory units, only, out of M total available. In one embodiment, the N units are sequential units, one after another. In one embodiment, the N units are not sequentially ordered units, i.e. not one after another, e.g. skipping every other units (e.g. starting from one of the units, going in one or both directions, until N is exhausted), or e.g. skipping every other 2 units, or e.g. N units randomly or semi-randomly or pseudo-randomly distributed between M units, or e.g. distributed between M units within or by any pattern or rule of distribution. Thus, e.g. based on the usage or need or requirements, one chooses one of the schemes above for the storage of the data, some of which have some partial redundancy for storage of data.

In one embodiment, as the time passes, the shorter term storages are erased more often, thus, reducing the redundancies gradually. Even the longer term storages can be erased or edited or updated, as the system becomes aware of the bad data or expired data. In one embodiment, for search and retrieval of Jim's salary or data, we start from the unit K-th memory, and go in one or both directions, toward $1^{st}$ and M-th memory units, until the system finds one or more values for Jim's salary, from one or more of the memory units. In one embodiment, for search, we can skip some of the units, randomly or in order or in a pattern, very similar to any of the variations of methods described above for the storage of data. So, basically, the search can be in any order we wish.

However, in one embodiment, we may already know that we have only stored these kinds of data in the long term memory, or only long term memory unit(s) has a substantial probability of having any information, if any at all, then we limit ourselves in those units or regions or range of units, for search, e.g. only look at units 3 and 4. So, in those situations, we just go directly to those units, to save time and resources, for efficiency. In one embodiment, we are looking for one value, only, and thus, we stop the search, once one value is found for Jim's salary. In one embodiment, we are looking for R separate values, and thus, we stop the search, once R values are found for Jim's salary, or until N is exhausted, or until the search pattern is exhausted. In one embodiment, we know the storage rules and patterns, so we can optimize the retrieval, e.g. in reverse of the storage rules and patterns.

In one embodiment, we have an indexing table between the memory units for mapping the data between those units. These search, retrieval, storage, query, and fuzzification or quantization methods, explained above, are very efficient techniques for large amount of data and analytics, and for long term storages, which are expensive or impossible for all data in our universe or set, e.g. Internet or Big Data.

One Example for Adjusting the Ranking:

In an Internet search engine, in one embodiment, when it presents the data or links to a user and the user goes to e.g. $5^{th}$ page on her screen and clicks on a link there, as the hit number 46 (ranked 46 for display to the user, or $N_{rank}$=46), skipping the first 4 pages or first 45 hits or links or web sites on display, that indicates that that selected link is very relevant to the user's search, as a feedback to the system, to adjust the weights or results for future similar searches, to reorder or re-rank or replace or exchange the list or items or importance or weights, based on a correction factor. Note that normally, most people would not go more than few pages or few hit lists in the ranking, if they cannot find good result soon (which is an inherent bias in the system). They would rather re-write their search query, instead. So, in one embodiment, the probability of selected items from bottom of the list goes down e.g. exponentially, as we go further down the list or ranking. So, in one embodiment, we can model that with an exponential function, as an example. So, e.g. if an item selected from the bottom, that indicates that the search engine was very off, and the error was high, and the correction is a major correction ($C_{rank}$). So, in one embodiment, we can write the correction ($C_{rank}$) based on a function of ($N_{rank}$-1), as:

$$C_{rank}=F_{rank}(N_{rank}-1)$$

Note that in one embodiment, for ($N_{rank}$=1), there is no correction needed (or correction is zero), and the difference ($N_{rank}$-1) is the parameter that we are interested in, as the distance to the first hit or link. In one embodiment, we have the exponential relationship, with the normalization or adjustment factor $K_{rank}$:

$$C_{rank}=K_{rank}[\exp(N_{rank}-1)-1]$$

Then, we use $C_{rank}$ to adjust the list or ranking, as a feedback to the system (which, in one embodiment, generally is not a linear function of or proportional to $C_{rank}$ at all). Of course, in one embodiment, this function grows very fast, and to dampen its growth, in one embodiment, we can add a denominator, $D_{Damp}$, to make it more manageable for our system and normalize the exponential function. So, in one embodiment, we will have:

$$C_{rank}=K_{rank}[\exp((N_{rank}-1)/D_{Damp})-1]$$

Of course, this is not the only way to make any adjustment on the system and ranking, and based on the purpose, other similar methods or corrections can be used, as well (like the ones currently used in industry, e.g. GOOGLE®'s PageRank algorithm). For example, in another embodiment, we have multiple pages of ranking for search on Internet web sites, and the system randomly selects a hit number from lower ranking, to highlight and bring up to show to the user, to see if the user selects that, as a feedback, which means that if selected by the user, the criteria should be changed to favor that randomly selected hit number, to come up in ranking for future searches. So, that would be our training sample or adjustment sample for scoring, relevance, or ranking. The scoring, relevance, or ranking can also be handled using Z-web, to build up or adjust, as time passes.

Fingerprints:

In one embodiment, for fingerprint recognition (or other similar biometrics or pattern recognition situations), we look for the features such as cusps (where 2 curves meet), grooves, curves, curvatures, angles, slopes, or fingerprint minutiae (e.g. splits, loops, "Y"-shapes, short curves, or the like). Then, we define multiple basic building blocks from which (or combination thereof) we can get all the features above in any fingerprint in our library. Then, we codify or symbolize the curves, cusps, fingerprint minutiae, or other features, based on those basic building blocks (or basic alphabets). For example, we have a shorthand notation, with the following grammar or rule:

| Y [left] | Y [right] | SHORTLOOP |

For example, for the above notation, we have a split curve, in the shape of "Y", which on the left branch of split, ends up with another split, in the shape of "Y", which on the right branch of split, ends up with a short loop (or circle or closed curve or oval). For example, the short loop is defined in our library, as a range or fuzzy parameter or crisp values or thresholds or sample training shapes from actual fingerprints. The qualifier or characteristic or adjective "Short", by itself, is a fuzzy parameter or value, as well. See e.g. FIG. 166 for such a system, for a general pattern recognition situation.

Now, in one embodiment, if we want to express the other side of the first split (the "right" side, in this example), we can it write as:

| Y [left] | Y [right] | SHORTLOOP |
| [right] | LONGLOOP | |

In this example, the right side ends up with a "long loop" feature, as defined in our library. The other splits and branches are also written in the same way, with the same grammar. Alternatively, we can write the same notation above this way, with a slightly different grammar:

| Y1 [left] | Y2 [right] | SHORTLOOP 1 |
| Y1 [right] | LONGLOOP3 | |

Here, we labeled the Y-shapes and other features, such as the SHORTLOOP, with an added counter or integer, attached to the name, so that we can keep track of which one we are following, e.g. when we have hundreds of them in our notation, describing a complete set of fingerprints from a person. Other useful descriptors for fingerprints are, e.g.: SHORTLINE, SHORTCURVE, SHARPANGLE, WIDEANGLE, and the like.

Once we map or codify our fingerprints in one of the grammar notations, we can store or compare them with others very easily, from library or database, for recognition or percentage or probability of match or verification of a person. This method can be used for iris recognition and the like, with components of iris or eye described this way, with its own vocabulary or building blocks and corresponding grammar to connect them together, in a compact way, for storage, comparison, training for neural networks, retrieval from database, matching, and scoring.

Note that curves, cusps, or Y-shapes can also be modeled with Z-nodes and Z-branches, as a Z-web, for storage, comparison, or manipulation, plus reliability factor and other Z-factors, when e.g. some of the curves are not very visible or erased partially or not available, which can be handled or modeled with reliability factor and other Z-factors.

Skeletons:

In one embodiment, we can use the skeletons method for the objects. For example, the Eiffel Tower can be simplified using the operator skeletons on the object or pixels, which is a well-known operator for image processing. For example, see page 545, of book Gonzalez et al., "Digital image processing", published 1993, by Addison-Wesley. Then, we can compare the skeleton of the unknown object with skeleton of the known objects or classes in the library, in a very fast and efficient way, to first find that the object is generally a "tower". Then, once we know it is a tower, then we can compare the full version of the object with those in the library or our knowledge base, in the "tower" category, which is a very limited class with limited number of members, which means more efficient search and faster search results, which is good for Big Data analytics or Internet, e.g. to find famous objects, figures, people, cities, or monuments.

The skeleton of an object can be described by mathematical formulation, simple geometrical figures (e.g. inverted "Y" shape, for the tower), or textual description (e.g. "inverted 'Y' shape"), as some examples. In one embodiment, we can describe the skeleton as a fuzzy parameter or description, which takes less space in memory and also may make the search narrower much faster, in a multiple step process for search. See e.g. FIG. 167 for such a system.

In one embodiment, we use fuzzification, or use low resolution version, or use small version (in size), such as thumbnail version of image, or use one of the components of its wavelet expansion, or use one of the components of its Fourier expansion, or use one of its filtered version, e.g. based on frequency filtering or spatial filtering, or use one of its averaged versions on neighboring pixels in image (instead of skeleton operator, method, or filter, above).

Music Recognition:

In one embodiment, for music recognition, or for sound, or voice, or lectures, or humming or whistling or beating sound (e.g. from mouth or by tapping on a desk by hand), or series of notes or harmonics or modulated waveforms or sinusoidal functions, we can identify the music or the notes or the like, using the sound bites or pieces, extracted from the original piece (e.g. from sound waveform, broken down to pieces when there is a relative silence or low intensity in the waveform, or we can do it in frequency domain, based on frequency analysis, as frequency components and their weights, e.g. by Fourier analysis), as its building blocks, to compare to the pattern or series of notes in the library, to match or find the right one. If other data, such as artist or singer is known, the Z-web can find that song easier or faster.

The patterns of sound can be represented by beating sounds or regular music notes, e.g. to mimic a famous song or music, e.g. "BEE-BEE-BEEM-BAM-BOOM----BEE-BEE-BEEM-BAM-BOOM", where symbol "-" denotes the unit of time for pause between sound pieces, which can be e.g. a fraction of a second. Then, the unit blocks used here for our dictionary of our basic sound pieces are: BEE, BEEM, BAM, and BOOM. Then, for all of our library of songs or music, we generate these pieces, to harmonize or normalize, to gather all possible basic sound pieces, to complete our dictionary of our basic sound pieces. The recognition for these series of codes or notes are done very similarly by other pattern recognition methods we mentioned in this disclosure.

That is an efficient way of generation, classification, recognition, and retrieval of original songs or music, from library or database, through these converted patterns, with relatively simple dictionary. The connection or series of these patterns can be mapped to a Z-web, as well, for recognition purposes. One application of this is for higher sales, encouraging more sales, introducing to friends, introducing similar songs, finding copyright infringers or trademark infringers on similar songs automatically on the web, or matching friends, which are all good for movie and music recording industries (e.g. choosing or finding specific ring tones for tel. sets).

Eigenvectors for Recognition:

In one embodiment, to learn the samples more efficiently for a learning machine, we want to use low dimensionality (reduce degrees of freedom for original data), using a transformation technique, e.g. using histograms, Ritz approximation or example-based presentation, Independent-Component Analysis, Gabor type filters, Karhunen-Loeve or Principal Component Analysis (PCA), Wavelets, or the like, to get a subspace of the original space.

For an object, e.g. a face or head, we have N number of models in library, with grid presentation, connecting multiple points with lines in-between, and the positions of the points are variable, or have fuzzy coordinate values, or are elastic, as shown in FIG. 168 and FIG. 177. In FIG. 177, we have shown 2 models: grid model (using feature points, such as eyes, as anchor points or corners or edges, for tessellation or tiling or covering the whole face) and region block model (or region model), which has $K_{RM}$ regions (e.g. 12) and $M_{RM}$ relationships (e.g. 26) between regions, shown by arrows or vectors, for relative positions or orientations between regions, e.g. their coordinates, their corners, their boundaries, their edges, their centers of mass, their nearest points or edges, or their geometrical centers. (Please note that for FIG. 177, we drew the 2 models partially on the faces, to make the point.) In one embodiment, the tiling can be done by user, expert human, computer trained machine, or a model based computer. In one embodiment, using those N models and the fuzzy parameters for coordinates of reference points, we can fit any given face or head. Now, we store the data in the database. Then, for future, we can compare and find the best match, based on those N classes, to narrow down the search, at the beginning In one embodiment, we use the autocorrelation matrix. In one embodiment, normalized aligned meshes or grids with the fuzzy parameters for coordinates of reference points. In one embodiment, we use the neural networks for learning machine. In one embodiment, we use the age progression on faces to modify the face or morph the face based on age transformation model. In one embodiment, we use the lighting adjustment, to normalize or transform the pixels accordingly, for better comparisons between images. In one embodiment, we use the face recognition against the mood or emotion of face model templates in the library, to find the mood or emotion, to conclude the psychology or intention of the subject, e.g. for marketing purposes.

In one embodiment, we use the model shown e.g. in FIG. 168 to morph the components of the object or face, based on the parameters and small changes on those parameters, e.g. in a chain sequence, e.g. for $\Delta X$, $\Delta Y$, and $\Delta \theta$ perturbations, e.g. for small distances and angles, e.g. for components, e.g. for eyes and nose. In one embodiment, the perturbations can be on pixel level, or on component level, such as eye, or on curves defining the edges and boundaries of components, e.g. eye. In one embodiment, the perturbations are on tiling, or on edge of tiling, or on corners of tiling, or on such coordinates, or on region model or rectangles or triangles, as shown e.g. in any of 2 models shown in FIG. 177.

In one embodiment, we use the eigenvectors for the face or head for recognition, with the object (e.g. face or head) as the linear combination of the eigenvectors or basis functions (e.g. 100-200 of them in the library), e.g. as shown in FIG. 169 or FIG. 170 or FIG. 178. In one embodiment, these are simplified face types or component of face types, e.g. nose or eye (e.g. see FIG. 170), or are similar to basis functions for Hadamard Transform or Discrete Cosine Transform (DCT), for images (e.g. see FIG. 169 or FIG. 178).

In one embodiment, we use the distance between them, as the measure of similarity, or to find the person. In one embodiment, we can generate the eigenvectors or basis functions using thousands of images of faces (as training samples), or get the common denominators for those images by comparing them (or get the difference or delta and subtract the difference from the original image), or filter those images to intentionally blur them with different filtering schemes or steps (to generate those different eigenvectors, e.g. using averaging filter on neighboring pixels, e.g. for 8 neighboring pixels). Mathematically, we can write e.g. for a given face, $F_{face}$, in terms of $N_{eigenvector}$ eigenvectors or basis functions, $V_{i-eigen}$, as their linear combination, with the coefficients $A_{i-eigen}$:

$$F_{face} = \Sigma_i A_{i-eigen} V_{i-eigen}$$

Wherein $i=1, 2, \ldots, N_{eigenvector}$, and the summation runs on variable i.

In one embodiment, we use the local feature analysis, for features on the face, e.g. mouth, nose, eyebrow, eye, ear, and the like, as can be represented as a superimposed image of separate images for different parts of the face, e.g. mouth, eye, and nose.

In one embodiment, if we have different basis functions or basis objects for recognition of different parts of the main object, e.g. for face, recognizing e.g. eye and mouth, as components of the face, then we look for similar basis functions or basis objects, e.g. for eye and mouth, to factor them together, in case they are the same or very similar, based on some fuzzy or crisp threshold or percentage or relative size or absolute size. Then, we save on the storage and calculation period, as the total number of basis functions or basis objects for all objects in our universe or set is reduced, making the process much faster. In addition, in one embodiment, we can do the parallel processing, because for most parts of the e.g. face, this can be processed at the same time for the same or common basis function. This is a huge advantage, in terms of processing time, e.g. in real-time or on-spot recognition, e.g. face recognition, e.g. at the airport.

In one embodiment, wavelets or Haar orthonormal or Fourier basis functions are used as simple black/white region rectangles or squares, or as resembling components of an object, or as resembling simple patterns, for face or object or pattern recognition, as we scan the image. In one embodiment, the wavelets or basis functions are used at different resolutions to scan the image to find all instances of such object in the image. In one embodiment, the wavelets or basis functions used at different resolutions are scanned simultaneously in parallel for faster search. In one embodiment, the wavelets or basis functions that look the same or similar for different objects at different resolutions are scanned or processed simultaneously in parallel for faster search.

In one embodiment, when we dot product the image with any given eigenvector or basis function (assuming orthogonal or orthonormal basis), then we get the coefficient corresponding for that eigenvector, for the linear combination formula mentioned above.

Feature Detection, Using Basis Objects or Basis Windows:

To find a face or other objects, one can use windows or filters that resemble their basis objects, as much as it is practical. The basis objects are the components of the object. For example, for the object of "face", we have basis objects as eye, mouth, nose, and the like. So, we design a window or filter that looks like a mouth or eye, or resemble them roughly, as shown in FIG. 170. Then, we use them as our basis windows. In one embodiment, the basis windows are rectangular or square, which are simpler to handle. In one embodiment, the basis windows are in free form shape. The examples are rectangles or squares of size 2×2 pixels, 2×4 pixels, 4×2 pixels, 3×6 pixels, 4×8 pixels, 32×32 pixels, and so on. The basis windows are divided into two sections, e.g.: black section and white section. For example, the black section resembles the eye or nose. In one embodiment, having black section and white section in fuzzy domain, we assign values between 0 and 1 to the black section and white section, as membership values. In one embodiment, having black section and white section in crisp domain, we assign values between 1 and 0 to the black section and white section, respectively, as an example.

In one embodiment, for the basis windows, the black section does not resemble any basis object at all, but it looks like an ordered geometrical basis function, in black/white or in grayscale or in color components, similar to Walsh basis functions (for example, see page 136 of book Gonzalez et al., "Digital image processing", published 1993, by Addison-Wesley), or similar to ordered Hadamard basis functions or Discrete Cosine Transform basis functions (for example, see pages 143 and 145 of book Gonzalez et al., "Digital image processing", published 1993, by Addison-Wesley), as shown in our FIG. 169 or FIG. 178, above.

In one embodiment, now, we express the image base on these basis windows, same as basis function representation. Or, in one embodiment, we can use the dot product of each of the basis windows with the image, to get the projection of the image on that basis window, which is similar to the component of the image on that basis window coordinate space. In one embodiment, the dot product is defined as the sum of multiplication of values of each pixel from image to that of the basis windows, as they overlap, within the basis window, and as the basis window moves across (or scans or traverses) the image.

In one embodiment, once we get the component of the image in those basis windows, we can store that in our database or compare that to those of the prior data or objects for comparison, match, and recognition, which can be a fuzzy recognition, based on fuzzy boundaries and membership functions and values, or can be crisp recognition based on e.g. a conventional threshold. The comparison can be based on degree of similarities or closeness between the coefficients of basis windows.

In one embodiment, we use the difference between the pixel values (e.g. color components values in RGB system or YMCK system, or intensity of pixels, or grayscale values of pixels) under black section and those under white section (which is an indication of contrast between the 2 sections) (e.g. see FIG. 169 or FIG. 178), for our metrics, for comparison purposes, for detection or recognition, when scanning the basis window across the image. In one embodiment, for multiple basis windows, we use the aggregate of all contributions or average values or summation or max or MAX or sup (as commonly known in Fuzzy Logic) or union or the like, from all the contributions from all basis windows. In one embodiment, we use the sum all pixel values under black section and/or those under white section.

In one embodiment, we use Kalman filters or motion vectors (e.g. for motion detection and prediction of moving object) for video frames, for objects in the frames, such as a human. In one embodiment, we use multiple frames in a video to find the frontal view of the person, as optimum position for face recognition, with higher accuracy rate. In one embodiment, we first find the face, roughly, and then find components of the object or face, e.g. eyes, and then get the relationship between components found, e.g. eyes and mouth, and then verify it is a real face, based on the found relationships, and then if it is a real face, then find who it is, based on the face library for all population or our universe or set (and other data or clues or hunches or tags or comments for the picture or person), e.g. using Z-web, to correlate them.

In one embodiment, we use Haar filters for recognition of the face. In one embodiment, we use Viola-Jones method for recognition of the face or object or components of the face, e.g. eyes. In one embodiment, we define an "integral image" as follows: For a given pixel position in the original image (i, j), we set the value for that position (or image coordinate (i, j)) as the sum of the all pixels (or pixel values) which are located to the left and top of the given pixel. See e.g. FIG. 179, the top figure. For pixel at point 4, that would define a region defined by the highlighted rectangle, between points 4 and 5, at the diagonal positions, in FIG. 179. Now, for our notation, for the sum of pixels for the 4 rectangles defined by points 1, 2, 3, and 4 (as diagonal points, with respect to point 5, at the top left corner), we will have: $S_{15}$, $S_{25}$, $S_{35}$, and $S_{45}$, respectively. Also, for the area of the rectangle defined between points 1, 2, 3, and 4, in FIG. 179 at top figure, for the sum of all pixels covered there, we will have the notation: $S_{goal}$. Then, we can write $S_{goal}$, in terms of other sums:

$$S_{goal} = S_{45} - S_{35} - S_{25} + S_{15}$$

In one embodiment, we use $S_{goal}$ for feature detection, e.g. for face, along with the sets shown in e.g. FIG. 178, top set or bottom set, to use the inherent contrast between eyes and nose and lips and other components or regions of the face. In one embodiment, we can define the integral image in a region of pixels with tilted boundaries, as shown at the bottom of FIG. 179, with lines at 45 degrees, with the corner point, point 4, in this case. In one embodiment, this can be used for frontal face detection. In one embodiment, we use AdaBoost or other similar methods to select a small number of critical features (out of a large set), for higher efficiency. In one embodiment, we add more complex classifiers, as cascade, for focusing more on important regions of the image (and ignoring the background), as focusing attention on features, and doing the process in multiple steps, for efficiency. In one embodiment, a series of classifiers are applied to every sub-window, for detection cascade, with first classifiers eliminating a large percentage of negative examples with relatively low processing power, in each step. In one embodiment, a multilayer cascaded classifier is trained with a set of face and non-face samples, using e.g. human tagged images or machine-tagged images. In one embodiment, the images are normalized for different light conditions. In one embodiment, multiple detectors are integrated or aggregated. In one embodiment, a majority voting scheme is applied for detectors.

In one embodiment, we use different sets for black-white regions as shown on top or bottom of FIG. 178, with rotated units in the bottom figure, or as shown in FIG. 169, on top or bottom figures. In one embodiment, the total pixel values for Black and White regions are calculated, separately. In one embodiment, we get the difference or delta between the total or summation of pixel values for Black and White regions (e.g. see FIG. 178 for the 2 sets, and their units), as the assigned value for that unit, for that image processing step. In one embodiment, we use the same basis functions for different parts of the face, but at different weights. So, we can factor them out for calculations or scans or storage, for efficiency.

Information Retrieval:

In one embodiment, for information retrieval or search engines, we use term frequency (TF) and inverse document frequency (IDF), as a term weighting method (or TF-IDF), including e.g. Zipf's law or its variations, and normalized for document length. In one embodiment, we use a vector matching representation (for possible partial matching), using non-binary weights to index terms in documents or queries (for degree of similarity). Thus, the cosine of angle between 2 given vectors is an indication of similarity of the 2 vectors, which can be obtained by a probability ranking principle, or ranking based on relevant and non-relevant information. In one embodiment, the feedback information comes from local analysis (which includes clustering of results and modified user query) and global analysis (which includes external thesaurus, interdocument similarities, and modified user query). In one embodiment, the TF, the IDF, ranking, and the weights are all fuzzy values and parameters, with fuzzy boundaries and thresholding for the indexes for searches or databases. This makes the search more flexible and powerful.

In one embodiment, for information retrieval, we look at eye tracking data and relevance of information at hand. There are 4 types of eye behavior: gazing on an object or part of the scene for more than a fraction of second for information acquisition and processing, scan path for eye, pupil dilation indicating interest on the object by human, and fast movement of the eye to locate interesting parts of the scene. These give indication of the interest and relevance on a given object or subject by a user. In one embodiment, clicks (including clicks in a query chain) are used as the user's behavior analysis and metrics of user preference.

In one embodiment, a user access through user interface or GUI to query engine, which gets index from indexer, which is connected to the crawler, which is connected to the web. In one embodiment, we have a cluster-based architecture for the search module, with each cluster containing an index of the whole collection, with the index partitioned among M servers, with N clusters making N replicas of the whole index. The user interacts with the frontend servers (i.e. queries and answers), which is connected to document servers and answer cache servers, as well as broker network, which is connected to its own load-balancing server, which is connected to its own cluster. Each of the N clusters contains M combinations of "index cache plus search cluster". In one embodiment, we have a distributed and parallel search engine, with a data parallel strategy and task parallel strategy.

In one embodiment, we have multiple indexes as hierarchical indexes, as improvement for performance, with the first one as small and fast index for most frequent queries, and the last one is the larger and slower index for not-most frequent queries. In one embodiment, we have distributed architecture, such as multisite architecture, due to limitation of the size of a single data center, e.g. due to cooling challenge and power requirements.

In one embodiment, we have a harvest architecture, with a user connected to the broker and also to object cache (which is connected to web site). The broker is connected to replication manager and other brokers, as well as gatherers (which gather information from anywhere, including the web site). In one embodiment, we have harvest architecture more efficient than conventional architecture.

In one embodiment, for ranking, we use domain names as an indication of confidence on quality of content, e.g. .GOV or .EDU. In one embodiment, for ranking, we use content parameter, structural parameter (e.g. for textual data, using a text anchor, for search or query, as a proxy text of the web page), link-based parameter (e.g. number of in-links and out-links to or from a page), web usage parameter (as a feedback from the user(s), e.g. extracted from clicks, number, frequency, how long, purchases, dollar amount, traffic, comments, tags, "favorite", LIKE flag, email to others, recommend to others, forward to others, text to others, or how often), or user parameter (e.g. user's IP address, language, geography, operating system, browser, or history (cookies)). In one embodiment, for ranking, we use Hypertext Induced Topic Search or PageRank (designed by GOOGLE®), which simulates a user navigating randomly on the web, which has problems for self-links and dead-end links, and which can be computed with an iterative algorithm. In one embodiment, we use machine learning to learn to rank, by training samples. In one embodiment, search engine ranking with our model of Z-web, including reliability factor and other Z-factors, becomes much improved.

Crawlers:

In one embodiment, for crawlers, we focus on one of the following goals: quality, volume, or being up-to-date. We can focus on one or two goals, or compromise on all three, as our final goal. In one embodiment, for crawlers, we have static and dynamic data, some private and some public, some indexable and some hidden, some reachable by links and some reachable by forms, only. In one embodiment, for crawlers, we have downloader connected to the web, and downloads pages and puts it in storage, from which a metadata is extracted and is given to the scheduler, which sends the URL to the downloader, for the scheduled download from the web, at a later time.

In one embodiment, for crawlers, we have downloader connected to the web, and the downloader contains short term scheduler and multi-threaded fetchers. The "multi-threaded fetchers" downloads pages and puts it in storage, which contains metadata, links, and rich text. From storage, the data goes to the long-term scheduler, which supplies the downloader, through short term scheduler. The short term scheduler feeds multi-threaded fetchers, which is connected to the web, to complete our loop, to get the data from the web, based on the schedule designed earlier. In one embodiment, for crawlers, we have parallel crawlers, for improving efficiency. In one embodiment, for crawlers, we have revisit policy, for creations, updates, and deletions. In one embodiment, for crawlers, we have multiple policies, to combine together.

Analysis on Various Types of Data:

In one embodiment, we get multimedia data, as input, which is then segmented, compressed, and stored. In addition, after segmentation step or after storage step, we summarize the data. Furthermore, after segmentation step, we extract the features and then index it, based on retrieval models in our library. In addition, after storage step and after indexing step, we display the result(s) to the user, e.g. on monitor of computer or smart phone or tablet, e.g. using user interface or GUI or browser or query engine or module or software. In one embodiment, usually, as we go from simple to more complex form of data (e.g. from text to image to video to music), we have more semantic gap between our knowledge and the meaning of the multimedia data. In one embodiment, we analyze the machine generated data, e.g. tables or lists or computer logs, for behavioral analysis for consumers for marketing purposes. In one embodiment, the retrieval is based on color, texture, or distinct points in the image (regardless of the image scale, e.g. corner of objects in the image).

In one embodiment, the speech recognition is based on Hidden-Markov Model (HMM), based on a word model with phonemes for the word, based on an acoustic phoneme model, based on e.g. state sequence diagram with self-loop feature (to construct or model the pronunciation of the word), e.g. with the probability of a specific Mel-Frequency Cesptral Coefficients (MFCC) vector (as an example), which transforms the broad shape for our spectrogram into a vector with low dimensionality, which can be accomplished with a DCT (Discrete Cosine Transform) with 10 to 20 coefficients.

In one embodiment, in video application, we get an abstract or summarization based on identification of the key-frames, based on the frames in video with the largest changes or deltas or differences between consecutive frames, e.g. based on motion vectors. Summaries and abstracts can be searched more efficiently than the original data. In one embodiment, in video application, the sequence of the key frames gives a general summary of the whole video (or storyline). In one embodiment, in face recognition, we use eigenfaces (i.e. eigenvectors and its summations or linear combinations), to store, reconstruct, summarize, compare, or recognize images or faces, very efficiently. The eigenfaces are stored in our library in advance, based on thousands of training sample images on a neural network, or based on filtering thousands of training sample images (based on different filters to get those eigenfaces).

In one embodiment, we combine or merge the models or results e.g. for audio-visual speech recognition, e.g. to combine acoustic data from speech with e.g. the facial expression of the speaker, to recognize the multimedia data. For example, if the shape of mouth (or face) looks like "smiling" face (based on templates, or based on real faces, or based on face formulations, or based on face grids, in our library, for comparison and determination), indicating happiness or mood of the speaker, then if the speech or sound is not clear and noisy, and the speech recognition is vague with respect to identification of e.g. one word, but with 2 choices, e.g. "sad" and "pad", then the system probably chooses "pad", as the better choice for recognition, because the word "sad" is the opposite of the mood of the speaker (i.e. happiness, in this example), making it the worst choice for recognition (for such a speech).

In one embodiment, first, we combine or merge audio and visual data together, and then we apply HMM on it, for analysis and recognition. In one embodiment, first, we apply HMM on each individual data component (e.g. audio and visual data), and then we combine them together at the end. In one embodiment, we segment the video, e.g. into mixed sound tracks (which is divided into speech, music, and sound effects) and video frames (which is divided into scenes or frames, and then divided into shots). In one embodiment, speech is recognized based on phoneme list in its corresponding library, sound effects are recognized based on known sound effects stored in its library or database, and music is recognized based on MIDI, tempo, score, notes, or any codes or instructions or symbols for expressing the music, stored in its library.

In one embodiment, for video segmentation, we use color information for transition frames or fading frames, using its peaks and valleys on the color component curves, plus pixel intensity curves, using its peaks and valleys, to find or mark the transition or important points in time or corresponding frames, and mark them accordingly, for segmentation and further analysis. In one embodiment, we segment the data of any type, including video, sound, and multimedia, based on sudden change in the sequence (or big delta or difference), e.g. based on an assumption or model, starting from time zero, and go on in time, until the assumption is broken drastically, which means that this is a good place to segment the sequence, and mark it accordingly (assuming that the noise level is low, for this case, and the sudden change is not due to the random noise, itself). In one embodiment, we use Bayesian model, for both sides of the potential boundary between segments, with 2 different model parameters, to fit the 2 sides better, to examine the potential boundary for segmentation, e.g. for speech.

Speech & Language Recognition:

For speech or language recognition, in one embodiment, we use anchors (as special characters that anchor regular expressions to particular places in a string), disjunction operator (or "pipe") (to search e.g. for "A OR B"), grouping, and parenthesis operator (e.g. to enclose a pattern), based on the operator precedence hierarchy (in the absence of parenthesis), e.g. in this order, from highest to lowest precedence, for one embodiment: parenthesis, counters, sequences & anchors, and disjunction.

In one embodiment, we use finite-state automation (FSA), with states, including start state and final state, with transitions, represented by arcs in the graph. The arcs are generally from one state to the next state or to same original state. The FSA can be deterministic or non-deterministic. In one embodiment, for a language, for strings, we have the following operations: intersection, difference, complementation, and reversal. In one embodiment, for morphological parser, we use lexicon, morphotactics, and orthographic rules (such as spelling rules). In one embodiment, we use finite-state lexicon or finite-state transducers or transducers and orthographic rules. In one embodiment, we use lexicon-free FST (or finite-state transducer) (the Porter stemming algorithm). In one embodiment, we use word and sentence tokenization, related to word segmentation and sentence segmentation.

In one embodiment, we use string distance or minimum edit distance, e.g. for spelling correction. In one embodiment, we use N-gram models, language models, word prediction, chain rule of probability, and Markov models, e.g. for speech recognition, handwriting recognition, and machine translation. In one embodiment, we use word counting in corpora (a computer readable collection of text or speech), with probabilities based on counting items.

In one embodiment, we use maximum likelihood estimation (MLE), normalization, N-gram probability, and relative frequency. In one embodiment, we use training and test sets or training corpus. In one embodiment, we use part-of-speech tagging (word classes, morphological classes, or lexical tags). In one embodiment, we use rule based tagging (e.g. hand written rules), HMM (Hidden Markov Model) and maximum entropy tagging (statistical techniques), memory based tagging, or transformation based tagging. In one embodiment, we use contextual spelling error correction. In one embodiment, e.g. to find the probability of the next letter in a sequence, we use HMM, maximum entropy Markov model (a sequence classifier or sequence labeler), weighted finite state automaton, or Markov chain. In one embodiment, we use the forward-backward algorithm for HMM training In one embodiment, we use phonetics for speech recognition, speech synthesis, and text-to-speech conversion. In one embodiment, we use phonological categories and variations of pronunciation. In one embodiment, we use waveform, Fourier analysis, sound spectrum, phonetically annotated corpus, or pronunciation dictionaries. In one embodiment, we use text normalization or sentence tokenization. In one embodiment, we use context-free grammar. In one embodiment, we use a treebank search, e.g. for a specific grammar. In one embodiment, we use dynamic programming parsing technique, Cocke-Kasami-Younger (CKY) algorithm (based on Chomsky normal form (CNF)), Earley method, or chart parsing.

In one embodiment, for a conversational agent, we have a speech recognition module, which feeds the natural language analysis or understanding module, which feeds a dialogue manager module, which is connected a task manager module. The dialogue manager module is also connected to natural language generation module, which is connected to a text-to-speech synthesis module.

In one embodiment, we have recursive phrase structure expansion, as in tree structure format, to segment the sentence and tag the components, e.g. for the sentence "The people sat.", we have, e.g.:

| S | NP | AT | "The" |
|---|----|----|-------|
| S | NP | NNS | "people" |
| S | VP | VBD | "sat" |

So, in the example above, we start from S on the top. Then, S splits into two branches NP and VP. Then, NP splits into 2 branches AT ("The") and NNS ("people"). However, VP has only one branch going out, as VBD ("sat"). Thus, this scans the whole sentence, based on its components and grammar, based on templates and tags, in our library, pre-defined, for matching. We can show this in tree structure, with arrows, as well. In this example, we have S for the original sentence, NP for noun phrase, VP for verb phrase, AT for articles, NNS for plural nouns, and VBD for the verb for the past tense. Of course, this is just an example, and any other set of notations would work, as well. Since some of the tags can be nested themselves, within itself, the tagging process above is recursive. In one embodiment, we use Penn Treebank, for our system.

In one embodiment, for machine translation, we use alignment lines between corresponding words and phrases, sometimes in different order in the sentence. In one embodiment, for machine translation, we use a pyramid (called Vauquois Triangle), starting from base as source language text, as input, and ending at other end at the base of pyramid, as output, as target language text. For the first level, we have words to words, direct translation. Then, on the $2^{nd}$ level, for synthetic structure, we have synthetic transfer. Then, on the $3^{rd}$ level, for semantic structure, we have semantic transfer. Then, on the top, at peak, we have interlingua. So, starting from input base on the bottom of the pyramid or triangle, going up between each level to the peak, we have morphological analysis input to the first level (words), which feeds parsing to the second level (synthetic structure), which feeds shallow synthetic analysis to the $3^{rd}$ level (semantic structure), which feeds conceptual analysis to the peak (interlingua), which feeds back down from the top, conceptual generation to lower level (semantic structure), which feeds semantic generation to the lower level (synthetic structure), which feeds synthetic generation to the lower level (words), which outputs morphological generation for target language text, at the bottom of the pyramid, at the other side. Therefore, now, we have a complete machine translation method and system here.

In one embodiment, for machine translation, we use statistical alignment lines, or we use offset alignment lines, using signal processing methods, e.g. on bit text maps, to correspond the matching text together in different languages. In one embodiment, for text categorization, we use decision trees, using conditional probability and training sets. In one embodiment, for ranking or recognition, we use the frequency and distribution of some keywords. In one embodiment, the keywords can be obtained from the related nodes in Z-web.

Learning Machines:

In one embodiment, for fitting the data points, the "overfitting" problem may cause that we use lower order curve fitting, even if they actually have higher order curve in reality in behavior. In one embodiment, for training, for more reliable data points, we set more weights, or increase the copies of that data point with the same ratio, as new training samples. In one embodiment, for the gradient descent method, if going stochastically, one data point at a time, we go toward the optimum point with the step size proportional to the reliability of that data, e.g. the higher the reliability factor (which is a part of the Z-factor), the higher the step size. In one embodiment, for learning machines, instead of using a single weight for a data point, we have a function of the weight, or a function of combination of the weight and the data point itself, as the new applied weight. In one embodiment, for learning machines, the expert knowledge or world knowledge determines the form of the formula or function or other requirements, down the road, for the learning process.

In one embodiment, e.g. for credit score for loan or risk analysis, if it turns out that e.g. the age is not a big factor, then the impact factor for age parameter is determined to be low (for loan determination goal or task). Then, for information regarding the age of the loan applicant, the age information does not have to be very reliable. For example, the age information with reliability factor of 75 percent is enough for our loan application, which is part of our Z-web for the loan applicant (person), as one of the Z-factors. That is, for low relevance factor or low impact factor (also part of Z-factors), we can relax the reliability factor of the data (reduce the min. threshold needed for the reliability factor of the data). In one embodiment, for low relevance factor or low impact factor, e.g. for age information, instead of using age as a value in linear models, we use square root of age (or log(x), or the like), in linear models, to de-emphasize or reduce the significance of the value of age in the analysis.

In one embodiment, e.g. for loan analysis, if there is a rule forbidding anybody less than 18 to get a loan, then instead of linear regression, we can use a non-linear function in there, or use a second order term for the cut-off age, or use the moment terms of the $2^{nd}$ order, to mimic the effect of the cut-off age. In one embodiment, e.g. for loan analysis, if it turns out that the age bracket is important, e.g. bracket or range of age between e.g. "low 40 to mid 50", then we have fuzzy range and parameters, rather than crisp number(s). In one embodiment, for stochastic gradient descent, we use more than one data points, e.g. get an average (or aggregate or median or weighted average) for 5 or 10 points for each step, to get a better result.

In one embodiment, for constructing kernels (K) for SVM, we can use basis functions (B) based on polynomials, Gaussians, or logistic sigmoids family of functions:

$$K(x,\dot{x})=B(x)^T B(\dot{x})=\Sigma_i B_i(x) B_i(\dot{x})$$

Wherein i runs from 1 to p, and T denotes the transpose of the matrix.

In one embodiment, for classification, e.g. for one million data points, we choose one thousand points only, randomly or uniformly, if possible (i.e. a subset), and find the support vector machines for the subset (derived SVM), which is much faster than that of the original data set, and then try the remaining data points (999,000 points, in this example) against the resulting the support vector machines and the support vectors, to adjust, if needed. Since, in average, for most cases, most of the original 1 million data points are far from the support vectors, and thus, not contributing to the support vectors, the adjustment is usually limited to (or required for) a small fraction of those remaining 999,000 points. This increases the efficiency of the calculation of the SVM.

In one embodiment, for adjusting the derived SVM result for 1000 points, we can find all the data points close to (or within) the region defined by (or surrounded by) the support vectors (points) of our derived SVM (or within union of those regions), out of those remaining 999,000 points. Let's assume there are M points like that, in that region, out of those remaining 999,000 points. Then, we can combine the M points with our original (1000) points, and calculate the SVM for the resulting (M+1000) points, again, which would be our final SVM result.

In one embodiment, for adjusting the derived SVM result for 1000 points, we can find all the data points close to (or within) the region defined by (or surrounded by) the support vectors of our derived SVM (or within union of those regions), out of those remaining 999,000 points. Let's assume there are M points like that, in that region, out of those remaining 999,000 points. Let's assume that those M points constitute an imaginary band (or imaginary rectangle covering those M points or band). Then, the band, when it is skeletonized (with image processing skeleton or thinning operator), becomes a single line, in the middle of the band, with a specific equation. Then, to adjust our derived SVM, to get the final SVM, we have multiple techniques, from any one of the following:
- Based on width and/or length of the band
- Based on width and/or length of the rectangle covering the band
- Based on equation of the skeleton line representing the band
- From the point where the derived SVM intersects the skeleton line, rotate the derived SVM toward the skeleton line, half way (or rotate with an angle somewhere in between)
- Match the skeleton line, or introduce the skeleton line, as our final SVM
- Shift, rotate, twist, and/or translate the derived SVM, toward the skeleton line
- Shift, rotate, twist, and/or translate the derived SVM, toward the band
- Shift, rotate, twist, and/or translate the derived SVM, toward the rectangle around the band
- For small changes, do not change the derived SVM at all, based on some thresholds
- Or any combination of the above In another version, we do the same method as above for 2 or more different subsets of original 1 million data points, e.g. N subsets. Then, we generate multiple (N) SVMs, one for each subset. Then, we get the average of those N SVMs, or a line in between of all of those N SVMs, or a line in between of all of those N SVMs with minimum total distance (or square of distance) to all of those N SVMs, or with minimum total angle with all of those N SVMs (when crossing them at one point), or choose a line or hyperplane for separation of clusters with coefficients in the equation of the line or hyperplane derived as the average (or median or the like) of those corresponding coefficients in those multiple N SVMs, or choose a combination of the above methods. So, from the above, we get a semi-final SVM result. Then, from the remaining data points, we adjust the semi-final SVM result, to get to the final SVM result, for all 1 million data points, with one of the methods mentioned above. This increases the efficiency of the calculation of the SVM result.

In one embodiment, we have lots of data coming in real time, as input. First, we calculate our first SVM for the first e.g. 1000 data points, and store the result in the library. Then, we adjust the first SVM result, based on the coming data (millions of points) in real time, as they come in, based on the methods shown above, as an approximation (similar to running average of data points coming in, in real time). Thus, we can handle large amount of data, in real time, to get the SVM, for classification, recognition, and verification purposes (or the like).

In one embodiment, to find a cluster, we start from a small region in N-dimensional feature space, with points in close proximity, as our original cluster. Then, we expand with circles (or hyperspheres) of small radius (or squares (hypercubes) of small dimensions), going beyond the boundary of the original region or cluster. If the small circles include enough points or have enough point density (above a threshold), then the circle is a part of the original region, and they get UNION-ed together, as sets or regions or points, as our new cluster region, and this continues, until the next expansion circles are empty or almost empty, which means that we get to a region between the clusters, and we stop in that direction. Once all directions and all around the boundary of the original region are exhausted, and after the growth of the region is stopped (in all directions), then that would be the final shape of our cluster. So, we found one complete cluster. Continuing on this, we find other clusters, and eventually, find all clusters available. Then, we can use them for the classification.

In the conventional SVM, we get a penalty, if we cross or get into the margin of the line separating the clusters, e.g. with a new data point. However, in one embodiment, we do not get penalized for crossing a new data point in that marginal band or region around the separation line (or hypersurface or plane), as long as that new point belongs to a cluster.

For learning machines, the minimum description length (MDL) principle (similar to Occam's Razor) states that the best hypothesis (for a given set of data) is the one that leads to the best compression of the data, or fewer bits to describe the data. Similarly, given two hypotheses that can explain the behavior of a given data, we prefer to choose the simpler (or less complex) hypothesis or model or assumption. Note that this is related to the Kolmogorov complexity (or algorithmic entropy, descriptive complexity, Kolmogorov-Chaitin complexity, or program-size complexity) for an object (e.g. a piece of text), which measures the computational resources needed to specify the object, e.g. the length of the shortest possible description of the object (in some description language or grammar). (Note that the Kolmogorov complexity is also related to polynomial-time computable problem.)

Please note that for learning machines, the VC dimension (Vapnik-Chervonenkis dimension) is a measure of the capacity of a statistical classification algorithm (e.g. the cardinality of the largest set of points that the algorithm can shatter (e.g. with the model making no errors, when evaluating that set of data points)).

For learning machines, the Falsifiability factor relates to the data that shows an assumption (or statement, hypothesis, or theory) is wrong. This is also part of the Z-factors in our Z-web. The Falsifiability factor depends on the size of data.

For example, to show some function is (or is not) linear, we need more than 2 points to prove (or disprove) such a statement, because one can pass a straight line through any 2 points.

In one embodiment, for fuzzy SVM, we have sets with fuzzy boundaries, and the members with membership values between 0 and 1. Thus, the margin of the line separating the clusters (or hyperplane, in general), with respect to the support vectors (designated points), are all fuzzy, and all correspond to their respective membership values (including the support vectors, themselves). So, for fuzzy SVM technique, the margin or band around our separating line is wider and "fuzzier" or "cloudier".

A Note on Zadeh's Z-Numbers and $Z^+$ Extension Principle:

In one embodiment, we use restricted-centered theory of reasoning and computation in an environment of uncertainty and imprecision (also called RRC), to enhance capability of reasoning and computation in an environment of uncertainty, imprecision and partiality of truth. The point of departure in RRC is a basic premise. In the real world, such environment is the norm, rather than exception. For example, for the question of "How long does it take to go from home to office?", we may have the answer, e.g. "Normally, about 45 minutes". These types of answers are RRC type (with restriction). The restriction by itself is a carrier of information. The restriction can be possibilistic (e.g. "X is large."). The restriction can be probabilistic (e.g. "X has a uniform probability distribution."). Or, the restriction can be both possibilistic and probabilistic (e.g. "Usually, X is large." or "It is very likely that there is a large decrease in the price of gold in the short term."), which can be expressed by Z-numbers.

In one embodiment, Z-numbers can be used e.g. for scheduling for adding the time periods together e.g. to find out the final arrival time to destination, which involves the addition of restrictions, e.g. going from A to B takes "about 5 hours, normally", and from B to C, it takes "roughly 3 hours, usually". So, we have 2 Z-numbers here. To get the final time, for going from A to C, we add them up, in Z-number domain, in the form of (A, B):

$$Z_{final} = Z_1 + Z_2 = (\text{About 5, Normally}) + (\text{Roughly 3, Usually})$$

We have shown the Z-number arithmetic elsewhere in this disclosure. So, using Z-number domain, we can find answers to everyday problems and process natural language information by humans, which would not be possible before (without Z-number domain).

For a given conventional theorem, we can add fuzzy logic generalization, to generalize the theory in the fuzzy domain, using fuzzy sets and fuzzy parameters. The structure of modes of reasoning and computation can be mathematical (which can be Type 1 or Type 2) and non-mathematical (which is Type 3, unprecisiated perceptions, related to f-valaidity). Type 1 is for measurements, related to p-validity, and Type 2 is for measurements plus percisiated perceptions. The restriction can be expressed as:

$$R(X): X \in A$$

The restrictions can be hard or soft. The restrictions can be direct or indirect. In one embodiment, the restriction can be a possibilistic restriction, e.g.:

$$R(X): X \text{ is } A \text{ (with } (r=\text{blank}))$$

In one embodiment, the restriction is Z-restriction, wherein X is a real-valued random variable. Then, we have Z-restriction (r=z, s is suppressed) being expressed as:

$$R(X): X \text{ iz } Z$$

where Z is a combination of possibilistic and probabilistic restrictions defined as:

$$Z: \text{Prob}(X \text{ is } A) \text{ is } B$$

Where A and B are fuzzy sets, e.g. from natural language processing. The ordered pair of (A, B) is Z-number, which we explained elsewhere in this disclosure. For example, the fuzzy number, B, is a possibilistic restriction on the certainty (probability) that X is A. Now, we have $Z^+$-restriction ($r=z^+$, s is suppressed) being expressed as:

$$R(X): X \text{ iz}^+ Z^+$$

$$Z^+ = (\text{Poss}(X), \text{Prob}(X))$$

Wherein $Z^+$ is an ordered pair, (Poss(X), Prob(X)), in which Poss(X) and Prob(X) are, respectively, the possibility and probability distributions of X. Note that $Z^+$ is more informative than Z. So, if (Z=(A, B)) and p is the underlying probability density function of X, then $$Z^+ = (A, p)$$

If Z is (A, B) and $Z^+$ is (A, p), then B is an indirect possibilistic restriction on ($\mu_A \cdot p$). p is explicit in $Z^+$ and implicit in Z. The ordered pair (A, p) is referred to as a $Z^+$-number. Now, we have Z-valuation as an ordered triple of the form (X,A,B), where X is a real-valued variable and (A,B) is a Z-number. Equivalently, a Z-valuation, (X,A,B), is a Z-restriction on X:

(X,A,B) → X iz (A,B)

For example, we have:

(length of car, short, very likely)

(stock value next July, sharp increase, extremely unlikely)

So, we can process and evaluate a lot of situations in our life, which is naturally expressed in our language in the Z-number domain (in contrast to crisp values, e.g. 3.1557 dollars). Then, we have Z-rule as a conditional restriction in which the antecedent and consequent are Z-valuations:

If $(X, A_1, B_1)$ then $(Y, A_2, B_2)$

For example:

If (consumer confidence, low, usually) then (unemployment, high, usually)

So, we can input these conditions or rules into our rule engine, or use it for prediction, control system, forecasting (economy, elections, and other events), social behavioral analysis, consumer behavioral analysis, predicting revolutions or unrest, detecting frauds, detecting unusual behaviors, detecting unusual patterns, finding liars or contradictions, resolving contradictions, and the like. In our daily life setting, much of the information in an environment of uncertainty and imprecision is represented as a collection of Z-valuations and Z-rules, which we call Z-information, as a whole. Any interpolation based on Z-numbers is called Z-interpolation, which is very important for our fuzzy control systems. In one embodiment, we model a piece of information as a restriction. In one embodiment, we model the meaning as a restriction. All of the above is foundations for computing with words (CWW), which is natural to the natural language processing or human understanding of a language.

In one embodiment, we use extension principles to compute the result, e.g. for probabilistic extension principle with a possibilistic restriction, we have:

$$Y = f(p)$$

$$\frac{R(p): g(p) \text{ is } A}{R(y)(f(A)): \mu_Y(q) = \sup_p \mu_A(g(p))}$$

subject to: $q = f(p)$ wherein p is a probability density function in R, and A is a fuzzy set in the space of probability density functions. For $Z^+$-extension principle, we have the restriction on X as a $Z^+$-restriction.

$$Y = f(X)$$

$$\frac{R(X): X \ iz^+(A, p)}{R(Y)(f(A, p)): R(Y) \ iz^+(f(A), f(p))}$$

where A is a fuzzy set which defines the possibility distribution of X, and p is the underlying probability density function of X. For Z-extension principle, we have the restriction on X as a Z-number:

$$Y = f(X)$$

$$\frac{R(X): X \ iz(A, B)}{R(Y)(f(A, B)): Y \ iz(f(A), C)}$$

where C is the certainty of f(A). Computation of C involves an application of the $Z^+$-extension principle, followed by an application of the probabilistic extension principle with a probabilistic restriction, (p·A is B). For example, sum of two Z-numbers is done by this method. For example, let's look at the steps for method to find the sum of two Z-numbers:

Let $X=(A_X,B_X)$ and $Y=(A_Y,B_Y)$. The sum of X and Y is a Z-number, $Z=(A_Z,B_Z)$. The sum of $(A_X,B_X)$ and $(A_Y,B_Y)$ is defined as:

$$(A_X,B_X)+(A_Y,B_Y)=(A_X+A_Y,B_Z)$$

where $(A_X+A_Y)$ is the sum of fuzzy numbers $A_X$ and $A_Y$ computed through the use of fuzzy arithmetic. Then, we compute $B_Z$. Let $p_X$ and $p_Y$ be the underlying probability density functions in the Z-valuations $(X,A_X,B_X)$ and $(Y,A_Y,B_Y)$, respectively. If $p_X$ and $p_Y$ were known, the underlying probability density function in Z is the convolution of $p_X$ and $p_Y$, $(p_Z=p_X \circ p_Y)$, which is expressed as (where R is real):

$$p_{X+Y}(v) = \int_R p_X(u) p_Y(v-u) du$$

We do not know $p_X$ and $p_Y$, but we know the restrictions on $p_X$ and $p_Y$, which are:

$$(\int_R \mu_{AX}(u) p_X(u) du) \text{ is } B_x$$

$$(\int_R \mu_{AY}(u) p_Y(u) du) \text{ is } B_y$$

Using extension principle, for restriction on $p_Z$, we have:

$$\mu_{pZ}(p_Z) = \sup_{p_X, p_Y}(\mu_{BX}(\int_R \mu_{AX}(u) p_X(u) du) \wedge \mu_{BY}(\int_R \mu_{AY}(u) p_Y(u) du))$$

subject to: $(p_Z = p_X \circ p_Y)$ $$(\int_R p_X(u) du) = 1$$

$$(\int_R p_Y(u) du) = 1$$

If we know $p_Z$, then we have:

$$B_Z = (\int_R \mu_{AZ}(u) p_Z(u) du)$$

Where:

$$\mu_{AZ}(u) = \sup_v(\mu_{AX}(v) \wedge \mu_{AY}(u-v))$$

Now, we apply extension principle, to get restriction on $B_Z$:

$$\mu_{BZ}(\omega) = \sup_{p_Z}(\mu_p z(p_Z))$$

subject to:

$$w = (\int_R \mu_{AZ}(u) p_Z(u) du)$$

We already got $(\mu_p z(p_Z))$. Thus, the sum of Z-numbers is completed now.

Another important transformation is f-transformation, in the context of f-geometry, which we draw the geometrical shapes with fuzzy boundaries, or with thick non-sharp cloudy boundaries, as if it is drawn by hand with a spray pen. Then, we will have the following f-concepts in f-geometry: f-point, f-triangle, f-line, f-parallel, f-circle, f-bisector, f-tangent, f-proof, f-perpendicular, f-median, f-altitude, f-definition, f-theorem, and the like.

In summary, Z-number domain is a powerful domain and tool for processing natural language data or our daily way of life, to better understand and process the information (efficiently and correctly).

Technical Notes:

In one embodiment, we use two learning machines which get trained by two images from binocular vision, or stereoscopic vision, or binocular disparity, or parallax, or as if they are a set of two eyes on somebody's head, e.g. for depth perception or binocular fusion, for a machine which can find the depth or perspective, based on its training, which is very valuable e.g. for a replacement for a human in a robotic vision or target detection or space missions (for automatic landing).

FIG. 128 shows some of the applications or modules, using the analyzer or processor taught in this invention, applying the methods taught in this invention, for various uses, with analyzer feeding data to or receiving data from the components, for various tasks. In one embodiment, the Big Data analytics is used for marketing, geolocation information, mobile users, fraud prevention, investing, and mortgage analysis.

In one embodiment, to do the data mining from Z-web, we can use "extract, transformation, and load" procedure, to our data warehouse, and then report it in various formats to the user, from the data warehouse, e.g. for batch reports and decision support systems reports, which can be multi-dimensional, rational, or hybrid, with queries based on natural language in free human language format, or based on templates. In one embodiment, the calculations are all done in the warehouse.

In one embodiment, the calculations are done outside the warehouse in a multi-dimensional database. The reporting can be done on CRM, e-business intelligence, web traffic analysis, and click stream analysis, for customer taste, complementary merchandise, gift suggestions, customer profile, marketing and sales, and the like. In one embodiment, for frequently asked questions or those with high probability, for retrieval or calculations, to avoid double work for retrieval or calculations very often, the system stores the results in the intermediate storages for quick access by other users, without double calculations, e.g. calculating the average salary of all teachers in all school districts in US once, and only once.

In one embodiment, we add hashing, compression of data, partitioning the data, clustering, and parallel processing to the data mining module. In one embodiment, we use Z-webs for prediction engines, using the data mining from Z-web, to e.g. predict what the user will buy for next year, e.g. in terms of fashion, color, and the like. From the prediction engines for human behaviors and emotion variables, one can predict social unrests and revolutions, or on an individual basis, the problems with a specific person, which helps predicting policing for crime prevention.

In one embodiment, we have learning machines with multiple search options: logic-based, cultural-related, or evolutionary or genetics search. For genetic algorithm or programming, we have to determine the set of terminals and functions, as well as the fitness measure and parameters for the run, e.g. number of generations and population size, plus the method for getting the result and how to terminate the run, based on some criteria. The genetic algorithm can be combined with our method of our invention for learning machines. In addition, for the way that nodes of Z-web evolve, we can use a genetic algorithm, to progressively improve the Z-web node values and Z-factors.

In one embodiment, we have a large set of facts, e.g. encyclopedia, and a set of formulas or relationships, e.g. for conversion of currency or length or weight or the like, e.g. between US Dollar and Euro, and a set of presentation tools, such as graphs or 2-D Cartesian drawings (for Y versus X axis) or tables, to present the raw facts in a presentable format or modified format, as required per query or search by user. For example, if the user wants to know "the population of US in 2000 according to US Census Bureau", in addition to the simple answer as an integer, the system presents all the available data for population, e.g. from 1900 to now, by a plot or graph in 2D on display for the user, as an extra information.

In one embodiment, a search engine can be customized for a user, based on her specific developed Z-web, with her preferences embedded in there. That also helps to find the right context e.g. for a word search with multiple meanings, to find the intention of the user automatically, from the Z-web. In one embodiment, the browsing habits or history or purchases or web sites or clicks are part of the customized feedback for the user, to modify her Z-web for future.

General Notes:

For all the systems taught here, one can use a microprocessor, processor, computer, computing device, controller, CPU, central processing module, processing unit, or controlling unit, to calculate, analyze, convert, and process the data, and it can store the information on a disk, hard drive, memory unit, storage unit, ROM, RAM, optical disc, magnetic unit, memory module, database, flash drive, removable drive, server, PC, RAID, tape, or the like. The information can be processed serially or in parallel. The communication between different units, devices, or modules are done by wire, cable, fiber optics, wirelessly, WiFi, Bluetooth, through network, Internet, copper interconnect, antenna, satellite dish, or the like.

In general, for all teachings of this disclosure, the changes or rules or commands or corrections can be in crisp values, e.g. 10 percent change or threshold or difference, or in one other embodiment, in Fuzzy domain, e.g. Fuzzy rules, commands, and corrections, e.g. large difference or large change, or can be expressed in combination of both Fuzzy and crisp rules and parameters. The Fuzzy rules and sets and their treatments are explained elsewhere in this disclosure.

Note that throughout this disclosure, "we" or "it" means "our system" or "our controller" or "processor" or "CPU" or "our computer" or "our system of invention or embodiment" or "one of our embodiments" or "our method of invention" or "system of invention" or "microprocessor" or "processing unit of our system" or "our device" or "server" or "our teaching based on our method or system or device", which is (or related to) a machine or device or hardware, and not referring to a human at all. We also (sometimes) use the words "we" or "our" as our teaching entity or "teacher" for our disclosure, which again means that we are talking about "our system" or "details of our system" or "our method" or "details of our method" or "how it works, based on components of our system or steps of our method" (and not referring to a human at all).

Any other teachings similar to here or variations of here are also meant to be included for protection under the current invention disclosure. All embodiments and examples are independent for teaching purposes, and they are not limiting the scope of the invention at all. However, they can be combined for or in our system, in any combination possible, with no limitation intended.

More Embodiments

Introduction (Video and Image Search Engines)

With powerful search in images and videos, more photos or videos become available as source of information which results in more growth in sharing the images as way of sharing information. The information becomes more available and hence more useful and valuable.

3D Model of Head and Body from Video

In one embodiment, using various frames of a video for a person, the analysis engine determines the motion and poses of the person (e.g., orientation) from a frame(s), extracts features (e.g., facial or body), and map those features to a 3D model for that person. Certain poses provide more reliability for certain features (or they may hide other features), e.g., front and side way poses expose different parts of a face with different reliability (based on projection angle to the camera or viewer).

The learning of the features take into account the reliability of a given feature based on the pose and the quality of the image (e.g., fuzziness, sharpness, contrast, scale).

Background Check Application

In one embodiment, applicants fill applications for example for getting hired by a company, receive medical benefit or insurance, e.g., Medicare or Medicaid, license to drive, license to practice law, license to become accountant, or gun license. The sources of the names/entities may be from the application or from a list (e.g., based on zip code, associated with a locality or an entity, including name/address pairs).

Application may be in form of name/value pair of information, in flat form or structured in a hierarchical form, e.g., XML, or in a database relational tables. See FIG. 206 for example. The analysis engine obtains or queries other search engines, databases, social media, and repositories to gather information and data related to the applicant or the items in the application related to the applicant.

Analysis engine incorporates the information in Z-web along with the reliability factors, e.g., based on the queries from various repositories and engines, and based on the relative weight/reliability of the source of information for a given query.

Z-web may be queries to obtain detailed or aggregate information and analysis regarding the application or the applicant (or the person or entity being investigated or being queried). Such results may be provided based on subscription (e.g., paid) to investigation agencies as the Z-web databases grow. Reliability of overall, subset or individual piece of the application may be determined.

The result may be organized by individual people even if they have similar or the same name, based on correlation with their images and associated documents, activities, and background. This approach disambiguates the labels/names and associated information for individual people or entities, based on reliability of information and match.

In one embodiment, to identify a person, e.g. the system is based on the hierarchy of the classifiers. First, it is established that the object is human for the first classifier, then it goes on to the ethnicity or facial features, as the second classifier, to separate people into groups of similar features, to limit the scope of the search, and have better weights for the learning machine. Then, it goes on to the third classifier, that identifies a person based on its database, on that region or ethnicity, specialized for that region or ethnicity, e.g. Northern Europe Scandinavian type people. This way, we can continue in more nested classifiers, or hierarchy, so that we get more accurate results at the end. So, potentially, for some large populations, with diverse shapes and features, we may go e.g. 3-10 steps, before we get to the final results.

Z-Web, with Reliability Factor or Z-Factors

In one embodiment, Z-web, the analyzer, and our search engine (Z-engine or Z-search engine) get the information from the user or social media, and analyze them. Alternatively, it crawls in the Internet, to get the data. Then, any search result from other conventional search engines, e.g. GOOGLE, can be refined, corrected, ordered, and edited, to be presented to a querying user, through a GUI or user interface, with high reliability or improved Z-factors, which is much more useful result for the user. The types that are handled are images, text, video, documents, metadata, voice, and the like. The processor for Z-web also indexes the web or Internet, and has features repository, for efficient navigation of web or Internet. For example, see FIG. 207.

Security Application

For example, see FIG. 208. In one embodiment, for example, at the airport, we have multiple cameras, as a person walks around, to monitor people, along with voice or sound capture, e.g. the sound of walking or foot on the ground or voice of people, to get walking patterns as a signature for a person, or voice recognition. It is non-intrusive. It can get the walking pattern, e.g. drunk person, or when person tilting toward left due to heavy bag or unusually heavy bag, to warn the authorities. It also detects the sweat on persons face, or facial expressions e.g. nervousness or agitation or anger, to get mood, behavior, state, status, or intention of the person. In one embodiment, it is for access control for a building. In one embodiment, it has a database of targeted individuals. In one embodiment, we have the pattern of walking combined with signature of walking combined with facial expressions. In one embodiment, it determines the invariant features e.g. size of nose, with variant features, e.g. size of mouth during big laugh, to find the right person, by databases (DB). In one embodiment, we convert the variant features to invariant counterparts, or normalize them, or convert to neutral ones, from databases, or using rules or models, to be able to compare or recognize them, against the known people.

In one embodiment, we have the pose e.g. bent back, or motion pattern e.g. the sequence or patterns of body pieces during walking or sitting, in motion or at stationary positions, for signatures for a person or person's behavior or intention or action, e.g. fast running or nervous running or running while looking backward (as guilty feeling). In one embodiment, we alert the authorities, and also track the specific person using multiple cameras, using the motor(s) or hinges or arms under each camera, to focus or zoom or follow a person in 3D coordinates, in 3 axes, for finding the person. In one embodiment, the system records the interesting events in storage, for later view and review and analysis, or marks the interesting parts, for partial storage, only.

Image of an Object (Versus Image Related to an Object (or Face or Person))

For example, see FIG. 209. In one embodiment, we get features from images and video, along with user identity, relationships, and annotations, to match features with labels, users, entities, to auto-annotate and apply matched relationships. Then, in one embodiment, for a new image and/or metadata of that image or video, the system extracts features, and then, the system matches with existing features or annotations, as mentioned above, e.g. based on rules and policy engine. Then, in one embodiment, for matched images, the system locates or identifies same or similar person, object, or entity, based on matched features, in various images, photos, audios, or videos (e.g. the location in video frames, e.g. at 30-50 second points or frames or ranges), e.g. based on annotations, including auto-annotations. In one embodiment, the system locates (for pictures) at what part of picture or body, and for videos, it locates at what track and timing or segment of track, using scene name or number or ID, or for frames, locating with location or position or coordinate (at which part(s) of the frame or image).

In one embodiment, we get confidence factor and reliability factor, as Z-factors. In one embodiment, we use it for dating sites or type of look search or FBI face search. In one embodiment, we get images of object A, rather than images related to object A. In one embodiment, we use video frame images or sequences or major changes. In one embodiment, we search by image or video piece (e.g. based on percentage of matches between single frames or series of frames, with a threshold(s)), for action sequences or emotion or pose or behavior, e.g. walking or drunk walking or explosion scene or sitting or rocket take-off, for human or animal or object, e.g. for similar to dictionary or reverse dictionary search. In one embodiment, we have self-annotate function, by user or friends. In one embodiment, we have auto-annotate function. In one embodiment, we have the data indexed or linked from the database. In one embodiment, we locate or identify the person or object in various videos or still images. In one embodiment, we use audio track or OCR for recognition analysis. In one embodiment, we name the person with real name that we had found. In one embodiment, we tag the person as person X, as a substitute, until we name the person later on, with his/her real name, when it is known to us. In one embodiment, we have video frames or pieces identified with its track or piece number or ID.

Image or Information Network (for People, Places, Concepts, or Objects)

For example, see FIG. 210. In one embodiment, we have a network of photos or images, with relationships between photos or people in the photos. In one embodiment, we have links, LIKE button results, and relationships, e.g. follower, groupie, fan, supporter, mentor, idle, friend, close friend, acquaintance, boss, dad, son, or co-worker. In one embodiment, we have navigation by UI, or by search engine (e.g. using criteria or analytics). In one embodiment, we have analytics, e.g. with web elements and links, e.g. to enhance metadata for links, e.g. using degrees, time periods, and the like. In one embodiment, we find or verify one object through one or more images or relationships.

In one embodiment, once uploaded the albums in our web site, by friends, a friend can link and go to others, by relationship web, and navigate through pictures or albums, using e.g. context, e.g. for friends or co-workers, for their corresponding links, optionally showing all links and relationships as an overlay to the albums and pictures, and optionally showing the images and links as miniature versions or thumbnails, for faster review and scanning by user.

In one embodiment, once uploaded the albums in our web site, by friends, one person can ask if there is a picture of these two people A and B in this or other albums, and if so, where? Then, the search engine finds it, if any, and gives the location to the user. In one embodiment, once uploaded the albums in our web site, by friends, one person can ask what relationship exists between person A and B, e.g. father, or friend-of-friend-of-friend, or son-in-law, or identify them by name (and any other related data about that person).

Image Recognition for People (or Objects)

For example, see FIG. 211 (as an example of Z-web). In one embodiment, we have two people called Jim and John, as 2 entities, with a third entity with the same name as Jim, but a different person. They have their own IDs and properties or attributes, and relationships, e.g. between 2 entities, e.g. friends, or father-son, with Z-factors between them, e.g. as reliability factor, e.g. with cross tables or pointers or arrows, showing them or referring to each other. In one embodiment, we distinguish between 2 people with same name (Jim), using images and other attributes, with Z-factors (e.g. reliability factor or confidence factor), or if they are the same person, merging the two entities as one "Jim", together.

In one embodiment, the system shows the nodes connected to the original node, in the Z-web, on screen or monitor for the user to see, for more research, search, hint, clue, or the like, pictorially or in text format or in voice format or bar-code or coded format or multimedia or mixed format or any other format. For example, if the user is searching for "outdoors", the system shows the picture of "outdoors", as well as e.g. a picture of "SUV" or "JEEP" automobile or "beach umbrella" or "flying kite", on the side of the screen, so that the user or her friends can select the side pictures and continue going deep with it, in one or more directions in the Z-web, for related concepts or objects or people, e.g. by clicking on them, to discover more in the Z-web and the knowledge base.

Auto-Annotation & Feature-Enabling Web Albums

For example, see FIG. 212. In one embodiment, we search e.g. by gender, or looking for a "red dress", color of dress, or "wedding dress", or looking for "cold weather", using indicators, e.g. hat, coat, GPS data (for location on hemisphere or planet Earth), ice, snow, time or season, or the like. In one embodiment, we look for bride in an album (image album or video library) for wedding, or wedding indicators, e.g. wedding dress, tags, comments, formal dress, cake, tie, or jacket. In one embodiment, we do the same in frames of video.

In one embodiment, we have a person with multiple images and video albums or archives, each from an occasion, e.g. trip to zoo, with metadata, e.g. GPS data for location on planet Earth, date, time, or camera or lens information or specifications. In one embodiment, we have ADD and DELETE and UPDATE functions to add or subtract or update or synchronize between 2 devices for some data, e.g. attributes, tags, metadata, and the like. In one embodiment, we have private and public areas for albums or display or distribution or sharing or access or input or comment or tagging or output or email capability. In one embodiment, we self or automatically organize or use or tag or annotate photos or videos or pieces of videos. In one embodiment, we find or detect expressions on face, e.g. smiling or anger, closed eyes, red eyes, not-front-face posture, foggy photo, half-head in photo, open-mouth in photo, not-focused lens photo, or other problems or features in the image. In one embodiment, we have those features optional with the user (interactive with user, with GUI).

In one embodiment, we have cross reference between final albums, or soft boundaries between album classifications, either automatically or manually. In one embodiment, one image can be in multiple albums, as referenced or as copies. In one embodiment, the processor fixes or highlights or separates or brings apart or collects the red eye images or other features or problems. In one embodiment, the processor fixes the red eye or other problems, using other images of the person, e.g. using his eyes in the good or approved pictures to replace the bad ones, automatically. In one embodiment, we have clusters based on camera ID or recording time periods, in albums.

In one embodiment, we can search by e.g. people's name, occasion, or time, or by the characteristics of a dress, e.g. type of dress, e.g. "wedding dress", or attributes, e.g. color, or objects, e.g. hat or type of "hat", or e.g. abstract level of relationship for web or semantic web, e.g. "bride", to search for "wedding dress", or "cold weather", to search for hat, snow, or ice, or search for concepts or environments, e.g. night or day (in the image, based on color, histogram, "Moon", "Sun", intensity, time, or the like). Then, in one embodiment, after search, we can organize and rank the results. The result is based on images, or parts of images with objects in them, or highlighted parts. In one embodiment, with a click of the mouse or selector on screen or monitor or display, the system goes or jumps or refers to other data about the image, or original image itself, or relationships for the image. In one embodiment, we can get the information about the body of the person, or infer the age of person, in the image, using the metadata (or the like). In one embodiment, we search e.g. for CASUAL EVENT, e.g. looking for casual dress, tie, or jacket, coming from a database or rule storage, to expand the search terms.

In one embodiment, first, for a user, it searches his own database, and then friends' databases, as default, or alternatively, set the order of search as the user wishes, to search in that order for those databases. In one embodiment, for search, one can use image, part of image, or annotation of image, as search term or part of search terms. In one embodiment, other terms can be combined logically, using AND or OR or NOT operators, or using fuzzy logic operators or modifiers, e.g. showing degree of match or membership values. In one embodiment, the features are extracted, and then are used as the search terms, without any text or typing by the user. In one embodiment, the user can share the annotations with friends or public. In one embodiment, for generalization or specification situation, e.g. one is looking for "animal" or "panda", which are related to the "animal zoo", to be used for search term. In one embodiment, for search, we use the attributes of e.g. "animal" for "panda", for search terms (where "panda" is a subset of "animal").

Dictionary of Images

For example, see FIG. 213. In one embodiment, we have dictionary of images, or reverse dictionary of images, for searches both ways. In one embodiment, we have a document and document reviewer, for rendering, e.g. with image and text on the same file or page or layout. In one embodiment, processor uses the figure caption or figure number in the text to get information about the image, e.g. as a match of figure numbers, e.g. for sources of metadata. In one embodiment, main processor uses tags, OCR, or natural language module, to understand the related text.

In one embodiment, the user can do the selection on the objects, or alternatively, it does that automatically. In one embodiment, the user can hover over the image to get data about the image or object in the image, e.g. using a mouse, or click on it (or the like). In one embodiment, the analysis is based on reference URL, or metadata associated or embedded, or sources of information, or figure caption. In one embodiment, for the URL for image, the URL is associated with annotations. In one embodiment, we have functions WHOIS? and LEARN, e.g. with the right click on the image, to identify (image, person, or object), or learn it (as a learning or training sample).

In one embodiment, we use URL, metadata, or whole image, to get annotations, reliability, link, and other metadata. In one embodiment, we use a processor or plug-in to do the function or method mentioned here in this disclosure. In one embodiment, the plug-in is interactive, to be able to enter data. In one embodiment, we have PDF reader, browser, or MICROSOFT WORD, for the reader or viewer. In one embodiment, for large documents, for the extracted data, it can be used for other images, e.g. using cached information for other instances. In one embodiment, we use web crawlers or bots for pre-capture, analysis, and indexing. In one embodiment, we have embedded data, with no reference. In one embodiment, we have referenced image or data.

In one embodiment, the plug-in has a corresponding user interface, communicating with Z-web and its databases. In one embodiment, there is a context, obtained from metadata, or from enclosing documents, or from user ID, or from reader's ID. In one embodiment, in one or more databases, we have well-known people or objects, or classes of them. In one embodiment, we have various thresholds for different matchings. In one embodiment, we have batch process before the user's view, based on web page or image, or document capture, or indexing process, or background process in network (e.g. not user-driven), e.g. using annotations. (Note that these can be before that process, or at the same time.) In one embodiment, some of the process can be done without user's involvement or reader's involvement. In one embodiment, the UI or drop-down menu is used for entry into database, for editing and entry, or for learning an image or object.

In one embodiment, we have reverse dictionary of photos, e.g. with a GUI, e.g. with a plug-in, e.g. with a right-click-mouse function, e.g. for WHOIS? function (to identify the person or object in the image), or UPLOAD function to upload, or ANNOTATE function to annotate, or LINK function to link, or the like. In one embodiment, for the match, we compare with user's album, friend's album, friend-of-friend's album, group's album, super-group's album, social network's album, or the like, in an expanding manner, for scope or reach or size or width. In one embodiment, for the match, we have a repository of famous people, places, objects, or the like, with corresponding thresholds or criteria, with corresponding Z-factors, e.g. reliability factor. In one embodiment, for a given image or picture, the system gets or extracts a concept or object, and from that, the system can get antonyms or synonyms for that concept or object, if any, pictorially or textually or both, displayed to the user, on GUI or monitor or display. In one embodiment, the system displays ads based on antonyms or synonyms or related concepts. In one embodiment, the system displays concepts related to the object, based on a thesaurus, slangs, proverbs, or idioms dictionary, fully pictorially, or half pictorially (mixed with text).

Context

For example, see FIG. 214. In one embodiment, the system gets an image in a context, and then it finds the interest points in there. In one embodiment, it uses multiple classifiers, using multiple databases, e.g. for people, objects (e.g. for home, office, or road), buildings, animals, or satellite images, e.g. with hierarchy of more specialized classifiers. In one embodiment, it uses semantic web, e.g. using the Z-web (with reliability factor or other Z-factors), to uniquely identify, and if needed, go deeper in the classifiers chain. When, e.g., we find a collection of objects as "computer, fax machine, and white board", we may infer from them e.g. the OFFICE, as the context or environment for the collection of those objects, based on a database for context (or rules or rules engine).

In one embodiment, it also uses dictionary, and common misspellings listing or rules for correction module, to try different versions or variations for possible match. In one embodiment, it looks for generic object, e.g. "human", rather than "Jim". In one embodiment, it has reliability factor for each level of recognition, e.g. 90 percent for the recognized object being "human" (at the top level), and 10 percent for that to be "Jim" (at a lower level, as a subset of the top level). In one embodiment, it uses semantic web, to e.g. get "pet", as the extra object to search for, when e.g. searching for the object "dog", to expand the scope of the search, for better and more comprehensive search (for "dog").

In one embodiment, e.g., we find 4 objects in the example of FIG. 214 (as localization of interest points), two of which are the human and the pet (as class identification), and the other 2 maybe not recognized, yet. Then, for the entity identification, we have identified them as e.g. Joe and his dog, e.g. called Dragon, which have some Z-factor (or reliability factor) associated with their respective identifications.

Application for Social Network or Using Social Network

For example, see FIG. 215. In one embodiment, e.g. in FIG. 215, we have user A's photo album is input and analyzed for match and recognition, e.g. recognizing A, based on extracted features and matching them. But e.g. person labeled X is not resolved or needs further verifications. So, we analyze user B's album, and the result goes to a resolver module, to resolve person C, as being the same X, using another module, in which we use e.g. a user's data, e.g. user A and social network as input, and found links based on that, e.g. for list of friends or co-workers, which helps the resolver module resolving the identity of X, as being equal to C. In one embodiment, person C and person B are the same. In one embodiment, e.g. the user is asked to help to resolve or verify identities, by the system, if possible, by a window or text dialog appearing on the screen. In one embodiment, the user is asked to resolve people based on the order of e.g. their frequency of appearances, e.g. as showing more importance for larger frequencies.

For example, see FIG. 216. In one embodiment, 2 people use each other's albums or photos, or cross-reference other one. In one embodiment, e.g. we get pictures for a group of people, as mutual friends, but not all know each other. Then, once all people are identified, and a new picture is input, then, we label the new one with known people, and send one or some or all people in the picture an email or notification or SMS or the like, about the picture or each other or the picture itself, e.g. in a social network setting. In one embodiment, we use contact list from email or the like, e.g. OUTLOOK, or the registration log or account for each user, or for friends. In one embodiment, we send the email to the user or friend or both. In one embodiment, we use the contact list as a guide for annotation or more links. In one embodiment, we let the users verify images of themselves or friends, e.g. in a game or by simple window inquiry by system. In one embodiment, the user wants to know the identity of the 2nd person, and initiates the query, or links it to his contact list. In one embodiment, the match is done, but with low reliability. So, it asks the user or friend to verify that match. In one embodiment, the system uses this introduction mechanism between people, to make people connected or friend in the big network, to expand it very fast.

In one embodiment, the user can invite one or multiple people in the photo, to join or become friend or linked or come in to his circle or social network, or send an email, texting, SMS, TWITTER, broadcast, warning, invitation, or notice, automatically, e.g. textually or verbally or symbolically or pictorially, e.g. by clicking on people or objects, or going or hovering over them, or with stylus, finger or pen, or by hand movement or pose nearby, or face gesture with camera(s), or eye tracking or pose with camera(s), or by RFIDs or tags or beacons or sensors or magnets or devices or transmitters or inductor devices or capacitor devices or reflectors or lenses or mirrors on fingers or hands or body or clothing or gloves or hat or helmet or eyeglasses or the like, or other similar ways.

Using Faces for Verification of Email Recipients

In one embodiment, for the email system, for the email listing, people's faces are shown for verification of recipients, so that the mail does not go to the wrong people, as with visual confirmation by the sender, for fewer mistakes. In one embodiment, for the email system, for the email listing, the list is done textually, or by voice recognition naming the people, initially, and then verified visually by user, using the pictures or images or faces of recipients, or other attributes or caricatures or other signatures or trademarks of people or well-known facts about people (visually). In one embodiment, for the email system, for the email listing, the list is done or selected visually by the user, from the beginning, in one step. In one embodiment, we perform auto-completion for email from figures, for multiple choices for figures (for candidates for a person).

Picture Selection Criteria

In one embodiment, we have a metrics for pose or quality of print or other quality of the picture, so that based on that, we can rank, sort, or search images, and present the listing or ranking or best one(s) to the user (or optionally to the user, for further narrowing down the choices), e.g. good pictures for the resume or for newspaper article, or a picture with a tie and jacket selected, or a best picture in a context, e.g. for beach ad, with a bathing suit, among one or more people, based on templates or rules, e.g. defining the good height to width ratio of a person, or defining muscular bodies for sports figure selection, e.g. based on some training samples or features detections on the body.

Searching (or Getting or Finding) Image of a Person (or Object)

In one embodiment, e.g. we have person A inputting the pictures or albums, which gets analyzed, and then, annotated or tagged, as in FIG. 217, e.g. to get "image of" a person, rather than image "related to" a person, which is much bigger scope and yields more as output, but sometimes not what exactly we are looking for. For example, for search of a person, as we can distinguish from the name, when searching for her name, in the images, we do not want to show a picture of the house of that person, but rather, we usually (in one embodiment) want to get the picture of the person herself. In one embodiment, as in FIG. 217, instead of "query for user A label", for "search engine, e.g. GOOGLE", we have "query for Entity 1 or 2 label".

In one embodiment, as in FIG. 218, e.g. we are querying for label A (e.g. somebody's name, e.g. person A). We get images from other search engines, and then we clean up the results, to get only the images of label A. In one embodiment, the system searches through other search engines, first, and then the system compares it with the annotated images we had had before. We also distinguish two entities with the same name, e.g. Entity n, with the same label A, e.g. "Jim", as the name for 2 different people. In one embodiment, the system lists e.g. the people with the same name, in a ranking order based on e.g. the proximity link they have with the user (e.g. how close they are). In one embodiment, we display the results with links and metadata, using GUI. In one embodiment, we have link proximity based on e.g. user, friends, or famous people. In one embodiment, we put the search results from other search engines, e.g. GOOGLE, at the end of our own search results, as secondary results (i.e. with lower quality), for user's view and reference or comparison. In one embodiment, for a user, we can e.g. bypass the step of "Search related images, e.g. from other search engines", as in FIG. 218, if we know the user (with his picture albums and friend links), to go directly to the step of "Search and match URL and label A", as in FIG. 218, which is fed from user's photo album and friends' links database.

In one embodiment, if the system finds a picture for person A, as verified, and knows where it came from, then that web site (as a source) has more weight, and can be explored further in depth to get more reliable information about person A.

In one embodiment, for the results from other search engines, for expansion, the system uses the URL for extracting more information, e.g. via web crawler and bot, e.g. in a batch process or background process.

Privacy

In one embodiment, we have private or public or semi-public or semi-private (or the like) settings for our sharing or displaying or reviewing or tagging or annotating or accessing or searching or browsing of images or objects or videos, for user, friends, family, co-worker, boss, employee, contractor, senior management, public, social network, college, school, classmate, roommate, household, shared device, shared account, friend-of-friend, friend-of-friend-of-friend, and so on, or the like. In one embodiment, we have government excluding list database, for specified individuals, to exclude for the rules, for the above functions, for privacy settings. In one embodiment, we have the intersection of the privacy settings of multiple users or contributors, in set of rules, parameters, settings, coverages, scopes, extensions, reach, neighboring groups, overlaps, members, access points, or the like. In one embodiment, we have the union (or AND or OR or logical operators or XOR or fuzzy operators or MAX or MIN or "max" or "min" or Max-Min or Min-Max or Sup or the like) of the privacy settings of multiple users or contributors, in set of rules, parameters, settings, coverages, scopes, extensions, reach, neighboring groups, overlaps, members, access points, or the like.

In one embodiment, the user determines or sets who can annotate, to whom, where, when, for whom, who can look at them, who can copy them, who can download them, who can print them, who can see the relationships, who can see the names, if his relationships can be combined with his friends', if his relationships can be combined with those of his friends-of-friends (and so on), if his relationships can be combined with those of general public, the scope of the combination of his relationships, names, dates, locations, pictures, or data with others', if his data can be used for statistical usage with no identification, if his data can be used for statistical usage with identification of his name, if his data can be used for non-profit purposes, if he gets any royalty or fee or licensing for usage of his data (and how much or based on what metrics), if he can swap his data with his friends or others, what part of his data can be public, if the system has to ask permission for usage of which part of his data on a case-by-case basis, or similar rules or constraints or permissions or situations, set by user or friends or both, or collectively, or conditionally, using menus, dialog windows, options, buttons, screen items or boxes, or the like.

Visual Indicator

In one embodiment, we have visual feedback or visual indicator for the images, e.g. having an extra border or overlay on top of or around the image frame, so that it has different colors or grey scale values or intensities or frequencies, indicating e.g. the reliability factor, e.g. going from light to dark green or blue, e.g. representing 0 to 100 percent reliability factor, or in fuzzy terms, e.g. going from very low to very high reliability factor or other Z-factors.

Games

In one embodiment, we have a game for friends, tagging names on pictures for people or objects, e.g. to get points, to accumulate, e.g. to get a prize or coupon or win a trip or exchange points with selection of awards or to get listed in the Hall of Fame of a specific game. In one embodiment, we have this method as a way of training for our learning machine. In one embodiment, we have this method as a fan club or game club or social network connector, linking people more and more. In one embodiment, we have this method to reduce uncertainty or conflict on naming or tagging objects or people. In one embodiment, we have weighted average or average or voting or weighted voting or consensus of users or friends, to get the final result from multiple people or users. In one embodiment, we have e.g. higher weights for people who have more experience, or experts, or people with higher score for credibility so far, or people who played more, or people who were ranked higher by others in the community or social network.

In one embodiment, the system has a game, in which the heads of people (or an object e.g. a car, or part of an object, e.g. tire on a car) in the image are exchanged or edited or replaced or hidden or switched or obscured, in which case the friends or other users have to guess, identify, name, tag, or replace the objects or heads for the match or partial match, to get points or rewards, or e.g. as a funny or entertaining game, for bringing the traffic to our web site, or for training our learning machine (as training samples or users' feedback or input for identification, as supervised learning). In one embodiment, the system has this done for components of the object, e.g. eyes only, to hide eye, or replace eye, or cover eye, or only show eye, or put eyeglasses on the eye, or put eye patch on the eye, or put a famous or funny eye on the face, or the like, which can be a very fun or funny game, for guess and identification between friends, as a game.

Social Network Application

In one embodiment, we have e.g. a social network application, such as FACEBOOK, running for a user, with pictures showing in the user's timeline or album, which may be addressable. In one embodiment, we have our overlay on top of the social network application, e.g. the timeline display, or modify the display. In one embodiment, we have the interactivity with the user. In one embodiment, we have code or data running or presented in or through the social network application or platform, or by the browser, or using or through or by their API (application programming interface) or SDK (software development kit or "devkit"). In one embodiment, the user goes through our analytics engine or processor, to log in with the social network application, through the intermediary, with e.g. URLs stored in a database. In one embodiment, there is a plug-in for this process. In one embodiment, there is no plug-in for this process. In one embodiment, the relationship between 2 people is identified from the social network application or web site.

In one embodiment, the system encourages more participation in social network and more traffic, e.g. for more ad revenue. In one embodiment, the system enables finding new friends with similar interests. In one embodiment, the system enables finding new friends with particular facial or body features, or dress taste, or food taste, or wine taste, or the like.

Advertisement

In one embodiment, we have images and videos annotated and analyzed, which make them searchable by others, e.g. for safety (by police or law enforcement) or for security (for access control or target-list). In one embodiment, the system searches for small scope, such as within user and her friends scope or radius, or alternatively, it can increase the scope e.g. for other databases, e.g. region-wide, famous people, city-wide, co-workers, and the like. In one embodiment, the system uses the information for ad or income or referral or recommendation or suggestion or customization, e.g. for travel or vacation for next Summer, for interest or experience of user or her friends, for her taste or history or circle of friends or type of people, for person's personality or profile or background, e.g. for airline tickets, flights, clothing, food, restaurant, car, sport, concert, accessory, wine, soft drink, luggage, eyeglasses, or the like, from pictures or images or videos. In one embodiment, the system applies in the context of family, business, friends, university, or the like, to customize the suggestions or advertisements.

At Store

In one embodiment, the system lets a user use a store (e.g. on-line), in which the store has a subscription to the Z-web (based on video or image analyzers), which it can query, to get e.g. the kind or brand for clothing, based on the context and preference, e.g. based on percentage, ranking, fuzzy membership, or fuzzy descriptor, e.g. "85 percent" "casual", or "mostly" "casual". In one embodiment, the system has one or more cameras at the physical store, tracking and analyzing the customer, e.g. for identification and analysis, e.g. based on face, way of walking, emotion, GPS data, smart phone ID, RFID tag, credit card ID, driving license ID, store card ID, coupon ID, or any other ID mechanisms, with store's database, getting the preferences or taste for the user, e.g. in coordination with rules database, styles database, and habits database. In one embodiment, the system uses a cookie for tracking purposes for the user, e.g. clicking patterns or behaviors.

Image Analysis

In one embodiment, the system uses statistics and patterns extracted from images, over time, e.g. to find anomalies, even if we do not know what we exactly are looking for at the beginning, to alert or warn user or others, e.g. finding a person with bathing suit in a black-tie event or formal dinner, or finding a person with formal dress at the beach, where all others having bathing suit, in the photo or image or video. In one embodiment, the system is used for medical images, e.g. to find cancer tumor, or satellite image to find a tank or car, or for spectrum analyzer to find peaks or valleys for the curve, e.g. to find elements or features or accessing quality in the matter or compound or specimen or sample, e.g. for semiconductor material, bridge analysis, blood analysis, chemical analysis, or the like, for training or recognition or classification later on.

Video (or Multimedia or Movie (Including Homemade Movie))

In one embodiment, the system uses video track and frames, to analyze motion, for people or objects or animals, e.g. getting the features, e.g. for sitting posture, running, falling down, eating, walking as drunk or sleepy, explosion, rocket take-off, and the like, which are searchable, e.g. to analyze scenes, e.g. to later gather individual scenes to find the storyline or summary for the whole video, or to find the context, or to classify the context (e.g. with a classifier, e.g. using 200-2000 features, for 1-10 million training samples).

In one embodiment, the system gets a video, and it identifies e.g. Abraham Lincoln, "war" scene, and "old style clothing", along with audio track which is transcribed to text for search, or searched by voice analyzer directly, which can identify the person in movie as e.g. Abraham Lincoln, as well, indicating a movie about Abraham Lincoln. In one embodiment, the system classifies the video as historical, or comedy, or the like, based on some rules and tags or labels or identifiers or indicators, or set of them, or rules engine, or fuzzy rules engine.

In one embodiment, the system has an input from a URL of a movie e.g. from YOUTUBE, or other content owners or repositories, with tags, description, title, top comments, or the like, from which we get keywords and concepts, to analyze, and then send to different classifiers or databases, e.g. specialized classifiers for a specific classification, e.g. face recognition module, or special ethnicity face recognition module for more accurate recognition at a later stage, e.g. to find or locate features in the movie, to index or store them for future use or current search. In one embodiment, the system has a UI or GUI for description of objects or scenes or images, textually, by menu, verbally, or pictorially, to search for them, to find them in the video or track or frame or range of frames, and to mark or flag the location or record the place and time in the video, or record the proximity to other objects or scenes in the video in a storage, for future search. This can be combined with a Z-web, or linked to a Z-web, as a "Z-link", for expressing or including relationships and Z-factors, including reliability factor.

In one embodiment, the system uses a web browser and plug-in for a movie e.g. from YOUTUBE, or other content owners or repositories, for a click, to jump to a location in the movie or track or frame series. In one embodiment, the system has a UI for getting or capturing LIKE locations, auto-capture, comment on scenes, user annotation on scenes, user notes on scenes, ask-friends for comments on scenes, or the like, or for communicating these to others, e.g. friends in social network, e.g. to encourage participation in this social interaction, which brings more traffic to our web site, or can be used for training purposes (by users' input or feedback or comments on scenes), or can be used for marketing or advertising purposes for movie or objects in the movie or characters in the movie, or can be used to collect public opinion about an event or subject, e.g. drunk driving and corresponding laws, or can be used as survey or voting or public behavior analysis, or can be used for platform for searching interesting things in this movie or all movies, which brings huge traffic to our web site.

In one embodiment, the system uses the email or other forms of communications, e.g. texting or SMS, to communicate or notify friends or others, about the actions or interactions mentioned above, using the mailing list or contact lists or other listing for such purpose. In one embodiment, the system analyzes the emails between friends, or comments posted or TWITTER sent or tags posted, to get some information about a particular video or image. In one embodiment, the system sends a small section of video or first frame or interesting frame or scene or tagged ones or flagged ones to the friend automatically, or with user's option or input, along with the location and position of the interesting scenes, e.g. with a link or code or actual piece or comments or tags or blogs or pointer to the piece, for the friend to review or view.

In one embodiment, the system uses the method above to rank movies and scenes automatically. In one embodiment, the system analyzes the most popular movies in display at the theaters currently or recently, to tag and annotate them for interesting scenes, for users come and add more to it, for a large attraction for such activities, e.g. movie fans around the world, e.g. for most liked scene, most watched scene, most ridiculous scene, funniest scene, most romantic scene, most emailed scene, most commented scene, most hated scene, or the like. In one embodiment, we have the user getting a video (plus audio) from YOUTUBE or similar site, with her browser and her PC. Then, the user accesses our server (which acts as a portal for movies for social network site, for and from members), which has analyzed the video accessed by the user already, or will do that very soon, by accessing the content owner web site, such as YOUTUBE, to give information to the user about the movie, as detailed above.

In one embodiment, for a site e.g. FACEBOOK, or other social networking sites, for a user, the system accesses the movies (URL), e.g. for title or description, recognizes people in e.g. home videos, and annotates them or tags them or flags them or puts notes on them or marks them, and then stores them, or sends email or text or notification or the like, regarding the content or with the content or with a piece of content, to one or more people involved in the video, or friends or family or group or network. In one embodiment, the collection of movies or videos are analyzed, e.g. for the background of the image. In one embodiment, people access the collections for view, comments, referrals, purchase (the video), rent, lease, ad view, review of other's comments, and the like, e.g. with the log-in, with the application at the social site.

In one embodiment, the system has IM (instant message) feature and blog between friends for comments. In one embodiment, the system has a mask feature for hiding images or objects or people, depending on the viewer or user, e.g. for privacy purpose or for game or for guessing challenge for friends. In one embodiment, the system classifies based on topics, e.g. funny video. In one embodiment, the selection is done by right click on image or object, or by hovering over the object by mouse or finger or stylus or other input or selection devices or methods.

Catalogs

In one embodiment, the system goes through web sites or databases, which are well-organized for different categories, e.g. on-line catalog, or e-commerce, or pet store, or book store, or AMAZON.COM, or EBAY, or libraries, or repositories, or the like, to define or learn species and subset of classes or subclasses or classification (usually designed by a human expert, previously, for the other web site), to learn from that in our system, automatically, e.g. traversing through the classification or catalog tree structure, node by node through branches, to learn the classification and relationships, e.g. "men's shirt" being under the category of (or as a subset of) "men's clothing".

Fashion

In one embodiment, the system looks for and analyzes models (people's identity), celebrities, friends, famous people, fashion dresses (clothing), eyeglasses, sportswear, shoes, watches, jewelry, accessories, or the like, e.g. with emphasis on patterns, trends, styles, colors, or the like, e.g. at occasions or events, such as OSCAR ceremony, using tags, footage, or metadata, e.g. for search to find an exact match or similar object(s), e.g. finding a similar or exact clothing at half price somewhere else, e.g. with the same brand or another brand, for shoppers on-line, or bargain hunters. Sometimes, people are interested in similar products (not exact or not the same), but at bargain price, with or by a non-brand name manufacturer. In one embodiment, the system looks for components of e.g. a dress or shirt, e.g. short sleeve or long sleeve, or components of clothing, e.g. pants, and compares it to a catalog or database or user's preference or user's history of purchase or public's preference or public's history of purchase, for matching. In one embodiment, the system is connected to a social network site, for interactions, comments, and referrals between members or friends.

In one embodiment, the same search engine can also be used to find the potential trademark or copyright infringers e.g. for the clothing or design industry, on Internet, automatically, which is compared with the list of authorized dealers or licensees, to see if that is included in there, or if that needs further review, by human or computer, to determine the exact nature of use or sale, e.g. for a specific web site on Internet.

Hand-Drawn Images

In one embodiment, the system lets the user input hand-drawn images, by tablet or mouse or stylus or finger or on-screen or the like, or input by scanner, or alternatively, using fuzzy descriptors using templates or pre-designed figures, as a combination of pieces, for input. Then, the engine searches for similar figures, e.g. as a reverse dictionary. This can be used for police to find the missing person or described person, matched with other images in the database or in video library.

In one embodiment, the system uses this engine for a game, for multi-user game or teams, to draw by hand by the first user, and other people guess the person intended, from library of famous people, or friends' images. In one embodiment, the game has a template library, to help finish the drawing for the user, to make it easier for matching, e.g. as auto-finish function, as the drawing is done with some simple or coarse strokes by the user, which resembles part or all of a specific design or figure in a template, for the system to present that template to the user, to be chosen as an option to substitute the strokes by the user, to reconstruct part or all of the face for the famous person or friend, in one or more steps. The system searches for such match, as well, to be compared with people's guesses. This can be used as a fun game, or as a training tool for our learning machine, for faces, with users' input or feedback.

In one embodiment, the system lets the user morph the hand-drawn image, e.g. by mouse dragging on the object borders or objects, or by transformations or templates or filters available to the user on computer menu or screen, to be used on selected objects, e.g. elongating the size of the chin or nose, based on computer model and template library, to get later matched by our system with another person or famous personality or friend, e.g. to be compared with people's guesses, e.g. as a fun game. The face game can be done on any other object, e.g. cars or houses, as well.

Semantic Web

In one embodiment, the system uses semantic web, through the Z-web, to get the relationships, e.g. to relate the "outdoors" to "river" and "hills", pictorially, as still single images or videos or video frames. In one embodiment, the system connects components to subcomponents or the object, or classes to subclasses, or to synonym, or to related objects, e.g. "car" related to "tire". In one embodiment, that could expand the search scope. In one embodiment, if one types or searches for "outdoors" (e.g. pictorially, e.g. starting from an image of "outdoors"), then some images of "river" and "hills" appear on the screen automatically, which can be further chained in a sequence for related concepts, for more display of more images, by computer automatically, or optionally, in a direction guided by the user, in a branch of a semantic web chosen by the user.

Video Analysis

In one embodiment, the system uses a video sequence, e.g. for a car, to get different views of a car, for the same car, from different perspectives and angles, from different frames. In one embodiment, the system uses a 3D (3-dimensional) model, and a learning machine, for those input samples from different views of the car, to learn the car in 3D, according to the 3D model of the car. In one embodiment, the system uses relative position, perspective, correlation, normal vector, facing vector (which is parallel to the vector which is normal to the face of the object), movement vector, motion vector for the video frames, and transparency of the surfaces, e.g. glass of the window for the car, to keep an account for the car and its components, e.g. tire, e.g. to track or follow the car, and also to help recognize the other objects in the video.

In one embodiment, the system uses a frame of the video that inherently is not fully complete, as a single still image. However, that frame gets completed using the neighboring frames in that sequence, to fill up the pixel or raster or scanning gaps (or interpolate or extrapolate), for a resulting complete single still image, representing that frame, which can be used for our image analysis or image or object recognition. Thus, in these situations, in one embodiment, such preprocessing is used for our video frames, to make them ready for our further analysis or search or recognition.

Human (or Object) Model in 3D

In one embodiment, the system uses a real human, with sensors or beacons on body parts or clothing to track his movements in 3D in a room, with detectors or cameras all over the room, at different angles, to capture him in 3D, based on e.g. about 20-40 anchor points on his body, usually at joints or major moving parts or natural hinges on human body parts, e.g. at knees. Alternatively, one can capture the real human movements through multiple cameras, with reflective surfaces on clothing or body parts, or using light sources, to get a 3D coordinates of the body parts, to track them in movements, e.g. walking, running, angry walking, or drunk walking, to model all those modes and postures and activities and emotions for human or animal, and capture and store them in our databases, for future reference or comparisons. These can be used for our supervised learning for our learning machine, for sequences defining a situation, e.g. being drunk, angry, or nervous, for video analysis, based on our built-up library of sequences and gestures. This can also be used for video analysis, to examine sequences for objects or animals, e.g. defining rocket take-off, or bird flying. This can also be used for analysis, as a dictionary or reverse-dictionary of gestures, modes, actions, postures, or emotions.

Using Camera for Social (or Business) Networking

In one embodiment, the user uses a camera to capture the images or videos, e.g. the one on his eye glasses or necklace or watch or phone or digital camera or tie or hat or helmet or hidden in his jacket or hidden in his pen or hidden in the pin on his jacket or the like, which transmits the data to outside, e.g. using wireless, wire, fiber optics, WIFI, 4G, BLUETOOTH, or the like. In one embodiment, the user triggers the image capture, using a button or menu or key or the like, e.g. visible to all. Or, in one embodiment, this is hidden from all, using e.g. a key with transmitter in his pocket, with a button to push, using his fingers, without others noticing, with a camera hidden in his clothing or accessories, e.g. eye glasses, so that the picture capture is not noticed at all, by others in the room. The key transmitter in his pocket transmits the command to take a picture or video to the hidden camera, to trigger the picture or video capture. In one embodiment, the user triggers such an event from a remote place, or based on a pre-determined time, or based on another event, or based on periodic time, or based on a third party, or based on a rule engine, or based on a condition being satisfied.

In one embodiment, the user also uses a microphone for speaker recognition or voice recognition or natural language processing. In one embodiment, the user sends the photo to analyzer for analysis and recognition, so that the name and other information for the person in photo are obtained and returned back to the user, e.g. on his phone or other mobile devices or his PC or IPAD or computing tablet. This is useful for parties, business meetings, social gatherings, networking events, social networking, or the like. This is useful for in-person meeting or by computer introduction. In one embodiment, the introduction is done by email or texting or phone or the like, to the 2nd person. In one embodiment, a connection request or friend request message is sent to the 2nd person, automatically. In one embodiment, this increases the social network or business network connections. In one embodiment, the system displays all related data for the person in the photo, to the 1st user, using tables or list or menu. In one embodiment, the Z-factor for the recognition is shown to the 1st user (e.g. the reliability factor).

In one embodiment, the 1st user connects or syncs to 2nd user wirelessly, when both of their phones or devices are in close vicinity, and after the invitation for friendship was sent by device of the 1st user to that of the 2nd user. The next step is by the 2nd user, to accept the invitation, if desired, to get connected by phone, email, other devices or means, or in social network, e.g. FACEBOOK account. This is a fast method of adding friends, using pictorial method, as described above.

In one embodiment, the 1st user wants to get connected or introduced to all the people in the photo, who are not already his friends, after recognizing all people in the photo, as much as possible, and figuring out who is not in his circle of friends, already, from the list of friends. So, the 1st user can use his common friends, if any, to make the connections, or send the invitation directly to the 2nd user, if the 2nd user's address or email is available. Thus, the introduction can go through a common friend's account, if applicable, e.g. by an email.

In one embodiment, the friends, common friends, friends-of-friends, friends-of-friends-of-friends (and so on), unknown people, recognized people, famous people, family members, co-workers, boss, teacher, or the like, are all identified by color frames or various shapes or markers or flags or the like, superimposed on the photo, visually, for the ease of use, for the user, for identification of people based on their class or type. In one embodiment, the other data, such as name or address or position in the company, are also tagged, written, linked, or coded by symbols or colors or the like, e.g. using a pop-up balloon or menu or window or box. In one embodiment, for any new photo, it is also analyzed, and the people who are not friends are identified (in those images or photos or videos), and then, they get contacted for friend-request (or the like), as explained above.

At Store

In one embodiment, there is a kiosk in a store with camera and other biometrics detectors and analyzers, e.g. fingerprint recognition, to verify the identification of the person, by image or face recognition or other recognition methods, such as signature recognition, or measuring the pen pressure during signing by the user on the sensitive pad at the kiosk (e.g. working with piezoelectric (sensor) or capacitance or electrical resistance variations or changes effect, based on amount of pressure, measuring with sensors on the pad's surface), as compared with the database of known people (and their known characteristics). In one embodiment, the kiosk acts as a recognition unit, verification unit, analyzing unit, coupon dispensing unit, and messaging unit (getting messages from store or advertisements or special price announcements, or from user's friend or spouse, as a reminder to buy something from the store).

In one embodiment, the display is on a big monitor in the store, in every corner, following the user on sequential monitors in the store, based on the user's location, e.g. in one embodiment, based on the GPS data, or triangulation, or using the smart phone location, so that the user can see the ads or messages clearly. In one embodiment, the direction of the movement of the user in store is tracked, e.g. by cameras, sensors, detectors, RFIDs, tags, GPS, smart phone location, or face recognizers, for various sections, e.g. shoe section, to target ads or messages for him, accordingly, for a specific brand, type, product, or merchandise, e.g. specific shoe, especially, if he had a history for purchase of that product in the store database. In one embodiment, for mobile devices, the lower resolution versions of images (or partial images or icons or thumbnails) are used for faster loading or retrieval or efficiency.

In one embodiment, emotion or mood or posture of the people in picture, or the person taking the picture (based on the opposite camera, on the camera phones with double cameras, taking the picture of the camera holder, automatically), is recorded and analyzed, for better ad targeting and marketing, in real time, or at a later time, e.g. to target the people in store or on Internet, e.g. based on personality, mood, and prior history of purchases and tastes (e.g. the bottle of wine at a person's hand in the picture, with a brand, which is identified on the bottle, using an OCR module, indicating his type of preference for "wine" and the identified brand, with a high certainty factor, or Z-factor).

Grammar or Standard Description Language for Image or Video

For describing the objects, images, videos, frames of videos, coordinates, positions, locations, objects hiding or covering other objects, types of objects, flags, comments, place holders in videos or albums, and the like, we use a grammar or standard description language or a set of tags and parameters for image or video. For example, for tagging or flagging a scene in a video, one can specify the time, for the location of the scene or frame, e.g.:

<t=14567 sec> or use the frame number in the sequence:

<N=234,459>

Or, for an object A in front of object B, we have the FRONT function:

A=Front (B)

Or, for the position of an object or pixel, we have the coordinates (x,y) on screen as, e.g.:

(34, 56)

expressed as e.g. in cm or meter, or number of pixels from the origin of the coordinate system.

In one embodiment, the related information is extracted from MPEG, JPEG, and other formats, e.g. from their headers or tracks or attachments or content or encoding scheme.

Video or Image Applications

In one embodiment, the system for video or image recognizer is used for access control, e.g. for building, elevator, airport, security, or government, or for anti-terrorism, or for police work, or for background check, or for employment verification. In one embodiment, the system is used for face or object detection and recognition in pictures or images, e.g. in albums or videos.

In one embodiment, the system is used for recognition of face with hats or eyeglasses, or eye tracking or movement (or pupil or iris) for mood or emotion analysis or sleepiness analysis or drunk-person analysis (e.g. based on some predetermined data on patterns previously reported and captured or tagged, for machine learning samples or in a database), or sweat on skin or face or clothing for mood or emotion analysis (or temperature of the environment analysis), or wrinkles on face or skin for age analysis (or mood or emotion analysis), or color of face or blood vessels on face or neck for age analysis (or mood or emotion analysis, or health analysis, e.g. for medical doctors), or recognizing taste or fashion (e.g. for clothing and food, e.g. for marketing purposes, e.g. for magazines or on-line catalogs or web sites), or recognizing posture, action, or pose (e.g. for mood, situation, or status analysis, e.g. resulting in the analysis that "Jim is running & he looks scared", or "RUNNING+SCARED" as attributes to JIM), or determining the context or environment for the scene or image or sound or music (as "scary" or "creepy" or "war zone" or "fighting" or "angry", which are also fuzzy parameters, in natural language processing, with assigned membership values or functions).

In one embodiment, the system is used for lip reading from a video, with templates of various sounds and pieces (e.g. collectively corresponding to words or phrases) corresponding to lip and mouth and face movements or poses or sequences stored in the database, for matching and recognition, beyond some probability or threshold or reliability factor or Z-factor, e.g. using Z-web analysis or using Hidden Markov Model (HMM), as explained in details elsewhere in this disclosure and the parent of this patent application.

In one embodiment, the system is used for hand gesture analysis from a video, with templates of sign language in different styles or languages, for translation to regular English or other languages or text or voice, or for analysis of hand gesture in other applications, e.g. for baseball game, or for construction workers in a noisy environment with critical results, or for codes between friends, or for special symbols between cultures or people, e.g. "V" sign, by 2 fingers, indicating VICTORY.

In one embodiment, the system is used for tracking and understanding video or camera images, e.g. for a computer or smart phone or tablet input (or computer game systems), e.g. for capturing and interpreting the finger(s), hand, body, face, eye, eyebrow, nose, mouth, hat on the head, eyeglasses on the head, and the like, for poses, gestures, sequences, movements, and the like, based on coded definitions or prior interpretations or stored sequences or videos or images or frames, for comparison and analysis, to match and interpret the meaning, e.g. to convert to text or computer commands or codes, e.g. to initiate an action on the device, or other functionalities or options on the device, e.g. emailing a file or picture to a friend.

Or, for example, the system interprets a "closed fist" for left hand and "circular motion" with right index finger as e.g. a command for "drawing a complete circle on the screen", on the drawing software, using pre-programmed sequences or commands or codes or executables on the drawing software, based on the library of hand motions, e.g. in the server farm, to initiate such an action, to draw a circle on the screen or display. In one embodiment, the system combines e.g. text commands and voice commands, as well, to e.g. move the circle (in the example above) around on the screen, e.g. for "move up" command, or using an "arrow-up" on the keyboard, to e.g. move the "circle" up on the display.

In one embodiment, e.g. for FIG. 220, when hovering on a person in the image, some menu or buttons or thumbnails appearing on the side of the screen, so that the user can select more details, or some links are associated with the image of the person, so that the user can jump to another location for more data or information.

In one embodiment, in addition to image or video recognizer, to supplement the Z-web analytics, the system uses voice and speaker recognizers, with text transcribe module, to recognize people or objects.

In one embodiment, for image or video, we train the simple objects (which e.g. have more distinct features, for ease of recognition), first, for our learning machine.

In one embodiment, the system tracks a person (or an object) in video frames, and once the system knows the identity of that person from another method, then the system replaces the ID tag for that person with his real name.

In one embodiment, the system shows the user a teaser or short version of a movie, and if the user likes it, the user can buy or rent or watch or download or use the rest or the whole movie or video, through the transaction module, or through the DRM (digital rights management) module.

In one embodiment, the system keeps or marks or demarcates the location where the user has gone so far, on the movie or on the tracks e.g. for video, as a placeholder, or flag, so that for next session, the user can continue from the previous placeholder or marker, or the user can repeat or review a section of the movie again, or send it to her friends, or archive it, or the like. In one embodiment, the system keeps a section of the video, selected based on major changes in the frames, e.g. in the scenes, as pieces, for representation of the video, e.g. as a summary, for ease of review or initial survey, e.g. for the user, or other search engines searching in our databases or archives or libraries.

In one embodiment, the system asks the user or friends or public to approve, confirm, verify, identify, disapprove, challenge, deny, feedback, opinion, vote for or against, or help request, for the purpose of identification, locating, narrowing down, comments, LIKE function (e.g. "I like it"), description, summarization, or verification, for a person or object or concept, e.g. in a video or image or sound piece (such as tagging as "embarrassing moment" by the user, e.g. for a "naked man" in the "formal party setting" in a picture or video), through a GUI or user interface, e.g. in game or dialog window, or collaboratively by multiple users, questioning or challenging the user(s), for input or answer or feedback or opinion or vote.

In one embodiment, the system classifies and cross-classifies the object or video or image in one or more classes, as in relational databases, with cross-links between them, so that one can search for the same video from multiple approaches or concepts or leads, and still ends up with the same result. In one embodiment, for the example above, the video or image is listed under the following categories: "embarrassing moment", "naked man", and "formal party setting", and it can be searched and reached to, from any of those categories or leads, which a user may remember later, e.g. remembering or searching as a "video containing an 'embarrassing moment'". This search or query can be accessed or initiated by another picture under "embarrassing moment", pictorially, or by verbal command by a user (using voice recognizer module) for a given search, e.g. mentioning the phrase "video containing an 'embarrassing moment'", to initiate a search by the search engine, or textually (e.g. user typing the search terms, or their logical combinations, or phrases, with the natural language processor module), or the like. In one embodiment, for an object, the degree of membership for each of those classes in classification is expressed as a soft boundary, e.g. as a fuzzy number or value, e.g. with corresponding membership functions or values.

3D Models and Templates

In one embodiment, the system uses the 3D model for faces (or objects) to get the non-frontal face poses, e.g. face at 30 degree to the right-hand side, or at 45 degree to the left side, or side-view, or half-back side view at 45 degree angle, for generating templates, for recognition purpose for any face or a new given face, as input. Since the video already has a person's face (or car or an object) at different angles in different frames (tracked), a movie (or video, MPEG, QUICKTIME, multimedia, or the like) is a good source of the training for our learning machine, for training samples, or to capture the patterns emerging, or to model the 3D templates, or to adjust such templates or models (or parameters for them), empirically.

In one embodiment, the system uses the 3D model for faces or heads, with family members have similar features in common, using both parents, as a starting point, or one parent, or sibling, or children, or grandparents, or grandkids, or cousins, or the like, for modeling and recognition purpose. In one embodiment, the system uses figure captions or comments or tags on the figures. In one embodiment, the system uses the 3D model to generate faces in other orientations, to reconstruct, or to interpolate between them, for recognition purpose. In one embodiment, the system uses the 3D sub-models, for poses and emotions and variations, e.g. sneezing face, e.g. starting from neutral front-looking face with no emotions, as the basis, and generating other situations, to store in the pose and emotion databases, for later comparisons, for recognition purpose. In one embodiment, the system uses e.g. thousands or millions of real images beforehand, to get the parameters for the 3D models and the 3D sub-models fixed, or trained by learning machine, for different templates for different classes of heads or faces, e.g. 30-300 classes and 10-30 sub-classes of templates, e.g. using tagged supervised learning, or human expert interactive learning, or voting scheme with multiple human users, or the like. In one embodiment, the system uses the same training samples multiple times, for training Information Layers In one embodiment, the system tags people (or objects) in images or videos, by one or more extra layers, for their names and other information, e.g. address and tel. numbers, for each layer, superimposed on the coordinate of the photo or image or video frame, with the layers stored with image, or separately, or remotely, or in our server farm, or in cloud, or in the social network site, or as attachments, or as a header, or as part of the content of the file, or as a parallel track, or as a separate track, or as a synchronized track, as one option being visible, or invisible, or sometimes visible, or partially visible, to the user's view or friends' view, based on settings by the user or the friends, e.g. chosen by the menus or buttons on screen or voice commands, for the display to the user or friends or public or group or social network or followers or fans or groupie or supporters or party or classmates or students or the like, on their mobile device, smart phone, PDA, pad, tablet, camera, watch, TV, monitor, display, or the like.

Relationship Distance

In one embodiment, the system shows or indicates, by text or pictorially or indicators or graphically or sound or color or size or objects or symbols or letters or order or ranking or shapes or music notes or patterns or the like, the relationships between people, e.g. the relationship distance, as how far they are from each other, or haw many steps or people-in-between apart, as a metrics, e.g. sister-in-law, or 2nd cousin, or friend-of-friend, or friend-of-cousin-of-sister-in-law, or boss's-son, or best-friend's-son, which is optionally represented by a fuzzy parameter or a crisp number or value or tag or adjective, e.g. "far" or "close" or "2 people apart" or "D=3.6 'people-distance' between them" or "2 people in between them", e.g. with a real number representing the strength of relationships between people, in a scale or axis, or normalized to one or 100 percent, or expressed as an inverse of a parameter or value.

Music Recognizer

In one embodiment, the system recognizes the song or lyrics (or music or ring tone or "beeping" sound or rhythm or "beating" sound or notes or music pieces or humming sound or whistling sound or sound of tapping on the table or sound made by mouth or sound made by or on any object or music instrument or body parts, e.g. clapping hands), to find the musician or song or music album, to direct the user to the e-store or regular store or web site, e.g. for participating stores or merchants, e.g. for service or sale or rent, e.g. to facilitate the commerce or sale or transaction, e.g. with a percentage of the deal, or for click fee referral, or for coupon for the store or product, e.g. for download, or CD, or listening, e.g. for ringtone, or any tone for functions on keyboard or computer or telephone or mobile device. In one embodiment, the system lets the user send recommendation to friends (in social network or group or club or email list or class), for the music, or forward the music directly.

Image Matching

In one embodiment, the system recognizes or matches faces or photos (or objects or pets or places or events or emotions or actions in a movie) very fast, using e.g. basis functions, or Haar wavelets or functions. In one embodiment, the system breaks down each image into multiple blocks, e.g. 5×5 pieces, or 5 sections on each dimension, or 25 blocks total. In one embodiment, the system finds the correlations for match with the database of known images, which are already analyzed and indexed. In one embodiment, the system uses N parameters, e.g. 4-20 parameters, calculated or extracted for each block, or middle blocks, or outer edge blocks, or corner blocks, or all blocks together, for matching or comparisons, for object or picture or face or people matching or recognition, e.g. against one or more thresholds.

In one embodiment, if one (or M) of the thresholds is passed with a large margin of approval (high certainty factor), then other thresholds or comparisons for other parameters are relaxed, in terms of acceptance criteria. That is, the system forgives them, as being a bit lower than the corresponding threshold. That is, the system counts the image as accepted or approved, as matched with the other picture in the database or library.

In one embodiment, if one (or P) of the blocks is passed with a large margin of approval (high certainty factor), then other blocks or comparisons for other blocks are relaxed, in terms of acceptance criteria, for the whole photo.

In one embodiment, if one (or P) of the blocks, with M thresholds combination, is passed with a large margin of approval (high certainty factor), then other blocks or parameters or comparisons for other blocks or parameters are relaxed, in terms of acceptance criteria, for the whole photo. (Please note that M, N, and P are positive integers for this example, here.)

In one embodiment, the system determines object shapes, histograms (e.g. for color, intensity, grey scale, or the like), range of parameters (e.g. for color, intensity, grey scale, or the like), or ratios of parameters, average of pixel values, total of pixel values, median of pixel values, rate of change of pixel values (e.g. intensity change of 20 points per pixel length in x-direction or horizontal direction), rate of change of rate-of-change of pixel values (2nd order difference or delta, or "acceleration" value), maximum value, minimum value for pixels, contrasts, patterns, standard deviation, variance, shape of distribution of the pixel values, location of distribution of the pixel values in the block, shape of the distribution for pixel values in the block with respect to the Normal or Gaussian distribution, for each block, for the image or photo or video frame or painting or cartoon or movie or the like, to get the values as parameters, for the comparison and matching, e.g. photo matching.

In one embodiment, the system evaluates the totality of all N parameters for matching photos or images or faces, or compares them using weights for more emphasis on some parameters, or adds all the scores for comparisons together for all parameters, or do a weighted average or score or vote for N parameters (e.g. N comparisons), e.g. against or versus one or more thresholds, e.g. N threshold values, or do a fuzzy comparison with no hard boundary or thresholding for any parameter, using fuzzy sets, fuzzy rules engine, or membership functions, for each or all parameter(s) or comparison(s).

In one embodiment, the system normalizes the values for parameters for comparisons. In one embodiment, the system compares in parallel. In one embodiment, the system compares in series for parameters. In one embodiment, the system processes in batch file, for speed or efficiency. In one embodiment, the system asks the user for help or comment or feedback or input or approval for recognition. In one embodiment, the user loads the images by uploading the file on web site, or email as attachment or content, or clicking on the file, or right-clicking on the image, or drag-and-dropping the file, or choosing the file by any other method. In one embodiment, the user opens an account for her pet on the pet social network for her pet's photos, for exchange with her friends and comments, or for pet store, or for pet adoption, or for finding a similar looking pet in the database, or for finding a lost pet (among pictures of the found pets).

SVM (Support Vector Machines)

In one embodiment, the system uses a continuum of points, represented by the density of points, or color coded based on the density of points, for classification purposes. In one embodiment, the system uses a continuum model, instead of discrete points, for classification. In one embodiment, the system converts back to the discrete points, after the boundary lines are drawn or found, and the classification is finalized, to find where the clusters are with respect to the individual points. In one embodiment, the system uses this method for fast classification of a large number of points. In one embodiment, the system uses an iterative process for classification. In one embodiment, the system uses this method e.g. for Big Data analysis or a large amount of images.

Landmark (or Feature) Recognizer

In one embodiment, for famous landmark recognizer, the system uses GPS data and travel guides, plus encyclopedia for geographical facts, to correlate data, and filter the images taken by individuals and posted on the web site, as photo album or video library, for clustering purpose and recognition tasks, e.g. geo-clustering, to validate landmarks' identifications. In one embodiment, for landmark recognizer, the system uses the unsupervised learning. In one embodiment, the system uses matching based on local features. In one embodiment, the system finds interesting points or features, e.g. using Laplacian-of-Gaussian filters. In one embodiment, the system then finds local descriptors, e.g. using multi-dimensional Gabor Wavelets, for texture features on local regions, e.g. using 50-200 dimensions. In one embodiment, the system then reduces the dimensionality of the features, e.g. by 50 percent, e.g. using Principle Component Analysis (PCA) technique, to simplify the problem by reducing dimensionality and calculations. In one embodiment, the system then compares the shapes geometrically, from the extracted interesting points or features above, to find the match against the library. In one embodiment, in this stage, the system uses e.g. affine transformations for geometrical matching for shapes. From here, in one embodiment, the system gets matching scores, which indicate the result of comparisons with the library of images or landmarks.

In one embodiment, furthermore, binomial distribution for the probability model or Bayes technique can be used for the object matching. In one embodiment, the system uses matching edges and overlap edges for various regions, as the metrics for comparisons. In one embodiment, the system uses graph clustering, for grouping together similar images. In one embodiment, the system uses tree method for matching. In one embodiment, the system uses parallel processing for computation efficiency.

Search Scope Based on Linked Groups/Entities/Individuals

In one embodiment, as for example depicted in FIG. 219, the focus of search starts with the data related to User A, such as features, metadata and annotation extracted from the user's data, e.g., albums and metadata. In one embodiment, the search is expanded to the databases associated with links to user A, e.g., based on social network settings, such as user A's friends, family, or colleagues' DBs. In one embodiment, the search is extended to the database of famous people or things (e.g., buildings, paintings, sites, logos) and general (e.g., generic) concepts (e.g., car, boat, road, river, water, liquid, glass). The search in general concepts may be extended further by semantic web. In one embodiment, the search is expanded to a business/company database. In one embodiment the search is expanded to a global or a regional search, based on features being searched. In one embodiment, the search services are based on subscription and fee.

GUI for Detected Features and Annotations

In one embodiment, as for example depicted in FIG. 220, a graphical user interface uses a surrounding border or fill (e.g., rectangular or rounded) to indicate that features on the image (e.g., faces) are detected. In one embodiment, one or more classes of annotation (e.g., names) are displayed next to the feature, based on the user preferences (e.g., on mouse over, display characteristics for font, size, format and location). In one embodiment, various color codes or continuum are used to indicate the reliability of the annotation, e.g., based on Z-web data. In one embodiment, fuzzy or coarse terms are used to indicate the values, e.g., the reliability. In one embodiment, the border or fill visual feedback is used to indicate the type of relationship between the objects in the image (e.g., to a particular object for example in the same or other images, or to a particular entity such as the user), such as friend, family, or colleague. In one embodiment, indicators are placed on the image to indicate more metadata or features may be displayed or links to other data (e.g., related to the object or entity indicated). In one embodiment, selecting the object prompts a user interface for entering/updating/correcting data or annotation regarding the object. In one embodiment, a preconfigured list of items is presented to the user based on the class of object detected, to enter or confirm or reject annotations related to the items (e.g., name and relation). In one embodiment, the annotation uses the contact list to pull information (e.g., name) from contact database.

Feature Detection Based on Context, e.g., Clothing and Fashion

In one embodiment, as for example depicted in FIG. 221, the feature detector is trained to detect clothing items worn on body parts. Such clothes are associated with the people wearing them, based on annotation or recognition (e.g., facial features). In one embodiment, the clothing and attributes (e.g., type and color) are extracted from the images or videos and are associated with the people (e.g., users) or models/brand/publishers (e.g., determined from metadata). A clothing item may be located by other recognition engines, and passed on to a dress/clothing detection engine, for further detail classification (such as hat or eyeglass).

In one embodiment, as for example depicted in FIG. 222, various features are detected, e.g., for clothing and dress, and various attributes are determined such as style and color. During a search, search terms are analyzed by a semantic/relation/reasoning engine to expand search terms based on concept-semantic, lexical relationship, cognitive synonyms databases/search engine and other knowledgebase to expand the search terms to determine the category of the search. In one embodiment, the categories of the objects detected (e.g., clothing/dress) or sub-categories (e.g., shirt, gown), are stored and used to limit the search expansion to such categories. In one embodiment, the user or a process may search for "bride" or "red dress" to find a white gown and red tie in images, respectively. In one embodiment, a search may be done by style, color, or a person (e.g., fashion model, brand, or a person, or a combination of matching criteria).

In one embodiment, as for example depicted in FIG. 223, a Conceptual-Semantic, Lexical Relationships, Cognitive Synonyms, or Knowledgebase is used to expand the search terms or find applicable categories to search for (e.g., matching) features in images and movies or other metadata, such as occasion/event or related to the footage. In one embodiment, the search results are used to facilitate labeling/autoannotation, as well as indexing. In one embodiment, one or more terms used in finding the results are displayed to the user.

In one embodiment, an image or movie (or a portion thereof) is used as a search term. In one embodiment, the features of the image/movie are determined and used to search for similar data/image containing same/similar attributes. In one embodiment, the features are presented to the user to indicate which feature is must be the focus of the search and be prioritized. In one embodiment, the search terms based on an image/movie is augmented/edited by the user to specify other filters (e.g., by specifying other attributes, logical constructs AND, OR, NOT, and other features from other images).

Correlation to Descriptive Features/Labels

In one embodiment, as for example depicted in FIG. 224, 3D objects in images or movies are detected based on models of parts and sub-parts. The features from the feature detector are correlated (e.g., by using a restricted Boltzmann machine, RBM) with descriptive labels and attributes, via a correlation layers (e.g., made up of stochastic sigmoid units with unidirectional weighted links. In one embodiment, the descriptive labels and features are organized in to body parts and components/subparts, and attributes include the surface properties such as transparency, color and texture. The geometrical model properties are used for surfaces and direction. Some attributes describe the state of relative position of the parts, e.g., a car door being closed or open (or the degree, e.g., based on cosine of the opening angle). Some attributes describe the constraint in arrangement (position, orientation) between the parts. In one embodiment, the attributes are learned via correlation layer through a supervised training. In one embodiment, the 3D model rendering parameters, e.g., perspective, scale, relative eye/camera orientation, applied from an object in the image, are applied to other objects in the image to facilitate their identification, for example, by holding the label units corresponding to perspective and orientation to those attributes when analyzing other objects in the image. In one embodiment, the training of the feature detector is done via rendering from a 3D model as a training set generator, including the rendering for occlusion and hidden surfaces based on the surface normal vector.

In one embodiment, video or sequence of highly correlated images/frames from different perspective are used in learning the 3D model or motion. In one embodiment, an empirical model is built via training with data obtained from sensors/detectors used for tracking the key portions of a physical object (e.g., in 3D tracking) In one embodiment, the 3D coordinates of each point is captured via triangulation with multiple sensors, and organized into a captured sequence of correlated movements. One embodiment uses a sequence of data to train the motion features, e.g., by using a RBM with multiple linked visible and hidden layers associated with various timeframes. In one embodiment, a supervised learning is used to label the learned (unsupervised) motions.

In one embodiment, relative distances of the objects detected in an image or frame are determined based on scale, orientation and perspective. In one embodiment, the changes in relative position of objects detected in sequence of images or frames are determined, by comparing those between images or frames.

In one embodiment, images/frames are built from various frames from the video, e.g., by decoding the video data. In one embodiment, raster lines are combined from sequential frames to make a full image/frame. In one embodiment, the changes in the video frames (e.g., motion vectors) are used to determine the potential motion of objects captured in the video. In one embodiment, the scale and motion of objects are used to determine whether the camera was in motion compared to background (e.g., looking outside from a moving train or car).

Individualized Correlators In one embodiment, as for example depicted in FIG. 225(a), learning individual correlators are used for individual labels or identities. For example, to recognize whether an image is of a particular person, among several other persons, each person is represented by a label, e.g., with value in [0, 1] to indicate its degree of membership of the image for that label. In one embodiment, each correlator is trained by a supervised learning approach. In one embodiment, additional people may be added to a group of people, and for each added person, an individualized correlator is trained to identify that person among the group, without retraining the other individualized correlators, as the diversity of the features (e.g., facial features) in a small groups (e.g., in a social network links) are generally met. In one embodiment, other correlators in for the group members are spot checked against the images of the added person, and if one or more prior individual correlators return positive indication (e.g., high label value over a threshold), then (e.g., based on rules and a rules engine) the correlators are trained using the larger set including the images of the added person, to adjust for differences in attributes.

In one embodiment, the individualized correlators tend to reduce the dimensionality of the feature space (to few labels), and therefore, they tend to occupy small foot print for efficient storage and transmission of the correlators. In one embodiment, the individualized correlators are used for rapid identification or matching of people or objects in multiple images or video (e.g., related or in the same album or related to the same user). In one embodiment, a reliability factor is used to determine the reliability of the identification. For example, in one embodiment, the weighted input from correlation layer units to a label unit is used as the basis for the reliability of the label (e.g., between [0,1]). In one embodiment, multiple positive label indication is used to reduce the reliability of identification or any of those labels. In one embodiment, the individualized correlators are used based on the proximity to the albums' owner/user, e.g., based on the social network list of links, e.g., friends, family, colleagues. In one embodiment, the preliminary features or metadata, if available, are used to order the candidate correlators for a given image. In one embodiment, the individualized correlators are defined by their structure (e.g., number of units) the bias on the units and the weights associated between the correlation units and label and feature units, respectively.

In one embodiment, as depicted for example in FIG. 225(b), the individualized correlators are used to determine group through a consolidation layer. The Group label Gk represents a set (crisp or fuzzy) set of individuals associated with the individualized correlators. In one embodiment, the consolidation layer provides for identification of several groups and sub-groups, given a set of people. In one embodiment, the consolidation layer is trained via a supervised learning approach.

Descriptive Correlators and Reconstruction

In one embodiment, as depicted for example in FIG. 226, the correlation layer is used to train the descriptive parameters of a model, give a trained feature detector (e.g., trained unsupervised). This allows for more general identification of people or object in a larger population as the feature space of the descriptive parameters is similar to the feature space of the features determined by the feature detector. In one embodiment, the feature detector is fine tuned, e.g., via a deep autoencoder and back propagation, to be able to reconstruct images accurately. In one embodiment, the eye/camera relationship to the object is modeled by perspective (e.g., infinity points), scale, and orientation (e.g., polar coordinate angles $(\theta,\phi)$) parameters. In one embodiment, invariant or semi-invariant parameters are more structural and core to the identification of a person or object, while the variant parameters (e.g., mouth open/closed, expressions such as smiling) may radically be different from image to image. In one embodiment, the invariant parameters are determined as those invariant with respect to different poses and expression of the same person or object, while variant parameters (values) tend to be in common for various people and object with the same or similar expressions. The parameters for part and sub-parts are nested in one embodiment, and the relationship between parts and parts and subparts are represented by constraint parameters (e.g., an angle between eyes and the tip of the nose). In one embodiment, the descriptive parameters are used in supervised learning (e.g., using a model renderer) to learn the correlation layer.

In one embodiment, a high level labels/parameters may have fuzzy values or discrete values. In one embodiment, the expressive parameters (e.g., smiling) are represented as modification to state and relationships for parts, with for example, parameters values controlling the degree of the modifications. In one embodiment, various 3D models of face/head/body are used to represent the skeleton or hard foundation features, soft (e.g., muscular) features used for expressive parameters, and skin parameters used for color and texture, as well as, various models for hair, teeth, eye glasses, and hats.

In one embodiment, a data is input to the feature detector and its descriptive parameters are derived from the correlation layer to the label layers. In one embodiment, the descriptive parameters are modified (e.g., by changing the expression from neutral to smiling), and the image is reconstructed (e.g., via a one pass top down reconstruction derived from the correlation layer through the feature detector (e.g., based on RBM)). In one embodiment, various poses and expression of a person detected in an image (based on the features) are generated by varying the descriptive labels and reconstruction (as for example described also our prior patent application).

In one embodiment, the features obtained from images (or frames of a video) at different pose (e.g., orientation) provide different reliability of features. For example, the features of an ear in an image may not be as reliable in frontal view compared to side view (e.g., for certain classes of ears). One embodiment used a combination of features and their reliability factors obtained from different poses provide for more reliable model of a face/head (or other object classes/types). One embodiment updates the feature parameter values as more data arrives. One embodiment uses fuzzy values to describe feature parameters. One embodiment uses a model to apply probability distribution and variance for different parameters projected from different poses. In one embodiment, a 3D rendering is used to estimate the reliability of obtaining feature in a pose by varying the feature parameters and estimating the corresponding partial derivatives (e.g., gradients) of the features obtained from the rendered projection, and estimating the sensitivity of the rendered image in such a pose with respect to the modeled feature parameter.

Video/Image Analysis, Annotation, and Classification

In one embodiment, as for example depicted in FIG. 227, frames of a video or movie are analyzed by building a frame, e.g., by decoding from I-frame (Intra-coded picture), P-frame (Predicted picture), or B-frame (Bi-predictive picture), or slices. An image analyzer is used to detect features (e.g., people and objects) on the frame, while a motion analyzer uses multiple frames to detect motion of objects in between the frames. For example, in one embodiment, macroblock segments are used to determine the potential movement between the frames. In one embodiment, features from the picture/image/frame/macroblock/slice are used and correlated to determine the correlation and identification of objects across the timeline. In one embodiment, the features from motion are determined. One embodiment, for example, uses encoded motion vectors (e.g., determined based on motion estimation or from other blocks e.g., in direct/skip mode of H.264) are used to determine regions of the frame that potentially corresponds to a moving object. In one embodiment, common features from scene are determined. In one embodiment, the determined features are associated with frames, group of frames, and scene. In one embodiment, the scene detection uses a collection of I-frames to determine major changes in the background or consistency of the image across frames. In one embodiment, a voice/sound analyzer feeds to a speaker recognition module that associates a tonal signature to a speaker. In one embodiment, a transcription module is used to create metadata (text) from spoken voices and associate the data to the timeline (ranges) or scene labels. In one embodiment, the voice of the speaker/object is matched (e.g., via temporal correlation/occurrence) and/or via motion of the mouth to a particular person or object detected in image. The correlation is used for resolution of the recognition of person/object in images/frames where the faces/bodies are not detected reliably, e.g., by combining the reliability information (e.g., via Bayesian inference and/or Z-web).

In one embodiment, the motion of the mouth movements in frames is used to detect the speaking intervals from the video, and their correlation (e.g., via regression) with the speaking intervals from the audio, e.g., via a comparison module, provides for an out of synch timing between the video and audio portion of a movie. In one embodiment, the multimedia/movie is edited/updated/recoded to fix the out of synch timing by shifting the track timing (for example for audio track) to match that of video track by the amount compensating for the out of synch interval. In one embodiment, the visual key points in video motion corresponding to sound/voice generation are used to correlate the sound/voice with the video. In one embodiment, statistical threshold is used to determine whether the mismatch is attributed to jitter or a consistent bias (e.g., out of synch issue).

In one embodiment, the scene or motion is characterized/classified/categorized based on matching template from knowledgebase or based on supervised training One embodiment auto-annotates the recognized features/attributes based on frame, location within frame, scene, or whole presentation.

In one embodiment, the users' DBs are used to match features with users, e.g., to specifically identify individuals in the video. In one embodiment, features are extracted from video/audio and associated with the objects/video/frame (e.g., in a database based of features). In one embodiment, the features are used to match objects within various frames/scenes in the video and other videos (e.g., related videos, for example, based on the metadata, category, and user/owner/channel).

In one embodiment, the user is prompted to annotate (e.g., via a GUI or voice annotation) the detected objects/people in video and/or audio. In one embodiment, for example, few frequently occurring detected objects and/or people are used to prompt the user for annotation and propagate the annotation automatically based on a reliability threshold to other objects/features detected, e.g., in the same video/audio, and other data in or related to the users (e.g., albums).

In one embodiment, a user selects a portion of the frame via a GUI (e.g., click and drag a rectangle/oval around or about a location), and use that as the search query to find similar object/person in the video or other videos. In one embodiment, the selected portion is analyzed by one or more image analyzers to detect features (e.g., classes of objects and/or detailed features for identification). In one embodiment, the corresponding audio track is used to correlate with a speaker, and extend the search on the audio track or transcript or captions (if any). In one embodiment, the search is made based on a voice segment. In one embodiment, the voice segment is used to extract tonal features and speech particularities for speaker recognition or for matching with voice signatures in a database. In one embodiment, the association of the speaker to the visual images/frames are used to find the same or similar speakers in the same video or others, and identify/annotate/localize.

In one embodiment, as for example depicted in FIG. 228, based on an identifier or a URL, a movie and its associated data (e.g., metadata, title, description, owner/uploader, channel, comments, likes, and statistics) are extracted from a repository. In one embodiment, the movie and its associated data are analyzed, e.g., by a video/audio analyzer and keyword/concept extraction/analyzer, to provide/generate features/annotation and metadata. In one embodiment, the features/annotations/metadata are used to classify/categorize/index the movie (including association with the URL or movie identifier). In one embodiment, the determined features (e.g., based on images/frames/locations within frames/scenes) are used for classification and indexing. In one embodiment, a semantic web or a concept relationship database are used to expand the annotation and enhance the indexing/search. In one embodiment, a user interface or a service is provided to receive the search/query, based on for example the URL or ID, image, voice, and other filtering metadata, and return candidate movies, location of features (temporal and spatial), annotations, and generated links, e.g., for annotations or recognized entities.

In one embodiment, for example, a product placement or class/type of objects are determined (e.g., a car or beverage) and used for targeted advertisement overlaid on the movie or on the side of movie playback frame, e.g., with links to other movies or ad webpage. In one embodiment, the duration of the advertisement is based on the duration of the presentation of the object on the video, e.g., for a minimum amount of time and/or for the duration/interval of the object display in the movie. In one embodiment, multiple objects are detected in the image or frame/scene, and the targeted ad is presented to the user, based on the user's preferences, characteristics, or previous buying habits or interests.

In one embodiment, the comments/annotation indicator or overlaid ad indicator moves with the object as the object's location is changed within the frame. In one embodiment, the corresponding indicators are placed at the side of the frame as to not interfere with the playback. In one embodiment, upon user's action (e.g., clicking on the indicators), the GUI shows identifies the corresponding object on the image/frame, e.g., with border/fill, tooltip or an annotation marker.

In one embodiment, a comment/annotation indicator moves/tracks with the object. In one embodiment, the comment/annotation indicator enters the scene or displayed if the object appears again or mentioned on the voice track, e.g., by overlaying and inclusion of the GUI for the indicator and detecting the location of the object (e.g., surrounding region/rectangle or center or a key location such as on a recognized part/subpart of the object).

In one embodiment, Kalman filtering is used to predict the location of object in subsequent frames for more efficient detection.

In one embodiment, the voice is input (e.g., via a UI such as a microphone) and used to annotate an image/video/frame (s)/scene or objects/motions/concepts recognized (e.g., selected) within the image/video/frame/scene. In one embodiment, the audio comment/annotation is transcribed by a transcript generator and the transcription is used for annotation.

In one embodiment, a user is provided with a GUI to reply on an annotation/comments for an object (e.g., detected or associated with a frame/scene/image), for example via a bubble/tooltip/comment box.

In one embodiment, the location (e.g., temporal and/or spatial) of an object is used as a reference (e.g., together with the identification or URL of the image/video/audio) for later usage, such as favorites, or for sharing (e.g., via email or posting to a social network). In one embodiment, the tags are made as part of the URL to indicate such reference, e.g., by generating identification codes/hash values for various objects/scenes/frames.

In one embodiment, the snapshot (e.g., a thumbnail) or a short duration of the movie is taken (e.g., upon user's action) and presented to the user to input annotation or comments at a later point.

In one embodiment, the links and GUI are provided (e.g., overlaid on images/frames) to provide one or more actions available to the user related to the object, e.g., based on the context of the scene, class/type/identity of the object. For example, clicking on a person in an image/frame brings up a popup menu showing the actions available for the object in the image, such as fixing red eye. In one embodiment, the action taken for one frame is also performed on other frames where the object appears and the action is applicable (for example, based on proximity of the other frames to selected frame). In one embodiment, a particular attribute (e.g., red eye or an expression) is searched in video/image by searching the applicable objects and their attributes/features. In one embodiment, the user is presented with search results and the action is taken on the selection of instances made by user. In one embodiment, the features of the object on the database are used to take the action (e.g., by determining the color of the person's eye from other images to fix the red eye issue in a particular image or set of frames).

In one embodiment, for example or an image, the action reconstructs the image or a portion of image (e.g., face) to change one or more attributes (e.g., descriptive labels). For example, in one embodiment, the user queries for a person in an album (e.g., his or her images) where the expression is not neutral or smiling, the mouth is open, or the eyes are shut. In one embodiment, the portions of the face (e.g., eyes, eyebrows, mouth, and chin) are reconstructed according to the descriptive labels. In one embodiment, a morph module is used to control the changes to the face based on model (e.g., 3D model) of the face/head and the features determined from the person (e.g., from other images/videos). In one embodiment, the reconstruction is made via a deep autoencoder or RBM invoked through a correlation layer connected to the label units, for a portion of the image (e.g., face).

In one embodiment, the reconstruction is used to modify clothes or their attributes such as color. In one embodiment, the reconstruction is used to remove items, e.g., eye glasses from the image, by specifying the state and expression for the eye and using the facial features from the database.

In one embodiment, a morph module/application is used to make adjustment to descriptive features/labels after recognizing the model features.

In one embodiment, GUI is provided for user to specify action annotations on the video, e.g., by placing annotation associated with the video track to change playback speed (e.g., slowdown) for a segment of video, zoom in to an object, and track an object. In one embodiment, the action annotations are shared by providing an identifier to the annotation(s) associated a given movie.

Video/Image Analysis and Annotation in Context of Social Network

In one embodiment, as for example depicted in FIG. 229, a user (A) logs in to an online application (e.g., social network), for example, via an annotator application (e.g., a cloud/web or a mobile/desktop application). The user then uses the annotator application to annotate an object in a movie or image (from a repository, e.g., referenced via a link/ID). In one embodiment, the user's annotations and/or autoannotations are associated to the user/group and stored in a database (as well as other features/objects detected/analyzed). In one embodiment, the annotation from user A is shared with others, e.g., based on groups, friends, or classmates/professor or are made public for to access/view. In one embodiment, the annotations are associated with the user's ID (e.g., from social network site). In one embodiment, the content provider or other commentators pre-allocate notes and comments, e.g., as annotations/comments, associated with the video. In one embodiment, the annotation is filtered based on the annotator's ID or group belonging (e.g., user A's friends). In one embodiment, the annotations are used in an educational/instructional settings; for example, a student/audience member comments on the portions or on objects (captured in the movie) of a lecture by a professor/teacher/presenter. In one embodiment, user B accesses the annotations to view along with the viewing the movie or image. In one embodiment, the annotations are provided to user B if user B is part of the group authorized to see/add/edit annotations, e.g., based on the social network settings obtained (e.g., friend's list) or other lists such as class roster (e.g., obtained via a structured listing or group association in an LDAP database). In one embodiment, the history of the annotations is kept in transactional DB, e.g., based on the time/date the annotations were made.

In one embodiment, comments/annotations are viewed or accessible per user or a group of users (e.g., who made the annotations). In one embodiment, one or more users are selected to filter the annotations/comments. In one embodiment, the annotations (including autoannotations) are organized by users, scenes, objects/people (detected) in the movie/image. In one embodiment, the user indication of "like" is associated with a location (e.g., if clicked) and frame time, range of frames (e.g., if user held the mouse down), scene, or object/people.

In one embodiment, when a user indicates "like" or other annotations on an image/movie, the person recognized on the image/movie automatically gets an indication of the annotation (e.g., with a link to annotation and location in the image/movie/frame/scene) via social network or other available form such as email from contact list (e.g., with the snap shot of movie or photo).

In one embodiment, the UI input such as mouse or touch input changes to a tool (e.g., "like" or question mark or emotion icons) to express action or emotion of the user for quick annotation upon users action (e.g., click or touch), for example, during the movie playback, to associate/perform the expression/action/annotation with association with the object/frame/scene. In one embodiment, a touch/click by the user provides a UI such as the popup menu for user to quickly select the action/emotion to use with respect the object selected (e.g., detected).

In one embodiment, the annotations and/or features are maintained in one or more databases which may be separate from the domain of the social network or the movie repository.

In one embodiment, the annotations may be specified as private (e.g., for the user's own usage) and not accessible to others (e.g., in social network or public), for example, for user's own favorite spots on the movie/scene/image.

In one embodiment, an annotation is used to indicate where the user left off viewing the movie for later playback from on or earlier spot on the movie. In one embodiment, the user is asked to annotate certain objects on the movie, e.g., in order to gather statistics of annotation to indicate whether the user actually viewed the movie/image, e.g., for online course or certification.

In one embodiment, the annotations are used to indicate a portion of movie or snap shot to share with others.

In one embodiment, a summary of a movie is specified by annotations marking the scenes/range of frames to include in the summary. The play back uses the annotation timestamps to jump to the selected segments (e.g., sequentially). In one embodiment, a summary may be annotated by searching based on objects/people/scenes detected based on image/movie analysis.

In one embodiment, the timings of the annotations are automatically adjusted based on the objects/scenes/features to account for a delay in a user's reaction in seeing an object and actually clicking/inputting/touching/acting.

In one embodiment, the annotation/comment on the scene is automatically associated or time stamped, based on the interval of the scene. In one embodiment, the categorical annotations (e.g., interesting) is used for quick annotation with automatic time stamp based on the current location of the playback, so others may jump (e.g., from a list of interesting locations) to the location on the movie.

In one embodiment, more useful comments or more specific to parts of the movie/object/people are made based on object/attribute detection in the image/video/audio and based on more recognizable user identification (e.g., based on the user name or ID from a social network). Higher value comments and annotations provide for higher value metadata for the advertisers for targeted advertising, or statistical analysis with more reliability or traceability. For example, in an embodiment, advertisement specific to portions of the movie or tailored to the user and various objects in the movie are provided to the viewing users. For example, one user may be presented with an advertisement and another user may be presented with another advertisement for the same segment of the movie, depending on various contexts of the segment and the user.

In one embodiment, the annotations are used for training. For example, in one embodiment, the user is prompted to annotate certain objects or segments. In one embodiment, the scenes are classified based on the annotations, metadata, and features detected, and the categorizations and features are used to index the scene for future search/query.

In one embodiment, the user annotations are played back in an audio output, e.g., in a translation scenario or in a short explanatory/commentary related to an object/scene, e.g., based on user preference.

In one embodiment, the annotation tools with GUI such as balloon with tips are used to place annotations over the frame. In one embodiment, the annotation tip/location automatically conforms/tracks to the object(s) on the frame/scene/image. In one embodiment, the voice annotations (e.g., emotional) from multiple users are combined and played back for a user, e.g., to give an impression of viewing the presentation live in a crowd.

In one embodiment, the annotations are used as a voting tool, e.g., to vote on objects/people detected in the image or video. For example, this can be used to vote on people or object appearing in the movie by directly interacting with UI overlaid on the movie frame.

In one embodiment, as for example depicted in FIG. 230, images and movies placed in albums or other areas (e.g., timeline feature in Facebook®) are analyzed and annotated (e.g., automatically). In one embodiment, an online application (2510) (e.g., a social network) communicates (2516) with the user's browser or application (e.g., running on a user's device) (2512) and provide information about the user's own (or others) information, e.g., timeline (2514), including associated data such as multimedia or images placed, e.g., on the timeline or albums, by the user or others, including sponsored ads/info for advertisements. In one embodiment, a first process or an application (2518) (e.g., a cloud or web application), e.g., adapted for the social network platform, receives information from on line application (2510) or the user's application (2512), e.g., when the user's application invokes a resource or process or function of the first application, based on a data received from the online application (2510), e.g., a URL of a resource associated with the first application. In one embodiment, the online application invokes the first application and provides information. In one embodiment, the information is obtained by the first application using the authorization of the user (e.g., a token obtained via a login process) from the online application 2510. In one embodiment, such information includes, for example, the user data/ID, movies, and images (e.g., associated with the timeline or albums) and/or respective identifiers or URLs. In one embodiment, the user ID and references (e.g., URL, or ID) associated with the movie or image are sent to a search/indexing engine/application/process (2520), to find features/annotations previously analyzed or obtained from such movie or image. If such information found, they are extracted (2522) from a database or Z-web (2524), e.g., including features, temporal/spatial locations, labels, autoannotations and users' annotations, for example, associated with user/group (e.g., for friends, colleagues, for example, based on social network setting), and processed/organized by a search engine (2520) and passed on (2526) to the user's browser or application (2512), via for example, the first process or application (2518), e.g., after reformatting and coding by the first process or application (2528), so that the information will be rendered and can be acted upon by the user via the user's application (2512). In one embodiment, when such annotation or features are not available in the database (2524), the movie or the image (or a portion thereof) is obtained by the Analytics engine (2520), e.g., via the on-line application (2510), a user's repository, a third party repository (e.g., a movie or image repository), or a search engine, e.g., based on an identifier such as URL or label/title/ID. In one embodiment, the movie or image is analyzed to find feature/locations and perform autoannotations, e.g., based on the user's data or data associated with the user (e.g., albums), or based on classification of other matched people and objects, e.g., based on similar context.

In one embodiment, the user's application includes a plug-in module (2530) which communicates the user ID and references (e.g., URL, or ID) associated with the movie or image are sends such information to a search/indexing engine/application/process (2520), e.g., via a second process or application (2532), such as a web application. Similarly, features, temporal/spatial locations, labels, autoannotations and users' annotations are extracted (2522) from a DB or Z-web (2524) and passed on to the plug-in, e.g., via the second application or process, and rendered in the user's application or browser (2512), e.g., via the plug-in (2530).

In one embodiment, the first and second application and process refer to the same application or process. In one embodiment, the first application/process or the second application/process are incorporated or part of the analytics/search engine. In one embodiment, the user's application or the user's repository may be on a mobile device. In one embodiment, the title/description or other metadata of the movie is used to search for the movie. In one embodiment, a pending analysis message is returned to the plug-in or the user's application, to indicate to the user that an analysis is scheduled and pending for a given image or movie of a part thereof. In one embodiment, the background task is associated with such image or movie to obtain and control the status of the task.

Search in Feature Space Via Hierarchical Clustering

In one embodiment, as for example depicted in FIG. 231, the clusters of data in the multi-dimensional (d) (e.g., a highly dimensional) feature space are formed to facilitate fast indexing and search. In such a situation, it may be more efficient to index (e.g., a nested index) based on clusters as opposed to indexing based on highly dimensional features. For example, for a given feature set associated with an image or object in an image, there may not be an exact match found in the database, and similar objects (in feature space) with close feature distance may be searched for. In one embodiment, non-variant (or semi-non-variant) features are used to form feature space and/or clusters in the feature space. In one embodiment, clusters are formed around a feature vector of a data point, e.g., during population of the feature space with the feature vectors. In one embodiment, the clusters are adjusted (added/subtracted), e.g., by using a clustering technique, based on monitoring the population and the density of the data points in clusters for efficient cluster-based search. Each cluster (including sub-cluster) is associated by its boundary (crisp or fuzzy) within the feature space, e.g., determined by a model (e.g., center and radius, PCA) or combination of the feature space subsets. In one embodiment, feature vector for a given data point X1 is determined, and its membership in various clusters (and levels) are determined. For example, based on the features, X1 is in cluster ID1, ID4, ID5, ID8, and ID9. In one embodiment, cross tables are used to track the association between clusters and sub-clusters. In one embodiment, clusters overlap to allow more flexibility for classification and search. In one embodiment, e.g., in a sparse feature space and/or when populating the feature space, when a point does not fit into any cluster at a given hierarchy level (e.g., Li, Li+1, and Li+2), a cluster is formed about that point (e.g., with a default extent/radius about the point for a given level and/or based on heuristics from other regions of the feature space), and the level records and cross tables are updated to account for the new cluster(s) and their relationships. In one embodiment, similar data points (e.g., to X1 or any arbitrary point in the feature space) are searched, by first analyzing the clusters the point belongs (which may include multiple path to the point due to the overlapping nature of the clusters). Then, similar data points are determined based on the located clusters. For example, in one embodiment, the data points in the same deep level cluster(s) that the searched point belongs are returned. For example, in one embodiment, based on the feature vector (e.g., for X1), deep clusters ID8 and ID9 are determined by traversing from the higher level clusters (e.g., ID2, ID4, and ID5) and matching/finding the lower level cluster candidates based on cross tables (between the levels). In one embodiment, based on the found clusters, the data points (e.g., X3) belonging to those clusters are returned (along with their maximum membership function in the union, if fuzzy clusters). In one embodiment, if the scope of returned data point is expanded by using the overlap between the clusters (e.g., of the same hierarchical level). The overlap between two clusters is determined, e.g., based on their extent in the feature space, or by determining if they share data points. For example, by joining a cross table by itself (e.g., Li+2 to X cross table) and grouping for unique cluster relationships, a cluster overlap result is obtained (e.g., for clusters in Li+2) and stored/updated (e.g., with records indicating the following overlap relationships: ID8-ID9, ID8-ID10, and ID9-ID10 at Li+2, and D3-ID4 and ID4-ID5 at Li+1). In one embodiment, based on overlap between the clusters, the (e.g., deep level) searched clusters (e.g., ID8 and ID9) are used to determine other overlapping clusters at the same level. For example, based on ID8 and ID9, cluster ID10 is determined as an overlapping cluster, and the data points associated with ID10 (e.g., X2) are also returned.

In one embodiment, e.g., through supervised learning, the clusters are labeled by higher order labels/features describing the clusters.

In one embodiment, the feature space is dependent on the feature extraction engine (e.g., RBM or deep autoencoder). In one embodiment, a mapping is made to facilitate a search across or between two feature space (e.g., corresponding to two feature extraction engine). For example, one extraction engine may be specialized to recognize detailed features of a face or particular ethnicities, or a particular types of vehicles or trees), while another feature extraction engine may recognize higher level features or different set of features at even a different dimensionality of feature space. In one embodiment, the same data point (e.g., from the same image) is used to determine the mapping. In one embodiment, a second feature space has levels, e.g., Kj, Kj+1, Kj+2. In one embodiment, similar hierarchies, cross tables, and overlap tables are determined between K levels and their corresponding data points. In one embodiment, the deep levels of both feature spaces (e.g., Li+2 and Kj+2) are used to determine the mapping at deep level, using the data point memberships in the clusters at those levels in the corresponding feature spaces. For example, if X3 belongs to $ID_9^{F1}$ and $ID_{20}^{F2}$, (where the superscript refers to a particular feature space, and subscript refers to an index/ID of the level in the corresponding feature space), then an overlap between feature spaces clusters are established, e.g., by joining feature spaces' deep level cluster and data point cross tables (e.g., based on common data points) and grouping based on unique cluster relationships across the feature space. The count of the grouping indicates how correlated the feature spaces may be. The correlation is taken to higher levels by grouping based on the cross tables of higher to lower level clusters (in each feature space). In one embodiment, a data point or an arbitrary point in one feature space is matched with the deep clusters (and/or overlapping clusters) or a higher level cluster(s) of that feature space. Then, the result (i.e., cluster IDs) are used to find corresponding clusters in another feature space and finding similar data points corresponding to those clusters or to determine labels/high level features on the second feature space. This provides for an efficient handoff from one feature detector to another.

The higher count associated with unique grouping (e.g., between deep level clusters of two feature spaces) indicates a higher measure of correlation between the clusters across the feature spaces, while a higher number of groupings indicates lack of specificity between the features of two feature space. These measures are dependent on specific portions of the feature space (e.g., dependent on specific clusters). In one embodiment, these statistical measures are used to decide which second detection engine to use based on the features detected by the first detection engine, e.g., in expert selection.

In one embodiment, as for example depicted in FIG. 232, the features of two feature spaces are correlated (based on the common data points), e.g., by learning using an RBM as correlation layer. Then, the feature vector form (e.g., from one feature detector) can be used through the feature space correlator to determine a candidate feature vectors(s) in the second feature space.

In one embodiment, the number of clusters (e.g., at deep level) is kept one or two orders of magnitude less than the number of data points. In one embodiment, clustering hierarchy in the feature space allows for efficient global search when the user database (including user's linked databases, such as friends albums) are not available or do not yield result with reliability or otherwise a global search is required.

SVM for Big Data Processing Based on Density Graph

In one embodiment, the classification learning of data requires a large dataset (e.g., few billions) which may not be handled by conventional SVM (Support Vector Machine) learning approach (e.g., limited to few thousand data points). In one embodiment, the density mapping of data is tracked in a resolution (e.g., non-uniform) corresponding to the number of grids/regions that can be handled by SVM training. The number of data points falling in each region or grid is tracked based on the incoming (e.g., labeled) data points, and a strength measure is associated with each grid or region in the feature space, for a given class, e.g., based on the (e.g., relative) number of the data points contained in the grid or region for a given class. The strength measure for each grid/region and class forms a density graph representing the data point densities for a given class. As the number of data points are increased the density map becomes more and more stable, while the conventional SVM approach for learning quickly hits its limit. The density graphs may be generated based on time slices associated with the data points (if time based). The density graphs may be combined in one embodiment, allowing the aggregation of such data from multiple processing units (e.g., in Cloud computing). In one embodiment, the density aggregation is achieved on a corresponding grid/region from multiple density graphs, by weighted summation of the densities based on the number of points supported by each density graph. In one embodiment, the density graph is updated in batch as the data arrives, e.g., by incrementing the strength associated for grid/region for a class. In one embodiment, if the number of data points associated with a grid or region is below a threshold, then in learning approach the data points are used directly instead of regions/grids. In such as case, for example, each such point is given a strength measure equivalent to a region/grid containing that single data point. In one embodiment, the SVM learning is done based on grids/regions (instead of data points) and the error function per grid/region is weighted based on the associated strength measure. In one embodiment, a representative point associated with grid/region (e.g., center of grid) is used to represent grid/region by a point with corresponding strength measure. SVM learning is then employed based on such points and their strength measures. In one embodiment, a region is split to two or more sub-region each represented by a point, e.g., with strength of the region distributed among those representative points. In one embodiment, the trigger to recalculate the SVM weights, occur after the change in the density strengths exceed a threshold. In one embodiment, large number of data samples may be used in learning via SVM by using SVM against the class density map instead of the individual points themselves. In one embodiment, the density/color graph forms a semi-continuum representation of the data points, as the basis for fast iterative learning from big data via SVM. In addition to classification by SVM, the resulting density graphs for various classes, also help predict the probability of the classification of a data point based on the location of the data point in the graph (i.e., region/grid) and the corresponding strength for a given class.

In one embodiment, for example as shown in FIG. 233, data is processed by multiple processors in parallel (labeled 1 through 5), e.g., in a computing cloud (e.g., with a distributed file system), and the results of processing are aggregated in a aggregation node (A).

In one embodiment, the density graphs are aggregated from distributed processing nodes in the aggregation node. In one embodiment, SVM weights are determined in multiple processing nodes and the aggregated weights are determined in the aggregation node.

Improving General GUI for Email Systems (or File Systems)

In one embodiment, we improve general GUI (graphical user interface or UI) for email systems or file systems or file hierarchy systems, on any computing or communication devices, with a user interface. In one embodiment, we are providing improvements for the performance of email systems in different aspects, e.g. in terms of reliability, efficiency, redundancies, safety, security, and convenience for the users. The system can be on a computer, PDA, tablet computer, phone, smart phone, electronic device, game device, e-book reader, game console, communication device, computing device, PC, server, terminal, kiosk, video game, entertainment device, music box, music player, multimedia device, movie player, calendar device, watch, clock, or the like.

The embodiment mentioned here can be applied to (and includes) SMS (Short Message Service), MMS (Multimedia Messaging Service), XMS (Extended Messaging Service), texting, voice message, multimedia message, video message, combination message, live messaging, instant message, chat session, blog, social media forum, voting forum, discussion forum, consumer forum, or the like, in which a message or information or data is transmitted or sent or pushed or pulled or downloaded or uploaded from or between point A and point B or 2 or more people or computer units or terminals, automatically (e.g. by a computer, microprocessor, or processor), based on a trigger or event, semi-automatically, or manually, e.g. by a user or a third party, acting on it, e.g. by pushing a button or choosing a menu item on the screen or display or monitor. Thus, this embodiment is for any form of communications, which is a superset of email systems.

In one embodiment, the system relates to dragging and dropping emails into different folders. In one embodiment, when a user wants to store an email into a specific folder (e.g. after reading an email), for storage for future reference, the user may make a mistake and put (or drag-and-drop) that email in to a wrong place or folder. To avoid such a mistake (or reduce the possibility of such problems, or increase the speed and efficiency of the user), the email system let the user choose or highlight a specific target folder beforehand (e.g. by clicking on the folder using the right button of the mouse, to choose or highlight the folder). Then, as long as the user has not reversed his highlight feature for a specific folder, the folder is activated (as described below).

In one embodiment, for a highlighted folder, the vicinity and neighboring area around the folder is designated as the folder itself, in terms of screen or display coordinates or position. That is, the area corresponding to the folder increases drastically, to cover the neighboring folders, by one or more folder spaces (folder or icon size, on screen or display or monitor), e.g. 2 folder-size on each side of the folder (e.g. in up and down directions), such that the neighboring folders cannot be selected anymore, and anything (any file) going near the highlighted folder will be attracted and dropped into the highlighted folder (or "Magnetic" folder) automatically (like a magnet pulling in the object, within its vicinity). This way, the user cannot make a mistake and put the file or email into a wrong folder or neighboring folder by mistake (i.e. effectively disabling the other neighboring folders, temporarily, for the sake of speed and accuracy). The speed of the process of drag-and-drop increases, as well, increasing the efficiency of the user.

In one embodiment, as an example, the user selects a folder by right clicking on it, and choose the option "Magnetic folder", to highlight the selected folder, which increases the size of the icon representing the selected folder from a rectangle with (G×H) pixels, dimensions in 2 orthogonal axes, e.g. to ((3G)×(3H)) pixel dimensions, or to ((5.6G+20)×(3.9H+50)) pixel dimensions, to scale the icon larger, for ease of use, for the user to see. However, the actual "magnetic" region (for the actual effective area, to attract the emails or files in that region) does not have to be the same as the visual icon's size (for the enlarged icon). In one embodiment, it is larger. In one embodiment, it is smaller. In one embodiment, it is the same size and region.

However, in one embodiment, to make it easier for the user, for one of the examples above, of the enlarged icon by a factor of 3, i.e., ((3G)×(3H)) pixel dimensions, e.g. centered at the original icon's position or coordinate, the system disables e.g. the neighboring 5 folders on either side (e.g. up and down, on screen), and also assigns a region of ((5G)× (5H)) pixel dimensions as the "magnetic" region (as defined above), around the point centered at the original icon's position or coordinate. Thus, for any file or email coming into that "magnetic" region, e.g. as dragged or selected by the user, the file or email automatically goes into the highlighted (selected) enlarged folder, making the mistakes by the user minimal (or none at all), for the email or file placements or arrangements.

In one embodiment, the user is now finished with the process, and thus, the user right-clicks on the "magnetic" or selected folder, to undo the property, or to unselect the folder, to get that back to a normal folder. In that case, both the icon apparent size for display and the real region of clickability go back to their respective original sizes, i.e. the sizes before any of the operations mentioned above.

In one embodiment, the user uses any method of selection, e.g. mouse, hovering, clicking, pen, stylus, pad, roller, tablet, finger on touch-sensitive screen, finger near display, finger pose (as detected by a camera on device and analyzed, as the meaning of the pose by the user's finger(s) or hand), or the like.

In one embodiment, this process can be done for multiple folders in the email hierarchy (or folder tree, pyramid, or hierarchy), which correspond to the folders that the specific user uses most often in a given session. In one embodiment, this can be suggested by the email system itself. That is, based on the prior usage of user A, or history or histogram, on the frequency of usage of different folders, the email system automatically identifies (and waits for the approval of the user), or optionally, even highlights or chooses the corresponding folders for the user (e.g. highlights the top 5 folders, or top 10 percent folders, in terms of frequency of usage or drag-and-drop function on the folder).

In one embodiment, the Magnetic folder is activated or deactivated using a key combination or sequence on keyboard (predetermined, default, pre-set, or customized by the user). In one embodiment, the Magnetic folder is deactivated, if the mouse stays on the folder's icon with no activity, for example, for more than 3 seconds. In one embodiment, the Magnetic folder's icon size gets enlarged by a factor of, for example, 3, to highlight the selection, and making it easier for the user. In one embodiment, the Magnetic folder gets activated automatically for a folder, when that folder is used, for example, 3 times in a row, or 10 times in the last 10 minutes. In one embodiment, the Magnetic folder is acting as an attraction pole or focal point, pulling the folders in, from the vicinity, to snap in the right folder, hence, the name, the "Magnetic" folder.

In one embodiment, the training on the system to learn the patterns is done using e.g. a neural network system, e.g. to analyze the emails or contents, e.g. to classify, to properly place the file or email or image in a correct folder or super-folder, even if the user makes a mistake for placement, with an optional feature, e.g. for warning or emailing or messaging to the user, if that happens.

Please note that all or some of the features and embodiments above can also be combined in the same email (or texting or telephone or communication or computer or tablet or smart phone or file) system. Please note that all the teachings in this embodiment are also applied to SMS, texting, emails, or telephone messages, and the system can notify the user through all or any communication methods, e.g. calling, emailing, texting, vibration on device, flashing light on device, special note or music or tone or ringtone on device, heating a resistive coil in device (for heat sensitivity, detected by the user), paging the person, or beeping the person, e.g. using a phone set, PDA, computer, laptop, IPAD, tablet computer, smart phone, GPS, wireless device, pager, walkie-talkie, two-way radios, one-way radios, intercom, broadcasting device, Internet, voice-over-IP, computer network, fiber optic, optical communication device, or other similar devices, or using the combinations of the above.

General Notes

For all the systems taught here, one can use a microprocessor, processor, computer, computing device, controller, CPU, central processing module, processing unit, or controlling unit, to calculate, analyze, convert, and process the data, and it can store the information on a disk, hard drive, memory unit, storage unit, ROM, RAM, optical disc, magnetic unit, memory module, database, flash drive, removable drive, server, PC, RAID, tape, or the like. The information can be processed serially or in parallel. The communication between different units, devices, or modules are done by wire, cable, fiber optics, wirelessly, WIFI, BLUETOOTH, through network, Internet, copper interconnect, antenna, satellite dish, or the like.

In general, for all teachings of this disclosure, including the above sections, the changes or rules or commands or corrections can be in crisp values, e.g. 10 percent change or threshold or difference, or in one other embodiment, in Fuzzy domain, e.g. Fuzzy rules, commands, and corrections, e.g. large difference or large change, or can be expressed in combination of both Fuzzy and crisp rules and parameters. The Fuzzy rules and sets and their treatments are explained elsewhere in this disclosure or incorporated by reference in our prior application(s).

In general, whatever we teach here for face can be applied to other objects and components or parts, as well, and vice versa. In general, whatever we teach here for image can also be applied to video, frames, movie, and the like, and vice versa.

Note that throughout this disclosure, "we" or "it" means "our system" or "our controller" or "processor" or "CPU" or "our computer" or "our system of invention or embodiment" or "one of our embodiments" or "our method of invention" or "system of invention" or "microprocessor" or "processing unit of our system" or "our device" or "server" or "our teaching based on our method or system or device", which is (or related to) a machine or device or hardware, and not referring to a human at all. We also (sometimes) use the words "we" or "our" as our teaching entity or "teacher" for our disclosure, which again means that we are talking about "our system" or "details of our system" or "our method" or "details of our method" or "how it works, based on components of our system or steps of our method" (and not referring to a human at all).

In this disclosure, video also refers to Video/Audio including other tracks such as captions and transcripts.

Some Examples/Embodiments

First Example

A system for tagging images or videos, said system comprising:

an image analyzer for finding features in an image or video;

a feature extractor for extracting features in said image or video;

a correlation module for relating different parameters from various databases or albums or repositories with respect to said extracted features;

a processor module for identifying said image or video or one or more objects in said image or video;

a tagging module for tagging on said image or video or said one or more objects in said image or video;

a commenting module for commenting on said image or video or said one or more objects in said image or video;

a demarcating module for marking on said image or video or said one or more objects in said image or video;

a notification module for notifying one or more people identified in said image or video;

an email module for sending said image or video, or its tags, comments, flags, or markers, or the links to such information, to said one or more people identified in said image or video;

a blog forum for people to interact on images or videos;

a web site for people to load image or video albums;

said web site displays information about said image or video, along with its tags, comments, flags, or markers, or the links to such information;

said system lets the people look at each other's image or video, along with its tags, comments, flags, or markers, or the links to such information, to interact with each other;

using said markers, a third party can review and comment on other people's interesting videos or images, as a social network place.

Other Examples

A system for searching images or videos, starting from an image, sound, text, video, or description.

A system for searching images or videos, as a reverse-dictionary for images or videos.

A system for searching images or videos, as a dictionary for images or videos.

Search engine for images or videos.

Search, based on hierarchical overlapping clusters in feature space, for global search.

A system for annotating video, which can be shared with his social network.

Using similar annotations, to annotate a target image or video, e.g. from other people's library or album.

A method of finding relationships between people or objects or concepts or animals in an image or video.

A system for matching target image or video with other videos or images.

A user interface or GUI, e.g. for automatic link, accessing a photo web, jumping to photo web, automatic search, and filtering topics, with crisp or fuzzy relationships.

A method of analysis and annotation beforehand, e.g. using ID or URL, so that later on, a plug-in recognizes and queries, to get information based on URL or ID, to render the information into the application, on image or video.

A method of connecting people together in a social network, using images and video.

A method of obtaining image of an object, from many more images initially extracted, which are just related to the object.

A system for semantic web analysis, to expand search terms, for more comprehensive search.

More Embodiments

Video and Image Annotations

In one embodiment, we have logical operations for images, objects in images, or annotations in the images. For example, we have "object A IN FRONT OF object B", "object A AND object B", "person A in image", "person A NEAR person B in photo", "A, but not B", or the like. In one embodiment, we have the relationships based on the users' annotations. In one embodiment, we have the relationships based on the system analyzing the objects and images and annotations. In one embodiment, the system lets the user search the relationships, images, objects, video and photo albums, or annotations, which includes tags, flags, LIKE, DISLIKE, comments, voice, text, music, notes, symbols, signs, patterns, codes, executables, pictures, videos, photos, albums, images, links, hierarchical structure (comments on comments), listing, numbers, files, folders, directory, or the like. In one embodiment, the system lets the user search, order, rank, list, and display the items.

In one embodiment, the system lets the user specify the location or frame number or frame time or range of time or starting time, for the annotations or attachments or insertions, e.g. in the video or movies or multimedia or voice or music track(s), to get incorporated or displayed or inserted or reviewed or searched or indexed or stored.

In one embodiment, the system searches in video or images for objects, people, sequences, actions (such as running or laughing), frames, pieces, patterns, features, or emotions (e.g. angry, or nervousness, as an indication for not being truthful, e.g. as a lie detector). The system can then auto-annotate, based on its findings and determinations, in addition to the user's annotations, for a complete set of annotations, or comparison of the annotations by user versus those of the system.

In one embodiment, the system sends an instant message (IM) or text or email, with all annotations attached, e.g. as a self-contained file structure. In one embodiment, the system uses XML (Extensible Markup Language, or the like) for tagging the images or videos. In one embodiment, the system uses plug-ins for mobile applications or devices, in addition to browser software.

In one embodiment, the user e.g. clicks on a button, e.g. on the menu or on the video, to specify the starting and stopping time ranges or frames or spots, e.g. for the piece of video or voice or music or multimedia, to specify where to annotate or insert the annotations or plug-in or attach a file or link to a site or link to a hyperlink (or the like). In one embodiment, the user e.g. clicks on a button or on screen, e.g. to halt or pause the movie and put comment in the meantime, and then restart the movie again. In one embodiment, when the user restarts the movie, the movie starts from e.g. 2 seconds before (as a rewind), so that the user does not miss any part of the movie. In one embodiment, when the user puts the annotations, using e.g. a single button or click or gesture or command, it is done in real-time, without pausing the video or movie.

In one embodiment, to show the number or concentration of comments or annotations to the user, the system shows or uses curves, counters (e.g. on screen or video or on the side bar), numbers on screen, color coded on axis, with separate colors for LIKE, DISLIKE, DISAPPROVE, APPROVE, NEUTRAL, NOCOMMENT, or the like, with color intensity e.g. reflecting the density of number of comments or importance of comments or most popular comments, e.g. for dark green, light green, dark blue, or light blue, with the time line for annotations parallel to the video track time line (marked), e.g. with the user be able to zoom-in on time line or axis, and e.g. showing a typical thumbnail picture from a video frame or a feature of the frame, as a typical frame or video, or e.g. showing a comment or start of a comment or summary of comment or name of the commentators or picture of the commentators, e.g. as a teaser, e.g. to attract more interactions and to solicit more comments e.g. from other users or friend of the original user or friend of who loaded the video or picture or image (e.g. on our site or third party's site or album) or general public or guests or close friends only.

In one embodiment, to show the number or concentration of comments or annotations to the user, the system shows or uses density of color or grayscale value for indication of concentration of comments for an axis of time for video, e.g. using dark blue or darker blue. In one embodiment, the system shows the concentration or density by dots on screen, near axis, at the time corresponding to the video frame. In one embodiment, the user can click and jump to the next comment on time axis, or next comment at the same time moment, using various menu options. The comment time axis is parallel or the same as the video frame time axis. In one embodiment, the comment time axis unit is a "second" or a fraction of second. In one embodiment, the comments are stacked on top of each other, or listed on a scroll bar fashion, in the order of time or reverse order of time. In one embodiment, the comment has an upper limit for durations, for time, or for storage limit. In one embodiment, the comment or frame icon, on screen, near the time axis, is enlarged as we move the mouse or selector across the time axis or comment scroll bar, vertically or horizontally, to show more details for the user, for fast review.

In one embodiment, to show the number or concentration of comments or annotations to the user, the system shows counter on the bottom, or superimposed on the video for small screen, e.g. for mobile devices, such as phones. In one embodiment, to make comments, no sign up is needed. In one embodiment, to make comments, sign up is mandatory, e.g. through FACEBOOK or other social media sites.

In one embodiment, the users regulate the quality of comments, as the comments that are offensive are reported, or the bad ones get bad score or rating, and push down in the list, for low chance of further review by others or users. In one embodiment, the voting or score is used for self-regulation by users, e.g. for reliable commentators, e.g. based on history. In one embodiment, as an example, the system sorts inversely, based on duration of comments, which indicates that the shorter comments are generally more specific, on topics, and so, should have higher ranking and should come up on the list, to the top (if everything else being equal). In one embodiment, as an example, the reverse is applied, as the longer comments are more descriptive and informative, based on the environment and context (depending on the situation).

In one embodiment, as an example, the system sorts inversely, based on spatial size of the boxed region in the image, as the smaller size of the boxed region generally indicates more specific object(s), or topic, and so, it should be more relevant and focused, and it should come up to the top of the list, with a higher score or ranking. In one embodiment, as an example, the reverse is applied, as the larger regions are more inclusive with more related objects, based on the environment and context (depending on the situation), and thus, it should be higher ranking in the list.

In one embodiment, the system applies cross album reference, or within one album, for pictures or videos or both, for one or more people, e.g. using annotations, e.g. using voice comments or annotations, e.g. between friends or community or group only, or between one's album only, or among all users or public.

In one embodiment, the user tells story or dialog between images, e.g. with marker or highlighter or clicks or mouse movements, e.g. to select a region or image or frame, e.g. as a storyteller, who can select, can combine, can link, can reference, can annotate, can relate, can sequence, or can summarize a series of e.g. images or objects, for a particular story or dialog, to be stored as a sequence or series of actions or objects or links or annotations or images or videos or voices or music or text or the like, for sharing, review, distribution, broadcast, sending, transmission, or the like, for the user, friends, family, group, party, class, public, guests, trusted entities, officials, government, or limited list, depending on the privacy or distribution or sharing settings, by the user.

In one embodiment, the user uses automatic sharing, which jumps to the link or place in the video or image or album, which is of interest, e.g. marked by others or user herself, beforehand. This can be used e.g. for class discussion, college project, or group project or homework, e.g.

between co-workers or classmates or professor or instructor or boss. In one embodiment, the system has templates for various types of videos. For example, for the instructional videos for courses, the comments are called Questions, Answers, and Comments. For scary movies, the comments are called Scary, Very Scary, and Comments. For funny movies, the comments are called Funny, Very Funny, and Comments. These can be flags or buttons, to be selected by the user, without any typing, to speed up the tagging process, during the playback of the video or movie.

In one embodiment, the user has the options in the menu or display or interface, for entry of comments and playback the comments, along with the video playing, or without the video. In one embodiment, the comments are searchable, along with the tags or flags, in voice, sound, text, images, or objects in the images, and can be indexed and stored beforehand. In one embodiment, the user has the option to share or send or link the comments or tags with public, friends, friends of friends, or customized individually. In one embodiment, the user has links to comments, to different time flags, on time axis, e.g. to link user's comments with her friends, or to accumulate them, or to jump between them, or to summarize the text or voice, or to use them as an anchor point(s) to start with, or to use flags as starting and ending points or frames, or to point to other similar or related video or content or comment or frames or points on axis, or to gather all similar or related videos or content or comment or frames or objects in videos.

In one embodiment, the user uses hierarchical comments, e.g. comments on comments, or chain, or sequence, or based on, or nested, or pyramid-type, or tree-type. In one embodiment, the user uses speaking balloon shapes on screen for comments (or other icons for voice, music, figure, text, video, or link, for display on screen of monitor or device). In one embodiment, the system tracks the speaker or person in video in different frames, with speaking balloon shapes on screen for comments, tagging along on the screen with the person or speaker. In one embodiment, the user has the option to stop the video, superimpose the comment on video, show the comment on the bottom, or track the object in video.

In one embodiment, the system is used for comments as e.g. to take a vote or use question or multiple answers or survey or plot, and e.g. notify or email the interested parties and subscribers or followers the statistics or results, e.g. with triggering the notifications happening above a threshold or number, e.g. how many people commented on a specific part of the video, or on the part of the video that the original user annotated, first, e.g. to see the reaction or comments of the user's friends or public, in general.

In one embodiment, the system is used for display, e.g. for multiple tracks for play back annotations as overlaid on video, or as preview snapshot with annotation over it, or as a window on the side, or annotation on still image or frame of video.

In one embodiment, the system is used for voice recognition and voice relationship in our video album or voice annotation, e.g. from video data used for our Z-web, for relationships between different people and objects, e.g. using recognition and transcription to text, e.g. to find the people's taste or preferences, e.g. for marketing. In one embodiment, the system is used to search transcription from voice. In one embodiment, the system is used to have voice recorded from text templates that people read and record beforehand (or for any message or interactive session). In one embodiment, the system is used e.g. to get the user's voice or voice signature or voice commands or typical messages for his friends.

In one embodiment, the system is used for the mobile device or phone to take a picture or video, by the user, and then the picture is analyzed fast by our software in the phone or laptop, to find all the faces, and mark them by box or rectangle (around the face) (box them). Then, the user can click on faces and can comment or tag them by voice and other data. Then, the comment and content goes to our repository for further analysis, and a copy goes to the user's social site or album site. In one embodiment, the user can also add a voice message and email that to a friend, using e.g. the screen menu choices. In one embodiment, when the phone is charging at night, the system does the calculations on the user's phone e.g. for the recognition and analysis, during idle times. In one embodiment, the user backs up the annotations in our repository, for safe keeping or storage, from his phone or mobile device or tablet.

In one embodiment, the system is used for mobile phone to take picture and video, and then tagged or commented or annotated by the user, e.g. using voice annotations, e.g. "The picture of me and dad, in Paris, 2006 Summer vacation, having fun". The annotation can be transcribed to text, and stored as text, as well. The figures can be searched (by voice recognition or text-basis), later on, from albums, e.g. using questions or hints, e.g. the following (to find the picture(s)):

"picture of me and my dad"
"Paris vacation"
"2006 vacation"
"fun vacations"
"Paris photos"
"travels"
"overseas photos?"

In one embodiment, the system provides templates for comments or provides links, for ease of user, or provides symbols or icons or tags, such as happy face or smiling face, for the user to click or drag-and-drop, to choose, e.g. from a menu, to include in the text or comments. In one embodiment, the system provides links or suggests links, e.g. as auto-link. In one embodiment, the user or her friends provide links or tags. In one embodiment, the system works using voice commands, in addition to text commands. In one embodiment, this is used for scientific collaborations, course review, classroom, co-workers, security, entertainment, fun activity, movie industry, and the like.

Privacy

In one embodiment, the user uses different classes or categories for privacy or sharing or display or emailing or producing or the like (e.g. for permission domain, for access, or for filtering view), e.g. for "myself", close friends, friends, casual friends, friend of friends, family, far relatives, public, one-time-visitors, guests, limited list, exceptions, or the like. In one embodiment, the user uses different classes or categories for comments coming e.g. from (or going to): anonymous, mine, friends, named people, verified people, famous people, public figures, politicians, popular people, popular comments, popular commentators, or the like (e.g. based on vote and ranking or feedback of others), e.g. to filter or select or narrow down the sources or recipients or direction of comments (or distribution or censoring, e.g. for kids).

In one embodiment, the system is used for permission for annotation or sharing annotation, e.g. propagates the permission, e.g. who can do it or see it. In one embodiment, a famous character opens up to everybody, as one extreme example, with minimum privacy setting. In one embodiment, the system is used with a model to start from zero permission and add to it gradually, or in an alternate model, start from full permission and chip away from that, to reduce the permission scope and level. In one embodiment, the public knowledge is open to all, e.g. available data on Internet. In one embodiment, once a picture is shown to public, the features can be extracted by the public, which cannot be undone (after the public disclosure). In one embodiment, if the image is not shared to public, and later, the image is deleted, then the extracted feature set from the image is also erased from the system, or can be used only for the user or his circle of friends, based on permission level or privacy level.

In one embodiment, the system is used for permission level based on the triangle of "feature-identity-picture" relationships, as the 3 corners of a triangle being FEATURE, IDENTITY, and PICTURE (or image). This means that, e.g. once one person, e.g. user 1, is identified by the user 2, e.g. from exposure of a picture of user 1 to user 2, then even if the picture is deleted by user 1, from the album, later on, user 2 can still remember the identity of user 1 in his head (keep the identity), which is the association of features with the identity of a person, as denoted by one side of the triangle mentioned above, which will be remaining (even after the picture or image is gone or erased). In one embodiment, the system or user can assign a permission setting for this association, too.

Video Conferencing

In one embodiment, the system is used for lie detector or body language or emotion analysis on video or in court or video conferencing, for conclusion about a person or his intention or his behavior.

In one embodiment, as described before in our prior disclosures, for the face recognition in an image, using basis function, first, the system finds the tilt or orientation, so that to rotate in the right direction, as normalized, and then the system finds the scale of at least a head or body, for the correct size of basis function, using one face or object as a normalization or scaling factor.

In one embodiment, the system is used for video conferencing, with information about attendees, and also image of the attendees, so that less information is transmitted, and still getting better image construction on the other side. For video conferencing, e.g. the system finds the 4 people in the room, and boxes their faces, and then transmits the faces once with high resolution, and then superimpose the emotions on faces (with minimum transmission cost) later. In one embodiment, the system transmits the rest of the objects at low resolution, or based on difference of frames. In one embodiment, the system reconstructs the faces at the other end, based on models or templates or simulations on expression of faces, without actual face transmission, just by tags indicating emotions, which is extremely low bandwidth transmission. The people on the other side can examine the facial expressions and body languages of the user, during video conference. This reduces the need for traveling for business meetings, which saves a lot of money for the businesses.

Event-Centric Social Network

In one embodiment, we have a social network that is event-centric, rather than individual-centric. In one embodiment, people are going to a real meeting or official event or party or social event (or a virtual one), and take pictures or videos (or audio), e.g. by their cell or mobile or smart phones or cameras or tablets, and put it (upload) on the event-based social website. Then, later on, they can go and comment on and annotate with voice, text, image, video, music, or symbols (or the like), on their own or others' albums at the party, so that they can continue their conversations, even after the party or event, for more interactions and communications between the members or participants of the party or event, to essentially re-do or re-live the party, and extend it forever, as much as desired.

In one embodiment, they have a private "room" or "lounge" for the private communications. In one embodiment, they have a professional or political gathering for a specific cause or topic. In one embodiment, they have a dating site for a subset of people, for finding a match, or connect people with similar interests, e.g. book club or yoga or rock climbing or wine tasting. In one embodiment, they can share or store the pictures or videos or corresponding comments, or hide them from some or all people or public or members (of the event or party). In one embodiment, they can have overlap between events. In one embodiment, they can merge 2 or more events, e.g. if they are started by 2 different members, for the same exact event. In one embodiment, the system lets the members know that they might have repetitious or same/similar events, e.g. based on time and GPS recorded, e.g. by cameras, as a suggestion for merger or combined events, if they desire, e.g. where at least one or two or majority or supermajority of members of each event desires so (or approves or consents to).

In one embodiment, they have one or more managing member(s). In one embodiment, they have a starting member or initiation member. In one embodiment, they have an approval member for new members to verify them as a member of the event or as a guest for the event. In one embodiment, they have an ejection rule, for an arbitration person, for disagreements or bad or rude behavior on site or toward each other. In one embodiment, they have a guest member (e.g. with limited rights or access or privacy on the site or party or event), or e.g. for people who missed the party (but invited already), or for people who may become interested in the subject of the event or party, to visit or browse or comment on others or interact with others, to encourage more interactions and networking. In one embodiment, the sign-up is mandatory. In one embodiment, the sign-up is through other web sites, e.g. FACEBOOK or TWITTER or GOOGLE sites, for using the same identification for the user, or for ease of use for the user, or if the user desires.

In one embodiment, the interactions are before, during, and after the real or virtual party, with or without host(s), or one or more hosts or mangers, with different degrees or levels of invitees or guests with different levels of access or privacy, for e.g. pictures, conversations, and inviting privileges or rights.

In one embodiment, the system automatically suggests friends or other events to others, based on date, location, GPS, names, title, tags, and friend circles. In one embodiment, the various events can be merged based on managers' approvals or consent, as one event or combination event, which carries all the conditions and rights or constraints of individuals or people on individual events.

In one embodiment, the system loaded on a phone and camera, e.g. as plug-in, to let the user take a picture or video, and upload them in our web site by users or automatically, with copies or invitations emailed to friends by users or automatically, and with annotations done by users or automatically, and the recognitions of people or objects done by users or automatically.

In one embodiment, an event is automatically suggested based on a photo or a video of a user. In one embodiment, a face recognition module is used to match the faces found in the photo and video with those in a database, e.g., based on a user's album, or in an album of another user directly or indirectly connected to the user. In one embodiment, similar photos across albums are determined (e.g., based on common persons, background, metadata, GPS/location, and time) to fit a criteria of belonging to the same or similar event. In one embodiment, an event is (e.g., automatically) suggested to a user (or users), and e.g., upon initiation, an event object is setup and the photo or video is associated with the event object (e.g., in a database). In one embodiment, one or more users or recognized people in the photos or videos are (e.g., automatically) sent an invitation to join or visit or attend the event using an email, SMS, message, or notification, e.g., automatically, by using a face recognition module or annotation on the video or photo and by matching the identity of recognized faces or annotated persons/entities to the contact mode of notification (e.g., via contact list, email database, or a social network).

As for example depicted in FIG. 234, in one embodiment, the album of user 101 includes one or more (104) images or videos (or audio) related to an event. In one embodiment, an album of user 102 includes one or more (105) images or videos (or audio) related to the same event. In one embodiment, one or more video/audio/images are annotated (manually or automatically), e.g., with identity (or classification) of the people/objects/entities and/or information about the event (e.g., birthday, conference, or party). In one embodiment, the automatic annotation uses facial locator/recognizer module(s) to find the facial features (e.g., description or abstract features) of a face in an image or video, and determine a match in the user's (and/or the user's contacts/connections') annotated facial database (e.g., with a reliability or certainty factor), and automatically annotate the recognized face/object in a particular image or video. The auto-annotation for an audio uses a speaker recognition module that recognizes the audio signatures of a speaker and finds a match with an identified or annotated feature signature in a database. In one embodiment, an event object is automatically suggested by a event generator module based on annotations, GPS data, time, album organization, image/video/audio metadata (e.g., filenames sequences) and/or matching attributes or rules, or created/initiated by a user. An event object (108 or 109) is associated with a collection of such images/videos/audio and annotations, e.g., in a database. In one embodiment, an annotation or recognition of person/object in an image/video/audio (e.g., 104 and/or 105) in an album or an event (e.g., 108 and/or 109, respectively), refers or points to or identifies (e.g., 121 and/or 122, respectively) other users (e.g., 102 and/or 101, respectively). In one embodiment, based on cross identification, relationships, location (GPS), time/date, and other metadata or annotations, an event matching module determines that various events (e.g., 108 and 109) or various collections (e.g., albums) refer to the same event. In one embodiment, a notification is automatically sent to the event managers to merge the events in one (e.g., 110). In one embodiment, the merge is done automatically, based on satisfaction of pre-determined criteria and/or user settings (e.g., including based on automatic acceptance of event mergers with certain users for certain dates/times). In one embodiment, the merge is achieved by associating an identifier (representing the merged event, 110) with the other event objects (108 and 109) identifiers, e.g., in a database. In one embodiment, annotations (e.g., in form of text, voice, or video), comments, blogs, or chats are added or associated with an event or objects (e.g., images, video, audio, other annotations or comments) associated with the event. In one embodiment, via annotation or face recognition module or speaker recognition module, a person (103) or object is recognized (e.g., in a database or social network). For example, in case of person or entity, a notification is (e.g., automatically) sent to the person (103) by a notifier module via for example, social network messaging, email, or SMS to participate in the event and/or contribute or upload material (e.g., image, video, audio) (106). In one embodiment, a person's albums are automatically searched for matching annotations or indicators (e.g., time/date or location/GPS) or similar group or sub-group of people or objects or similar background or scene in the image/video/audio to suggest incorporation of such material into the event by the person or entity (103). In one embodiment, the image/video/audio (or their references or addresses) are added to the event automatically, based for example on user settings, criteria, or rules. In one embodiment, events (e.g., 110 and 112) are overlapped based on one or more criteria or relationships (e.g., based on people, time, subject, or location proximity). In one embodiment, authorized users may browse or navigate between events. In one embodiment, a person (e.g., 111) may be invited to participate in an event (e.g., 110) by one or more users or participants (e.g., 103) of the event. In one embodiment, event messages are sent as notifications to event participants, e.g., when a user adds a comment or annotation. In one embodiment, a notification is sent to the participants identified by a particular image/video/audio, person contributing the object, or to invitees, based upon a user making an annotation or comment on the image/video/audio. In one embodiment, more events (e.g., 113) may be merged together (e.g., 114), for example, by associating an identifier of merged event (114) with those of merging events (e.g., 113 and 110).

In one embodiment, as depicted for example in FIG. 235, an event or party object may be extended to a social application, such as a dating application. For example, users (e.g., 201 and 202) participating in an event (e.g., a party) (200) may indicate comments or indicators (e.g., private comment/indicator only visible to each user) such as "Wink" or "Like" (e.g., 203 and 204) on other people (e.g., 205 and 206) that appear in images/video/audio in the event. In one embodiment, a matching module determines a cross/mutual interest between people (e.g., 201 and 202, based on 206 and 205, respectively identified as the same people) and automatically sends those people notifications regarding the cross/mutual interest. In one embodiment, the capability to indicate such comments or indicator by a person may be limited by a total number or other rules, e.g., associated with the event or per user. In one embodiment the notification of mutual/cross interest is sent based on satisfying one or more rules and conditions based associated with the event or the users. For example, in one embodiment, the "Wink" indicator may not be sent to more than (for example) two people. For example, in one embodiment, a user may set a rule or setting not to accept a notification of cross interest, if the other user has given similar indication to more than a set number of people (e.g. three) in the event. In one embodiment, the notifications to a person for a mutual/cross interest are prioritized or filtered based on various factors, such as, the number similar indications sent by another person to other people. In one embodiment, people may tag their comments, conversations, chats, or annotations as private as to one or more other users. In one embodiment, a user may invite another user to an event. In one embodiment, a semi-private "Wink" or "Like" indicator from a user (e.g., 202) on an object (e.g., 206) representing or referring to a user or a person (e.g., 201), is visible or notified to the referred person (201) automatically, based on the event setting or the users' settings. In one embodiment, the private or semi-private indicators are matched or compared across various events, e.g., a mutual/cross interest between two users/entities can be matched when each interest indicator occurred in different event, e.g., by propagating the mutual/cross interest to the user level from the event domain.

FIG. 236 depicts an embodiment for event centric social network.

One Embodiment of the System (and its Components)

In one embodiment, as an example, the system comprises the following components (with the following functions, as described elsewhere in this or our prior disclosures, in more details):

- Our Next Generation Search Engine, using image, video, voice, annotations, text, and the like
  - Find objects, people, emotions, subjects, actions, context, environment, relationships, patterns, fashion, or the like, through images, videos, voice, text, and the like
  - Relevant and reliable search e.g. for images and videos (e.g. using Z-factors)
  - Relationships between text, image, sound, voice, and other forms of data (e.g. using Z-web)
- Automated Image Organizer and Relationship Manager
  - Search for people
  - Logical operations (e.g. AND, OR, NOT, or a combination)
  - Multiple User Albums Cross Identifier
  - For video and still image
- Z-web platform and relations knowledgebase
  - Expanding Z-web database, with corresponding Z-factors
  - To interface or make inquiry or query about an object or relationship in Z-web, with corresponding Z-factors (called "Z-inquiry")
- Pose and expression auto-editor (e.g. for human faces, e.g. for smiling face, for editing automatically)
- On-line Image or Video Finder/Search (e.g. based on text or image query)
  - People Finder/Search
  - Video Finder/Search
  - Image Finder/Search
  - Segment Finder/Search
  - Object Finder/Search
  - Action Finder/Search
  - Logical operations (e.g. AND, OR, NOT, or a combination)
- On-line Image and Video Annotator
  - Annotate on the timeline of video (e.g., "like", "don't like", comments, flags, placeholders, pointers, insertions, notes, markers, share comments, email comments, notify about other's comments, or the like)
  - Annotate parts of the image (e.g. identify, "like", recommend, note, link). The part is marked by the user or automatically suggested by the system, e.g., by the face-object locator module.
  - Annotate using text, voice, image, video, doodle, symbol, drawing, music, link, or the like
  - Annotations tagged with topics (e.g. pre-configured, dynamic)
  - Annotate on other annotations, e.g. blog or hierarchy
  - Annotations for: location, event, date/time, type (political, comedy, drama, news, sports, etc., which is useful for marketing and ads), starting points or markers in the movie or scenes (shared, or e.g. can be emailed)
  - Shared (social network)
  - Play-back annotations, e.g. voice annotations
  - Searchable annotations
  - Categorized annotations
  - Organized based on commented portion
  - Filter based on friends
  - Privacy level of comments
  - Organized based on commenter (or commentator or annotator) (e.g., famous people) (order or filter based on commenter (e.g., ID or ranking))
  - Show current comments (close to current time)
  - Preview of the comment, e.g. using a mouse hovering over a thumbnail image or an icon, representing the comment
  - Organized based on named comments, versus anonymous comments
  - Show summary count or density of comments (or e.g. types, e.g. with color codes, e.g. for LIKE, DISLIKE, etc.)
  - Comments or annotations, as thumbnails or icons or buttons or symbols on screen of device
  - Interactive with user (e.g. put forth photos or parts or segments, and ask NL (natural language) questions) (e.g. use prior questions and annotations, to guide for words, using templates or rules or decision trees)
  - Cross-Album user annotation or comment, e.g., voice annotation, covering multiple images and parts
  - Storyline by user (e.g. with marker, highlighter, or object selector)
  - Order or filter based on commented part of image (content)
  - Order based on types of annotation and rankings of annotations
  - Search or organize by annotation, topic, annotators, type, location, or coordinates in time or space
  - Follow a topic or person, with auto-notification
  - Transcription of voice to searchable text
  - Annotate video and images from other sources or stored at our site
  - Using mobile devices, for capture, annotations, and transmission or storage of videos and images
- Services (based on Ad, subscription, software licensing)
  - Video annotation (public or private)
  - Image Search
  - Video Search
- Library of voice annotations
  - Voice recognition
  - Speaker recognition
  - Transcribe to text
- Behavior and trend analysis
  - Marketing value
  - Targeted ads and income
- For social gatherings (or formal meetings or events)
  - Photo and video album after the party
  - Annotations and comments for photo and video album after the party (including voice annotation)
  - More interactions and relationships after the party
  - Parties
  - Virtual parties
  - Invitations to join, before or after the party
  - Community of people (matching people, e.g. book club)
  - Dating site (with common interest or friend, or using friend's recommendation) (knowledgeable matching, based on the other person's interests or comments or annotations) (facial or features matching, using our image search engine, within the album): generating subscription and income Professional services (for formal meetings or events) (e.g. video conferencing)

Image Editing, e.g., automatic finding and changing expressions, e.g., smiling, closing mouth, opening eyes, red eyes (automatic correcting or editing, using correct color and texture, from surrounding color of skin or face)

In one embodiment, the system unlocks information and maximizes value of images and videos, by extracting reliable and relevant information from image and video, e.g. for expressions and actions, within images and videos, which is also searchable, by the user, e.g. in the albums (for the user or his friends), with self or auto or cross annotations. In one embodiment, the system is used for Big Data analysis, as well. In one embodiment, the system is used for instructional video (e.g. targeted communication, via objects within a video), fashion (e.g. search to find same or similar dress, or compare prices in catalogs, for bargain prices), security (e.g. for airports or entry to a building or elevator or room or computer), travel industry, entertainment industry, movie or music industry, or the like.

Video and Image Recognition

In one embodiment, the system changes resolution during the recognition process, for an image or video, e.g., once the face is detected in the frame or image, then to recognize the face, the resolution used goes higher, dynamically, e.g., based on a rules engine.

In one embodiment, the system recognizes the arrangement of the objects in an image, e.g., object A located in front of object B, or covers object B, or on the left side of object B. In one embodiment, the system uses different focuses for distances or depths for various objects in the image (located at different distances or depths), for recognition purposes. In one embodiment, the system uses an incomplete line or abrupt discontinuity in borders or boundaries as an indication of another object covering the first object (as hidden, or located on the back).

In one embodiment, the system recognizes the objects in a video, using only pieces of the video, for selected frames or selected regions in a frame. In one embodiment, the system uses the recognized objects for the ad revenue, e.g. from the manufacturer or store, skipping the middleman, e.g. for connecting the chain of object-content owner-distributor-shows-middleman-ads, e.g. which can be shown on ad-track, e.g. for a video, parallel to the video normal track, on timeline or time axis.

Eye-Glasses as Computer Monitor or Display or Computer Interface

In one embodiment, the eyeglasses are used for monitor or computer interface. The image is projected at a focal length $f_1$, on eyeglasses, from the perspective of the user, at a distance $f_1$. However, for people who wear prescription eyeglasses, they cannot wear both at the same time. So, for them, the focal length is $f_2$, i.e., at a distance of $f_2$. So, the difference is $\Delta f = abs(f_2 - f_1)$, as the absolute value of the difference. Thus, we have a correction on the focal length equal to $\Delta f$. So, the user can put her prescription parameters for her eyeglasses in the system to adjust for focal length for monitor or display of the computer, or the system determines her eye problem, or reads her medical chart or history, to adjust based on $\Delta f$. The eye astigmatism can also be corrected with correction on display, such that the user does not need the conventional eyeglasses for that, to view the monitor on computer eyeglasses directly. In this case, the correction is on tilt ($\Delta \alpha$), curvature (e.g. Gaussian curvature form), angle ($\Delta \theta$), envelop, or shape. So, basically, the image is formed, by considering the user's eye problem already included in the position, angle, curvature, and tilt of the image rays and image formation, on an image plane, which is distanced (at $f_2$) and centered (in both directions of coordinates, with deviation at $\Delta x$ and $\Delta y$), accordingly.

Using Templates to Store Information

In one embodiment, for remembering or recalling or storing the numbers or poems, the system uses rhymes or templates to fit in the text or voice information, as an envelope or carrier data or shell. The templates are stored in a database. The templates generally reduce the size of the data stored. The templates represent patterns in nature or information for compression of data received or observed, in most cases. For example, to store a telephone number, e.g. (734) 435-1214, the system breaks it down as: 734, 435, 12, and 14, to be stored as 4 integer numbers. Or, the voice can be stored as a rhyme or poem type information for the telephone number. For example, we can have the rhyme for telephone number above as: "DaDaDa-DaDaDe-DaDe-DaDa", as an envelope or shell or template for the 4 integer numbers above.

Using Templates for Voice Generation

In one embodiment, for text to voice conversion, the system has templates based on voice-actors or the user herself, with voice pre-recorded, for various emotions, e.g. angry, happy, laughing, scared, nervous, and the like, which can be detected from natural language processing or learning from the context or words used in proximity, or which can be detected from image recognition on the video or image from the face (emotion or expression detection) or body language or action or pose of the subject under study, as described elsewhere in our disclosures. Then, the text will be converted to the voice using that template, e.g., saying "Watch out!" using a Nervous or Shouting (or combined both) template voice option(s), as this phrase usually refers to an urgency of information, or for the sender or originator of information. In one embodiment, the user or a third party tags the emotions or context. In one embodiment, the system does the tagging automatically, e.g. based on the teachings on emotion recognition (taught elsewhere in our disclosures), and then selects the proper template(s) from the template database, to be used for text-to-voice conversion, as output as voice.

Sound Recognition

In one embodiment, for voice recognition or natural language processing, the system uses fuzzy or soft boundary clusters, to e.g. find or separate or distinguish words or partial words or phrases in voice or text form. In general, the system uses fuzzy or soft boundary clusters or recognitions for any data recognition, e.g. in image or video or text or OCR, to combine all, and get better recognition on correlations of the individual recognitions.

In one embodiment, for sound recognition, one can have signatures or clusters or features recognized and stored in a database, or through a learning machine module or neural network weights, such as sounds for bomb or thunderstorm or gunshot or footstep or barking of a dog or coughing a person or sneezing of a person or pattern of footsteps, to be able to e.g. recognize gunshot, type of gun, identity of a person, size of the lung of a person, height of a person, weight of a person, knee or foot problem for a person, identity of a dog, or type of dog or other animals, by matching and recognizing against the database or taught learning machine, to e.g. add this recognition with other signatures or recognitions on text or OCR or picture or video or tags or comments or user's own identifications, to be able to get a better combined recognition result.

In one embodiment, for sound recognition, one can have multiple sound recorders or sensors installed on e.g. a post or fixed location, or moved as mobile recorder, e.g. with GPS or location recorder, around town or building or airport or street, for security purposes, to recognize the sound, and then by triangulation, GPS, or optical, sonar, laser, or other methods, find the location and distance of the source, to automatically notify authorities e.g. for coming storm or gunshot or bomb or car accident, by sound signatures in the database, for any event desired, for public safety, or other purposes, which can be also combined with the video or image feed, for better recognition or redundancies or accuracy.

Recognition Based on Style of Writing or Text or Speech

In one embodiment, the system recognizes the author or user based on style of writing of that person, as stored or scanned before in a database, as signature or features for that person, e.g. how often he makes a new paragraph, phrases used, use of commas, correct or incorrect patterns of usage of grammar or abbreviations or phrases, slangs used, topics used, words used, common words, type of words used, length of text or paragraphs, numbering formats, indexing formats, conclusion formats, logic used, formality of text, or the like, to correlate to a person, in addition to signature or handwriting recognitions or others, if available, to combine for better recognitions. The Z-factor or reliability factor comes in here as a factor for correct recognition, from competing parameters, e.g. those mentioned above.

The same analysis applies to speech and voice or lecture or song or lyrics, converted to text or analyzed as sound only, or both text and sound analysis, for pauses, words, slangs, tone of voice, common words, mistakes, or topics used, frequency of words used, frequency spectrum of sound and peaks and relative sizes and locations, Fourier coefficients, loudness, emphasis, accent, localized words, e.g. in Australian English usage, or per city usage or slang, formats, grammar, or the like, for recognition of person, verification, identification of level of education, background, family history, place of birth, expertise, sanity of a person, type of person, anger level, danger level, reliability, or reasonableness of a person, or social unrest collectively on a website or log or network, as a metrics or predictor parameter for possible revolution in a country or unrest, or political or social opinions, or voting on a movie or topics, collectively.

Using Hardware

In one embodiment, the system is based on hardware, with analog devices, for learning and recognition purposes, for faster and parallel processing, e.g. to be able to handle Big Data and face recognition in a very short amount of time, or in real time. So, e.g. the devices are stacked physically in 3-D (dimensional), on top of each other, e.g. using Si-via-hole technology, to be able to process the data faster, with a processor at each node in circuit, for parallel processing. In one embodiment, the matrix or vector manipulation can be approximated by the function of the device, as the speed is the main concern, and the results are still very good for recognition accuracy and reliability.

In one embodiment, the system is based on multiple-step step-wise interposer(s), as layers in between, in semiconductor processing for connectivity, for hardware, to connect many terminals or metal contacts to many other terminals or metal contacts or devices, in a large scale, for full connectivity between them, with many electrical connections in 3D, e.g. stacked vertically and crossing each other in a horizontal projection plane, without actually touching each other or shortening the circuit or shortening the terminals. So, the interposer is done e.g. at 20 steps, so that it can shift the location of a first terminal in horizontal plane X-Y coordinates, gradually, to be able to connect to a second terminal or metal contact or device, at a location that crosses it at a 2D projection horizontal plane X-Y coordinates, but in reality, that is clear from it electrically, i.e., not crossing each other in 3D, i.e., not shortening it electrically, for a full connection of many terminals or devices to many other terminals or devices (electrically).

In one embodiment, the system above is used for neural network simulations or actual hardware implementation of that, with nodes and layers, using devices on substrate in different layers of semiconductor structure, to connect to other devices or terminals or metal contacts, using e.g. a 20-step interposer metal connector or conductor (as a middle or inserted or intermediary or "translator" or adaptor or sandwiched layer), for full connection between layers (electrically), to represent and mimic neural networks (with nodes and layers, plus bias feed). In one embodiment, the system also has a 2D, horizontal plane X-Y coordinates, electrical distribution lines (or bus, e.g. in multiple of rows and columns) on substrate, for massive interconnects between devices or terminals, in the combination that is desired, or for bias voltage on each node, or for control of each node, or for weights.

In one embodiment, the system uses the hierarchical algorithm, or tree decision making, for which each node is a recognizer of a feature which may be real, e.g. eye or iris, or a combination of features of the face, e.g. ($2W_{eye}/L_{nose}$) for eye width and nose length, or abstract value, which is not readily derivable from features of the face. So, by using the depth and width of the hierarchy, the system controls the accuracy, speed, and level of recognition, in view of constraints of the computing power or time delays. In some cases, some general high level recognition can be accomplished on the surface, without full analysis, and some parts of the hierarchy can be idle and not used at all, for faster calculations and result (e.g. for ethnicity recognition or gender recognition, without recognizing the identity of the person). Note that each node depends on decisions of its sub-nodes (all or a majority or some of those sub-nodes), under its domain, under its branch.

In one embodiment, the system uses quantum computing using e.g. qubits (quantum bits), which is different from binary digital format, to represent the states and situations which are not in binary logic, e.g. in fuzzy domain, which relates to our current and prior inventions and disclosures, e.g. Z-numbers, Z-factors, and Z-web (or which are expressed in fuzzy clustering or soft boundary clustering, e.g. for recognition and classification purposes).

Face and Object Recognition or Tracking

In one embodiment, the system uses eigenvector for faces (eigenfaces), as described in our prior disclosures, to average human face in 2D or 3D models, as a model or template. One way to do this is to average hundreds of faces in real life photos or images, by normalizing on the size first, and then superimposing or combining them (e.g. averaging, weighted averaging, combining, adding, aggregating, union or intersection logical operations on pixel level, or superimposing two images, pixel by pixel, or region by region). Another way is to use an averaging filter on an image of face or head, to fuzzify or unsharpen the image or lines, or as defocused image through an optical lens, or through a dirty or scratched lens, to produce such murky or foggy or muddy or cloudy effect (on clarity of picture or face), to produce such eigenfaces, as our basis functions.

In one embodiment, then, any new face is a linear combination of those eigenfaces ($F_i$, e.g. about 100 or 200 of them), ($\Sigma_i \alpha_i F_i$), in our database, or alternatively, as a morphable variation of an eigenface, using a number of parameters to adjust features, e.g. nose, mouth, and eyes, to fit the model, e.g. $L_{mouth}$ or $W_{nose}$, to change the size or boundaries of the objects or features, e.g. mouth or nose, by some delta or small differences or perturbations or variations, e.g. $\Delta L_{mouth}$ or $\Delta W_{nose}$, for length of mouth or width of nose, to roughly fit the original eigenface. So, to store the information about the new face, we only need to store the coefficient of the linear combination in the example above ($\alpha_i$), or the small differences or perturbations or variations ($\Delta L_{mouth}$ or $\Delta W_{nose}$), plus the identity of the original eigenface ($F_O$), which is small data for storage or comparison or retrieval from a database, for more efficiency and higher speed.

In one embodiment, we have various amount or angle of lighting or camera or lens or focus or available colors or grey scale or texture, as variations of the faces. In one embodiment, we have various poses and angles and emotions (e.g. laughing or serious look) and views and perspectives, as variations of the faces. In one embodiment, we have various locations, e.g. frontal pose in the center of the image, or 45 degree side pose in the corner of top left of the image or photo, as variations of the faces. In one embodiment, we have various accessories, e.g. hair, eyeglasses, hat, or beard, as variations of the faces. These variations can be used for training purposes, or recognizing a person, or defining a person, or learning faces, or finding the orientation or environment of the face or camera or lens. So, once one parameter is taken as given, the others can be obtained from that, as the consequence or correspondence, after the training or learning mechanism above.

Once we find a good match, e.g. 92 percent match on $\alpha_i$, then we can detect a person or identity, from a database of known people, or for the ones who were previously detected in another camera or video. In one embodiment, to find the overall match for all $\alpha_i$, we get the minimum value for all $\alpha_i$ match scores, or get the multiplication of all $\alpha_i$ match scores, or the average of all $\alpha_i$ match scores. In one embodiment, this can be used for fitting score for matching a model or variations of a model or template. In one embodiment, we have hierarchical matching, with hierarchical classes or subclasses, for templates or models or eigenfaces or types of faces stored, for faster matching or comparisons. In one embodiment, we have separate databases or classes for different ages, genders, ethnicities, races, head types, or the like, to make the analysis and learning more accurate.

In one embodiment, we get lip reading with the emotion detection, on the face or lip or mouth, for sequence of configurations, as an action in video, for sequence of frames, to detect the words or emotion on the word, e.g. angry and shouting, for conversion to text or voice later on, for dictation or transcribing or storage. The templates on the training for the library of words and emotions or combinations of them are stored, based on supervised learning on known samples and videos, for future recognition of unknown input. The lip reading plus voice recognition are used for video caption generation.

In one embodiment, the model of the face or head is based on 3D scanning or laser scanning or digitizer, from real faces and heads, to be stored in a computer or database. In one embodiment, the beacons or tags or reflectors or RFIDs or transmitters are attached to the face or head, for digitization or recording or scanning of the face or head.

In one embodiment, the system transfers one face to another, using the model, to simulate the talking of one person, based on talking from another person, using the same words for imitation, based on word and mouth or face configuration and sequence correspondence, already learned or stored in a database. The various sequences are simulated based on parameters for that pose or emotion or sequence (which requires prior learning on many samples, or pattern recognition for supervised learning, or based on model for face or talking or mouth or shapes for various words captured and learned from many sequences beforehand), or actually taken as pictures and stored for that person, which requires prior tagging and classification for variations for that person.

In one embodiment, the system estimates the date or age of the picture from a rules engine, with correspondence on hair styles, clothing styles, wrinkles on picture, car models, and other objects in the picture, to be used for the current age of the person (as picture age can be added to the estimated age of the person in the picture at that time, which is based on the features of the face for different age ranges for male and female, already learned or classified based on many samples, e.g. through supervised learning).

In one embodiment, the system adjusts the color or background or contrast, to improve the contrast between face and background or other objects, so that recognition is done more accurately. In one embodiment, the system defines anchor points for the features on the face or objects for tracking them in the video, for better recognition, or for compression of data defining the video.

In one embodiment, first, the face is located in an image, e.g. using Viola-Jones algorithm. Then, two or more images of a person are captured at 2 or more different bands of spectrum of light, using different detectors or sensors or cameras, at different ranges of frequencies. Then, the captured images are aligned and normalized, for the referencing or comparison to each other. Then, the accessories, e.g. hair or eyeglasses, are removed from the image. Then, the system normalizes or equalizes the histogram from the images, to reduce any environmental effects or camera effects. Then, any of the methods below can be applied, for face recognition (or other methods we described in our prior disclosures). In one embodiment, the system uses grayscale image or infrared image of the face or object, as the basis, for recognition.

In one embodiment, the system uses the Principal Component Analysis (PCA) for face recognition, as a feature extractor, which relates to an orthogonal transformation to convert a set of possibly correlated variables observations into a set of uncorrelated variable values (principal components), with usually fewer variables. The first principal component has the largest possible variance, and each other component has the highest possible variance, with the condition that it is uncorrelated with or orthogonal to previous components. A feature subset selection method is used to reduce dimensionality and enhance the speed for classification. In one embodiment, the system also uses moment invariants to enhance the performance of face recognition.

In one embodiment, the system uses Kalman filter for tracking face in video. It can also be used to track an object in video, to compensate for the shaky camera or moving base line or coordinate system, to reduce the effect, for better result and more stable image, for better recognition of the other objects in the frame.

In one embodiment, the system uses multiple versions of image in different resolutions or spatial frequencies to store for comparison for face recognition, for faster or more efficient comparisons, at different stages and levels of accuracy, e.g. for hierarchical comparisons.

In one embodiment, the system uses eye movement or tracking, with one or more cameras on screen, for detecting the focus of the eye for the user, e.g. as a mouse or selector on screen, so that the user interface becomes faster and easier, for selection of menus or buttons or actions on screen, which can be combined with blinking fast, or twisting mouth, or hand gesture, or other facial or body movements or gestures, with tracking or recognition of such gestures, to mean a function or action, e.g. mouse click or selection of the point on screen, by the user, for easier user interface. In one embodiment, the system detects the eye gazing or focusing point on the screen using a light (possibly invisible), to shine on the eye and detect the reflection using sensors in front of the eyes, to extrapolate the gazing position, based on head and eye for the sitting position for the user, for the positions and coordinates as detected by the sensors in front of the user.

In one embodiment, the system uses hierarchical algorithm for recognition. In one embodiment, the system selects to ignore some features or regions of image. In one embodiment, the system uses Gaussian filters or convolution or matrix equivalent or kernel to focus on a region or center of Gaussian curve and defocus on the surroundings of that region. That is equivalent to the vision of a person who needs an eyeglass to see properly, and uses the eyeglass for a view of a center of a region, and for the surrounding or rest of the regions, she does not use any eyeglasses for any correction and sees the world murky or cloudy or unfocussed. So, we apply that principal to our system (our recognition machine) for viewing different regions, for field of view or window, that can be moved around, as time passes, to focus on the neighboring region(s), as sliding focused window, if needed.

In one embodiment, the system learns how to learn. In one embodiment, the system learns how to emphasize or focus or de-emphasize or de-focus on some features or regions of image, using a learning machine module.

In one embodiment, the system uses fixed camera for security e.g. at buildings, streets, or airports. Thus, the background is fixed or limited in variations, which can easily and rapidly be learned or distinguished or subtracted or marked or separated. Thus, the objects or foregrounds can be extracted or understood or distinguished much faster.

In one embodiment, the system uses real parallel lines on sides of e.g. rectangle or square shapes, e.g. a box or building or street, to get their infinite horizon points or point or line for perspective, by finding the intersection of such lines in the image at infinite point, far away, or use the natural boundaries, such as ocean and sky boundary in the image, to find the "infinite" or horizon line and horizontal axis or plane or direction of gravity, to normalize or understood or rotate or recognize or make correction in tilt for the image or components or objects in the image.

In one embodiment, the system uses the biggest deltas or changes or differences, to find the frame major changes in video, e.g. relative deltas, to know the background is changed at that point, to go deep and find the background again, for the new series of the frames, again, and store the new background somewhere in memory for further analysis of the new frame series in that sequence.

In one embodiment, the system uses a standard language or grammar or alphabet sets for input or description of an image or object (or voice or text or other data, as well), for Internet or search engine, using combination of e.g. tags, text, labels, geometrical shapes, pieces, unit objects, unit pieces, image alphabets, or sound alphabets, a subset of which is with interface with humans and is human-readable, to be used for processing, storing, inputting, interfacing, or the like, with humans and other machines, for data or input or recognition or compression or summarization or indexing or storage or description purposes. For example, an image of an object or insect is described based on a collection and relative position of a series of geometrical units, such as rectangles or triangles, as they are located in front of another geometrical unit, to form the final image, as we see it in the picture or image. For example, we have:

2 SQUAREs directly on TOP LEFT and TOP RIGHT of 1 TRIANGLE

TRIANGLE color: RED (color code: 237)

In one embodiment, the system asks the user to help to tag, for objects or people, to identify or verify, for fee or free, to correlate or vote between users, or based on the prior history and credibility of the user, or e.g. as a weighted average, or e.g. as measured as a Z-factor for the user for the reliability of information measure, or combine Z-factors of many users for combination of many information, some of which may seem contradictory or partially contradictory in conventional logic system, or e.g. using template or guided path for the user to answer or multiple choice or hierarchical choices for faster result, which is much more accurate and more efficient than that of other (conventional) methods, e.g. AMAZON Mechanical Turk for labeling, from multi-user response or crowd-sourcing, using public input.

In one embodiment, the system classifies e.g. a bird, e.g. a Cardinal, as a male and female, due to various or different appearances, or various colors due to different seasons or climates for animals, as a separate clusters or classifications, that are later related or connected by tags and extra information, to be in the same or under the same family or name or umbrella. In one embodiment, the system classifies the Cardinal, as a bird, and carries both information with the object, for the fact that all description of BIRD carries here, as inheritance, for simplicity for recognition for faster result, to describe the parameters or units defining a bird in an image (or sound or the like), from a template for BIRD in a database, already populated or learned. For example, see the example above, for the description of an insect with geometrical units or alphabets.

In one embodiment, the system gets a video, and to summarize the video, it overlaps the deltas or differences on top of each other, on a fixed background, e.g. for a fixed camera in an airport, or normalize on a fixed background from multiple cameras or moving camera, for security, for all activities observed e.g. in that part of the airport for the past week, which then can be detected for specific person, activity, object, action, or sequence, e.g. for suspicious activities, e.g. to alarm the police or authorities. So, in this case, the images of people potentially overlap on a specific space or coordinate in an image on background, but the system keeps track of them as separate objects, for analysis, or focusing more later, if needed.

Search Based on Image

In one embodiment, a search query is made based on images or parts of a video, e.g., by user selecting one or more objects/persons from the image or part of video. In one embodiment, prior to the selection, an object/face/person/speaker locator/recognition module analyzes the image/video/audio. In one embodiment, the analyzer module determines the bounding boxes or borders of the objects/faces/bodies in images and/or video frames. In one embodiment, the selection module uses the bounding boxes or borders to determine objects/persons/faces being selected. In one embodiment, user selection (e.g., indicated by a point or a region on image, video frame or a point or an interval in video frame or audio track) is processed by a locator/recognition module to determine objects/faces/bodies within or at the vicinity of the selection spatial and/or temporal indicators. In one embodiment, the query module provides logical combination between the audio/visual search elements (e.g., AND, OR, NOT). In one embodiment, the signatures/features of the selected entities are determined for search in a database or index based on similar features. In one embodiment, the search features are used to locate the objects in live feeds prior to indexing the features of the live feed. In one embodiment, the search query includes descriptive test of the objects/persons. For example, in one embodiment, a search query is constructed by selecting a person and a bag or brief case from one or more video frames. In one embodiment, multiple objects are selected from image/video frames to indicate that they represent the same object/person/face (e.g., taken at different poses or at different occlusions). In one embodiment, the features representing the object/person/face are combined or enhanced based on the reliability of the features from different sources.

Extending the Feature Space Clusters to Encyclopedia Samples

In one embodiment, a learning machine/module is trained to determine features of a class or species of objects, e.g., in via a non-supervised training. In one embodiment, the features are correlated with a set of descriptive features or principle components through a supervised training or using a correlation module. In one embodiment, clusters of sub-species are identified in the feature space, e.g., via SVM. In one embodiment, the range or extent of clusters are estimated in the feature space for the identified clusters. In one embodiment, encyclopedia samples (e.g., few images for a given sub-species) are used to determine the representative features (points or region) in the feature space. In one embodiment, the extent or ranges of other sub-species are used as the basis to estimate or make initial assumption as to the extent of the cluster for represented by few samples in the feature space for an encyclopedia sub-species. In one embodiment, a search based on an image of an object in the class uses the trained learning machine to determine the features of the object from the searched image. In one embodiment, the featured so determined are associated with one or more clusters, including those based on encyclopedia samples, to determine candidate subspecies close to the searched image. In one embodiment, candidate subspecies are determined based on the extent of the corresponding clusters and the point/region in feature space represented by searched object.

Applications

The teachings here have applications e.g. for fashion e.g. clothing search (and supplier web address or store search, with price comparison), security, language translation e.g. for travel industry, application of "Who is at my door?", using camera, to search for dangerous people in a database, and application of "What is this object?", using camera, to search for an object captured by camera, in a database or on Internet or in a network, for search based on image, text, OCR, and sound, or other input, as explained here.

Other Embodiments

There is a great wealth of information in image and video content, which cannot be obtained from text data. People and machines generate ever increasing volume of images and videos, e.g., using mobile devices with cameras. Search for an object by text alone is inadequate. Current image search engines deliver incomplete knowledge, with unreliable or irrelevant results. By analyzing/recognizing images, highly targeted and more relevant ads may be supplied to the users. In one embodiment, a search engine platform for image and/or video is used, e.g., for recognition of objects and/or humans, with high reliability, relevance, and speed. One embodiment results in high rate of click through and/or conversion for display ads relevant to the displayed items on webpages. Appendix 4 (slides including photographic images) depicts various embodiments of the invention.

A problem scenario (as for example depicted in Fig. B1 of Appendix 4): A user sees an item, e.g., in a store or at a party or on a website, and wants to have it. The item may be hard to describe by words beyond few generic terms. In typical search engines (by words) the desired item may be lost within the vast amount of returned search results (due to generic terms which are typically used out of context from just about anywhere within a reference document) or totally absent from the search result despite the user's additional search terms (because the original item may not have been described (by words) with all those search terms in the first place). The problem for the user includes getting mixed images and items from various merchants with no time to sort through the results (even if the desired item is there), and not being taken to the targeted (desired) product item (webpage). In addition, the result set typically includes items that may or may not have all the characteristics described by those search words (but only some of them). Merchants also have a problem in determining the desired item based on image taken by the user or identified by the user, especially when words/label description are often not detailed or sufficient or do not match the search words. In case of advertising in a publisher's webpage, the merchant or advertiser is limited to an inefficient method of advertising, because they do not have an automated mechanism to match the images on the webpage to similar products in their catalogs, and as the result the user is not led to the desired product even if the user click or selects the ad. This leads to an inefficient advertising which fails to lead the user to the desired product and potentially miss a sale opportunity.

One embodiment converts such a disconnect to a sales opportunity, via a deep image analysis, search, and recommendation (as for example depicted in Fig. B2 of Appendix 4). For example, in e-commerce, using an image search engine for clothing and accessories (e.g., for coat, dress, jacket, pants, short, skirt, suit, sweater, shirt, blouse, wedding dress, swimsuit, socks, tie, shoe, handbag, hat, glasses, watch, brooch, necklace, bracelet, ring, scarf, pin, and earring), the user's desired object is located. One embodiment enables highly targeted ads based on the merchants catalog items and the images from publishers' webpage that are shown to users. One embodiment enables a one-stop shop, as a front for retailers and as a major entry point to e-commerce. One embodiment searches and matches merchant catalog items (or other indexed images/objects) based on the images from the user, e.g., from photo album, camera, email, or the Internet. In one embodiment, the items searched for are hard to describe by words. In one embodiment, the user (e.g., browser) is taken to the catalog item webpage, saving the user time and trouble of sorting through thousands of irrelevant items. In one embodiment, the exact, similar and matching items are shown/provided to the user, based on color, pattern, or style identified/recognized in the image. In one embodiment, complementary items (e.g., in an outfit), e.g., by pattern, style, size, material, model, brand, price, and merchant, are shown/provided to the user, in a computing device such as a mobile device, laptop, or desktop.

Figs. B3 and B4 of Appendix 4 depict examples of ways to connect the user to the item/product through "See & Shop" (or S&S) platform (referring to a platform for matching the images selected/provided by user or appearing on a publisher's webpage with images in other repositories such as merchants' catalogs, through methods including image recognition). In one embodiment, the images in publishers' webpages (e.g., in fashion websites) are automatically matched to the items in merchants' catalogs. Such a match is of great value to both merchants/advertisers and publishers, as the ads based on such a match are highly relevant to the consumer's interest and immediately present while the user is viewing the webpage.

Image Analyzer and Search Platform

In one embodiment, as for example depicted in FIG. 237, the images or catalog items from a repository (e.g., a third party catalog) or a service (e.g., accessed via API through for example Web Service, SOAP, lightweight REST, HTTP) are obtained, for example by an automated crawler or an iterative procedure, and the items are cached. In one embodiment, the catalog items are obtained through extraction from the corresponding web pages. In one embodiment, rules/templates associated with a catalog or a portion of catalog are used to control or guide the extraction or used for validation of the data extracted. In one embodiment, the rules are implemented in an interface module used for extraction of the data from webpages or catalog. In one embodiment, the rules include the hierarchy of the catalog items and the hierarchy of the presentation of the catalog items provided. In one embodiment, in addition to image(s) of the catalog item, its corresponding webpage URL (e.g., used as the user landing page for referral or ad) and/or other descriptions are extracted and cached.

In one embodiment, a catalog analyzer module manages the analysis of catalog items by taking a catalog item from the cache (or from the original service or repository) and uses the image(s) to determine the features of the object(s) contained therein, via an image analyzer engine. In one embodiment, the image analyzer engine uses other descriptive information to apply rules and parameters (for example in fashion). For example, in one embodiment, if the description indicates that the item is a dress, the rules will indicate to use the dress recognition engine (as opposed to shoe recognition engine), or the rules will indicate to use dress locator engine, or apply higher weight to dress recognition, or resolve ambiguity to its favor.

In one embodiment, the image analyzer engine identifies a set of features for the image analyzed, e.g., via a variety of methods such as SIFT, CPA, neural networks, and/or hierarchical approach to object recognition. In one embodiment, the features are stored in a repository and indexed for fast lookup based on the features and associated description (e.g., a distilled description), URL of the image, and merchant related information.

In one embodiment, the catalog items are queried or crawled to update changes to the catalog. In one embodiment, the catalog items and/or their changes are received via a feed via push or pull or against the repository or service.

In one embodiment, as for example depicted in FIG. 238, a user's computing device sends or uploads an image to a server (e.g., a merchant server or website). In one embodiment, the user captures the image via built-in camera on the computing device (e.g., a mobile device) or from an album repository on the device. In one embodiment, the user via the computing device provides a URI for the image (e.g., residing in a cloud or network) to the server and the image is uploaded to the server based on the URI. In one embodiment, the image includes meta tags (e.g., GPS information, time/date, camera information, and/or annotations) or such information is uploaded/pulled/pushed separately to the server. In one embodiment, the server transmits the image (and/or meta data) to an analyzer and search platform (server) to determine the features of the image and find a match to the image based on those features (and/or the meta data and/or other criteria) with catalog items in the same or other merchants' catalogs. In one embodiment, the platform indicates the image query to a tracker module which stores the information about the query in a query database, based on rules associated with the query (e.g., accounting for querying the same image). In one embodiment, the query tracking is used as a basis to account for or monitor the service provided to the merchant, e.g., for billing purposes or satisfying a subscription agreement. In one embodiment, the provided images and/or metadata are stored/cached in an image/metadata database/file system (e.g., a distributed file system based on Hadoop and map/reduce). In one embodiment, the image is analyzed by an image analyzer engine to determine the features of the object(s) contained in the image. In one embodiment, the identified features are stored and indexed in a repository based on the features and/or other associated metadata. In one embodiment, a search module uses the features determined from the image to search for similar or exact features of other images/items in a feature/description repository to find one or more matches for the image. In one embodiment, the search is accelerated via indexing the features of previously analyzed images. In one embodiment, the indexing uses fuzzy values and intervals. In one embodiment, the search provides one or more potential matching results to a match maker module. In one embodiment, the feature values (fuzzy, crisp, labels) are also provided for coded features (i.e., the features that are descriptive). In one embodiment, the similarity factor for overall and for individual features are determined and provided. In one embodiment, the matches are determined from the items in the merchant's catalog, e.g., by filtering the search using the items associated with the merchant. In one embodiment, a merchant selector module uses the identity of the merchant and/or other factors to filter the results or search. An example of such factor may be the context or type of objects being analyzed.

In an embodiment, as for example depicted in Fig. B19 of Appendix 4, the user uses the camera on a mobile device to take a photo of an item via the merchant's mobile application (or other applications). The mobile application sends the image to the image analyzer and search platform (for example directly through API, or via the merchant's server) for determining the features on the object on the image. The platform analyzes the image, determines the features, and searches the features against the features/description of the catalog items of the merchant (e.g., previously analyzed and stored in a repository/database). In one embodiment, the match maker module uses the potential matches and/or coded features and provides matched items based on the similarity factors and context (e.g., from merchant) to the platform server to provide to the merchant server or the mobile device. In one embodiment, the matched catalog item(s) is shown to the user with the corresponding catalog item information such as model, price/discount, options (colors), and sizes. In one embodiment, the user has the option to select the item (for example by placing the item in electronic basket) for purchase. In one embodiment, the other matches are also shown to the user as similar results to give the user an option to select from those matches. In one embodiment, the user is shown the items in the catalog that are similar to the search result. In one embodiment, the user information is also received from the merchant and stored in a repository. In one embodiment, the automatic and reliable search from the image lets the user get to the relevant item in the merchant's catalog. This may increase the competitive sales conversion for the merchant as the merchant would be able to convert a potential sale from a competitor (e.g., displaying the item on a shelf). In one embodiment, the image recognition and search serve is provided to the merchant based on per query or subscription or platform license or as a percentage of the sale or based on the search result and volume/accuracy levels (e.g., above a certain similarity level or reliability threshold).

In one embodiment, a search/analysis platform provides a service to a merchant without interfering with the look & feel of the merchant's application to the user. In one embodiment, the platform closes the critical disconnect between the user's intention to buy an item depicted in an image or seen in a store and the merchant's ability to reliably provide to the user the highly relevant item from its catalog. In one embodiment, the reliable and accurate image recognition and search provides specific and relevant search results to what the user is searching for. This in turn yields high click rate and conversion rate for the merchant. It also creates an opportunity for competitive conversion, i.e., for the merchant to convert a sale that would have otherwise gone to a competitor having the item on display.

See & Shop Mobile App

In one embodiment, as for example depicted in Fig. B18 of Appendix 4, the user uses a (e.g., mobile) computing device to take a picture (or video) of an item (or select a video or picture from album). The mobile application sends the image or video to the search and analysis platform to determine the features of the object in the image and search for one or more catalog items (e.g., from analyzed merchant catalogs), in order to display matched catalog items from one or more merchant to the user. In one embodiment, when the user clicks on the item, the user is taken to the corresponding merchant's webpage for the item. In one embodiment, where the user uses the search/shopping application with the intent and attention on buying, there is a high click rate (on displayed merchants' items) and purchase of the item (conversion rate) from the merchants. In one embodiment, the number of clicks is monitored/tracked by invoking a tracking module/service, to be used as a basis for payment per click by merchants. In one embodiment, a reliable and accurate image recognition and search provides highly relevant search results which the user is after. This, in turn, yields high click rate and conversion rate for the merchant. Therefore, in one embodiment, the application offers a highly fruitful source of revenue for on-line merchants by presenting to the user highly relevant items from merchants' catalog, in response to the user's query intended to purchase such specific items.

In one embodiment, as for example depicted in FIG. 239, a mobile application on a mobile device sends an image (or video) to an application server. In one embodiment, the image includes other metadata such as GPS and/or date/time. In one embodiment, the user logs in and is provided an interface to manage the user's profile and preferences. In one embodiment, the user may choose to save or delete the image on a repository. In one embodiment, the image is analyzed to extract features of the object(s) contained by an image analyzer module. In one embodiment, a search module uses the features identified (and/or other associated meta data with the image and/or the features) to search and determine similar matches to the (catalog) items based on the features and/or metadata associated with those items. In one embodiment, potential matches and/or coded features are determined (e.g., based on similarity threshold on the object and/or or one or more features of the object). In one embodiment, a prioritizer module provides one or more factors or rules to select or rank merchants and catalog items. In one embodiment, a match maker module selects the matches based on priority, relevance (e.g., similarity of the features and reliability of the match), meta data from the image and items, context from the user (e.g., a set of priority features extracted from a user interface where the user specifies the features the user places higher emphasis for match). In one embodiment, the feature search module uses the user's priority features to select the potential matches, e.g., by assigning different ranges of tolerances for various features to be matches.

In one embodiment, the matched items are transmitted to the user's device (e.g., mobile application or browser), and the user selects one or more items. In one embodiment, through a user interface, the user selects item(s) to be added to a user's wish list, and the items are stored in a repository managed by the user via a user interface through an application server. In one embodiment, the user selects (e.g., by clicking) the item and the mobile application displays the landing webpage of the associated merchant's website for the user on the user's computing device. The user's selection of the item is indicated to a tracker module which records the click/selections in a repository for accounting and reporting, based on a set of rules for determining whether to count a click.

See & Shop Anywhere (Plug-in)

Fig. B5 of Appendix 4 depicts an embodiment where the browser includes or has a plug-in (or bookmarklet or a code/script) at executes on the browser and/or the user's computing device. Such plug-in identifies images on the webpage (of the publisher). For example, a script is executed that iterate through the document object model or the window object to identify elements associated with images, e.g., based on tags, IDs, and/or source's URL (e.g., ending with .jpg or .bmp). In one embodiment, the images are filtered based on criteria such as size of the image (e.g., minimum size). In one embodiment, the script determines whether to identify the images based on the domain name (e.g., as positive filter to include or negative filter to exclude).

In one embodiment, with a See & Shop browser plug-in (extension), the user has See & Shop capability at his/her fingertip just about anywhere the user browses the Internet, with no need for any special code on the website being viewed.

In one embodiment, the textual descriptions provided with the image on a typical webpage may be inadequate or irrelevant to describe the image on the webpage (e.g., in fashion). One embodiment bridges the disconnect between the user's intention to buy/get an item depicted in an image and the merchant's ability to reliably provide to the user relevant item from its catalog.

In one embodiment, the user invokes the See & Shop plug-in (e.g., by clicking on a button or toolbar) while viewing the webpage with the image (as for example depicted in Fig. B5 of Appendix 4). In one embodiment, a script analyzes the document object model to determine images contained (e.g., by iterative or recursive walk thru or query against the object model). In one embodiment, the script communicates the image or an image identifier(s) (e.g., URL) to a See & Shop server (e.g., by POST or GET method, or by calling an API). In one embodiment, XML and/or JavaScript Object Notation (JSON) is used to communicate data. In one embodiment, JSON with padding (JSONP) is used to communicate data (e.g., via a function container), e.g., via script element injection into DOM.

In one embodiment, an automatic analysis, search and recommendation platform provides specific and relevant search results from merchants' catalogs. This yields high click rate and conversion rate for the merchant. In one embodiment, a competitive advantage to the merchants results by providing relevant items to the user when the user decides to shop for an item in an ad hoc manner, while conventional ads on the same webpage conversion would miss the opportunity. Therefore, such an application offers a highly fruitful source of revenue for on-line merchants by presenting to the user highly relevant items from merchants' catalog, in response to the user's ad hoc query intended to shop for such specific items.

In one embodiment, as for example depicted in FIG. 244, a crawler module receives images and/or content from a publisher's website (e.g., via automated exploring the links or via a template/rule set) or the publisher's content management system (e.g., via API or feed). In one embodiment, the crawled webpages and/or images are cached (including the corresponding websites, webpages, and URIs or other unique identifiers) in a database or storage. In one embodiment, the scheduler module sets up the cached images for analysis, for example by placing a status tag in a database indicating when or the order to run the analysis for an image or indicating whether an image should be analyzed during the next batch process or indicating the image should have a priority process. In one embodiment, the rules for scheduling the analysis are stored in a rules database and/or implemented in a rules engine or code/script. In one embodiment, the scheduling module or one or more of its elements run as background process or as service. In one embodiment, the scheduler initiates an image analysis run by instantiating or triggering an instance of the process. In one embodiment, a scheduler module initiates a crawl task for a website or one or more webpages. In one embodiment, the application server requests/triggers an image analysis directly or via a scheduler module. In one embodiment, the image and/or URL of image is received by the application server from the publisher's website and/or the browser (e.g., via the plug-in or scripts downloaded from the publisher's website and/or a web server). In one embodiment, the application server stores the image and URL (and other meta data) in a storage or database (e.g., indexed). In one embodiment, the application server determines if an image received already exists in its database, based on its URI. In one embodiment, an image is provided by the application server or from the database, and analyzed by the image analyzer engine to identify the features of the object(s) contained in the image. In one embodiment, if the image already exists in the database, the application server uses that image instead of downloading it from the publisher's website. In one embodiment, the image analyzer receives the image from a database or from an application server. In one embodiment, an application server modifies the priority or order of the image analysis for an image scheduled to be analyzed, e.g., when a plug-in or the browser forward the image or its URI to an application server. In one embodiment, the identified features by the image analyzer engine is indexed based on the features and/or other meta data (or description including the image URI) and stored in a repository or database.

In one embodiment, as depicted for example in FIG. 240, the plug-in sends the URL(s) of image(s) from a publisher's webpage loaded in a user's browser. In one embodiment, the user selects which image(s) should be used, via a user interface through the plug-in or scripts. In one embodiment, an application server receives the image from the publisher's website based on the image URL. In one embodiment, the application server determines if the image is already in the database/repository based on its URI. In one embodiment, the image and/or its meta data (including description corresponding to the image) and/or URI are stored/cached in a database or repository (with index for fast lookup and query), for example via the application server or a crawler module. In one embodiment, a feature finder module determines the feature of the image. In one embodiment, the feature finder module queries a database and/or repository to determine if the image is in the database or repository. In one embodiment, a query is made to the repository or database for indexed features/description which contains previously analyzed features and/or description. In one embodiment, such query is made even if the actual image does not reside in a database or repository. In one embodiment, the query to retrieve feature/description uses the image meta data or URI or an identifier (e.g., a primary key) as selection filter for the query. In one embodiment, the identified features are used (e.g., by feature finder module) to search for other items (e.g., catalog items) matching the features (e.g., by a feature search module). In one embodiment, the image is analyzed by an image analyzer module to determine its features, and the features/meta data/descriptions/URI are indexed (by an indexer) and stored in a database or repository. In one embodiment, a feature search module provides potential matches and/or descriptive features and/or the degrees of similarity or reliability of the match to a mach maker module. In one embodiment, the mach maker module uses the catalog items to provide matched items, e.g., based on priority or ranking factors related to the merchants (such as the pay per click or pay per action amounts, inventory status, and/or inventory replenishing/restocking rate). In one embodiment, the application server provides the matched items to the browser for display to the user. In one embodiment, the user makes one or more selections on the items. In one embodiment, the user selection(s) is provided to the application server (e.g., by the browser and/or plug-in/ scripts). In one embodiment, the application server uses a tracker module to track the click events (or selection) made by the user on the item (corresponding to a merchant) in a click database or repository for purpose of accounting or reporting, based on click rules from a rules database or rules engine. In one embodiment, the application server provides landing page URLs corresponding to the matched items along with the matched items and/or in response to the user's selection. In one embodiment, the browser goes to the merchant's catalog item webpage directly via the landing page URI or indirectly via a temporary landing page used for measuring traffic/actions and/or shortening URLs and/or obfuscation to circumvent the attempts to bypass the process.

See & Shop Enabled Webpage

In one embodiment, as for example depicted in Figs. B7, B8, and B9 of Appendix 4, a publisher's webpage is includes (i.e., enabled by) scripts or code corresponding to See & Shop platform. For example, the code/script when executed or rendered in a user's browser provides the user with a visual feedback (e.g., a button or an icon on the display or over an image on the webpage to indicate to the user the presence of the service (even without having plug-in/extension installed on the browser). In one embodiment, when a user selects an image or hover the mouse or selector over the image, a visual feedback provides the user with the area on the image, based on the analysis of the features of an object (e.g., a top or blouse bounding or grounding rectangles). In one embodiment, the item(s) matched to the object in the image is displayed to the user in an overlay or in a hovering pane or window, e.g., with a rolling display of selectable options for the user. In one embodiment, the browser goes to the merchant's catalog item webpage (landing page) upon selection the corresponding option to choose. In one embodiment, the browser goes to a temporary forwarding landing page before getting forwarded/directed to the merchant's landing webpage, e.g., for the purpose of accounting/reporting traffic.

In one embodiment, as for example depicted in FIG. 241, the content provider/publisher's website directs or provides the user's browsers with scripts corresponding to See & Shop platform. In one embodiment, the scripts/code analyze the webpage (or rendered document object model) to determine images on the webpage, e.g., belonging to the same nodal hierarchy as elements (e.g., HTML elements) having a particular ID or class. In this way, the webpage images may be marked with elements that are used as nodes/anchors to determine images automatically without modification to the code for the image. In one embodiment, the image code is provided with an ID or class, marking the image for analysis and/or referral and/or ad display. In one embodiment, the script/code provide the application server with the URLs and/or IDs associated with the images on the webpage or corresponding images to the reference nodes in the tree hierarchy. In one embodiment, the images are retrieved from the publisher's website by the application server based on the URI or other identifiers. In one embodiment, a crawler or a process retrieves images and/or meta data and/or other descriptions from the publisher's website and/or its content management service, e.g., to cache and analyze by image analyzer engine to extract features corresponding to those images. In one embodiment, the application server provides matched items to the browser for display and selection by the user, e.g., at a hovering pane or IFrame. In one embodiment, the retrieved data (e.g., the bounding or grounding boxes for objects in the image) is used by the scripts to provide an interactive user interface overlaid on the image on the webpage, by for example dynamically adding new visual elements of controlling visual elements on the webpage, e.g., via jQuery and AJAX. In one embodiment, data is transmitted between the browser and the application server using XML, JSON and/or JASONP.

See & Shop Anywhere Website

In one embodiment, as for example depicted in Figs. B5 and B6 of Appendix 4, a website/interface/portal is provided for users to provide user management interface, e.g., registration and sing-in. In one embodiment, the browser is forwarded to the website via the plug-in and/or the corresponding scripts/code from a publisher's website. In one embodiment, the user uploads images (and/or annotations) of his/her wardrobe via the website and the platform provides suggestions for matches with other items based on analyzed outfits from collection of outfit images (e.g., from popular fashion sites) as well as the complementary matching items from merchants' catalogs. In one embodiment, the analysis and search platform analyzes an outfit and determines the objects in the outfit and makes a relationship between the features of the objects (or the objects) corresponding to the outfit. In one embodiment, such stored/indexed relationship is used to make recommendation for complementary items for an object in an image (e.g., from wardrobe or taken by a camera or from a webpage). In one embodiment, for an object identified in an image, matched items from merchant catalogs are provided to the user (e.g., for blouse or skirt) along with meta data including price, label, reviews, and merchant and description.

In one embodiment, the user uploads an image via website from a local or mobile device or via a URL, for search within the merchants' catalog or other repositories/caches. In one embodiment, the user is provided a wish list to store items of interest in a database or repository, e.g., from the uploaded or referenced image or from a catalog item. In one embodiment, a background process searches and finds matches to the items in the user's wish list. In one embodiment, a process orders the matches based on the user preference, e.g., price, brand, and particular rules based on features of the object.

In one embodiment, the image search uses multiple query images. In one embodiment, the query images are analyzed to ascertain the features. In one embodiment, the common or clustered features of the queried images are used as the basis/filter for search. In one embodiment, the user indicated the particular feature the user is seeking from a particular query image. In one embodiment, the search is cone based on the collection of the particular features specified from various query images (e.g., a strap similar to shoe No. 1, a heel similar to shoe No. 2, a texture similar to shoe No. 3). In one embodiment, the user is provided an interface to select the parts/features from a query image. In one embodiment, the user is provided with an interface summarizing the coded/descriptive features of an object with value of each feature provided as discrete, (semi) continuous, or fuzzy (label or range), e.g., based on the image analysis of the object and/or meta data and/or description and/or annotations and/or (cluster class label). In one embodiment, the user is provided with an interface to modify the features or parameters, e.g., via a fuzzy slider or ruler Fuzzy ruler or via a graphical interface that uses mouse or touch to change the parameters graphically on a graphical model (with anchor points to drag on a path), e.g., to make the sleeve shorter or longer. In one embodiment, the graphical model is posed/chosen/rendered to mimic/approximate the pose of the object in the image. In one embodiment, the user's refined/redesigned parameters/features are used to search for matched images/items in merchant catalog or other repositories. In one embodiment, the search is performed iteratively as the user modifies the feature/parameter value. In one embodiment, the user is provided with search results/items as the user modifies the parameters/features. In one embodiment, the user is provided with an interface to eliminate a feature or add a feature from a list of features based on the context of the object.

In one embodiment, the user is provided with an option to shop with a friend. The user is provided with an interface to put comments or add images (e.g., matches) on a blog or an item from a friend's wish list. In one embodiment, the user gets a point or incentive to find a match between an object in an image and a merchant's item, via an interface provided from the platform. In one embodiment, the user may share points with friends. In one embodiment, the user specifies his/her styles, by for example uploading outfit images or by categories. In one embodiment, the user is provided results of search based on his/her preferences or styles. In one embodiment, the user is provided an interface to make or give suggestions via a social network to friends/circles/members. In one embodiment, the suggestions are displayed to user(s) with an ad based on merchants' catalog items that match the features of the image referred to or referred in the suggestion.

Intelligent Matching

In one embodiment, as for example depicted in Fig. B10 of Appendix 4 or FIG. 248, an image from a webpage (or another source) is analyzed and features of the object(s) contained in the image are determined via an image analysis engine or manually (e.g., by crowd sourcing). In one embodiment, an image (or multiple images at different poses) from a merchant's catalog item is analyzed and the features of the object(s) contained in that image are determined via an image analysis engine or manually (e.g., by crowd sourcing). In one embodiment, an intelligent matching module (or via a crowd source), a match is determined between the images, e.g., from the publisher's webpage and the merchant's catalog item, e.g., based on the features determined, meta data, and/or description. In one embodiment, the level of match (e.g., reliability or accuracy) is determined based on the closeness of the features and the context of the match (e.g., matching the clothing, shoes, faces, background, characteristics of the people in the image if any). In one embodiment, the match associates the image (and its URI), its corresponding element/node/frame/hierarchy on the webpage, the webpage URI, the domain/website, and/or the publisher identification to the item catalog identifier, merchant's identifier, image (or images) matched with and the corresponding URI(s), the description of the item, and/or the webpage for the catalog item (landing page).

In one embodiment, See & Shop platform automatically matches the images in publishers' webpages (e.g., in fashion websites) to the items in merchants' catalogs. This match is of great value to both merchants/advertisers and publishers:

Merchants/advertisers would be willing to bid/pay higher CPM (cost per impression) when they know that the click though rate and conversion rate on their ads will be higher and overall will reduce their cost. In addition, merchants are also willing to pay higher CPC (cost per click) because the landing page will point to the very item that the consumer is looking for, based on the interested image on the publisher's website.

Publishers are willing to receive less CPC (cost per click) for ads that are highly relevant to the consumer's interest, because the higher click rate for the relevant ads overall increases the revenue for the publisher for those ads. In addition, the publishers are willing to demand less CPM (cost per impression) because the relevant ads to their content of their webpages will appear as less of the distraction to the users of the website and more of a convenient service for them to purchase.

See & Shop can capitalize on these market positions for ad and create or form a basis for a targeted ad exchange based on image matching.

In one embodiment, See & Shop platform provides a subscription or transaction based service to merchants/advertisers, publishers, and/or ad exchanges to evaluate the number of or quality of matches (e.g., in form of a summary report) or the actual matches. In one embodiment, an interface is provided for merchants to compare two different items to the number of matches meeting a quality threshold to publishers' webpages. One embodiment integrates the user traffic data to those website to provide/estimate/predict/ compare the advertisers/merchants' relative potential revenue from those items. In one embodiment, an interface is provided to predict/estimate relative potential ad revenue for publishers from different images placed in the content of their webpages, by determining the number and quality of the matches with merchant's items. In one embodiment, merchants/advertisers and/or publishers query the platform to obtain such estimates, based on subscription or transactional basis. In one embodiment, the predictive module uses the heuristics, historical data on revenue generation, click rates, relevance, sites traffic, context to determine the user's behavior, e.g., click rate and conversion rate on a particular ad, e.g., based on similar ads/categories appearing on similar websites from similar merchants at similar price ranges.

Matching information, in one embodiment, is the basis for a new marketplace for targeted and highly relevant ads based on the match between the webpage images and items in merchants' catalogs. In contrast to irrelevant and ignorable ads, the high relevancy of the matched ads turns the user's interest on the webpage/image into intent to shop.

Crowd-Based Matching

In one embodiment, as for example depicted in Figs. B11 and B12 of Appendix 4 or FIGS. 249 and 250, a crowd source is used to find matches between images from publishers' websites and merchants' catalog items. In one embodiment, an application and/or a browser plug-in provided to a user to identify or select images from various (e.g., publishers') websites/webpages. In one embodiment, the user activates the plug-in, e.g., by clicking on a toolbar for the plug-in. The script/code associated with the plug-in processes the user's action (e.g., mouse click or touch) as an event within a document object model or window to determine an image selected by the user (based on the position of the event). In one embodiment, the script/code determines the source/URI of the image, associated meta data or description (based on for example predetermined or learned template associated with the webpage), the webpage URI, the domain, the publisher (e.g., based on matching the domain to a publisher in a database, or entry by the user), and/or the hierarchical node where the image appears on the webpage. In one embodiment, a plug-in or an application is used to similarly let a user pickup/identify images and webpages corresponding to an on-line catalog item from a merchant. In one embodiment, the user specifies a match between the images from the publisher's webpage and the merchant's catalog item via an interface for entering the match, e.g., by giving the user the ability to run through, search and filter the picked up records based on meta data, description and/or features obtained from automatic image recognition. In one embodiment, an automatic process chooses the images from catalogs and publishers and present to the user to determine the potential matches, the degree of match, the degree of match for various features, and/or annotations by the user. In one embodiment, the match determined by a user is automatically presented to another user via a user interface, along with other images/options to verify the match (e.g., via consensus). In one embodiment, a record of consensus and rejections are monitored per user to determine the effectiveness of the user's matching capabilities or monitor the user's improvement over time. In one embodiment, when a user makes a match between an image (e.g., in a publisher's website) and another (e.g., in a merchant's catalog), the user is automatically provided similar items from the same or different merchant(s) to the user to indicate the degree of similarity between the matches or relative degree of similarity between the matches for overall and per various features presented. In one embodiment, more matches are created and stored based on the user's input for such options. In one embodiment, the user matches of input are used to train one or more components of an image recognition engine, e.g., in an iterative (stochastic) mode or batch mode.

In one embodiment, the result of automatic match and crowd source are reconciled together along with their respective reliability factors. As the reliability of the automatic match increases, in one embodiment, the volume of matches are increased. In one embodiment, the matches are provided to an image-based ad/referral engine, e.g., for service to an ad or referral network.

Extended Matching

In one embodiment, a match (e.g., provided by a user or automatically by a feature matching search engine) is extended to other matches, by comparing an image signature (e.g., block hash/signature) and searching for other images with the same or very similar signature (i.e., finding the instances of the same image or a cropped portion or a scaled version or somewhat) for example in an index repository or database. In one embodiment, the catalog items and webpages (e.g., of publishers) are crawled or gathered and a hash signature from the images associated with them are stored in an index database or repository based on the hash signature, the URI of the page and/or image. In one embodiment, a match (whether generated automatically or via crowd source) is extended to other matches by comparing the signature of the images associated with the match and searching for other such images in the repository/database have the same or similar signature indicating that the images are of the same content. In one embodiment, new matches are expanded based on other combinations between the images with the same or similar signature. For example, when the same image (with the same signature) appears on another publisher's website or webpage, the match is extended or a new match created for that image/webpage/website/publisher. Also, when a catalog item from a manufacturer or a brand in a merchant website uses the same image (e.g., provided from the brand/manufacturer) as another merchant for the same item, then a match involving such a catalog item is extended and or created for the other catalog item. In one embodiment, matches are extended based on images appearing in social/bookmarking networks. In one embodiment, a user or an automated process determines a match between an image appearing in a social/bookmarking network (e.g., Pinterest fashion). In one embodiment, the web link URI (from where the image was extracted/pinned) and/or meta data (e.g., associated description and/or number of associated pins) are queried or extracted via a process (e.g., by crawling, using template or a macro, script/plug-in, or an API) from the social network interface. In one embodiment, a process identifies the image on the referenced webpage (e.g., at a publisher's website) based on, for example, signature block, URI, or description/meta data. In one embodiment, the referenced image may also have links/bookmarks/pins in the same or other social/bookmarking network. In one embodiment, a process determines the additional links to social/bookmarking network to identify instances of the image in (referenced/pinned), e.g., recursively using a crawler and repeating the process. The found instances are used to extend the matches.

Match Extension Via Image Hash/Signature

In one embodiment, the matches are extended by querying an image signature from a repository (e.g., indexed) of image signatures associated with images/URIs. In one embodiment, a search engine, e.g., a search-by-image module, is used to obtain one or more instances of the same (or portion of or scaled or with slightly intensity/color modified) image with, for example, their associated URIs/meta data/description/webpages/websites. In one embodiment, as for example depicted in FIG. 247, a process crawls/scans a webpage (and images). In one embodiment, a process creates a set of hash/signature keys for an image. In one embodiment, the image hash/signature(s), URI, hash/signature ID, meta data, and/or description are stored in a (e.g., indexed) database or repository. In one embodiment, a service provides a search by image (hash/signature), e.g., by determining the signature/hash for the queried image (e.g., uploaded or retrieved by a link) and searching the signature/hash in an indexed database, or looking up the image (or it hash/signature) in a database (indexed) based on a URI. In one embodiment, the service or an extracting process provides the signature ID or hash ID (unique or primary/composite key) based on the query. In one embodiment, the hash/signature ID (or a code/script related thereto) is associated (e.g., in a database) with one or more matches that are associated with the image corresponding to the hash/signature ID. In one embodiment, an ad finder module determines/constructs a (relevant matching) ad with a merchant's catalog item/image to appear in the ad when a user is viewing the webpage with the image, e.g., by resolving/selecting the matches (e.g., by IDs) based on association with hash/signature IDs associated with the (e.g., publisher's) image/webpage URI or identifier. In one embodiment, the ad network scripts for the webpage (e.g., executing on the client side or server side) invoke the lookup or the query to determine whether a image-based match (ad) is available for the image or webpage (e.g., based on the query whether a hash ID associated with the image also has any associated match ID in the database).

In one embodiment, the match reliability and/or context is stored in a database or repository. In one embodiment, an ad selection process uses the reliability of the match and/or the context in selecting among various ads.

Image-Based Ad for Tagged/Marked Images/Links in Social Network

In one embodiment, as for example depicted in FIG. 246, a user tags an image or webpage (e.g., via tagging buttons such as Facebook's "Like" or Pinterest's "Pin" or via script/plug-ins/bookmarklets) from a publisher's website. In one embodiment, the tagged image/video/link appears in the corresponding social network page. In one embodiment, the image/page in publisher's website is crawled/scanned and image(s) identified, e.g., by an automated process. Social buttons/bookmarking elements are identified for a given set of social network, e.g., by identifying the HTML tags within the webpage. In one embodiment, unique characteristics of the tags are determined, e.g., the publisher's ID and application ID, Type identification, URI of the image and/or the page. In one embodiment, the image is analyzed to determine the features of the object(s) within the image. In one embodiment, one or more features are used to search and match with merchants' catalog items (e.g., based on features, descriptions, and meta data). In on e embodiment, the social network/bookmarking identifier(s) is associated with the match and/or indexed for quick look up in a database or repository. In one embodiment, the social network platform manages/stores the tags (e.g., liked links, image URI, referenced webpage/website info) in a repository/database. In one embodiment, a social match finder module/process uses identifying attributes of the image/video/link (e.g., the image/page URI, publisher's ID) that associate these to the publisher's webpage/image, to query for one or more matches associated with the publisher's webpage/image. In one embodiment, an ad is selected and setup via an ad maker module for display via an ad script on the social network webpage on or at the vicinity of the displayed tagged image/video/link. In one embodiment, the ad scripts are associated with an application running on the social network platform. In one embodiment, the impressions of the ad and user click/selection of the ad are tracked automatically by executing a script or calling an API.

Block Signature

In one embodiment, a process makes a set of signature/hash from an image, for quick search and indexing. In one embodiment, various transformations and/or aggregate functions are used to generate signature from the pixel map of the image, e.g., DCT (discrete cosine transform) wavelet, averaging, contrast, variation measures, and/or intensity measures. In one embodiment, an image is reduced to a thumbnail to take a signature, e.g., by down sampling (fat pixels) or resolution reduction (e.g., spatial and/or color resolution). In one embodiment, an image is fuzzied or unsharpened, e.g., via convolution with for example a Gaussian. In one embodiment, a process uses edge detection (e.g., Canny, Canny-Deriche, Differential, Sobel, Prewitt, and Roberts cross), corner detection (e.g., Moravec corner detection, Harris operator, Shi and Tomasi, Forstner corner detector, Level curve curvature, Laplacian of Gaussian (LoG) feature detection, difference of Gaussians (DoG) feature detection, and determinant of the Hessian (DoH) feature detection, affine-adapted interest point operators, Wang and Brady corner detection, smallest univalue segment assimilating nucleus (SUSAN), Trajkovic and Hedley corner detector, accelerated segment test (AST) based feature detector, and features from accelerated segment test (FAST)), blob detection (e.g., LoG, DoG, DoH, maximally stable extremal regions (MSER), and principal curvature-based region detector (PCBR)), ridge detection, Hough transform, affine invariant feature detection, affine shape adaptation, Harris affine region detector, Hessian affine region detector, Scale-invariant feature transform (SIFT), speeded up robust features (SURF) detector, gradient location and orientation histogram (GLOH), histogram of oriented gradients (HOG), scale-space, and Pyramid. In one embodiment, an image is segmented to one or more (e.g., overlapping) regions, such as rectangle/blocks, and a signature/hash is obtained for each block. In one embodiment, the block follows a sliding window (up and/or down) with threshold. In one embodiment, hash/signatures are associated with context dependent weights. In one embodiment, the block size and number of blocks are dynamically chosen. In one embodiment, the block size is fixed or proportional to the image size. In one embodiment, the block size is determined based on the intensity and/or color/grayscale variation/histogram.

Incentive Based Crowd Matching and Point Trading Platform

In one embodiment, the user receives an incentive for providing one or more matches between a given image (e.g., an image from a publisher's webpage) and merchants' catalog items via a user interface. In one embodiment, the user receives an incentive, for example, the product for free or at a discount, e.g., based on the performance of the provided match to generate clicks from users/consumers and/or to generate sales (or action) for the item or for the merchant. In one embodiment, a payment from merchant to an ad network is made based on cost per click or pay per click (CPC or PPC) (e.g., specified as a bid for advertizing or referral) or cost per action (CPA) (e.g., commission specified in form of per action or per sales price). In one embodiment, as for example depicted in Figs. B13 and B14 of Appendix 4 or FIGS. 251 and 252, users provide matches to the platform via a user interface, and the scripts from the publisher web pages (and/or the scripts from See & Shop platform) and/or plug-in show the ads or referral marks (e.g., icons) to a consumer when viewing the publisher's webpage. In one embodiment, when the consumer selects the referral icon, ad, or otherwise selects an item displayed on the webpage (or overlaid on it), e.g., based on the ad or referral match based on image, the browser is forwarded or taken to a landing page on the merchant or advertiser's site, e.g., via the ad network (e.g., based on Shop & See platform). In one embodiment, a fraction of Pay-for-Click or commission amount from the advertiser for the services of the ad network/See & Shop platform is provided, for example, as point(s) to user, e.g., up to the value of the item. As more consumers click on the ads or make purchases at the merchant based on the referral or ads, the user earns more point corresponding to the match provided by the user. In one embodiment, users trade points using a point trading platform (or module). For example, the module is accessed via See & Shop website when the user logs-in. In one embodiment, other users can sign up and participate as well in trading points with currency. In one embodiment, a valuation module predicts the future value of a point for a match based on the heuristics from consumer's clicks and conversions. In one embodiment, users are provided an interface to estimate the time it takes for the points for a match to grow to full value. In one embodiment, a future (estimate) value of points is provided, e.g., via a user interface, based on heuristics, e.g., the click through rate and/or conversion rate, the type of publisher's website, the time webpage or content was created/updated and/or the number of days or clicks previously done on the ad since ad was in place on the webpage (and/or website and/or other websites).

In one embodiment, the point value corresponding to a match is modified based on trading between users, e.g., via a point trading platform where the users log-in to manage and trade the points. In one embodiment, other users may participate in the point trading who have not created a match, through a user interface viewing what points/matches are up for trading. In one embodiment, an interface is provided for users to hedge against or for future point value of a match. In one embodiment, a new point value is assigned to a match based on the point trading. In one embodiment, a user interface is provided for the users to assign the matches. In one embodiment, a user interface is provided for specifying a point threshold for a match, such that when the point value reaches (or exceeds) the threshold, a process allocates the excess point to another eligible match. In one embodiment, a minimum point threshold (e.g., a ratio) is used to specify the minimum points required before the points are eligible for trading on the match (e.g., points added via trading). In one embodiment, a maximum point (cumulative) value/ratio is used for a match to determine the eligible points allowed for trading from the match. For example, in one embodiment, for a maximum point on a match set at $(1+x) \cdot$(Full Point Value), the amount of point earned on the match allowed to be traded out is ($x \cdot$Full Point Value). In one embodiment, there is no restriction on the trading out the points that were previously traded in for a match.

In one embodiment, a user uses the full point of a match to purchase (e.g., for free) the item (associated with the match or an equivalent item) from the merchant through an e-commerce interface or via a coupon generated based on the points associated with the match. In one embodiment, the user uses a partial point on a match to purchase an item from the merchant at a discount. In one embodiment, upon usage of the points to purchase an item, the points are released back to the platform (i.e., out of the trading). In one embodiment, the user can opt for various coupon options having different point values, e.g., at 25%, 50%, 75% and 100%. In one embodiment, the user can use the point for purchase based on the coupon ratios available for the match and for the current point value. In one embodiment, a user can gift his/her points on a match to another user (i.e., one sided trade).

In one embodiment, the user is given different levels of points (e.g., compared to full value of the item) depending on the level of the task, such as finding the match, finding a number of matches for the same image, judging the match found by someone else, and selecting a match among the choices (e.g., automatically) presented to the user by a selection interface. In one embodiment, performing different tasks (e.g., judging a match suggested by someone else) is a prerequisite for a match made by the user to be eligible for earning point or eligible to earn point for the user (e.g., while being eligible to be gifted or to earn points for other uses).

In one embodiment, catalog items and/or publishers' webpages/images are gathered/fed and/or crawled and stored in a repository. In one embodiment, an interface is provided to the user (e.g., for a crowd source) to specify a match. In one embodiment, the user uses a plug-in/script or an application to pick/tag/mark an item (e.g., webpage, image, and/or description) on a publisher's website. In one embodiment, the user uses a plug-in/script to pick/tag/mark an item from a merchant's catalog. In one embodiment, a user is provided with an interface to associate merchant's catalog items with publisher's images/webpages, such as a graphical drag and drop interface for arranging the corresponding images side by side or in a hierarchy. In one embodiment, for example as the automated analysis engine is getting trained, the user is provided with suggestion from the automated search engine from the merchant catalog items (or other repositories) for the user to verify the match with a publisher's image or specify degree of match (e.g., based on various features of the object in the image). In one embodiment, a user interface is provided to a user to select matches or similar items from the merchant's catalog (or multiple merchants' catalogs), for example, by automatically selecting items and displaying them to the user for selection of similar objects or features and the degree of similarity or dissimilarity (e.g., graphically via a fuzzy slider/ruler or a selection of checkboxes/buttons associated with choices).

In one embodiment, the matches provided by the user are automatically compared for consensus of the result. In one embodiment, various combination of images are provided to the user to eliminate/reduce inconsistencies or verify the choices among the users, e.g., combining two or more images from one selection with other images and showing the new selection to the same or other users for further selection and input.

In one embodiment, an interface is provided to mark and select matches to be consolidated in earning points among the selected users (e.g., with verified consensus of the users), for example to allow the points to be automatically consolidated (for example for a charity or for benefit of a user or a third party).

Image-Based Ads for Video

In one embodiment, as for example depicted in FIG. 245, a video is analyzed (e.g., by scene/frame via a scene selector module) and the timing information (e.g., from video track) and object features and spatial information (e.g., via an image analyzer engine) are extracted. In one embodiment, the timing and spatial information are stored in a database or repository to be used for example in creating an object track (e.g., a fashion track) for the video. In one embodiment, the features/description extracted are stored in a feature database (e.g., indexed) to be used for example for matching with other item/images (e.g., merchants' catalogs). In one embodiment, a track generator module, assigns tags/IDs (e.g., reference or key identifiers (Ref. ID)) to a track (e.g., fashion track) by associating the timing information to the tags. In one embodiment, a spatial track (e.g., fashion track) is setup to carry the spatial information (e.g., the grounding box of the object or an outline of the object, for example per frame or per multiple frames, or an aggregate box covering the object in multiple frames) and the attributes such as the coordinates and types of the spatial indicator (outline, rectangle, ellipse/oval, region/blob/silhouette of the object). In one embodiment, the object (e.g., fashion) track (including its media information such as blob description) is added to the video, for example by creating a new video or by creating a link to the track stored separate from the video using a unique identifier/link for later retrieval.

In one embodiment, the video is distributed by various methods such as publishing on web, as part of TV/cable programming, or through a content distribution network. In one embodiment, a user views or playbacks the video (e.g., in TV, DVD, browser or a viewing application). In one embodiment, the user interactions are captured, e.g., via a TV/multi gadget remote control from the TV/cable box or from the service provider capturing the user's input, or via the playback application/browser. In one embodiment, the user selection/interaction is captured for example including the video identifier, selection in time and location, and/or the Ref. ID corresponding to the user's selection.

In one embodiment, analyze, search, and match maker modules provide and/or store the match between the features/descriptions of the objects in the video with images/items (e.g., from merchants' catalogs). In one embodiment, the matches (or the features) are associated with Ref. IDs to provide an association hook to the video (fashion/object) track for fast lookup when a user selects an item, e.g., during the video playback.

In one embodiment, upon the user's selection, one or more matched catalog items are shown to the user in an interactive display (e.g., on the same webpage, or at the corner overlaid section of the TV screen), for example based on selection of the items, for example, by an ad network or referral network, for example by using the bidding information from the merchant/advertisers/agencies and the Ref. ID extracted from the user's selection and querying the corresponding matches.

In one embodiment, the matched items are automatically displayed to the user (e.g., at the side/corner of the screen or overlaid on video playback) without the user first selecting an object on the fashion/object track. In one embodiment, the playback triggers the auto display of the ads/items/images based on the timing of Ref. IDs from the object track and the matches associated with those identifiers. In one embodiment, an indicator of available match is displayed to the user during the playback for the user to select (if interested), for example, based on the spatial coordinates and types associated with the object/fashion track. In one embodiment, the textual information extracted from the matches are encoded in a text track (similar to the closed caption) and displayed to the user during the playback, with its timing based on the object's timing from the object/fashion track.

In one embodiment, where the video is interrupted for ad display by the content/service provider, a set of processes render and display interactive ads based on images (e.g., cropped) from the video and merchants' catalog items that are matched to those images from the video, based on Ref. ID.

Image Ad/Referral Network

In one embodiment, as for example depicted in Figs. B11 or B15 of Appendix 4 or FIG. 249 or 253, an ad network/exchange based on matching images is used to display merchant's catalog items within content of ad next to an image on a webpage, twit, email, document, or other forms of content delivery. In one embodiment, the ad network chooses between the various merchants' catalog item for an ad, based on for example, merchant's bid on PPC related to a collection or a subset of its catalog items, merchant's bid in fix amount and/or based on item's sales price, relevance of context, reliability and degree of the similarity in match the match, user's preference or perceived preference to a feature or a type/class of object (for example, in a multi-object situation such as an outfit that may produce matches with various classes of items), relevance factors, merchant's score/traffic, merchant's in-stock status for a matched item, merchant's re-stocking rate for a merchandise, publisher's restriction/filters to exclude certain or certain types of merchants and merchant's restriction/filters to exclude certain or certain types of publishers. In one embodiment, for example, the ranking order is higher for more relevant match, more reliable match, more similar match, in-stock status, higher merchant's score, and/or higher merchant's bid or commission (based on impression, click through, or conversion—with heuristic rates used for normalizing the bid basis and weights associated with preference between such bases). In one embodiment, a ranking function is calculated based on for example, weighted dependency on such ranking factors with linear, quadratic, polynomial, or exponential, or reciprocal (e.g., inverse of powers of inverse) dependencies. In one embodiment, the weights and dependencies are modified by automated process (e.g., via optimization methods or genetic algorithms), for example, to optimize for maximum sustainable return.

In one embodiment, as for example depicted in FIG. 242, an ad network or a referral/commission network based on image is used to associate the publisher's image (on a webpage) to a merchant's catalog item. In one embodiment, one or more scripts or codes are downloaded to the user's browser or application (or executed on server) that are associated with See & Shop platform for ad/referral network. An ad server provides configured ads based on standard configurations (sizes, location, and appearance (color/font/fields), personalization for user, and personalization of message) or custom configuration provided for example by merchant/advertiser/agencies or publisher. An ad configuration repository is used for example with a user interface to specify or provide the configuration, e.g., in form of script/XML/HTML code/form.

In one embodiment, a tracker module tracks the number of impression of the ad and click through events based on click/impression rules in one or more databases, for example, for financial, reporting, or aggregation purposes. A financial module determines the amounts receivable from merchants and communicates the invoice for a period (e.g., daily, weekly, monthly) and/or based on a threshold amounts to the advertiser/merchant, e.g., via an invoicing/payment module or system. In one embodiment, a portal for merchants/advertisers or publishers are provided to sign up, sign in, and manage their profiles and view their accounts via an account management module, and upload or provide their bids or parameters (e.g., daily limits, exclusions/filters) via a user interface or an API.

In one embodiment, as for example indicated by Figs. B11 and B12 of Appendix 4 or FIGS. 249 and 250, a process generates product demand forecast to matched merchant, based on the traffic, bid, and heuristics. For example, when an image/webpage from a high traffic website is matched with a merchant's catalog item (or a process indicates that matches with such an item or class of items exists with an aggregated high traffic websites), based on one or more reporting threshold amounts, the merchant is automatically receives such notice with for example the repost indicting the demand forecast for the item based on the matches to help inventory management and ordering process. In one embodiment, this service is provided as subscription and/or per transaction and/or per commission. In one embodiment, such matches with other merchant's catalog items are used by a process to report to affiliated merchants/advertisers with demand forecast for inclusion of the product in the inventory. In one embodiment, the newly added item to the inventory is reported by the merchant via an API call or data communication to the See & Shop platform (e.g., along with the report ID) to extend the match to the newly added item. In one embodiment, the newly proposed match is automatically checked to verify the image/description match to reduce mistakes or abuse.

In one embodiment, merchants/advertisers/agencies bid for an ad corresponding for an image/webpage of a publisher based on the match information provided to them. In one embodiment, publishers bid for referral/commission/PPC from a merchant/merchant catalog item(s) based on the match information provided to them. In one embodiment, the bids are resolved based on the supply (of the merchant/advertiser's ad budget or of the publisher's limited real estate for ad display) and demand (of advertiser for the webpage ad or of publisher for a particular merchant/catalog item(s)). In one embodiment, the supply and demand are resolved in an ad/referral exchange/network based on relevance, traffic volume, context, reliability and similarity factors, and optimization of the return.

In one embodiment, the publishers are paid for a portion of the referral/commission/PPC for hosting the ad on their webpages. In one embodiment, the publishers (e.g., weblogs) share their ad revenue with the contributors of the content (e.g., the blogger).

In one embodiment, the users act as direct or indirect publisher's of the content, e.g., when tagging and recommending to their friends or others certain images or webpages, e.g., via social networks, bookmarking, twit, email, and sharing personal images. In one embodiment, an ad or code/script accompanies the user's communication to display matched items based on the image/text in the content of the user communication. In one embodiment, the click rate is higher for the referral or ads related to messages or communications and from trusted sources and individuals. In one embodiment, the messages are send/posted on behalf of the user from the See & Shop platform, e.g., by using the user's login authorization to post messages to the social/bookmarking networks. In one embodiment, the posted message includes links/scripts (e.g., in addition to static content) associated to the platform, such that when viewed by recipient or others, the script/code execute and the ad content is provided to the viewer and the accounting for the views/impression is made by a tracker module.

See & Shop Ads

In one embodiment, as for example depicted in Figs. B16 and B17 of Appendix 4, Ads based on matching images (based on features of objects in the image) automatically provide relevant images of items from various merchants' catalogs that match the items in an image on a webpage to a user viewing the webpage. In one embodiment, the scripts supporting the ads are incorporated in the webpage or fed to the browser to place the ads next to or at the vicinity of the image(s) on the webpage, e.g., by the content provider of the website, e.g., in order to participate in a highly effective ad revenue sharing based on such Ads. In one embodiment, the ad essentially lets the content provider (e.g., fashion or news site) offer See & Shop capability to its users, based on the content it provides while it shares a portion of the ad/referral revenue. In conventional ad models, the content providers have little control over the ads appearing on their fashion webpages (such as a political ads, miracle diets, or walk-in tubs). These conventional ads are at best related to previous webpages visited by the user (or others sharing the Internet connection from the same private network), e.g., tracked via tracking mechanisms such as Google's DoubleClick cookies. Such ads have been proven to produce relatively low click rates.

In one embodiment, the users click rate on ads are increased based on user's interest in the images viewed on the publisher's webpage and by providing relevant ad based on the image the user is likely to be interested in, at the time the user is actually viewing the image on the webpage. For example, for fashion, this is because, the user is potentially interested in the content of fashion webpages (which are highly visual, yet difficult or inconvenient or impractical to describe by words in details) which most likely includes the images on the webpage; therefore, the user is potentially more interested in the ads that reflect the items in such images than the irrelevant ads or those remotely related to the subject of the webpage. Also, the user may not view such highly relevant ads as distracting, especially when they are inviting the user to shop what the user likely finds interesting on the webpage to begin with (e.g., fashion and celebrities wearing such or visually similar items). In one embodiment, the user is more likely to shop for the items the user immediately sees on the interested images, especially if such items are readily displayed on the ads on the same webpage, the click rate and conversion rate (to sale) with such Ads is considerably higher. This translates to more effective advertisement and a new basis for revenue for the image ad exchange/network.

Figure 243A:
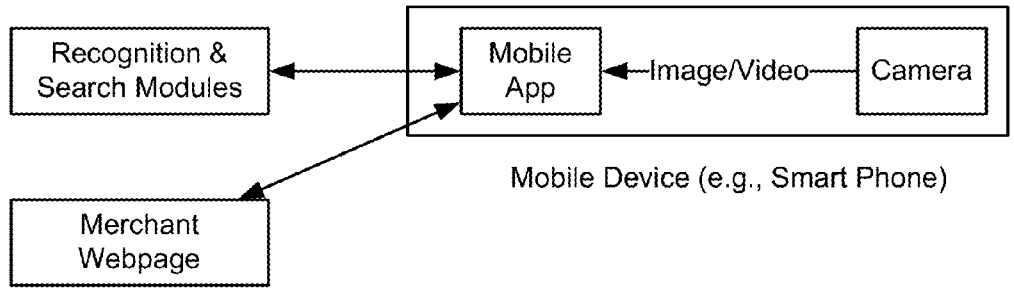
Figure 243B:
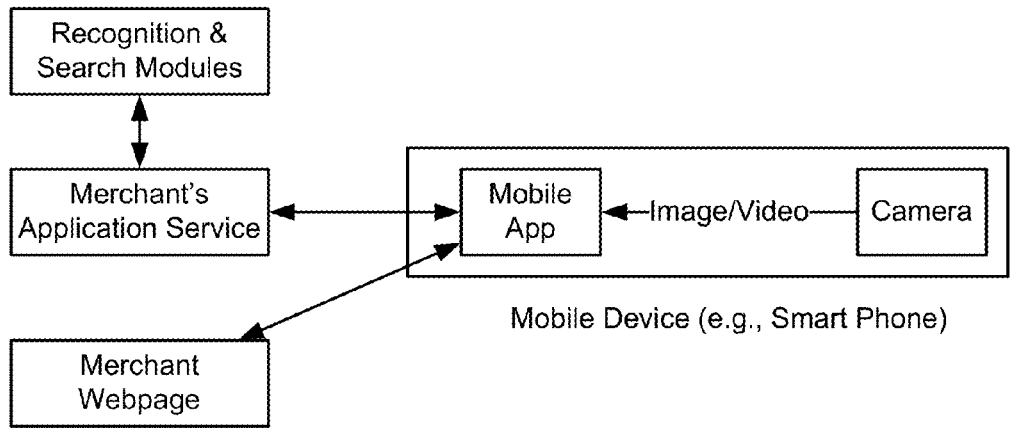
Figure 243C:
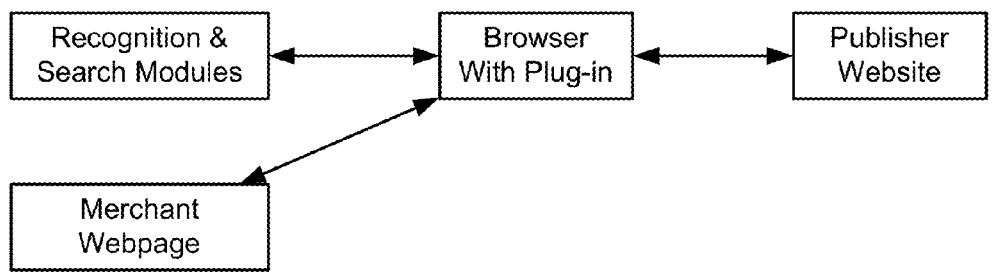
Figure 243D:
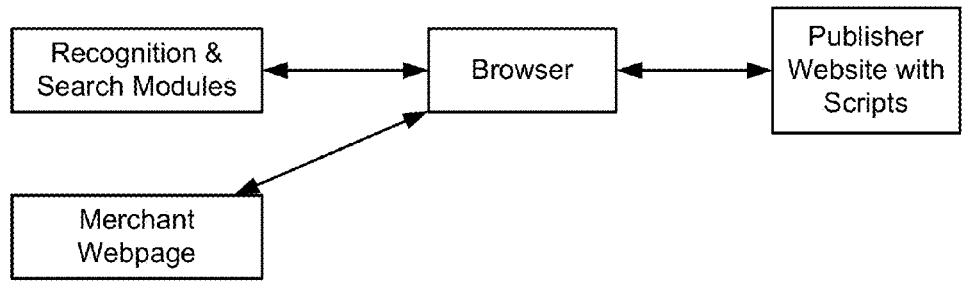
Figure 243E:
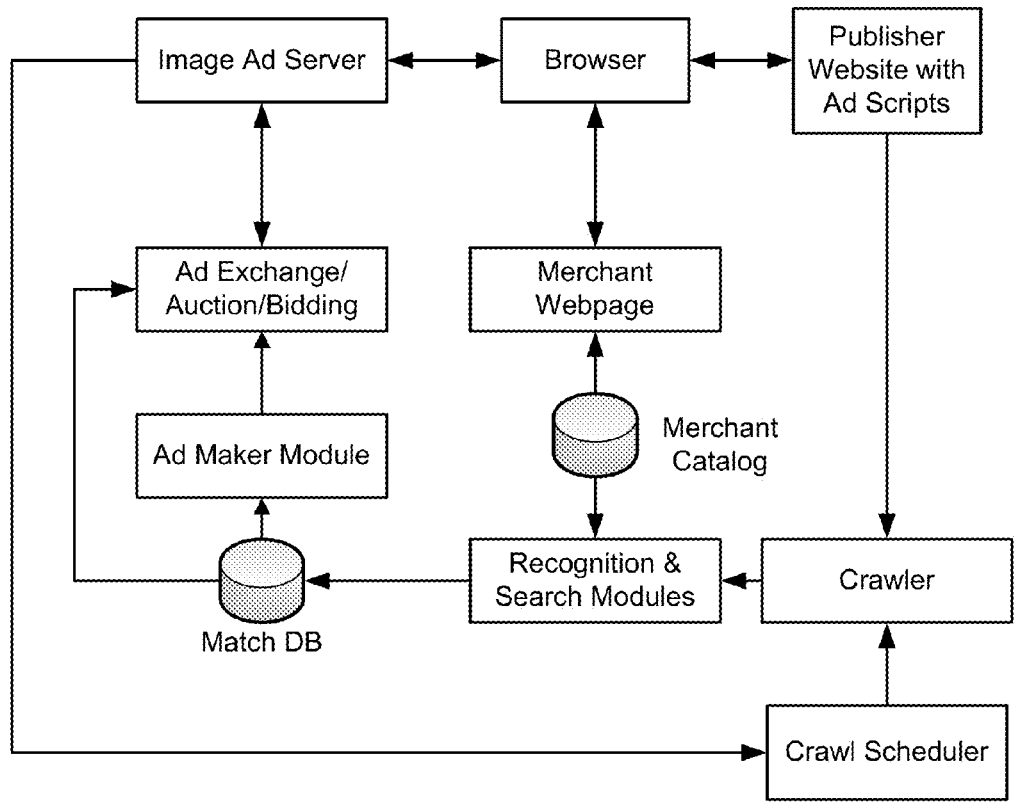

In one embodiment, as for example depicted in FIGS. 242 and 243(e), a set of processes (e.g., automated) scan/crawl the publisher's webpages and/or merchants' catalog items, analyze the features/descriptions of the images, search the features/descriptions and determine potential matches, select one or more matches for display in an ad on a webpage in vicinity or on an image associated with the match selected. In one embodiment, the scripts/codes for the ad on the webpage (corresponding to the ad network) execute on the user's browser (client side). In one embodiment, additional script/code/data are loaded e.g., from ad serve or ad network platform, e.g., to manage the user interface for the ad for the user and provide the links, referral landing page, graphics, and messages (e.g., personal messages). In one embodiment, a temporary landing page of link is provided to the user interface, such that when the user clicks on the ad (or a portion thereof), the browser is forwarded to a resource on the ad network to, for example, track the click, and/or provide a landing page forwarding link to the merchant's catalog item. In such a way, in one embodiment, the potential for abuse is reduced.

In one embodiment, the scripts on a webpage (e.g., publishers) when executed invoke a process in the platform (e.g., by calling a resource or an API) to detect whether the webpage/images(s) were scanned/crawled recently (e.g., based on a configuration for duration). In one embodiment, a crawling session is scheduled or performed to scan/crawl the webpage (or website), as for example depicted in FIG. 244, for an embodiment.

In one embodiment, when there is no match immediately available for ad based on image(s) on the webpage (e.g., publisher's), the platform/ad exchange/ad network uses other methods to provide context based ads for display. For example, a process uses other matches for the webpages on the same or other websites, e.g., within the same category/context (e.g., based on the words/text on the webpage such as titles). In one embodiment, the platform defers or falls back on an ad network/exchange based on words, by providing the ad configuration/page URL/publisher's ID (for the ad network) to the fall back network, and provide the ad content to the webpage (via script) provided by the fall back ad network.

In-Image Ads or Referral

In one embodiment, the referral or ad scripts on a webpage or a plug-in script (in a browser) displace overlaid icons/markers/buttons/ads on the corresponding image, as for example depicted in Figs. B17 or B7-B8 of Appendix 4. In one embodiment, the script uses jQuery and/or AJAX and/or JSON and/or JSONP to achieve user interactive responsiveness and communication with the platform servers. In one embodiment, the in-image ads/referrals are invoked by user selecting an icon/button overlaid on the image (for example as depicted in Fig. B17 of Appendix 4) or in vicinity of the image (as depicted on Figs. B7, B8 or B9 of Appendix 4) or in a tool bar (for example as depicted in Fig. B5 of Appendix 4). In one embodiment, the in-image ad invocation includes events such as mouse over, opening/refreshing the webpage, and/or based on time an number of times (randomly or configured). In one embodiment, an in-image ad/referral pane or overlaid element slides up or appears (e.g., limited to a region on the image) and/or dismissed/disappears (e.g., by user action on a close box/button and/or based on time). In one embodiment, other matches show up via sliding up/down within the overlaid region (e.g., at the bottom of the image) or displayed in an automatically rolling fashion (e.g., based on a configurable time duration) as for example depicted in Fig. B17 of Appendix 4. In one embodiment, the user is provided with an interface to manually roll the matches, click to go to See & Shop website (with the parameters indicated by the image and webpage URI or assigned identifiers), click on items to go to merchant catalog item webpage (i.e., merchant's landing page) (e.g., directly or indirectly).

In one embodiment, the publisher does not need to replace dedicated ad real estate on a webpage from one ad network to another. In one embodiment, the image ad/referral network use overlaid panes/IFrames/Windows/regions over or close to the image to display the items/ads.

Extension of Word-Based Ad Network

In one embodiment, a service/process provides (e.g., supplements) the advertisers' bids on word-based ad networks with the description of the catalog items, e.g., as an additional bid on behalf of the merchant/advertiser/agency. In one embodiment, a service/process provides (e.g., supplements) the publisher's webpage word representation/signature (e.g., extracted by a crawl/search engine) by the description of the objects contained in the image(s) on the webpage, e.g., on behalf of the publishers for example if participating in bidding process. In one embodiment, the ad network uses the supplementary information for matching based on words and/or bidding on words, e.g., in determining relevance and ranking for selecting an ad to display.

In one embodiment, once the word ad network selects, for example, a regular/generic ad from a merchant/advertiser for display on a publisher's webpage, a process is used to query whether there is any match based on image from the same merchant/advertiser and the publisher (e.g., based on their IDs or domain name of merchant's generic landing page and the publisher's website). In such a case, the word ad network makes a request (e.g., via an API) to display (e.g., more relevant) an image-based ad from an image ad matching engine (as for example depicted in Fig. B10 of Appendix 4 or FIG. 248). Then the ad network renders the ad based on the matching information provided by the matching engine (for example, landing page, images, labels, features, and/or relevance, as depicted in Fig. B12 of Appendix 4 or FIG. 250) to display on the user's device (e.g., in a browser, an application, or the application launching pad interface). In one embodiment, the word ad network delegate the ad display to the image-based ad network, e.g., by receiving the script/code/parameters used to display the image-based ads on the user's device. In one embodiments, the image-based ad/referral scripts/codes are executed (for example on the user's device) to display the image/catalog item on the ad. In one embodiment, a match ID (e.g., temporary placeholder ID/link/URI) is provided to the word ad network to relay to the browser (e.g., along with corresponding scripts) so that when scripts execute on the browser, the temporary ID is provided to the platform for retrieving the match for display as an ad to the user. In one embodiment, the temporary ID is used so that the word ad network is prevented to perform data mining on the image-ad network/platform. In one embodiment, the request to process an ad (e.g., by a script) on the image-ad network is check to determine whether the request is from a user's browser/application or from a process in the network (e.g., based on the http headers/signatures and IP addresses), in order to eliminate or reduce data mining.

In one embodiment, the word ad network is extended through a hint attribute/parameter. In one embodiment, a publisher adds image-based scripts/elements to its webpage for downloading to the user's web browser (and/or executing on the serer side). The script locates the hint attribute associated to an element associated with the word ad network/exchange (e.g., on the document object model or the source code), for example by querying for the signature tags/classes. In one embodiment, a code/script supplements the hint attribute with description related to the image on the webpage (e.g., based on the image feature analysis and description). In one embodiment, a code/script supplements the hint attribute with description related to one or more items from merchants' catalogs (e.g., based on matching). In one embodiment, a script/code tags/provides/supplements the hint attribute with an identifier associated with hints based on image (e.g., stored on image-based ad/referral network/platform). In one embodiment, the word ad network processes the hints (supplemented) and uses the descriptions/words for better matching with the associated merchant (or their catalog items) for more relevant ad (e.g., as a heightened relevance factor) in auction for word process to select an ad to display. In one embodiment, the identifier is queried by a process to provide hint records obtained for example based on image analysis. In one embodiment, the platform is queried for a hint for a publisher's webpage/image even if an ID was supplemented by a script (e.g., on the user's browser).

Connecting User to Product

In various embodiments, the user is referred to a product in variety of ways. FIGS. 243(a) through 243(e) demonstrate for example several such ways.

In one embodiment, as for example depicted in FIG. 243(a), user using a (e.g., mobile) computing device (e.g., equipped with a camera) takes a video or image (or pick one from album) and recognition and search platform provides a matching item in a merchant's catalog and provides the match(es) to the user/mobile phone to navigate to the merchant's webpage. One embodiment, for example, is illustrated in Fig. B18 of Appendix 4.

In one embodiment, as for example depicted in FIG. 243(b), the (e.g., mobile) application communicates with a service (e.g., merchant's application server or website) and provides the image/video. The merchant service uses recognition and search modules to provide a match from the catalog and provides that to the user's device, e.g., to navigate to the item's webpage. One embodiment, for example, is illustrated in Fig. B19 of Appendix 4.

In one embodiment, as for example depicted in FIG. 243(c), a user's browser installed with a plug-in/extension/code picks/identifies an image/video on a publisher's website and recognition and search modules provide a merchant's catalog item webpage matching an object user specified on the video/image. One embodiment, for example, is illustrated in Fig. B5 of Appendix 4.

In one embodiment, as for example depicted in FIG. 243(d), the user, using a browser, navigates to a publisher's website having script/code associated with the page (client and/or server side), such as referral or ad scripts. Via scripts, the browser uses the recognition and search modules to get a link and navigate to the landing page of merchant's catalog item. Examples of some embodiment are illustrated in Figs. B7, B8, B9, B16, and B17 of Appendix 4.

In one embodiment, as for example depicted in FIG. 243(e), the content of the publisher's webpages/images are crawled/gathered and analyzed and matched with catalog items from merchants, and ads are dynamically created for display to the user when an ad exchange/network selects the ad (match) for display on the publisher's webpage/website via an ad server which is invoked or communicated with ad/referral scripts associated with the web page (e.g., client side or server side).

Miscellaneous

PPC (pay per click), PPA (pay per action), and PPM (pay per impression) may be used interchangeably in various embodiments.

In one embodiment, OCR is used to recognize text from various parts of image. In one embodiment SIFT is used to recognize logos on various parts of image. In one embodiment, bar code recognition is used to read a bar code data from the image.

Merchants' catalog and/or catalog items (or updates thereof) may be retrieved from agencies, e.g., working with merchants (and/or receiving feeds from merchants), in various embodiments.

Image and video are used interchangeably in various embodiments. The ad/referral display may be in-image, on video track, overlaid or between the playback segments, in various embodiments.

In one embodiment, a discount or coupon from the merchants is automatically issued to the platform for use in the incentive-based crown sourcing and point trading, based on the ad click through/impression/conversion volume/rate.

In one embodiment, various publishers' websites (e.g., focusing on models and celebrities) are crawled and images analyzed and correlated to the individual celebrities, by a set of automated and/or manual methods. In one embodiment, a service is provided to web publishers that display a celebrity wearing an outfit or a clothing/accessory that match the image displayed in the webpage, e.g., on or at the vicinity of the webpage image. In one embodiment, a service is provided to a merchant to display a celebrity wearing an outfit or a clothing/accessory that match the image displayed in the merchant's catalog item webpage or a summary/category page. In one embodiment, a service is provided to suggest other clothing items or object based on the outfit worn be a celebrity, from the same or various merchants' catalog items. In one embodiment, for example, a celebrity(ies) dedicated website uses the service (referral) to increase referral revenue based on the image content. In one embodiment, a plug-in/code is provided to display matching outfit worn by various celebrities on or next to an image in a webpage, e.g., having similar or matching objects with the outfit worn by the celebrity. In one embodiment, when a user clicks or selects the outfit image f the celebrity, the user's browser navigates to a website where the outfit image was posted, a website for analyzing or for showing the analyzed outfit and various matching catalog items, or a merchant's webpage for the matching catalog item. In one embodiment, a webpage/window/tab is displayed with a portion (e.g., on top) managed by See & Shop platform scripts/codes/webpage, e.g., having controls/buttons to navigate to merchants' webpages for various outfit items, e.g., at another portion of the page (e.g., at the bottom), e.g., via IFrame. In one embodiment See & Shop tool bars are overlaid and the various merchants' pages appear on a different pane/window/tab, so that the user can navigate back and forth without losing/leaving See & Shop control/tool bar.

In various embodiments, process or service is implemented or executed on a computing device (e.g., mobile, server, desktop), platform, or computing cloud.

In one embodiment, the user enters his/her input at a user interface comprising of a Fuzzy ruler/slider to adjust the level of relevance desired for matching different features of an object.

In one embodiment, near real-time ad is generated (e.g., based on near real-time image analysis) when a user communicates (e.g., the user twits, emails, blogs, likes, or posts), with the ad displaying an item from a merchant's catalog that matches with the image being communicated. In one embodiment, the user sending the communication is provided with points, incentive, or rewards, for inclusion of the ad with the communication.

In one embodiment, the merchants are provided an interface to bid on images or category of images, e.g., with one or more particular features (e.g., ascertained from a collection of photos, for example automatically and/or by words/description), and/or bid differently for various features (e.g., in a weighted bidding). In one embodiment, feature bidding allows the highly relevant matches e.g., between publisher's webpage/image and a merchant's catalog item(s).

In one embodiment, the number of likes/tags/pins for a particular item/image/webpage is used to prioritize the analysis and match finding for such an item, as the number of likes/tags/pins is related to the interest level for that item. In one embodiment, it is used as a factor in bidding among entities (e.g., publishers) for a match (e.g., is there is a limited supply of allocated ad budget). In one embodiment, the social/bookmarking network (e.g., Pinterest) is used to retag/repin items to collect in them in a collection (e.g., board) with links/pointers (e.g., on a button) pointing to a URI/resource/link on a website (e.g., See & Shop platform) with the request for placeholder links initiating a request for match query for the item and forwarding the browser to a merchant's catalog landing page associated to a matching item or to See & Shop website with the image (or URL or another identifier) as a parameter to display the image and the matching items from various merchants.

Recognition

In one embodiment, an optimization (e.g., used in training image recognition engine/component) is based on fuzzy constraint, or the constraints are made fuzzy through aggregation and simplification to reduce the complexity of the constraint surface in feature space. In one embodiment, the aggregated fuzzy constraint is used in Lagrange optimization or one with KKT condition.

In one embodiment, especially when the data (e.g., training samples) features are not readily forming a simple ellipsoidal distribution in feature space, the data is used to determine the principal components of clusters of data, i.e., the feature space is decomposition to ellipsoid like distributions in a hierarchical PCA. In recognition process, the data features are evaluated against the frost few principal components, and then against the first few principal component of sub cluster, and so on. These series of top principal components, in one embodiment, represent various features of the object at different levels of granularity. In one embodiment, this provides for fast search through hierarchy of feature clusters. In one embodiment, the training is also simplified and made in steps, by for example ignoring certain detailed features/labels for initial feature classifications. The series of feature values for top components provide a signature for the item.

In one embodiment, as a preprocessing step for recognition, a thumbnail silhouette of the image is used as an initial stage to determine the outline of the object (e.g., background separation), high level classification of the object(s) and pose estimation. In one embodiment, the expert recognition system is selected based on the classification and the portion of the image associated with the subpart of the object is used for further recognition and detailed classification of the subpart (e.g., in context of the object). Recognition of the various subparts is used in Bayesian probability method to estimate the likelihood of various sub-classification of other parts, e.g., based on the analysis of the training samples and/or user feedback and/or reliability and certainty factors from other recognition methods.

In one embodiment, for a given class of objects (e.g., shoes or footwear), a general basis for description is used to describe features (for example in an XML hierarchy or based on web/graph relationship) for quick comparison of the coded/described features between the objects from different images, e.g., used during training, indexing or search processes.

In one embodiment a fuzzy SVM is used to train a classifier. In one embodiment, the membership function of the training data is made to be fuzzy, i.e., the data point may partially belong to a particular class. In one embodiment, the slack error function may be constant, linear or quadratic with respect to the slack from margin. In one embodiment, the slack error function for each point is weighted by a complement membership function imposed by the classifier (e.g., based on the classifier line and its margin). In one embodiment, the complement membership function is 1 when the point is misclassified and it is outside of the margin around the center line, and less than 1 when it is within the margin around the center line (e.g., proportional to slack). In one embodiment, the classifier line may be considered as a fuzzy line classifier. The line refers to hyper plane. In one embodiment, the hyper plane is on a transform space (e.g., based on a kernel).

Emotion Recognition

In one embodiment, from the voice or text or typing or handwriting, one can get the emotion of the speaker or writer, as well as the intention, truthfulness, and type of personality. The parameters are pitch, volume, pause frequency, pause length, emphasis, loudness, speed, timing, energy, pressure on keyboard, computer input surface, or paper, vocabulary used, frequency of voice, relative or absolute values, relative to normal behavior, head, mouth, body, hand language and movements, speed/frequency of blinking, speed/frequency of breathing, skin color, skin wrinkles, facial form, lip form, neck position, range of voice, speed of typing, and the like. For the parameters given above, we have an N dimensional space, which we can train the system to recognize the person in different conditions, or use it on many users/people, to get the clusters separated out in the N dimensional space for different conditions, and marked accordingly during the training. Then, next time, when we get a point in that N dimensional feature space, we can find out the condition and its relative degree of that condition, e.g., "very-angry", which is also a fuzzy parameter, based on the position of the point with respect to the cluster of "anger", e.g., its position with respect to the cluster's center and boundary, to set the degree of the condition or the relative strength. For example, the center of cluster may be regarded as the highest strength for that condition, as one embodiment.

More Embodiments

We present a method and system for iterative preprocessing for training a support vector machine, e.g., for a large dataset, based on balancing the center of mass of input data, e.g., within a variable margin about the hyperplane. At each iteration, the input data is projected on the hyperplane (or on a vector parallel to the hyperplane), and the imbalance of the center of mass for different classes within a variable margin is used to update the direction of the hyperplane within the feature space, in addition to other factors including the estimate of slack error changes due data points entering and exiting the margin. In one embodiment, an estimate for the margin and the regularization constant is provided based on scanning/counting an ordered list of projected data points on a direction perpendicular to the hyperplane. In one embodiment, a fuzzy membership function for data points is used as an input (or estimated), for example, to determine center of mass and/or count data points which violate the margin. In one embodiment, non-linear SVM, e.g., based on kernels, such as (homogeneous or inhomogeneous) Polynomial, Gaussian radial basis function (RBF), or hyperbolic tangent, is used for training from input dataset, and the required dimension is estimated for the feature space (represented via a set of orthonormal feature vectors) based on a set of points in input space that provide coverage on all or substantially all data points via kernel (e.g., Gaussian) and provide sufficient information to uniquely identify a data point of a series of (e.g., neighboring) data points.

Appendix 5 includes slides of presentation "Preprocessing Method for Support Vector Machines Based on Center of Mass", presented on Dec. 16, 2013, at The Third Annual World Conference on Soft Computing, WCSC 2013, in San Antonio, Tex.

SVM Quadratic Dual Form

Support vector machines (SVMs) are powerful tools for classification of input data based on structural risk minimization. SVM uses a hyperplane (within the input space, in case of linear SVM, or in a feature space, in case of non-linear SVM) to separate the input data based on their classification while maximizing the margin from the input data. In case of inseparable dataset, a soft margin version of SVM is used to allow for misclassification error by imposing a penalty, e.g., proportional with the Euclidian distance from the class margin. In such a case, a regularization parameter is used as a tradeoff mechanism between the maximizing the margin and minimizing the error penalty. The appropriate level of tradeoff is determined by a validation step to estimate the out-of-sample error.

N number of samples $(x_i, y_i)$ are used for training an SVM, where $x_i \in \mathbb{R}^d$ and $y_i \in \{-1, 1\}$ (denoting the classification of the data sample). A hyperplane classifier is sought to separate the input data according to their classification:

$$f(x) = \text{sign}(u_i) = \text{sign}(w \cdot x_i + b) = \begin{cases} +1 & \text{if } y_i = +1 \\ -1 & \text{if } y_i = -1 \end{cases} \quad (19)$$

Direction of w is perpendicular to the hyperplane, and its inverse of magnitude represents the margin between the hyperplane (having plane number 0) and the margin surface having the plane number $u_i$ set to +1 or -1 (e.g., at the nearest class data points in a linearly separable case):

$$y_i u_i = y_i(w \cdot x_i + b) \geq 1, \forall i = 1 \text{ to } N \quad (20)$$

As an example of when the dataset is not linearly separable, a slack (or error) parameter is used to still classify the data point correctly within the slack from the class margin:

$$y_i u_i = y_i(w \cdot x_i + b) \geq 1 - \xi_i, \xi_i \geq 0, \forall i = 1 \text{ to } N \quad (21)$$

To maximize the margin $\|w\|^{-1}$, an objective function is formed to minimize $(w \cdot w)$ as well as the slack errors, based on the trade off parameter C, subject to (21):

$$\text{Minimize} \left( \frac{1}{2} w \cdot w + C \sum_{i=1}^{N} \xi_i \right) \quad (22)$$

The solution may be found at the saddle point of the Lagrangian:

$$L(w, b, \alpha_i, \beta_i) = \quad (23)$$
$$\frac{1}{2} w \cdot w + C \sum_{i=1}^{N} \xi_i - \sum_{i=1}^{N} \alpha_i(y_i(w \cdot x_i + b) - 1 + \xi_i) - \sum_{i=1}^{N} \beta_i \xi_i$$

where $\alpha_i, \beta_i \geq 0$, and the Lagrangian is minimized w.r.t. (w, b) and maximized w.r.t. $(\alpha_i, \beta_i)$, yielding:

$$w = \sum_{i=1}^{N} \alpha_i y_i x_i \quad (24)$$

$$\sum_{i=1}^{N} \alpha_i y_i = 0 \quad (25)$$

$$\alpha_i + \beta_i = C, 0 \le \alpha_i, \beta_i \le C, \quad (26)$$

The modified Lagrangian in dual form (i.e., by substituting (24) and using (25) and (26)) is quadratic in $\alpha_i$, and it is minimized w.r.t. $\alpha_i$, subject to constraint (26):

$$\mathcal{L}'(\alpha) = \sum_{i=1}^{N} \alpha_i - \frac{1}{2} \sum_{i=1}^{N} \sum_{j=1}^{N} \alpha_i \alpha_j y_i y_j (x_i \cdot x_j) \quad (27)$$

In a non-linear case, where the optimization is performed in a feature space $\mathcal{Z}$, the vector product in (25) would become $(z_i \cdot z_j)$, where $z_i = \phi(x_i)$ is the corresponding feature vector and the dot product in space Z may be expressed as a corresponding kernel $\mathcal{K}(x_i \cdot x_j)$ in $\mathcal{X}$ domain satisfying Mercer condition. The solution for (27) provides a set of $\{\alpha_i\}$ where most are typically zeros, indicating the corresponding data points that are outside the margin (with zero slack). A non-zero $\alpha_i$ represents an $x_i$ which is at the margin or violating the margin with a non-zero slack. The KKT (Karush-Kuhn-Tucker) conditions for the solution are:

$$\begin{cases} y_i u_i > 1 & \Leftrightarrow \quad \alpha_i = 0 \\ y_i u_i = 1 & \Leftrightarrow \quad 0 \le \alpha_i \le C \\ y_i u_i < 1 & \Leftrightarrow \quad \alpha_i = C \end{cases} \quad (28)$$

The classification hypothesis may be expressed by the few non-zero $\alpha_i$'s (by substituting (24) in (19)) with their corresponding $x_i$'s denoted as support vectors (SVs):

$$f(x) = \text{sign}\left(\sum_{\alpha_i > 0} \alpha_i y_i \mathcal{K}(x_i, x) + b\right) \quad (29)$$

While most $\alpha_i$'s are typically zero, the performance of quadratic (QD) programming solvers suffer for large datasets due to large size of (N×N) kernel matrix with $\mathcal{K}(x_i, x_j)$ elements. Various embodiments can address this issue, such as "chunking" to break down a larger QD problem into series of smaller ones, or breaking the problem to the smallest chunk in pair-wise sequential minimal optimization. In addition, the solver repeats the optimization by varying the values of C and/or kernel parameter(s) within a wide exponential range, and a grid search is used to determine the optimum hyperparameter(s) likely to minimize out of sample error (e.g., estimated by validation dataset). Another embodiment eliminates the subset of input dataset, via fuzzy clustering, to reduce the workload.

1 Preprocessing for SVM Using Center of Mass

While any data point might be a support vector (as anticipated by (27)), we present a preprocessing approach to quickly identify the potential SVs in linear SVM, as the initial starting point for QD solvers in order to speed up the optimization process. The approach also estimates the margin and C to narrow the range of C's needed for use with validation. An extension of this approach to non-linear SVM is suggested where the assumption is that relatively few SVs would support the hyperplane having a relatively low dimensionality.

1.1 Leverage Model of Lagrange Multipliers

The relations (24) and (25) suggest a view of leverage for the data points (depicted in solid black in FIG. 254) at or inside the margin about the hyperplane.

Per (28), $\alpha$ for the points inside the margin gets limited to C, while those at the margin may have $\alpha$ between 0 and C. Furthermore, $\alpha_i y_i$ provides the polarity to the "force" $\alpha_i$ excreted on the margin by the corresponding data point. For example, such force by "circle" class (having y=+1) is pointing down, while those from "square" class (with y=−1) are pointing in opposite direction. Equation (25) may be rewritten as a force balance equation:

$$\sum_{i_+} \alpha_{i_+} = \sum_{i_-} \alpha_{i_-} \left(= \frac{1}{2} \sum_{i=1}^{N} \alpha_i\right) \quad (30)$$

where $i_+$ and $i_-$ are indexes for non-zero $\alpha_i$'s corresponding to "circle" and "square" classes (i.e., y=+1 and −1), respectively. The soft margin SVM that allows errors (with slack) limits the value of $\alpha$ to C (tradeoff parameter). This can be interpreted as the "skin" of the soft margin only being able to support a point force up to C before getting penetrated. In other words, the force on the margin builds up from 0 to C, as the point is "pushed" from outside the margin through the "skin"

The "force" model (with $\alpha$ playing the role of force) can be extended to a "leverage" model (with torque) by observing that the RHS of (24) resembles a torque $\alpha_i y_i x_i$ having $x_i$ as its leverage. To exploit this property, we project (24) on a direction perpendicular to w (denoted by unit vector $\hat{w}_\perp$):

$$\sum_{i=1}^{N} \alpha_i y_i (x_i \cdot \hat{w}_\perp) = \left(\sum_{i=1}^{N} \alpha_i y_i x_i\right) \cdot \hat{w}_\perp = w \cdot \hat{w}_\perp = 0 \quad (31)$$

where m is the margin. Note that in $\mathcal{D}$ dimensional space of w, there are $(\mathcal{D}-1)$ independent $\hat{w}_\perp$ per $\hat{w}$ (unit vector in direction of w, also denoted as $\hat{w}_\parallel$). Equation (31) implies that, at the solution, the torque from the forces ($\alpha_i y_i$) balance so not to tilt $\hat{w}$ in the direction of $\hat{w}_\perp$. It should be noted that if $x_i$'s are offset by a arbitrary fixed vector q, Equation (24) (as well as (31)) remain invariant under such translation due to (25):

$$\sum_{i=1}^{N} \alpha_i y_i (x_i - q) = \sum_{i=1}^{N} \alpha_i y_i x_i - \left(\sum_{i=1}^{N} \alpha_i y_i\right) q = w - 0 = w \quad (32)$$

By placing q on the hyperplane (u=0), Equation (31) demonstrates that the torques balance around such a pivot point in any of $\hat{w}_\perp$ direction(s), as for example depicted in FIG. 255.

This also implies that the "center of mass" for "circle class" (for solid circles) should have the same projection on $\hat{w}_\perp$ as the center of mass for "square class" (solid squares), when the optimum solution is at hand. This is because the torque from a set of points from one class can be represented from the torque from their corresponding center of mass. Note that the center of mass for such points is weighted by their corresponding force ($\alpha$) as shown below:

$$\left(\sum_{i_+} \alpha_{i_+}\right) \cdot COM_+ = \sum_{i_+} \alpha_{i_+} x_{i_+}, \quad (33)$$

-continued $$\left(\sum_{i_-} \alpha_{i_-}\right) \cdot COM_- = \sum_{i_-} \alpha_{i_-} x_{i_-}$$

Given (30) and (24), Equation (31) may be written as follows:

$$COM_+ \cdot \hat{w}_\perp = COM_- \cdot \hat{w}_\perp \text{ or } (COM_+ - COM_-) \cdot \hat{w}_\perp = 0 \quad (34)$$

In cases that the number of points violating the margin (from both classes) are significantly higher than those exactly on the margin, one can assume that most of $\alpha_i$'s are limited to C, and the determination of the center of mass is simplified to a class member head count (violating the margin) and its projection on $\hat{w}_\perp$.

It is noteworthy that the projection on the direction of w (i.e., on $\hat{w}$ or $\hat{w}_\parallel$) produces the inverse of margin:

$$\sum_{i=1}^{N} \alpha_i y_i (x_i \cdot \hat{w}_\parallel) = \left(\sum_{i=1}^{N} \alpha_i y_i x_i\right) \cdot \hat{w}_\parallel \quad (35)$$

$$= w \cdot \hat{w}_\parallel$$

$$= \|w\|$$

$$= m^{-1}$$

To setup the problem, for the first iteration, $COM_\pm$ are determined from all class data points via (33) (by ignoring $\alpha_i$'s, e.g., by setting them to 1). The initial $w_{init}$ is estimated as follows:

$$\hat{w}_{init} = \frac{COM_+ - COM_-}{\|COM_+ - COM_-\|} \quad (36)$$

A set of $\hat{w}_\perp$'s is determined for $\hat{w}_{init}$, for example by reconstructing a successive pair-wise rotation matrices that aligns the unit vector associated with the last coordinate to $\hat{w}_{init}$. Same transformation provides a set of $(\mathcal{D}-1)$ orthonormal $\hat{w}_\perp$'s by operating on the other unit vectors of other $(\mathcal{D}-1)$ dimensions.

1.2 Scanning Through Ordered Projection Values

Next, $x_i$'s are projected onto $\hat{w}_{init}$ (or $\hat{w}_\parallel$) (see FIG. 256), and they are sorted based on the projected values ($p_i$):

$$p_i = x_i \cdot \hat{w}_\parallel \quad (37)$$

Next, for a given set of percentage of population (e.g., 1%, 5%, 10%, 20% . . . of the class with less members), scan/count from low end of $p_i$ for y=+1 class (denoted as $p_{start+}$) and high end of $p_i$ for y=−1 class (denoted as $p_{start-}$) as shown in FIG. 256. The count can also be sequential from each sorted list, for example, based on margin or percentage change. If the data set happens to be separable by $\hat{w}_\parallel$, $p_{start+}$ is more than $p_{start-}$, and their average (denoted as $p_{m0}$) marks the hyperplane candidate for zero error, and half of their difference corresponds to its margin.

If $p_{start+}$ is less than $p_{start-}$ (i.e., not linearly separable in $\hat{w}_\parallel$ direction), the count/scan continues until the class markers on projected pass each other. In such a case, the prior position of the markers (before passing each other), $p_{m0+}$ and $p_{m0-}$, are used to mark a zero-margin hyperplane candidate under $\hat{w}_\parallel$, for example by taking an average value. The slack error is tracked by simply adding the projected values during the scan/count (to be later offset and scaled by the position of the hyperplane and size of the margin, respectively) as shown in (43) and (41). At given class counter positions, $p_{m1+}$ and $p_{m1-}$ (see FIG. 256), the hyperplane parameters are estimated as follows:

$$m = \frac{1}{2}(p_{m1+} - p_{m1-}) \quad (38)$$

and $$w = \|w\| \hat{w}_\parallel$$

$$= m^{-1} \hat{w}_\parallel$$

$$b = u - \frac{\hat{w}_\parallel \cdot x}{m}\bigg|_{at\ hyperplane} \quad (39)$$

$$= 0 - \frac{(p_{m1+} + p_{m1-})}{2\ m}$$

$$= \frac{p_{m1+} + p_{m1-}}{p_{m1+} - p_{m1-}}$$

$$\underset{(scaled\ by\ C)}{Est.Slack\ Err} \approx C \cdot [\mathcal{F}_+(N_{m1+}) + \mathcal{F}_-(N_{m1-})],$$

where $$\mathcal{F}_\pm(N_{m1\pm}) = N_{m1\pm} \cdot \left[\frac{1}{m}\left(p_{m1\pm} - \frac{1}{N_{m1\pm}} \sum_{\substack{i_\pm \\ scanned}} p_{i_\pm}\right) \cdot y_\pm\right] \quad (40)$$

$$= N_{m1\pm} \cdot \left[\frac{1}{m}(p_{m1\pm} - COM_{scanned\pm} \cdot \hat{w}_\parallel)\right]$$

where $N_{m1+}$ and $N_{m1-}$ are number of class points counted/scanned corresponding to $p_{m1+}$ and $p_{m1-}$ projection class markers. $COM_{scanned\pm}$ is the center of mass for the scanned data point for a class. In a synchronous counting between classes, where the counts are the same ($N_{m1}$) and the class errors are weighted equally, the estimated slack error is:

$$\underset{(scaled\ by\ C)}{Est.Slack\ Err} \approx C \cdot N_{m1} \cdot \left[2 - \frac{1}{m \cdot N_{m1}}\left(\sum_{\substack{i_+ \\ scanned}} p_{i_+} - \sum_{\substack{i_- \\ scanned}} p_{i_-}\right)\right] = \quad (41)$$

$$C \cdot N_{m1} \cdot \left[2 - \frac{1}{m}(COM_{scanned+} - COM_{scanned-}) \cdot \hat{w}_\parallel\right]$$

In this scheme, during one scan/count, various error levels are estimated for a given count $N_{m1}$ or percentage of the population (based on $N_{m1}$). Summations over $p_i$'s in (40) and (41) represent a cumulative running sum as the counting progresses. Similarly, $COM_\pm$ or their projections on $\hat{w}_{\perp,k}$ or $\hat{w}_\parallel$ are determined as running sums based on the scanned data points. Objective function (22) and its elements as well as misclassification ratio (MR) data points can be estimated and tracked:

$$Obj\ Func. \approx \frac{1}{2\ m^2} + \underset{(scaled\ by\ C)}{Est.\ Slack\ Err} \approx \quad (42)$$

$$\frac{1}{2\ m^2} + C \cdot [\mathcal{F}_+(N_{m1+}) + \mathcal{F}_-(N_{m1-})]$$

$$MR \approx \frac{1}{N}\bigg[ \quad (43)$$

$$IndexLookup\left(\frac{p_{m1+} + p_{m1-}}{2}\right)\bigg|_+ + IndexLookupRev\left(\frac{p_{m1+} + p_{m1-}}{2}\right)\bigg|_-\bigg]$$

where IndexLookup and IndexLookupRev determine the number of misclassified data points in each class, by looking up the index of the projection value of hyperplane in the ordered list of the projected values of $x_i$'s onto $\hat{w}_\parallel$.

Per (38) and (43), a relationship between margin m and in-sample misclassification rate MCR is determined for each candidate $\hat{w}_\|$ being iterated, based on the scan through various values of $N_{m1\mp}$. In addition, $\mathcal{F}_\mp(N_{m1\mp})$ as a measure of slack error is made independent of C, per (40). Therefore, the relationship between the objective function (42) and C may conveniently be determined for a candidate $\hat{w}_\|$ without rescanning the dataset. Thus, a range of appropriate C may be estimated, for example, as an order of magnitude below and above the range of $(2m^2[\mathcal{F}_+(N_{m1+})+\mathcal{F}_-(N_{m1-})])^{-1}$ for various $N_{m1\mp}$ encountered during the same scan.

1.3 Predictive Tilting Based on Center of Mass and In/Out Adjustments

For data points on the margin boundary, (24) and (31) may be used to determine the effect of trade off $\Delta\alpha$ between two margin points $x_1$ and $x_2$ of the same class (e.g., y=+1) with opposite $\Delta\alpha$:

$$\Delta w = \Delta\left(\sum_{i=1}^{N} \alpha_i y_i x_i\right) \quad (44)$$
$$= \Delta\alpha y(x_2 - x_1)$$

Given $x_1$ and $x_2$ are on the margin, $(x_2-x_1)$ is perpendicular to $\hat{w}_\|$. Therefore, the effect is a tilt to w in the direction of $(x_2-x_1)$. The amount of tilt is proportional to $\|x_2-x_1\|$, i.e., the tradeoff in $\alpha$ for far away points has larger impact on tilting w. The concept applies to points of different classes (having the same $\Delta\alpha$ per (30) and opposite signs for y's). Based on (44), we describe an efficient method for providing $\Delta w$ for the subsequent iteration.

In addition to projection of data points on $\hat{w}_\|$, the data point(s) $x_i$ are also projected on $\hat{w}_\perp$'s, and sorted accordingly (see for example FIG. 255):

$$p_{i,k} = x_i \cdot \hat{w}_{\perp,k} \quad (45)$$

where k indexes over $(\mathcal{D}-1)$ independent $\hat{w}_\perp$'s corresponding to $\hat{w}_\|$. For a given $\hat{w}_\|$, assume the margin, $m_{opt}$, and offset, $b_{opt}$, are optimized as to (42) for a given C, per previous section. Thus, an update to $\hat{w}_\|$ should be in form of a small tilt, $\Delta w$, perpendicular to $\hat{w}_\|$ (see FIG. 257).

The small tilt maintains the magnitude of $\hat{w}_\|$, and therefore, the corresponding portion of the objective function $$\left(\frac{1}{2m^2}\right)$$

does not change. However, the tilt impacts slack errors (see (22)) in three ways based on: a) points staying in violation of the margin having different slack error, b) points going out of margin violation reducing slack error, and c) points coming into margin and increasing slack error, as depicted in FIG. 257.

Assuming the tilt pivot point, PV, is located on the hyperplane, the change in $u_i$ due to $\Delta w$ becomes:

$$\Delta u_i = \Delta w \cdot (x_i - PV) \quad (46)$$

Let $\Delta w$ be aligned to $\hat{w}_{\perp,k}$, so that $\Delta w = \|\Delta w\|\hat{w}_{\perp,k}$. Then:

$$\Delta u_i = \|\Delta w\|(p_{i,k} - PV \cdot \hat{w}_{\perp,k}) \quad (47)$$

Let $S_{in\text{-}pri}$ be a set of in-margin data points prior to the tilt (i.e., including those that stay in and go out after the tilt). The total change in plane numbers is:

$$\sum_{i_\pm \in S_{in\text{-}pri}} \Delta u_i = \|\Delta w\|\left(\sum_{i_\pm \in S_{in\text{-}pri}} p_{i_\pm,k} - N_{in\text{-}pri_\pm} PV \cdot \hat{w}_{\perp,k}\right) \quad (48)$$
$$= \|\Delta w\| \cdot N_{in\text{-}pri_\pm}(COM_\pm - PV) \cdot \hat{w}_{\perp,k}$$

where $N_{in\text{-}pri_\pm}$ denotes the number of data points from each class in $S_{in\text{-}pri}$; $i_\pm$ indexes points over each class; and $COM_\pm$ is the center of mass for each class of data point in $S_{in\text{-}pri}$, given by $$COM_\pm = \frac{1}{N_{in\text{-}pri_\pm}} \sum_{i_\pm \in S_{in\text{-}pri}} x_{i_\pm}$$

The change in slack error for $S_{in\text{-}pri}$ becomes:

$$\sum_{i \in S_{in\text{-}pri}} \Delta\xi_i = \sum_{i \in S_{in\text{-}pri}} -y_i \cdot \Delta u_i \quad (49)$$
$$= -\|\Delta w\| \cdot N_{in\text{-}pri}(COM_+ - COM_-) \cdot \hat{w}_{\perp,k}$$

where it is assumed that $N_{in\text{-}pri_\pm}$ are equal and denoted by $N_{in\text{-}pri}$ (resulting in elimination of PV). As depicted in FIG. 258, the imbalance in $COM_\pm$ can be used to reorient $\hat{w}_\|$ via $\Delta w$ in reducing the slack error.

However, the expression for $\Delta\xi$ is now adjusted by those points going out and coming into the margin after the tilt by considering both $u_i$ and $\Delta u_i$ to account for double counting of those going out (denoted by $S_{out\text{-}after}$) which were included in $S_{in\text{-}pri}$, as well as those coming into the margin after the tilt (denoted by $S_{in\text{-}after}$).

$$\sum_{i \in S_{in\text{-}after}} \Delta\xi_i = \sum_{i \in S_{in\text{-}after}} (1 - y_i \cdot (u_i + \Delta u_i)) \quad (50a)$$

Further simplification results:

$$\sum_{i \in S_{in\text{-}after}} \Delta\xi_i = \quad (50b)$$
$$N_{in\text{-}after} - (N_{in\text{-}after_+} - N_{in\text{-}after_-})(b - \|\Delta w\|PV \cdot \hat{w}_{\perp,k}) -$$
$$\sum_{i_+ \in S_{in\text{-}after_+}} \frac{1}{m}\left(p_{i_+} + \frac{\|\Delta w\|}{\|w\|}p_{i_+,k}\right) +$$
$$\sum_{i_- \in S_{in\text{-}after_-}} \frac{1}{m}\left(p_{i_-} + \frac{\|\Delta w\|}{\|w\|}p_{i_-,k}\right)$$

where $N_{in\text{-}after_\pm}$ are the number data points for each class coming into the margin after the tilt, and $N_{in\text{-}after}$ is the sum of $(N_{in\text{-}after_+} + N_{in\text{-}after_-})$. The expression for the adjustment of slack error for data points going out of the margin is quite similar, except for minus sign (as the errors are reduced) and labels switching from in to out:

$$\sum_{i \in S_{out\text{-}after}} \Delta\xi_i = \sum_{i \in S_{out\text{-}after}} (-1 + y_i \cdot (u_i + \Delta u_i)) \quad (51)$$

Therefore, at each iteration, (49) may readily be evaluated for a given $\|\Delta w\|$, based on tracking of the running sum of $p_{i,k}$ in (48) or center of masses in (49), during the scanning of the ordered list of projected data (37). While (49) is explicitly proportional to $\|\Delta w\|$, (50) and (51) are only indirectly related to $\|\Delta w\|$, through $N_{in\text{-}after}$ and $N_{out\text{-}after}$. It would be reasonable for most affected points be from regions far from the pivot point per (46) where $\Delta u_i$ is greater.

The following approach is adopted to control the tilt so that the scan of projected data along $\hat{w}_\parallel$ would provide the required data for evaluating (49), (50), and (51). Based on the scanning of $p_{m1+}$ and $p_{m1-}$ projection class markers, Equations (38)-(43) provide applicable hyperplane (if any) and its associated objective function and slack error for various $N_{m1}$'s. Therefore, around the marker positions corresponding to margin, $m_{opt}$, and offset, $b_{opt}$, other neighboring markers provide information, e.g., for a larger margin $m_2$, as depicted in FIG. 259.

The markers corresponding to $m_2$ are adopted to effectively limit $\|\Delta w\|$, so that the set of data points going into the margin ($S_{in\text{-}after}$) due to the tilt would be limited to those data points entering margin $m_2$ when margin is expanded from $m_{opt}$ in $\hat{w}_\parallel$ direction (denoted as $S_{m_2\text{-}m_{opt}}$), provided that:

$$\frac{\|\Delta w\|}{\|w\|} \leq \frac{\Delta L}{L} = \frac{m_2 - m_{opt}}{L} \qquad (52)$$
$$= \frac{\Delta m}{L}$$

where L is the full extent of data points in $\hat{w}_{\perp,k}$ direction from the pivot point, and the pivot may be taken at the extremes of the range or near a center of mass (e.g., where $COM_\pm$ project on $\hat{w}_{\perp,k}$). Practically, the margin markers which control the margin boundaries are used to determine the limit for $\Delta L$. For example, $$\frac{\|\Delta w\|}{\|w\|} \leq \frac{p_{m2\pm} - p_{opt\pm}}{L} \qquad (53)$$

where $p_{m2\pm}$ and $p_{opt\pm}$ are the projections of the margin $m_2$ and $m_{opt}$ on $\hat{w}_\parallel$. Consequently, $S_{in\text{-}after} \subset S_{m_2\text{-}m_{opt}}$, and therefore, a search for elements are $S_{in\text{-}after}$ becomes limited to a relatively small dataset $S_{m_2\text{-}m_{opt}}$. In evaluating (52), it is first checked whether a given point in $S_{m_2\text{-}m_{opt}}$ has entered the tilted margin (e.g., via evaluating $y_i u_i$ or using (47)). Similar check is made for determining $S_{out\text{-}after}$ using (47) where the updated $u_i$ indicates whether a point in $S_{in\text{-}pri}$ has moved out of margin (i.e., to $S_{out\text{-}after}$).

To determine if objective function may be minimized by tilting w, (49), (50), and (51) are added for a given $\|\Delta w\|$ to check if the total slack error (denoted as a functional $\Delta \xi_{\perp,k}(\|\Delta w\|)$) is reduced for a particular $\hat{w}_{\perp,k}$. If so, $\Delta w$ adopts a component from $\hat{w}_{\perp,k}$ in proportion to the corresponding error reduction:

$$\Delta w = \eta \sum_{\forall \hat{w}_{\perp,k}} (-\Delta \xi_{\perp,k}(\|\Delta w\|)) \hat{w}_{\perp,k} \qquad (54)$$

where $\eta$ is a learning step parameter. In one approach, the contribution to $\Delta w$ is made if $(\Delta \xi_{\perp,k}(\|\Delta w\|)) < -\epsilon$, where $\epsilon$ is a threshold parameter. In another approach, the contribution is made when $(|\Delta \xi_{\perp,k}(\|\Delta w\|)| > \epsilon)$, allowing for taking the step in an opposite direction that of increasing slack error.

The next step of iteration is performed by updating the candidate w according to (54), and it stops for example when the objective function (42) does not improve significantly or a maximum iteration count has reached.

1.4 Estimation of Lagrange Multipliers

Based on the above preprocessing iterations, a set of candidate hyperplanes are generated for various values of C. According to KKT condition (28), $\alpha_i$'s are generated for bounded parameters (i.e., $\alpha_i=0$ or C). For any data point at margin, initialize $\alpha_i$ to C/2, and/or use (31) to determine such $\alpha_i$'s based on the distribution of unbounded parameters across $\hat{w}_{\perp,k}$.

One of the advantages of this approach is that quite immediately in its iterations, proper scale of C is readily determined.

2 Extension to Non-Linear SVM 2.1 A Case of RBF (Gaussian) Kernel

Equation (27) after kernel substitution for feature space becomes:

$$\mathcal{L}'(\alpha) = \sum_{i=1}^{N} \alpha_i - \frac{1}{2} \sum_{i=1}^{N} \sum_{j=1}^{N} \alpha_i \alpha_j y_i y_j \mathcal{K}(x_i, x_j) \qquad (55)$$

In the following approach, instead of attempting to break the problem of (N×N) quadratic form in (27), we make an assumption that in a relatively low dimensional space scenario, there are significantly more points in the margin than those exactly at the margin, and we attempt to find an approximate solution in the non-linear space via a low dimensional decomposition.

To have low number of support vectors with RBF (Gaussian) kernel, the data points need to be well represented or covered in $\langle^d$ via several kernels centered around few central points to be uniquely identifiable, e.g., through triangulation. This requirement helps to ensure that in the feature space the dimensions represented by the central points provide dimensional coverage for other data points in the dataset. Therefore, in $\langle^d$, we assign at least d+1 such centers to basically allow for triangulation. However, the requirement calls for coverage as well, so that a given point in the dataset would have non-trivial kernel values with respect to at least d+1 central points. RBF (proximity) kernel in input space is between (0,1], with the coverage dependent on the bandwidth parameter $\sigma$ as shown in (56):

$$\mathcal{K}(x_i, x_j) = \exp(-\gamma \|x_i - x_j\|^2), \qquad (56)$$
$$\gamma = \frac{1}{2\sigma^2}$$

Therefore, the coverage of each central point extends to at most several $\sigma$'s. Too small a $\sigma$ creates islands out of each input dataset, resulting in high dimensionality, high number of SVs, and relatively high out of sample error. In other words, the learning process memorizes the training data instead of learning the overall pattern for small $\sigma$. On the other hand, too large a $\sigma$, it will have difficulty negotiating stronger curves than the shape of the kernel allows.

Let there be l such centers in $\langle^d$ covering the input dataset, denoted as $G_j$ with j=1 to l. Because of coverage of every $x_i$, the set of $\mathcal{K}(x_i, G_j)$'s representing proximity to the centers triangulate $x_i$ with sufficient accuracy. Therefore, in the transform space Z, there are at least d+1 non-trivial dot products between $z_i$ and $H_j$ (i.e., the respective transformed counterparts of $x_i$ and $G_j$) to provide dimensionality coverage:

$$\mathcal{K}(x_i, G_j) = z_i \cdot H_j \tag{57}$$

Because of triangulation, $H_j$ define 1 dimensional space in feature space capable of supporting similar number of SVs. Note that given neighboring $G_j$ are within coverage of their closest centers as well (with non-trivial cross kernel), the set of $H_j$'s do not quite form an orthogonal basis in Z. However, with modifications in Z domain, an orthonormal set of feature vectors $\hat{v}_j$ may be constructed based on $H_j$. The first $\hat{v}_1$ is taken in the same direction as $H_1$, and the rest are determined, for example, by iterative subtraction process, so that $\hat{v}_j$ retain basic characteristics of the corresponding $H_j$ as much as possible:

$$\hat{v}_1 = \frac{H_1}{\|H_1\|} \tag{58}$$

$$= \frac{H_1}{\sqrt{\mathcal{K}(G_1, G_1)}}$$

or $$H_1 = (H_1 \cdot \hat{v}_1) \hat{v}_1$$

$$\hat{v}_2 = \frac{V_2}{\|V_2\|},$$

where $$V_2 = H_2 - (H_2 \cdot \hat{v}_1)\hat{v}_1$$

$$\hat{v}_3 = \frac{V_3}{\|V_3\|},$$

where $$V_3 = H_3 - (H_3 \cdot \hat{v}_2)\hat{v}_2 - (H_3 \cdot \hat{v}_1)\hat{v}_1$$

...

$$\hat{v}_j = \frac{V_j}{\|V_j\|},$$

where $$V_j = H_j - \sum_{j'=1}^{j-1} (H_j \cdot \hat{v}_{j'}) \hat{v}_{j'}$$

Note that $\|V_j\|$ as $\sqrt{V_j \cdot V_j}$ may be expressed via dot products of $H_1$ through $H_j$, and therefore, accessible in terms of cross kernels of $G_j$'s: $\mathcal{K}(G_{j'}, G_{j''})$.

All transformed data points $z_i$'s (including $H_j$'s) as well as hyperplane related vectors (e.g., $\hat{w}_\|$ and $\hat{w}_{\perp,k}$) may be expressed based on the orthonormal set of $\hat{v}_j$'s. For example:

$$H_1 = \sqrt{\mathcal{K}(G_1, G_1)} \, \hat{v}_1 \tag{59}$$

$$H_2 = \|V_2\| \hat{v}_2 + (H_2 \cdot \hat{v}_1) \hat{v}_1$$

$$H_3 = \|V_3\| \hat{v}_3 + (H_3 \cdot \hat{v}_2) \hat{v}_2 + (H_3 \cdot \hat{v}_1) \hat{v}_1$$

...

-continued $$H_j = \|V_j\| \hat{v}_j + \sum_{j'=1}^{j-1} (H_j \cdot \hat{v}_{j'}) \hat{v}_{j'}$$

$$= \sum_{j'=1}^{j} h_{j,j'} \hat{v}_{j'},$$

where $$h_{j,j'} = 0 \text{ for } j' > j$$

where $h_{j,j'}$'s are expressed via cross kernel of $G_j$'s. Similarly, for a $z_i$:

$$z_i = \sum_{j=1}^{l} z_{i,j} \hat{v}_j \tag{60}$$

On the basis of orthonormal set of $\hat{v}_j$'s, a lower triangular matrix $\mathcal{H}$ is constructed by transposing $H_j$'s as rows of $\mathcal{H}$:

$$\mathcal{H} = \begin{bmatrix} \cdots \\ H_j^T \\ \cdots \end{bmatrix} \tag{61}$$

$$= [h_{j,j'}]_{l \times l}$$

The components of $z_i$, i.e., $z_{i,j}$'s, are determined by inverting $\mathcal{H}$ as follows:

$$\mathcal{H} z_i = \begin{bmatrix} \cdots \\ H_j^T \\ \cdots \end{bmatrix} z_i \tag{62}$$

$$= \begin{bmatrix} \cdots \\ H_j \cdot z_i \\ \cdots \end{bmatrix}_{l \times 1}$$

$$= \begin{bmatrix} \cdots \\ \mathcal{K}(G_j, x_i) \\ \cdots \end{bmatrix}_{l \times 1}$$

Therefore:

$$z_i = \begin{bmatrix} \cdots \\ z_{i,j} \\ \cdots \end{bmatrix} \tag{63}$$

$$= \mathcal{H}^{-1} \begin{bmatrix} \cdots \\ \mathcal{K}(G_j, x_i) \\ \cdots \end{bmatrix}_{l \times 1}$$

The above shows that a slice of original kernel matrix in (55) is used to deal with the data in feature space. The coverage and triangulation in input space implies redundancy in the kernel matrix. In other words, if two input points $x_1$ and $x_2$ may be located in $\langle^d$ based on their kernels (or distances) to $G_j$'s, then per (63), $\mathcal{K}(x_1, x_2)$ (which is $(z_1 \cdot z_2)$) may be expressed in terms of $\mathcal{K}(G_j, x_1)$'s, $\mathcal{K}(G_j, x_2)$'s, and $\mathcal{K}(G_j, G_{j'})$'s. The accuracy in which this is possible can be used as a validation of coverage and triangulation to ensure the dimensionality of the feature space can support decomposition in (60) and (63).

The machinery of previous sections can thus be brought to bear in the feature space, as all expressions are convertible to dot products (such as projections of the data points on certain directions).

EXAMPLES

Example for Z-Advanced-1

A method for recognition of faces from a still image or video frame, said method comprising:
receiving a still image or video frame through an input interface;
preprocessing said still image or video frame;
recognizing a first class of image for said still image or video frame;
if said first class of image for said still image or video frame comprises face or human, then sending said still image or video frame to a face recognizer module;
said face recognizer module accessing a first basis function from a first library of basis functions, stored in a first basis function storage, corresponding to a first component of face;
said face recognizer module accessing a second basis function from a second library of basis functions, stored in a second basis function storage, corresponding to a second component of face;
a computing processor applying said first basis function across said still image or video frame to detect said first component of face;
said computing processor applying said second basis function across said still image or video frame to detect said second component of face;
said computing processor accessing a relationship between said first component of face and said second component of face;
assigning a first node and a second node on a relational web to represent said first component of face and said second component of face, respectively;
assigning a first branch connecting said first node and said second node on said relational web to represent said relationship between said first component of face and said second component of face;
assigning a first Z-factor, a second Z-factor, and a third Z-factor to said first node, said second node, and said first branch, respectively;
wherein Z-factor is a mathematical set of factors comprising one or more of reliability factor, confidence factor, truth factor, expertise factor, bias factor, knowledge factor, usefulness factor, and relevance factor;
said computing processor analyzing said first Z-factor, said second Z-factor, and said third Z-factor for said first node, said second node, and said first branch;
said computing processor detecting one or more faces in said still image or video frame, with a fourth Z-factor, based on said analysis step;
said computing processor comparing said detected one or more faces with said fourth Z-factor against a library of faces, each with its own said Z-factor, stored in a first face storage;
if said detected one or more faces match or correspond to a first face in said library of faces, then outputting identity or identification number of said first face, as identification for said detected one or more faces from said still image or video frame, along with a fifth Z-factor corresponding to said matching or correspondence to said first face.

Example for Zadeh-101-Cont-1

A method for determining a Z-valuation, said method comprising:
inputting one or more rules into a rules engine, wherein said rules engine is run by a processor device;
receiving one or more fact information by said rules engine;
setting up one or more protoforms in a first memory location or unit;
establishing one or more relationships related to said one or more protoforms;
extracting a first attribute from said one or more relationships;
filtering possible reciprocal relationships from a first database, wherein said possible reciprocal relationships are selected based on said first attribute;
determining a first reciprocal relationship based on said filtering step;
determining a first consequential attribute based on said first attribute;
determining one or more synonym attributes based on said first attribute, wherein said one or more synonym attributes reside on a second memory location or unit;
instantiating a first supplemental relationship based on said one or more synonym attributes, said first reciprocal relationship, or said first consequential attribute;
expanding one or more additional relationships by matching a first set of attributes to a first set of general rules from a knowledge base, stored on a second database;
determining a first Z-valuation based on said first supplemental relationship.

Example for Zadeh-101

A method for fuzzy logic control, said method comprising:
an input module receiving a precisiated proposition associated with a protoform;
a fuzzy logic inference engine evaluating a first fuzzy logic rule from a fuzzy logic rule repository;
wherein said fuzzy logic inference engine is in or loaded on or executed on or implemented in a computing device;
wherein said computing device comprises one or more of following: computer, processor device, integrated circuit, microprocessor, or server;
wherein said fuzzy logic rule repository comprises one or more fuzzy logic rules;
wherein said first fuzzy logic rule comprises an antecedent part and a consequent part;
wherein said precisiated proposition comprises a Z-valuation;
wherein said Z-valuation is in a form of ordered triple (X, A, B), representing a statement assignment of X to a pair (A, B);
wherein X represents a variable, A is a fuzzy logic set in domain of X, and B is a fuzzy logic set representing a certainty indicator of X being possiblistically restricted by said fuzzy logic set A; and
said evaluating step comprises:
a test score evaluation module assigning a first test score to a candidate probability distribution for X based on said Z-valuation;

wherein said candidate probability distribution belongs to a set of candidate probability distributions;

said test score evaluation module assigning a second test score to said antecedent part based on said antecedent part, said set of candidate probability distributions, and said first test score; and said fuzzy logic inference engine determining whether said antecedent part is satisfied beyond a threshold, based on said second test score.

Example for Zadeh-101-Cont

A method of search for an item, said method comprising:
a first input module receiving a first item;
wherein said first item is associated with a first Z-number;
a second input module receiving a second item;
wherein said second item is associated with a second Z-number;
a relevance analysis module generating one or more first relevant items from said first item, using a relevance storage database;
said relevance analysis module generating one or more second relevant items from said one or more first relevant items;
said relevance analysis module generating one or more third relevant items from said second item;
a correlation degree module receiving said one or more second relevant items and said one or more third relevant items;
wherein said one or more second relevant items are associated with a third Z-number;
wherein said one or more third relevant items are associated with a fourth Z-number;
wherein said third Z-number is dependent on said first Z-number;
wherein said fourth Z-number is dependent on said second Z-number;
said correlation degree module analyzing a correlation between said one or more second relevant items and said one or more third relevant items, using one or more correlation rules, from a correlation rule storage, based on said third Z-number and said fourth Z-number;
based on said correlation analysis, a computing device deciding whether to connect said one or more second relevant items with said one or more third relevant items;
if said one or more second relevant items is connected with said one or more third relevant items, then associating said second item with said first item.

Example for ZAdvanced-1-Cont

A method of storage for data in a computer media, said method comprising:
an input module receiving a first data;
a computing processor module fuzzifying said first data, to produce a second data;
said computing processor module fuzzifying said second data, to produce a third data;
a storage management module storing said first data in a first memory unit;
said storage management module storing said second data in a second memory unit;
said storage management module storing said third data in a third memory unit;
wherein said first memory unit is for short term storage;
wherein said second memory unit is for medium term storage;
wherein said third memory unit is for long term storage;
accessing said first data, said second data, or said third data, through an interface;
after a first expiration date, said storage management module deleting said first data from said first memory unit;
after a second expiration date, said storage management module deleting said second data from said second memory unit;
wherein said second expiration date is after said first expiration date.

Example for ZAdvanced-1-Cont

A method of searching for an item in an image or video, said method comprising:
an input module receiving an image or video frame;
an object recognizer recognizing an object in said image or video frame;
a computing processor unit accessing a database for list of one or more items related to said object;
said computing processor unit receiving information about statistics of position of said one or more items with respect to position of said object;
wherein said object corresponds to a first node on a Z-web;
wherein said one or more items correspond to a second node on said Z-web;
wherein a first Z-factor relates said first node to said second node on said Z-web;
said computing processor unit defining a radius or region of search on said image or video frame, based on said position of said one or more items with respect to position of said object, and based on said first Z-factor;
an item recognizer searching for said one or more items within said radius or region of search on said image or video frame.

Example for ZAdvanced-1-Cont

A method for supervised descriptive training of a recognition system, said method comprising:
rendering an image based on a model driven by invariant or semi-invariant parameters, variant parameters, and pose parameters;
wherein said pose parameters comprise one or more of orientation, position, and scaling type parameters;
wherein said invariant or semi-invariant parameters are invariant or semi-invariant with respect to different poses and expression of same person or object rendered by said model;
wherein value of said variant parameters are in common for various people or objects with same or similar expressions rendered by said model;
detecting or classifying a feature set from said image;
taking an optimization step in training a correlation layer using said feature set and one or more of said invariant or semi-invariant parameters, said variant parameters, and said pose parameters, as input to said correlation layer; and
wherein said correlation layer comprises stochastic sigmoid units and unidirectional weighted links.

Example for ZAdvanced-2-Prov-Cont

A method for feature space translator, said method comprising:
selecting or generating training data or image from a model renderer or a database;

detecting or classifying a first feature set from said training data or image by a first feature detector;

detecting or classifying a second feature set from said training data or image by a second feature detector;

taking an optimization step in training a correlation layer using said first feature set and said second feature set as input to said correlation layer;

wherein said correlation layer comprises stochastic sigmoid units and unidirectional weighted links; and wherein said correlation layer, upon training, outputs a translated feature set, given a third feature set as input to said correlation layer.

Example for ZAdvanced-1-Cont

A method for geometrical abstraction for a recognition system, said method comprising:

an input module receiving an image or video frame;

an object recognizer unit recognizing an object in said image or video frame;

a computing processor applying a skeleton operator or thinning filter to said object in said image or video frame, to produce a basic shape;

a matching module comparing said basic shape with members of symbols library, geometrical objects library, and alphabets library;

describing said basic shape with said members of said symbols library, said geometrical objects library, and said alphabets library;

said matching module comparing said basic shape with combinations of said members of said symbols library, said geometrical objects library, and said alphabets library;

encoding said basic shape with combinations of said members of said symbols library, said geometrical objects library, and said alphabets library;

associating a Z-factor to said described basic shape and said encoded basic shape;

storing said described basic shape and said encoded basic shape in a geometrical descriptor database;

receiving another item in an image or video;

based on said geometrical descriptor database for said object and said another item, comparing said object to said another item.

Example for ZAdvanced-1-Cont

A system for feature detection with reliability, said system comprising:

one or more layers of stochastic units;

one or more weighted links associating a first stochastic unit of said one or more layers of stochastic units with one or more linked units;

a layer of input units;

wherein a set of data is input to one or more of clamped input units in said layer of input units;

a set of detected features;

wherein said set of detected features are associated with a top layer of said one or more layers of stochastic units;

wherein an energy measure corresponding to said set of data is determined based on factors comparing said one or more of clamped input units, said one or more weighted links, and said one or more layers of stochastic units;

wherein a reliability or conformity measure corresponding to said set of detected features is determined based on said energy measure and a baseline.

APPENDICES

Please note that Appendices 1-5 teaches the details of the inventions, which are accompanied here with this filing, and also incorporated by reference from the parents and prior applications/patents/provisionals mentioned on this current spec.

For the current inventions, we can combine any and all the systems and methods of our own prior applications, which we have priority claim for, as mentioned on the current spec/application, to provide very efficient and fast algorithms for image processing, learning machines, NLP, pattern recognition, classification, SVM, deep learning, and the like, for all the applications and usages mentioned here in this disclosure, with all tools, systems, and methods provided here.

Other Embodiments

In one embodiment, as for example depicted in FIG. 261, the extent of the connectivity between the visible units and higher units are limited (local extent). This helps reduce the number of parameters for better regularization. In one embodiment, the local extent may be uniform across the image or vary in size or shape. In one embodiment, the higher level cells may connect to the visible units via overlapping and/or non-overlapping local extent (fan-out). Similar limitation of local extent may be imposed between higher layers, as well.

In one embodiment, as for example depicted in FIG. 261, the local extent is defined by a patch of visible units, for example in a rectangular, circular, or polynomial (e.g., hexagonal) form. In one embodiment, some patches may overlap and some patches may not overlap each other. In one embodiment, the pattern of the patch arrangements may be a regular of non-uniform across the image.

In one embodiment, as for example depicted in FIG. 262, a portion or all of the visible layer/cells are divided to (overlapping and/or non-overlapping) patches, and a feature set $\{k_1, \ldots, k_n\}$ is used to drive the features from the cells/visible units from patches (e.g., patch i and j in FIG. 262). Such feature sets may include various functionalities, such as convolution, averaging, contrast, edge detection, color representation (e.g., based on DCT or other transformations). Each k in feature set may be multidimensional depending on the corresponding feature. In one embodiment, feature k may be a linear combination of the underlying cell attributes (e.g., color, or value) with a non-linear function (e.g., tan h or sigmoid) applied to the result. In one embodiment, some features may be deterministic and some features may be probabilistic (e.g., the resulting function determines the probability of the feature value (e.g., to be on/off)). In one embodiment, the weights and offsets (e.g., $w_{i,k1}$, $b_{i,k1}$) related to patch i and the feature set are represented by vectors, arrays, and/or tensors.

In one embodiment, the same feature sets having the same weights/biases are used for multiple patches (overlapping or non-overlapping). In such an embodiment, the total number of parameters (degrees of freedom) relating the visible units to the feature sets are reduced drastically which helps the regularization (i.e., avoids overfitting during the training) and provides translational invariance, i.e., learning a line piece in one patch implies learning it in other patches. In such an embodiment, a collection of such reusable features are treated as standard feature sets that may be applied to all sorts of input images, as they contain the basic image processing common to many types of images. In one embodiment, only a subset of features are evaluated at a given time for a given patch to conserve computational resources (e.g., CPU cycles and memory), based on other information or triggers. In one embodiment, upon automatic inference, more features are activated to get evaluated for a patch, e.g., where the inference module/engine indicates that a feature is expected in or about the patch's location (e.g., with a probability above a threshold) or randomly selected based on an exploration mode.

In one embodiment, the features are further combined at higher layers for more complex (abstract) features. With increasing layers, the locality may be reduced due to fan-out. In one embodiment, at a level where the features are potentially liked to any/every visible unit, the subsequent levels are more fully connected (in contrast to sparse connections from the visible layer).

The localization of the concepts (e.g., circle, ellipse, line, or other free form geometries) from upper layers is achieved by driving down at each layer based on fan-out extent. For example, to determine potential intercept points of the circle and a line recognized at upper layers, a reconstruction along the fan-out cells are used to determine cells in common to both fan-outs. In driving down the layers, the concept would change from high level (e.g., circle) to arc/pieces to pixels in the visible layer.

In one embodiment, as for example depicted in FIG. 263, the feature set may detect geometric features such as lines, arcs, segments, dash lines. In one embodiment, such a feature set may be used at various layers, where the lower layers have more limited coverage extend of the visible layer due to fan-out limitation. In one embodiment, feature sets (e.g., averaging) may be used in subsequent layers to effectively form a thumbnail at a higher layer. The similar feature sets (e.g., detecting geometrical shapes) would be used regardless of the scale reduction toward higher layers, to detect, for example, a small circle in a lower layer, and a larger circle at a higher layer. In one embodiment, use of various pre-learned or pre-defined feature sets helps with the regularization and reduces duplicity in learning features.

In one embodiment, as for example depicted in FIG. 264, the feature detection occurs based on other features, e.g., via inference or pattern. For example, when a stroke or line is detected in one block or patch, the detection attributes would indicate a pattern or direction which is used, for example with other information, to infer which other patch(es) might contain this or other features. In one embodiment, features are sub-detected sequentially. In one embodiment, sub-features are detected in parallel from various existing sub-features. In one embodiment, the inference as to which portion/location/area of the image may have features is learned via known training samples, by learning the relationships (e.g., arrangements) between features.

In one embodiment, the range of weights, biases, and/or input values are granularized (e.g., using fuzzy sets) and the dot product is made based on fuzzy sets.

In one embodiment, an image patch is normalized, e.g., by getting average intensity/color and contrast/direction/DCT features of the patch.

In one embodiment, a kernel is used in feature detection/classification, with discrete values. In one embodiment, input values of the training samples (and/or weights/biases) use discrete values. In one embodiment, discrete values are in $\{-1, 0, +1\}$. In one embodiment, a (proximity) kernel is defined as $\oplus(x_i \otimes y_i)$, where $(x_i \otimes y_i)$ is defined as +1 when $x_i=y_i$; −1 when $x_i=-y_i$ and $x_i \neq 0$; and 0 otherwise; and where $\oplus(\ldots)$ is defined as in various forms, such as +1 when none of the constituents is −1 and majority of constituents +1 (or their summation is above a threshold value); 0 when none of the constituents is −1 and majority of constituents are 0; and −1 otherwise.

In one embodiment, the learning process of the learning machine uses a statistical approach to hypothesis parameters by keeping track of those values over time during fitting the data fitting, with more weight given to those parameters occurring more often.

In one embodiment, as for example depicted in FIG. 265, the patches and/or unit coverage with a patch are arranged in a radial fashion. In one embodiment, the feature detectors for connected to the patches or the units are restricted to have their weights follow the symmetry (e.g., either be the same or correlated at different angles), so that once the detector learns a feature in an image, it would be able to detect same feature rotated at a somewhat different angle.

In one embodiment, the dot products and non-linear functions used for neural cells are implemented via electronics, e.g., using a circuit depicted in FIG. 266. Other variations of the circuit or its equivalents may be used. Weights (including the bias) are input to gates of the transistors to modulate the current. At low voltage (on $x_i$ side), the current is approximately linear with $x_i$ and dependent of the transconductance (which depends on the gate voltage). The current in the transistor can be made proportional to both $x_i$ and $w_i$ (or inverse thereof). The operational amplifier in negative feedback creates a virtual ground that forces the sum of the currents of the input transistors to pass through one of the clamping diodes (depending on the direction) by adjusting the output of the operational amplifier. The output voltage follows back-to-back inverted turn-on diode characteristics that resemble sigmoid or step functions. In one embodiment, the weights are provided to the circuit using a programmable device (e.g., FPGA), memory device (with connected paths to transistors), ASIC, buffers, and/or serial input.

In one embodiment, an ad network uses image recognition platform to match on-line images (e.g., on a publisher's webpage, posting, message, email, or a Tweet) to one or more visual items (or attributes derived from visual items) such as merchants/advertisers' catalog items. In one embodiment, (a) publisher and/or merchant/advertiser aggregators are used to scale the system to reach more merchants and publishers, (b) the system uses consistent and fewer interfaces, (c) the system reuses the image-based ads for webpages/images that are shared, pinned (e.g., in content aggregators such as Pinterest), or tagged/liked (e.g., in social networks, such as Facebook), or contain identical images (e.g., based on hash/block signature assigned to crawled images), in order to create a multiplier effect on the ad reach and revenue generation, and/or (d) relevant image-based ads (e.g., on social network applications such as Facebook wall/timeline next to a friend's liked image, pinned/tagged images, e.g., as in Pinterest, or shared images or webpages) are significantly more rewarding and much less annoying alternative to irrelevant native ads, on a desktop or mobile settings.

One embodiment uses a deep level cognitive approach for recognition, in contrast to traditional approaches that (a) have many training samples only to learn what to ignore (e.g., a flower decoration on vamp of the shoe) (b) provide results in generic classification and identification of objects, and (c) treat the whole image as only one object with many parts/attributes. In one embodiment, a deep cognitive approach uses a learnable recursive inference approach to treat objects as flexible collection of features (components) and the learning encompasses the components relationships in a model layer. In one embodiment, the learning continues when unexpected or one-off components are encountered. In one embodiment, far less number of training samples is required to recognize complex objects (where in some instances, there may not even be enough training samples for conventional methods when object's loose component variation increases). In one embodiment, the untying of the learning of loose components and their arrangements, require less number of training samples, and it provides flexibility in learning/recognizing the integration arrangements of various components and features for making inference about where/what features may be found in the input data (e.g., image).

In one embodiment, as for example depicted in FIG. 267, a recursive approach is used to build knowledge from data (e.g., image, voice, video, text). In one embodiment, the data (e.g., image) is further explored based on the prior knowledge (e.g., is that a glove or a hand? Does the color match the face?). In one embodiment, expected features are confirmed and more refined features are extracted. In one embodiment, unexpected features are learned, and may be later used as particular search term (e.g., a narrow red band on the heel cap). In one embodiment, recurring features are re-prioritized in the recursive recognition. In one embodiment, the system learns to infer or learns to search for features, e.g., based on detection of known features (e.g., in training samples or previously detected features), learn effective discovery process/rules (e.g., as in learning the rules of a game by simulating the games) and optimizing based on cost of success (finding feature) and failure (not finding feature) (e.g., based on CPU usage or memory requirement). The learning will capture the patterns of the relationships between the components of the objects and the inference follows the spatial relationships of the components (e.g., probabilistically or by generation or reconstruction of the phantom samples, for example, by clamping the visual and/or hidden layer(s) to the found feature; or e.g., by executing captured rules). For example, a person's head or a hand in an image leads to body and infers orientation of the body (parts). In one embodiment, the search for features uses stochastic approach, so that the search has a chance to stumble upon unexpected features and/or have a coverage of the data (e.g., image).

In one embodiment, functional attributes/features can be targeted and learned. For example, consider a shoe object. Different shoe styles have various (common/uncommon) attributes or components (e.g., sole, platform, vamp). What makes a shoe "a shoe" is various (flexible) combinations of such components & attributes in particular or fuzzy arrangements. Designer shoes have their own attributes, e.g.: red band at the sole, flower decoration on toe box, fluffy decoration on the counter, logo on the outer side. In one embodiment, such combinations, arrangements, and relationships are learned, and the learned relationships are used as predictor of features and their locations/arrangements in presence or absence of other features, e.g., shape/geometry, relative position, hidden surfaces/coverage. Functional abstraction is an attribute at the high level, e.g., vamp extends platform to cover front of foot.

One embodiment uses predictive feature detection. In one embodiment, the inference module predicts where the features might be based on the initial recognition. This approach provides feature discovery in exploratory/recursive manner. In one embodiment, the approach takes a coarse to fine window/field of focus (including finer effective pixel size) to get (or confirm) additional fine features, e.g., based on initial confirmation. In one embodiment, detecting one feature leads to other features via inference module. In one embodiment, when detection fails to confirm the presence of the expected or inferred feature, a detection module captures the new or one-off feature(s) for later classification, or the inference module adjusts initial recognition assumptions.

One embodiment uses soft classification for training, based on soft similarities and soft dissimilarities, e.g., by using soft class boundaries. In one embodiment, interest points/locations are used in training to learn spatial features/relations and to provide anchors for further exploration of features. In one embodiment, such interest points are used to learn 3D model of the object from multiple image of the same or similar object from various perspective. In one embodiment, hidden features/points/surfaces are learned in the model layer.

One embodiment uses progressive feature selection and prioritization. In one embodiment, the feature selection and prioritization are used for efficiency, e.g., the detection looks for hands first or faces first, or run parallel, and then it looks for other body parts. In one embodiment, the priority and selection of features are learned or determined, e.g., based on strong correlations and frequency of features, e.g., in training samples and/or later detected input data. In one embodiment, some of one-off features are gradually categorized as common features, e.g., based on occurrences and/or cost functions, e.g., in one embodiment, it is less costly to look for common features before others (as strong predictors of other features).

In one embodiment, a fuzzy match between features is used during search. For example, consider features indicating narrow red band on high heel. "Red" may be matched with reddish, and fuzzy attributes such as "Narrow", "wide", "high", "short" would be relative to other features and to the same feature present in other images.

In one embodiment, a recursive inference module uses patterns of the features detected to predict the potential location/existence (and their likelihood) of other features. One embodiment uses a recursive inference to feed the model layer with data from the same data/image (or sequence of images as in a video) to look for other expected features to confirm and fine tune the model or discover new and/or unexpected features (e.g., a decorative flower on the vamp of the shoe). One embodiment uses component level approach to determine the similarity measure of data/images for search at the image level, at the component level, or both. Such component level approach enables fast search at the component level. One embodiment uses simultaneously search for a mix of features derived from multiple datasets (e.g., images). For example, the user can search for a shoe having a high heel similar to the shoe in one image, toe cap similar to a shoe in another image, and a flower decoration similar to a shoe in yet another image. In one embodiment, by untying the learning of loose components and their arrangements, the training requires less number of training samples, and it provides flexibility in learning/recognizing the integration arrangements of various components and features for making inference. One embodiment uses component masking between recursive feature detections which makes the later fine feature detection more efficient and accurate both in terms of learning and recognition. In one embodiment, a new object representation may be conceived and searched by new combinations of features the user may specify via a user interface, e.g., a shoe with a red band on its sole (like shoe #1) and decorative flower on its vamp (like shoe #2).

Some object categories have highly integrated components (e.g., in face recognition for frontal (naked) face). In such an example, visual attributes (nose, eyes, lips, chin, etc.) are always present and tightly integrated together. Such categories of objects may be learned and recognized in one-go (i.e., by capturing the highly integrated pattern of arrangement along with the components in one-go). However, in the other extreme, for example, a scene from a street (with people and objects loosely integrated with respect to each other) would be difficult to learn or be recognized using such one-go approach, because it would require an very large number of training samples and very deep (many layered) neural network, based on traditional methods, which would also be hard to converge (i.e., impossible or hard to learn in one shot due to loose patterns, sparsity, and one-off situations). In practice, various complex objects (e.g., shoe, or faces with hats/beards/glasses) fall somewhere in between in the spectrum of Integration Flexibility. In one embodiment, the recursive inference approach takes advantage of the integration flexibility and provides more efficient and accurate recognition and search.

by changing the view perspective (and/or illumination) of an object. Such learning may be used, in one embodiment, to learn the structural and overall shape of the object and its orientation, for fast recognition and masking, e.g., prior to make fine recognition of features of the object. The outline/mask of the object is also learned during the training, in one embodiment. In one embodiment, the mask is applied to visible units (e.g., during recognition) by, for example, ignoring units outside the masked portion, or forcing a highly contrastive unit value for outside units neighboring the mask periphery, based on the inside units at the periphery. In one embodiment, when learning a training object, a mask is used to limit the training image to the inside mask portion of the visible units. One embodiment, during training, either unclamps the other visible units (outside of mask) or set them to highly contrastive values, based on the visible units inside the mask.

TABLE 1

Comparison of an embodiment with traditional approach

| Characteristic | Recursive Inference Deep Level Approach | Traditional Learning Approach |
|---|---|---|
| Image/data size | Can be large | Limited to small size due to limited $1^{st}$ layer visible units set prior to learning |
| Image/data isolation | Can learn to find features | The features in the images are required to be isolated to begin with, e.g., with features restricted to occupy good fraction of the image (e.g., at least 1/3) |
| Fine features | Can be detected during recursion | Ignored completely, as not being a principal feature |
| Detection Level | Fine & detailed down to components | Generic categorization |
| Component integration flexibility | Scalable and flexible | Not scalable or flexible |
| Training approach | Mix of training of components for feature detectors and training of the integration arrangement for inference | Training in one-go requires far more training samples (even if possible to learn more loosely arranged components) |
| Learning additional/unexpected features | Guided by inference | Impossible. Requires full retraining of everything (i.e., old and new features), as the weights and parameters all have to be changed |
| Size of training samples | Limited number of samples would be enough to deal with components and their arrangements. | Much larger training samples needed to deal with more loosely integrated or flexible components (with no guarantee that training may even be successful) |
| Training/recognition cost of complex objects | Less expensive with less number of calculations. Learning of loose components may be separately optimized. | More expensive with more calculations required for more layers to hardwire, with more training samples. It is even more likely to overfit the data with excessive number of parameters (i.e., not learning the patterns, but memorizing the training samples). |

In one embodiment, human subjects are used to learn the inference, by automatically monitoring the movement of eye's focus and/or field of view on displayed images/objects to determine which features are visited/located/revisited and in which order and/or frequency. This data is used as part of the training set for the inference module/engine to learn how to locate other features when it locates a feature in an image/data.

In one embodiment, the model layer is fed with detected features of the same object, for example from a video or multiple images, to improve the features or confirm. In one embodiment, the images are simulated or prepared manually One embodiment uses a cognitive layer in addition to the deep neural network. In one embodiment, the relationships of object components (e.g., hand and face) are learned and used to infer expected position and state of other features (e.g., the hand with respect to the position of the face).

In one embodiment, l coverage $G_j$ points/centers are used in $\langle$ d, covering the input dataset for training an SVM. In one embodiment, clustering is used to determine candidate center points. In one embodiment, $G_j$ is initially randomly chosen and the choice is validated against decomposition in transformed space. For each scanned input data point, $x_i$, the decomposition of $\mathcal{K}(x_i, x_i)$ or $\mathcal{K}(G_j, x_i)$ is evaluated, and if it the validation fails beyond a threshold, then $x_i$ is assigned to be the next center, $G_{j+1}$. If all/coverage $G_j$ points/centers are assigned in this manner, the remaining data points are validated similarly. If there is a failure, then either the number of centers are increased, or a previously assigned center is given up in favor of the new one, e.g., based on closeness of previously selected centers based on $\mathcal{K}(G_j, G_{j'})$.

In one embodiment, an image ad network detects efforts to bypass the ad network by putting dummy unknown web sites, so that if a publisher attempts to bypass the network and reuse ad landing page link, the attempt can be detected, logged, and notified.

In one embodiment, a layer of cognitive processing with rules engine is used with a deep learning machine, e.g., using Z number for rules (e.g., having a rule that in summer, people usually wear short sleeve shirts, or people usually wear short sleeve shirts with cargo pants) to match, infer, recognize, or correlate objects in images.

In one embodiment, a 3D model is learned by using a rotating/pivoting controllable pedestal as a platform to support an object and/or camera and take pictures/videos for training, e.g., a shoe out of a class as a representative, to teach the learning machine recognize the orientation attributes.

In one embodiment, the ads displaying the items of the competitor merchants are not displayed on the merchant's webpage, by filtering the matching sources or limiting the source to the particular merchant. In one embodiment, the visual ads are based on the image, text, and history/behavior of user.

In one embodiment, the consensus voting is used with for crowd tagging, so that bad actors or mistakes are detected, and a person making repeated mistake (e.g., beyond threshold is identified and notified, or dropped).

In one embodiment, when a feature selection occurs often enough (e.g., with CPU cost lowered), the feature selector is moved up in a priority to an earlier pass at the data/image.

In one embodiment, the fine level detection of a component is done as a later task, e.g., asynchronously or as needed, for example, a deep recognition for detecting the seams on the shoe may be done at a later time or based on triggers (demand, number of inquiries).

In one embodiment, a learning machines discovers new patterns in a class, such as a new shoe, by for example detecting unelected features. In an embodiment, such features are stored for later correlation and pattern recognition, as the instances increase.

In one embodiment, a face recognition engine recognizes/detects micro expressions (e.g., happy, angry, sad, contempt, etc.) for behavior analysis (e.g., for humans) by frame by frame analysis, e.g., for automation for psychological analysis.

In one embodiment, the tone of skin, hair color, and/or eye color is detected and matched with clothing and shoes and/or lip stick and other accessories, automatically, based on fashion rules and color rules.

In one embodiment, the SVM use (proximity) kernels based on similarity measures assigned, e.g., by crowd tagging, as the input to kernel matrix, e.g. indicating the similarities between objects and/or object components, e.g., shoes, shoe laces and other features of the shoe. One embodiment, uses similarity measures on the component/feature level. One embodiment isolates the feature, e.g., via correlation. One embodiment determines several labels (for components) and assess similarities on the components via their labels, tag components (e.g., red band on the heel).

One embodiment uses a cognition module to capture abstract rules (e.g., what a shoe is), e.g., by using subject matter expert and also crowd sourcing.

In one embodiment, the input impression is summarized and fuzzified, e.g., 30-35 C temperature outside with probability of about 25 percent becomes low 30s with low probability.

In one embodiment, geometric features are detected separate form functional features (e.g., hat or shoe). In one embodiment, functional features (e.g., shoe vamp) are correlated.

In one embodiment, additional training samples are creates by offsetting, rotating, re-coloring, adding noise, adding contrast to the original image.

In one embodiment, the delta between the expected feature and unexpected feature is learned, e.g., a red spot on a shoe which expected based on the model layer. If encountered many times, then this is taken as a feature to detect earlier in the recursive process. So, the model gets richer, and the system learns and grows the model.

In one embodiment, the training commences with simple (e.g., computer generated simple images), with no exceptional features, gradually expands to richer feature, and finds patterns with these exceptions, as correlation, and append to model for next rounds of recognition.

In one embodiment, the priority of processing of information (e.g., parallel and sequential, or mix) is optimized.

In one embodiment, one or more object components are detected first (e.g., head, face, hand, shoe), and then, the inference module uses the model layer or learned patterns (e.g., via a neural network) infers the rest of body (e.g., shirt and elbow). The feature detectors then zoom/locate the interest areas sequentially or in parallel, for confirmation or fine detection. For example, a component that looks like zipper on shirt, based on structure, shape or position, may further be fine detected to conclude that it is a zipper. In one embodiment, the detection tasks are prioritized (e.g., scheduled for execution asynchronously).

In one embodiment, model can anticipate by recognizing component (or a label), e.g., an object is recognized to be a cat, even from its paws or part of body.

In one embodiment, the training samples includes cartoonish, simple silhouette, shadow shape images.

In one embodiment, a GPU hardware is used for image processing and calculations, e.g., related to the neural networks.

In one embodiment, multiple specialized recognizers are used for recognition of shoe, head, hand, in parallel, each doing its own focus and duty, with its own neural net, which is very small compared to general purpose neural net.

One embodiment uses multiple basis functions for various objects such as face locating and shoe locating simultaneously in parallel.

One embodiment uses different weights for features/components for recognition/search, as some are more important than the others or more relevant in the context, e.g., in recognizing an individual in a specific race faster, based on, e.g., more primary features for that subset.

The invention claimed is:
1. A system for feature detection, said system comprising:
one or more processors;
multiple input units;
wherein a second set of data determines a first subset of said multiple input units to be clamped to a first set of data;
wherein in clamping a first input unit of said multiple input units, said one or more processors dynamically set a value of said first input unit in a first memory unit associated with said first input unit to a corresponding value from said first set of data;

one or more layers of stochastic units, comprising a first stochastic unit;

wherein said first stochastic unit has one or more links traceable to a second subset of said multiple input units, wherein a local coverage extent associated with said first stochastic unit limits said one or more links;

wherein said one or more links represent first weighted connections between said first stochastic unit and second units;

wherein said second units are among said second subset of said multiple input units or from said one or more layers of stochastic units between said first stochastic unit and said multiple input units;

wherein said one or more processors set a memory unit associated with said first stochastic unit to a first value generated based on weighted sum of values of memory units associated with said second units per said first weighted connections represented by said one or more links;

wherein said one or more processors detect sub-features associated with a higher layer of said one or more layers of stochastic units, based on sub-features detected by a lower layer of said one or more layers of stochastic units;

one or more output units;

wherein said one or more processors set a memory unit associated with said one or more output units to a value indicating a detected feature based on one or more said detected sub-features associated with one or more layers of one or more units of said one or more layers of stochastic units;

wherein said one or more processors determine an energy measure corresponding to said first set of data, based on factors comprising of said first weighted connections, said one or more layers of stochastic units, and said first set of data clamped to said first subset of said multiple input units;

wherein in said determining said energy measure, a contribution of said energy measure from said first stochastic unit is reduced by a coverage factor of said first stochastic unit;

wherein said coverage factor of said first stochastic unit is determined based on a value representing fraction of input units within said second subset of said multiple input units traceable from said first stochastic unit that are also in said first subset of said multiple input units clamped to said first set of data;

wherein said one or more processors output to a second memory unit a value representing a quality measure associated with said detected feature determined based on said energy measure and a baseline.

2. The system for feature detection as recited in claim 1, wherein said system is feeding or is fed by an ad network.

3. The system for feature detection as recited in claim 1, wherein one or more units of said multiple input units not belonging to said first subset of said multiple input units are reconstructed based on said one or more layers of stochastic units or said detected feature.

4. The system for feature detection as recited in claim 1, wherein said system is part of an image ad network.

5. The system for feature detection as recited in claim 1, wherein said system recognizes objects or people.

6. The system for feature detection as recited in claim 1, wherein said first stochastic unit is binary.

7. The system for feature detection as recited in claim 1, wherein said system recognizes emotions.

8. The system for feature detection as recited in claim 1, wherein said system recognizes human behavior.

9. The system for feature detection as recited in claim 1, wherein said system matches ads with merchant catalogs.

10. The system for feature detection as recited in claim 1, wherein said system recognizes natural language.

11. The system for feature detection as recited in claim 1, wherein said system recognizes voice.

12. The system for feature detection as recited in claim 1, wherein said system is a part of a search engine.

13. The system for feature detection as recited in claim 1, wherein said system is connected to or associated with a web.

14. The system for feature detection as recited in claim 1, wherein said system recognizes patterns in social networks.

15. The system for feature detection as recited in claim 1, wherein said system recognizes actions in video.

16. The system for feature detection as recited in claim 1, wherein said system is associated with a classifier.

17. The system for feature detection as recited in claim 1, wherein said system recognizes components of an object.

18. The system for feature detection as recited in claim 1, wherein said system learns by itself.

19. A system for feature detection with reliability measure, said system comprising:

one or more processors;

multiple input units;

wherein a second set of data determines a first subset of said multiple input units to be clamped to a first set of data;

wherein in clamping a first input unit of said multiple input units, said one or more processors dynamically set a value of said first input unit in a first memory unit associated with said first input unit to a corresponding value from said first set of data;

one or more layers of stochastic units, comprising a first stochastic unit;

wherein said first stochastic unit has one or more links traceable to a second subset of said multiple input units, wherein a local coverage extent associated with said first stochastic unit limits said one or more links;

wherein said one or more links represent first weighted connections between said first stochastic unit and second units;

wherein said second units are among said second subset of said multiple input units or from said one or more layers of stochastic units between said first stochastic unit and said multiple input units;

wherein said one or more processors set a memory unit associated with said first stochastic unit to a first value generated based on weighted sum of values of memory units associated with said second units per said first weighted connections represented by said one or more links;

wherein said one or more processors detect sub-features associated with a higher layer of said one or more layers of stochastic units, based on sub-features detected by a lower layer of said one or more layers of stochastic units;

one or more output units;

wherein said one or more processors set a memory unit associated with said one or more output units to a value indicating a detected feature based on one or more said detected sub-features associated with one or more layers of one or more units of said one or more layers of stochastic units;

wherein said one or more processors determine an energy measure corresponding to said first set of data, based on factors comprising of said first weighted connections, said one or more layers of stochastic units, and said first set of data clamped to said first subset of said multiple input units;

wherein in said determining said energy measure, a contribution of said energy measure from said first stochastic unit is reduced by a coverage factor of said first stochastic unit;

wherein said coverage factor of said first stochastic unit is determined based on a value representing fraction of input units within said second subset of said multiple input units traceable from said first stochastic unit that are also in said first subset of said multiple input units clamped to said first set of data;

wherein said one or more processors output to a second memory unit a value representing a quality measure associated with said detected feature determined based on said energy measure and a baseline;

wherein said quality measure indicates a degree of conformity, a degree of confidence, relative probability, or a degree of reliability associated with said detected feature for said first set of data.

20. A system for feature detection with conformity measure, said system comprising:
one or more processors;
multiple input units;
wherein a second set of data determines a first subset of said multiple input units to be clamped to a first set of data;
wherein in clamping a first input unit of said multiple input units, said one or more processors dynamically set a value of said first input unit in a first memory unit associated with said first input unit to a corresponding value from said first set of data;
one or more layers of stochastic units, comprising a first stochastic unit;
wherein said first stochastic unit has one or more links traceable to a second subset of said multiple input units, wherein a local coverage extent associated with said first stochastic unit limits said one or more links;
wherein said one or more links represent first weighted connections between said first stochastic unit and second units;
wherein said second units are among said second subset of said multiple input units or from said one or more layers of stochastic units between said first stochastic unit and said multiple input units;
wherein said one or more processors set a memory unit associated with said first stochastic unit to a first value generated based on weighted sum of values of memory units associated with said second units per said first weighted connections represented by said one or more links;
wherein said one or more processors detect sub-features associated with a higher layer of said one or more layers of stochastic units, based on sub-features detected by a lower layer of said one or more layers of stochastic units;
one or more output units;
wherein said one or more processors set a memory unit associated with said one or more output units to a value indicating a detected feature based on one or more said detected sub-features associated with one or more layers of one or more units of said one or more layers of stochastic units;

wherein said one or more processors determine an energy measure corresponding to said first set of data, based on factors comprising of said first weighted connections, said one or more layers of stochastic units, and said first set of data clamped to said first subset of said multiple input units;

wherein in said determining said energy measure, a contribution of said energy measure from said first stochastic unit is reduced by a coverage factor of said first stochastic unit;

wherein said coverage factor of said first stochastic unit is determined based on a value representing fraction of input units within said second subset of said multiple input units traceable from said first stochastic unit that are also in said first subset of said multiple input units clamped to said first set of data;

wherein said one or more processors output to a second memory unit a value representing a quality measure associated with said detected feature determined based on said energy measure and a baseline;

wherein said local coverage extent associated with said first stochastic unit is defined by a patch shape covering said second units.

21. The system for feature detection as recited in claim 20, wherein said patch shape is circular, square-shape, rectangular, hexagonal, or polygonal.

22. The system for feature detection as recited in claim 20, wherein pattern of arrangement of said patch shape is non-uniformly distributed.

23. The system for feature detection as recited in claim 20, wherein pattern of arrangement of said patch shape is regularly distributed.

24. The system for feature detection as recited in claim 1, wherein one or more units of said multiple input units not belonging to said first subset of said multiple input units are initialized randomly.

25. The system for feature detection as recited in claim 1, wherein one or more units of said multiple input units are stochastic.

26. The system for feature detection as recited in claim 1, wherein in said determining said energy measure corresponding to said first set of data, a contribution to said energy measure from a unit of said first subset of said multiple input units is ignored.

27. The system for feature detection as recited in claim 1, wherein said coverage factor of said first stochastic unit is determined or estimated based on coverage factors associated with said second units.

28. The system for feature detection as recited in claim 1, wherein said coverage factor of said first stochastic unit is determined or estimated based on a value representing fraction of said multiple input units belonging to said first subset of said multiple input units clamped to said first set of data.

29. The system for feature detection as recited in claim 1, wherein a weight value represented by one of said first weighted connections between said first stochastic unit and second units is shared with one of second weighted connections of a second stochastic unit.

* * * * *